US012709628B2

(12) United States Patent
Bregman et al.

(10) Patent No.: US 12,709,628 B2

(45) Date of Patent: Aug. 18, 2026

(54) STAT6 MODULATORS AND USES THEREOF

(71) Applicant: Recludix Pharma, Inc., San Diego, CA (US)

(72) Inventors: Howard Bregman, Melrose, MA (US); John Yeoman, Medford, MA (US); Jennifer Downing, Clinton, MA (US); Samuel K. Reznik, Cambridge, MA (US); Ernest Allen Sickmier, Needham, MA (US); Giovanni Cianchetta, Boxford, MA (US); Rishi G. Vaswani, Lexington, MA (US); Neil Bifulco, Sudbury, MA (US); Xia Tian, Cambridge, MA (US); Andrew Tasker, Simi Valley, CA (US); Brian Hodous, Arlington, MA (US)

(73) Assignee: Recludix Pharma, Inc., San Diego, CA (US)

( * ) Notice: Subject to any disclaimer, the term of this patent is extended or adjusted under 35 U.S.C. 154(b) by 0 days.

(21) Appl. No.: 19/267,357

(22) Filed: Jul. 11, 2025

(65) Prior Publication Data

US 2026/0015373 A1 Jan. 15, 2026

Related U.S. Application Data

(60) Provisional application No. 63/743,999, filed on Jan. 10, 2025, provisional application No. 63/670,686, filed on Jul. 12, 2024.

(51) Int. Cl.
*C07F 9/6561* (2006.01)
*A61K 31/675* (2006.01)

(52) U.S. Cl.
CPC .......... *C07F 9/6561* (2013.01); *A61K 31/675* (2013.01)

(58) Field of Classification Search
CPC ............................ C07F 9/6561; A61K 31/675
See application file for complete search history.

(56) References Cited

U.S. PATENT DOCUMENTS

| | | | |
|---|---|---|---|
| 2002/0068063 | A1 | 6/2002 | Deshaies et al. |
| 2004/0225146 | A1 | 11/2004 | Kolb et al. |
| 2009/0123480 | A1 | 5/2009 | Wang et al. |
| 2013/0190340 | A1 | 7/2013 | Hedstrom et al. |
| 2014/0302523 | A1 | 10/2014 | Crews et al. |
| 2014/0356322 | A1 | 12/2014 | Crews et al. |
| 2015/0274738 | A1 | 10/2015 | Gray et al. |
| 2015/0291562 | A1 | 10/2015 | Crew et al. |
| 2016/0022642 | A1 | 1/2016 | Crews et al. |
| 2016/0214972 | A1 | 7/2016 | Jin et al. |
| 2016/0272639 | A1 | 9/2016 | Crew et al. |
| 2017/0008904 | A1 | 1/2017 | Crew et al. |
| 2017/0037004 | A1 | 2/2017 | Crew et al. |
| 2017/0121321 | A1 | 5/2017 | Crews et al. |
| 2017/0281784 | A1 | 10/2017 | Wang et al. |
| 2018/0009779 | A1 | 1/2018 | Bradner |
| 2018/0118733 | A1 | 5/2018 | Harling et al. |
| 2018/0134684 | A1 | 5/2018 | Bradner et al. |
| 2018/0147202 | A1 | 5/2018 | Crew et al. |
| 2019/0076539 | A1 | 3/2019 | Phillips et al. |
| 2019/0076540 | A1 | 3/2019 | Phillips et al. |
| 2019/0076541 | A1 | 3/2019 | Phillips et al. |
| 2019/0076542 | A1 | 3/2019 | Phillips et al. |
| 2020/0121693 | A1 | 4/2020 | Pache et al. |
| 2023/0295197 | A1 | 9/2023 | Wang et al. |
| 2023/0295200 | A1 | 9/2023 | Wang et al. |
| 2025/0179103 | A1 | 6/2025 | Bifulco et al. |
| 2025/0215029 | A1 | 7/2025 | Bregman et al. |
| 2025/0215030 | A1 | 7/2025 | Bifulco et al. |

FOREIGN PATENT DOCUMENTS

| | | | |
|---|---|---|---|
| AU | 2023351608 | A1 | 5/2025 |
| CN | 120230147 | A | 7/2025 |
| WO | 2002020740 | A2 | 3/2002 |
| WO | 2006091837 | A2 | 8/2006 |
| WO | 2010077589 | A2 | 7/2010 |
| WO | 2012003281 | A2 | 1/2012 |
| WO | 2012078559 | A2 | 6/2012 |
| WO | 2013106643 | A2 | 7/2013 |
| WO | 2013106646 | A2 | 7/2013 |
| WO | 2014063061 | A1 | 4/2014 |
| WO | 2014108452 | A1 | 7/2014 |
| WO | 2014182928 | A2 | 11/2014 |
| WO | 2015160845 | A2 | 10/2015 |
| WO | 2016100184 | A1 | 6/2016 |
| WO | 2016105518 | A1 | 6/2016 |
| WO | 2016118666 | A1 | 7/2016 |
| WO | 2016149668 | A1 | 9/2016 |
| WO | 2016169989 | A1 | 10/2016 |
| WO | 2016197032 | A1 | 12/2016 |

(Continued)

OTHER PUBLICATIONS

Andrés, R. M. et al. (2013). "Studies Of JAK/STAT 3 Expression And Signalling In Psoriasis Identifies STAT 3-S Er727 Phosphorylation As A Modulator Of Transcriptional Activity," Experimental Dermatology 22(5):323-328. Bai, L. et al. (2019). "A Potent And Selective Small-Molecule Degrader Of STAT3 Achieves Complete Tumor Regression In Vivo," Cancer Cell 36(5):498-511.

Cai, Q. et al. (Mar. 28, 2011). "A Potent And Orally Active Antagonist (SM-406/AT-406) Of Multiple Inhibitor Of Apoptosis Proteins (Iaps) In Clinical Development For Cancer Treatment," Journal Of Medicinal Chemistry 54 (8):2714-2726.

Campbell, I. L. (2005, e-pub. Jan. 15, 2005). "Cytokine-Mediated Inflammation, Tumorigenesis, And Disease-Associated JAK/STAT/SOCS Signaling Circuits In The CNS," Brain Research Reviews 48(2):166-177.

Gao, B. et al. (2012). "STAT Proteins—Key Regulators Of Anti-Viral Responses, Inflammation, And Tumorigenesis In The Liver," Journal Of Hepatology 57(2):430-441.

(Continued)

*Primary Examiner* — Kortney L. Klinkel
*Assistant Examiner* — Richard Grant Peckham
(74) *Attorney, Agent, or Firm* — MORRISON & FOERSTER LLP

(57) ABSTRACT

The present disclosure relates generally to STAT6 modulators and uses thereof, and more specifically to compounds, salts, and compositions thereof useful for treating conditions associated with STAT6.

50 Claims, No Drawings

(56) References Cited

FOREIGN PATENT DOCUMENTS

| | | | |
|---|---|---|---|
| WO | 2016197114 | A1 | 12/2016 |
| WO | 2017007612 | A1 | 1/2017 |
| WO | 2017011371 | A1 | 1/2017 |
| WO | 2017011590 | A1 | 1/2017 |
| WO | 2017079267 | A1 | 5/2017 |
| WO | 2017117473 | A1 | 7/2017 |
| WO | 2017117474 | A1 | 7/2017 |
| WO | 2017161119 | A1 | 9/2017 |
| WO | 2017176708 | A1 | 10/2017 |
| WO | 2017176957 | A1 | 10/2017 |
| WO | 2017176958 | A1 | 10/2017 |
| WO | 2017197036 | A1 | 11/2017 |
| WO | 2017197046 | A1 | 11/2017 |
| WO | 2017197051 | A1 | 11/2017 |
| WO | 2017197055 | A1 | 11/2017 |
| WO | 2017197056 | A1 | 11/2017 |
| WO | 2020198435 | A1 | 10/2020 |
| WO | 2020205467 | A1 | 10/2020 |
| WO | 2020206424 | A1 | 10/2020 |
| WO | 2021188696 | A1 | 9/2021 |
| WO | 2021195481 | A1 | 9/2021 |
| WO | 2022077010 | A1 | 4/2022 |
| WO | 2023133336 | A1 | 7/2023 |
| WO | 2023164680 | A1 | 8/2023 |
| WO | 2023192960 | A1 | 10/2023 |
| WO | 2023250058 | A1 | 12/2023 |
| WO | 2024030628 | A1 | 2/2024 |
| WO | 2024064080 | A1 | 3/2024 |
| WO | 2024071439 | A1 | 4/2024 |
| WO | 2024148041 | A1 | 7/2024 |
| WO | 2024173291 | A1 | 8/2024 |
| WO | 2024233639 | A2 | 11/2024 |
| WO | 2024238598 | A2 | 11/2024 |
| WO | 2024238603 | A2 | 11/2024 |
| WO | 2025049820 | A1 | 3/2025 |
| WO | 2025049821 | A1 | 3/2025 |
| WO | 2025103477 | A1 | 5/2025 |
| WO | 2025147320 | A1 | 7/2025 |
| WO | 2025147509 | A1 | 7/2025 |
| WO | 2025/218706 | A1 | 10/2025 |
| WO | 2025/228404 | A1 | 11/2025 |

OTHER PUBLICATIONS

Gardino, A.K. et al. (2025). "Recludix Platform Has Unlocked Development Of Oral, Reversible Small Molecule Inhibitors Of SH2 Domains," Poster, presented at the FASEB Signal Transduction in the Immune System Conference, Scottsdale, AZ, USA, Jun. 28-Jul. 2, 2025, one page.
Gollob, J. et al. (May 2025). "Revolutionizing Immunology: Oral Medicines with Biologics-like Activity," Kymera Therapeutics, 9 pages.
Goropevsek, A. et al. (2017, e-pub. May 23, 2016). "The Role Of STAT Signaling Pathways In The Pathogenesis Of Systemic Lupus Erythematosus," Clinical Reviews In Allergy & Immunology 52(2):164-181.
Grote, K. et al. (2005). "JANUS Under Stress—Role Of JAK/STAT Signaling Pathway In Vascular Diseases," Vascular Pharmacology 43(5):357-363.
Gurzov, E. N. et al. (2016). "The JAK/STAT Pathway In Obesity And Diabetes," The FEBS Journal 283 (16):3002-3015.
Heidel, K. M. et al. (2019, e-pub. Aug. 30, 2019). "Phosphonate Prodrugs: An Overview And Recent Advances," Future Medicinal Chemistry 11(13):1625-1643.
Hodge, L. S. et al. (Feb. 13, 2014, e-pub. Dec. 11, 2013). "Constitutive Activation Of STAT5A And STAT5B Regulates IgM Secretion In Waldenstrom's Macroglobulinemia," Blood, The Journal of the American Society of Hematology 123(7):1055-1058.
Jatiani, S. S. et al. (2010). "JAK/STAT Pathways In Cytokine Signaling And Myeloproliferative Disorders: Approaches For Targeted Therapies," Genes & Cancer 1(10):979-993.
Knight, J. M. et al. (2018, e-pub. May 8, 2018). "Small Molecule Targeting Of The STAT5/6 Src Homology 2 (SH2) Domains To Inhibit Allergic Airway Disease," Journal of Biological Chemistry 293(26):10026-10040.
Lai, P. S. et al. (2015, e-pub. Sep. 22, 2015). "A STAT Inhibitor Patent Review: Progress Since 2011," Expert Opinion On Therapeutic Patents 25(12):1397-1421.
Lee, J. et al. (Oct. 2, 2022). "Discovery Of E3 Ligase Ligands For Target Protein Degradation," Molecules 27 (19):6515, 23 pages.
Luh, L. M. et al. (2020). "Prey For The Proteasome: Targeted Protein Degradation—A Medicinal Chemist's Perspective," Angewandte Chemie International Edition 59(36):15448-15466.
Maple, H. J. et al. (Oct. 2019). "Developing Degraders: Principles And Perspectives On Design And Chemical Space," MedChemComm 10(10):1755-1764.
Mehellou, Y. et al. (Aug. 9, 2017). "The Protide Prodrug Technology: From The Concept To The Clinic: Miniperspective," Journal of medicinal chemistry 61(6):2211-2226.
Metz, P. et al. (2025). "Highly Selective And Reversible STAT6 Inhibition Demonstrates Potential For Differentiated Efficacy And Safety Profile In Type 2 Allergic Inflammation," Poster, presented at the ATS 2025 International Conference, San Francisco, CA, USA, May 18-21, 2025, one page.
O'Shea, J. J. et al. (Jan. 10, 2013). "JAKs and STATs in Immunity, Immunodeficiency, And Cancer," New England Journal of Medicine 368(2):161-170.
Oh, C.K. et al. (Mar. 1, 2010). "Investigational Therapeutics Targeting The IL-4/IL-13/STAT-6 Pathway For The Treatment Of Asthma", European Respiratory Review 19(115):46-54.
Ortiz-Munoz, G. et al. (Apr. 2009). "Suppressors Of Cytokine Signaling Modulate JAK/STAT-Mediated Cell Responses During Atherosclerosis," Arteriosclerosis, Thrombosis, And Vascular Biology 29(4):525-531.
Pubchem (Aug. 16, 2010). "[2-[[(3S,6S)-3-[[(2S)-5-amino-1-(benzylamino)-1,5-dioxopentan-2-yl]carbamoyl]-5-oxo-1,2,3,6,7,8,9,9a-octahydropyrrolo[1,2-a]azepin-6-yl]carbamoyl]-1H-indol-5-yl]methylphosphonic acid," PubChem CID 46840597, 8 pages.
Rauch, I. et al. (Jan.-Mar. 2013, e-pub. Jan. 1, 2013). "The Regulation Of Inflammation By Interferons And Their STATs," Jak-stat 2(1):e23820, 14 pages.
Recludix Pharma (2024). "Corporate Presentation: Evercore ISI Emerging Private Biotech Conference 2024," 23 pages.
Recludix Pharma (Apr. 2024). "Corporate Presentation: Unlocking New Therapeutic Possibilities," 25 pages.
Recludix Pharma (Feb. 8, 2023). "Guggenheim Oncology Conference: Unlocking New Therapeutic Possibilities," 26 pages.
Recludix Pharma (Jan. 15, 2025). "JP Morgan Healthcare Conference: Unlocking New Therapeutic Possibilities," 25 pages.
Recludix Pharma (Jan. 2023). "Corporate Presentation: JP Morgan Healthcare Conference," 31 pages.
Recludix Pharma (Jan. 2023). "JP Morgan Healthcare Conference: Unlocking New Therapeutic Possibilities," 26 pages.
Recludix Pharma (Jan. 2024). "Corporate Presentation: Unlocking New Therapeutic Possibilities," 25 pages.
Recludix Pharma (Jan. 2025). "Corporate Presentation: Unlocking New Therapeutic Possibilities," 33 pages.
Recludix Pharma (Jul. 20, 2023). "Recludix Pharma Enters into a Strategic Collaboration with Sanofi to Advance Novel Oral STAT6 Inhibitor in Multiple Immunological and Inflammatory Indications," located at https://recludixpharma.com/recludix-pharma-enters-into-a-strategic-collaboration-with-sanofi-to-advance-novel-oral-stat6-inhibitor-in-multiple-immunological-and-inflammatory-indications/, 2 pages.
Recludix Pharma (Jul. 2023). "Corporate Presentation: Unlocking New Therapeutic Possibilities," 26 pages.
Recludix Pharma (Jul. 2024). "Corporate Presentation: Unlocking New Therapeutic Possibilities," 26 pages.
Recludix Pharma (Jul. 2025). "Corporate Presentation: Unlocking New Therapeutic Possibilities," 30 pages.
Recludix Pharma (Jun. 2025). "Corporate Presentation: Unlocking New Therapeutic Possibilities," 30 pages.

(56) References Cited

OTHER PUBLICATIONS

Recludix Pharma (Mar. 14, 2023). "Oppenheimer Annual Healthcare Conference: Unlocking New Therapeutic Possibilities," 27 pages.
Recludix Pharma (May 19, 2025). "Recludix Pharma Presents Data Demonstrating Potent Efficacy and High Selectivity of a STAT6 Inhibitor in Preclinical Asthma Model," located at https://recludixpharma.com/recludix-pharma-presents-data-demonstrating-potent-efficacy-and-high-selectivity-of-a-stat6-inhibitor-in-preclinical-asthma-model/, 3 pages.
Recludix Pharma (May 2022). "Corporate Presentation: Unlocking New Therapeutic Possibilities," 25 pages.
Recludix Pharma (Nov. 2021). "Corporate Presentation: Unlocking New Therapeutic Possibilities," 28 pages.
Recludix Pharma (Sep. 2023). "Corporate Presentation: Unlocking New Therapeutic Possibilities," 26 pages.
Recludix Pharma (Sep. 2024). "Corporate Presentation: Unlocking New Therapeutic Possibilities," 26 pages.
Sanofi (Dec. 7, 2023). "R&D Day: Play to Win," 154 pages.
Sugimoto, K. (Sep. 7, 2008). "Role Of STAT3 In Inflammatory Bowel Disease," World Journal Of Gastroenterology: WJG 14(33):5110-5114.
Sun, H. et al. (2008, e-pub. Oct. 28, 2008). "Structure-Based Design, Synthesis, Evaluation, And Crystallographic Studies Of Conformationally Constrained Smac Mimetics As Inhibitors Of The X-Linked Inhibitor Of Apoptosis Protein (XIAP)," Journal Of Medicinal Chemistry 51(22):7169-7180, 42 pages.
Sun, H. et al. (2010, e-pub. Aug. 4, 2010). "Nonpeptidic And Potent Small-Molecule Inhibitors Of Ciap-1/2 And XIAP Proteins," Journal Of Medicinal Chemistry 53(17):6361-6367.
Tamiya, T. et al. (May 2011). "Suppressors Of Cytokine Signaling (SOCS) Proteins And JAK/STAT Pathways: Regulation Of T-Cell Inflammation By SOCS1 And SOCS3," Arteriosclerosis, Thrombosis, And Vascular Biology 31 (5):980-985.
Toure, M. et al. (2016). "Small-Molecule PROTACS: New Approaches To Protein Degradation," Angewandte Chemie International Edition 55(6):1966-1973.
Turkson, J. et al. (2000). "STAT Proteins: Novel Molecular Targets For Cancer Drug Discovery," Oncogene 19 (56):6613-6626.
Uehara, T. et al. (Apr. 24, 2017). "Selective Degradation Of Splicing Factor Capera By Anticancer Sulfonamides," Nature Chemical Biology 13(6):675-680.
Varfolomeev, E. et al. (Nov. 16, 2007). "IAP Antagonists Induce Autoubiquitination Of C-Iaps, NF-Kb Activation, And Tnfα-Dependent Apoptosis," Cell 131(4):669-681.
Walker, J. G. et al. (2005). "The Jak-STAT Pathway In Rheumatoid Arthritis," The Journal Of Rheumatology 32 (9):1650-1653.
Wang, A. et al. (Mar. 8, 2024). "53901. Potent and Selective Oral STAT6 Degraders Inhibit IL-4 and IL-13 Functions in Human Cells and Block TH2 Inflammation in a Mouse Model of Atopic Dermatitis," Poster, presented at American Academy of Dermatology, San Diego, CA, Mar. 8-12, 2024, five pages.
Wang, A. et al. (May 16-21, 2024). "Potent and Selective Oral STAT6 Degrader, KT-621, Inhibits IL-4 and IL-13 Functions in Human Cells and Blocks Th2 Inflammation in House Dust Mite Models of Asthma Prophylactically and Therapeutically," Poster No. P1564, ATS Annual Meeting 2025, May 16-21, 2025, San Francisco, CA, 1 page.
Wang, A. et al. (May 17-22, 2024). "Potent and Selective Oral STAT6 Degraders Inhibit IL-4 and IL-13 Functions in Human Cells and Block TH2 Inflammation in a House Dust Mite Mouse Model of Asthma," Poster No. 813, ATS Annual Meeting Kymera Therapeutics, May 17-22, 2024, San Diego, CA, one page.
Wang, A. et al. (May 18-21, 2024). "Potent and Selective Oral STAT6 Degraders Inhibit IL-4 and IL-13 Functions in Human Cells and Block TH2 Inflammation In Vivo in a Mouse Model," Poster No. Tu1488, Digestive Disease Week 2024, May 18-22, 2024, Washington D.C., 1 page.
Wang, A. et al. (Oct. 24-28, 2024). "Potent and Selective Oral STAT6 Degrader, KT-621, Inhibits IL-4 and IL-13 Functions in Human Cells and Blocks TH2 Inflammation In Vivo," Poster, presented at ACAAI 2024 Annual Scientific Meeting, Boston, MA, Oct. 24-28, 2024, one page.
Wang, A. et al. (Sep. 25-28, 2024). "Potent and Selective Oral STAT6 Degrader, KT-621, Inhibits IL-4 and IL-13 Functions in Human Cells and Blocks TH2 Inflammation In Vivo," EADV Congress, Sep. 25-28, 2024, Amsterdam, Netherlands, 1 page.
Zhou, H. et al. (2019). "Structure-Based Discovery Of SD-36 As A Potent, Selective, And Efficacious PROTAC Degrader Of STAT3 Protein," Journal Of Medicinal Chemistry 62(24):11280-11300.
Zhou, H. et al. (May 10, 2021). "SD-91 As A Potent And Selective STAT3 Degrader Capable Of Achieving Complete And Long-Lasting Tumor Regression," ACS Medicinal Chemistry Letters 12(6):996-1004.
International Search Report and Written Opinion mailed on Oct. 13, 2025 for PCT Application No. PCT/US2025/037404, filed on Jul. 11, 2025, 14 pages.

STAT6 MODULATORS AND USES THEREOF

CROSS REFERENCE TO RELATED APPLICATIONS

This application claims priority benefit to U.S. Provisional Application Nos. 63/670,686, filed Jul. 12, 2024, and 63/743,999, filed Jan. 10, 2025, the disclosures of each of which are hereby incorporated herein by reference in their entireties for all purposes.

FIELD

The present disclosure relates generally to STAT6 modulators and uses thereof, and more specifically to compounds, salts, and compositions thereof useful for treating conditions associated with STAT6.

BACKGROUND

The Signal Transducer and Activator of Transcription (STAT) family of proteins consists of transcription factors that play an essential role in the regulation of cell processes, such as proliferation, differentiation, apoptosis and angiogenesis. Seven STAT genes have been identified in the human genome: STAT1, STAT2, STAT3, STAT4, STAT5a, STAT5b, and STAT6.

Recent studies have shown that STAT6 signaling is essential for IL-4- and IL-13-induced epithelial mesenchymal transition (EMT) and aggressiveness of colorectal cancer cells (CRC) cells. STAT6 is involved in several aspects of inflammatory disease and other related conditions.

Given their role in the regulation of cell processes, modulating the activity of one or more STAT proteins, particularly STAT6, represent a pivotal area of investigation for the treatment of cancer, inflammatory conditions, and other therapeutic needs. Therefore, there is a substantial need to supply modulators of STAT, particularly STAT6 modulators.

BRIEF SUMMARY

The present disclosure provides compounds of Formula (I), compositions thereof, and methods of using these compounds and compositions thereof for the treatment of diseases or conditions associated with STAT, in particular STAT6.

In one aspect, provided is a compound of Formula (I):

(I)

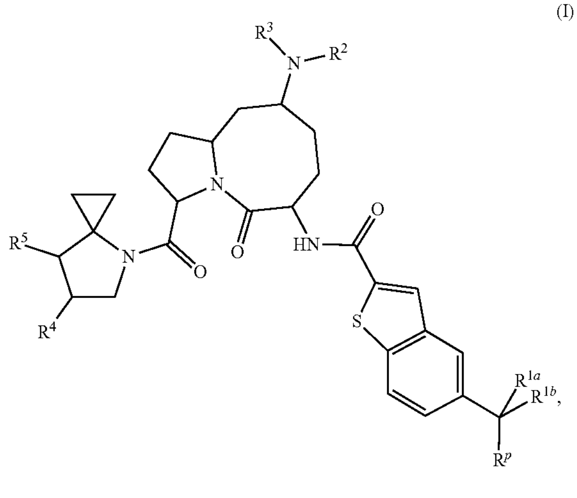

or a pharmaceutically acceptable salt thereof, wherein: $R^{1a}$ and $R^{1b}$ are each independently H or halogen; $R^2$ is H, $(C_1$-$C_6)$alkyl, or $(C_3$-$C_6)$cycloalkyl; $R^3$ is $(C_1$-$C_6)$alkyl, halo$(C_1$-$C_6)$alkyl, $(C_3$-$C_6)$cycloalkyl, 3- to 7-membered heterocyclyl, —$(C_1$-$C_6)$alkylene-$(C_3$-$C_6)$cycloalkyl, or —$(C_1$-$C_6)$alkylene-(3- to 7-membered heterocyclyl), wherein $(C_1$-$C_6)$alkyl, $(C_3$-$C_6)$cycloalkyl, $(C_3$-$C_6)$cycloalkyl of —$(C_1$-$C_6)$alkylene-$(C_3$-$C_6)$cycloalkyl, or (3- to 7-membered heterocyclyl) of —$(C_1$-$C_6)$alkylene-(3- to 7-membered heterocyclyl) is each substituted with 0, 1, 2, 3, 4, or 5 substituents each independently selected from the group consisting of $(C_1$-$C_6)$alkyl, $(C_1$-$C_6)$alkoxy, cyano, halogen, halo$(C_1$-$C_6)$alkyl, and halo$(C_1$-$C_6)$alkoxy, or $R^2$ and $R^3$ together with the nitrogen atom to which they are attached form 5- to 7-membered heterocyclyl substituted with 0, 1, 2, or 3 substituents each independently selected from the group consisting of $(C_1$-$C_6)$alkyl, $(C_1$-$C_6)$alkoxy, cyano, halogen, halo$(C_1$-$C_6)$alkyl, and halo$(C_1$-$C_6)$alkoxy; $R^4$ is H, $(C_6$-$C_{10})$aryl, or 5- to 10-membered heteroaryl, wherein $(C_6$-$C_{10})$aryl or 5- to 10-membered heteroaryl is each substituted with 0, 1, 2, or 3 substituents each independently selected from the group consisting of halogen, cyano, $(C_1$-$C_6)$alkyl, $(C_1$-$C_6)$alkoxy, halo$(C_1$-$C_6)$alkyl, halo$(C_1$-$C_6)$alkoxy, and —$NR^{4a}R^{4b}$, wherein: each $R^{4a}$ and $R^{4b}$ is independently H or $(C_1$-$C_6)$alkyl; $R^5$ is H, cyano, or $(C_1$-$C_6)$alkoxy; and $R^P$ is phosphonic acid, phosphonate, phosphonamidate, or phosphondiamidate.

DETAILED DESCRIPTION

The following description is presented to enable a person of ordinary skill in the art to make and use the various embodiments. Descriptions of specific methods, techniques, and applications are provided only as examples. Various modifications to the examples described herein will be readily apparent to those of ordinary skill in the art, and the general principles defined herein may be applied to other examples and applications without departing from the spirit and scope of the various embodiments. Thus, the various embodiments are not intended to be limited to the examples described herein and shown, but are to be accorded the scope consistent with the claims.

Definitions

As used in the present specification, the following words and phrases are generally intended to have the meanings as set forth below, except to the extent that the context in which they are used indicates otherwise.

Throughout this application, unless the context indicates otherwise, references to a compound of Formula (I) include all subgroups defined herein, such as Formula (I-A-1), (I-A-2), (I-A-3), (I-A-4), (I-A-5), (I-A-6), (I-B-1), (I-B-2), (I-B-3), (I-B-4), (I-B-5), (I-B-6), (I-C-1), (I-C-2), (I-C-3), (I-C-4), (I-C-5), (I-C-6), (I-D-1), (I-D-2), (I-D-3), (I-D-4), (I-D-5), (I-D-6), (I-E-1), (I-E-2), (I-E-3), (I-E-4), (I-E-5), (I-E-6), (I-F-1), (I-F-2), (I-F-3), (I-F-4), (I-F-5), (I-F-6), (I-G-1), (I-G-2), (I-G-3), (I-G-4), (I-G-5), (I-G-6), (I-H-1), (I-H-2), (I-H-3), (I-H-4), (I-H-5), (I-H-6), (I-J-1), (I-J-2), (I-J-3), (I-J-4), (I-J-5), or (I-J-6) including all substructures, subgenera, preferences, embodiments, examples, and particular compounds defined and/or described herein. In some embodiments, references to a compound of Formula (I) and subgroups thereof include ionic forms, stereoisomers, rotamers, tautomers, oxides (e.g., N-oxides, S-oxides), esters, prodrugs, isotopologues, and/or protected forms thereof.

When used in connection to describe a chemical group that may have multiple points of attachment, a hyphen (-) designates the point of attachment(s) of that group. For example, —NHC(O)OH means that the point of attachment for this group occurs on the nitrogen atom.

As used herein, "$C_X$-$C_Y$" or "($C_x$-$C_y$)" in reference to or preceding the name of a chemical group (e.g., alkyl, alkoxy, cycloalkyl, aryl) refers to the group having from X to Y carbon atoms, for example a ($C_1$-$C_6$)alkyl refers to an alkyl having 1, 2, 3, 4, 5, or 6 carbon atoms. The terms "halo" and "halogen" refer to an atom selected from fluorine (fluoro, —F), chlorine (chloro, —Cl), bromine (bromo, —Br), and iodine (iodo, —I).

Unless otherwise specified, the term "alkyl" when used alone or as part of a larger moiety, such as "haloalkyl", and the like, means saturated straight-chain or branched monovalent hydrocarbon radical. For example, "($C_1$-$C_6$)alkyl" includes methyl, ethyl, propyl, isopropyl, n-butyl, 1-methylpropyl, isobutyl, tert-butyl, pentyl, isopentyl, neopentyl, and hexyl. The term "alkylene" when used alone or as part of a larger moiety, such as "alkylene-cycloalkyl", and the like, means saturated straight-chain or branched divalent hydrocarbon radical, for example, $—CH_2—$, $—CH_2CH_2—$, $—CH_2CH_2CH_2—$, $—CH_2CH_2CH_2CH_2—$, $—CH(CH_3)—$, and $—C(CH_3)_2—$.

The term "haloalkyl" includes mono, poly, and perhaloalkyl groups where the halogens are independently selected from fluorine, chlorine, bromine, and iodine. In some embodiments, the halogen is fluorine. For example, haloalkyl includes chloromethyl, dichloromethyl, trichloromethyl, fluoromethyl, difluoromethyl, trifluoromethyl, 1,2-difluoroethyl, 2,2,2-trifluoroethyl, and 1,1,2,2-tetrafluoroethyl.

"Alkoxy" means an alkyl radical attached through an oxygen linking atom, represented by —O-alkyl. For example, "($C_1$-$C_4$)alkoxy" includes methoxy, ethoxy, proproxy, and butoxy.

"Haloalkoxy" is a haloalkyl group which is attached to another moiety via an oxygen atom such as, e.g., $—OCHF_2$ or $—OCF_3$.

The term "oxo" means the group =O.

The term "imino" means the group =NH.

Unless otherwise specified, the term "heteroaryl" refers to a 5- to 12-membered aromatic radical containing 1-4 heteroatoms selected from N, O, and S. In some instances, nitrogen atoms in a heteroaryl may be quaternized. The term "heteroaryl" may be used interchangeably with the terms "heteroaryl ring", "heteroaryl group", or "heteroaromatic". A heteroaryl group may be mono- or bi-cyclic. Monocyclic heteroaryl includes, for example, pyridyl, pyridazinyl, pyrimidinyl, pyrazinyl, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, etc. Bicyclic heteroaryls include groups in which a monocyclic heteroaryl ring is fused to one or more aryl or heteroaryl rings. Nonlimiting examples include indolyl, benzooxazolyl, benzooxodiazolyl, indazolyl, benzimidazolyl, benzthiazolyl, benzothiopheneyl, quinolinyl, quinazolinyl, quinoxalinyl, pyrrolopyridinyl, pyrrolopyrimidinyl, pyrrolopyridinyl, thienopyridinyl, thienopyrimidinyl, indolizinyl, purinyl, cinnolinyl, naphthyridinyl, and pteridinyl. It will be understood that when specified, optional substituents on a heteroaryl group may be present on any substitutable position and, include, e.g., the position at which the heteroaryl is attached (where valency permits).

Unless otherwise specified, the term "heterocyclyl" means a 4- to 12-membered saturated or partially unsaturated heterocyclic ring containing 1 to 4 heteroatoms independently selected from N, O, and S. The terms "heterocycle", "heterocyclyl", "heterocyclyl ring", "heterocyclic group", "heterocyclic moiety", and "heterocyclic radical", are used interchangeably herein. A heterocyclyl ring can be attached to its pendant group at any heteroatom or carbon atom that results in a stable structure. A heterocyclyl group may be mono- or bicyclic (e.g., a bridged, fused, or spiro bicyclic ring). Examples of monocyclic saturated or partially unsaturated heterocyclic radicals include, without limitation, azetidinyl, tetrahydrofuranyl, tetrahydrothienyl, terahydropyranyl, pyrrolidinyl, pyrrolidonyl, piperidinyl, oxazolidinyl, piperazinyl, dioxanyl, dioxolanyl, morpholinyl, dihydrofuranyl, dihydropyranyl, dihydropyridinyl, tetrahydropyridinyl, dihydropyrimidinyl, tetrahydropyrimidinyl, dihydrooxadizolyl, and dihydroisoxazolyl. Bi-cyclic heterocyclyl groups include, e.g., unsaturated heterocyclic radicals fused to another unsaturated heterocyclic radical, cycloalkyl, aryl, or heteroaryl ring, such as for example, benzodioxolyl, dihydrobenzodioxinyl, dihydrobenzofuranyl, dihydrobenzothiophenyl, 5-oxa-2,6-diazaspiro[3.4]oct-6-enyl, 6-thia-2,7-diazaspiro[3.4]octanyl, 2,6-diazaspiro[3.3]heptanyl, spiro[indoline-3,3'-pyrrolidine]-yl, thiochromanyl, and the like. It will be understood that when specified, optional substituents on a heterocyclyl group may be present on any substitutable position and, include, e.g., the position at which the heterocyclyl is attached (where valency permits).

The term "spiro" refers to two rings that shares one ring atom (e.g., carbon).

The term "fused" refers to two rings that share two adjacent ring atoms with one another.

The term "bridged" refers to two rings that share three adjacent ring atoms with one another.

The term "aryl" refers to an aromatic carbocyclic single ring or two fused ring system containing 6 to 10 carbon atoms. Examples include phenyl, indanyl, tetrahydronaphthalene, and naphthyl. In some embodiments, the aryl is phenyl or naphthyl. In some embodiments, the aryl is phenyl.

The term "cycloalkyl", used alone or as part of a larger moiety, refers to a saturated cyclic aliphatic monocyclic or bicyclic ring system, including spirocyclic ring system that may be referred to as "spirocycloalkyl", having from, unless otherwise specified, 3 to 10 carbon ring atoms. Monocyclic cycloalkyl groups include, without limitation, cyclopropyl, cyclobutyl, cyclopentyl, cyclopentenyl, cyclohexyl, cyclohexenyl, cycloheptyl, cycloheptenyl, and cyclooctyl. It will be understood that when specified, optional substituents on a cycloalkyl or cycloaliphatic group may be present on any substitutable position and, include, e.g., the position at which the cycloalkyl group is attached.

The term "N-linked amino acid" refers to an amino acid that is attached to the indicated moiety via the main-chain amino group. For example, N-linked alanine can be represented by $—NHCH(CH_3)C(O)OH$. N-linked amino acids can be substituted or unsubstituted.

The term "N-linked amino acid ester" refers to an N-linked amino acid where the main-chain carboxylic acid group and/or any other carboxylic acid group(s) has been converted to an ester group. N-linked amino acid esters can be substituted or unsubstituted.

The term "amino acid" refers to any amino acid (both standard and non-standard amino acids, and both natural and non-natural amino acids), including, but not limited to, α-amino acids, 3-amino acids, γ-amino acids, and 6-amino acids. Examples of suitable amino acids include, but are not limited to, alanine, asparagine, aspartate, cysteine, glutamate, glutamine, glycine, proline, serine, tyrosine, arginine, histidine, isoleucine, leucine, lysine, methionine, phenylalanine, threonine, tryptophan, and valine. Additional examples of suitable amino acids include, but are not limited to, ornithine, hypusine, 2-aminoisobutyric acid, dehydroalanine, gamma-aminobutyric acid, citrulline, beta-alanine, alpha-ethyl-glycine, alpha-propyl-glycine and norleucine.

Non-natural amino acids are known in the art and include, e.g., alpha-alkyl amino acids (e.g., alpha methyl), alpha-alkylalkoxy amino acids (e.g., alpha $—CH_2OCH_3$), N-methyl amino acids, homo-amino acids, etc.

The term "phosphonic acid," as used herein, refers to an organophosphorous group containing a P(═O) moiety where the phosphorous atom is bonded to a carbon atom (herein the point of attachment of $R^P$) and two hydroxy groups, i.e., $—P(═O)(OH)_2$. The term "phosphonate," as used herein, refers to an organophosphorous group containing a P(═O) moiety where the phosphorous atom is bonded to a carbon atom (herein the point of attachment of $R^P$) and two monovalent oxygen-linked groups, up to one of which may be hydroxy, and the other or both of which may be a non-hydroxy group, such as alkyloxy, aryloxy, cycloalkyloxy, heteroaryloxy, or heterocyclyloxy. The term "phosphonamidate," as used herein, refers to an organophosphorous group containing a P(═O) moiety where the phosphorous atom is bonded to a carbon atom (herein the point of attachment of $R^P$), one monovalent oxygen-linked group, such as hydroxy, alkyloxy, aryloxy, cycloalkyloxy, heteroaryloxy, or heterocyclyloxy, and one monovalent nitrogen-linked group, such as alkylamino, arylamino, cycloalkylamino, heteroarylamino, heterocyclylamino, N-linked amino acid, N-linked amino acid ester, N-linked heteroaryl, or N-linked heterocyclyl. The term "phosphondiamidate," as used herein, refers to an organophosphorous group containing a P(═O) moiety where the phosphorous atom is bonded to a carbon atom (herein the point of attachment of $R^P$) and two monovalent nitrogen-linked group, such as alkylamino, arylamino, cycloalkylamino, heteroarylamino, heterocyclylamino, N-linked amino acid, N-linked amino acid ester, N-linked heteroaryl, or N-linked heterocyclyl.

The term "substituted" refers to one or more hydrogen radical of the designated group being replaced with the radical(s) of a moiety other than hydrogen. Unless otherwise noted, the substituent(s) can be in any position(s), provided that the respective compound is sufficiently stable and pharmaceutically acceptable. Reference to a group being substituted by, for example, 0, 1, 2, or 3 substituents indicates the group is optionally substituted, that is the group may be unsubstituted (have zero substituents) or may be substituted with one, two, or three substituents.

Compounds having one or more chiral centers can exist in various stereoisomeric forms. Stereoisomers are compounds that differ only in their spatial arrangement. Stereoisomers include all diastereomeric, enantiomeric, and epimeric forms as well as racemates and mixtures thereof. A "geometric isomer" refers to stereoisomers that differ in the orientation of substituent group in relationship to a carbon-carbon double bond, a cycloalkyl ring, or a bridged bicyclic system. Atoms (other than H) on each side of a carbon-carbon double bond may be in an E (substituents are on opposite sides of the carbon-carbon double bond) or Z (substituents are oriented on the same side) configuration. "Cis" refers to substituents oriented on the same side of a double bond or ring, whereas "trans" refers to substituents oriented on opposite sides of a double bond or ring.

When the stereochemical configuration at a chiral center in a compound having one or more chiral centers is depicted by its chemical name (e.g., where the configuration is indicated in the chemical name by "R" or "S") or structure (e.g., the configuration is indicated by "wedge" bonds), the enrichment of the indicated configuration relative to the opposite configuration is greater than 50%, 60%, 70%, 80%, 90%, 99% or 99.9%. "Enrichment of the indicated configuration relative to the opposite configuration" is a mole percent and is determined by dividing the number of compounds with the indicated stereochemical configuration at the chiral center(s) by the total number of all of the compounds with the same or opposite stereochemical configuration in a mixture.

When a geometric isomer is depicted by name or structure, the enrichment of the indicated isomer relative to the opposite isomer is greater than 50%, 60%, 70%, 80%, 90%, 99% or 99.9%. "Enrichment of the indicated isomer relative to the opposite isomer" is a mole percent and is determined by dividing the number of compounds with the indicated geometrical configuration by the total number of all of the compounds with the same or opposite geometrical configuration in a mixture.

When a disclosed compound is named or depicted by structure without indicating stereochemistry, it is understood that the name or the structure encompasses one of the possible stereoisomers or geometric isomers free of the others, or a mixture of the encompassed stereoisomers or geometric isomers.

The terms "subject" and "patient" may be used interchangeably, and means a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment.

The term "inhibit," "inhibition" or "inhibiting" includes a decrease in the baseline activity of a biological activity or process.

The term "pharmaceutically acceptable excipient" refers to a compound suitable for use in contact with recipient animals, particularly mammals, and more particularly humans, and having a toxicity, irritation, or allergic response commensurate with a reasonable benefit/risk ratio, and effective for their intended use.

As used herein, the term "pharmaceutically acceptable salt" refers to salts that are, within the scope of sound medical judgment, suitable for administration to a subject without undue toxicity, irritation, allergic response, or other undesired effect, commensurate with a reasonable benefit/risk ratio. Pharmaceutically acceptable salts of the compounds describe herein include those derived from suitable inorganic and organic acids and bases.

The term "effective amount" or "therapeutically effective amount" refers to an amount of a compound described herein that is sufficient to achieve the desired biological effect. In some embodiments, the effective amount is sufficient to achieve the desired therapeutic effect (such as treatment of a condition recited herein) under the conditions of administration by modulating, e.g., inhibiting STAT, in particular STAT6. The therapeutically effective amount will vary depending on the compound, the disease or condition and its severity and the age, weight, or other characteristics of the subject to be treated.

The term "administer," "administering," and "administration," refer to contacting a subject with a compound or composition, or to prescribing, instructing, managing, or supervising the contacting of a subject with a compound or a composition by the subject or by another.

Compounds

Compounds and salts thereof (such as pharmaceutically acceptable salts) are detailed herein, including in the Brief Summary and in the appended claims. Also provided are the use of all of the compounds described herein, including any and all stereoisomers, including geometric isomers (e.g., cis/trans, E/Z isomers), enantiomers, diastereomers, and mixtures thereof in any ratio including racemic mixtures, and salts of the compounds described herein, as well as methods of making such compounds. Any compound described herein may also be referred to as a drug.

In one aspect, provided is a compound of Formula (I):

(I)

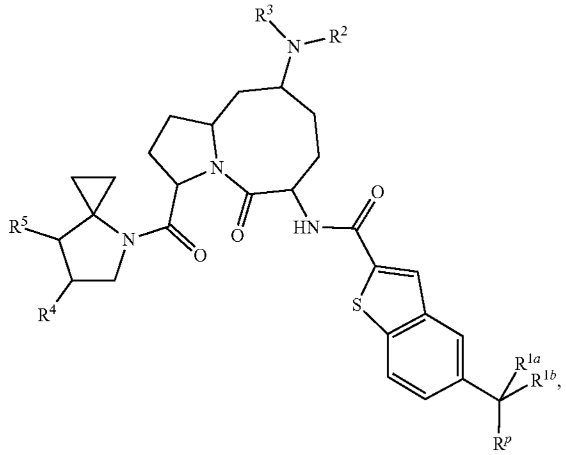

or a pharmaceutically acceptable salt thereof, wherein:

$R^{1a}$ and $R^{1b}$ are each independently H or halogen;

$R^2$ is H, $(C_1\text{-}C_6)$alkyl, or $(C_3\text{-}C_6)$cycloalkyl;

$R^3$ is $(C_1\text{-}C_6)$alkyl, halo$(C_1\text{-}C_6)$alkyl, $(C_3\text{-}C_6)$cycloalkyl, 3- to 7-membered heterocyclyl, —$(C_1\text{-}C_6)$alkylene-$(C_3\text{-}C_6)$cycloalkyl, or —$(C_1\text{-}C_6)$alkylene-(3- to 7-membered heterocyclyl), wherein $(C_1\text{-}C_6)$alkyl, $(C_3\text{-}C_6)$cycloalkyl, $(C_3\text{-}C_6)$cycloalkyl of —$(C_1\text{-}C_6)$alkylene-$(C_3\text{-}C_6)$cycloalkyl, or (3- to 7-membered heterocyclyl) of —$(C_1\text{-}C_6)$alkylene-(3- to 7-membered heterocyclyl) is each substituted with 0, 1, 2, 3, 4, or 5 substituents each independently selected from the group consisting of $(C_1\text{-}C_6)$alkyl, $(C_1\text{-}C_6)$alkoxy, cyano, halogen, halo$(C_1\text{-}C_6)$alkyl, and halo$(C_1\text{-}C_6)$alkoxy, or $R^2$ and $R^3$ together with the nitrogen atom to which they are attached form 5- to 7-membered heterocyclyl substituted with 0, 1, 2, or 3 substituents each independently selected from the group consisting of $(C_1\text{-}C_6)$alkyl, $(C_1\text{-}C_6)$alkoxy, cyano, halogen, halo$(C_1\text{-}C_6)$alkyl, and halo$(C_1\text{-}C_6)$alkoxy;

$R^4$ is H, $(C_6\text{-}C_{10})$aryl, or 5- to 10-membered heteroaryl, wherein $(C_6\text{-}C_{10})$aryl or 5- to 10-membered heteroaryl is each substituted with 0, 1, 2, or 3 substituents each independently selected from the group consisting of halogen, cyano, $(C_1\text{-}C_6)$alkyl, $(C_1\text{-}C_6)$alkoxy, halo$(C_1\text{-}C_6)$alkyl, halo$(C_1\text{-}C_6)$alkoxy, and —$NR^{4a}R^{4b}$, wherein: each $R^{4a}$ and $R^{4b}$ is independently H or $(C_1\text{-}C_6)$alkyl;

$R^5$ is H, cyano, or $(C_1\text{-}C_6)$alkoxy; and $R^P$ is phosphonic acid, phosphonate, phosphonamidate, or phosphondiamidate.

In some embodiments, the compound of Formula (I), or a pharmaceutically acceptable salt thereof, is a compound of Formula (I-A-1), (I-A-2), (I-A-3), (I-A-4), (I-A-5), or (I-A-6), or a pharmaceutically acceptable salt thereof:

(I-A-1)

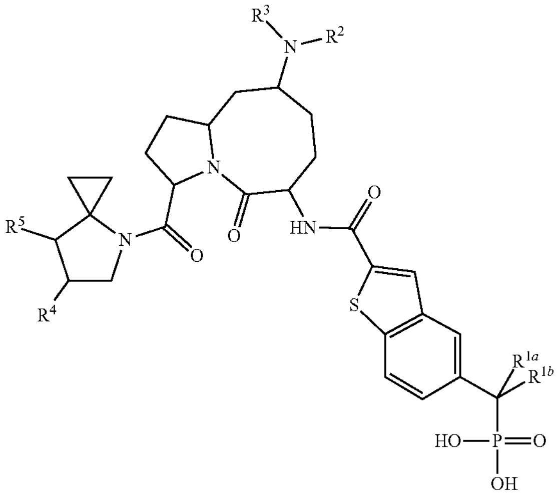

(I-A-2)

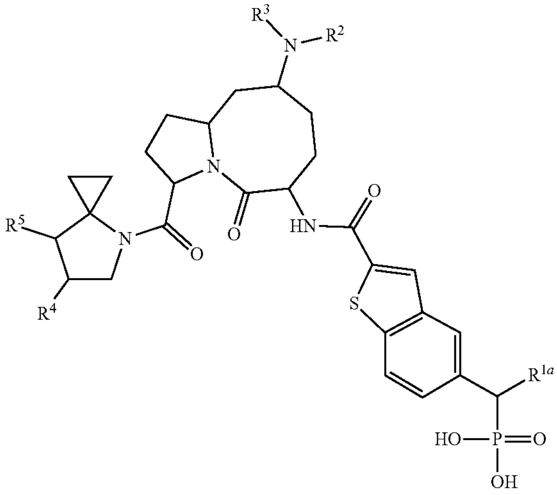

-continued
(I-A-3)
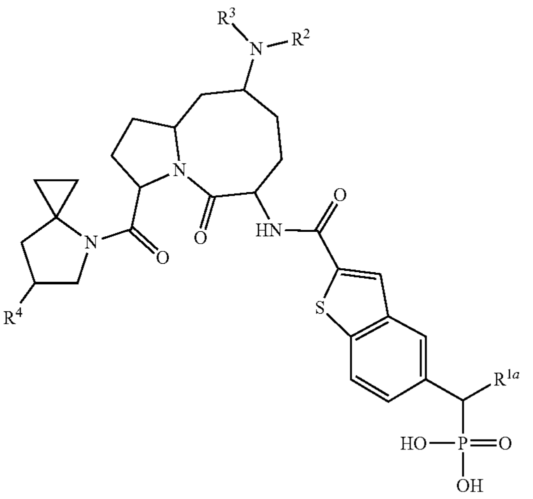
(I-A-4)
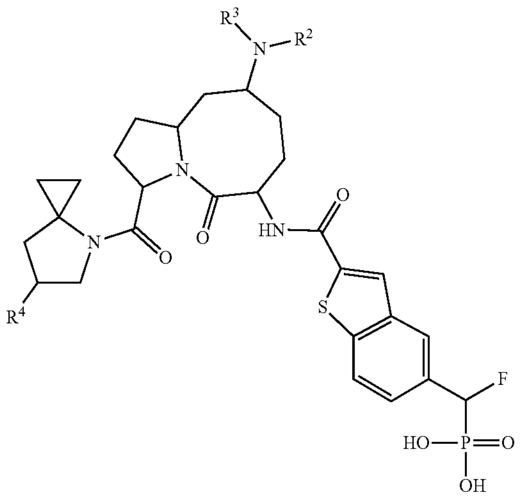
(I-A-5)
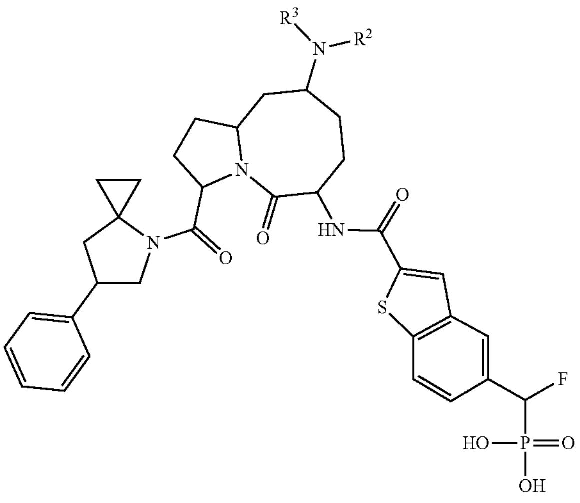
-continued
(I-A-6)
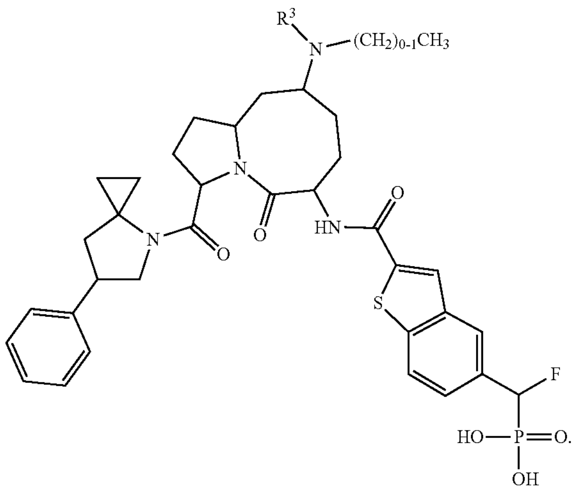
In some embodiments, the compound of Formula (I), or a pharmaceutically acceptable salt thereof, is a compound of Formula (I-B-1), (I-B-2), (I-B-3), (I-B-4), (I-B-5), or (I-B-6), or a pharmaceutically acceptable salt thereof:
(I-B-1)
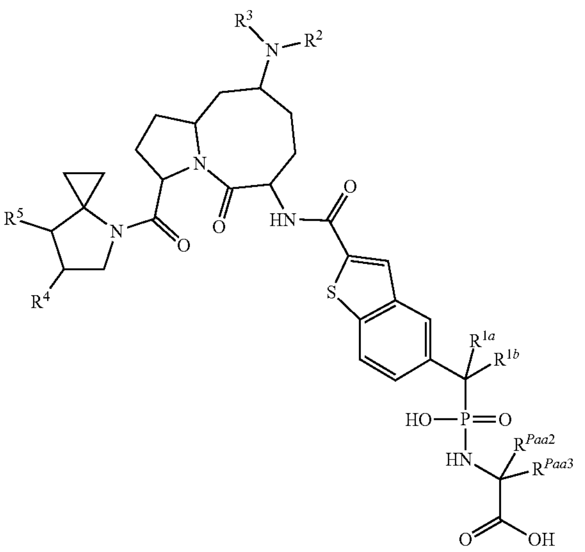

-continued
(I-B-2)
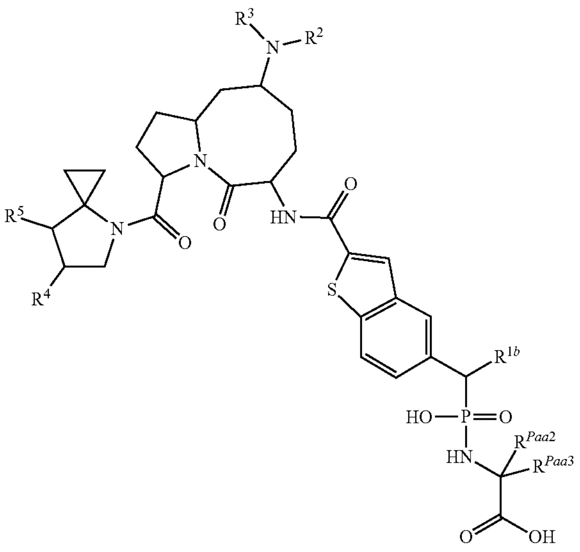
(I-B-3)
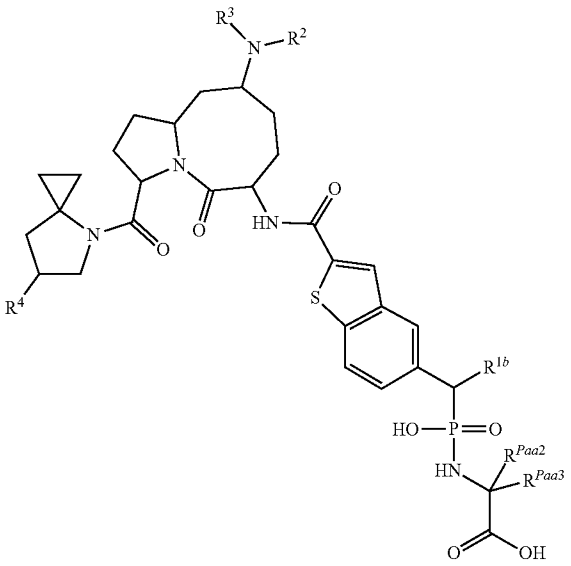
-continued
(I-B-4)
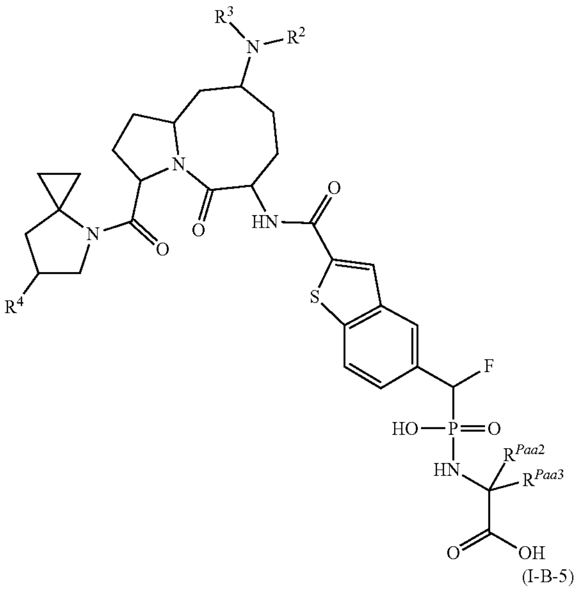
(I-B-5)
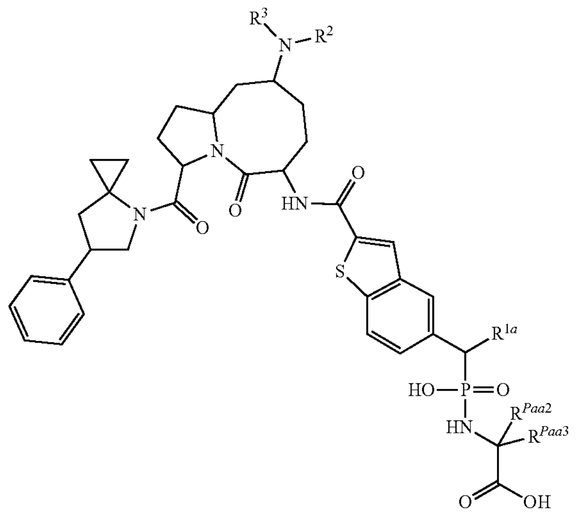
(I-B-6)
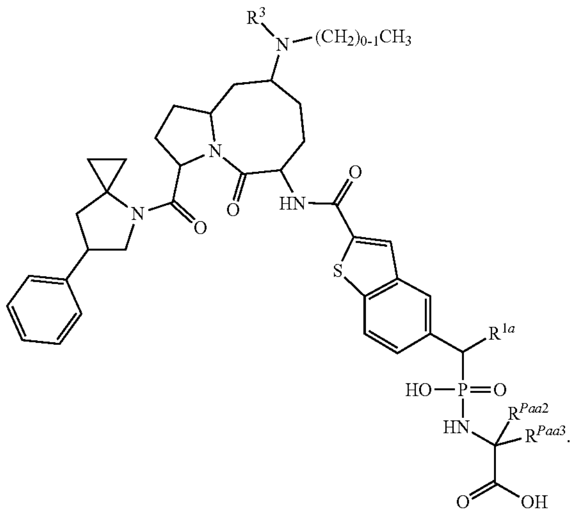

wherein $R^{Paa2}$ is H or $(C_1-C_6)$alkyl; and $R^{Paa2}$ is H, $(C_1-C_6)$alkyl, —$(C_1-C_6)$alkylene-$(C_1-C_6)$alkoxy, or —$(C_1-C_6)$alkylene-$(C_6-C_{10})$aryl; or $R^{Paa2}$ and $R^{Paa3}$ together with the carbon atom to which they are attached form $(C_3-C_6)$cycloalkyl.

In some embodiments, the compound of Formula (I), or a pharmaceutically acceptable salt thereof, is a compound of Formula (I-C-1), (I-C-2), (I-C-3), (I-C-4), (I-C-5), or (I-C-6), or a pharmaceutically acceptable salt thereof:

(I-C-1)

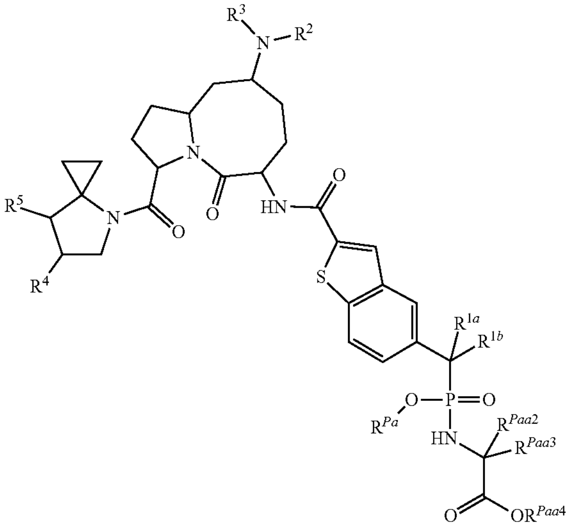

(I-C-2)

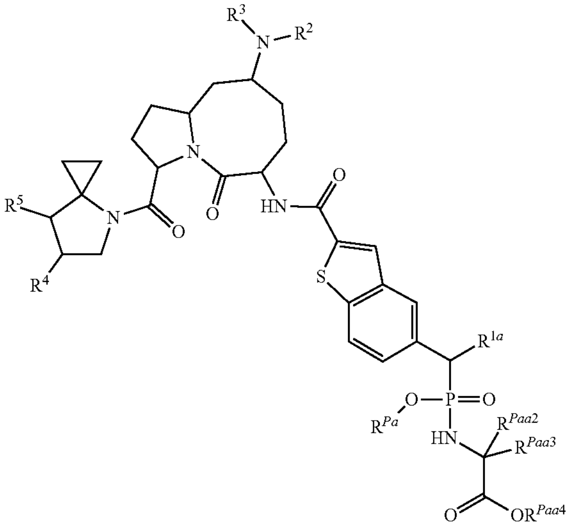

-continued (I-C-3)

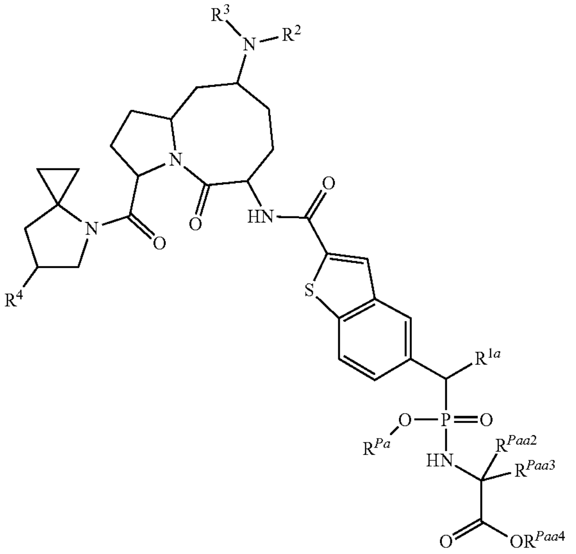

(I-C-4)

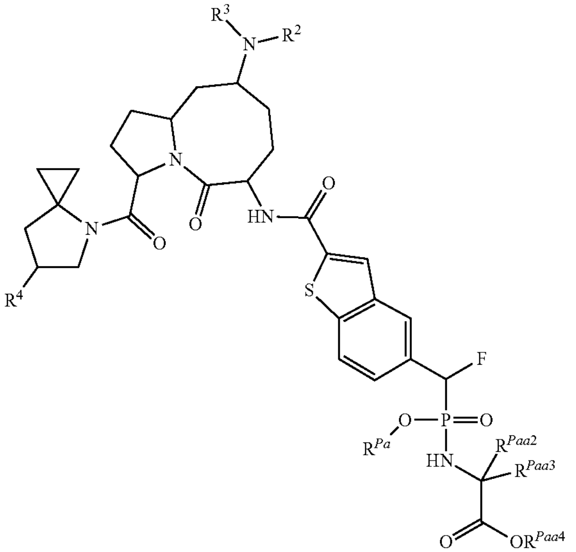

(I-C-5)

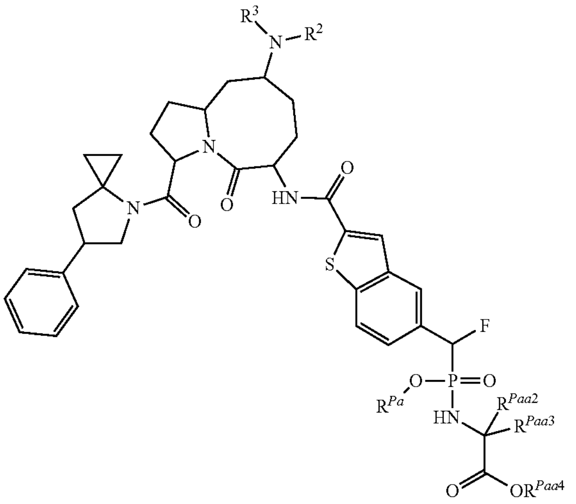

-continued (I-C-6)

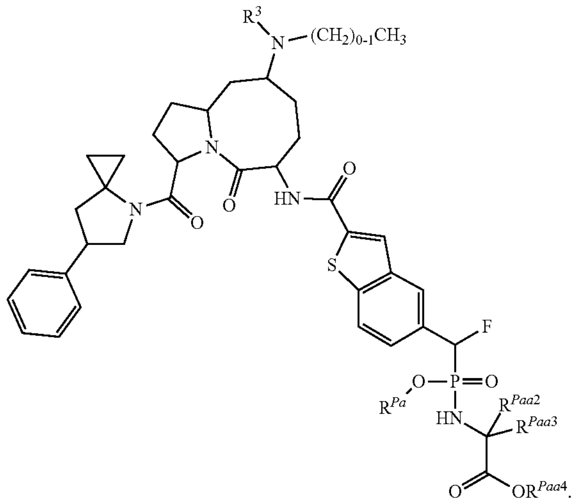

wherein $R^{Pa}$ is $(C_1\text{-}C_6)$alkyl, halo$(C_1\text{-}C_6)$alkyl, $(C_6\text{-}C_{10})$aryl, or $(C_3\text{-}C_6)$cycloalkyl, wherein $(C_1\text{-}C_6)$alkyl is substituted with 0, 1, 2, or 3 substituents each independently selected from the group consisting of halo and $(C_1\text{-}C_6)$alkoxy; $R^{Paa2}$ is H or $(C_1\text{-}C_6)$alkyl; $R^{Paa3}$ is H, $(C_1\text{-}C_6)$alkyl, —$(C_1\text{-}C_6)$alkylene-$(C_1\text{-}C_6)$alkoxy, or —$(C_1\text{-}C_6)$alkylene-$(C_6\text{-}C_{10})$aryl; or $R^{Paa2}$ and $R^{Paa3}$, together with the carbon atom to which they are attached form $(C_3\text{-}C_6)$cycloalkyl; and $R^{Paa4}$ is $(C_1\text{-}C_6)$alkyl, halo$(C_1\text{-}C_6)$alkyl, —$(C_1\text{-}C_6)$alkylene-$(C_1\text{-}C_6)$alkoxy, $(C_3\text{-}C_6)$cycloalkyl, $(C_5\text{-}C_8)$spirocycloalkyl, —$(C_1\text{-}C_6)$alkylene-$(C_6\text{-}C_{10})$aryl, —$(C_1\text{-}C_6)$alkylene-$(C_1\text{-}C_6)$alkoxy, —$(C_1\text{-}C_6)$alkylene-$(C_3\text{-}C_7)$cycloalkyl, 3- to 7-membered heterocyclyl, or —$(C_1\text{-}C_6)$alkylene-(3- to 7-membered heterocyclyl), wherein $(C_1\text{-}C_6)$alkyl, $(C_3\text{-}C_6)$cycloalkyl, $(C_5\text{-}C_8)$spirocycloalkyl, or $(C_3\text{-}C_7)$cycloalkyl of —$(C_1\text{-}C_6)$alkylene-$(C_3\text{-}C_7)$cycloalkyl is each substituted with 0, 1, 2, or 3 independently selected halogen.

In some embodiments, the compound of Formula (I), or a pharmaceutically acceptable salt thereof, is a compound of Formula (I-D-1), (I-D-2), (I-D-3), (I-D-4), (I-D-5), or (I-D-6), or a pharmaceutically acceptable salt thereof:

(I-D-1)

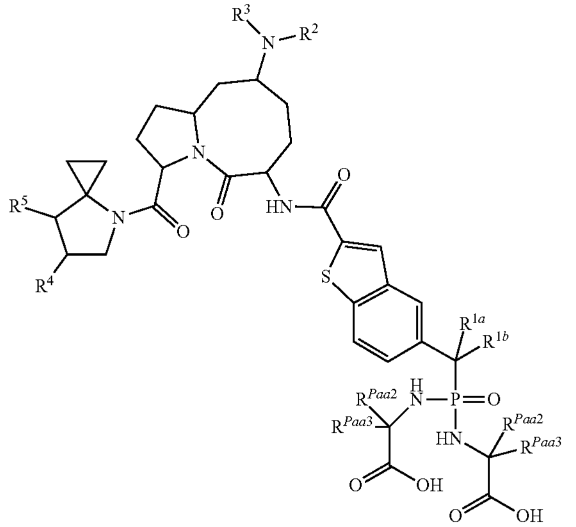

-continued (I-D-2)

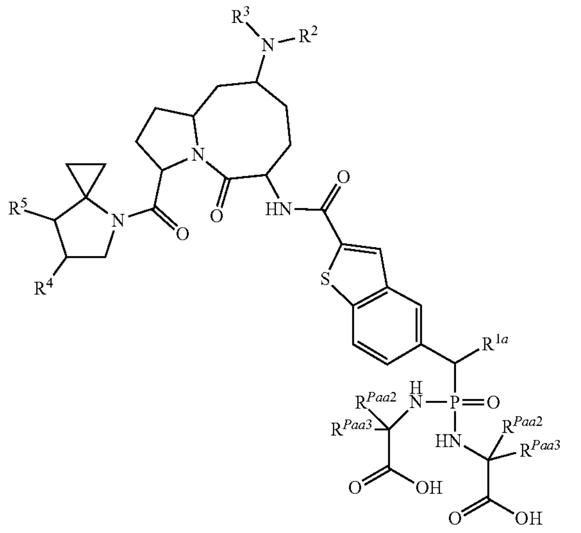

(I-D-3)

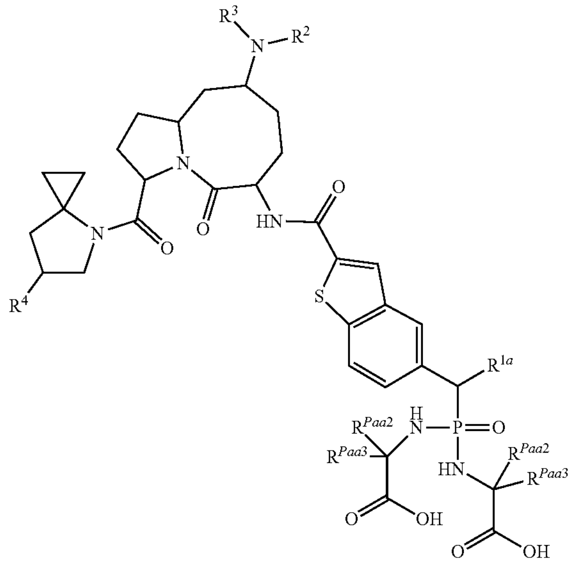

-continued (I-D-4)

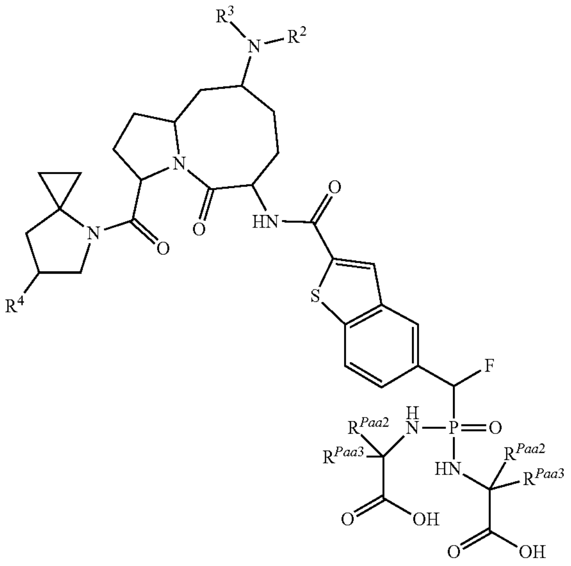

(I-D-5)

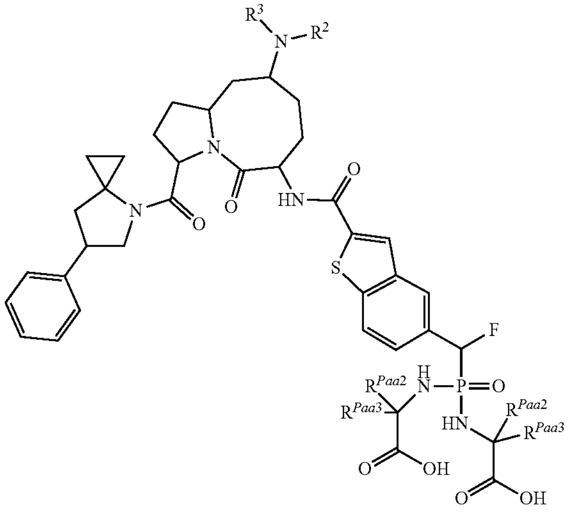

(I-D-6)

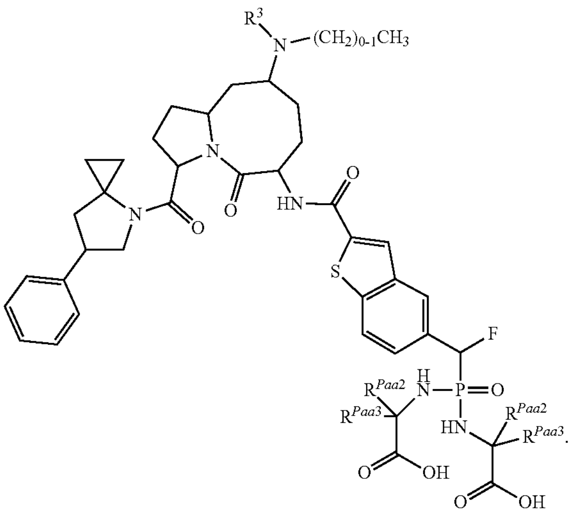

wherein each $R^{Paa2}$ is independently H or $(C_1-C_6)$alkyl; and each $R^{Paa3}$ is independently H, $(C_1-C_6)$alkyl, $-(C_1-C_6)$alkylene-$(C_1-C_6)$alkoxy, or $-(C_1-C_6)$alkylene-$(C_6-C_{10})$aryl; or $R^{Paa2}$ and $R^{Paa3}$ together with the carbon atom to which they are attached form $(C_3-C_6)$cycloalkyl.

In some embodiments, the compound of Formula (I), or a pharmaceutically acceptable salt thereof, is a compound of Formula (I-E-1), (I-E-2), (I-E-3), (I-E-4), (I-E-5), or (I-E-6, or a pharmaceutically acceptable salt thereof:

(I-E-1)

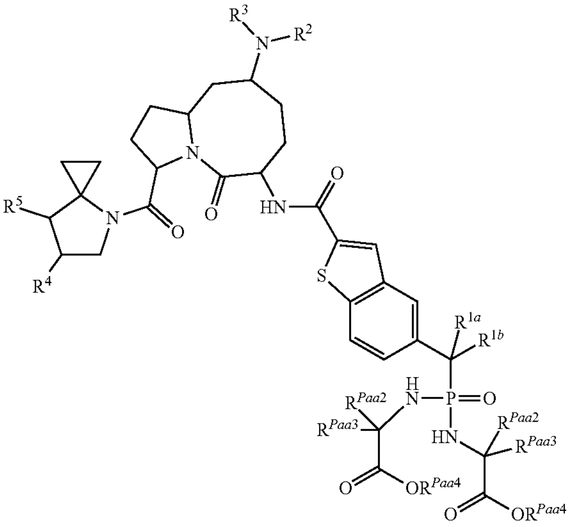

(I-E-2)

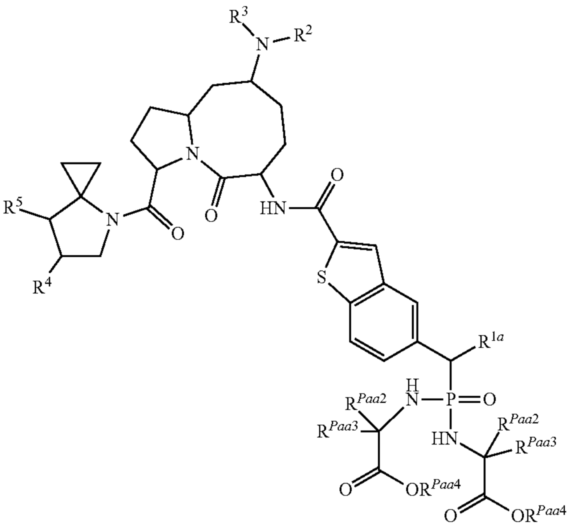

-continued (I-E-3)

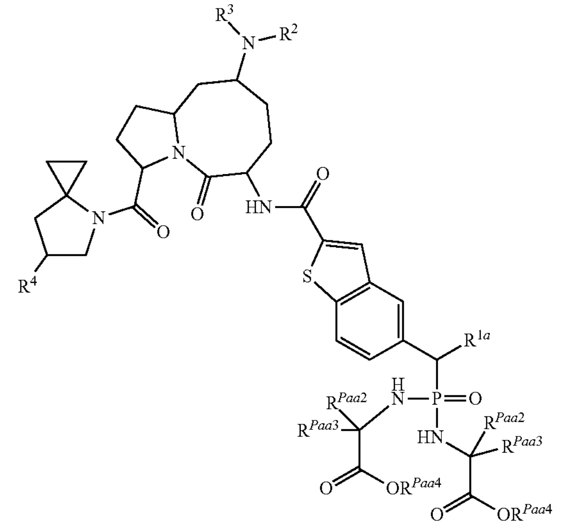

(I-E-4)

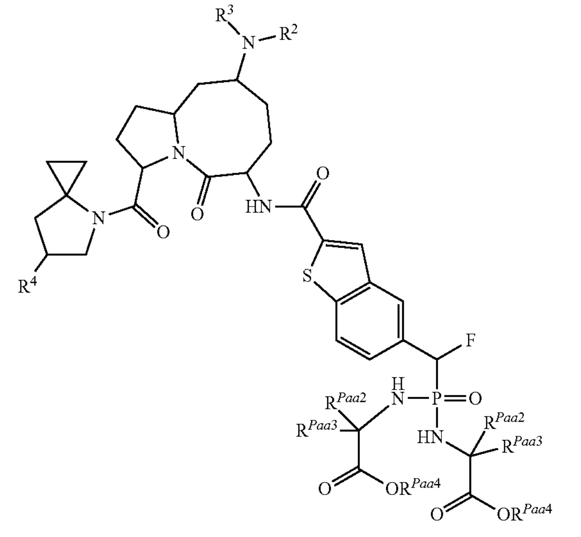

(I-E-5)

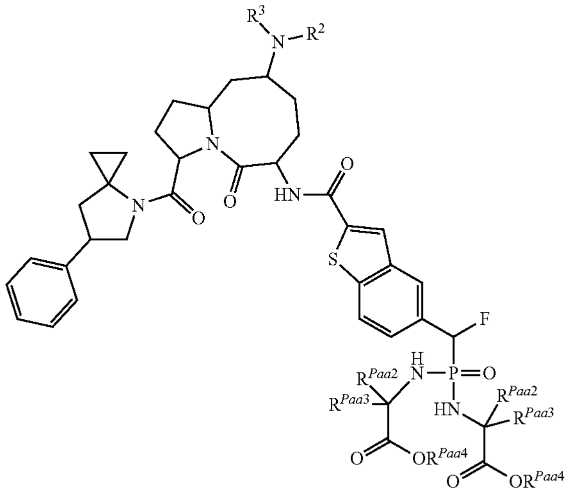

-continued (I-E-6)

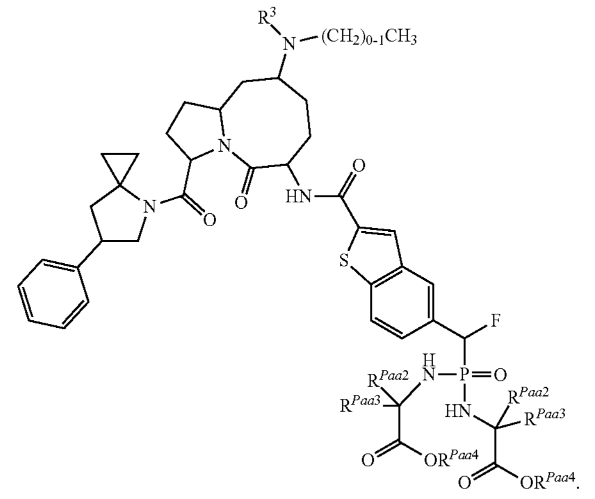

wherein $R^{Paa2}$ is H or $(C_1\text{-}C_6)$alkyl; $R^{Paa3}$ is H, $(C_1\text{-}C_6)$alkyl, $—(C_1\text{-}C_6)$alkylene-$(C_1\text{-}C_6)$alkoxy, or $—(C_1\text{-}C_6)$alkylene-$(C_6\text{-}C_{10})$aryl; or $R^{Paa2}$ and $R^{Paa3}$, together with the carbon atom to which they are attached form $(C_3\text{-}C_6)$cycloalkyl; and $R^{Paa4}$ is $(C_1\text{-}C_6)$alkyl, halo$(C_1\text{-}C_6)$alkyl, $—(C_1\text{-}C_6)$alkylene-$(C_1\text{-}C_6)$alkoxy, $(C_3\text{-}C_6)$cycloalkyl, $(C_5\text{-}C_8)$spirocycloalkyl, $—(C_1\text{-}C_6)$alkylene-$(C_6\text{-}C_{10})$aryl, $—(C_1\text{-}C_6)$alkylene-$(C_1\text{-}C_6)$alkoxy, $—(C_1\text{-}C_6)$alkylene-$(C_3\text{-}C_7)$cycloalkyl, 3- to 7-membered heterocyclyl, or $—(C_1\text{-}C_6)$alkylene-(3- to 7-membered heterocyclyl), wherein $(C_1\text{-}C_6)$alkyl, $(C_3\text{-}C_6)$cycloalkyl, $(C_5\text{-}C_8)$spirocycloalkyl, or $(C_3\text{-}C_7)$cycloalkyl of $—(C_1\text{-}C_6)$alkylene-$(C_3\text{-}C_7)$cycloalkyl is each substituted with 0, 1, 2, or 3 independently selected halogen. In some embodiments, the compound of Formula (I), or a pharmaceutically acceptable salt thereof, is a compound of Formula (I-F-1), (I-F-2), (I-F-3), (J-F-4), (I-F-5), or (I-F-6), or a pharmaceutically acceptable salt thereof:

(I-F-1)

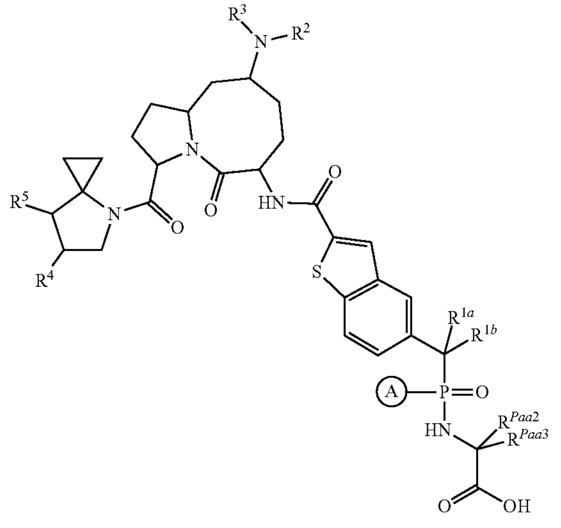

-continued (I-F-2)

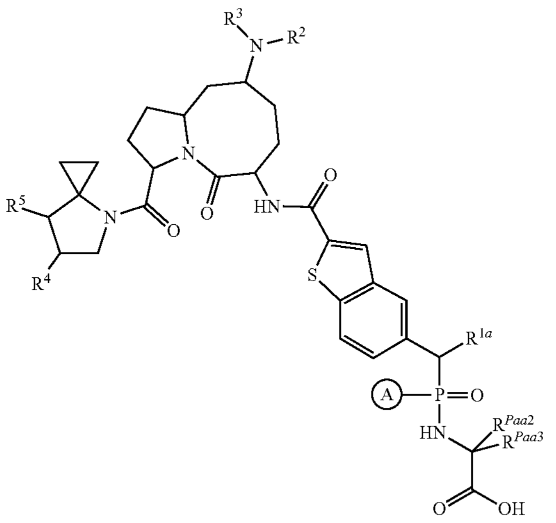

(I-F-3)

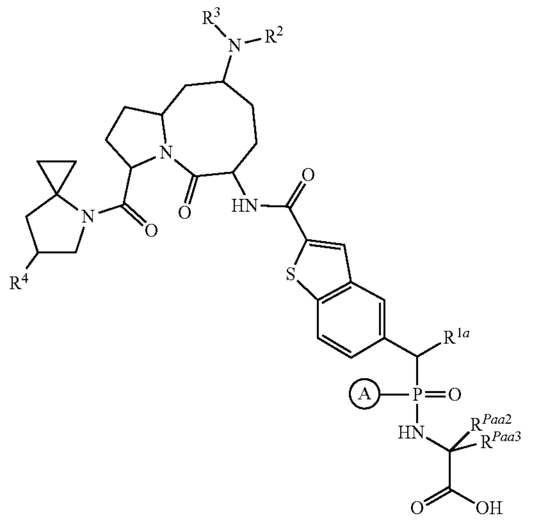

(I-F-4)

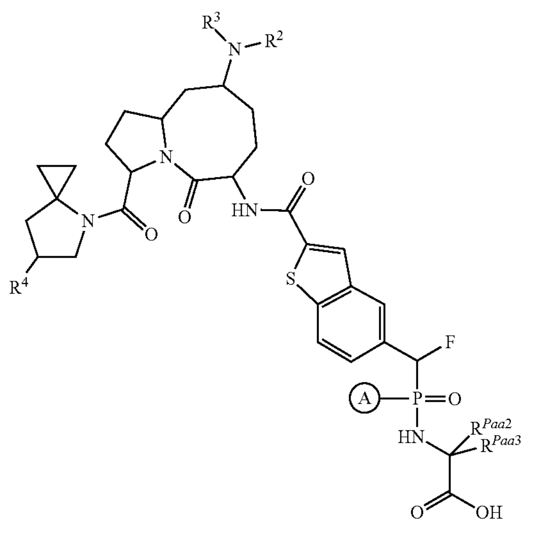

-continued (I-F-5)

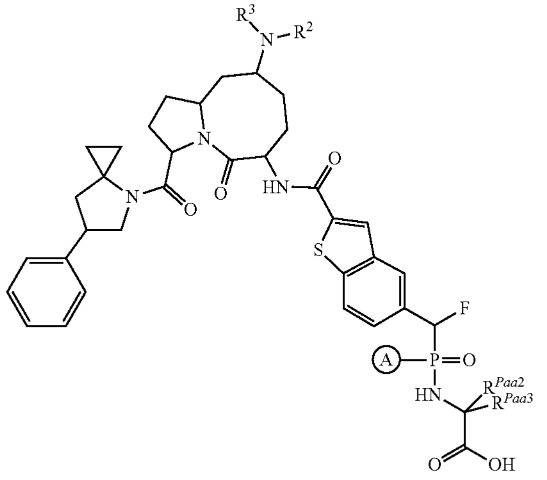

(I-F-6)

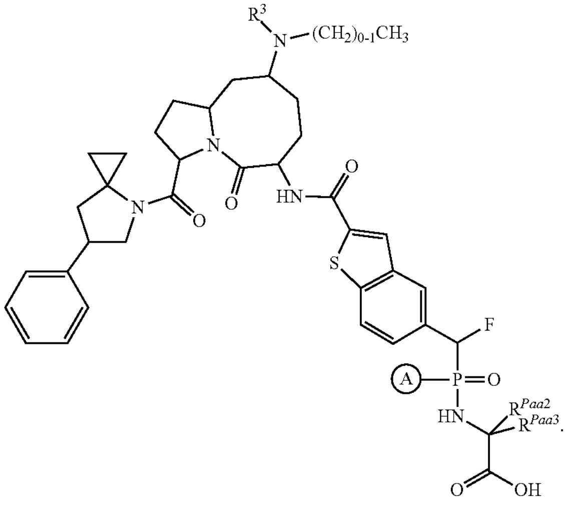

wherein $R^{Paa2}$ is H or $(C_1\text{-}C_6)$alkyl; $R^{Paa3}$ is H, $(C_1\text{-}C_6)$alkyl, $—(C_1\text{-}C_6)$alkylene-$(C_1\text{-}C_6)$alkoxy, or $—(C_1\text{-}C_6)$alkylene-$(C_6\text{-}C_{10})$aryl; or $R^{Paa2}$ and $R^{Paa3}$, together with the carbon atom to which they are attached form $(C_3\text{-}C_6)$cycloalkyl; and Ring A is

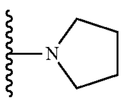 [SMILES: *N1CCCC1]

substituted with 0, 1, 2, or 3 substituents each independently selected from the group consisting of halo, oxo, COOH, and $—C(O)OR^{PE}$; and each $R^{PE}$ is independently $(C_1\text{-}C_6)$alkyl, halo$(C_1\text{-}C_6)$alkyl, $—(C_1\text{-}C_6)$alkylene-$(C_1\text{-}C_6)$alkoxy, $(C_3\text{-}C_6)$cycloalkyl, $(C_5\text{-}C_8)$spirocycloalkyl, $—(C_1\text{-}C_6)$alkylene-$(C_6\text{-}C_{10})$aryl, $—(C_1\text{-}C_6)$alkylene-$(C_1\text{-}C_6)$alkoxy, $—(C_1\text{-}C_6)$alkylene-$(C_3\text{-}C_7)$cycloalkyl, 3- to 7-membered heterocyclyl, or $—(C_1\text{-}C_6)$alkylene-(3- to 7-membered heterocyclyl), wherein $(C_1\text{-}C_6)$alkyl, $(C_3\text{-}C_6)$cycloalkyl, $(C_5\text{-}C_8)$spirocycloalkyl, or $(C_3\text{-}C_7)$cycloalkyl of $—(C_1\text{-}C_6)$alkylene-$(C_3\text{-}C_7)$cycloalkyl is each substituted with 0, 1, 2, or 3 independently selected halogen.

In some embodiments, the compound of Formula (I), or a pharmaceutically acceptable salt thereof, is a compound of Formula (I-G-1), (I-G-2), (I-G-3), (I-G-4), (I-G-5), or (I-G-6), or a pharmaceutically acceptable salt thereof:
(I-G-1)
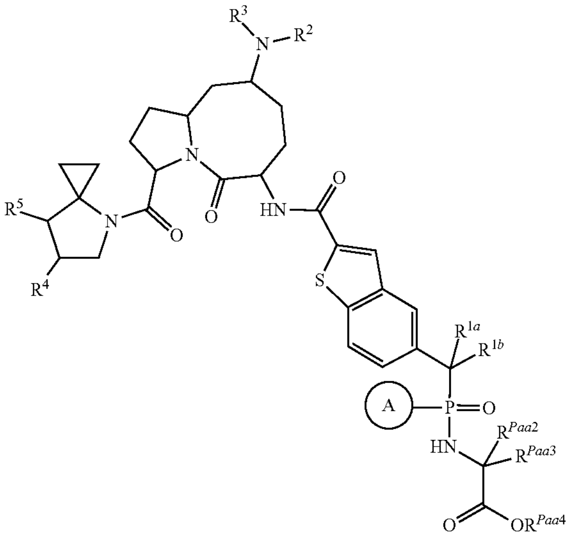
(I-G-2)
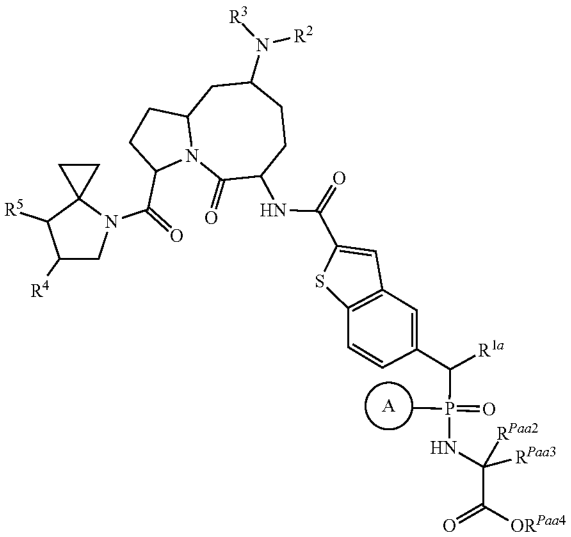
-continued
(I-G-3)
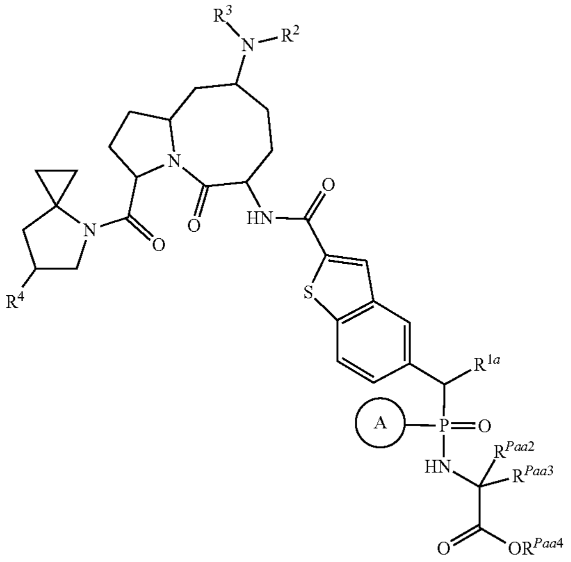
(I-G-4)
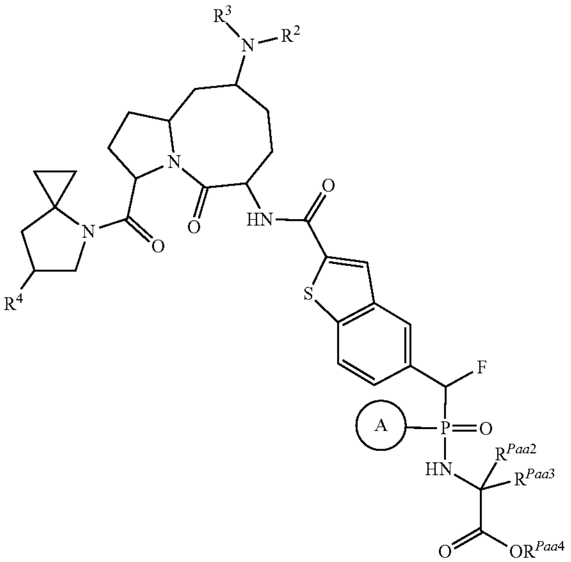

-continued (I-G-5)

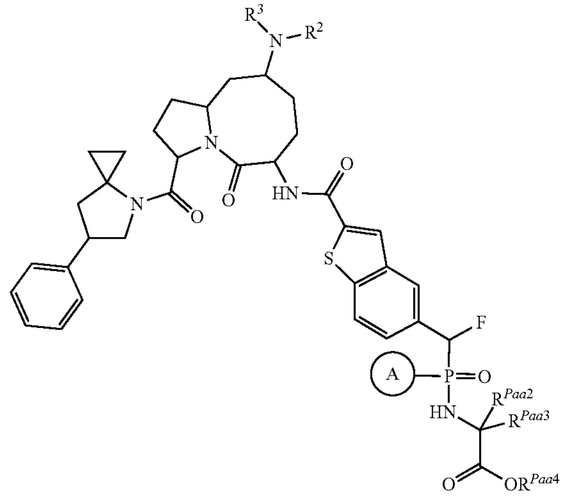

(I-G-6)

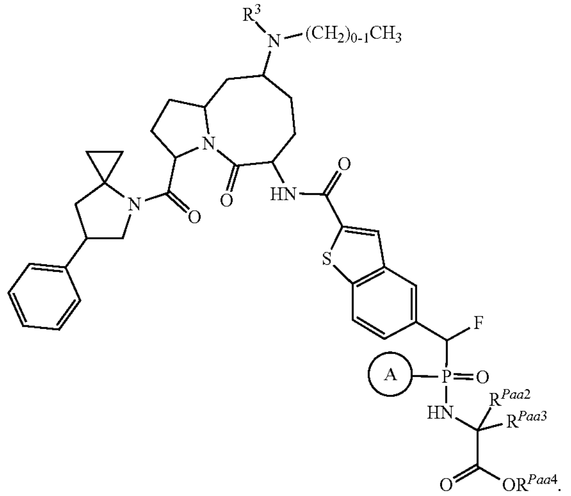

wherein $R^{Paa2}$ is H or $(C_1\text{-}C_6)$alkyl; $R^{Paa3}$ is H, $(C_1\text{-}C_6)$alkyl, —$(C_1\text{-}C_6)$alkylene-$(C_1\text{-}C_6)$alkoxy, or —$(C_1\text{-}C_6)$alkylene-$(C_6\text{-}C_{10})$aryl; or $R^{Paa2}$ and $R^{Paa3}$, together with the carbon atom to which they are attached form $(C_3\text{-}C_6)$cycloalkyl; $R^{Paa4}$ is $(C_1\text{-}C_6)$alkyl, halo$(C_1\text{-}C_6)$alkyl, —$(C_1\text{-}C_6)$alkylene-$(C_1\text{-}C_6)$alkoxy, $(C_3\text{-}C_6)$cycloalkyl, $(C_5\text{-}C_8)$spirocycloalkyl, —$(C_1\text{-}C_6)$alkylene-$(C_6\text{-}C_{10})$aryl, —$(C_1\text{-}C_6)$alkylene-$(C_1\text{-}C_6)$alkoxy, —$(C_1\text{-}C_6)$alkylene-$(C_3\text{-}C_7)$cycloalkyl, 3- to 7-membered heterocyclyl, or —$(C_1\text{-}C_6)$alkylene-(3- to 7-membered heterocyclyl), wherein $(C_1\text{-}C_6)$alkyl, $(C_3\text{-}C_6)$cycloalkyl, $(C_5\text{-}C_8)$spirocycloalkyl, or $(C_3\text{-}C_7)$cycloalkyl of —$(C_1\text{-}C_6)$alkylene-$(C_3\text{-}C_7)$cycloalkyl is each substituted with 0, 1, 2, or 3 independently selected halogen; and Ring A is

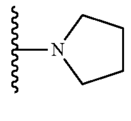 [SMILES: *N1CCCC1]

substituted, with 0, 1, 2, or 3 substituents each independently selected from the group consisting of halo, oxo, COOH, and —C(O)$OR^{PE}$; and each $R^{PE}$ is independently $(C_1\text{-}C_6)$alkyl, halo$(C_1\text{-}C_6)$alkyl, —$(C_1\text{-}C_6)$alkylene-$(C_1\text{-}C_6)$alkoxy, $(C_3\text{-}C_6)$cycloalkyl, $(C_5\text{-}C_8)$spirocycloalkyl, —$(C_1\text{-}C_6)$alkylene-$(C_6\text{-}C_{10})$aryl, —$(C_1\text{-}C_6)$alkylene-$(C_1\text{-}C_6)$alkoxy, —$(C_1\text{-}C_6)$alkylene-$(C_3\text{-}C_7)$cycloalkyl, 3- to 7-membered heterocyclyl, or —$(C_1\text{-}C_6)$alkylene-(3- to 7-membered heterocyclyl), wherein $(C_1\text{-}C_6)$alkyl, $(C_3\text{-}C_6)$cycloalkyl, $(C_5\text{-}C_8)$spirocycloalkyl, or $(C_3\text{-}C_7)$cycloalkyl of —$(C_1\text{-}C_6)$alkylene-$(C_3\text{-}C_7)$cycloalkyl is each substituted with 0, 1, 2, or 3 independently selected halogen.

In some embodiments, the compound of Formula (I), or a pharmaceutically acceptable salt thereof, is a compound of Formula (I-H-1), (I-H-2), (I-H-3), (I-H-4), (I-H-5), or (I-H-6), or a pharmaceutically acceptable salt thereof:

(I-H-1)

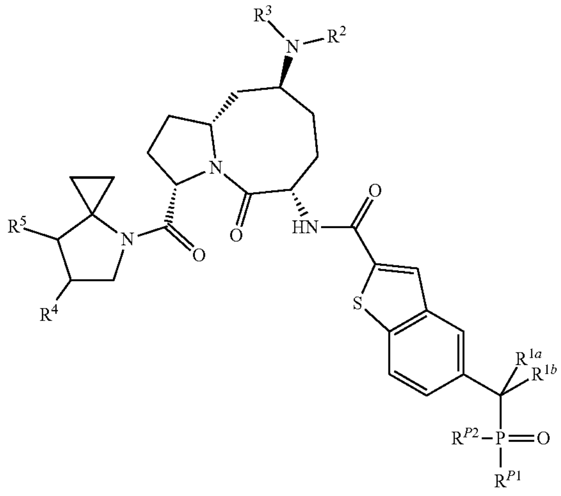

(I-H-2)

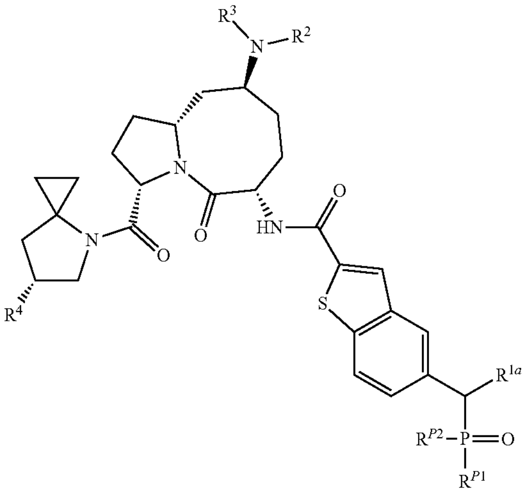

-continued (I-H-3)

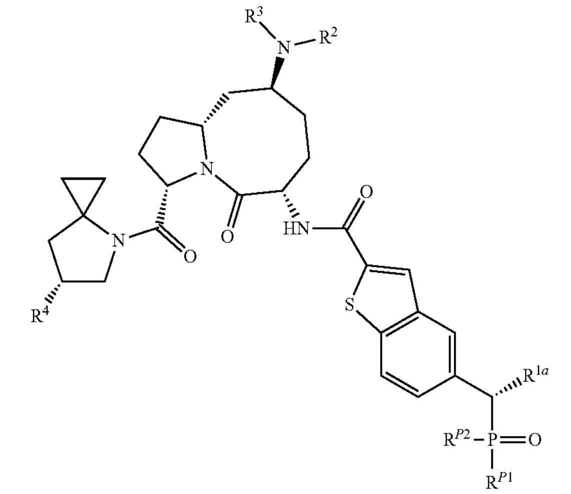

(I-H-4)

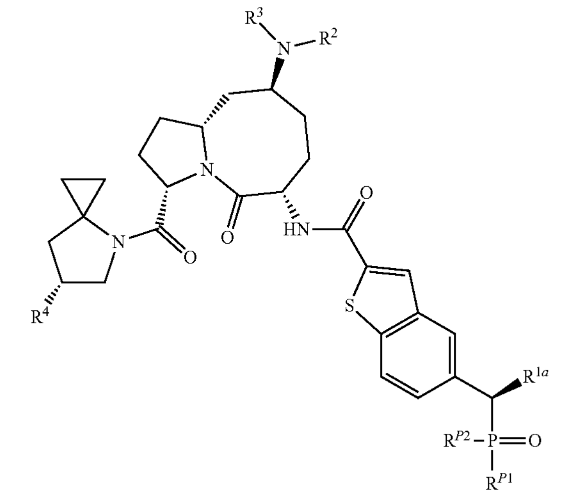

(I-H-5)

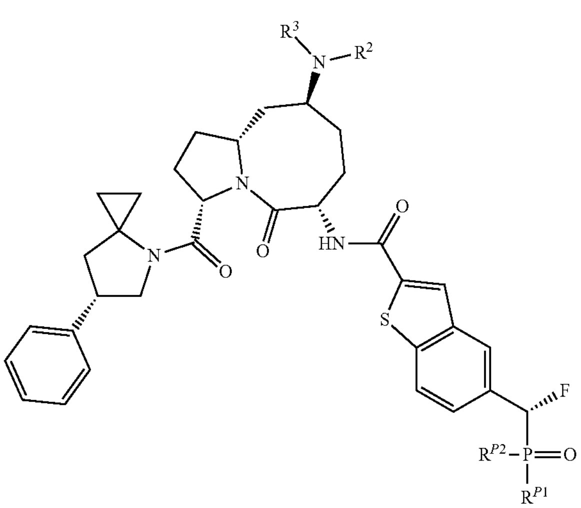

-continued (I-H-6)

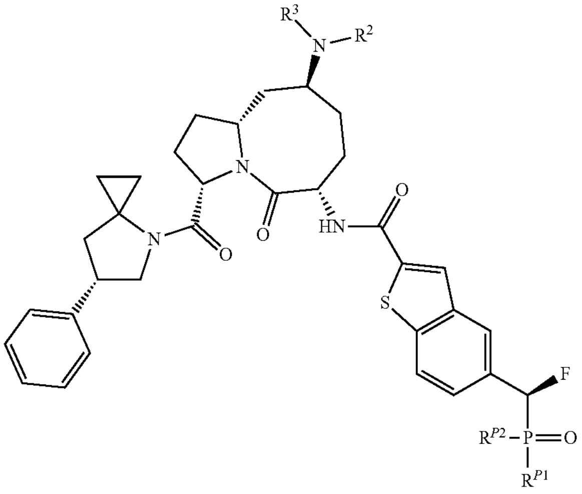

wherein $R^{P1}$ and $R^{P2}$ are each independently —OH, —$OR^{Pa}$, —$NR^{Paa1}$ $CR^{Paa2}R^{Paa3}C(O)OH$, $NR^{Paa1}CR^{Paa2}R^{Paa3}(O)OR^{Paa4}$, or Ring A; Ring A is

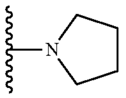

substituted with 0, 1, 2, or 3 substituents each independently selected from the group consisting of halo, oxo, COOH, and —$C(O)OR^{PE}$; $R^{Pa}$ is independently $(C_1$-$C_6)$alkyl, halo$(C_1$-$C_6)$alkyl, $(C_6$-$C_{10})$aryl, or $(C_3$-$C_6)$cycloalkyl, wherein $(C_1$-$C_6)$alkyl is substituted with 0, 1, 2, or 3 substituents each independently selected from the group consisting of halo and $(C_1$-$C_6)$alkoxy; each $R^{PE}$ is independently $(C_1$-$C_6)$alkyl, halo$(C_1$-$C_6)$ alkyl, —$(C_1$-$C_6)$alkylene-$(C_1$-$C_6)$alkoxy, $(C_3$-$C_6)$cycloalkyl, $(C_5$-$C_8)$spirocycloalkyl, —$(C_1$-$C_6)$alkylene-$(C_6$-$C_{10})$aryl, —$(C_1$-$C_6)$alkylene-$(C_1$-$C_6)$alkoxy, —$(C_1$-$C_6)$alkylene-$(C_3$-$C_7)$cycloalkyl, 3- to 7-membered heterocyclyl, or —$(C_1$-$C_6)$alkylene-(3- to 7-membered heterocyclyl), wherein $(C_1$-$C_6)$alkyl, $(C_3$-$C_6)$cycloalkyl, $(C_5$—$C_8)$spirocycloalkyl, or $(C_3$-$C_7)$cycloalkyl of —$(C_1$-$C_6)$alkylene-$(C_3$-$C_7)$cycloalkyl is each substituted with 0, 1, 2, or 3 independently selected halogen; each $R^{Paa1}$ is independently H or $(C_1$-$C_6)$alkyl; each $R^{Paa2}$ is independently H or $(C_1$-$C_6)$alkyl; each $R^{Paa3}$ is independently H, $(C_1$-$C_6)$alkyl, —$(C_1$-$C_6)$alkylene-$(C_1$-$C_6)$alkoxy, or —$(C_1$-$C_6)$alkylene-$(C_6$-$C_{10})$aryl; or $R^{Paa2}$ and $R^{Paa3}$, together with the carbon atom to which they are attached form $(C_3$-$C_6)$cycloalkyl; and each $R^{Paa4}$ is independently $(C_1$-$C_6)$alkyl, halo$(C_1$-$C_6)$alkyl, —$(C_1$-$C_6)$alkylene-$(C_1$-$C_6)$alkoxy, $(C_3$-$C_6)$cycloalkyl, $(C_5$-$C_8)$spirocycloalkyl, —$(C_1$-$C_6)$alkylene-$(C_6$-$C_{10})$aryl, —$(C_1$-$C_6)$ alkylene-$(C_1$-$C_6)$alkoxy, —$(C_1$-$C_6)$alkylene-$(C_3$-$C_7)$ cycloalkyl, 3- to 7-membered heterocyclyl, or —$(C_1$-$C_6)$alkylene-(3- to 7-membered heterocyclyl), wherein $(C_1$-$C_6)$alkyl, $(C_3$-$C_6)$cycloalkyl, $(C_5$-$C_8)$spirocycloalkyl, or $(C_3$-$C_7)$cycloalkyl of —$(C_1$-$C_6)$alkylene-$(C_3$-$C_7)$cycloalkyl is each substituted with 0, 1, 2, or 3 independently selected halogen.

In some embodiments, $R^{1a}$ and $R^{1b}$ are each independently H or halogen. In some embodiments, $R^2$ is H, $(C_1-C_6)$alkyl, or $(C_3-C_6)$cycloalkyl. In some embodiments, $R^3$ is $(C_1-C_6)$alkyl, halo$(C_1-C_6)$alkyl, $(C_3-C_6)$cycloalkyl, 3- to 7-membered heterocyclyl, —$(C_1-C_6)$alkylene-$(C_3-C_6)$cycloalkyl, or —$(C_1-C_6)$alkylene-(3- to 7-membered heterocyclyl), wherein $(C_1-C_6)$alkyl, $(C_3-C_6)$cycloalkyl, $(C_3-C_6)$cycloalkyl of —$(C_1-C_6)$alkylene-$(C_3-C_6)$cycloalkyl, or (3- to 7-membered heterocyclyl) of —$(C_1-C_6)$alkylene-(3- to 7-membered heterocyclyl) is each substituted with 0, 1, 2, 3, 4, or 5 substituents each independently selected from the group consisting of $(C_1-C_6)$alkyl, $(C_1-C_6)$alkoxy, cyano, halogen, halo$(C_1-C_6)$alkyl, and halo$(C_1-C_6)$alkoxy. In some embodiments, $R^2$ and $R^3$ together with the nitrogen atom to which they are attached form 5- to 7-membered heterocyclyl substituted with 0, 1, 2, or 3 substituents each independently selected from the group consisting of $(C_1-C_6)$alkyl, $(C_1-C_6)$alkoxy, cyano, halogen, halo$(C_1-C_6)$alkyl, and halo$(C_1-C_6)$alkoxy. In some embodiments, $R^4$ is H, $(C_6-C_{10})$aryl, or 5- to 10-membered heteroaryl, wherein $(C_6-C_{10})$aryl or 5- to 10-membered heteroaryl is each substituted with 0, 1, 2, or 3 substituents each independently selected from the group consisting of halogen, cyano, $(C_1-C_6)$alkyl, $(C_1-C_6)$alkoxy, halo$(C_1-C_6)$alkyl, halo$(C_1-C_6)$alkoxy, and —$NR^{4a}R^{4b}$, wherein: each $R^{4a}$ and $R^{4b}$ is independently H or $(C_1-C_6)$alkyl. In some embodiments, $R^5$ is H, cyano, or $(C_1-C_6)$alkoxy. In some embodiments, $R^P$ is phosphonic acid, phosphonate, phosphonamidate, or phosphondiamidate.

In some embodiments, $R^{1a}$ is F. In some embodiments, $R^{1b}$ is H. In some embodiments, $R^{1a}$ is F and $R^{1b}$ is H. In some embodiments, $R^{1a}$ and $R^{1b}$ are each F.

In some embodiments, $R^2$ is methyl or ethyl.

In some embodiments, $R^3$ is $(C_1-C_6)$alkyl, halo$(C_1-C_6)$alkyl, $(C_3-C_6)$cycloalkyl, 3- to 7-membered heterocyclyl, or —$(C_1-C_6)$alkylene-(3- to 7-membered heterocyclyl). In some embodiments, $R^3$ is halo$(C_1-C_6)$alkyl. In some embodiments, $R^3$ is $(C_3-C_6)$cycloalkyl substituted with 0, 1, 2, or 3 substituents each independently selected from the group consisting of halogen, cyano, halo$(C_1-C_6)$alkyl, and halo$(C_1-C_6)$alkoxy. In some embodiments, $R^3$ is 3- to 7-membered heterocyclyl. In some embodiments, $R^3$ is —$(C_1-C_6)$alkylene-[3- to 7-membered heterocyclyl substituted with 0 or 1 $(C_1-C_6)$alkyl]. In some embodiments, $R^3$ is $(C_1-C_6)$alkyl substituted with 0, 1, 2, 3, 4, or 5 substituents each independently selected from the group consisting of halo, $(C_1-C_6)$alkoxy, and halo$(C_1-C_6)$alkoxy. In some embodiments, $R^3$ is

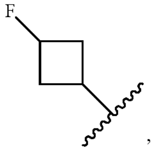,
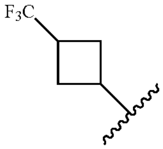,
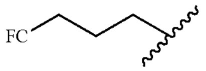,
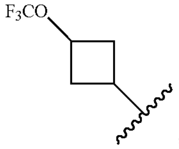,
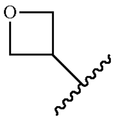,
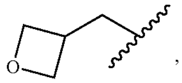,
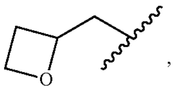,
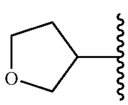,
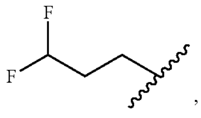, -continued

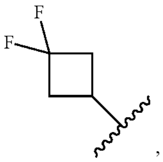,
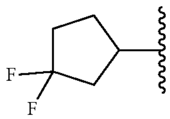,
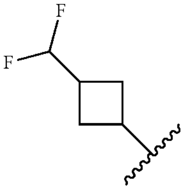,
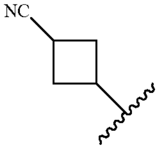,
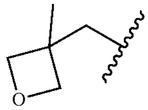,
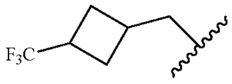,
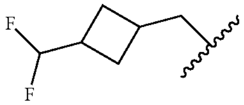,
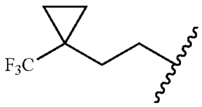,
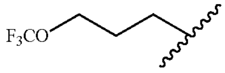,
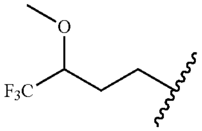,
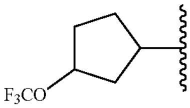, or
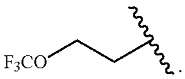.

In some embodiments,

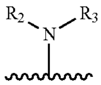

of Formula (I) is

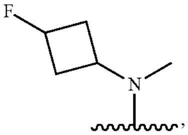,
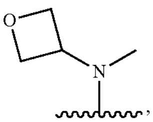,
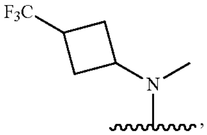,
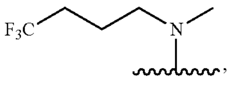,
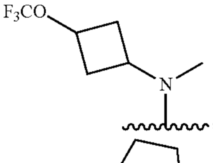,
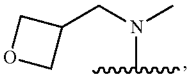,
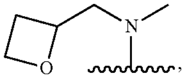,
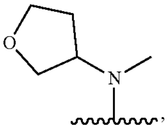,
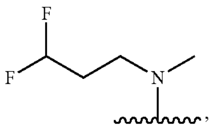,
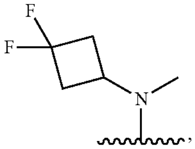, -continued

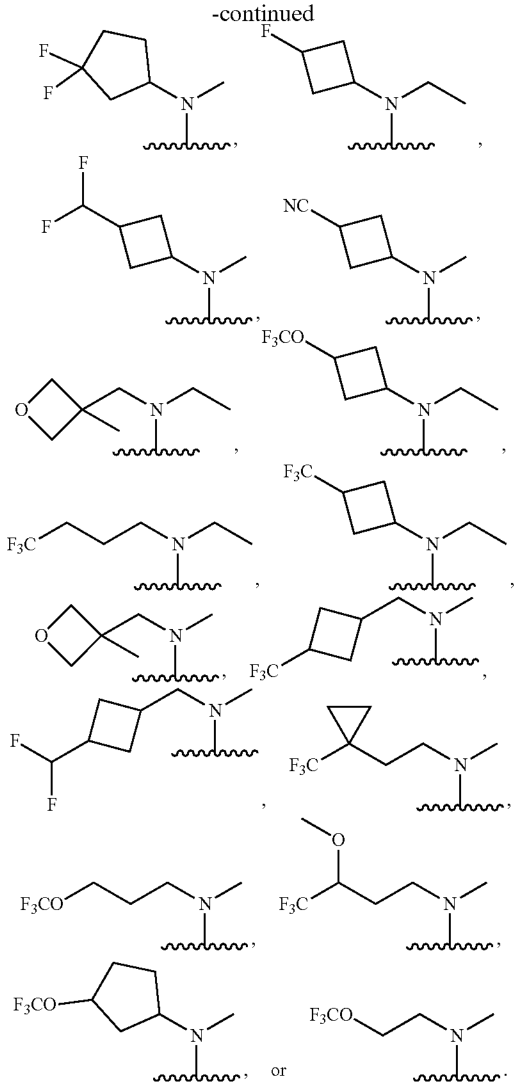

In some embodiments, $R^2$ and $R^3$ together with the nitrogen atom to which they are attached form 6-membered heterocyclyl.

In some embodiments,

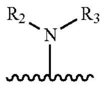

of Formula (I) is

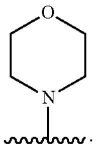

In some embodiments, $R^4$ is H. In some embodiments, $R^4$ is $(C_6\text{-}C_{10})$aryl or 5- to 10-membered heteroaryl. In some embodiments, $R^4$ is phenyl substituted with 0, 1, 2, or 3 halogen.

In some embodiments, $R^4$ is

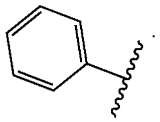 [SMILES: *c1ccccc1]

In some embodiments, $R^4$ is

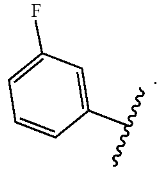 [SMILES: *c1cccc(F)c1]

In some embodiments, $R^4$ is pyridinyl substituted with 0 or 1 —$NR^{4a}R^{4b}$. In some embodiments, $R^4$ is

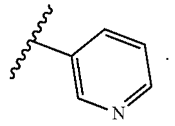 [SMILES: *c1cccnc1]

In some embodiments, $R^4$ is

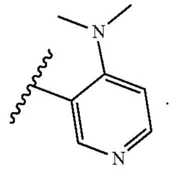 [SMILES: *c1cnccc1N(C)C]

In some embodiments, $R^5$ is H. In some embodiments, $R^5$ is cyano. In some embodiments, $R^5$ is methoxy.

In some embodiments, $R^P$ is

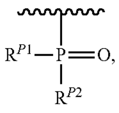

wherein $R^{P1}$ and $R^{P2}$ are each independently —OH, —$OR^{Pa}$, N-linked amino acid, N-linked amino acid ester, or Ring A. In some embodiments, Ring A is

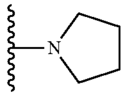

substituted with 0, 1, 2, or 3 substituents each independently selected from the group consisting of halo, oxo, COOH, and —$C(O)OR^{PE}$. In some embodiments, $R^{Pa}$ is independently $(C_1\text{-}C_6)$alkyl, halo$(C_1\text{-}C_6)$alkyl, $(C_6\text{-}C_{10})$aryl, or $(C_3\text{-}C_6)$ cycloalkyl, wherein $(C_1\text{-}C_6)$alkyl is substituted with 0, 1, 2, or 3 substituents each independently selected from the group consisting of halo and ($C_1$-$C_6$)alkoxy. In some embodiments, each $R^{PE}$ is independently ($C_1$-$C_6$)alkyl, halo($C_1$-$C_6$)alkyl, —($C_1$-$C_6$)alkylene-($C_1$-$C_6$)alkoxy, ($C_3$-$C_6$)cycloalkyl, ($C_5$-$C_8$)spirocycloalkyl, —($C_1$-$C_6$)alkylene-($C_6$-$C_{10}$)aryl, —($C_1$-$C_6$)alkylene-($C_1$-$C_6$)alkoxy, —($C_1$-$C_6$)alkylene-($C_3$-$C_7$)cycloalkyl, 3- to 7-membered heterocyclyl, or —($C_1$-$C_6$)alkylene-(3- to 7-membered heterocyclyl), wherein ($C_1$-$C_6$)alkyl, ($C_3$-$C_6$)cycloalkyl, ($C_5$-$C_8$)spirocycloalkyl, or ($C_3$-$C_7$)cycloalkyl of —($C_1$-$C_6$)alkylene-($C_3$-$C_7$)cycloalkyl is each substituted with 0, 1, 2, or 3 independently selected halogen.

In some embodiments, $R^P$ is

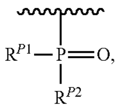

wherein $R^{P1}$ and $R^{P2}$ are each independently —OH, —$OR^{Pa}$, —$NR^{Paa1}CR^{Paa2}R^{Paa3}C(O)OH$, —$NR^{Paa1}CR^{Paa2}R^{Paa3}C(O)OR^{Paa4}$, or Ring A. In some embodiments, Ring A is

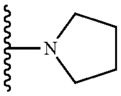 [SMILES: *N1CCCC1]

substituted with 0, 1, 2, or 3 substituents each independently selected from the group consisting of halo, oxo, COOH, and —$C(O)OR^{PE}$. In some embodiments, $R^{Pa}$ is independently ($C_1$-$C_6$)alkyl, halo($C_1$-$C_6$)alkyl, ($C_6$-$C_{10}$)aryl, or ($C_3$-$C_6$)cycloalkyl, wherein ($C_1$-$C_6$)alkyl is substituted with 0, 1, 2, or 3 substituents each independently selected from the group consisting of halo and ($C_1$-$C_6$)alkoxy. In some embodiments, each $R^{PE}$ is independently ($C_1$-$C_6$)alkyl, halo($C_1$-$C_6$)alkyl, —($C_1$-$C_6$)alkylene-($C_1$-$C_6$)alkoxy, ($C_3$-$C_6$)cycloalkyl, ($C_5$-$C_8$)spirocycloalkyl, —($C_1$-$C_6$)alkylene-($C_6$-$C_{10}$)aryl, —($C_1$-$C_6$)alkylene-($C_1$-$C_6$)alkoxy, —($C_1$-$C_6$)alkylene-($C_3$-$C_7$)cycloalkyl, 3- to 7-membered heterocyclyl, or —($C_1$-$C_6$)alkylene-(3- to 7-membered heterocyclyl), wherein ($C_1$-$C_6$)alkyl, ($C_3$-$C_6$)cycloalkyl, ($C_5$-$C_8$)spirocycloalkyl, or ($C_3$-$C_7$)cycloalkyl of —($C_1$-$C_6$)alkylene-($C_3$-$C_7$)cycloalkyl is each substituted with 0, 1, 2, or 3 independently selected halogen. In some embodiments, each $R^{Paa1}$ is independently H or ($C_1$—$C_6$)alkyl. In some embodiments, each $R^{Paa2}$ is independently H or ($C_1$-$C_6$)alkyl, and each $R^{Paa3}$ is independently H, ($C_1$-$C_6$)alkyl, —($C_1$-$C_6$)alkylene-($C_1$-$C_6$)alkoxy, or —($C_1$-$C_6$)alkylene-($C_6$-$C_{10}$)aryl; or $R^{Paa2}$ and $R^{Paa3}$, together with the carbon atom to which they are attached form ($C_3$-$C_6$)cycloalkyl. In some embodiments, each $R^{Paa4}$ is independently ($C_1$-$C_6$)alkyl, halo($C_1$-$C_6$)alkyl, —($C_1$-$C_6$)alkylene-($C_1$-$C_6$)alkoxy, ($C_3$-$C_6$)cycloalkyl, ($C_5$-$C_8$)spirocycloalkyl, —($C_1$-$C_6$)alkylene-($C_6$-$C_{10}$)aryl, —($C_1$-$C_6$)alkylene-($C_1$-$C_6$)alkoxy, —($C_1$-$C_6$)alkylene-($C_3$-$C_7$)cycloalkyl, 3- to 7-membered heterocyclyl, or —($C_1$-$C_6$)alkylene-(3- to 7-membered heterocyclyl), wherein ($C_1$-$C_6$)alkyl, ($C_3$-$C_6$)cycloalkyl, ($C_5$-$C_8$)spirocycloalkyl, or ($C_3$-$C_7$)cycloalkyl of —($C_1$-$C_6$)alkylene-($C_3$-$C_7$)cycloalkyl is each substituted with 0, 1, 2, or 3 independently selected halogen.

In some embodiments, $R^P$ is

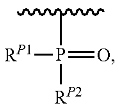

wherein $R^{P1}$ and $R^{P2}$ are each —OH.

In some embodiments, $R^P$ is

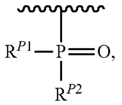

wherein $R^{P1}$ is —OH and $R^{P2}$ is N-linked amino acid. In some embodiments, $R^P$ is

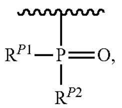

wherein $R^{P1}$ is —OH and $R^{P2}$ is N-linked amino acid ester.

In some embodiments, $R^P$ is

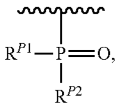

wherein $R^{P1}$ is —$OR^{Pa}$ and $R^{P2}$ is N-linked amino acid ester. In some embodiments, $R^{Pa}$ is ($C_1$-$C_6$)alkyl, halo($C_1$-$C_6$)alkyl, ($C_6$-$C_{10}$)aryl, or ($C_3$-$C_6$)cycloalkyl, wherein ($C_1$-$C_6$)alkyl is substituted with 0, 1, 2, or 3 substituents each independently selected from the group consisting of halo and ($C_1$-$C_6$)alkoxy.

In some embodiments, $R^P$ is

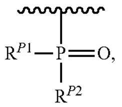

wherein $R^{P1}$ and $R^{P2}$ are each independently N-linked amino acid.

In some embodiments, $R^P$ is

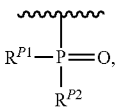

wherein $R^{P1}$ and $R^{P2}$ are each independently N-linked amino acid ester.

In some embodiments, $R^P$ is

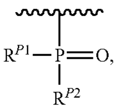

wherein $R^{P1}$ is N-linked amino acid and $R^{P2}$ is Ring A, wherein Ring A is

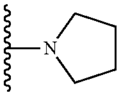 [SMILES: *N1CCCC1]

substituted with 0, 1, 2, or 3 substituents each independently selected from the group consisting of halo, oxo, and —COOH.

In some embodiments, $R^P$ is

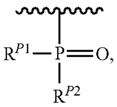

wherein $R^{P1}$ is N-linked amino acid ester and $R^{P2}$ is Ring A, wherein Ring A is

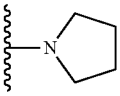 [SMILES: *N1CCCC1]

substituted with 0, 1, 2, or 3 substituents each independently selected from the group consisting of halo, oxo, and ester.

In some embodiments, $R^{Pa}$ is phenyl. In some embodiments $R^{Pa}$ is ethyl. In some embodiments, $R^{Pa}$ is —$CH_2CF_3$. In some embodiments, $R^{Pa}$ is

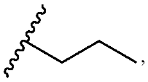, 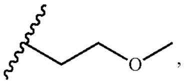, 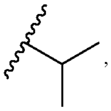,

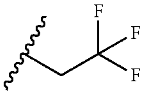, 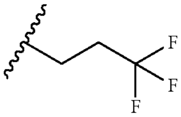, cyclopropyl, cyclopentyl, or cyclohexyl. In some embodiments, $R^{Pa}$ is

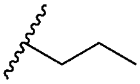, 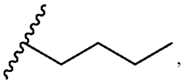, 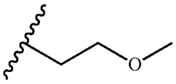,

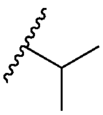, 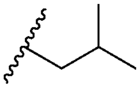, 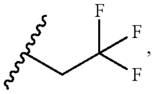,

-continued

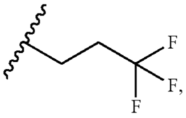

cyclopropyl, cyclopentyl, or cyclohexyl.

In some embodiments, $R^{P2}$ is

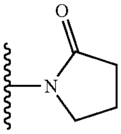 or 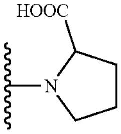.

In some embodiments, $R^{P2}$ is Ring A, wherein Ring A is

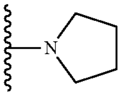

substituted with 0, 1, 2, or 3 substituents each independently selected from the group consisting of halo, oxo, and —C(O)$OR^{PE}$. In some embodiments, each $R^{PE}$ is independently $(C_1\text{-}C_6)$alkyl, halo$(C_1\text{-}C_6)$alkyl, —$(C_1\text{-}C_6)$alkylene-$(C_1\text{-}C_6)$alkoxy, $(C_3\text{-}C_6)$cycloalkyl, $(C_5\text{-}C_8)$spirocycloalkyl, —$(C_1\text{-}C_6)$alkylene-$(C_6\text{-}C_{10})$aryl, —$(C_1\text{-}C_6)$alkylene-$(C_1\text{-}C_6)$alkoxy, —$(C_1\text{-}C_6)$alkylene-$(C_3\text{-}C_7)$cycloalkyl, 3- to 7-membered heterocyclyl, or —$(C_1\text{-}C_6)$alkylene-(3- to 7-membered heterocyclyl), wherein $(C_1\text{-}C_6)$alkyl, $(C_3\text{-}C_6)$cycloalkyl, $(C_5\text{-}C_8)$spirocycloalkyl, or $(C_3\text{-}C_7)$cycloalkyl of —$(C_1\text{-}C_6)$alkylene-$(C_3\text{-}C_7)$cycloalkyl is each substituted with 0, 1, 2, or 3 independently selected halogen. In some embodiments, each $R^{PE}$ is independently ethyl,

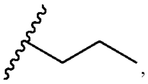, 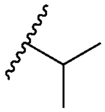, 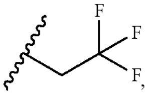

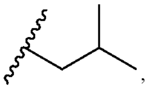, 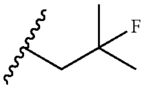, 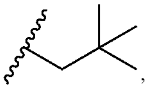,

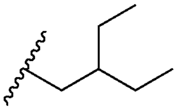, 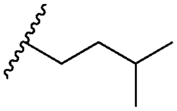,

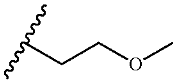, 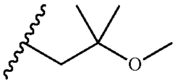, 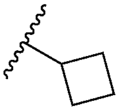,

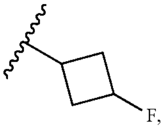 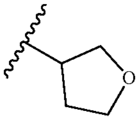, 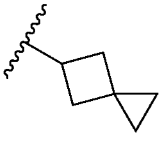,

-continued

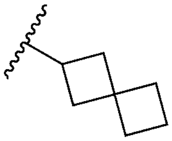 , 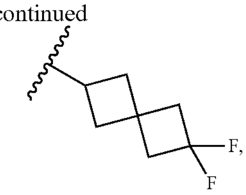

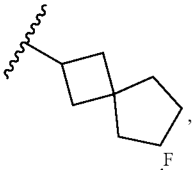 , 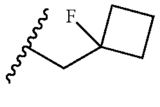 ,

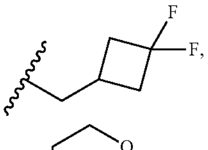 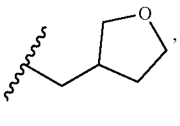 ,

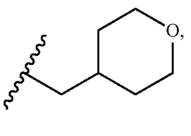 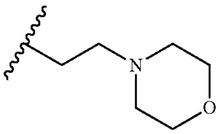 , or

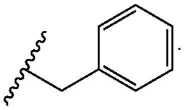 .

In some embodiments, each $R^{PE}$ is

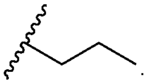 [SMILES: *CCC] .

In some embodiments, $R^{P2}$ is

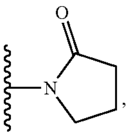 , 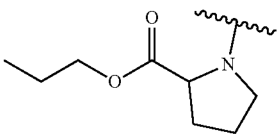 ,

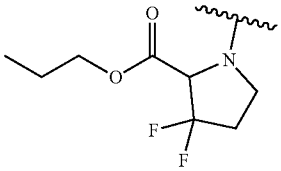 , or

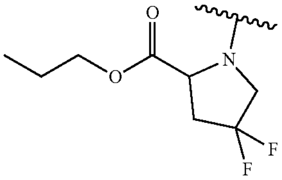 .

In some embodiments, each N-linked amino acid is independently N-linked α-amino acid. In some embodiments, each N-linked amino acid ester is independently N-linked α-amino acid ester.

In some embodiments, each N-linked amino acid is independently $—NR^{Paa1}CR^{Paa2}R^{Paa3}C(O)OH$. In some embodiments, each N-linked amino acid ester is independently $—NR^{Paa1}CR^{Paa2}R^{Paa3}C(O)OR^{Paa4}$.

In some embodiments, each $R^{Paa1}$ is independently H or $(C_1-C_6)$alkyl. In some embodiments, each $R^{Paa2}$ is independently H or $(C_1-C_6)$alkyl, and each $R^{Paa3}$ is independently H, $(C_1-C_6)$alkyl, $—(C_1-C_6)$alkylene-$(C_1-C_6)$alkoxy, or $—(C_1-C_6)$alkylene-$(C_6-C_{10})$aryl; or $R^{Paa2}$ and $R^{Paa3}$, together with the carbon atom to which they are attached form $(C_3-C_6)$cycloalkyl.

In some embodiments, $R^{Paa1}$ is H. In some embodiments, $R^{Paa1}$ is methyl.

In some embodiments, $R^{Paa2}$ is H. In some embodiments, $R^{Paa2}$ is methyl.

In some embodiments, $R^{Paa3}$ is methyl. In some embodiments, $R^{Paa3}$ is ethyl,

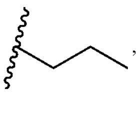 , 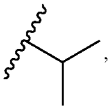 , or $—CH_2OCH_3$. In some embodiments, $R^{Paa3}$ is

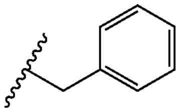 .

In some embodiments, $R^{Paa2}$ and $R^{Paa3}$, together with the carbon atom to which they are attached form cyclopropyl.

In some embodiments, each $R^{Paa4}$ is independently $(C_1-C_6)$alkyl, halo$(C_1-C_6)$alkyl, $—(C_1-C_6)$alkylene-$(C_1-C_6)$alkoxy, $(C_3-C_6)$cycloalkyl, $(C_5-C_8)$spirocycloalkyl, $—(C_1-C_6)$alkylene-$(C_6-C_{10})$aryl, $—(C_1-C_6)$alkylene-$(C_1-C_6)$alkoxy, $—(C_1-C_6)$alkylene-$(C_3-C_7)$cycloalkyl, 3- to 7-membered heterocyclyl, or $—(C_1-C_6)$alkylene-(3- to 7-membered heterocyclyl), wherein $(C_1-C_6)$alkyl, $(C_3-C_6)$cycloalkyl, $(C_5-C_8)$spirocycloalkyl, or $(C_3-C_7)$cycloalkyl of $—(C_1-C_6)$alkylene-$(C_3-C_7)$cycloalkyl is each substituted with 0, 1, 2, or 3 independently selected halogen. In some embodiments, each $R^{Paa4}$ is independently ethyl,

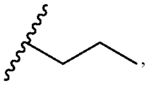 , 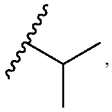 , 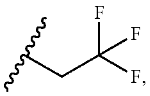

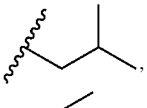 , 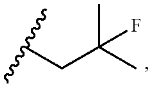 , 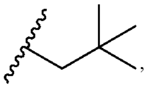 ,

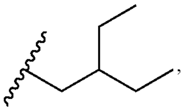 , 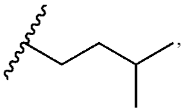 , 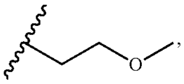 ,

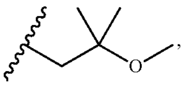 , 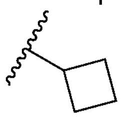 , 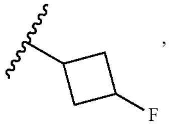

-continued

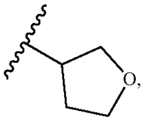, 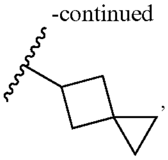, 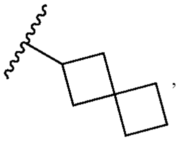,

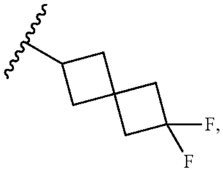, 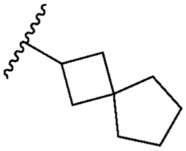,

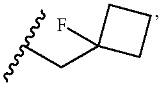, 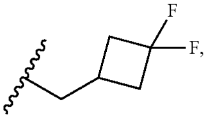,

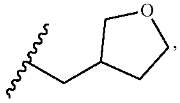, 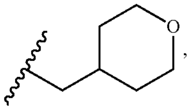,

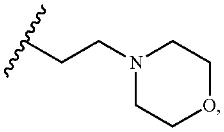 or 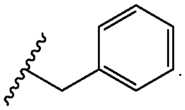.

In some embodiments, $R^{Paa4}$ is

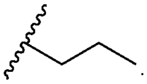 [SMILES: *CCC].

In some embodiments, $R^{Paa4}$ is ethyl,

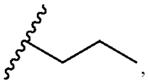, 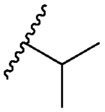, 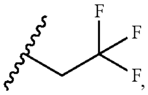,

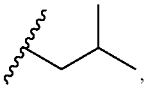, 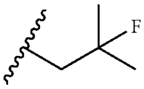, 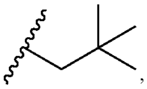,

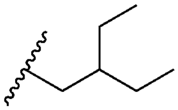, 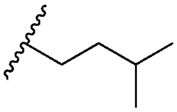,

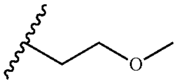, or 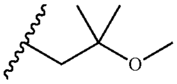.

In some embodiments, $R^{Paa4}$ is

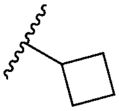, 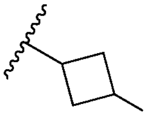, 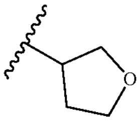,

-continued

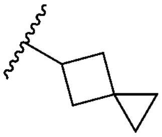, 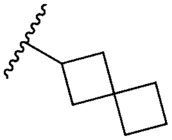,

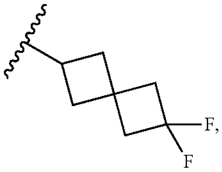, 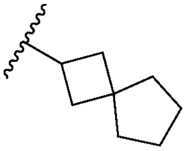,

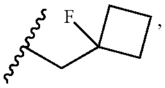, 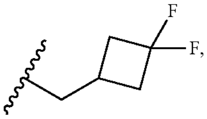, 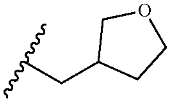,

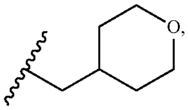, 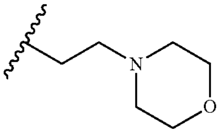, or

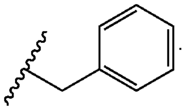.

In some embodiments, provided herein are compounds of Table 1A, Table 1B, Table 1C, and pharmaceutically acceptable salts thereof. See Example 1.

In one aspect, provided herein is a parent drug. In some embodiments, a prodrug can be metabolized to produce the parent drug. In some embodiments, the prodrug can be metabolized to produce an intermediate metabolite. In some embodiments, the intermediate metabolite can be further metabolized to produce the parent drug. In some embodiments, the prodrug can be metabolized by enzymes such as carboxyesterase and/or phosphoramidase to produce the parent drug. In some embodiments, the prodrug is a ProTide prodrug analog (see, e.g., Mehellou, et al., J. Med. Chem. 61(6) 2211-2226 (2018). In some embodiments, the prodrug has an $R^P$ selected from those present in molecules described herein in the representative procedures for synthesis of phosphoryl groups of Example 1.

In some embodiments, the parent drug is the compound of Formula (I-A-1), (I-A-2), (I-A-3), (I-A-4), (I-A-5), or (I-A-6), or a pharmaceutically acceptable salt thereof. In some embodiments, the parent drug is a compound of Formula (I), wherein $R^P$ is

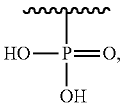, or a pharmaceutically acceptable salt thereof. In some embodiments, the parent drug is a compound selected from the group consisting of the compounds of Table 1A, or a pharmaceutically acceptable salt thereof.

In some embodiments, the compound, or a pharmaceutically acceptable salt thereof, is a parent drug selected from the group consisting of:

(fluoro(2-((9-((3-fluorocyclobutyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)phosphonic acid;
(fluoro(2-((9-(methyl(3-(trifluoromethyl)cyclobutyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)phosphonic acid;
(fluoro(2-((9-(methyl(4,4,4-trifluorobutyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)phosphonic acid;
(fluoro(2-((9-(methyl(3-(trifluoromethoxy)cyclobutyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)phosphonic acid;
(fluoro(2-((9-(methyl(3-(trifluoromethoxy)cyclobutyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)phosphonic acid;
((2-((3-(7-cyano-6-phenyl-4-azaspiro[2.4]heptane-4-carbonyl)-9-morpholino-5-oxodecahydropyrrolo[1,2-a]azocin-6-yl)carbamoyl)benzo[b]thiophen-5-yl)fluoromethyl)phosphonic acid;
(fluoro(2-((9-morpholino-5-oxo-3-(6-(pyridin-3-yl)-4-azaspiro[2.4]heptane-4-carbonyl)decahydropyrrolo[1,2-a]azocin-6-yl)carbamoyl)benzo[b]thiophen-5-yl)methyl)phosphonic acid;
((2-((3-(6-(4-(dimethylamino)pyridin-3-yl)-4-azaspiro[2.4]heptane-4-carbonyl)-9-morpholino-5-oxodecahydropyrrolo[1,2-a]azocin-6-yl)carbamoyl)benzo[b]thiophen-5-yl)fluoromethyl)phosphonic acid;
(fluoro(2-((9-morpholino-5-oxo-3-(6-(pyridin-3-yl)-4-azaspiro[2.4]heptane-4-carbonyl)decahydropyrrolo[1,2-a]azocin-6-yl)carbamoyl)benzo[b]thiophen-5-yl)methyl)phosphonic acid;
(fluoro(2-((9-morpholino-5-oxo-3-(6-(pyridin-3-yl)-4-azaspiro[2.4]heptane-4-carbonyl)decahydropyrrolo[1,2-a]azocin-6-yl)carbamoyl)benzo[b]thiophen-5-yl)methyl)phosphonic acid;
((2-((3-(7-cyano-6-(pyridin-3-yl)-4-azaspiro[2.4]heptane-4-carbonyl)-9-morpholino-5-oxodecahydropyrrolo[1,2-a]azocin-6-yl)carbamoyl)benzo[b]thiophen-5-yl)fluoromethyl)phosphonic acid;
((2-((3-(6-(4-(dimethylamino)pyridin-3-yl)-4-azaspiro[2.4]heptane-4-carbonyl)-9-morpholino-5-oxodecahydropyrrolo[1,2-a]azocin-6-yl)carbamoyl)benzo[b]thiophen-5-yl)fluoromethyl)phosphonic acid;
(fluoro(2-((9-(methyl(oxetan-3-yl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)phosphonic acid;
(fluoro(2-((9-(methyl(oxetan-3-ylmethyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)phosphonic acid;
(fluoro(2-((9-(methyl((oxetan-2-yl)methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)phosphonic acid;
(fluoro(2-((9-(methyl(oxetan-3-yl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)phosphonic acid;
(fluoro(2-((9-(methyl((oxetan-2-yl)methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)phosphonic acid;
(fluoro(2-((9-(methyl(tetrahydrofuran-3-yl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)phosphonic acid;
(fluoro(2-((9-(methyl(tetrahydrofuran-3-yl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)phosphonic acid;
((2-((9-((3,3-difluoropropyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)fluoromethyl)phosphonic acid;
(fluoro(2-((9-((3-fluorocyclobutyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)phosphonic acid;
(fluoro(2-((9-((3-fluorocyclobutyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)phosphonic acid;
2,2,2-trifluoroacetic acid compound with ((2-((9-((3,3-difluorocyclobutyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)fluoromethyl)phosphonic acid;
(fluoro(2-((9-(methyl((oxetan-2-yl)methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)phosphonic acid;
((2-((9-((3,3-difluorocyclobutyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)fluoromethyl)phosphonic acid;
(fluoro(2-((9-(methyl(tetrahydrofuran-3-yl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)phosphonic acid;
(fluoro(2-((3-(6-(3-fluorophenyl)-4-azaspiro[2.4]heptane-4-carbonyl)-9-(methyl(oxetan-3-yl)amino)-5-oxodecahydropyrrolo[1,2-a]azocin-6-yl)carbamoyl)benzo[b]thiophen-5-yl)methyl)phosphonic acid;

-continued (fluoro(2-((9-(methyl(tetrahydrofuran-3-yl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)phosphonic acid;
((2-((9-((3,3-difluoropropyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)fluoromethyl)phosphonic acid;
(fluoro(2-((9-((3-fluorocyclobutyl)(methyl)amino)-5-oxo-3-(6-(pyridin-3-yl)-4-azaspiro[2.4]heptane-4-carbonyl)decahydropyrrolo[1,2-a]azocin-6-yl)carbamoyl)benzo[b]thiophen-5-yl)methyl)phosphonic acid.;
(fluoro(2-((9-(methyl((oxetan-2-yl)methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)phosphonic acid;
((2-((9-((3,3-difluorocyclopentyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)fluoromethyl)phosphonic acid;
((2-((9-(ethyl(3-fluorocyclobutyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)fluoromethyl)phosphonic acid;
((2-((9-(ethyl(3-fluorocyclobutyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)fluoromethyl)phosphonic acid;
((2-((9-((3-(difluoromethyl)cyclobutyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)fluoromethyl)phosphonic acid;
((2-((9-((3,3-difluorocyclopentyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)fluoromethyl)phosphonic acid;
((2-((9-((3-cyanocyclobutyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)fluoromethyl)phosphonic acid;
(fluoro(2-((9-(methyl(4,4,4-trifluorobutyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)phosphonic acid;
(fluoro(2-((9-((3-fluorocyclobutyl)(methyl)amino)-5-oxo-3-(4-azaspiro[2.4]heptane-4-carbonyl)decahydropyrrolo[1,2-a]azocin-6-yl)carbamoyl)benzo[b]thiophen-5-yl)methyl)phosphonic acid;
((2-((9-((3-cyanocyclobutyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)fluoromethyl)phosphonic acid;
2,2,2-trifluoroacetic acid compound with ((2-((9-(ethyl((3-methyloxetan-3-yl)methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)fluoromethyl)phosphonic acid;
((2-((9-(ethyl(3-(trifluoromethoxy)cyclobutyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)fluoromethyl)phosphonic acid;
((2-((9-(ethyl(4,4,4-trifluorobutyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)fluoromethyl)phosphonic acid;
((2-((9-(ethyl(4,4,4-trifluorobutyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)fluoromethyl)phosphonic acid;
((2-((9-(ethyl(3-(trifluoromethyl)cyclobutyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)fluoromethyl)phosphonic acid;
((2-((9-(ethyl(3-(trifluoromethyl)cyclobutyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)fluoromethyl)phosphonic acid;
((2-((9-(ethyl(3-(trifluoromethoxy)cyclobutyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)fluoromethyl)phosphonic acid;
(fluoro(2-((9-(methyl((3-(trifluoromethyl)cyclobutyl)methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)phosphonic acid;
(fluoro(2-((9-(methyl((3-(trifluoromethyl)cyclobutyl)methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)phosphonic acid;
(fluoro(2-((9-(methyl(2-(1-(trifluoromethyl)cyclopropyl)ethyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)phosphonic acid;
(fluoro(2-((9-(methyl(3-(trifluoromethoxy)cyclobutyl)amino)-5-oxo-3-(4-azaspiro[2.4]heptane-4-carbonyl)decahydropyrrolo[1,2-a]azocin-6-yl)carbamoyl)benzo[b]thiophen-5-yl)methyl)phosphonic acid;
(fluoro(2-((9-(methyl(3-(trifluoromethoxy)propyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)phosphonic acid;
(fluoro(2-((9-(methyl(4,4,4-trifluoro-3-methoxybutyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)phosphonic acid;

-continued

| |
|---|
| (fluoro(2-((9-morpholino-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)phosphonic acid; |
| ((2-((9-((3,3-difluorocyclopentyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)fluoromethyl)phosphonic acid; |
| (fluoro(2-((9-(methyl((3-methyloxetan-3-yl)methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)phosphonic acid; |
| (fluoro(2-((9-(methyl(3-(trifluoromethoxy)cyclopentyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)phosphonic acid; |
| (difluoro(2-((9-(methyl(3-(trifluoromethoxy)cyclobutyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)phosphonic acid; |
| (fluoro(2-((9-(methyl(3-(trifluoromethoxy)cyclobutyl)amino)-5-oxo-3-(6-(pyridin-3-yl)-4-azaspiro[2.4]heptane-4-carbonyl)decahydropyrrolo[1,2-a]azocin-6-yl)carbamoyl)benzo[b]thiophen-5-yl)methyl)phosphonic acid; |
| (fluoro(2-((9-(methyl(3-(trifluoromethoxy)cyclobutyl)amino)-5-oxo-3-(6-(pyridin-3-yl)-4-azaspiro[2.4]heptane-4-carbonyl)decahydropyrrolo[1,2-a]azocin-6-yl)carbamoyl)benzo[b]thiophen-5-yl)methyl)phosphonic acid; |
| (fluoro(2-((3-(7-methoxy-6-phenyl-4-azaspiro[2.4]heptane-4-carbonyl)-9-(methyl(3-(trifluoromethoxy)cyclobutyl)amino)-5-oxodecahydropyrrolo[1,2-a]azocin-6-yl)carbamoyl)benzo[b]thiophen-5-yl)methyl)phosphonic acid; |
| (fluoro(2-((3-(7-methoxy-6-phenyl-4-azaspiro[2.4]heptane-4-carbonyl)-9-(methyl(3-(trifluoromethoxy)cyclobutyl)amino)-5-oxodecahydropyrrolo[1,2-a]azocin-6-yl)carbamoyl)benzo[b]thiophen-5-yl)methyl)phosphonic acid; |
| (fluoro(2-((9-(methyl(3,3,3-trifluoro-2-methoxypropyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)phosphonic acid; |
| (fluoro(2-((9-(methyl(2-(trifluoromethoxy)ethyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)phosphonic acid; and |
| (fluoro(2-((9-(methyl(3-(trifluoromethyl)cyclobutyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)phosphonic acid, |

and pharmaceutically acceptable salts thereof.

In some embodiments, the prodrug is a compound of Formula (I), wherein $R^P$ is

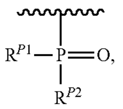

wherein $R^{P1}$ and $R^{P2}$ are each independently —$OR^{Pa}$, or a pharmaceutically acceptable salt thereof.

In some embodiments, the prodrug is the compound of Formula (I-C-1), (I-C-2), (I-C-3), (I-C-4), (I-C-5), or (I-C-6), or a pharmaceutically acceptable salt thereof. In some embodiments, the prodrug is a compound of Formula (I), wherein $R^P$ is

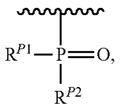

wherein $R^{P1}$ is —$OR^{Pa}$ and $R^{Paa2}$ is N-linked amino acid ester, or a pharmaceutically acceptable salt thereof. In some embodiments, the intermediate metabolite of the prodrug is the compound of Formula (I-B-1), (I-B-2), (I-B-3), (I-B-4), (I-B-5), or (I-B-6), or a pharmaceutically acceptable salt thereof. In some embodiments, the intermediate metabolite of the prodrug is a compound of Formula (I), wherein $R^P$ is

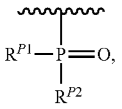

wherein $R^{P1}$ is —OH and $R^{Paa2}$ is N-linked amino acid, or a pharmaceutically acceptable salt thereof. In some embodiments, the intermediate metabolite is a compound of formula (I), wherein $R^P$ is

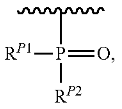

wherein $R^{P1}$ is —OH, and $R^{P2}$ is

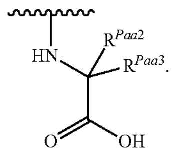

In some embodiments, the intermediate metabolite is a compound of formula (I), wherein $R^P$ is

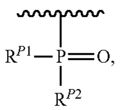

wherein $R^{P1}$ is —OH, and $R^{P2}$ is

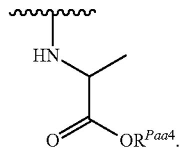

In some embodiments, the intermediate metabolite is a compound of formula (I), wherein $R^P$ is

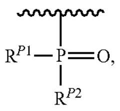

wherein $R^{P1}$ is —OH, and $R^{P2}$ is

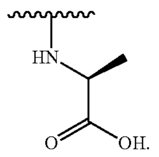 [SMILES: *N[C@@H](C)C(=O)O]

In some embodiments, the prodrug is the compound of Formula (I-E-1), (I-E-2), (I-E-3), (I-E-4), (I-E-5), or (I-E-6), or a pharmaceutically acceptable salt thereof. In some embodiments, the prodrug is a compound of Formula (I), wherein $R^P$ is

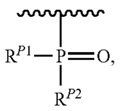

wherein $R^{P1}$ and $R^{P2}$ are each independently N-linked amino acid ester, or a pharmaceutically acceptable salt thereof. In some embodiments, the intermediate metabolite of the prodrug is the compound of Formula (I-D-1), (I-D-2), (I-D-3), (I-D-4), (I-D-5), or (I-D-6), or a pharmaceutically acceptable salt thereof. In some embodiments, the intermediate metabolite of the prodrug is a compound of Formula (I), wherein $R^P$ is

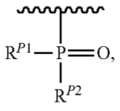

wherein $R^{P1}$ and $R^{P2}$ are each independently N-linked amino acid, or a pharmaceutically acceptable salt thereof.

In some embodiments, the prodrug is the compound of Formula (I-G-1), (I-G-2), (I-G-3), (I-G-4), (I-G-5), or (I-G-

6), or a pharmaceutically acceptable salt thereof, wherein Ring A is substituted with 0, 1, 2, or 3 substituents each independently selected from the group consisting of halo, oxo, and ester. In some embodiments, the prodrug is a compound of Formula (I), wherein $R^P$ is

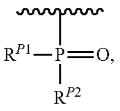

wherein $R^{P1}$ is N-linked amino acid ester and $R^{P2}$ is Ring A, wherein Ring A is

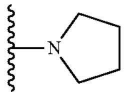

substituted with 0, 1, 2, or 3 substituents each independently selected from the group consisting of halo, oxo, and ester, or a pharmaceutically acceptable salt thereof. In some embodiments, the intermediate metabolite of the prodrug is the compound of Formula (I-F-1), (I-F-2), (I-F-3), (I-F-4), (I-F-5), or (I-F-6), or a pharmaceutically acceptable salt thereof, wherein Ring A is substituted with 0, 1, 2, or 3 substituents each independently selected from the group consisting of halo, oxo, and —COOH. In some embodiments, the intermediate metabolite of the prodrug is a compound of Formula (I), wherein $R^P$ is

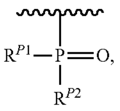

wherein $R^{P1}$ is N-linked amino acid and $R^{P2}$ is Ring A, wherein Ring A is

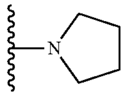 [SMILES: *N1CCCC1]

substituted with 0, 1, 2, or 3 substituents each independently selected from the group consisting of halo, oxo, and —COOH, or a pharmaceutically acceptable salt thereof.

In some embodiments, the prodrug is a compound selected from the group consisting of the compounds of Table 1C, or a pharmaceutically acceptable salt thereof. In some embodiments, the intermediate metabolite is a compound selected from the group consisting of the compounds of Table 1B, or a pharmaceutically acceptable salt thereof.

In some embodiments, the intermediate metabolite is a compound of formula (I), wherein $R^P$ is

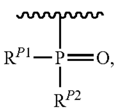

wherein $R^{P1}$ is —OH, and $R^{Paa2}$ is N-linked amino acid ester. In some embodiments, the intermediate metabolite is a compound of formula (I), wherein $R^P$ is

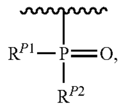

wherein $R^{P1}$ is —OH, and $R^{P2}$ is

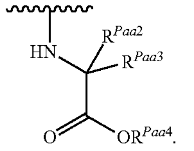

In some embodiments, the intermediate metabolite is a compound of formula (I), wherein $R^P$ is

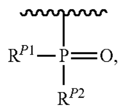

wherein $R^{P1}$ is —OH, and $R^{P2}$ is

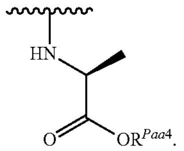

In some embodiments, the intermediate metabolite is a compound of formula (I), wherein $R^P$ is

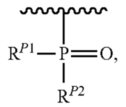

wherein $R^{P1}$ is —OH, $R^{P2}$ is

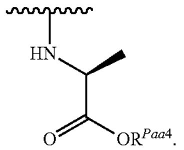

and $R^{Paa4}$ is

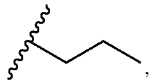, 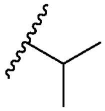, 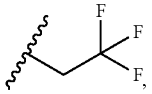, 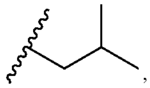, 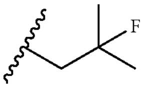, 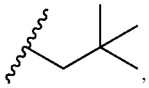, 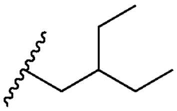, 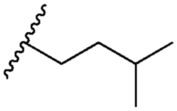, 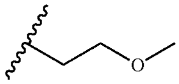, or 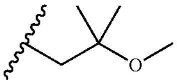.

In some embodiments, the intermediate metabolite is a compound of formula (I), wherein $R^P$ is

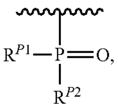

wherein $R^{P1}$ is —OH, $R^{P2}$ is

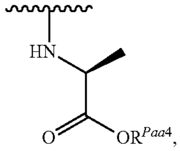

and $R^{Paa4}$ is

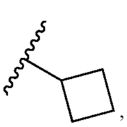, 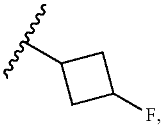, 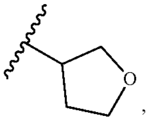, 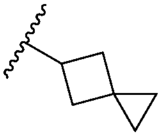, 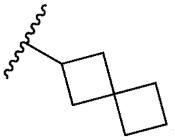, 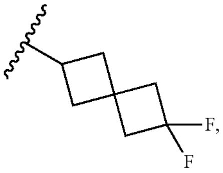, 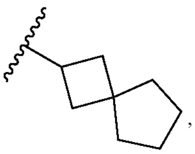, 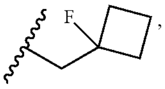, 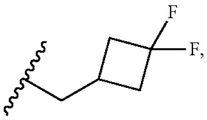, 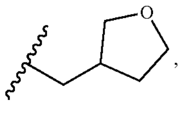, -continued
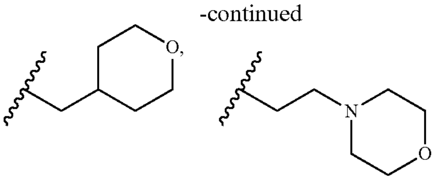
, or
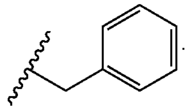
In some embodiments, the intermediate metabolite is a compound of formula (I), wherein $R^P$ is
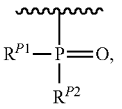
wherein $R^{P1}$ is —OH, $R^{P2}$ is
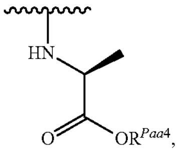
and $R^{Paa4}$ is
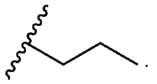 [SMILES: *CCC]
In some embodiments, the compound of Formula (I), or a pharmaceutically acceptable salt thereof, is a compound of Formula (I-J-1), (I-J-2), (I-J-3), (I-J-4), (I-J-5), or (I-J-6), or a pharmaceutically acceptable salt thereof:
(I-J-1)
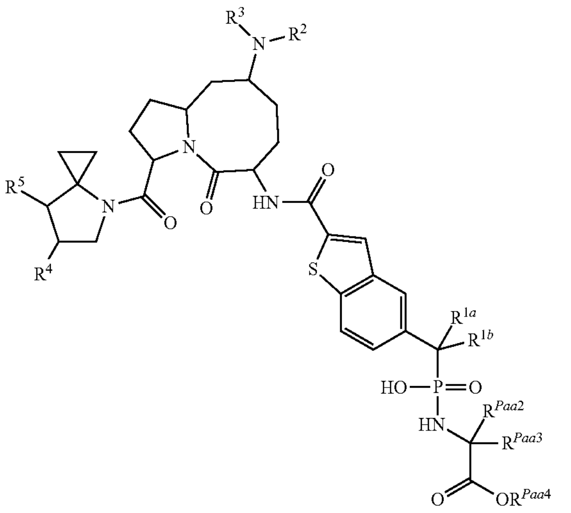
-continued
(I-J-2)
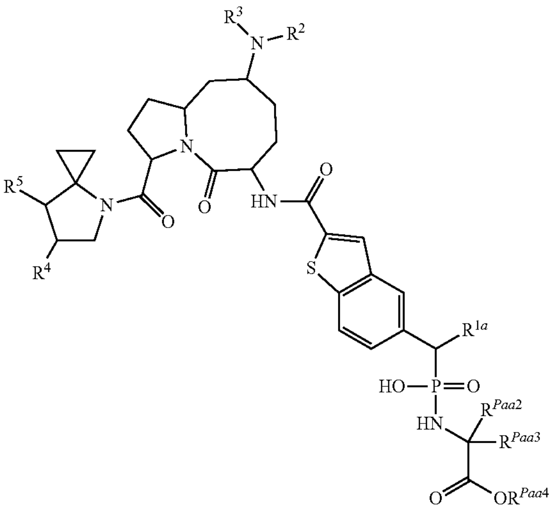
(I-J-3)
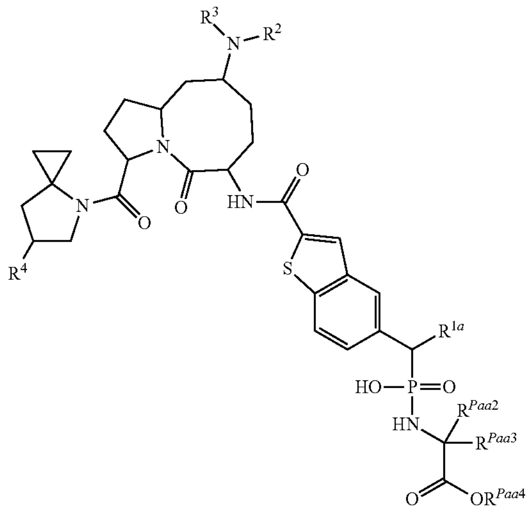

-continued (I-J-4)

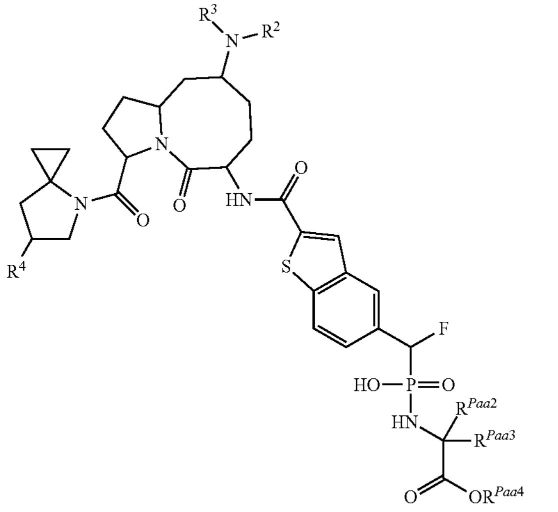

(I-J-5)

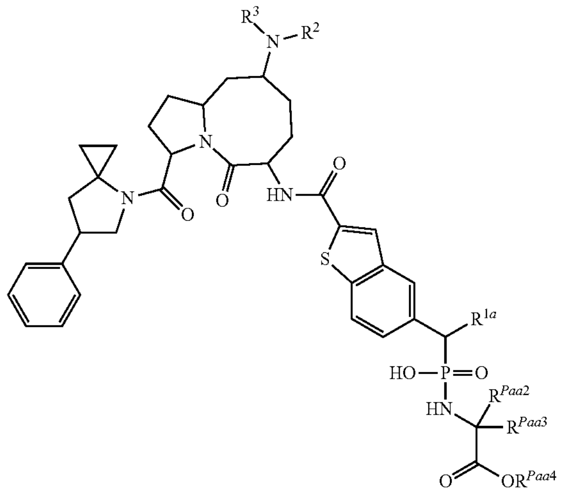

-continued (I-J-6)

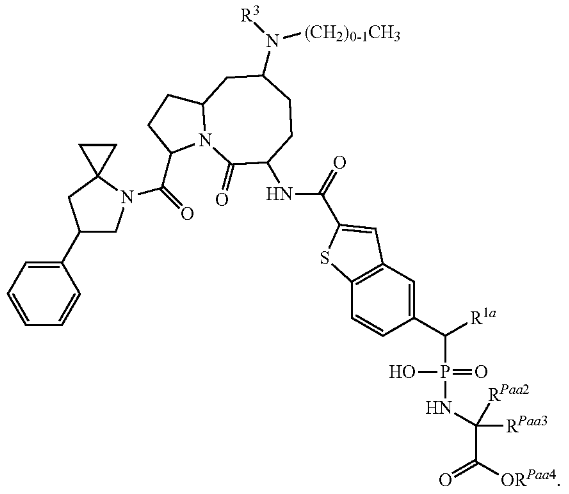

wherein $R^{Paa2}$ is H or $(C_1\text{-}C_6)$alkyl; and $R^{Paa3}$ is H, $(C_1\text{-}C_6)$alkyl, $-(C_1\text{-}C_6)$alkylene-$(C_1\text{-}C_6)$alkoxy, or $-(C_1\text{-}C_6)$alkylene-$(C_6\text{-}C_{10})$aryl; or $R^{Paa2}$ and $R^{Paa3}$ together with the carbon atom to which they are attached form $(C_3\text{-}C_6)$cycloalkyl; and $R^{Paa4}$ is $(C_1\text{-}C_6)$ alkyl.

In some embodiments, the compound, or a pharmaceutically acceptable salt thereof, is an intermediate metabolite selected from the group consisting of:

((fluoro(2-((9-((3-fluorocyclobutyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(hydroxy)phosphoryl)-alanine;

((fluoro(2-((9-(methyl(3-(trifluoromethoxy)cyclobutyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(hydroxy)phosphoryl)-alanine;

((fluoro(2-((9-(methyl(3-(trifluoromethoxy)cyclobutyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(hydroxy)phosphoryl)-alanine;

((fluoro(2-((9-(methyl(3-(trifluoromethyl)cyclobutyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(hydroxy)phosphoryl)-alanine;

((fluoro(2-((9-(methyl(4,4,4-trifluorobutyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(hydroxy)phosphoryl)-alanine;

(((2-((9-((3,3-difluoropropyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)fluoromethyl)(hydroxy)phosphoryl)-alanine;

((fluoro(2-((9-((3-fluorocyclobutyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(hydroxy)phosphoryl)-alanine;

(((2-((9-(ethyl(3-fluorocyclobutyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)fluoromethyl)(hydroxy)phosphoryl)-alanine;

((fluoro(2-((9-(methyl((3-methyloxetan-3-yl)methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(hydroxy)phosphoryl)-alanine;

-continued

| |
|---|
| ((fluoro(2-((9-(methyl(3-(trifluoromethyl)cyclobutyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(hydroxy)phosphoryl)-alanine; |
| (((2-((9-((3-cyanocyclobutyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)fluoromethyl)(hydroxy)phosphoryl)-alanine; |
| (((2-((9-((3,3-difluorocyclopentyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)fluoromethyl)(hydroxy)phosphoryl)-alanine; |
| ((fluoro(2-((9-((3-fluorocyclobutyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-6-yl)methyl)(hydroxy)phosphoryl)-alanine; |
| ((fluoro(2-((9-(methyl(4,4,4-trifluorobutyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(hydroxy)phosphoryl)-alanine; |
| ((fluoro(2-((9-((3-fluorocyclobutyl)(methyl)amino)-5-oxo-3-(4-azaspiro[2.4]heptane-4-carbonyl)decahydropyrrolo[1,2-a]azocin-6-yl)carbamoyl)benzo[b]thiophen-5-yl)methyl)(hydroxy)phosphoryl)-alanine; |
| (((2-((9-(ethyl(3-(trifluoromethoxy)cyclobutyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)fluoromethyl)(hydroxy)phosphoryl)-alanine; |
| (((2-((9-(ethyl(4,4,4-trifluorobutyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)fluoromethyl)(hydroxy)phosphoryl)-alanine; |
| (((2-((9-((3-(difluoromethyl)cyclobutyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)fluoromethyl)(hydroxy)phosphoryl)-alanine; |
| ((fluoro(2-((9-(methyl(tetrahydrofuran-3-yl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(hydroxy)phosphoryl)-alanine; |
| ((fluoro(2-((9-(methyl((oxetan-2-yl)methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(hydroxy)phosphoryl)-alanine; |
| ((fluoro(2-((9-(methyl(oxetan-3-yl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(hydroxy)phosphoryl)-alanine; |
| ((fluoro(2-((9-(methyl((oxetan-2-yl)methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(hydroxy)phosphoryl)-alanine; |
| ((fluoro(2-((9-(methyl((oxetan-2-yl)methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(hydroxy)phosphoryl)-alanine; |
| ((fluoro(2-((9-morpholino-5-oxo-3-(6-(pyridin-3-yl)-4-azaspiro[2.4]heptane-4-carbonyl)decahydropyrrolo[1,2-a]azocin-6-yl)carbamoyl)benzo[b]thiophen-5-yl)methyl)(hydroxy)phosphoryl)-alanine; |
| ((fluoro(2-((9-((3-fluorocyclobutyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(hydroxy)phosphoryl)-alanine; |
| (((2-((9-(ethyl(4,4,4-trifluorobutyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)fluoromethyl)(hydroxy)phosphoryl)-alanine; |
| (((2-((9-(ethyl(3-(trifluoromethoxy)cyclobutyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)fluoromethyl)(hydroxy)phosphoryl)-alanine; and |
| ((fluoro(2-((9-(methyl(oxetan-3-yl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(hydroxy)phosphoryl)-alanine, |

and pharmaceutically acceptable salts thereof.

In some embodiments, the compound, or a pharmaceutically acceptable salt thereof, is a prodrug selected from the group consisting of:

| |
|---|
| propyl (((2-((9-((3,3-difluoropropyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)fluoromethyl)(phenoxy)phosphoryl)-alaninate; |
| propyl (((2-((9-((3,3-difluorocyclobutyl)(methyl)amino)-5-oxo-3-(6-phenyl-4-azaspiro[2.4]heptane-4-carbonyl)decahydropyrrolo[1,2-a]azocin-6-yl)carbamoyl)-2,3-dihydrobenzo[b]thiophen-5-yl)fluoromethyl)(phenoxy)phosphoryl)-alaninate; |
| propyl (((2-((9-((3,3-difluorocyclobutyl)(methyl)amino)-5-oxo-3-(6-phenyl-4-azaspiro[2.4]heptane-4-carbonyl)decahydropyrrolo[1,2-a]azocin-6-yl)carbamoyl)-2,3-dihydrobenzo[b]thiophen-5-yl)fluoromethyl)(phenoxy)phosphoryl)-alaninate; |
| propyl ((fluoro(2-((9-(methyl(3-(trifluoromethyl)cyclobutyl)amino)-5-oxo-3-(6-phenyl-4-azaspiro[2.4]heptane-4-carbonyl)decahydropyrrolo[1,2-a]azocin-6-yl)carbamoyl)-2,3-dihydrobenzo[b]thiophen-5-yl)methyl)(phenoxy)phosphoryl)-alaninate; |

-continued propyl ((fluoro(2-((9-(methyl(3-(trifluoromethoxy)cyclobutyl)amino)-5-oxo-3-(6-phenyl-4-azaspiro[2.4]heptane-4-carbonyl)decahydropyrrolo[1,2-a]azocin-6-yl)carbamoyl)-2,3-dihydrobenzo[b]thiophen-5-yl)methyl)(phenoxy)phosphoryl)-alaninate;
propyl ((fluoro(2-((9-(methyl(3-(trifluoromethoxy)cyclobutyl)amino)-5-oxo-3-(6-phenyl-4-azaspiro[2.4]heptane-4-carbonyl)decahydropyrrolo[1,2-a]azocin-6-yl)carbamoyl)-2,3-dihydrobenzo[b]thiophen-5-yl)methyl)(phenoxy)phosphoryl)-alaninate;
propyl ((fluoro(2-((9-(methyl(3-(trifluoromethoxy)cyclobutyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
propyl ((fluoro(2-((9-(methyl(4,4,4-trifluorobutyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
propyl (((2-((9-((3,3-difluoropropyl)(methyl)amino)-5-oxo-3-(6-phenyl-4-azaspiro[2.4]heptane-4-carbonyl)decahydropyrrolo[1,2-a]azocin-6-yl)carbamoyl)-2,3-dihydrobenzo[b]thiophen-5-yl)fluoromethyl)(phenoxy)phosphoryl)-alaninate;
propyl ((fluoro(2-((9-(methyl(3-(trifluoromethyl)cyclobutyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
propyl (((2-((9-((3,3-difluoropropyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)fluoromethyl)(phenoxy)phosphoryl)-alaninate;
propyl (((2-((9-((3,3-difluoropropyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)fluoromethyl)(phenoxy)phosphoryl)-alaninate;
propyl ((fluoro(2-((9-(methyl(3-(trifluoromethyl)cyclobutyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
cyclobutyl ((fluoro(2-((9-((3-fluorocyclobutyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
cyclobutyl ((fluoro(2-((9-((3-fluorocyclobutyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
propyl ((fluoro(2-((9-((3-fluorocyclobutyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
propyl ((fluoro(2-((9-((3-fluorocyclobutyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
propyl ((fluoro(2-((9-(methyl((oxetan-2-yl)methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
propyl ((fluoro(2-((9-((3-fluorocyclobutyl)(methyl)amino)-5-oxo-3-(6-phenyl-4-azaspiro[2.4]heptane-4-carbonyl)decahydropyrrolo[1,2-a]azocin-6-yl)carbamoyl)-2,3-dihydrobenzo[b]thiophen-5-yl)methyl)(phenoxy)phosphoryl)-alaninate;
propyl ((fluoro(2-((9-(methyl((oxetan-2-yl)methyl)amino)-5-oxo-3-(6-phenyl-4-azaspiro[2.4]heptane-4-carbonyl)decahydropyrrolo[1,2-a]azocin-6-yl)carbamoyl)-2,3-dihydrobenzo[b]thiophen-5-yl)methyl)(phenoxy)phosphoryl)-alaninate;
propyl ((fluoro(2-((9-(methyl((oxetan-2-yl)methyl)amino)-5-oxo-3-(6-phenyl-4-azaspiro[2.4]heptane-4-carbonyl)decahydropyrrolo[1,2-a]azocin-6-yl)carbamoyl)-2,3-dihydrobenzo[b]thiophen-5-yl)methyl)(phenoxy)phosphoryl)-alaninate;
propyl ((fluoro(2-((9-(methyl(tetrahydrofuran-3-yl)amino)-5-oxo-3-(6-phenyl-4-azaspiro[2.4]heptane-4-carbonyl)decahydropyrrolo[1,2-a]azocin-6-yl)carbamoyl)-2,3-dihydrobenzo[b]thiophen-5-yl)methyl)(phenoxy)phosphoryl)-alaninate;
propyl ((fluoro(2-((9-((3-fluorocyclobutyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
propyl ((fluoro(2-((9-(methyl(tetrahydrofuran-3-yl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
propyl ((fluoro(2-((9-((3-fluorocyclobutyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
propyl ((fluoro(2-((9-(methyl(oxetan-3-ylmethyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
propyl ((fluoro(2-((9-(methyl(tetrahydrofuran-3-yl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
propyl ((fluoro(2-((9-((3-fluorocyclobutyl)(methyl)amino)-5-oxo-3-(6-(pyridin-3-yl)-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
propyl ((fluoro(2-((9-morpholino-5-oxo-3-(6-(pyridin-3-yl)-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
propyl ((fluoro(2-((9-(methyl(oxetan-3-yl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;

-continued propyl (((2-((3-(6-(4-(dimethylamino)pyridin-3-yl)-4-azaspiro[2.4]heptane-4-carbonyl)-9-morpholino-5-oxodecahydropyrrolo[1,2-a]azocin-6-yl)carbamoyl)benzo[b]thiophen-5-yl)fluoromethyl)(phenoxy)phosphoryl)-alaninate;
propyl ((fluoro(2-((9-(methyl(tetrahydrofuran-3-yl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
propyl ((fluoro(2-((9-morpholino-5-oxo-3-(6-(pyridin-3-yl)-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
propyl ((fluoro(2-((9-(methyl(oxetan-3-yl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
propyl ((fluoro(2-((9-(methyl(oxetan-3-yl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
propyl ((fluoro(2-((3-(6-(3-fluorophenyl)-4-azaspiro[2.4]heptane-4-carbonyl)-9-(methyl(oxetan-3-yl)amino)-5-oxodecahydropyrrolo[1,2-a]azocin-6-yl)carbamoyl)benzo[b]thiophen-5-yl)methyl)(phenoxy)phosphoryl)-alaninate;
propyl ((fluoro(2-((9-(methyl(oxetan-3-yl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
propyl (((2-((3-(7-cyano-6-phenyl-4-azaspiro[2.4]heptane-4-carbonyl)-9-morpholino-5-oxodecahydropyrrolo[1,2-a]azocin-6-yl)carbamoyl)benzo[b]thiophen-5-yl)fluoromethyl)(phenoxy)phosphoryl)-alaninate;
propyl ((fluoro(2-((9-morpholino-5-oxo-3-(6-(pyridin-3-yl)-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
propyl ((fluoro(2-((9-morpholino-5-oxo-3-(6-(pyridin-3-yl)-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
propyl ((fluoro(2-((9-morpholino-5-oxo-3-(6-(pyridin-3-yl)-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
propyl ((fluoro(2-((9-morpholino-5-oxo-3-(6-(pyridin-3-yl)-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
propyl ((fluoro(2-((9-morpholino-5-oxo-3-(6-(pyridin-3-yl)-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
propyl (((2-((3-(7-cyano-6-(pyridin-3-yl)-4-azaspiro[2.4]heptane-4-carbonyl)-9-morpholino-5-oxodecahydropyrrolo[1,2-a]azocin-6-yl)carbamoyl)benzo[b]thiophen-5-yl)fluoromethyl)(phenoxy)phosphoryl)-alaninate;
propyl (((2-((3-(7-cyano-6-(pyridin-3-yl)-4-azaspiro[2.4]heptane-4-carbonyl)-9-morpholino-5-oxodecahydropyrrolo[1,2-a]azocin-6-yl)carbamoyl)benzo[b]thiophen-5-yl)fluoromethyl)(phenoxy)phosphoryl)-alaninate;
propyl (((2-((3-(6-(4-(dimethylamino)pyridin-3-yl)-4-azaspiro[2.4]heptane-4-carbonyl)-9-morpholino-5-oxodecahydropyrrolo[1,2-a]azocin-6-yl)carbamoyl)benzo[b]thiophen-5-yl)fluoromethyl)(phenoxy)phosphoryl)-alaninate;
propyl (((2-((3-(6-(4-(dimethylamino)pyridin-3-yl)-4-azaspiro[2.4]heptane-4-carbonyl)-9-morpholino-5-oxodecahydropyrrolo[1,2-a]azocin-6-yl)carbamoyl)benzo[b]thiophen-5-yl)fluoromethyl)(phenoxy)phosphoryl)-alaninate;
propyl (((2-((3-(6-(4-(dimethylamino)pyridin-3-yl)-4-azaspiro[2.4]heptane-4-carbonyl)-9-morpholino-5-oxodecahydropyrrolo[1,2-a]azocin-6-yl)carbamoyl)benzo[b]thiophen-5-yl)fluoromethyl)(phenoxy)phosphoryl)-alaninate;
isopropyl ((fluoro(2-((9-morpholino-5-oxo-3-(6-(pyridin-3-yl)-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
isopropyl ((fluoro(2-((9-morpholino-5-oxo-3-(6-(pyridin-3-yl)-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
propyl ((fluoro(2-((9-(methyl((oxetan-2-yl)methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
benzyl (((2-((9-((3,3-difluoropropyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)fluoromethyl)(phenoxy)phosphoryl)-alaninate;
propyl 2-((((2-((9-((3,3-difluoropropyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)fluoromethyl)(phenoxy)phosphoryl)amino)butanoate;
2-methoxyethyl (((2-((9-((3,3-difluoropropyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)fluoromethyl)(phenoxy)phosphoryl)-alaninate;
propyl (((2-((9-(ethyl(3-fluorocyclobutyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)fluoromethyl)(phenoxy)phosphoryl)-alaninate;
propyl (((2-((9-(ethyl(3-fluorocyclobutyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)fluoromethyl)(phenoxy)phosphoryl)-alaninate;

-continued isopropyl (((2-((9-((3,3-difluoropropyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)fluoromethyl)(phenoxy)phosphoryl)-alaninate;
ethyl (((2-((9-((3,3-difluoropropyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)fluoromethyl)(phenoxy)phosphoryl)-alaninate;
propyl ((fluoro(2-((9-(methyl(tetrahydrofuran-3-yl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
propyl ((fluoro(2-((9-(methyl(tetrahydrofuran-3-yl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
cyclobutyl ((fluoro(2-((9-((3-fluorocyclobutyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
cyclobutyl ((fluoro(2-((9-((3-fluorocyclobutyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
propyl ((fluoro(2-((9-((3-fluorocyclobutyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(2,2,2-trifluoroethoxy)phosphoryl)-alaninate;
propyl ((fluoro(2-((9-((3-fluorocyclobutyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(2,2,2-trifluoroethoxy)phosphoryl)-alaninate;
propyl (((2-((9-((3-cyanocyclobutyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)fluoromethyl)(phenoxy)phosphoryl)-alaninate;
(3,3-difluorocyclobutyl)methyl ((fluoro(2-((9-((3-fluorocyclobutyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
(3,3-difluorocyclobutyl)methyl ((fluoro(2-((9-((3-fluorocyclobutyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
isopropyl ((fluoro(2-((9-((3-fluorocyclobutyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
isopropyl ((fluoro(2-((9-((3-fluorocyclobutyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
propyl (((2-((9-((3-(difluoromethyl)cyclobutyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)fluoromethyl)(phenoxy)phosphoryl)-alaninate;
propyl (((2-((9-((3-(difluoromethyl)cyclobutyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)fluoromethyl)(phenoxy)phosphoryl)-alaninate;
3-fluorocyclobutyl ((fluoro(2-((9-((3-fluorocyclobutyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
3-fluorocyclobutyl ((fluoro(2-((9-((3-fluorocyclobutyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
2-ethylbutyl ((fluoro(2-((9-((3-fluorocyclobutyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
neopentyl ((fluoro(2-((9-((3-fluorocyclobutyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
3-fluorocyclobutyl ((fluoro(2-((9-((3-fluorocyclobutyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
3-fluorocyclobutyl ((fluoro(2-((9-((3-fluorocyclobutyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
isopropyl (ethoxy(fluoro(2-((9-((3-fluorocyclobutyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)phosphoryl)-alaninate;
2-ethylbutyl ((fluoro(2-((9-((3-fluorocyclobutyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
neopentyl ((fluoro(2-((9-((3-fluorocyclobutyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
propyl ((fluoro(2-((9-((3-fluorocyclobutyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
propyl ((fluoro(2-((9-(methyl(4,4,4-trifluorobutyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;

-continued isopropyl (ethoxy(fluoro(2-((9-((3-fluorocyclobutyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)phosphoryl)-alaninate;
propyl ((fluoro(2-((9-((3-fluorocyclobutyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
propyl ((fluoro(2-((9-((3-fluorocyclobutyl)(methyl)amino)-5-oxo-3-(4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
isopropyl (ethoxy(fluoro(2-((9-((3-fluorocyclobutyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)phosphoryl)-alaninate;
propyl ((fluoro(2-((9-(methyl(4,4,4-trifluorobutyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(2,2,2-trifluoroethoxy)phosphoryl)-alaninate;
propyl ((fluoro(2-((9-((3-fluorocyclobutyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(propoxy)phosphoryl)-alaninate;
cyclobutyl ((fluoro(2-((9-((3-fluorocyclobutyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(2,2,2-trifluoroethoxy)phosphoryl)-alaninate;
propyl (((2-((9-((3,3-difluorocyclopentyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)fluoromethyl)(2,2,2-trifluoroethoxy)phosphoryl)-alaninate;
propyl ((fluoro(2-((9-(methyl(4,4,4-trifluorobutyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(2,2,2-trifluoroethoxy)phosphoryl)-alaninate;
propyl (cyclopropoxy(fluoro(2-((9-((3-fluorocyclobutyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)phosphoryl)-alaninate;
isopropyl (ethoxy(fluoro(2-((9-((3-fluorocyclobutyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)phosphoryl)-alaninate;
isopropyl ((fluoro(2-((9-((3-fluorocyclobutyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(2,2,2-trifluoroethoxy)phosphoryl)-alaninate;
propyl (((2-((9-((3,3-difluorocyclopentyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)fluoromethyl)(2,2,2-trifluoroethoxy)phosphoryl)-alaninate;
propyl ((fluoro(2-((9-(methyl(3-(trifluoromethoxy)cyclobutyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(2,2,2-trifluoroethoxy)phosphoryl)-alaninate;
propyl ((fluoro(2-((9-(methyl(3-(trifluoromethoxy)cyclobutyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(2,2,2-trifluoroethoxy)phosphoryl)-alaninate;
propyl (((2-((9-(ethyl((3-methyloxetan-3-yl)methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)fluoromethyl)(phenoxy)phosphoryl)-alaninate;
propyl (((2-((9-(ethyl(3-(trifluoromethoxy)cyclobutyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)fluoromethyl)(phenoxy)phosphoryl)-alaninate;
propyl (((2-((9-(ethyl(4,4,4-trifluorobutyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)fluoromethyl)(phenoxy)phosphoryl)-alaninate;
propyl (((2-((9-(ethyl(4,4,4-trifluorobutyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)fluoromethyl)(phenoxy)phosphoryl)-alaninate;
cyclobutyl ((fluoro(2-((9-((3-fluorocyclobutyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(2,2,2-trifluoroethoxy)phosphoryl)-alaninate;
isopropyl ((fluoro(2-((9-((3-fluorocyclobutyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(2,2,2-trifluoroethoxy)phosphoryl)-alaninate;
isobutyl ((fluoro(2-((9-((3-fluorocyclobutyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
isobutyl ((fluoro(2-((9-((3-fluorocyclobutyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
cyclobutyl (ethoxy(fluoro(2-((9-((3-fluorocyclobutyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)phosphoryl)-alaninate;
cyclobutyl (ethoxy(fluoro(2-((9-((3-fluorocyclobutyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)phosphoryl)-alaninate;
propyl (((2-((9-(ethyl(3-(trifluoromethyl)cyclobutyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)fluoromethyl)(phenoxy)phosphoryl)-alaninate;

-continued propyl (((2-((9-(ethyl(3-(trifluoromethyl)cyclobutyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)fluoromethyl)(phenoxy)phosphoryl)-alaninate;
propyl (((2-((9-((3-cyanocyclobutyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)fluoromethyl)(2,2,2-trifluoroethoxy)phosphoryl)-alaninate;
cyclobutyl (((2-((9-((3-cyanocyclobutyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)fluoromethyl)(phenoxy)phosphoryl)-alaninate;
cyclobutyl (((2-((9-((3-cyanocyclobutyl) (methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)fluoromethyl)(phenoxy)phosphoryl)-alaninate;
cyclobutyl ((fluoro(2-((9-(methyl(3-(trifluoromethyl)cyclobutyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
propyl ((fluoro(2-((9-(methyl(3-(trifluoromethyl)cyclobutyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(2,2,2-trifluoroethoxy)phosphoryl)-alaninate;
propyl ((fluoro(2-((9-(methyl(4,4,4-trifluorobutyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
propyl (cyclopropoxy(fluoro(2-((9-(methyl(3-(trifluoromethoxy)cyclobutyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)phosphoryl)-alaninate;
propyl (cyclopropoxy(fluoro(2-((9-(methyl(3-(trifluoromethyl)cyclobutyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)phosphoryl)-alaninate;
isopropyl ((fluoro(2-((9-(methyl(3-(trifluoromethoxy)cyclobutyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
propyl (((2-((9-(ethyl(3-(trifluoromethoxy)cyclobutyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)fluoromethyl)(phenoxy)phosphoryl)-alaninate;
propyl ((fluoro(2-((9-(methyl(4,4,4-trifluorobutyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
isopropyl ((fluoro(2-((9-(methyl(3-(trifluoromethoxy)cyclobutyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate 2,2,2-trifluoroacetate;
isobutyl (cyclopropoxy(fluoro(2-((9-(methyl(3-(trifluoromethoxy)cyclobutyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)phosphoryl)-alaninate;
cyclobutyl (ethoxy(fluoro(2-((9-(methyl(3-(trifluoromethoxy)cyclobutyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)phosphoryl)-alaninate;
cyclobutyl ((fluoro(2-((9-(methyl(3-(trifluoromethoxy)cyclobutyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
cyclobutyl ((fluoro(2-((9-(methyl(3-(trifluoromethoxy)cyclobutyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
propyl N-((fluoro(2-((9-(methyl(3-(trifluoromethoxy)cyclobutyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-O-methyl-serinate;
propyl 2-(((fluoro(2-((9-(methyl(3-(trifluoromethoxy)cyclobutyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)amino)-2-methylpropanoate;
propyl ((fluoro(2-((9-(methyl(3-(trifluoromethoxy)cyclobutyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-phenylalaninate;
isobutyl ((fluoro(2-((9-(methyl((3-(trifluoromethyl)cyclobutyl)methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
isobutyl (((2-((9-(((3-(difluoromethyl)cyclobutyl)methyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)fluoromethyl)(phenoxy)phosphoryl)-alaninate;
isobutyl ((fluoro(2-((9-(methyl(2-(1-(trifluoromethyl)cyclopropyl)ethyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
isobutyl ((fluoro(2-((9-(methyl(3-(trifluoromethoxy)cyclobutyl)amino)-5-oxo-3-(4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
isobutyl ((fluoro(2-((9-(methyl(3-(trifluoromethoxy)propyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
isobutyl ((fluoro(2-((9-(methyl(3-(trifluoromethyl)cyclobutyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;

-continued isobutyl ((fluoro(2-((9-(methyl(4,4,4-trifluorobutyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
isobutyl ((fluoro(2-((9-(methyl(4,4,4-trifluorobutyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
propyl ((fluoro(2-((9-(methyl(4,4,4-trifluoro-3-methoxybutyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
propyl (((2-((9-(((3-(difluoromethyl)cyclobutyl)methyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)fluoromethyl)(phenoxy)phosphoryl)-alaninate;
propyl ((fluoro(2-((9-(methyl(2-(1-(trifluoromethyl)cyclopropyl)ethyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
propyl ((fluoro(2-((9-(methyl(3-(trifluoromethoxy)propyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
propyl ((fluoro(2-((9-(methyl(3-(trifluoromethoxy)propyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
propyl (((2-((9-((3,3-difluorocyclopentyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)fluoromethyl)(phenoxy)phosphoryl)-alaninate;
propyl (((2-((9-((3,3-difluorocyclopentyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)fluoromethyl)(phenoxy)phosphoryl)-alaninate;
propyl ((fluoro(2-((9-(methyl(4,4,4-trifluorobutyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
propyl ((fluoro(2-((9-morpholino-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
propyl ((fluoro(2-((9-(methyl((3-methyloxetan-3-yl)methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
propyl ((fluoro(2-((9-(methyl(oxetan-3-yl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
isobutyl (((2-((9-((3,3-difluoropropyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)fluoromethyl)(phenoxy)phosphoryl)-alaninate;
propyl N-(((2-((9-((3,3-difluoropropyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)fluoromethyl)(phenoxy)phosphoryl)-O-methyl-serinate;
propyl 2-((((2-((9-((3,3-difluoropropyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)fluoromethyl)(phenoxy)phosphoryl)amino)-2-methylpropanoate;
isopropyl 2-((((2-((9-((3,3-difluoropropyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)fluoromethyl)(phenoxy)phosphoryl)amino)butanoate;
propyl ((difluoro(2-((9-(methyl(3-(trifluoromethoxy)cyclobutyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)prolinate;
propyl 1-(ethoxy(fluoro(2-((9-(methyl(3-(trifluoromethoxy)cyclobutyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)phosphoryl)-3,3-difluoropyrrolidine-2-carboxylate;
propyl ((difluoro(2-((9-(methyl(3-(trifluoromethoxy)cyclobutyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
dipropyl 2,2'-(((fluoro(2-((9-(methyl(3-(trifluoromethoxy)cyclobutyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)phosphoryl)bis(azanediyl))dipropionate;
isobutyl (cyclopropoxy(fluoro(2-((9-(methyl(3-(trifluoromethoxy)cyclobutyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)phosphoryl)-alaninate;
propyl 1-(((fluoro(2-((9-((3-fluorocyclobutyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)amino)cyclopropane-1-carboxylate;
isobutyl ((fluoro(2-((9-(methyl(3-(trifluoromethoxy)cyclopentyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
isobutyl ((fluoro(2-((9-(methyl(3-(trifluoromethoxy)cyclopentyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;

-continued propyl ((fluoro(2-((9-(methyl(3-(trifluoromethoxy)cyclopentyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
(1-fluorocyclobutyl)methyl ((fluoro(2-((9-((3-fluorocyclobutyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
propyl ((fluoro(2-((9-((3-fluorocyclobutyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(3,3,3-trifluoropropoxy)phosphoryl)-alaninate;
propyl ((fluoro(2-((9-(methyl(3-(trifluoromethoxy)cyclobutyl)amino)-5-oxo-3-(6-(pyridin-3-yl)-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
propyl ((fluoro(2-((9-(methyl(3-(trifluoromethoxy)cyclobutyl)amino)-5-oxo-3-(6-(pyridin-3-yl)-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
propyl ((fluoro(2-((3-(7-methoxy-6-phenyl-4-azaspiro[2.4]heptane-4-carbonyl)-9-(methyl(3-(trifluoromethoxy)cyclobutyl)amino)-5-oxodecahydropyrrolo[1,2-a]azocin-6-yl)carbamoyl)benzo[b]thiophen-5-yl)methyl)(phenoxy)phosphoryl)-alaninate;
propyl ((fluoro(2-((3-(7-methoxy-6-phenyl-4-azaspiro[2.4]heptane-4-carbonyl)-9-(methyl(3-(trifluoromethoxy)cyclobutyl)amino)-5-oxodecahydropyrrolo[1,2-a]azocin-6-yl)carbamoyl)benzo[b]thiophen-5-yl)methyl)(phenoxy)phosphoryl)-alaninate;
propyl ((fluoro(2-((9-(methyl(3,3,3-trifluoro-2-methoxypropyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
propyl ((fluoro(2-((9-(methyl(2-(trifluoromethoxy)ethyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
propyl ((fluoro(2-((9-(methyl(2-(trifluoromethoxy)ethyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
propyl ((fluoro(2-((9-((3-fluorocyclobutyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(2-oxopyrrolidin-1-yl)phosphoryl)-alaninate;
cyclobutyl ((fluoro(2-((9-(methyl((3-methyloxetan-3-yl)methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
propyl ((fluoro(2-((9-(methyl((3-methyloxetan-3-yl)methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(2,2,2-trifluoroethoxy)phosphoryl)-alaninate;
(tetrahydrofuran-3-yl)methyl ((fluoro(2-((9-(methyl(3-(trifluoromethyl)cyclobutyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
propyl ((fluoro(2-((9-(methyl(3-(trifluoromethyl)cyclobutyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(2,2,2-trifluoroethoxy)phosphoryl)-alaninate;
isopropyl (ethoxy(fluoro(2-((9-(methyl(3-(trifluoromethyl)cyclobutyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)phosphoryl)-alaninate;
isopropyl (ethoxy(fluoro(2-((9-(methyl(4,4,4-trifluorobutyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)phosphoryl)-alaninate;
propyl (ethoxy((2-((9-(ethyl(3-fluorocyclobutyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)fluoromethyl)phosphoryl)-alaninate;
2-morpholinoethyl (((2-((9-((3,3-difluoropropyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)fluoromethyl)(phenoxy)phosphoryl)-alaninate;
neopentyl (((2-((9-((3,3-difluoropropyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)fluoromethyl)(phenoxy)phosphoryl)-alaninate;
propyl (((2-((9-((3,3-difluoropropyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)fluoromethyl)(phenoxy)phosphoryl)-prolinate;
2-methoxy-2-methylpropyl ((fluoro(2-((9-((3-fluorocyclobutyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
6,6-difluorospiro[3.3]heptan-2-yl ((fluoro(2-((9-((3-fluorocyclobutyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
(tetrahydrofuran-3-yl)methyl ((fluoro(2-((9-((3-fluorocyclobutyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
(tetrahydrofuran-3-yl)methyl ((fluoro(2-((9-((3-fluorocyclobutyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
(tetrahydro-2H-pyran-4-yl)methyl ((fluoro(2-((9-((3-fluorocyclobutyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;

-continued isobutyl 2-(((fluoro(2-((9-((3-fluorocyclobutyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)amino)butanoate;
isopentyl ((fluoro(2-((9-((3-fluorocyclobutyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
propyl 2-(((fluoro(2-((9-((3-fluorocyclobutyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)amino)pentanoate;
propyl ((cyclohexyloxy)(fluoro(2-((9-((3-fluorocyclobutyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)phosphoryl)-alaninate;
propyl ((cyclopentyloxy)(fluoro(2-((9-((3-fluorocyclobutyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)phosphoryl)-alaninate;
propyl ((fluoro(2-((9-((3-fluorocyclobutyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(isopropoxy)phosphoryl)-alaninate;
neopentyl ((fluoro(2-((9-((3-fluorocyclobutyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(2,2,2-trifluoroethoxy)phosphoryl)-alaninate;
propyl ((fluoro(2-((9-((3-fluorocyclobutyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(2-methoxyethoxy)phosphoryl)-alaninate;
spiro[3.3]heptan-2-yl ((fluoro(2-((9-((3-fluorocyclobutyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
propyl ((fluoro(2-((9-((3-fluorocyclobutyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-valinate;
tetrahydrofuran-3-yl ((fluoro(2-((9-((3-fluorocyclobutyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
tetrahydrofuran-3-yl ((fluoro(2-((9-((3-fluorocyclobutyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
2-fluoro-2-methylpropyl ((fluoro(2-((9-((3-fluorocyclobutyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
(tetrahydrofuran-3-yl)methyl ((fluoro(2-((9-((3-fluorocyclobutyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
(tetrahydrofuran-3-yl)methyl ((fluoro(2-((9-((3-fluorocyclobutyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
(tetrahydro-2H-pyran-4-yl)methyl ((fluoro(2-((9-((3-fluorocyclobutyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
propyl 4,4-difluoro-1-((fluoro(2-((9-(methyl(3-(trifluoromethoxy)cyclobutyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)pyrrolidine-2-carboxylate;
propyl N-((fluoro(2-((9-(methyl(3-(trifluoromethoxy)cyclobutyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(2,2,2-trifluoroethoxy)phosphoryl)-N-methyl-alaninate;
2-ethylbutyl (ethoxy(fluoro(2-((9-(methyl(3-(trifluoromethoxy)cyclobutyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)phosphoryl)-alaninate;
propyl N-(ethoxy(fluoro(2-((9-(methyl(3-(trifluoromethoxy)cyclobutyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)phosphoryl)-N-methyl-alaninate;
propyl (ethoxy(fluoro(2-((9-(methyl(3-(trifluoromethoxy)cyclobutyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)phosphoryl)-prolinate;
spiro[3.4]octan-2-yl ((fluoro(2-((9-((3-fluorocyclobutyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
spiro[2.3]hexan-5-yl ((fluoro(2-((9-((3-fluorocyclobutyl)(methyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate;
propyl ((fluoro(2-((9-(methyl(3-(trifluoromethyl)cyclobutyl)amino)-5-oxo-3-(6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-alaninate,
propyl 2-(((fluoro(2-((9-(methyl(3-(trifluoromethoxy)cyclobutyl)amino)-5-oxo-3-(6-phenyl-4-azaspiro[2.4]heptane-4-carbonyl)decahydropyrrolo[1,2-a]azocin-6-yl)carbamoyl)-2,3-dihydrobenzo[b]thiophen-5-yl)methyl)(isobutoxy)phosphoryl)amino)-2-methylpropanoate;
propyl 2-(((fluoro(2-((9-(methyl(3-(trifluoromethoxy)cyclobutyl)amino)-5-oxo-3-((S)-6-phenyl-4-azaspiro[2.4]heptane-4-carbonyl)decahydropyrrolo[1,2-a]azocin-6-yl)carbamoyl)-2,3-dihydrobenzo[b]thiophen-5-yl)methyl)(isopropoxy)phosphoryl)amino)-2-methylpropanoate;

-continued

| |
|---|
| propyl 2-((butoxy(fluoro(2-((9-(methyl(3-(trifluoromethoxy)cyclobutyl)amino)-5-oxo-3-(6-phenyl-4-azaspiro[2.4]heptane-4-carbonyl)decahydropyrrolo[1,2-a]azocin-6-yl)carbamoyl)-2,3-dihydrobenzo[b]thiophen-5-yl)methyl)phosphoryl)amino)-2-methylpropanoate; |
| propyl 2-(((fluoro(2-((9-(methyl(3-(trifluoromethoxy)cyclobutyl)amino)-5-oxo-3-(6-phenyl-4-azaspiro[2.4]heptane-4-carbonyl)decahydropyrrolo[1,2-a]azocin-6-yl)carbamoyl)-2,3-dihydrobenzo[b]thiophen-5-yl)methyl)(propoxy)phosphoryl)amino)-2-methylpropanoate; and |
| propyl 2-((ethoxy(fluoro(2-((9-(methyl(3-(trifluoromethoxy)cyclobutyl)amino)-5-oxo-3-(6-phenyl-4-azaspiro[2.4]heptane-4-carbonyl)decahydropyrrolo[1,2-a]azocin-6-yl)carbamoyl)-2,3-dihydrobenzo[b]thiophen-5-yl)methyl)phosphoryl)amino)-2-methylpropanoate; |

and pharmaceutically acceptable salts thereof.

In some embodiments, the compound, or a pharmaceutically acceptable salt thereof, is selected from the group consisting of parent drugs A3, A4, A5, A6, A7, A8, A11, A13, A14, A18, A19, A20, A21, A22, A23, A25, A30, A32, A33, A35, A36, A37, A38, A40, A42, A43, A44, A47, A48, A49, A50, A52, A53, A55, A57, A58, A59, A60, A61, and A65, and pharmaceutically acceptable salts thereof. In some embodiments, the compound, or a pharmaceutically acceptable salt thereof, is selected from the group consisting of compounds A3, A4, A5, A6, A7, A8, A11, A13, A14, A18, A19, A20, A21, A22, A23, A25, A30, A32, A33, A35, A36, A37, A38, A40, A42, A43, A44, A47, A48, A49, A50, A52, A53, A55, A57, A58, A59, A60, A61, and A65, prodrugs or intermediate metabolites thereof, and pharmaceutically acceptable salts of any of the foregoing.

In some embodiments, the compound, or a pharmaceutically acceptable salt thereof, is selected from the group consisting of prodrugs C4, C5, C6, C7, C8, C10, C13, C17, C19, C23, C25, C53, C54, C61, C63, C64, C65, C66, C68, C70, C71, C73, C74, C75, C82, C83, C84, C89, C90, C91, C92, C93, C94, C96, C97, C96, C97, C102, C103, C015, C016, C017, C110, C111, C114, C116, C118, C121, C122, C123, C124, C125, C126, C127, C132, C133, C135, C136, C137, C140, C141, C143, C144, C148, C155, C156, C160, C162, C170, C173, C175, C176, C177, C180, C182, C185, C186, C188, C189, C194, C195, C197, C198, C205, C208, and C209, and pharmaceutically acceptable salts thereof.

Any variation or embodiment of $R^{1a}$, $R^{1b}$, $R^2$, $R^3$, $R^4$, $R^{4a}$, $R^{4b}$, $R^5$, $R^P$, $R^{P1}$, $R^{P2}$, $R^{Pa}$, $R^{PE}$, $R^{Paa1}$, $R^{Paa2}$, $R^{Paa3}$, $R^{Paa4}$, or Ring A provided herein can be combined with every other variation or embodiment of $R^{1a}$, $R^{1b}$, $R^2$, $R^3$, $R^4$, $R^{4a}$, $R^{4b}$, $R^5$, $R^P$, $R^{P1}$, $R^{P2}$, $R^{Pa}$, $R^{PE}$, $R^{Paa1}$, $R^{Paa2}$, $R^{Paa3}$, $R^{Paa4}$, or Ring A the same as if each and every combination had been individually and specifically described.

As used herein, when any variable occurs more than one time in a chemical formula, its definition on each occurrence is independent of its definition at every other occurrence.

Methods of Synthesis

Compounds of Formula (I), and those described herein may be prepared in various ways as generally described below and more specifically in the Examples hereinafter (such as the schemes provided in the Examples below). General synthetic routes to compounds of Formula (I), and some examples of starting materials used to synthesize compounds of Formula (I) are shown and described herein. The routes shown and described herein are illustrative only and are not intended, nor are they to be construed, to limit the scope of the claims in any manner whatsoever. Those skilled in the art will be able to recognize modifications of the disclosed syntheses and to devise alternate routes based on the disclosures herein; all such modifications and alternate routes are within the scope of the claims.

Certain stereochemical centers have been left unspecified and certain substituents have been eliminated in the following schemes for the sake of clarity and are not intended to limit the teaching of the schemes in any way. Furthermore, individual isomers, enantiomers, and diastereomers may be separated or resolved by one of ordinary skill in the art at any convenient point in the synthesis of compounds of the invention, by methods such as selective crystallization techniques or chiral chromatography (See for example, J. Jacques, et al., "*Enantiomers, Racemates, and Resolutions*", John Wiley and Sons, Inc., 1981, and E. L. Eliel and S. H. Wilen, "*Stereochemistry of Organic Compounds*", Wiley-Interscience, 1994).

Compounds of Formula (I), (I-A-1), (I-A-2), (I-A-3), (I-A-4), (I-A-5), (I-A-6), (I-B-1), (I-B-2), (I-B-3), (I-B-4), (I-B-5), (I-B-6), (I-C-1), (I-C-2), (I-C-3), (I-C-4), (I-C-5), (I-C-6), (I-D-1), (I-D-2), (I-D-3), (I-D-4), (I-D-5), (I-D-6), (I-E-1), (I-E-2), (I-E-3), (I-E-4), (I-E-5), (I-E-6), (I-F-1), (I-F-2), (I-F-3), (I-F-4), (I-F-5), (I-F-6), (I-G-1), (I-G-2), (I-G-3), (I-G-4), (I-G-5), (I-G-6), (I-H-1), (I-H-2), (I-H-3), (I-H-4), (I-H-5), (I-H-6), (I-J-1), (I-J-2), (I-J-3), (I-J-4), (I-J-5), or (I-J-6) can be prepared according to Scheme A, Scheme B, Scheme C, Scheme D, Scheme E, or Scheme F, wherein the $R^{1a}$, $R^{1b}$, $R^2$, $R^3$, $R^4$, $R^{4a}$, $R^{4b}$, $R^5$, $R^P$, $R^{Pa}$, $R^{Paa2}$, $R^{Paa3}$, and $R^{Paa4}$, are as defined for Formula (I) or any applicable variations thereof as detailed herein.

Methods for preparing compound (A) or a salt of thereof, are shown herein, as shown in Scheme A. The method of preparing compound (A) can be applied to prepare the starting material for Schemes B-F.

Scheme A

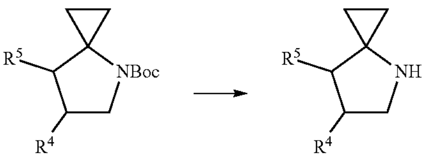

(a) (b)

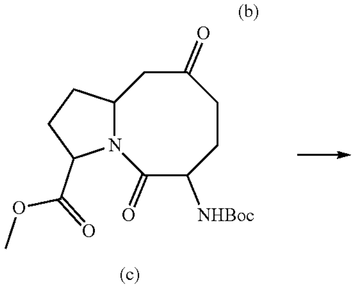

(c)

-continued

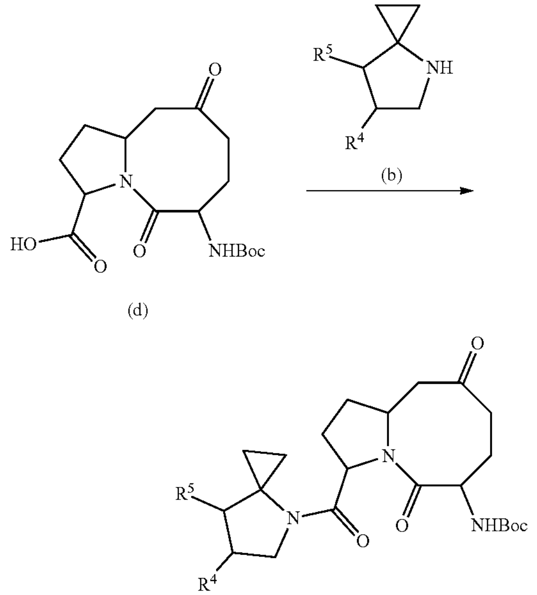

(d)

(A)

In one aspect, provided herein is a method of preparing a compound of formula (A), (A)

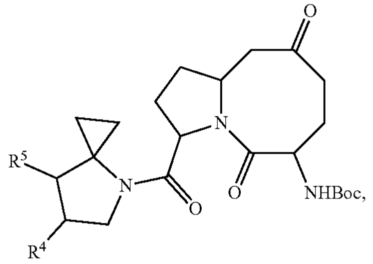

or a salt thereof, comprising contacting a compound of formula (d)

(d)

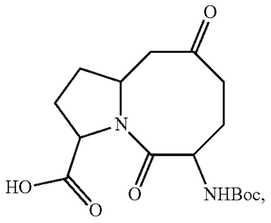

or a salt thereof, with a compound of formula (b), (b)

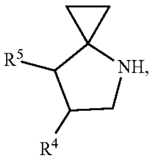

or a salt thereof, in the presence of a coupling reagent and an aliphatic amine. In some embodiments, the coupling reagent comprises O-(7-Azabenzotriazol-1-yl)-N,N,N',N'-tetramethyluronium hexafluorophosphate (HATU). In some embodiments, the aliphatic amine comprises triethylamine. In some embodiments, the contacting of the compound of formula (d) or a salt thereof with a compound of formula (b) or a salt thereof is carried out at a temperature between about 20° C. and about 30° C. In some embodiments, the contacting of the compound of formula (d) or a salt thereof with a compound of formula (b) or a salt thereof is carried out at a temperature between about 20° C. and about 25° C. In some embodiments, the contacting of the compound of formula (d) or a salt thereof with a compound of formula (b) or a salt thereof is carried out at a temperature of about 25° C. In some embodiments, the contacting of the compound of formula (d) or a salt thereof with a compound of formula (b) or a salt thereof is carried out for about one hour to five hours. In some embodiments, the contacting of the compound of formula (d) or a salt thereof with a compound of formula (b) or a salt thereof is carried out for about one hour to three hours. In some embodiments, the contacting of the compound of formula (d) or a salt thereof with a compound of formula (b) or a salt thereof is carried out for about two hours.

In some embodiments, the compound of Formula (d) or a salt thereof is prepared by contacting a compound of Formula (c), (c)

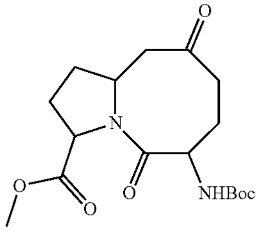

or a salt thereof, with a strong base in the presence of a polar aprotic solvent. In some embodiments, the strong base comprises a metal hydroxide. In some embodiments, the strong base comprises $LiOH \cdot H_2O$. In some embodiments, the polar aprotic solvent comprises tetrahydrofuran. In some embodiments, the contacting of the compound of Formula (c) or a salt thereof with a strong base in the presence of a polar aprotic solvent is carried out at a temperature between about 10° C. and 30° C. In some embodiments, the contacting of the compound of Formula (c) or a salt thereof with a strong base in the presence of a polar aprotic solvent is carried out at a temperature between about 15° C. and 25° C. In some embodiments, the contacting of the compound of Formula (c) or a salt thereof with a strong base in the presence of a polar aprotic solvent is carried out at a temperature of about 20° C. In some embodiments, the contacting of the compound of Formula (c) or a salt thereof with a strong base in the presence of a polar aprotic solvent is carried out for about one hour to five hours. In some embodiments, the contacting of the compound of Formula (c) or a salt thereof with a strong base in the presence of a polar aprotic solvent is carried out for about one hour to three hours. In some embodiments, the contacting of the compound of Formula (c) or a salt thereof with a strong base in the presence of a polar aprotic solvent is carried out for about two hours.

In one aspect, provided herein is a method of preparing a compound of formula (b)

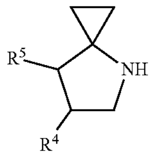

or a salt thereof, comprising contacting a compound of Formula (a), (a)

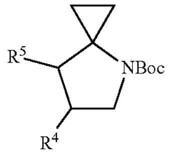

or a salt thereof with a strong organic acid. In some embodiments, the strong organic acid comprises trifluoroacetic acid. In some embodiments, the contacting of the compound of Formula (a) or a salt thereof is carried out at a temperature between about 20° C. and about 30° C. In some embodiments, the contacting of the compound of Formula (a) or a salt thereof is carried out at a temperature between about 20° C. and about 25° C. In some embodiments, the contacting of the compound of Formula (a) or a salt thereof is carried out at a temperature of about 25° C. In some embodiments, the contacting of the compound of Formula (a) or a salt thereof is carried out for about one hour to five hours. In some embodiments, the contacting of the compound of Formula (a) or a salt thereof is carried out for about one hour to three hours. In some embodiments, the contacting of the compound of Formula (a) or a salt thereof is carried out for about two hours.

Methods for preparing compound (D) or a salt of thereof, are shown herein, as shown in Scheme B. The method of preparing compound (D) can be applied to prepare the starting material for Schemes C-F.

Scheme B.

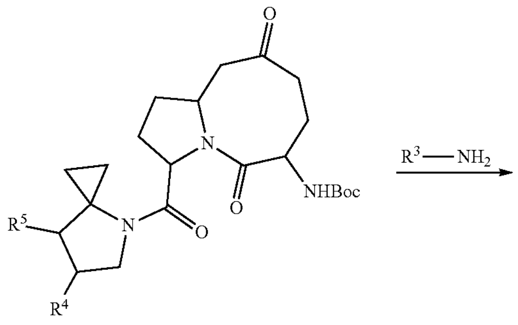

(A)

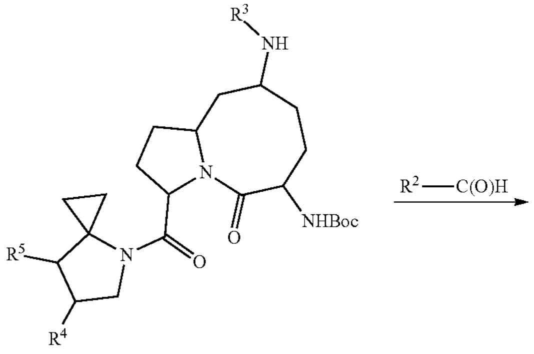

(B)

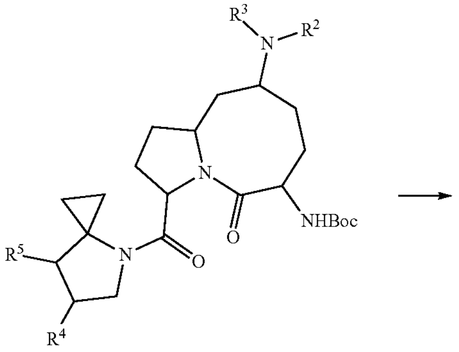

(C)

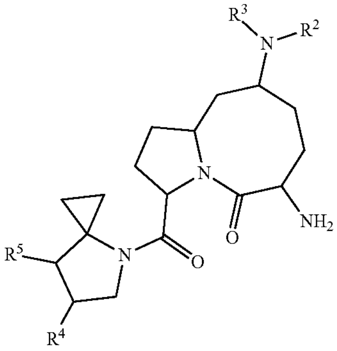

(D)

In some embodiments, the compound of Formula (D) or a salt thereof is prepared by contacting a compound of Formula (C),

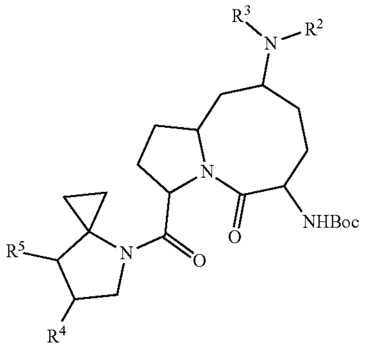
(C)

or a salt thereof, with a strong organic acid and a polar aprotic solvent. In some embodiments, the strong organic acid comprises trifluoroacetic acid. In some embodiments, the polar aprotic solvent comprises dichloromethane. In some embodiments, the contacting of the compound of Formula (C) or a salt thereof is carried out at a temperature between about 20° C. and about 30° C. In some embodiments, the contacting of the compound of Formula (C) or a salt thereof is carried out at a temperature between about 20° C. and about 25° C. In some embodiments, the contacting of the compound of Formula (C) or a salt thereof is carried out at a temperature of about 25° C. In some embodiments, the contacting of the compound of Formula (C) or a salt thereof is carried out for about 30 minutes to two hours. In some embodiments, the contacting of the compound of Formula (C) or a salt thereof is carried out for about one hour to two hours. In some embodiments, the contacting of the compound of Formula (C) or a salt thereof is carried out for about one hour.

In some embodiments, the compound of Formula (C) or a salt thereof is prepared by contacting a compound of Formula (B),

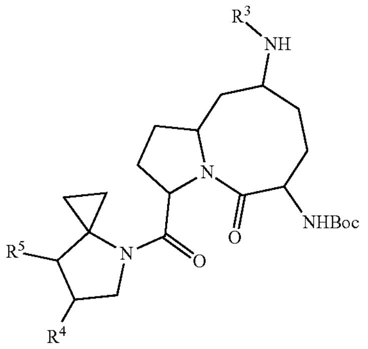
(B)

or a salt thereof, with $R^2$—C(O)H and one or more polar protic solvents. In some embodiments, the polar protic solvents comprise methanol or sodium borohydride, or both.

In some embodiments, the contacting of the compound of Formula (B) or a salt thereof is carried out at a temperature between about 20° C. and about 30° C. In some embodiments, the contacting of the compound of Formula (B) or a salt thereof is carried out at a temperature between about 20° C. and about 25° C. In some embodiments, the contacting of the compound of Formula (B) or a salt thereof is carried out at a temperature of about 25° C.

In some embodiments, the compound of Formula (B) or a salt thereof is prepared by contacting a compound of Formula (A),

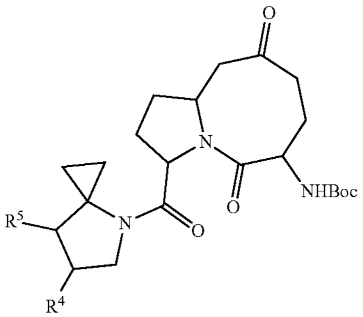
(A)

or a salt thereof, with $R^3$—$NH_2$. In some embodiments, the contacting of the compound of Formula (A) or a salt thereof with $R^3$—$NH_2$ is carried out in the presence of a catalyst, a polar protic solvent, and a mild reducing agent. In some embodiments, the catalyst is a metal halide. In some embodiments, the catalyst comprises zinc chloride. In some embodiments, the polar protic solvent comprises methanol. In some embodiments, the mild reducing agent comprises sodium cyanoborohydride. In some embodiments, the contacting of the compound of Formula (A) or a salt thereof with $R^3$—$NH_2$ is carried out at a temperature between about 40° C. and about 60° C. In some embodiments, the contacting of the compound of Formula (A) or a salt thereof with $R^3$—$NH_2$ is carried out at a temperature between about 50° C. and about 60° C. In some embodiments, the contacting of the compound of Formula (A) or a salt thereof with $R^3$—$NH_2$ is carried out at a temperature of about 55° C. to 15 hours. In some embodiments, the contacting of the compound of Formula (A) or a salt thereof with $R^3$—$NH_2$ is carried out for about 11 to 14 hours. In some embodiments, the contacting of the compound of Formula (A) or a salt thereof with $R^3$—$NH_2$ is carried out for about 12 hours.

Methods for preparing a parent compound, intermediate metabolite, or a prodrug, or a salt of any of the foregoing are shown herein, as shown in Scheme C.

Scheme C.
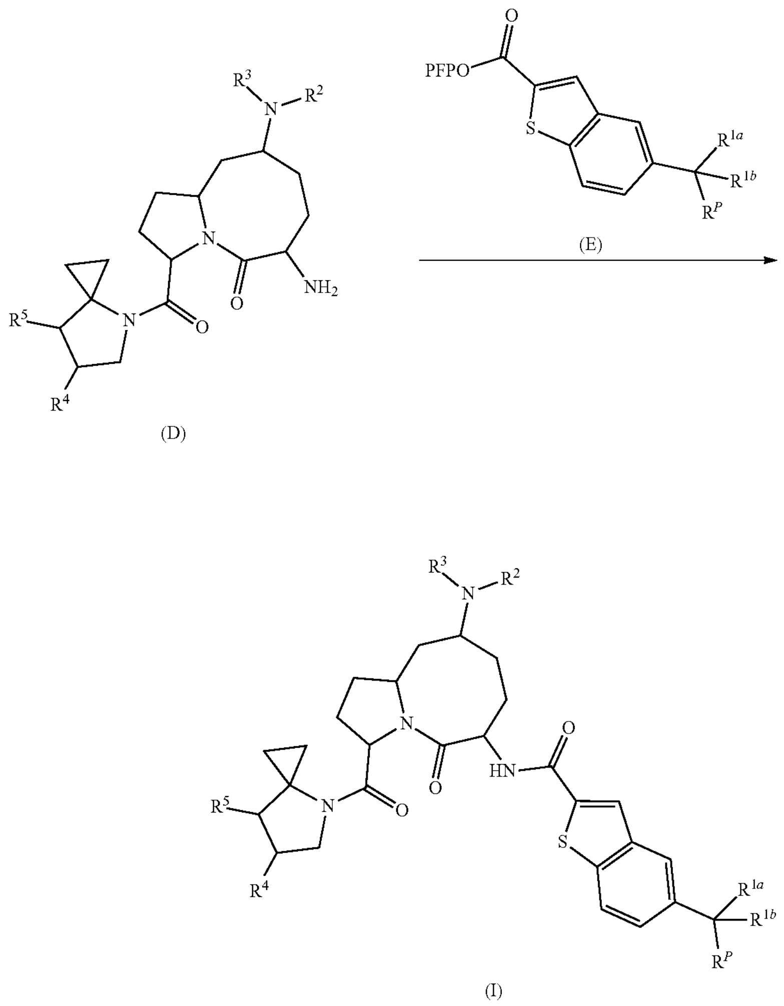
In one aspect, provided herein is a method of preparing a compound of formula
(I)
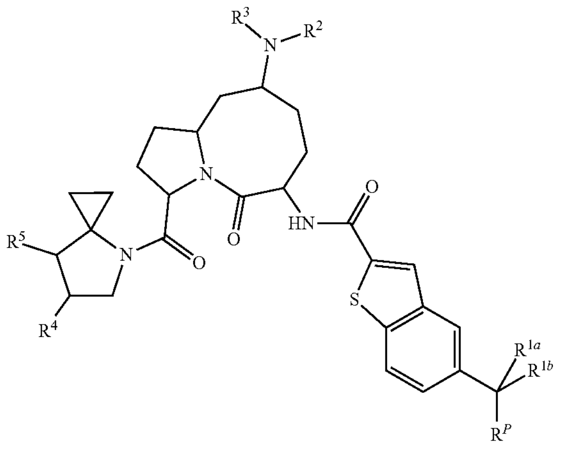
or a salt thereof, comprising contacting a compound of Formula (D),
(D)
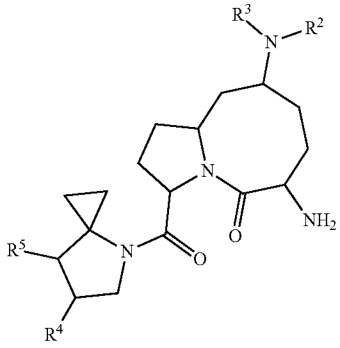

or a salt thereof with a compound of Formula (E), (E)

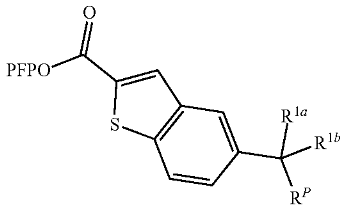

or a salt thereof. PFP is perfluorophenyl. In some embodiments, the contacting of the compound of Formula (D) or a salt thereof with the compound of Formula (E) or a salt thereof is carried out in the presence of a polar aprotic solvent and an aliphatic amine. In some embodiments, the polar aprotic solvent comprises dimethylformamide. In some embodiments, the aliphatic amine comprises triethylamine. In some embodiments, the contacting of the compound of Formula (D) or a salt thereof with the compound of Formula (E) or a salt thereof is carried out at a temperature between about 20° C. and about 30° C. In some embodiments, the contacting of the compound of Formula (D) or a salt thereof with the compound of Formula (E) or a salt thereof is carried out at a temperature between about 20° C. and about 25° C. In some embodiments, the contacting of the compound of Formula (D) or a salt thereof with the compound of Formula (E) or a salt thereof is carried out at a temperature of about 25° C. In some embodiments, the contacting of the compound of Formula (D) or a salt thereof with the compound of Formula (E) or a salt thereof is carried out for about 30 minutes to two hours. In some embodiments, the contacting of the compound of Formula (D) or a salt thereof with the compound of Formula (E) or a salt thereof is carried out for about one hour to two hours. In some embodiments, the contacting of the compound of Formula (D) or a salt thereof with the compound of Formula (E) or a salt thereof is carried out for about one hour.

Methods for preparing a parent compound or a salt thereof are shown herein, as shown in Scheme D.

Scheme D.

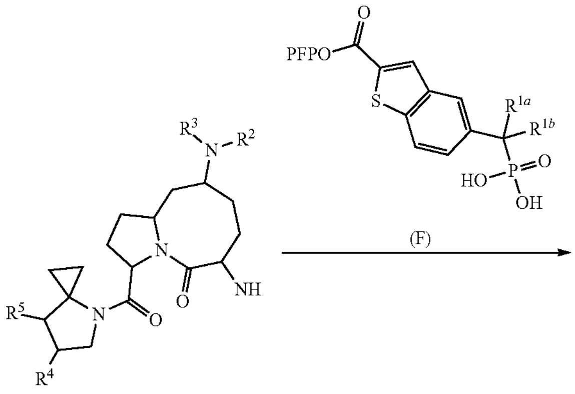

(D)

-continued

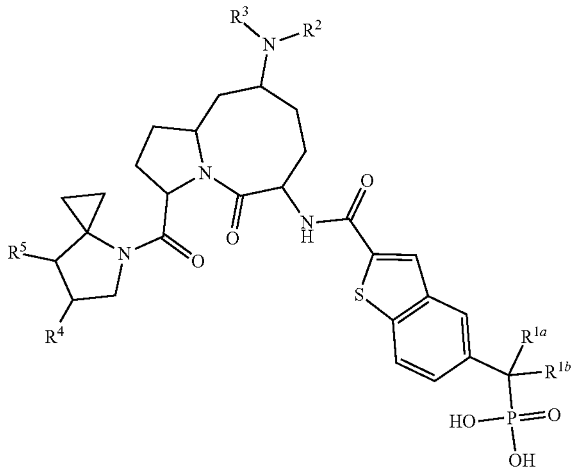

(I-A-1)

In one aspect, provided herein is a method of preparing a parent compound of formula (I-A-1)

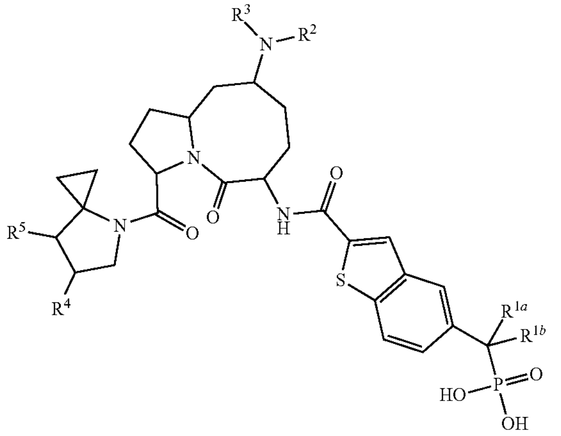

or a salt thereof, comprising contacting a compound of Formula (D)

(D)

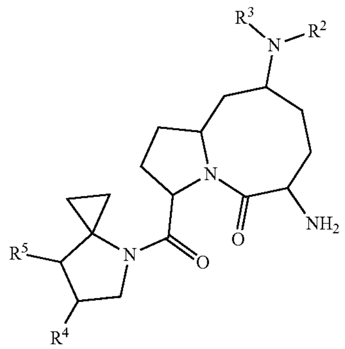

or a salt thereof with a compound of Formula (F),

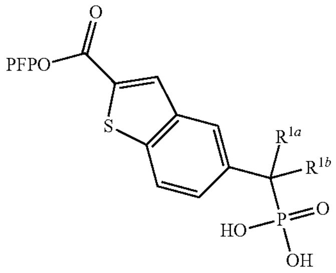

(F)

or a salt thereof. In some embodiments, the contacting of the compound of Formula (D) or a salt thereof with the compound of Formula (F) or a salt thereof is carried out in the presence of a polar aprotic solvent and an aliphatic amine. In some embodiments, the polar aprotic solvent comprises dimethylformamide. In some embodiments, the aliphatic amine comprises triethylamine. In some embodiments, the contacting of the compound of Formula (D) or a salt thereof with the compound of Formula (F) or a salt thereof is carried out at a temperature between about 20° C. and about 30° C. In some embodiments, the contacting of the compound of Formula (D) or a salt thereof with the compound of Formula (F) or a salt thereof is carried out at a temperature between about 20° C. and about 25° C. In some embodiments, the contacting of the compound of Formula (D) or a salt thereof with the compound of Formula (F) or a salt thereof is carried out at a temperature of about 25° C. In some embodiments, the contacting of the compound of Formula (D) or a salt thereof with the compound of Formula (F) or a salt thereof is carried out for about 30 minutes to two hours. In some embodiments, the contacting of the compound of Formula (D) or a salt thereof with the compound of Formula (F) or a salt thereof is carried out for about one hour to two hours. In some embodiments, the contacting of the compound of Formula (D) or a salt thereof with the compound of Formula (F) or a salt thereof is carried out for about one hour.

Methods for preparing a prodrug or intermediate metabolite or a salt thereof are shown herein, as shown in Scheme E.

Scheme E.

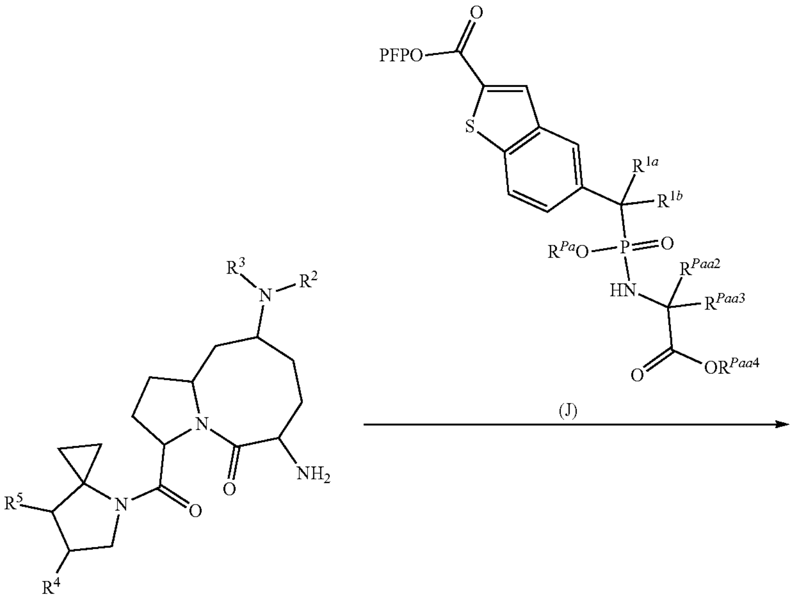

(J)

(D)

-continued

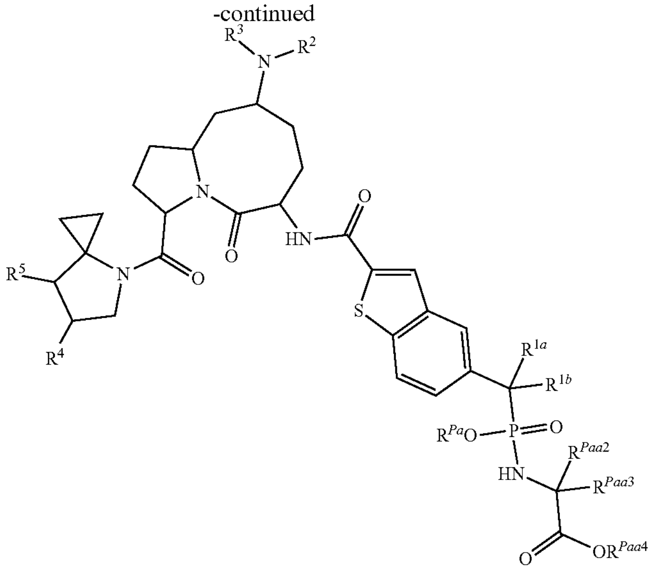

(I-C-1)

In some embodiments, provided herein is a method of preparing a prodrug of the formula (I-C-1)

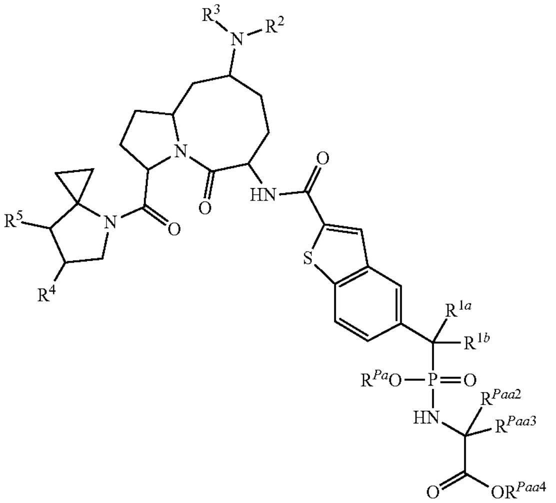

or a salt thereof, comprising contacting a compound of Formula (D), (D)

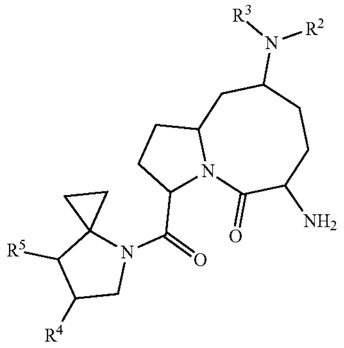

or a salt thereof, with a compound of Formula (J)

(J)

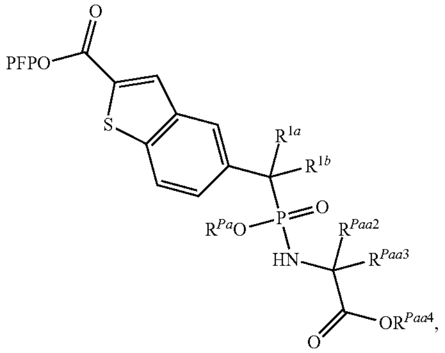

or a salt thereof. In some embodiments, the contacting of the compound of Formula (D) or a salt thereof with the compound of Formula (J) or a salt thereof is carried out in the presence of a polar aprotic solvent and an aliphatic amine. In some embodiments, the polar aprotic solvent comprises dimethylformamide. In some embodiments, the aliphatic amine comprises triethylamine. In some embodiments, the contacting of the compound of Formula (D) or a salt thereof with the compound of Formula (J) or a salt thereof is carried out at a temperature between about 20° C. and about 30° C. In some embodiments, the contacting of the compound of Formula (D) or a salt thereof with the compound of Formula (J) or a salt thereof is carried out at a temperature between about 20° C. and about 25° C. In some embodiments, the contacting of the compound of Formula (D) or a salt thereof with the compound of Formula (J) or a salt thereof is carried out at a temperature of about 25° C. In some embodiments, the contacting of the compound of Formula (D) or a salt thereof with the compound of Formula (J) or a salt thereof is carried out for about 30 minutes to two hours. In some embodiments, the contacting of the compound of Formula (D) or a salt thereof with the compound of Formula (J) or a salt thereof is carried out for about one hour to two hours. In some embodiments, the contacting of the compound of Formula (D) or a salt thereof with the compound of Formula (F) or a salt thereof is carried out for about one hour.

Methods for preparing an intermediate metabolite or a salt thereof are shown herein, as shown in Scheme F.

Scheme F.

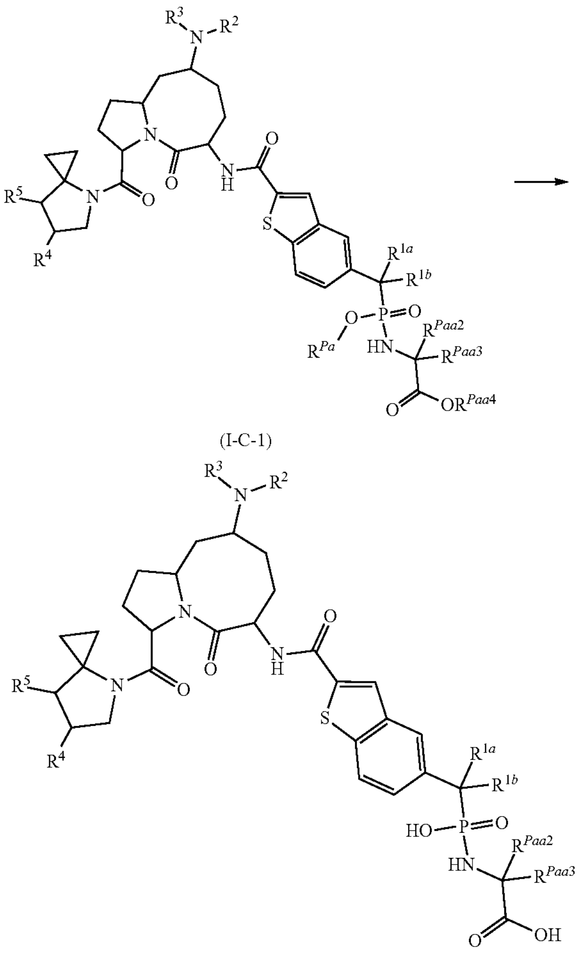

(I-C-1)

(I-B-1)

In some embodiments, provided herein is a method of preparing an intermediate metabolite of the formula (I-B-1)

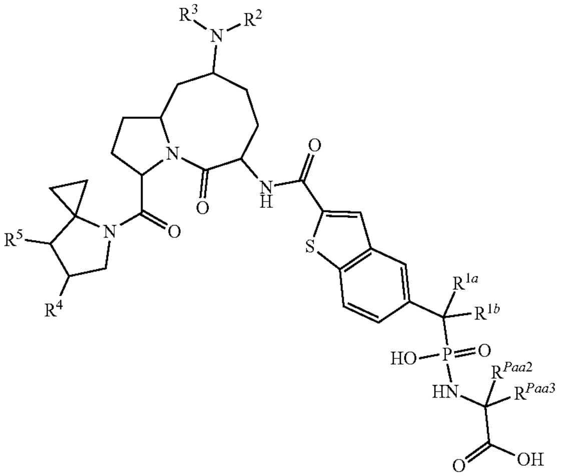

or a salt thereof, comprising contacting a compound of Formula (I-C-1), (I-C-1)

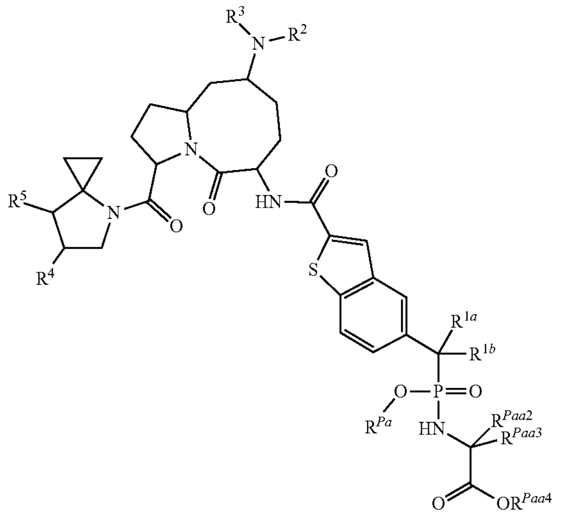

or a salt thereof, with a strong base in the presence of a polar aprotic solvent. In some embodiments, the strong base comprises a metal hydroxide. In some embodiments, the strong base comprises LiOH—$H_2O$. In some embodiments, the polar aprotic solvent comprises tetrahydrofuran. In some embodiments, the contacting of the compound of Formula (I-C-1) or a salt thereof with a strong base in the presence of a polar aprotic solvent is carried out at a temperature between about 10° C. and 30° C. In some embodiments, the contacting of the compound of Formula (I-C-1) or a salt thereof with a strong base in the presence of a polar aprotic solvent is carried out at a temperature between about 15° C. and 25° C. In some embodiments, the contacting of the compound of Formula (I-C-1) or a salt thereof with a strong base in the presence of a polar aprotic solvent is carried out at a temperature of about 20° C. In some embodiments, the contacting of the compound of Formula (I-C-1) or a salt thereof with a strong base in the presence of a polar aprotic solvent is carried out for about one hour to five hours. In some embodiments, the contacting of the compound of Formula (I-C-1) or a salt thereof with a strong base in the presence of a polar aprotic solvent is carried out for about one hour to three hours. In some embodiments, the contacting of the compound of Formula (I-C-1) or a salt thereof with a strong base in the presence of a polar aprotic solvent is carried out for about two hours.

Uses, Formulation, and Administration

In one aspect, provided herein is a pharmaceutical composition comprising a compound of Formula (I) or a prodrug thereof, or a pharmaceutically acceptable salt thereof, as an active ingredient. Such a pharmaceutical composition comprises a therapeutically effective amount of at least one compound of Formula (I) or a prodrug thereof, or a pharmaceutically acceptable salt thereof, and at least one pharmaceutically acceptable excipient. One or more pharmaceutically acceptable excipient is selected, in accordance with the pharmaceutical form and method of administration desired, from customary excipients. For examples of such excipients, see Remington's Pharmaceutical Sciences (20th ed., Mack Publishing Co. 2000).

In certain aspects, a pharmaceutical composition described herein is formulated for administration to a patient in need of such composition. Pharmaceutical compositions described herein may be administered orally, topically, transdermally, by inhalation, nasally, or buccally, or parenterally. In some embodiments, the pharmaceutical composition is administered orally. Appropriate unit administration forms include oral forms such as tablets, soft or hard capsules, powders, granules, and oral solutions or suspensions; forms for inhalative administration such as an inhaler spray; and forms for topical administration, such as creams, gels, ointments, and lotions.

A specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound described herein in the composition will also depend upon the particular compound in the pharmaceutical composition.

In one aspect, provided herein are methods of treating a disease or condition in a subject in need thereof. In some embodiments, the method comprises administering to the subject in need thereof a therapeutically effective amount of a compound of Formula (I), or a pharmaceutically acceptable salt thereof. In some embodiments, the method comprises administering to the subject in need thereof a therapeutically effective amount of a parent drug described herein. In some embodiments, the method comprises administering to the subject in need thereof a therapeutically effective amount of an intermediate metabolite described herein. In some embodiments, the method comprises administering to the subject in need thereof a therapeutically effective amount of a prodrug described herein. In some embodiments, the disease or condition is responsive to the modulation (e.g., inhibition) of STAT6.

In one aspect, provided is a method of administering a parent drug compound of Formula (I), or a pharmaceutically acceptable salt thereof, to a subject, wherein the method comprises administering to the subject a prodrug, or a pharmaceutically acceptable salt thereof, of the parent drug compound of Formula (I), or a pharmaceutically acceptable salt thereof. In some embodiments, the prodrug once administered to the subject is metabolized in the subject to the parent drug compound of Formula (I). In some embodiments, the prodrug once administered to the subject is first metabolized to an intermediate metabolite and subsequently to the parent drug compound of Formula (I). In some embodiments, the parent drug compound of Formula (I) is a compound selected from the groups consisting of the compounds in Table 1A, or a pharmaceutically acceptable salt thereof. In some embodiments, the prodrug is a compound of Formula (I), or a pharmaceutically acceptable salt thereof, e.g., a compound selected from the group consisting of the compounds in Table 1C, or a pharmaceutically acceptable salt thereof. In some embodiments, the intermediate metabolite is a compound of Formula (I), or a pharmaceutically acceptable salt thereof, e.g., a compound selected from the group consisting of the compounds in Table 1B, or a pharmaceutically acceptable salt thereof.

In one aspect, provided is a method of administering an intermediate metabolite compound of Formula (I), or a pharmaceutically acceptable salt thereof, to a subject, wherein the method comprises administering to the subject a prodrug, or a pharmaceutically acceptable salt thereof, of the intermediate metabolite compound of Formula (I), or a pharmaceutically acceptable salt thereof. In some embodiments, the prodrug once administered to a subject is metabolized in the subject to the intermediate metabolite of Formula (I). In some embodiments the intermediate metabolite compound of Formula (I) is a compound selected from the groups consisting of the compounds in Table 1B, or a pharmaceutically acceptable salt thereof. In some embodiments the prodrug is a compound of Formula (I), or a pharmaceutically acceptable salt thereof, e.g., a compound selected from the group consisting of the compounds in Table 1C, or a pharmaceutically acceptable salt thereof.

In some embodiments, a compound of Formula (I) is selective for inhibition of STAT6 vs. STAT1, STAT2, STAT3, STAT4, STAT5a, and/or STAT5b. In some embodiments, a compound of Formula (I) is at least about 100, 200, 300, 400, 500, 600, 700, 800, 900, 1000, 1250, 1500, 1750, 2000, 2500, 3000, 3500, 4000, 4500, 5000, 6000, 7000, 8000, 9000, or 10000 times selective for STAT6 vs. STAT1, STAT3, and/or STAT4. In some embodiments, a compound of Formula (I) is at least about 100, 200, 300, 400, 500, 600, 700, 800, 900, 1000, 1250, 1500, 1750, 2000, 2500, 3000, 3500, 4000, 4500, 5000, 6000, 7000, 8000, 9000, or 10000 times selective for STAT6 vs. STAT1, STAT2, STAT3, and/or STAT4. In some embodiments, a compound of Formula (I) is at least about 100, 200, 300, 400, 500, 600, 700, 800, 900, 1000, 1250, 1500, 1750, 2000, 2500, 3000, 3500, 4000, 4500, 5000, 6000, 7000, 8000, 9000, or 10000 times selective for STAT6 vs. STAT1, STAT2, STAT3, STAT4, STAT5a, and/or STAT5b.

In some embodiments, a compound of Formula (I) inhibits IL-4 and/or IL-13 induced expression of thymus- and activation-regulated chemokine (TARC) (also known as, CC chemokine ligand 17 (CCL17)). In some embodiments, a compound of Formula (I) inhibits IL-4 and/or IL-13 induced expression of TARC in human peripheral blood mononuclear cells (PBMCs). In some embodiments, the $IC_{50}$ for inhibition of IL-4 and/or IL-13 induced TARC expression (e.g., in human PBMCs) is less than or equal to about 500 nM, about 100 nM, about 50 nM, about 10 nM, about 5 nM, or about 1 nM.

In some embodiments, a compound of Formula (I) inhibits IL-4 induced expression of CD23 (also known as, Fc epsilon RII (FcεRII)). In some embodiments, a compound of Formula (I) inhibits IL-4 induced expression of CD23 in human PBMCs. In some embodiments, the IC50 for inhibition of IL-4 induced CD23 expression (e.g., in human PBMCs) is less than or equal to about 500 nM, about 100 nM, about 50 nM, about 10 nM, about 5 nM, or about 1 nM.

In some embodiments, a compound of Formula (I) inhibits T helper 2 (Th2) cell function. In some embodiments, the $IC_{50}$ for inhibition of Th2 cell function is less than or equal to about 500 nM, about 100 nM, about 50 nM, about 10 nM, about 5 nM, or about 1 nM. In some embodiments, inhibition of Th2 cell function is measured based on change in expression of IL-5. In some embodiments, a compound of Formula (I) inhibits T helper 2 (Th2) cell function selectively compared to inhibition of other T cell functions, for example, T cell activation, Th helper 1 (Th1) cell function, and/or T helper 17 (Th17) cell function. In some embodiments, the inhibition of Th2 cell function relative to inhibition of T cell activation is greater than or equal to about 30×, about 50×, about 100×, about 300×, about 500×, or about 1000×. In some embodiments, inhibition of T cell activation is measured based on change in expression of CD25. In some embodiments, the inhibition of Th2 cell function relative to inhibition of Th1 cell function is greater than or equal to about 30×, about 50×, about 100×, about 300×, about 500×, or about 1000×. In some embodiments, inhibition of Th1 cell function is measured based on change in expression of IFNγ. In some embodiments, the inhibition of Th2 cell function relative to inhibition of Th17 cell function is greater than or equal to about 30×, about 50×, about 100×, about 300×, about 500×, or about 1000×. In some embodiments, inhibition of Th1 cell function is measured based on change in expression of IL-17A. In some embodiments, a compound of Formula (I) inhibits T helper 2 (Th2) cell function selectively compared to modulation of hematologic homeostasis, for example inhibition of erythropoietin(EPO)-induced STAT5-driven transcription and/or thrombopoietin (TPO)-induced STAT5-driven transcription. In some embodiments, the inhibition of Th2 cell function relative to inhibition of EPO induced STAT5-driven transcription is greater than or equal to about 30×, about 50×, about 100×, about 300×, about 500×, or about 1000×. In some embodiments, the inhibition of Th2 cell function relative to inhibition of TPO induced STAT5-driven transcription is greater than or equal to about 30×, about 50×, about 100×, about 300×, about 500×, or about 1000×.

In some embodiments, oral administration (e.g., P.O. in dogs) of a prodrug compound of Formula (I) provides durable bioavailability of the corresponding parent drug compound of Formula (I). In some embodiments, the oral administration (e.g., P.O. in dogs) of the prodrug compound of Formula (I) enables durable bioavailability of the parent drug in PBMCs. In some embodiments, the bioavailability is characterized by an effective concentration (e.g., in PBMCs) of the parent drug about 2 hours, about 6 hours, about 12 hours, or about 24 hours after dosing of the prodrug. In some embodiments, the bioavailability is characterized by an effective concentration (e.g., in PBMCs) of the parent drug averaged over about 6 hours, about 12 hours, or about 24 hours after dosing of the prodrug. In some embodiments the effective concentration (e.g., in PBMCs) is at least about 50 ng/mL, at least about 100 ng/mL, at least about 200 ng/mL, at least about 300 ng/mL, at least about 400 ng/mL, at least about 500 ng/mL, at least about 600 ng/mL, at least about 700 ng/mL, at least about 800 ng/mL, at least about 900 ng/mL, or at least about 1000 ng/mL. In some embodiments, the bioavailability is characterized by an area under the curve (AUC) of cellular concentration (e.g., ng/mL in PBMCs) over about 2 hours, about 6 hours, about 12 hours, or about 24 hours after dosing of the prodrug. In some embodiments, the AUC over 24 hours post-dosing is at least about 1200 ng*h/mL, at least about 2400 ng*h/mL, at least about 4800 ng*h/mL, at least about 7200 ng*h/mL, at least about 9600 ng*h/mL, at least about 12000 ng*h/mL, at least about 14400 ng*h/mL, at least about 16800 ng*h/mL, at least about 19200 ng*h/mL, or at least about 21600 ng*h/mL, at least about 24000 ng*h/mL.

In some embodiments, oral administration (e.g., P.O. in dogs) of a prodrug compound of Formula (I) the method enables durable and/or selective inhibition of pSTAT6. In some embodiments, the oral administration of a prodrug compound of Formula (I) enables therapeutically effective inhibition of pSTAT6. In some embodiments, therapeutically effective inhibition of pSTAT6 is characterized by the percentage of pSTAT6-positive cells (e.g., in whole blood, PBMCs, myeloid cells, lymphocytes) following oral administration compared to predose control. In some embodiments, the maximum percentage of pSTAT6-positive cells (e.g., in whole blood, PBMCs, myeloid cells, lymphocytes) compared to predose control following initial dose response is less than about 90%, is less than about 80%, is less than about 70%, is less than about 60%, less than about 50%, less than about 40%, less than about 30%, less than about 20%, or less than about 10%. In some embodiments, a prodrug compound of Formula (I) inhibits pSTAT6 (e.g., depletes the percentage of pSTAT6-positive cells compared to predose control to less than about 90%, less than about 80%, less than about 70%, less than about 60%, less than about 50%, less than about 40%, less than about 30%, less than about 20%, or less than about 10%) with dosing twice per day (e.g., P.O., BID in dogs). In some embodiments, a prodrug compound of Formula (I) inhibits pSTAT6 (e.g., depletes the percentage of pSTAT6-positive cells compared to predose control to less than about 90%, less than about 80%, less than about 70%, less than about 60%, less than about 50%, less than about 40%, less than about 30%, less than about 20%, or less than about 10%) with dosing once per day (e.g., P.O., QD in dogs).

In one aspect, provided herein is a method of treating a disease or condition responsive to the modulation (e.g., inhibition) of STAT6 in a subject in need thereof, comprising administering to the subject a therapeutically effective amount of a compound of Formula (I) or a prodrug thereof, or a pharmaceutically acceptable salt thereof, or a pharmaceutical composition comprising a compound of Formula (I) or a prodrug thereof, or a pharmaceutically acceptable salt thereof.

Also provided is the use of a compound of Formula (I) or a prodrug thereof, or a pharmaceutically acceptable salt thereof, or a pharmaceutical composition comprising a compound of Formula (I) or a prodrug thereof, or a pharmaceutically acceptable salt thereof, for the manufacture of a medicament. Also provided is the use of a compound of Formula (I) or a prodrug thereof, or a pharmaceutically acceptable salt thereof, or a pharmaceutical composition comprising a compound of Formula (I) or a prodrug thereof, or a pharmaceutically acceptable salt thereof, for the manufacture of a medicament for treating a disease or condition responsive to the modulation (e.g., inhibition) of STAT6. Also provided is a compound of Formula (I) or a prodrug thereof, or a pharmaceutically acceptable salt thereof, or a pharmaceutical composition comprising a compound of Formula (I) or a prodrug thereof, or a pharmaceutically acceptable salt thereof, for use as a drug. Also provided is a compound of Formula (I) or a prodrug thereof, or a pharmaceutically acceptable salt thereof, or a pharmaceutical composition comprising a compound of Formula (I) or a prodrug thereof, or a pharmaceutically acceptable salt thereof, for use in treating a disease or condition responsive to the modulation (e.g., inhibition) of STAT6. In some embodiments, the compound is selected from the group consisting of the parent drugs in Table 1A, or a pharmaceutically acceptable salt thereof. In some embodiments, the compound is selected from the group consisting of the parent drugs in Table 1A, or a prodrug or intermediate metabolite thereof, or a pharmaceutically acceptable salt thereof. In some embodiments, the compound is selected from the group consisting of the prodrugs in Table 1C, or a pharmaceutically acceptable salt thereof. In some embodiments, the compound, or a pharmaceutically acceptable salt thereof, is selected from the group consisting of parent drugs A3, A4, A5, A6, A7, A8, A11, A13, A14, A18, A19, A20, A21, A22, A23, A25, A30, A32, A33, A35, A36, A37, A38, A40, A42, A43, A44, A47, A48, A49, A50, A52, A53, A55, A57, A58, A59, A60, A61, A65, and pharmaceutically acceptable salts thereof. In some embodiments, the compound, or a pharmaceutically acceptable salt thereof, is selected from the group consisting of compounds A3, A4, A5, A6, A7, A8, A11, A13, A14, A18, A19, A20, A21, A22, A23, A25, A30, A32, A33, A35, A36, A37, A38, A40, A42, A43, A44, A47, A48, A49, A50, A52, A53, A55, A57, A58, A59, A60, A61, and A65, prodrugs or intermediate metabolites thereof, and pharmaceutically acceptable salts of any of the foregoing. In some embodiments, the compound, or a pharmaceutically acceptable salt thereof, is selected from the group consisting of prodrugs C4, C5, C6, C7, C8, C10, C13, C17, C19, C23, C25, C53, C54, C61, C63, C64, C65, C66, C68, C70, C71, C73, C74, C75, C82, C83, C84, C89, C90, C91, C92, C93, C94, C96, C97, C96, C97, C102, C103, C015, C016, C017, C110, C111, C114, C116, C118, C121, C122, C123, C124, C125, C126, C127, C132, C133, C135, C136, C137, C140, C141, C143, C144, C148, C155, C156, C160, C162, C170, C173, C175, C176, C177, C180, C182, C185, C186, C188, C189, C194, C195, C197, C198, C205, C208, and C209, and pharmaceutically acceptable salts thereof.

In one aspect, the disease or condition responsive to the modulation (e.g., inhibition) of STAT6 is selected from the group consisting of an inflammatory disorder, autoimmune disorder, an allergic disorder, and a skin disorder. In some embodiments, the disease or condition is associated with T helper type 2 (Th2) inflammation. In some embodiments, the disease or condition is selected from the group consisting of atopic dermatitis, prurigo nodularis, asthma, chronic rhinosinusitis with nasal polyps, eosinophilic esophagitis, and chronic obstructive pulmonary disease.

In another aspect, provided herein is a method of modulating the activity of STAT6, comprising contacting a biological sample with or administering to a subject in need thereof a compound of Formula (I) or a prodrug thereof, or a pharmaceutically acceptable salt thereof, or a pharmaceutical composition comprising a compound of Formula (I) or a prodrug compound thereof, or a pharmaceutically acceptable salt thereof. In some embodiments, the method inhibits the activity of STAT6. In some embodiments, the method inhibits the activity of phospho-STAT6 (pSTAT6). In some embodiments, the method inhibits the activity of STAT6 and pSTAT6. In some embodiments, the method inhibits the phosphorylation of STAT6 to pSTAT6, for example by a JAK protein (e.g., JAK1). In some embodiments, the method inhibits the dimerization of pSTAT6. In some embodiments, the method inhibits the translocation of pSTAT6 into the nucleus.

ENUMERATED EMBODIMENTS

The following enumerated embodiments are representative of some aspects of the invention.

1. A compound of Formula (I),

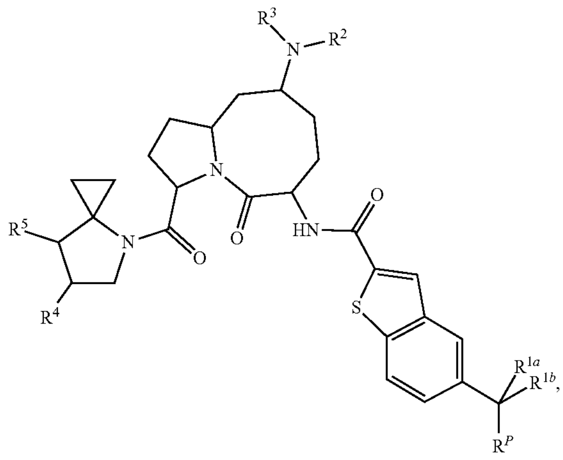

(I)

or a pharmaceutically acceptable salt thereof, wherein:

$R^{1a}$ and $R^{1b}$ are each independently H or halogen;

$R^2$ is H, $(C_1-C_6)$alkyl, or $(C_3-C_6)$cycloalkyl;

$R^3$ is $(C_1-C_6)$alkyl, halo$(C_1-C_6)$alkyl, $(C_3-C_6)$cycloalkyl, 3- to 7-membered heterocyclyl, —$(C_1-C_6)$alkylene-$(C_3-C_6)$cycloalkyl, or —$(C_1-C_6)$alkylene-(3- to 7-membered heterocyclyl), wherein $(C_1-C_6)$alkyl, $(C_3-C_6)$cycloalkyl, $(C_3-C_6)$cycloalkyl of —$(C_1-C_6)$alkylene-$(C_3-C_6)$cycloalkyl, or (3- to 7-membered heterocyclyl) of —$(C_1-C_6)$alkylene-(3- to 7-membered heterocyclyl) is each substituted with 0, 1, 2, 3, 4, or 5 substituents each independently selected from the group consisting of $(C_1-C_6)$alkyl, $(C_1-C_6)$alkoxy, cyano, halogen, halo$(C_1-C_6)$alkyl, and halo$(C_1-C_6)$alkoxy, or $R^2$ and $R^3$ together with the nitrogen atom to which they are attached form 5- to 7-membered heterocyclyl substituted with 0, 1, 2, or 3 substituents each independently selected from the group consisting of $(C_1-C_6)$alkyl, $(C_1-C_6)$alkoxy, cyano, halogen, halo$(C_1-C_6)$alkyl, and halo$(C_1-C_6)$alkoxy;

$R^4$ is H, $(C_6-C_{10})$aryl, or 5- to 10-membered heteroaryl, wherein $(C_6-C_{10})$aryl or 5- to 10-membered heteroaryl is each substituted with 0, 1, 2, or 3 substituents each independently selected from the group consisting of halogen, cyano, $(C_1-C_6)$alkyl, $(C_1-C_6)$alkoxy, halo$(C_1-C_6)$alkyl, halo$(C_1-C_6)$alkoxy, and —$NR^{4a}R^{4b}$, wherein: each $R^{4a}$ and $R^{4b}$ is independently H or $(C_1-C_6)$alkyl;

$R^5$ is H, cyano, or $(C_1-C_6)$alkoxy; and $R^P$ is phosphonic acid, phosphonate, phosphonamidate, or phosphondiamidate.

2. The compound of embodiment 1, or a pharmaceutically acceptable salt thereof, wherein $R^{1a}$ is F.

3. The compound of embodiment 1, or a pharmaceutically acceptable salt thereof, wherein $R^{1b}$ is H.

4. The compound of embodiment 1, or a pharmaceutically acceptable salt thereof, wherein $R^{1a}$ is F and $R^{1b}$ is H.

5. The compound of embodiment 1, or a pharmaceutically acceptable salt thereof, wherein $R^{1a}$ and $R^{1b}$ are each F.

6. The compound of any one of embodiments 1 to 5, or a pharmaceutically acceptable salt thereof, wherein $R^2$ is methyl or ethyl.

7. The compound of any one of embodiments 1 to 6, or a pharmaceutically acceptable salt thereof, wherein $R^3$ is $(C_1-$ $C_6$)alkyl, halo($C_1$-$C_6$)alkyl, ($C_3$-$C_6$)cycloalkyl, 3- to 7-membered heterocyclyl, or —($C_1$-$C_6$)alkylene-(3- to 7-membered heterocyclyl).

8. The compound of embodiment 7, or a pharmaceutically acceptable salt thereof, wherein $R^3$ is halo($C_1$-$C_6$)alkyl.

9. The compound of embodiment 7, or a pharmaceutically acceptable salt thereof, wherein $R^3$ is ($C_3$-$C_6$)cycloalkyl substituted with 0, 1, 2, or 3 substituents each independently selected from the group consisting of halogen, cyano, halo($C_1$-$C_6$)alkyl, and halo($C_1$-$C_6$)alkoxy.

10. The compound of embodiment 7, or a pharmaceutically acceptable salt thereof, wherein $R^3$ is 3- to 7-membered heterocyclyl.

11. The compound of embodiment 7, or a pharmaceutically acceptable salt thereof, wherein $R^3$ is —($C_1$-$C_6$)alkylene-[3- to 7-membered heterocyclyl substituted with 0 or 1 ($C_1$-$C_6$)alkyl].

12. The compound of embodiment 7, or a pharmaceutically acceptable salt thereof, wherein $R^3$ is ($C_1$-$C_6$)alkyl substituted with 0, 1, 2, 3, 4, or 5 substituents each independently selected from the group consisting of halo, ($C_1$-$C_6$)alkoxy, and halo($C_1$-$C_6$)alkoxy.

13. The compound of embodiment 7, or a pharmaceutically acceptable salt thereof, wherein $R^3$ is

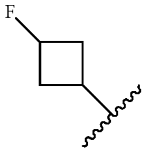, 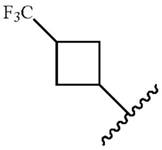, 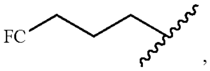,

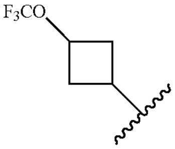, 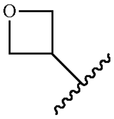, 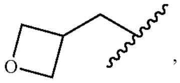,

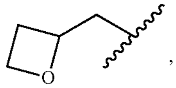, 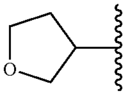, 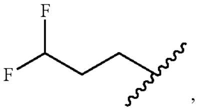,

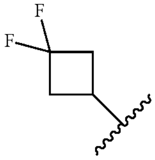, 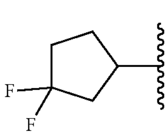, 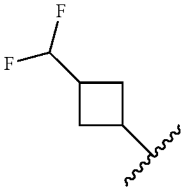,

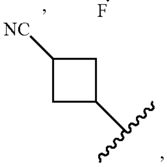, 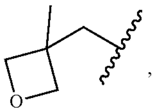,

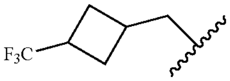, 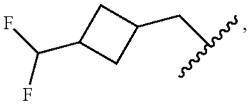,

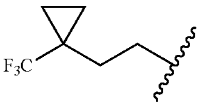, 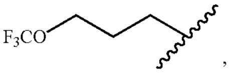,

-continued

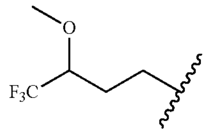, 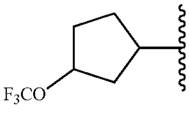, or

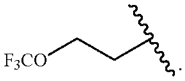.

14. The compound of embodiment 7, or a pharmaceutically acceptable salt thereof, wherein

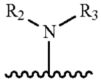

of Formula (I) is

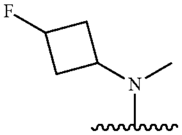, 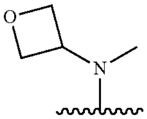, 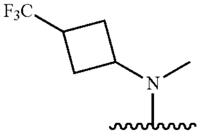,

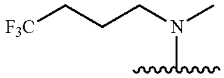, 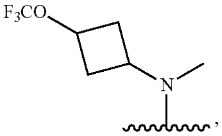,

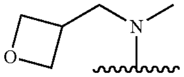, 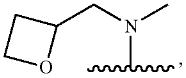,

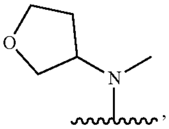, 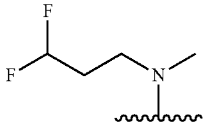,

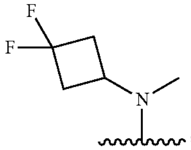, 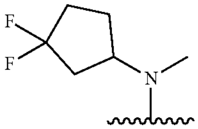,

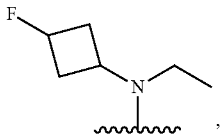, 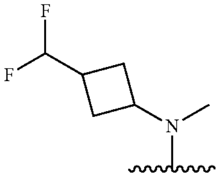,

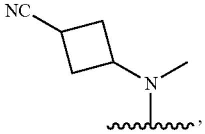, 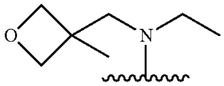,

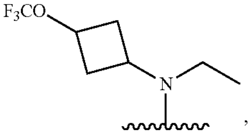, 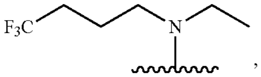,

-continued

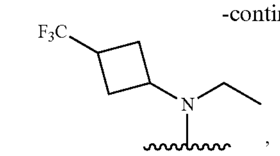, 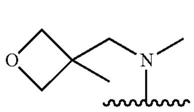, 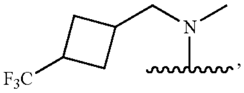, 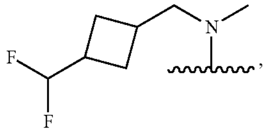, 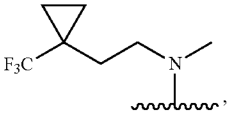, 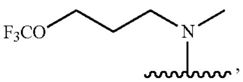, 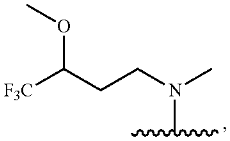, 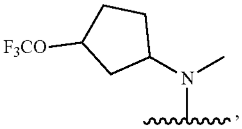, or 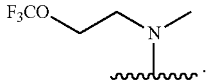.

15. The compound of any one of embodiments 1 to 5, or a pharmaceutically acceptable salt thereof, wherein $R^2$ and $R^3$ together with the nitrogen atom to which they are attached form 6-membered heterocyclyl.

16. The compound of embodiment 15, or a pharmaceutically acceptable salt thereof, wherein

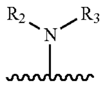

of Formula (I) is

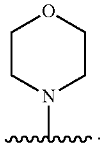 [SMILES: *N1CCOCC1].

17. The compound of any one of embodiments 1 to 16, or a pharmaceutically acceptable salt thereof, wherein $R^4$ is H.

18. The compound of any one of embodiments 1 to 16, or a pharmaceutically acceptable salt thereof, wherein $R^4$ is $(C_6\text{-}C_{10})$aryl or 5- to 10-membered heteroaryl.

19. The compound of embodiment 18, or a pharmaceutically acceptable salt thereof, wherein $R^4$ is phenyl substituted with 0, 1, 2, or 3 halogen.

20. The compound of embodiment 19, or a pharmaceutically acceptable salt thereof, wherein $R^4$ is

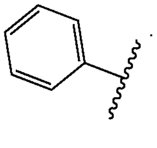 [SMILES: *c1ccccc1].

21. The compound of embodiment 19, or a pharmaceutically acceptable salt thereof, wherein $R^4$ is

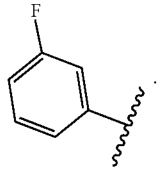 [SMILES: *c1cccc(F)c1].

22. The compound of embodiment 18, or a pharmaceutically acceptable salt thereof, wherein $R^4$ is pyridinyl substituted with 0 or 1 —$NR^{4a}R^{4b}$.

23. The compound of embodiment 22, or a pharmaceutically acceptable salt thereof, wherein $R^4$ is

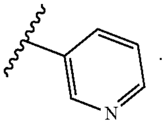 [SMILES: *c1cccnc1].

24. The compound of embodiment 22, or a pharmaceutically acceptable salt thereof, wherein $R^4$ is

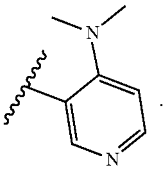 [SMILES: *c1cnccc1N(C)C].

25. The compound of any one of embodiments 1 to 24, or a pharmaceutically acceptable salt thereof, wherein $R^5$ is H.

26. The compound of any one of embodiments 1 to 24, or a pharmaceutically acceptable salt thereof, wherein $R^5$ is cyano.

27. The compound of any one of embodiments 1 to 24, or a pharmaceutically acceptable salt thereof, wherein $R^5$ is methoxy.

28. The compound of any one of embodiments 1 to 27, or a pharmaceutically acceptable salt thereof, wherein $R^P$ is

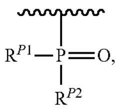, wherein $R^{P1}$ and $R^{P2}$ are each independently —OH, —$OR^{Pa}$, N-linked amino acid, N-linked amino acid ester, or

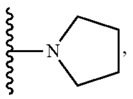, wherein

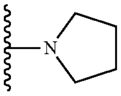 [SMILES: *N1CCCC1]

is substituted with 0, 1, 2, or 3 substituents each independently selected from the group consisting of halo, oxo, COOH, and —C(O)OR$^{PE}$, wherein:

each R$^{Pa}$ is independently ($C_1$-$C_6$)alkyl, halo($C_1$-$C_6$)alkyl, ($C_6$-$C_{10}$)aryl, or ($C_3$-$C_6$)cycloalkyl, wherein ($C_1$-$C_6$)alkyl is substituted with 0, 1, 2, or 3 substituents each independently selected from the group consisting of halo and ($C_1$-$C_6$)alkoxy; and each R$^{PE}$ is independently ($C_1$-$C_6$)alkyl, halo($C_1$-$C_6$)alkyl, —($C_1$-$C_6$)alkylene-($C_1$-$C_6$)alkoxy, ($C_3$-$C_6$)cycloalkyl, ($C_5$-$C_8$)spirocycloalkyl, —($C_1$-$C_6$)alkylene-($C_6$-$C_{10}$)aryl, —($C_1$-$C_6$)alkylene-($C_1$-$C_6$)alkoxy, —($C_1$-$C_6$)alkylene-($C_3$-$C_7$)cycloalkyl, 3- to 7-membered heterocyclyl, or —($C_1$-$C_6$)alkylene-(3- to 7-membered heterocyclyl), wherein ($C_1$-$C_6$)alkyl, ($C_3$-$C_6$)cycloalkyl, ($C_5$-$C_8$)spirocycloalkyl, or ($C_3$-$C_7$)cycloalkyl of —($C_1$-$C_6$)alkylene-($C_3$-$C_7$)cycloalkyl is each substituted with 0, 1, 2, or 3 independently selected halogen.

29. The compound of any one of embodiments 1 to 27, or a pharmaceutically acceptable salt thereof, wherein R$^P$ is

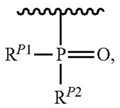

wherein R$^{P1}$ and R$^{P2}$ are each independently —OH, —OR$^{Pa}$, —NR$^{Paa1}$CR$^{Paa2}$R$^{Paa3}$C(O)OH, —NR$^{Paa1}$CR$^{Paa2}$R$^{Paa3}$C(O)OR$^{Paa4}$, or

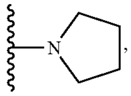, wherein

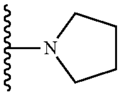 [SMILES: *N1CCCC1]

is substituted with 0, 1, 2, or 3 substituents each independently selected from the group consisting of halo, oxo, COOH, and —C(O)OR$^{PE}$, wherein:

each R$^{Pa}$ is independently ($C_1$-$C_6$)alkyl, halo($C_1$-$C_6$)alkyl, ($C_6$-$C_{10}$)aryl, or ($C_3$-$C_6$)cycloalkyl, wherein ($C_1$-$C_6$)alkyl is substituted with 0, 1, 2, or 3 substituents each independently selected from the group consisting of halo and ($C_1$-$C_6$)alkoxy; each R$^{PE}$ is independently ($C_1$-$C_6$)alkyl, halo($C_1$-$C_6$)alkyl, —($C_1$-$C_6$)alkylene-($C_1$-$C_6$)alkoxy, ($C_3$-$C_6$)cycloalkyl, ($C_5$-$C_8$)spirocycloalkyl, —($C_1$-$C_6$)alkylene-($C_6$-$C_{10}$)aryl, —($C_1$-$C_6$)alkylene-($C_1$-$C_6$)alkoxy, —($C_1$-$C_6$)alkylene-($C_3$-$C_7$)cycloalkyl, 3- to 7-membered heterocyclyl, or —($C_1$-$C_6$)alkylene-(3- to 7-membered heterocyclyl), wherein ($C_1$-$C_6$)alkyl, ($C_3$-$C_6$)cycloalkyl, ($C_5$-$C_8$)spirocycloalkyl, or ($C_3$-$C_7$)cycloalkyl of —($C_1$-$C_6$)alkylene-($C_3$-$C_7$)cycloalkyl is each substituted with 0, 1, 2, or 3 independently selected halogen;

each R$^{Paa1}$ is independently H or ($C_1$-$C_6$)alkyl;

each R$^{Paa2}$ is independently H or ($C_1$-$C_6$)alkyl, and each R$^{Paa3}$ is independently H, ($C_1$-$C_6$)alkyl, —($C_1$-$C_6$)alkylene-($C_1$-$C_6$)alkoxy, or —($C_1$-$C_6$)alkylene-($C_6$-$C_{10}$)aryl; or R$^{Paa2}$ and R$^{Paa3}$, together with the carbon atom to which they are attached form ($C_3$-$C_6$)cycloalkyl; and each R$^{Paa4}$ is independently ($C_1$-$C_6$)alkyl, halo($C_1$-$C_6$)alkyl, —($C_1$-$C_6$)alkylene-($C_1$-$C_6$)alkoxy, ($C_3$-$C_6$)cycloalkyl, ($C_5$-$C_8$)spirocycloalkyl, —($C_1$-$C_6$)alkylene-($C_6$-$C_{10}$)aryl, —($C_1$-$C_6$)alkylene-($C_1$-$C_6$)alkoxy, —($C_1$-$C_6$)alkylene-($C_3$-$C_7$)cycloalkyl, 3- to 7-membered heterocyclyl, or —($C_1$-$C_6$)alkylene-(3- to 7-membered heterocyclyl), wherein ($C_1$-$C_6$)alkyl, ($C_3$-$C_6$)cycloalkyl, ($C_5$-$C_8$)spirocycloalkyl, or ($C_3$-$C_7$)cycloalkyl of —($C_1$-$C_6$)alkylene-($C_3$-$C_7$)cycloalkyl is each substituted with 0, 1, 2, or 3 independently selected halogen.

30. The compound of any one of embodiments 1 to 27, or a pharmaceutically acceptable salt thereof, wherein R$^P$ is

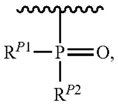

wherein R$^{P1}$ and R$^{P2}$ are each —OH.

31. The compound of any one of embodiments 1 to 27, or a pharmaceutically acceptable salt thereof, wherein R$^P$ is

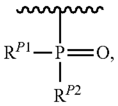

wherein R$^{P1}$ is —OH and R$^{Paa2}$ is N-linked amino acid.

32. The compound of any one of embodiments 1 to 27, or a pharmaceutically acceptable salt thereof, wherein R$^P$ is

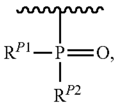

wherein R$^{P1}$ is —OR$^P$a and R$^{Paa2}$ is N-linked amino acid ester, wherein R$^{Pa}$ is ($C_1$-$C_6$)alkyl, halo($C_1$-$C_6$)alkyl, ($C_6$-$C_{10}$)aryl, or ($C_3$-$C_6$)cycloalkyl, wherein ($C_1$-$C_6$)alkyl is substituted with 0, 1, 2, or 3 substituents each independently selected from the group consisting of halo and ($C_1$-$C_6$)alkoxy.

33. The compound of any one of embodiments 1 to 27, or a pharmaceutically acceptable salt thereof, wherein R$^P$ is

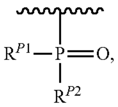

wherein $R^{P1}$ and $R^{Paa2}$ are each independently N-linked amino acid.

34. The compound of any one of embodiments 1 to 27, or a pharmaceutically acceptable salt thereof, wherein $R^P$ is

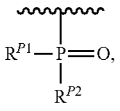

wherein $R^{P1}$ and $R^{P2}$ are each independently N-linked amino acid ester.

35. The compound of any one of embodiments 1 to 27, or a pharmaceutically acceptable salt thereof, wherein $R^P$ is

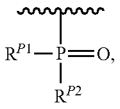

$R^{P2}$, wherein $R^{P1}$ is N-linked amino acid and $R^{P2}$ is

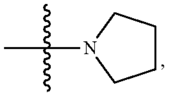

wherein

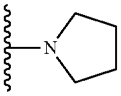 [SMILES: *N1CCCC1]

is substituted with 0, 1, 2, or 3 substituents each independently selected from the group consisting of halo, oxo, and —COOH.

36. The compound of any one of embodiments 1 to 27, or a pharmaceutically acceptable salt thereof, wherein $R^P$ is

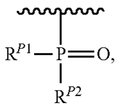

wherein $R^{P1}$ is N-linked amino acid ester and $R^{P2}$ is

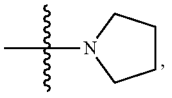 [SMILES: *N1CCCC1]

wherein

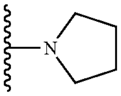 [SMILES: *N1CCCC1]

is substituted with 0, 1, 2, or 3 substituents each independently selected from the group consisting of halo, oxo, and ester.

37. The compound of embodiment 32, or a pharmaceutically acceptable salt thereof, wherein $R^{Pa}$ is phenyl.

38. The compound of embodiment 32, or a pharmaceutically acceptable salt thereof, wherein $R^{Pa}$ is ethyl.

39. The compound of embodiment 32, or a pharmaceutically acceptable salt thereof, wherein $R^{Pa}$ is $—CH_2CF_3$.

40. The compound of embodiment 32, or a pharmaceutically acceptable salt thereof, wherein $R^{Pa}$ is

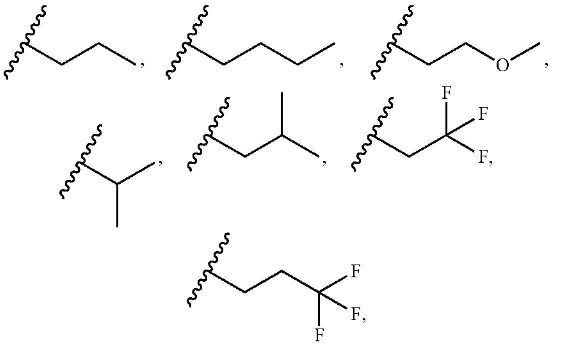

cyclopropyl, cyclopentyl, or cyclohexyl.

41. The compound of embodiment 35, or a pharmaceutically acceptable salt thereof, wherein $R^2$ is

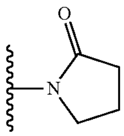

or

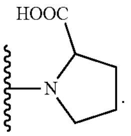

42. The compound of embodiment 36, or a pharmaceutically acceptable salt thereof, wherein $R^{P2}$ is

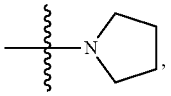

wherein

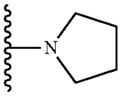

is substituted with 0, 1, 2, or 3 substituents each independently selected from the group consisting of halo, oxo, and $—C(O)OR^{PE}$, wherein each $R^{PE}$ is independently $(C_1\text{-}C_6)$alkyl, halo$(C_1\text{-}C_6)$alkyl, $—(C_1\text{-}C_6)$alkylene-$(C_1\text{-}C_6)$alkoxy, $(C_3\text{-}C_6)$cycloalkyl, $(C_5\text{-}C_8)$spirocycloalkyl, $—(C_1\text{-}C_6)$alkylene-$(C_6\text{-}C_{10})$aryl, $—(C_1\text{-}C_6)$alkylene-$(C_1\text{-}C_6)$alkoxy, $—(C_1\text{-}C_6)$alkylene-$(C_3\text{-}C_7)$cycloalkyl, 3- to 7-membered heterocyclyl, or $—(C_1\text{-}C_6)$alkylene-(3- to 7-membered heterocyclyl), wherein $(C_1\text{-}C_6)$alkyl, $(C_3\text{-}C_6)$cycloalkyl, $(C_5\text{-}C_8)$spirocycloalkyl, or $(C_3\text{-}C_7)$cycloalkyl of $—(C_1\text{-}C_6)$alkylene-($C_3$-$C_7$)cycloalkyl is each substituted with 0, 1, 2, or 3 independently selected halogen.

43. The compound of embodiment 42, or a pharmaceutically acceptable salt thereof, wherein each $R^{PE}$ is independently ethyl,

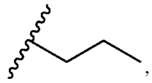,
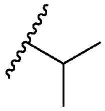,
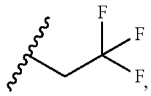
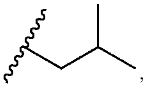,
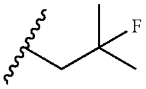,
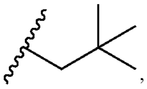,
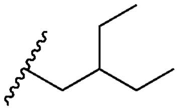,
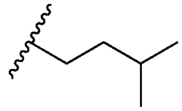,
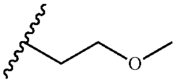,
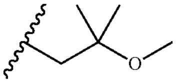,
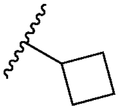,
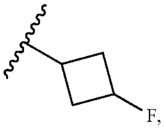
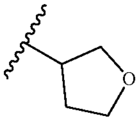,
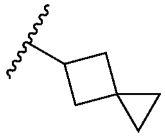,
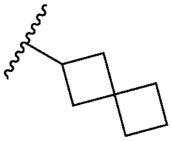,
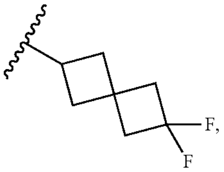
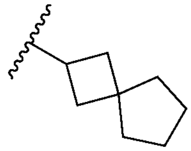,
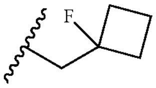,
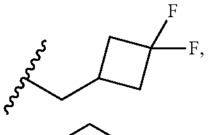
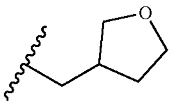,
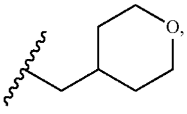
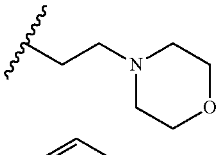, or
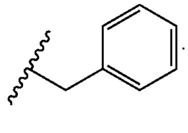.

44. The compound of embodiment 43, or a pharmaceutically acceptable salt thereof, wherein each $R^{PE}$ is

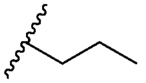.

45. The compound of embodiment 36, or a pharmaceutically acceptable salt thereof, wherein $R^2$ is

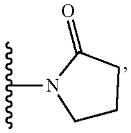,
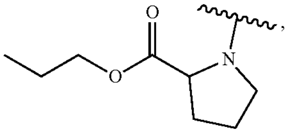,
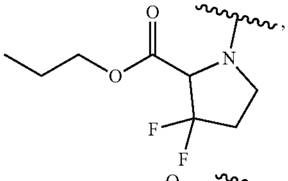, or
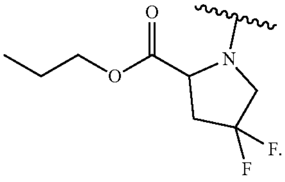

46. The compound of any one of embodiments 31, 33, 35, and 41, or a pharmaceutically acceptable salt thereof, wherein each N-linked amino acid is independently N-linked α-amino acid.

47. The compound of embodiment 46, or a pharmaceutically acceptable salt thereof, wherein each N-linked amino acid is independently —$NR^{Paa1}CR^{Paa2}R^{Paa3}C(O)OH$, wherein:

each $R^{Paa1}$ is independently H or ($C_1$-$C_6$)alkyl; and each $R^{Paa2}$ is independently H or ($C_1$-$C_6$)alkyl, and each $R^{Paa3}$ is independently H, ($C_1$-$C_6$)alkyl, —($C_1$-$C_6$)alkylene-($C_1$-$C_6$)alkoxy, or —($C_1$-$C_6$)alkylene-($C_6$-$C_{10}$)aryl; or $R^{Paa2}$ and $R^{Paa3}$, together with the carbon atom to which they are attached form ($C_3$-$C_6$)cycloalkyl.

48. The compound of any one of embodiments 32, 34, 36, 37 to 40, and 42 to 45, or a pharmaceutically acceptable salt thereof, wherein each N-linked amino acid ester is independently N-linked α-amino acid ester.

49. The compound of embodiment 48, or a pharmaceutically acceptable salt thereof, wherein each N-linked amino acid ester is independently —$NR^{Paa1}CR^{Paa2}R^{Paa3}C(O)OR^{Paa4}$, wherein:

each $R^{Paa1}$ is independently H or ($C_1$-$C_6$)alkyl;

each $R^{Paa2}$ is independently H or ($C_1$-$C_6$)alkyl, and each $R^{Paa3}$ is independently H, ($C_1$-$C_6$)alkyl, —($C_1$-$C_6$)alkylene-($C_1$-$C_6$)alkoxy, or —($C_1$-$C_6$)alkylene-($C_6$-$C_{10}$)aryl; or $R^{Paa2}$ and $R^{Paa3}$, together with the carbon atom to which they are attached form ($C_3$-$C_6$)cycloalkyl; and each $R^{Paa4}$ is independently ($C_1$-$C_6$)alkyl, halo($C_1$-$C_6$)alkyl, —($C_1$-$C_6$)alkylene-($C_1$-$C_6$)alkoxy, ($C_3$-$C_6$)cycloalkyl, ($C_5$-$C_8$)spirocycloalkyl, —($C_1$-$C_6$)alkylene-($C_6$-$C_{10}$)aryl, —($C_1$-$C_6$)alkylene-($C_1$-$C_6$)alkoxy, —($C_1$-$C_6$)alkylene-($C_3$-$C_7$)cycloalkyl, 3- to 7-membered heterocyclyl, or —($C_1$-$C_6$)alkylene-(3- to 7-membered heterocyclyl), wherein ($C_1$-$C_6$)alkyl, ($C_3$-$C_6$)cycloalkyl, ($C_5$-$C_8$)spirocycloalkyl, or ($C_3$-$C_7$)cycloalkyl of —($C_1$-$C_6$)alkylene-($C_3$-$C_7$)cycloalkyl is each substituted with 0, 1, 2, or 3 independently selected halogen.

50. The compound of embodiment 49, or a pharmaceutically acceptable salt thereof, wherein each $R^{Paa4}$ is independently ethyl,

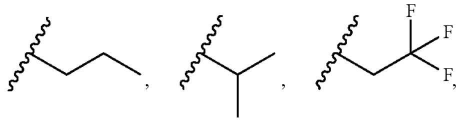

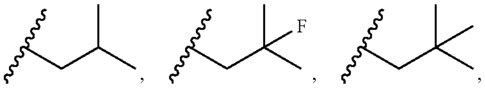

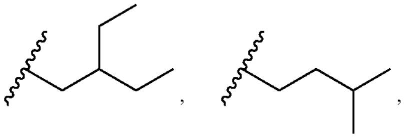

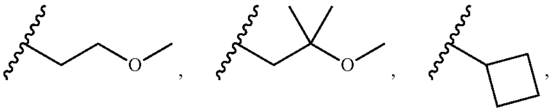

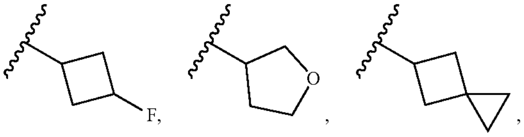

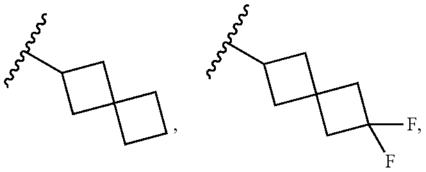

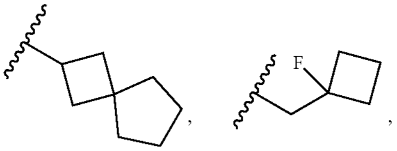

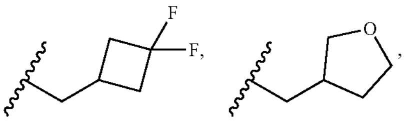

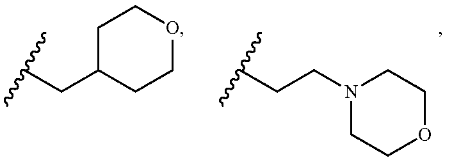

, or

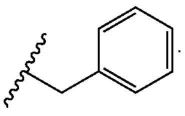

51. The compound of embodiment 50, or a pharmaceutically acceptable salt thereof, wherein $R^{Paa4}$ is ethyl

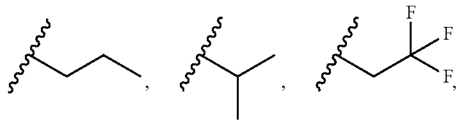

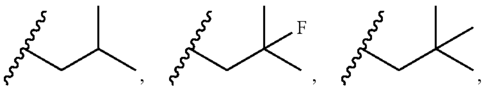

-continued

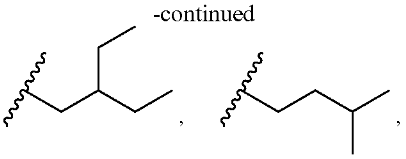

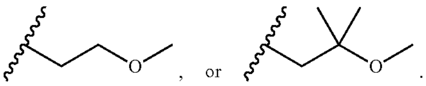

52. The compound of embodiment 50, or a pharmaceutically acceptable salt thereof, wherein $R^{Paa4}$ is

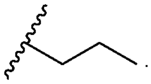 [SMILES: *CCC]

53. The compound of Embodiment 50, or a pharmaceutically acceptable salt thereof, wherein $R^{Paa4}$ is

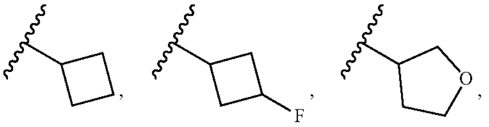

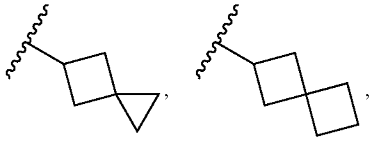

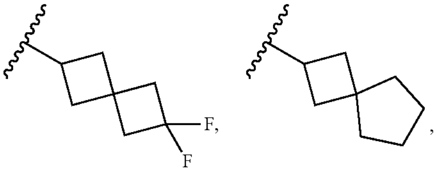

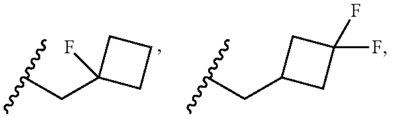

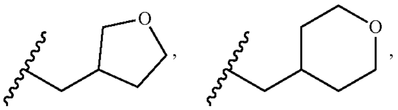

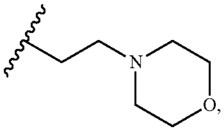

or

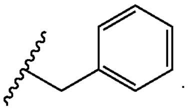 [SMILES: *Cc1ccccc1]

54. The compound of any one of embodiments 47 and 49 to 53, or a pharmaceutically acceptable salt thereof, wherein $R^{Paa1}$ is H.

55. The compound of any one of embodiments 47 and 49 to 53, or a pharmaceutically acceptable salt thereof, wherein $R^{Paa1}$ is methyl.

56. The compound of any one of embodiments 47 and 49 to 55, or a pharmaceutically acceptable salt thereof, wherein $R^{Paa2}$ is H.

57. The compound of any one of embodiments 47 and 49 to 55, or a pharmaceutically acceptable salt thereof, wherein $R^{Paa2}$ is methyl.

58. The compound of any one of embodiments 47 and 49 to 57, or a pharmaceutically acceptable salt thereof, wherein $R^{Paa3}$ is methyl.

59. The compound of any one of embodiments 47 and 49 to 57, or a pharmaceutically acceptable salt thereof, wherein $R^{Paa3}$ is ethyl,

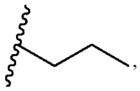,
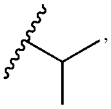, or $—CH_2OCH_3$.

60. The compound of any one of embodiments 47 and 49 to 57, or a pharmaceutically acceptable salt thereof, wherein $R^{Paa3}$ is

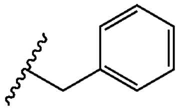.

61. The compound of any one of embodiments 47 and 49 to 53 or a pharmaceutically acceptable salt thereof, wherein $R^{Paa2}$ and $R^{Paa3}$, together with the carbon atom to which they are attached form cyclopropyl.

62. The compound of embodiment 1, or a pharmaceutically acceptable salt thereof, wherein the compound is selected from the group consisting of the compounds of Table 1A, Table 1B, and Table 1C.

63. A pharmaceutical composition comprising the compound of any one of embodiments 1 to 62, or a pharmaceutically acceptable salt thereof; and a pharmaceutically acceptable excipient.

64. A medicament comprising a compound of any one of embodiments 1 to 62, or a pharmaceutically acceptable salt thereof, or the pharmaceutical composition of embodiment 63.

65. A method of treating a disease or condition responsive to the modulation (e.g., inhibition) of STAT6 in a subject in need thereof, the method comprising administering to the subject in need thereof a therapeutically effective amount of the compound of any one of embodiments 1 to 62, or a pharmaceutically acceptable salt thereof, or the pharmaceutical composition of embodiment 63.

66. A compound of any one of embodiments 1 to 62, or a pharmaceutically acceptable salt thereof, or the pharmaceutical composition of embodiment 63, for use as a drug.

67. A compound of any one of embodiments 1 to 62, or a pharmaceutically acceptable salt thereof, or the pharmaceutical composition of embodiment 63, for use in the treatment of a disease or condition responsive to the modulation (e.g., inhibition) of STAT6 in a subject.

68. Use of a compound of any one of embodiments 1 to 62, or a pharmaceutically acceptable salt thereof, or the pharmaceutical composition of embodiment 63, for use in the preparation of a medicament.

69. The use of embodiment 67, wherein the medicament is intended for the treatment of a disease or condition responsive to the modulation (e.g., inhibition) of STAT6 in a subject.

70. The method of embodiment 65, the compound for use of embodiment 67, or the use of embodiment 69, wherein the disease or condition is selected from the group consisting of an inflammatory disorder, autoimmune disorder, an allergic disorder, and a skin disorder.

71. The method of embodiment 65, the compound for use of embodiment 67, or the use of embodiment 69, wherein the disease or condition is selected from the group consisting of atopic dermatitis, prurigo nodularis, asthma, chronic rhinosinusitis with nasal polyps, eosinophilic esophagitis, and chronic obstructive pulmonary disease.

EXAMPLES

The presently disclosed subject matter will be better understood by reference to the following Examples, which are provided as exemplary of the invention, and not by way of limitation.

Abbreviations used in the Examples include the following:

ACN, MeCN—acetonitrile
AIBN—Azobisisobutyronitrile
AcOH—acetic acid
BSA—Bovine serum albumin
CMPI—2-chloro-1-methylpyridinium iodide
CST—cell signaling technology
DCM—dichloromethane
DEA—diethanoloamine
DFT—density functional theory
DIEA—N,N-diisopropylethylamine
DMAP—4-Dimethylaminopyridine
DME—dimethyl ether
DMF—dimethylformamide
DMSO—dimethyl sulfoxide
DTT—Dithiothreitol
EA, EtOAc—ethyl acetate
EDCI—1-Ethyl-3-(3-dimethylaminopropyl)carbodiimide hydrochloride
EDTA—Ethylenediaminetetraacetic acid
ESI—electrospray ionization
FA—formic acid
FBS—fetal bovine serum
HATU—1-[Bis(dimethylamino)methylene]-1H-1,2,3-triazolo[4,5-b]pyridinium 3-oxide hexafluorophosphate (Hexafluorophosphate Azabenzotriazole Tetramethyl Uronium)
HEPES—4-(2-Hydroxyethyl)piperazine-1-ethane-sulfonic acid
HPLC—high-performance liquid chromatography
IMDM—Iscove's Modified Dulbecco's Medium
IPA—isopropyl alcohol
LCMS—liquid chromatography-mass spectrometry
LDA—Lithium diisopropylamide
MeOH—methyl alcohol
MS—mass spectrometry
MSD—meso scale discovery
NBS—N-Bromosuccinimide
NMR—nuclear magnetic resonance
PBS—phosphate buffered saline
PE—phycoerythrin
PK—pharmacokinetic
PMBC—peripheral blood mononuclear cells
qPCR—quantitative polymerase chain reaction
RBC—red blood cell
RT—retention time
SFC—supercritical fluid chromatography
SM—starting material TEA—triethylamine
TFA—trifluoroacetic acid
THF—tetrahydrofuran
TLC—thin layer chromatography
TMSBr—Bromotrimethylsilane
TMSI—Trimethylsilyl iodide
VCD—vibrational circular dichroism
aq—aqueous
eq—equivalents
Hz—hertz
MHz—megahertz
h, hr—hour
g—gram
mg—milligram
L—liter
mL—milliliter
uL—microliter
m/z—mass-to-charge ratio
mm—millimeter
nm—nanometer
um—micrometer
min—minute
mol—mole
mmol—millimole
umol—micromole
M—molarity
mM—millimolar
N—normality

Example 1: Preparation of Compounds

The compounds of Formula (I) were prepared by adapting or following the procedures outlined in the following schemes and examples. For example, the representative procedures for the combination of cores, pyrrolidine groups, northern amines, and phosphoryl groups are not limited to the examples below and may be adapted to form other compounds of Formula (I) by utilizing the appropriate intermediates and/or starting materials (e.g., pyrrolidine groups, northern amines, and/or phosphoryl groups). In some embodiments, the compounds of Formula (I) or starting materials or intermediates thereto were prepared by adapting or following procedures described in WO 2023/133336, paragraphs [0085]-[001573](EXEMPLIFICATION: Preparation of Compounds), WO 2023/164680 paragraphs [0019]-[00801](EXEMPLIFICATION: Preparation of Compounds), or WO 2023/192960, paragraphs [0085]-[00784](EXEMPLIFICATION: Preparation of Compounds), each of which is incorporated herein by reference in its entirety.

Compound names were generated using the software built into ChemDraw. To the extent that there are discrepancies between the name of a compound and its depicted structure, the depicted chemical structure is to be taken as the appropriate compound.

Representative Procedures for Combination of Cores, Pyrrolidine Groups, Northern Amines, and Phosphoryl Groups:

The compounds of Formula (I) in Tables 1A, 1B, and 1C were prepared according to the general schemes and exemplary procedures for the combination of cores, pyrrolidine groups, northern amines, and phosphoryl groups with the appropriate starting materials, intermediates, and modifications.

Preparation of tert-butyl ((3S,6S,10aR)-5,9-dioxo-3-((S)-6-phenyl-4-azaspiro[2.4]heptane-4-carbonyl) decahydropyrrolo[1,2-a]azocin-6-yl)carbamate (Int 1)

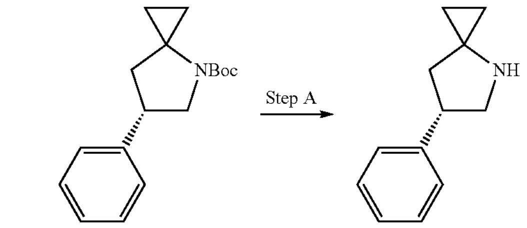

1 2

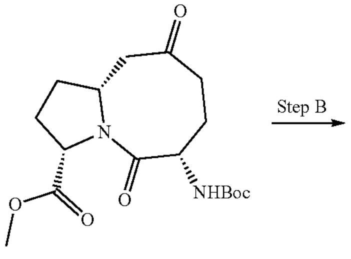

3

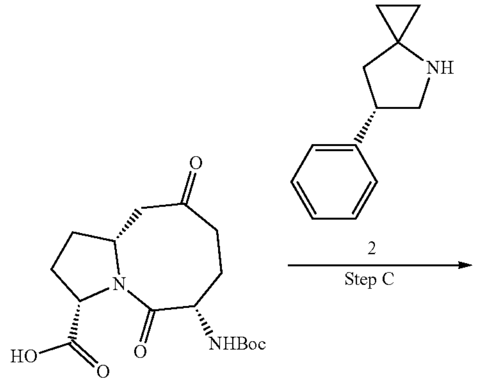

4

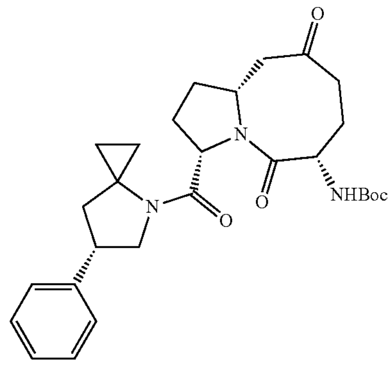

Int 1

Step A: (S)-6-phenyl-4-azaspiro[2.4]heptane

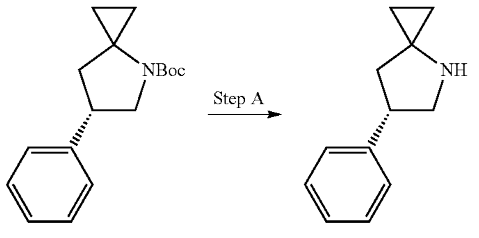

1 2

To a solution of tert-butyl (S)-6-phenyl-4-azaspiro[2.4]heptane-4-carboxylate (1, 20 g, 73.3 mmol, 1.0 eq.) in DCM (210 mL) was added trifluoroacetic acid (TFA) (70 mL), and the resulting mixture was stirred at room temperature for 2 hrs. After completion, the reaction mixture concentrated under reduced pressure to give crude (S)-6-phenyl-4-azaspiro[2.4]heptane (TFA salt) (2, 20 g, quant.) as a white solid, which was used in next Step directly without further purification. LCMS (ESI): m/z=174 $[M+H]^+$.

Step B: (3S,6S,10aR)-6-((tert-butoxycarbonyl)amino)-5,9-dioxodecahydropyrrolo[1,2-a]azocine-3-carboxylic acid

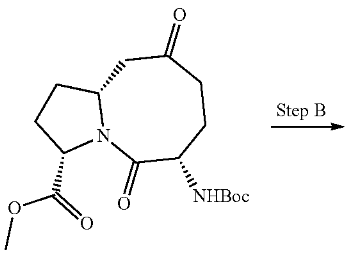

3

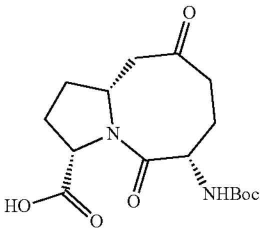

4

To a solution of methyl (3S,6S,10aR)-6-((tert-butoxycarbonyl)amino)-5,9-dioxodecahydropyrrolo[1,2-a]azocine-3-carboxylate (3, 30 g, 84.7 mmol, 1.0 eq.) in THF/$H_2O$ (300 mL/60 mL) was added LiOH·$H_2O$ (10.4 g, 254 mmol, 3.0 eq.), and the resulting mixture was stirred at room temperature for 2 hrs. After completion, the reaction mixture was cooled down in an ice bath, then neutralized carefully with HCl (aq., 1 N) until the pH was adjusted to pH=5-6. The resulting mixture was extracted with DCM (300 mL×3), and the combined organic layers were washed with brine (100 mL×2), dried over with anhydrous $Na_2SO_4$, then concentrated under reduced pressure to give crude (3S,6S,10aR)-6-((tert-butoxycarbonyl)amino)-5,9-dioxodecahydropyrrolo[1,2-a]azocine-3-carboxylic acid (4, 26 g, quant.) as a white solid, which was used in next Step directly without further purification. LCMS (ESI): m/z=341 $[M+H]^+$.

Step C: tert-butyl ((3S,6S,10aR)-5,9-dioxo-3-((S)-6-phenyl-4-azaspiro[2.4]heptane-4-carbonyl)decahydropyrrolo[1,2-a]azocin-6-yl)carbamate

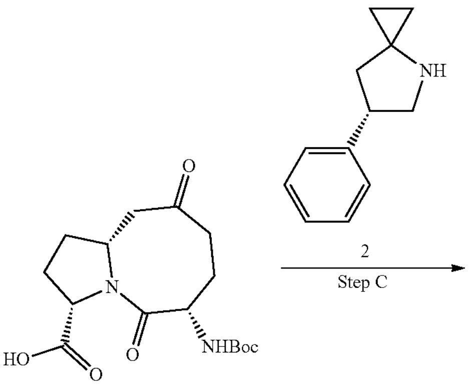

4

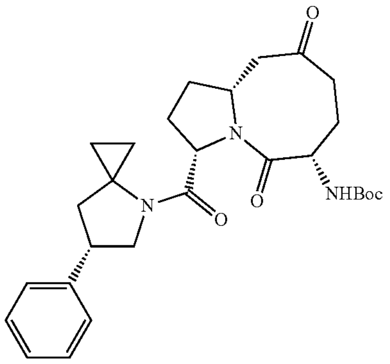

Int 1

A solution of (3S,6S,10aR)-6-((tert-butoxycarbonyl)amino)-5,9-dioxodecahydropyrrolo[1,2-a]azocine-3-carboxylic acid (4, 26 g, 76.5 mmol, 1.0 eq.) and HATU (32 g, 84.2 mmol, 1.1 eq.) in DMF (500 mL) was stirred for 15 min, then TEA (38.6 g, 383 mmol, 5.0 eq.) and (S)-6-phenyl-4-azaspiro[2.4]heptane (TFA salt) (2, 13.3 g, 76.5 mmol, 1.0 eq.) were added, and the resulting mixture was stirred at room temperature for additional 2 hrs. After completion, the reaction was poured into $H_2O$ (1 L), and the suspension was filtered. The wet cake was slurried with $H_2O$ (1 L) and then filtered. The filter cake was washed with $H_2O$ (100 mL×3). The wet cake was dried to afford tert-butyl ((3S,6S,10aR)-5,9-dioxo-3-((S)-6-phenyl-4-azaspiro[2.4]heptane-4-carbonyl)decahydropyrrolo[1,2-a]azocin-6-yl)carbamate (Int 1, 34 g, 68.6 mmol, 90%) as a white solid. LCMS (ESI): m/z=496 $[M+H]^+$.

Preparation of tert-butyl ((3S,6S,9S,10aR)-9-morpholino-5-oxo-3-((S)-6-phenyl-4-azaspiro[2.4]heptane-4-carbonyl)decahydropyrrolo[1,2-a]azocin-6-yl)carbamate

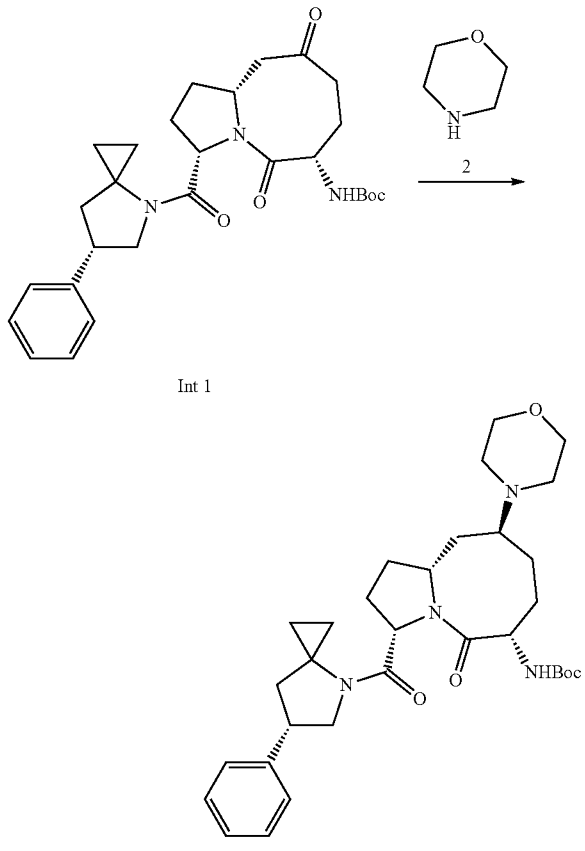

Int 1

3

To a mixture of tert-butyl ((3S,6S,10aR)-5,9-dioxo-3-((S)-6-phenyl-4-azaspiro[2.4]heptane-4-carbonyl)decahydropyrrolo[1,2-a]azocin-6-yl)carbamate (Int 1, 3 g, 6.06 mmol, 1.0 eq.) and morpholine (2, 2.64 g, 30.3 mmol, 5 eq.) in MeOH (100 mL) was added $ZnCl_2$ (8.12 g, 60.6 mmol, 10 eq.). The resulting mixture was stirred at 55° C. for 1 hr under $N_2$, then $NaBH_3CN$ (1.27 g, 20.2 mmol, 10.0 eq.) was added to the reaction mixture in five portions (2 eq/hour) and the resulting mixture was stirred at 55° C. overnight under $N_2$. After completion, the reaction mixture was concentrated under reduced pressure to remove MeOH (15 mL left). The residue was poured into $H_2O$ (150 mL) and then the suspension was filtered. The wet cake was dissolved in DCM (100 mL), dried over anhydrous $Na_2SO_4$ and concentrated under reduced pressure. The filtrate above was then extracted with DCM (50 mL×3). The organic layers were combined and washed with brine (100 mL), dried over anhydrous $Na_2SO_4$, and concentrated under reduced pressure. The residue was purified by reverse phase chromatography using a 120 g C18 cartridge eluting with a gradient of 5-80% MeCN in water (with 0.1% $NH_4OH$) to afford the desired product as a white solid (3, 1.48 g, 2.61 mmol, 43% yield). LCMS (ESI): m/z=567.2 $[M+H]^+$.

Preparation of (3S,6S,9S,10aR)-6-amino-9-((3,3-difluoropropyl)(methyl)amino)-3-((S)-6-phenyl-4-azaspiro[2.4]heptane-4-carbonyl)octahydropyrrolo[1,2-a]azocin-5(1H)-one (5)

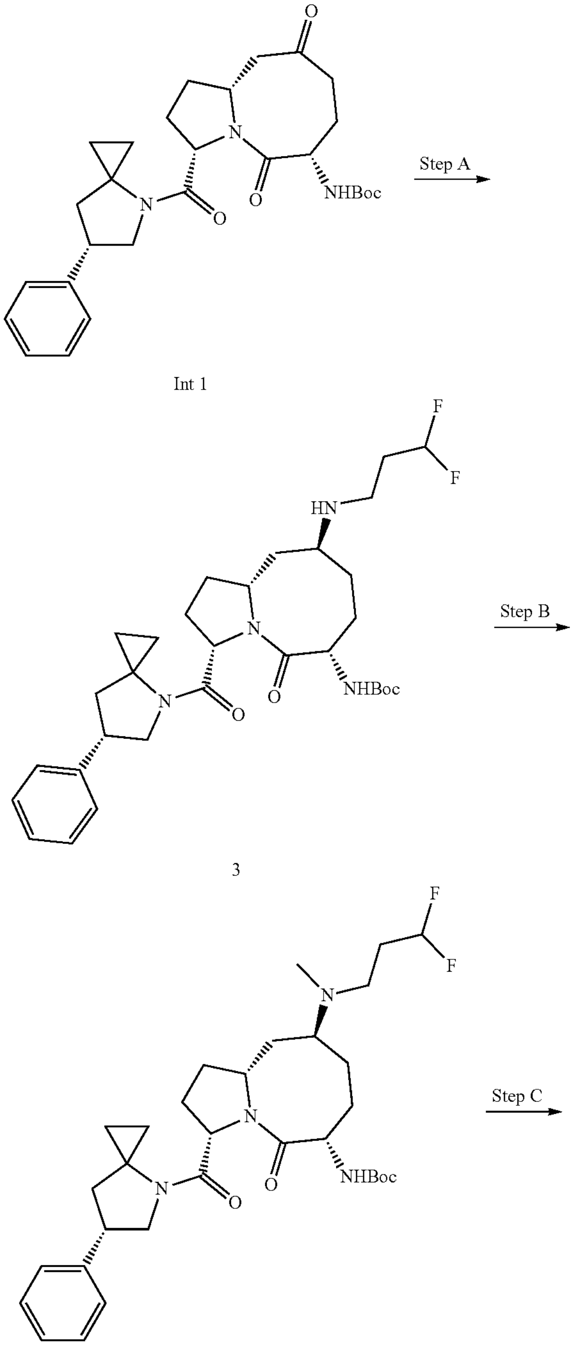

Int 1

3

4

-continued

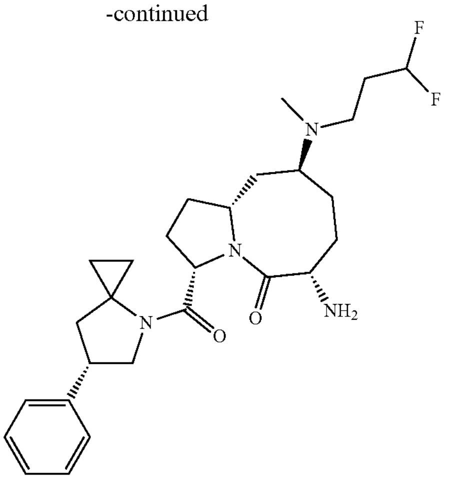

5

Step A: tert-butyl ((3S,6S,10aR)-9-((3,3-difluoropropyl)amino)-5-oxo-3-((S)-6-phenyl-4-azaspiro[2.4]heptane-4-carbonyl)decahydropyrrolo[1,2-a]azocin-6-yl)carbamate

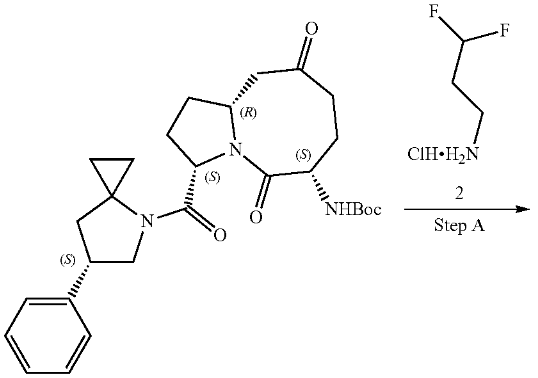

Int 1

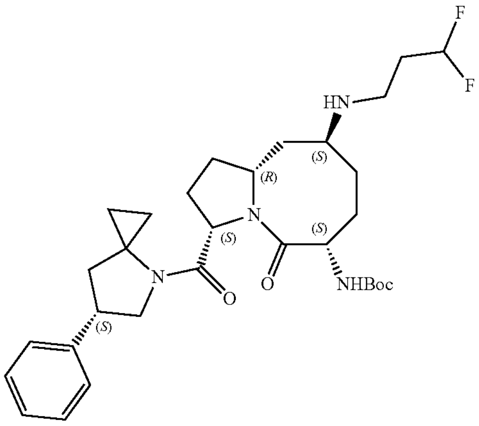

3

To a mixture of tert-butyl ((3S,6S,10aR)-5,9-dioxo-3-((S)-6-phenyl-4-azaspiro[2.4]heptane-4-carbonyl)decahydropyrrolo[1,2-a]azocin-6-yl)carbamate (Int 1, 1 g, 2.02 mmol, 1.0 eq.) and 3,3-difluoropropan-1-amine hydrochloride (2, 0.35 g, 3.64 mmol, 1.8 eq.) in MeOH (20 mL) was added $ZnCl_2$ (1.35 g, 10.1 mmol, 5.0 eq.). The resulting mixture was stirred at 55° C. for 1 hr under $N_2$, then $NaBH_3CN$ (1.27 g, 20.2 mmol, 10.0 eq.) was added to the reaction mixture in five portions and the resulting mixture was stirred at 55° C. overnight under $N_2$. The reaction mixture was used in the next Step directly without further purification. LCMS (ESI): m/z=575.4[M+H]$^+$.

Step B: tert-butyl ((3S,6S,9S,10aR)-9-((3,3-difluoropropyl)(methyl)amino)-5-oxo-3-((S)-6-phenyl-4-azaspiro[2.4]heptane-4-carbonyl)decahydropyrrolo[1,2-a]azocin-6-yl)carbamate

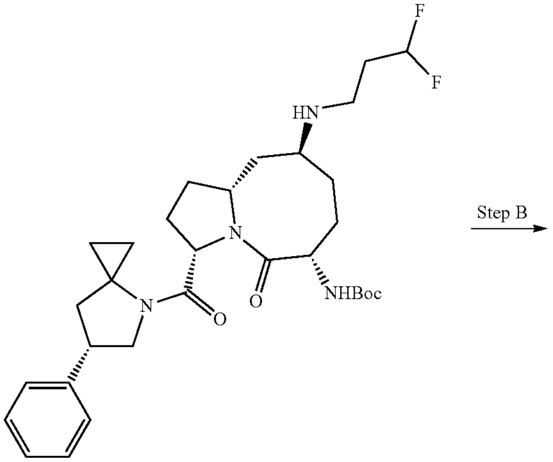

3

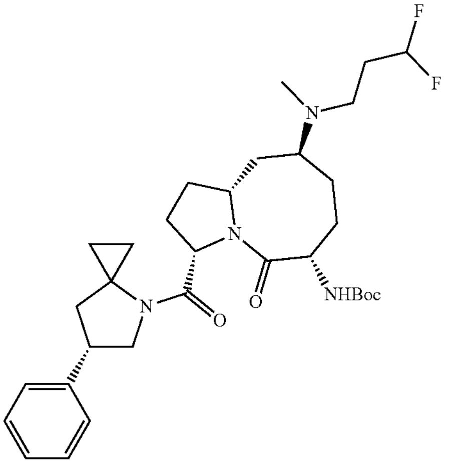

major
4

To a mixture of tert-butyl ((3S,6S,10aR)-9-((3,3-difluoropropyl)amino)-5-oxo-3-((S)-6-phenyl-4-azaspiro[2.4]heptane-4-carbonyl)decahydropyrrolo[1,2-a]azocin-6-yl) carbamate (3, Step B above, crude.) were added $CH_2O$ (2 mL, 30 wt % in water) and $NaBH_3CN$ (0.26 g, 4.04 mmol, 2.0 eq.). The resulting mixture was stirred at 55° C. for 30 min under $N_2$. After completion, the reaction mixture was concentrated under reduced pressure to remove MeOH. The residue was poured into $H_2O$ (50 mL) and then the suspension was filtered. The wet cake was dissolved in DCM (100 mL), dried over anhydrous $Na_2SO_4$ and concentrated under reduced pressure. The filtrate above was then extracted with DCM (20 mL×3). The organic layers were combined and washed with brine (50 mL), dried over anhydrous $Na_2SO_4$, and concentrated under reduced pressure. The residue was purified by reverse phase chromatography using a 120 g C18 cartridge eluting with a gradient of 5-80% ACN in water (with 0.1% $NH_3H_2O$) to afford the desired product as a white solid (4, 700 mg, 12.0 mmol, 59% yield over 2 Steps) LCMS (ESI): m/z=589.2 $[M+H]^+$.

Step C: (3S,6S,9S,10aR)-6-amino-9-((3,3-difluoropropyl)(methyl)amino)-3-((S)-6-phenyl-4-azaspiro[2.4]heptane-4-carbonyl)octahydropyrrolo[1,2-a]azocin-5(1H)-one

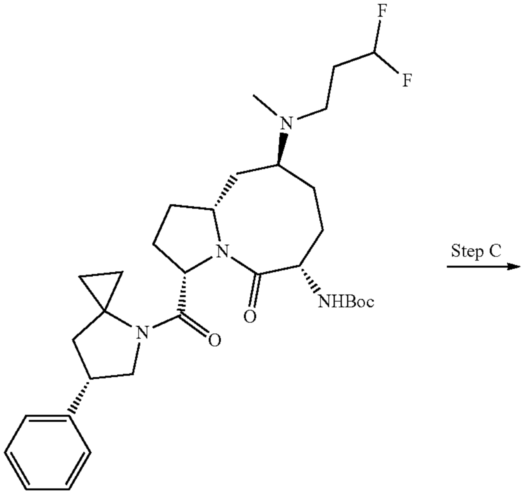

4

-continued

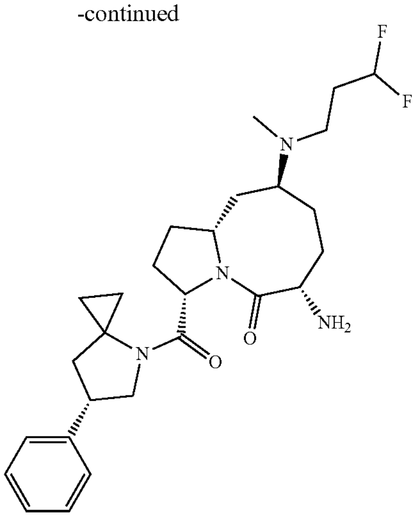

5

To a solution of tert-butyl ((3S,6S,9S,10aR)-9-((3,3-difluoropropyl)(methyl)amino)-5-oxo-3-((S)-6-phenyl-4-azaspiro[2.4]heptane-4-carbonyl)decahydropyrrolo[1,2-a]azocin-6-yl)carbamate (4, 600 mg, 1.02 mmol, 1.0 eq.) in DCM (10 mL) was added TFA (3 mL), and the resulting mixture was stirred at room temperature for 2 hrs. After completion, the reaction mixture concentrated under reduced pressure to give crude (3S,6S,9S,10aR)-6-amino-9-((3,3-difluoropropyl)(methyl)amino)-3-((S)-6-phenyl-4-azaspiro[2.4]heptane-4-carbonyl)octahydropyrrolo[1,2-a]azocin-5(1H)-one (TFA salt) (5, 600 mg, quant.) as a white solid, which was used in next Step directly without further purification. LCMS (ESI): m/z=489.4 $[M+H]^+$.

Preparation of propyl (((R)-(2-(((3S,6S,9S,10aR)-9-((3,3-difluoropropyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)(phenoxy)phosphoryl)-L-alaninate (prodrug C1), ((R)-(2-(((3S,6S,9S,10aR)-9-((3,3-difluoropropyl)(methyl)amino)-5-oxo-3-((R)-6-phenyl-4-azaspiro[2.4]heptane-4-carbonyl)decahydropyrrolo[1,2-a]azocin-6-yl)carbamoyl)benzo[b]thiophen-5-yl)fluoromethyl)phosphonic acid (parent drug A20)

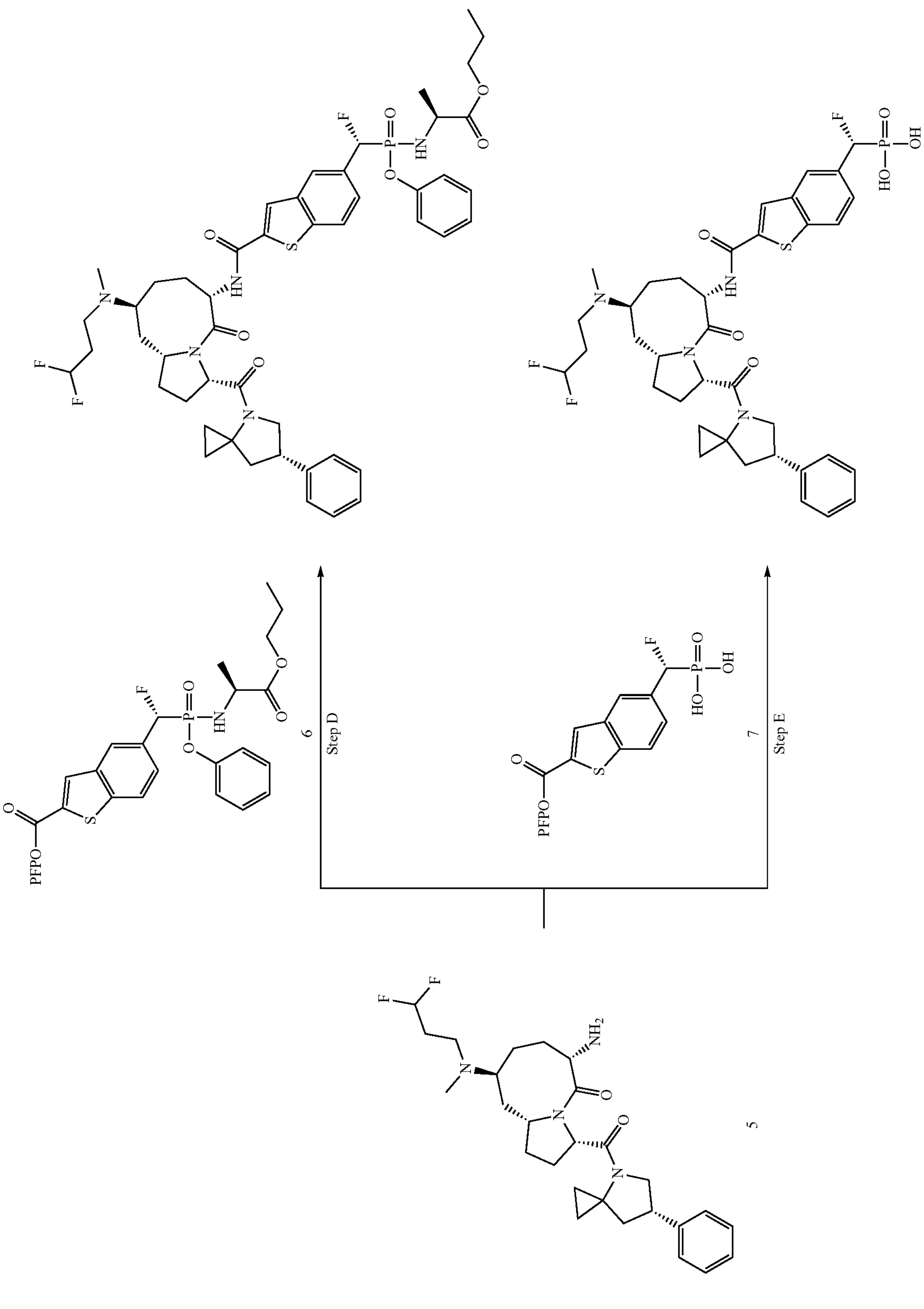
6
Step D
7
Step E
5

Step D: propyl (((R)-(2-(((3S,6S,9S,10aR)-9-((3,3-difluoropropyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)(phenoxy)phosphoryl)-L-alaninate (Compound C1)

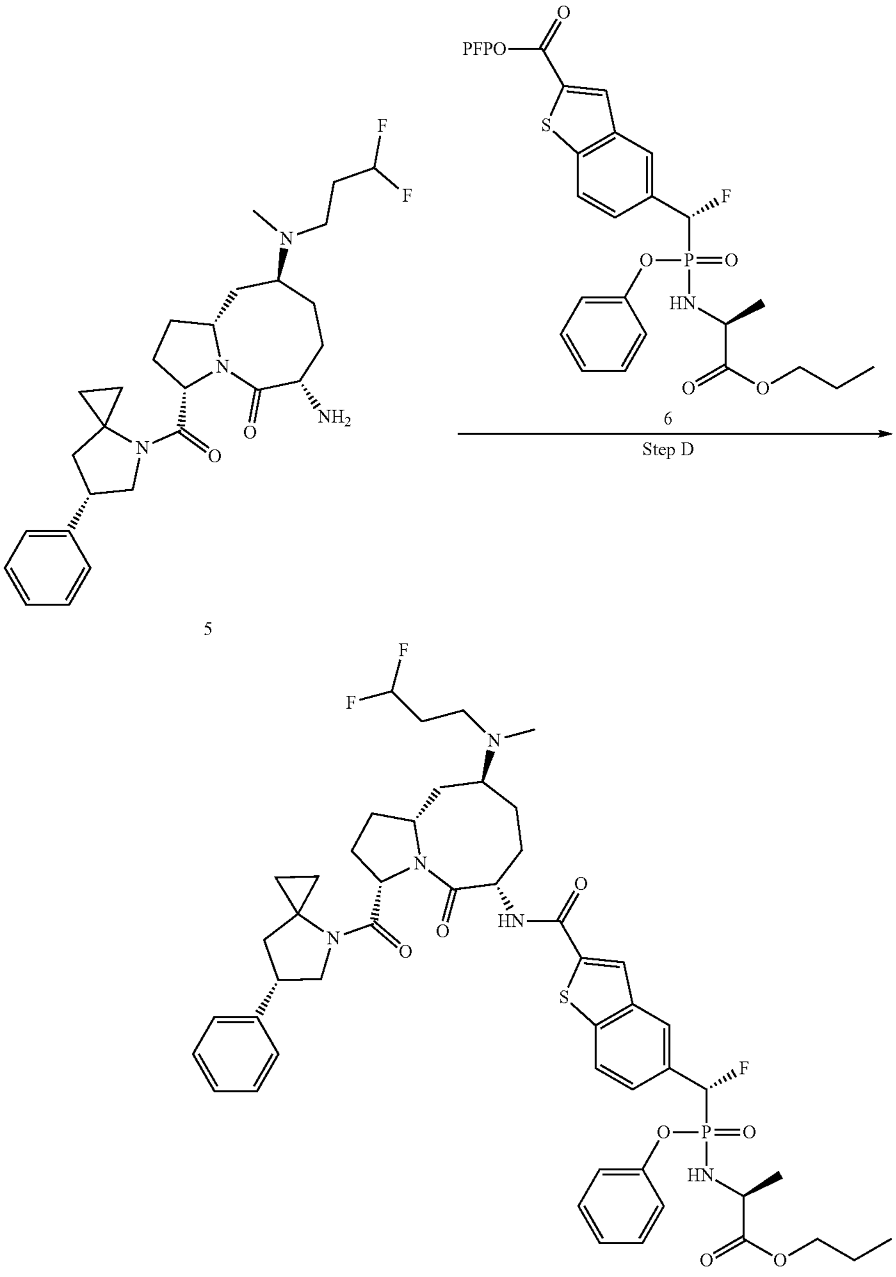

5

To a solution of (3S,6S,9S,10aR)-6-amino-9-((3,3-difluoropropyl)(methyl)amino)-3-((S)-6-phenyl-4-azaspiro[2.4]heptane-4-carbonyl)octahydropyrrolo[1,2-a]azocin-5(1H)-one (TFA salt) (5, 600 mg, 1.02 mmol, 1.0 eq.) and TEA (515 mg, 5.1 mmol, 5.0 eq.) in DMF (5 mL) was added perfluorophenyl 5-((1R)-fluoro((((S)-1-oxo-1-propoxypropan-2-yl)amino)(phenoxy)phosphoryl)methyl)benzo[b]thiophene-2-carboxylate (6, 650 mg, 1.02 mmol, 1.0 eq.) at room temperature. The resulting mixture was stirred at room temperature for additional 2 hrs. After completion, the reaction mixture was poured into $H_2O$ (50 mL) and then the suspension was filtered. The wet cake was dissolved in DCM (100 mL), dried over anhydrous $Na_2SO_4$ and concentrated under reduced pressure. The mixture was dissolved in DMF (30 mL) and purified by reverse phase chromatography using a 120 g C18 cartridge eluting with a gradient of 5-80% ACN in water (with 0.1% TFA) to afford the desired product (700 mg, TFA salt) as a white solid. The TFA salt was dissolved in DCM (50 mL) and washed with 5% $NaHCO_3$ (aq.) (50 mL×4); following by deionized water (50 mL×4). The combined aqueous layers were was extracted with DCM (50 mL×2), then the combined DCM layers concentrated under reduced pressure to give propyl (((R)-(2-(((3S,6S,9S,10aR)-9-((3,3-difluoropropyl)(methyl)

amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)(phenoxy)phosphoryl)-L-alaninate (520 mg, 53.7% yield over 2 Steps) as a white solid. $^1$H NMR (400 MHz, DMSO) δ 8.82-8.71 (m, 1H), 8.27 (s, 1H), 8.09-8.03 (m, 2H), 7.64-7.57 (m, 1H), 7.38-7.28 (m, 6H), 7.24-7.14 (m, 4H), 6.26-6.20 (m, 1H), 6.16-5.92 (m, 2H), 4.83-4.72 (m, 1H), 4.53-4.42 (m, 1H), 4.36-4.26 (m, 1H), 4.16-4.06 (m, 1H), 3.95-3.70 (m, 4H), 3.58-3.49 (m, 1H), 3.08-2.90 (m, 1H), 2.45-2.32 (m, 2H), 2.25-2.18 (m, 1H), 2.17-1.36 (m, 20H), 1.17-1.09 (m, 3H), 0.85-0.75 (m, 3H), 0.52-0.40 (m, 2H). LCMS (ESI): m/z=950.8 [M+H]$^+$.

Step E: ((R)-(2-(((3S,6S,9S,10a10aR)-9-((3,3-difluoropropyl)(methyl)amino)-5-oxo-3-((R)-6-phenyl-4-azaspiro[2.4]heptane-4-carbonyl)decahydropyrrolo[1,2-a]azocin-6-yl)carbamoyl)benzo[b]thiophen-5-yl)fluoromethyl)phosphonic acid (Compound A20)

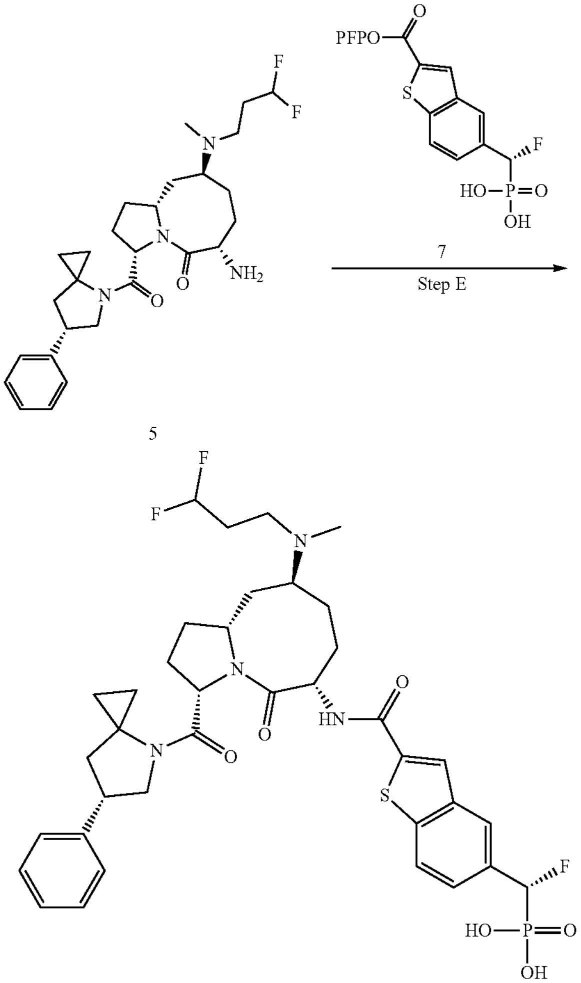

To a solution of (3S,6S,9S,10aR)-6-amino-9-((3,3-difluoropropyl)(methyl)amino)-3-((S)-6-phenyl-4-azaspiro[2.4]heptane-4-carbonyl)octahydropyrrolo[1,2-a]azocin-5(1H)-one (TFA salt) (5, 60 mg, 0.1 mmol, 1.0 eq.) and TEA (51 mg, 0.5 mmol, 5.0 eq.) in DMF (1 mL) was added (R)-(fluoro(2-((perfluorophenoxy)carbonyl)benzo[b]thiophen-5-yl)methyl)phosphonic acid (7, 65 mg, 0.1 mmol, 1.0 eq.) at room temperature. The resulting mixture was stirred at room temperature for additional 2 hrs. After completion, the reaction mixture was purified by reverse phase chromatography using a 40 g C18 cartridge eluting with a gradient of 5-50% ACN in water (with 0.1% TFA) to afford the desired product (75 mg, TFA salt) as a white solid. Then the TFA salt was dissolved in DMF (2 mL) and purified by reverse phase chromatography using a 40 g C18 cartridge eluting with a gradient of 5-50% ACN in water (with 0.1% $NH_4HCO_3$) to give ((R)-(2-(((3S,6S,9S,10aR)-9-((3,3-difluoropropyl)(methyl)amino)-5-oxo-3-((R)-6-phenyl-4-azaspiro[2.4]heptane-4-carbonyl)decahydropyrrolo[1,2-a]azocin-6-yl)carbamoyl)benzo[b]thiophen-5-yl)fluoromethyl)phosphonic acid (free base) (45 mg, 58.5% yield over 2 Steps) as a white solid. $^1$H NMR (400 MHz, DMSO) δ 8.87-8.67 (m, 1H), 8.24 (s, 1H), 8.03 (d, J=8.4 Hz, 1H), 7.98 (s, 1H), 7.53 (d, J=8.4 Hz, 1H), 7.38-7.29 (m, 4H), 7.26-7.19 (m, 1H), 6.40-6.03 (m, 1H), 5.91-5.75 (m, 1H), 4.81 (s, 1H), 4.60-4.50 (m, 2H), 4.17-4.09 (m, 1H), 3.85-3.70 (m, 2H), 3.57-3.51 (m, 1H), 3.35-3.19 (m, 2H), 2.80-2.69 (m, 3H), 2.49-2.42 (m, 1H), 2.39-1.70 (m, 14H), 1.56 (s, 1H), 0.59-0.42 (m, 2H). LCMS (ESI): m/z=761.5 [M+H]$^+$.

Preparation of (((R)-(2-(((3S,6S,9S,10aR)-9-((3,3-difluoropropyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)(hydroxy)phosphoryl)-L-alanine

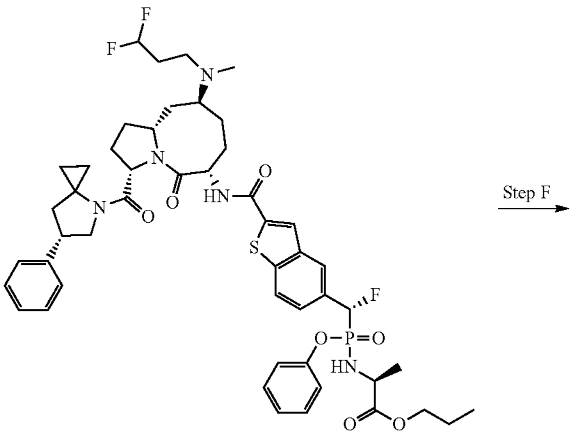

-continued

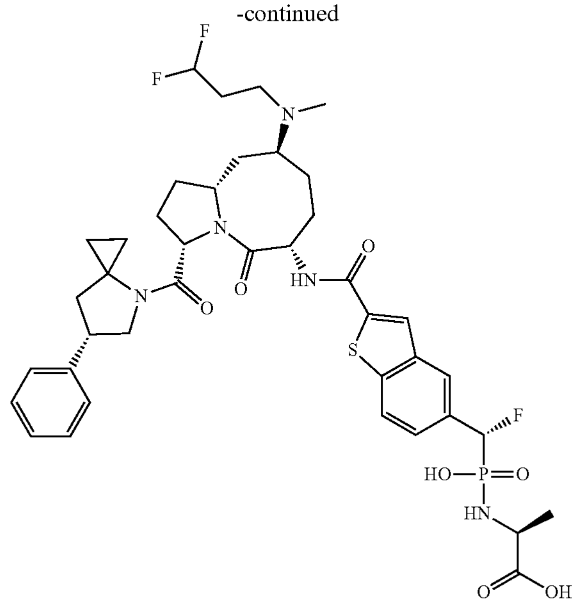

Step F: (((R)-(2-(((3S,6S,9S,10aR)-9-((3,3-difluoropropyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)(hydroxy)phosphoryl)-L-alanine (Compound B6)

To a solution of propyl (((R)-(2-(((3S,6S,9S,10aR)-9-((3,3-difluoropropyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)(phenoxy)phosphoryl)-L-alaninate (200 mg, 0.21 mmol, 1.00 eq) in THF (3 mL) was added LiOH·$H_2O$ (2 M, 1 mL, 10 eq) at 20° C. and stirred at 20° C. for 2 hrs. LCMS showed that SM was consumed and desired MS (0%-30% method) was detected. The mixture was concentrated to remove methanol. The water phase was purified by prep-HPLC (column: Waters Xbridge C18 150*50 mm*10 um; mobile phase: [water($NH_4HCO_3$)-ACN]; gradient: 10%-30% B over 10 min) and lyophilized to give (((R)-(2-(((3S,6S,9S,10aR)-9-((3,3-difluoropropyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)(hydroxy)phosphoryl)-L-alanine (110 mg, 132 mol, 63% yield,) as a white solid. $^1H$ NMR (400 MHz, DMSO) δ 8.70 (d, J=7.4 Hz, 1H), 8.20 (s, 1H), 7.92 (d, J=8.1 Hz, 2H), 7.54 (d, J=8.5 Hz, 1H), 7.38-7.28 (m, 4H), 7.22 (t, J=7.1 Hz, 1H), 6.10 (t, J=57.2 Hz, 1H), 5.61 (dd, J=45.7, 7.6 Hz, 1H), 4.81-4.69 (m, 1H), 4.49 (t, J=8.3 Hz, 1H), 4.34 (s, 1H), 4.10 (t, J=8.6 Hz, 1H), 3.74 (t, J=9.8 Hz, 1H), 3.58-3.37 (m, 2H), 3.28-2.98 (m, 2H), 2.45-2.30 (m, 2H), 2.29-2.15 (m, 3H), 2.14-2.05 (m, 2H), 2.04-1.93 (m, 4H), 1.92-1.35 (m, 9H), 1.06 (d, J=6.8 Hz, 3H), 0.53-0.41 (m, 2H). LCMS: m/z=832.5 (M+H)+.

Representative Procedures for Syntheses of Cores:

Synthesis of (3S,6S,10aS)-6-((tert-butoxycarbonyl)amino)-5-oxodecahydropyrrolo[1,2-a]azocine-3-carboxylic acid

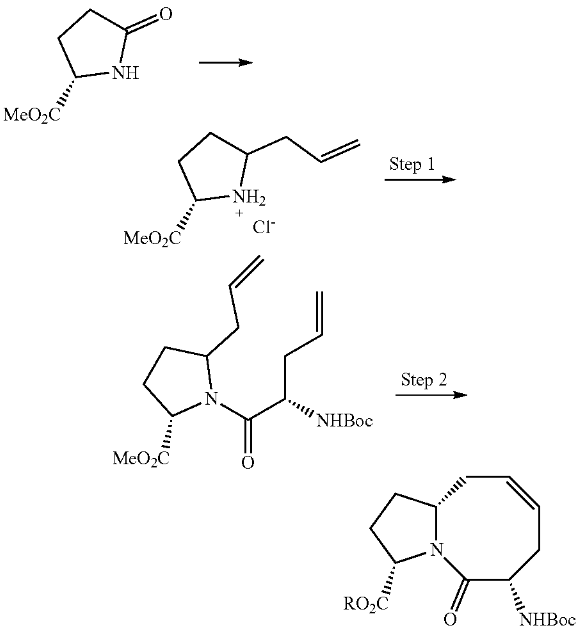

Step 1: Preparation of methyl (2S)-5-allyl-1-((S)-2-((tert-butoxycarbonyl)amino)pent-4-enoyl)pyrrolidine-2-carboxylate To a cooled (0° C.) solution of methyl (2S)-5-allylpyrrolidine-2-carboxylate hydrochloride (200 g, 972 mmol, 1.00 eq) and (S)-2-((tert-butoxycarbonyl)amino)pent-4-enoic acid (209 g, 972 mmol, 1.00 eq) in $CH_2Cl_2$ (1.60 L) was added $Et_3N$ (406 mL, 2.92 mol, 3.00 eq) and 2-chloro-1-methylpyridinium iodide (CMPI) (273 g, 1.07 mol, 1.10 eq). The solution was warmed to 25° C. and stirred for 1 h. The mixture was poured into water (5.0 L), extracted with $CH_2Cl_2$ (2.00 L×3). The combined organic layers were washed with brine (2.0 L), dried over $Na_2SO_4$, filtered and concentrated under reduced pressure. Six individual batches of equal scale were performed in parallel and combined during work up. The resulting residue was purified by column chromatography (petroleum ether:EtOAc=100:1 to 10:1) to give methyl (2S)-5-allyl-1-((S)-2-((tert-butoxycarbonyl)amino)pent-4-enoyl)pyrrolidine-2-carboxylate (1.18 kg, 3.22 mol, 55.2% yield) as yellow oil. $^1H$ NMR (400 MHz, $CDCl_3$) δ 5.84-5.78 (m, 2H), 5.17-4.99 (m, 5H), 4.50-4.34 (m, 3H), 3.76-3.70 (m, 3H), 2.50-2.15 (m, 6H), 1.96-1.91 (m, 2H), 1.41 (s, 9H).

Step 2: Preparation of methyl (3S,6S,10aR,Z)-6-((tert-butoxycarbonyl)amino)-5-oxo-1,2,3,5,6,7,10,10a-octahydropyrrolo[1,2-a]azocine-3-carboxylate To a solution of methyl (2S)-5-allyl-1-((S)-2-((tert-butoxycarbonyl)amino)pent-4-enoyl)pyrrolidine-2-carboxylate (200 g, 546 mmol, 1.00 eq) in $CH_2Cl_2$ (2.00 L) was added 1st generation Grubbs catalyst (44.9 g, 54.6 mmol, 0.10 eq) at 25° C. The solution was subsequently heated to 50° C. and stirred for 36 h. Six individual batches of equal scale were performed in parallel and combined during work up. The combined reaction mixtures were concentrated to give a residue. The residue was purified by column chromatography (petroleum ether:EtOAc=100:1 to 0:1) twice to give a crude product. The crude product was triturated with petroleum ether (2.00 L) for 12 h and filtered. The filter cake was dried under reduced pressure to give methyl (3S,6S,10aR,Z)-6-((tert-butoxycarbonyl)amino)-5-oxo-1,2,3,5,6,7,10,10a-octahydropyrrolo[1,2-a]azocine-3-carboxylate (510 g, 1.40 mol, 51.3% yield, 92.9% purity) as a solid. LCMS (ESI) m/z=361.2 $[M+Na]^+$; $^1H$ NMR (400 MHz, $CDCl_3$) δ 5.82-5.80 (m, 1H), 5.73-5.71 (m, 1H), 5.58-5.56 (m, 1H), 4.88-4.85 (m, 1H), 4.52-4.49 (m, 1H), 4.16-4.14 (m, 1H), 3.71 (s, 3H), 2.81-2.74 (m, 2H), 2.45-2.38 (m, 1H), 2.33-2.24 (m, 1H), 2.14-2.05 (m, 2H), 1.98-1.93 (m, 2H), 1.43 (s, 9H).

Synthesis of (3S,6S,9R,10aR)-6-{[(tert-butoxy)carbonyl]amino}-9-hydroxy-5-oxo-decahydropyrrolo[1,2-a]azocine-3-carboxylic acid, (3S,6S,9S,10aR)-6-((tert-butoxycarbonyl)amino)-9-hydroxy-5-oxodecahydropyrrolo[1,2-a]azocine-3-carboxylic acid, (3S,6S,8S,10aR)-6-((tert-butoxycarbonyl)amino)-8-hydroxy-5-oxodecahydropyrrolo[1,2-a]azocine-3-carboxylic acid, (3S,6S,8R,10aR)-6-((tert-butoxycarbonyl)amino)-8-hydroxy-5-oxodecahydropyrrolo[1,2-a]azocine-3-carboxylic acid

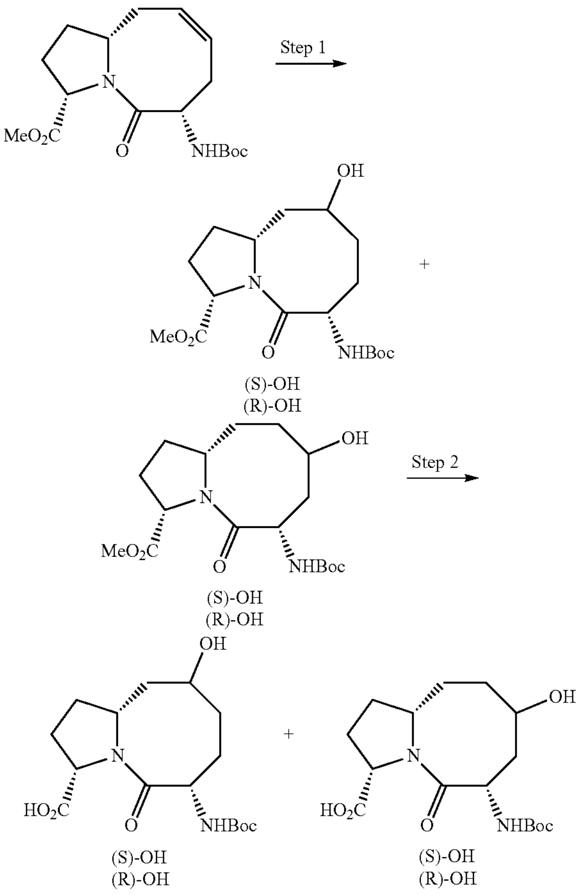

Step 1: Preparation of methyl (3S,6S,10aR)-6-((tert-butoxycarbonyl)amino)-9-hydroxy-5-oxodecahydro-pyrrolo[1,2-a]azocine-3-carboxylate and methyl (3S,6S,10aR)-6-((tert-butoxycarbonyl)amino)-8-hydroxy-5-oxodecahydropyrrolo[1,2-a]azocine-3-carboxylate

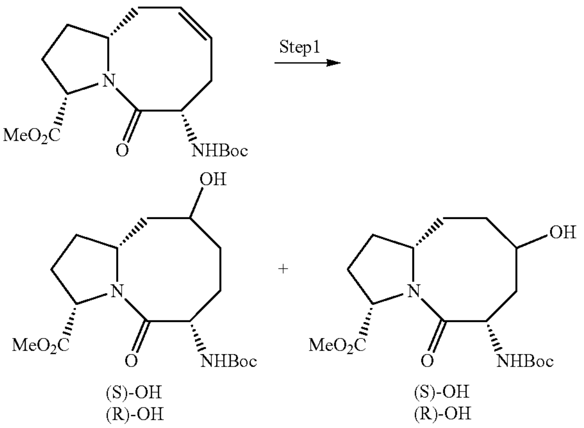

Methyl (3S,6S,10aR)-6-((tert-butoxycarbonyl)amino)-9-hydroxy-5-oxodecahydropyrrolo[1,2-a]azocine-3-carboxylate and methyl (3S,6S,10aR)-6-((tert-butoxycarbonyl)amino)-8-hydroxy-5-oxodecahydropyrrolo[1,2-a]azocine-3-carboxylate were prepared starting from methyl (3S,6S,10aR,Z)-6-((tert-butoxycarbonyl)amino)-5-oxo-1,2,3,5,6,7,10,10a-octahydropyrrolo[1,2-a]azocine-3-carboxylate and utilizing similar protocols established in Journal of Medicinal Chemistry (2010), 53(17), 6361-6367.

The mixture of alcohol diastereoisomers and regioisomers were separated by reverse phase chromatography [C18 cartridge eluting with a gradient of 5-40% MeOH in water (with 0.1% formic acid)] followed by chiral SFC separation [Lux i-Cellulose-5 21.2×250 mm 5 um column, column temp=40° C., flow rate 75 mL/min, 20% MeOH, cycle time: 5 min]. A representative reaction starting from methyl (3S,6S,10aR,Z)-6-((tert-butoxycarbonyl)amino)-5-oxo-1,2,3,5,6,7,10,10a-octahydropyrrolo[1,2-a]azocine-3-carboxylate (4.3 g, 12.7 mmol) afforded the following products:

Peak 1: Methyl (3S,6S,9R,10aR)-6-{[(tert-butoxy)carbonyl]amino}-9-hydroxy-5-oxo-decahydropyrrolo[1,2-a]azocine-3-carboxylate (760 mg, 2.13 mmol, 16.8% yield) as a white solid. LCMS (ESI) m/z=357.2 $[M+H]^+$.

Peak 2: Methyl (3S,6S,9S,10aR)-6-{[(tert-butoxy)carbonyl]amino}-9-hydroxy-5-oxo-decahydropyrrolo[1,2-a]azocine-3-carboxylate (375 mg, 19% yield) as a clear thick oil. LCMS (ESI) m/z=357.2 $[M+H]^+$.

Peak 3: Methyl (3S,6S,8R,10aR)-6-{[(tert-butoxy)carbonyl]amino}-8-hydroxy-5-oxo-decahydropyrrolo[1,2-a]azocine-3-carboxylate (795 mg, 40% yield) as a white foam. LCMS (ESI) m/z=357.2 $[M+H]^+$.

Peak 4: Methyl (3S,6S,8S,10aR)-6-{[(tert-butoxy)carbonyl]amino}-8-hydroxy-5-oxo-decahydropyrrolo[1,2-a]azocine-3-carboxylate (600 mg, 30% yield) as a white solid. LCMS (ESI) m/z=357.2 $[M+H]^+$.

Step 2: Preparation of (3S,6S,9R,10aR)-6-{[(tert-Butoxy)carbonyl]amino}-9-hydroxy-5-oxo-decahydropyrrolo[1,2-a]azocine-3-carboxylic acid

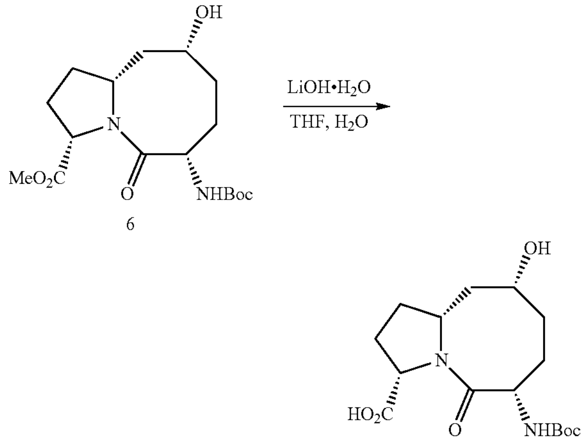

6

C9

To a solution of methyl (3S,6S,9R,10aR)-6-{[(tert-butoxy)carbonyl]amino}-9-hydroxy-5-oxo-decahydropyrrolo[1,2-a]azocine-3-carboxylate (Peak 1) (1.08 g, 3.03 mmol, 1 eq) in a mixture of THF (24 mL) and water (8 mL) was added LiOH—$H_2O$ (380 mg, 9.08 mmol, 3.0 eq). The reaction mixture was stirred at room temperature for 2 hours. The reaction was subsequently concentrated under reduced pressure to remove tetrahydrofuran. The crude residue was purified by reverse phase chromatography [C18 cartridge eluting with a gradient of 5-60% Acetonitrile in water (with 0.1% formic acid)] to give (3S,6S,9R,10aR)-6-{[(tert-butoxy)carbonyl]amino}-9-hydroxy-5-oxo-decahydropyrrolo[1,2-a]azocine-3-carboxylic acid (780 mg, 76% yield) as a white solid. LCMS (ESI) m/z=343.2 $[M+H]^+$.

The intermediates in the table below were prepared according to the general procedure described above starting from the appropriate starting materials.

| Name | Structure | LCMS |
|---|---|---|
| (3S,6S,9S,10aR)-6-((tert-butoxycarbonyl)amino)-9-hydroxy-5-oxodecahydropyrrolo[1,2-a]azocine-3-carboxylic acid | 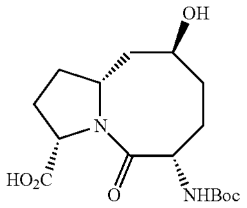 [SMILES: CC(C)(C)OC(=O)N[C@H]1CC[C@H](O)C[C@H]2CC[C@@H](C(=O)O)N2C1=O] Peak 2 of starting material core used for synthesis | 343.2 $[M + H]^+$ |
| (3S,6S,8S,10aR)-6-((tert-butoxycarbonyl)amino)-8-hydroxy-5-oxodecahydropyrrolo[1,2-a]azocine-3-carboxylic acid | 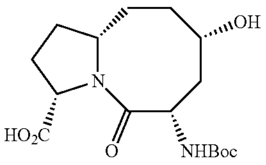 [SMILES: CC(C)(C)OC(=O)N[C@H]1C[C@@H](O)CC[C@H]2CC[C@@H](C(=O)O)N2C1=O] Peak 4 of starting material core used for synthesis | 343.2 $[M + H]^+$ |
| (3S,6S,8R,10aR)-6-((tert-butoxycarbonyl)amino)-8-hydroxy-5-oxodecahydropyrrolo[1,2-a]azocine-3-carboxylic acid | 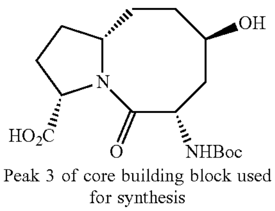 Peak 3 of core building block used for synthesis | 343.2 $[M + H]^+$ |

Synthesis of methyl (3S,6S,10aR)-6-{[(tert-butoxy)carbonyl]amino}-5,9-dioxo-decahydropyrrolo[1,2-a]azocine-3-carboxylate and methyl (3S,6S,10aR)-6-{[(tert-butoxy)carbonyl]amino}-5,8-dioxo-decahydropyrrolo[1,2-a]azocine-3-carboxylate

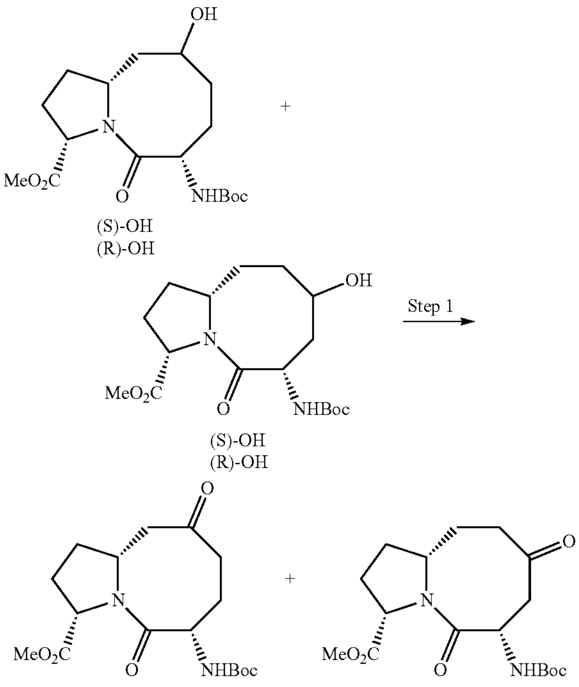

Methyl (3S,6S,10aR)-6-{[(tert-butoxy)carbonyl]amino}-5,9-dioxo-decahydropyrrolo[1,2-a]azocine-3-carboxylate and methyl (3S,6S,10aR)-6-{[(tert-butoxy)carbonyl]amino}-5,8-dioxo-decahydropyrrolo[1,2-a]azocine-3-carboxylate were prepared using the protocol described in US 2009/0123480. The crude reaction mixture was purified by reverse phase chromatography using a [C18 cartridge eluting with a gradient of 5-100% acetonitrile in water (with 0.1% FA)] to give a mixture of ketone isomers (1.2 g) as a beige solid. The resultant ketone isomers were separated chiral SFC separation (Column Lux i-Cellulose-5 21.2×250 mm 5 um column, flow rate 75 mL/min, 15% MeOH) to give methyl (3S,6S,10aR)-6-{[(tert-butoxy)carbonyl]amino}-5,9-dioxo-decahydropyrrolo[1,2-a]azocine-3-carboxylate (9) (424 mg, 35.6% yield) as a white solid and methyl (3S,6S,10aR)-6-{[(tert-butoxy)carbonyl]amino}-5,8-dioxo-decahydropyrrolo[1,2-a]azocine-3-carboxylate (433 mg, 36.3% yield) as a white solid.

Methyl (3S,6S,10aR)-6-{[(tert-butoxy)carbonyl]amino}-5,9-dioxo-decahydropyrrolo[1,2-a]azocine-3-carboxylate: LCMS (ESI) m/z=299.1 $[M+H]^+$; $^1H$ NMR: (400 MHz, $CDCl_3$) δ 5.27 (d, J=8.1 Hz, 1H), 4.59 (t, J=8.7 Hz, 1H), 4.45-4.31 (m, 2H), 3.80 (s, 3H), 3.20 (td, J=12.5, 4.9 Hz, 1H), 3.06 (t, J=12.0 Hz, 1H), 2.47-2.15 (m, 5H), 2.13-2.00 (m, 1H), 1.87 (dd, J=12.1, 7.0 Hz, 1H), 1.68-1.62 (m, 1H), 1.41 (s, 9H).

Methyl (3S,6S,10aR)-6-{[(tert-butoxy)carbonyl]amino}-5,8-dioxo-decahydropyrrolo[1,2-a]azocine-3-carboxylate: LCMS (ESI) m/z=299.1 $[M+H]^+$; $^1H$ NMR: (400 MHz, $CDCl_3$) δ 5.56 (d, J=7.6 Hz, 1H), 5.13 (ddd, J=12.2, 7.6, 4.9 Hz, 1H), 4.51 (t, J=8.8 Hz, 1H), 4.33-4.23 (m, 1H), 3.73 (s, 3H), 3.07 (dd, J=13.8, 4.5 Hz, 1H), 2.96 (td, J=11.9, 2.9 Hz, 1H), 2.65-2.50 (m, 2H), 2.36-1.91 (m, 4H), 1.90-1.76 (m, 2H), 1.45 (s, 9H).

Representative Procedures for Syntheses of Pyrrolidine Groups:

Synthesis of (rel-trans)-6-phenyl-4-azaspiro[2.4]heptane-7-carbonitrile TFA salt

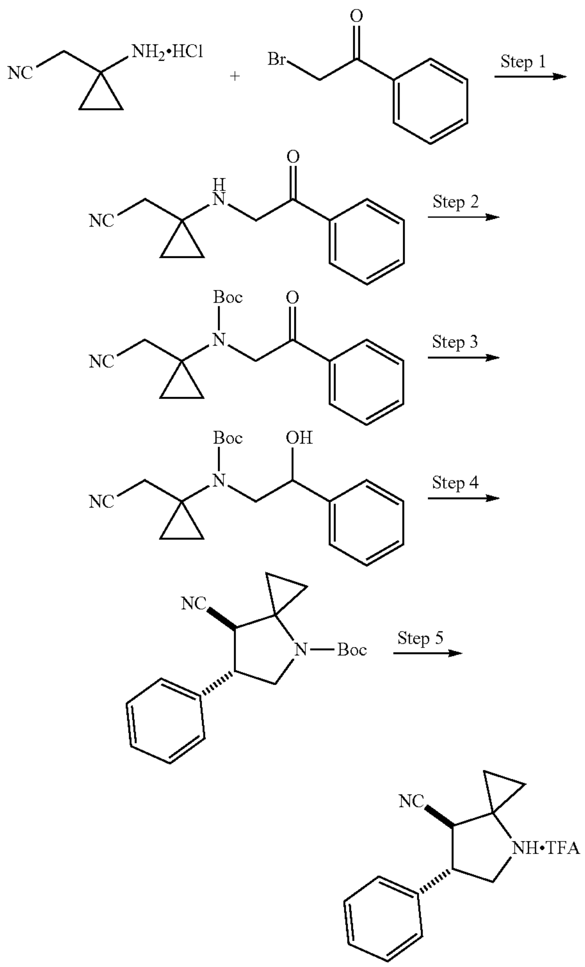

Step 1: 2-{1-[(2-oxo-2-phenylethyl)amino]cyclopropyl}acetonitrile

To a solution of 2-(1-aminocyclopropyl)acetonitrile hydrochloride (10.7 g, 81.0 mmol, 1 eq) in N,N-dimethylformamide (250 mL) were added 2-bromo-1-phenylethan-1-one (16.1 g, 81.0 mmol, 1 eq) followed by potassium phosphate tribasic (42.8 g, 202 mmol, 2.5 eq). The mixture was stirred at room temperature for 4 h. A yellowish mixture was observed over time. The reaction was quenched with the addition of 1 N HCl (600 mL, pH=1) at room temperature. The aqueous solution was washed with EtOAc (2×500 mL) then basified with 1 N NaOH aqueous solution (until pH=9, 600 mL) then extracted with EtOAc (2×600 mL). The combined organic extracts were washed with brine (2×300 mL), dried over sodium sulfate, filtered and concentrated under reduced pressure to give crude 2-{1-[(2-oxo-2-phenylethyl)amino]cyclopropyl}acetonitrile (12.5 g, 72%) as a clear pale orange liquid. LCMS (ESI) m/z=215.2 $[M+H]^+$. 1H NMR (400 MHz, DMSO-d6) δ 7.97 (d, J=7.6 Hz, 2H), 7.66 (t, J=7.1 Hz, 1H), 7.54 (t, J=7.1 Hz, 2H), 4.25 (s, 2H), 2.79 (s, 2H), 0.76-0.70 (m, 2H), 0.61-0.56 (m, 1H).

Step 2: tert-butyl N-[1-(cyanomethyl)cyclopropyl]-N-(2-oxo-2-phenylethyl)carbamate To a solution of 2-{1-[(2-oxo-2-phenylethyl)amino] cyclopropyl}acetonitrile (12.5 g, 58.3 mmol, 1 eq) in THF (150 mL) were added water (150 mL) and sodium bicarbonate (4.89 g, 58.3 mmol, 1.0 eq) followed by di-tert-butyl dicarbonate (25.3 g, 116 mmol, 2 eq). The reaction was stirred for 48 h at room temperature. The reaction was concentrated under reduced pressure (to remove THF) then diluted with EtOAc (250 mL) and water (50 mL). The phases were separated and the aqueous phase was back-extracted with EtOAc (2×250 mL). The combined organic layers were dried with sodium sulfate, filtered and concentrated under reduced pressure. The crude residue was purified flash-chromatography on silica gel eluting with 1-25% EtOAc in heptane to give tert-butyl N-[1-(cyanomethyl) cyclopropyl]-N-(2-oxo-2-phenylethyl)carbamate (14.3 g, 78%) as a white solid. LCMS (ESI) m/z=215.2 (M-Boc+2H), 259.2 (M-t-Bu+2H). $^1$H NMR (400 MHz, DMSO-$d_6$ at 80° C.) δ 7.97 (d, J=7.2 Hz, 2H), 7.67 (t, J=7.1 Hz, 1H), 7.55 (t, J=7.1 Hz, 2H), 4.73 (s, 2H), 2.87 (s, 2H), 1.54-1.24 (m, 9H), 1.04-0.99 (m, 2H), 0.94-0.90 (m, 2H).

Step 3: tert-butyl N-[1-(cyanomethyl)cyclopropyl]-N-(2-hydroxy-2-phenylethyl)carbamate To a solution of tert-butyl N-[1-(cyanomethyl)cyclopropyl]-N-(2-oxo-2-phenylethyl)carbamate (14.33 g, 45.4 mmol, 1 eq) in methanol (260 mL) at 0° C. was added sodium borohydride (1.71 g, 45.4 mmol, 1.0 eq) portion wise over 10 min. The reaction was stirred for 20 min at room temperature. The reaction was quenched with 1 N HCl (100 mL) and concentrated under reduced pressure (to remove MeOH). The crude residue was extracted with EtOAc (3×200 mL). The combined organic layers were over sodium sulfate, filtered and concentrated under reduced pressure to give tert-butyl N-[1-(cyanomethyl)cyclopropyl]-N-(2-hydroxy-2-phenylethyl)carbamate (14.7 g, 100%) as a clear pale pink oil. 1H NMR (400 MHz, DMSO-d6 at 80° C.) δ 7.38-7.23 (m, 5H), 5.51 (br. s, 1H), 4.89-4.72 (m, 1H), 3.39-3.27 (m, 1H), 3.21-3.13 (m, 1H), 3.04-2.90 (m, 1H), 2.68-2.60 (m, 1H), 1.48 (s, 9H), 0.83-0.65 (m, 4H).

Step 4: tert-butyl (rel-trans)-7-cyano-6-phenyl-4-azaspiro[2.4]heptane-4-carboxylate To a solution of tert-butyl N-[1-(cyanomethyl)cyclopropyl]-N-(2-hydroxy-2-phenylethyl)carbamate (12 g, 37.9 mmol, 1 eq) in THF (650 mL) at −15° C. were added diethyl phosphorochloridate (5.74 mL, 39.7 mmol, 1.05 eq) followed by dropwise addition of 1 M LiHMDS in THF (94.7 mL, 94.7 mmol, 2.5 eq) over 30 min. The reaction was stirred at −15° C. for 30 min. The reaction was quenched with 1N HCl (200 mL) and concentrated under reduced pressure (to remove THF). The crude residue was purified flash-chromatography on silica gel eluting with 1-8% EtOAc in heptane to give rac-tert-butyl (rel-trans)-7-cyano-6-phenyl-4-azaspiro[2.4]heptane-4-carboxylate (3.7 g, 33%) as a clear oil. LCMS (ESI) m/z=243.2 $(M\text{-}t\text{-}Bu+2H)^+$. $^1$H NMR (400 MHz, DMSO-$d_6$) δ 7.59-7.21 (m, 5H), 4.01 (d, J=10.5 Hz, 1H), 3.90 (dd, J=10.5, 7.8 Hz, 1H), 3.69 (q, J=10.2 Hz, 1H), 3.45 (t, J=10.0 Hz, 1H), 1.96-1.83 (m, 1H), 1.48-1.41 (m, 1H), 1.40-1.32 (m, 9H), 0.92-0.77 (m, 1H), 0.74-0.61 (m, 1H).

rac-tert-butyl (6R,7S)-7-cyano-6-phenyl-4-azaspiro[2.4]heptane-4-carboxylate was submitted to chiral SFC separation (SFC conditions: Column Lux Amylose 1, 30×250 mm 5 um column, 9.25 mg/inj, concentration 18.5 mg/mL, Column T=40° C., Flow rate 100 mL/min, 10% MeOH, cycle time: 2 min) to give tert-butyl (6R,7S)-7-cyano-6-phenyl-4-azaspiro[2.4]heptane-4-carboxylate (1.57 g, 5.26 mmol, 42% recovery, 99.9% ee) as a white solid and tert-butyl (6S,7R)-7-cyano-6-phenyl-4-azaspiro[2.4]heptane-4-carboxylate (1.57 g, 0.70 mmol, 42% recovery, 99.9% ee) as a white solid.

The assignment of absolute stereochemical configuration was made by comparing experimental vibrational circular dichroism (VCD) spectra with theoretical VCD spectra obtained from DFT calculations.

Step 5: (rel-trans)-6-phenyl-4-azaspiro[2.4]heptane-7-carbonitrile TFA salt

To a solution of a tert-butyl (rel-trans)-7-cyano-6-phenyl-4-azaspiro[2.4]heptane-4-carboxylate (32 mg, 0.1072 mmol, 1 eq) in methylene chloride (4 mL) was added TFA (1 mL). The reaction was stirred at room temperature for 2 h. The reaction was concentrated under reduced pressure to give crude (rel-trans)-6-phenyl-4-azaspiro[2.4]heptane-7-carbonitrile TFA salt (21.2 mg, 99%) as a thick oil. LCMS (ESI) m/z=229.2 $[M+H]^+$.

Synthesis of racemic-(6S,7R)-6-(3-methoxyphenyl)-4-azaspiro[2.4]heptane-7-carbonitrile

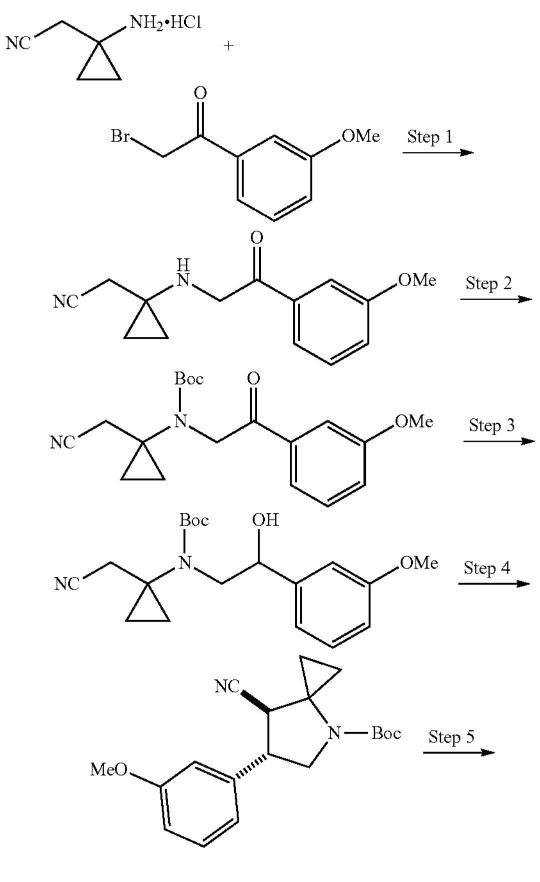

-continued

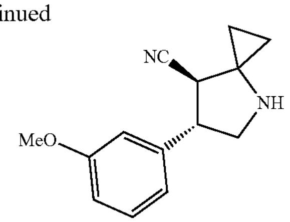

Step 1: Preparation of 2-(1-((2-(3-methoxyphenyl)-2-oxoethyl)amino)cyclopropyl)acetonitrile To a solution of 2-(1-aminocyclopropyl)acetonitrile hydrochloride (367 mg, 3.82 mmol, 1.0 eq) in DMF (10 mL) were added 2-bromo-1-(3-methoxyphenyl)ethan-1-one (918 mg, 4.01 mmol, 1.05 eq) and $NaHCO_3$ (801 mg, 9.54 mmol, 2.5 eq). The mixture was stirred at room temperature for 20 h. The reaction was diluted with MeCN and filtered. The filtrate was concentrated under reduced pressure. The crude solution was purified by reverse phase chromatography on a Cis cartridge eluting with 5-60% MeCN in basic water (10 mM $NH_4HCO_3$ (pH=10) buffer). The pure fractions were concentrated under reduced pressure to give 2-(1-((2-(3-methoxyphenyl)-2-oxoethyl)amino)cyclopropyl)acetonitrile (522 mg, 55.9%) as an orange oil. LCMS (ESI) m/z=245.1 $[M+H]^+$. $^1H$ NMR (400 MHz, $CDCl_3$) δ 7.53-7.51 (m, 1H), 7.49-7.46 (m, 1H), 7.38 (t, J=7.9 Hz, 1H), 7.16-7.10 (m, 1H), 4.25 (s, 2H), 3.86 (s, 3H), 2.58 (s, 2H), 0.89-0.84 (m, 2H), 0.74-0.70 (m, 2H).

The intermediates in the table below were prepared using the method described above in Step 1 for the preparation of 2-(1-((2-(3-methoxyphenyl)-2-oxoethyl)amino)cyclopropyl)acetonitrile utilizing the appropriate starting materials and modifications.

| Name | Structure | LCMS |
| --- | --- | --- |
| 2-(1-((2-(3-fluorophenyl)-2-oxoethyl)amino)cyclopropyl)acetonitrile | 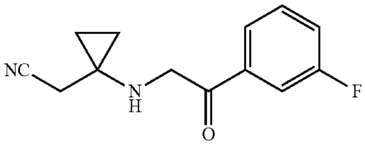 [SMILES: N#CCC1(NCC(=O)c2cccc(F)c2)CC1] | 233.2 $[M + H]^+$ |

Step 2: Preparation of tert-butyl (1-(cyanomethyl)cyclopropyl)(2-(3-methoxyphenyl)-2-oxoethyl)carbamate To a solution of 2-(1-((2-(3-methoxyphenyl)-2-oxoethyl)amino)cyclopropyl)acetonitrile (522 mg, 2.13 mmol, 1 eq) in THF (1 mL) were added water (1 mL) and $NaHCO_3$ (178 mg, 2.13 mmol, 1.0 eq) followed by di-tert-butyl dicarbonate (929 mg, 4.26 mmol, 2 eq) at 0° C. The reaction was warmed up to room temperature and stirred for 48 h at room temperature. The reaction was diluted with MeCN and filtered. The filtrate was concentrated under reduced pressure. The crude residue was purified by reverse phase chromatography on a Cis cartridge eluting with 5-80% MeCN in water (with 0.1% formic acid) to give tert-butyl (1-(cyanomethyl)cyclopropyl)(2-(3-methoxyphenyl)-2-oxoethyl)carbamate (400 mg, 54.5%) as a sticky oil. LCMS (ESI) m/z=245.2 $[(M\text{-}Boc)^+2H]^+$.

The intermediates in the table below were prepared using the method described above in Step 2 for the preparation of tert-butyl (1-(cyanomethyl)cyclopropyl)(2-(3-methoxyphenyl)-2-oxoethyl)carbamate utilizing the appropriate starting materials and modifications.

| Name | Structure | LCMS |
| --- | --- | --- |
| tert-butyl (1-(cyanomethyl)cyclopropyl)(2-(3-fluorophenyl)-2-oxoethyl)carbamate | 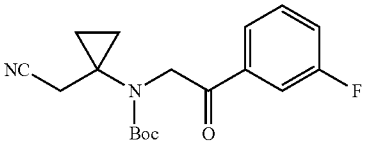 [SMILES: CC(C)(C)OC(=O)N(CC(=O)c1cccc(F)c1)C1(CC#N)CC1] | 277.2 $[(M\text{-}tBu) + 2H]^+$ |

Step 3: Preparation of tert-butyl (1-(cyanomethyl) cyclopropyl)(2-hydroxy-2-(3-methoxyphenyl)ethyl) carbamate To a solution of tert-butyl (1-(cyanomethyl)cyclopropyl) (2-(3-methoxyphenyl)-2-oxoethyl)carbamate (193 mg, 0.5603 mmol, 1 eq) in methanol (10 mL) at 0° C. was added $NaBH_4$ (21.1 mg, 0.5603 mmol, 1.0 eq). The reaction was stirred for 2 h at room temperature. The reaction was quenched with 1 N HCl (1 mL) and concentrated under reduced pressure. The crude residue was purified by reverse phase chromatography on a Cis cartridge eluting with 5-60% MeCN in water (with 0.1% formic acid) to give tert-butyl (1-(cyanomethyl)cyclopropyl)(2-hydroxy-2-(3-methoxyphenyl)ethyl)carbamate (144 mg, 74.2%) as a thick clear oil. $^1$H NMR (400 MHz, DMSO-$d_6$) δ 7.26 (t, J=7.8 Hz, 1H), 6.91-6.80 (m, 3H), 5.56-5.48 (m, 1H), 4.88-4.71 (m, 1H), 3.75 (s, 3H), 3.40-3.30 (m, 1H), 3.19-3.10 (m, 1H), 3.04-2.92 (m, 1H), 2.73-2.61 (m, 1H), 1.46 (s, 9H), 1.32-1.20 (m, 1H), 0.84-0.62 (m, 3H).

The intermediates in the table below were prepared using the method described above in Step 3 for the preparation of tert-butyl (1-(cyanomethyl)cyclopropyl)(2-hydroxy-2-(3-methoxyphenyl)ethyl)carbamate utilizing the appropriate starting materials and modifications.

| Name | Structure | LCMS | NMR |
|---|---|---|---|
| tert-butyl (1-(cyanomethyl)cyclopropyl)(2-(3-fluorophenyl)-2-hydroxyethyl)carbamate | 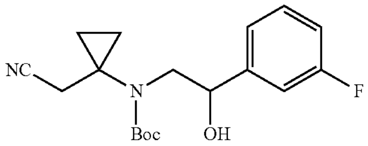 [SMILES: CC(C)(C)OC(=O)N(CC(O)c1cccc(F)c1)C1(CC#N)CC1] | 261.2 [(M-tBu-OH) + 2H]$^+$ | |

Step 4: Preparation of racemic-tert-butyl (6S,7R)-7-cyano-6-(3-methoxyphenyl)-4-azaspiro[2.4]heptane-4-carboxylate To a solution of tert-butyl (1-(cyanomethyl)cyclopropyl) (2-hydroxy-2-(3-methoxyphenyl)ethyl)carbamate (115 mg, 0.3319 mmol, 1 eq) in THF (10 mL) at −15° C. were added diethyl phosphorochloridate (50.3 μL, 0.3484 mmol, 1.05 eq) followed by dropwise addition of 1 M LiHMDS in THF (829 μL, 0.8297 mmol, 2.5 eq). The reaction was stirred at −15° C. for 2 h. The reaction was quenched with 1 N HCl (1 mL) and concentrated under reduced pressure. The crude residue was purified by reverse phase chromatography on a Cis cartridge eluting with 5-70% MeCN in water (with 0.1% formic acid) to give racemic-tert-butyl (6S,7R)-7-cyano-6-(3-methoxyphenyl)-4-azaspiro[2.4]heptane-4-carboxylate (50.0 mg, 46.2%) as a white solid. LCMS (ESI) m/z=273.2 [(M-t-Bu)$^+$2H]$^+$. $^1$H NMR (400 MHz, $C_6D_6$) δ 7.03-6.98 (m, 1H), 6.66-6.61 (m, 2H), 6.53-6.49 (m, 1H), 3.72-3.62 (m, 1H), 3.29 (s, 3H), 3.25-3.18 (m, 1H), 3.04-2.96 (m, 1H), 2.71 (d, J=10.5 Hz, 1H), 2.38-1.93 (m, 1H), 1.75-1.47 (m, 1H), 1.37 (s, 9H), 1.09-1.02 (m, 1H), 0.45-0.39 (m, 1H).

The intermediates in the table below were prepared using the method described above in Step 4 for the preparation of racemic-tert-butyl (6S,7R)-7-cyano-6-(3-methoxyphenyl)-4-azaspiro[2.4]heptane-4-carboxylate utilizing the appropriate starting materials and modifications.

| Name | Structure |
|---|---|
| Racemic-tert-butyl (6R,7S)-7-cyano-6-(3-fluorophenyl)-4-azaspiro[2.4]heptane-4-carboxylate | 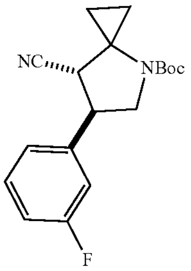 [SMILES: CC(C)(C)OC(=O)N1C[C@@H](c2cccc(F)c2)[C@H](C#N)C12CC2] |

Step 5: Preparation of racemic-(6S,7R)-6-(3-methoxyphenyl)-4-azaspiro[2.4]heptane-7-carbonitrile To a solution of a tert-butyl (6R,7S)-7-cyano-6-(3-methoxyphenyl)-4-azaspiro[2.4]heptane-4-carboxylate (44 mg, 0.1339 mmol, 1 eq) in methylene chloride (2 mL) was added TFA (0.5 mL). The reaction was stirred at room temperature for 2 h. The reaction was concentrated under reduced pressure to give crude racemic-(6S,7R)-6-(3-methoxyphenyl)-4-azaspiro[2.4]heptane-7-carbonitrile (30.5 mg, 99%, TFA salt) as a thick oil. LCMS (ESI) m/z=229.2 [M+H]$^+$.

The intermediates in the table below were prepared using the method described above in Step 5 for the preparation of racemic-(6S,7R)-6-(3-methoxyphenyl)-4-azaspiro[2.4]heptane-7-carbonitrile utilizing the appropriate starting materials and modifications.

| Name | Structure | LCMS |
| --- | --- | --- |
| Racemic-(6R,7S)-6-(3-fluorophenyl)-4-azaspiro[2.4]heptane-7-carbonitrile (TFA salt) | 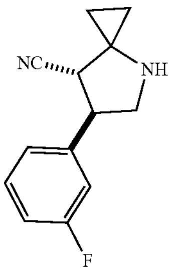 [SMILES: N#C[C@H]1[C@H](c2cccc(F)c2)CNC12CC2] | 217.2 [M + H]+ |

Synthesis of racemic-trans-6-(pyridin-3-yl)-4-azaspiro[2.4]heptane-7-carbonitrile

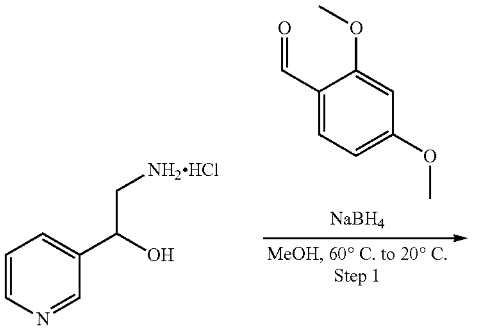

1

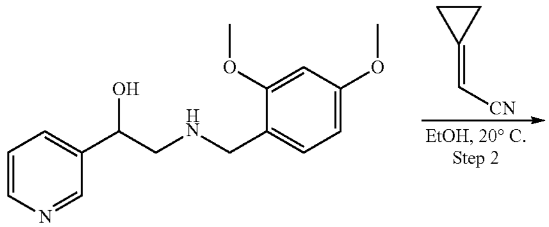

2

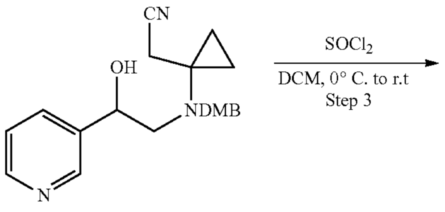

3

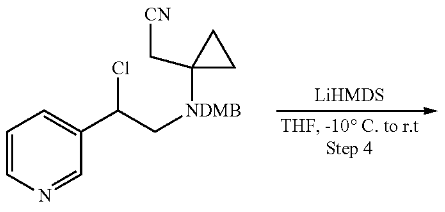

4

-continued

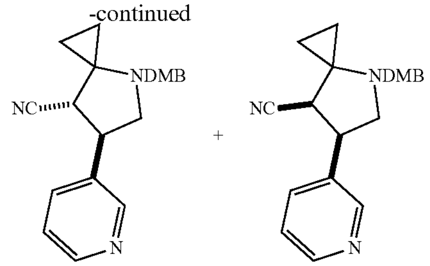

5A 5B

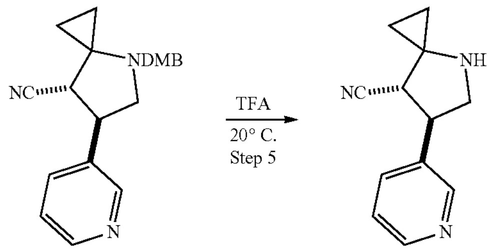

5A 6

Step 1: Preparation of 2-((2,4-dimethoxybenzyl) amino)-1-(pyridin-3-yl)ethan-1-ol A solution of 2-amino-1-(pyridin-3-yl)ethan-1-ol dihydrochloride (1, 2.8 g, 13.2 mmol, 1 eq.) and 2,4-dimethoxybenzaldehyde (2.19 g, 13.2 mmol, 1 eq.) in MeOH (10 mL) was stirred at 60° C. for 0.5 h, then $NaBH_4$ (1.50 g, 39.5 mmol, 3 eq.) was added at 20° C. and the reaction mixture was stirred at 20° C. for 16 h under $N_2$ atmosphere. After completion, the reaction mixture was poured into ice-$NH_4Cl$ (100 mL), then extracted with EtOAc (50 mL×3). The organic layers were combined and washed with brine (100 mL), dried over anhydrous $Na_2SO_4$, and concentrated under reduced pressure to afford 2-((2,4-dimethoxybenzyl)amino)-1-(pyridin-3-yl)ethan-1-ol (2, 2.50 g, 8.67 mmol, 66%) as a yellow oil. LCMS (ESI): m/z=289.2 $[M+H]^+$. $^1H$ NMR (400 MHz, DMSO) δ 8.52 (d, J=2.0 Hz, 1H), 8.44 (dd, J=4.8, 1.6 Hz, 1H), 7.71 (dt, J=7.8, 1.8 Hz, 1H), 7.33 (dd, J=7.7, 4.9 Hz, 1H), 7.13 (d, J=8.2 Hz, 1H), 6.52 (d, J=2.3 Hz, 1H), 6.45 (dd, J=8.2, 2.4 Hz, 1H), 5.46 (s, 1H), 4.70 (t, J=6.0 Hz, 1H), 3.74 (d, J=3.2 Hz, 6H), 3.64 (d, J=4.7 Hz, 2H), 3.17 (d, J=5.1 Hz, 1H), 2.70-2.62 (m, 2H).

Step 2: Preparation of 2-(1-((3,4-dimethylbenzyl)(2-hydroxy-2-(pyridin-3-yl)ethyl)amino)cyclopropyl) acetonitrile To a mixture of 2-((2,4-dimethoxybenzyl)amino)-1-(pyridin-3-yl)ethan-1-ol (2, 2.5 g, 8.67 mmol, 1 eq.) in EtOH (5 mL) was added 2-cyclopropylideneacetonitrile in PE solution (1.36 g, 17.3 mmol, 2 eq.) and the resulting mixture was stirred at 20° C. for 1 h under $N_2$ atmosphere. After completion, the reaction mixture was concentrated under reduced pressure to give a residue. The residue was purified by flash column chromatography on silica gel to get 2-(1-((3,4-dimethylbenzyl)(2-hydroxy-2-(pyridin-3-yl)ethyl)amino)cyclopropyl)acetonitrile (3, 2.40 g, 6.53 mmol, 75%) as a pale-yellow oil. LCMS (ESI): m/z=368.2 $[M+H]^+$. $^1H$ NMR (400 MHz, DMSO) δ 8.40 (dd, J=4.7, 1.6 Hz, 1H), 8.30 (d, J=1.8 Hz, 1H), 7.54 (dt, J=7.8, 1.8 Hz, 1H), 7.28 (dd, J=7.8, 4.8 Hz, 1H), 7.18 (d, J=8.3 Hz, 1H), 6.54 (d, J=2.3 Hz, 1H), 6.47 (dd, J=8.3, 2.4 Hz, 1H), 4.99 (d, J=3.1 Hz, 1H), 4.28 (dd, J=9.8, 6.6 Hz, 1H), 3.85-3.71 (m, 8H), 2.94-2.71 (m, 4H), 0.60-0.31 (m, 3H), 0.06 (s, 1H).

Step 3: Preparation of 2-(1-((2-chloro-2-(pyridin-3-yl)ethyl)(3,4-dimethylbenzyl)amino)cyclopropyl)acetonitrile $SOCl_2$ in DCM solution (3, 281 mg, 2.37 mmol, 1.2 eq.) was added to a solution 2-(1-((3,4-dimethylbenzyl)(2-hydroxy-2-(pyridin-3-yl)ethyl)amino)cyclopropyl)acetonitrile (3, 730 mg, 1.98 mmol, 1 eq.) in DCM (10 mL) at 0° C. The solution was stirred at room temperature for 0.5 h. After completion, the reaction mixture was quenched with $NaHCO_3$ (aq., sat.) (20 mL), then extracted with EtOAc (50 mL×2). The organic layers were combined and washed with brine (100 mL), dried over anhydrous $Na_2SO_4$, and concentrated under reduced pressure. The residue was purified by flash column chromatography on silica gel to afford 2-(1-((2-chloro-2-(pyridin-3-yl)ethyl)(3,4-dimethylbenzyl)amino)cyclopropyl)acetonitrile (4, 310 mg, 0.80 mmol, 41%) as an oil. LCMS (ESI): m/z=386.2 $[M+H]^+$. $^1H$ NMR (400 MHz, DMSO) δ 8.50 (dd, J=4.8, 1.5 Hz, 1H), 8.31 (d, J=1.9 Hz, 1H), 7.64-7.57 (m, 1H), 7.37 (dd, J=7.9, 4.8 Hz, 1H), 7.13 (d, J=8.3 Hz, 1H), 6.55 (d, J=2.3 Hz, 1H), 6.49 (dd, J=8.3, 2.4 Hz, 1H), 4.62 (t, J=7.2 Hz, 1H), 3.81-3.72 (m, 8H), 3.36-3.23 (m, 2H), 2.91-2.75 (m, 2H), 0.61-0.38 (m, 3H), 0.06--0.04 (m, 1H).

Step 4: Preparation of racemic-trans-4-(3,4-dimethylbenzyl)-6-(pyridin-3-yl)-4-azaspiro[2.4]heptane-7-carbonitrile & racemic-cis-4-(3,4-dimethylbenzyl)-6-(pyridin-3-yl)-4-azaspiro[2.4]heptane-7-carbonitrile To a solution of 2-(1-((2-chloro-2-(pyridin-3-yl)ethyl)(3,4-dimethylbenzyl)amino)cyclopropyl)acetonitrile (4, 310 mg, 0.80 mmol, 1 eq.) in THF (10 mL) was added LiHMDS (202 mg, 2.00 mmol, 2.5 eq.) dropwise at −10° C. and the solution was stirred at room temperature for 1 hr. After completion, the reaction mixture was quenched with $NH_4Cl$ (aq., sat.) (15 mL), then extracted with EtOAc (15 mL×2). The organic layers were combined and washed with brine (10 mL), dried over anhydrous $Na_2SO_4$, and concentrated under reduced pressure. The residue was purified by flash column chromatography on silica gel to afford racemic-trans-4-(3,4-dimethylbenzyl)-6-(pyridin-3-yl)-4-azaspiro[2.4]heptane-7-carbonitrile (5 A, 75 mg, 0.21 mmol, 27%) and cis-4-(3,4-dimethylbenzyl)-6-(pyridin-3-yl)-4-azaspiro[2.4]heptane-7-carbonitrile (5B, 55.0 mg, 0.16 mmol, 20%) as a yellow oil. LCMS (ESI): m/z=350.2 $[M+H]^+$.

Step 5: Preparation of racemic-trans-6-(pyridin-3-yl)-4-azaspiro[2.4]heptane-7-carbonitrile A solution of racemic-trans-4-(3,4-dimethylbenzyl)-6-(pyridin-3-yl)-4-azaspiro[2.4]heptane-7-carbonitrile (5 A, 100 mg, 0.29 mmol, 1 eq.) in TFA (5 mL) was stirred at 20° C. overnight under $N_2$. After completion, the reaction mixture was quenched with $NaHCO_3$ (aq., sat.) (20 mL), then extracted with EtOAc (20 mL×2). The organic layers were combined and washed with brine (100 mL), dried over anhydrous $Na_2SO_4$, and concentrated under reduced pressure to afford racemic-trans-6-(pyridin-3-yl)-4-azaspiro[2.4]heptane-7-carbonitrile (6, 55.0 mg, quant.) as an oil for next Step without further purification. LCMS (ESI): m/z=199.9 $[M+H]^+$.

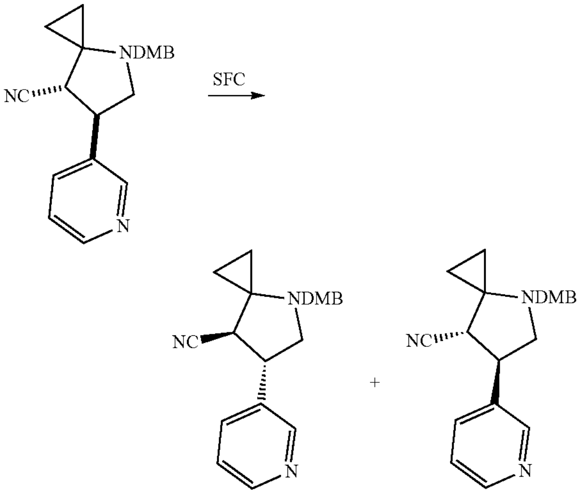

Peak 1 Peak 2

Rac-(6R,7S)-4-(2,4-dimethoxybenzyl)-6-(pyridin-3-yl)-4-azaspiro[2.4]heptane-7-carbonitrile (8 g) was separated by chiral SFC to afford (6S,7R)-4-(2,4-dimethoxybenzyl)-6-(pyridin-3-yl)-4-azaspiro[2.4]heptane-7-carbonitrile (Peak 1, 4.0 g, 50%) and (6R,7S)-4-(3,4-dimethoxybenzyl)-6-(pyridin-3-yl)-4-azaspiro[2.4]heptane-7-carbonitrile (Peak 2, 3.2 g, 40%) as a white solid. Absolute stereochemical configuration was assigned arbitrarily as drawn.

Peak 1: Retention time: 1.946 min; >99% ee.

Peak 2: Retention time: 2.456 min; >99% ee.

Analytical method: Column: ChiralPak IG, 100×4.6 mm I.D., 5 um, Mobile phase: A for $CO_2$ and B for ethanol (0.05% DEA), Gradient: 8 min @B 30%, Flow rate: 2.5 mL/min, Back pressure: 100 bar, Column temperature: 35° C.

SFC method: Instrument: Waters Thar 80 preparative SFC, Column: ChiralPak IG, 250×21.2 mm I.D., 5 μm, Mobile phase: A for $CO_2$ and B for EtOH+0.1% $NH_3H_2O$, Gradient: B 30%, Flow rate: 40 mL/min, Back pressure: 100 bar, Column temperature: 35° C., Wavelength: 220 nm, Cycle-time: 5.2 min, Eluted time: 3 H.

The intermediates in the table below were prepared using the method described above in Step 5 for racemic-trans-6-(pyridin-3-yl)-4-azaspiro[2.4]heptane-7-carbonitrile utilizing the appropriate starting materials and modifications.

| Name | Structure | LCMS |
|---|---|---|
| (6S,7R)-6-(pyridin-3-yl)-4-azaspiro[2.4]heptane-7-carbonitrile | 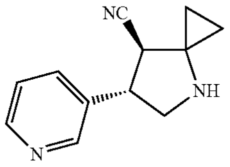 [SMILES: N#C[C@@H]1[C@@H](c2cccnc2)CNC12CC2] | 199.9 [M + H]$^+$ |
| (6R,7S)-6-(pyridin-3-yl)-4-azaspiro[2.4]heptane-7-carbonitrile | 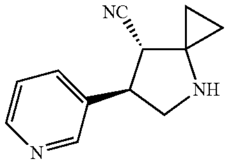 [SMILES: N#C[C@H]1[C@H](c2cccnc2)CNC12CC2] | 199.9 [M + H]$^+$ |

Synthesis of tert-butyl (R)-6-(pyridin-3-yl)-4-azaspiro[2.4]heptane-4-carboxylate and tert-butyl (S)-6-(pyridin-3-yl)-4-azaspiro[2.4]heptane-4-carboxylate

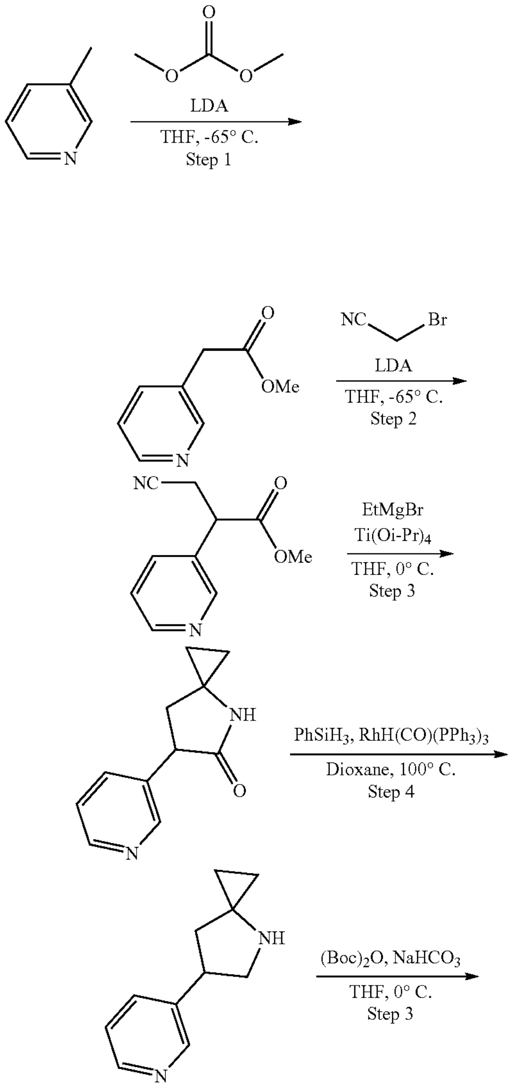

-continued

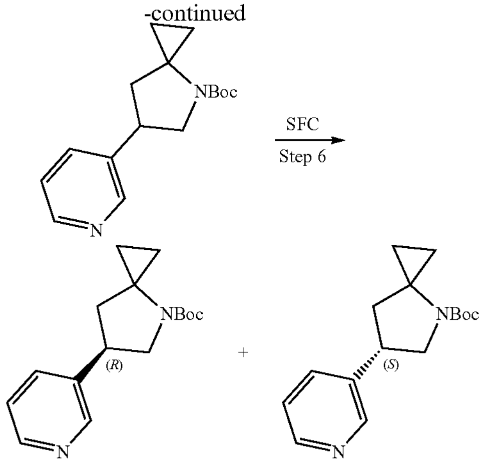

Step 1: Preparation of methyl 2-(pyridin-3-yl)acetate

To a solution of 3-methylpyridine (1, 30 g, 322 mmol, 1.0 eq.) in THF (600 mL) was added dropwise LDA (193 mL, 386 mmol, 2M, 1.2 eq.) at −65° C. under $N_2$ atmosphere. The reaction solution was stirred at −65° C. for 1 h and dimethyl carbonate (57 g, 483 mmol, 1.5 eq.) was added into the reaction mixture. After addition, the mixture was stirred at −65° C. for an additional 1 hr. After completion, the reaction mixture was quenched with saturated $NH_4Cl$ (aq.) solution (500 mL) at 0° C., then extracted with EtOAc (500 mL×2). The organic layers were combined and washed with brine (150 mL), dried over anhydrous $Na_2SO_4$ and concentrated under reduced pressure. The residue was purified by flash column chromatography on silica gel to afford methyl 2-(pyridin-3-yl)acetate (2, 25.0 g, 165 mmol, 51%) as a yellow oil. LCMS (ESI): m/z=152 [M+H]$^+$. $^1$H NMR (400 MHz, $CDCl_3$) δ 8.60-8.48 (m, 2H), 7.68-7.60 (m, 1H), 7.29-7.23 (m, 1H), 3.71 (s, 3H), 3.64 (s, 2H).

Step 2: Preparation of methyl 3-cyano-2-(pyridin-3-yl)propanoate

To a solution of LDA (99.0 mL, 198 mmol, 2M, 1.5 eq.) in THF (400 mL) was added dropwise a solution of methyl 2-(pyridin-3-yl)acetate (2, 20 g, 132 mmol, 1.0 eq.) at −65° C. under $N_2$ atmosphere. The reaction solution was stirred at −65° C. for 1 h and 2-bromoacetonitrile (18.9 g, 158 mmol, 1.2 eq.) was added into the reaction mixture. After addition, the mixture was stirred at −65° C. for an additional 1 h. After completion, the reaction mixture was quenched with saturated ice-$NH_4Cl$ (aq.) solution (500 mL), then extracted with EtOAc (500 mL×3). The organic layers were combined and washed with brine (500 mL), dried over anhydrous $Na_2SO_4$ and concentrated under reduced pressure. The residue was purified by flash column chromatography on silica gel to afford methyl 3-cyano-2-(2-methoxypyridin-4-yl)propanoate (3, 20.5 g, 107 mmol, 82%) as a yellow oil. LCMS (ESI): m/z=191 $[M+H]^+$. $^1H$ NMR (400 MHz, $CDCl_3$) δ 8.62 (dd, J=4.8, 1.5 Hz, 1H), 8.57 (d, J=2.2 Hz, 1H), 7.69-7.61 (m, 1H), 7.34 (dd, J=7.9, 4.8 Hz, 1H), 4.00 (t, J=7.5 Hz, 1H), 3.75 (s, 3H), 3.07 (dd, J=16.9, 7.1 Hz, 1H), 2.88 (dd, J=16.9, 7.9 Hz, 1H).

Step 3: Preparation of 6-(pyridin-3-yl)-4-azaspiro[2.4]heptan-5-one

To a solution of methyl 3-cyano-2-(pyridin-3-yl)propanoate (3, 20.5 g, 107 mmol, 1.0 eq.) and Titanium tetraisopropanolate (36.8 g, 128 mmol, 1.2 eq.) in THF (400 mL) was added dropwise EtMgBr (80 mL, 240 mmol, 3M, 2.25 eq.) at 0° C. After addition, the reaction mixture was stirred at 0° C. for 1 hr. After completion, the reaction mixture was quenched by addition of HCl aqueous solution (140 mL, 2N) at 0° C. The suspension was warmed to room temperature and filtered. The filtrate was poured into ice-water (500 mL) and extracted with EtOAc (200 mL×2). The organic layers were combined, washed with brine (500 mL), dried over anhydrous $Na_2SO_4$, and concentrated under reduced pressure. The residue was purified by flash column chromatography on silica gel to afford 6-(pyridin-3-yl)-4-azaspiro[2.4]heptan-5-one (4, 9.2 g, 48.8 mmol, 46%) as a yellow solid. LCMS (ESI): m/z=189 $[M+H]^+$. $^1H$ NMR (400 MHz, $CDCl_3$) δ 8.59 (d, J=2.1 Hz, 1H), 8.53 (dd, J=4.8, 1.5 Hz, 1H), 7.74-7.65 (m, 1H), 7.29 (dd, J=8.0, 4.9 Hz, 1H), 7.00 (s, 1H), 3.91 (t, J=8.7 Hz, 1H), 2.53 (dd, J=12.9, 9.3 Hz, 1H), 2.33 (dd, J=12.9, 8.2 Hz, 1H), 1.00-0.68 (m, 4H).

Step 4: Preparation of 6-(pyridin-3-yl)-4-azaspiro[2.4]heptane

To a solution of 6-(pyridin-3-yl)-4-azaspiro[2.4]heptan-5-one (4, 3.0 g, 15.9 mmol, 1.0 eq.) and methanidylidyneoxidanium tris(triphenylphosphane) hydrogen rhodium (729 mg, 795 mmol, 0.05 eq.) in dioxane (60 mL) was added phenylsilane (10.32 g, 95.4 mmol, 6.0 eq.). The reaction solution was stirred at 100° C. for 12 h. After completion, the reaction mixture was concentrated under reduced pressure to give a residue. The residue was triturated with 1N HCl (200 mL) at 25° C. for 0.5 h and then filtered. The filtrate was extracted with EtOAc (100 mL×2). The organic layers were combined, dried over anhydrous $Na_2SO_4$ and concentrated under reduced pressure. The residue was purified by Biotage® C18 column chromatography to afford 6-(pyridin-3-yl)-4-azaspiro[2.4]heptane (5, 2.2 g, 12.62 mmol, 79%) as a brown solid. LCMS (ESI): m/z=175$[M+H]^+$. $^1H$ NMR (400 MHz, $CDCl_3$) δ 8.55-8.46 (m, 2H), 7.72-7.62 (m, 1H), 7.31-7.25 (m, 1H), 3.84-3.71 (m, 2H), 3.40-3.28 (m, 1H), 2.32-2.17 (m, 2H), 1.52-1.37 (m, 2H), 0.91-0.76 (m, 2H).

Step 5: Preparation of tert-butyl 6-(pyridin-3-yl)-4-azaspiro[2.4]heptane-4-carboxylate To a solution of 6-(pyridin-3-yl)-4-azaspiro[2.4]heptane (5, 8 g, 45.9 mmol, 1 eq.) in THF/$H_2O$ (80 mL/10 mL) were added $NaHCO_3$ (7.7 g, 91.7 mmol, 2 eq.) and $Boc_2O$ (12 g, 55.1 mmol, 1.2 eq.). The solution was stirred at room temperature for 4 h. After completion, the reaction mixture was diluted with $H_2O$ (100 mL) and extracted with EtOAc (100 mL×3). The organic layers were combined and washed with brine (100 mL), dried over anhydrous $Na_2SO_4$, and concentrated under reduced pressure. The residue was purified by flash column chromatography on silica gel to afford tert-butyl 6-(pyridin-3-yl)-4-azaspiro[2.4]heptane-4-carboxylate (6, 6.7 g, 24.5 mmol, 53%) as a white solid. LCMS (ESI): m/z=275 $[M+H]^+$.

Step 6: Preparation of tert-butyl (R)-6-(pyridin-3-yl)-4-azaspiro[2.4]heptane-4-carboxylate and tert-butyl (S)-6-(pyridin-3-yl)-4-azaspiro[2.4]heptane-4-carboxylate tert-butyl 6-(pyridin-3-yl)-4-azaspiro[2.4]heptane-4-carboxylate (6, 6.7 g) was separated by chiral SFC to afford tert-butyl (R)-6-(pyridin-3-yl)-4-azaspiro[2.4]heptane-4-carboxylate (Peak 1, 3 g, 45%) and tert-butyl (S)-6-(pyridin-3-yl)-4-azaspiro[2.4]heptane-4-carboxylate (Peak 2, 3.1 g, 46%). LCMS (ESI): m/z=275 $[M+H]^+$. SFC method: Instrument: Waters Thar 80 preparative SFC Column: ChiralPak C-IG, 250×21.2 mm I.D., 5 μm Mobile phase: A for $CO_2$ and B for MEOH+0.1% $NH_3H_2O$, Gradient: B 45% Flow rate: 40 mL/min, Back pressure: 100 bar, Column temperature: 35° C., Wavelength: 220 nm Cycle-time: 25 min Eluted time: 7H. The assignment of absolute stereochemical configuration was made by comparison of experimental vibrational circular dichroism (VCD) spectra with theoretical VCD spectra obtained from DFT calculations.

Synthesis of (R)-6-phenyl-4-azaspiro[2.4]heptane and (S)-6-phenyl-4-azaspiro[2.4]heptane

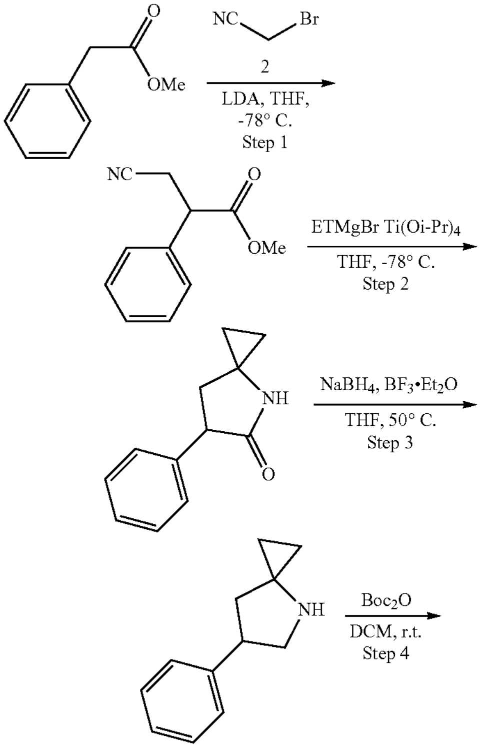

-continued

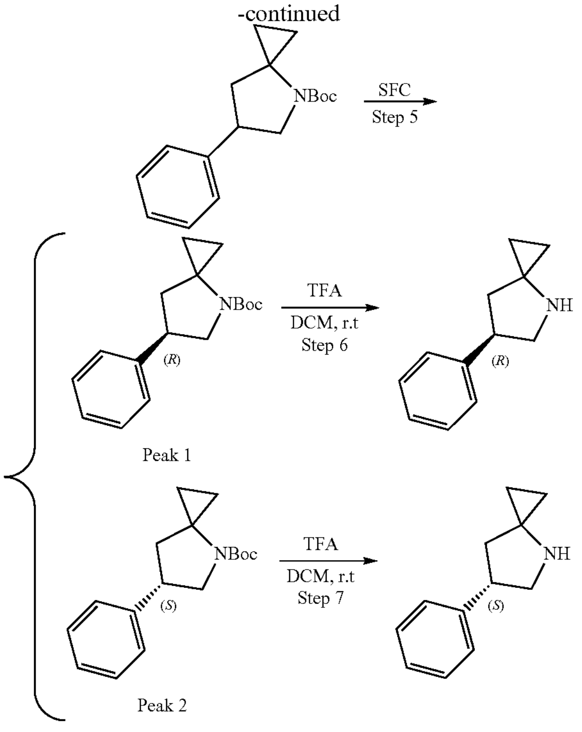

Step 1: Preparation of methyl 3-cyano-2-phenylpropanoate

To a solution of LDA (5.95 mL, 47.8 mmol, 1.2 eq) in THF (80 mL) was added dropwise methyl 2-phenylacetate (6 g, 39.9 mmol, 1.0 eq) at −78° C. under $N_2$ atmosphere. The reaction solution was stirred at −78° C. for 0.5 h and 2-bromoacetonitrile (5.25 g, 43.8 mmol, 1.1 eq) was introduced into the reaction. After addition, the mixture was stirred at −78° C. for 0.5 h. After completion, the reaction mixture was quenched with saturated ice-$NH_4Cl$ (aq.) solution (500 mL), then extracted with EtOAc (500 mL×3). The organic layers were combined and washed with brine (500 mL), dried over anhydrous $Na_2SO_4$ and concentrated under reduced pressure. The residue was purified by flash column chromatography on silica gel to afford methyl 3-cyano-2-phenylpropanoate (6.20 g, 32.7 mmol, 82%) as a yellow oil. LCMS (ESI): m/z=190 $[M+H]^+$.

Step 2: Preparation of 6-phenyl-4-azaspiro[2.4]heptan-5-one

To a solution of methyl 3-cyano-2-phenylpropanoate (6.2 g, 32.7 mmol, 1 eq) in THF (50 mL) was added dropwise $Ti(Oi\text{-}Pr)_4$ (10.2 g, 35.9 mmol, 1.1 eq) at −78° C. The reaction solution was stirred at −78° C. for 10 min and EtMgBr (72 mL, 71.9 mmol, 2.2 eq) was added dropwise into the reaction mixture. The reaction was stirred at −78° C. for 10 min then warmed up to room temperature for 0.5 h. After completion, the reaction mixture was quenched with $H_2O$ (5 mL), followed by 10% aqueous HCl (50 mL) and EtOAc (500 mL). And 10% aq. NaOH solution was added to the resulting clear mixture until the pH was adjusted pH=8-9. The filtrate was extracted with EtOAc (200 mL×2). The organic layers were combined, washed with brine (500 mL), dried over anhydrous $Na_2SO_4$ and concentrated under reduced pressure. The residue was purified by flash column chromatography on silica gel to afford 6-phenyl-4-azaspiro[2.4]heptan-5-one (9.2 g, 48.8 mmol, 46%) as a yellow solid. LCMS (ESI): m/z=188.2 $[M+H]^+$. $^1H$ NMR (400 MHz, $CDCl_3$) δ 7.39-7.24 (m, 6H), 3.86 (dd, J=9.4, 7.6 Hz, 1H), 2.51 (dd, J=12.9, 9.4 Hz, 1H), 2.29 (dd, J=12.9, 7.6 Hz, 1H), 0.85-0.88 (m, 1H), 0.87-0.81 (m, 1H), 0.76-0.64 (m, 2H).

Step 3: Preparation of 6-phenyl-4-azaspiro[2.4]heptane

To a solution of 6-phenyl-4-azaspiro[2.4]heptan-5-one (2.2 g, 11.7 mmol, 1 eq) in THF (100 mL) was added $NaBH_4$ (2.21 g, 58.5 mmol, 5 eq) at 0° C., then Boron trifluoride etherate (8.30 g, 58.5 mmol, 5 eq) was added dropwise to the mixture. The mixture was stirred at room temperature for 5 h and then stirred at 50° C. overnight. After completion, the reaction mixture was quenched with $NaHCO_3$ aqueous solution (20 mL) and extracted with EtOAc (20 mL×2). The organic layers were combined, washed with brine (500 mL), dried over anhydrous $Na_2SO_4$ and concentrated under reduced pressure. The residue was purified by C18 column chromatography to afford 6-phenyl-4-azaspiro[2.4]heptane (1.50 g, 8.65 mmol, 74%) as an oil. LCMS (ESI): m/z=174.3 $[M+H]^+$.

Step 4: Preparation of tert-butyl 6-phenyl-4-azaspiro[2.4]heptane-4-carboxylate To a solution of 6-phenyl-4-azaspiro[2.4]heptane (1.2 g, 6.92 mmol, 1 eq), DIEA (1.78 g, 13.8 mmol, 2 eq) and DMAP (84.5 mg, 692 μmol, 0.1 eq) in DCM (20 mL) was added di-tert-butyl dicarbonate (301 mg, 1.38 mmol, 1.2 eq) at room temperature. The reaction solution was stirred at room temperature for 5 h. After completion, the reaction mixture was concentrated under reduced pressure. The residue was purified by flash chromatography on silica gel to get tert-butyl 6-phenyl-4-azaspiro[2.4]heptane-4-carboxylate (1.50 g, 5.48 mmol, 79%) as a white solid. LCMS (ESI): m/z=218.3 $[(M\text{-}tBu)+H]^+$. $^1H$ NMR (400 MHz, $CDCl_3$) δ 7.38-7.19 (m, 5H), 3.98 (s, 1H), 3.54-3.39 (m, 2H), 2.48-2.27 (m, 1H), 1.95 (dd, J=12.2, 5.5 Hz, 1H), 1.52 (s, 2H), 1.43 (s, 9H), 0.55-0.42 (m, 2H)

Step 5: Preparation of tert-butyl (R)-6-phenyl-4-azaspiro[2.4]heptane-4-carboxylate and tert-butyl (S)-6-phenyl-4-azaspiro[2.4]heptane-4-carboxylate Tert-butyl 6-phenyl-4-azaspiro[2.4]heptane-4-carboxylate (1.50 g, 5.48 mmol) was further separated by Chiral SFC to give: SFC Method: Instrument: SHIMADZU PREP SOLUTION SFC, Column: ChiralPak IH, 250×21.2 mm I.D., 5 μm, Mobile phase: A for $CO_2$ and B for MeOH+0.1% $NH_3H_2O$, Gradient: B 10%, Flow rate: 10 mL/min, Back pressure: 100 bar, Column temperature: 35° C., Wavelength: 220 nm, Cycle-time: 4 min, Eluted time: 4 h. Absolute stereochemistry was arbitrarily assigned.

Peak 1: tert-butyl (R)-6-phenyl-4-azaspiro[2.4]heptane-4-carboxylate or tert-butyl (S)-6-phenyl-4-azaspiro[2.4]heptane-4-carboxylate (600 mg, 40%); Retention time: 3.287 min, 99% ee. LCMS (ESI): m/z=218.3 $[(M\text{-}tBu)+H]^+$. $^1H$ NMR (400 MHz, $CDCl_3$) δ 7.35-7.21 (m, 5H), 3.99 (s, 1H), 3.54-3.40 (m, 2H), 2.37 (dd, J=13.9, 8.8 Hz, 1H), 1.96 (dd, J=12.1, 5.5 Hz, 1H), 1.43 (s, 9H), 0.57-0.41 (m, 2H).

Peak 2: tert-butyl (S)-6-phenyl-4-azaspiro[2.4]heptane-4-carboxylate or tert-butyl (R)-6-phenyl-4-azaspiro[2.4]heptane-4-carboxylate (600 mg, 40%); Retention time: 3.582 min, 97% ee. LCMS (ESI): m/z=218.3 [(M-tBu)+H]$^+$. $^1$H NMR (400 MHz, $CDCl_3$) δ 7.37-7.20 (m, 5H), 3.99 (s, 1H), 3.56-3.38 (m, 2H), 2.37 (dd, J=13.8, 8.8 Hz, 1H), 1.96 (dd, J=12.1, 5.5 Hz, 1H), 1.43 (s, 9H), 0.58-0.42 (m, 2H).

Analytical method: Column: (R,R)-Whelk-O1, 250×4.6 mm I.D., 5 um, Mobile phase: A for $CO_2$ and B for IPA (0.05% DEA), Gradient: 10 min @B 20%, Flow rate: 2.0 mL/min, Back pressure: 100 bar, Column temperature: 35° C.

Step 6: Preparation of (R)-6-phenyl-4-azaspiro[2.4]heptane or (S)-6-phenyl-4-azaspiro[2.4]heptane To the solution of tert-butyl (R)-6-phenyl-4-azaspiro[2.4]heptane-4-carboxylate or tert-butyl (S)-6-phenyl-4-azaspiro[2.4]heptane-4-carboxylate (60 mg, 219 μmol, 1 eq, Peak 1) in DCM (2 mL) was added TFA (1 mL) at room temperature. The solution was stirred at room temperature. for 2 h. After completion, the reaction mixture was concentrated under reduced pressure to give (R)-6-phenyl-4-azaspiro[2.4]heptane or (S)-6-phenyl-4-azaspiro[2.4]heptane (70.0 mg, quant.) as an oil, which was used in next Step directly without further purification. LCMS (ESI): m/z=174.2 [M+H]$^+$.

Step 7: Preparation of (S)-6-phenyl-4-azaspiro[2.4]heptane or (R)-6-phenyl-4-azaspiro[2.4]heptane To the solution of tert-butyl (6S)-6-phenyl-4-azaspiro[2.4]heptane-4-carboxylate or tert-butyl (R)-6-phenyl-4-azaspiro[2.4]heptane-4-carboxylate (60 mg, 219 μmol, 1 eq, Peak 2) in DCM (2 mL) was added TFA (1 mL) at room temperature. The solution was stirred at room temperature. for 2 h. After completion, the reaction mixture was concentrated under reduced pressure to give (S)-6-phenyl-4-azaspiro[2.4]heptane or (R)-6-phenyl-4-azaspiro[2.4]heptane (70.0 mg, quant.) as an oil, which was used in next Step directly without further purification. LCMS (ESI): m/z=174.2 [M+H]$^+$.

Preparation of N,N-dimethyl-3-(4-azaspiro[2.4]heptan-6-yl)pyridin-4-amine

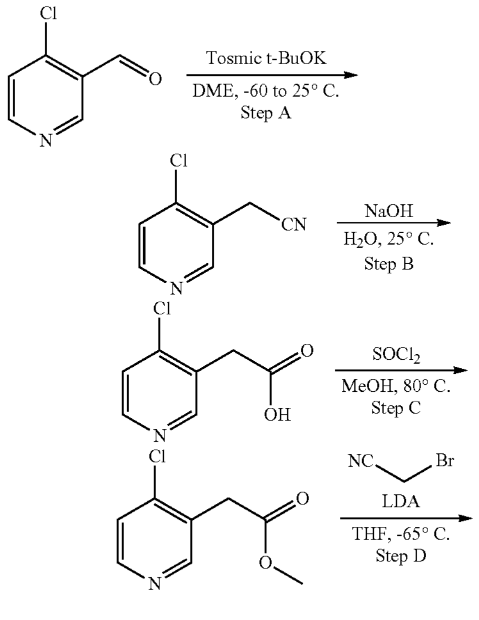

-continued

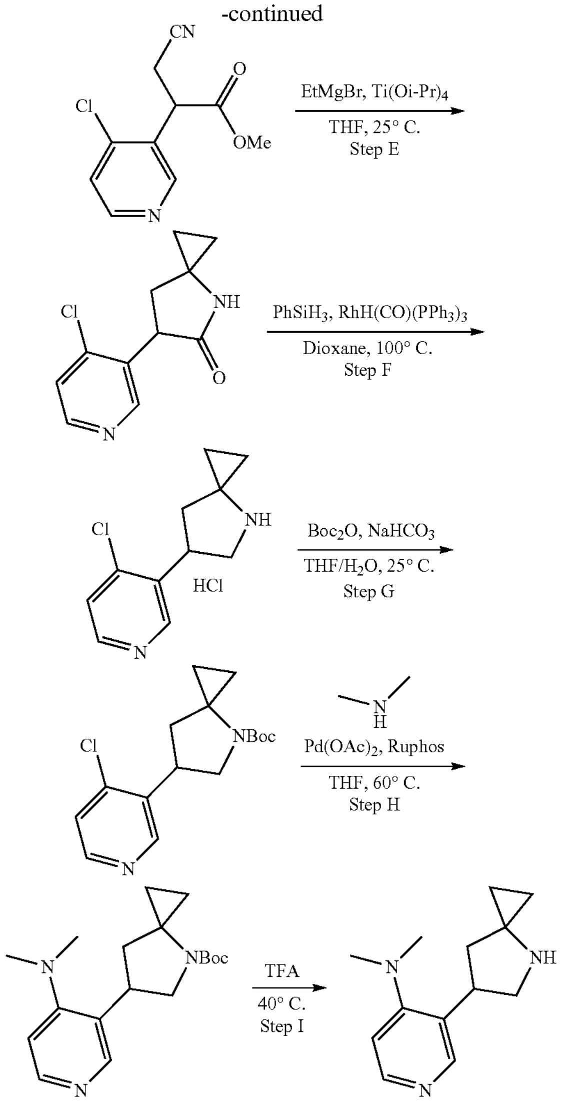

Step A: 2-(4-chloropyridin-3-yl)acetonitrile

To a solution of t-BuOK (15.8 g, 141 mmol, 2 eq.) in DME (100 mL) was added TosMIC (16.5 g, 84.7 mmol, 1.2 eq.) at 25° C. The reaction mixture was cooled to −60° C. 4-chloronicotinaldehyde (10 g, 70.6 mmol, 1 eq.) in DME (100 mL) was added dropwise to the mixture at −60° C. The reaction was stirred at −60° C. for 1 hr, then warmed up to 25° C. and stirred for 2 hrs under $N_2$ atmosphere. MeOH (100 mL) was added to the mixture, and the reaction mixture was heated to 80° C. and stirred at 80° C. for 0.5 hrs under $N_2$ atmosphere. After completion, the reaction mixture was quenched by adding $H_2O$ (200 mL), then extracted with EtOAc (100 mL×3). The organic layers were combined and washed with brine (150 mL), dried over anhydrous $Na_2SO_4$, and concentrated under reduced pressure. The residue was purified by flash column chromatography on silica gel to afford 2-(4-chloropyridin-3-yl)acetonitrile (4.2 g, 27.5 mmol, 39%) as a yellow solid. LC-MS (ESI) m/z=153 [M+H]$^+$.

Step B: 2-(4-chloropyridin-3-yl)acetic acid 2-(4-chloropyridin-3-yl)acetonitrile (4.2 g, 27.5 mmol, 1.0 eq.) was added to a solution of sodium hydroxide (9 g, 225 mmol, 8.2 eq.) in $H_2O$ (51 mL) at 25° C. The reaction mixture was heated to 100° C. and stirred for 1 hr. After completion, the reaction mixture was cooled down in an ice bath, then acidified carefully with HCl (con.) until the pH was adjusted to pH=1. The resulting mixture was dissolved in MeOH (50 mL). The suspension was filtered through a pad of Celite, the filter cake was washed with MeOH (10 mL). The combined filtrates were concentrated under reduced pressure to give 2-(4-chloropyridin-3-yl)acetic acid (4.0 g, 23.3 mmol, 85%) as a brown solid. LC-MS (ESI) m/z=172 $[M+H]^+$.

Step C: methyl 2-(4-chloropyridin-3-yl)acetate

To a solution of 2-(4-chloropyridin-3-yl)acetic acid (4 g, 23.3 mmol, 1 eq.) in MeOH (50 mL) was added dropwise thionyl chloride (13.7 g, 116 mmol, 5 eq.) at 25° C. The reaction mixture was heated to 80° C. and stirred for 1 hr. After completion, the reaction mixture was concentrated under reduce pressure. The product was dissolved in water (100 mL), the aqueous phase was neutralized carefully with $NaHCO_3$ (aq.) until the pH was adjusted to pH=9. The resulting mixture was extracted with EtOAc (100 mL×2), and the combined organic layers were washed with brine (100 mL), dried over with anhydrous $Na_2SO_4$, then concentrated under reduced pressure. The residue was purified by flash column chromatography on silica gel to afford methyl 2-(4-chloropyridin-3-yl)acetate (4.0 g, 21.5 mmol, 93%) as a yellow oil. LCMS (ESI): m/z=186 $[M+H]^+$.

Step D: methyl 2-(4-chloropyridin-3-yl)-3-cyanopropanoate

To a solution of methyl 2-(4-chloropyridin-3-yl)acetate (3 g, 16.1 mmol, 1 eq.) in dry THF (10 mL) was added LDA (9.7 mL, 19.3 mmol, 1.2 eq.) slowly at −65° C. under nitrogen. The mixture was stirred for additional 1 hr at −65° C., then 2-bromoacetonitrile (2.31 g, 19.3 mmol, 1.2 eq.) was added drop-wisely, after addition, the reaction mixture was stirred at −65° C. for 1 hr. After completion, the reaction mixture was quenched by adding sat. $NH_4Cl$ (100 mL), then extracted with EtOAc (100 mL×2). The organic layers were combined and washed with brine (100 mL), dried over anhydrous $Na_2SO_4$, and concentrated under reduced pressure. The residue was purified by flash column chromatography on silica gel to afford methyl 2-(4-chloropyridin-3-yl)-3-cyanopropanoate (3.0 g, 13.3 mmol, 83%) as a yellow oil. LC-MS (ESI) m/z=225 $[M+H]^+$ Step E: 6-(4-chloropyridin-3-yl)-4-azaspiro[2.4]heptan-5-one To a solution of methyl 2-(4-chloropyridin-3-yl)-3-cyanopropanoate (1 g, 4.45 mmol, 1 eq.) and titanium isopropoxide (1.58 g, 5.56 mmol, 1.25 eq.) in THF (30 mL) was added dropwise EtMgBr (3.7 mL, 11.1 mmol, 2.5 eq.) at 25° C. for 2 hrs. The reaction mixture was stirred at 25° C. for 0.5 hrs under $N_2$ atmosphere. After completion, the reaction mixture was diluted with $H_2O$ (10 mL), then extracted with EtOAc (20 mL×3). The organic layers were combined and washed with brine (150 mL), dried over anhydrous $Na_2SO_4$, and concentrated under reduced pressure. The residue was purified by flash column chromatography on silica gel to afford 6-(4-chloropyridin-3-yl)-4-azaspiro[2.4]heptan-5-one (500 mg, 2.25 mmol, 51%) as a yellow oil. LC-MS (ESI) m/z=223 $[M+H]^+$ Step F: 6-(4-chloropyridin-3-yl)-4-azaspiro[2.4]heptane hydrochloride To a solution of 6-(4-chloropyridin-3-yl)-4-azaspiro[2.4]heptan-5-one (500 mg, 2.24 mmol, 1.0 eq.) in dioxane (10 mL) were added lambda1-rhodium(1+) formyl radical tris (triphenylphosphine) hydride (103 mg, 112 μmol, 0.05 eq.) and phenylsilane (1.45 g, 13.4 mmol, 6 eq.) at 25° C. The reaction mixture was heated to 100° C. and stirred for 12 hrs under $N_2$ atmosphere. After completion, the reaction mixture was cooled to 25° C. and acidified carefully with HCl/dioxane (4 M) until the pH was adjusted to pH=1. The resulting mixture was concentrated under reduce pressure. The residue was triturated with $H_2O$ (10 mL) and filtered. The filtrate was concentrate under reduce pressure to give 6-(4-chloropyridin-3-yl)-4-azaspiro[2.4]heptane hydrochloride (200 mg, 815 μmol, 36%) as a yellow solid. LC-MS (ESI) m/z=209 $[M+H]^+$.

Step G: tert-butyl 6-(4-chloropyridin-3-yl)-4-azaspiro[2.4]heptane-4-carboxylate To a solution of 6-(4-chloropyridin-3-yl)-4-azaspiro[2.4]heptane hydrochloride (200 mg, 958 μmol, 1 eq.) and sodium bicarbonate (402 mg, 4.79 mmol, 5 eq.) in a mixture of $H_2O$ (5 mL) and THF (5 mL) was added di-tert-butyl dicarbonate (312 mg, 1.43 mmol, 1.5 eq.) at 25° C. The reaction mixture was stirred at 25° C. for 2 hrs. After completion, the reaction mixture was diluted with $H_2O$ (10 mL), then extracted with EtOAc (20 mL×3). The organic layers were combined and washed with brine (15 mL), dried over anhydrous $Na_2SO_4$, and concentrated under reduced pressure. The residue was purified by flash column chromatography on silica gel to afford tert-butyl 6-(4-chloropyridin-3-yl)-4-azaspiro[2.4]heptane-4-carboxylate (200 mg, 647 μmol, 68%) as a yellow oil. LC-MS (ESI) m/z=309 $[M+H]^+$.

Step H: tert-butyl 6-(4-(dimethylamino)pyridin-3-yl)-4-azaspiro[2.4]heptane-4-carboxylate To a mixture of tert-butyl 6-(4-chloropyridin-3-yl)-4-azaspiro[2.4]heptane-4-carboxylate (100 mg, 0.32 mmol, 1 eq.), dimethylamine (0.64 mmol, 2.0 eq., 1 M in THF), and t-BuONa (61 mg, 0.64 mmol, 2.0 eq.) in THF (2 mL) were added $Pd(OAc)_2$ (5 mg, 32 μmol, 0.1 eq.) and Ruphos (30 mg, 64 μmol, 0.2 eq.). The suspension was degassed under vacuum and purged with $N_2$ several times. The resulting mixture was stirred at 60° C. for 0.5 hrs. After completion, the mixture was concentrated under reduced pressure. The residue was purified by flash column chromatography on silica gel to give tert-butyl 6-(4-(dimethylamino)pyridin-3-yl)-4-azaspiro[2.4]heptane-4-carboxylate (70 mg, 0.22 mmol, 69%) as a yellow oil. LCMS (ESI): m/z=318 $[M+H]^+$.

Step 1: N,N-dimethyl-3-(4-azaspiro[2.4]heptan-6-yl)pyridin-4-amine

A solution of tert-butyl 6-(4-(dimethylamino)pyridin-3-yl)-4-azaspiro[2.4]heptane-4-carboxylate (100 mg, 0.31 mmol, 1.0 eq.) in TFA (0.5 mL) was stirred at 40° C. for 6 hrs. After completion, the reaction mixture was concentrated under reduced pressure to afford N,N-dimethyl-3-(4-azaspiro[2.4]heptan-6-yl)pyridin-4-amine (100 mg, quant.) (TFA salt) as a brown solid, which was used without further purification. LCMS (ESI): m/z=218 $[M+H]^+$.

Representative Procedures for Syntheses of Phosphoryl Groups:

Synthesis of 5-((diethoxyphosphoryl)difluoromethyl)benzo[b]thiophene-2-carboxylic acid

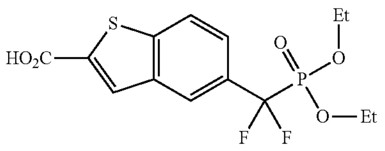 [SMILES: CCOP(=O)(OCC)C(F)(F)c1ccc2sc(C(=O)O)cc2c1]

5-((diethoxyphosphoryl)difluoromethyl)benzo[b]thiophene-2-carboxylic acid was prepared according to the protocol described in WO 2020/205467 (e.g., paragraphs [0560-0565], which are incorporated herein).

Synthesis of (difluoro(2-((4-nitrophenoxy)carbonyl)benzo[b]thiophen-5-yl)methyl)phosphonic acid

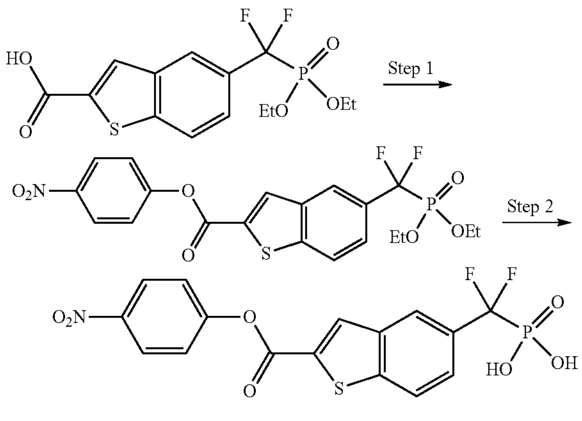

Step 1: Preparation of 4-nitrophenyl 5-((diethoxyphosphoryl)difluoromethyl)benzo[b]thiophene-2-carboxylate To a mixture of 5-[(diethoxyphosphoryl)difluoromethyl]-1-benzothiophene-2-carboxylic acid (10.0 g, 27.4 mmol), EDCI (7.85 g, 41.0 mmol) and DMAP (836 mg, 6.85 mmol) in $CH_2Cl_2$ (80 mL) was stirred at room temperature. After 15 min, 4-nitrophenol (4.75 g, 34.2 mmol) was added and the resulting yellow mixture was stirred at room temperature for 18 h. The reaction was quenched with water (30 mL) and the product was extracted with $CH_2Cl_2$ (10 mL×2). The combined organic extracts were washed with brine, dried with sodium sulfate, filtered and concentrated in vacuo. The crude residue was purified by reverse phase chromatography [C18 cartridge eluting with a gradient of 5-100% acetonitrile in water] and the appropriate fractions were concentrated to give 4-nitrophenyl 5-((diethoxyphosphoryl)difluoromethyl)benzo[b]thiophene-2-carboxylate (7.80 g, 16.0 mmol, 59.0% yield) as a yellow solid. LCMS m/z=486.2 $[M+H]^+$; $^1$H NMR (400 MHz, DMSO-$d_6$) δ 8.32-8.37 (m, 3H), 8.22 (s, 1H), 8.01 (d, J=9.1 Hz, 1H), 7.77 (d, J=7.8 Hz, 1H), 7.51-7.45 (m, 2H), 4.14-4.32 (m, 4H), 1.34 (t, J=7.8 Hz, 6H).

Step 2: Preparation of (difluoro(2-((4-nitrophenoxy)carbonyl)benzo[b]thiophen-5-yl)methyl)phosphonic acid To a cooled (0° C.) solution of 4-nitrophenyl 5-((diethoxyphosphoryl)difluoromethyl)benzo[b]thiophene-2-carboxylate (4.47 g, 9.20 mmol) in $CH_2Cl_2$ (39 mL) was added N,O-bis(trimethylsilyl)trifluoroacetamide (12.1 mL, 46.0 mmol) and iodotrimethylsilane (5.23 mL, 36.8 mmol) as a solution in $CH_2Cl_2$ (10 mL). The reaction mixture was gradually allowed to warm to ambient temperatures. To the reaction mixture was added a mixture of 2:1 $H_2O$/acetonitrile (with 0.1% TFA) (50 mL) and precipitation of product was observed. The volatiles were removed in vacuo and the crude residue was suspended in a mixture of acetonitrile/water solution (1:1 v/v, 100 mL). The suspension was filtered, the solids were washed with a 2:1 mixture acetonitrile/water solution, and the solid were dried under reduced pressure to afford [difluoro({2-[(4-nitrophenoxy)carbonyl]-1-benzothiophen-5-yl})methyl]phosphonic acid (6.5 g, 94%) as a beige solid. The filtrate was concentrated to 50% of solvent volume and the resulting suspension was filtered and washed with 1:2 acetonitrile/water solution. The solid was dried under reduced pressure to afford additional [difluoro({2-[(4-nitrophenoxy)carbonyl]-1-benzothiophen-5-yl})methyl]phosphonic acid (0.4 g) as a beige solid. Both products were lyophilized to give (difluoro(2-((4-nitrophenoxy)carbonyl)benzo[b]thiophen-5-yl)methyl)phosphonic acid (6.90 g, 16.0 mmol, 98.0% yield). $^1$H NMR (400 MHz, DMSO-$d_6$) δ 7.66-7.74 (m, 3H), 8.27 (d, J=8.3 Hz, 1H), 8.30 (s, 1H), 8.36-8.41 (m, 2H), 8.66 (s, 1H).

The intermediates in the table below was prepared using a similar protocol outlined above for synthesis of [difluoro({2-[(4-nitrophenoxy)carbonyl]-1-benzothiophen-5-yl})methyl]phosphonic acid and utilizing the appropriate intermediate(s) as starting material(s).

| Name | Structure | LC-MS |
| --- | --- | --- |
| (difluoro(2-((perfluorophenoxy)carbonyl)benzo[b]thiophen-5-yl)methyl)phosphonic acid | 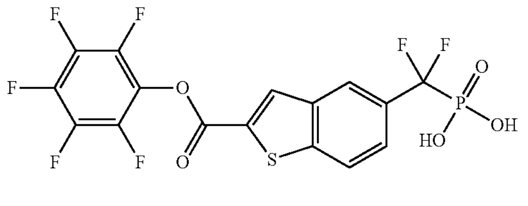 [SMILES: O=C(Oc1c(F)c(F)c(F)c(F)c1F)c1cc2cc(C(F)(F)P(=O)(O)O)ccc2s1] | 475.0 $[M + H]^+$ |

-continued

| Name | Structure | LC-MS |
|---|---|---|
| (R)-(fluoro(2-((perfluorophenoxy)carbonyl)benzo[b]thiophen-5-yl)methyl)phosphonic acid | 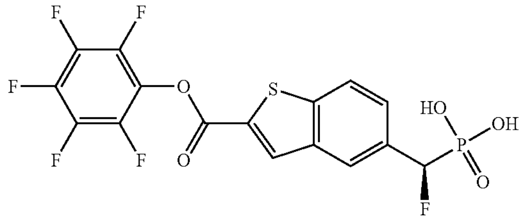 [SMILES: O=C(Oc1c(F)c(F)c(F)c(F)c1F)c1cc2cc([C@H](F)P(=O)(O)O)ccc2s1] | 457 [M + H]+ |
| (S)-(fluoro(2-((perfluorophenoxy)carbonyl)benzo[b]thiophen-5-yl)methyl)phosphonic acid | 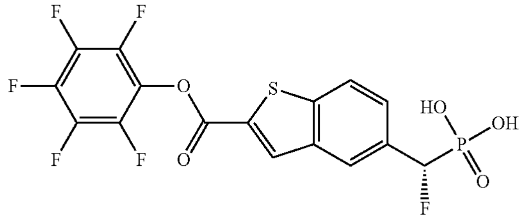 [SMILES: O=C(Oc1c(F)c(F)c(F)c(F)c1F)c1cc2cc([C@@H](F)P(=O)(O)O)ccc2s1] | 457 [M + H]+ |

Synthesis of ((2-((perfluorophenoxy)carbonyl)benzo[b]thiophen-5-yl)methyl)phosphonic acid

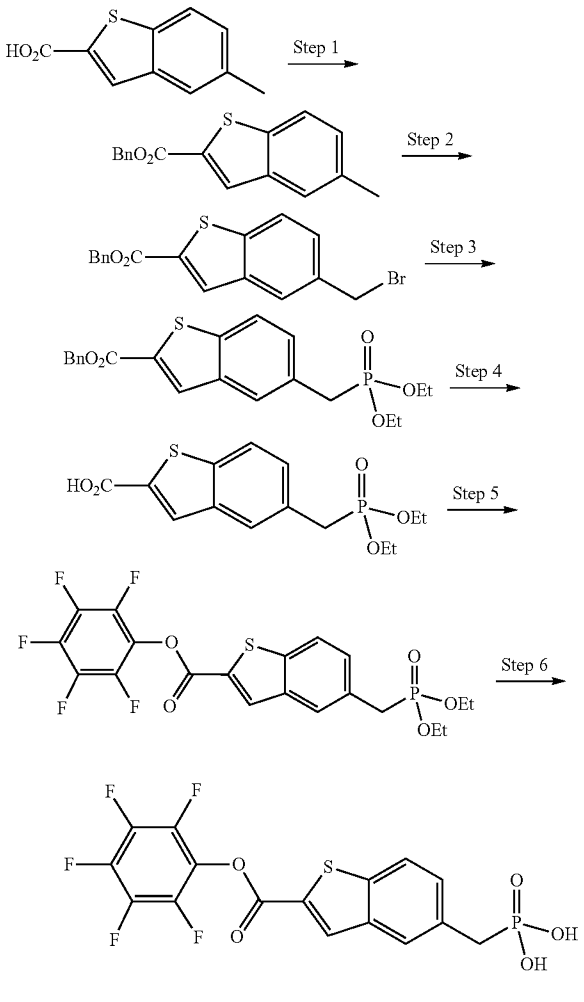

Preparation of 5-methylbenzo[b]thiophene-2-carboxylic acid

5-Methylbenzo[b]thiophene-2-carboxylic acid was prepared according to the procedure described in WO 2016/100184 (e.g., paragraphs [0281]-[0284], which are incorporated by reference herein).

Step 1: Preparation of benzyl 5-methylbenzo[b]thiophene-2-carboxylate

To a solution of 5-methylbenzo[b]thiophene-2-carboxylic acid (21.2 g, 110.0 mmol, 1.0 eq) and $K_2CO_3$ (30.4 g, 220.0 mmol, 2.0 eq) in DMF (200 mL) was added benzyl bromide (20.6 g, 121.0 mmol, 1.1 eq). The mixture was stirred at room temperature for 14 h. The reaction mixture was poured into ice water (400 mL) and stirred for 5 min. The resulting solids were filtered, and the filter cake was washed with water (50 mL), dried in vacuum to give benzyl 5-methylbenzo[b]thiophene-2-carboxylate (30.1 g, 106.0 mmol, 97% yield) as a yellow solid. $^1H$ NMR (400 MHz, $CDCl_3$) δ 8.01 (s, 1H), 7.71 (t, J=12.2 Hz, 1H), 7.65 (s, 1H), 7.46 (d, J=6.8 Hz, 2H), 7.42-7.35 (m, 3H), 7.29-7.26 (m, 1H), 5.38 (s, 2H), 2.47 (s, 3H).

Step 2: Preparation of benzyl 5-(bromomethyl)benzo[b]thiophene-2-carboxylate

To a solution of benzyl 5-methylbenzo[b]thiophene-2-carboxylate (15.0 g, 53.1 mmol, 1.0 eq) and NBS (10.3 g, 58.4 mmol, 1.1 eq) in $CCl_4$ (30 mL) was added benzoyl peroxide (1.3 g, 5.31 mmol, 0.1 eq). The reaction flask was subjected to three cycles of evacuation and backfilling with $N_2$ (g). The mixture was stirred at 80° C. for 16 h under constant atmosphere of $N_2$ (g). The reaction mixture was concentrated under reduced pressure. The residue was purified by flash column chromatography on silica gel to give benzyl 5-(bromomethyl)benzo[b]thiophene-2-carboxylate (6.80 g, 18.8 mmol, 36% yield) as a yellow solid.

Step 3: Preparation of benzyl 5-((diethoxyphosphoryl)methyl)benzo[b]thiophene-2-carboxylate A solution of benzyl 5-(bromomethyl)benzo[b]thiophene-2-carboxylate (10.3 g, 28.5 mmol, 1.0 eq) dissolved in triethyl phosphite (30.0 g, 180.0 mmol, 6.3 eq) was stirred at 100° C. for 5 h. The reaction mixture was concentrated under reduced pressure directly, the residue was purified by flash column chromatography on silica gel to give benzyl 5-((diethoxyphosphoryl)methyl)benzo[b]thiophene-2-carboxylate (6.5 g, 15.5 mmol, 55% yield) as a colorless oil. LCMS (ESI) m/z=419 $[M+H]^+$; $^1H$ NMR (400 MHz, $CDCl_3$) δ 8.04 (s, 1H), 7.80 (d, J=8.3 Hz, 2H), 7.49-7.33 (m, 6H), 5.39 (s, 2H), 4.08-3.93 (m, 4H), 3.26 (d, J=21.5 Hz, 2H), 1.24 (t, J=7.1 Hz, 6H).

Step 4: Preparation of 5-((diethoxyphosphoryl)methyl)benzo[b]thiophene-2-carboxylic acid To a solution of benzyl 5-((diethoxyphosphoryl)methyl)benzo[b]thiophene-2-carboxylate (5.6 g, 13.3 mmol, 1.0 eq) in dissolved in a mixture of THF (80 mL) and $H_2O$ (10 mL) was added LiOH (1.10 g, 26.6 mmol, 2.0 eq). The mixture was stirred at room temperature for 3 h and subsequently acidified with aqueous solution of 1 N HCl (adjusted to pH ~3-4). The product precipitated out of solution upon acidification. The resulting solids were filtered, the filter cake was washed with water (20 mL×2), and the solids were dried under vacuum to give 5-((diethoxyphosphoryl)methyl)benzo[b]thiophene-2-carboxylic acid (3.9 g, 11.8 mmol, 88.9% yield) as a white solid. LCMS (ESI) m/z=329 $[M+H]^+$.

Step 5: Preparation of perfluorophenyl 5-((diethoxyphosphoryl)methyl)benzo[b]thiophene-2-carboxylate To a cooled (0° C.) solution of 5-((diethoxyphosphoryl)methyl)benzo[b]thiophene-2-carboxylic acid (3.9 g, 11.8 mmol, 1.0 eq) in $CH_2Cl_2$ (50 mL) was added oxalyl chloride (2.2 g, 17.7 mmol, 1.5 eq) followed by addition of two drops of DMF. The mixture was stirred at 0° C. for 30 min, followed by evaporation of the reaction mixture to dryness. The resulting solids were dissolved in $CH_2Cl_2$ (50 mL), followed by addition of $Et_3N$ (3.6 g, 35.4 mmol, 3.0 eq) and pentafluorophenol (2.6 g, 14.1 mmol, 1.2 eq). The resulting mixture was stirred at room temperature for additional 2 h and subsequently, poured over $H_2O$ (30 mL). The bi-phasic solution was extracted with EtOAc (30 mL×3). The combined organic layers were dried over $MgSO_4$, filtered and concentrated under reduced pressure, the residue was purified by column chromatography on silica gel to give perfluorophenyl 5-((diethoxyphosphoryl)methyl)benzo[b]thiophene-2-carboxylate (4.7 g, 9.5 mmol, 81% yield) as a white solid. LCMS (ESI) m/z=419 $[M+H]^+$; $^1H$ NMR (400 MHz, $CDCl_3$) δ 8.29 (s, 1H), 7.88 (d, J=9.1 Hz, 2H), 7.51 (d, J=8.4 Hz, 1H), 4.14-3.94 (m, 4H), 3.29 (d, J=21.5 Hz, 2H), 1.26 (t, J=7.0 Hz, 6H).

Step 6: Preparation of ((2-((perfluorophenoxy)carbonyl)benzo[b]thiophen-5-yl)methyl)phosphonic acid To a solution of perfluorophenyl 5-((diethoxyphosphoryl)methyl)benzo[b]thiophene-2-carboxylate (4.7 g, 9.5 mmol, 1.0 eq) in $CH_2Cl_2$ (60 mL) was added bromotrimethylsilane (12 mL). The mixture was stirred at room temperature for 14 h and subsequently concentrated under reduced pressure. The residue was purified by C18 column chromatography to give ((2-((perfluorophenoxy)carbonyl)benzo[b]thiophen-5-yl)methyl)phosphonic acid (3.7 g, 8.4 mmol, 89% yield) as a white solid. LCMS (ESI) m/z=439 $[M+H]^+$.

Synthesis of (R)- or (S)-5-((diethoxyphosphoryl)fluoromethyl)benzo[b]thiophene-2-carboxylic acid and (S)-5-((diethoxyphosphoryl)fluoromethyl)benzo[b]thiophene-2-carboxylic acid

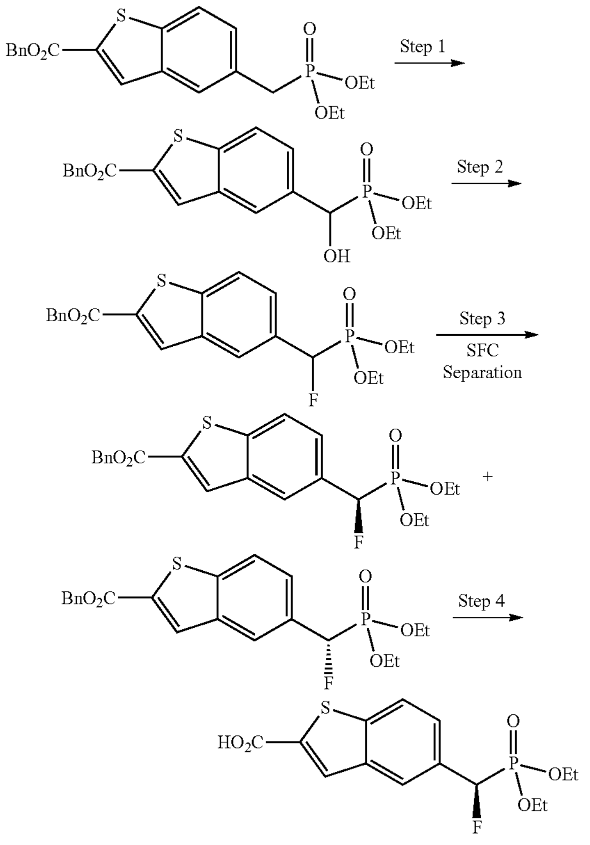

Step 1: rac-benzyl 5-((diethoxyphosphoryl)(hydroxy)methyl)benzo[b]thiophene-2-carboxylate To a cooled (−78° C.) solution of benzyl 5-((diethoxyphosphoryl)methyl)benzo[b]thiophene-2-carboxylate (2.4 g, 5.73 mmol, 1 eq) in THF (75 mL) and 2-(benzenesulfonyl)-3-phenyloxaziridine (2.97 g, 11.4 mmol, 2 eq) was added a 1 M solution of NaHMDS (11.4 mL, 11.4 mmol, 2 eq) in THF. A deep purple solution was observed upon addition of base that changed to orange after complete addition of the base. The mixture was stirred for an additional 10 min, followed by addition of aqueous saturated $NH_4Cl$ (50 mL). The mixture was warmed to ambient temperatures and EtOAc (75 mL) and water (25 mL) was added. After stirring for an additional 30 min, the phases were separated. The aqueous layer was extracted with EtOAc (125 mL×2). The combined organic extracts were dried with anhydrous sodium sulfate, filtered, concentrated under reduced pressure. Another batch of equal scale was performed and combined for purification. The combined material (6.42 mmol, 12.15 mmol in total) was purified by flash chromatography (20%-100%=EtOAc:heptane) to give rac-benzyl 5-((diethoxyphosphoryl)(hydroxy)methyl)benzo[b]thiophene-2-carboxylate (3.69 g, 8.49 mmol, 70%) as a white sticky solid. LCMS (ESI) m/z=869.4 [2M+H]$^+$; $^1$H NMR (400 MHz, $CDCl_3$) δ 8.10 (s, 1H), 8.04-8.00 (m, 1H), 7.88 (d, J=8.6 Hz, 1H), 7.61 (d, J=8.6 Hz, 1H), 7.51-7.47 (m, 2H), 7.46-7.35 (m, 3H), 5.42 (s, 2H), 5.17 (dd, J=10.4, 4.5 Hz, 1H), 4.18-3.95 (m, 4H), 3.10-2.99 (m, 1H), 1.33-1.20 (m, 6H).

Step 2: rac-benzyl 5-((diethoxyphosphoryl)fluoromethyl)benzo[b]thiophene-2-carboxylate To a cooled (−78° C.) solution (under $N_2$ (g)) of rac-benzyl 5-((diethoxyphosphoryl)(hydroxy)methyl)benzo[b]thiophene-2-carboxylate (cc) (1.56 g, 3.59 mmol, 1 eq) in $CH_2Cl_2$ (30 mL) was added (diethylamino)sulfur trifluoride (568 L, 4.30 mmol, 1.2 eq). The reaction was stirred for 15 min, followed by addition of aqueous saturated $NaHCO_3$ (50 mL). After warming to room temperature, the product was extracted with $CH_2Cl_2$ (50 mL×3). The combined organic layers were dried over sodium sulfate, filtered and concentrated under reduced pressure. The crude residue was purified by reverse phase chromatography on C18 cartridge (eluting with 5-80% acetonitrile in water) to give rac-benzyl 5-((diethoxyphosphoryl)fluoromethyl)benzo[b]thiophene-2-carboxylate (650 mg, 1.48 mmol, 41.6%) as a thick clear oil. LCMS (ESI) m/z=873.2 [2M+H]$^+$; $^1$H NMR (400 MHz, $CDCl_3$) δ 8.12 (s, 1H), 8.02-7.99 (m, 1H), 7.92 (d, J=8.7 Hz, 1H), 7.61 (d, J=8.7 Hz, 1H), 7.51-7.51 (m, 2H), 7.46-7.36 (m, 3H), 5.82 (dd, J=44.4, 7.5 Hz, 1H), 5.42 (s, 2H), 4.21-4.02 (m, 4H), 1.34-1.26 (m, 6H).

Step 3: Preparation of benzyl (R)-5-((diethoxyphosphoryl)fluoromethyl)benzo[b]thiophene-2-carboxylate and benzyl (S)-5-((diethoxyphosphoryl)fluoromethyl)benzo[b]thiophene-2-carboxylate rac-Benzyl 5-((diethoxyphosphoryl)fluoromethyl)benzo[b]thiophene-2-carboxylate (650 mg, 1.48 mmol) was submitted to chiral SFC separation (Column: Lux i-Amylose 3, 21.2×250 mm 5 um column, 75 mL/min, 40% MeOH) to give benzyl (R)- or (S)-5-((diethoxyphosphoryl)fluoromethyl)benzo[b]thiophene-2-carboxylate (304 mg, 0.70 mmol, 46.8% recovery, 99.9% ee) as a thick clear oil (Peak 1) and benzyl (R)- or (S)-5-((diethoxyphosphoryl)fluoromethyl)benzo[b]thiophene-2-carboxylate (317 mg, 0.73 mmol, 49% recovery, 99.9% ee) as a thick clear oil (Peak 2). Note: Fastest eluting enantiomer by SFC was arbitrarily assigned as (R)-5-(fluoro(phosphono)methyl)benzo[b]thiophene-2-carboxylic acid and slowest eluting enantiomer by SFC as (S)-5-(fluoro(phosphono)methyl)benzo[b]thiophene-2-carboxylic acid. HPLC method for analysis of enantiomeric excess: Lux Cellulose-3 150 mm 45% $H_2O$+0.05% TFA/55% MeCN 1 mL/min 8 min.

Step 4: Preparation of (R)- or (S)-5-((diethoxyphosphoryl)fluoromethyl)benzo[b]thiophene-2-carboxylic acid To a mixture of 10% Pd/C (60 mg, 50% wet) and benzyl (R)-5-((diethoxyphosphoryl)fluoromethyl)benzo[b]thiophene-2-carboxylate (Peak 1) (60 mg, 0.1374 mmol, 1 eq) in THF (5 mL) was degassed with $N_2$ (g) for 5 min. To the mixture was bubbled $H_2$ (g) for 5 min then the reaction was allowed to stir at room temperature under $H_2$ (g) (1 atm). The reaction mixture was stirred until consumption of starting material was detected by LCMS. The reaction mixture was subsequently sparged $N_2$ (g) for 15 min and filtered over a pad of Celite®. The filter cake was washed with 2-MeTHF and the filtrate was concentrated to give (R)- or (S)-5-((diethoxyphosphoryl)fluoromethyl)benzo[b]thiophene-2-carboxylic acid (47.4 mg, 0.0137 mmol, 99%) as a thick clear oil. LCMS (ESI) m/z=347.2 [M+H]$^+$.

The intermediates in the table below was prepared using the procedure outlined above (in Step 4) starting from benzyl (S)- or (R)-5-((diethoxyphosphoryl)fluoromethyl)benzo[b]thiophene-2-carboxylate (Peak 2) and using the appropriate reagents.

| Name | Structure | LCMS |
|---|---|---|
| (S)-or (R)-5-((diethoxyphosphoryl)fluoromethyl)benzo[b]thiophene-2-carboxylic acid | 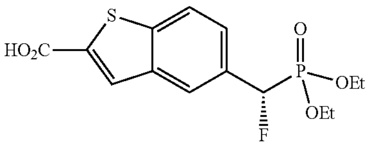 [SMILES: CCOP(=O)(OCC)[C@H](F)c1ccc2sc(C(=O)O)cc2c1] or 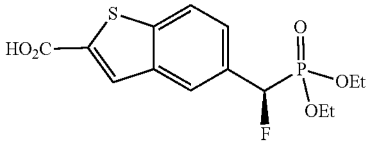 [SMILES: CCOP(=O)(OCC)[C@@H](F)c1ccc2sc(C(=O)O)cc2c1] | 347.2 [M + H]$^+$ |

Preparation of 5-(((((S)-1-isopropoxy-1-oxopropan-2-yl)amino)(phenoxy)phosphoryl)methyl)benzo[b]thiophene-2-carboxylic acid

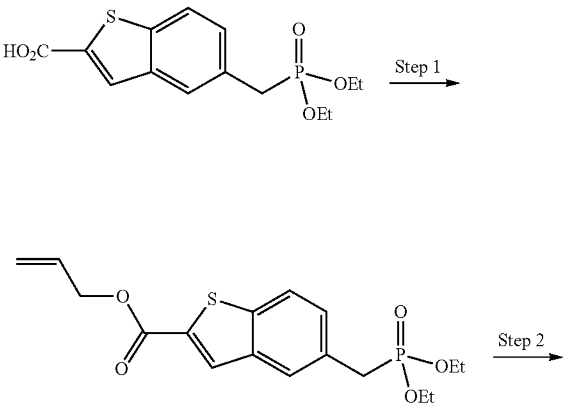

-continued

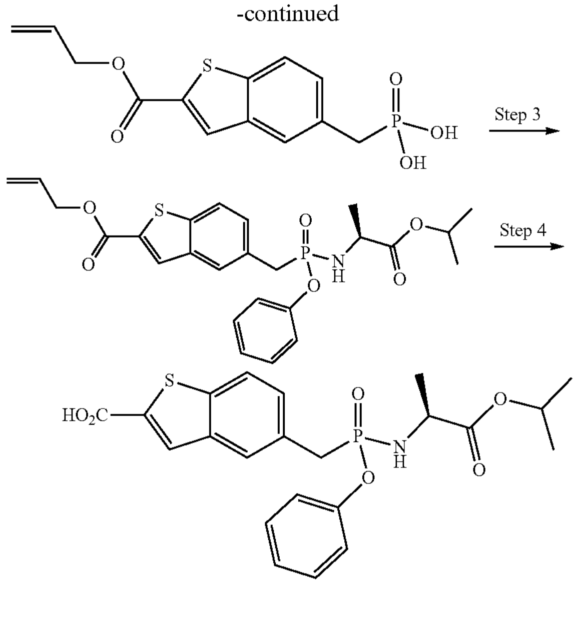

Step 1: Preparation of allyl 5-((diethoxyphosphoryl) methyl)benzo[b]thiophene-2-carboxylate To a suspension of 5-((diethoxyphosphoryl)methyl)benzo[b]thiophene-2-carboxylic acid (1.0 g, 3.0 mmol, 1.0 eq) and $K_2CO_3$ (839 mg, 6.1 mmol, 2.0 eq) in DMF (20 mL) was added 3-bromoprop-1-ene (440 mg, 3.6 mmol, 1.2 eq). The mixture was stirred at room temperature for 14 h and poured over water (30 mL). The mixture was extracted with EtOAc (25 mL×3). The combined organic layers were dried over $Na_2SO_4$, filtered, and concentrated under reduced pressure, the residue was purified by column chromatography to give allyl 5-((diethoxyphosphoryl)methyl)benzo[b]thiophene-2-carboxylate (0.980 g, 2.7 mmol, 88% yield) as a light-yellow solid. LCMS (ESI) m/z=369 $[M+H]^+$; $^1H$ NMR (400 MHz, $CDCl_3$) δ 8.04 (s, 1H), 7.84-7.77 (m, 2H), 7.45-7.37 (m, 1H), 6.18-5.94 (m, 1H), 5.49-5.39 (m, 1H), 5.36-5.28 (m, 1H), 4.87-4.83 (m, 2H), 4.08-3.97 (m, 4H), 3.27 (d, J=21.4 Hz, 2H), 1.25 (t, J=7.1 Hz, 6H).

Step 2: Preparation of ((2-((allyloxy)carbonyl)benzo [b]thiophen-5-yl)methyl)phosphonic acid To a solution of allyl 5-((diethoxyphosphoryl)methyl) benzo[b]thiophene-2-carboxylate (980 mg, 2.7 mmol, 1.0 eq) in $CH_2Cl_2$ (15 mL) was added bromotrimethylsilane (3 mL). The mixture was stirred at room temperature for 14 h and subsequently concentrated under reduced pressure. The resulting residue was triturated with $H_2O$ (5 mL) and the resulting precipitates were filtered. The filter cake was washed with $H_2O$ (5 mL×2) and dried under reduced pressure to give ((2-((allyloxy)carbonyl)benzo[b]thiophen-5-yl) methyl)phosphonic acid (0.710 g, 2.3 mmol, 86% yield) as a white solid. LCMS (ESI) m/z=313 $[M+H]^+$; $^1H$ NMR (400 MHz, DMSO-$d_6$) δ 8.20 (s, 1H), 7.96 (d, J=8.4 Hz, 1H), 7.92-7.83 (m, 1H), 7.50-7.38 (m, 1H), 6.12-5.98 (m, 1H), 5.46-5.38 (m, 1H), 5.32-5.27 (m, 1H), 4.85-4.80 (m, 2H), 3.08 (d, J=21.2 Hz, 2H).

Step 3: Preparation of allyl 5-(((((S)-1-isopropoxy-1-oxopropan-2-yl)amino)(phenoxy)phosphoryl) methyl)benzo[b]thiophene-2-carboxylate To a cooled (0° C.) solution (under a constant stream of $N_2$ (g)) of ((2-((allyloxy)carbonyl)benzo[b]thiophen-5-yl) methyl)phosphonic acid (2.80 g, 8.96 mmol, 1 eq) and catalytic DMF (1 drop) in dry $CH_2Cl_2$ (50 mL) was added oxalyl chloride (3.40 g, 26.8 mmol, 3 eq). After effervescence of gas ceased, the mixture was warmed at 40° C. After 2 h, the mixture was cooled to room temperature and concentrated in vacuo to give yellow solids. The solids were subsequently diluted $CH_2Cl_2$ (50 mL) and cooled to 0° C. To the cooled solution was added phenol (0.843 g, 8.96 mmol, 1 eq) and $Et_3N$ (4.53 g, 44.8 mmol, 5 eq). After complete addition, the mixture was warmed to room temperature and stirred for 1 h, followed by introduction of propan-2-yl (2S)-2-aminopropanoate (1.75 g, 13.4 mmol, 1.5 eq) to the mixture. After stirring for an additional 2 h, the mixture was concentrated to dryness. The residue was purified by C18 column (elution 50%-80% acetonitrile in water) to give allyl 5-(((((S)-1-isopropoxy-1-oxopropan-2-yl)amino)(phenoxy) phosphoryl)methyl)benzo[b]thiophene-2-carboxylate (2.23 g, 4.44 mmol, 49.6% yield) as white solids. LCMS (ESI) m/z=502.0 $[M+H]^+$; $^1H$ NMR (400 MHz, $CDCl_3$) δ 8.05 (d, J=6.9 Hz, 1H), 7.91-7.80 (m, 2H), 7.53-7.43 (m, 1H), 7.29 (d, J=8.1 Hz, 2H), 7.18-7.09 (m, 3H), 6.05 (ddd, J=16.1, 10.9, 5.6 Hz, 1H), 5.48-5.40 (m, 1H), 5.32 (dd, J=10.4, 1.2 Hz, 1H), 4.98-4.87 (m, 1H), 4.85 (d, J=5.7 Hz, 2H), 4.04-3.85 (m, 1H), 3.44 (dd, J=20.7, 14.1 Hz, 2H), 3.12 (t, J=10.9 Hz, 1H), 1.21-1.10 (m, 9H).

Step 4: Preparation of 5-(((((S)-1-isopropoxy-1-oxopropan-2-yl)amino)(phenoxy)phosphoryl) methyl)benzo[b]thiophene-2-carboxylic acid A solution of allyl 5-(((((S)-1-isopropoxy-1-oxopropan-2-yl)amino)(phenoxy)phosphoryl)methyl)benzo[b]thiophene-2-carboxylate (90 mg, 0.1794 mmol, 1 eq), pyrrolidine (12.7 mg, 179 μmol, 1 eq), $Pd(PPh_3)_4$ (10.3 mg, 8.97 μmol, 0.05 eq) in $CH_2Cl_2$ (5 mL) was stirred under $N_2$ (g). After 2 h, the reaction was concentrated in vacuo. The residue was purified by C18 column (elution 30%-70% acetonitrile in water) to yield 5-(((((S)-1-isopropoxy-1-oxo-propan-2-yl)amino)(phenoxy)phosphoryl)methyl)benzo[b] thiophene-2-carboxylic acid (64.0 mg, 0.1386 mmol, 77.4% yield) as white solids. LCMS (ESI) m/z 462.1 $[M+H]^+$.

The intermediates in the table below were prepared using the described above for synthesis of 5-(((((S)-1-isopropoxy-1-oxopropan-2-yl)amino)(phenoxy)phosphoryl)methyl) benzo[b]thiophene-2-carboxylic acid and utilizing the appropriate utilizing the appropriate starting materials and modifications.

| Name | Structure | LCMS |
|---|---|---|
| 5-(fluoro(((S)-1-isopropoxy-1-oxopropan-2-yl)amino)(phenoxy)phosphoryl)methyl)benzo[b]thiophene-2-carboxylic acid | 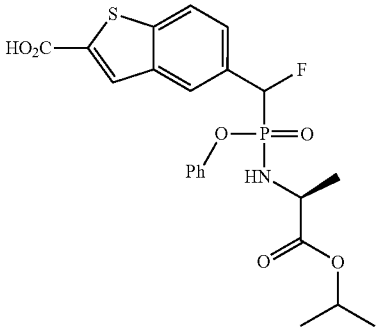 [SMILES: CC(C)OC(=O)[C@H](C)NP(=O)(Oc1ccccc1)C(F)c1ccc2sc(C(=O)O)cc2c1] | 480.1 [M + H]+ |
| 5-(((((S)-1-isopropoxy-1-oxopropan-2-yl)amino)(2,2,2-trifluoroethoxy)phosphoryl)methyl)benzo[b]thiophene-2-carboxylic acid | 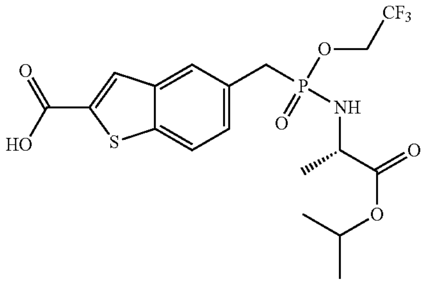 [SMILES: CC(C)OC(=O)[C@H](C)NP(=O)(Cc1ccc2sc(C(=O)O)cc2c1)OCC(F)(F)F] | 468.2 [M + H]+ |
| 5-(((4-chlorophenoxy)(((S)-1-isopropoxy-1-oxopropan-2-yl)amino)phosphoryl)methyl)benzo[b]thiophene-2-carboxylic acid | 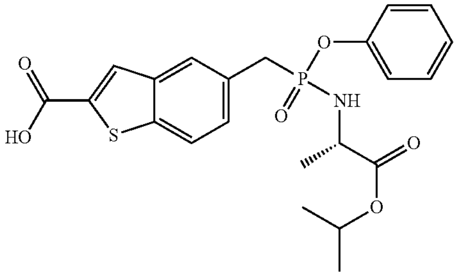 [SMILES: CC(C)OC(=O)[C@H](C)NP(=O)(Cc1ccc2sc(C(=O)O)cc2c1)Oc1ccccc1] | 496.2 [M + H]+ |
| 5-(((2-chlorophenoxy)(((S)-1-isopropoxy-1-oxopropan-2-yl)amino)phosphoryl)methyl)benzo[b]thiophene-2-carboxylic acid | 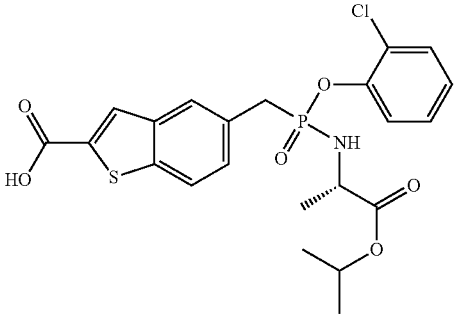 [SMILES: CC(C)OC(=O)[C@H](C)NP(=O)(Cc1ccc2sc(C(=O)O)cc2c1)Oc1ccccc1Cl] | 496.2 [M + H]+ |

Synthesis of 5-(((((S)-1-(benzyloxy)-1-oxopropan-2-yl)amino)(phenoxy)phosphoryl)difluoromethyl)benzo[b]thiophene-2-carboxylic acid

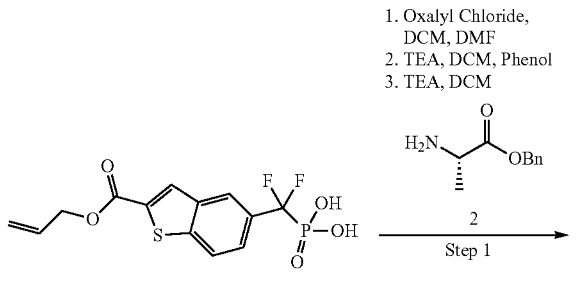

1

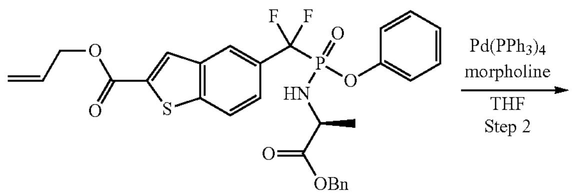

3

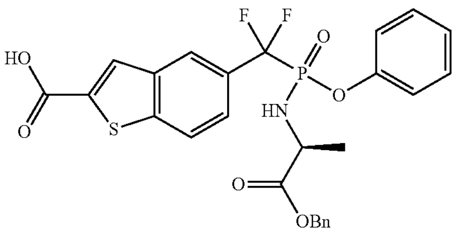

4

Step 1: Preparation of allyl 5-(((((S)-1-(benzyloxy)-1-oxopropan-2-yl)amino)(phenoxy)phosphoryl)difluoromethyl)benzo[b]thiophene-2-carboxylate To a solution of ((2-((allyloxy)carbonyl)benzo[b]thiophen-5-yl)difluoromethyl)phosphonic acid (300 mg, 861 μmol, 1 eq) in DCM (5 mL) at 0° C. were added 2 drops of DMF (cat.) followed by dropwise addition of oxalyl chloride (220 μL, 2.58 mmol, 3 eq). The reaction was warmed up to room temperature and stirred for 16 h. The reaction mixture was concentrated under reduced pressure and dried completely under high vacuum for 30 min. to give a yellow solid. The yellow solid was diluted in DCM (5 mL) and cooled to 0° C. A solution of phenol (89.1 mg, 947 μmol, 1.1 eq) and triethylamine (599 μL, 4.30 mmol, 5 eq) in DCM (1 mL, dried on $Na_2SO_4$) was slowly added to the yellow solution. The reaction mixture was stirred at 0° C. for 2 min. and then warmed up to room temperature and stirred for 2 h. A solution of L-alanine benzyl ester p-toluenesulfonate salt (453 mg, 1.29 mmol, 1.5 eq) in DCM (1 mL, dried on $Na_2SO_4$) was slowly added to the yellow solution. The reaction mixture was stirred at room temperature for 18 h. The solvent was removed in vacuo. The crude product was purified by reverse phase chromatography on a 50 g Cis cartridge eluting with a gradient of 5-100% acetonitrile in water. The pure fractions were combined and concentrated under reduced pressure to give allyl 5-(((((S)-1-(benzyloxy)-1-oxopropan-2-yl)amino)(phenoxy)phosphoryl)difluoromethyl)benzo[b]thiophene-2-carboxylate (196 mg, 38.8%) as a yellow oil. LCMS (ESI) m/z=586.2.

The intermediates in the table below were prepared using the method described above in Step 1 for the preparation of allyl 5-(((((S)-1-(benzyloxy)-1-oxopropan-2-yl)amino)(phenoxy)phosphoryl)difluoromethyl)benzo[b]thiophene-2-carboxylate and utilizing the appropriate starting materials and modifications.

| Name | Structure | NMR; LCMS |
|---|---|---|
| butyl (2S)-1-(((2-((allyloxy)carbonyl)benzo[b]thiophen-5-yl)difluoromethyl)(phenoxy)phosphoryl)-4,4-difluoropyrrolidine-2-carboxylate | 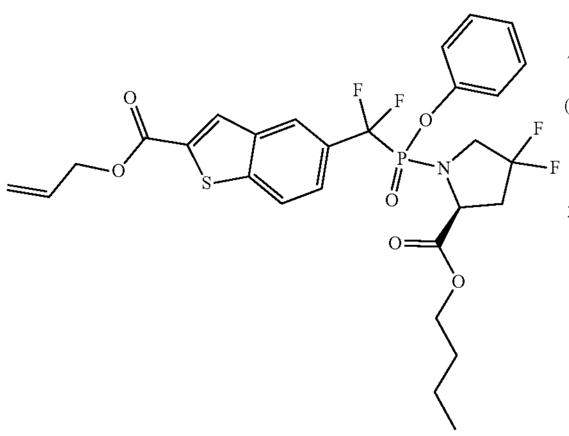 | $^1H$ NMR (400 MHz, $CDCl_3$) δ 8.19 (s, 1H), 8.12 (s, 1H), 7.99-7.91 (m, 1H), 7.79-7.73 (m, 1H), 7.35-7.02 (m, 5H), 6.12-5.98 (m, 1H), 5.50-5.41 (m, 1H), 5.38-5.28 (m, 1H), 4.89-4.84 (m, 2H), 4.81-4.73 (m, 0.8H), 4.47-4.38 (m, 0.2H), 4.29-3.96 (m, 2H), 3.88-3.64 (m, 2H), 2.76-2.43 (m, 2H), 1.61-1.50 (m, 2H), 1.39-1.23 (m, 2H), 0.90 (t, J = 7.3 Hz, 3H); 614.2 [M + H]$^+$ |

-continued

| Name | Structure | NMR; LCMS |
| --- | --- | --- |
| butyl (((2-((allyloxy)carbonyl)benzo[b]thiophen-5-yl)difluoromethyl)(phenoxy)phosphoryl)-L-prolinate | 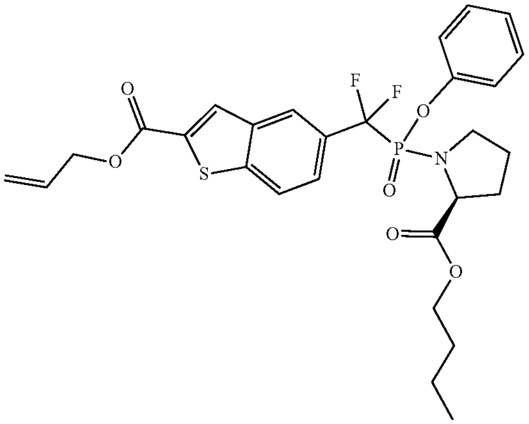 | 542.3 $[M + H]^+$ |

Step 2: Preparation of 5-(((((S)-1-(benzyloxy)-1-oxopropan-2-yl)amino)(phenoxy)phosphoryl)difluoromethyl)benzo[b]thiophene-2-carboxylic acid To a stirred solution of allyl 5-(((((S)-1-(benzyloxy)-1-oxopropan-2-yl)amino)(phenoxy)phosphoryl)difluoromethyl)benzo[b]thiophene-2-carboxylate (196 mg, 334 μmol, 1 eq) in THF (5 mL) were added morpholine (143 μL, 1.67 mmol, 5 eq) and $Pd(PPh_3)_4$ (38.5 mg, 33.4 μmol, 0.10 eq) under nitrogen. The reaction mixture was stirred 1 h at room temperature. The reaction mixture was directly purified by reverse phase chromatography on a 50 g C18 cartridge eluting with a gradient of 5-100% acetonitrile in water (with 0.1% formic acid). The pure fractions were concentrated under reduced pressure to give 5-(((((S)-1-(benzyloxy)-1-oxopropan-2-yl)amino)(phenoxy)phosphoryl)difluoromethyl)benzo[b]thiophene-2-carboxylic acid (164 mg, 90.1%) as a light brown solid. $^1$H NMR (400 MHz, $CDCl_3$) δ 8.22-8.09 (m, 1H), 7.88-7.76 (m, 2H), 7.66-7.59 (m, 1H), 7.43-7.29 (m, 7.6H), 7.26-7.15 (m, 2.4H), 5.24 (s, 1H), 5.13 (s, 1H), 4.83-4.67 (m, 0.5H), 4.62-4.44 (m, 0.5H), 4.39-4.14 (m, 1H), 1.50-1.35 (m, 3H).

The intermediates in the table below were prepared using the method described above in Step 2 for the preparation of 5-(((((S)-1-(benzyloxy)-1-oxopropan-2-yl)amino)(phenoxy)phosphoryl)difluoromethyl)benzo[b]thiophene-2-carboxylic acid and utilizing the appropriate starting materials and modifications.

| Name | Structure | LCMS |
| --- | --- | --- |
| 5-((((S)-2-(butoxycarbonyl)-4,4-difluoropyrrolidin-1-yl)(phenoxy)phosphoryl)difluoromethyl)benzo[b]thiophene-2-carboxylic acid | 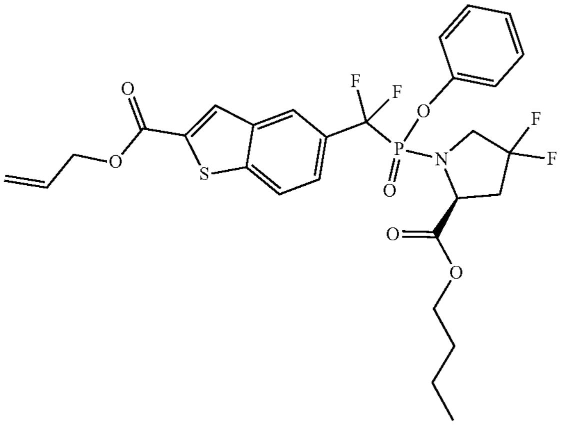 | 574.2 $[M + H]^+$ |

-continued

| Name | Structure | LCMS |
| --- | --- | --- |
| 5-((((S)-2-(butoxycarbonyl)pyrrolidin-1-yl)(phenoxy)phosphoryl)difluoromethyl) benzo[b]thiophene-2-carboxylic acid | 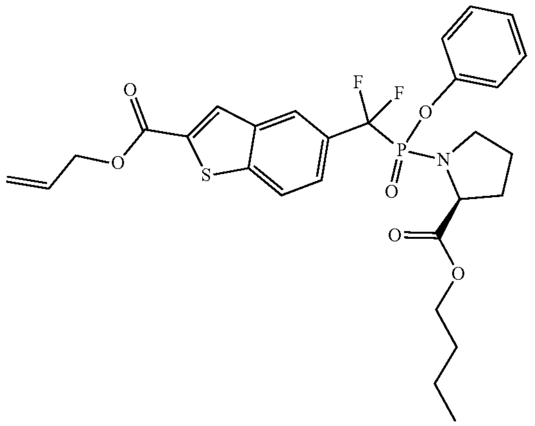 | 537.8 $[M + H]^+$ |

Synthesis of 5-(((((S)-1-butoxy-1-oxopropan-2-yl) amino)(naphthalen-1-yloxy)phosphoryl)difluoromethyl)benzo[b]thiophene-2-carboxylic acid

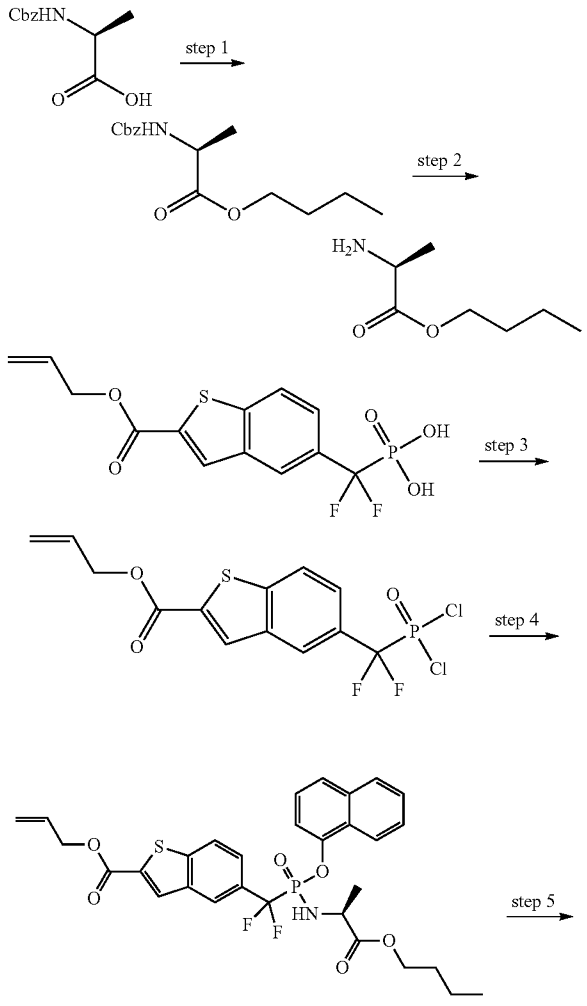

-continued

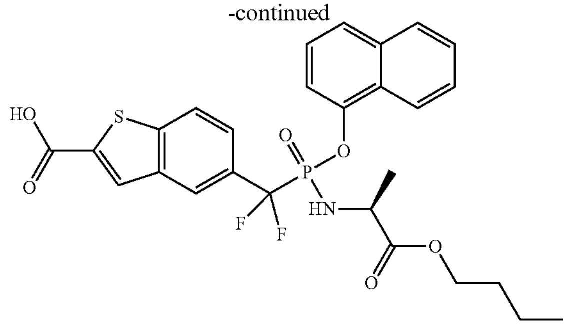

Step 1: Preparation of butyl ((benzyloxy)carbonyl)-L-alaninate

To a solution of ((benzyloxy)carbonyl)-L-alanine (5 g, 22 mmol, 1 eq) in DMF (50 mL) was added 1-chlorobutane (2.1 g, 22 mmol, 1 eq) and dipotassium carbonate (6.2 g, 45 mmol, 2 eq), the mixture was stirred at 60° C. for 1 h to give yellow solution. The mixture was diluted with water (200 mL) and extracted with EtOAc (200 mL×2), the combined organic layers were washed with saturated brine (200 mL×2), dried over $Na_2SO_4$, filtered and concentrated under reduced pressure to give a residue. The residue was purified by column chromatography to give butyl ((benzyloxy)carbonyl)-L-alaninate (3.6 g, 13 mmol, 57.8% yield) as a yellow oil. LCMS (ESI) m/z=280.0

Step 2: Preparation of butyl L-alaninate

To a solution of butyl ((benzyloxy)carbonyl)-L-alaninate (3 g, 11 mmol, 1 eq) in THF (30 mL) was added Pd/C (3 g, 10%) under $N_2$, the mixture was stirred at 25° C. for 2 h under $H_2$ (15 Psi). The reaction mixture was filtered and the filter was concentrated to give butyl L-alaninate (1.7 g, crude) as a yellow oil. LCMS (ESI) m/z=146.1 $[M+H]^+$.

Step 3: Preparation of allyl 5-((dichlorophosphoryl) difluoromethyl)benzo[b]thiophene-2-carboxylate To a solution of ((2-((allyloxy)carbonyl)benzo[b]thiophen-5-yl)difluoromethyl)phosphonic acid (0.2 g, 0.57 mmol, 1 eq) in DCM (5 mL) was added dimethylformamide (0.42 mg, 5.7 μmol, 0.01 eq), the mixture was stirred at 0° C. for 5 min, then a solution of oxalyl chloride (0.22 g, 1.7 mmol, 3 eq) in DCM (5 mL) was added to the mixture, the mixture was stirred at 40° C. for 15 min to give yellow solution. The reaction mixture was concentrated under reduced pressure to give allyl 5-((dichlorophosphoryl)difluoromethyl)benzo[b]thiophene-2-carboxylate (0.2 g, crude) as a yellow oil. LCMS (ESI) m/z=377.0 [M+H]$^+$.

Step 4: Preparation of allyl 5-(((((S)-1-butoxy-1-oxopropan-2-yl)amino)(naphthalen-1-yloxy)phosphoryl)difluoromethyl)benzo[b]thiophene-2-carboxylate To a solution of allyl 5-((dichlorophosphoryl)difluoromethyl)benzo[b]thiophene-2-carboxylate (0.2 g, 0.52 mmol, 1 eq) in DCM (10 mL) was added naphthalen-1-ol (60 mg, 0.42 mmol, 0.8 eq), the mixture was stirred at 0° C. for 5 min, then a solution of N,N-diisopropylethylamine (0.2 g, 1.6 mmol, 3.0 eq) in DCM (10 mL) was added to the mixture, then a solution of butyl L-alaninate (75 mg, 0.52 mmol, 1 eq) in DCM (10 mL) was added to the mixture, the mixture was stirred at 0° C. for 30 min to give yellow solution. The reaction mixture was concentrated under reduced pressure to give a residue. The residue was purified by column chromatography to give allyl 5-(((((S)-1-butoxy-1-oxopropan-2-yl)amino)(naphthalen-1-yloxy)phosphoryl)difluoromethyl)benzo[b]thiophene-2-carboxylate (0.15 g, 0.24 mmol, 46.4% yield) as a yellow oil. LCMS (ESI) m/z=602.1 [M+H]$^+$.

Step 5: Preparation of 5-(((((S)-1-butoxy-1-oxopropan-2-yl)amino)(naphthalen-1-yloxy)phosphoryl)difluoromethyl)benzo[b]thiophene-2-carboxylic acid To a solution of allyl 5-(((((S)-1-butoxy-1-oxopropan-2-yl)amino)(naphthalen-1-yloxy)phosphoryl)difluoromethyl)benzo[b]thiophene-2-carboxylate (0.14 g, 0.23 mmol, 1 eq) in DCM (1.0 mL) was added $Pd(PPh_3)_4$ (27 mg, 23 μmol, 0.1 eq), the mixture was stirred at 0° C. for 5 min, then pyrrolidine (17 mg, 0.23 mmol, 1 eq) was added to the mixture, the mixture was stirred at 25° C. for 5 min to give yellow solution. The reaction mixture was concentrated under reduced pressure to give a residue. The residue was purified by reversed phase (TFA) to give 5-(((((S)-1-butoxy-1-oxopropan-2-yl)amino)(naphthalen-1-yloxy)phosphoryl)difluoromethyl)benzo[b]thiophene-2-carboxylic acid (97 mg, 0.17 mmol, 74.6% yield) as a yellow oil. LCMS (ESI) m/z=562.1 [M+H]$^+$.

Synthesis of ((2-((allyloxy)carbonyl)benzo[b]thiophen-5-yl)methyl)phosphonic acid and ((2-((allyloxy)carbonyl)benzo[b]thiophen-5-yl)fluoromethyl)phosphonic acid

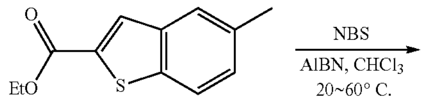

1

-continued

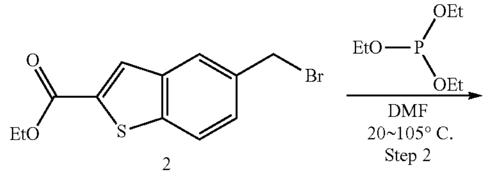

2

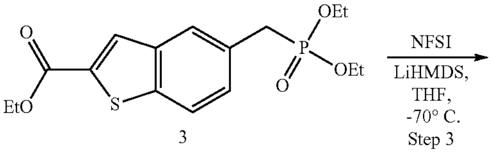

3

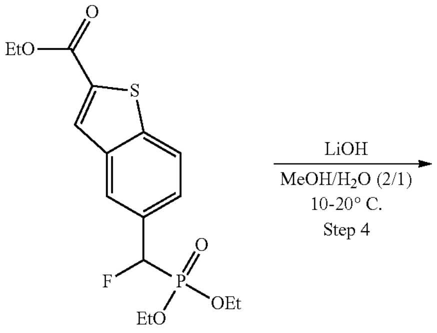

4

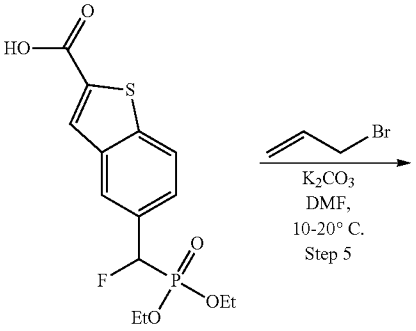

5

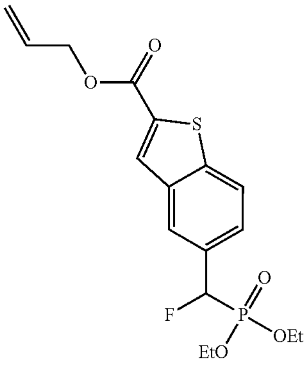

6

-continued

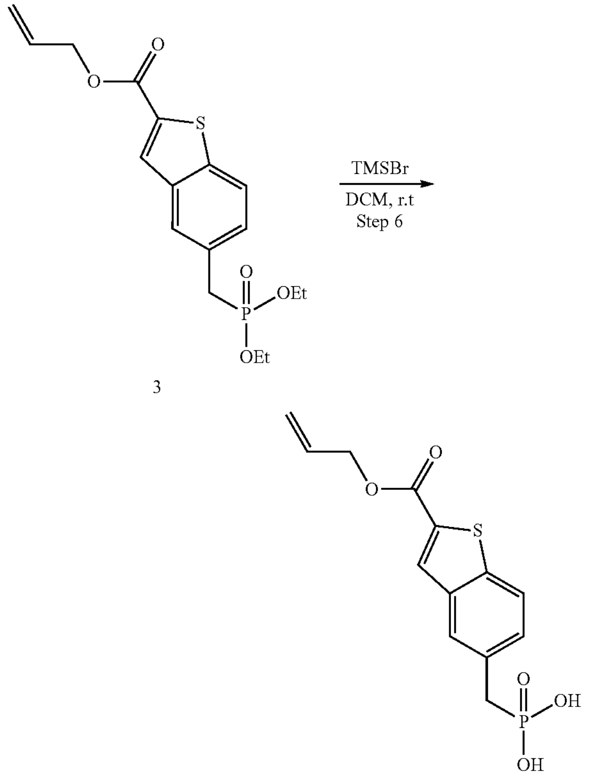

3

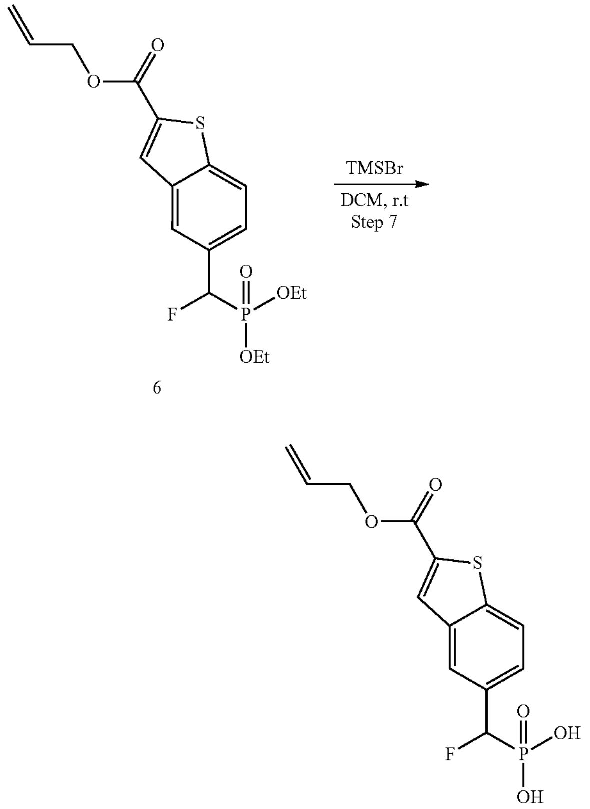

6

Ethyl 5-methylbenzo[b]thiophene-2-carboxylate was prepared according to the procedure described in WO 2016/100184 (e.g., paragraphs [0281]-[0284], which are incorporated by reference herein).

Step 1: Preparation of ethyl 5-(bromomethyl)benzo[b]thiophene-2-carboxylate

To a solution of ethyl 5-methylbenzo[b]thiophene-2-carboxylate (1, 7.3 kg, 33.1 mol, 1.0 eq.) in $CHCl_3$ (58 L) stirred at 20° C. was added AIBN (544 g, 3.31 mol, 0.10 eq.) and NBS (6.19 kg, 34.8 mol, 1.05 eq.). The mixture was heated from 30° C. to 50° C. over 4 h and was then heated to 60° C. and stirred for 12 hours. After completion, the reaction mixture was cooled to 10° C. and 15% $Na_2SO_3$ (20 L) was added. The organic layers were washed with $H_2O$ (20 L*2), dried over $Na_2SO_4$, and concentrated under reduced pressure at 45° C. to afford ethyl 5-(bromomethyl)benzo[b]thiophene-2-carboxylate (2, 9.50 kg, 23.5 mol, 70.9% yield, 74.0% purity) as a yellow solid. LCMS (ESI): m/z=298.9 $[M+H]^+$. $^1H$ NMR (400 MHz, $CDCl_3$) δ 8.034 (s, 1H), 7.89-7.84 (m, 2H), 7.50 (d, J=9.6 Hz, 1H), 4.64 (s, 2H), 4.45-4.40 (m, 2H), 1.45-1.41 (m, 3H).

Step 2: Preparation of ethyl 5-((diethoxyphosphoryl)methyl)benzo[b]thiophene-2-carboxylate To a solution of ethyl 5-(bromomethyl)benzo[b]thiophene-2-carboxylate (2, 9.50 kg, 31.8 mol, 1.0 eq.) in DMF (28.5 L) stirred at 20° C. was added triethyl phosphite (5.8 kg, 34.9 mol, 1.1 equiv). The mixture was heated to 100° C. and stirred for 5 h. After completion, the reaction mixture was cooled to 15° C., poured into $H_2O$ (50.0 L), and extracted with EtOAc (20 L*2). The combined organics were washed with $H_2O$ (20 L*2) and brine (10 L), dried over $Na_2SO_4$, and concentrated under reduced pressure at 45° C. to give a residue. Crude residue was purified by silica gel chromatography (Petroleum ether/Ethyl acetate=100/1 to 1/1, Petroleum ether/Ethyl acetate=0/1) to afford ethyl 5-((diethoxyphosphoryl)methyl)benzo[b]thiophene-2-carboxylate (3, 5.24 kg, 14 mol, 44.4% yield) as yellow solid. LCMS (ESI): m/z=356.9 $[M+H]^+$. $^1H$ NMR (400 MHz, $CDCl_3$) δ 8.02 (s, 1H), 7.82-7.80 (m, 2H), 7.41 (d, J=2.0 Hz, 1H), 4.44-4.41 (m, 2H), 4.05-4.01 (m, 4H), 3.27 (d, J=21.6 Hz, 2H), 1.46-1.42 (m, 3H), 1.27-1.23 (m, 6H).

Step 3: Preparation of ethyl 5-((diethoxyphosphoryl)fluoromethyl)benzo[b]thiophene-2-carboxylate Three batches were carried out in parallel.

To a solution of ethyl 5-((diethoxyphosphoryl)methyl)benzo[b]thiophene-2-carboxylate (3, 250 g, 702 mmol, 1.00 eq) and N-(benzenesulfonyl)-N-fluorobenzenesulfonamide (221 g, 702 mmol, 1.00 eq) in THF (2.50 L) was added dropwise LiHMDS (1 M, 702 mL, 1.00 eq) at −70° C. under $N_2$. The mixture was stirred at −70° C. for 3 h. Following completion, the reaction mixture was poured into saturated $NH_4Cl$ aqueous solution (5.00 L) slowly at 0° C. and the mixture was stirred at 0° C. for 0.5 hr. Then three batches were combined to workup. The mixture was extracted with ethyl acetate (5.00 L*3). The organic layers were combined, washed with brine (5.00 L), dried over anhydrous $Na_2SO_4$ and concentrated under reduced pressure. The residue was purified by column chromatography ($SiO_2$, petroleum ether/ethyl acetate=1/0-3/1, $R_f$=0.30, petroleum ether/ethyl acetate=1/1) to give ethyl 5-((diethoxyphosphoryl)fluoromethyl)benzo[b]thiophene-2-carboxylate (4, 357 g, 928 mmol, 44.1% yield) as yellow oil. LCMS (ESI): m/z=375.0 $[M+H]^+$. $^1H$ NMR (400 MHz, $CDCl_3$) δ 8.07 (s, 1H), 8.00 (s, 1H), 7.90 (d, J=8.4 Hz, 1H), 7.59 (d, J=8.8 Hz, 1H), 5.88-5.75 (m, 1H), 4.45-4.40 (m, 2H), 4.15-4.05 (m, 4H), 1.45-1.41 (m 3H), 1.31-1.28 (m, 6H).

Step 4: Preparation of 5-((diethoxyphosphoryl)fluoromethyl)benzo[b]thiophene-2-carboxylic acid To a solution of ethyl 5-((diethoxyphosphoryl)fluoromethyl)benzo[b]thiophene-2-carboxylate (4, 252 g, 673 mmol, 1.00 eq) in MeOH (1.80 L) was added $H_2O$ (760 mL) and $LiOH{\cdot}H_2O$ (56.5 g, 1.35 mol, 2.00 eq) at 10-20° C. under $N_2$. The mixture was stirred at 10-20° C. for 1 hr. TLC (petroleum ether/ethyl acetate=1/1) showed that compound 4 was consumed ($R_f$=0.30) and desired spot ($R_f$=0.10) was formed. The reaction mixture was quenched by $H_2O$ (2.50 L) and then adjusted pH to 3-4 with HCl (aq. 1M). The mixture was extracted with dichloromethane (2.50 L*3). The combined organic layers were dried over anhydrous $Na_2SO_4$ and concentrated under reduced pressure to give 5-((diethoxyphosphoryl)fluoromethyl)benzo[b]thiophene-2-carboxylic acid (5, 222 g, 626 mmol, 93.0% yield) as a white solid.

Step 5: Preparation of allyl 5-((diethoxyphosphoryl)fluoromethyl)benzo[b]thiophene-2-carboxylate Two batches were carried out in parallel.

To a solution of 5-((diethoxyphosphoryl)fluoromethyl)benzo[b]thiophene-2-carboxylic acid (5, 178 g, 514 mmol, 1.00 eq) in DMF (1.78 L) was added $K_2CO_3$ (142 g, 1.03 mol, 2.00 eq) and allyl bromide (68.4 g, 565 mmol, 1.10 eq) at 10-20° C. The mixture was stirred at 10-20° C. for 12 h. TLC (petroleum ether/ethyl acetate=0/1) showed that compound 5 was consumed ($R_f$=0.60) and a new spot ($R_f$=0.70) was formed. The reaction mixture was diluted with $H_2O$ (6.00 L), extracted with ethyl acetate (2.00 L*3). The organic layers were combined. The mixture was washed with brine (2.00 L) and $NH_4Cl$ (2.00 L), dried over anhydrous $Na_2SO_4$ and concentrated under reduced pressure to give allyl 5-((diethoxyphosphoryl)fluoromethyl)benzo[b]thiophene-2-carboxylate (6, 388 g, 985 mmol, 95.8% yield) as yellow oil.

Step 6: Preparation of ((2-((allyloxy)carbonyl)benzo[b]thiophen-5-yl)methyl)phosphonic acid To a solution of allyl 5-((diethoxyphosphoryl)methyl)benzo[b]thiophene-2-carboxylate (3, 50 g, 136 mmol, 1.0 eq.) in DCM (5 L) was added TMSBr (411 g, 2.71 mol, 20.0 eq.) dropwise at 0° C. After addition, the reaction mixture was allowed to warm to room temperature and stirred for an additional 12 h. The reaction progress was monitored by LCMS. After completion, the reaction mixture was concentrated under reduced pressure and water was added. The resulting mixture was filtered and the filter cake was washed with water (2 L), then dried in vacuum to afford ((2-((allyloxy)carbonyl)benzo[b]thiophen-5-yl)methyl)phosphonic acid (40.3 g, 129 mmol, 95%) as a yellow solid. $^1H$ NMR (400 MHz, DMSO-$d_6$) δ 8.20 (s, 1H), 7.96 (d, J=8.4 Hz, 1H), 7.87 (s, 1H), 7.43 (d, J=8.4 Hz, 1H), 6.10-5.98 (m, 1H), 5.46-5.37 (m, 1H), 5.33-5.24 (m, 1H), 4.86-4.77 (m, 2H), 3.08 (d, J=21.2 Hz, 2H). LCMS (ESI) m/z=313.1 $[M+H]^+$.

Step 7: Preparation of ((2-((allyloxy)carbonyl)benzo[b]thiophen-5-yl)fluoromethyl)phosphonic acid To a solution of allyl 5-((diethoxyphosphoryl)fluoromethyl)benzo[b]thiophene-2-carboxylate (6, 5.2 g, 13.5 mmol, 1.0 eq.) in DCM (500 mL) was added TMSBr (41.1 g, 270 mmol, 20.0 eq.) dropwise at 0° C. After the addition, the reaction mixture was allowed to warm to room temperature and stirred for an additional 12 h. The reaction progress was monitored by LCMS. After completion, the reaction mixture was concentrated under reduced pressure and water was added. The resulting mixture was filtered and the filter cake was washed with water (200 mL), then dried in vacuum to afford ((2-((allyloxy)carbonyl)benzo[b]thiophen-5-yl)fluoromethyl)phosphonic acid (3.1 g, 9.37 mmol, 69%) as a yellow solid. $^1H$ NMR (400 MHz, DMSO-$d_6$) δ 8.32 (s, 1H), 8.14-8.05 (m, 2H), 7.59 (d, J=8.4 Hz, 1H), 6.12-5.99 (m, 1H), 5.84 (dd, J=44.3, 8.2 Hz, 1H), 5.49-5.40 (m, 1H), 5.35-5.27 (m, 1H), 4.88-4.81 (m, 2H). LCMS (ESI): m/z=329.1 $[M-H]^-$.

Chiral Separation of allyl 5-((diethoxyphosphoryl)fluoromethyl)benzo[b]thiophene-2-carboxylate Rac-allyl 5-((diethoxyphosphoryl)fluoromethyl)benzo[b]thiophene-2-carboxylate (617 g, 1.62 mol, 1.00 eq) was purified by SFC to give allyl (S)-5-((diethoxyphosphoryl)fluoromethyl)benzo[b]thiophene-2-carboxylate (Peak 1) and allyl (R)-5-((diethoxyphosphoryl)fluoromethyl)benzo[b]thiophene-2-carboxylate (Peak 2).

Preparative SFC method: Instrument: Waters 350 Preparative SFC. Column: REGIS (S,S) WHELK-O1, 250×50 mm I.D., 10 μm. Mobile phase: A for $CO_2$ and B for MEOH (Neu). Gradient: B 30%. Flow rate: 220 g/min. Back pressure: 100 bar. Column temperature: 35° C. Wavelength: 220 nm. Cycle-time: 3.3 min.

Analytical SFC method: Column: Kromasil (S,S) WHELK-01, 50×4.6 mm I.D., 3.5 μm. Mobile phase: A for $CO_2$ and B for MEOH (0.05% DEA). Gradient: B 5 to 40% Flow rate: 3 mL/min. Back pressure: 100 bar. Column temperature: 35° C. Wavelength: 220 nm.

allyl (S)-5-((diethoxyphosphoryl)fluoromethyl)benzo[b]thiophene-2-carboxylate (Peak 1, 267 g, 685 mmol, 39.7% yield, >99% ee, RT=1.36 min) was obtained as yellow oil. LCMS (ESI): m/z=387.1 $[M+H]^+$.

allyl (R)-5-((diethoxyphosphoryl)fluoromethyl)benzo[b]thiophene-2-carboxylate (Peak 2, 270 g, 676 mmol, 39.2% yield, >99% ee, RT=1.55 min) was obtained as yellow oil. LCMS (ESI): m/z=387.1 $[M+H]^+$.

Assignment of absolute stereochemical configuration was made by comparison of experimental vibrational circular dichroism (VCD) spectra with theoretical VCD spectra obtained from DFT calculations.

The intermediates in the table below were prepared using the method described above in Step 7 for the preparation of ((2-((allyloxy)carbonyl)benzo[b]thiophen-5-yl)fluoromethyl)phosphonic acid and utilizing the appropriate starting materials and modifications.

| Name | Structure | LCMS |
|---|---|---|
| (S)-((2-((allyloxy)carbonyl)benzo[b]thiophen-5-yl)fluoromethyl)phosphonic acid | 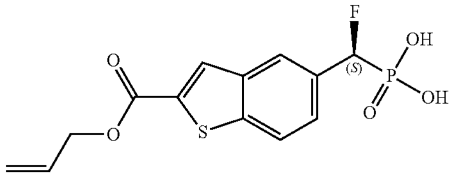 | 329 [M − H]⁻ |
| (R)-((2-((allyloxy)carbonyl)benzo[b]thiophen-5-yl)fluoromethyl)phosphonic acid | 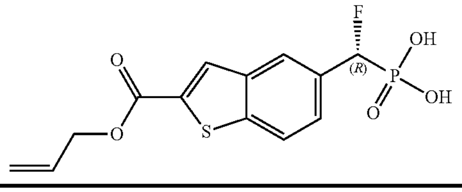 | 329 [M − H]⁻ |

Synthesis of 5-(((2,6-dimethylphenoxy)(((S)-1-oxo-1-propoxypropan-2-yl)amino)phosphoryl)methyl)benzo[b]thiophene-2-carboxylic acid

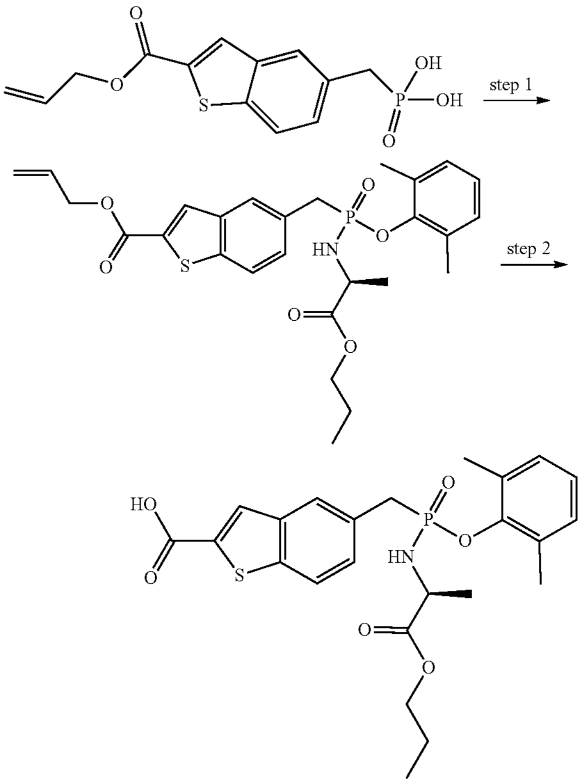

Step 1: Preparation of allyl 5-(((2,6-dimethylphenoxy)(((S)-1-oxo-1-propoxypropan-2-yl)amino)phosphoryl)methyl)benzo[b]thiophene-2-carboxylate To a suspension of ((2-((allyloxy)carbonyl)benzo[b]thiophen-5-yl)methyl)phosphonic acid (0.150 g, 480 μmol, 1 eq) and 1 drop of DMF (cat.) in DCM (4 mL) at 0° C. was added oxalyl chloride (122 μL, 1.44 mmol, 3 eq) and the mixture was stirred for 2 days at room temperature. The reaction was concentrated under reduced pressure and then dried under high vacuum for 20 min. The crude residue was diluted in toluene (5 mL). A solution of 2,6-dimethylphenol (58.6 mg, 480 μmol, 1 eq) and triethylamine (333 μL, 2.40 mmol, 5 eq) in toluene (2 mL, dried with sodium sulfate) was added to the mixture and stirred at 90° C. for 3 h. Propyl (2S)-2-aminopropanoate hydrochloride (80.4 mg, 480 μmol, 1 eq) was added at once at 90° C. and the reaction was stirred at 90° C. for 2 h. The reaction was cooled down to room temperature and quenched with 2 drops of water and toluene was removed under reduced pressure. The product was purified by reverse phase chromatography on a 100 g Cis cartridge eluting with a gradient of 5-100% acetonitrile in water (with 0.1% formic acid) to afford allyl 5-(((2,6-dimethylphenoxy)(((S)-1-oxo-1-propoxypropan-2-yl)amino)phosphoryl)methyl)benzo[b]thiophene-2-carboxylate (50.0 mg, 19.6%) as a pale yellow oil. LCMS (ESI) m/z=530.4 $[M+H]^+$.

The intermediates in the table below were prepared using the method described above in Step 1 for the preparation of allyl 5-(((2,6-dimethylphenoxy)(((S)-1-oxo-1-propoxypropan-2-yl)amino)phosphoryl)methyl)benzo[b]thiophene-2-carboxylate and utilizing the appropriate starting materials and modifications.

| Name | Structure | NMR; LCMS |
|---|---|---|
| allyl 5-((((2-methyl-3-oxo-3-propoxypropyl)amino)(phenoxy)phosphoryl)methyl)benzo[b]thiophene-2-carboxylate | 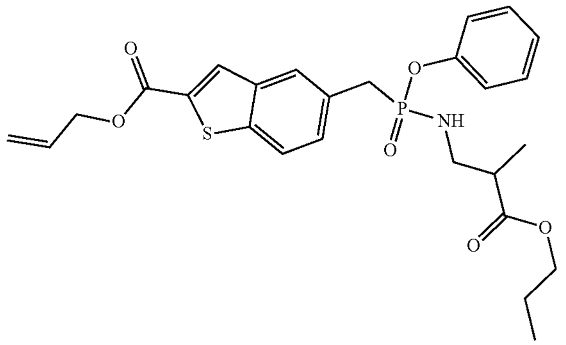 [SMILES: C=CCOC(=O)c1cc2cc(CP(=O)(NCC(C)C(=O)OCCC)Oc3ccccc3)ccc2s1] | $^1H$ NMR (400 MHz, $CDCl_3$) δ 8.07-8.02 (m, 1H), 7.88-7.80 (m, 2H), 7.50-7.43 (m, 1H), 7.33-7.27 (m, 2H), 7.19-7.10 (m, 3H), 6.11-5.99 (m, 1H), 5.49-5.41 (m, 1H), 5.36-5.30 (m, 1H), 4.89-4.83 (m, 2H), 4.03-3.85 (m, 2H), 3.47-3.36 (m, 2H), 3.14-2.95 (m, 3H), 2.43-2.31 (m, 1H), 1.64-1.51 (m, 2H), 1.01 (d, J = 7.3 Hz, 3H), 0.92-0.83 (m, 3H); 516.4 $[M + H]^+$ |
| butyl (2S)-1-(((2-((allyloxy)carbonyl)benzo[b]thiophen-5-yl)methyl)(phenoxy)phosphoryl)-4,4-difluoropyrrolidine-2-carboxylate | 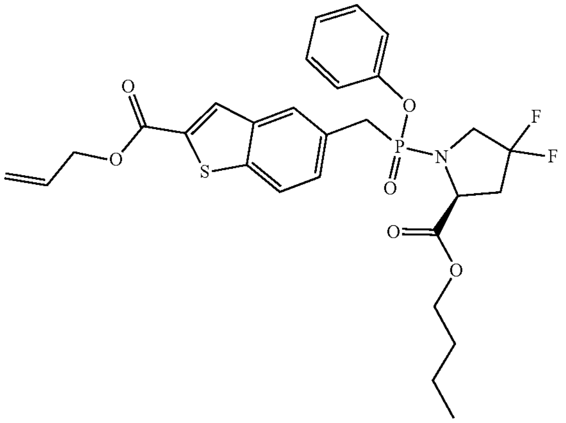 [SMILES: C=CCOC(=O)c1cc2cc(CP(=O)(Oc3ccccc3)N3CC(F)(F)C[C@H]3C(=O)OCCCC)ccc2s1] | $^1H$ NMR (400 MHz, $CDCl_3$) δ 8.10-8.02 (m, 1H), 8.00-7.89 (m, 1H), 7.88-7.80 (m, 1H), 7.63-7.50 (m, 1H), 7.37-7.10 (m, 5H), 6.14-5.98 (m, 1H), 5.49-5.42 (m, 1H), 5.39-5.28 (m, 1H), 4.89-4.83 (m, 2H), 4.73-4.67 (m, 0.4H), 4.30-4.23 (m, 0.6H), 4.23-4.02 (m, 2H), 3.82-3.59 (m, 1H), 3.58-3.41 (m, 2H), 3.31-3.04 (m, 1H), 2.54-2.20 (m, 2H), 1.70-1.48 (m, 2H), 1.45-1.15 (m, 2H), 0.98-0.88 (m, 3H); 578.4 $[M + H]^+$ |
| allyl 5-(((((S)-1-oxo-1-propoxybutan-2-yl)amino)(phenoxy)phosphoryl)methyl)benzo[b]thiophene-2-carboxylate | 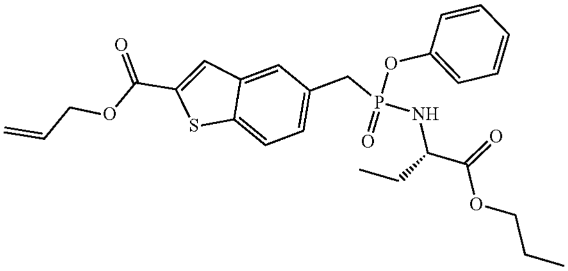 [SMILES: C=CCOC(=O)c1cc2cc(CP(=O)(N[C@@H](CC)C(=O)OCCC)Oc3ccccc3)ccc2s1] | $^1H$ NMR (400 MHz, $CDCl_3$) δ 8.09-8.00 (m, 1H), 7.93-7.81 (m, 2H), 7.56-7.44 (m, 1H), 7.33-7.27 (m, 2H), 7.19-7.04 (m, 3H), 6.12-6.00 (m, 1H), 5.49-5.42 (m, 1H), 5.37-5.30 (m, 1H), 4.89-4.82 (m, 2H), 4.05-3.87 (m, 3H), 3.51-3.39 (m, 2H), 3.33-3.07 (m, 1H), 1.63-1.46 (m, 4H), 0.93-0.83 (m, 3H), 0.78-0.59 (m, 3H); 516.2 $[M + H]^+$ |
| allyl 5-((((4-oxo-4-propoxybutan-2-yl)amino)(phenoxy)phosphoryl)methyl)benzo[b]thiophene-2-carboxylate | 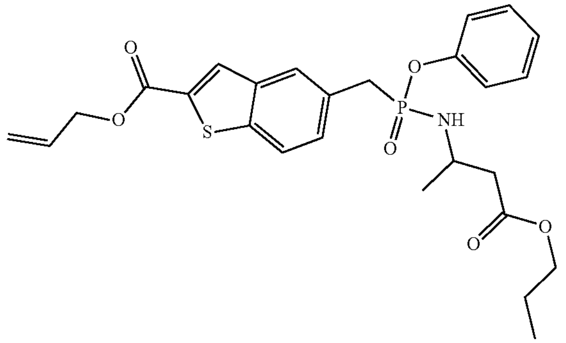 [SMILES: C=CCOC(=O)c1cc2cc(CP(=O)(NC(C)CC(=O)OCCC)Oc3ccccc3)ccc2s1] | $^1H$ NMR (400 MHz, $CDCl_3$) δ 8.07-8.02 (m, 1H), 7.90-7.78 (m, 2H), 7.50-7.44 (m, 1H), 7.34-7.27 (m, 2H), 7.21-7.08 (m, 3H), 6.13-5.99 (m, 1H), 5.49-5.41 (m, 1H), 5.36-5.30 (m, 1H), 4.89 (m, 2H) 4.03-3.86 (m, 2H), 3.80-3.64 (m, 1H), 3.48-3.36 (m, 2H), 3.33-3.12 (m, 1H), 2.34-2.14 (m, 2H), 1.67-1.50 (m, 2H), 1.10-0.97 (m, 3H), 0.95-0.85 (m, 3H); 516.2 $[M + H]^+$ |

-continued

| Name | Structure | NMR; LCMS |
|---|---|---|
| butyl (((2-((allyloxy)carbonyl)benzo[b]thiophen-5-yl)methyl)(phenoxy)phosphoryl)-L-prolinate | 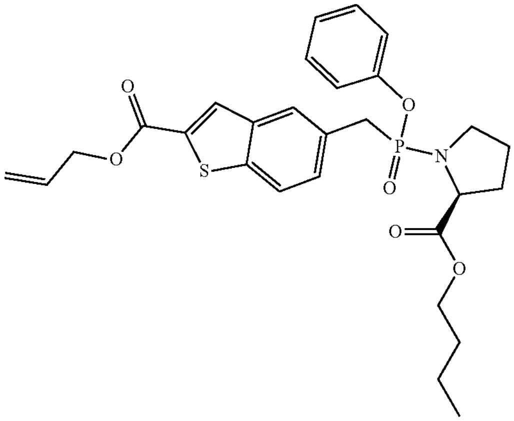 [SMILES: C=CCOC(=O)c1cc2cc(CP(=O)(Oc3ccccc3)N3CCC[C@H]3C(=O)OCCCC)ccc2s1] | 542.3 [M + H]$^+$ |
| allyl 5-(((((S)-1-butoxy-1-oxopropan-2-yl)amino)(naphthalen-1-yloxy)phosphoryl)methyl)benzo[b]thiophene-2-carboxylate | 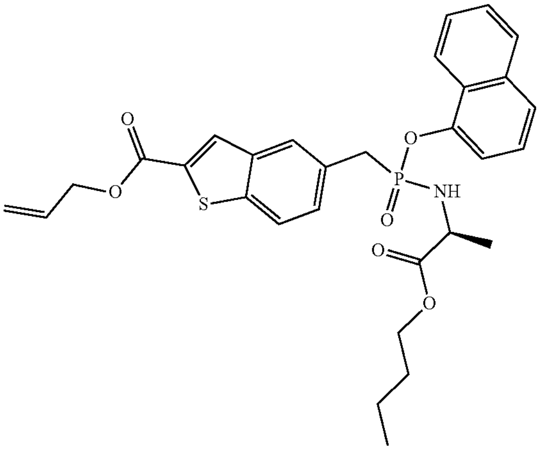 [SMILES: C=CCOC(=O)c1cc2cc(CP(=O)(N[C@@H](C)C(=O)OCCCC)Oc3cccc4ccccc34)ccc2s1] | 566.1 [M + H]$^+$ |
| allyl 5-(((((S)-3-methyl-1-oxo-1-propoxybutan-2-yl)amino)(phenoxy)phosphoryl)methyl)benzo [b]thiophene-2-carboxylate | 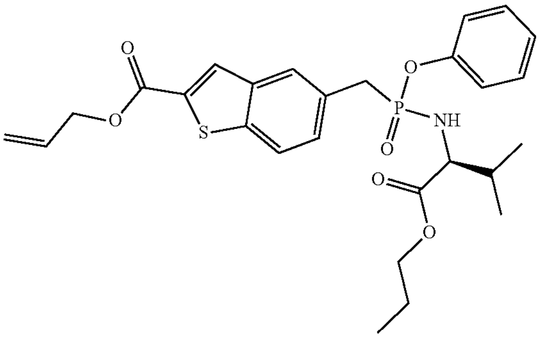 [SMILES: C=CCOC(=O)c1cc2cc(CP(=O)(N[C@H](C(=O)OCCC)C(C)C)Oc3ccccc3)ccc2s1] | $^1$H NMR (400 MHz, CDCl3) δ 8.05 (d, J = 6.0 Hz, 1H), 7.92-7.80 (m, 2H), 7.55-7.45 (m, 1H), 7.30-7.27 (m, 1H), 7.27-7.24 (m, 1H), 7.15-7.08 (m, 3H), 6.13-5.99 (m, 1H), 5.45 (td, J = 1.2, 17.2 Hz, 1H), 5.36-5.31 (m, 1H), 5.31 (s, 1H), 4.86 (d, J = 5.6 Hz, 2H), 4.03-3.90 (m, 1H), 3.86-3.75 (m, 1H), 3.50-3.39 (m, 2H), 3.21-3.03 (m, 1H), 1.94-1.83 (m, 1H), 1.59-1.50 (m, 2H), 0.91-0.86 (m, 3H), 0.85-0.78 (m, 3H), 0.67 (dd, J = 4.0, 6.8 Hz, 3H) |
| allyl 5-(((((S)-1-((R)-sec-butoxy)-1-oxopropan-2-yl)amino)(phenoxy)phosphoryl)methyl) benzo[b]thiophene-2-carboxylate | 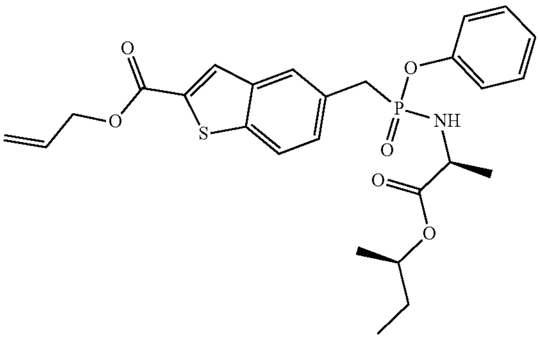 [SMILES: C=CCOC(=O)c1cc2cc(CP(=O)(N[C@@H](C)C(=O)O[C@H](C)CC)Oc3ccccc3)ccc2s1] | $^1$H NMR (400 MHz, CDCl3) δ 8.04 (d, J = 6.4 Hz, 1H), 7.90-7.79 (m, 2H), 7.48 (m, 1H), 7.30-7.27 (m, 1H), 7.25 (d, J = 2.0 Hz, 1H), 7.17-7.09 (m, 3H), 6.09-5.99 (m, 1H), 5.47-5.40 (m, 1H), 5.33-5.29 (m, 1H), 4.85 (d, J = 5.6 Hz, 2H), 4.81-4.71 (m, 1H), 4.01-3.90 (m, 1H), 3.48-3.38 (m, 2H), 1.55-1.43 (m, 2H), 1.18-1.14 (m, 3H), 1.14-1.09 (m 3H), 0.83 (s, 3H) |

-continued

| Name | Structure | NMR; LCMS |
|---|---|---|
| allyl 5-(((((S)-1-oxo-1-propoxypropan-2-yl)amino)(2,2,2-trifluoroethoxy)phosphoryl)methyl)benzo[b]thiophene-2-carboxylate | 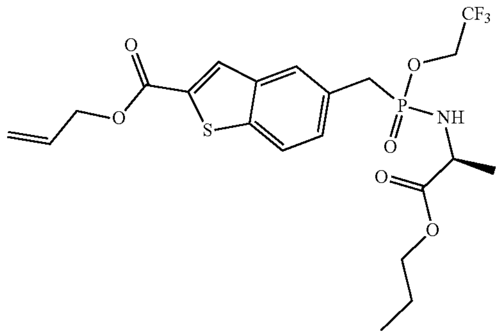 [SMILES: C=CCOC(=O)c1cc2cc(CP(=O)(N[C@@H](C)C(=O)OCCC)OCC(F)(F)F)ccc2s1] | $^1H$ NMR (400 MHz, $CDCl_3$) δ 8.08-8.01 (m, 1H), 7.86-7.79 (m, 2H), 7.47-7.37 (m, 1H), 6.12-5.98 (m, 1H), 5.45 (dd, J = 1.6, 17.2 Hz, 1H), 5.33 (dd, J = 1.2, 10.4 Hz, 1H), 4.86 (d, J = 5.6 Hz, 2H), 4.33-4.16 (m, 2H), 4.10-3.93 (m, 2H), 3.43-3.31 (m, 2H), 3.21-2.96 (m, 1H), 1.66-1.54 (m, 3H), 1.35 (d, J = 7.2 Hz, 2H), 1.26 (d, J = 7.2 Hz, 1H), 0.95-0.88 (m, 3H) |
| allyl 5-(((((S)-1-ethoxy-1-oxo-3-phenylpropan-2-yl)amino)(phenoxy)phosphoryl)methyl)benzo[b]thiophene-2-carboxylate | 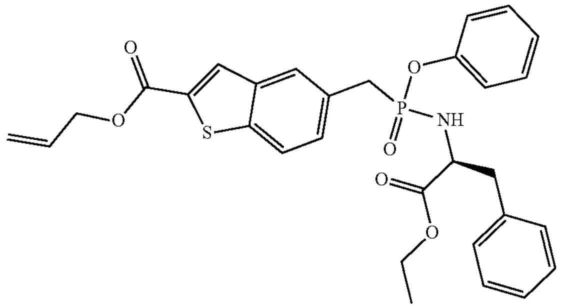 [SMILES: C=CCOC(=O)c1cc2cc(CP(=O)(N[C@@H](Cc3ccccc3)C(=O)OCC)Oc3ccccc3)ccc2s1] | 564 $[M + H]^+$ |
| allyl 5-(((((S)-1-(benzyloxy)-4-methyl-1-oxopentan-2-yl)amino)(phenoxy)phosphoryl)methyl)benzo[b]thiophene-2-carboxylate | 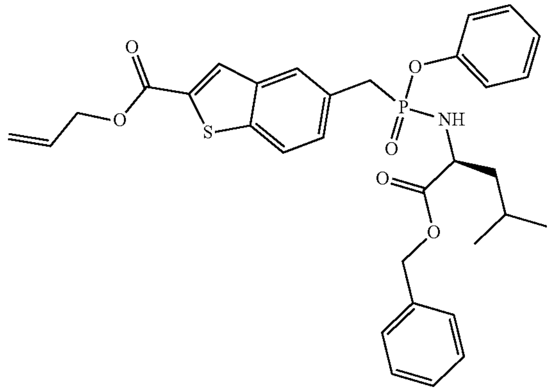 [SMILES: C=CCOC(=O)c1cc2cc(CP(=O)(N[C@@H](CC(C)C)C(=O)OCc3ccccc3)Oc3ccccc3)ccc2s1] | 592 $[M + H]^+$ |
| allyl 5-(((((S)-1-(benzyloxy)-1-oxopropan-2-yl)amino)(phenoxy)phosphoryl)methyl)benzo[b]thiophene-2-carboxylate | 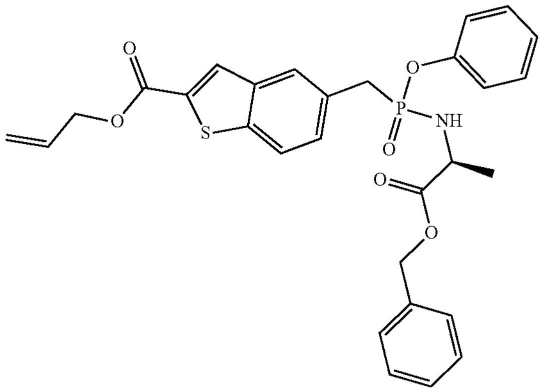 [SMILES: C=CCOC(=O)c1cc2cc(CP(=O)(N[C@@H](C)C(=O)OCc3ccccc3)Oc3ccccc3)ccc2s1] | 550 $[M + H]^+$ |

-continued

| Name | Structure | NMR; LCMS |
|---|---|---|
| isopropyl (((2-((allyloxy)carbonyl)ben-zo[b]thiophen-5-yl)methyl)(phenoxy)phos-phoryl)-L-prolinate | 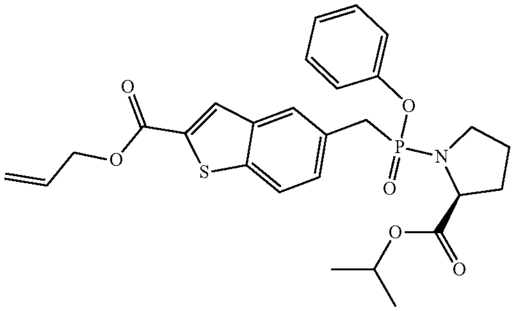 [SMILES: C=CCOC(=O)c1cc2cc(CP(=O)(Oc3ccccc3)N3CCC[C@H]3C(=O)OC(C)C)ccc2s1] | 528 [M + H]+ |
| allyl 5-(((((S)-2-oxoTHF-3-yl)amino)(phenoxy)phos-phoryl)methyl)benzo[b]thiophene-2-carboxylate | 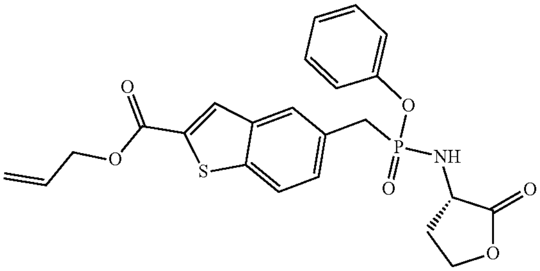 [SMILES: C=CCOC(=O)c1cc2cc(CP(=O)(N[C@H]3CCOC3=O)Oc3ccccc3)ccc2s1] | 472.1 [M + H]+ |
| allyl 5-(((((S)-1-(benzyloxy)-1-oxo-4-phenylbutan-2-yl)amino)(phenoxy)phos-phoryl)methyl)benzo[b]thiophene-2-carboxylate | 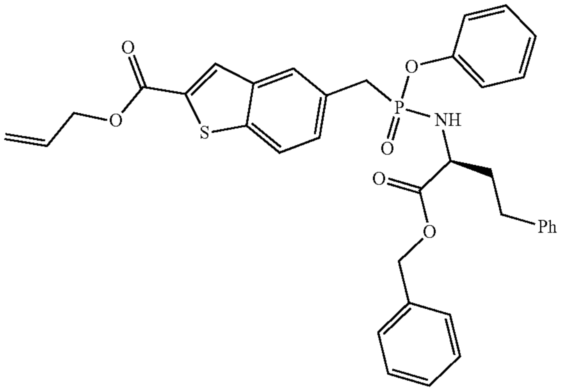 [SMILES: C=CCOC(=O)c1cc2cc(CP(=O)(N[C@@H](CCc3ccccc3)C(=O)OCc3ccccc3)Oc3ccccc3)ccc2s1] | 640 [M + H]+ |
| allyl 5-(((((S)-1-ethoxy-1-oxopropan-2-yl)amino)(phenoxy)phos-phoryl)methyl)benzo[b]thiophene-2-carboxylate | 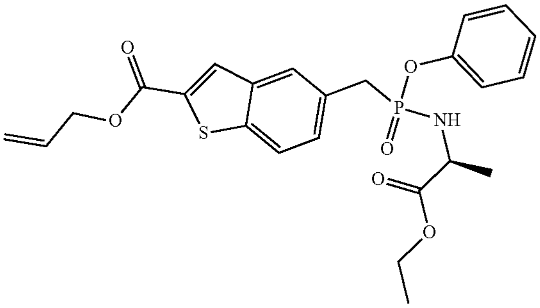 [SMILES: C=CCOC(=O)c1cc2cc(CP(=O)(N[C@@H](C)C(=O)OCC)Oc3ccccc3)ccc2s1] | 488 [M + H]+ |

-continued

| Name | Structure | NMR; LCMS |
|---|---|---|
| allyl 5-(((((S)-3-methoxy-1-oxo-1-propoxypropan-2-yl)amino)(phenoxy)phosphoryl)methyl)benzo[b]thiophene-2-carboxylate | 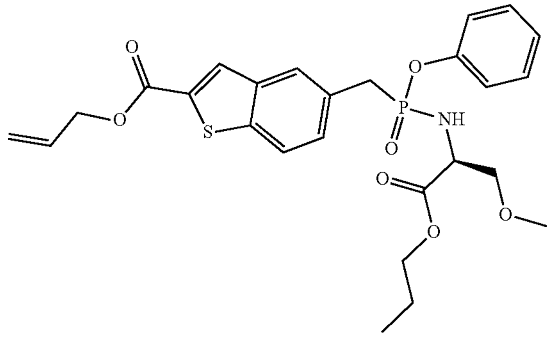 [SMILES: C=CCOC(=O)c1cc2cc(CP(=O)(N[C@@H](COC)C(=O)OCCC)Oc3ccccc3)ccc2s1] | 532 $[M + H]^+$ |
| allyl 5-(((((S)-4-methoxy-1-oxo-1-propoxybutan-2-yl)amino)(phenoxy)phosphoryl)methyl)benzo[b]thiophene-2-carboxylate | 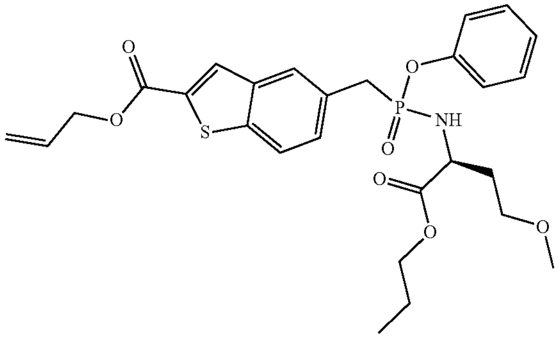 [SMILES: C=CCOC(=O)c1cc2cc(CP(=O)(N[C@@H](CCOC)C(=O)OCCC)Oc3ccccc3)ccc2s1] | 546 $[M + H]^+$ |
| allyl 5-(((((S)-1-oxo-1-propoxy-3-(pyridin-2-yl)propan-2-yl)amino)(phenoxy)phosphoryl)methyl)benzo[b]thiophene-2-carboxylate | 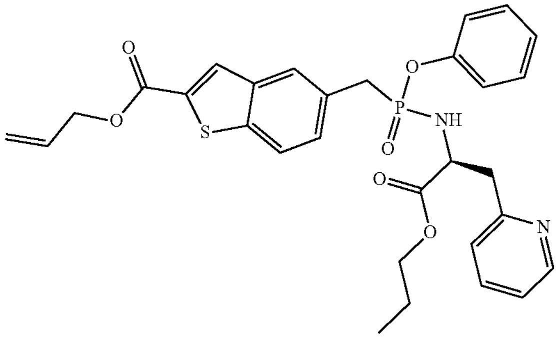 [SMILES: C=CCOC(=O)c1cc2cc(CP(=O)(N[C@@H](Cc3ccccn3)C(=O)OCCC)Oc3ccccc3)ccc2s1] | 579 $[M + H]^+$ |
| allyl 5-((phenoxy((1-(propoxycarbonyl)cyclopropyl)amino)phosphoryl)methyl)benzo[b]thiophene-2-carboxylate | 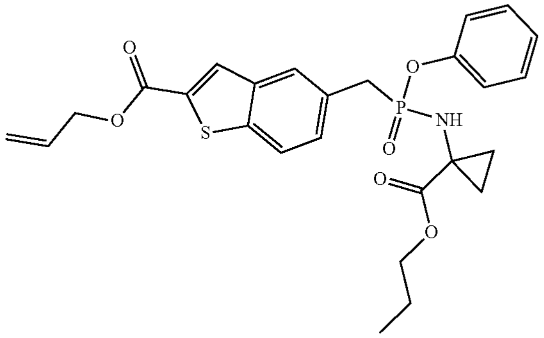 [SMILES: C=CCOC(=O)c1cc2cc(CP(=O)(NC3(C(=O)OCCC)CC3)Oc3ccccc3)ccc2s1] | 514.1 $[M + H]^+$ |

Step 2: Preparation of 5-(((2,6-dimethylphenoxy)(((S)-1-oxo-1-propoxypropan-2-yl)amino)phosphoryl)methyl)benzo[b]thiophene-2-carboxylic acid To a stirred solution of allyl 5-(((2,6-dimethylphenoxy)(((S)-1-oxo-1-propoxypropan-2-yl)amino)phosphoryl)methyl)benzo[b]thiophene-2-carboxylate (50 mg, 94.4 μmol, 1 eq) in THF (4 mL) were added morpholine (40.6 μL, 472 μmol, 5 eq) and $Pd(PPh_3)_4$ (3.27 mg, 2.83 μmol, 0.03 eq) under nitrogen. The reaction mixture was stirred at room temperature 1 h. The solvent was removed under reduced pressure and the product was directly purified by reverse phase chromatography on a 100 g Cis cartridge eluting with a gradient of 5-80% acetonitrile in water (with 0.1% formic acid) to afford 5-(((2,6-dimethylphenoxy)(((S)-1-oxo-1-propoxypropan-2-yl)amino)phosphoryl)methyl)benzo[b]

thiophene-2-carboxylic acid (36.0 mg, 77.9%) as a pale yellow solid. $^{1}H$ NMR (400 MHz, $CDCl_3$) δ 7.93-7.84 (m, 1H), 7.83-7.71 (m, 2H), 7.48-7.36 (m, 1H), 7.08-6.93 (m, 3H), 4.17-3.98 (m, 3H), 3.59-3.42 (m, 2H), 2.37 (s, 3H), 2.30 (s, 3H), 1.65-1.57 (m, 2H), 1.27-1.22 (m, 3H), 1.15-1.11 (m, 1H), 0.94-0.88 (m, 3H).

The intermediates in the table below were prepared using the method described above in Step 2 for the preparation of 5-(((2,6-dimethylphenoxy)(((S)-1-oxo-1-propoxypropan-2-yl)amino)phosphoryl)methyl)benzo[b]thiophene-2-carboxylic acid and utilizing the appropriate starting materials and modifications.

| Name | Structure | NMR; LCMS |
|---|---|---|
| 5-((((2-methyl-3-oxo-3-propoxypropyl)amino)(phenoxy)phosphoryl)methyl)benzo[b]thiophene-2-carboxylic acid | 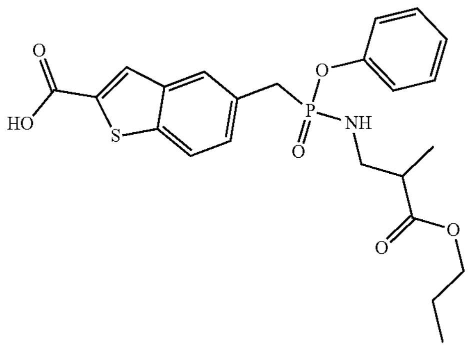 [SMILES: CCCOC(=O)C(C)CNP(=O)(Cc1ccc2sc(C(=O)O)cc2c1)Oc1ccccc1] | $^{1}H$ NMR (400 MHz, DMSO-$d_6$) δ 13.39 (br. s., 1H), 8.10-8.05 (m, 1H), 8.01-7.88 (m, 2H), 7.51-7.44 (m, 1H), 7.39-7.28 (m, 2H), 7.22-7.05 (m, 3H), 5.22-5.10 (m, 1H), 3.96-3.82 (m, 2H), 3.47-3.36 (m, 2H), 3.10-2.94 (m, 1H), 2.86-2.70 (m, 1H), 2.36-2.22 (m, 1H), 1.56-1.45 (m, 2H), 0.90 (dd, J = 10.3, 7.1 Hz, 3H), 0.86-0.78 (m, 3H); 476.2 $[M + H]^+$ |
| 5-((((S)-2-(butoxycarbonyl)-4,4-difluoropyrrolidin-1-yl)(phenoxy)phosphoryl)methyl)benzo[b]thiophene-2-carboxylic acid | 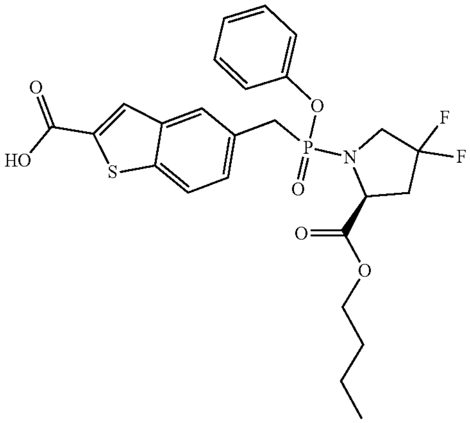 [SMILES: CCCCOC(=O)[C@@H]1CC(F)(F)CN1P(=O)(Cc1ccc2sc(C(=O)O)cc2c1)Oc1ccccc1] | $^{1}H$ NMR (400 MHz, DMSO-$d_6$) δ 13.49 (br. s., 1H), 8.14-8.06 (m, 1H), 8.04-7.91 (m, 2H), 7.55-7.47 (m, 1H), 7.40-7.28 (m, 2H), 7.25-7.06 (m, 3H), 4.67-4.56 (m, 0.4H), 4.35-4.28 (m, 0.6H), 4.08-3.69 (m, 3H), 3.68-3.42 (m, 3H), 2.73-2.30 (m, 2H), 1.55-1.37 (m, 2H), 1.35-1.18 (m, 2H), 0.91-0.77 (m, 3H); 538.2 $[M + H]^+$ |
| 5-(((((S)-1-oxo-1-propoxybutan-2-yl)amino)(phenoxy)phosphoryl)methyl)benzo[b]thiophene-2-carboxylic acid | 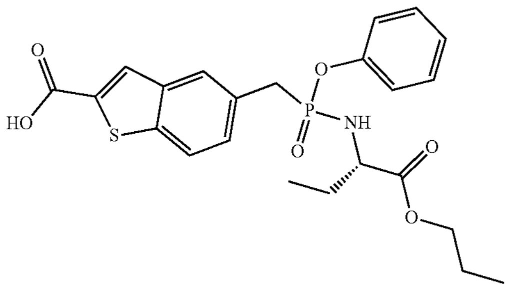 [SMILES: CCCOC(=O)[C@H](CC)NP(=O)(Cc1ccc2sc(C(=O)O)cc2c1)Oc1ccccc1] | $^{1}H$ NMR (400 MHz, $CD_3OD$) δ 8.01 (s, 1H), 7.97-7.83 (m, 2H), 7.54-7.47 (m, 1H), 7.36-7.25 (m, 2H), 7.21-7.11 (m, 3H), 3.95-3.65 (m, 3H), 3.61-3.43 (m, 2H), 1.59-1.40 (m, 4H), 0.86 (q, J = 7.6 Hz, 3H), 0.73-0.63 (m, 3H); 476.2 $[M + H]^+$ |
| 5-((((4-oxo-4-propoxybutan-2-yl)amino)(phenoxy)phosphoryl)methyl)benzo[b]thiophene-2-carboxylic acid | 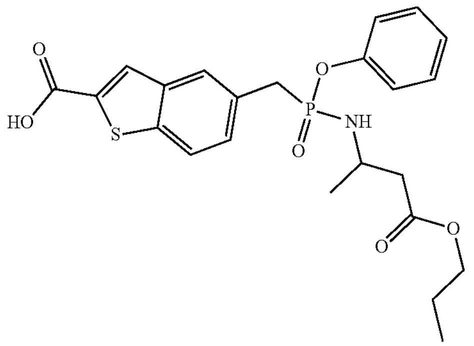 [SMILES: CCCOC(=O)CC(C)NP(=O)(Cc1ccc2sc(C(=O)O)cc2c1)Oc1ccccc1] | $^{1}H$ NMR (400 MHz, DMSO-$d_6$) δ 13.47 (br. s., 1H), 8.08 (s, 1H), 8.02-7.89 (m, 2H), 7.53-7.45 (m, 1H), 7.39-7.27 (m, 2H), 7.17-7.09 (m, 3H), 5.22-5.04 (m, 1H), 3.92-3.80 (m, 2H), 3.61-3.45 (m, 1H), 3.45-3.25 (m, 3H), 2.30-2.13 (m, 2H), 1.55-1.44 (m, 2H), 0.93-0.86 (m, 3H), 0.85-0.79 (m, 3H); 476.2 $[M + H]^+$ |

-continued

| Name | Structure | NMR; LCMS |
|---|---|---|
| 5-((((S)-2-(butoxycarbonyl)pyrrolidin-1-yl)(phenoxy)phosphoryl)methyl)benzo[b]thiophene-2-carboxylic acid | 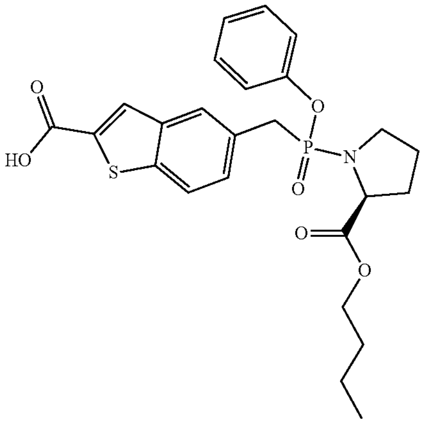 [SMILES: CCCCOC(=O)[C@@H]1CCCN1P(=O)(Cc1ccc2sc(C(=O)O)cc2c1)Oc1ccccc1] | 502.1 [M + H]$^+$ |
| 5-(((((S)-1-butoxy-1-oxopropan-2-yl)amino)(naphthalen-1-yloxy)phosphoryl)methyl)benzo[b]thiophene-2-carboxylic acid | 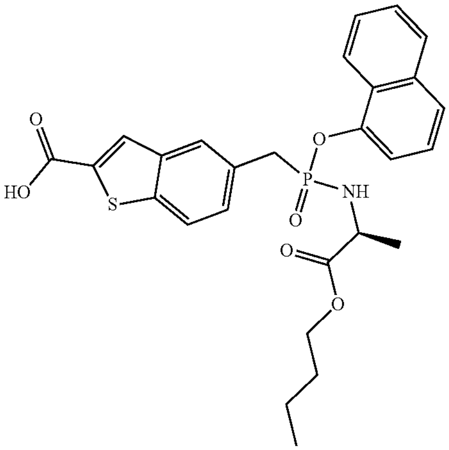 [SMILES: CCCCOC(=O)[C@H](C)NP(=O)(Cc1ccc2sc(C(=O)O)cc2c1)Oc1cccc2ccccc12] | 526.1 [M + H]$^+$ |
| 5-(((((S)-3-methyl-1-oxo-1-propoxybutan-2-yl)amino)(phenoxy)phosphoryl)methyl)benzo[b]thiophene-2-carboxylic acid | 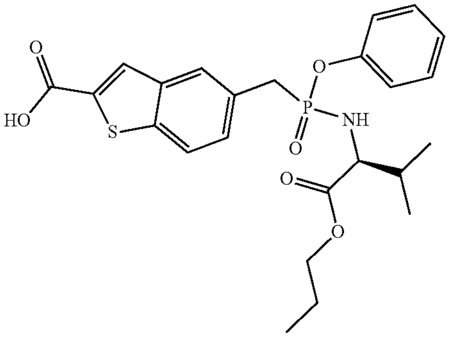 [SMILES: CCCOC(=O)[C@@H](NP(=O)(Cc1ccc2sc(C(=O)O)cc2c1)Oc1ccccc1)C(C)C] | 490.3 [M + H]$^+$ |
| 5-(((((S)-1-((R)-sec-butoxy)-1-oxopropan-2-yl)amino)(phenoxy)phosphoryl)methyl)benzo[b]thiophene-2-carboxylic acid | 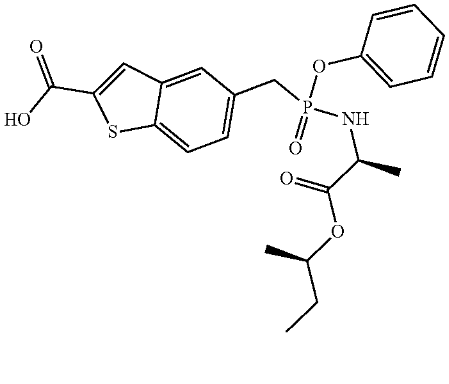 [SMILES: CC[C@@H](C)OC(=O)[C@H](C)NP(=O)(Cc1ccc2sc(C(=O)O)cc2c1)Oc1ccccc1] | 476.8 [M + H]$^+$ |

-continued

| Name | Structure | NMR; LCMS |
| --- | --- | --- |
| 5-(((((S)-1-oxo-1-propoxypropan-2-yl)amino)(2,2,2-trifluoroethoxy)phosphoryl)methyl)benzo[b]thiophene-2-carboxylic acid | 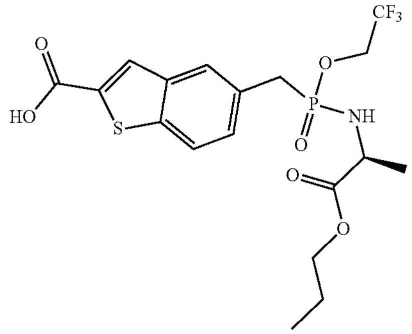 [SMILES: CCCOC(=O)[C@H](C)NP(=O)(Cc1ccc2sc(C(=O)O)cc2c1)OCC(F)(F)F] | $^{1}$H NMR (400 MHz, $CDCl_3$) δ 7.83 (s, 1H), 7.81-7.75 (m, 2H), 7.32 (dd, J = 2.0, 8.4 Hz, 1H), 4.50-4.29 (m, 2H), 4.18-3.98 (m, 2H), 3.87-3.62 (m, 1H), 3.46-3.32 (m, 2H), 1.72-1.64 (m, 2H), 1.42 (dd, J = 7.2, 17.2 Hz, 3H), 0.96 (q, J = 7.2 Hz, 3H) |
| 5-(((((S)-1-ethoxy-1-oxo-3-phenylpropan-2-yl)amino)(phenoxy)phosphoryl)methyl)benzo[b]thiophene-2-carboxylic acid | 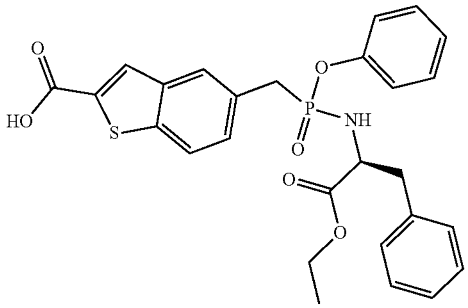 [SMILES: CCOC(=O)[C@H](Cc1ccccc1)NP(=O)(Cc1ccc2sc(C(=O)O)cc2c1)Oc1ccccc1] | 524 [M + H]$^+$ |
| 5-(((((S)-1-(benzyloxy)-4-methyl-1-oxopentan-2-yl)amino)(phenoxy)phosphoryl)methyl)benzo[b]thiophene-2-carboxylic acid | 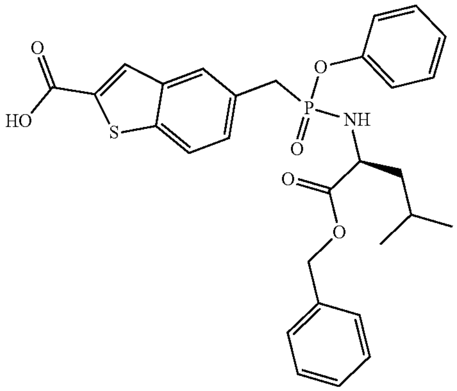 [SMILES: CC(C)C[C@H](NP(=O)(Cc1ccc2sc(C(=O)O)cc2c1)Oc1ccccc1)C(=O)OCc1ccccc1] | 552 [M + H]$^+$ |
| 5-(((((S)-1-(benzyloxy)-1-oxopropan-2-yl)amino)(phenoxy)phosphoryl)methyl)benzo[b]thiophene-2-carboxylic acid | 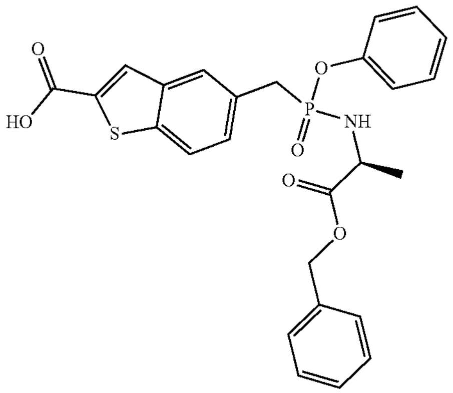 [SMILES: C[C@H](NP(=O)(Cc1ccc2sc(C(=O)O)cc2c1)Oc1ccccc1)C(=O)OCc1ccccc1] | 510 [M + H]$^+$ |

-continued

| Name | Structure | NMR; LCMS |
| --- | --- | --- |
| 5-((((S)-2-(isopropoxycarbonyl)pyrrolidin-1-yl)(phenoxy)phosphoryl)methyl)benzo[b]thiophene-2-carboxylic acid | 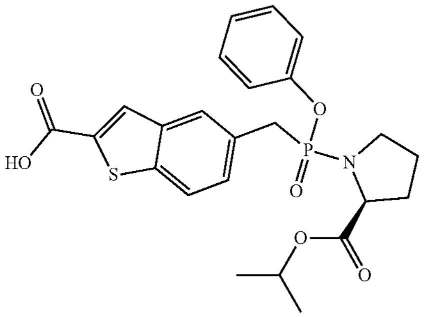 [SMILES: CC(C)OC(=O)[C@@H]1CCCN1P(=O)(Cc1ccc2sc(C(=O)O)cc2c1)Oc1ccccc1] | 488 [M + H]+ |
| 5-(((((S)-2-oxoTHF-3-yl)amino)(phenoxy)phosphoryl)methyl)benzo[b]thiophene-2-carboxylic acid | 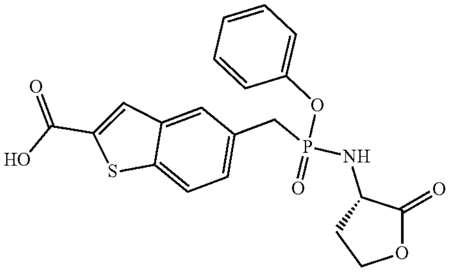 [SMILES: O=C(O)c1cc2cc(CP(=O)(N[C@H]3CCOC3=O)Oc3ccccc3)ccc2s1] | 432 [M + H]+ |
| 5-(((((S)-1-(benzyloxy)-1-oxo-4-phenylbutan-2-yl)amino)(phenoxy)phosphoryl)methyl)benzo[b]thiophene-2-carboxylic acid | 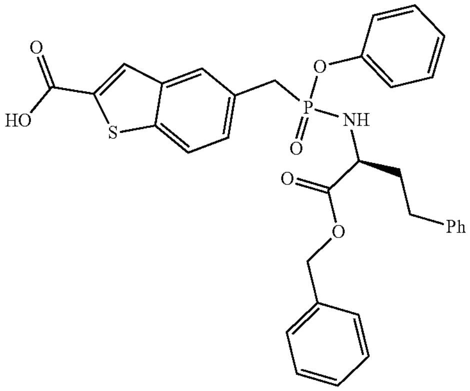 [SMILES: O=C(O)c1cc2cc(CP(=O)(N[C@@H](CCc3ccccc3)C(=O)OCc3ccccc3)Oc3ccccc3)ccc2s1] | 600 [M + H]+ |
| 5-(((((S)-1-ethoxy-1-oxopropan-2-yl)amino)(phenoxy)phosphoryl)methyl)benzo[b]thiophene-2-carboxylic acid | 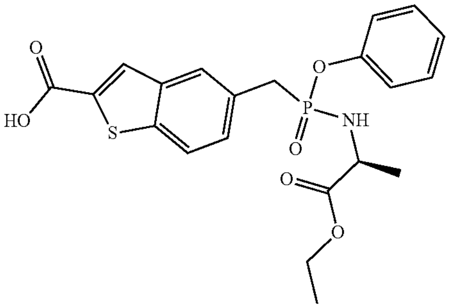 [SMILES: CCOC(=O)[C@H](C)NP(=O)(Cc1ccc2sc(C(=O)O)cc2c1)Oc1ccccc1] | 448 [M + H]+ |

-continued

| Name | Structure | NMR; LCMS |
| --- | --- | --- |
| 5-(((((S)-3-methoxy-1-oxo-1-propoxypropan-2-yl)amino)(phenoxy)phosphoryl)methyl)benzo[b]thiophene-2-carboxylic acid | 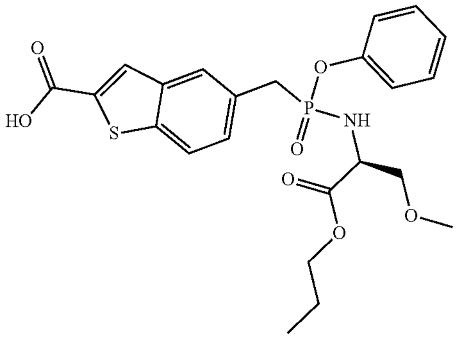 [SMILES: CCCOC(=O)[C@H](COC)NP(=O)(Cc1ccc2sc(C(=O)O)cc2c1)Oc1ccccc1] | 492 [M + H]+ |
| 5-(((((S)-4-methoxy-1-oxo-1-propoxybutan-2-yl)amino)(phenoxy)phosphoryl)methyl)benzo[b]thiophene-2-carboxylic acid | 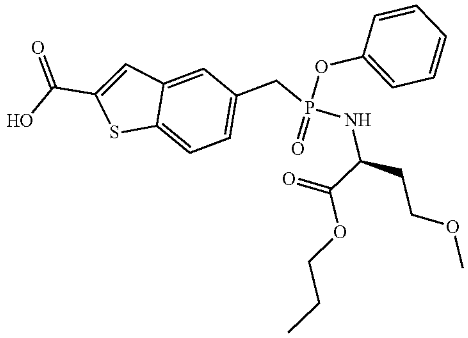 | 546 [M + H]+ |
| 5-(((((S)-1-oxo-1-propoxy-3-(pyridin-2-yl)propan-2-yl)amino)(phenoxy)phosphoryl)methyl)benzo[b]thiophene-2-carboxylic acid | 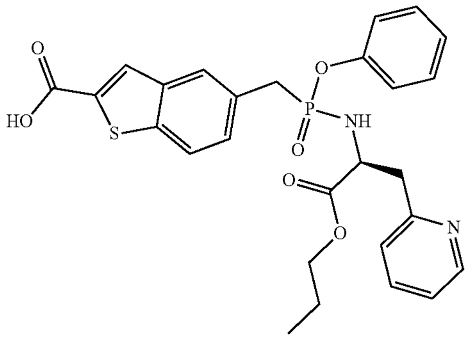 [SMILES: CCCOC(=O)[C@H](Cc1ccccn1)NP(=O)(Cc1ccc2sc(C(=O)O)cc2c1)Oc1ccccc1] | 539 [M + H]+ |
| 5-((phenoxy((1-(propoxycarbonyl)cyclopropyl)amino)phosphoryl)methyl)benzo[b]thiophene-2-carboxylic acid | 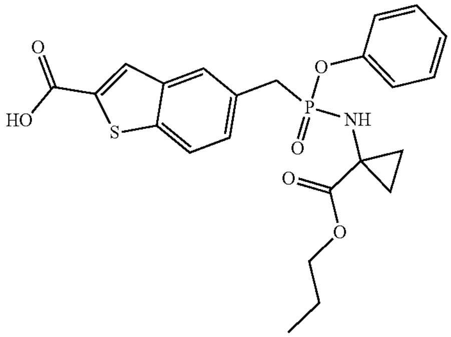 [SMILES: CCCOC(=O)C1(NP(=O)(Cc2ccc3sc(C(=O)O)cc3c2)Oc2ccccc2)CC1] | 474.0 [M + H]+ |

Synthesis of 5-((morpholino(((S)-1-oxo-1-propoxy-propan-2-yl)amino)phosphoryl)methyl)benzo[b]thiophene-2-carboxylic acid

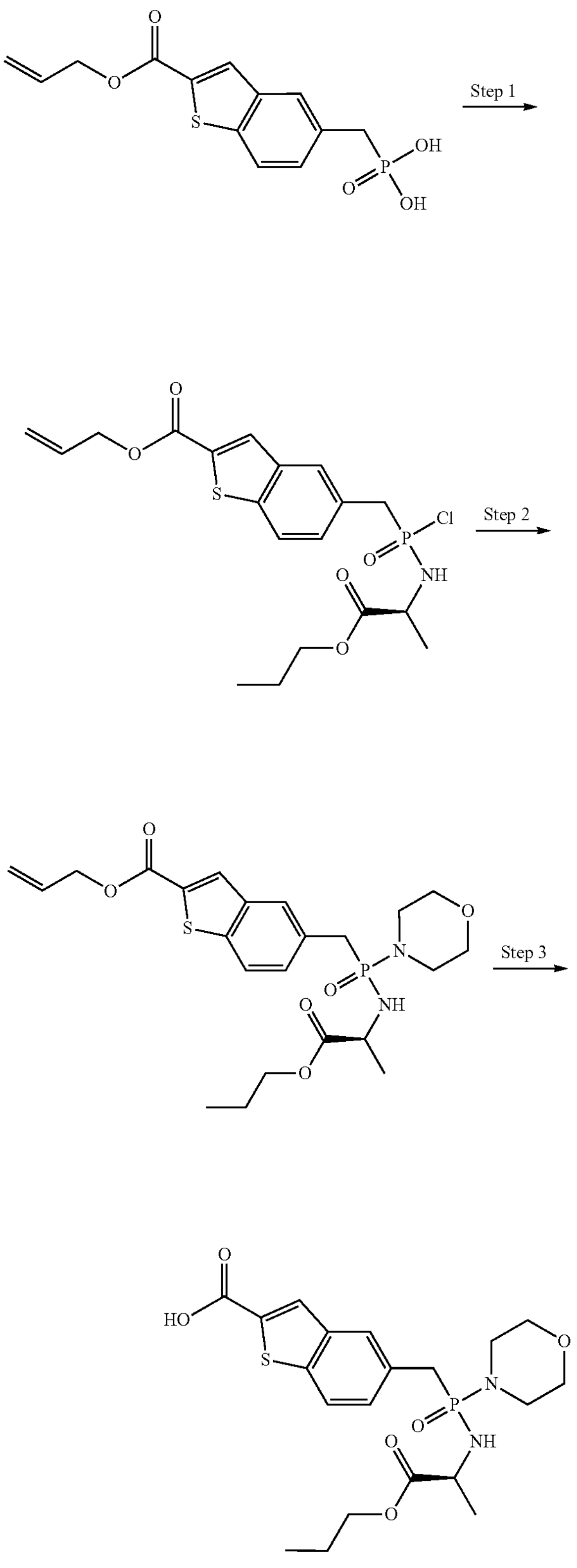

Step 1: Synthesis of allyl 5-((chloro(((S)-1-oxo-1-propoxypropan-2-yl)amino)phosphoryl)methyl)benzo[b]thiophene-2-carboxylate Oxalyl chloride (10 mL) was added dropwise to the solution of ((2-((allyloxy)carbonyl)benzo[b]thiophen-5-yl)methyl)phosphonic acid (1 g, 3.20 mmol, 1.0 eq.) in dry DCM (20 mL) and DMF (1 drop) at 20° C. The reaction mixture was stirred at 25° C. for an additional 1 hr. The reaction was monitored by pipetting out a small amount of crude sample and quenching it with MeOH to ensure bis-Cl phosphoryl chloride had been formed completely (bis-methoxy phosphonate was observed by LCMS). After completion, the excess oxalyl chloride and solvent were removed under reduced pressure to afford allyl 5-((dichlorophosphoryl)methyl)benzo[b]thiophene-2-carboxylate (960 mg, 2.74 mmol, 86%). allyl 5-((dichlorophosphoryl)methyl)benzo[b]thiophene-2-carboxylate (100 mg, 251 μmol, 1.0 eq.) was re-dissolved in anhydrous DCM (2 mL), then added to a mixture of propyl L-alaninate (36 mg, 276 μmol, 1.1 eq.) and triethylamine (101 mg, 1.00 mmol, 4.0 eq.) in anhydrous DCM (2 mL) at 0° C. The reaction was allowed to warm to 25° C., and stirred for an additional 15 min. The reaction progress was monitored by LCMS, and after completion, the reaction mixture was used in next Step directly without further purification.

Step 2: Synthesis of allyl 5-((morpholino(((S)-1-oxo-1-propoxypropan-2-yl)amino)phosphoryl)methyl)benzo[b]thiophene-2-carboxylate Allyl 5-((chloro(((S)-1-oxo-1-propoxypropan-2-yl)amino)phosphoryl)methyl)benzo[b]thiophene-2-carboxylate (200 mg, 450 μmol, 1.0 eq.) as a solution in DCM (5 mL) was added to a solution of morpholine (196 mg, 2.25 mmol, 5 eq.) and triethylamine (TEA) (273 mg, 2.7 mmol, 6 eq.) in DCM (1 mL). The mixture was stirred at 25° C. for 15 min, at which time LCMS showed formation of product. The mixture was concentrated under reduced pressure. The residue was purified by Biotage® C18 column chromatography to give allyl 5-((morpholino(((S)-1-oxo-1-propoxypropan-2-yl)amino)phosphoryl)methyl)benzo[b]thiophene-2-carboxylate (82 mg, 0.17 mmol, 38%) as a white solid. LCMS (ESI): m/z=495 $[M+H]^+$.

The intermediates in the table below were prepared using the method described above in Step 2 for the preparation of allyl 5-((morpholino(((S)-1-oxo-1-propoxypropan-2-yl)amino)phosphoryl)methyl)benzo[b]thiophene-2-carboxylate and utilizing the appropriate starting materials and modifications.

| Name | Structure | LCMS |
| --- | --- | --- |
| allyl 5-(((2-methoxyethoxy)(((S)-1-oxo-1-propoxypropan-2-yl)amino)phosphoryl)methyl)benzo[b]thiophene-2-carboxylate | 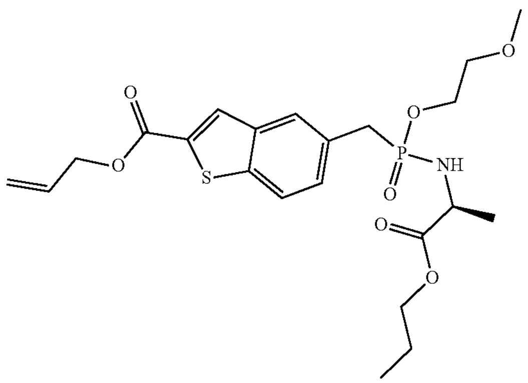 [SMILES: C=CCOC(=O)c1cc2cc(CP(=O)(N[C@@H](C)C(=O)OCCC)OCCOC)ccc2s1] | 484 [M + H]+ |
| allyl 5-((ethoxy(((S)-1-oxo-1-propoxypropan-2-yl)amino)phosphoryl)methyl)benzo[b]thiophene-2-carboxylate | 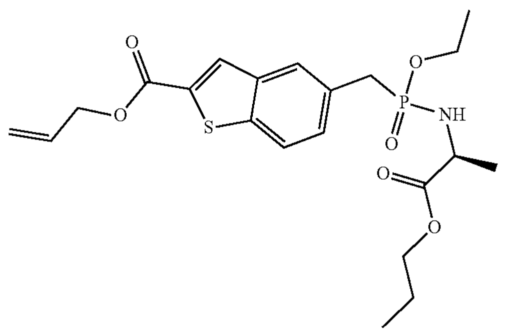 | 438 [M + H]+ |
| allyl 5-(((2,2-difluoropropoxy)(((S)-1-oxo-1-propoxypropan-2-yl)amino)phosphoryl)methyl)benzo[b]thiophene-2-carboxylate | 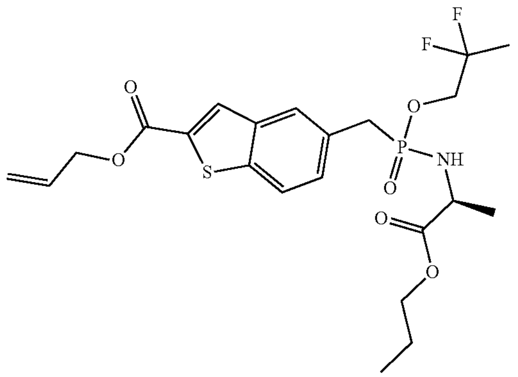 | 490 [M + H]+ |

Step 3: Synthesis of 5-((morpholino(((S)-1-oxo-1-propoxypropan-2-yl)amino)phosphoryl)methyl)benzo[b]thiophene-2-carboxylic acid To a solution of allyl 5-((morpholino(((S)-1-oxo-1-propoxypropan-2-yl)amino)phosphoryl)methyl)benzo[b]thiophene-2-carboxylate (82 mg, 0.17 mmol, 1.0 eq) in DCM (3 mL) were added $Pd(PPh_3)_4$ (20 mg, 17 μmol, 0.1 eq.) and pyrrolidine (12 mg, 0.17 mmol, 1.0 eq.). The mixture was purged and degassed with $N_2$ (three times), then stirred at 25° C. for 0.5 h. After completion, the mixture was concentrated under reduced pressure. The residue was purified by Biotage® C18 column chromatography to give 5-((morpholino(((S)-1-oxo-1-propoxypropan-2-yl)amino)phosphoryl)methyl)benzo[b]thiophene-2-carboxylic acid (50 mg, 0.11 mmol, 65%) as a white solid. LCMS (ESI): m/z=455 $[M+H]^+$.

The intermediates in the table below were prepared using the method described above in Step 3 for the preparation of 5-((morpholino(((S)-1-oxo-1-propoxypropan-2-yl)amino)phosphoryl)methyl)benzo[b]thiophene-2-carboxylic acid and utilizing the appropriate starting materials and modifications.

| Name | Structure | LCMS |
| --- | --- | --- |
| 5-(((2-methoxyethoxy)(((S)-1-oxo-1-propoxypropan-2-yl)amino)phosphoryl)methyl)benzo[b]thiophene-2-carboxylic acid | 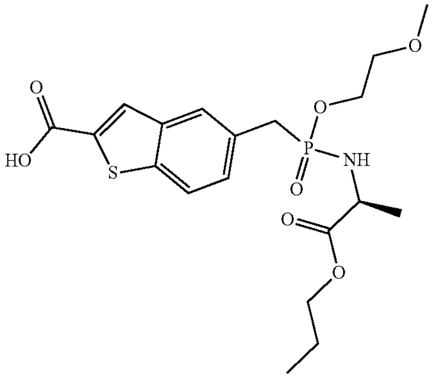 [SMILES: CCCOC(=O)[C@H](C)NP(=O)(Cc1ccc2sc(C(=O)O)cc2c1)OCCOC] | 444 [M + H]+ |
| 5-((ethoxy(((S)-1-oxo-1-propoxypropan-2-yl)amino)phosphoryl)methyl)benzo[b]thiophene-2-carboxylic acid | 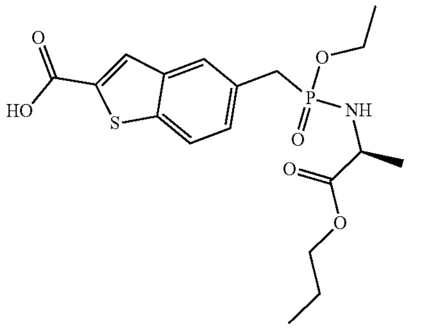 [SMILES: CCCOC(=O)[C@H](C)NP(=O)(Cc1ccc2sc(C(=O)O)cc2c1)OCC] | 414 [M + H]+ |
| 5-(((2,2-difluoropropoxy)(((S)-1-oxo-1-propoxypropan-2-yl)amino)phosphoryl)methyl)benzo[b]thiophene-2-carboxylic acid | 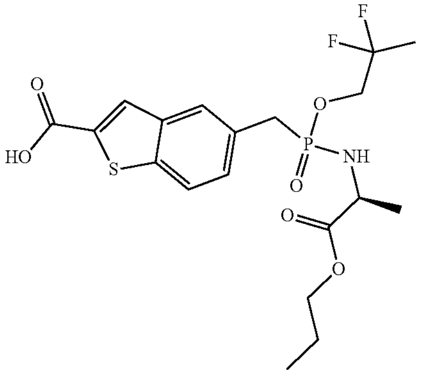 | 450 [M + H]+ |

Synthesis of 5-(((((S)-4-methoxy-1-oxo-1-propoxybutan-2-yl)amino)(phenoxy)phosphoryl)methyl)benzo[b]thiophene-2-carboxylic acid

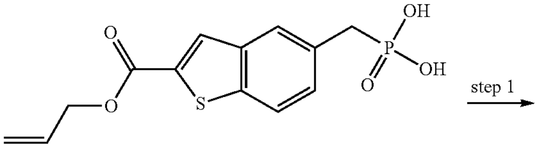

-continued

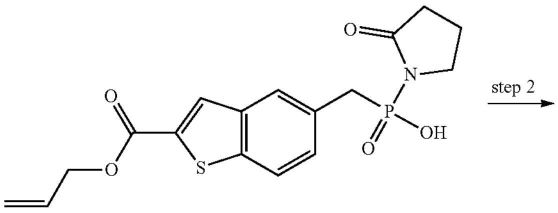

-continued

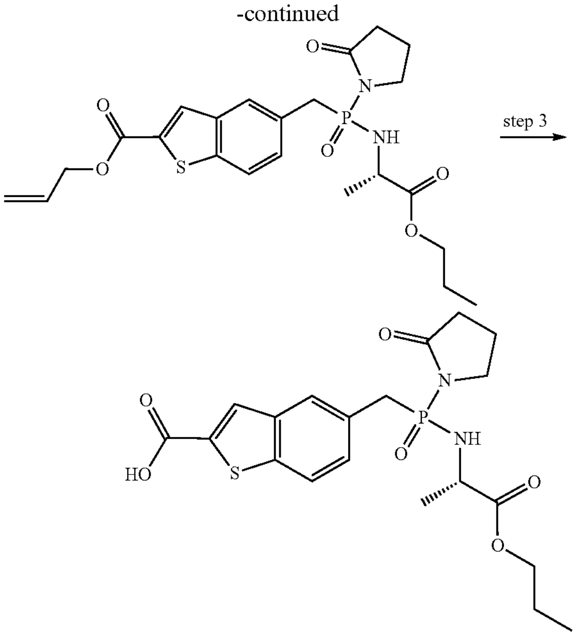

Step 1: Preparation of ((2-((allyloxy)carbonyl)benzo[b]thiophen-5-yl)methyl)(2-oxopyrrolidin-1-yl)phosphinic acid Oxalyl chloride (10 mL) was added dropwise to the solution of ((2-((allyloxy)carbonyl)benzo[b]thiophen-5-yl)methyl)phosphonic acid (300 mg, 960 μmol, 1 eq.) in dry DCM (20 mL) and DMF (0.1 mL) at 0° C. The reaction mixture was stirred at 40° C. for an additional 1 hr. The reaction was monitored by pipetting out a small amount of crude sample and quenching it with MeOH to ensure bis-Cl phosphoryl chloride had been formed completely (bis-methoxy phosphonate was observed by LCMS). After completion, the excess oxalyl chloride and solvent were removed under reduced pressure to afford allyl 5-((dichlorophosphoryl)methyl)benzo[b]thiophene-2-carboxylate (300 mg). The residue (300 mg, 859 μmol, 1 eq.) was re-dissolved in anhydrous DCM (5 mL), then added to a mixture of pyrrolidin-2-one (218 mg, 2.57 mmol, 3 eq.) and TEA (259 mg, 2.57 mmol, 3 eq.) in anhydrous DCM (10 mL) at 0° C. The reaction was allowed to warm to 25° C. and stirred for an additional 2 h. After completion, the reaction mixture was concentrated under reduced pressure. The residue was purified by Biotage® C18 column chromatography to give ((2-((allyloxy)carbonyl)benzo[b]thiophen-5-yl)methyl)(2-oxopyrrolidin-1-yl)phosphinic acid (100 mg, 263 μmol, 31%) as a colorless oil. LCMS (ESI): m/z=380 [M+H]$^+$.

Step 2: Preparation of allyl 5-(((((S)-1-oxo-1-propoxypropan-2-yl)amino)(2-oxopyrrolidin-1-yl)phosphoryl)methyl)benzo[b]thiophene-2-carboxylate Oxalyl chloride (201 mg, 1.59 mmol, 5 eq.) was added dropwise to the solution of ((2-((allyloxy)carbonyl)benzo[b]thiophen-5-yl)methyl)(2-oxopyrrolidin-1-yl)phosphinic acid (100 mg, 320 μmol, 1 eq.) in dry DCM (5 mL) and DMF (0.1 mL) at 0° C. The reaction mixture was stirred at 40° C. for an additional 1 hr. The reaction was monitored by pipetting out a small amount of crude sample and quenching it with MeOH to ensure mono-Cl phosphoryl chloride had been formed completely (mono-methoxy phosphonate was observed by LCMS). After completion, the excess oxalyl chloride and solvent were removed under reduced pressure to afford allyl 5-((chloro(2-oxopyrrolidin-1-yl)phosphoryl)methyl)benzo[b]thiophene-2-carboxylate (100 mg). The residue (100 mg, 251 μmol, 1 eq.) was re-dissolved in anhydrous DCM (10 mL), then added to a mixture of propyl L-alaninate (65.8 mg, 502 μmol, 2 eq.) and TEA (101 mg, 1.00 mmol, 4 eq.) in anhydrous DCM (10 mL) at 0° C. The reaction was allowed to warm to 25° C. and stirred for an additional 2 h. After completion, the reaction mixture was concentrated under reduced pressure. The residue was purified by Biotage® C18 column chromatography to give allyl 5-(((((S)-1-oxo-1-propoxypropan-2-yl)amino)(2-oxopyrrolidin-1-yl)phosphoryl)methyl)benzo[b]thiophene-2-carboxylate (23.0 mg, 46.6 μmol, 19%) as a colorless oil. LCMS (ESI): m/z=493 [M+H]$^+$.

Step 3: Preparation of 5-(((((S)-1-oxo-1-propoxypropan-2-yl)amino)(2-oxopyrrolidin-1-yl)phosphoryl)methyl)benzo[b]thiophene-2-carboxylic acid To a solution of allyl 5-(((((S)-1-oxo-1-propoxypropan-2-yl)amino)(2-oxopyrrolidin-1-yl)phosphoryl)methyl)benzo[b]thiophene-2-carboxylate (22 mg, 44.6 μmol, 1 eq) in DCM (2 mL) were added Pd($PPh_3$)$_4$ (5 mg, 4.46 μmol, 0.1 eq.) and pyrrolidine (3 mg, 44.6 μmol, 1.0 eq.). The mixture was purged and degassed with $N_2$ (three times), then stirred at 25° C. for 0.5 h. After completion, the mixture was quenched with HCl aqueous solution (1 N) and extracted with DCM (10 mL×3). The organic layers were combined and washed with brine (15 mL), dried over anhydrous $Na_2SO_4$, and concentrated under reduced pressure. The residue was purified by Biotage® C18 column chromatography to give 5-(((((S)-4-methoxy-1-oxo-1-propoxybutan-2-yl)amino)(phenoxy)phosphoryl)methyl)benzo[b]thiophene-2-carboxylic acid (13.0 mg, 28.7 μmol, 65%) as a colorless oil. LCMS (ESI): m/z=453 [M+H]$^+$.

Synthesis of 5-((bis((S)-2-(propoxycarbonyl)pyrrolidin-1-yl)phosphoryl)methyl)benzo[b]thiophene-2-carboxylic acid

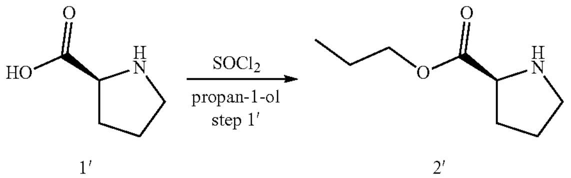

1′ 2′

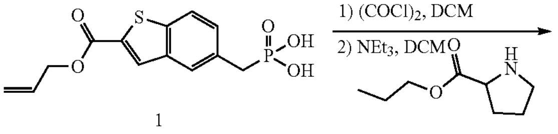

1

2 step 1

-continued

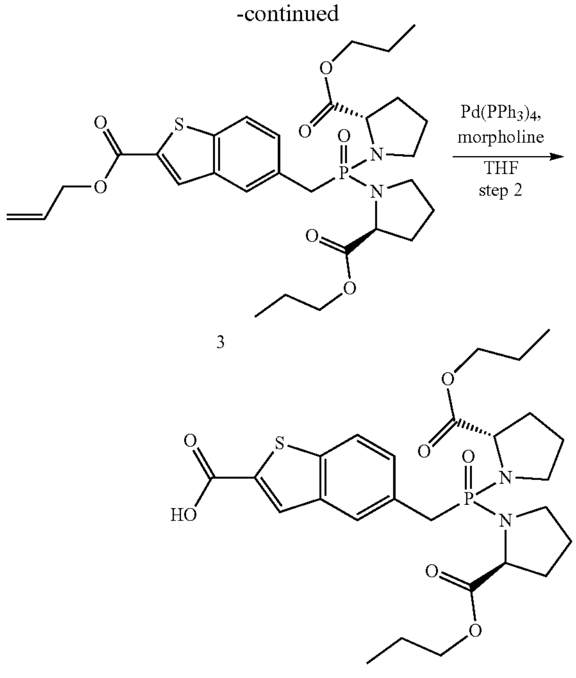

3

4 to room temperature overnight. The reaction was concentrated under reduced pressure and then dried under high vacuum during 30 min. The crude residue was diluted in DCM (10 mL, dried with $Na_2SO_4$) and cooled down to 0° C. A solution of propyl L-prolinate (603 mg, 3.84 mmol, 4 eq) and triethylamine (668 μL, 4.80 mmol, 5 eq) in DCM (3 mL, dried with $Na_2SO_4$) was added and the mixture was stirred at room temperature for 3 d. The reaction was concentrated under reduced pressure and the crude residue was purified by reverse phase chromatography on a 150 g Cis cartridge eluting with 5-100% MeCN in water (with 0.1% formic acid) to give propyl dipropyl (((2-((allyloxy)carbonyl)benzo[b]thiophen-5-yl)methyl)phosphoryl)(S)-di-L-prolinate (274 mg, 48.3%) as an orange oil. LCMS (ESI): m/z=591.2 $[M+H]^+$.

The intermediates in the table below were prepared using the method described above in Step 2 for the preparation of dipropyl (((2-((allyloxy)carbonyl)benzo[b]thiophen-5-yl)methyl)phosphoryl)(S)-di-L-prolinate and utilizing the appropriate starting materials and modifications.

| Name | Structure | LCMS |
| --- | --- | --- |
| dibutyl 2,2'-(((2-((allyloxy)carbonyl)benzo[b]thiophen-5-yl)methyl)phosphoryl)bis(azanediyl))(2S,2'S)-dipropionate | 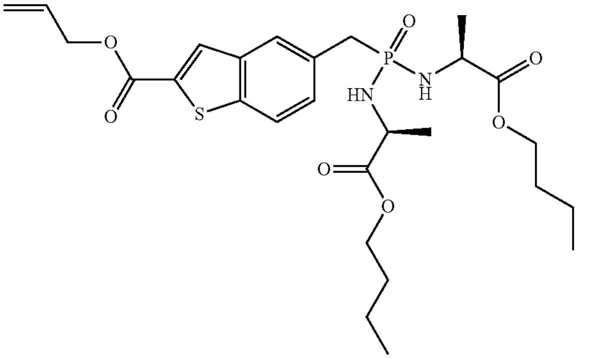 [SMILES: C=CCOC(=O)c1cc2cc(CP(=O)(N[C@@H](C)C(=O)OCCCC)N[C@@H](C)C(=O)OCCCC)ccc2s1] | 567 $[M + H]^+$ |

Step 1: Preparation of propyl L-prolinate

To a solution of (2S)-pyrrolidine-2-carboxylic acid (2.00 g, 17.3 mmol, 1 eq) in propan-1-ol (13.0 mL, 266 mmol) at −78° C. was added dropwise thionyl chloride (3.76 mL, 51.9 mmol, 3 eq). The mixture was allowed to warm to room temperature and then heated at 80° C. overnight. The reaction mixture was concentrated under reduced pressure and the crude propyl L-prolinate (2.62 g, 16.6 mmol, 96.6%) was isolated as an orange sticky oil that was used directly in the next Step. LCMS (ESI): m/z=158.1 $[M+H]^+$.

Step 2: Preparation of dipropyl (((2-((allyloxy)carbonyl)benzo[b]thiophen-5-yl)methyl)phosphoryl) (S)-di-L-prolinate To a solution of ((2-((allyloxy)carbonyl)benzo[b]thiophen-5-yl)methyl)phosphonic acid (300 mg, 0.9606 mmol, 1 eq) in DCM (10 mL) at 0° C. were added 2 drops of DMF (cat) and oxalyl chloride (246 μL, 2.88 mmol, 3 eq). The solution was stirred at 0° C. and was allowed to warm slowly

Step 3: Preparation of 5-((bis((S)-2-(propoxycarbonyl)pyrrolidin-1-yl)phosphoryl)methyl)benzo[b] thiophene-2-carboxylic acid To a solution of propyl dipropyl (((2-((allyloxy)carbonyl) benzo[b]thiophen-5-yl)methyl)phosphoryl)(S)-di-L-prolinate (274 mg, 0.4638 mmol, 1 eq) in THF (30 mL) were added morpholine (199 μL, 2.31 mmol, 5 eq) and $Pd(PPh_3)_4$ (53.5 mg, 0.04638 mmol, 0.10 eq). The reaction mixture was stirred at room temperature for 2 h and THF was removed under reduced pressure. The crude residue was purified by reverse phase chromatography on a 100 g Cis cartridge eluting with 5-100% MeCN in water (with 0.1% formic acid) to give 5-((bis((S)-2-(propoxycarbonyl)pyrrolidin-1-yl)phosphoryl)methyl)benzo[b]thiophene-2-carboxylic acid (203 mg, 79.6%) as a white solid. LCMS (ESI): m/z=551.2 $[M+H]^+$.

The intermediates in the table below were prepared using the method described above in Step 2 for the preparation of 5-((bis((S)-2-(propoxycarbonyl)pyrrolidin-1-yl)phosphoryl) methyl)benzo[b]thiophene-2-carboxylic acid and utilizing the appropriate starting materials and modifications.

| Name | Structure | LCMS |
|---|---|---|
| 5-((bis(((S)-1-butoxy-1-oxopropan-2-yl)amino)phosphoryl)methyl)benzo[b]thiophene-2-carboxylic acid | 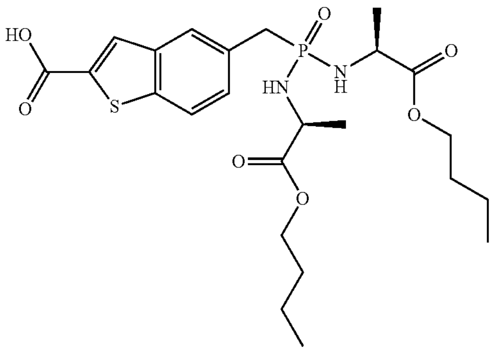 [SMILES: CCCCOC(=O)[C@H](C)NP(=O)(Cc1ccc2sc(C(=O)O)cc2c1)N[C@@H](C)C(=O)OCCCC] | 527 [M + H]+ |

Synthesis of 5-(((((S)-1-isopropoxy-3-methoxy-1-oxopropan-2-yl)amino)(phenoxy)phosphoryl)methyl)benzo[b]thiophene-2-carboxylic acid

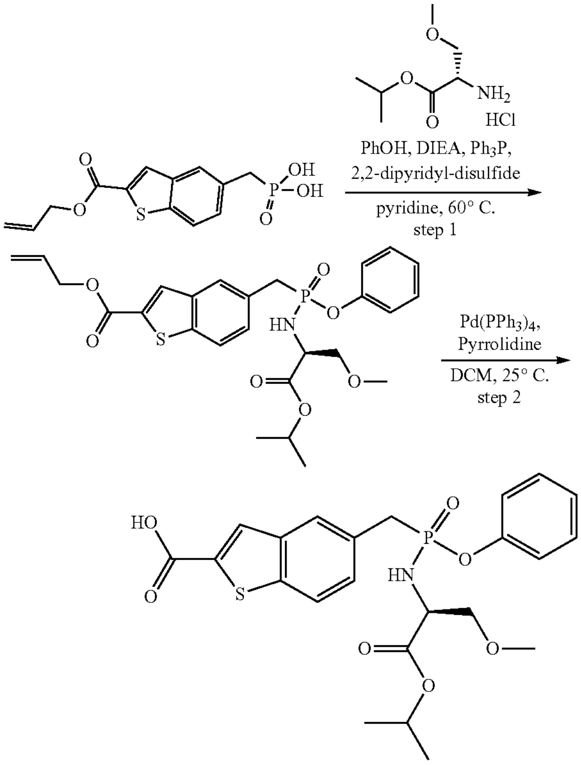

Step 1: Preparation of allyl 5-(((((S)-1-isopropoxy-3-methoxy-1-oxopropan-2-yl)amino)(phenoxy)phosphoryl)methyl)benzo[b]thiophene-2-carboxylate To a solution of ((2-((allyloxy)carbonyl)benzo[b]thiophen-5-yl)methyl)phosphonic acid (49.3 mg, 158 μmol, 1 eq.), propan-2-yl (2S)-2-amino3-methoxypropanoate hydrochloride (31.2 mg, 158 μmol, 1 eq.) and phenol (19.3 mg, 206 μmol, 1.3 eq.) in pyridine (3 mL) were added N,N-diisopropylethylamine (162 mg, 1.26 mmol, 8 eq.), 2,2-dipyridyl-disulfide (140 mg, 635 mol, 4 eq.) and triphenylphosphine (166 mg, 635 mol, 4 eq.) at 25° C. The mixture was heated to 60° C. and stirred at 60° C. for 48 h under $N_2$ atmosphere. After completion, the reaction mixture was concentrated under reduced pressure. The residue was purified by Biotage® C18 column chromatography to afford allyl 5-(((((S)-1-isopropoxy-3-methoxy-1-oxopropan-2-yl)amino)(phenoxy)phosphoryl)methyl)benzo[b]thiophene-2-carboxylate (35.0 mg, 65.8 mol, 42%) as a yellow solid. LCMS (ESI): m/z=532 $[M+H]^+$.

The intermediates in the table below were prepared using the method described above in Step 1 for the preparation of allyl 5-(((((S)-1-isopropoxy-3-methoxy-1-oxopropan-2-yl)amino)(phenoxy)phosphoryl)methyl)benzo[b]thiophene-2-carboxylate and utilizing the appropriate starting materials and modifications.

| Name | Structure | LCMS |
|---|---|---|
| allyl 5-((((1-isopropoxy-2-methyl-1-oxopropan-2-yl)amino)(phenoxy)phosphoryl)methyl)benzo[b]thiophene-2-carboxylate | 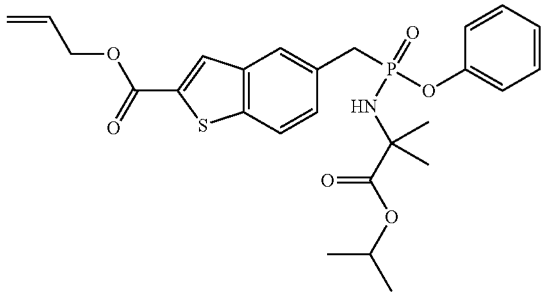 [SMILES: C=CCOC(=O)c1cc2cc(CP(=O)(NC(C)(C)C(=O)OC(C)C)Oc3ccccc3)ccc2s1] | 516.2 [M + H]+ |

-continued

| Name | Structure | LCMS |
|---|---|---|
| diisopropyl 2,2'-((((2-((allyloxy)carbonyl)benzo[b]thiophen-5-yl)methyl)phosphoryl)bis(azanediyl))(2S, 2'S)-dipropionate | 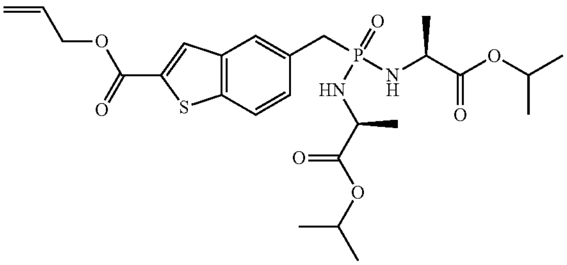 [SMILES: C=CCOC(=O)c1cc2cc(CP(=O)(N[C@@H](C)C(=O)OC(C)C)N[C@@H](C)C(=O)OC(C)C)ccc2s1] | 539 [M + H]+ |
| allyl 5-((((2-methyl-1-oxo-1-propoxypropan-2-yl)amino)(phenoxy)phosphoryl)methyl)benzo[b]thiophene-2-carboxylate | 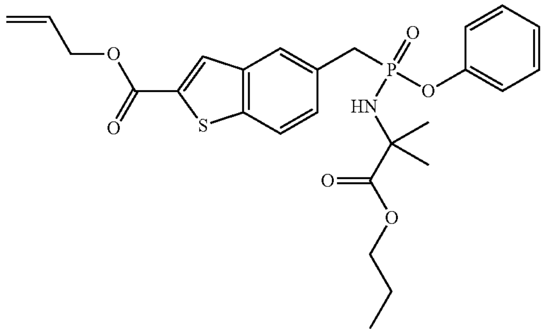 [SMILES: C=CCOC(=O)c1cc2cc(CP(=O)(NC(C)(C)C(=O)OCCC)Oc3ccccc3)ccc2s1] | 516.1 [M + H]+ |

Step 2: Preparation of 5-(((((S)-1-isopropoxy-3-methoxy-1-oxopropan-2-yl)amino)(phenoxy)phosphoryl)methyl)benzo[b]thiophene-2-carboxylic acid To a solution of allyl 5-(((((S)-1-isopropoxy-3-methoxy-1-oxopropan-2-yl)amino)(phenoxy)phosphoryl)methyl) benzo[b]thiophene-2-carboxylate (2, 150 mg, 282 μmol, 1 eq) in DCM (5 mL) were added $Pd(PPh_3)_4$ (65.1 mg, 56.4 μmol, 0.2 eq.) and pyrrolidine (20.0 mg, 282 μmol, 1.0 eq.). The mixture was purged and degassed with $N_2$ (three times), then stirred at 25° C. for 1 hr. After completion, the mixture was concentrated under reduced pressure. The residue was purified by Biotage® C18 column chromatography to give 5-(((((S)-1-isopropoxy-3-methoxy-1-oxopropan-2-yl) amino)(phenoxy)phosphoryl)methyl)benzo[b]thiophene-2-carboxylic acid (120 mg, 244 μmol, 87%) as a yellow solid. LCMS (ESI): m/z=492.1 $[M+H]^+$.

The intermediates in the table below were prepared using the method described above in Step 2 for the preparation of 5-(((((S)-1-isopropoxy-3-methoxy-1-oxopropan-2-yl) amino)(phenoxy)phosphoryl)methyl)benzo[b]thiophene-2-carboxylic acid and utilizing the appropriate starting materials and modifications.

| Name | Structure | LCMS |
|---|---|---|
| 5-((((1-isopropoxy-2-methyl-1-oxopropan-2-yl)amino)(phenoxy)phosphoryl)methyl) benzo[b]thiophene-2-carboxylic acid | 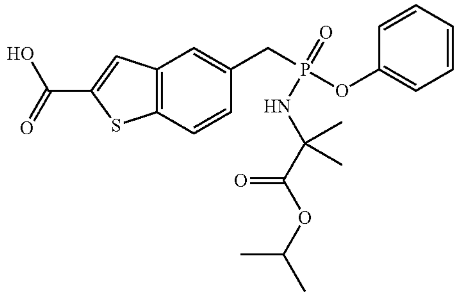 [SMILES: CC(C)OC(=O)C(C)(C)NP(=O)(Cc1ccc2sc(C(=O)O)cc2c1)Oc1ccccc1] | 476.5 [M + H]+ |

-continued

| Name | Structure | LCMS |
|---|---|---|
| 5-((bis(((S)-1-isopropoxy-1-oxopropan-2-yl)amino)phosphoryl)methyl)benzo[b]thiophene-2-carboxylic acid | 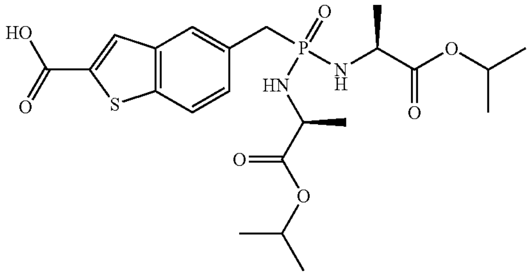 [SMILES: CC(C)OC(=O)[C@H](C)NP(=O)(Cc1ccc2sc(C(=O)O)cc2c1)N[C@@H](C)C(=O)OC(C)C] | 499 [M + H]+ |
| 5-((((2-methyl-1-oxo-1-propoxypropan-2-yl)amino)(phenoxy)phosphoryl)methyl) benzo[b]thiophene-2-carboxylic acid | 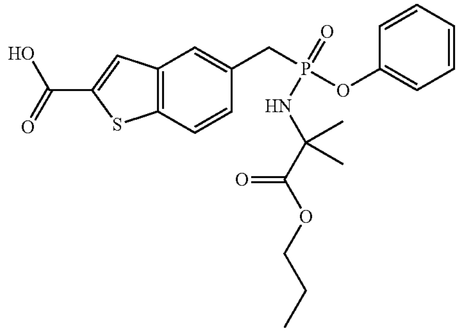 [SMILES: CCCOC(=O)C(C)(C)NP(=O)(Cc1ccc2sc(C(=O)O)cc2c1)Oc1ccccc1] | 476.2 [M + H]+ |

Synthesis of 5-(1-fluoro-1-((((S)-1-oxo-1-propoxypropan-2-yl)amino)(phenoxy)phosphoryl)ethyl) benzo[b]thiophene-2-carboxylic acid

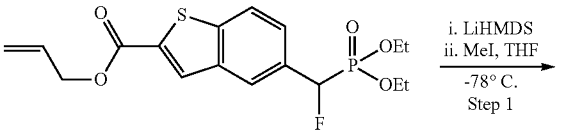

1

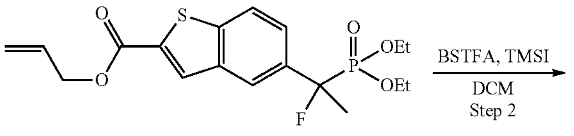

2

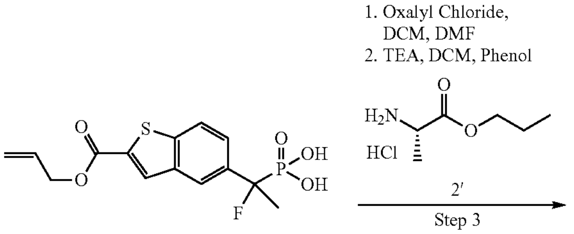

3

-continued

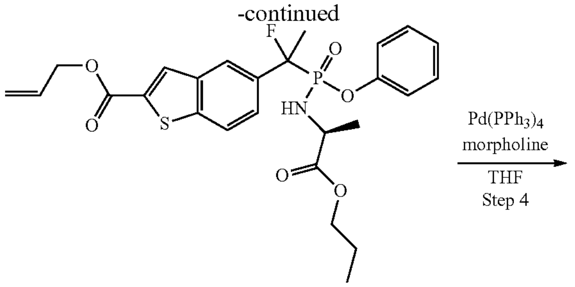

4

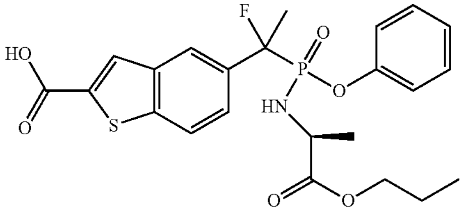

5

Step 1: Preparation of allyl 5-(1-(diethoxyphosphoryl)-1-fluoroethyl)benzo[b]thiophene-2-carboxylate To a solution of allyl 5-((diethoxyphosphoryl)fluoromethyl)benzo[b]thiophene-2-carboxylate (2.66 g, 6.88 mmol, 1 eq) in THF (50 mL) at −78° C. were added 1 M LiHMDS in THF (6.88 mL, 6.88 mmol, 1 eq) and methyl iodide (850 μL, 13.7 mmol, 2 eq) dropwise. The mixture was stirred at −78° C. for 5 min. The reaction was quenched with a saturated aqueous solution of ammonium chloride (30 mL), warmed up to room temperature and the product was extracted with EtOAc (2×100 mL). The combined organic extracts were dried with sodium sulfate, filtered and concentrated under reduced pressure. The crude material was purified by reverse phase chromatography on a 150 g Cis cartridge eluting with a gradient of 5-80% acetonitrile in water (with 0.1% formic acid). The fractions were combined and concentrated under reduced pressure to give allyl 5-(1-(diethoxyphosphoryl)-1-fluoroethyl)benzo[b]thiophene-2-carboxylate (1.44 g, 52.3%) as a brown oil. LCMS (ESI) m/z=401.2

Step 2: Preparation of (1-(2-((allyloxy)carbonyl) benzo[b]thiophen-5-yl)-1-fluoroethyl)phosphonic acid To a solution of allyl 5-(1-(diethoxyphosphoryl)-1-fluoroethyl)benzo[b]thiophene-2-carboxylate (1.44 g, 3.59 mmol, 1 eq) in DCM (30 mL) at 0° C. were added N,O-bis(trimethylsilyl)trifluoroacetamide (4.74 mL, 17.9 mmol) followed by slow addition of trimethylsilyl iodide (1.52 mL, 10.7 mmol, 3 eq) in DCM (2 mL). The solution was stirred at 0° C. for 1 h. The reaction was quenched with the addition of a 2:1 solution of water and acetonitrile (with 0.1% TFA) (2 mL). The solvent was removed under reduced pressure. The crude residue was purified by reverse phase chromatography on a 150 g Cis cartridge eluting with a gradient of 5-60% acetonitrile in water (with 0.1% formic acid). The combined fractions were concentrated and freeze-dried to give (1-(2-((allyloxy)carbonyl)benzo[b]thiophen-5-yl)-1-fluoroethyl)phosphonic acid (887 mg, 72.1%) as a pale-yellow solid. $^{1}$H NMR (400 MHz, DMSO-$d_6$) 11.84-11.05 (m, 2H), 8.34-8.28 (m, 1H), 8.12-8.02 (m, 2H), 7.66-7.56 (m, 1H), 6.12-5.98 (m, 1H), 5.49-5.39 (m, 1H), 5.35-5.27 (m, 1H), 4.89-4.81 (m, 2H), 1.96-1.78 (m, 3H).

Step 3: Preparation of allyl 5-(1-fluoro-1-((((S)-1-oxo-1-propoxypropan-2-yl)amino)(phenoxy)phosphoryl)ethyl)benzo[b]thiophene-2-carboxylate To a suspension of (1-(2-((allyloxy)carbonyl)benzo[b]thiophen-5-yl)-1-fluoroethyl)phosphonic acid (160 mg, 464 µmol, 1 eq) and 1 drop of DMF (cat) in DCM (30 mL) at 0° C. was added oxalyl chloride (118 µL, 1.39 mmol, 3 eq) and the reaction was stirred for 20 h. The reaction was concentrated under reduced pressure and then dried under high vacuum during 10 min. The crude residue was diluted in 1,2-dichloroethane (3 mL) and a solution of phenol (43.6 mg, 464 µmol, 1 eq) and triethylamine (322 µL, 2.32 mmol, 5 eq) in 1,2-dichloroethane (3 mL, dried with $Na_2SO_4$) was added to the mixture which was stirred at 45° C. for 3 h. Propyl (2S)-2-aminopropanoate hydrochloride (77.7 mg, 464 µmol, 1 eq) in dichloromethane (10 mL, dried with $Na_2SO_4$) was added directly to the solution and stirred at room temperature overnight. The reaction mixture was quenched with water and the dichloromethane was removed in vacuo. The product was purified by reverse phase chromatography on a 50 g Cis cartridge eluting with a gradient of 5-100% acetonitrile in water (with 0.1% formic acid) to afford allyl 5-(1-fluoro-1-((((S)-1-oxo-1-propoxypropan-2-yl)amino)(phenoxy)phosphoryl)ethyl)benzo[b]thiophene-2-carboxylate (30.0 mg, 12%). $^{1}$H NMR (400 MHz, $CDCl_3$) δ 8.12-8.02 (m, 2H), 7.93-7.82 (m, 1H), 7.72-7.64 (m, 1H), 7.38-7.28 (m, 1H), 7.25-7.13 (m, 2H), 7.09-7.00 (m, 1H), 7.00-6.92 (m, 1H), 6.13-5.98 (m, 1H), 5.45 (br d, J=17.1 Hz, 1H), 5.33 (br d, J=10.5 Hz, 1H), 4.86 (br d, J=4.9 Hz, 2H), 4.25-4.11 (m, 0.5H), 4.10-4.00 (m, 1H), 3.95-3.76 (m, 1H), 3.68-3.48 (m, 1.25H), 3.45-3.36 (m, 0.25H), 2.44-2.74 (m, 1H), 2.17-2.01 (m, 3H), 1.70-1.59 (m, 1H), 1.56-1.46 (m, 0.5H), 1.45-1.33 (m, 0.5H), 1.32-1.23 (m, 1.5H), 1.13-1.05 (m, 0.5H), 0.97-0.89 (m, 1.5H), 0.87-0.80 (m, 0.5H), 0.80-0.72 (m, 1H).

Step 4: Preparation of 5-(1-fluoro-1-((((S)-1-oxo-1-propoxypropan-2-yl)amino)(phenoxy)phosphoryl) ethyl)benzo[b]thiophene-2-carboxylic acid To a stirred solution of allyl 5-(1-fluoro-1-((((S)-1-oxo-1-propoxypropan-2-yl)amino)(phenoxy)phosphoryl)ethyl) benzo[b]thiophene-2-carboxylate (30 mg, 56.2 µmol, 1 eq) in THF (3 mL) were added morpholine (24.1 µL, 281 µmol, 5 eq) and $Pd(PPh_3)_4$ (3.24 mg, 2.81 µmol, 0.05 eq) under nitrogen. The reaction mixture was stirred at room temperature for 1 h. The reaction was concentrated and the crude was directly purified by reverse phase chromatography on a 50 g Cis cartridge eluting with a gradient of 5-100% acetonitrile in water (with 0.1% formic acid) to afford 5-(1-fluoro-1-((((S)-1-oxo-1-propoxypropan-2-yl)amino)(phenoxy)phosphoryl)ethyl)benzo[b]thiophene-2-carboxylic acid (30.0 mg, 108%) as a beige solid. LCMS (ESI) m/z=494.2 $[M+H]^+$.

Synthesis of perfluorophenyl 5-(((((S)-1-oxo-1-propoxypropan-2-yl)amino)(phenoxy)phosphoryl) methyl)benzo[b]thiophene-2-carboxylate

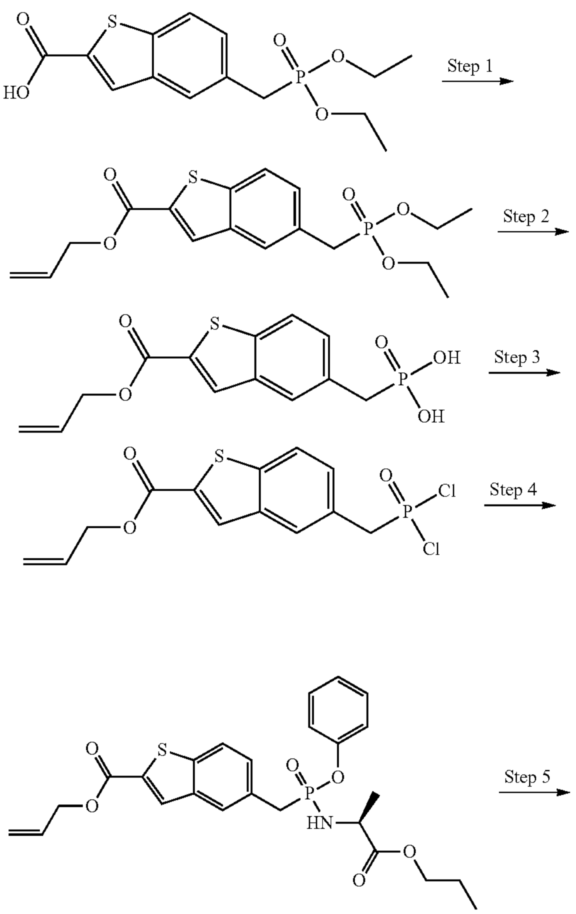

-continued

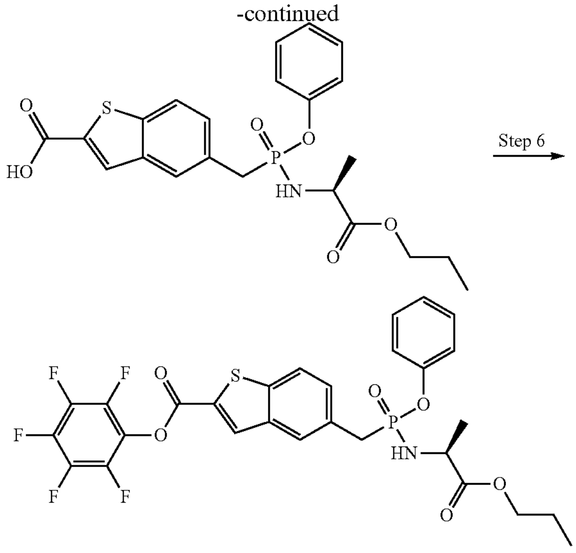

Step 1: Preparation of allyl 5-((diethoxyphosphoryl)methyl)benzo[b]thiophene-2-carboxylate To a solution of 5-((diethoxyphosphoryl)methyl)benzo[b]thiophene-2-carboxylic acid (25 g, 76 mmol, 1 eq) in DMF (250 mL) was added $Na_2CO_3$ (20 g, 190 mmol, 2.5 eq) and 3-bromoprop-1-ene (23 g, 190 mmol, 2.5 eq), the mixture was stirred at 25° C. for 12 h. The mixture was diluted with water (500 mL) and extracted with EtOAc (500 mL×3). The combined organic layers were washed with brine (500 mL×3), dried over anhydrous $Na_2SO_4$, filtered and concentrated under reduced pressure to give a residue. The residue was purified by flash silica gel chromatography to give allyl 5-((diethoxyphosphoryl)methyl)benzo[b]thiophene-2-carboxylate (25 g, 68 mmol, 89% yield) as a white solid. $^1H$ NMR (400 MHz, $CDCl_3$) δ 7.97 (s, 1H), 7.79-7.67 (m, 2H), 7.39-7.28 (m, 1H), 6.05-5.88 (m, 1H), 5.43-5.33 (m, 1H), 5.29-5.20 (m, 1H), 4.83-4.73 (m, 2H), 4.00-3.88 (m, 4H), 3.29-3.11 (m, 2H), 1.18 (d, J=6.4 Hz, 6H).

Step 2: Preparation of ((2-((allyloxy)carbonyl)benzo[b]thiophen-5-yl)methyl)phosphonic acid To a solution of allyl 5-((diethoxyphosphoryl)methyl)benzo[b]thiophene-2-carboxylate (25 g, 68 mmol, 1 eq) in DCM (250 mL) was added TMSI (54 g, 272 mmol, 4 eq) in a dropwise manner at 0° C., the mixture was stirred at 0° C. for 1 h. The reaction mixture was concentrated under reduced pressure to give a yellow oil. The oil was purified by reversed phase (TFA) to lyophilized to give ((2-((allyloxy)carbonyl)benzo[b]thiophen-5-yl)methyl)phosphonic acid (13 g, 42 mmol, 61% yield) as a white solid. LCMS (ESI) m/z=313.2 $[M+H]^+$.

Step 3: Preparation of allyl 5-((dichlorophosphoryl)methyl)benzo[b]thiophene-2-carboxylate To a solution of ((2-((allyloxy)carbonyl)benzo[b]thiophen-5-yl)methyl)phosphonic acid (2.0 g, 6.4 mmol, 1 eq) in DCM (30 mL) was added DMF (0.09 mL) and was cooled to 0° C., then oxalic dichloride (2.4 g, 19.2 mmol, 3 eq) was dropwise, after that the reaction was warmed to 40° C. and was stirred 1 h to give a yellow clean solution. The reaction mixture was concentrated under reduced pressure to give allyl 5 ((dichlorophosphoryl)methyl)benzo[b]thiophene-2-carboxylate (2.0 g, crude) as a brassy yellow solid. LCMS (ESI) m/z=341.2 $[M+H]^+$.

Step 4: Preparation of allyl 5-(((((S)-1-oxo-1-propoxypropan-2-yl)amino)(phenoxy)phosphoryl)methyl)benzo[b]thiophene-2-carboxylate To a solution of allyl 5-((dichlorophosphoryl)methyl)benzo[b]thiophene-2-carboxylate (2.0 g, crude, 1 eq) in DCM (40 mL) was cooled to 0° C. and was added a solution of phenol (0.43 g, 4.58 mmol, 1 eq) in DCM (8 mL), then ethylbis(propan-2-yl)amine (2.2 g, 17 mmol, 3 eq) in DCM (50 mL) was dropwise over 0.5 h. Then propyl L-alaninate hydrochloride (1.44 g, 1.58 mmol, 1.5 eq) in DCM (8 mL) was added, the mixture was stirred at 0° C. for 0.5 h. The reaction mixture was concentrated under reduced pressure to give a residue. The residue was purified by column chromatography to give allyl 5-(((((S)-1-oxo-1-propoxypropan-2-yl)amino)(phenoxy)phosphoryl)methyl)benzo[b]thiophene-2-carboxylate (1.4 g, 2.8 mmol, 43.8% yield) as a yellow oil. LCMS (ESI) m/z=502.2 $[M+H]^+$.

Step 5: Preparation of 5-(((((S)-1-oxo-1-propoxypropan-2-yl)amino)(phenoxy)phosphoryl)methyl)benzo[b]thiophene-2-carboxylic acid To a solution of allyl 5-(((((S)-1-oxo-1-propoxypropan-2-yl)amino)(phenoxy)phosphoryl)methyl)benzo[b]thiophene-2-carboxylate (1.4 g, 2.8 mmol) in DCM (20 mL) was added $Pd(PPh_3)_4$ (0.3 g, 0.3 mmol, 0.1 eq) and pyrrolidine (0.4 g, 5.6 mmol, 2 eq). Then the reaction was stirred at 25° C. for 15 min to give a yellow clean solution. The reaction mixture was concentrated under reduced pressure to give a residue. The residue was purified by reversed phase (TFA) to freeze-drying to give 5-(((((S)-1-oxo-1-propoxypropan-2-yl)amino)(phenoxy)phosphoryl)methyl)benzo[b]thiophene-2-carboxylic acid (1.1 g, 2.4 mmol, 85.9% yield) as a yellow oil. LCMS (ESI) m/z=461.9 $[M+H]^+$. $^1H$ NMR (400 MHz, $CDCl_3$) δ 7.91-7.86 (m, 1H), 7.84-7.76 (m, 2H), 7.45-7.38 (m, 1H), 7.38-7.31 (m, 2H), 7.27-7.15 (m, 3H), 4.28-3.95 (m, 3H), 3.56-3.42 (m, 2H), 1.64 (td, J=7.2, 14.0 Hz, 2H), 1.33-1.18 (m, 3H), 0.93 (dt, J=4.8, 7.2 Hz, 3H).

Step 6: Preparation of perfluorophenyl 5-(((((S)-1-oxo-1-propoxypropan-2-yl)amino)(phenoxy)phosphoryl)methyl)benzo[b]thiophene-2-carboxylate To a solution of 5-(((((S)-1-oxo-1-propoxypropan-2-yl)amino)(phenoxy)phosphoryl)methyl)benzo[b]thiophene-2-carboxylic acid (19 g, 41 mmol, 1 eq) and pyridine (11 g, 0.14 mol, 3.5 eq) in DMF (100 mL) was cooled to 0° C., then the solution of perfluorophenyl 2,2,2-trifluoroacetate (57 g, 0.21 mol, 5 eq) was dropwise added to the mixture at 0° C. Then the mixture was stirred at 0° C. for 1 h to give a yellow solution. The mixture was diluted with water (500 mL) and extracted with EtOAc (500 mL×3), the combined organic layers were dried over $Na_2SO_4$, filtered and concentrated under reduced pressure to give a residue. The residue was purified by flash silica gel chromatography to give perfluorophenyl 5-(((((S)-1-oxo-1-propoxypropan-2-yl)amino)(phenoxy)phosphoryl)methyl)benzo[b]thiophene-2-carboxylate (17 g, 27 mmol, 65% yield) was obtained as a yellow oil. LCMS (ESI) m/z=628.1 $[M+H]^+$. $^1H$ NMR (400 MHz, $CDCl_3$) δ 8.33-8.23 (m, 1H), 8.03-7.85 (m, 2H), 7.60-7.53 (m, 1H), 7.28 (s, 2H), 7.20-7.05 (m, 3H), 4.08-3.87 (m, 3H), 3.55-3.42 (m, 2H), 1.63-1.52 (m, 2H), 1.19-1.15 (m, 3H), 0.95-0.83 (m, 3H).

Synthesis of perfluorophenyl 5-((S)-fluoro((R)-(((S)-1-oxo-1-propoxypropan-2-yl)amino)(phenoxy)phosphoryl)methyl)benzo[b]thiophene-2-carboxylate
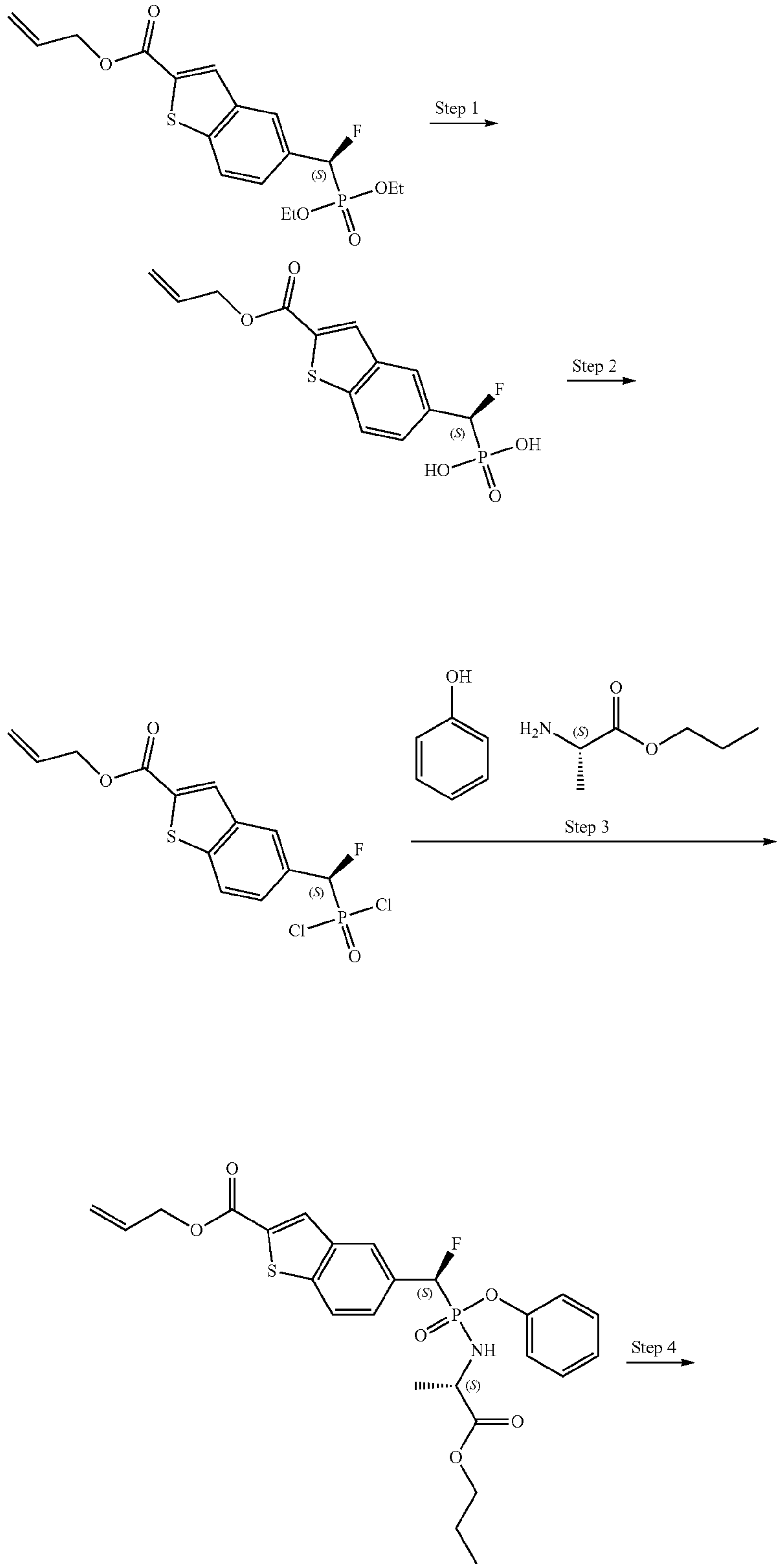

-continued

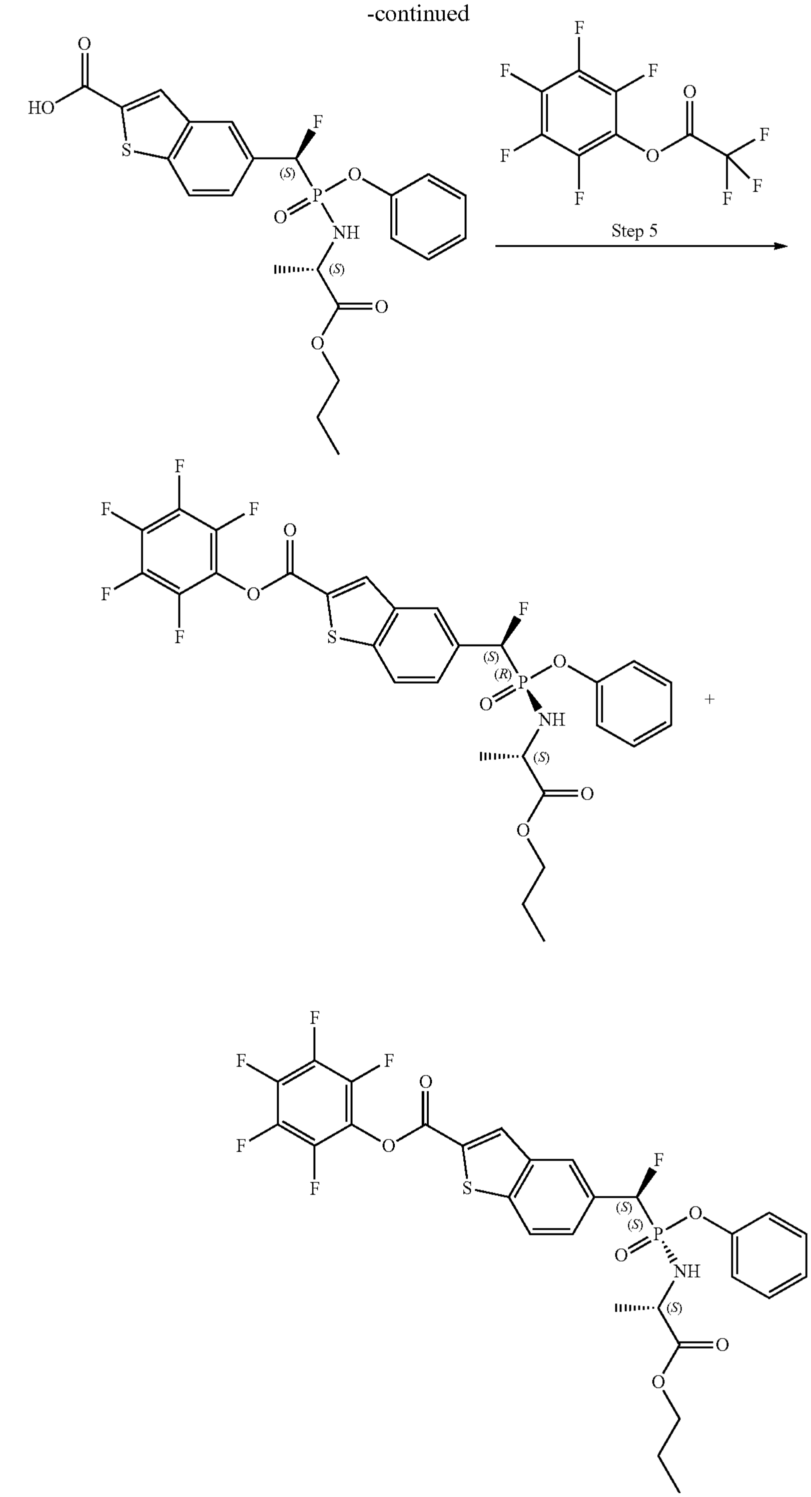

Step 1: Preparation of (S)-((2-((allyloxy)carbonyl) benzo[b]thiophen-5-yl)fluoromethyl)phosphonic acid To a solution of allyl (S)-5-((diethoxyphosphoryl)fluoromethyl)benzo[b]thiophene-2-carboxylate (20 g, 52 mmol, 1 eq) in methylene chloride (500 mL) was added trimethylsilyl iodide (21 g, 0.10 mol, 2 eq). The mixture was stirred at 0° C. for 1 hour to give a brown solution. The reaction mixture was concentrated under reduced pressure to give a residue. The reaction residue was purified by prep-HPLC (TFA) to lyophilized to give (S)-((2-((allyloxy)carbonyl) benzo[b]thiophen-5-yl)fluoromethyl)phosphonic acid (12 g, 36 mmol, 70% yield) as a brown solid. LCMS (ESI) m/z=330.9

Step 2: Preparation of allyl (S)-5-((dichlorophosphoryl)fluoromethyl)benzo[b]thiophene-2-carboxylate To a solution of (S)-((2-((allyloxy)carbonyl)benzo[b]thiophen-5-yl)fluoromethyl)phosphonic acid (11 g, 33 mmol, 1 eq) in methylene chloride (200 mL) was added dimethylformamide (0.24 g, 3.3 mmol, 0.1 eq) at 0° C. under $N_2$ atmosphere, then oxalyl chloride (13 g, 0.10 mol, 3 eq) was added dropwise and stirred at 0° C. for 30 minutes and warmed to 40° C. for 1 hour to give a brown solution. The reaction mixture was concentrated under reduced pressure to give allyl (S)-5-((dichlorophosphoryl)fluoromethyl)benzo[b]thiophene-2-carboxylate (11 g crude) as a yellow solid. LCMS (ESI) m/z=358.9.

Step 3: Preparation of allyl 5-((1S)-fluoro((((S)-1-oxo-1-propoxypropan-2-yl)amino)(phenoxy)phosphoryl)methyl)benzo[b]thiophene-2-carboxylate To a solution of (S)-5-((dichlorophosphoryl)fluoromethyl)benzo[b]thiophene-2-carboxylate (11 g, 30 mmol, 1 eq) in methylene chloride (150 mL) was added phenol (2.2 g, 24 mmol, 0.8 eq) in methylene chloride (20 mL) in 10 minutes at 0° C., then the solution of N,N-diisopropylethylamine (12 g, 90 mmol, 3 eq) in methylene chloride (200 mL) was dropwise over 1.5 hours and the mixture was stirred at 25° C. for 5 minutes to give a yellow clean solution then the solution of propyl (2S)-2-aminopropanoate (3.9 g, 30 mmol, 1 eq) in methylene chloride (20 mL) was added, the mixture was stirred at 25° C. for 1 hour to give a yellow clean solution. The reaction mixture was concentrated under reduced pressure to give a residue. The residue was purified by flash silica gel chromatography to give allyl 5-((1S)-fluoro((((S)-1-oxo-1-propoxypropan-2-yl)amino)(phenoxy)phosphoryl)methyl)benzo[b]thiophene-2-carboxylate (7.4 g, 14.2 mmol, 47% yield) as a yellow solid. LCMS (ESI) m/z=520.2

Step 4: Preparation of 5-((1S)-fluoro((((S)-1-oxo-1-propoxypropan-2-yl)amino)(phenoxy)phosphoryl)methyl)benzo[b]thiophene-2-carboxylic acid To a solution of allyl 5-((1S)-fluoro((((S)-1-oxo-1-propoxypropan-2-yl)amino)(phenoxy)phosphoryl)methyl)benzo[b]thiophene-2-carboxylate (3.5 g, 6.7 mmol, 1 eq) in methylene chloride (40 mL) at 0° C. under $N_2$ atmosphere, then pyrrolidine (0.38 g, 5.4 mmol, 0.8 eq) and $Pd(PPh_3)_4$ (0.7 g, 0.67 mmol, 0.11 eq) was added dropwise and stirred at 0° C. for 10 minutes and warmed to 25° C. for 10 minutes to give a brown solution. The reaction mixture was concentrated under reduced pressure to give a residue. The reaction residue was purified by prep-HPLC (TFA) to lyophilized to give 5-((1S)-fluoro((((S)-1-oxo-1-propoxypropan-2-yl)amino)(phenoxy)phosphoryl)methyl)benzo[b]thiophene-2-carboxylic acid (2.8 g, 5.9 mmol, 87% yield) as a white solid. $^1H$ NMR (400 MHz, $CDCl_3$) δ 8.10 (d, J=11.2 Hz, 2H), 7.97 (d, J=8.4 Hz, 1H), 7.66 (d, J=8.4 Hz, 1H), 7.38-7.30 (m, 2H), 7.19 (d, J=7.6 Hz, 3H), 6.20-5.99 (m, 1H), 4.05-3.77 (m, 3H), 1.68-1.42 (m, 2H), 1.22 (d, J=7.2 Hz, 3H), 0.89-0.85 (m, 3H)

Step 5: Preparation of perfluorophenyl 5-((S)-fluoro((R)-(((S)-1-oxo-1-propoxypropan-2-yl)amino)(phenoxy)phosphoryl)methyl)benzo[b]thiophene-2-carboxylate and perfluorophenyl 5-((S)-fluoro((S)-(((S)-1-oxo-1-propoxypropan-2-yl)amino)(phenoxy)phosphoryl)methyl)benzo[b]thiophene-2-carboxylate To a solution of 5-((1S)-fluoro((((S)-1-oxo-1-propoxypropan-2-yl)amino)(phenoxy)phosphoryl)methyl)benzo[b]thiophene-2-carboxylic acid (3.0 g, 6.3 mmol, 1 eq) in pyridine (15 mL) at 0° C. under $N_2$ atmosphere, then 2,3,4,5,6-pentafluorophenyl 2,2,2-trifluoroacetate (5.2 g, 19 mmol, 3 eq) was added dropwise and stirred at 0° C. for 10 minutes and warmed to 25° C. for 1 hour to give a brown solution. The reaction mixture was concentrated under reduced pressure to give a residue. The residue was purified by flash silica gel chromatography in 3:1 Petroleum ether/ethyl acetate to give the separated Phos isomers. The analogous (R)—F isomer was made in a similar manner. Analytical data for all 4 isomers are listed in the table below. SFC conditions used in the peak assignments are as follows: Chiralpak AS-3 50×4.6 mm I.D., 3 um. Mobile phase: Phase A for $CO_2$, and Phase B for EtOH (0.05% DEA); Gradient elution: B in A from 5% to 40%. Flow rate: 3 mL/min; Detector: PDA; Column Temp: 35C; Back Pressure: 100 Bar.

| Name | Structure | LCMS | NMR |
| --- | --- | --- | --- |
| perfluorophenyl 5-((S)-fluoro((R)-(((S)-1-oxo-1-propoxypropan-2-yl)amino)(phenoxy)phosphoryl)methyl)benzo[b]thiophene-2-carboxylate | 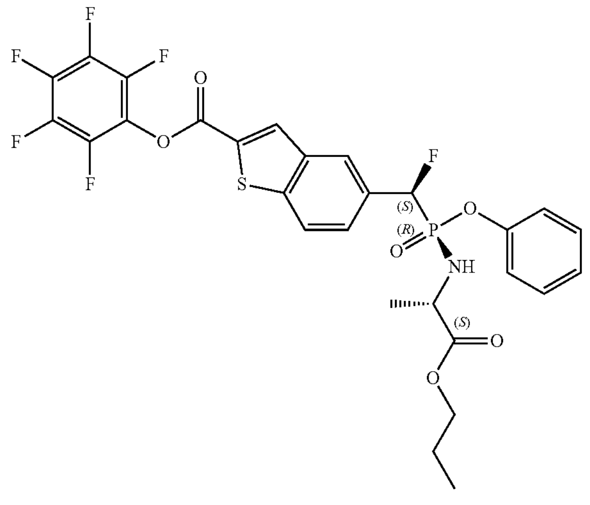 | 645.9 $[M + H]^+$ | $^1H$ NMR (400 MHz, $CD_3OD$) δ 8.52 (s, 1H), 8.25 (s, 1H), 8.14 (d, J = 8.4 Hz, 1H), 7.81 (d, J = 8.4 Hz, 1H), 7.39-7.32 (m, 2H), 7.27-7.16 (m, 3H), 6.25-6.01 (m, 1H), 4.00 (t, J = 6.8 Hz, 2H), 3.92-3.82 (m, 1H), 1.63-1.52 (m, 2H), 1.14 (d, J = 7.2 Hz, 3H), 0.90 (t, J = 7.2 Hz, 3H) |
| or | or | | |

-continued

| Name | Structure | LCMS | NMR |
|---|---|---|---|
| perfluorophenyl 5-((S)-fluoro((S)-(((S)-1-oxo-1-propoxypropan-2-yl)amino)(phenoxy)phosphoryl)methyl)benzo[b]thiophene-2-carboxylate | 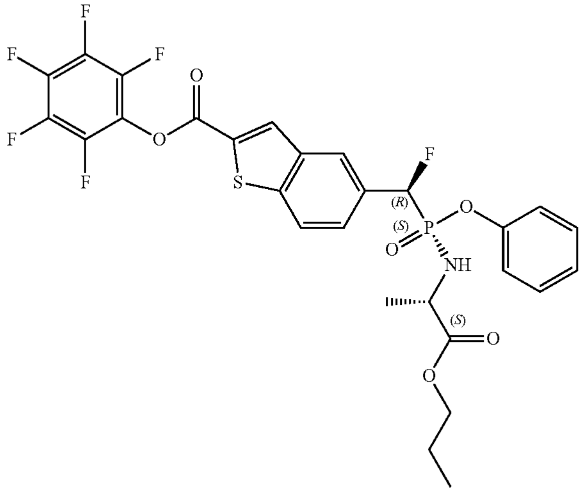<br>CFTE-27B, SFC Peak 2<br>Ret. Time = 1.46 Minutes | | |
| perfluorophenyl 5-((S)-fluoro((R)-(((S)-1-oxo-1-propoxypropan-2-yl)amino)(phenoxy)phosphoryl)methyl)benzo[b]thiophene-2-carboxylate | 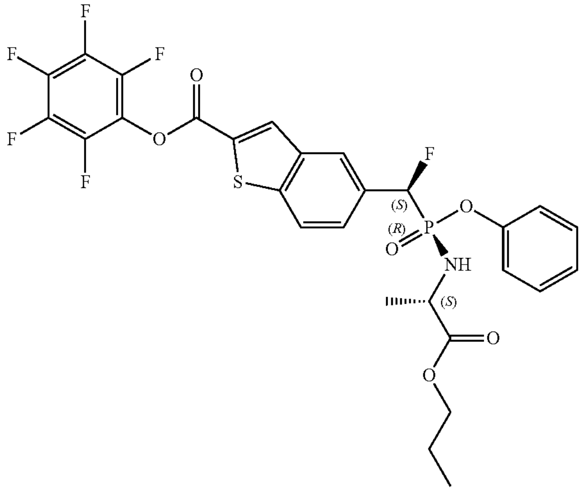 | 646.0 [M + H]+ | $^{1}H$ NMR (400 MHz, $CD_3OD$) δ 8.51 (s, 1H), 8.27 (s, 1H), 8.11 (d, J = 8.4 Hz, 1H), 7.79 (d, J = 8.8 Hz, 1H), 7.40-7.33 (m, 2H), 7.25-7.18 (m, 3H), 6.27-6.08 (m, 1H), 4.03-3.85 (m, 3H), 1.63-1.51 (m, 2H), 1.25 (d, J = 7.2 Hz, 3H), 0.89 (t, J = 7.6 Hz, 3H) |
| or | or | | |
| perfluorophenyl 5-((S)-fluoro((S)-(((S)-1-oxo-1-propoxypropan-2-yl)amino)(phenoxy)phosphoryl)methyl)benzo[b]thiophene-2-carboxylate | 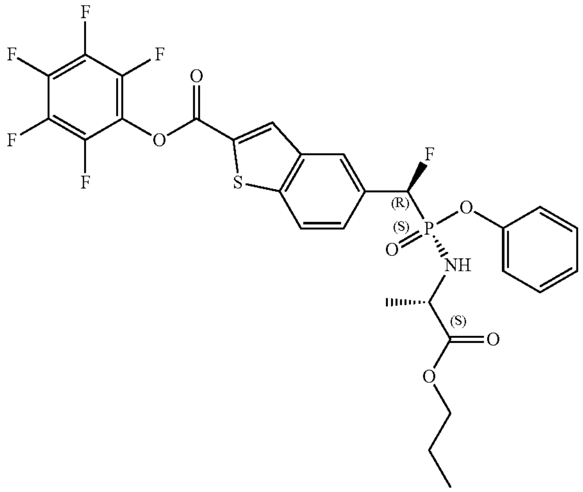 | | |

-continued

| Name | Structure | LCMS | NMR |
|---|---|---|---|
| | CFTE-27A, SFC Peak 1<br>Ret. Time = 0.89 Minutes | | |
| perfluorophenyl 5-((R)-fluoro((R)-(((S)-1-oxo-1-propoxypropan-2-yl)amino)(phenoxy)phosphoryl)methyl)benzo[b]thiophene-2-carboxylate | 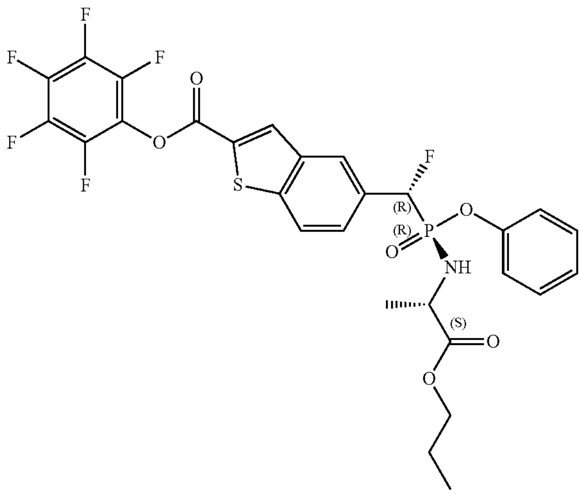 | 645.9<br>$[M + H]^+$ | $^1H$ NMR (400 MHz, $CD_3OD$) δ 8.50-8.44 (m, 1H), 8.26-8.18 (m, 1H), 8.13-8.03 (m, 1H), 7.81-7.72 (m, 1H), 7.41-7.28 (m, 2H), 7.27-7.11 (m, 3H), 6.22-6.00 (m, 1H), 4.01-3.94 (m, 2H), 3.93-3.83 (m, 1H), 1.63-1.51 (m, 2H), 1.23 (d, J = 7.2 Hz, 3H), 0.93-0.83 (m, 3H) |
| or | or | | |
| perfluorophenyl 5-((R)-fluoro((S)-(((S)-1-oxo-1-propoxypropan-2-yl)amino)(phenoxy)phosphoryl)methyl)benzo[b]thiophene-2-carboxylate | 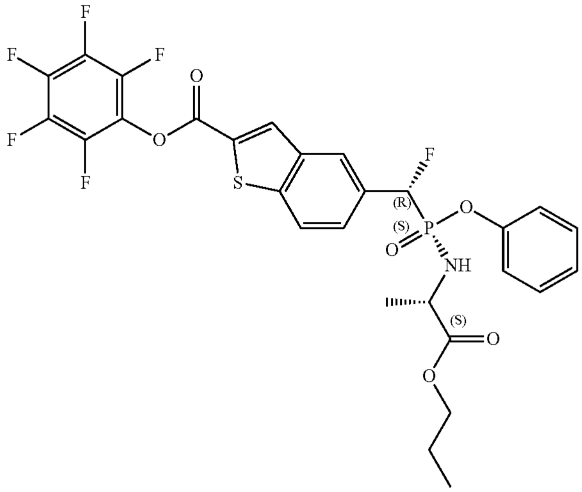 | | |
| | CFTE-28A, SFC Peak 2<br>Ret. Time = 1.95 Minutes | | |

-continued

| Name | Structure | LCMS | NMR |
|---|---|---|---|
| perfluorophenyl 5-((R)-fluoro((R)-(((S)-1-oxo-1-propoxypropan-2-yl)amino)(phenoxy)phosphoryl)methyl)benzo[b]thiophene-2-carboxylate | 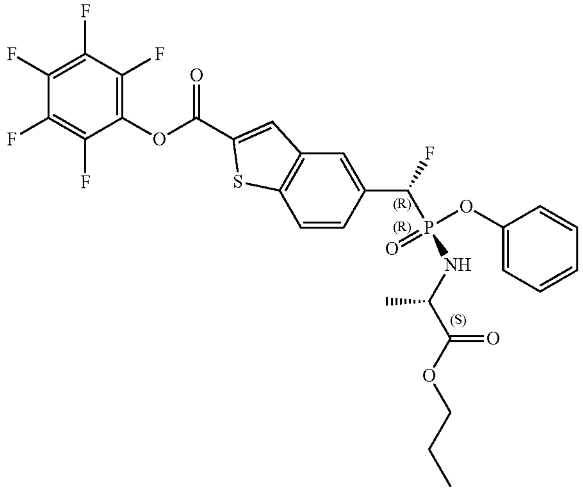 | 646.1 $[M + H]^+$ | $^1H$ NMR (400 MHz, METHANOL-d4) δ 8.40 (s, 1H), 8.17-8.06 (m, 1H), 8.04-7.95 (m, 1H), 7.75-7.64 (m, 1H), 7.29-7.18 (m, 2H), 7.14-6.98 (m, 3H), 6.18-5.93 (m, 1H), 3.87-3.79 (m, 1H), 3.79-3.67 (m, 2H), 1.48-1.36 (m, 2H), 1.15-1.09 (m, 3H), 0.76 (t, J = 7.6 Hz, 3H) |
| or | or | | |
| perfluorophenyl 5-((R)-fluoro((S)-(((S)-1-oxo-1-propoxypropan-2-yl)amino)(phenoxy)phosphoryl)methyl)benzo[b]thiophene-2-carboxylate | 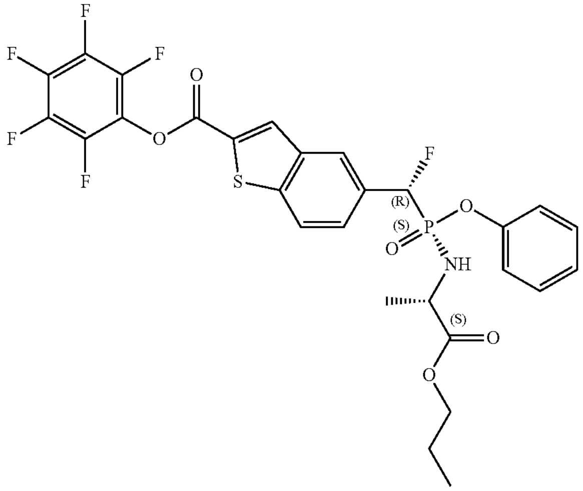 CFTE-28B, SFC Peak 1 Ret. Time = 1.51 Minutes | | |

The intermediates in the table below were prepared using the synthetic procedure described above Synthesis of perfluorophenyl 5-((S)-fluoro((R)-(((S)-1-oxo-1-propoxypropan-2-yl)amino)(phenoxy)phosphoryl)methyl)benzo[b]thiophene-2-carboxylate and utilizing the appropriate starting materials and modifications.

| Name | Structure | LCMS | NMR |
|---|---|---|---|
| perfluorophenyl 5-((S)-fluoro((R)-(((S)-1-isopropoxy-1-oxopropan-2-yl)amino)(phenoxy)phosphoryl)methyl)benzo[b]thiophene-2-carboxylate | 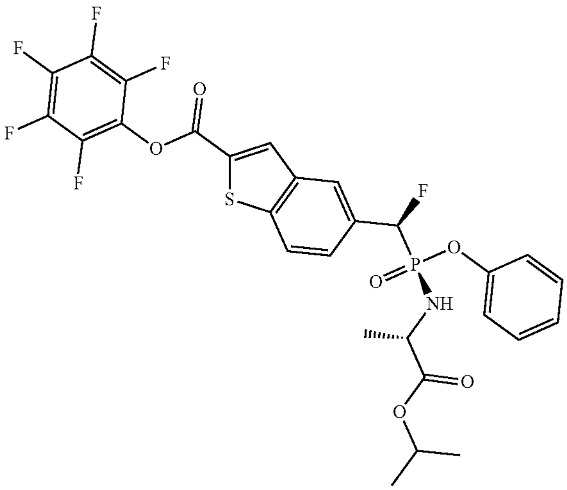 [SMILES: CC(C)OC(=O)[C@H](C)N[P@](=O)(Oc1ccccc1)[C@H](F)c1ccc2sc(C(=O)Oc3c(F)c(F)c(F)c(F)c3F)cc2c1] | 646.2 [M + H]+ | |
| or | or | | |
| perfluorophenyl 5-((S)-fluoro((S)-(((S)-1-isopropoxy-1-oxopropan-2-yl)amino)(phenoxy)phosphoryl)methyl)benzo[b]thiophene-2-carboxylate | 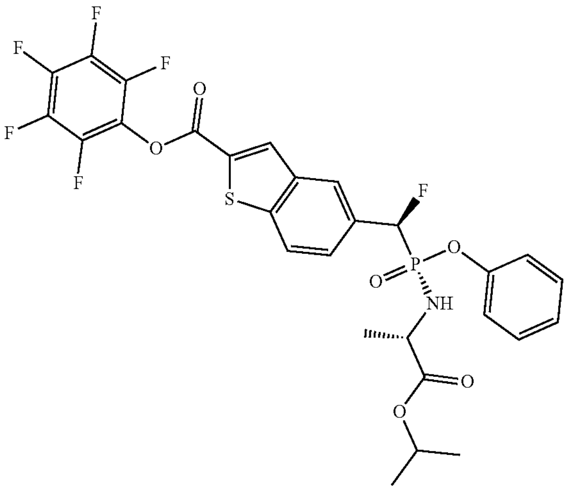 [SMILES: CC(C)OC(=O)[C@H](C)N[P@@](=O)(Oc1ccccc1)[C@H](F)c1ccc2sc(C(=O)Oc3c(F)c(F)c(F)c(F)c3F)cc2c1] | | |
| perfluorophenyl 5-((S)-fluoro((R)-(((S)-1-isopropoxy-1-oxopropan-2-yl)amino)(phenoxy)phosphoryl)methyl)benzo[b]thiophene-2-carboxylate | 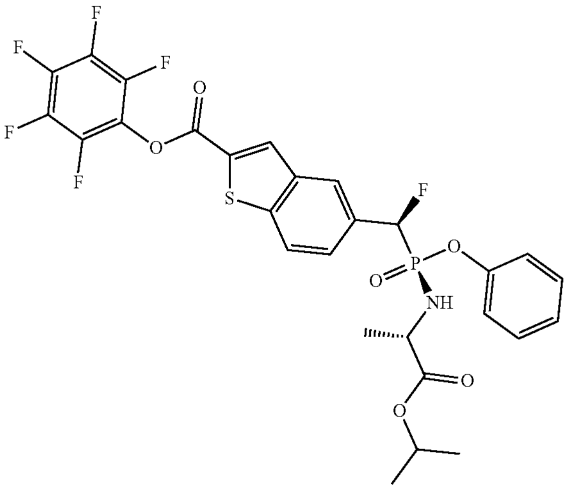 [SMILES: CC(C)OC(=O)[C@H](C)N[P@](=O)(Oc1ccccc1)[C@H](F)c1ccc2sc(C(=O)Oc3c(F)c(F)c(F)c(F)c3F)cc2c1] | 646.2 [M + H]+ | $^1$H NMR (400 MHz, $CDCl_3$) δ 8.36 (s, 1H), 8.14 (s, 1H), 8.02-7.95 (m, 1H), 7.76 (d, J = 8.4 Hz, 1H), 7.32-7.28 (m, 2H), 7.18-7.14 (m, 1H), 7.12 (d, J = 8.0 Hz, 2H), 6.10-5.94 (m, 1H), 5.05 (m, 1H), 4.20-4.09 (m, 1H), 3.68 (t, J = 10.4 Hz, 1H), 1.32 (d, J = 7.2 Hz, 3H), 1.30-1.24 (m, 6H) |
| or | or | | |

-continued

| Name | Structure | LCMS | NMR |
|---|---|---|---|
| perfluorophenyl 5-((S)-fluoro((S)-(((S)-1-isopropoxy-1-oxopropan-2-yl)amino)(phenoxy)phosphoryl)methyl)benzo[b]thiophene-2-carboxylate | 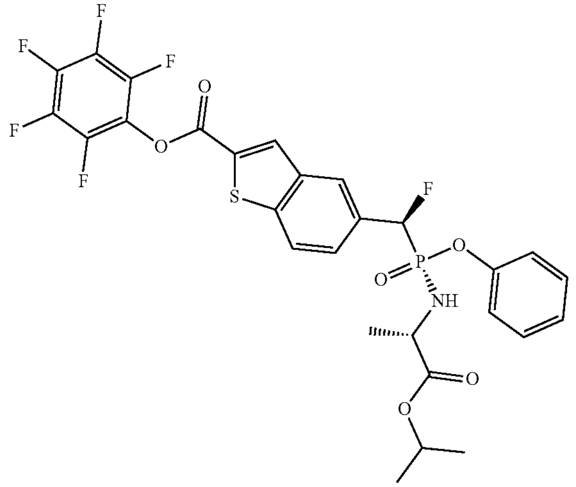 [SMILES: CC(C)OC(=O)[C@H](C)N[P@@](=O)(Oc1ccccc1)[C@H](F)c1ccc2sc(C(=O)Oc3c(F)c(F)c(F)c(F)c3F)cc2c1] | | |

The intermediates in the table below were prepared using the synthetic procedure described above for allyl 5-((1S)-fluoro((((S)-1-oxo-1-propoxypropan-2-yl)amino)(phenoxy)phosphoryl)methyl)benzo[b]thiophene-2-carboxylate and utilizing the appropriate starting materials and modifications.

| Name | Structure | LCMS |
|---|---|---|
| allyl 5-((1R)-fluoro((((S)-1-oxo-1-propoxypropan-2-yl)amino)(phenoxy)phosphoryl)methyl)benzo[b]thiophene-2-carboxylate | 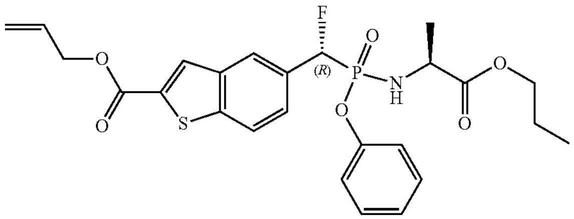 | 520.1 $[M + H]^+$ |

The chiral intermediates in the table below were obtained by chiral SFC separation of the corresponding P-isomer mixtures, which were prepared using the synthetic procedure described above for allyl 5-((S) fluoro((((S)-h-oxo-1 propoxypropan-2-yl)amino)(phenoxy)phosphoryl)methyl)benzo[b]thiophene-2-carboxylate and utilizing the appropriate starting materials and modifications. Absolute stereochemical configuration at phosphorus is arbitrarily assigned as drawn.

| Name | Structure | LCMS | Preparative SFC conditions for separation |
|---|---|---|---|
| allyl 5-((S)-fluoro((R)-(((S)-1-oxo-1-propoxypropan-2-yl)amino)(phenoxy)phosphoryl)methyl)benzo[b]thiophene-2-carboxylate | 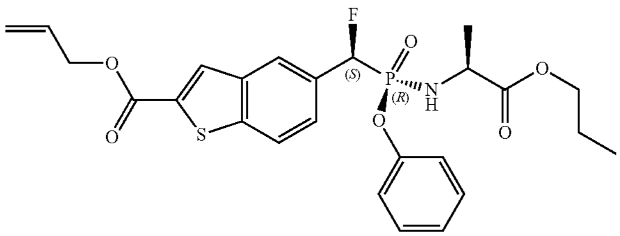 (Peak 1, RT = 4.46 min) | 520.2 $[M + H]^+$ | ChiralPak R,R-WHELK 250 × 21.2 mm 5 μm column; Mobile phase: A for $CO_2$ and B for MeOH + 0.1% $NH_3H_2O$; Gradient: B 50%; Flow rate: 40 mL/min; Back pressure: 100 bar; Column temperature: 35° C.; Wavelength: 220 nm; Cycle-time: |

-continued

| Name | Structure | LCMS | Preparative SFC conditions for separation |
|---|---|---|---|
| allyl 5-((S)-fluoro((S)-(((S)-1-oxo-1-propoxypropan-2-yl)amino)(phenoxy)phosphoryl)methyl)benzo[b]thiophene-2-carboxylate | 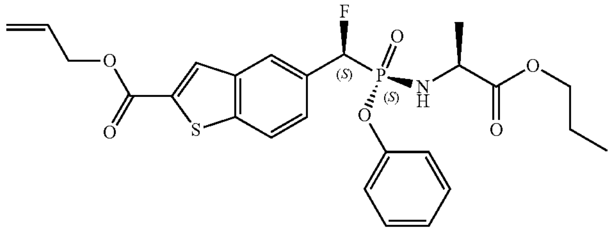 (Peak 2, RT = 6.54 min) | 520.2 [M + H]+ | 11 min |
| allyl 5-((R)-fluoro((R)-(((S)-1-oxo-1-propoxypropan-2-yl)amino)(phenoxy)phosphoryl)methyl)benzo[b]thiophene-2-carboxylate | 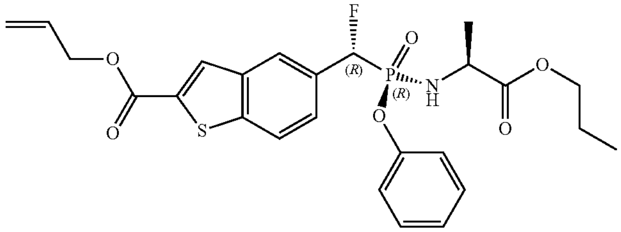 (Peak 1, RT = 2.72 min) | 520.2 [M + H]+ | ChiralPak IH 250 × 21.2 mm 5 μm column; Mobile phase: A for $CO_2$ and B for MeOH + 0.1% $NH_3H_2O$; Gradient: B 35%; Flow rate: 40 mL/min; Back pressure: 100 bar; Column temperature: 35° C.; Wavelength: 220 nm; Cycle-time: 5 min |
| allyl 5-((R)-fluoro((S)-(((S)-1-oxo-1-propoxypropan-2-yl)amino)(phenoxy)phosphoryl)methyl)benzo[b]thiophene-2-carboxylate | 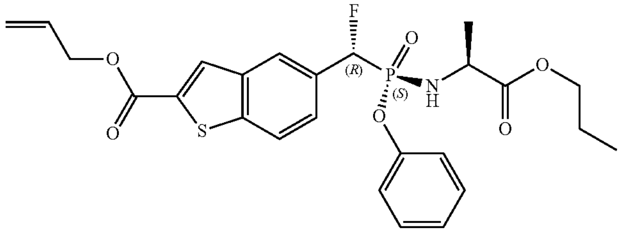 (Peak 2, RT = 4.11 min) | 520.2 [M + H]+ | |

The intermediates in the table below were prepared using the synthetic procedure described above for 5-((1S)-fluoro((((S)-1-oxo-1-propoxypropan-2-yl)amino)(phenoxy)phosphoryl)methyl)benzo[b]thiophene-2-carboxylic acid and utilizing the appropriate starting materials and modifications.

| Name | Structure | LCMS |
|---|---|---|
| 5-((S)-fluoro((R)-(((S)-1-oxo-1-propoxypropan-2-yl)amino)(phenoxy)phosphoryl)methyl)benzo[b]thiophene-2-carboxylic acid | 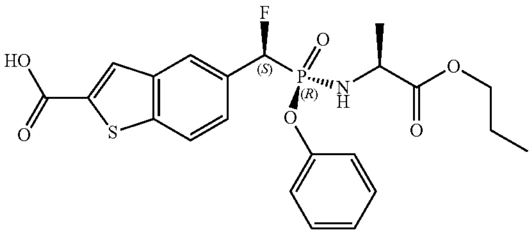 | 480.1 [M + H]+ |
| 5-((S)-fluoro((S)-(((S)-1-oxo-1-propoxypropan-2-yl)amino)(phenoxy)phosphoryl)methyl)benzo[b]thiophene-2-carboxylic acid | 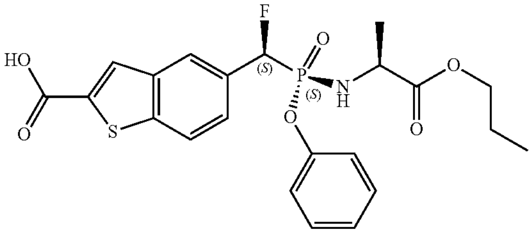 | 480.1 [M + H]+ |

-continued

| Name | Structure | LCMS |
|---|---|---|
| 5-((R)-fluoro((R)-(((S)-1-oxo-1-propoxypropan-2-yl)amino)(phenoxy)phosphoryl)methyl)benzo[b]thiophene-2-carboxylic acid | 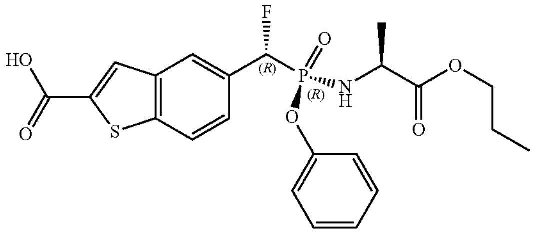 | 480.1 $[M + H]^+$ |
| 5-((R)-fluoro((S)-(((S)-1-oxo-1-propoxypropan-2-yl)amino)(phenoxy)phosphoryl)methyl)benzo[b]thiophene-2-carboxylic acid | 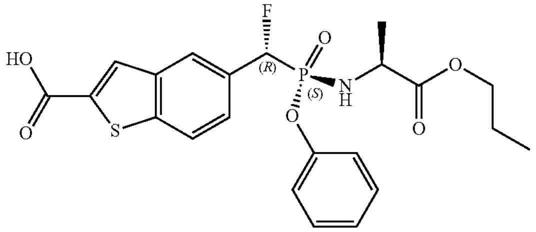 | 480.1 $[M + H]^+$ |

The intermediates in the table below were prepared using the protocol described above for synthesis of 5-(((((S)-1-isopropoxy-1-oxopropan-2-yl)amino)(phenoxy)phosphoryl)methyl)benzo[b]thiophene-2-carboxylic acid and utilizing the appropriate starting materials and modifications.

| Name | Structure | LCMS |
|---|---|---|
| 5-(((((S)-1-ethoxy-1-oxopropan-2-yl)amino)(2,2,2-trifluoroethoxy)phosphoryl)fluoromethyl)benzo[b]thiophene-2-carboxylic acid | 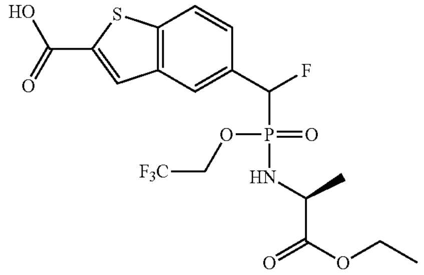 [SMILES: CCOC(=O)[C@H](C)NP(=O)(OCC(F)(F)F)C(F)c1ccc2sc(C(=O)O)cc2c1] | 472.1 $[M + H]^+$ |
| 5-(((((S)-1-oxo-1-propoxypropan-2-yl)amino)(2,2,2-trifluoroethoxy)phosphoryl)methyl)benzo[b]thiophene-2-carboxylic acid | 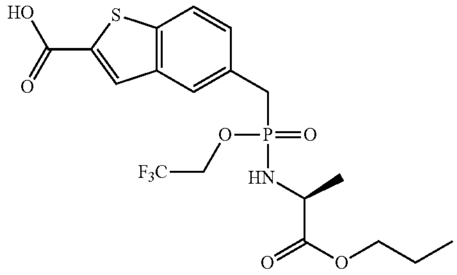 [SMILES: CCCOC(=O)[C@H](C)NP(=O)(Cc1ccc2sc(C(=O)O)cc2c1)OCC(F)(F)F] | 468.0 $[M + H]^+$ |
| 5-(fluoro((((S)-1-oxo-1-propoxypropan-2-yl)amino)(2,2,2-trifluoroethoxy)phosphoryl)methyl)benzo[b]thiophene-2-carboxylic acid | 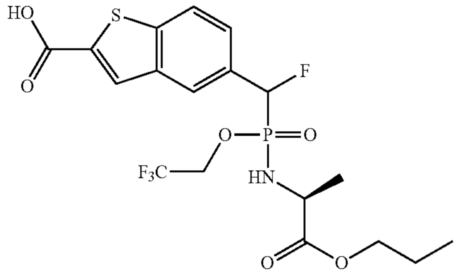 [SMILES: CCCOC(=O)[C@H](C)NP(=O)(OCC(F)(F)F)C(F)c1ccc2sc(C(=O)O)cc2c1] | 485.9 $[M + H]^+$ |

-continued

| Name | Structure | LCMS |
| --- | --- | --- |
| 5-(fluoro(((S)-1-oxo-1-propoxybutan-2-yl)amino)(phenoxy)phosphoryl)methyl)benzo[b]thiophene-2-carboxylic acid | 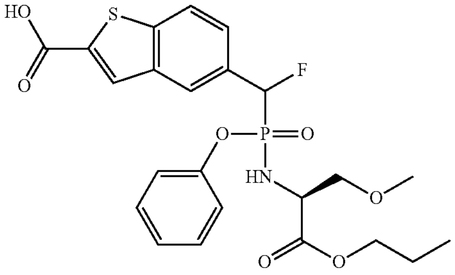 | 494.1 [M + H]+ |
| 5-(fluoro(((S)-3-methoxy-1-oxo-1-propoxypropan-2-yl)amino)(phenoxy)phosphoryl)methyl)benzo[b]thiophene-2-carboxylic acid | 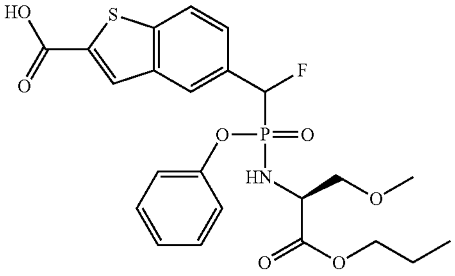 [SMILES: CCCOC(=O)[C@H](COC)NP(=O)(Oc1ccccc1)C(F)c1ccc2sc(C(=O)O)cc2c1] | 510.2 [M + H]+ |

Synthesis of perfluorophenyl 5-((R)-fluoro((S)-(((S)-1-(neopentyloxy)-1-oxopropan-2-yl)amino)(phenoxy)phosphoryl)methyl)benzo[b]thiophene-2-carboxylate and perfluorophenyl 5-((R)-fluoro((R)-(((S)-1-(neopentyloxy)-1-oxopropan-2-yl)amino)(phenoxy)phosphoryl)methyl)benzo[b]thiophene-2-carboxylate

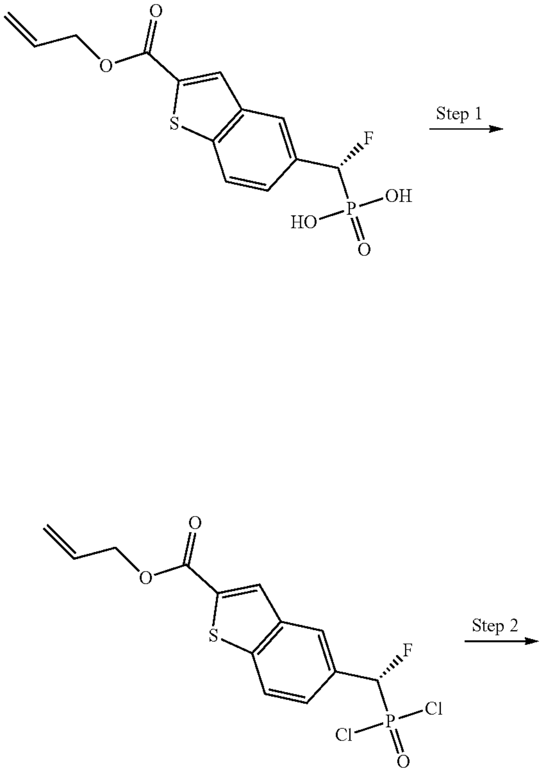

-continued

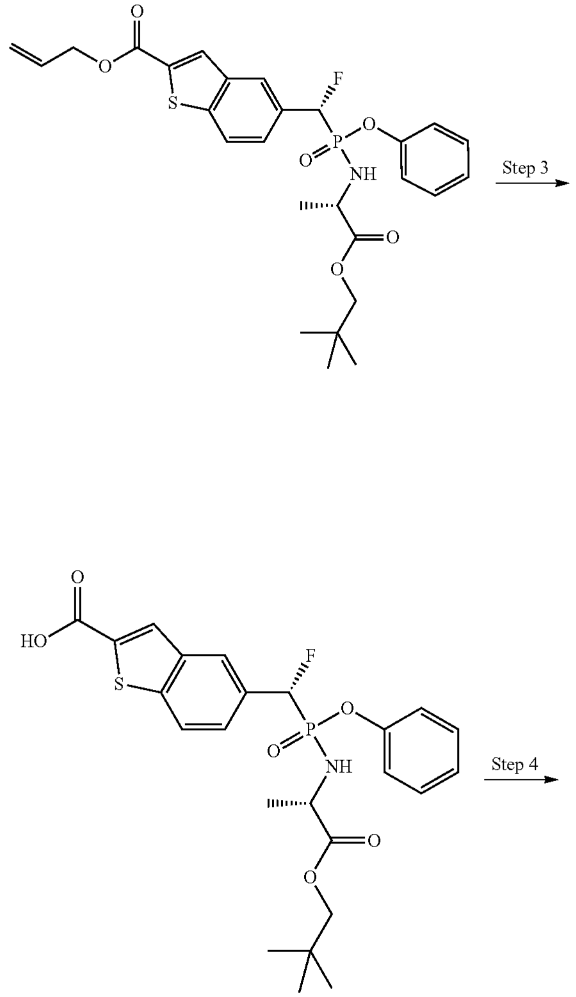

-continued

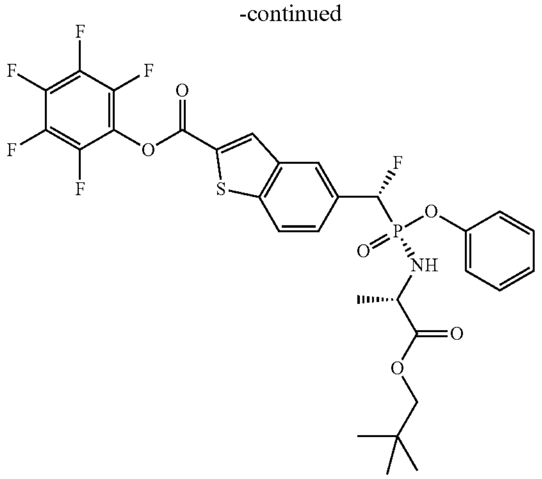

+

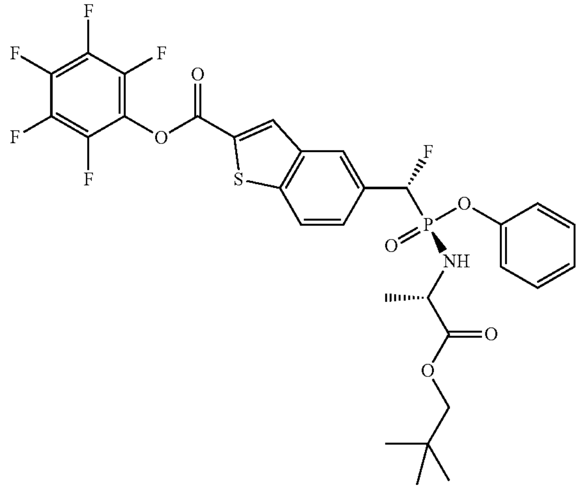

Step 1: Preparation of allyl (R)-5-((dichlorophosphoryl)fluoromethyl)benzo[b]thiophene-2-carboxylate To a solution of (R)-((2-((allyloxy)carbonyl)benzo[b]thiophen-5-yl)fluoromethyl)phosphonic acid (2.0 g, 6.1 mmol, 1.0 eq) in DCM (30 mL) was added 3 drops of DMF (0.03 mL) cooled to 0° C., then the reaction was added oxalyl chloride (2.3 g, 18.1 mmol, 3 eq) slowly, after that the reaction was warmed to 45° C. and stirred 20 min to give a yellow clean solution. The reaction mixture was concentrated under reduced pressure to give allyl (R)-5-((dichlorophosphoryl)fluoromethyl)benzo[b]thiophene-2-carboxylate (2.0 g, crude) as a yellow oil and was used into the next Step without further purification. LCMS (ESI) m/z=358.9 $[M+H]^+$.

Step 2: Preparation of allyl 5-((1R)-fluoro((((S)-1-(neopentyloxy)-1-oxopropan-2-yl)amino)(phenoxy)phosphoryl)methyl)benzo[b]thiophene-2-carboxylate To a solution of allyl (R)-5-((dichlorophosphoryl)fluoromethyl)benzo[b]thiophene-2-carboxylate (2.0 g, 5.4 mmol, 1.0 eq) in DCM (40 mL) was cooled to 0° C. and was added a solution of phenol (0.5 g, 5.4 mmol, 1.0 eq) in DCM (10 mL), then the mixture was added N,N-diisopropylethylamine (2.1 g, 16 mmol, 3.0 eq) in DCM (40 mL) dropwise. The reaction was stirred at 0° C. for 10 min and was added 2,2-dimethylpropyl (2S)-2-aminopropanoate (0.9 g, 5.4 mmol, 1.0 eq) in DCM (20 mL). Then the reaction was warmed to 25° C. and stirred for 1 h to give a light-yellow clean solution. The reaction mixture was concentrated under reduced pressure to give a residue. The residue was purified by flash column chromatography on silica gel to get allyl 5-((1R)-fluoro((((S)-1-(neopentyloxy)-1-oxopropan-2-yl)amino)(phenoxy)phosphoryl)methyl)benzo[b]thiophene-2-carboxylate (1.7 g, 3.1 mmol, 57% yield) was obtained as a yellow oil. LCMS (ESI) m/z=548.2. $^1H$ NMR (400 MHz, $CDCl_3$) δ 8.10 (s, 1H), 8.07-7.99 (m, 1H), 7.91 (d, J=8.4 Hz, 1H), 7.68-7.59 (m, 1H), 7.41-7.25 (m, 3H), 7.23-7.06 (m, 3H), 6.12-5.90 (m, 2H), 5.48-5.44 (m, 1H), 5.39-5.30 (m, 1H), 4.87 (d, J=5.6 Hz, 2H), 4.22-4.07 (m, 2H), 3.90-3.83 (m, 1H), 3.74-3.63 (m, 2H), 1.38-1.30 (m, 3H), 0.92 (s, 9H).

Step 3: Preparation of 5-((1R)-fluoro((((S)-1-(neopentyloxy)-1-oxopropan-2-yl)amino)(phenoxy)phosphoryl)methyl)benzo[b]thiophene-2-carboxylic acid To a solution of allyl 5-((1R)-fluoro((((S)-1-(neopentyloxy)-1-oxopropan-2-yl)amino)(phenoxy)phosphoryl)methyl)benzo[b]thiophene-2-carboxylate (1.7 g, 3.1 mmol, 1.0 eq) in DCM (20 mL) was added pyrrolidine (0.4 g, 6.2 mmol, 2.0 eq) and $Pd(PPh_3)_4$ (0.4 g, 0.3 mmol, 0.1 eq). Then the reaction stirred for 15 min to give a yellow clean solution. The reaction mixture was concentrated under reduced pressure to give a residue. The residue was purified by reversed phase (TFA) to lyophilized to give 5-((1R)-fluoro((((S)-1-(neopentyloxy)-1-oxopropan-2-yl)amino)(phenoxy)phosphoryl)methyl)benzo[b]thiophene-2-carboxylic acid (1.3 g, 2.6 mmol, 83% yield) as a white solid. LCMS (ESI) m/z=508.2

Step 4: Preparation of perfluorophenyl 5-((R)-fluoro((S)-(((S)-1-(neopentyloxy)-1-oxopropan-2-yl)amino)(phenoxy)phosphoryl)methyl)benzo[b]thiophene-2-carboxylate and perfluorophenyl 5-((R)-fluoro((R)-(((S)-1-(neopentyloxy)-1-oxopropan-2-yl)amino)(phenoxy)phosphoryl)methyl)benzo[b]thiophene-2-carboxylate To a solution of 5-((1R)-fluoro((((S)-1-(neopentyloxy)-1-oxopropan-2-yl)amino)(phenoxy)phosphoryl)methyl)benzo[b]thiophene-2-carboxylic acid (1.2 g, 2.4 mmol, 1.0 eq) in pyridine (100 mL) was added 2,3,4,5,6-pentafluorophenyl 2,2,2-trifluoroacetate (0.66 g, 2.4 mmol, 1.0 eq) at 0° C., the mixture was stirred at 25° C. for 10 min to give a yellow clean solution. The reaction mixture was concentrated under reduced pressure to give a residue. The residue was purified by flash column chromatography on silica gel to give perfluorophenyl 5-((R)-fluoro((S)-(((S)-1-(neopentyloxy)-1-oxopropan-2-yl)amino)(phenoxy)phosphoryl)methyl)benzo[b]thiophene-2-carboxylate or perfluorophenyl 5-((R)-fluoro((R)-(((S)-1-(neopentyloxy)-1-oxopropan-2-yl)amino)(phenoxy)phosphoryl)methyl)benzo[b]thiophene-2-carboxylate (0.4 g, 0.59 mmol, 25% yield, Rt=1.883 min, Peak 2) as a yellow oil and perfluorophenyl 5-((R)-fluoro((R)-(((S)-1-(neopentyloxy)-1-oxopropan-2-yl)amino)(phenoxy)phosphoryl)methyl)benzo[b]thiophene-2-carboxylate or perfluorophenyl 5-((R)-fluoro((S)-(((S)-1-(neopentyloxy)-1-oxopropan-2-yl)amino)(phenoxy)phosphoryl)methyl)benzo[b]thiophene-2-carboxylate (0.50 g, 0.74 mmol, 32% yield, Rt=1.442 min, Peak 1) as a yellow oil.

Peak 2: perfluorophenyl 5-((R)-fluoro((S)-(((S)-1-(neopentyloxy)-1-oxopropan-2-yl)amino)(phenoxy)phosphoryl)methyl)benzo[b]thiophene-2-carboxylate: LCMS (ESI)

m/z=674.0 $[M+H]^+$. $^1H$ NMR (400 MHz, $CDCl_3$) δ 8.34 (s, 1H), 8.09 (s, 1H), 7.97 (d, J=8.4 Hz, 1H), 7.68 (d, J=8.4 Hz, 1H), 7.40-7.35 (m, 2H), 7.32-7.27 (m, 2H), 7.24-7.19 (m, 1H), 6.07-5.89 (m, 1H), 4.16-4.05 (m, 1H), 3.88-3.76 (m, 2H), 3.72-3.64 (m, 1H), 1.15 (d, J=7.2 Hz, 3H), 0.91 (s, 9H)

Peak 1: perfluorophenyl 5-((R)-fluoro((R)-(((S)-1-(neopentyloxy)-1-oxopropan-2-yl)amino)(phenoxy)phosphoryl)methyl)benzo[b]thiophene-2-carboxylate or perfluorophenyl 5-((R)-fluoro((S)-(((S)-1-(neopentyloxy)-1-oxopropan-2-yl)amino)(phenoxy)phosphoryl)methyl)benzo[b]thiophene-2-carboxylate: LCMS (ESI) m/z=674.0 $[M+H]^+$. $^1H$ NMR (400 MHz, $CDCl_3$) δ 8.34 (s, 1H), 8.12 (s, 1H), 7.96 (d, J=8.4 Hz, 1H), 7.74 (d, J=8.4 Hz, 1H), 7.29 (s, 1H), 7.25 (s, 1H), 7.16-7.05 (m, 3H), 6.13-5.96 (m, 1H), 4.22-4.10 (m, 1H), 3.89-3.83 (m, 1H), 3.73-3.66 (m, 1H), 3.62-3.54 (m, 1H), 1.33 (d, J=7.2 Hz, 3H), 0.92 (s, 9H).

Synthesis of 5-(difluoro((((S)-1-isopropoxy-1-oxopropan-2-yl)amino)(phenoxy)phosphoryl)methyl)benzo[b]thiophene-2-carboxylic acid

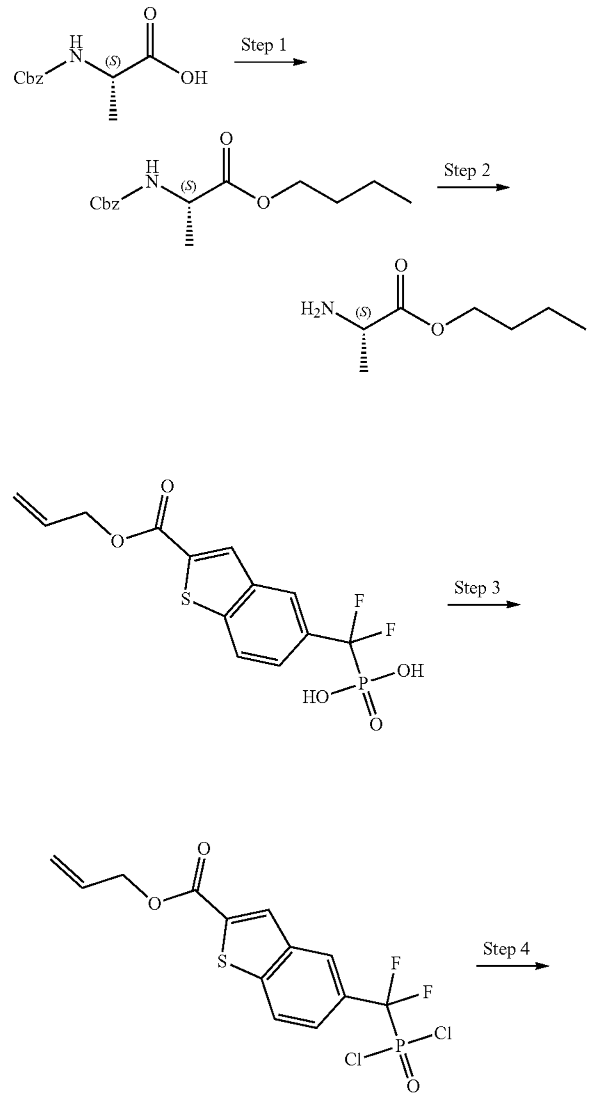

-continued

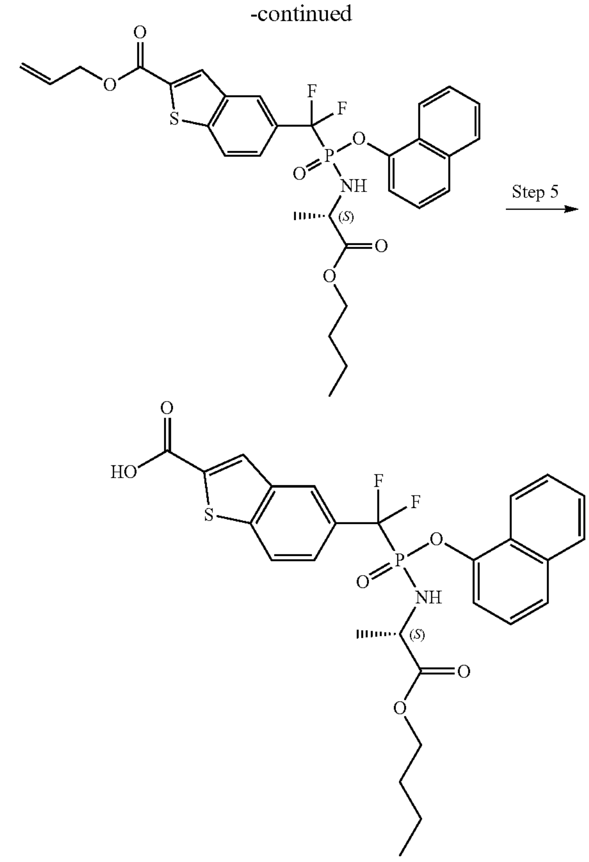

Step 1: Preparation of allyl 5-((diethoxyphosphoryl)difluoromethyl)benzo[b]thiophene-2-carboxylate To a solution of 5-((diethoxyphosphoryl)difluoromethyl)benzo[b]thiophene-2-carboxylic acid (5 g, 14 mmol, 1 eq) in dimethyl sulfoxide (40 mL) was added disodium carbonate (4.3 g, 41 mmol, 3 eq) and 3-bromoprop-1-ene (1.7 g, 14 mmol, 1 eq), the mixture was stirred at 25° C. for 12 h to give a white suspension. The mixture was diluted with water (200 mL) and extracted with EtOAc (200 mL×2), the combined organic layers were washed with saturated brine (200 mL×2), dried over $Na_2SO_4$, filtered and concentrated under reduced pressure to give a residue. The residue was purified by column chromatography to give allyl 5-((diethoxyphosphoryl)difluoromethyl)benzo[b]thiophene-2-carboxylate (4.6 g, 11.3 mmol, 83% yield) as a white oil. $^1H$ NMR (400 MHz, $CDCl_3$) δ 8.17-8.13 (m, 2H), 7.96 (d, J=8.8 Hz, 1H), 7.70 (d, J=8.4 Hz, 1H), 6.13-5.99 (m, 1H), 5.50-5.42 (m, 1H), 5.37-5.32 (m, 1H), 4.87 (d, J=5.6 Hz, 2H), 4.27-4.12 (m, 4H), 1.33 (t, J=7.2 Hz, 6H).

Step 2: Preparation of ((2-((allyloxy)carbonyl)benzo[b]thiophen-5-yl)difluoromethyl)phosphonic acid To a solution of allyl 5-((diethoxyphosphoryl)difluoromethyl)benzo[b]thiophene-2-carboxylate (4.6 g, 11.3 mmol, 1 eq) in DCM (40 mL) was added iodotrimethylsilane (9.0 g, 45 mmol, 4 eq) at 0° C., the mixture was stirred at 0° C. for 2 h. The reaction mixture was concentrated under reduced pressure to give a residue. The residue was purified by reversed phase (TFA) to give ((2-((allyloxy) carbonyl)benzo

[b]thiophen-5-yl)difluoromethyl)phosphonic acid (2.3 g, 6.6 mmol, 58% yield) as a white solid. LCMS (ESI) m/z=348.7

Step 3: Preparation of allyl 5-((dichlorophosphoryl) difluoromethyl)benzo[b]thiophene-2-carboxylate To a solution of ((2-((allyloxy) carbonyl)benzo[b]thiophen-5-yl)difluoromethyl)phosphonic acid (1 g, 2.9 mmol, 1 eq) in DCM (3 mL) was added DMF (21 mg, 0.29 mmol, 0.1 eq), oxalic dichloride (1.2 g, 28 mmol, 3 eq) was dropwise at 0° C., the mixture was stirred at 40° C. for 1 h to give a yellow solution. The reaction mixture was concentrated under reduced pressure to give allyl 5-((dichlorophosphoryl) difluoromethyl)benzo[b]thiophene-2-carboxylate (1 g, crude) as a yellow solid. LCMS (ESI) m/z=376.6.

Step 4: Preparation of allyl 5-(((((S)-1-butoxy-1-oxopropan-2-yl)amino)(naphthalen-1-yloxy)phosphoryl)difluoromethyl)benzo[b]thiophene-2-carboxylate To a solution of prop-2-en-1-yl 5-[(dichlorophosphoryl) difluoromethyl]-1-benzothiophene-2-carboxylate (0.2 g, 0.52 mmol, 1 eq) in methylene chloride (10 mL) was added naphthalen-1-ol (60 mg, 0.42 mmol, 0.8 eq), the mixture was stirred at 0° C. for 5 min, then a solution of N,N-diisopropylethylamine (0.2 g, 1.6 mmol, 3.0 eq) in methylene chloride (10 mL) was added to the mixture, then a solution of butyl (2S)-2-aminopropanoate (75 mg, 0.52 mmol, 1 eq) in methylene chloride (10 mL) was added to the mixture, the mixture was stirred at 0° C. for 30 min to give yellow solution. The reaction mixture was concentrated under reduced pressure to give a residue.

The residue was purified by column chromatography to give prop-2-en-1-yl 5-[({[(2S)-1-butoxy-1-oxopropan-2-yl] amino}(naphthalen-1-yloxy)phosphoryl)difluoromethyl]-1-benzothiophene-2-carboxylate (0.15 g, 0.24 mmol, 46.4% yield) as a yellow oil. LCMS (ESI) m/z=602.1

Step 5: Preparation of 5-(((((S)-1-butoxy-1-oxopropan-2-yl)amino)(naphthalen-1-yloxy)phosphoryl) difluoromethyl)benzo[b]thiophene-2-carboxylic acid To a solution of prop-2-en-1-yl 5-[({[(2S)-1-butoxy-1-oxopropan-2-yl]amino}(naphthalen-1-yloxy)phosphoryl)difluoromethyl]-1-benzothiophene-2-carboxylate (0.14 g, 0.23 mmol, 1 eq) in methylene chloride (1.0 mL) was added $Pd(PPh_3)_4$ (27 mg, 23 μmol, 0.1 eq), the mixture was stirred at 0° C. for 5 min, then pyrrolidine (17 mg, 0.23 mmol, 1 eq) was added to the mixture, the mixture was stirred at 25° C. for 5 min to give yellow solution. The reaction mixture was concentrated under reduced pressure to give a residue. The residue was purified by reversed phase (TFA) to give 5-[({[(2S)-1-butoxy-1-oxopropan-2-yl]amino}(naphthalen-1-yloxy)phosphoryl)difluoromethyl]-1-benzothiophene-2-carboxylic acid (97 mg, 0.17 mmol, 74.6% yield) as a yellow oil. LCMS (ESI) m/z=562.1.

Synthesis of 5-(((((S)-1-butoxy-1-oxopropan-2-yl) (methyl)amino)(phenoxy)phosphoryl)methyl)benzo [b]thiophene-2-carboxylic acid

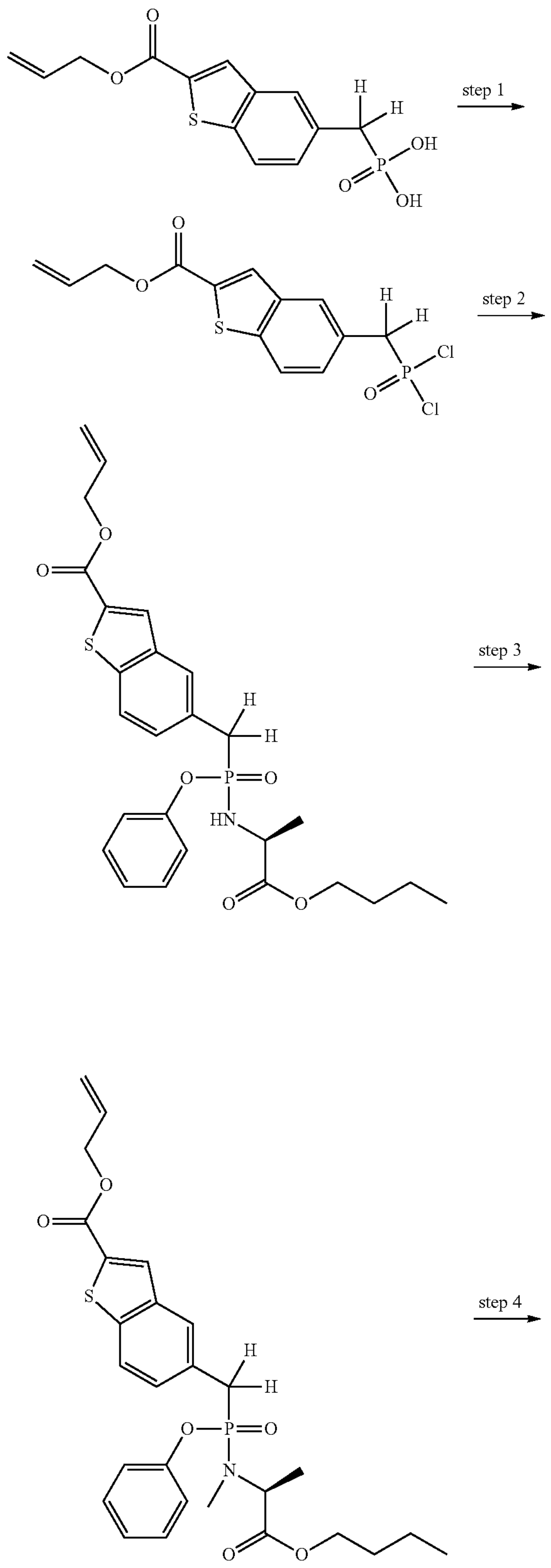

-continued

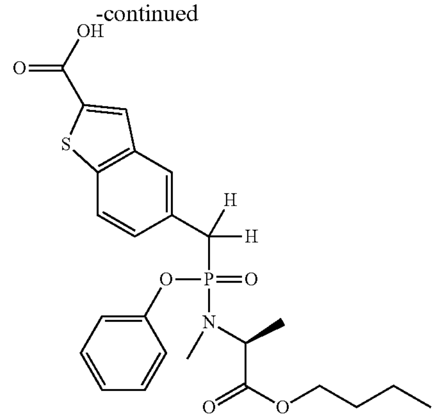

Step 1: Preparation of allyl 5-((dichlorophosphoryl) methyl)benzo[b]thiophene-2-carboxylate To a solution of ((2-((allyloxy)carbonyl)benzo[b]thiophen-5-yl)methyl)phosphonic acid (0.1 g, 0.32 mmol, 1 eq) in DCM (2 mL) was added DMF (2.3 mg, 32 μmol, 0.1 eq). The mixture was stirred at 0° C. for 5 min, then a solution of oxalyl chloride (0.12 g, 0.96 mmol, 3 eq) in DCM (2 mL) was added to the mixture, the mixture was stirred at 40° C. for 1 h to give yellow solution. The reaction mixture was concentrated under reduced pressure to give allyl 5-((dichlorophosphoryl)methyl)benzo[b]thiophene-2-carboxylate (0.100 g, crude) as a yellow oil. LCMS (ESI) m/z=341.0 (MeOH quench)

Step 2: Preparation of allyl 5-(((((S)-1-butoxy-1-oxopropan-2-yl)amino)(phenoxy)phosphoryl) methyl)benzo[b]thiophene-2-carboxylate To a solution of allyl 5-((dichlorophosphoryl)methyl) benzo[b]thiophene-2-carboxylate (0.10 g, 0.29 mmol, 1 eq) in DCM (2 mL) was added phenol (22 mg, 0.23 mmol, 0.8 eq) at 0° C. for 30 min, then a solution of DIEA (0.1 g, 0.86 mmol, 3.0 eq) in DCM (2 mL) was added to the mixture at 0° C. for 15 min, then a solution of butyl L-alaninate (42 mg, 0.29 mmol, 1 eq) in DCM (2 mL) was added to the mixture at 0° C. for 15 min to give yellow solution. The reaction mixture was concentrated under reduced pressure to give a residue. The residue was purified by column chromatography to give allyl 5-(((((S)-1-butoxy-1-oxopropan-2-yl) amino)(phenoxy)phosphoryl)methyl)benzo[b]thiophene-2-carboxylate (80 mg, 0.15 mmol, 80% yield,) as a yellow oil. LCMS (ESI) m/z=516.2 [M+H]$^+$.

Step 3: Preparation of allyl 5-(((((S)-1-butoxy-1-oxopropan-2-yl)(methyl)amino)(phenoxy)phosphoryl)methyl)benzo[b]thiophene-2-carboxylate To a solution of allyl 5-(((((S)-1-butoxy-1-oxopropan-2-yl)amino)(phenoxy)phosphoryl)methyl)benzo[b]thiophene-2-carboxylate (0.2 g, 0.39 mmol, 1 eq) in THF (5 mL) was added LDA (83 mg, 0.77 mmol, 2 eq) and methyl iodide (0.55 g, 3.9 mmol, 10 eq), the mixture was stirred at −70° C. for 15 min to give yellow solution. The reaction mixture was added water (0.5 mL) and concentrated under reduced pressure to give a residue. The residue was purified by column chromatography to give allyl 5-(((((S)-1-butoxy-1-oxopropan-2-yl)(methyl)amino)(phenoxy)phosphoryl) methyl)benzo[b]thiophene-2-carboxylate (60 mg, 0.11 mmol, 28% yield) as a yellow oil. LCMS (ESI) m/z=530.2 [M+H]$^+$.

Step 4: Preparation of 5-(((((S)-1-butoxy-1-oxopropan-2-yl)(methyl)amino)(phenoxy)phosphoryl) methyl)benzo[b]thiophene-2-carboxylic acid To a solution of allyl 5-(((((S)-1-butoxy-1-oxopropan-2-yl)(methyl)amino)(phenoxy)phosphoryl)methyl)benzo[b] thiophene-2-carboxylate (60 mg, 0.11 mmol, 1 eq) in DCM (2 mL) was added pyrrolidine (6.4 mg, 90 μmol, 0.8 eq) and $Pd(PPh_3)_4$ (1.3 mg, 1.1 μmol, 0.01 eq), the mixture was stirred at 25° C. for 5 min to give yellow solution. The reaction mixture was added water and concentrated under reduced pressure to give a residue. The residue was purified by reversed phase (TFA) then lyophilized to give 5-(((((S)-1-butoxy-1-oxopropan-2-yl)(methyl)amino)(phenoxy)phosphoryl)methyl)benzo[b]thiophene-2-carboxylic acid (49 mg, 99 μmol, 88% yield) as a yellow oil. LCMS (ESI) m/z=490.1 [M+H]$^+$.

Synthesis of perfluorophenyl 5-(fluoro((((S)-1-oxo-1-propoxypropan-2-yl)amino)(phenoxy)phosphoryl) methyl)benzo[b]thiophene-2-carboxylate

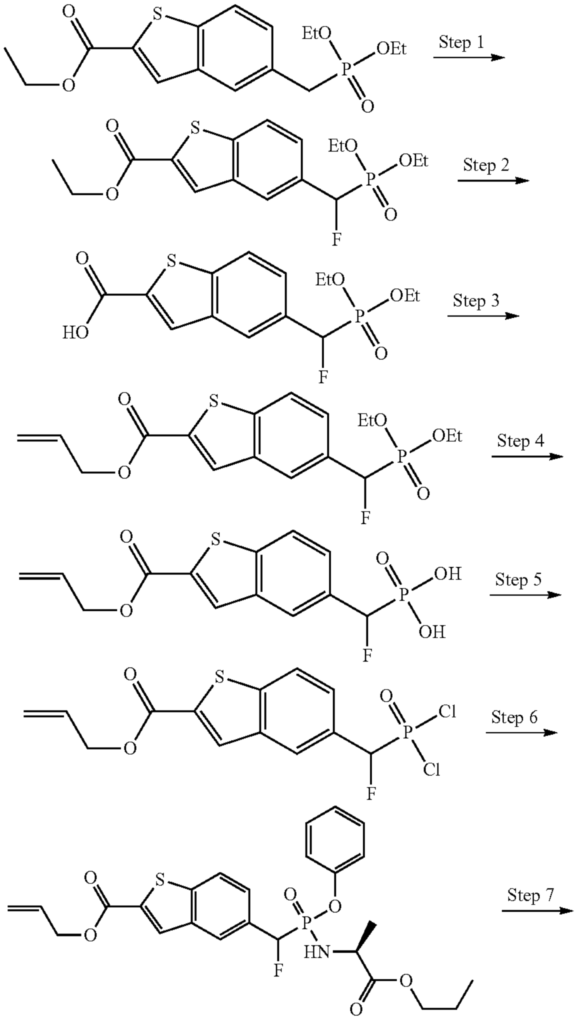

-continued

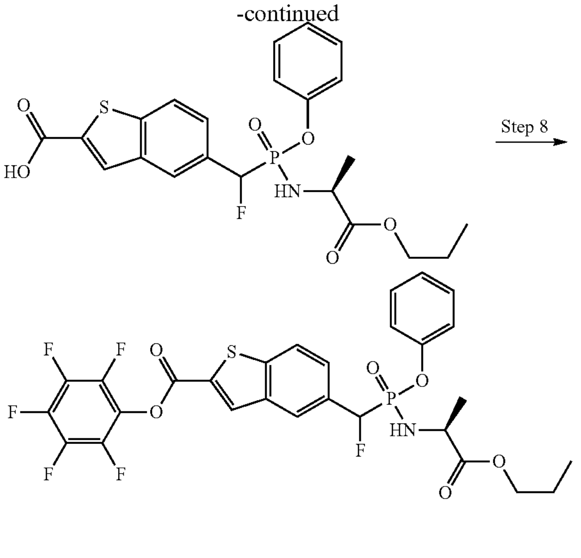

Step 1: Preparation of ethyl 5-((diethoxyphosphoryl)fluoromethyl)benzo[b]thiophene-2-carboxylate To a solution of ethyl 5-((diethoxyphosphoryl)methyl)benzo[b]thiophene-2-carboxylate (58 g, 0.16 mol, 1 eq) in THF (600 mL) was added lithium bis(trimethylsilyl)azanide (170 mL, 0.17 mol, 1.1 eq, 1.0 M in THF) at −70° C., then N-(benzenesulfonyl)-N-fluorobenzenesulfonamide (54 g, 0.17 mol, 1.1 eq) was added at −70° C., then stirred at −70° C. for 0.5 h. The reaction mixture was quenched by water (500 mL) at −70° C., then extracted with EtOAc (500 mL×2), the combined organic layers were washed with saturated brine (400 mL×2), dried over $Na_2SO_4$, filtered and concentrated under reduced pressure to give a residue. The residue was purified by flash silica gel chromatography to give ethyl 5-((diethoxyphosphoryl)fluoromethyl)benzo[b]thiophene-2-carboxylate (26 g, 67 mmol, 43% yield) as a yellow oil. $^1$H NMR (400 MHz, $CDCl_3$) δ 8.00 (s, 1H), 7.92 (s, 1H), 7.83 (d, J=8.4 Hz, 1H), 7.51 (d, J=8.4 Hz, 1H), 5.84-5.63 (m, 1H), 4.39-4.29 (m, 2H), 4.09-3.96 (m, 4H), 1.35 (t, J=7.1 Hz, 3H), 1.23-1.19 (m, 6H).

Step 2: Preparation of 5-((diethoxyphosphoryl)fluoromethyl)benzo[b]thiophene-2-carboxylic acid To a solution of ethyl 5-((diethoxyphosphoryl)fluoromethyl)benzo[b]thiophene-2-carboxylate (15 g, 40 mmol, 1 eq) in THF (40 mL) was dropwise added LiOH—$H_2O$ (1.8 g, 44 mmol, 1.1 eq) in $H_2O$ (40 mL) at 0° C. and stirred at 25° C. for 1 h to give a yellow solution. The reaction mixture was extracted with EtOAc (80 mL), then the aqueous phase was used 1M HCl to adjust the pH=4-3 extracted with EtOAc (100 mL×2), the combined organic layers were dried over $Na_2SO_4$, filtered and concentrated under reduced pressure to give 5-((diethoxyphosphoryl)fluoromethyl)benzo[b]thiophene-2-carboxylic acid (11 g, crude) as a white solid. LCMS (ESI) m/z=346.8 $[M+H]^+$.

Step 3: Preparation of allyl 5-((diethoxyphosphoryl)fluoromethyl)benzo[b]thiophene-2-carboxylate To a solution of 5-((diethoxyphosphoryl)fluoromethyl)benzo[b]thiophene-2-carboxylic acid (11 g, 32 mmol, 1 eq) in DMF (120 mL) was added sodium carbonate (6.7 g, 63 mmol, 2 eq) and stirred at 25° C. for 30 min, then 3-bromoprop-1-ene (7.7 g, 63 mmol, 2 eq) was added in it and stirred at 25° C. for 5 h to give a white suspension. The reaction mixture was diluted with water (300 mL) and extracted with EtOAc (400 mL×3), the combined organic layers were washed with saturated brine (500 mL×3), dried over $Na_2SO_4$, filtered and concentrated under reduced pressure to give a residue. The residue was purified by column chromatography to give allyl 5-((diethoxyphosphoryl)fluoromethyl)benzo[b]thiophene-2-carboxylate (10 g, 26 mmol, 82% yield) as a white solid. $^1$H NMR (400 MHz, $CDCl_3$) δ 8.10 (s, 1H), 8.05-7.98 (m, 1H), 7.91 (d, J=8.4 Hz, 1H), 7.59 (d, J=8.4 Hz, 1H), 6.13-5.97 (m, 1H), 5.91-5.71 (m, 1H), 5.52-5.40 (m, 1H), 5.33 (dd, J=1.2, 10.4 Hz, 1H), 4.86 (dd, J=1.2, 5.6 Hz, 2H), 4.19-4.03 (m, 4H), 1.33-1.24 (m, 6H).

Step 4: Preparation of ((2-((allyloxy)carbonyl)benzo[b]thiophen-5-yl)fluoromethyl)phosphonic acid To a solution of allyl 5-((diethoxyphosphoryl)fluoromethyl)benzo[b]thiophene-2-carboxylate (9 g, 23 mmol, 1 eq) and (E)-(trimethylsilyl 2,2,2-trifluoro-N-(trimethylsilyl)ethanimidate) (18 g, 70 mmol, 3 eq) in DCM (100 mL) was added iodotrimethylsilane (16 g, 93 mmol, 4 eq) at 0° C. and stirred at 0° C. for 1 h to give a brown solution. The reaction mixture was concentrated under reduced pressure to give a residue. The crude was purified by reverse phase chromatography (TFA) then lyophilization to give ((2-((allyloxy)carbonyl)benzo[b]thiophen-5-yl)fluoromethyl)phosphonic acid (6.0 g, 18 mmol, 78% yield) as a yellow solid. $^1$H NMR (400 MHz, DMSO-$d_6$) δ 8.31 (s, 1H), 8.14-8.05 (m, 2H), 7.59 (d, J=8.4 Hz, 1H), 6.13-5.98 (m, 1H), 5.90-5.76 (m, 1H), 5.44 (dd, J=1.6, 17.2 Hz, 1H), 5.31 (dd, J=1.6, 10.4 Hz, 1H), 4.86-4.83 (m, 2H).

Step 5: Preparation of allyl 5-((dichlorophosphoryl)fluoromethyl)benzo[b]thiophene-2-carboxylate To a solution of ((2-((allyloxy)carbonyl)benzo[b]thiophen-5-yl)fluoromethyl)phosphonic acid (2 g, 6.0 mmol, 1 eq) and DMF (88 mg, 1.2 mmol, 0.2 eq) in DCM (20 mL) was added oxalic dichloride (2.7 g, 21 mmol, 3.5 eq) at 0° C. and stirred at 40° C. for 0.5 h to give a yellow solution. The reaction mixture was concentrated under reduced pressure to give allyl 5-((dichlorophosphoryl)fluoromethyl)benzo[b]thiophene-2-carboxylate (2.2 g, crude) as a yellow solid. LCMS (ESI) m/z=717.1 (MeOH quench)

Step 6: Preparation of allyl 5-(fluoro((((S)-1-oxo-1-propoxypropan-2-yl)amino)(phenoxy)phosphoryl)methyl)benzo[b]thiophene-2-carboxylate To a solution of allyl 5-((dichlorophosphoryl)fluoromethyl)benzo[b]thiophene-2-carboxylate (2.2 g, 6.0 mmol, 1 eq) in DCM (20 mL), the solution was under $N_2$ and cooled to 0° C., then phenol (0.56 g, 6.0 mmol, 1 eq) in DCM (10 mL) was added in it, ethylbis(propan-2-yl)amine (3.1 g, 24 mmol, 4 eq) in DCM (60 mL) was dropwise added in it and stirred at 0° C. for 5 min, 3,3,3-trifluoropropyl (2S)-2-aminopropanoate (0.91 g, 6.0 mmol, 1 eq) in DCM (20 mL) was added in it and stirred at 0° C. for 10 min to give a yellow solution. The reaction mixture was concentrated under reduced pressure to give a residue. The residue was purified by column chromatography to give allyl 5-(fluoro((((S)-1-oxo-1-propoxypropan-2-yl)amino)(phenoxy)phosphoryl)methyl)benzo[b]thiophene-2-carboxylate (1.1 g, 1.9 mmol, 33% yield) as a white solid. $^1$H NMR (400 MHz, $CDCl_3$) δ 8.11-8.07 (m, 1H), 8.05-7.99 (m, 1H), 7.93-7.86

(m, 1H), 7.67-7.58 (m, 1H), 7.40-7.32 (m, 1H), 7.27-7.17 (m, 2H), 7.15-7.05 (m, 2H), 6.10-5.89 (m, 2H), 5.50-5.42 (m, 1H), 5.34 (dd, J=1.2, 10.4 Hz, 1H), 4.87 (d, J=5.6 Hz, 2H), 4.22-4.08 (m, 1H), 4.00-3.76 (m, 1H), 3.69-3.51 (m, 1H), 1.67-1.59 (m, 2H), 1.33-1.26 (m, 3H), 0.96-0.89 (m, 3H).

Step 7: Preparation of 5-(fluoro((((S)-1-oxo-1-propoxypropan-2-yl)amino)(phenoxy)phosphoryl)methyl)benzo[b]thiophene-2-carboxylic acid To a solution of allyl 5-(fluoro((((S)-1-oxo-1-propoxypropan-2-yl)amino)(phenoxy)phosphoryl)methyl)benzo[b]thiophene-2-carboxylate (1 g, 1.9 mmol, 1 eq) and pyrrolidine (82 mg, 1.2 mmol, 0.6 eq) in DCM (10 mL) was added $Pd(PPh_3)_4$ (0.22 g, 0.19 mmol, 0.1 eq) and stirred at 25° C. for 1 h to give a yellow solution. The reaction mixture was concentrated under reduced pressure to give a residue. The crude was purified by reverse phase chromatography (TFA) then lyophilized to give 5-(fluoro((((S)-1-oxo-1-propoxypropan-2-yl)amino)(phenoxy)phosphoryl)methyl)benzo[b]thiophene-2-carboxylic acid (0.70 g, 1.5 mmol, 76% yield) as a white solid. $^1H$ NMR (400 MHz, $CDCl_3$) δ 8.15-7.91 (m, 1H), 7.90-7.79 (m, 2H), 7.70-7.51 (m, 1H), 7.46-7.29 (m, 3H), 7.25-7.15 (m, 2H), 6.15-5.98 (m, 1H), 4.24-4.05 (m, 3H), 1.79-1.58 (m, 2H), 1.41-1.22 (m, 3H), 0.96 (dd, J=12.4, 19.6 Hz, 3H).

Step 8: Preparation of perfluorophenyl 5-(fluoro((((S)-1-oxo-1-propoxypropan-2-yl)amino)(phenoxy)phosphoryl)methyl)benzo[b]thiophene-2-carboxylate To a solution of 5-(fluoro((((S)-1-oxo-1-propoxypropan-2-yl)amino)(phenoxy)phosphoryl)methyl)benzo[b]thiophene-2-carboxylic acid (0.70 g, 1.5 mmol, 1 eq) and pyridine (0.57 g, 7.2 mmol, 5 eq) in DMF (10 mL) was added 2,3,4,5,6-pentafluorophenyl 2,2,2-trifluoroacetate (2.0 g, 7.2 mmol, 5 eq) and stirred at 25° C. for 0.5 h to give a yellow solution. The reaction mixture was diluted with water (50 mL) and extracted with EtOAc (50 mL×2), the combined organic layers were washed with saturated brine (40 mL×2), dried over $Na_2SO_4$, filtered and concentrated under reduced pressure to give a residue. The residue was purified by column chromatography to give perfluorophenyl 5-(fluoro((((S)-1-oxo-1-propoxypropan-2-yl)amino)(phenoxy)phosphoryl)methyl)benzo[b]thiophene-2-carboxylate (0.80 g, 1.2 mmol, 86% yield) as a white solid. LCMS (ESI) m/z=646.1 $[M+H]^+$. $^1H$ NMR (400 MHz, $CDCl_3$) δ 8.38-8.30 (m, 1H), 8.15-8.07 (m, 1H), 8.02-7.91 (m, 1H), 7.78-7.63 (m, 1H), 7.43-7.34 (m, 1H), 7.31-7.28 (m, 1H), 7.25-7.17 (m, 1H), 7.16-7.06 (m, 2H), 6.13-5.89 (m, 1H), 4.11-4.01 (m, 2H), 3.70-3.51 (m, 1H), 1.72-1.59 (m, 3H), 1.32 (d, J=7.2 Hz, 2H), 0.99-0.87 (m, 3H).

Synthesis of ((2-((perfluorophenoxy)carbonyl)benzo[b]thiophen-5-yl)methyl)phosphonic acid

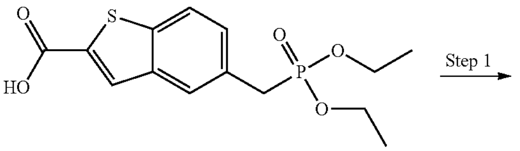

-continued

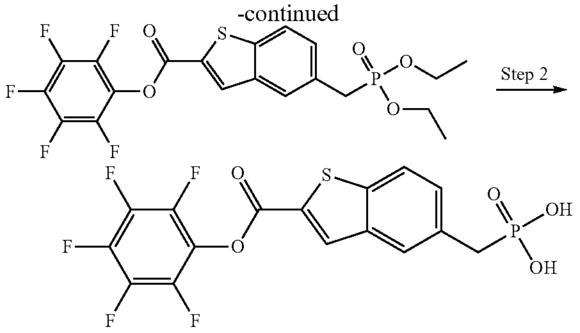

Step 1: Preparation of ((2-((perfluorophenoxy)carbonyl)benzo[b]thiophen-5-yl)methyl)phosphonic acid To a solution of 5-((diethoxyphosphoryl)methyl)benzo[b]thiophene-2-carboxylic acid (2 g, 6.1 mmol, 1 eq) in dimethylformamide (100 mL) was added pyridine (1.9 g, 24 mmol, 4 eq), the mixture was stirred at 0° C. for 5 min, then 2,3,4,5,6-pentafluorophenyl 2,2,2-trifluoroacetate (6.8 g, 24 mmol, 4 eq) was added to the mixture, the mixture was stirred at 25° C. for 15 min to give yellow solution. The mixture was diluted with water (50 mL) and extracted with EtOAc (50 mL×2), the combined organic layers were washed with saturated brine (40 mL×2), dried over $Na_2SO_4$, filtered and concentrated under reduced pressure to give a residue. The residue was purified by column chromatography to give perfluorophenyl 5-((diethoxyphosphoryl)methyl)benzo[b]thiophene-2-carboxylate (1.4 g, 2.9 mmol, 47% yield) as a yellow oil. LCMS (ESI) m/z=495.0

Step 2: Preparation of ((2-((perfluorophenoxy)carbonyl)benzo[b]thiophen-5-yl)methyl)phosphonic acid To a solution of perfluorophenyl 5-((diethoxyphosphoryl)methyl)benzo[b]thiophene-2-carboxylate (1.4 g, 2.8 mmol, 1 eq) in DCM (10 mL) was added trimethylsilyl iodide (2.3 g, 11 mmol, 4 eq), the mixture was stirred at 0° C. for 15 min to give yellow solution. The reaction mixture was concentrated under reduced pressure to give a residue. The residue was purified by reversed phase (TFA) to give ((2-((perfluorophenoxy)carbonyl)benzo[b]thiophen-5-yl)methyl)phosphonic acid (0.9 g, 2.1 mmol, 74% yield) as a white solid. LCMS (ESI) m/z=438.9 $[M+H]^+$. $^1H$ NMR (400 MHz, $CD_3OD$) δ 8.41 (s, 1H), 8.01-7.94 (m, 2H), 7.60-7.55 (m, 1H), 3.32-3.32 (m, 1H), 3.26 (s, 1H).

Synthesis of (fluoro(2-((perfluorophenoxy)carbonyl)benzo[b]thiophen-5-yl)methyl)phosphonic acid

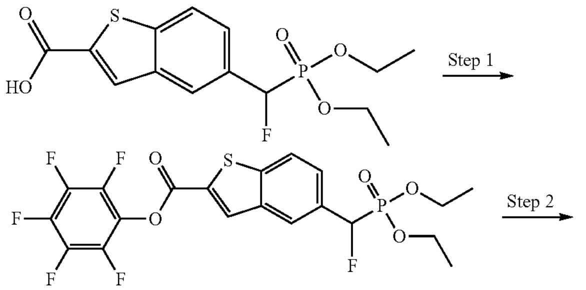

-continued

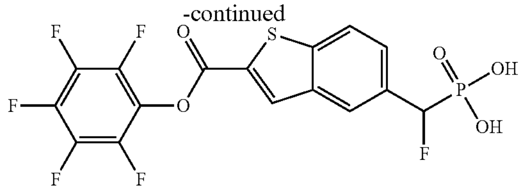

Step 1: Preparation of perfluorophenyl 5-((diethoxyphosphoryl)fluoromethyl)benzo[b]thiophene-2-carboxylate To a solution of 5-[(diethoxyphosphoryl)(fluoro)methyl]-1-benzothiophene-2-carboxylic acid (5 g, 14.40 mmol, 1 eq) in piperidine (6.13 g, 72 mmol, 5 eq) was added 2,3,4,5,6-pentafluorophenyl 2,2,2-trifluoroacetate (12 g, 43.20 mmol, 3 eq), the mixture was stirred at 0° C. for 30 min to give a brown clean solution. The reaction mixture was concentrated under reduced pressure to give a residue. The residue was diluted with water (200 mL) and extracted with EtOAc (500 mL×2), the combined organic layers were washed with saturated brine (500 mL×2), dried over $Na_2SO_4$, filtered and concentrated under reduced pressure to give a residue. The residue was purified by flash silica gel chromatography to give perfluorophenyl 5-((diethoxyphosphoryl)fluoromethyl)benzo[b]thiophene-2-carboxylate (6.50 g, 11.70 mmol, 81.40%) as a yellow oil. LCMS (ESI) m/z=513.1 $[M+H]^+$. $^1H$ NMR (400 MHz, $CDCl_3$) δ 8.35 (s, 1H), 8.08 (s, 1H), 7.98 (d, J=8.4 Hz, 1H), 7.67 (d, J=8.4 Hz, 1H), 5.93-5.77 (m, 1H), 4.22-4.17 (m, 1H), 4.16-4.13 (m, 1H), 4.13-4.11 (m, 1H), 4.10-4.06 (m, 1H), 1.34-1.31 (m, 3H), 1.30-1.27 (m, 3H).

Step 2: Preparation of (fluoro(2-((perfluorophenoxy)carbonyl)benzo[b]thiophen-5-yl)methyl)phosphonic acid To a solution of perfluorophenyl 5-((diethoxyphosphoryl)fluoromethyl)benzo[b]thiophene-2-carboxylate (6 g, 12 mmol, 1 eq) in DCM (60 mL) was dropwise TMSI (9.3 g, 47 mmol, 4 eq) at 0 C, the mixture was stirred at 0° C. for 1 h. The reaction mixture was concentrated under reduced pressure to give a yellow oil. The oil was purified by reversed phase (TFA) to lyophilized to give (fluoro(2-((perfluorophenoxy)carbonyl)benzo[b]thiophen-5-yl)methyl)phosphonic acid (3.0 g, 6.6 mmol, 56% yield) as a white solid. LCMS (ESI) m/z=457.2 $[M+H]^+$. $^1H$ NMR (400 MHz, $CD_3OD$) δ 8.48 (s, 1H), 8.17 (s, 1H), 8.07 (d, J=8.4 Hz, 1H), 7.73 (d, J=8.4 Hz, 1H), 5.97-5.78 (m, 1H).

Synthesis of 5-((1S)-fluoro(phenoxy((S)-2-(propoxycarbonyl)pyrrolidin-1-yl)phosphoryl)methyl)benzo[b]thiophene-2-carboxylic acid

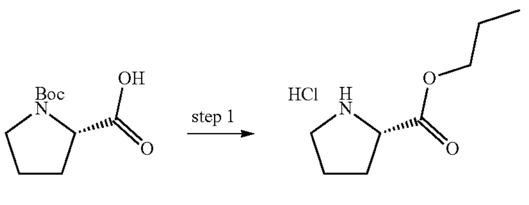

-continued

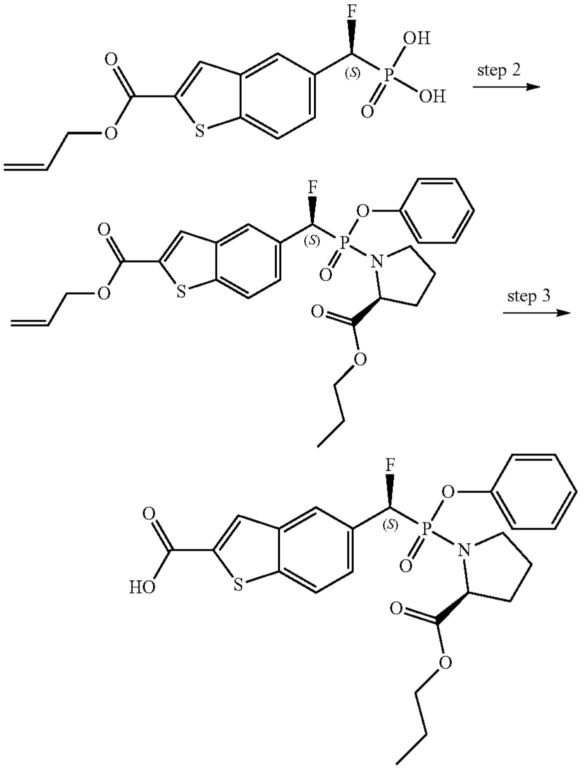

Step 1: Preparation of propyl L-prolinate hydrochloride

Thionyl chloride (2.01 mL, 27.8 mmol, 3 eq) was added dropwise to a solution of (tert-butoxycarbonyl)-L-proline (2.00 g, 9.29 mmol, 1 eq) in propan-1-ol (20 mL, 332 μmol, eq) at 0° C. The mixture was allowed to warm to ambient temperature and then heated at 80° C. overnight. The reaction mixture was concentrated under reduced pressure to give crude propyl L-prolinate hydrochloride (1.85 g, 103%) as a brown oil. $^1H$ NMR (400 MHz, DMSO-$d_6$) δ 4.36-4.33 (m, 1H), 4.18-4.07 (m, 2H), 3.26-3.14 (m, 2H), 2.32-2.22 (m, 1H), 2.01-1.85 (m, 3H), 1.66-1.59 (m, 2H), 0.92-0.89 (m, 3H).

The intermediates in the table below were prepared using the method described above in Step 1 for the preparation of propyl L-prolinate hydrochloride and utilizing the appropriate starting materials and modifications.

| Name | Structure | LCMS |
| --- | --- | --- |
| propyl (S)-azetidine-2-carboxylate (HCl salt) | 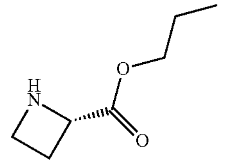 | 144.2 $[M+H]^+$ |

Step 2: Preparation of propyl (((S)-(2-((allyloxy)carbonyl)benzo[b]thiophen-5-yl)fluoromethyl)(phenoxy)phosphoryl)-L-prolinate To a solution of (S)-((2-((allyloxy)carbonyl)benzo[b]thiophen-5-yl)fluoromethyl)phosphonic acid (500 mg, 1.51 mmol, 1 eq) and DMF (2 drops) in DCM (15 mL) was added dropwise oxalyl chloride (1.02 mL, 12.0 mmol, 8 eq). The reaction mixture was stirred 2 h at room temperature under $N_2$. The reaction mixture was concentrated under reduced pressure and dried completely under high vacuum for 30 min. to give a yellow solid. The yellow solid was diluted in DCM (15 mL, dried on $Na_2SO_4$) and cooled down to 0° C. A solution of phenol (134 mg, 1.43 mmol, 0.95 eq) and triethylamine (1.26 mL, 9.06 mmol, 6.0 eq) in DCM (5 mL, dried on $Na_2SO_4$) was slowly added onto the solution. The reaction mixture was stirred at 0° C. for 2 min. and then warmed up to room temperature and stirred for 18 h. A solution of propyl L-prolinate hydrochloride (584 mg, 3.02 mmol, 2 eq) in DCM (5 mL, dried on $Na_2SO_4$) was slowly added onto the orange solution. The reaction mixture was stirred at room temperature for 4 h. Water (1 mL) was added. The solvent was removed under reduced pressure. The crude residue was purified by reverse phase chromatography on a 150 g Cis cartridge eluting with 5-100% MeCN in water. The pure fractions were then concentrated under reduced pressure to give propyl (((S)-(2-((allyloxy)carbonyl)benzo[b]thiophen-5-yl)fluoromethyl)(phenoxy)phosphoryl)-L-prolinate (320 mg, 38.8%) as a yellow oil. LCMS (ESI): m/z=546.2 $[M+H]^+$. $^1H$ NMR (400 MHz, $CDCl_3$) δ 8.17-8.04 (m, 2H), 7.94-7.86 (m, 1H), 7.79-7.62 (m, 1H), 7.34-7.28 (m, 2H), 7.24-7.20 (m, 1H), 7.19-7.03 (m, 2H), 6.10-6.00 (m, 1H), 5.49-5.31 (m, 2H), 4.89-4.84 (m, 2H), 4.57-4.22 (m, 1H), 4.15-3.96 (m, 2H), 3.66-3.21 (m, 1H), 3.13-2.67 (m, 1H), 2.18-2.04 (m, 1H), 1.97-1.86 (m, 1H), 1.83-1.46 (m, 5H), 1.00-0.86 (m, 3H).

The intermediates in the table below were prepared using the method described above in Step 2 for the preparation of propyl (((S)-(2-((allyloxy)carbonyl)benzo[b]thiophen-5-yl)fluoromethyl)(phenoxy)phosphoryl)-L-prolinate and utilizing the appropriate starting materials and modifications.

Step 3: Preparation of 5-((1S)-fluoro(phenoxy((S)-2-(propoxycarbonyl)pyrrolidin-1-yl)phosphoryl)methyl)benzo[b]thiophene-2-carboxylic acid To a solution of propyl (((S)-(2-((allyloxy)carbonyl)benzo[b]thiophen-5-yl)fluoromethyl)(phenoxy)phosphoryl)-L-prolinate (320 mg, 586 μmol, 1 eq) in THF (6 mL) were added morpholine (251 μL, 2.92 mmol, 5 eq) and $Pd(PPh_3)_4$ (13.5 mg, 11.7 μmol, 0.02 eq). The reaction mixture was stirred at room temperature for 1 h. The reaction mixture was concentrated to a volume of 2 mL under $N_2$. The crude product was purified by reverse phase chromatography on a 100 g Cis cartridge eluting with 5-80% MeCN in water (with 0.1% formic acid). The combined fractions were concentrated under reduced pressure and then freeze dried to give 5-((1S)-fluoro(phenoxy((S)-2-(propoxycarbonyl)pyrrolidin-1-yl)phosphoryl)methyl)benzo[b]thiophene-2-carboxylic acid (172 mg) as a white solid which was re-purified by reverse phase chromatography on a 275 g Cis cartridge eluting with 5-80% MeCN in water (with 0.1% formic acid). The combined fractions were concentrated under reduced pressure and then freeze dried to give 5-((1S)-fluoro(phenoxy((S)-2-(propoxycarbonyl)pyrrolidin-1-yl)phosphoryl)methyl)benzo[b]thiophene-2-carboxylic acid (75.0 mg, 25.3%) as a white solid. LCMS (ESI): m/z=506.0 $[M+H]^+$. $^1H$ NMR (400 MHz, DMSO-$d_6$) δ 13.58 (br. s., 1H), 8.21-8.10 (m, 2H), 7.73-7.63 (m, 1H), 7.41-7.31 (m, 3H), 7.30-7.16 (m, 2H), 7.12-7.08 (m, 1H), 6.86-6.28 (m, 1H), 4.43-3.41 (m, 4H), 3.19-2.82 (m, 1H), 2.10-1.61 (m, 4H), 1.57-1.45 (m, 2H), 0.92-0.72 (m, 3H).

The intermediates in the table below were prepared using the method described above in Step 3 for the preparation of 5-((1S)-fluoro(phenoxy((S)-2-(propoxycarbonyl)pyrrolidin-1-yl)phosphoryl)methyl)benzo[b]thiophene-2-carboxylic acid and utilizing the appropriate starting materials and modifications.

| Name | Structure | LCMS |
|---|---|---|
| propyl (2S)-1-(((S)-(2-((allyloxy)carbonyl)benzo[b]thiophen-5-yl)fluoromethyl)(phenoxy)phosphoryl)azetidine-2-carboxylate | 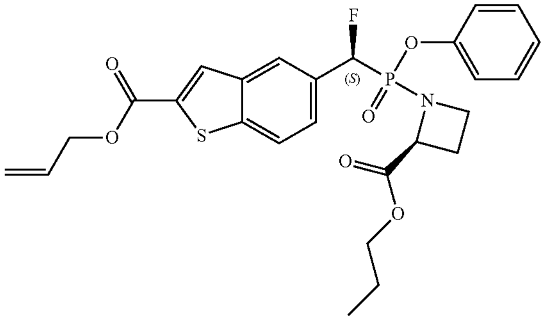 | 532.2 $[M + H]^+$ |

| Name | Structure | LCMS |
|---|---|---|
| 5-((1S)-fluoro(phenoxy((S)-2-(propoxycarbonyl)azetidin-1-yl)phosphoryl)methyl)benzo[b]thiophene-2-carboxylic acid | 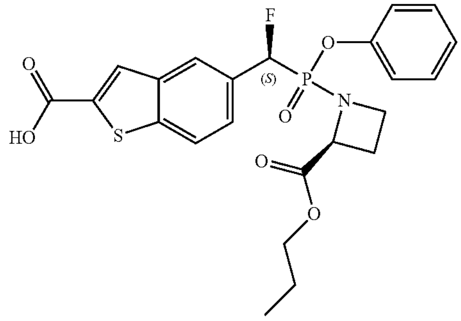 | 492.2 [M + H]$^+$ |

Synthesis of 5-((1R)-fluoro((((S)-1-(2-methoxy-2-methylpropoxy)-1-oxopropan-2-yl)amino)(phenoxy)phosphoryl)methyl)benzo[b]thiophene-2-carboxylic acid

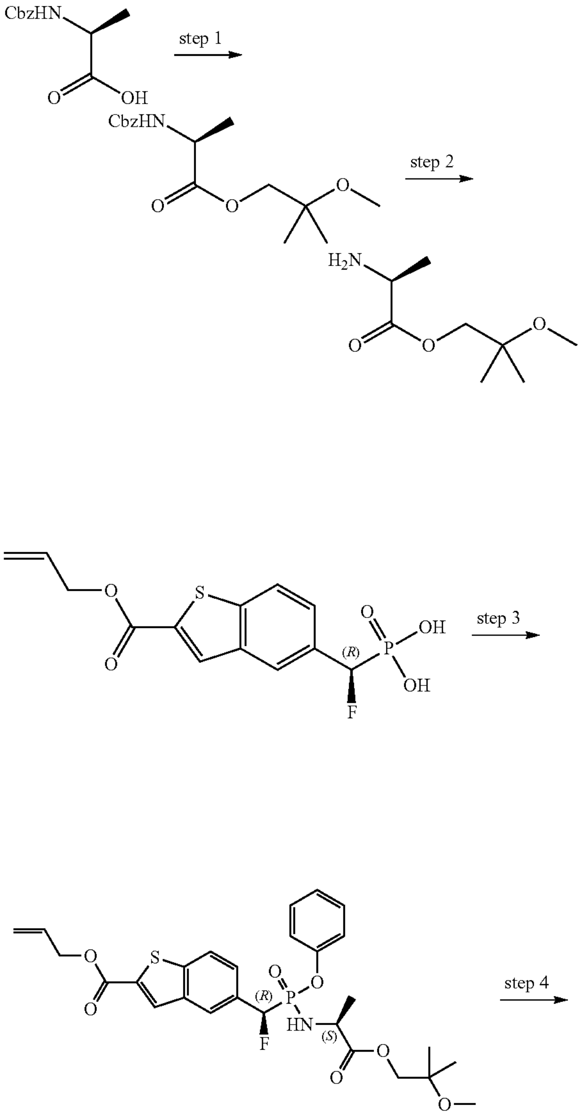

-continued

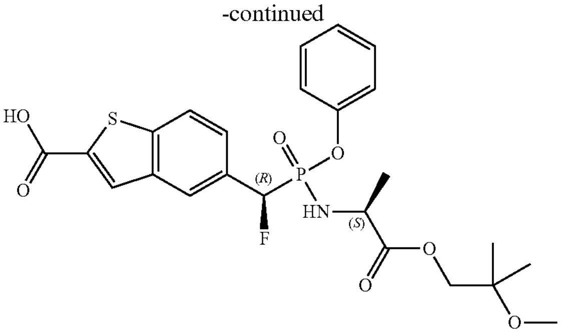

Step 1: Preparation of 2-methoxy-2-methylpropyl ((benzyloxy)carbonyl)-L-alaninate To a solution of ((benzyloxy)carbonyl)-L-alanine (1.64 g, 7.34 mmol, 1 eq.) and 2-methoxy-2-methylpropan-1-ol (916 mg, 8.80 mmol, 1.2 eq.) in ACN (20 ml) were added EDCI (1.68 g, 8.80 mmol, 1.2 eq.) and DMAP (1.07 g, 8.80 mmol, 1.2 eq.). The mixture was stirred at 25° C. for 16 h. After completion, the reaction mixture was diluted with $H_2O$ (10 mL) and extracted with DCM (10 mL×3). The organic layers were combined and washed with brine (10 mL), dried over anhydrous $Na_2SO_4$, and concentrated under reduced pressure. The residue was purified by flash column chromatography on silica gel to afford 2-methoxy-2-methylpropyl ((benzyloxy)carbonyl)-L-alaninate (2, 1.63 g, 5.27 mmol, 72%) as a colorless oil. LCMS (ESI): m/z=310 [M+H]$^+$.

The intermediates in the table below were prepared using the method described above in Step 1 for the preparation of 2-methoxy-2-methylpropyl ((benzyloxy)carbonyl)-L-alaninate and utilizing the appropriate starting materials and modifications.

| Name | Structure | LCMS |
|---|---|---|
| (tetrahydro-2H-pyran-4-yl)methyl ((benzyloxy)carbonyl)-L-alaninate | 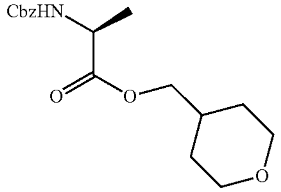 [SMILES: C[C@H](NC(=O)OCc1ccccc1)C(=O)OCC1CCOCC1] | 322 $[M+H]^+$ |
| pyridazin-3-ylmethyl ((benzyloxy)carbonyl)-L-alaninate | 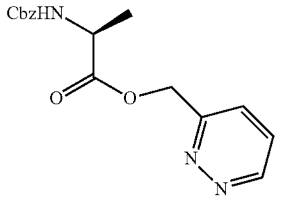 | 282 $[M+H]^+$ |
| oxetan-3-ylmethyl((benzyloxy)carbonyl)-L-alaninate | 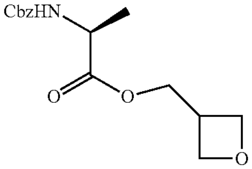 [SMILES: C[C@H](NC(=O)OCc1ccccc1)C(=O)OCC1COC1] | 294 $[M+H]^+$ |
| (3-methyloxetan-3-yl)methyl ((benzyloxy)carbonyl)-L-alaninate | 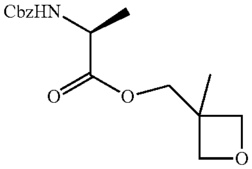 [SMILES: C[C@H](NC(=O)OCc1ccccc1)C(=O)OCC1(C)COC1] | 308 $[M+H]^+$ |

Step 2: Preparation of 2-methoxy-2-methylpropyl L-alaninate

To a solution of 2-methoxy-2-methylpropyl ((benzyloxy) carbonyl)-L-alaninate (1.5 g, 4.84 mmol, 1.0 eq.) in EtOAc (15 ml) was added Pd/C (150 mg) under nitrogen. The suspension was degassed under vacuum and purged with $H_2$ several times. The resulting mixture was stirred at room temperature for 14 h. After completion, the suspension was filtered through a pad of Celite®, the filter cake was washed with MeOH (20 mL). The combined filtrates were concentrated to dryness to give 2-methoxy-2-methylpropyl L-alaninate (640 mg, 3.65 mmol, 75%) as a colorless oil. LCMS (ESI): m/z=176 $[M+H]^+$.

The intermediates in the table below were prepared using the method described above in Step 2 for the preparation of 2-methoxy-2-methylpropyl ((benzyloxy)carbonyl)-L-alaninate and utilizing the appropriate starting materials and modifications.

| Name | Structure | LCMS |
|---|---|---|
| (tetrahydro-2H-pyran-4-yl)methyl L-alaninate | 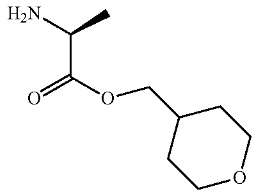 | 188 $[M+H]^+$ |
| pyridazin-3-ylmethyl L-alaninate | 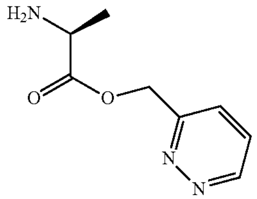 | 182 $[M+H]^+$ |

-continued

| Name | Structure | LCMS |
| --- | --- | --- |
| oxetan-3-ylmethyl L-alaninate | 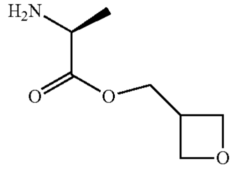 | 160 [M + H]+ |
| (3-methyloxetan-3-yl)methyl L-alaninate | 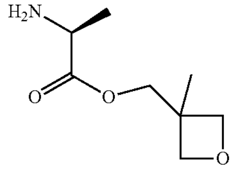 | 147.1 [M + H]+ |

Step 3: Preparation of allyl 5-((1R)-fluoro((((S)-1-(2-methoxy-2-methylpropoxy)-1-oxopropan-2-yl)amino)(phenoxy)phosphoryl)methyl)benzo[b]thiophene-2-carboxylate Oxalyl chloride (576 mg, 4.54 mmol, 5 eq.) was added dropwise to the solution of (R)-((2-((allyloxy)carbonyl)benzo[b]thiophen-5-yl)fluoromethyl)phosphonic acid (300 mg, 0.91 mmol, 1 eq.) in dry DCM (10 mL) and DMF (1 drop) at 25° C. The reaction mixture was stirred at 40° C. for an additional 0.5 hr. The reaction was monitored by pipetting out a small amount of crude sample and quenching it with MeOH to ensure bis-Cl phosphoryl chloride had been formed completely (bis-methoxy phosphonate was observed by LCMS). After completion, the excess oxalyl chloride and solvent were removed under reduced pressure. The residue was re-dissolved in anhydrous DCM (10 mL), then added to a mixture of phenol (88.8 mg, 0.94 mmol, 1.05 eq.) and TEA (908 mg, 8.98 mmol, 10.0 eq.) in anhydrous DCM (5 mL) at 0° C. The reaction was stirred for 0.5 h. Then 2-methoxy-2-methylpropyl L-alaninate (313 mg, 1.79 mmol, 2 eq.) was added at 0° C. and the resulting mixture was stirred at 20° C. for 1 h under $N_2$. After completion, the reaction mixture was concentrated under reduced pressure. The residue was purified by Biotage® C18 column chromatography to give allyl 5-((1R)-fluoro((((S)-1-(2-methoxy-2-methylpropoxy)-1-oxopropan-2-yl)amino)(phenoxy)phosphoryl)methyl)benzo[b]thiophene-2-carboxylate (45.0 mg, 80 μmol, 9%) as a yellow solid. LCMS (ESI): m/z=564.0 $[M+H]^+$.

The intermediates in the table below were prepared using the method described above in Step 3 for the preparation of allyl 5-((1R)-fluoro((((S)-1-(2-methoxy-2-methylpropoxy)-1-oxopropan-2-yl)amino)(phenoxy)phosphoryl)methyl)benzo[b]thiophene-2-carboxylate and utilizing the appropriate starting materials and modifications.

| Name | Structure | LCMS |
| --- | --- | --- |
| allyl 5-((1R)-fluoro((((S)-1-oxo-1-((tetrahydro-2H-pyran-4-yl)methoxy)propan-2-yl)amino)(phenoxy)phosphoryl)methyl)benzo[b]thiophene-2-carboxylate | 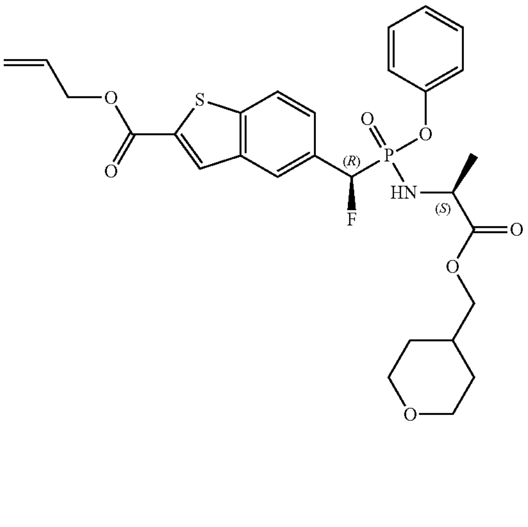 | 576 [M + H]+ |

-continued

| Name | Structure | LCMS |
| --- | --- | --- |
| allyl 5-((1R)-fluoro((((S)-1-oxo-1-(pyridazin-3-ylmethoxy)propan-2-yl)amino)(phenoxy)phosphoryl)methyl)benzo[b]thiophene-2-carboxylate | 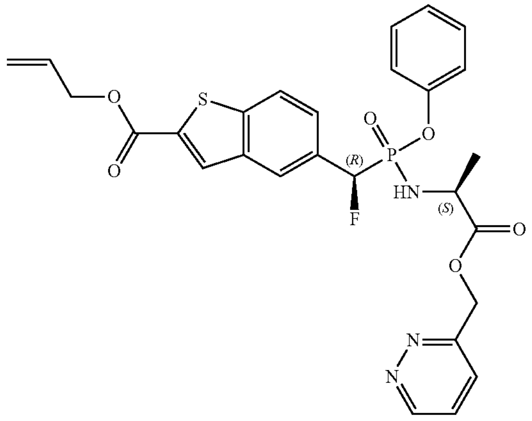 | 570 [M + H]+ |
| allyl 5-((1R)-fluoro((((S)-1-(oxetan-3-ylmethoxy)-1-oxopropan-2-yl)amino)(phenoxy)phosphoryl)methyl)benzo[b]thiophene-2-carboxylate | 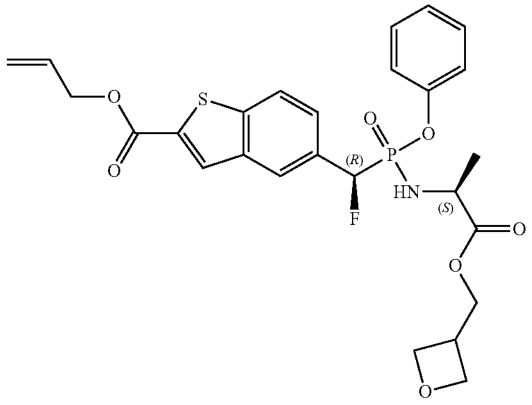 | 548 [M + H]+ |
| allyl 5-((1R)-fluoro((((S)-1-((3-methyloxetan-3-yl)methoxy)-1-oxopropan-2-yl)amino)(phenoxy)phosphoryl)methyl)benzo[b]thiophene-2-carboxylate | 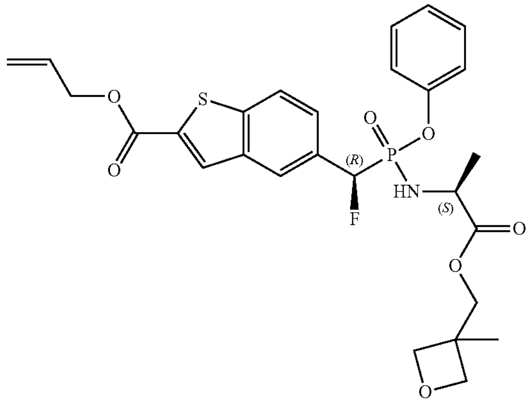 | 562 [M + H]+ |

Step 4: Preparation of 5-((1R)-fluoro((((S)-1-(2-methoxy-2-methylpropoxy)-1-oxopropan-2-yl)amino)(phenoxy)phosphoryl)methyl)benzo[b]thiophene-2-carboxylic acid To a solution of allyl 5-((1R)-fluoro((((S)-1-(2-methoxy-2-methylpropoxy)-1-oxopropan-2-yl)amino)(phenoxy)phosphoryl)methyl)benzo[b]thiophene-2-carboxylate (45.0 mg, 80 μmol, 1.0 eq) in DCM (6 mL) were added $Pd(PPh_3)_4$ (5 mg, 8 μmol, 0.1 eq.) and pyrrolidine (6 mg, 80 μmol, 1.0 eq.). The mixture was purged and degassed with $N_2$ (three times), then stirred at 25° C. for 1 hr. After completion, the mixture was concentrated under reduced pressure. The residue was purified by Biotage® C18 column chromatography to give 5-((1R)-fluoro((((S)-1-(2-methoxy-2-methylpropoxy)-1-oxopropan-2-yl)amino)(phenoxy)phosphoryl)methyl)benzo[b]thiophene-2-carboxylic acid (40 mg, 76 μmol, 95%) as a colorless oil. LCMS (ESI): m/z=524 $[M+H]^+$.

The intermediates in the table below were prepared using the method described above in Step 4 for the preparation of 5-((1R)-fluoro((((S)-1-(2-methoxy-2-methylpropoxy)-1-oxopropan-2-yl)amino)(phenoxy)phosphoryl)methyl)benzo[b]thiophene-2-carboxylic acid and

| Name | Structure | LCMS |
|---|---|---|
| 5-((1R)-fluoro((((S)-1-oxo-1-((tetrahydro-2H-pyran-4-yl)methoxy)propan-2-yl)amino)(phenoxy)phosphoryl)methyl)benzo[b]thiophene-2-carboxylic acid | 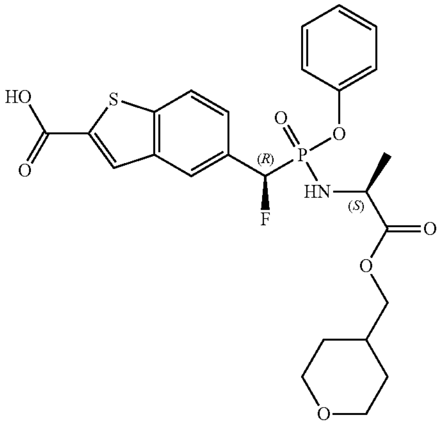 | 536 [M + H]+ |
| 5-((1R)-fluoro((((S)-1-oxo-1-(pyridazin-3-ylmethoxy)propan-2-yl)amino)(phenoxy)phosphoryl)methyl)benzo[b]thiophene-2-carboxylic acid | 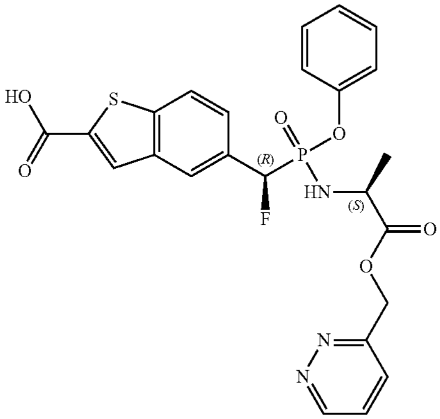 | 530 [M + H]+ |
| 5-((1R)-fluoro((((S)-1-(oxetan-3-ylmethoxy)-1-oxopropan-2-yl)amino)(phenoxy)phosphoryl)methyl)benzo[b]thiophene-2-carboxylic acid | 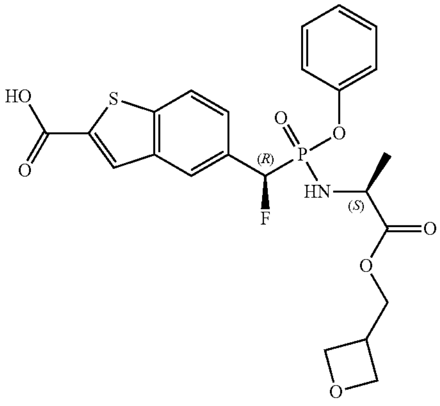 | 508 [M + H]+ |

-continued

| Name | Structure | LCMS |
|---|---|---|
| 5-((1R)-fluoro(((S)-1-((3-methyloxetan-3-yl)methoxy)-1-oxopropan-2-yl)amino)(phenoxy)phosphoryl)methyl)benzo[b]thiophene-2-carboxylic acid | 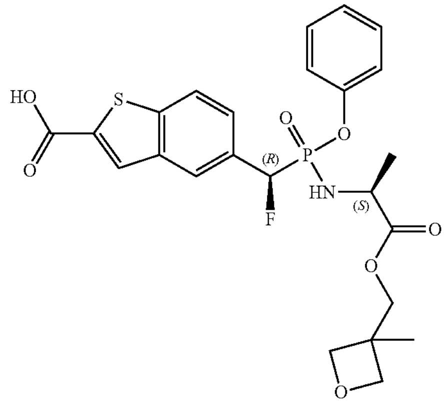 | 522 [M + H]+ |

Synthesis of 5-((1R)-fluoro((((S)-1-((1-methyl-1H-tetrazol-5-yl)methoxy)-1-oxopropan-2-yl)amino)(phenoxy)phosphoryl)methyl)benzo[b]thiophene-2-carboxylic acid

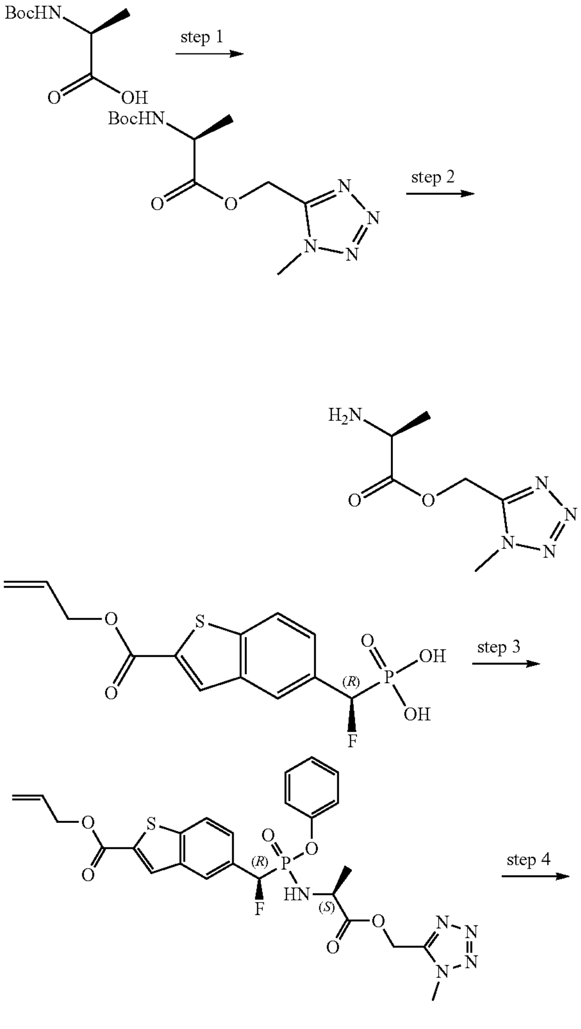

-continued

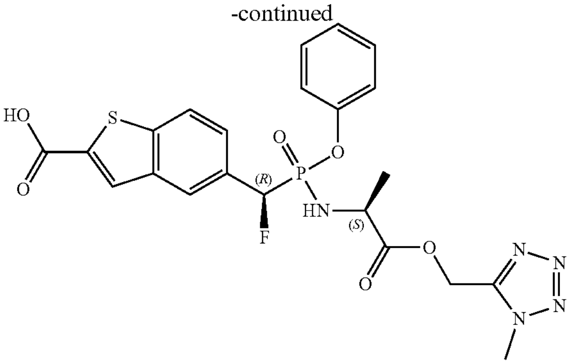

Step 1: Preparation of (1-methyl-1H-tetrazol-5-yl)methyl (tert-butoxycarbonyl)-L-alaninate To a solution of (tert-butoxycarbonyl)-L-alanine (1 g, 5.28 mmol, 1 eq.) and (1-methyl-1H-1,2,3,4-tetrazol-5-yl)methanol (903 mg, 7.92 mmol, 1.5 eq.) in DCM (15 ml) were added $T_3P$ (50%) (5.02 g, 15.8 mmol, 3 eq.), DMAP (32.2 mg, 264 μmol, 0.05 eq.) and 4-methylmorpholine (1.59 g, 15.8 mmol, 3 eq.). The mixture was stirred at room temperature for 2 h. After completion, the reaction mixture was diluted with $H_2O$ (10 mL) and extracted with DCM (10 mL×3). The organic layers were combined and washed with brine (10 mL), dried over anhydrous $Na_2SO_4$, and concentrated under reduced pressure. The residue was purified by flash column chromatography on silica gel to afford (1-methyl-1H-tetrazol-5-yl)methyl (tert-butoxycarbonyl)-L-alaninate (900 mg, 3.15 mmol, 60%) as a colorless oil. LCMS (ESI): m/z=286 $[M+H]^+$.

The intermediates in the table below were prepared using the method described above in Step 1 for the preparation of (1-methyl-1H-tetrazol-5-yl)methyl (tert-butoxycarbonyl)-L-alaninate and utilizing the appropriate starting materials and modifications.

| Name | Structure | LCMS | NMR |
|---|---|---|---|
| (4-methyl-4H-1,2,4-triazol-3-yl)methyl(tert-butoxycarbonyl)-L-alaninate | 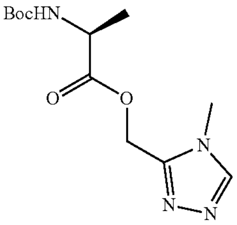 [SMILES: C[C@H](NC(=O)OC(C)(C)C)C(=O)OCc1nncn1C] | 285 [M + H]+ | |
| 2-methoxyethyl N-(tert-butoxycarbonyl)-O-methyl-L-serinate | 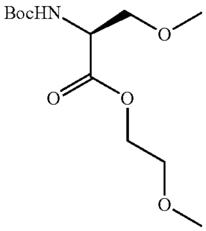 [SMILES: COCCOC(=O)[C@H](COC)NC(=O)OC(C)(C)C] | 278 [M + H]+ | $^1$H NMR (400 MHz, DMSO-$d_6$) δ 7.19-7.07 (m, 1H), 4.28-4.10 (m, 3H), 3.61-3.46 (m, 4H), 3.28-3.19 (m, 6H), 1.38 (s, 9H). |
| 2-methoxyethyl(tert-butoxycarbonyl)-L-alaninate | 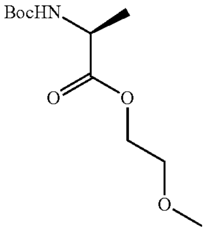 [SMILES: COCCOC(=O)[C@H](C)NC(=O)OC(C)(C)C] | 248 [M + H]+ | |
| propyl(tert-butoxycarbonyl)-L-alaninate | 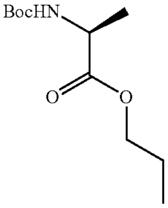 [SMILES: CCCOC(=O)[C@H](C)NC(=O)OC(C)(C)C] | | |
| propyl N-(tert-butoxycarbonyl)-O-methyl-L-serinate | 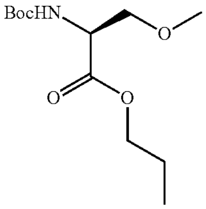 [SMILES: CCCOC(=O)[C@H](COC)NC(=O)OC(C)(C)C] | 262 [M + H]+ | |
| pyridin-2-ylmethyl(tert-butoxycarbonyl)-L-alaninate | 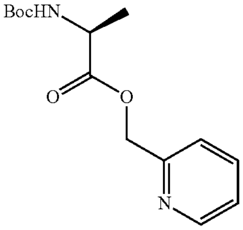 [SMILES: C[C@H](NC(=O)OC(C)(C)C)C(=O)OCc1ccccn1] | 281 [M + H]+ | |
| isobutyl(tert-butoxycarbonyl)-L-alaninate | 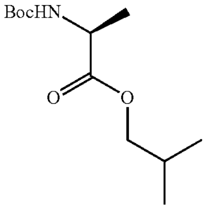 [SMILES: CC(C)COC(=O)[C@H](C)NC(=O)OC(C)(C)C] | 246 [M + H]+ | |

-continued

| Name | Structure | LCMS | NMR |
|---|---|---|---|
| cyclopropyl(tert-butoxycarbonyl)-L-alaninate | 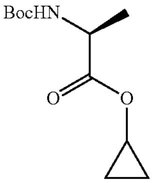 [SMILES: C[C@H](NC(=O)OC(C)(C)C)C(=O)OC1CC1] | 230 [M + H]+. | |
| neopentyl(tert-butoxycarbonyl)-L-alaninate | 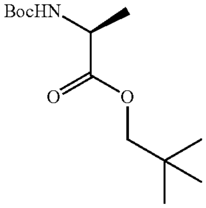 [SMILES: C[C@H](NC(=O)OC(C)(C)C)C(=O)OCC(C)(C)C] | 260 [M + H]+ | |

Step 2: Preparation of (1-methyl-1H-tetrazol-5-yl)methyl L-alaninate

A solution of (1-methyl-1H-tetrazol-5-yl)methyl (tert-butoxycarbonyl)-L-alaninate (600 mg, 2.10 mmol, 1 eq) in HCl/EA (10 mL) was stirred at room temperature for 1 hr. After completion, the reaction mixture was concentrated under reduced pressure to give crude (1-methyl-1H-tetrazol-5-yl)methyl L-alaninate (390 mg, quant.)(HCl salt) as a white solid, which was used in next Step directly without further purification. LCMS (ESI): m/z=186 $[M+H]^+$.

The intermediates in the table below were prepared using the method described above in Step 2 for the preparation of (1-methyl-1H-tetrazol-5-yl)methyl L-alaninate and utilizing the appropriate starting materials and modifications.

| Name | Structure | LCMS | NMR |
|---|---|---|---|
| (4-methyl-4H-1,2,4-triazol-3-yl)methyl L-alaninate (HCl Salt) | 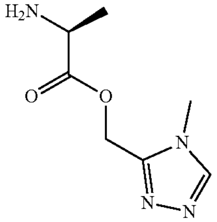 | 185 [M + H]+ | |
| 2-methoxyethyl O-methyl-L-serinate (HCl salt) | 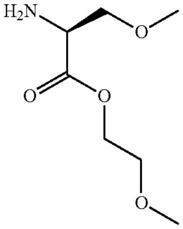 | | $^1$H NMR (400 MHz, DMSO-$d_6$) δ 8.84 (s, 2H), 4.29-4.22 (m, 2H), 3.87-3.75 (m, 2H), 3.58-3.56 (m, 3H), 3.31-3.25 (m, 6H) |
| 2-methoxyethyl L-alaninate (HCl salt) | 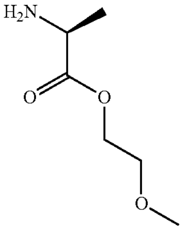 | 148 [M + H]+ | |

-continued
| Name | Structure | LCMS | NMR |
|---|---|---|---|
| propyl L-alaninate (HCl salt) | 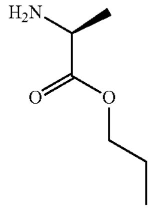 | | |
| propyl O-methyl-L-serinate (HCl salt) | 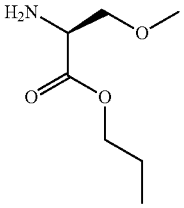 | 162 [M + H]+ | |
| pyridin-2-ylmethyl L-alaninate (HCl salt) | 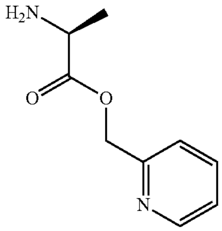 | 181 [M + H]+ | |
| isobutyl L-alaninate (HCl salt) | 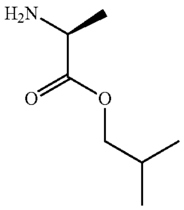 | 146 [M + H]+ | |
| cyclopropyl L-alaninate (HCl salt) | 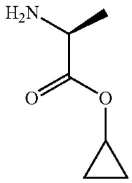 | 130 [M + H]+ | |
| benzyl L-alaninate (HCl salt) | 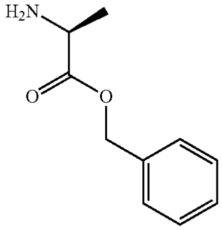 | 180 [M + H]+ | |
| neopentyl L-alaninate (HCl salt) | 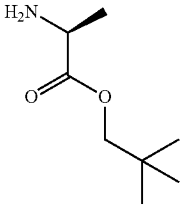 | 160 [M + H]+ | |

Step 3: Preparation of allyl 5-((1R)-fluoro((((S)-1-((1-methyl-1H-tetrazol-5-yl)methoxy)-1-oxopropan-2-yl)amino)(phenoxy)phosphoryl)methyl)benzo[b]thiophene-2-carboxylate Oxalyl chloride (1.05 g, 8.35 mmol, 5 eq.) was added dropwise to a solution of (R)-((2-((allyloxy)carbonyl)benzo[b]thiophen-5-yl)fluoromethyl)phosphonic acid (550 mg, 1.67 mmol, 1 eq.) in dry DCM (10 mL) and DMF (1 drop) at 25° C. The reaction mixture was stirred at 40° C. for an additional 0.5 hr. The reaction was monitored by pipetting out a small amount of crude sample and quenching it with MeOH to ensure bis-Cl phosphoryl chloride had been formed completely (bis-methoxy phosphonate was observed by LCMS). After completion, the excess oxalyl chloride and solvent were removed under reduced pressure. The residue was re-dissolved in anhydrous DCM (10 mL), then added to a mixture of phenol (146 mg, 1.56 mmol, 1.05 eq.) and TEA (752 mg, 7.45 mmol, 5 eq.) in anhydrous DCM (5 mL) at 0° C. The reaction was stirred for 0.5 h. Then (1-methyl-1H-tetrazol-5-yl)methyl L-alaninate (3, 551 mg, 2.98 mmol, 2 eq.) was added at 0° C. and the resulting mixture was stirred at 20° C. for 1 h under $N_2$. After completion, the reaction mixture was concentrated under reduced pressure. The residue was purified by Biotage® C18 column chromatography to give allyl 5-((1R)-fluoro((((S)-1-((1-methyl-1H-tetrazol-5-yl)methoxy)-1-oxopropan-2-yl)amino)(phenoxy)phosphoryl)methyl)benzo[b]thiophene-2-carboxylate (90.0 mg, 156 μmol, 11%) as a yellow oil. LCMS (ESI): m/z=574 $[M+H]^+$.

The intermediates in the table below were prepared using the method described above in Step 3 for the preparation of allyl 5-((1R)-fluoro((((S)-1-((1-methyl-1H-tetrazol-5-yl)methoxy)-1-oxopropan-2-yl)amino)(phenoxy)phosphoryl)methyl)benzo[b]thiophene-2-carboxylate and utilizing the appropriate starting materials and modifications.

| Name | Structure | LCMS |
| --- | --- | --- |
| allyl 5-((1R)-fluoro((((S)-1-((4-methyl-4H-1,2,4-triazol-3-yl)methoxy)-1-oxopropan-2-yl)amino)(phenoxy)phosphoryl)methyl)benzo[b]thiophene-2-carboxylate | 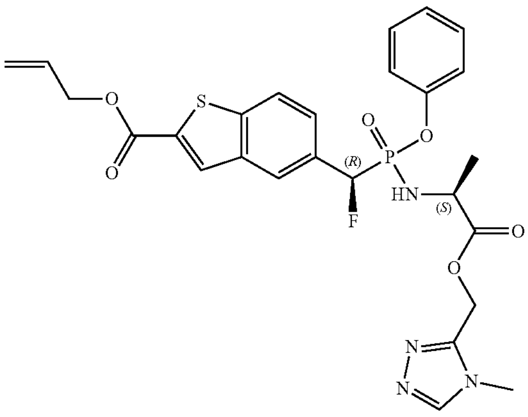 | 573 $[M + H]^+$ |
| allyl 5-((1R)-fluoro((((S)-3-methoxy-1-(2-methoxyethoxy)-1-oxopropan-2-yl)amino)(phenoxy)phosphoryl)methyl)benzo[b]thiophene-2-carboxylate | 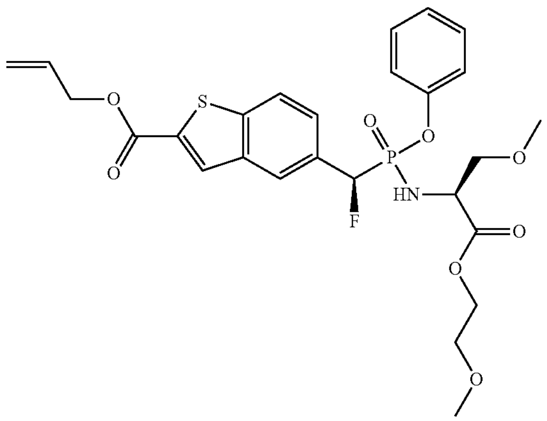 [SMILES: C=CCOC(=O)c1cc2cc([C@H](F)P(=O)(N[C@@H](COC)C(=O)OCCOC)Oc3ccccc3)ccc2s1] | 566 $[M + H]^+$ |

-continued

| Name | Structure | LCMS |
| --- | --- | --- |
| allyl 5-((1R)-fluoro((((S)-1-(2-methoxyethoxy)-1-oxopropan-2-yl)amino)(phenoxy)phosphoryl)methyl)benzo[b]thiophene-2-carboxylate | 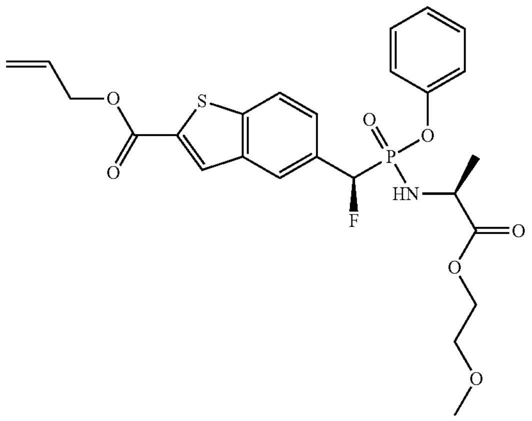 [SMILES: C=CCOC(=O)c1cc2cc([C@H](F)P(=O)(N[C@@H](C)C(=O)OCCOC)Oc3ccccc3)ccc2s1] | 536 [M + H]$^+$ |
| allyl 5-((1R)-fluoro((((S)-1-(2-methoxyethoxy)-1-oxopropan-2-yl)amino)(2,2,2-trifluoroethoxy)phosphoryl)methyl)benzo[b]thiophene-2-carboxylate | 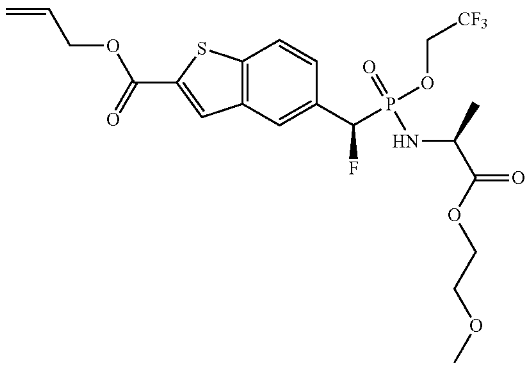 [SMILES: C=CCOC(=O)c1cc2cc([C@H](F)P(=O)(N[C@@H](C)C(=O)OCCOC)OCC(F)(F)F)ccc2s1] | 542 [M + H]$^+$ |
| allyl 5-((1R)-fluoro((((S)-1-oxo-1-propoxypropan-2-yl)amino)(phenoxy)phosphoryl)methyl)benzo[b]thiophene-2-carboxylate | 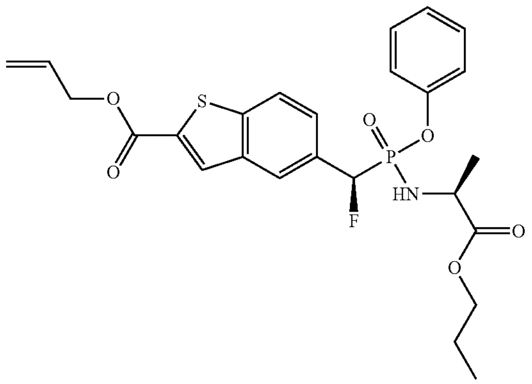 [SMILES: C=CCOC(=O)c1cc2cc([C@H](F)P(=O)(N[C@@H](C)C(=O)OCCC)Oc3ccccc3)ccc2s1] | 520 [M + H]$^+$ |
| allyl 5-((1R)-fluoro((((S)-3-methoxy-1-oxo-1-propoxypropan-2-yl)amino)(phenoxy)phosphoryl)methyl)benzo[b]thiophene-2-carboxylate | 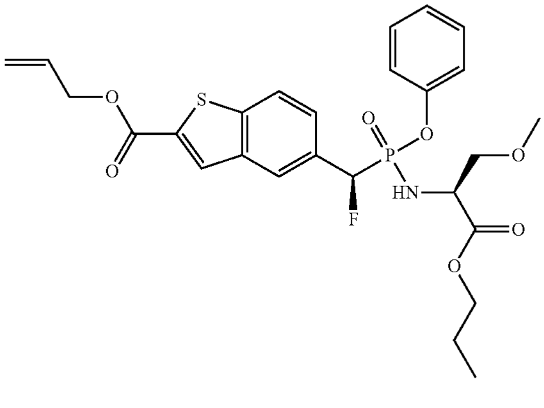 [SMILES: C=CCOC(=O)c1cc2cc([C@H](F)P(=O)(N[C@@H](COC)C(=O)OCCC)Oc3ccccc3)ccc2s1] | 550 [M + H]$^+$ |

-continued

| Name | Structure | LCMS |
| --- | --- | --- |
| allyl 5-((1R)-fluoro((((S)-1-oxo-1-(pyridin-2-ylmethoxy)propan-2-yl)amino)(phenoxy)phosphoryl)methyl)benzo[b]thiophene-2-carboxylate | 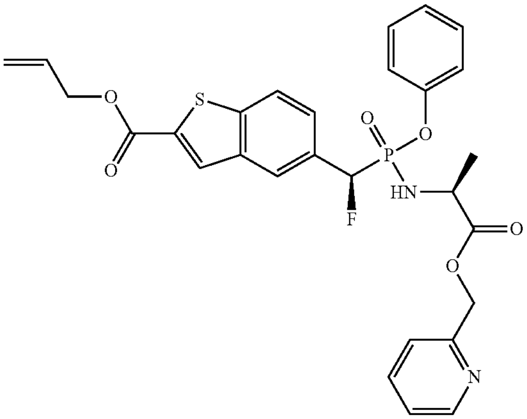 [SMILES: C=CCOC(=O)c1cc2cc([C@H](F)P(=O)(N[C@@H](C)C(=O)OCc3ccccn3)Oc3ccccc3)ccc2s1] | 569 [M + H]+ |
| allyl 5-((1R)-fluoro((((S)-1-isobutoxy-1-oxopropan-2-yl)amino)(phenoxy)phosphoryl)methyl)benzo[b]thiophene-2-carboxylate | 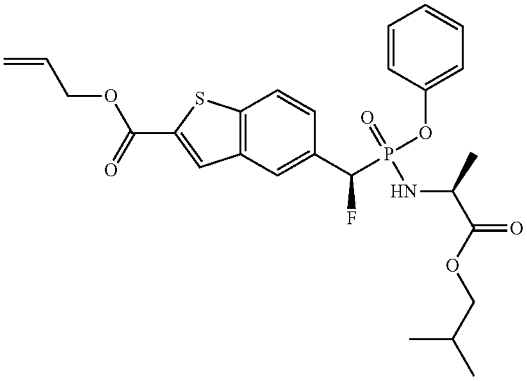 [SMILES: C=CCOC(=O)c1cc2cc([C@H](F)P(=O)(N[C@@H](C)C(=O)OCC(C)C)Oc3ccccc3)ccc2s1] | 534 [M + H]+ |
| allyl 5-((1R)-((((S)-1-cyclopropoxy-1-oxopropan-2-yl)amino)(phenoxy)phosphoryl)fluoromethyl)benzo[b]thiophene-2-carboxylate | 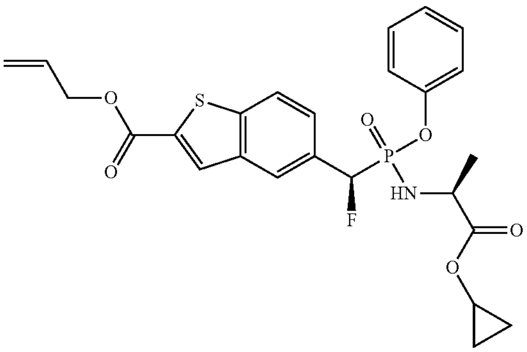 [SMILES: C=CCOC(=O)c1cc2cc([C@H](F)P(=O)(N[C@@H](C)C(=O)OC3CC3)Oc3ccccc3)ccc2s1] | 518 [M + H]+ |
| allyl 5-((1R)-((((S)-1-(2-ethylbutoxy)-1-oxopropan-2-yl)amino)(phenoxy)phosphoryl)fluoromethyl)benzo[b]thiophene-2-carboxylate | 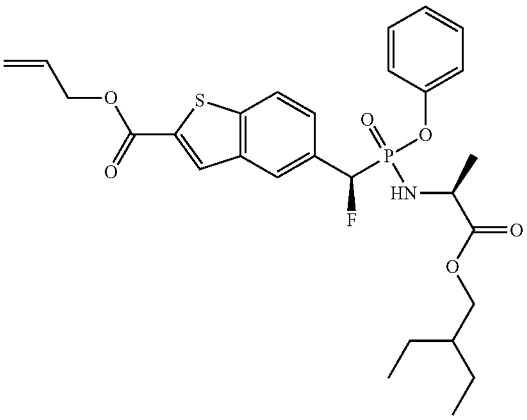 [SMILES: C=CCOC(=O)c1cc2cc([C@H](F)P(=O)(N[C@@H](C)C(=O)OCC(CC)CC)Oc3ccccc3)ccc2s1] | 562 [M + H]+ |

-continued

| Name | Structure | LCMS |
| --- | --- | --- |
| allyl 5-((1R)-((((S)-1-(benzyloxy)-1-oxopropan-2-yl)amino)(phenoxy)phosphoryl)fluoro-methyl)benzo[b]thiophene-2-carboxylate | 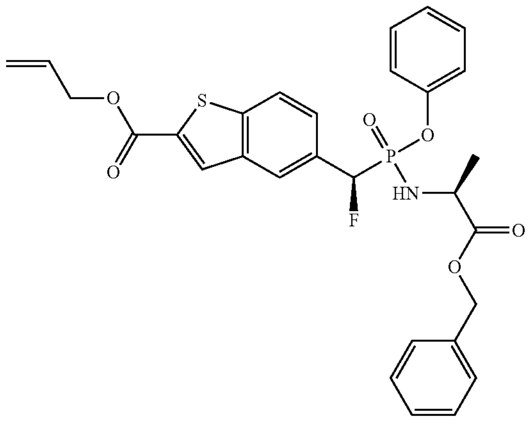 [SMILES: C=CCOC(=O)c1cc2cc([C@H](F)P(=O)(N[C@@H](C)C(=O)OCc3ccccc3)Oc3ccccc3)ccc2s1] | 568 [M + H]+ |
| allyl 5-((1R)-fluoro((((S)-1-(neopentyloxy)-1-oxopropan-2-yl)amino)(phenoxy)phoephoryl)meth-yl)benzo[b]thiophene-2-carboxylate | 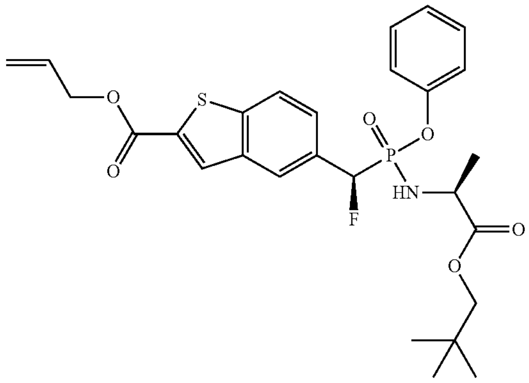 [SMILES: C=CCOC(=O)c1cc2cc([C@H](F)P(=O)(N[C@@H](C)C(=O)OCC(C)(C)C)Oc3ccccc3)ccc2s1] | 548 [M + H]+ |
| allyl 5-((1R)-((2,6-dimethylphenoxy)(((S)-1-oxo-1-propoxypropan-2-yl)amino)phosphoryl)fluoromethyl) benzo[b]thiophene-2-carboxylate | 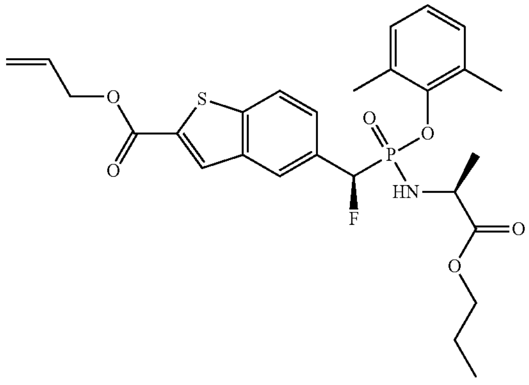 [SMILES: C=CCOC(=O)c1cc2cc([C@H](F)P(=O)(N[C@@H](C)C(=O)OCCC)Oc3c(C)cccc3C)ccc2s1] | 548 [M + H]+ |

Step 4: Preparation of 5-((1R)-fluoro((((S)-1-((1-methyl-1H-tetrazol-5-yl)methoxy)-1-oxopropan-2-yl)amino)(phenoxy)phosphoryl)methyl)benzo[b] thiophene-2-carboxylic acid To a solution of allyl 5-((1R)-fluoro((((S)-1-((1-methyl-1H-tetrazol-5-yl)methoxy)-1-oxopropan-2-yl)amino)(phenoxy)phosphoryl)methyl)benzo[b]thiophene-2-carboxylate (90 mg, 156 μmol, 1 eq.) in DCM (5 mL) were added $Pd(PPh_3)_4$ (9.0 mg, 7.8 μmol, 0.05 eq.) and pyrrolidine (11.0 mg, 156 μmol, 1.0 eq.). The mixture was purged and degassed with $N_2$ (three times), then stirred at 25° C. for 1 hr. After completion, the mixture was concentrated under reduced pressure. The residue was purified by Biotage® C18 column chromatography to give 5-((1R)-fluoro((((S)-1-((1-methyl-1H-tetrazol-5-yl)methoxy)-1-oxopropan-2-yl)amino)(phenoxy)phosphoryl)methyl)benzo[b]thiophene-2-carboxylic acid (50.0 mg, 93.7 μmol, 60%) as a yellow oil. LCMS (ESI): m/z=534 $[M+H]^+$.

The intermediates in the table below were prepared using the method described above in Step 4 for the preparation of 5-((1R)-fluoro((((S)-1-((1-methyl-1H-tetrazol-5-yl)methoxy)-1-oxopropan-2-yl)amino)(phenoxy)phosphoryl)methyl)benzo[b]thiophene-2-carboxylic acid and utilizing the appropriate starting materials and modifications.

| Name | Structure | LCMS |
|---|---|---|
| 5-((1R)-fluoro((((S)-1-((4-methyl-4H-1,2,4-triazol-3-yl)methoxy)-1-oxopropan-2-yl)amino)(phenoxy)phosphoryl)methyl)benzo[b]thiophene-2-carboxylic acid | 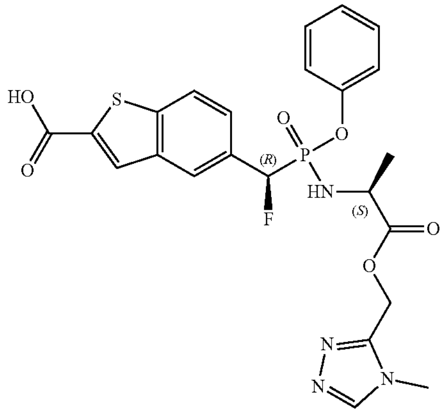 | 533 [M + H]$^+$ |
| 5-((1R)-fluoro((((S)-3-methoxy-1-(2-methoxyethoxy)-1-oxopropan-2-yl)amino)(phenoxy)phosphoryl)methyl)benzo[b]thiophene-2-carboxylic acid | 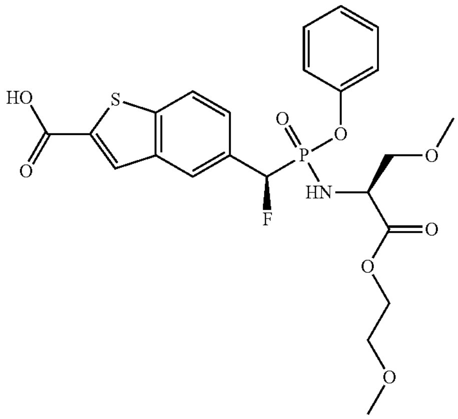 [SMILES: COCCOC(=O)[C@H](COC)NP(=O)(Oc1ccccc1)[C@@H](F)c1ccc2sc(C(=O)O)cc2c1] | 526 [M + H]$^+$ |
| 5-((1R)-fluoro((((S)-1-(2-methoxyethoxy)-1-oxopropan-2-yl)amino)(phenoxy)phosphoryl)methyl)benzo[b]thiophene-2-carboxylic acid | 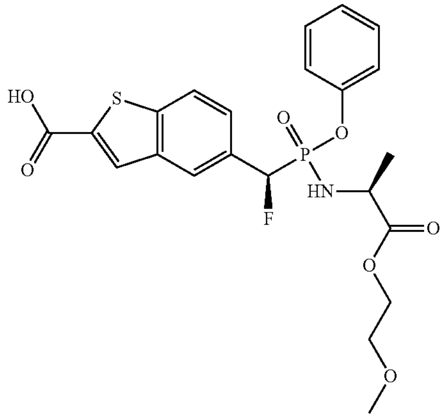 [SMILES: COCCOC(=O)[C@H](C)NP(=O)(Oc1ccccc1)[C@@H](F)c1ccc2sc(C(=O)O)cc2c1] | 496 [M + H]$^+$ |
| 5-((1R)-fluoro((((S)-1-(2-methoxyethoxy)-1-oxopropan-2-yl)amino)(2,2,2-trifluoroethoxy)phosphoryl)methyl)benzo[b]thiophene-2-carboxylic acid | 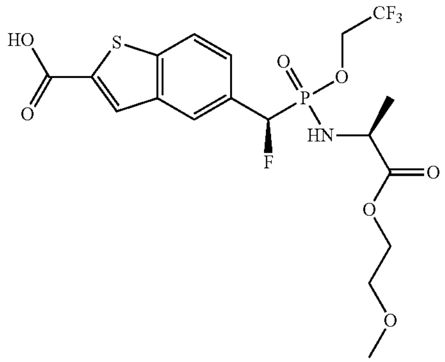 [SMILES: COCCOC(=O)[C@H](C)NP(=O)(OCC(F)(F)F)[C@@H](F)c1ccc2sc(C(=O)O)cc2c1] | 502 [M + H]$^+$ |

-continued

| Name | Structure | LCMS |
| --- | --- | --- |
| 5-((1R)-fluoro((((S)-1-oxo-1-propoxypropan-2-yl)amino)(phenoxy)phosphoryl)methyl)benzo[b]thiophene-2-carboxylic acid | 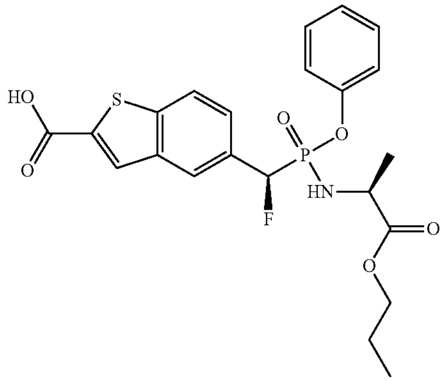 [SMILES: CCCOC(=O)[C@H](C)NP(=O)(Oc1ccccc1)[C@@H](F)c1ccc2sc(C(=O)O)cc2c1] | 480 [M + H]+ |
| 5-((1R)-fluoro((((S)-3-methoxy-1-oxo-1-propoxypropan-2-yl)amino)(phenoxy)phosphoryl)methyl)benzo[b]thiophene-2-carboxylic acid | 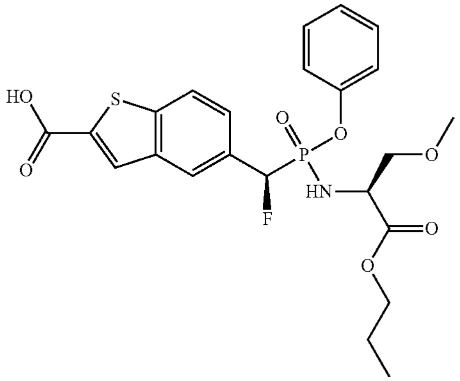 [SMILES: CCCOC(=O)[C@H](COC)NP(=O)(Oc1ccccc1)[C@@H](F)c1ccc2sc(C(=O)O)cc2c1] | 510 [M + H]+ |
| 5-((1R)-fluoro((((S)-1-oxo-1-(pyridin-2-ylmethoxy)propan-2-yl)amino)(phenoxy)phosphoryl)methyl)benzo[b]thiophene-2-carboxylic acid | 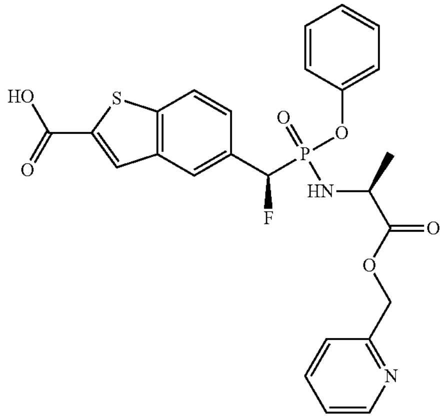 [SMILES: C[C@H](NP(=O)(Oc1ccccc1)[C@@H](F)c1ccc2sc(C(=O)O)cc2c1)C(=O)OCc1ccccn1] | 529 [M + H]+ |
| 5-((1R)-fluoro((((S)-1-isobutoxy-1-oxopropan-2-yl)amino)(phenoxy)phosphoryl)methyl)benzo[b]thiophene-2-carboxylic acid | 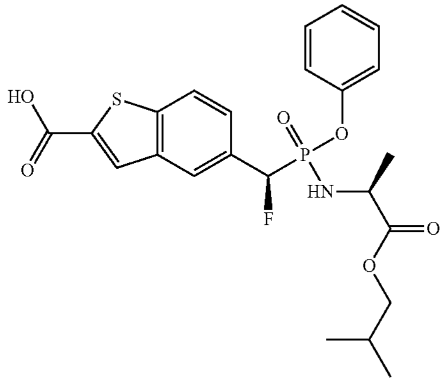 [SMILES: CC(C)COC(=O)[C@H](C)NP(=O)(Oc1ccccc1)[C@@H](F)c1ccc2sc(C(=O)O)cc2c1] | 494 [M + H]+ |

-continued

| Name | Structure | LCMS |
| --- | --- | --- |
| 5-((1R)-((((S)-1-cyclopropoxy-1-oxopropan-2-yl)amino)(phenoxy)phosphoryl)fluoro-methyl)benzo[b]thiophene-2-carboxylic acid | 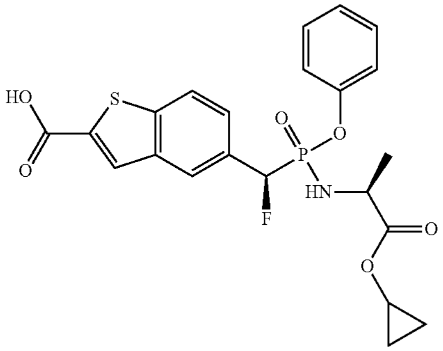 [SMILES: C[C@H](NP(=O)(Oc1ccccc1)[C@@H](F)c1ccc2sc(C(=O)O)cc2c1)C(=O)OC1CC1] | 478 [M + H]$^+$ |
| 5-((1R)-((((S)-1-(2-ethylbutoxy)-1-oxopropan-2-yl)amino)(phenoxy)phosphoryl)fluoro-methyl)benzo[b]thiophene-2-carboxylic acid | 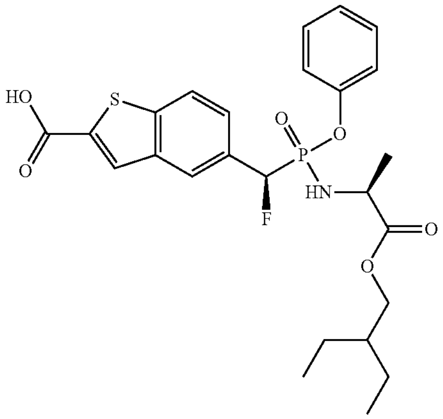 [SMILES: CCC(CC)COC(=O)[C@H](C)NP(=O)(Oc1ccccc1)[C@@H](F)c1ccc2sc(C(=O)O)cc2c1] | 522 [M + H]$^+$ |
| 5-((1R)-((((S)-1-(benzyloxy)-1-oxopropan-2-yl)amino)(phenoxy)phosphoryl)fluoro-methyl)benzo[b]thiophene-2-carboxylic acid | 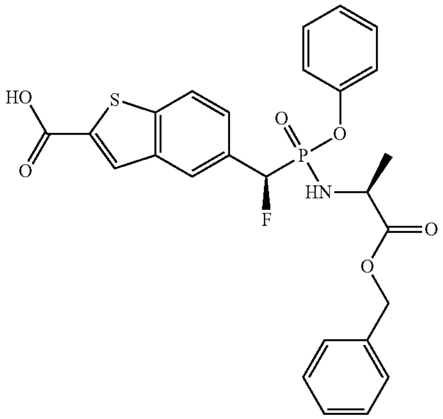 [SMILES: C[C@H](NP(=O)(Oc1ccccc1)[C@@H](F)c1ccc2sc(C(=O)O)cc2c1)C(=O)OCc1ccccc1] | 528 [M + H]$^+$. |

-continued

| Name | Structure | LCMS |
| --- | --- | --- |
| 5-((1R)-((2,6-dimethylphenoxy)(((S)-1-oxo-1-propoxypropan-2-yl)amino)phosphoryl)fluoromethyl)benzo[b]thiophene-2-carboxylic acid | 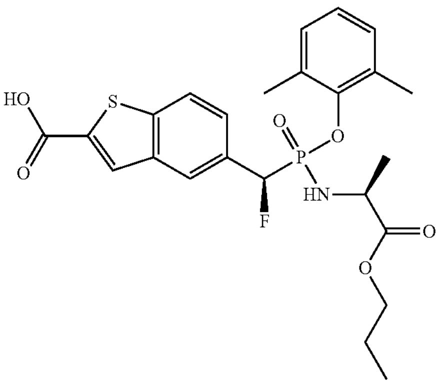 [SMILES: CCCOC(=O)[C@H](C)NP(=O)(Oc1c(C)cccc1C)[C@@H](F)c1ccc2sc(C(=O)O)cc2c1] | 508 [M + H]$^+$ |

Synthesis of 5-((1R)-fluoro((3-(2-methoxyethoxy)phenoxy)(((S)-1-oxo-1-propoxypropan-2-yl)amino)phosphoryl)methyl)benzo[b]thiophene-2-carboxylic acid

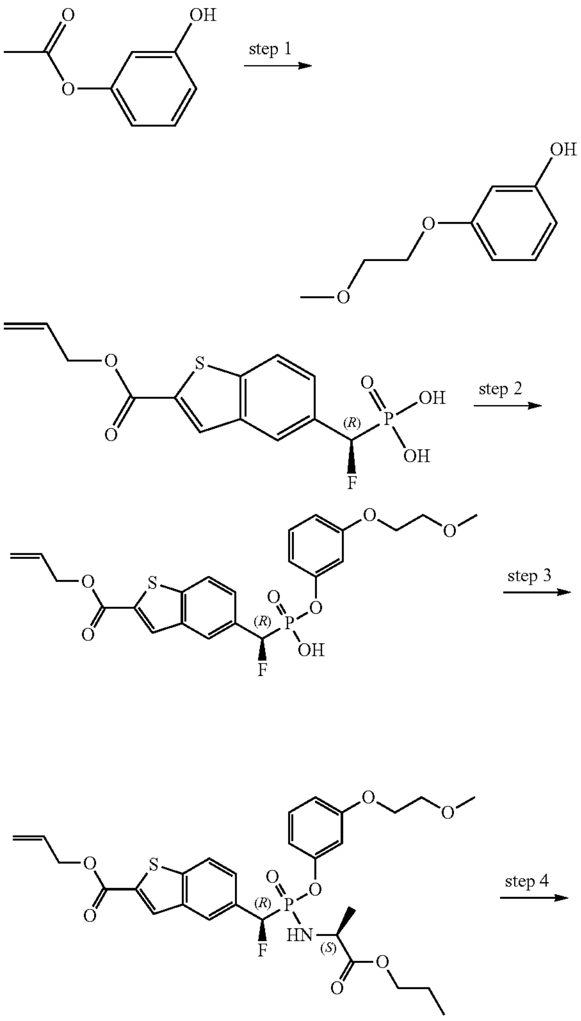

-continued

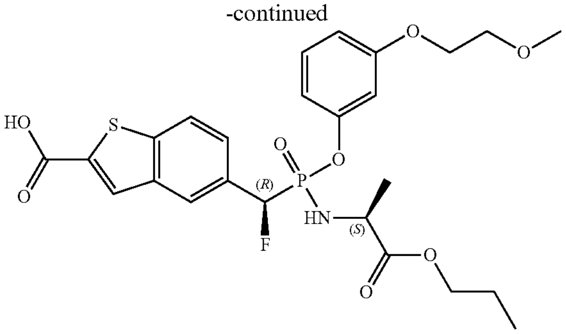

Step 1: Preparation of 3-(2-methoxyethoxy)phenol

To a solution of 3-hydroxyphenyl acetate (5 g, 32.9 mmol, 1.0 eq.) and $K_2CO_3$ (13.6 g, 98.7 mmol, 3.0 eq.) in DMF (100 ml) was added 2-methoxyethyl 4-methylbenzenesulfonate (11.4 g, 49.4 mmol, 1.5 eq.). The mixture was stirred at 80° C. for 4 h. After completion, the reaction was cooled to room temperature and 20% NaOH (aq.) was added into the reaction mixture. The resulting mixture was stirred for 0.5 h and then quenched with HCl (1 N, aq.), diluted with $H_2O$ (100 mL) and extracted with DCM (100 mL×3). The organic layers were combined and washed with brine (100 mL), dried over anhydrous $Na_2SO_4$, and concentrated under reduced pressure. The residue was purified by flash column chromatography on silica gel to afford 3-(2-methoxyethoxy)phenol (4 g, 23.8 mmol, 72%) as a colorless oil. LCMS (ESI): m/z=169 [M+H]$^+$.

Step 2: Preparation of allyl 5-((1R)-fluoro(hydroxy(3-(2-methoxyethoxy)phenoxy)phosphoryl)methyl)benzo[b]thiophene-2-carboxylate Oxalyl chloride (3.82 g, 30.3 mmol, 5 eq.) was added dropwise to a solution of (R)-((2-((allyloxy)carbonyl)benzo[b]thiophen-5-yl)fluoromethyl)phosphonic acid (3, 2 g, 6.06 mmol, 1 eq.) in dry DCM (30 mL) and DMF (1 drop) at 25° C. The reaction mixture was stirred at 40° C. for an additional 0.5 h. The reaction was monitored by pipetting out a small amount of crude sample and quenching it with MeOH to ensure bis-Cl phosphoryl chloride had been formed completely (bis-methoxy phosphonate was observed by LCMS). After completion, the excess oxalyl chloride and solvent were removed under reduced pressure. The residue was re-dissolved in anhydrous DCM (20 mL), then added to a mixture of 3-(2-methoxyethoxy)phenol (1.07 g, 6.36 mmol, 1.05 eq.) and TEA (6.12 g, 60.6 mmol, 10.0 eq.) in anhydrous DCM (10 mL) at 0° C. The reaction was stirred for 0.5 h. After completion, the reaction mixture was concentrated under reduced pressure. The residue was purified by Biotage® C18 column chromatography to give allyl 5-((1R)-fluoro(hydroxy(3-(2-methoxyethoxy)phenoxy)phosphoryl)methyl)benzo[b]thiophene-2-carboxylate (2.00 g, 4.17 mmol, 69%) as a yellow solid. LCMS (ESI): m/z=481 [M+H]$^+$.

Step 3: Preparation of allyl 5-((1R)-fluoro((3-(2-methoxyethoxy)phenoxy)(((S)-1-oxo-1-propoxypropan-2-yl)amino)phosphoryl)methyl)benzo[b]thiophene-2-carboxylate Oxalyl chloride (2.63 g, 20.85 mmol, 5 eq.) was added dropwise to the solution of allyl 5-((1R)-fluoro(hydroxy(3-(2-methoxyethoxy)phenoxy)phosphoryl)methyl)benzo[b]thiophene-2-carboxylate (2 g, 4.17 mmol, 1 eq.) in dry DCM (10 mL) and DMF (1 drop) at 25° C. The reaction mixture was stirred at 40° C. for an additional 0.5 h. The reaction was monitored by pipetting out a small amount of crude sample and quenching it with MeOH to ensure mono-$C_1$ phosphoryl chloride had been formed completely (mono-methoxy phosphonate was observed by LCMS). After completion, the excess oxalyl chloride and solvent were removed under reduced pressure. The residue was re-dissolved in anhydrous DCM (20 mL), then added to a mixture of propyl L-alaninate (1.09 g, 8.34 mmol, 2.0 eq.) and TEA (4.21 g, 41.7 mmol, 10.0 eq.) in anhydrous DCM (20 mL) at 0° C. The reaction was stirred for 0.5 h. After completion, the reaction mixture was concentrated under reduced pressure. The residue was purified by Biotage® C18 column chromatography to give allyl 5-((1R)-fluoro((3-(2-methoxyethoxy)phenoxy)(((S)-1-oxo-1-propoxypropan-2-yl)amino)phosphoryl)methyl)benzo[b]thiophene-2-carboxylate (1.8 g, 3.04 mmol, 73%) as a yellow solid. LCMS (ESI): m/z=594 [M+H]$^+$.

Step 4: 5-((1R)-fluoro((3-(2-methoxyethoxy)phenoxy)(((S)-1-oxo-1-propoxypropan-2-yl)amino)phosphoryl)methyl)benzo[b]thiophene-2-carboxylic acid To a solution of allyl 5-((1R)-fluoro((3-(2-methoxyethoxy)phenoxy)(((S)-1-oxo-1-propoxypropan-2-yl)amino)phosphoryl)methyl)benzo[b]thiophene-2-carboxylate (900 mg, 1.52 mmol, 1.0 eq) in DCM (6 mL) were added $Pd(PPh_3)_4$ (175 mg, 152 μmol, 0.1 eq.) and pyrrolidine (109 mg, 1.52 mmol, 1.0 eq.). The mixture was purged and degassed with $N_2$ three times, then stirred at 25° C. for 1 hr. After completion, the mixture was concentrated under reduced pressure. The residue was purified by Biotage® C18 column chromatography to give 5-((1R)-fluoro((3-(2-methoxyethoxy)phenoxy)(((S)-1-oxo-1-propoxypropan-2-yl)amino)phosphoryl)methyl)benzo[b]thiophene-2-carboxylic acid (370 mg, 0.67 mmol, 44%) as a white solid. LCMS (ESI): m/z=554 [M+H]$^+$.

Synthesis of perfluorophenyl 5-(fluoro((((S)-1-oxo-1-(3,3,3-trifluoropropoxy)propan-2-yl)amino)(phenoxy)phosphoryl)methyl)benzo[b]thiophene-2-carboxylate

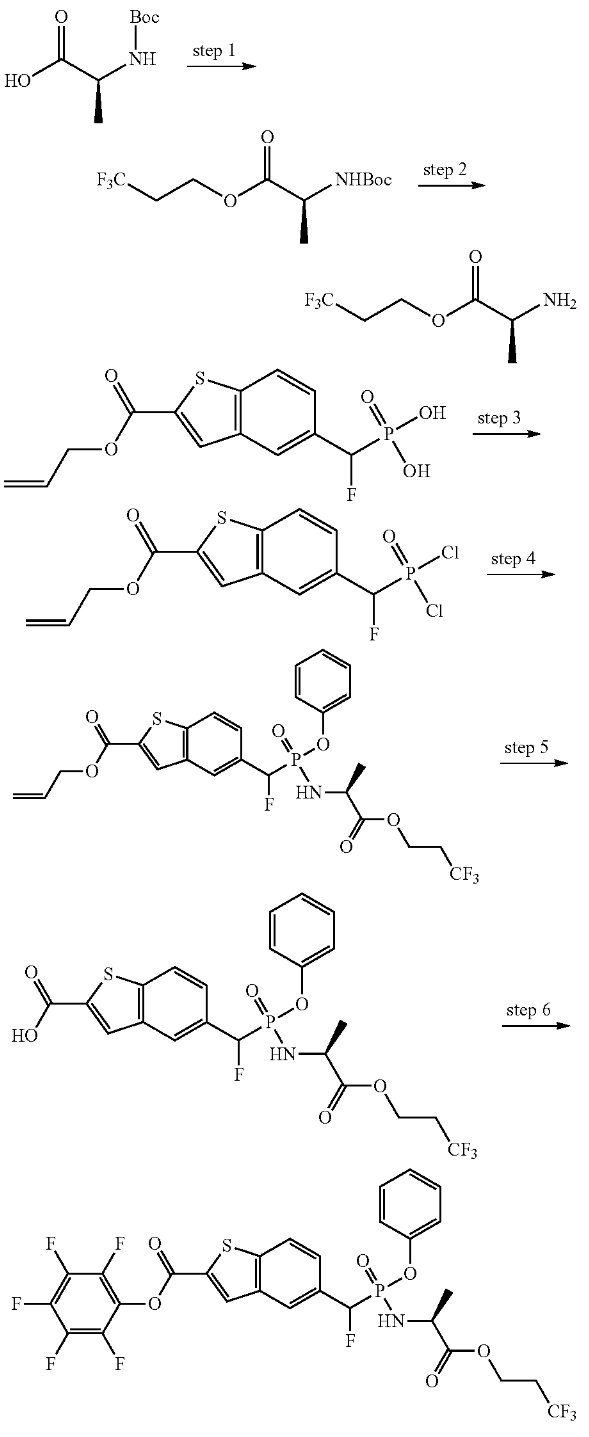

Step 1: Preparation of (S)-3,3,3-trifluoropropyl 2-((tert-butoxycarbonyl)amino)propanoate To a solution of (S)-2-((tert-butoxycarbonyl)amino)propanoic acid (5 g, 26.4 mmol, 1 eq) in dimethylformamide (50 mL) was added 3-chloro-1,1,1-trifluoropropane (10 g, 79 mmol, 3 eq) and $K_2CO_3$ (7.3 g, 53 mmol, 2 eq). The mixture was stirred at 60° C. for 16 h to give a white suspension. The mixture was diluted with water (250 mL) and extracted with EtOAc (1 L×3), the combined organic layers were washed with saturated brine (1 L×3), dried over $Na_2SO_4$, filtered and concentrated under reduced pressure to give a residue. The residue was purified by flash silica gel chromatography to give a (S)-3,3,3-trifluoropropyl 2-((tert-butoxycarbonyl)amino)propanoate (4.5 g, 15 mmol, 20% yield) as an off-white solid. LCMS (ESI) m/z=286.1 $[M+H]^+$.

Step 2: Preparation of (S)-3,3,3-trifluoropropyl 2-aminopropanoate

The (S)-3,3,3-trifluoropropyl 2-((tert-butoxycarbonyl)amino)propanoate (2 g, 7.0 mmol, 1 eq) was dissolved in DCM (20 mL) and HCL/dioxane (20 mL), the reaction solution was stirred at 25° C. for 1 h. The reaction mixture was concentrated under reduced pressure to give a (S)-3,3,3-trifluoropropyl 2-aminopropanoate (1.1 g, crude) as an off-white solid. $^1H$ NMR (400 MHz, $CD_3OD$) δ 4.59-4.40 (m, 2H), 4.15 (q, J=7.2 Hz, 1H), 2.75-2.61 (m, 2H), 1.56 (d, J=7.2 Hz, 3H).

Step 3: Preparation of allyl 5-((dichlorophosphoryl)fluoromethyl)benzo[b]thiophene-2-carboxylate To a solution of ((2-((allyloxy)carbonyl)benzo[b]thiophen-5-yl)fluoromethyl)phosphonic acid (0.90 g, 2.7 mmol, 1 eq) in DCM (9 mL) was added N,N-dimethylformamide (20 mg, 0.27 mmol, 0.1 eq) at 25° C., then cooled to 0° C., then oxalic dichloride (1.2 g, 9.5 mmol, 3.5 eq) was added at 0° C., then stirred at 40° C. for 0.5 h. The reaction mixture was concentrated under reduced pressure to give 5-((dichlorophosphoryl)fluoromethyl)benzo[b]thiophene-2-carboxylate (1.0 g, crude) as a yellow oil. LCMS (ESI) m/z=368.0 $[M+H]^+$.

Step 4: Preparation of allyl 5-(fluoro((((S)-1-oxo-1-(3,3,3-trifluoropropoxy)propan-2-yl)amino)(phenoxy)phosphoryl)methyl)benzo[b]thiophene-2-carboxylate To a solution of allyl 5-((dichlorophosphoryl)fluoromethyl)benzo[b]thiophene-2-carboxylate (1.0 g, 2.7 mmol, 1 eq) in DCM (4 mL), the solution was under $N_2$ and cooled to 0° C., then phenol (0.20 g, 2.2 mmol, 0.8 eq) in DCM (4 mL) was added in it, ethylbis(propan-2-yl)amine (1.4 g, 11 mmol, 4 eq) in DCM (20 mL) was dropwise added in it and stirred at 0° C. for 5 min, (S)-3,3,3-trifluoropropyl 2-aminopropanoate (0.60 g, 3.3 mmol, 1.2 eq) in DCM (4 mL) was added in it and stirred at 0° C. for 10 min to give a yellow solution. The reaction mixture was concentrated under reduced pressure to give a residue. The residue was purified by flash silica gel chromatography to give a product 5-(fluoro((((S)-1-oxo-1-(3,3,3-trifluoropropoxy)propan-2-yl)amino)(phenoxy)phosphoryl)methyl)benzo[b]thiophene-2-carboxylate (0.70 g, 1.2 mmol, 44% yield) as a white solid. LCMS (ESI) m/z=574.1

Step 5: Preparation of 5-(fluoro((((S)-1-oxo-1-(3,3,3-trifluoropropoxy)propan-2-yl)amino)(phenoxy)phosphoryl)methyl)benzo[b]thiophene-2-carboxylic acid To a solution of 5-(fluoro((((S)-1-oxo-1-(3,3,3-trifluoropropoxy)propan-2-yl)amino)(phenoxy)phosphoryl)methyl)benzo[b]thiophene-2-carboxylate (0.58 g, 1.0 mmol, 1 eq) and $Pd(PPh_3)_4$ (0.17 g, 0.15 mmol, 1.5 eq) in DCM (5 mL) was added pyrrolidine (50 mg, 0.71 mmol, 0.7 eq) at 0° C. The mixture was stirred at 25° C. for 0.5 h to give a yellow suspension. The reaction mixture was filtrated. The filtered and concentrated under reduced pressure to give a residue. The residue was purified by reverse phase (TFA) to lyophilized to give 5-(fluoro((((S)-1-oxo-1-(3,3,3-trifluoropropoxy)propan-2-yl)amino)(phenoxy)phosphoryl)methyl)benzo[b]thiophene-2-carboxylic acid (0.38 g, 0.71 mmol, 70% yield) as a yellow solid. LCMS (ESI) m/z=534.1 $[M+H]^+$.

Step 6: Preparation of perfluorophenyl 5-(fluoro((((S)-1-oxo-1-(3,3,3-trifluoropropoxy)propan-2-yl)amino)(phenoxy)phosphoryl)methyl)benzo[b]thiophene-2-carboxylate To a solution of 5-(fluoro((((S)-1-oxo-1-(3,3,3-trifluoropropoxy)propan-2-yl)amino)(phenoxy)phosphoryl)methyl)benzo[b]thiophene-2-carboxylic acid (0.40 g, 0.75 mmol, 1 eq) in dimethylformamide (4 mL) was added pyridine (0.18 g, 2.2 mmol, 3 eq), then perfluorophenyl 2,2,2-trifluoroacetate (1.0 g, 3.7 mmol, 5 eq) was added in the mixture at 0° C. to give a yellow solution. The mixture was diluted with water (20 mL) and extracted with EtOAc (20 mL×2), the combined organic layers were washed with saturated brine (20 mL×2), dried over $Na_2SO_4$, filtered and concentrated under reduced pressure to give a residue. The residue was purified by column chromatography to give a product perfluorophenyl 5-(fluoro((((S)-1-oxo-1-(3,3,3-trifluoropropoxy)propan-2-yl)amino)(phenoxy)phosphoryl)methyl)benzo[b]thiophene-2-carboxylate (0.45 mg, 0.64 mmol, 86% yield) as a white solid. LCMS (ESI) m/z=700.0 $[M+H]^+$.

Syntheses of perfluorophenyl 5-((diethoxyphosphoryl)difluoromethyl)benzo[b]thiophene-2-carboxylate

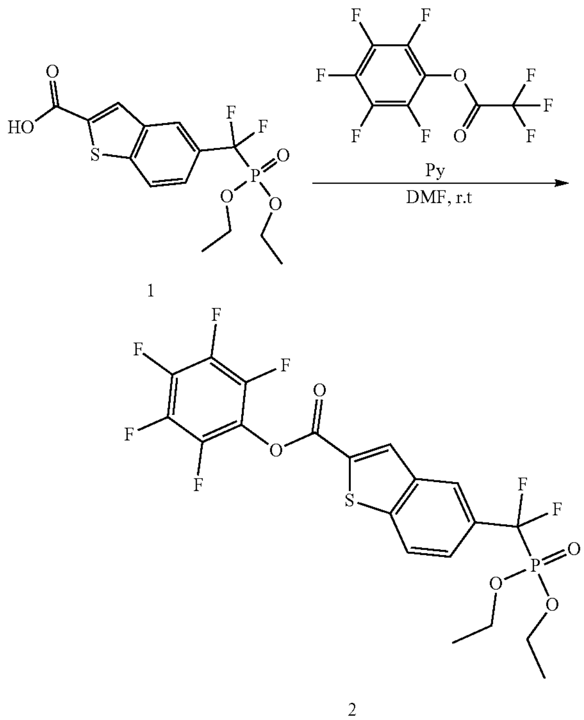

1

2

To a solution of 5-((diethoxyphosphoryl)difluoromethyl)benzo[b]thiophene-2-carboxylic acid (1, 3.64 g, 9.99 mmol, 1 eq.) in DMF (30 mL) were added pyridine (1.60 mL, 19.9 mmol, 2 eq.) and 2,3,4,5,6-pentafluorophenyl 2,2,2-trifluoroacetate (2.55 mL, 14.9 mmol, 1.5 eq.) under $N_2$ with stirring. The resulting mixture was stirred at room temperature for 1 hr. After completion, the reaction mixture was poured into $H_2O$ (20 mL), then extracted with EtOAc (50 mL×3). The organic layers were combined and washed with brine (50 mL), dried over anhydrous $Na_2SO_4$, and concentrated under reduced pressure to afford perfluorophenyl 5-((diethoxyphosphoryl)difluoromethyl)benzo[b]thiophene-2-carboxylate (2, 5.20 g, quant.) as a white solid. LCMS (ESI) m/z=531.0 $[M+H]^+$.

Preparation of 5-(((benzylamino)(((S)-1-isopropoxy-1-oxopropan-2-yl)amino)phosphoryl)methyl)benzo[b]thiophene-2-carboxylic acid

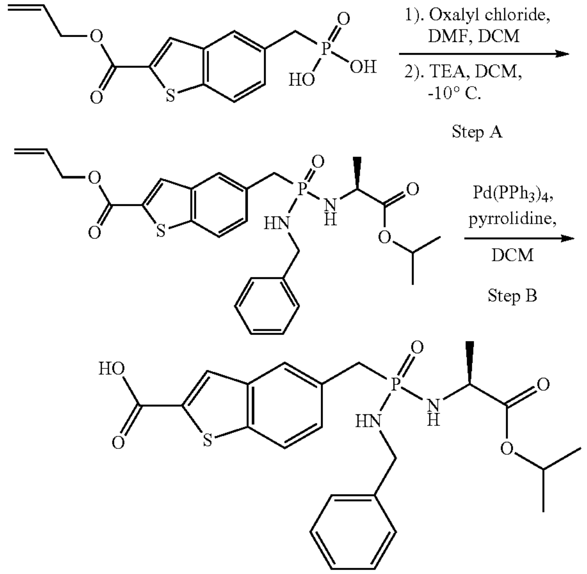

Step A: allyl 5-(((benzylamino)(((S)-1-isopropoxy-1-oxopropan-2-yl)amino)phosphoryl)methyl)benzo[b]thiophene-2-carboxylate Oxalyl chloride (814.4 mg, 6.4 mmol, 10 eq.) was added dropwise to the solution of ((2-((allyloxy)carbonyl)benzo[b]thiophen-5-yl)methyl)phosphonic acid (200 mg, 0.64 mmol, 1.0 eq.) in dry DCM (6 mL) and DMF (1 drop) at 0° C. The reaction was allowed to warm to 40° C., then stirred for additional 1-2 hrs. The reaction was monitored by pipetting out a small amount of crude sample and quenching it with MeOH to ensure bis-Cl phosphoryl chloride allyl 5-((dichlorophosphoryl)methyl)benzo[b]thiophene-2-carboxylate had been formed completely (bis-methoxy phosphonate was observed by LCMS). After completion, the excess of oxalyl chloride and solvent were removed under reduced pressure, and the residue was re-dissolved in anhydrous DCM (5 mL). To the solution was then added $BnNH_2$ (64.8 mg, 0.64 mmol, 1.0 eq.) in anhydrous DCM (2 mL) and $Et_3N$ (194.32 mg, 1.92 mmol, 3.0 eq.) at −40° C. The reaction was monitored by pipetting out a small amount of crude sample and quenching it with MeOH to ensure the most of the product was allyl 5-(((benzylamino)chlorophosphoryl)methyl)benzo[b]thiophene-2-carboxylate (mono-methoxy phosphonate was observed by LCMS). To the solution was then added isopropyl L-alaninate (107.2 mg, 0.64 mmol, 1.0 eq.) in anhydrous DCM (2 mL) at −40° C. The reaction was allowed to warm to room temperature and stirred for additional 2 hrs. After completion, the reaction was quenched by adding $H_2O$ (10 mL), and extracted with DCM (10 mL×3). The organic layers were combined and washed with brine (20 mL), dried over anhydrous $Na_2SO_4$, and concentrated under reduced pressure. The residue was purified by flash column chromatography on silica gel to afford allyl 5-(((benzylamino)(((S)-1-isopropoxy-1-oxopropan-2-yl)amino)phosphoryl)methyl)benzo[b]thiophene-2-carboxylate (100 mg, 194.33 μmol, 30%). LCMS (ESI): m/z=515.2 $[M+H]^+$.

Step B: 5-(((benzylamino)(((S)-1-isopropoxy-1-oxopropan-2-yl)amino)phosphoryl)methyl)benzo[b]thiophene-2-carboxylic acid A solution of allyl 5-(((benzylamino)(((S)-1-isopropoxy-1-oxopropan-2-yl)amino)phosphoryl)methyl)benzo[b]thiophene-2-carboxylate (100 mg, 194 μmol, 1 eq.), $Pd(PPh_3)_4$ (22.47 mg, 19.4 μmol, 0.1 eq.) and pyrrolidine (13.8 mg, 194 μmol, 1 eq.) in DCM (3 mL) was stirred at room temperature for 1 hr. After completion, the reaction mixture was concentrated under reduced pressure. The residue was purified by flash column chromatography on silica gel to afford 5-(((benzylamino)(((S)-1-isopropoxy-1-oxopropan-2-yl)amino)phosphoryl)methyl)benzo[b]thiophene-2-carboxylic acid (70 mg, 147.5 μmol, 76%). LCMS (ESI): m/z=475.1 $[M+H]^+$.

Synthesis of 5-((bis(((S)-1-isopropoxy-1-oxopropan-2-yl)amino)phosphoryl)methyl)benzo[b]thiophene-2-carboxylic acid

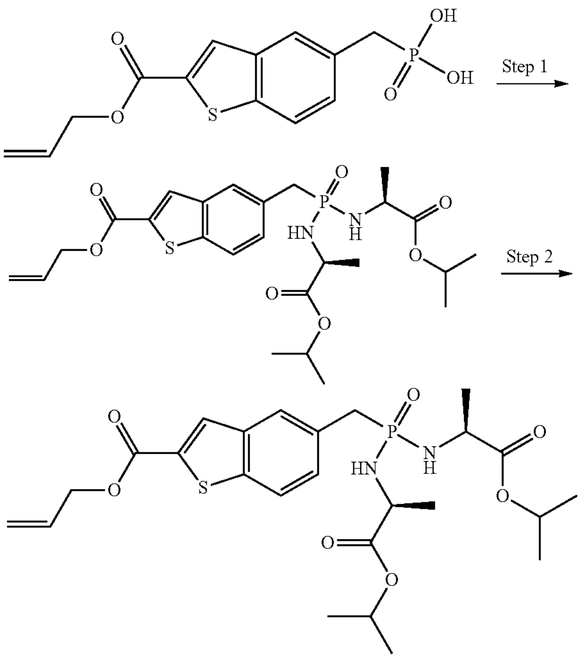

Step 1: Preparation of diisopropyl 2,2'-((((2-((allyloxy)carbonyl)benzo[b]thiophen-5-yl)methyl)phosphoryl)bis(azanediyl))(2S,2'S)-dipropionate To a solution of ((2-((allyloxy)carbonyl)benzo[b]thiophen-5-yl)methyl)phosphonic acid (300 mg, 960 µmol, 1.0 eq.) in dry DCM (10 mL) and DMF (cat.) at 0° C. was added oxalyl chloride (609 mg, 4.80 mmol, 5.0 eq.) dropwise. The reaction mixture was allowed to warm to 40° C., then stirred for additional 1-2 h. The reaction was monitored by pipetting out a small amount of crude sample and quenching it with MeOH to ensure bis-Cl phosphoryl chloride had been formed completely (bis-methoxy phosphonate was observed by LCMS). After completion, the excess of oxalyl chloride and solvent were removed under reduced pressure, and the residue was re-dissolved in anhydrous DCM (5 mL). This solution was then added to a mixture of isopropyl L-alaninate (502 mg, 3.83 mmol, 4.0 eq.) and N,N-diisopropylethylamine (620 mg, 4.80 mmol, 5.0 eq.) in anhydrous DCM (10 mL) at 0° C. The reaction was allowed to warm to room temperature and stirred for additional 18 h. The progress was monitored by LCMS. After completion, the reaction was quenched by adding $H_2O$ (10 mL) and extracted with DCM (10 mL×3). The organic layers were combined and washed with brine (20 mL), dried over anhydrous $Na_2SO_4$, and concentrated under reduced pressure. The residue was purified by flash column chromatography on silica gel to afford diisopropyl 2,2'-((((2-((allyloxy)carbonyl)benzo[b]thiophen-5-yl)methyl)phosphoryl)bis(azanediyl))(2S,2'S)-dipropionate (70.0 mg, 129 µmol, 14% yield). LCMS (ESI): m/z=539.2 $[M+H]^+$.

Step 2: Preparation of 5-((bis(((S)-1-isopropoxy-1-oxopropan-2-yl)amino)phosphoryl)methyl)benzo[b]thiophene-2-carboxylic acid To a solution of diisopropyl 2,2'-((((2-((allyloxy)carbonyl)benzo[b]thiophen-5-yl)methyl)phosphoryl)bis(azanediyl))(2S,2'S)-dipropionate (70 mg, 129 µmol, 1.0 eq.) in DCM (1 mL) was added pyrrolidine (9.17 mg, 129 µmol, 1.0 eq.) and $Pd(PPh_3)_4$ (14.9 mg, 12.9 µmol, 0.1 eq.) under $N_2$, and the resulting mixture was stirred at room temperature for 2 h. After completion, the reaction mixture was cooled down in an ice-bath, then neutralized carefully with HCl (aq. 1M) until the pH was adjusted to pH=4-6. The resulting mixture was extracted with DCM (10 mL×3), and the combined organic layers were washed with brine (10 mL×2), dried over anhydrous $Na_2SO_4$, then concentrated under reduced pressure. The residue was purified by Biotage® C18 column chromatography to give 5-((bis(((S)-1-isopropoxy-1-oxopropan-2-yl)amino)phosphoryl)methyl)benzo[b]thiophene-2-carboxylic acid (70.0 mg, 140 µmol, 108%, 60% purity) as a colorless oil. LCMS (ESI): m/z=499.2 $[M+H]^+$.

Synthesis of 5-(difluoro(((2-isopropoxy-2-oxoethyl)amino)(phenoxy)phosphoryl)methyl)benzo[b]thiophene-2-carboxylic acid

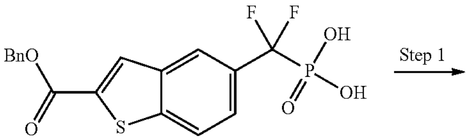

-continued

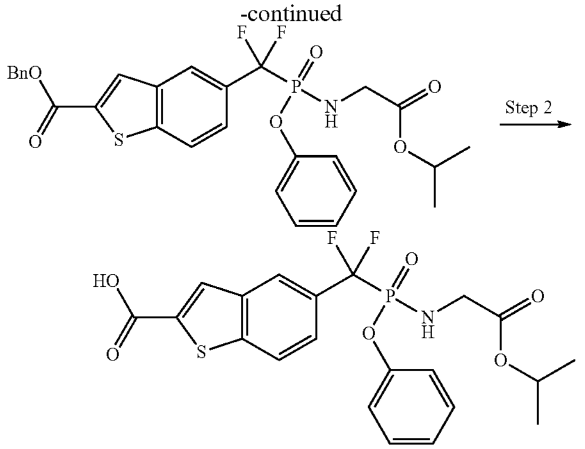

Step 1: Preparation of benzyl 5-(difluoro(((2-isopropoxy-2-oxoethyl)amino)(phenoxy)phosphoryl)methyl)benzo[b]thiophene-2-carboxylate To a solution of ((2-((benzyloxy)carbonyl)benzo[b]thiophen-5-yl)difluoromethyl)phosphonic acid (300 mg, 753 µmol, 1 eq) in methylene chloride (8 mL) at 0° C. was added 2 drops of DMF (cat.) followed by dropwise addition of oxalyl chloride (192 µL, 2.25 mmol, 3 eq). The reaction was warmed up to room temperature and stirred for 2 h. The reaction was not soluble at first but became a clear solution upon adding oxalyl chloride and warming up to room temperature. The reaction was concentrated under reduced pressure. Then, the latter was diluted in methylene chloride (8 mL) and the solution was cooled down to −78° C. A solution of phenol (56.6 mg, 602 µmol, 0.8 eq) and triethylamine (155 µL, 1.12 mmol, 1.5 eq) in DCM (1 mL) was slowly added on the yellow solution over 5 min. The reaction mixture was stirred at −78° C. for 15 min., then warmed up to room temperature and stirred for 2 h. The reaction mixture was cooled down to −78° C. A solution of propan-2-yl 2-aminoacetate (88.2 mg, 753 µmol, 1 eq) and triethylamine (155 µL, 1.12 mmol, 1.5 eq) in DCM (1 mL) was slowly added on the yellow solution over 5 min. The reaction mixture was stirred at −78° C. for 15 min., then warmed up to room temperature and stirred for 18 h. Water (2-3 drops) was added and the reaction was concentrated under reduced pressure. The crude residue was purified by reverse phase chromatography on a 50 g Cis cartridge eluting with 5-100% MeCN in water (with 0.1% formic acid) to give benzyl 5-(difluoro(((2-isopropoxy-2-oxoethyl)amino)(phenoxy)phosphoryl)methyl)benzo[b]thiophene-2-carboxylate (90.0 mg, 156 µmol, 20.8% yield) as a yellow oil. LCMS: m/z=574.2 $[M+H]^+$.

Step 2: Preparation of 5-(difluoro(((2-isopropoxy-2-oxoethyl)amino)(phenoxy)phosphoryl)methyl)benzo[b]thiophene-2-carboxylic acid To a solution of benzyl 5-(difluoro(((2-isopropoxy-2-oxoethyl)amino)(phenoxy)phosphoryl)methyl)benzo[b]thiophene-2-carboxylate (90 mg, 156 µmol, 1 eq) in anhydrous tetrahydrofuran (10 mL) under nitrogen was added 10% palladium on carbon (50% wet) (166 mg, 78.0 µmol, 0.5 eq). Hydrogen was bubbled for 5 min. and the reaction mixture was stirred at room temperature for 18 h under hydrogen (1 atm). Nitrogen was bubbled int the mixture and it was then filtered over Celite (rinsing with 2-MeTHF) and concentrated under reduced pressure. The isolated product 5-(difluoro(((2-isopropoxy-2-oxoethyl)amino)(phenoxy) phosphoryl)methyl)benzo[b]thiophene-2-carboxylic acid was used without further purification. LCMS: m/z=484.2 $[M+H]^+$.

The intermediates in the table below were prepared according to the procedure described for the synthesis of 5-(difluoro(((2-isopropoxy-2-oxoethyl)amino)(phenoxy) phosphoryl)methyl)benzo[b]thiophene-2-carboxylic acid utilizing the appropriate starting materials.

| Name | Structure | LCMS; NMR |
|---|---|---|
| 5-(difluoro((((S)-3-isopropoxy-2-methyl-3-oxopropyl)amino)(phenoxy)phosphoryl) methyl)benzo[b]thiophene-2-carboxylic acid | 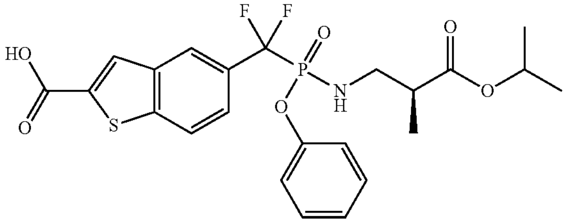 [SMILES: CC(C)OC(=O)[C@@H](C)CNP(=O)(Oc1ccccc1)C(F)(F)c1ccc2sc(C(=O)O)cc2c1] | 512.4 $[M + H]^+$ |
| 5-(difluoro((((S)-1-isopropoxy-1-oxo-3-phenylpropan-2-yl)amino)(phenoxy) phosphoryl)methyl) benzo[b]thiophene-2-carboxylic acid | 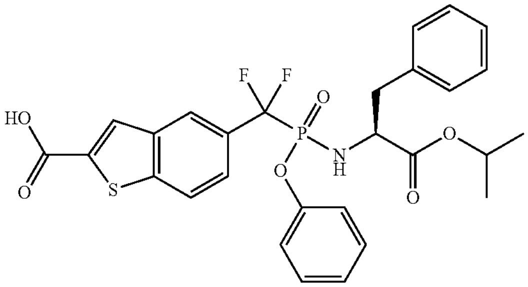 [SMILES: CC(C)OC(=O)[C@H](Cc1ccccc1)NP(=O)(Oc1ccccc1)C(F)(F)c1ccc2sc(C(=O)O)cc2c1] | 574.2 $[M + H]^+$ |
| 5-(((((S)-1-(benzyloxy)-1-oxo-4-phenylbutan-2-yl)amino)(phenoxy) phosphoryl)difluoromethyl)benzo[b]thiophene-2-carboxylic acid | 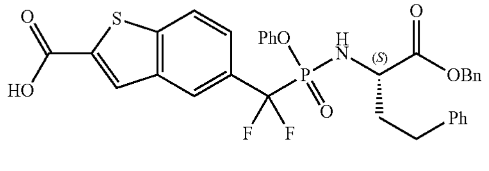 | 636.4 [M+H]+ |
| 5-(((((S)-1-(benzyloxy)-4-methyl-1-oxopentan-2-yl)amino)(phenoxy) phosphoryl)difluoromethyl)benzo[b]thiophene-2-carboxylic acid | 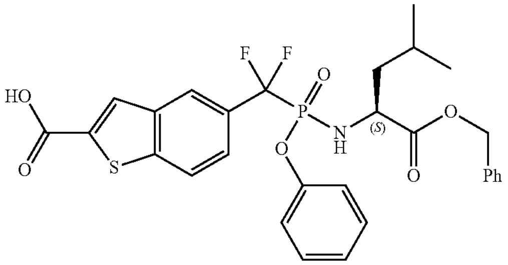 | (400 MHz, DMSO-$d_6$) δ 13.67 (br. s., 1H), 8.28-8.13 (m, 3H), 7.73-7.63 (m, 1H), 7.42-7.27 (m, 7H), 7.23-7.06 (m, 3H), 6.79 (td, J = 14.9, 10.6 Hz, 1H), 5.09-4.88 (m, 2H), 3.88-3.64 (m, 1H), 1.49-1.28 (m, 3H), 0.72-0.54 (m, 6H); 588.2 [M + H]+ |

Synthesis of perfluorophenyl 5-((1R)-(ethoxy((2-methyl-1-oxo-1-propoxypropan-2-yl)amino)phosphoryl)fluoromethyl)benzo[b]thiophene-2-carboxylate

Step A: propyl 2-((tert-butoxaycarbonyl)amino)-2-methylpropanoate

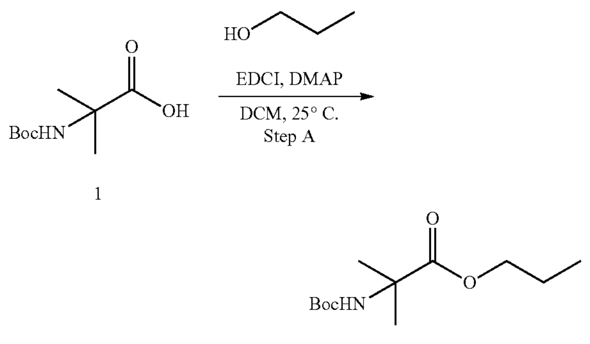

1

2

To a solution of 2-((tert-butoxycarbonyl)amino)-2-methylpropanoic acid (1, 2.0 g, 9.8 mmol, 1.0 eq.), EDCI (2.8 g, 14.7 mmol, 1.5 eq.) and DMAP (1.79 g, 14.7 mmol, 1.5 eq.) in DCM (30 mL) was added propan-1-ol (588 mg, 9.8 mmol, 1.0 eq.). The reaction mixture was stirred at 25° C. for 12 hrs. After completion, the mixture was diluted with water (30 mL) and extracted with DCM (30 mL×3), the organic layers were washed with saturated brine (30 mL×2), dried over anhydrous $Na_2SO_4$ and concentrated under reduced pressure. The residue was purified by flash chromatography on C18 (20%-80% ACN in $H_2O$) to afford propyl 2-((tert-butoxycarbonyl)amino)-2-methylpropanoate (2, 2.2 g, 9.0 mmol, 92%) as a colorless oil. LCMS (ESI): m/z=246 $[M+H]^+$.

Step B: propyl 2-amino-2-methylpropanoate hydrochloride

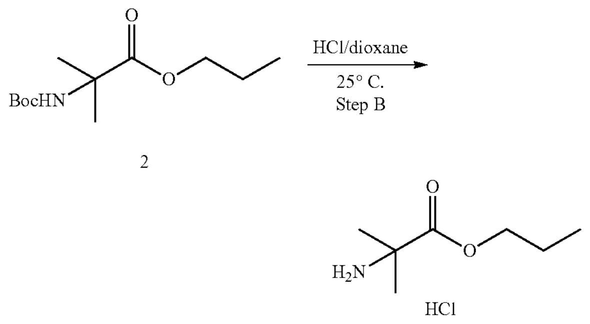

2

3

A solution of propyl 2-((tert-butoxycarbonyl) amino)-2-methylpropanoate (2, 2.2 g, 9.0 mmol, 1.0 eq.) in 4M HCl/dioxane (20 mL) was stirred at 25° C. for 2 hrs. After completion, the reaction mixture was concentrated under reduced pressure to give propyl 2-amino-2-methylpropanoate hydrochloride (3, 1.63 g, 9.0 mmol, crude) as a white solid, which was used in the next step directly without further purification. LCMS (ESI): m/z=146 $[M+H]^+$.

Step C: (R)-((2-((allyloxy)carbonyl)benzo[b]thiophen-5-yl)fluoromethyl)phosphonic acid

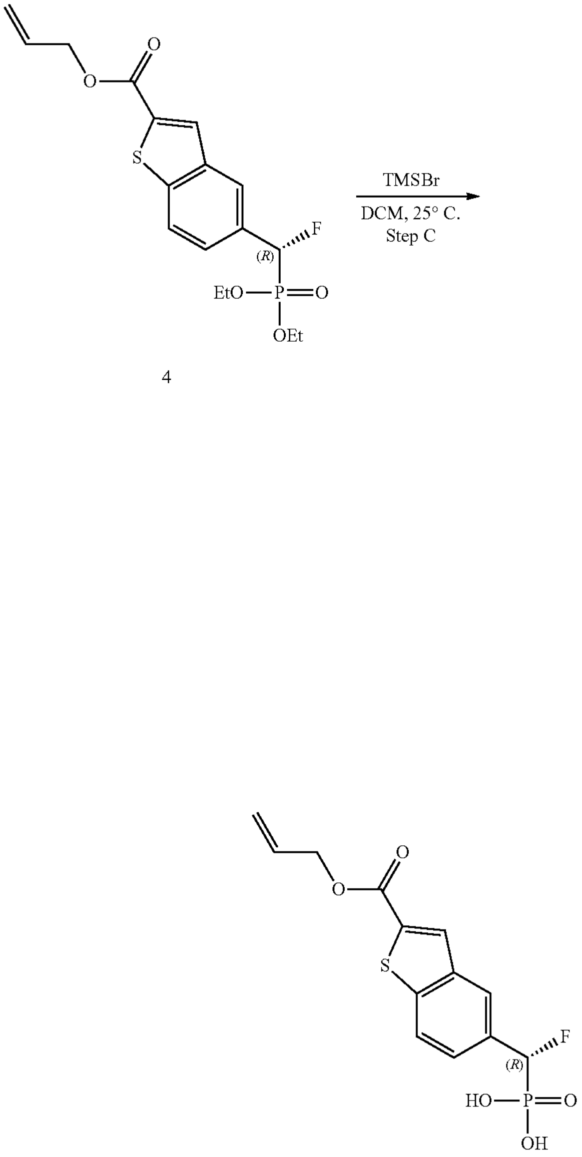

4

5

To a solution of methyl allyl (R)-5-((diethoxyphosphoryl)fluoromethyl)benzo[b]thiophene-2-carboxylate (4, 50 g, 130 mmol, 1.0 eq.) in DCM (500 mL) was added TMSBr (100 ml, 766 mol, 5.9 eq.). The resulting mixture was stirred at 25° C. for 16 hrs. After completion, the mixture was concentrated under reduced pressure. The residue was purified by flash chromatography on C18 to give (R)-((2-((allyloxy)carbonyl)benzo[b]thiophen-5-yl)fluoromethyl) phosphonic acid (5, 35 g, 106 mmol, 81%) as a white solid. LCMS (ESI): m/z=331 $[M+H]^+$.

Step D: allyl 5-((1R)-(ethoxy((2-methyl-1-oxo-1-propoxypropan-2-yl)amino)phosphoryl)fluoromethyl)benzo[b]thiophene-2-carboxylate

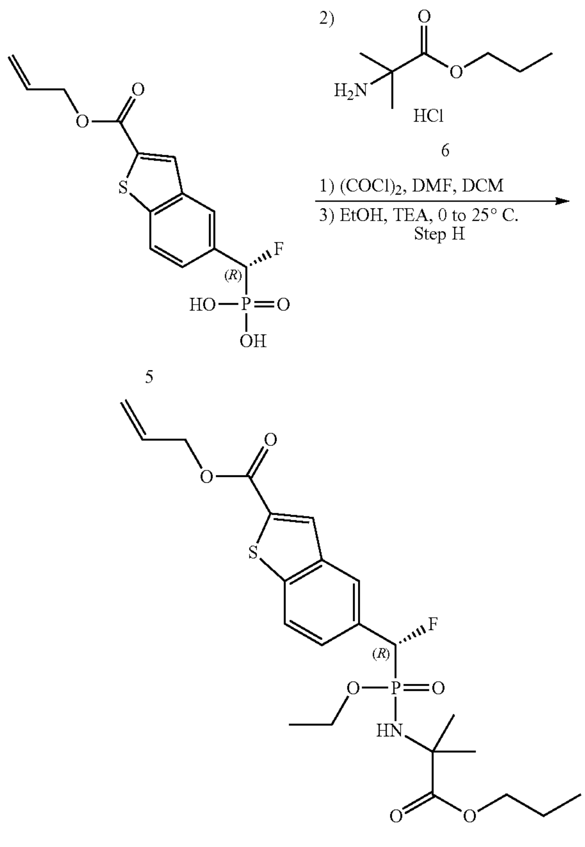

To a solution of allyl 5-((1R)-(ethoxy((2-methyl-1-oxo-1-propoxypropan-2-yl)amino)phosphoryl)fluoromethyl) benzo[b]thiophene-2-carboxylate (5, 5 g, 15.2 mmol, 1.0 eq.) in DCM (60 mL) were added oxalyl chloride (9.6 g, 75.6 mmol, 5.0 eq.) and DMF (0.1 mL) at 25° C. The reaction mixture was stirred at 25° C. for 2 hrs under $N_2$ atmosphere. The reaction solvent was removed under reduce pressure, the residue was dissolved in DCM (60 mL), triethylamine (7.73 g, 76.5 mmol, 5 eq.) was added to the above mixture at 0° C., then a solution of propyl 2-amino-2-methylpropanoate hydrochloride (6, 3.04 g, 16.7 mmol, 1.1 eq.) in DCM (10 mL) was added to the above mixture dropwise at 0° C. EtOH (6.7 g, 76.5 mmol, 5.0 eq.) was added dropwise after the reaction was stirred at 0° C. for 30 min under $N_2$ atmosphere. The reaction mixture was stirred at 25° C. for 16 hrs under $N_2$ atmosphere. After completion, the reaction mixture was poured into water (100 mL) and extracted with DCM (100 mL×2), the combined organic layers were washed with brine (100 mL), dried over anhydrous $Na_2SO_4$ and concentrated under reduced pressure. The residue was purified by flash chromatography on C18 to give allyl 5-((1R)-(ethoxy((2-methyl-1-oxo-1-propoxypropan-2-yl)amino)phosphoryl)fluoromethyl)benzo[b]thiophene-2-carboxylate (7, 3.0 g, 6.18 mmol, 40%) as a yellow solid. LCMS (ESI): m/z=486 $[M+H]^+$.

Step E: 5-((1R)-(ethoxy((2-methyl-1-oxo-1-propoxypropan-2-yl)amino)phosphoryl)fluoromethyl)benzo[b]thiophene-2-carboxylic acid

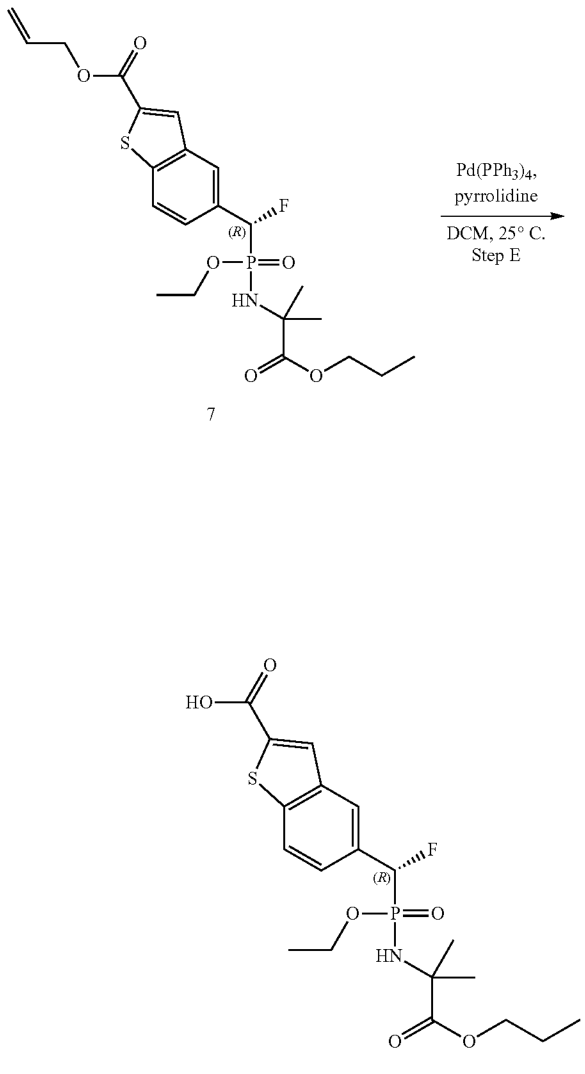

To a solution of allyl 5-((1R)-(ethoxy((2-methyl-1-oxo-1-propoxypropan-2-yl)amino)phosphoryl)fluoromethyl) benzo[b]thiophene-2-carboxylate (7, 3.0 g, 6.18 mmol, 1.0 eq.) and pyrrolidine (439 mg, 6.18 mmol, 1.0 eq.) in DCM (30 mL) was added, $Pd(PPh_3)_4$ (358 mg, 0.31 mmol, 0.05 eq.). The resulting mixture was stirred at 25° C. for 0.5 hrs under $N_2$ atmosphere. After completion, the mixture was adjusted to pH=5 with 1N HCl. The reaction mixture was poured into water (30 mL) and extracted with DCM (30 mL×2), the combined organic layers were washed with brine (30 mL), dried over anhydrous $Na_2SO_4$ and concentrated under reduced pressure to afford 5-((1R)-fluoro((((S)-1-((1s,3R)-3-fluorocyclobutoxy)-1-oxopropan-2-yl)amino)(phenoxy)phosphoryl)methyl)benzo[b]thiophene-2-carboxylic acid (8, 3.0 g, crude) as a yellow solid, which was used in the next step directly without further purification. LCMS (ESI): m/z=446 $[M+H]^+$.

Step F: perfluorophenyl 5-((1R)-(ethoxy((2-methyl-1-oxo-1-propoxypropan-2-yl)amino)phosphoryl)fluoromethyl)benzo[b]thiophene-2-carboxylate

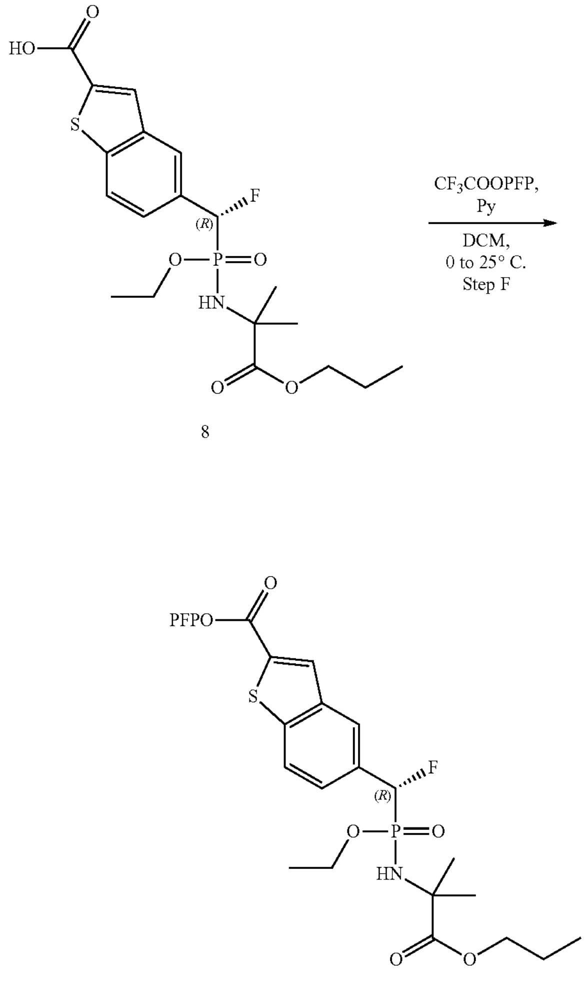

8

9

To a solution of 5-((1S)-fluoro((((S)-1-isobutoxy-1-oxopropan-2-yl)amino)(phenoxy)phosphoryl)methyl)benzo[b]thiophene-2-carboxylic acid (8, 3.0 g, crude) in DCM (30 mL) were added pyridine (1.95 g, 24.7 mmol, 4.0 eq.) and $CF_3COOPFP$ (4.34 g, 15.5 mmol, 2.5 eq.) at 0° C. The reaction mixture was warmed up to 25° C. and stirred for 2 hrs. After completion, the reaction mixture was poured into water (30 mL) and extracted with DCM (30 mL×2), the combined organic layers were washed with brine (30 mL), dried over anhydrous $Na_2SO_4$ and concentrated under reduced pressure. The crude was purified by flash chromatography on C18 (0-90% acetonitrile in $H_2O$ with TFA) to afford perfluorophenyl 5-((1R)-(ethoxy((2-methyl-1-oxo-1-propoxypropan-2-yl)amino)phosphoryl)fluoromethyl)benzo[b]thiophene-2-carboxylate (9, 2.7 g, 4.42 mmol, 71%) as a white solid. $^1H$ NMR (400 MHz, DMSO-$d_6$) δ 8.74 (s, 1H), 8.26-8.15 (m, 2H), 7.67 (d, J=8.6 Hz, 1H), 6.05-5.85 (m, 1H), 5.41 (m, 1H), 4.09-3.94 (m, 4H), 1.63-1.51 (m, 2H), 1.33 (m, 3H), 1.26-1.14 (m, 6H), 0.88 (m, 3H). LCMS (ESI): m/z=612 $[M+H]^+$.

Scheme G. General scheme for dimethyl glycine alkoxy benzothiophene esters

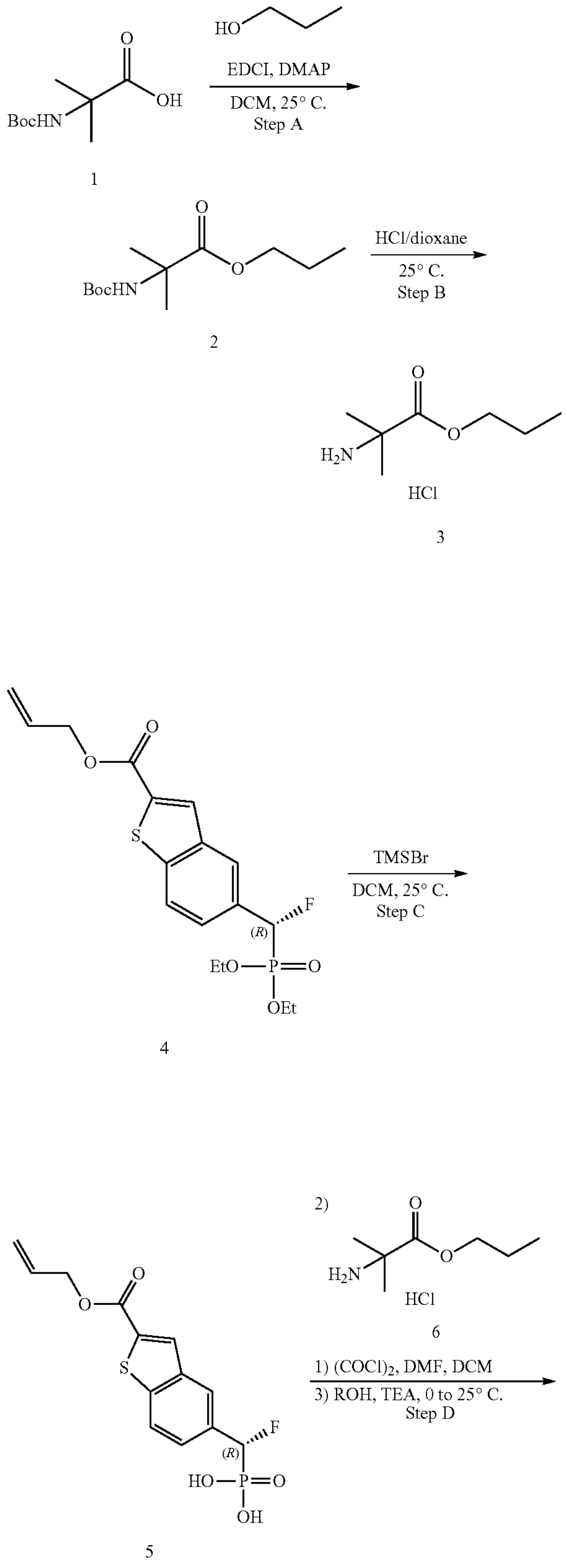

1

2

3

4

5

6

-continued

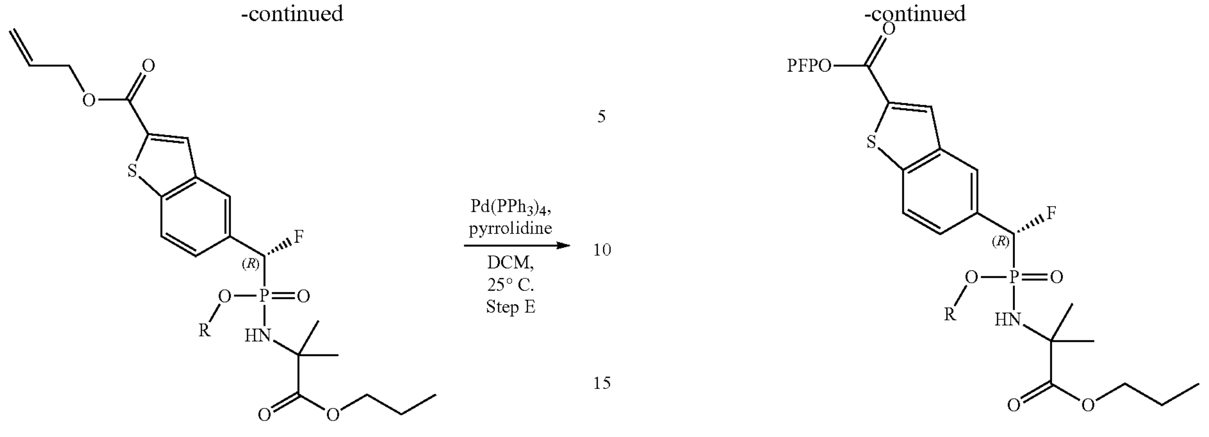

7

9

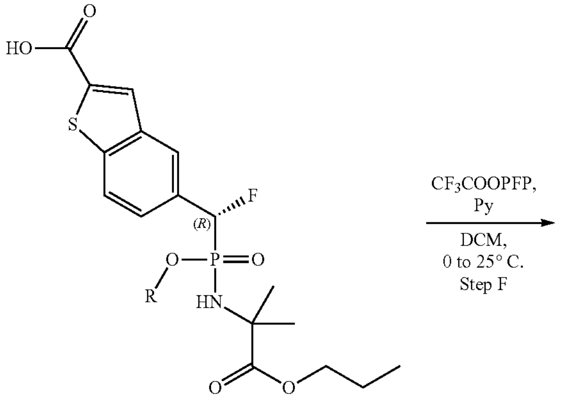

8

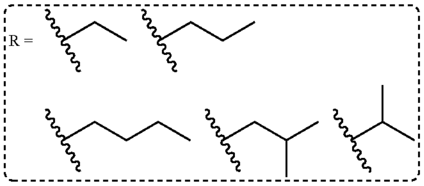

The intermediates in the table below were prepared using a similar protocol outlined above for synthesis of perfluorophenyl 5-((1R)-(ethoxy((2-methyl-1-oxo-1-propoxypropan-2-yl)amino)phosphoryl)fluoromethyl)benzo[b]thiophene-2-carboxylate and utilizing the appropriate intermediate(s) as starting material(s).

| Name | Structure | LC-MS |
| --- | --- | --- |
| propyl 2-((ethoxy((1R)-fluoro(2-(((1-fluoro-2$\lambda^1$-diphosphaneyl)oxy)carbonyl)benzo[b]thiophen-5-yl)methyl)phosphoryl)amino)-2-methylpropanoate | 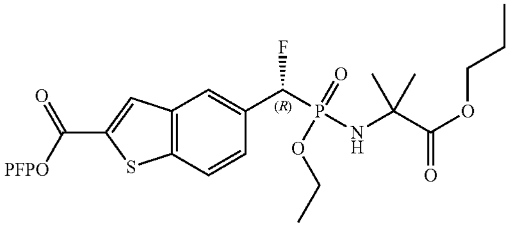 | 612 [M + H]+ |
| propyl 2-((((1R)-fluoro(2-(((1-fluoro-2$\lambda^1$-diphosphaneyl)oxy)carbonyl)benzo[b]thiophen-5-yl)methyl)(propoxy)phosphoryl)amino)-2-methylpropanoate | 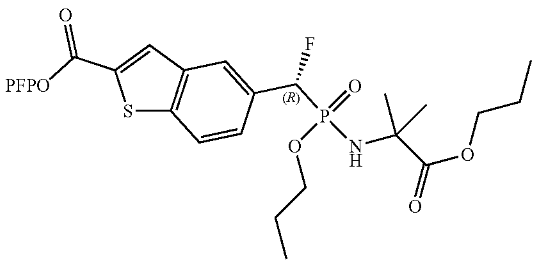 | 626 [M + H]+ |

-continued

| Name | Structure | LC-MS |
| --- | --- | --- |
| propyl 2-((butoxy((1R)-fluoro(2-(((1-fluoro-2λ[1]-diphosphaneyl)oxy)carbonyl)benzo[b]thiophen-5-yl)methyl)phosphoryl)amino)-2-methylpropanote | 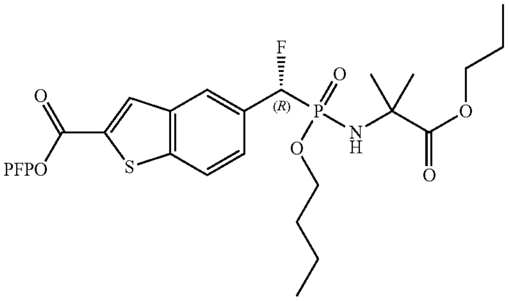 | 640 $[M + H]^+$ |
| propyl 2-((((1R)-fluoro(2-(((1-fluoro-2λ[1]-diphosphaneyl)oxy)carbonyl)benzo[b]thiophen-5-yl)methyl)(isopropoxy)phosphoryl)amino)-2-methylpropanote | 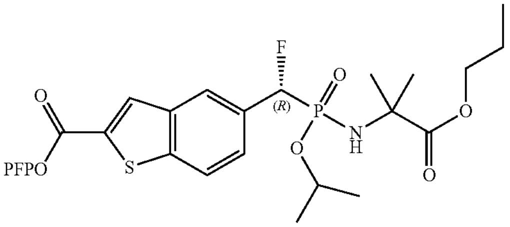 | 626 $[M + H]^+$ |
| propyl 2-((((1R)-fluoro(2-(((1-fluoro-2λ[1]-diphosphaneyl)oxy)carbonyl)benzo[b]thiophen-5-yl)methyl)(isobutoxy)phosphoryl)amino)-2-methylpropanote | 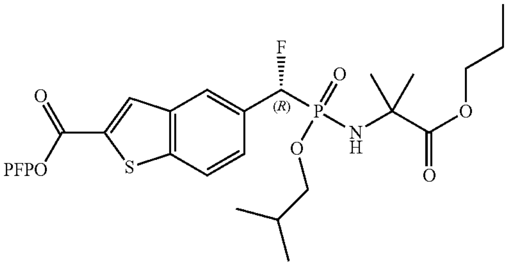 | 640 $[M + H]^+$ |

Synthesis of propyl ((S)-((S)-fluoro(2-(((3S,6S,9S,10aR)-9-(((1s,3R)-3-fluorocyclobutyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate (Compound C17), ((S)-fluoro(2-(((3S,6S,9S,10aR)-9-(((1s,3R)-3-fluorocyclobutyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)phosphonic acid (Compound A1), and propyl ((R)-((S)-fluoro(2-(((3S,6S,9S,10aR)-9-(((1s,3R)-3-fluorocyclobutyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate (Compound C25)

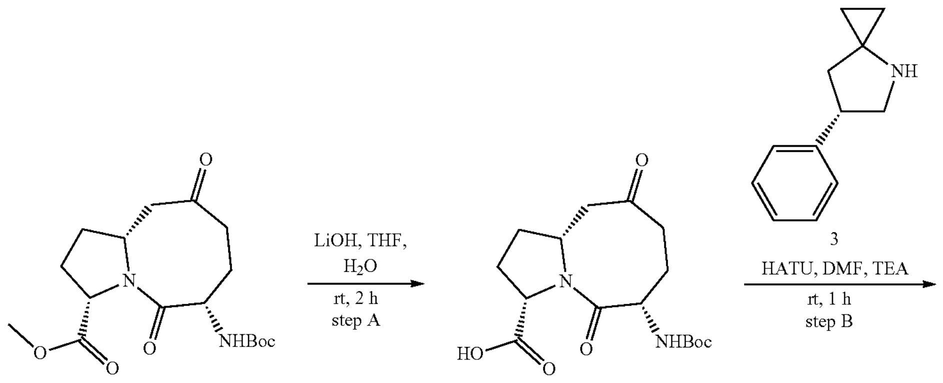

1 2

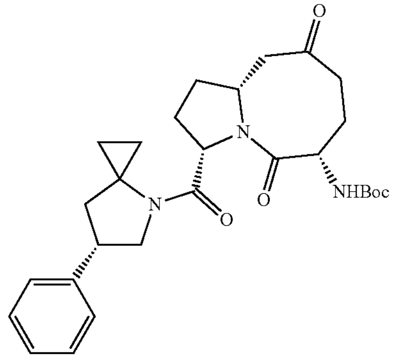

4

-continued
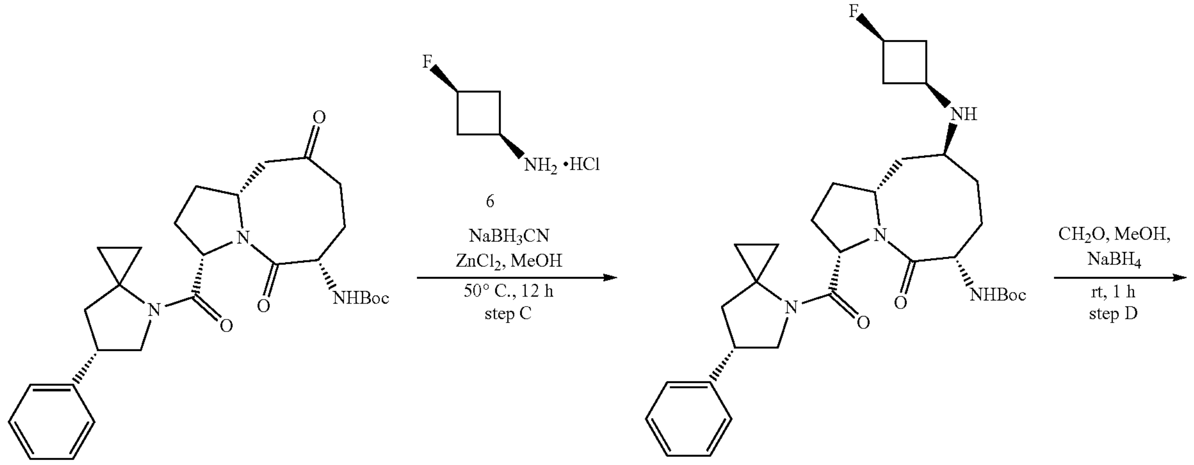
5 7
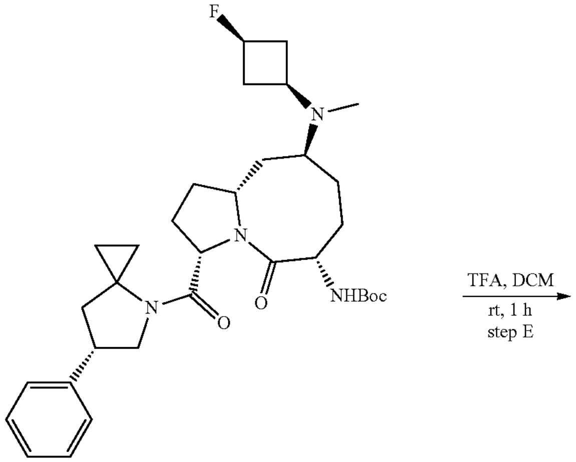
8
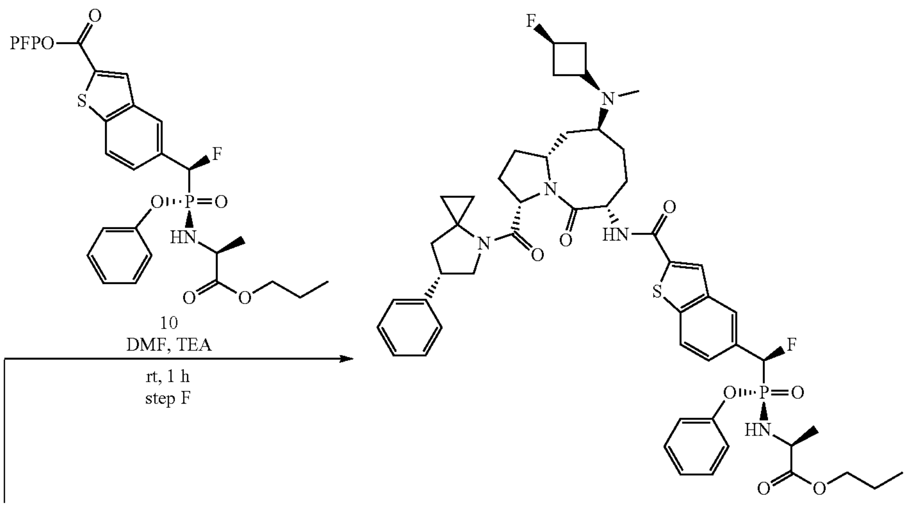

-continued
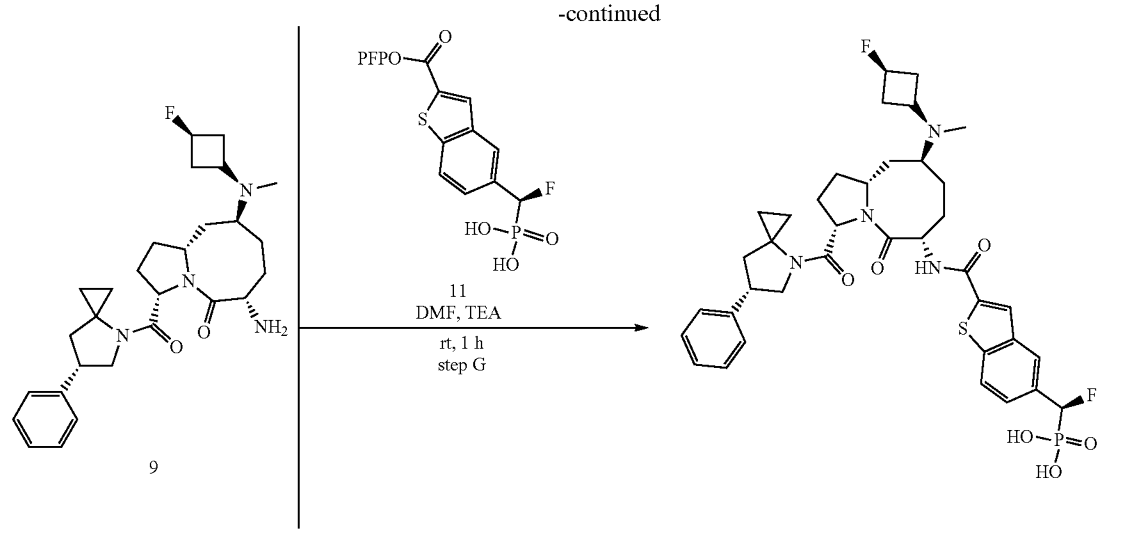
9
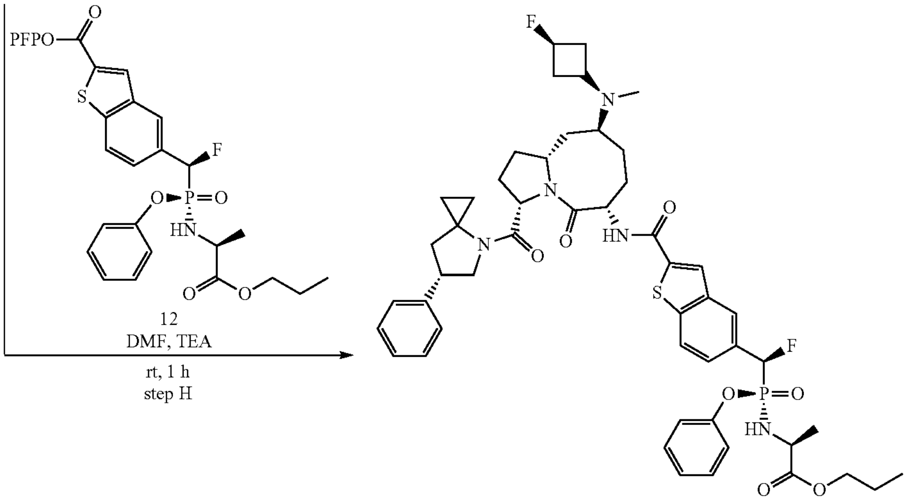
Step A: (3S,6S,10aR)-6-((tert-butoxycarbonyl) amino)-5,9-dioxodecahydropyrrolo[1,2-a]azocine-3-carboxylic acid
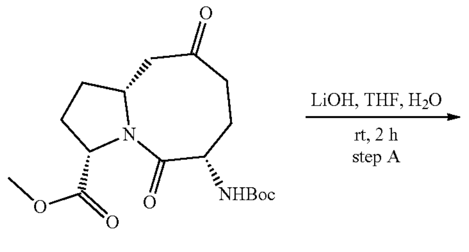
1
-continued
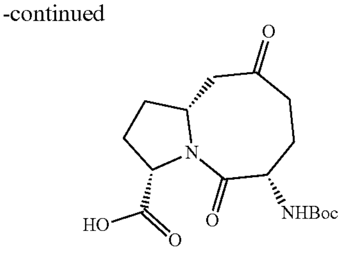
2
To a solution of methyl (3S,6S,10aR)-6-((tert-butoxycarbonyl)amino)-5,9-dioxodecahydropyrrolo[1,2-a]azocine-3-carboxylate (1, 10 g, 28.2 mmol, 1.0 eq.) in THF (50 mL), $H_2O$ (50 mL) was added LiOH—$H_2O$ (3.6 g, 84.7 mmol, 3.0 eq.). The solution was stirred for 2 h at room temperature and the pH was adjusted to pH=3 with 1M HCl (aq.), then extracted with EtOAc (100 mL×3), the organic layers were combined and washed with brine (100 mL), then dried over $Na_2SO_4$, filtered, then concentrated under vacuum to afford (3S,6S,10aR)-6-((tert-butoxycarbonyl)amino)-5,9-dioxo-decahydropyrrolo[1,2-a]azocine-3-carboxylic acid (2, 9.3 g, 27.4 mmol, 97.2% yield) as a white solid. LCMS (ESI): m/z=341 $[M+H]^+$.

Step B: tert-butyl ((3S,6S,10aR)-5,9-dioxo-3-((R)-6-phenyl-4-azaspiro[2.4]heptane-4-carbonyl)decahydropyrrolo[1,2-a]azocin-6-yl)carbamate

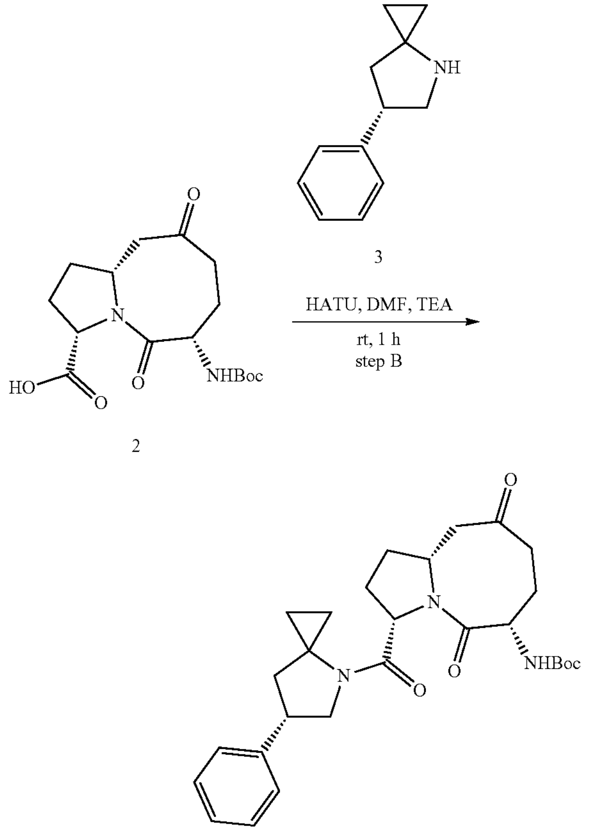

3

2

4

To a solution of (3S,6S,10aR)-6-((tert-butoxycarbonyl)amino)-5,9-dioxodecahydropyrrolo[1,2-a]azocine-3-carboxylic acid (2, 9 g, 26.5 mmol, 1.0 eq.) in DMF (100 mL) was added HATU (10.1 g, 26.5 mmol, 1 eq.), TEA (8.0 g, 79.0 mmol, 3 eq.), (R)-6-phenyl-4-azaspiro[2.4]heptane (3, 4.6 g, 26.5 mmol, 1 eq). The resulting mixture was stirred for 1 h at room temperature and the solution was poured into $H_2O$ (400 mL), then extracted with EtOAc (100 mL×3), the organic layers were combined and washed with brine (100 mL×3), then dried over $Na_2SO_4$, then concentrated under vacuum, the crude product was purified by C18 column to afford tert-butyl ((3S,6S,10aR)-5,9-dioxo-3-((R)-6-phenyl-4-azaspiro[2.4]heptane-4-carbonyl)decahydropyrrolo[1,2-a]azocin-6-yl)carbamate (4, 10 g, 20.2 mmol, 77% yield) as a white solid. LCMS (ESI): m/z=496 $[M+H]^+$.

Step C: tert-butyl ((3S,6S,9S,10aR)-9-(((1s,3R)-3-fluorocyclobutyl)amino)-5-oxo-3-((R)-6-phenyl-4-azaspiro[2.4]heptane-4-carbonyl)decahydropyrrolo[1,2-a]azocin-6-yl)carbamate

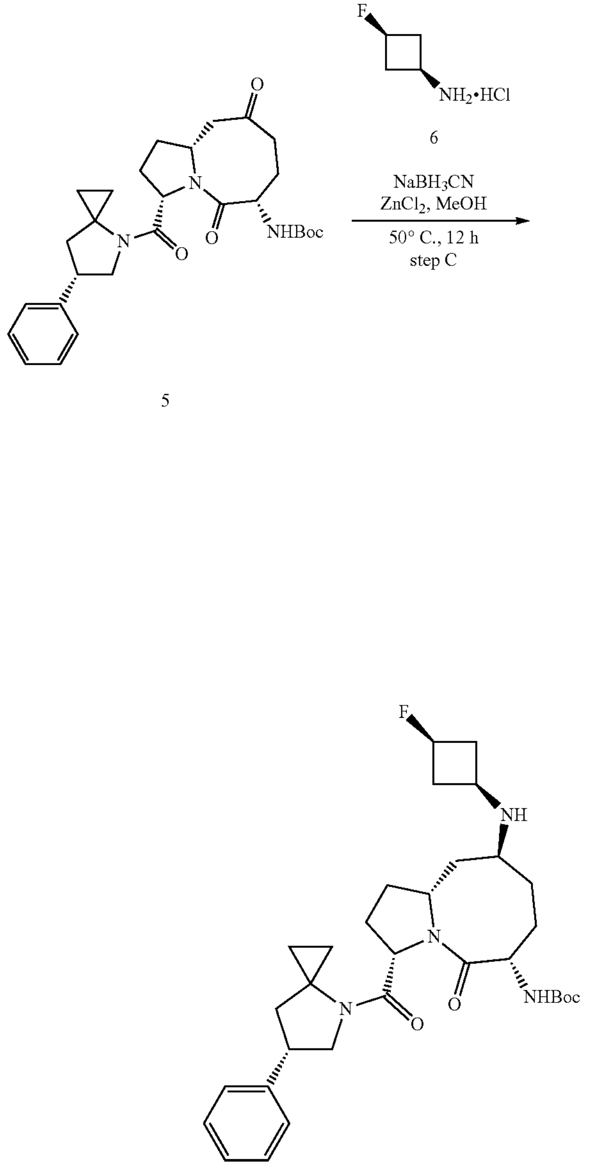

6

5

7

To a solution of tert-butyl ((3S,6S,10aR)-5,9-dioxo-3-((R)-6-phenyl-4-azaspiro[2.4]heptane-4-carbonyl)decahydropyrrolo[1,2-a]azocin-6-yl)carbamate (5, 3 g, 6.06 mmol, 1.0 eq.) in MeOH (60 mL) was added (1s,3s)-3-fluorocyclobutan-1-amine hydrochloride (6, 1.14 g, 9.09 mmol, 1.5 eq.), $ZnCl_2$ (8.3 g, 60.6 mmol, 10.0 eq.), the solution was stirred for 2 hr at 50° C. under an atmosphere of $N_2$. Then $NaBH_3CN$ (3.81 g, 60.6 mmol, 10.0 eq.) was added portion wise every 30 mins (2 eq. (762 mg each time) added 5 times), then the resulting mixture was stirred at 50° C. for 12 hr, then cooled to room temperature. The resulting mixture was used to next step without further workup. LCMS (ESI): m/z=569 $[M+H]^+$.

Step D: tert-butyl ((3S,6S,9S,10aR)-9-(((1s,3R)-3-fluorocyclobutyl)(methyl)amino)-5-oxo-3-((R)-6-phenyl-4-azaspiro[2.4]heptane-4-carbonyl)decahydropyrrolo[1,2-a]azocin-6-yl)carbamate

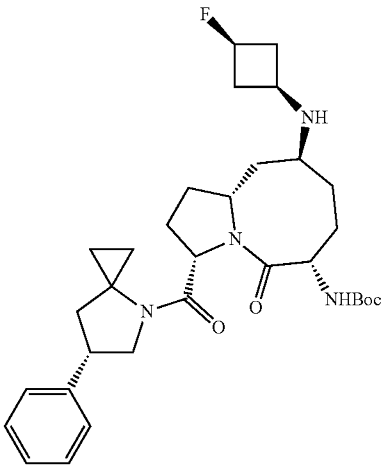

7

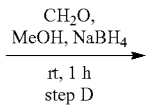

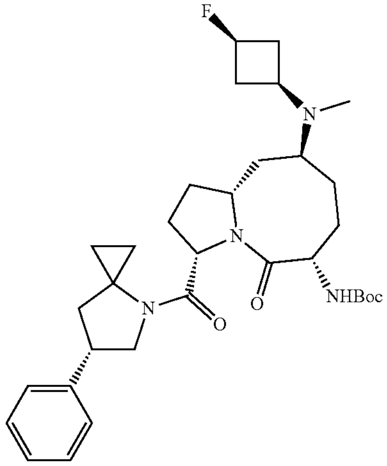

8

To the above mixture (step C) was added 40% formaldehyde aqueous (3 mL) at room temperature, the mixture was stirred for 30 mins, then $NaBH_4$ (1.15 g, 30.3 mmol, 5 eq.) was added in several portions during 30 mins, the mixture was stirred for additional 30 mins. The reaction was quenched by $NH_4Cl$ (sat. aq.), diluted with $H_2O$ (200 mL) and extracted with EtOAc (100 mL×3). The organic solution was dried over $Na_2SO_4$, filtered, then concentrated under vacuum. the crude product was purified by C18 column (MeCN:$H_2O$ (0.1% ammonium hydroxide)=5%-70%) to afford tert-butyl ((3S,6S,9S,10aR)-9-(((1s,3R)-3-fluorocyclobutyl)(methyl)amino)-5-oxo-3-((R)-6-phenyl-4-azaspiro[2.4]heptane-4-carbonyl)decahydropyrrolo[1,2-a]azocin-6-yl)carbamate (8, 2.8 g, 4.81 mmol, 79.4% yield two steps) as a white solid. LCMS (ESI): m/z=583 $[M+H]^+$.

Step E: (3S,6S,9S,10aR)-6-amino-9-(((1s,3R)-3-fluorocyclobutyl)(methyl)amino)-3-((R)-6-phenyl-4-azaspiro[2.4]heptane-4-carbonyl)octahydropyrrolo[1,2-a]azocin-5(1H)-one

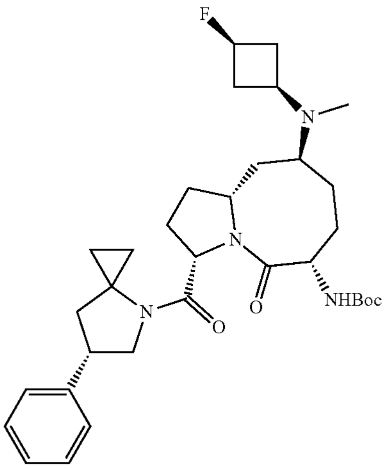

8

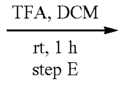

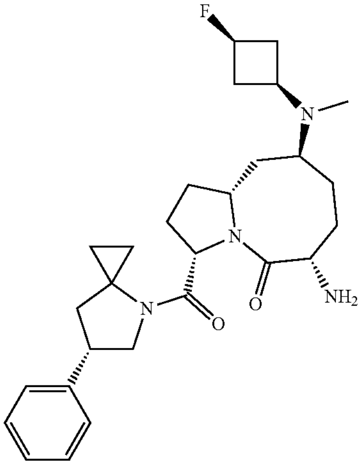

9

To a solution of tert-butyl ((3S,6S,9S,10aR)-9-(((1s,3R)-3-fluorocyclobutyl)(methyl)amino)-5-oxo-3-((R)-6-phenyl-4-azaspiro[2.4]heptane-4-carbonyl)decahydropyrrolo[1,2-a]azocin-6-yl)carbamate (8, 2.8 g, 4.81 mmol, 1.0 eq.) in DCM (30 mL) was added TFA (15 mL). The solution was stirred for 1 hr. at room temperature. The resulting mixture was concentrated to dryness under reduced pressure to afford crude product (3S,6S,9S,10aR)-6-amino-9-(((1s,3R)-3-fluorocyclobutyl)(methyl)amino)-3-((R)-6-phenyl-4-azaspiro[2.4]heptane-4-carbonyl)octahydropyrrolo[1,2-a]azocin-5(1H)-one (9, 2.8 g, TFA salt) as a yellow oil. LCMS (ESI): m/z=483 $[M+H]^+$.

Step F: propyl ((S)-((S)-fluoro(2-(((3S,6S,9S,10aR)-9-(((1s,3R)-3-fluorocyclobutyl)(methyl)amino)-5-oxo-3-((R)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate To a solution of (3S,6S,9S,10aR)-6-amino-9-(((1s,3R)-3-fluorocyclobutyl)(methyl)amino)-3-((R)-6-phenyl-4-azaspiro[2.4]heptane-4-carbonyl)octahydropyrrolo[1,2-a]azocin-5(1H)-one (9, 954 mg, 1.70 mmol, 1 eq) in DMF (10 mL) was added TEA (515 mg, 5.10 mmol, 3 eq.), propyl ((S)-((1S)-fluoro(2-(((1-fluoro-211-diphosphanyl)oxy)car-

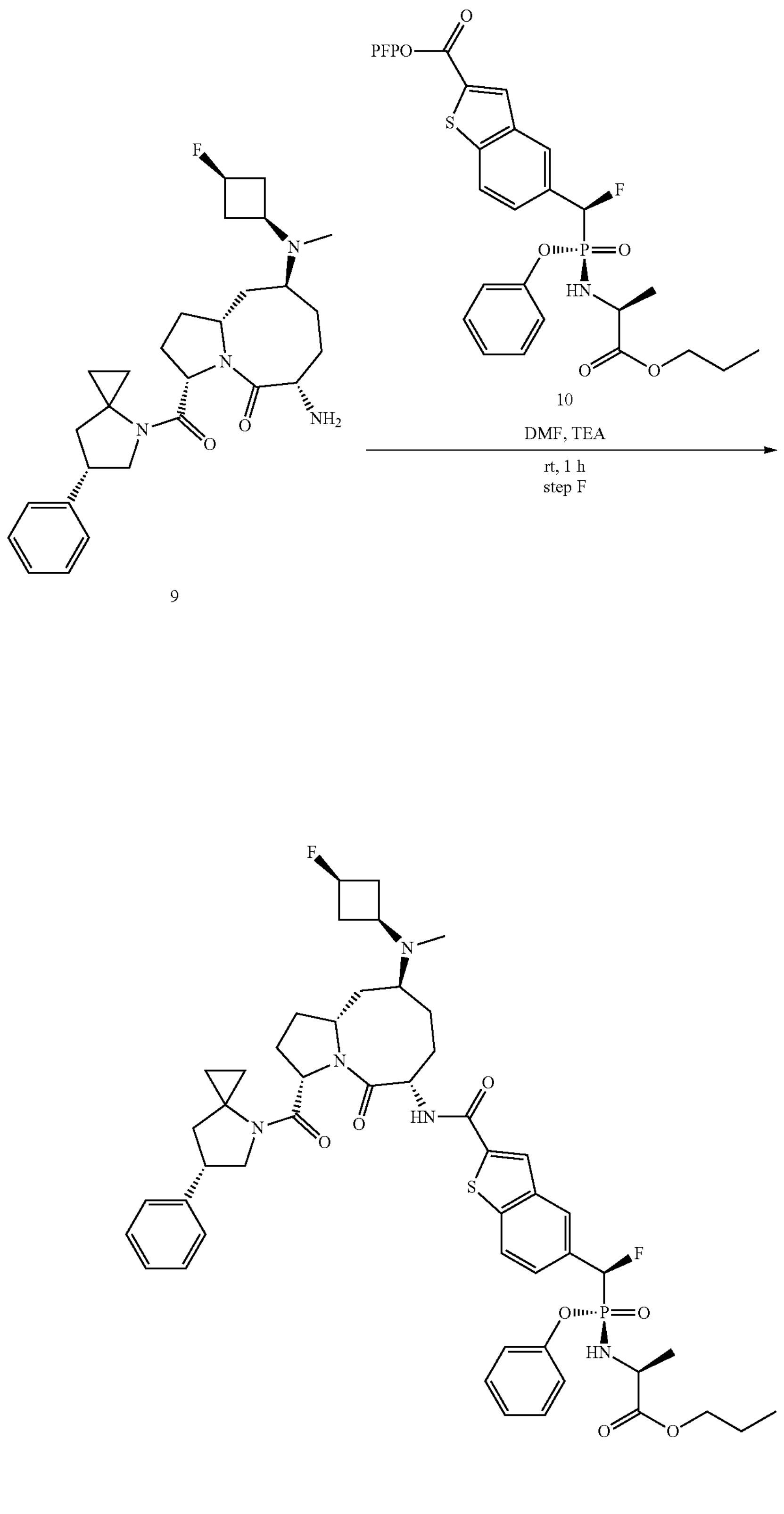

10

9 bonyl)benzo[b]thiophen-5-yl)methyl)(phenoxy)phosphoryl)-L-alaninate (10, 825 mg, 1.70 mmol, 1 eq.). The solution was stirred for 1 hr at room temperature. The crude product was purified by C18 column chromatography (MeCN:$H_2O$ (0.1% $NH_4CO_3$)=5%-80%) to afford propyl ((S)-((S)-fluoro(2-(((3S,6S,9S,10aR)-9-(((1s,3R)-3-fluorocyclobutyl)(methyl)amino)-5-oxo-3-((R)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate (Compound C17, 1.09 g, 1.16 mmol, 68.1%) as white solid. LCMS (ESI): m/z=944.6 $[M+H]^+$. $^1H$ NMR (400 MHz, DMSO-$d_6$) δ (ppm) 10.21-9.42 (m, 1H), 8.94-8.74 (m, 1H), 8.30-8.24 (m, 1H), 8.12-8.04 (m, 2H), 7.65-7.58 (m, 1H), 7.40-7.28 (m, 6H), 7.25-7.16 (m, 4H), 6.24-6.08 (m, 2H), 5.01-4.78 (m, 2H), 4.60-4.48 (m, 2H), 4.19-4.10 (m, 1H), 3.94-3.88 (m, 2H), 3.80-3.67 (m, 3H), 3.59-3.50 (m, 2H), 3.42-3.04 (m, 1H), 2.83-2.62 (m, 2H), 2.61-2.55 (m, 3H), 2.48-2.35 (m, 2H), 2.26-1.47 (m, 15H), 0.95 (d, J=7.1 Hz, 3H), 0.84-0.78 (m, 3H), 0.62-0.44 (m, 2H). $^{19}F$ NMR (377 MHz, DMSO-$d_6$) δ (ppm) −167.05 (s), −193.13--195.64 (m). $^{31}P$ NMR (162 MHz, DMSO-$d_6$) δ (ppm) 16.93 (d, J=82.4 Hz).

Step G: ((S)-fluoro(2-(((3S,6S,9S,10aR)-9-(((1s,3R)-3-fluorocyclobutyl)(methyl)amino)-5-oxo-3-((R)-6-phenyl-4-azaspiro[2.4]heptane-4-carbonyl)decahydropyrrolo[1,2-a]azocin-6-yl)carbamoyl)benzo[b]thiophen-5-yl)methyl)phosphonic acid

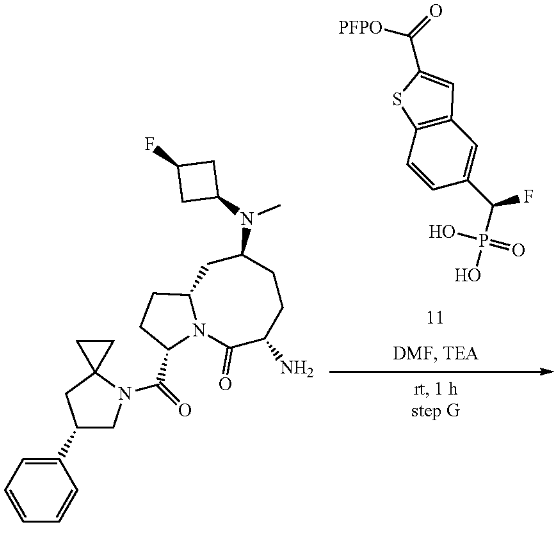

9

-continued

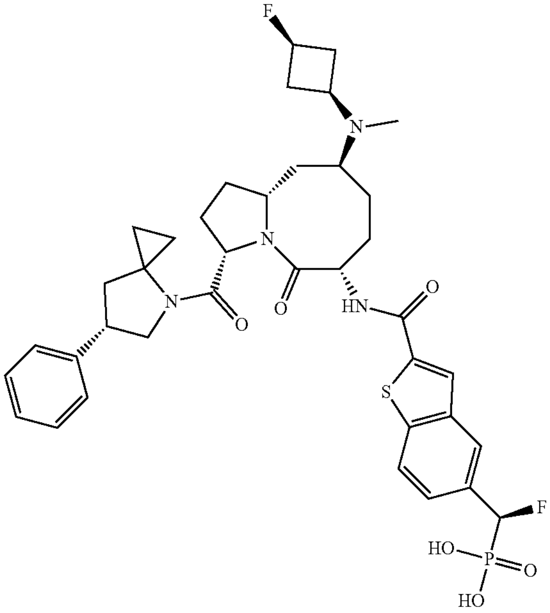

To a solution of (3S,6S,9S,10aR)-6-amino-9-{methyl[(1s,3s)-3-fluorocyclobutyl]amino}-3-[(6R)-6-phenyl-4-azaspiro[2.4]heptane-4-carbonyl]-decahydropyrrolo[1,2-a]azocin-5-one (9, 40 mg, 82.8 μmol, 1 eq.) in DMF (3 mL) was added N,N-diisopropylethylamine (53.5 mg, 414 μmol, 5 eq.) and [(S)-fluoro({2-[(2,3,4,5,6-pentafluorophenoxy)carbonyl]-1-benzothiophen-5-yl})methyl]phosphonic acid (11, 37.7 mg, 82.8 μmol, 1 eq.) 25° C. The reaction mixture was stirred at 25° C. for 1 hr. The crude product was purified by prep-HPLC (C18, 0-50% acetonitrile in $H_2O$ with TFA) to afford [(S)-(2-{[(3S,6S,9S,10aR)-9-{methyl[(1s,3s)-3-fluorocyclobutyl]amino}-5-oxo-3-[(6R)-6-phenyl-4-azaspiro[2.4]heptane4-carbonyl]-decahydropyrrolo[1,2-a]azocin-6-yl]carbamoyl}-1-benzothiophen-5-yl)(fluoro)methyl]phosphonic acid (Compound A1, 30.0 mg, 39.7 μmol, 48.0%) as a white solid. LCMS (ESI): m/z=755.3 $[M+H]^+$. $^1H$ NMR (400 MHz, DMSO-d6) δ (ppm) 10.26-9.53 (m, 1H), 8.91-8.72 (m, 1H), 8.25 (s, 1H), 8.05-7.95 (m, 2H), 7.53 (d, J=8.5 Hz, 1H), 7.38-7.29 (m, 4H), 7.25-7.18 (m, 1H), 5.82 (dd, J=44.4, 7.9 Hz, 1H), 4.99-4.81 (m, 2H), 4.61-4.49 (m, 2H), 4.19-4.11 (m, 1H), 3.86-3.68 (m, 2H), 3.65-3.48 (m, 2H), 3.41-3.05 (m, 1H), 2.79-2.62 (m, 2H), 2.57 (s, 3H), 2.48-2.34 (m, 2H), 2.31-1.50 (m, 13H), 0.63-0.41 (m, 2H). $^{19}F$ NMR (377 MHz, DMSO-$d_6$) δ (ppm) −166.57--167.90 (m), −193.77--195.72 (m). $^{31}P$ NMR (162 MHz, DMSO-$d_6$) δ (ppm) 10.91 (d, J=81.7 Hz), 6 (ppm) 10.81 (d, J=79.8 Hz).

Step H: propyl ((R)-((S)-fluoro(2-(((3S,6S,9S,10aR)-9-(((1s,3R)-3-fluorocyclobutyl)(methyl)amino)-5-oxo-3-((R)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate

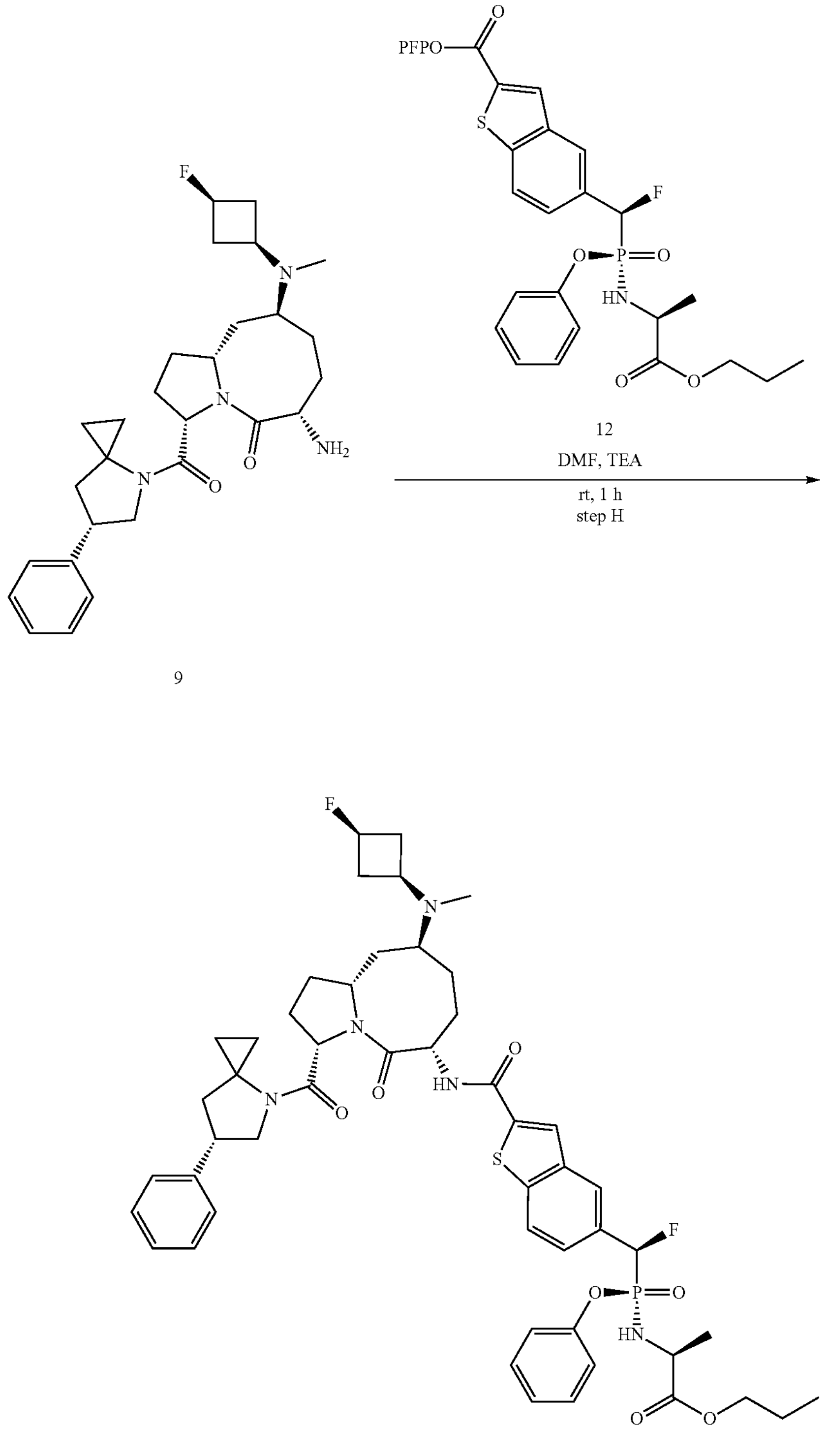

9

To a solution of (3S,6S,9S,10aR)-6-amino-9-(((1s,3R)-3-fluorocyclobutyl)(methyl)amino)-3-((R)-6-phenyl-4-azaspiro[2.4]heptane-4-carbonyl)octahydropyrrolo[1,2-a]azocin-5(1H)-one (9, 954 mg, 1.70 mmol, 1 eq.) in DMF (10 mL) was added TEA (515 mg, 5.10 mmol, 3 eq.), perfluorophenyl-5-((S)-fluoro((R)-(((S)-1-oxo-1-propoxypropan-2-yl)amino)(phenoxy)phosphoryl)methyl)benzo[b]thiophene-2-carboxylate (12, 825 mg, 1.70 mmol, 1 eq.). The solution was stirred for 1 hr at room temperature. The crude product was purified by C18 column chromatography (MeCN:$H_2O$ (0.1% TFA)=5%-50%) to afford propyl ((R)-((S)-fluoro(2-(((3S,6S,9S,10aR)-9-(((1s,3R)-3-fluorocyclobutyl)(methyl)amino)-5-oxo-3-((R)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate (Compound C25, 724 mg, 0.767 mmol, 60.3%) as white solid. LCMS (ESI): m/z=944.6 $[M+H]^+$. $^1H$ NMR (400 MHz, DMSO-$d_6$) δ (ppm) 10.05-9.43 (m, 1H), 8.94-8.75 (m, 1H), 8.32-8.21 (m, 1H), 8.11-7.98 (m, 2H), 7.60 (d, J=8.7 Hz, 1H), 7.39-7.25 (m, 6H), 7.24-7.09 (m, 4H), 6.32-6.14 (m, 2H), 5.04-4.75 (m, 2H), 4.64-4.44 (m, 2H), 4.22-4.06 (m, 1H), 3.97-3.82 (m, 3H), 3.79-3.69 (m, 2H), 3.56-3.53 (m, 2H), 3.36-2.99 (m, 1H), 2.84-2.62 (m, 2H), 2.61-2.55 (m, 3H), 2.48-2.31 (m, 2H), 2.26-1.43 (m, 15H), 1.17 (d, J=7.0 Hz, 3H), 0.81 (t, J=7.4 Hz, 3H), 0.63-0.44 (m, 2H). (TFA salt). $^{19}F$ NMR (376 MHz, DMSO) δ (ppm) −166.86--167.58 (m), −195.89--196.42 (m). $^{31}P$ NMR (162 MHz, DMSO-d6) δ (ppm) 17.34 (d, J=86.8 Hz).

Synthesis of propyl (((R)-fluoro(2-(((3S,6S,9S,10aR)-9-(((1s,3R)-3-fluorocyclobutyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(2,2,2-trifluoroethoxy)phosphoryl)-L-alaninate (Compound C64)

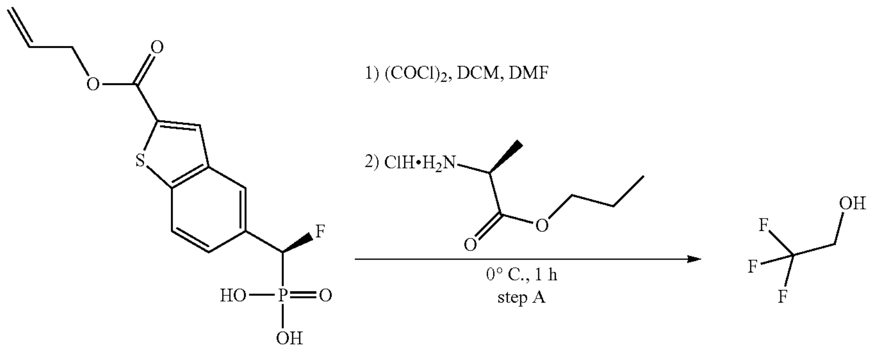

1

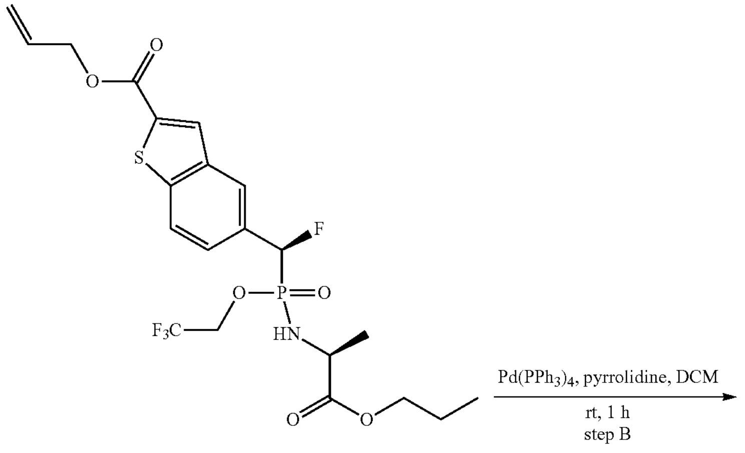

2

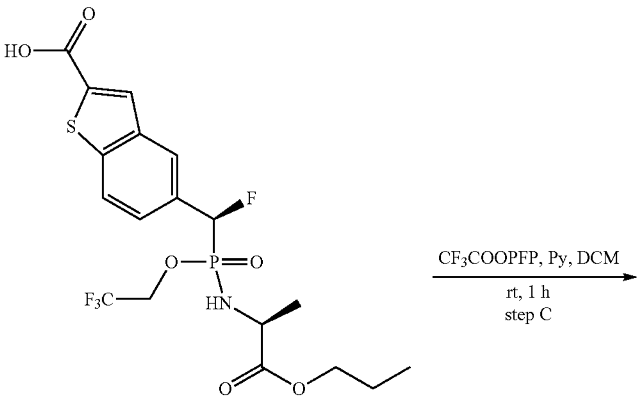

3

-continued
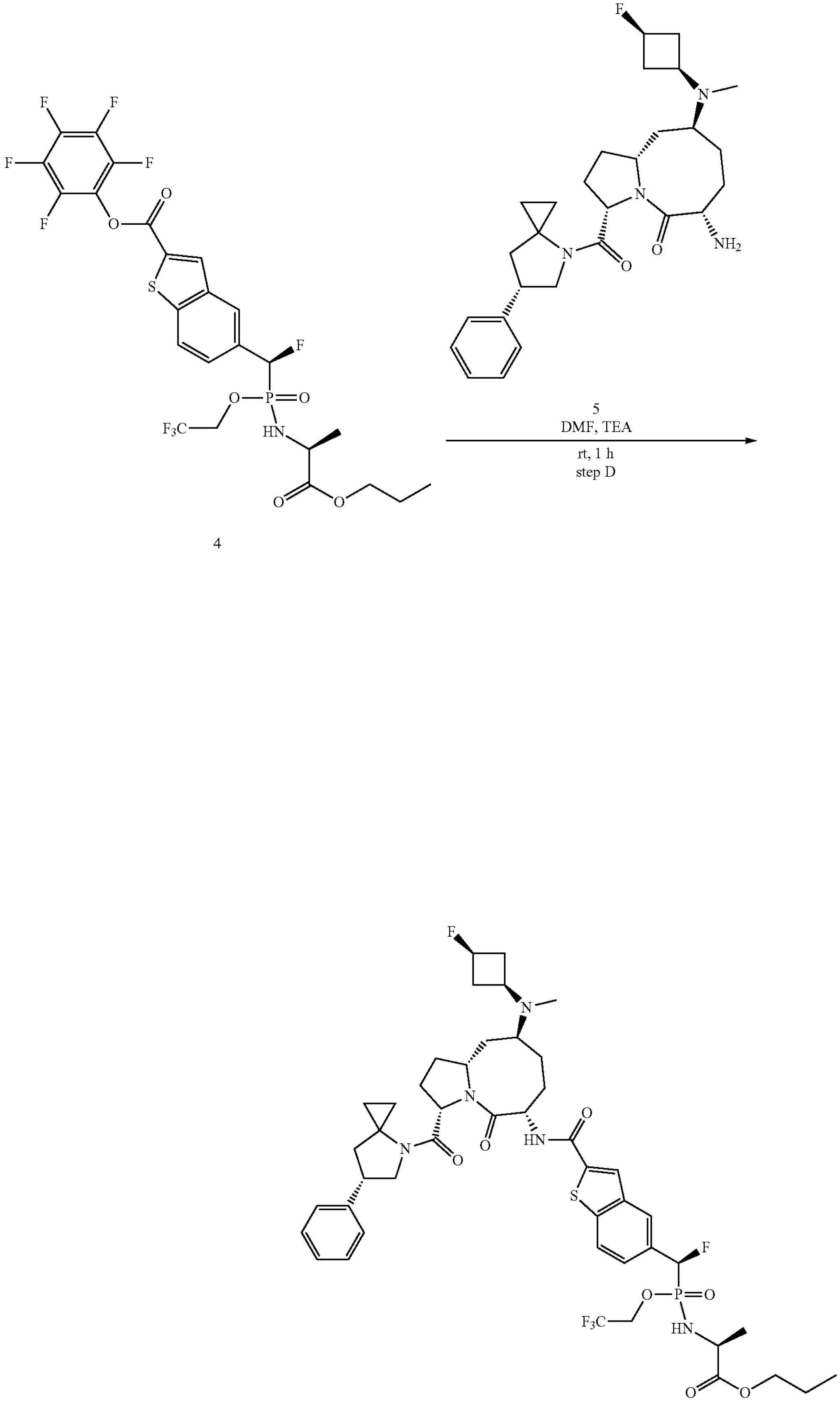
4

Step A: allyl 5-((1S)-fluoro((((S)-1-oxo-1-propoxypropan-2-yl)amino)(2,2,2-trifluoroethoxy)phosphoryl)methyl)benzo[b]thiophene-2-carboxylate

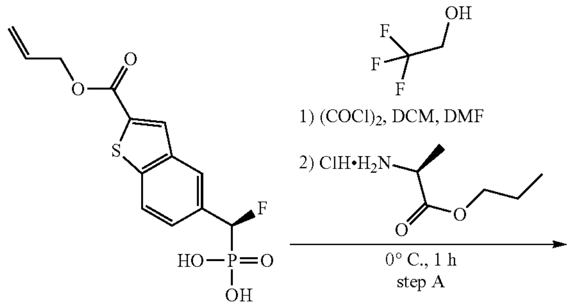

1

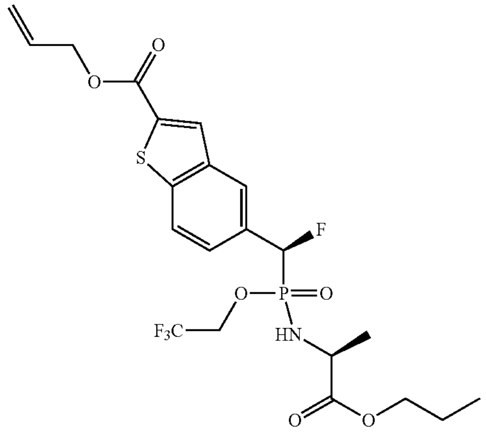

2

To a solution of (S)-((2-((allyloxy)carbonyl)benzo[b]thiophen-5-yl)fluoromethyl)phosphonic acid (1, 1.3 g, 3.94 mmol, 1 eq.) in DCM (20 mL) was added DMF (catalytic amount), and oxalyl chloride (2.5 g, 19.7 mmol, 5 eq.). The resulting mixture was stirred for 1 h at room temperature, then DCM was removed under reduced pressure. The residue was redissolved in DCM (20 mL) and cooled to 0° C., and 2,2,2-trifluoroethan-1-ol (394 mg, 3.94 mmol, 1 eq.) was added to the solution, TEA (2 g, 19.7 mmol, 5 eq.) was added dropwise to the solution, the mixture was stirred for 1 h at 0° C. Propyl L-alaninate hydrochloride (1.32 g, 7.88 mmol, 2 eq.) was added to the mixture, then stirred for 10 mins, then $H_2O$ (50 mL) was added to the solution, and extracted with DCM (50 mL×2), the organic layers were combined and washed with brine (20 mL×3), then dried over $Na_2SO_4$, filtered, and concentrated to dryness under reduced pressure. The crude product was purified by silica gel column chromatography to afford allyl 5-((1S)-fluoro((((S)-1-oxo-1-propoxypropan-2-yl)amino)(2,2,2-trifluoroethoxy)phosphoryl)methyl)benzo[b]thiophene-2-carboxylate (2, 860 mg, 1.64 mmol, 41.6% yield) as a colorless oil. LCMS (ESI): m/z=526 $[M+H]^+$.

Step B: 5-((1S)-fluoro((((S)-1-oxo-1-propoxypropan-2-yl)amino)(2,2,2-trifluoroethoxy)phosphoryl)methyl)benzo[b]thiophene-2-carboxylic acid

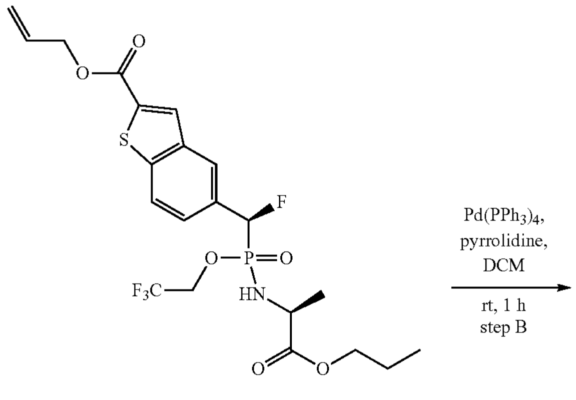

2

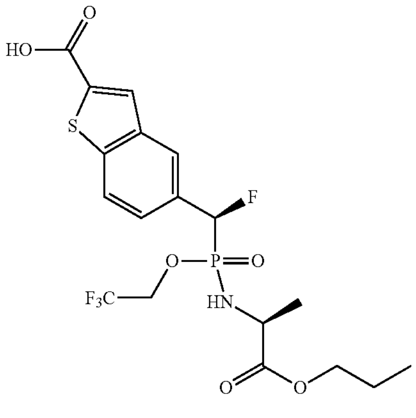

3

To a solution of allyl 5-((1S)-fluoro((((S)-1-oxo-1-propoxypropan-2-yl)amino)(2,2,2-trifluoroethoxy)phosphoryl)methyl)benzo[b]thiophene-2-carboxylate (2, 860 mg, 1.64 mmol, 1 eq.) in DCM (10 mL) was added $Pd(PPh_3)_4$ (184 mg, 0.16 mmol, 0.1 eq.), and pyrrolidine (116 mg, 1.64 mmol, 1 eq.). The resulting mixture was stirred for 1 h at room temperature under $N_2$ atmosphere. The mixture was adjusted to pH=3-4 with 1 M HCl (aq.), then extracted with DCM (20 mL×3), and the organic layers were combined and washed with brine (20 mL×2) dried over $Na_2SO_4$, filtered, and concentrated to dryness under reduced pressure to afford crude product 5-((1S)-fluoro((((S)-1-oxo-1-propoxypropan-2-yl)amino)(2,2,2-trifluoroethoxy)phosphoryl)methyl)benzo[b]thiophene-2-carboxylic acid (3, 650 mg, 1.34 mmol, 81.7% yield) as a yellow solid. LCMS (ESI): m/z=486 $[M+H]^+$.

Step C: perfluorophenyl 5-((1S)-fluoro((((S)-1-oxo-1-propoxypropan-2-yl)amino)(2,2,2-trifluoroethoxy)phosphoryl)methyl)benzo[b]thiophene-2-carboxylate

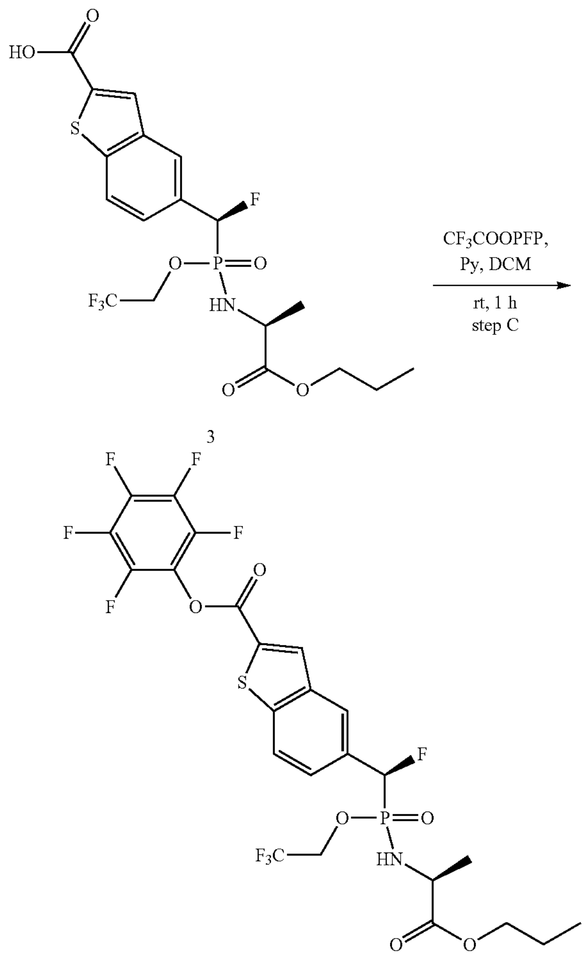

3

4

To a solution of 5-((1S)-fluoro((((S)-1-oxo-1-propoxypropan-2-yl)amino)(2,2,2-trifluoroethoxy)phosphoryl)methyl)benzo[b]thiophene-2-carboxylic acid (3, 650 mg, 1.34 mmol, 1 eq.) in DCM (10 mL) was added pyridine (317 mg, 4.02 mmol, 3 eq.), perfluorophenyl 2,2,2-trifluoroacetate (750 mg, 2.68 mmol, 2 eq.). The resulting mixture was stirred for 1 h at room temperature and $H_2O$ (20 mL) was added to quench the reaction, which was then extracted with DCM (30 mL×2). The organic layers were combined and washed with brine (20 mL×2), dried over $Na_2SO_4$, and concentrated to dryness under reduced pressure. The crude product was purified by silica gel column chromatography to afford perfluorophenyl 5-((1S)-fluoro((((S)-1-oxo-1-propoxypropan-2-yl)amino)(2,2,2-trifluoroethoxy)phosphoryl)methyl)benzo[b]thiophene-2-carboxylate (4, 700 mg, 1.08 mmol, 80% yield) as a white solid. LCMS (ESI): m/z=652 $[M+H]^+$.

Step D: propyl (((S)-fluoro(2-(((3S,6S,9S,10aR)-9-(((1s,3R)-3-fluorocyclobutyl)(methyl)amino)-5-oxo-3-((S)-6-phenyl-4-azaspiro[2.4]heptane-4-carbonyl) decahydropyrrolo[1,2-a]azocin-6-yl)carbamoyl) benzo[b]thiophen-5-yl)methyl)(2,2,2-trifluoroethoxy)phosphoryl)-L-alaninate

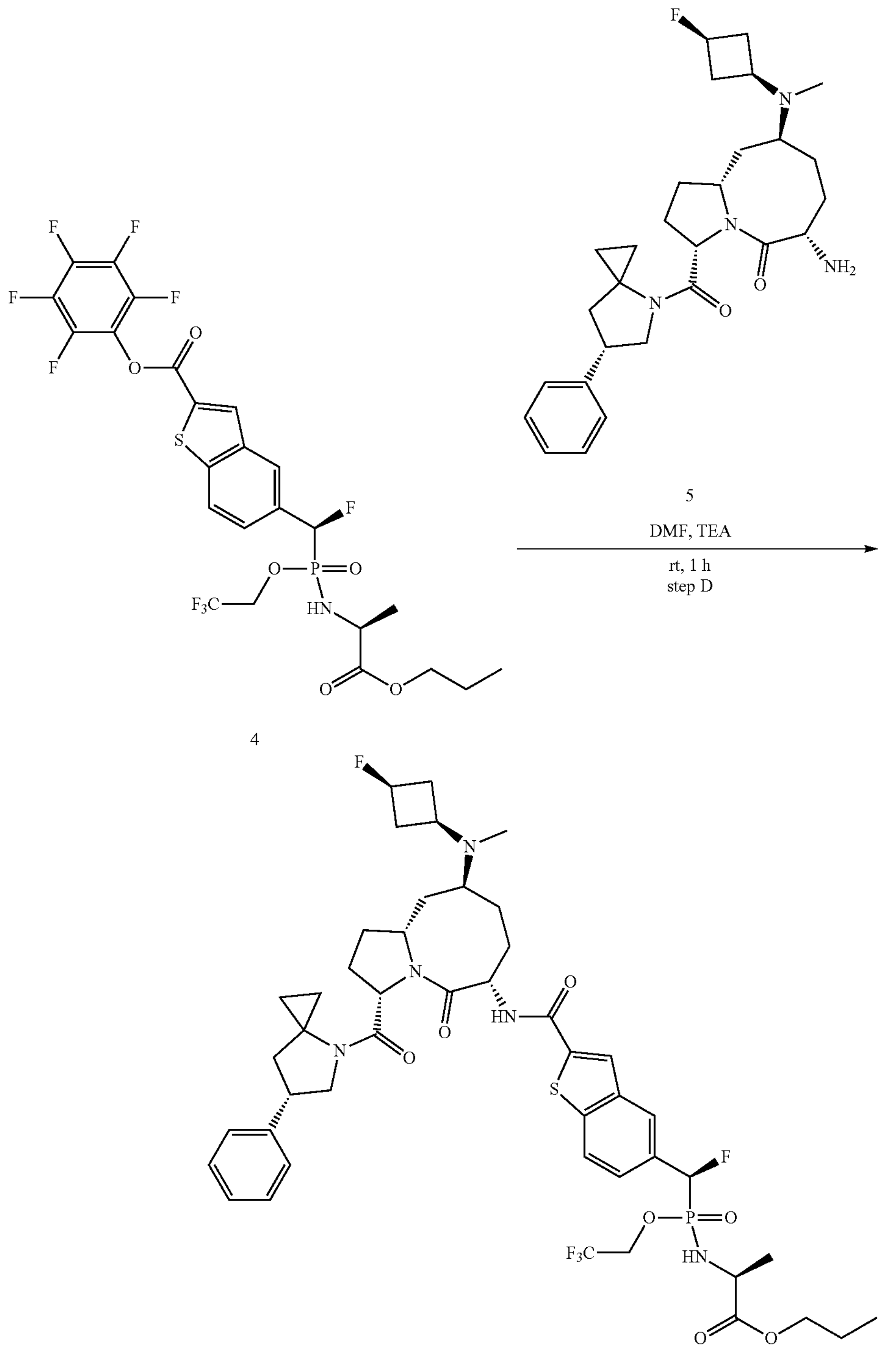

To a solution of perfluorophenyl 5-((1S)-fluoro((((S)-1-oxo-1-propoxypropan-2-yl)amino)(2,2,2-trifluoroethoxy) phosphoryl)methyl)benzo[b]thiophene-2-carboxylate (4, 30 mg, 0.046 mml, 1 eq.) in DMF (3 mL) was added (3S,6S, 9S,10aR)-6-amino-9-(((1s,3R)-3-fluorocyclobutyl)(methyl) amino)-3-((S)-6-phenyl-4-azaspiro[2.4]heptane-4-carbonyl) octahydropyrrolo[1,2-a]azocin-5(1H)-one (5, 22 mg, 0.046 mmol, 1 eq.), TEA (14 mg, 0.138 mmol, 3 eq.). The resulting mixture was stirred for 1 h at room temperature. The crude product was purified by Prep-HPLC to afford propyl (((S)-fluoro(2-(((3S,6S,9S,10aR)-9-(((1s,3R)-3-fluorocyclobutyl) (methyl)amino)-5-oxo-3-((S)-6-phenyl-4-azaspiro[2.4]heptane-4-carbonyl)decahydropyrrolo[1,2-a]azocin-6-yl) carbamoyl)benzo[b]thiophen-5-yl)methyl)(2,2,2-trifluoroethoxy)phosphoryl)-L-alaninate (Compound C64), 19 mg, 0.020 mmol, 45.6% yield) as a white solid. LCMS (ESI): m/z=950 [M+H]+. $^{1}$H NMR (400 MHz, DMSO-$d_6$) δ (ppm) 8.86-8.75 (m, 1H), 8.30-8.22 (m, 1H), 8.10-8.02 (m, 1H), 8.01-7.95 (m, 1H), 7.56-7.47 (m, 1H), 7.37-7.27 (m, 4H), 7.24-7.18 (m, 1H), 6.27-5.91 (m, 2H), 4.92-4.68 (m, 2H), 4.66-4.42 (m, 3H), 4.36-4.24 (m, 1H), 4.16-4.08 (m, 1H), 4.05-3.93 (m, 2H), 3.84-3.50 (m, 3H), 3.08-2.93 (m, 1H), 2.64-2.56 (m, 1H), 2.44-2.31 (m, 2H), 2.30-1.45 (m, 21H), 1.31-1.01 (m, 3H), 0.89-0.82 (m, 3H), 0.58-0.39 (m, 2H). $^{19}$F NMR (376 MHz, DMSO-$d_6$) δ (ppm) −73.67 (d, J=22.8 Hz), −165.29 (s), −195.24 (d, J=83.7 Hz), −197.01 (d, J=86.2 Hz). $^{31}$P NMR (162 MHz, DMSO-d6) δ (ppm) 21.32 (d, J=84.0 Hz), 20.98 (d, J=86.2 Hz).

Synthesis of ((R)-fluoro(2-(((3S,6S,9S,10aR)-9-(methyl((1s,3R)-3-(trifluoromethoxy)cyclobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)phosphonic acid (Compound A4) and propyl ((R)-((1R)-fluoro(2-(((3S,6S,9S,10aR)-9-(methyl((1s,3R)-3-(trifluoromethoxy)cyclobutyl)amino)-5-oxo-3-((S)-6-phenyl-4-azaspiro[2.4]heptane-4-carbonyl)decahydropyrrolo[1,2-a]azocin-6-yl)carbamoyl)-2,3-dihydrobenzo[b]thiophen-5-yl)methyl)(phenoxy)phosphoryl)-L-alaninate (Compound C5)

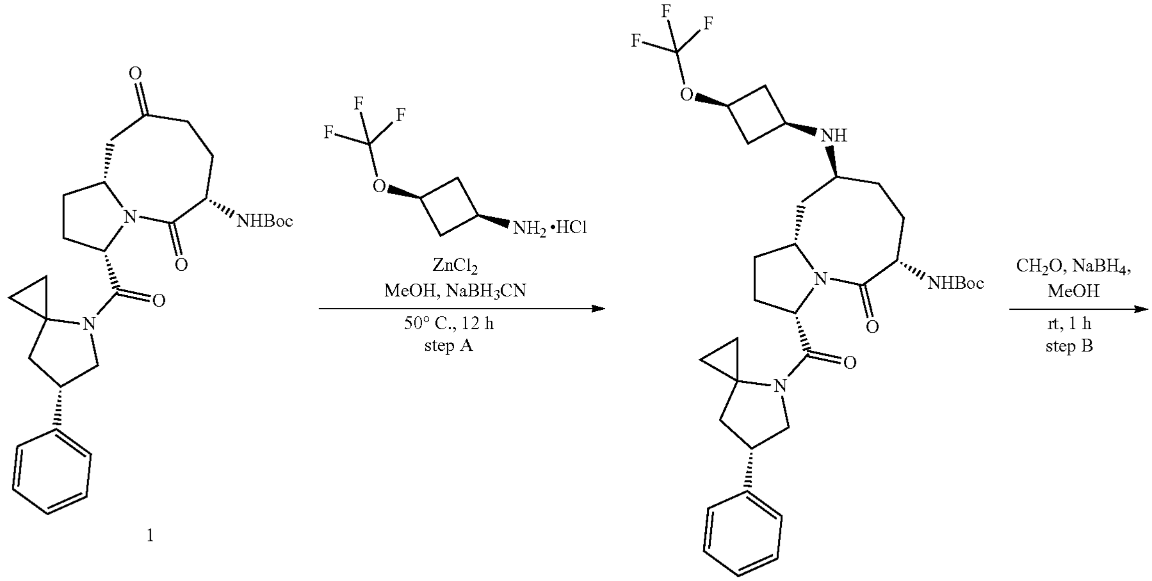

1

2

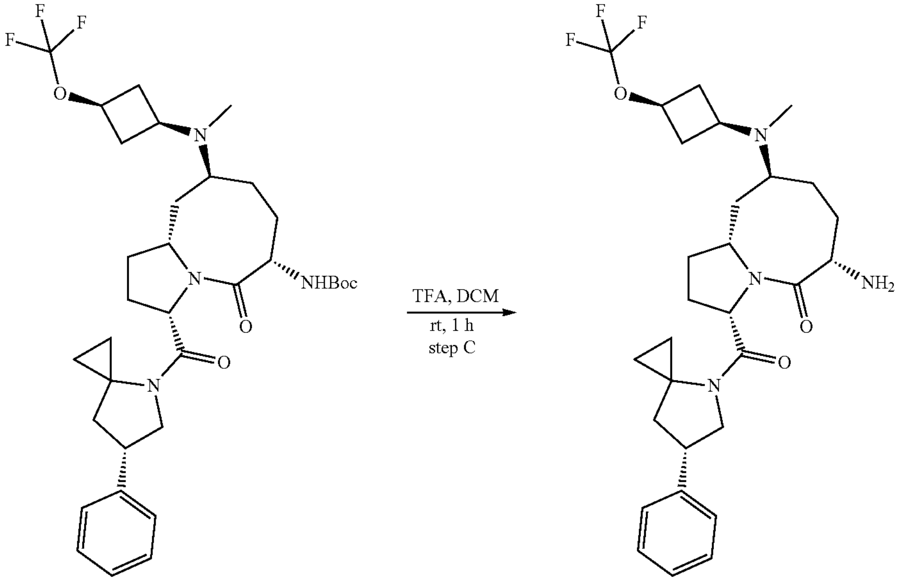

3

4

-continued
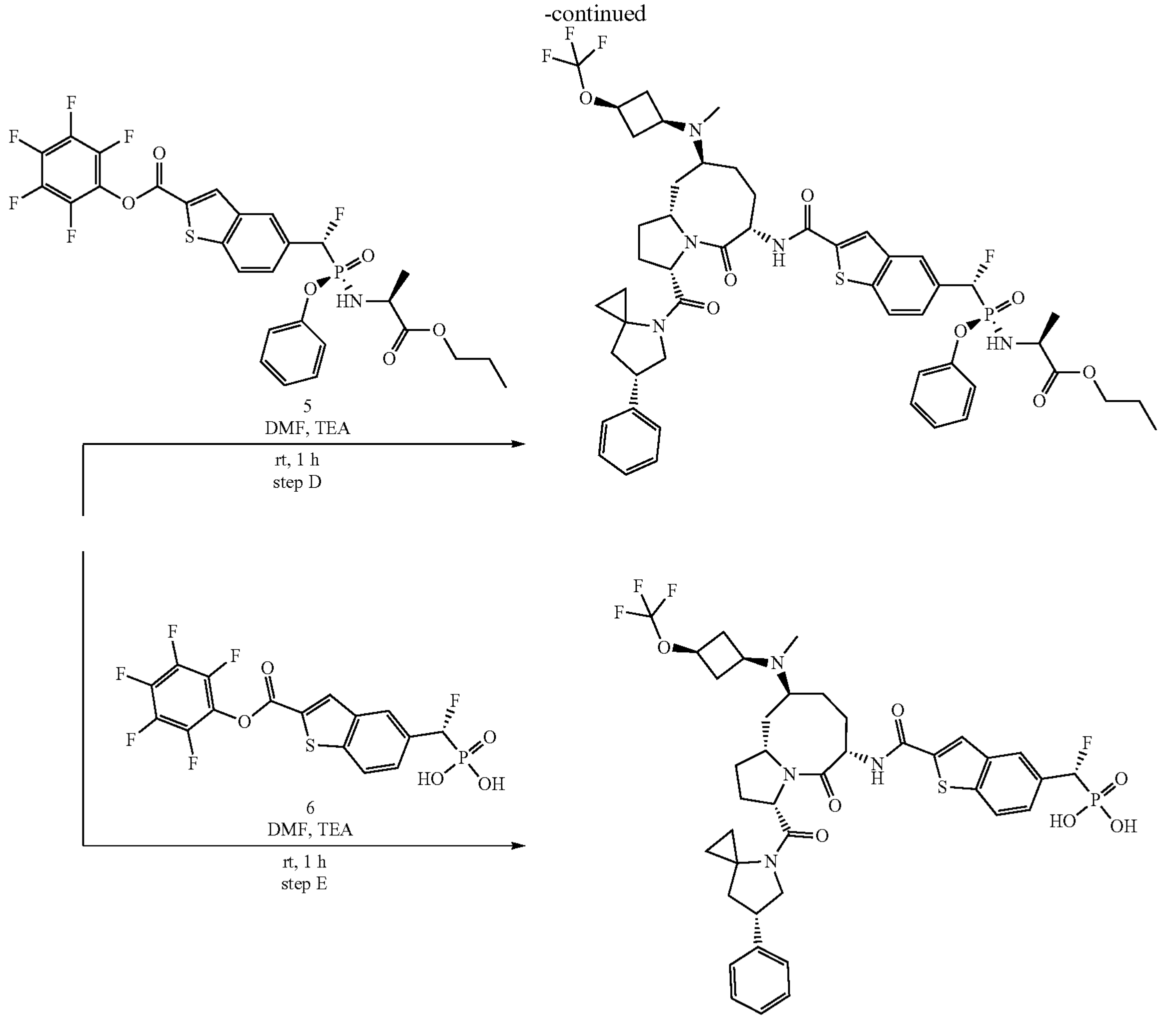
Step A: tert-butyl ((3S,6S,9S,10aR)-5-oxo-3-((S)-6-phenyl-4-azaspiro[2.4]heptane-4-carbonyl)-9-(((1 s, 3R)-3-(trifluoromethoxy)cyclobutyl)amino)decahydropyrrolo[1,2-a]azocin-6-yl)carbamate
-continued
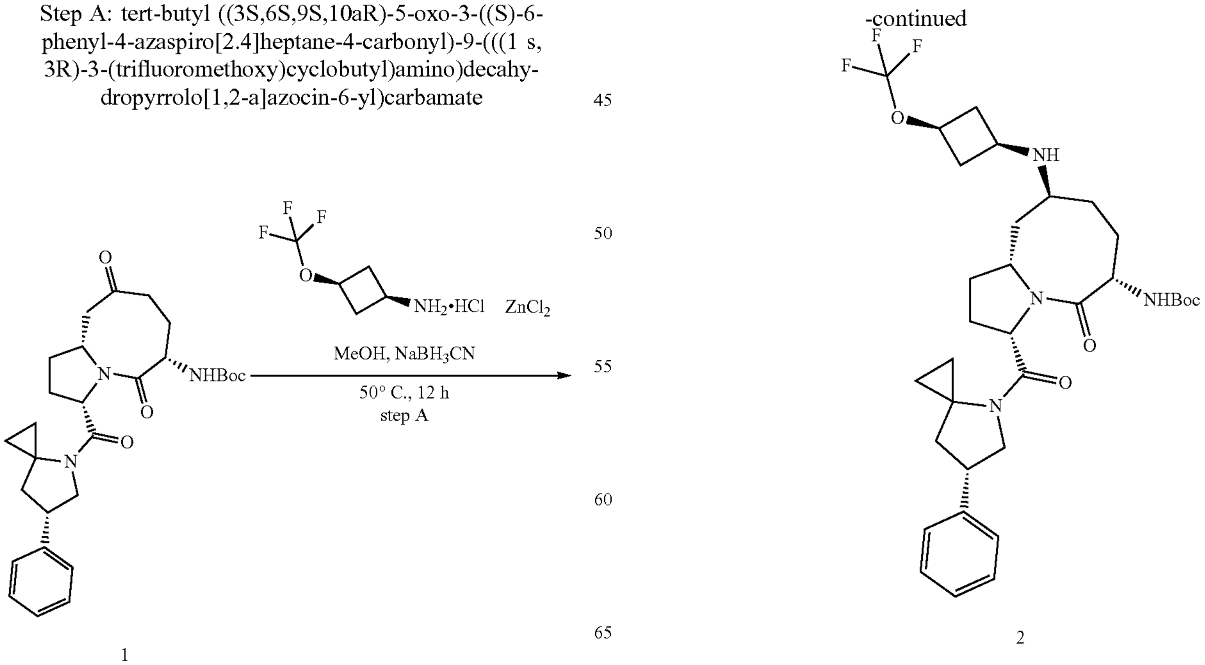
1
2

To a solution of tert-butyl ((3S,6S,10aR)-5,9-dioxo-3-((S)-6-phenyl-4-azaspiro[2.4]heptane-4-carbonyl)decahydropyrrolo[1,2-a]azocin-6-yl)carbamate (1, 1.5 g, 3.03 mmol, 1 eq.) in MeOH (20 mL) was added (1s,3s)-3-(trifluoromethoxy)cyclobutan-1-amine hydrochloride (868 mg, 4.55 mml, 1.5 eq.), $ZnCl_2$ (4.13 g, 30.3 mmol, 10 eq.). The mixture was stirred for 1 h at 50° C., then $NaBH_3CN$ (1.91 g, 30.3 mmol, 10 eq.) added portion wise every 30 mins (2 eq. (382 mg each time) added 5 times). The mixture was stirred for 12 h at 50° C., then cooled to room temperature. The resulting mixture was used in the next step directly without further workup. LCMS (ESI): m/z=635 $[M+H]^+$.

Step B: tert-butyl ((3S,6S,9S,10aR)-9-(methyl((1s,3R)-3-(trifluoromethoxy)cyclobutyl)amino)-5-oxo-3-((S)-6-phenyl-4-azaspiro[2.4]heptane-4-carbonyl)decahydropyrrolo[1,2-a]azocin-6-yl)carbamate

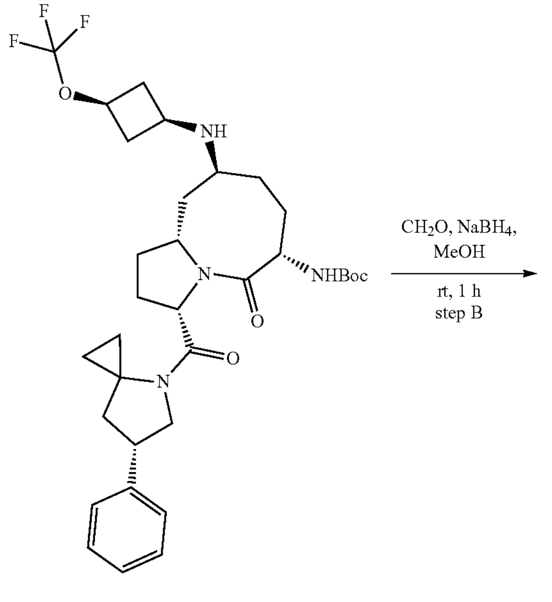

2

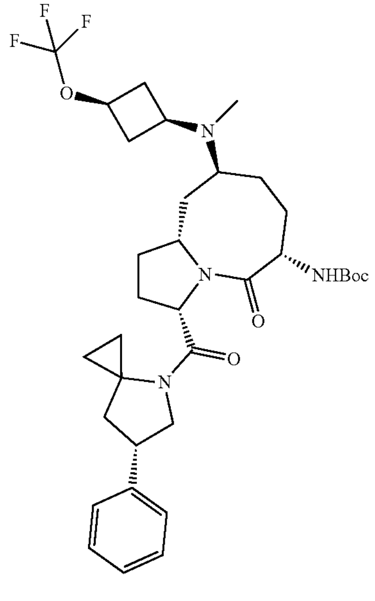

3

To a above mixture (step A) was added 40% formaldehyde (1 mL) at room temperature, the mixture was stirred for 10 min, then $NaBH_4$ (1.15 g, 30.3 mmol, 10 eq.) was added to the mixture in several portions during 20 mins, stirred for additional 30 mins, LCMS show that the reaction was completed. The reaction was quenched by $NH_4Cl$ (sat. aq.), diluted with $H_2O$ (200 mL) and extracted with EtOAc (100 mL×3). The organic layers were dried over $Na_2SO_4$, concentrated to dryness under reduced pressure, and the crude product was purified by C18 column (MeCN:$H_2O$ (0.1% ammonium hydroxide)=5%-70%) to afford tert-butyl ((3S,6S,9S,10aR)-9-(methyl((1s,3R)-3-(trifluoromethoxy)cyclobutyl)amino)-5-oxo-3-((S)-6-phenyl-4-azaspiro[2.4]heptane-4-carbonyl)decahydropyrrolo[1,2-a]azocin-6-yl)carbamate (3, 1 g, 1.54 mmol, 76.9% yield, two steps) as a white solid. LCMS (ESI): m/z=649 $[M+H]^+$.

Step C: (3S,6S,9S,10aR)-6-amino-9-(methyl((1s,3R)-3-(trifluoromethoxy)cyclobutyl)amino)-3-((S)-6-phenyl-4-azaspiro[2.4]heptane-4-carbonyl)octahydropyrrolo[1,2-a]azocin-5(1H)-one

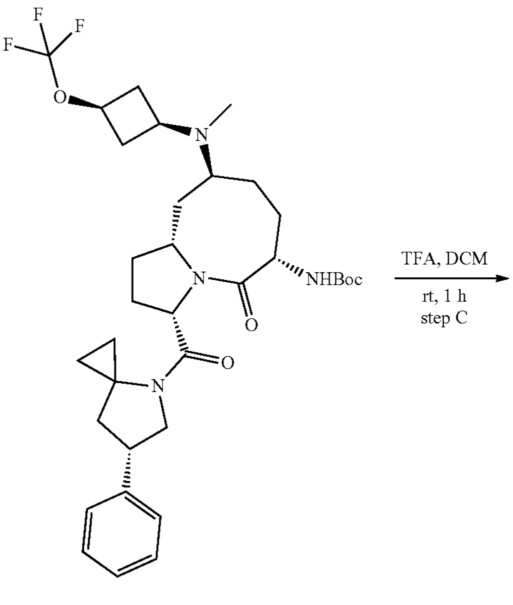

3

-continued

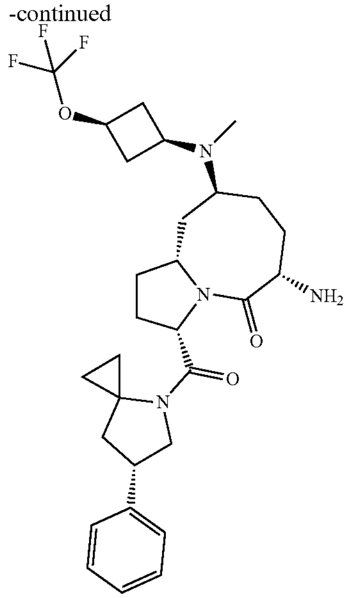

4

To a solution of tert-butyl ((3S,6S,9S,10aR)-9-methyl(1s,3R)-3-(trifluoromethoxy)cyclobutyl)amino)-5-oxo-3-((S)-6-phenyl-4-azaspiro[2.4]heptane-4-carbonyl)decahydropyrrolo[1,2-a]azocin-6-yl)carbamate (3, 30 mg, 0.046 mmol) in DCM (2 mL) was added TFA (2 mL), The resulting mixture was stirred for 1 h at room temperature and was concentrated under reduced pressure to afford crude product (3S,6S,9S,10aR)-6-amino-9-(methyl((1s,3R)-3-(trifluoromethoxy)cyclobutyl)amino)-3-((S)-6-phenyl-4-azaspiro[2.4]heptane-4-carbonyl)octahydropyrrolo[1,2-a]azocin-5(1H)-one (4, 30 mg, TFA salt) as a yellow oil which used in the next step without further purification. LCMS (ESI): m/z=549 $[M+H]^+$.

Step D: propyl ((R)-((R)-fluoro(2-(((3S,6S,9S,10aR)-9-(methyl((1s,3R)-3-(trifluoromethoxy)cyclobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate

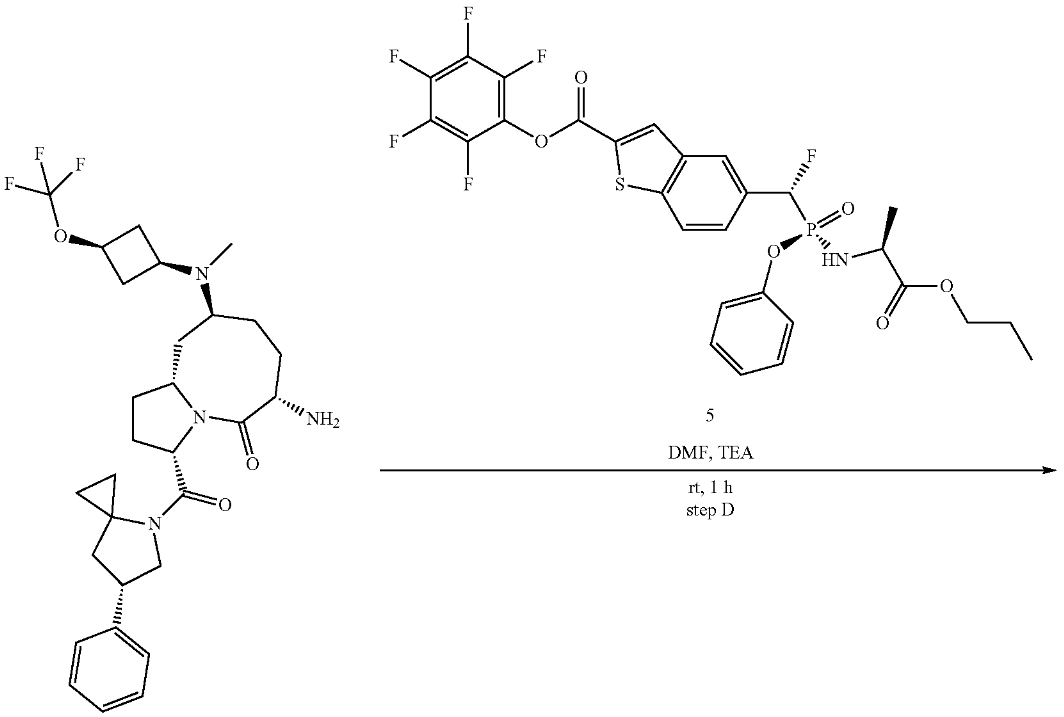

4

5

-continued

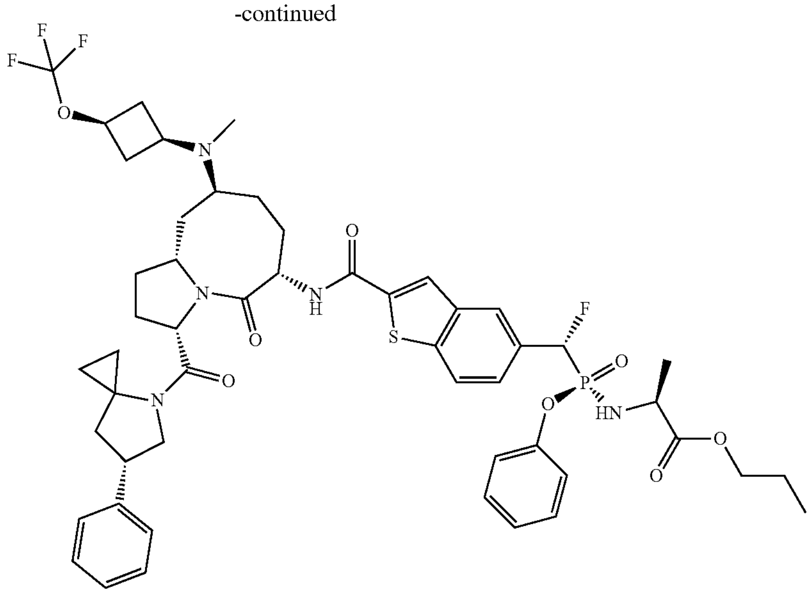

To a solution of (3S,6S,9S,10aR)-6-amino-9-(methyl((1s, 3R)-3-(trifluoromethoxy)cyclobutyl)amino)-3-((S)-6-phenyl-4-azaspiro[2.4]heptane-4-carbonyl)octahydropyrrolo[1, 2-a]azocin-5(1H)-one (4, 30 mg, TFA salt) in DMF (2 mL) was added TEA (9.4 mg, 0.093 mmol, 2 eq.), perfluorophenyl 5-((R)-fluoro((R)-(((S)-1-oxo-1-propoxypropan-2-yl) amino)(phenoxy)phosphoryl)methyl)benzo[b]thiophene-2-carboxylate (5, 30 mg, 0.046 mmol, 1 eq). The resulting mixture was stirred for 1 h at room temperature and the crude product was purified by Prep-HPLC to afford propyl ((R)-((R)-fluoro(2-(((3S,6S,9S,10aR)-9-(methyl((1s,3R)-3-(trifluoromethoxy)cyclobutyl)amino)-5-oxo-3-((S)-6-phenyl-4-azaspiro[2.4]heptane-4-carbonyl)decahydropyrrolo[1, 2-a]azocin-6-yl)carbamoyl)benzo[b]thiophen-5-yl)methyl) (phenoxy)phosphoryl)-L-alaninate (Compound C5, 24 mg, 0.024 mmol) as a white solid. LCMS (ESI): m/z=1010.7 $[M+H]^+$. $^1H$ NMR (400 MHz, DMSO-$d_6$) δ (ppm) 8.79 (d, J=7.6 Hz, 1H), 8.27 (s, 1H), 8.13-7.98 (m, 2H), 7.60 (d, J=8.6 Hz, 1H), 7.40-7.26 (m, 6H), 7.23-7.12 (m, 4H), 6.29-6.03 (m, 2H), 4.71 (t, J=8.5 Hz, 1H), 4.57-4.43 (m, 2H), 4.34-4.24 (m, 1H), 4.12 (t, J=8.7 Hz, 1H), 3.87-3.68 (m, 4H), 3.60-3.47 (m, 1H), 3.08-2.92 (m, 1H), 2.72-2.58 (m, 2H), 2.46-2.09 (m, 5H), 2.03-1.92 (m, 6H), 1.90-1.47 (m, 9H), 1.46-1.35 (m, 2H), 1.13 (d, J=7.1 Hz, 3H), 0.77 (t, J=7.4 Hz, 3H), 0.56-0.37 (m, 2H). $^{19}F$ NMR (376 MHz, DMSO-$d_6$) δ (ppm) −57.57 (s), −194.28 (d, J=83.0 Hz). $^{31}P$ NMR (162 MHz, DMSO-$d_6$) δ (ppm) 17.32 (d, J=83.5 Hz).

Step E: ((R)-fluoro(2-(((3S,6S,9S,10aR)-9-(methyl ((1s,3R)-3-(trifluoromethoxy)cyclobutyl)amino)-5-oxo-3-((S)-6-phenyl-4-azaspiro[2.4]heptane-4-carbonyl)decahydropyrrolo[1,2-a]azocin-6-yl) carbamoyl)benzo[b]thiophen-5-yl)methyl) phosphonic acid

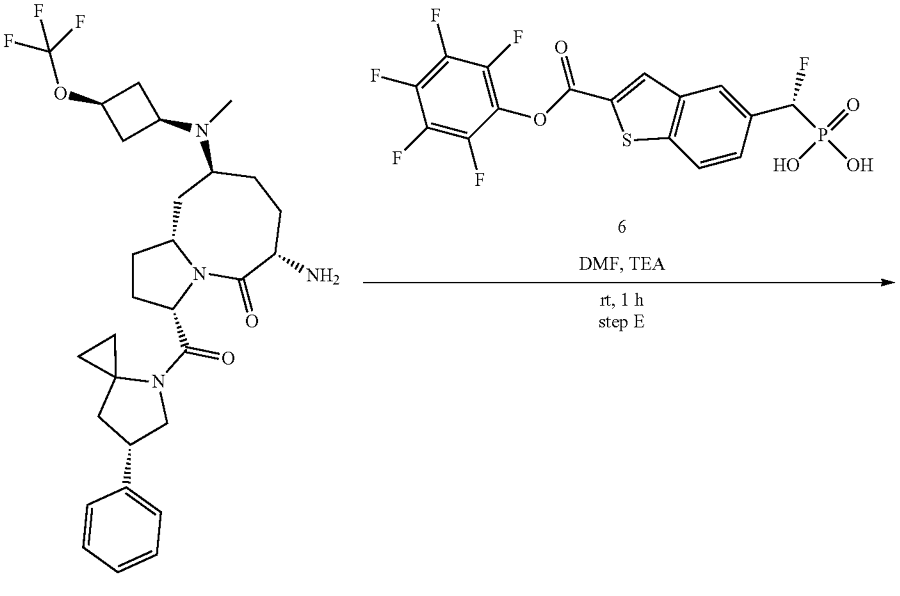

4

-continued

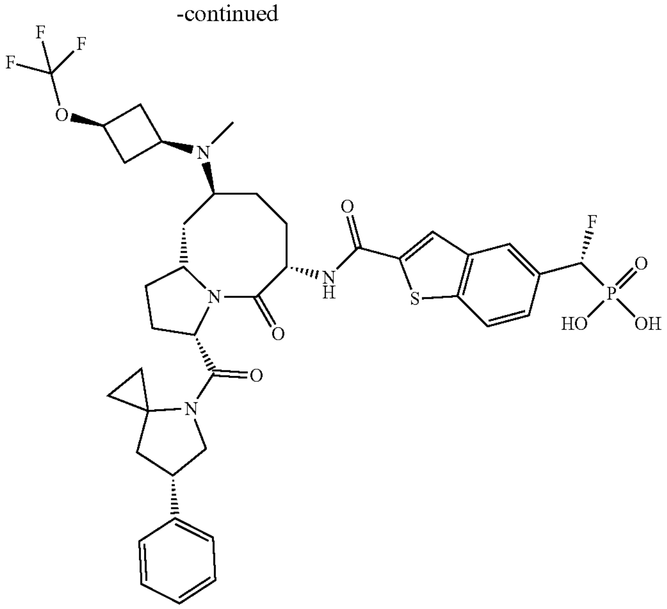

To a solution of (3S,6S,9S,10aR)-6-amino-9-(methyl((1s,3R)-3-(trifluoromethoxy)cyclobutyl)amino)-3-((S)-6-phenyl-4-azaspiro[2.4]heptane-4-carbonyl)octahydropyrrolo[1,2-a]azocin-5(1H)-one (4, 30 mg, TFA salt) in DMF (2 mL) was added TEA (9.4 mg, 0.093 mmol, 2 eq.), (R)-(fluoro(2-((perfluorophenoxy)carbonyl)benzo[b]thiophen-5-yl)methyl)phosphonic acid (6, 21.1 mg, 0.046 mmol, 1 eq.). The resulting mixture was stirred for 1 h at room temperature, and the crude product was purified by Prep-HPLC to afford ((R)-fluoro(2-(((3S,6S,9S,10aR)-9-(methyl((1s,3R)-3-(trifluoromethoxy)cyclobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)phosphonic acid (Compound A4, 12 mg, 0.015 mmol) as a white solid. LCMS (ESI): m/z=821.2 $[M+H]^+$. 1H NMR (400 MHz, $CD_3OD-d_4$) δ (ppm) 8.13-8.00 (m, 2H), 7.92 (d, J=8.5 Hz, 1H), 7.70 (d, J=8.5 Hz, 1H), 7.34-7.15 (m, 5H), 5.79-5.60 (m, 1H), 4.67-4.46 (m, 3H), 4.40-4.28 (m, 1H), 3.99-3.75 (m, 2H), 3.75-3.64 (m, 1H), 3.57-3.42 (m, 1H), 3.05-2.91 (m, 1H), 2.87-1.19 (m, 21H), 0.56-0.33 (m, 2H). $^{19}F$ NMR (376 MHz, $CD_3OD-d_4$) δ (ppm) −61.08 (s), −195.27 (d, J=77.8 Hz). $^{31}P$ NMR (162 MHz, $CD_3OD-d_4$) δ (ppm) 9.67 (d, J=76.4 Hz).

Synthesis of ((S)-fluoro(2-(((3S,6S,9S,10aR)-9-(methyl((1s,3R)-3-(trifluoromethoxy)cyclobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)phosphonic acid (Compound A5)

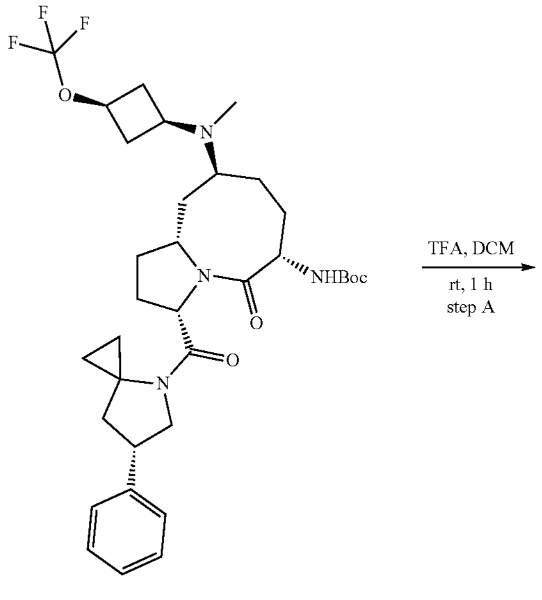

1

-continued
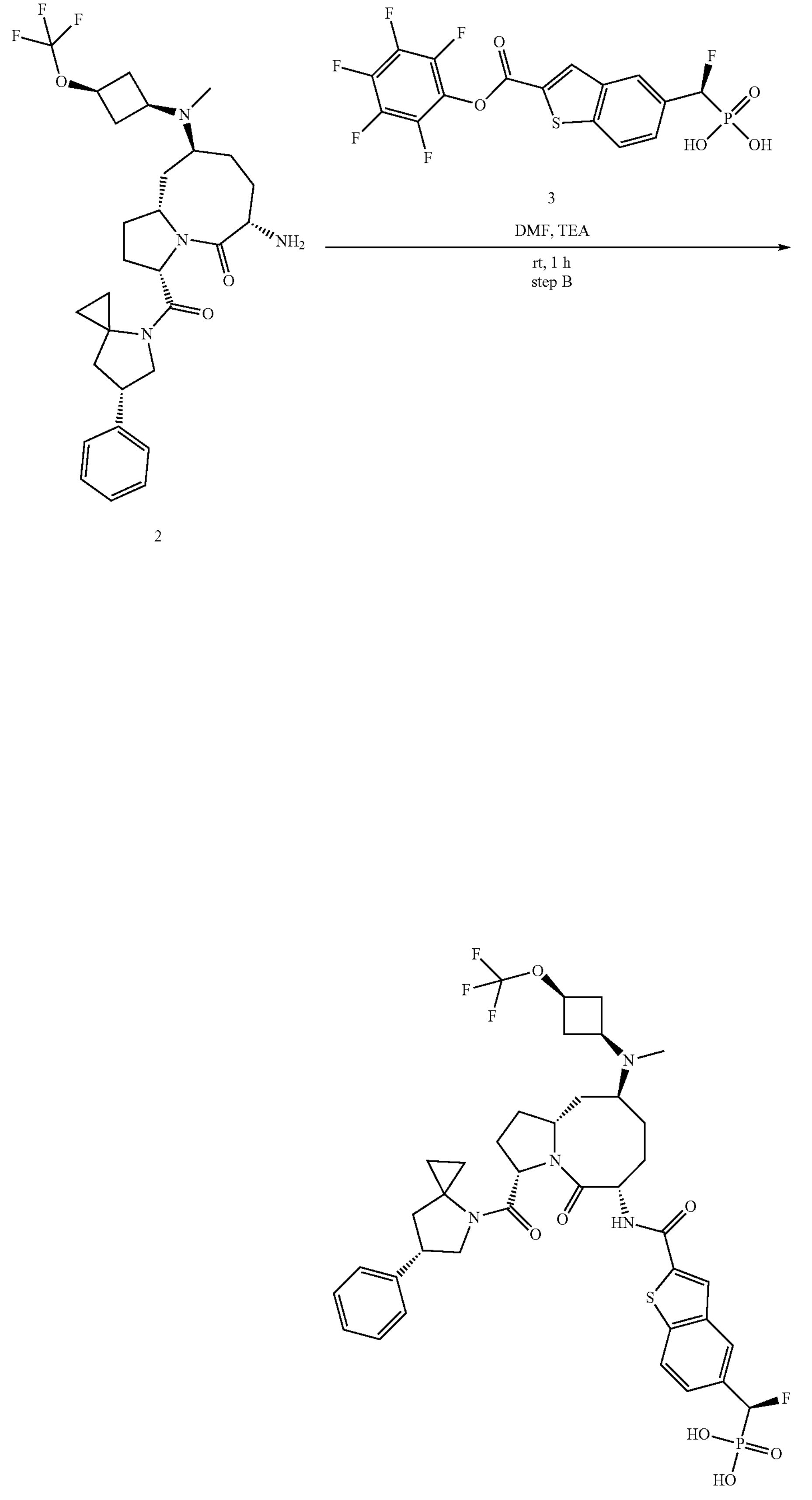
3
2

Step A: (3S,6S,9S,10aR)-6-amino-9-(methyl((1s,3R)-3-(trifluoromethoxy)cyclobutyl)amino)-3-((S)-6-phenyl-4-azaspiro[2.4]heptane-4-carbonyl)octahydropyrrolo[1,2-a]azocin-5(1H)-one

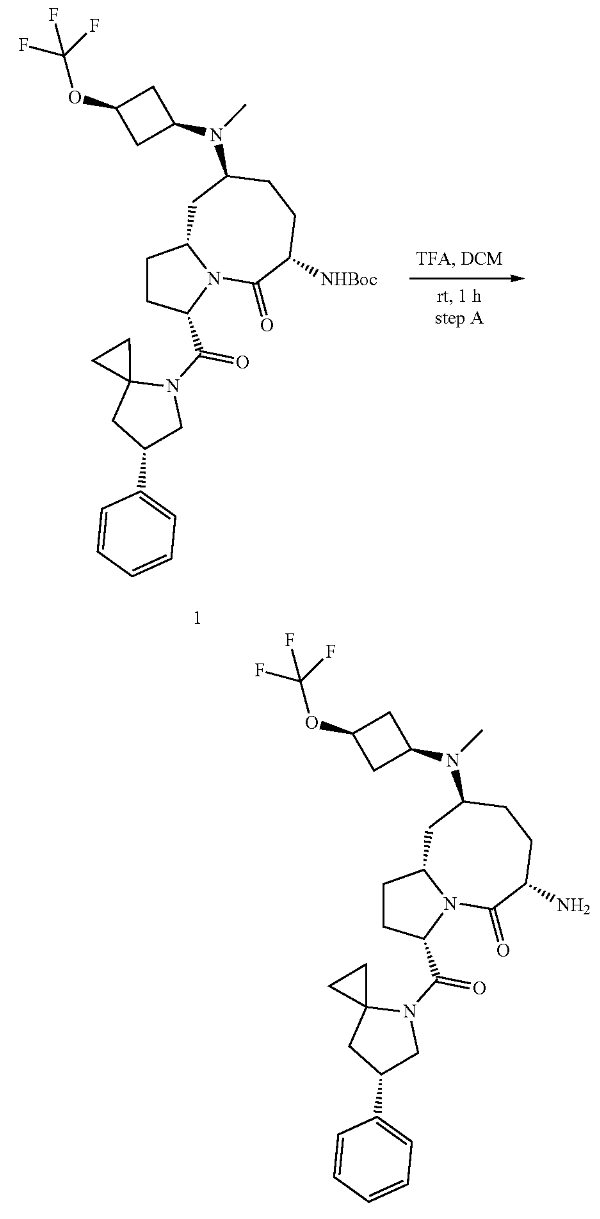

1

2

To a solution of tert-butyl ((3S,6S,9S,10aR)-9-(methyl((1s,3R)-3-(trifluoromethoxy)cyclobutyl)amino)-5-oxo-3-((S)-6-phenyl-4-azaspiro[2.4]heptane-4-carbonyl)decahydropyrrolo[1,2-a]azocin-6-yl)carbamate (1, 30 mg, 0.046 mmol) in DCM (2 mL) was added TFA (2 mL), The resulting mixture was stirred for 1 h at room temperature. The resulting solution was concentrated under reduced pressure to afford crude product (3S,6S,9S,10aR)-6-amino-9-(methyl((1s,3R)-3-(trifluoromethoxy)cyclobutyl)amino)-3-((S)-6-phenyl-4-azaspiro[2.4]heptane-4-carbonyl)octahydropyrrolo[1,2-a]azocin-5(1H)-one (2, 30 mg, TFA salt) as a yellow oil which used in the next step without further purification. LCMS (ESI): m/z=549 $[M+H]^+$.

Step B: ((S)-fluoro(2-(((3S,6S,9S,10aR)-9-(methyl((1s,3R)-3-(trifluoromethoxy)cyclobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)phosphonic acid

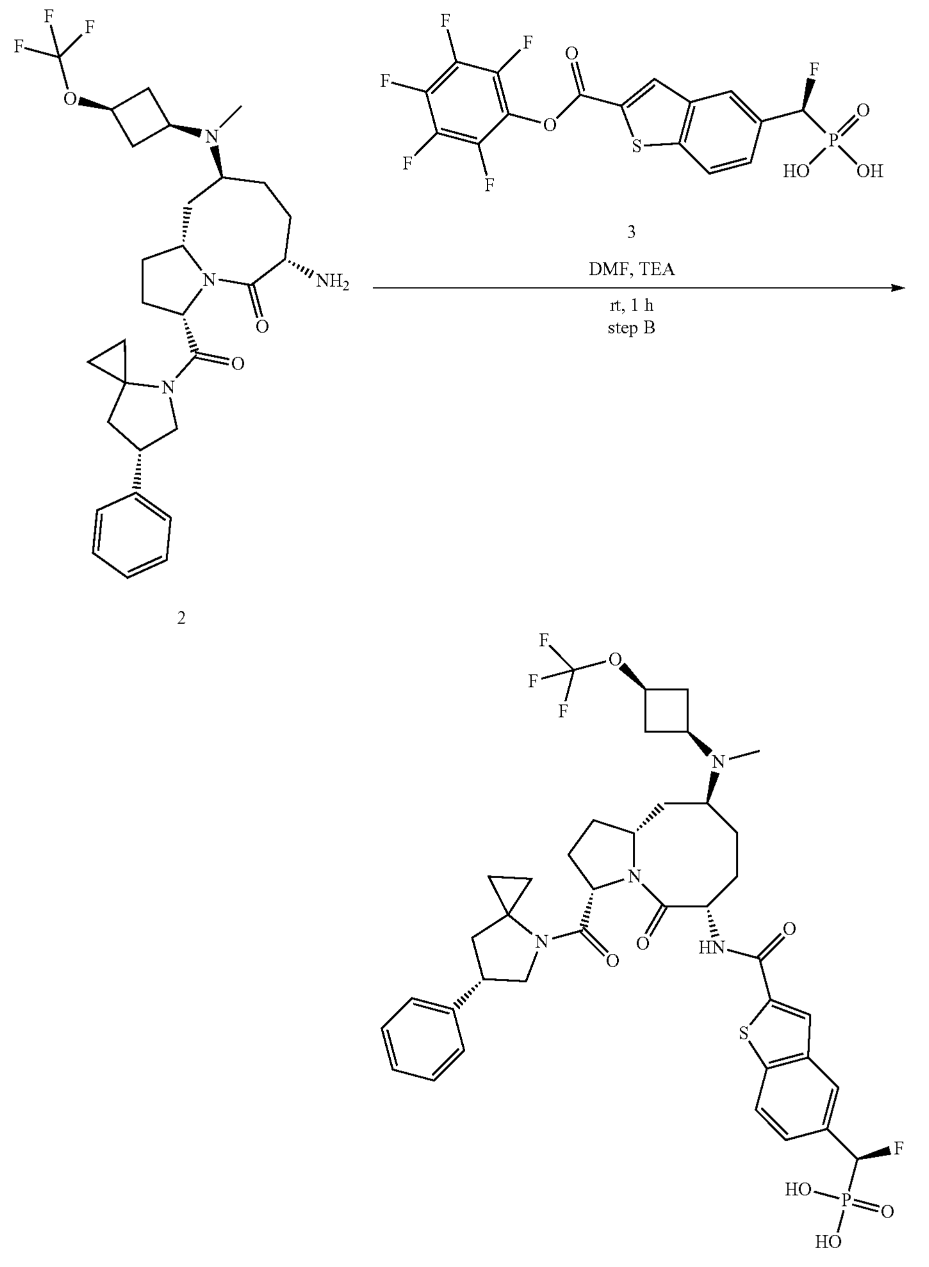

3

2

To a solution of (3S,6S,9S,10aR)-6-amino-9-(methyl((1s,3R)-3-(trifluoromethoxy)cyclobutyl)amino)-3-((S)-6-phenyl-4-azaspiro[2.4]heptane-4-carbonyl)octahydropyrrolo[1,2-a]azocin-5(1H)-one (2, 30 mg, TFA salt) in DMF (2 mL) was added TEA (9.4 mg, 0.093 mmol, 2 eq.), (S)-(fluoro(2-((perfluorophenoxy)carbonyl)benzo[b]thiophen-5-yl)methyl)phosphonic acid (3, 21.1 mg, 0.046 mmol, 1 eq.). The resulting mixture was stirred for 1 h at room temperature, and the crude product was purified by Prep-HPLC to afford ((S)-fluoro(2-(((3S,6S,9S,10aR)-9-(methyl((1s,3R)-3-(trifluoromethoxy)cyclobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)phosphonic acid (Compound A5, 18 mg, 0.022 mmol) as a white solid. LCMS (ESI): m/z=821.3 $[M+H]^+$. $^1$H NMR (400 MHz, $CD_3OD-d_4$) δ (ppm) 8.12-8.01 (m, 2H), 7.87 (d, J=8.4 Hz, 1H), 7.62 (d, J=8.5 Hz, 1H), 7.35-7.26 (m, 4H), 7.20 (t, J=7.0 Hz, 1H), 5.78-5.54 (m, 1H), 4.67 (d, J=10.1 Hz, 1H), 4.59-4.48 (m, 2H), 4.42-4.35 (m, 1H), 3.99 (t, J=8.6 Hz, 1H), 3.88 (t, J=9.7 Hz, 1H), 3.63-3.46 (m, 2H), 3.23-3.17 (m, 1H), 2.91-2.81 (m, 1H), 2.71-2.61 (m, 1H), 2.60-2.50 (m, 1H), 2.40-1.57 (m, 21H), 0.54-0.41 (m, 2H). $^{19}$F NMR (376 MHz, $CD_3OD-d_4$) δ (ppm) −60.66−−61.44 (m), −196.29 (d, J=77.8 Hz). $^{31}$P NMR (162 MHz, $CD_3OD-d_4$) δ (ppm) 9.73 (d, J=75.8 Hz).

Synthesis of isobutyl (cyclopropoxy((S)-fluoro(2-(((3S,6S,9S,10aR)-9-(methyl((1s,3R)-3-(trifluoromethoxy)cyclobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)phosphoryl)-L-alaninate (Compound C156)
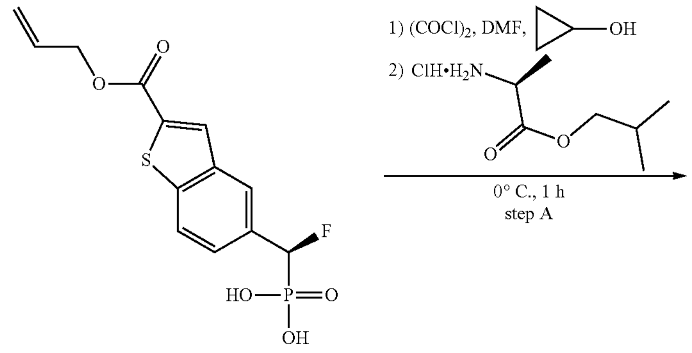
1
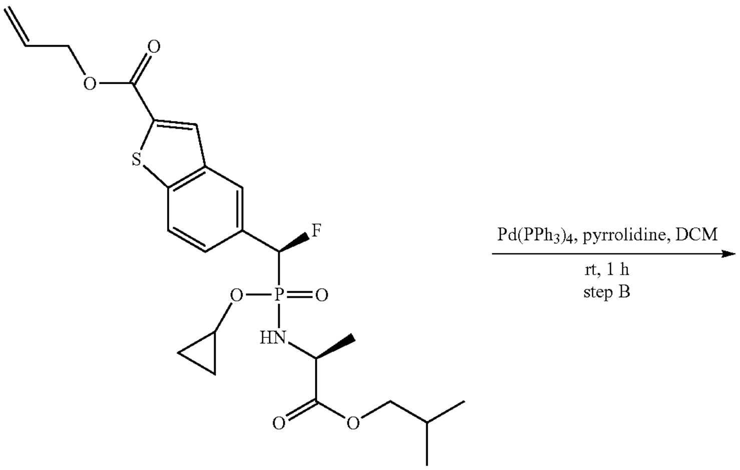
2
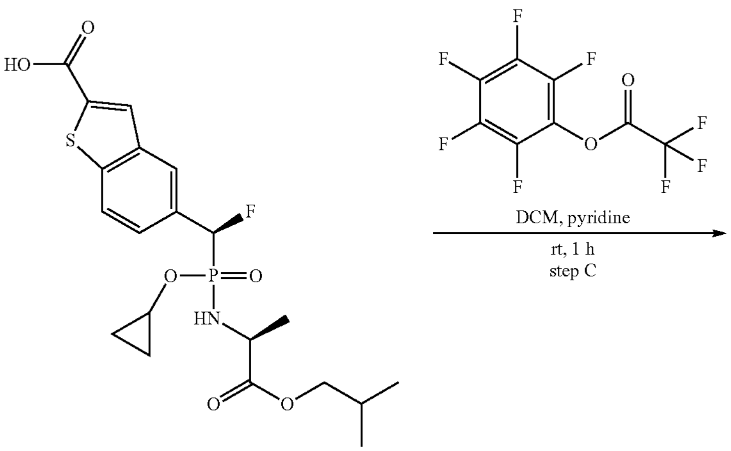
3

-continued
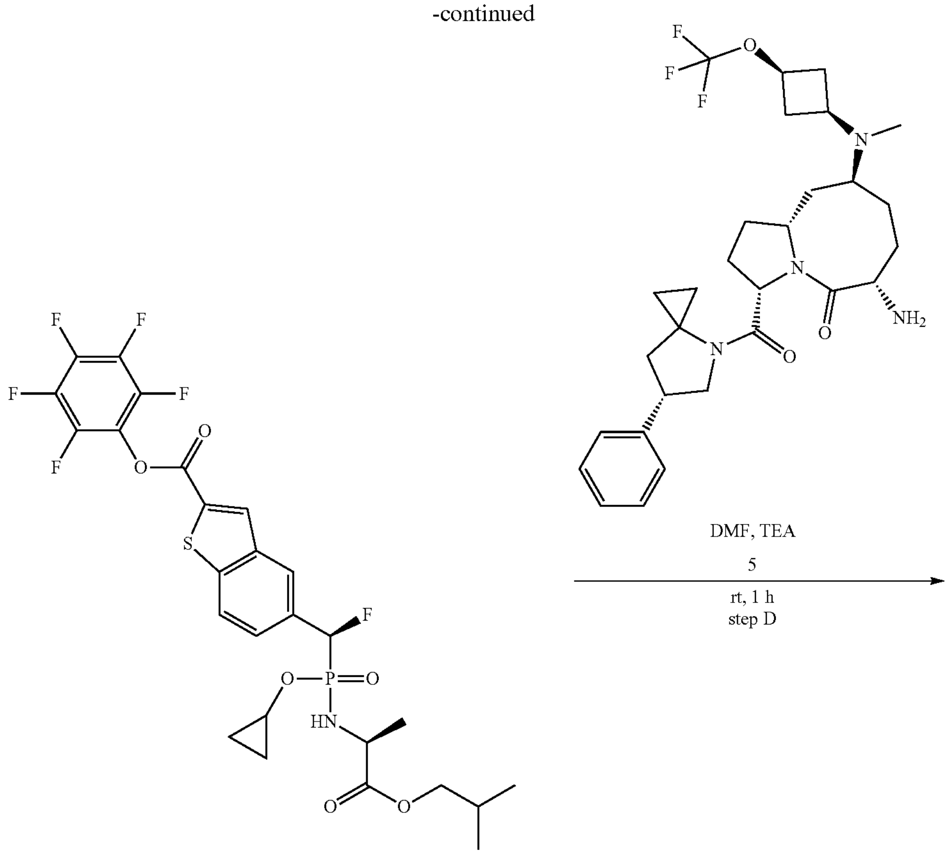
4
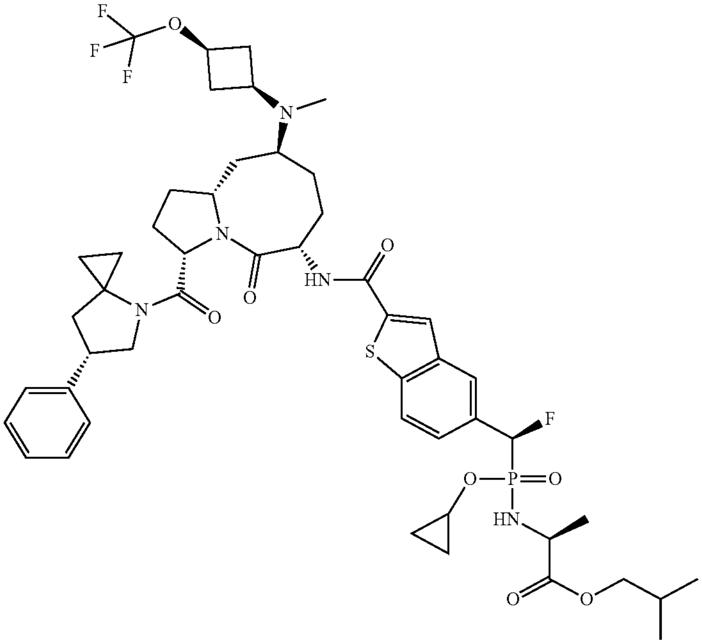

Step A: allyl 5-((1S)-(cyclopropoxy(((S)-1-isobutoxy-1-oxopropan-2-yl)amino)phosphoryl)fluoromethyl)benzo[b]thiophene-2-carboxylate

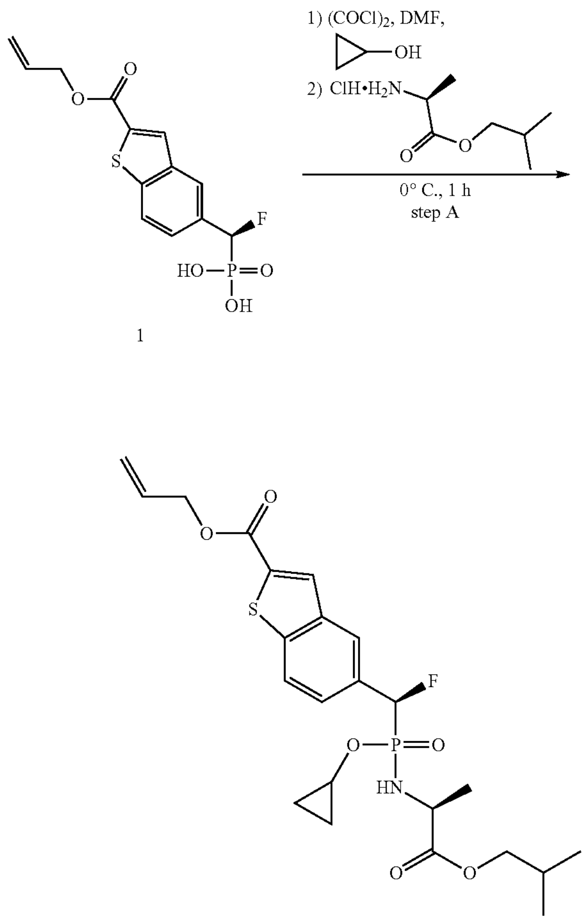

1

2

To a solution of (S)-((2-((allyloxy)carbonyl)benzo[b]thiophen-5-yl)fluoromethyl)phosphonic acid (1, 1 g, 3.03 mmol, 1 eq.) in DCM (20 mL) was added DMF (1 drop), and oxalyl chloride (1.92 g, 15.15 mmol, 5 eq.). The resulting mixture was stirred for 1 h at room temperature, then DCM was evaporated to dryness under reduced pressure to remove the excess oxalyl chloride, then redissolved in dry DCM (20 mL), the solution was cooled down to 0° C., cyclopropanol (176 mg, 3.03 mmol, 1 eq.) was added, followed by TEA (1.53 g, 15.15 mmol, 5 eq.) dropwise. The resulting mixture was stirred for 1 h at 0° C., then isobutyl L-alaninate hydrochloride (1.1 g, 6.06 mmol, 2 eq.) was added to the solution, then stirred for 10 min at 0° C. The reaction was quenched by adding $H_2O$ (20 mL), then extracted with DCM (20 mL×2), the organic layers were combined and washed with brine (20 mL), then dried over $Na_2SO_4$, then concentrated under reduced pressure, the crude product was purified by silica gel column to afford allyl 5-((1S)-(cyclopropoxy(((S)-1-isobutoxy-1-oxopropan-2-yl)amino)phosphoryl)fluoromethyl)benzo[b]thiophene-2-carboxylate (2, 500 mg, 1.01 mmol, 33% yield) as a white solid. LCMS (ESI): m/z=498 $[M+H]^+$.

Step B: 5-((1S)-(cyclopropoxy(((S)-1-isobutoxy-1-oxopropan-2-yl)amino)phosphoryl)fluoromethyl)benzo[b]thiophene-2-carboxylic acid

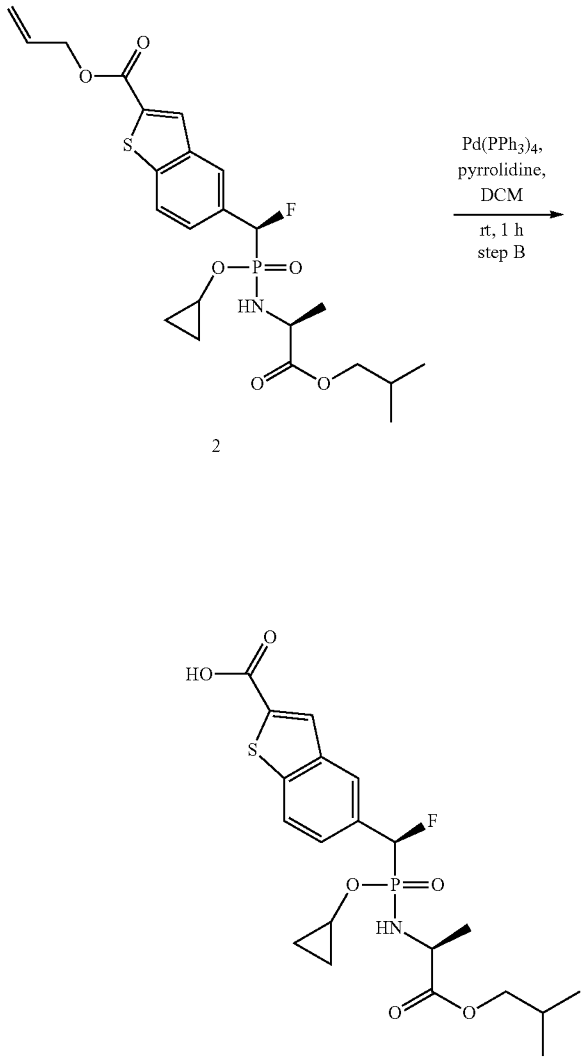

2

3

To a solution of allyl 5-((1S)-(cyclopropoxy(((S)-1-isobutoxy-1-oxopropan-2-yl)amino)phosphoryl)fluoromethyl)benzo[b]thiophene-2-carboxylate (2, 500 mg, 1.01 mmol, 1 eq.) in DCM (10 mL) was added $Pd(PPh_3)_4$ (115 mg, 0.1 mmol, 0.1 eq.), pyrrolidine (71 mg, 1.01 mmol, 1 eq.). The resulting mixture was stirred for 1 h at room temperature under the atmosphere of $N_2$. The reaction was quenched by adding $H_2O$ (10 mL), and adjusted pH=3 with 1 M HCl (aq.). Then extracted with DCM (10 mL×3), the organic layers were combined and washed with brine (20 mL), dried over $Na_2SO_4$, then concentrated to dryness under reduced pressure to afford crude product 5-((1S)-(cyclopropoxy(((S)-1-isobutoxy-1-oxopropan-2-yl)amino)phosphoryl)fluoromethyl)benzo[b]thiophene-2-carboxylic acid (3, 450 mg, 0.98 mmol, 97% yield) as a yellow solid, which was used in next step without further purification. LCMS (ESI): m/z=458 $[M+H]^+$.

Step C: perfluorophenyl 5-((1S)-(cyclopropoxy(((S)-1-isobutoxy-1-oxopropan-2-yl)amino)phosphoryl)fluoromethyl)benzo[b]thiophene-2-carboxylate

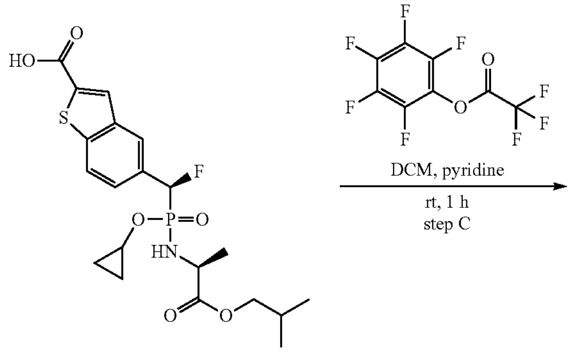

3

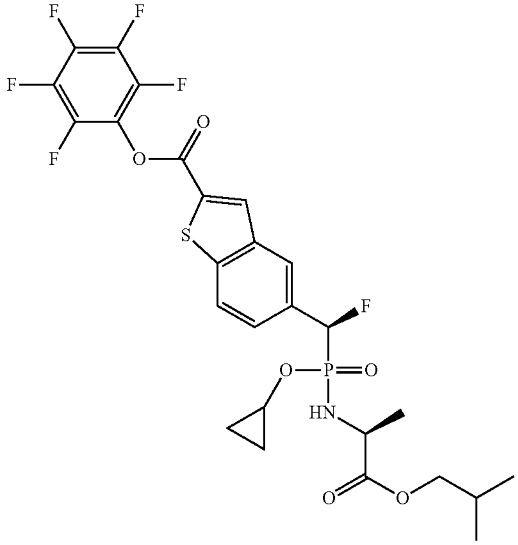

4

To a solution of 5-((1S)-(cyclopropoxy(((S)-1-isobutoxy-1-oxopropan-2-yl)amino)phosphoryl)fluoromethyl)benzo[b]thiophene-2-carboxylic acid (3, 450 mg, 0.98 mmol, 1 eq.) in DCM (5 mL) was added pyridine (233 mg, 2.95 mmol, 3 eq.), perfluorophenyl 2,2,2-trifluoroacetate (276 mg, 1.97 mmol, 2 eq.). The resulting mixture was stirred for 1 h at room temperature, LCMS show that the reaction was completed. $H_2O$ (10 mL) was added to the solution, which was adjusted to pH=3 with 1M HCl (aq.), then extracted with DCM (10 mL×3). The organic layers were combined and washed with brine, dried over $Na_2SO_4$, concentrated to dryness under reduced pressure the crude product was purified by C18 column to afford perfluorophenyl 5-((1S)-(cyclopropoxy(((S)-1-isobutoxy-1-oxopropan-2-yl)amino)phosphoryl)fluoromethyl)benzo[b]thiophene-2-carboxylate (4, 500 mg, 0.80 mmol, 81.6% yield) as a white solid. LCMS (ESI): m/z=624 $[M+H]^+$.

Step D: isobutyl (cyclopropoxy((S)-fluoro(2-(((3S,6S,9S,10aR)-9-(methyl((1s,3R)-3-(trifluoromethoxy)cyclobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)phosphoryl)-L-alaninate To a solution of perfluorophenyl 5-((1S)-(cyclopropoxy(((S)-1-isobutoxy-1-oxopropan-2-yl)amino)phosphoryl)fluoromethyl)benzo[b]thiophene-2-carboxylate (4, 30 mg, 0.048 mmol, 1 eq.) in DMF (2 mL) was added TEA (9.7 mg, 0.096 mmol, 2 eq.), (3S,6S,9S,10aR)-6-amino-9-(methyl((1s,3R)-3-(trifluoromethoxy)cyclobutyl)amino)-3-((S)-6-

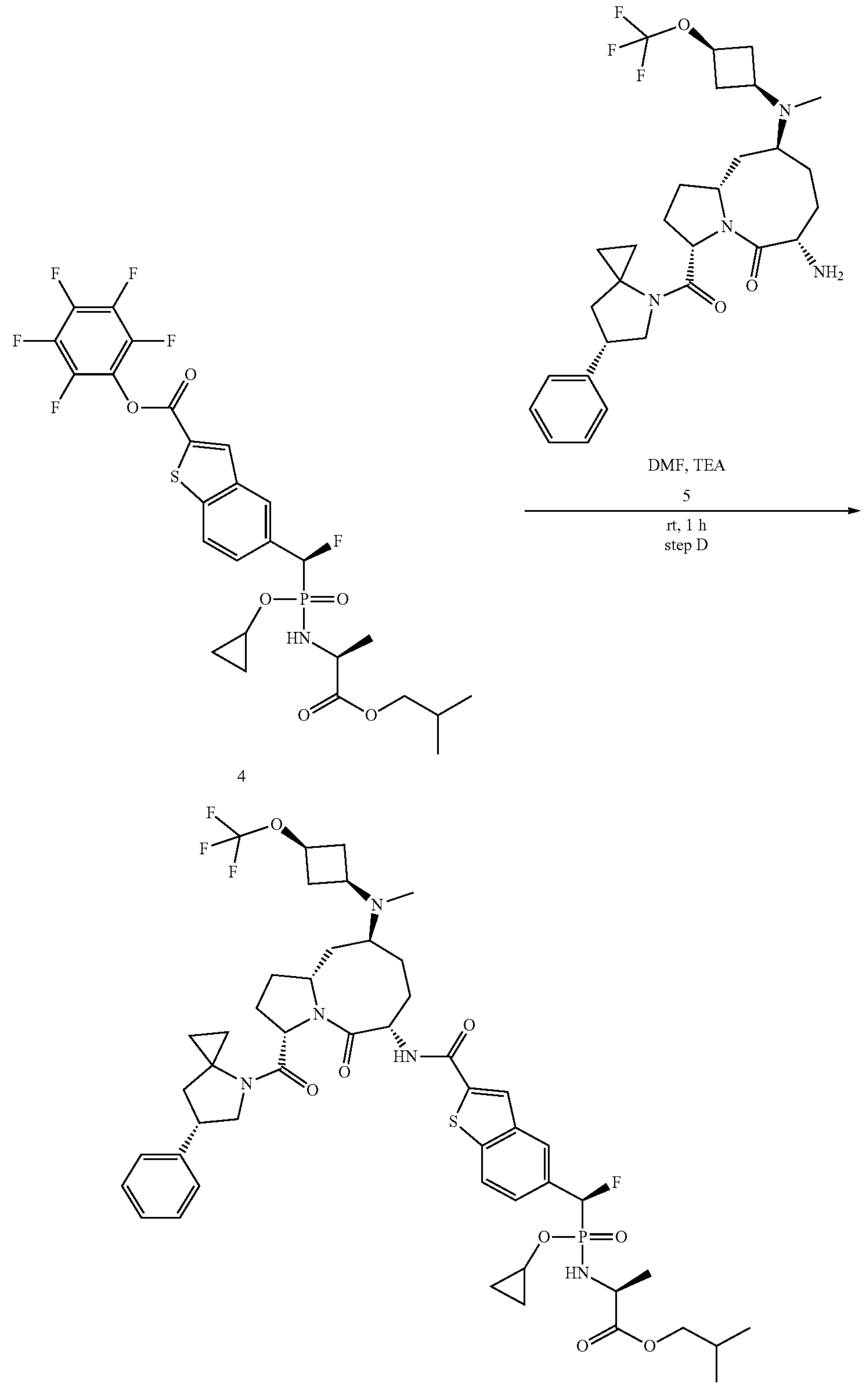

phenyl-4-azaspiro[2.4]heptane-4-carbonyl)octahydropyrrolo[1,2-a]azocin-5(1H)-one (5, 26 mg, 0.048 mmol, 1 eq.). The resulting mixture was stirred for 1 h at room temperature. The crude product was purified by Prep-HPLC to afford isobutyl (cyclopropoxy((S)-fluoro(2-(((3S,6S,9S,10aR)-9-(methyl((1s,3R)-3-(trifluoromethoxy)cyclobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)phosphoryl)-L-alaninate (Compound C156, 26 mg, 0.026 mmol) as a white solid. LCMS (ESI): m/z=988 $[M+H]^+$. $^1$H NMR (400 MHz, DMSO-$d_6$) δ (ppm) 8.87-8.70 (m, 1H), 8.32-8.20 (m, 1H), 8.08-7.98 (m, 1H), 7.98-7.92 (m, 1H), 7.55-7.44 (m, 1H), 7.38-7.26 (m, 4H), 7.24-7.17 (m, 1H), 6.11-5.60 (m, 2H), 4.78-4.64 (m, 1H), 4.59-4.42 (m, 2H), 4.36-4.23 (m, 1H), 4.17-4.06 (m, 1H), 4.02-3.86 (m, 1H), 3.86-3.60 (m, 4H), 3.59-3.46 (m, 1H), 3.08-2.92 (m, 1H), 2.74-2.57 (m, 2H), 2.47-2.29 (m, 2H), 2.28-2.18 (m, 1H), 2.17-2.08 (m, 2H), 2.05-1.92 (m, 6H), 1.90-1.45 (m, 10H), 1.32-0.97 (m, 3H), 0.89-0.82 (m, 6H), 0.81-0.62 (m, 2H), 0.61-0.53 (m, 2H), 0.54-0.35 (m, 2H). $^{19}$F NMR (376 MHz, DMSO-$d_6$) δ (ppm) −57.57 (s), −193.97 (d, J=81.1 Hz), −196.49 (d, J=82.0 Hz). $^{31}$P NMR (162 MHz, DMSO-$d_6$) δ (ppm) 19.89 (d, J=82.2 Hz), 19.58 (d, J=80.7 Hz).

Synthesis of ((R)-fluoro(2-(((3S,6S,9S,10aR)-9-(methyl((1s,3R)-3-(trifluoromethyl)cyclobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)phosphonic acid (Compound A2)

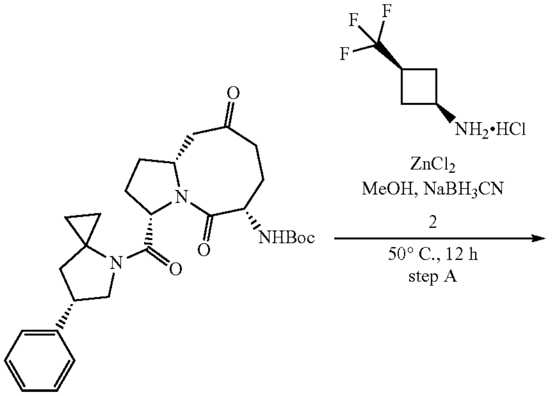

1

-continued

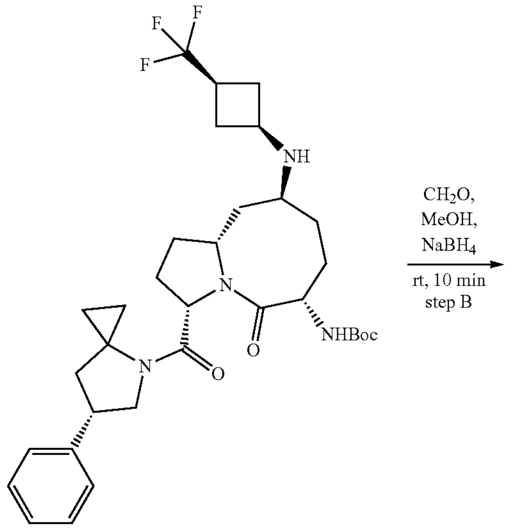

3

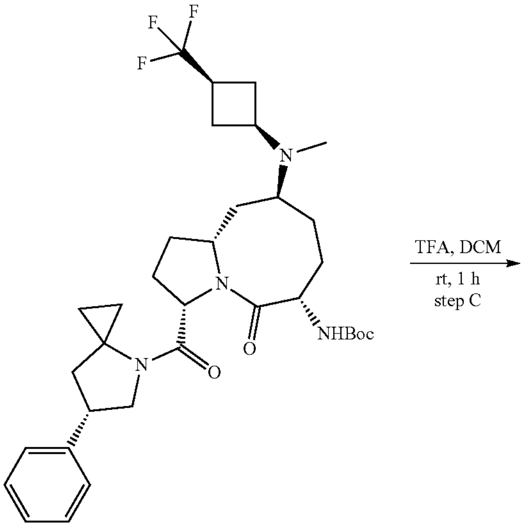

4

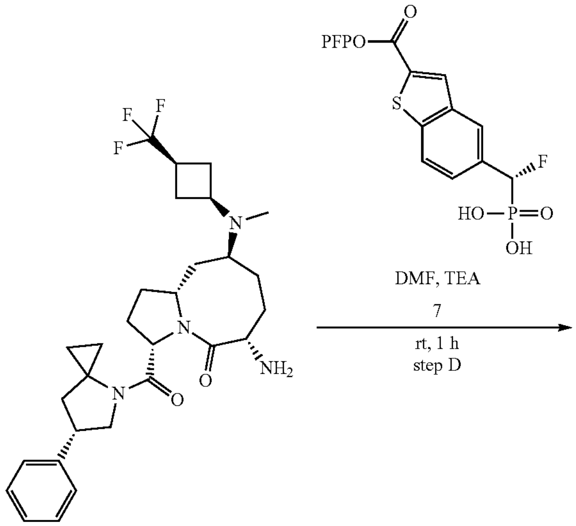

5

-continued

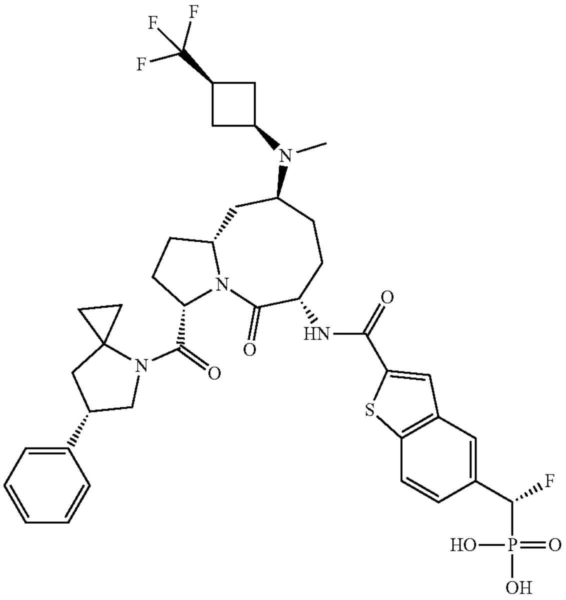

Step A: tert-butyl ((3S,6S,9S,10aR)-5-oxo-3-((S)-6-phenyl-4-azaspiro[2.4]heptane-4-carbonyl)-9-(((1s,3R)-3-(trifluoromethyl)cyclobutyl)amino)decahydropyrrolo[1,2-a]azocin-6-yl)carbamate

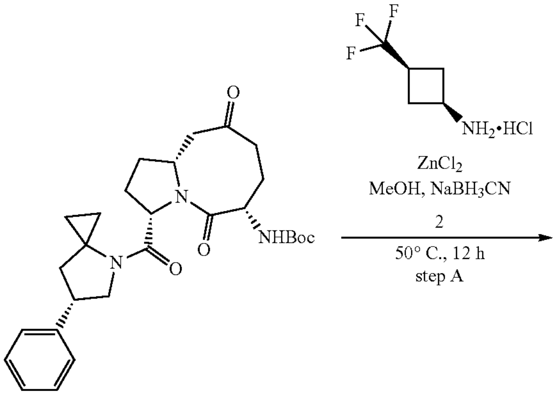

1

-continued

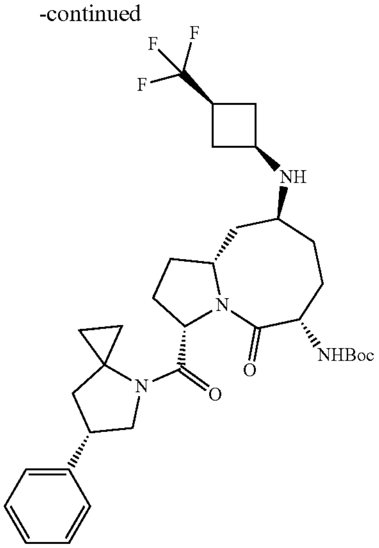

3

To a solution of tert-butyl ((3S,6S,10aR)-5,9-dioxo-3-((R)-6-phenyl-4-azaspiro[2.4]heptane-4-carbonyl)decahydropyrrolo[1,2-a]azocin-6-yl)carbamate (1, 1 g, 2.02 mmol, 1 eq.) in MeOH (20 mL) was added (1s,3s)-3-(trifluoromethyl)cyclobutan-1-amine hydrochloride (2, 530 mg, 3.03 mmol, 1.5 eq.), $ZnCl_2$ (2.77 g, 20.2 mmol, 10 eq.), and the solution was stirred at 50° C. for 2 hr under the atmosphere of $N_2$, then $NaBH_3CN$ (1.27 g, 20.2 mmol, 10 eq.) added portion wise every 30 mins (2 eq. (254 mg each time) added 5 times). The solution was stirred at 50° C. for additional 12 hr, then cooled to room temperature and used to next step without further workup. LCMS (ESI): m/z=619 $[M+H]^+$.

Step B: tert-butyl ((3S,6S,9S,10aR)-9-(methyl((1s,3R)-3-(trifluoromethyl)cyclobutyl)amino)-5-oxo-3-((S)-6-phenyl-4-azaspiro[2.4]heptane-4-carbonyl)decahydropyrrolo[1,2-a]azocin-6-yl)carbamate

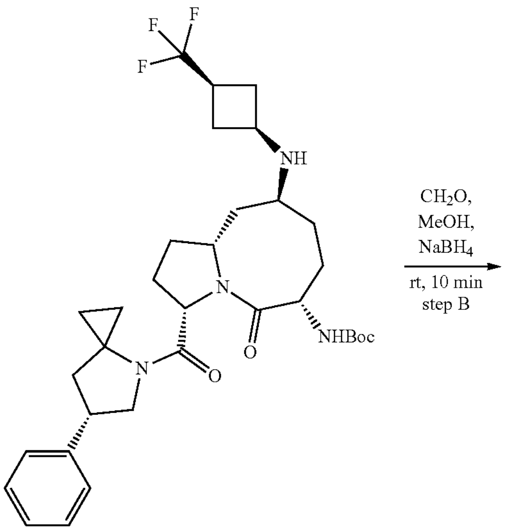

3

-continued

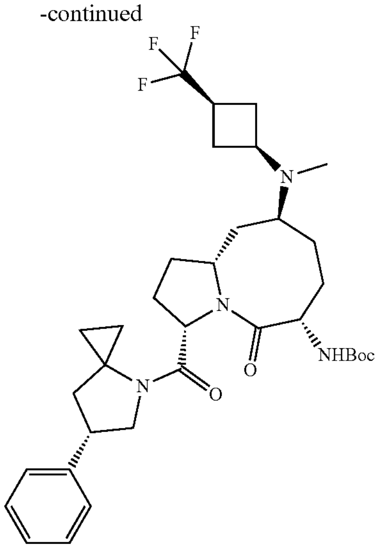

4

To the above mixture (step A) was added 40% formaldehyde aqueous (3 mL) at room temperature, the mixture was stirred for 30 min, then $NaBH_4$ (383 mg, 10.1 mmol, 5 eq.) was added in several portions and the resulting mixture was stirred for additional 30 min. The resulting mixture was cooled down to 0° C. and was quenched by $NH_4Cl$ (sat. aq), diluted with $H_2O$ (80 mL) and extracted with EtOAc (50 mL×3), the organic layers were combined and washed with brine (50 mL), dried over $Na_2SO_4$, filtered, then concentrated to dryness under reduced pressure. The crude product was purified by C18 column (MeCN:$H_2O$ (0.1% ammonium hydroxide)=5%-70%) to afford tert-butyl ((3S,6S,9S,10aR)-9-(methyl((1s,3R)-3-(trifluoromethyl)cyclobutyl)amino)-5-oxo-3-((S)-6-phenyl-4-azaspiro[2.4]heptane-4-carbonyl) decahydropyrrolo[1,2-a]azocin-6-yl)carbamate (4, 1 g, 1.58 mmol, 78.9% yield two steps) as a white solid. LCMS (ESI): m/z=633 [M+H]$^+$.

Step C: (3S,6S,9S,10aR)-6-amino-9-(methyl((1s,3R)-3-(trifluoromethyl)cyclobutyl)amino)-3-((S)-6-phenyl-4-azaspiro[2.4]heptane-4-carbonyl)octahydropyrrolo[1,2-a]azocin-5(1H)-one

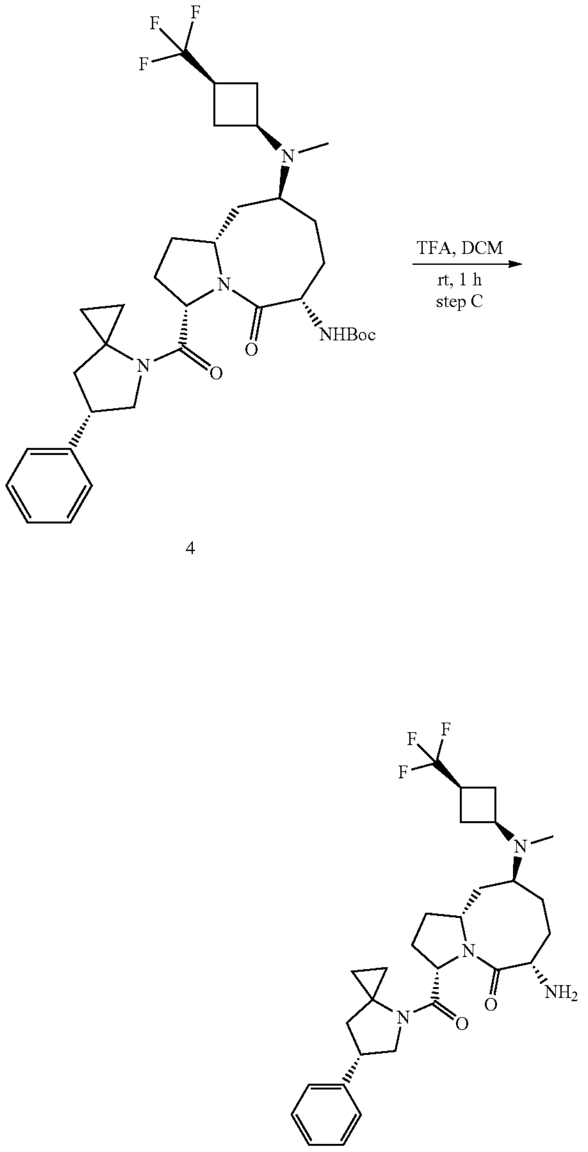

4

5

To a solution of tert-butyl ((3S,6S,9S,10aR)-9-(methyl((1s,3R)-3-(trifluoromethyl)cyclobutyl)amino)-5-oxo-3-((S)-6-phenyl-4-azaspiro[2.4]heptane-4-carbonyl)decahydropyrrolo[1,2-a]azocin-6-yl)carbamate (4, 30 mg, 0.047 mmol) in DCM (2 mL) was added TFA (2 mL). The resulting mixture was stirred for 1 h at room temperature and concentrated to dryness under reduced pressure to afford crude product (3S,6S,9S,10aR)-6-amino-9-(methyl((1s,3R)-3-(trifluoromethyl)cyclobutyl)amino)-3-((S)-6-phenyl-4-azaspiro[2.4]heptane-4-carbonyl)octahydropyrrolo[1,2-a]azocin-5(1H)-one (5, 30 mg, TFA salt) as a yellow oil which was used in the next step without further purification. LCMS (ESI): m/z=533 [M+H]$^+$.

Step D: ((R)-fluoro(2-(((3S,6S,9S,10aR)-9-(methyl((1s,3R)-3-(trifluoromethyl)cyclobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)phosphonic acid

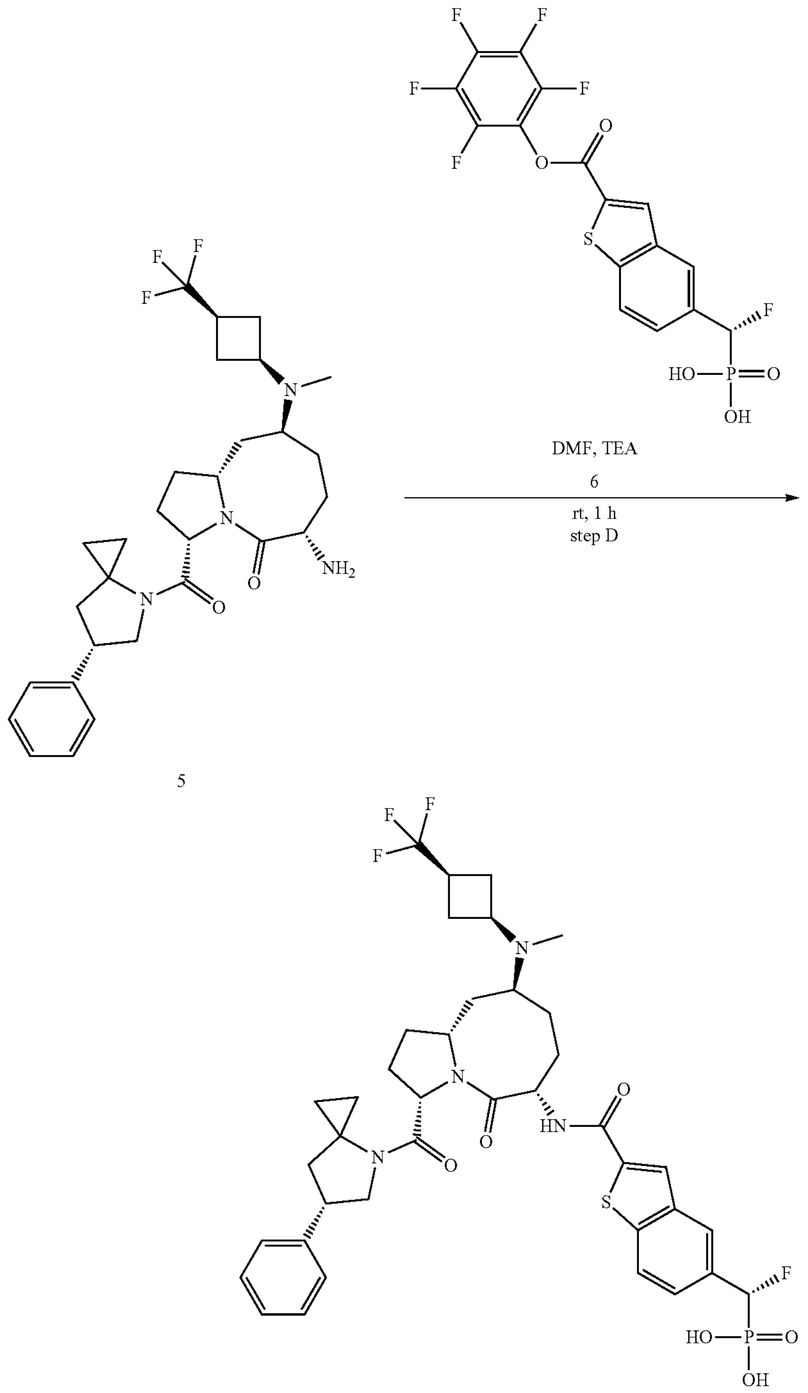

5

To a solution of (3S,6S,9S,10aR)-6-amino-9-(methyl((1s,3R)-3-(trifluoromethyl)cyclobutyl)amino)-3-((S)-6-phenyl-4-azaspiro[2.4]heptane-4-carbonyl)octahydropyrrolo[1,2-a]azocin-5(1H)-one (5, 30 mg, TFA salt) in DMF (2 mL) was added TEA (9.6 mg, 0.095 mmol, 2 eq.) and (R)-(fluoro(2-((perfluorophenoxy)carbonyl)benzo[b]thiophen-5-yl)methyl)phosphonic acid (6, 21.6 mg, 0.047 mmol, 1 eq.). The resulting mixture was stirred for 1 h at room temperature and the crude product was purified by Prep-HPLC to afford ((R)-fluoro(2-(((3S,6S,9S,10aR)-9-(methyl((1s,3R)-3-(trifluoromethyl)cyclobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)phosphonic acid (Compound A2, 18 mg) as a white solid. LCMS (ESI): m/z=805 $[M+H]^+$. $^1H$ NMR (400 MHz, $CD_3OD-d_4$) δ (ppm) 8.05 (s, 2H), 7.89 (d, J=8.5 Hz, 1H), 7.66 (d, J=8.4 Hz, 1H), 7.36-7.27 (m, 4H), 7.23-7.17 (m, 1H), 5.76-5.53 (m, 1H), 4.69-4.60 (m, 2H), 4.51-4.44 (m, 1H), 4.05-3.80 (m, 4H), 3.59-3.51 (m, 1H), 2.93-2.58 (m, 6H), 2.49-2.29 (m, 4H), 2.20-2.12 (m, 2H), 2.02-1.58 (m, 10H), 0.57-0.45 (m, 2H). $^{19}$F NMR (376 MHz, $CD_3OD-d_4$) δ (ppm) −74.51 (s), −195.88 (s). $^{31}$P NMR (162 MHz, $CD_3OD-d_4$) δ (ppm) 9.78 (d, J=74.9 Hz).
Synthesis of ((S)-tetrahydrofuran-3-yl)methyl (((R)-fluoro(2-(((3S,6S,9S,10aR)-9-(methyl((1s,3R)-3-(trifluoromethyl)cyclobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate (Compound C174)
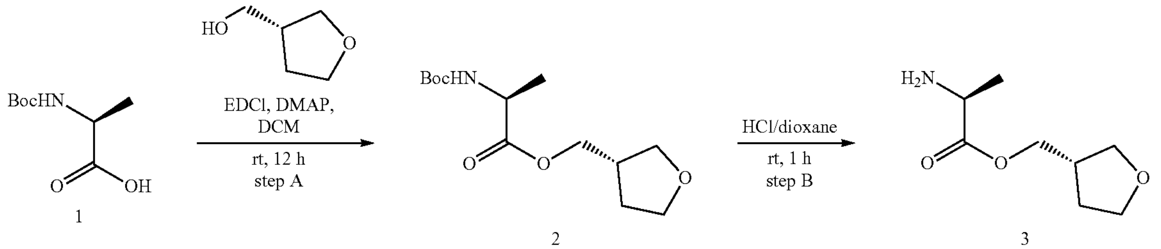
1 2 3
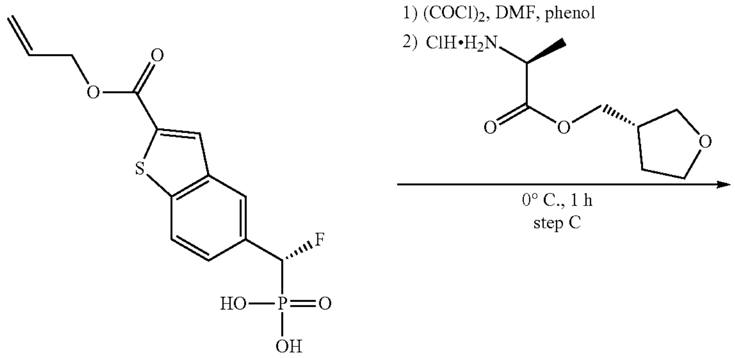
4
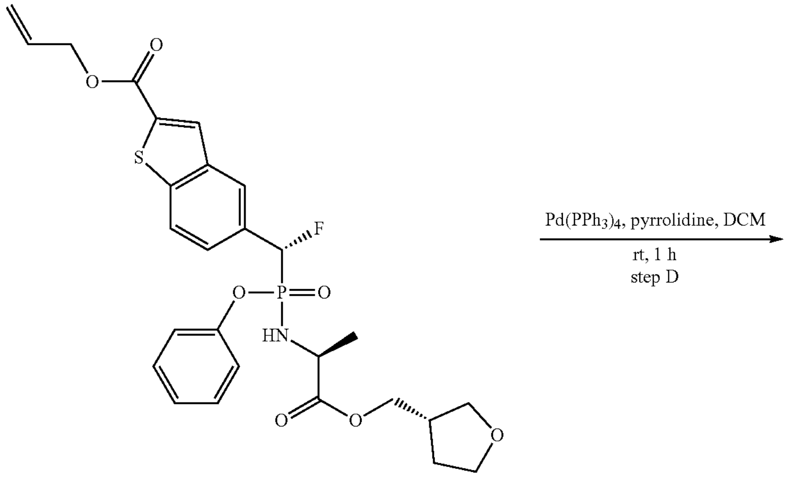
5

-continued
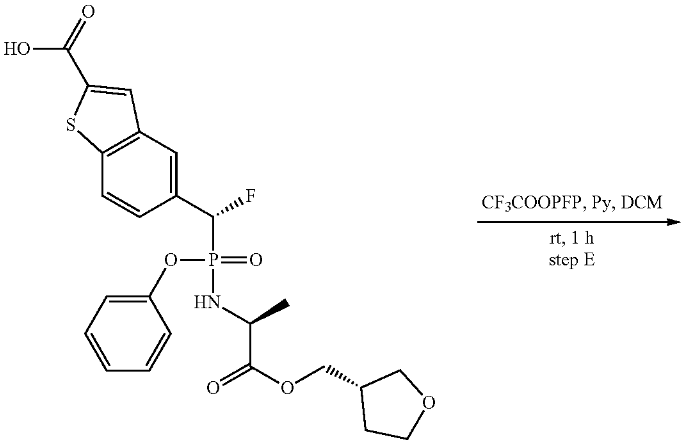
6
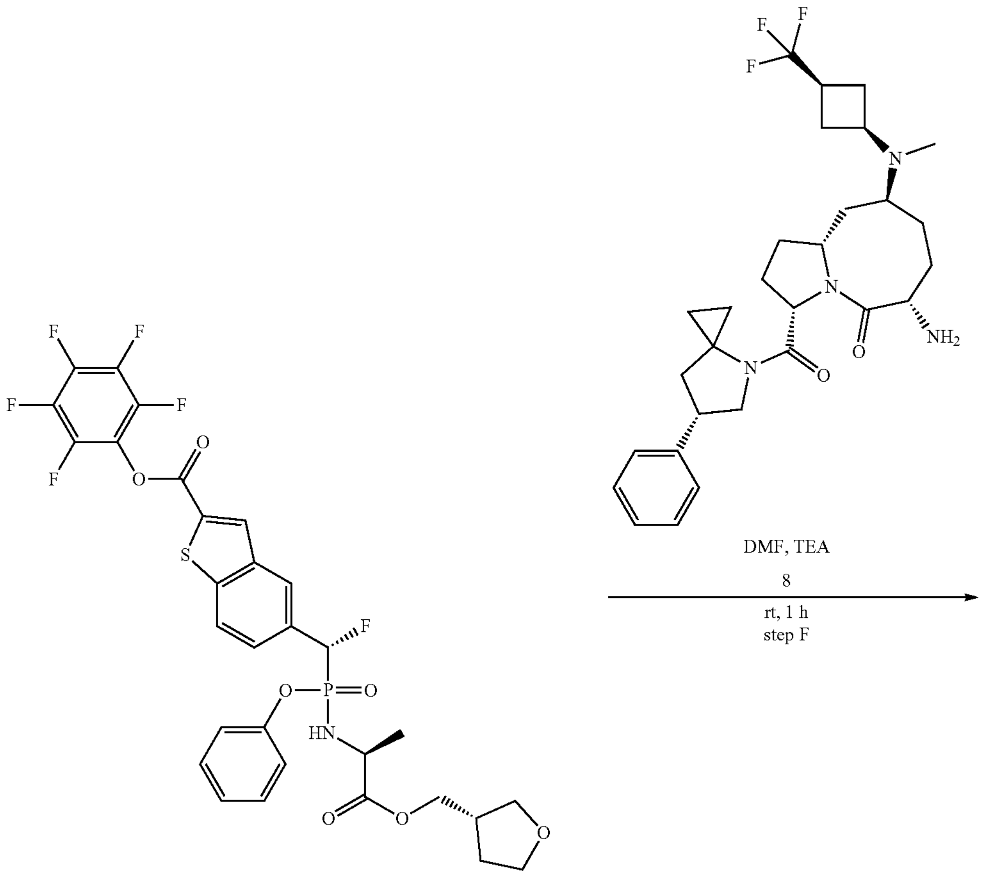
7

-continued

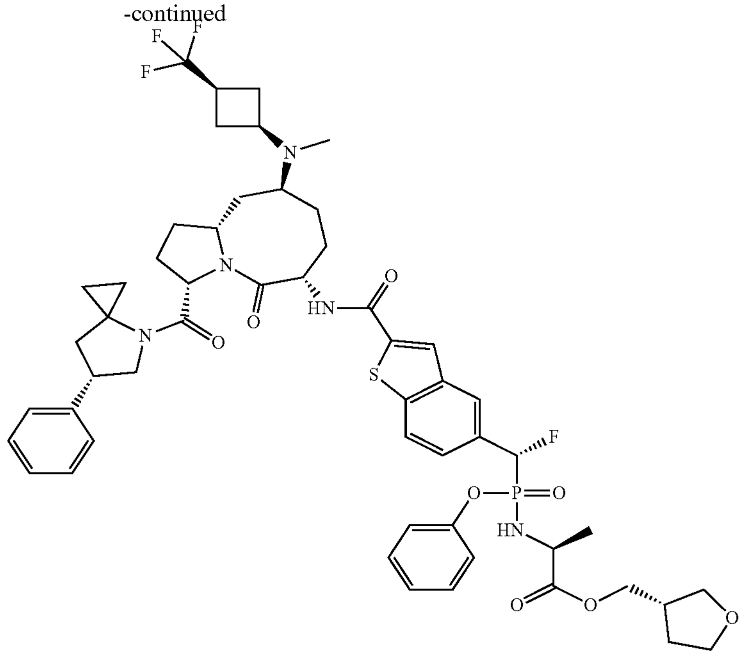

Step A: ((S)-tetrahydrofuran-3-yl)methyl (tert-butoxycarbonyl)-L-alaninate

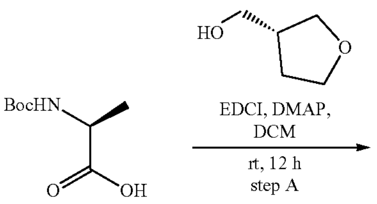

1

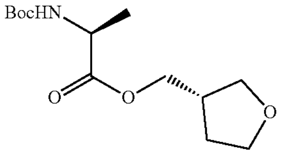

2

To a solution of (tert-butoxycarbonyl)-L-alanine (1, 2 g, 10.58 mmol, 1 eq.) in DCM (20 mL) was added (R)-(tetrahydrofuran-3-yl)methanol (1.08 g, 10.58 mmol, 1 eq.), DMAP (1.42 g, 11.64 mmol, 1.1 eq.) and EDCI (2.23 g, 11.64 mmol, 1.1 eq.). The solution was stirred for 12 h at room temperature and was quenched by adding $H_2O$ (20 mL), then extracted with DCM (20 mL×2). The organic layers were combined and washed with brine (20 mL), dried over $Na_2SO_4$, filtered, and concentrated to dryness under reduced pressure. The crude product was purified by silica gel column to afford ((S)-tetrahydrofuran-3-yl)methyl (tert-butoxycarbonyl)-L-alaninate (2, 2.5 g, 9.16 mmol, 86.5% yield) as a colorless oil. LCMS (ESI): m/z=274 $[M+H]^+$.

Step B: ((S)-tetrahydrofuran-3-yl)methyl L-alaninate hydrochloride

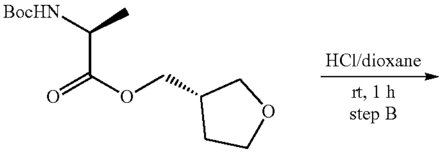

2

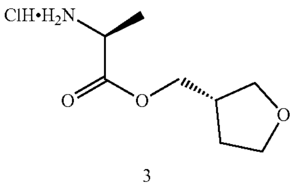

3

To a solution of ((S)-tetrahydrofuran-3-yl)methyl (tert-butoxycarbonyl)-L-alaninate (2, 2.5 g, 9.16 mmol) in dioxane (5 mL) was added 4M HCl in dioxane (10 mL). The solution was stirred for 1 hr at room temperature, LCMS showed that the reaction was completed. The solution was concentrated under vacuum to afford ((S)-tetrahydrofuran-3-yl)methyl L-alaninate hydrochloride (3, 1.9 g, 9.1 mmol, 99% yield) as a white solid (HCl salt). LCMS (ESI): m/z=174 $[M+H]^+$.

Step C: ((S)-tetrahydrofuran-3-yl)methyl L-alaninate hydrochloride

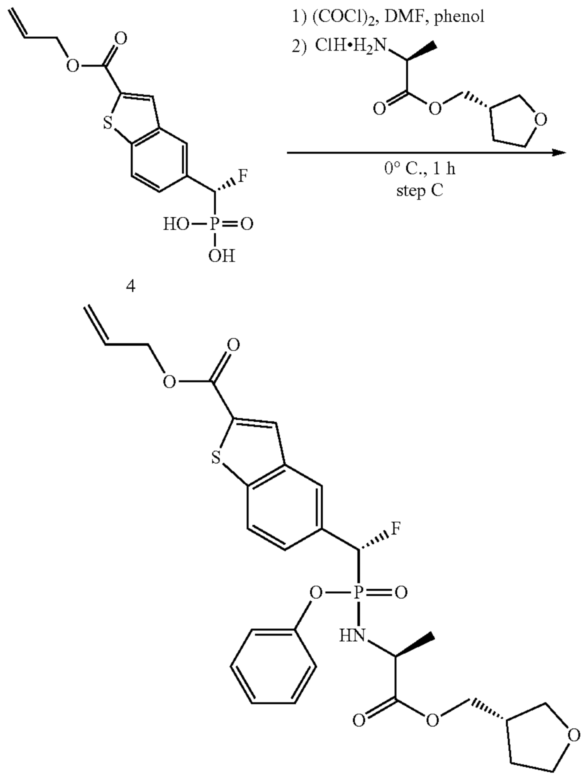

4

5

To a solution of (R)-((2-((allyloxy)carbonyl)benzo[b]thiophen-5-yl)fluoromethyl)phosphonic acid (4, 1.3 g, 3.94 mmol, 1 eq.) in DCM (20 mL) was added DMF (1 drop) and oxalyl chloride (2.5 g, 19.7 mmol, 5 eq). The resulting mixture was stirred for 1 h at room temperature, then excess oxalyl chloride was removed under reduced pressure. The residue was redissolved in DCM (20 mL) and cooled to 0° C., phenol (285 mg, 3.94 mmol, 1 eq) was added to the solution, TEA (2 g, 19.7 mmol, 5 eq.) was added dropwise, the mixture was stirred for 1 h at 0° C., ((S)-tetrahydrofuran-3-yl)methyl L-alaninate (1.27 g, 7.88 mmol, 2 eq.) was added, then the resulting mixture was stirred for additional 10 min. The reaction was quenched by adding $H_2O$ (50 mL), then extracted with DCM (50 mL×2), the organic layers were combined and washed with brine, then dried over $Na_2SO_4$, filtered, and concentrated to dryness under reduced pressure. The crude product was purified by silica gel column chromatography to afford allyl 5-((1R)-fluoro((((S)-1-oxo-1-(((S)-tetrahydrofuran-3-yl)methoxy)propan-2-yl)amino)(phenoxy)phosphoryl)methyl)benzo[b]thiophene-2-carboxylate (5, 800 mg, 1.43 mmol, 47% yield) as a colorless oil. LCMS (ESI): m/z=562 $[M+H]^+$.

Step D: 5-((1R)-fluoro((((S)-1-oxo-1-(((S)-tetrahydrofuran-3-yl)methoxy)propan-2-yl)amino)(phenoxy)phosphoryl)methyl)benzo[b]thiophene-2-carboxylic acid

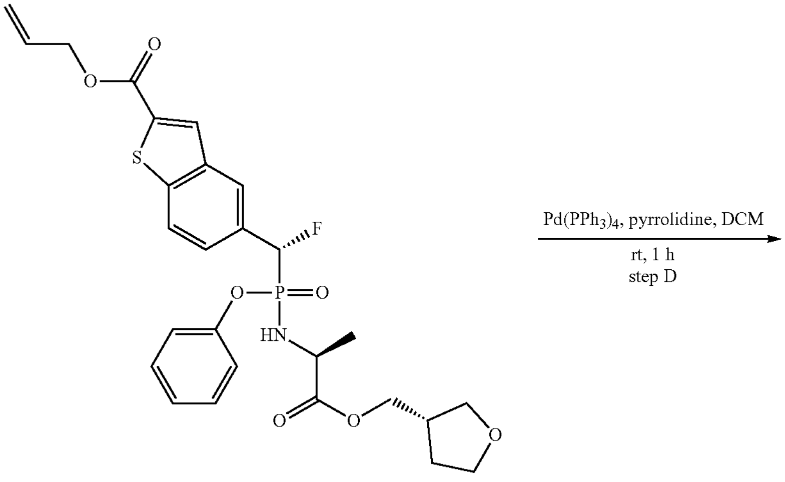

5

-continued

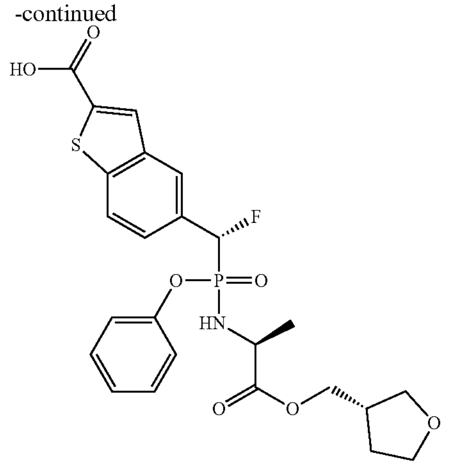

6

To a solution of allyl 5-((1R)-fluoro((((S)-1-oxo-1-(((S)-tetrahydrofuran-3-yl)methoxy)propan-2-yl)amino)(phenoxy)phosphoryl)methyl)benzo[b]thiophene-2-carboxylate (5, 800 mg, 1.43 mmol, 1 eq.) in DCM (10 mL) was added $Pd(PPh_3)_4$ (165 mg, 0.14 mmol, 0.1 eq.) and pyrrolidine (101 mg, 1.43 mmol, 1 eq.). The resulting mixture was stirred for 1 h at room temperature under the atmosphere of $N_2$. The pH was adjusted pH=3 with 1M HCl (aq.), then extracted with DCM (20 mL×2). The organic layers were combined and washed with brine (20 mL), dried over $Na_2SO_4$, filtered and the resulting mixture was concentrated to dryness under reduced pressure to afford crude product 5-((1R)-fluoro((((S)-1-oxo-1-(((S)-tetrahydrofuran-3-yl)methoxy)propan-2-yl)amino)(phenoxy)phosphoryl)methyl)benzo[b]thiophene-2-carboxylic acid (6, 700 mg, 1.34 mmol, 94% yield) as a yellow solid. LCMS (ESI): m/z=522 $[M+H]^+$.

Step E: perfluorophenyl 5-((1R)-fluoro((((S)-1-oxo-1-(((S)-tetrahydrofuran-3-yl)methoxy)propan-2-yl)amino)(phenoxy)phosphoryl)methyl)benzo[b]thiophene-2-carboxylate

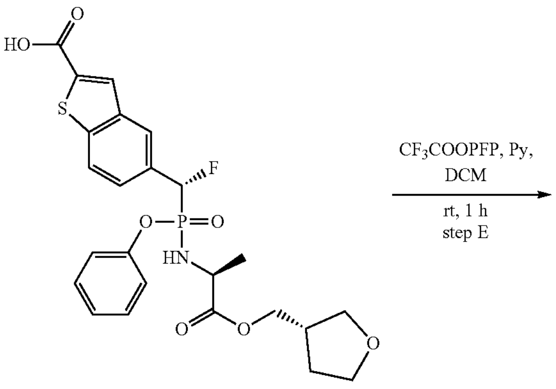

6

-continued

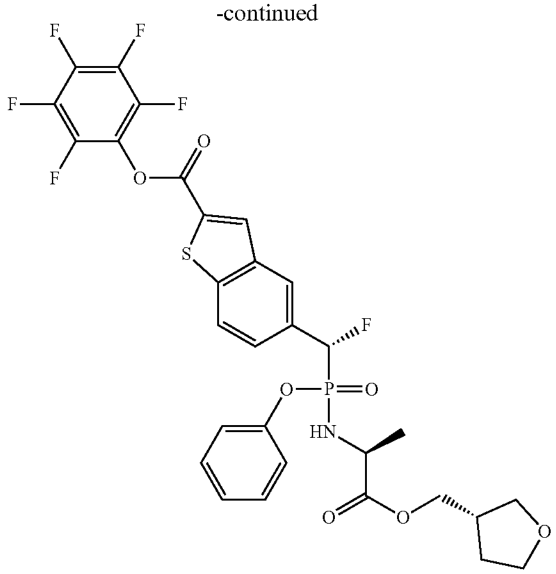

7

To a solution of 5-((1R)-fluoro((((S)-1-oxo-1-(((S)-tetrahydrofuran-3-yl)methoxy)propan-2-yl)amino)(phenoxy)phosphoryl)methyl)benzo[b]thiophene-2-carboxylic acid (6, 700 mg, 1.34 mmol, 1 eq.) in DCM (10 mL) was added pyridine (318 mg, 4.03 mmol, 3 eq.) and perfluorophenyl 2,2,2-trifluoroacetate (753 mg, 2.69 mmol, 2 eq.). The resulting mixture was stirred for 1 h at room temperature, and the reaction was quenched by adding $H_2O$ (20 mL), then extracted with DCM (20 mL×2). The organic layers were combined and washed with brine, dried over $Na_2SO_4$, concentrated to dryness under reduced pressure. The crude product was purified by silica gel column chromatography to afford perfluorophenyl 5-((1R)-fluoro((((S)-1-oxo-1-(((S)-tetrahydrofuran-3-yl)methoxy)propan-2-yl)amino)(phenoxy)phosphoryl)methyl)benzo[b]thiophene-2-carboxylate (7, 700 mg, 1.02 mmol, 76% yield) as a white solid. LCMS (ESI): m/z=688 $[M+H]^+$.

Step F: ((S)-tetrahydrofuran-3-yl)methyl (((R)-fluoro(2-(((3S,6S,9S,10aR)-9-(methyl((1s,3R)-3-(trifluoromethyl)cyclobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate
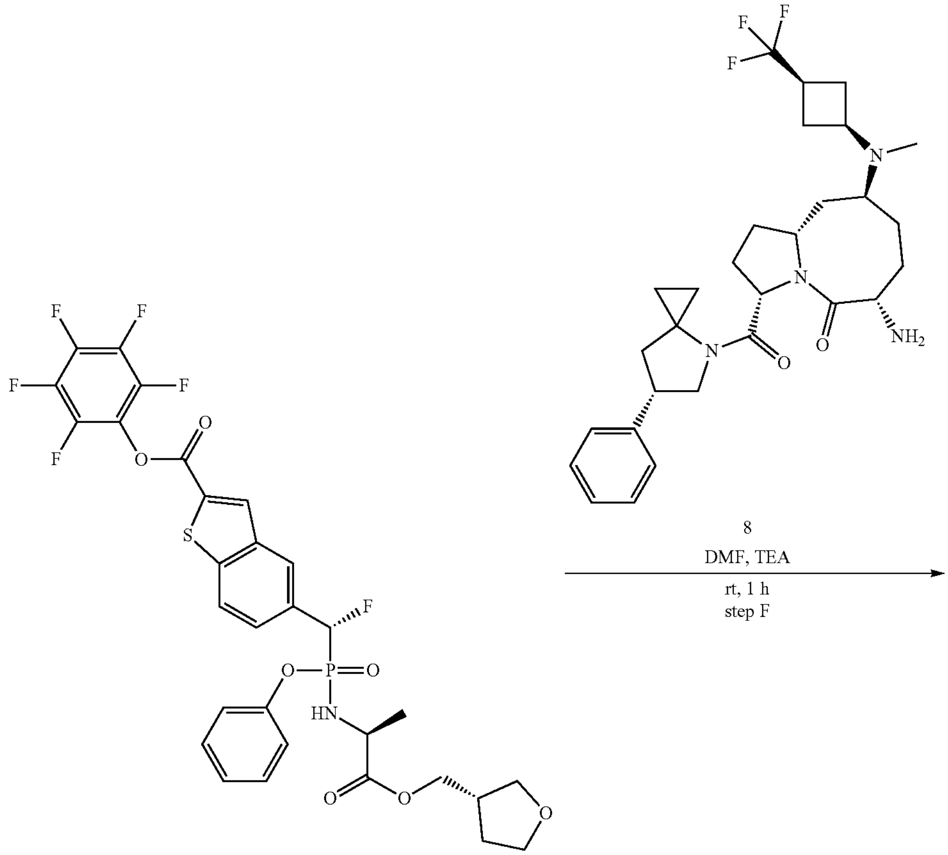
7

-continued

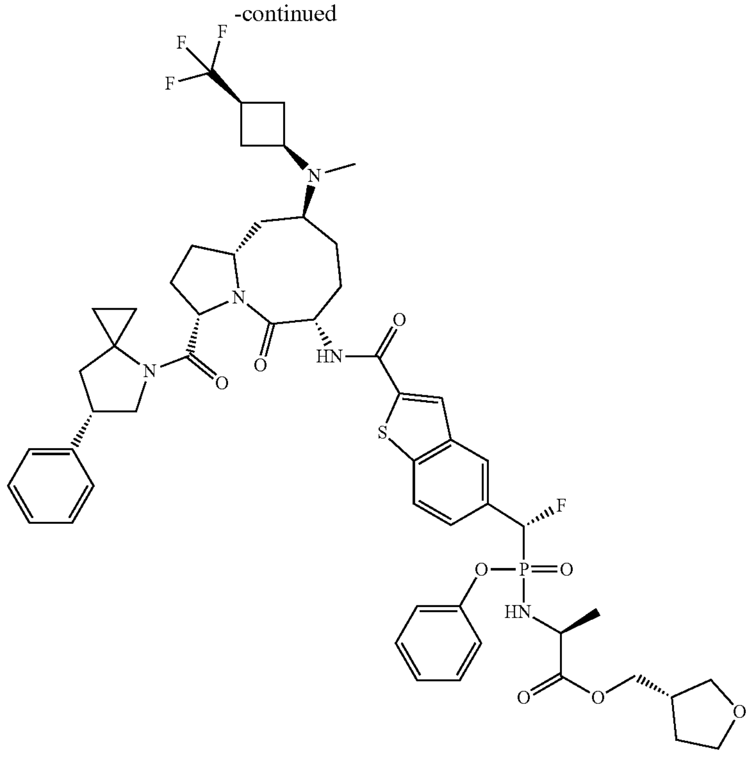

To a solution of perfluorophenyl 5-((1R)-fluoro((((S)-1-oxo-1-(((S)-tetrahydrofuran-3-yl)methoxy)propan-2-yl)amino)(phenoxy)phosphoryl)methyl)benzo[b]thiophene-2-carboxylate (7, 20 mg, 0.029 mml, 1 eq.) in DMF (3 mL) was added (3S,6S,9S,10aR)-6-amino-9-(methyl((1s,3R)-3-(trifluoromethyl)cyclobutyl)amino)-3-((S)-6-phenyl-4-azaspiro[2.4]heptane-4-carbonyl)octahydropyrrolo[1,2-a]azocin-5(1H)-one (8, 16 mg, 0.029 mmol, 1 eq.), TEA (5.9 mg, 0.058 mmol, 2 eq). The resulting mixture was stirred for 1 hr at room temperature. The crude product was purified by Prep-HPLC to afford ((S)-tetrahydrofuran-3-yl)methyl (((R)-fluoro(2-(((3S,6S,9S,10aR)-9-(methyl((1s,3R)-3-(trifluoromethyl)cyclobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate (Compound C174, 17 mg, 0.016 mmol) as a white solid. LCMS (ESI): m/z=1036 $[M+H]^+$. $^1H$ NMR (400 MHz, DMSO-$d_6$) δ (ppm) 8.78 (d, J=7.1 Hz, 1H), 8.27 (s, 1H), 8.10-8.00 (m, 2H), 7.60 (d, J=8.3 Hz, 1H), 7.40-7.26 (m, 6H), 7.23-7.12 (m, 4H), 6.29-6.07 (m, 2H), 4.76-4.66 (m, 1H), 4.48 (t, J=8.4 Hz, 1H), 4.34-4.22 (m, 1H), 4.12 (t, J=8.6 Hz, 1H), 3.98-3.84 (m, 1H), 3.81-3.49 (m, 7H), 3.07-2.92 (m, 2H), 2.83-2.69 (m, 1H), 2.40-2.19 (m, 4H), 2.14-2.03 (m, 3H), 2.02-1.90 (m, 6H), 1.88-1.33 (m, 12H), 1.17-1.05 (m, 3H), 0.52-0.37 (m, 2H). $^{19}F$ NMR (376 MHz, DMSO-$d_6$) δ (ppm) −71.25 (s), −194.09 (d, J=82.9 Hz), −196.24 (d, J=85.9 Hz). $^{31}P$ NMR (162 MHz, DMSO-$d_6$) δ (ppm) 17.35 (d, J=82.7 Hz), 17.09 (d, J=85.8 Hz).

Synthesis of ((R)-fluoro(2-(((3S,6S,9S,10aR)-9-(methyl(4,4,4-trifluorobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)phosphonic acid (Compound A3)
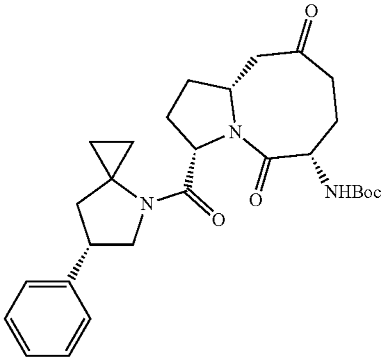
1
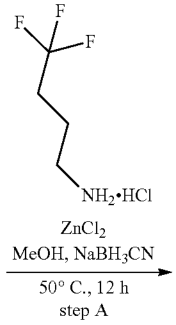
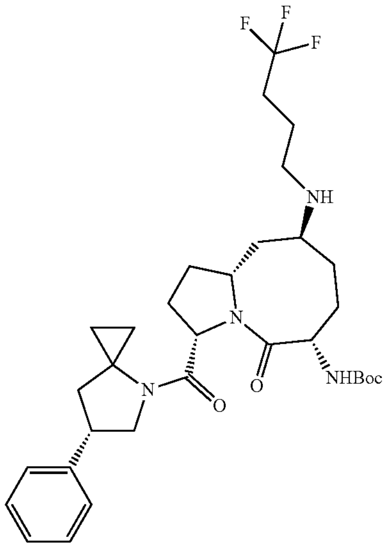
2
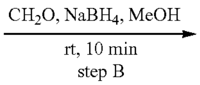
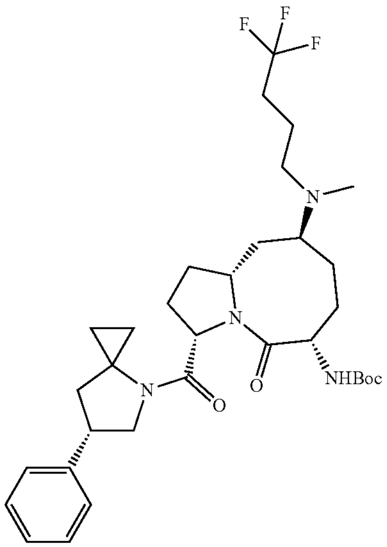
3
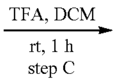

-continued
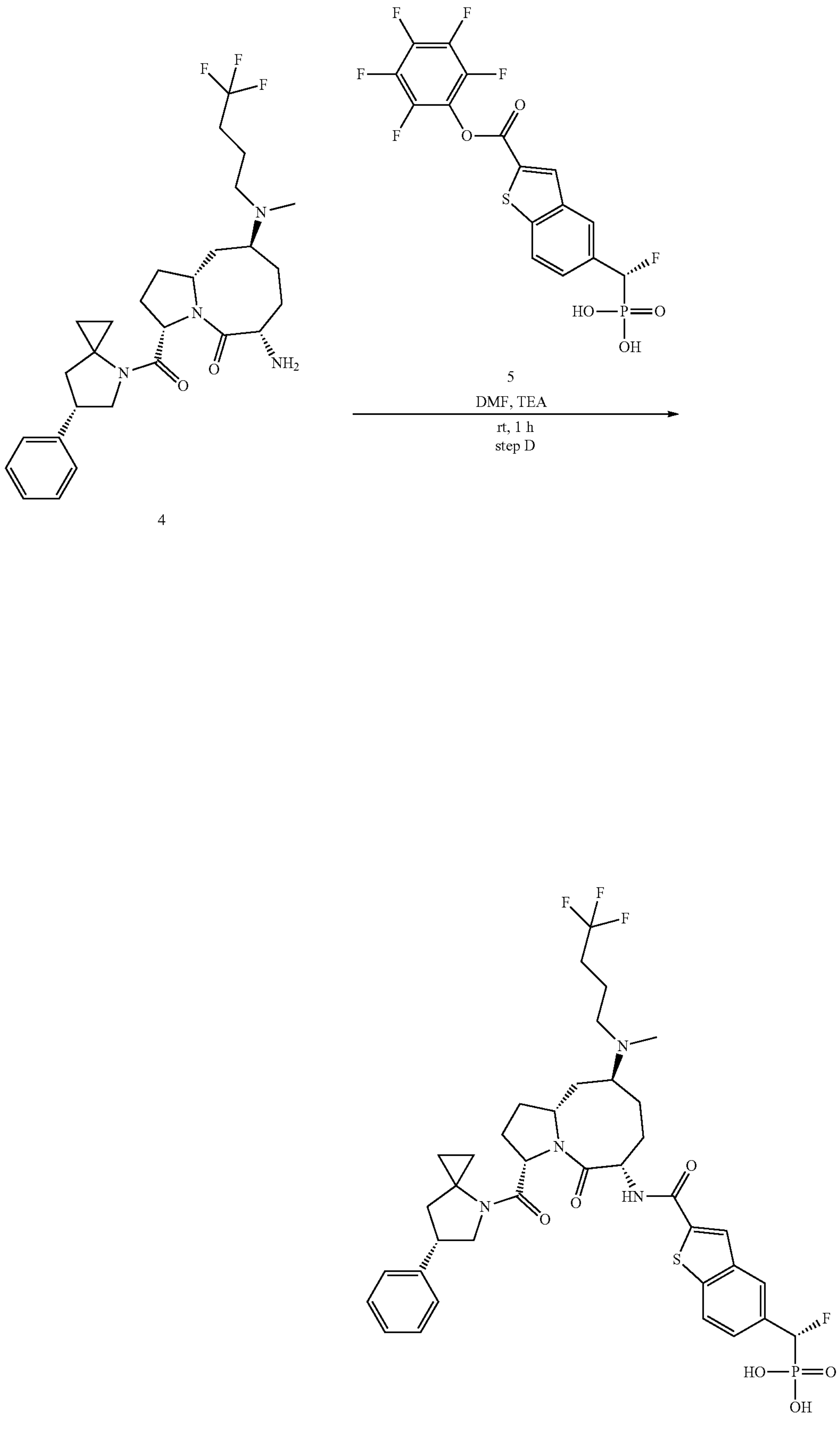
4

Step A: tert-butyl ((3S,6S,9S,10aR)-5-oxo-3-((S)-6-phenyl-4-azaspiro[2.4]heptane-4-carbonyl)-9-((4,4,4-trifluorobutyl)amino)decahydropyrrolo[1,2-a]azocin-6-yl)carbamate

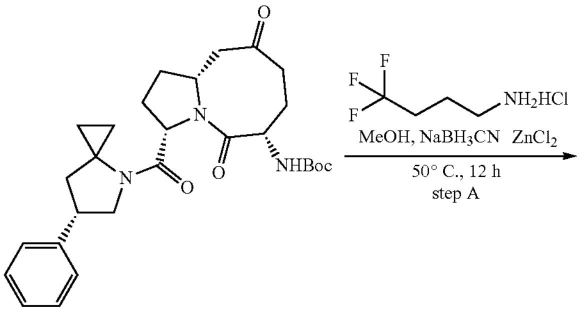

1

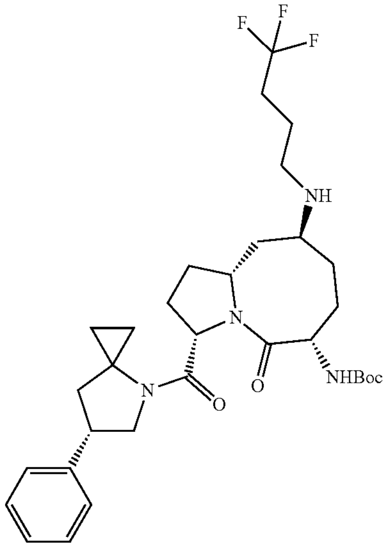

2

To a solution of tert-butyl ((3S,6S,10aR)-5,9-dioxo-3-((S)-6-phenyl-4-azaspiro[2.4]heptane-4-carbonyl)decahydropyrrolo[1,2-a]azocin-6-yl)carbamate (1, 2 g, 4.04 mmol, 1 eq.) in MeOH (40 mL) was added 4,4,4-trifluorobutan-1-amine hydrochloride (988 mg, 6.06 mml, 1.5 eq.), $ZnCl_2$ (5.5 g, 40.4 mmol, 10 eq.). The resulting mixture was stirred for 1 h at 50° C., then $NaBH_3CN$ (2.54 g, 40.4 mmol, 10 eq.) was added portion wise every 30 mins (2 eq. (508 mg each time) added 5 times). The reaction mixture was stirred at 50° C. for additional 12 h, LCMS show that the reaction was completed. Then cooled to room temperature, the mixture was used to the next step directly without further workup. LCMS (ESI): m/z=607 $[M+H]^+$.

Step B: tert-butyl ((3S,6S,9S,10aR)-9-(methyl(4,4,4-trifluorobutyl)amino)-5-oxo-3-((S)-6-phenyl-4-azaspiro[2.4]heptane-4-carbonyl)decahydropyrrolo[1,2-a]azocin-6-yl)carbamate

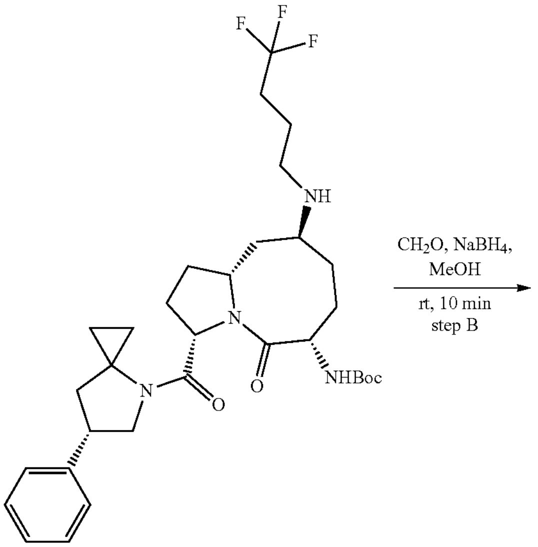

2

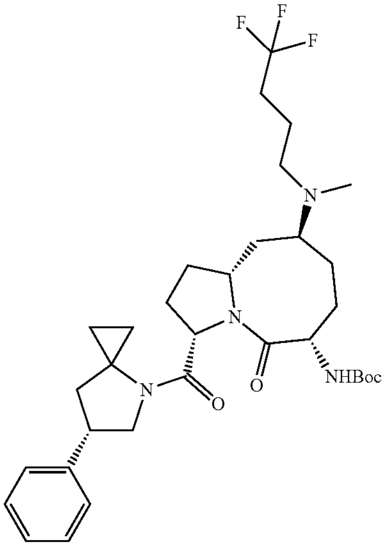

3

To the above mixture (step A) was added 40% formaldehyde (2 mL) at room temperature and the mixture was stirred for 10 min, then $NaBH_4$ (1.53 g, 40.4 mmol, 10 eq.) was added to the mixture, stirred for another 10 min. The reaction mixture was cooled down to 0° C. and quenched by $NH_4Cl$ (sat. aq.), diluted with $H_2O$ (100 mL) and extracted with EtOAc (50 mL×3). The organic layers were combined and washed with brine (20 mL), dried over $Na_2SO_4$, filtered, then concentrated to dryness under reduced pressure, the crude product was purified by C18 column (MeCN:$H_2O$ (0.1% ammonium hydroxide)=5%-70%) to afford tert-butyl ((3S,6S,9S,10aR)-9-(methyl(4,4,4-trifluorobutyl)amino)-5-oxo-3-((S)-6-phenyl-4-azaspiro[2.4]heptane-4-carbonyl)

decahydropyrrolo[1,2-a]azocin-6-yl)carbamate (3, 1.5 g, 2.42 mmol, 80% yield, two steps) as a white solid. LCMS (ESI): m/z=621 [M+H]+.

Step C: (3S,6S,9S,10aR)-6-amino-9-(methyl(4,4,4-trifluorobutyl)amino)-3-((S)-6-phenyl-4-azaspiro[2.4]heptane-4-carbonyl)octahydropyrrolo[1,2-a]azocin-5(1H)-one

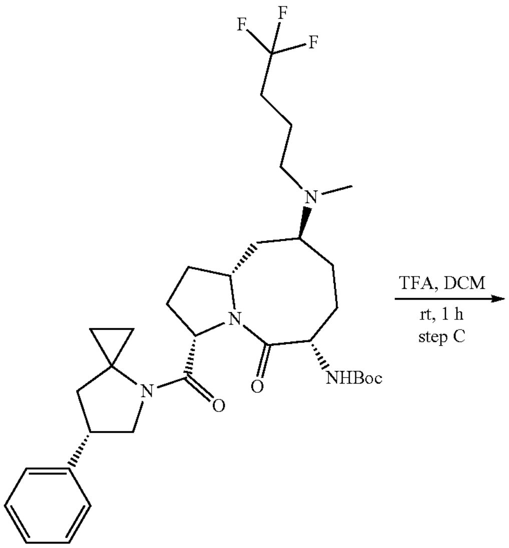

3

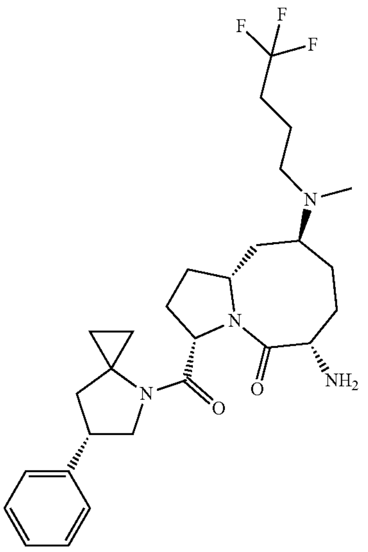

4

To a solution of tert-butyl ((3S,6S,9S,10aR)-9-(methyl(4,4-trifluorobutyl)amino)-5-oxo-3-((S)-6-phenyl-4-azaspiro[2.4]heptane-4-carbonyl)decahydropyrrolo[1,2-a]azocin-6-yl)carbamate (3, 20 mg, 0.032 mmol) in DCM (2 mL) was added TFA (2 mL), the resulting mixture was stirred for 1 h at room temperature then concentrated to dryness under reduced pressure to afford crude product (3S,6S,9S,10aR)-6-amino-9-(methyl(4,4,4-trifluorobutyl)amino)-3-((S)-6-phenyl-4-azaspiro[2.4]heptane-4-carbonyl)octahydropyrrolo[1,2-a]azocin-5(1H)-one (4, 20 mg, TFA salt) as a yellow oil which used in the next step without further purification. LCMS (ESI): m/z=521 [M+H]+.

Step D: ((R)-fluoro(2-(((3S,6S,9S,10aR)-9-(methyl (4,4,4-trifluorobutyl)amino)-5-oxo-3-((S)-6-phenyl-4-azaspiro[2.4]heptane-4-carbonyl)decahydropyrrolo [1,2-a]azocin-6-yl)carbamoyl)benzo[b]thiophen-5-yl)methyl)phosphonic acid

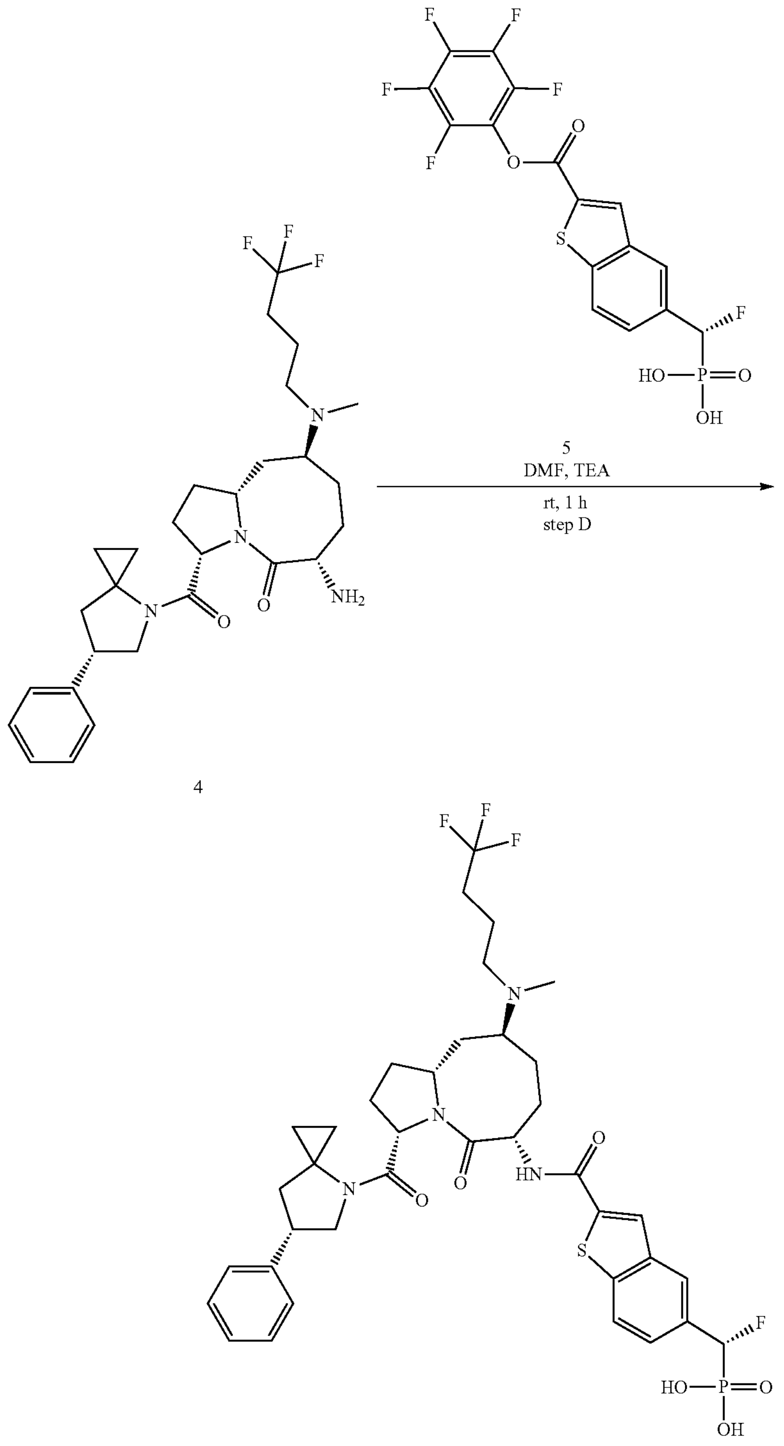

4

To a solution of (3S,6S,9S,10aR)-6-amino-9-(methyl(4,4,4-trifluorobutyl)amino)-3-((S)-6-phenyl-4-azaspiro[12.4] heptane-4-carbonyl)octahydropyrrolo[1,2-a]azocin-5(1H)-one (4, 20 mg, TFA salt) in DMF (2 mL) was added TEA (6.5 mg, 0.065 mmol, 2 eq.), and (R)-(fluoro(2-((perfluorophenoxy)carbonyl)benzo[ib]thiophen-5-yl)methyl)phosphonic acid (6, 14.67 mg, 0.032 mmol, 1 eq). The resulting mixture was stirred for 1 h at room temperature. The crude product was purified by Prep-HPLC to afford ((R)-fluoro(2-(((3S,6S,9S,10aR)-9-(methyl(4,4,4-trifluorobutyl)amino)-5-oxo-3-((S)-6-phenyl-4-azaspiro[2.4]heptane-4-carbonyl) decahydropyrrolo[1,2-a]azocin-6-yl)carbamoyl)benzo[b] thiophen-5-yl)methyl)phosphonic acid (Compound A3, 9 mg, 0.011 mmol) as a white solid. LCMS (ESI): m/z=793 $[M+H]^+$. $^1H$ NMR (400 MHz, $CD_3OD-d_4$) δ (ppm) 8.09 (s, 1H), 8.05 (s, 1H), 7.94 (d, J=8.5 Hz, 1H), 7.70 (d, J=8.6 Hz, 1H), 7.38-7.26 (m, 4H), 7.22 (d, J=6.7 Hz, 1H), 5.79-5.58 (m, 1H), 4.64-4.47 (m, 2H), 4.38-4.21 (m, 1H), 4.07-3.80 (m, 2H), 3.77-3.63 (m, 1H), 3.58-3.47 (m, 1H), 3.14-2.94 (m, 2H), 2.73-2.60 (m, 3H), 2.53-1.47 (m, 19H), 0.60-0.36 (in, 2H). $^{19}F$ NMR (377 MHz, $CD_3OD-d_4$) δ (ppm) −66.25~−68.60 (m), −193.51~−198.61 (m). $^{31}P$ NMR (162 MHz, $CD_3OD-d_4$) δ (ppm) 9.79 (d, J=76.6 Hz).

Synthesis of isobutyl ((S)-((R)-fluoro(2-(((3S,6S,9S,10aR)-9-(methyl(4,4,4-trifluorobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate (Compound C135)

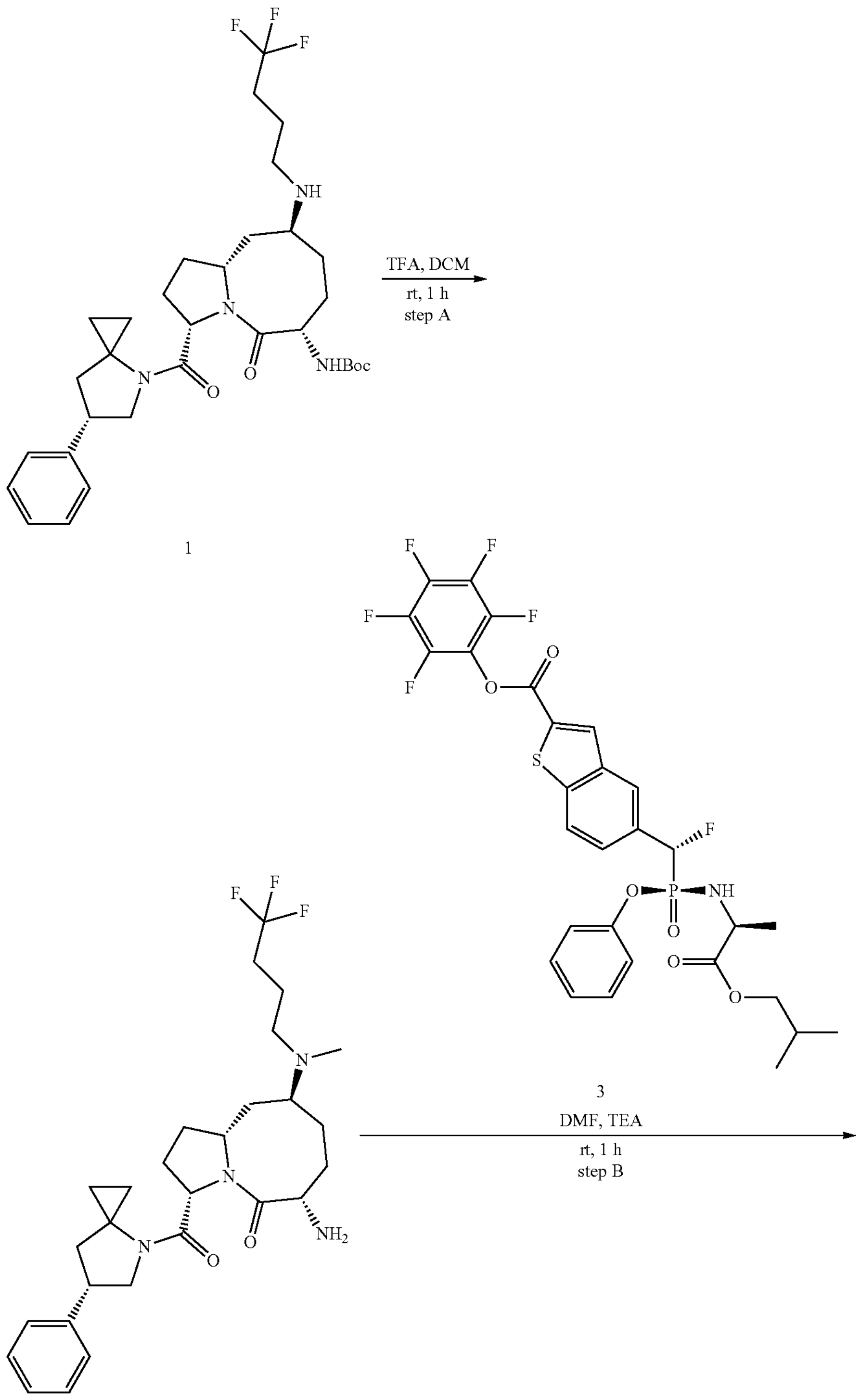

1

3

2

-continued

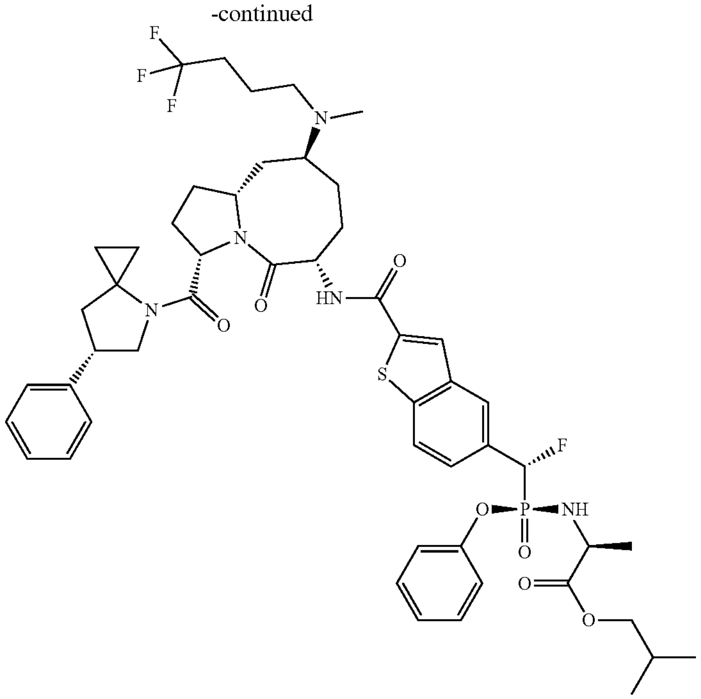

Step A: (3S,6S,9S,10aR)-6-amino-9-(methyl(4,4,4-trifluorobutyl)amino)-3-((S)-6-phenyl-4-azaspiro[2.4]heptane-4-carbonyl)octahydropyrrolo[1,2-a]azocin-5(1H)-one

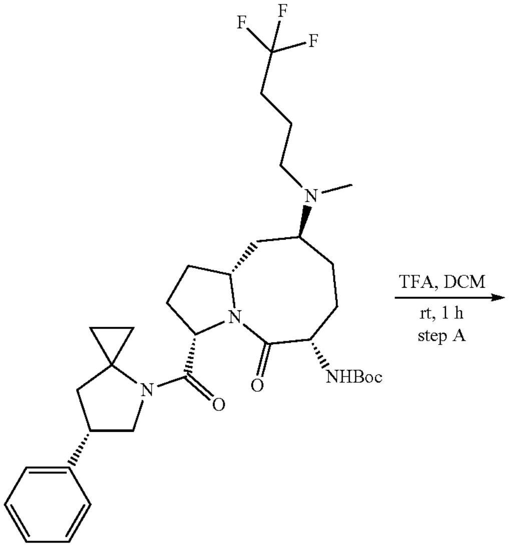

1

-continued

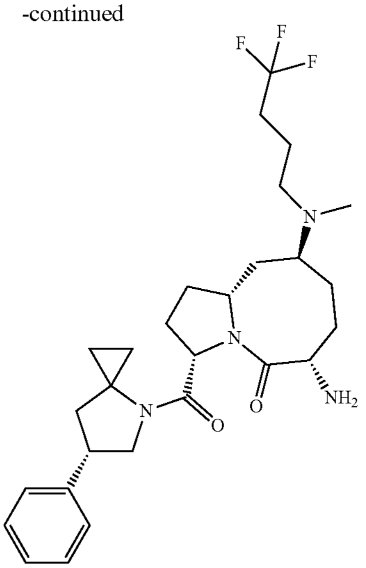

2

To a solution of tert-butyl ((3S,6S,9S,10aR)-9-(methyl(4,4,4-trifluorobutyl)amino)-5-oxo-3-((S)-6-phenyl-4-azaspiro[2.4]heptane-4-carbonyl)decahydropyrrolo[1,2-a]azocin-6-yl)carbamate (1, 20 mg, 0.032 mmol) in DCM (2 mL) was added TFA (2 mL) and the resulting mixture was stirred for 1 h at room temperature. The resulting mixture was concentrated to dryness under reduced pressure to afford crude product (3S,6S,9S,10aR)-6-amino-9-(methyl(4,4,4-trifluorobutyl)amino)-3-((S)-6-phenyl-4-azaspiro[2.4]heptane-4-carbonyl)octahydropyrrolo[1,2-a]azocin-5(1H)-one (2, 20 mg, TFA salt) as a yellow oil which used in the next step without further purification. LCMS (ESI): m/z=521 $[M+H]^+$.

Step B: isobutyl ((S)-((R)-fluoro(2-(((3S,6S,9S,10aR)-9-(methyl(4,4,4-trifluorobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate
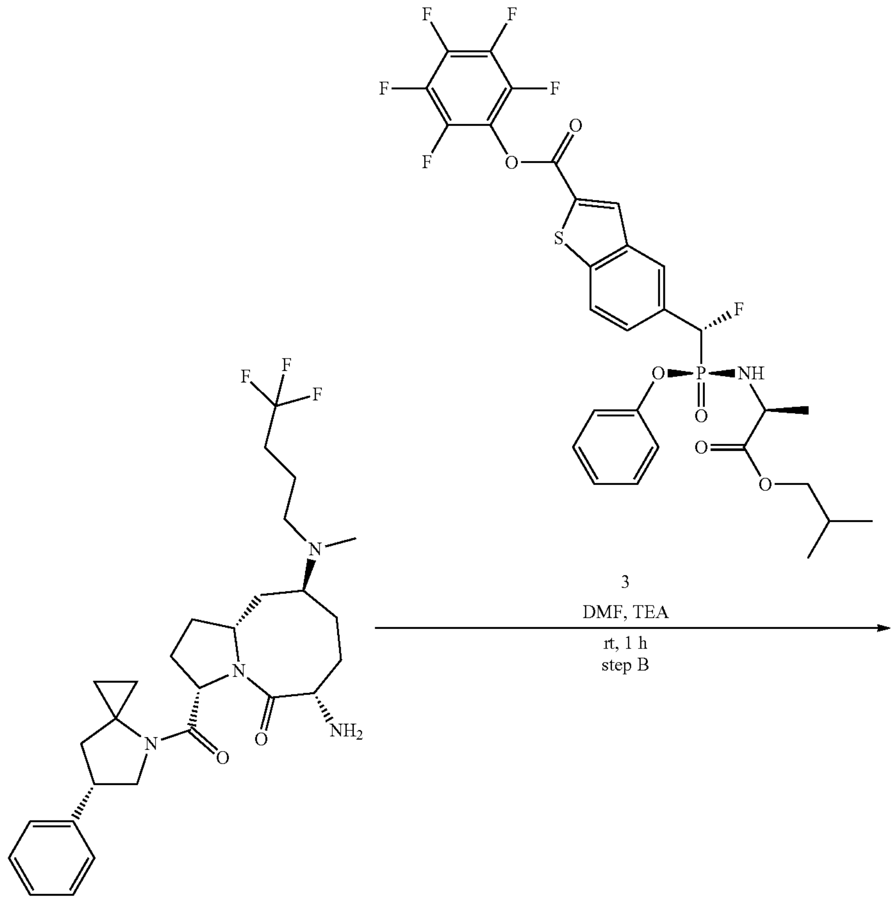

-continued

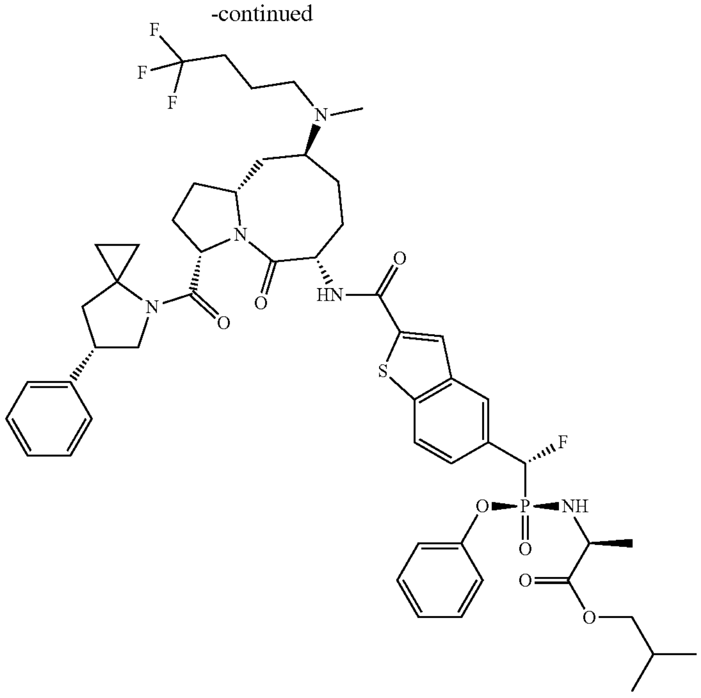

To a solution of (3S,6S,9S,10aR)-6-amino-9-(methyl(4,4,4-trifluorobutyl)amino)-3-((S)-6-phenyl-4-azaspiro[2.4]heptane-4-carbonyl)octahydropyrrolo[1,2-a]azocin-5(1H)-one (2, 20 mg, TFA salt) in DMF (2 mL) was added TEA (6.5 mg, 0.065 mmol, 2 eq.), and perfluorophenyl 5-((R)-fluoro((S)-(((S)-1-isobutoxy-1-oxopropan-2-yl)amino)(phenoxy)phosphoryl)methyl)benzo[b]thiophene-2-carboxylate (3, 21.2 mg, 0.032 mmol, 1 eq). The resulting mixture was stirred for 1 h at room temperature. The crude product was purified by Prep-HPLC to afford isobutyl ((S)-((R)-fluoro(2-(((3S,6S,9S,10aR)-9-(methyl(4,4,4-trifluorobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate (Compound C135, 10 mg, 0.010 mmol) as a white solid. LCMS (ESI): m/z=996 $[M+H]^+$. $^1H$ NMR (400 MHz, DMSO-$d_6$) δ (ppm) 8.85-8.67 (m, 1H), 8.34-8.18 (m, 1H), 8.12-7.99 (m, 2H), 7.68-7.53 (m, 1H), 7.39-7.14 (m, 10H), 6.32-6.07 (m, 2H), 4.89-4.69 (m, 1H), 4.56-4.40 (m, 1H), 4.36-4.21 (m, 1H), 4.16-4.04 (m, 1H), 3.85-3.67 (m, 4H), 3.58-3.44 (m, 1H), 3.01-2.85 (m, 1H), 2.46-2.17 (m, 7H), 2.14-2.08 (m, 3H), 2.05-1.95 (m, 3H), 1.87-1.52 (m, 11H), 1.19-1.07 (m, 3H), 0.89-0.75 (m, 6H), 0.54-0.37 (m, 2H). $^{19}F$ NMR (376 MHz, DMSO-$d_6$) δ (ppm) −64.55 (s), −196.27 (d, J=85.8 Hz). $^{31}P$ NMR (162 MHz, DMSO-$d_6$) δ (ppm) 17.08 (d, J=86.2 Hz). (free base).

Synthesis of ((R)-(2-(((3S,6S,9S,10aR)-9-((3,3-difluoropropyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)phosphonic acid (Compound A20)

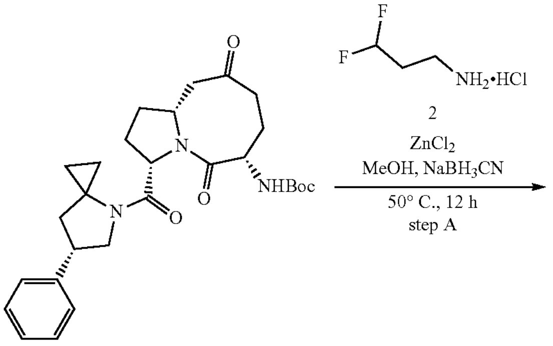

1

-continued
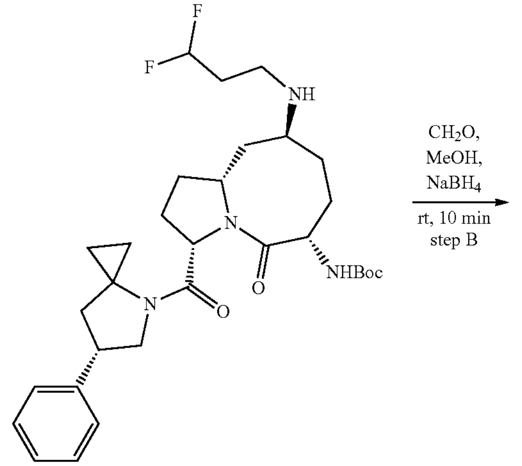
3
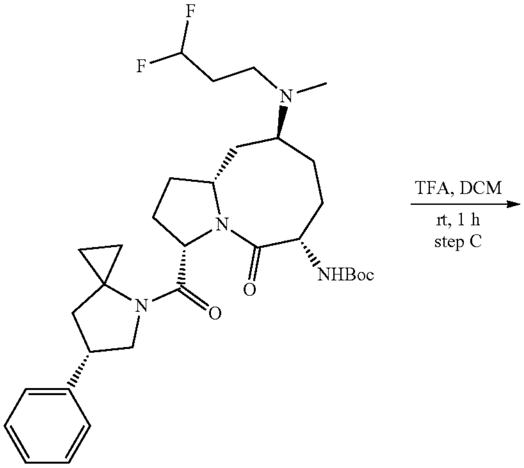
4
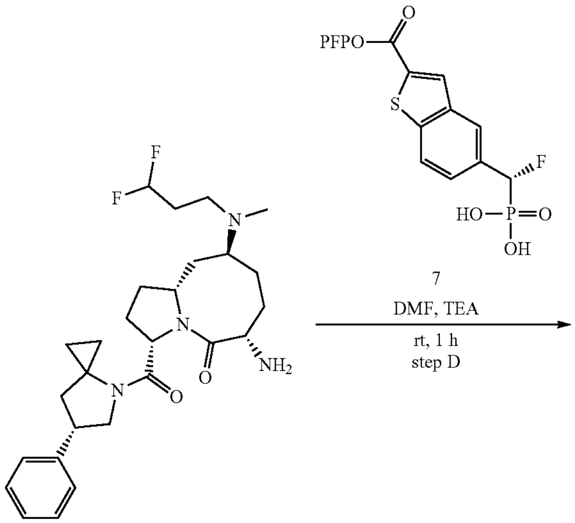
5
-continued
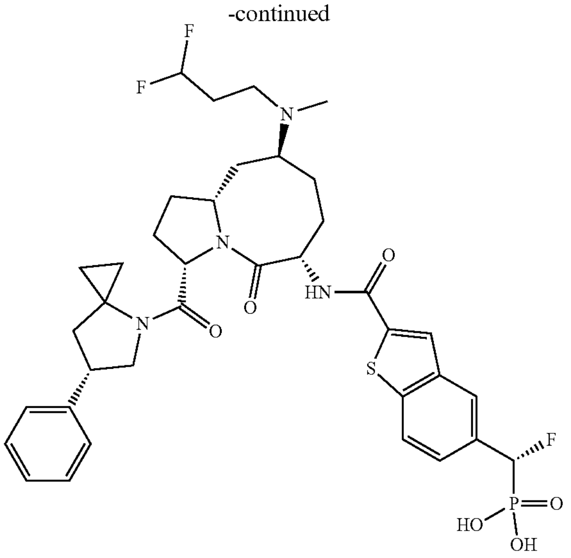
Step A: tert-butyl ((3S,6S,9S,10aR)-9-((3,3-difluoropropyl)amino)-5-oxo-3-((R)-6-phenyl-4-azaspiro[2.4]heptane-4-carbonyl)decahydropyrrolo[1,2-a]azocin-6-yl)carbamate
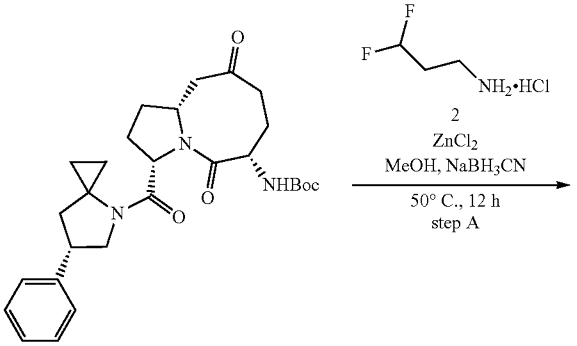
1
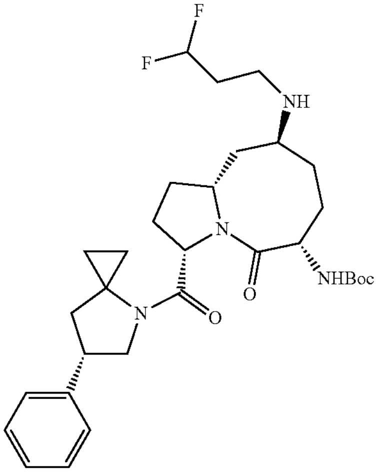
3
To a solution of tert-butyl ((3S,6S,10aR)-5,9-dioxo-3-((R)-6-phenyl-4-azaspiro[2.4]heptane-4-carbonyl)decahydropyrrolo[1,2-a]azocin-6-yl)carbamate (1, 1.5 g, 3.03 mmol, 1 eq.) in MeOH (30 mL) was added 3,3-difluoropropan-1-amine hydrochloride (2, 595 mg, 4.55 mmol, 1.5 eq.), $ZnCl_2$ (4.2 g, 30.3 mmol, 10 eq.) and the solution was stirred for 2 hr at 50° C. under the atmosphere of $N_2$. Then $NaBH_3CN$ (1.90 g, 30.3 mmol, 10 eq.) was added portion wise every 30 mins (2 eq. (380 mg each time) added 5 times). The solution was stirred for 12 hr at 50° C., then cooled to room temperature and used in the next step without further workup. LCMS (ESI): m/z=575 $[M+H]^+$.

Step B: tert-butyl ((3S,6S,9S,10aR)-9-((3,3-difluoropropyl)(methyl)amino)-5-oxo-3-((R)-6-phenyl-4-azaspiro[2.4]heptane-4-carbonyl)decahydropyrrolo[1,2-a]azocin-6-yl)carbamate

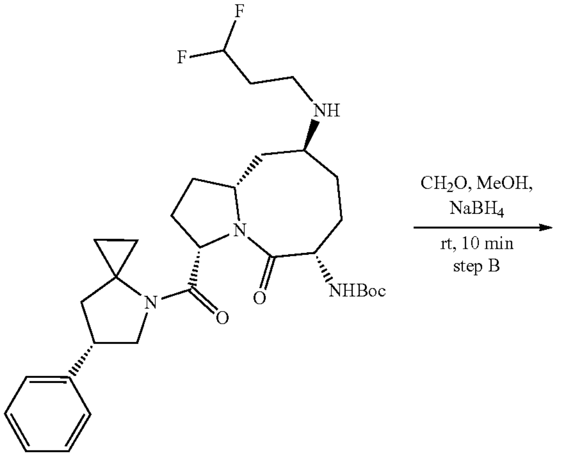

3

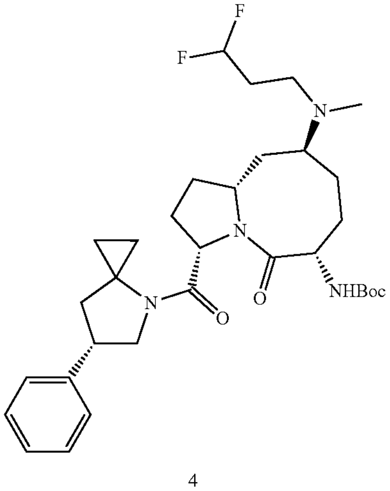

4

To the above mixture (step A) was added 40% formaldehyde aqueous (1.5 mL) at room temperature and the mixture was stirred for 10 min, then $NaBH_4$ (565 mg, 15.2 mmol, 5 eq.) was added in portions, and the mixture was stirred for additional 10 min. The reaction mixture was cooled down to 0° C., quenched by $NH_4Cl$ (sat. aq), diluted with $H_2O$ (100 mL), then extracted with EtOAc (50 mL×3), the organic layers were combined and washed with brine (20 mL), dried over $Na_2SO_4$, then concentrated to dryness under reduced pressure, and purified by C18 column (MeCN:$H_2O$ (0.1% ammonium hydroxide)=5%-70%) to tert-butyl ((3S,6S,9S,10aR)-9-((3,3-difluoropropyl)(methyl)amino)-5-oxo-3-((R)-6-phenyl-4-azaspiro[2.4]heptane-4-carbonyl)decahydropyrrolo[1,2-a]azocin-6-yl)carbamate (4, 1.5 g, 2.55 mmol, 84% yield two steps) as a white solid. LCMS (ESI): m/z=589 $[M+H]^+$.

Step C: (3S,6S,9S,10aR)-6-amino-9-((3,3-difluoropropyl)(methyl)amino)-3-((R)-6-phenyl-4-azaspiro[2.4]heptane-4-carbonyl)octahydropyrrolo[1,2-a]azocin-5(1H)-one

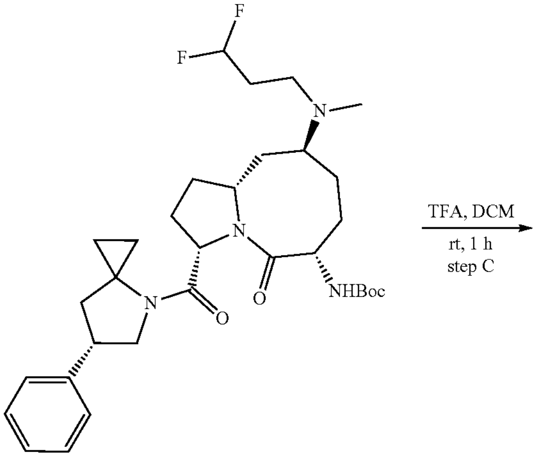

4

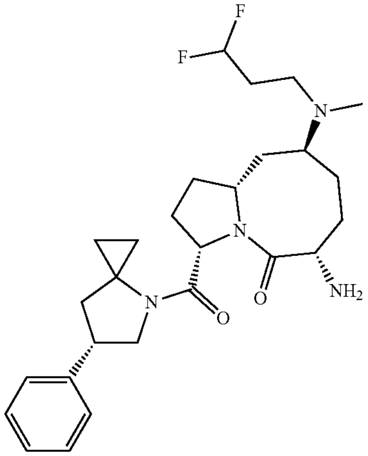

5

To a solution of tert-butyl ((3S,6S,9S,10aR)-9-((3,3-difluoropropyl)(methyl)amino)-5-oxo-3-((R)-6-phenyl-4-azaspiro[2.4]heptane-4-carbonyl)decahydropyrrolo[1,2-a]azocin-6-yl)carbamate (4, 20 mg, 0.034 mmol) in DCM (2 mL) was added TFA (2 mL). The resulting mixture was stirred for 1 h at room temperature, and concentrated to dryness under reduced pressure to afford crude product (3S,6S,9S,10aR)-6-amino-9-((3,3-difluoropropyl)(methyl)amino)-3-((R)-6-phenyl-4-azaspiro[2.4]heptane-4-carbonyl)octahydropyrrolo[1,2-a]azocin-5(1H)-one (5, 20 mg, TFA salt) as a yellow oil which was used in the next step without further purification. LCMS (ESI): m/z=489 $[M+H]^+$.

Step D: ((R)-(2-(((3S,6S,9S,10aR)-9-((3,3-difluoropropyl)(methyl)amino)-5-oxo-3-((R)-6-phenyl-4-azaspiro[2.4]heptane-4-carbonyl)decahydropyrrolo[1,2-a]azocin-6-yl)carbamoyl)benzo[b]thiophen-5-yl)fluoromethyl)phosphonic acid

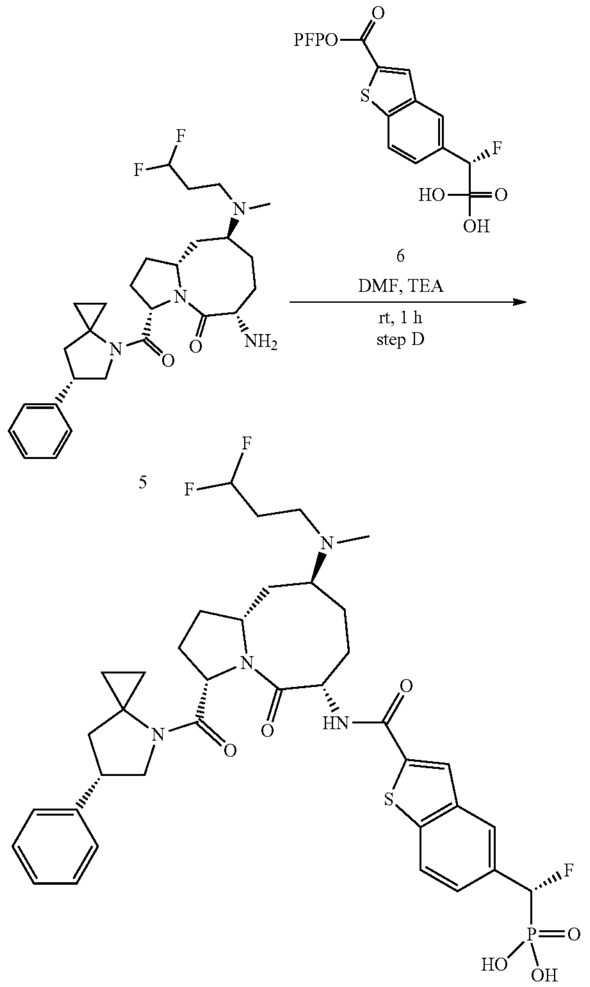

To a solution of (3S,6S,9S,10aR)-6-amino-9-((3,3-difluoropropyl)(methyl)amino)-3-((R)-6-phenyl-4-azaspiro[2.4]heptane-4-carbonyl)octahydropyrrolo[1,2-a]azocin-5(1H)-one (5, 20 mg, TFA salt) in DMF (2 mL) was added TEA (6.9 mg, 0.068 mmol, 2 eq.), (R)-(fluoro(2-((perfluorophenoxy)carbonyl)benzo[b]thiophen-5-yl)methyl)phosphonic acid (6, 15.5 mg, 0.034 mmol, 1 eq.). The resulting mixture was stirred for 1 hr at room temperature, LCMS show that the reaction was completed. The crude product was purified by Prep-HPLC to afford ((R)-(2-(((3S,6S,9S,10aR)-9-((3,3-difluoropropyl)(methyl)amino)-5-oxo-3-((R)-6-phenyl-4-azaspiro[2.4]heptane-4-carbonyl)decahydropyrrolo[1,2-a]azocin-6-yl)carbamoyl)benzo[b]thiophen-5-yl)fluoromethyl)phosphonic acid (Compound A20, 13 mg) as a white solid. LCMS (ESI): m/z=761 $[M+H]^+$. 1H NMR (400 MHz, DMSO-$d_6$) δ (ppm) 8.87-8.67 (m, 1H), 8.24 (s, 1H), 8.03 (d, J=8.4 Hz, 1H), 7.98 (s, 1H), 7.53 (d, J=8.4 Hz, 1H), 7.38-7.29 (m, 4H), 7.26-7.19 (m, 1H), 6.40-6.03 (m, 1H), 5.91-5.75 (m, 1H), 4.81 (s, 1H), 4.60-4.50 (m, 2H), 4.17-4.09 (m, 1H), 3.85-3.70 (m, 2H), 3.57-3.51 (m, 1H), 3.35-3.19 (m, 2H), 2.80-2.69 (m, 3H), 2.49-2.42 (m, 1H), 2.39-1.70 (m, 14H), 1.56 (s, 1H), 0.59-0.42 (m, 2H). $^{19}F$ NMR (377 MHz, DMSO-$d_6$) δ (ppm) −116.26 (d, J=78.4 Hz), −194.89 (d, J=80.9 Hz). $^{31}P$ NMR (162 MHz, DMSO-$d_6$) δ (ppm) 10.94 (d, J=81.0 Hz).

Synthesis of benzyl (((R)-(2-(((3S,6S,9S,10aR)-9-((3,3-difluoropropyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)(phenoxy)phosphoryl)-L-alaninate (Compound C52)
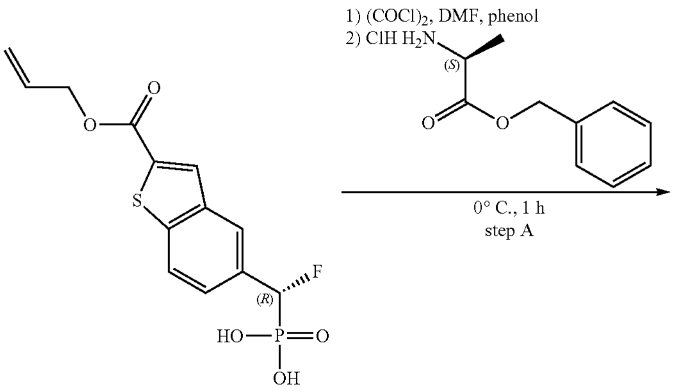
1
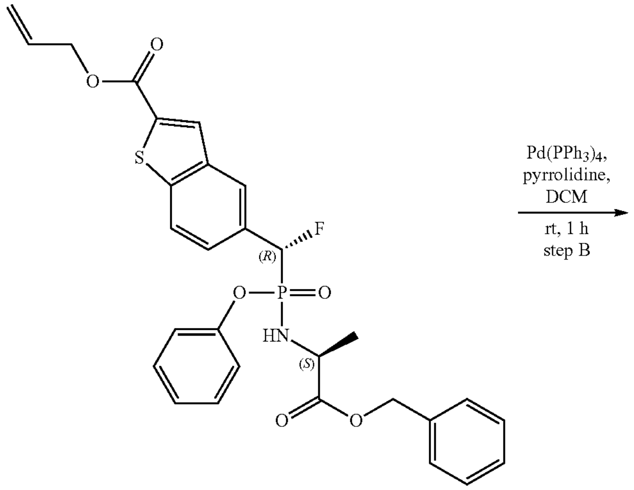
2
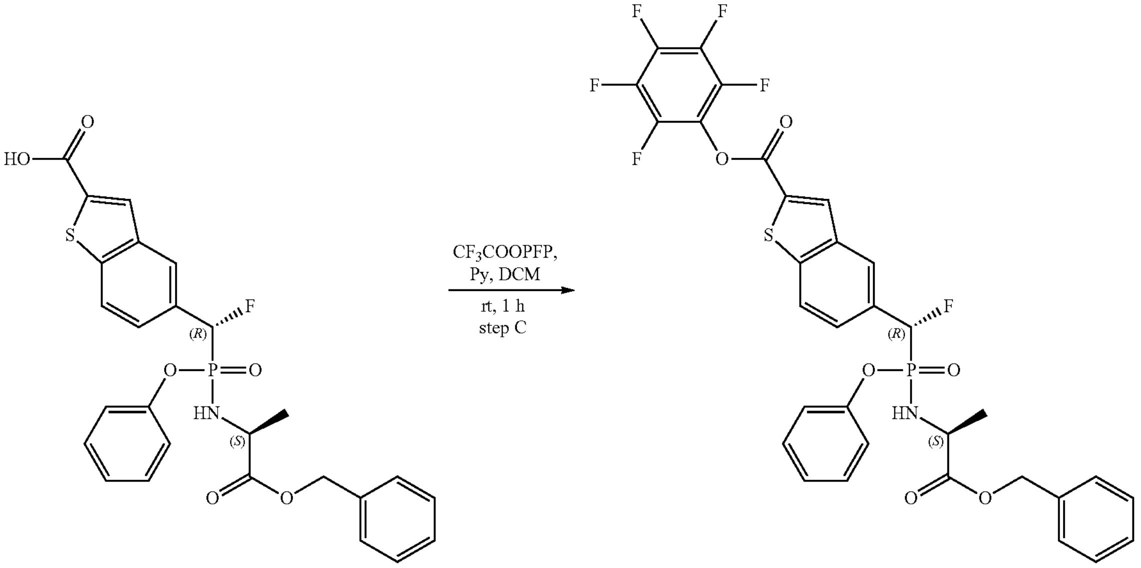
3
4

-continued
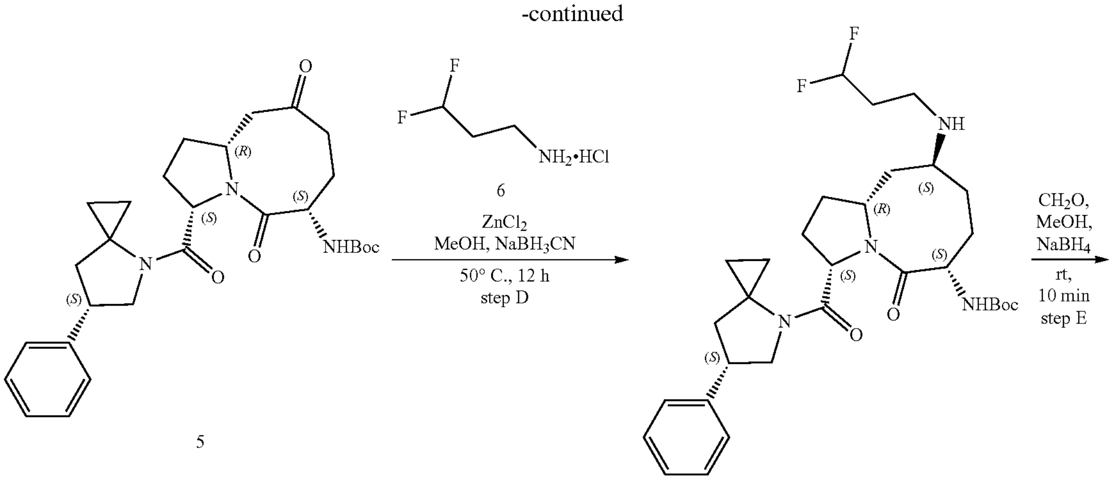
5
6
7
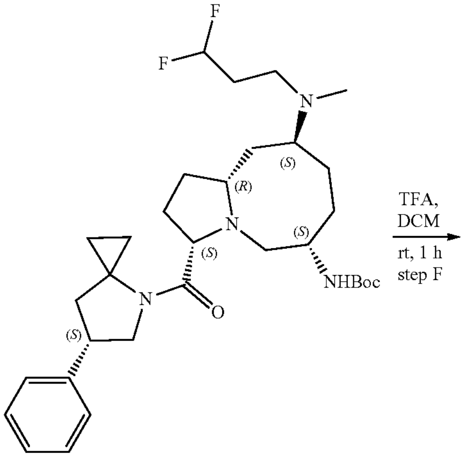
8

-continued
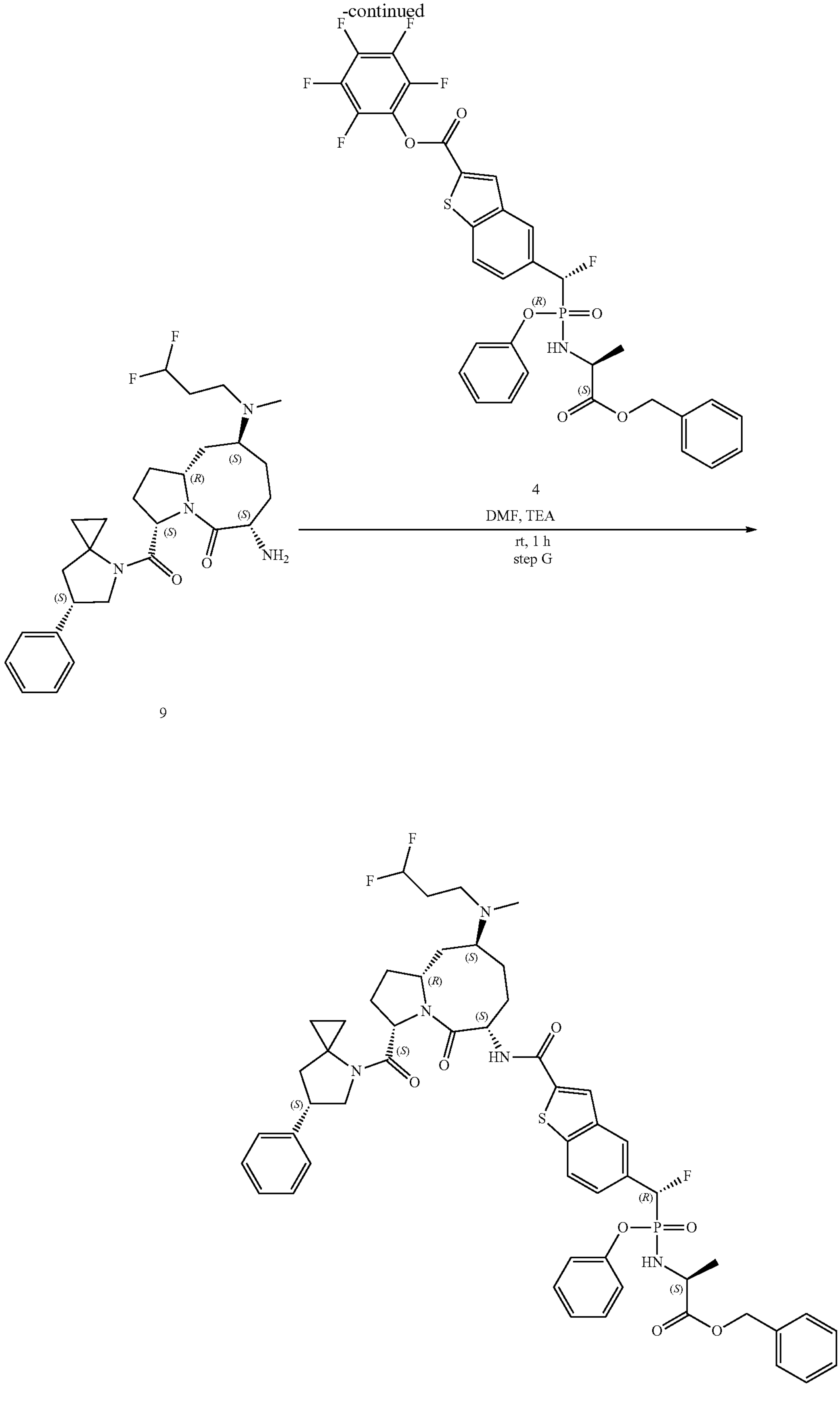
4
9

Step A: allyl 5-((1R)—((((S)-1-(benzyloxy)-1-oxopropan-2-yl)amino)(phenoxy)phosphoryl)fluoromethyl)benzo[b]thiophene-2-carboxylate

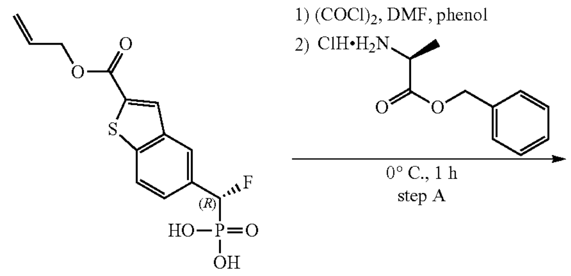

1

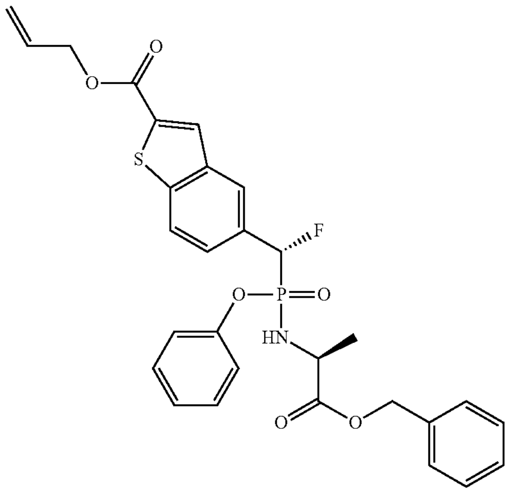

2

To a solution of (R)-((2-((allyloxy)carbonyl)benzo[b]thiophen-5-yl)fluoromethyl)phosphonic acid (1, 1.3 g, 3.94 mmol, 1 eq.) in DCM (20 mL) was added DMF (1 drop), oxalyl chloride (2.5 g, 19.7 mmol, 5 eq). The resulting mixture was stirred for 1 h at room temperature, then excess oxalyl chloride was removed under reduced pressure. The residue was redissolved in DCM (20 mL) and cooled to 0° C., phenol (285 mg, 3.94 mmol, 1 eq) was added to the solution, TEA (2 g, 19.7 mmol, 5 eq.) was added dropwise to the solution at 0° C., the mixture was stirred for 1 h at 0° C., benzyl L-alaninate hydrochloride (1.69 g, 7.88 mmol, 2 eq.) was added to the solution, then stirred for additional 10 min. The resulting mixture was quenched by adding $H_2O$ (50 mL), then extracted with DCM (50 mL×2), and the organic layers were combined and washed with brine, then dried over $Na_2SO_4$, filtered, and concentrated to dryness under reduced pressure. The crude product was purified by silica gel column chromatography to afford allyl 5-((1R)—((((S)-1-(benzyloxy)-1-oxopropan-2-yl)amino)(phenoxy)phosphoryl)fluoromethyl)benzo[b]thiophene-2-carboxylate (2, 800 mg, 1.41 mmol, 36% yield) as a colorless oil. LCMS (ESI): m/z=568 $[M+H]^+$.

Step B: 5-((1R)-fluoro((((S)-1-oxo-1-(((S)-tetrahydrofuran-3-yl)methoxy)propan-2-yl)amino)(phenoxy)phosphoryl)methyl)benzo[b]thiophene-2-carboxylic acid

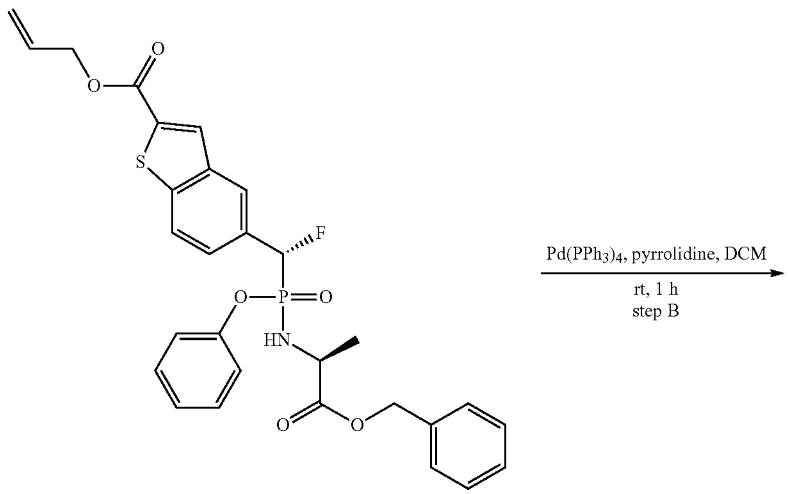

2

-continued

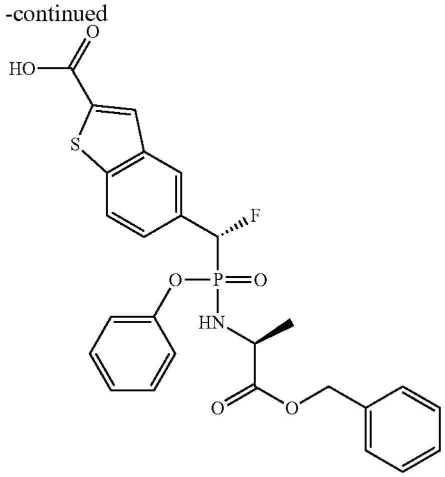

3

To a solution of allyl 5-((1R)—((((S)-1-(benzyloxy)-1-oxopropan-2-yl)amino)(phenoxy)phosphoryl)fluoromethyl) benzo[b]thiophene-2-carboxylate (2, 800 mg, 1.41 mmol, 1 eq.) in DCM (10 mL) was added $Pd(PPh_3)_4$ (165 mg, 0.14 mmol, 0.1 eq.) and pyrrolidine (100 mg, 1.41 mmol, 1 eq.). The resulting mixture was stirred for 1 h at room temperature under the atmosphere of $N_2$, LCMS show that the reaction was completed, adjusted pH=3 with 1M HCl (aq.), then extracted with DCM (20 mL×2). The organic layers were combined and washed with brine (20 mL) dried over $Na_2SO_4$, filtered, and concentrated to dryness under reduced pressure to afford crude product 5-((1R)—((((S)-1-(benzyloxy)-1-oxopropan-2-yl)amino)(phenoxy)phosphoryl)fluoromethyl)benzo[b]thiophene-2-carboxylic acid (3, 700 mg, 1.32 mmol, 94% yield) as a yellow solid. LCMS (ESI): m/z=528 $[M+H]^+$.

Step C: perfluorophenyl 5-((1R)—((((S)-1-(benzyloxy)-1-oxopropan-2-yl)amino)(phenoxy)phosphoryl)fluoromethyl)benzo[b]thiophene-2-carboxylate

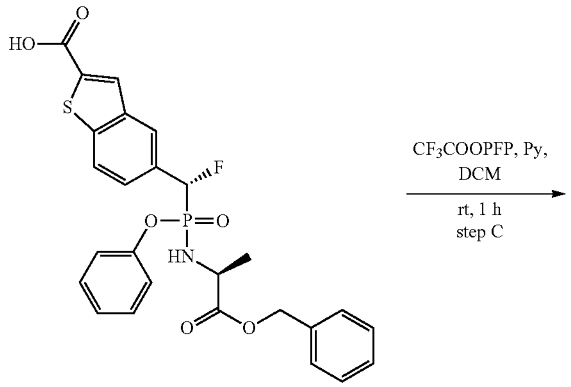

3

-continued

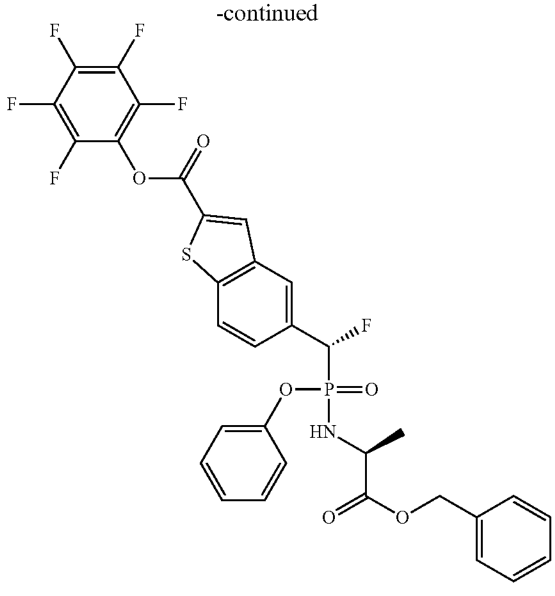

4

To a solution of 5-((1R)—((((S)-1-(benzyloxy)-1-oxopropan-2-yl)amino)(phenoxy)phosphoryl)fluoromethyl)benzo[b]thiophene-2-carboxylic acid (3, 700 mg, 1.32 mmol, 1 eq.) in DCM (10 mL) was added pyridine (313 mg, 3.96 mmol, 3 eq.), perfluorophenyl 2,2,2-trifluoroacetate (739 mg, 2.64 mmol, 2 eq.). The resulting mixture was stirred for 1 h at room temperature and was quenched by adding $H_2O$ (20 mL), then extracted with DCM (20 mL×2), the organic layers were combined and washed with brine, dried over $Na_2SO_4$, filtered, then concentrated under vacuum. The crude product was purified by silica gel column chromatography to afford perfluorophenyl 5-((1R)—((((S)-1-(benzyloxy)-1-oxopropan-2-yl)amino)(phenoxy)phosphoryl)fluoromethyl)benzo[b]thiophene-2-carboxylate (4, 700 mg, 1.01 mmol, 76% yield) as a white solid. LCMS (ESI): m/z=694 $[M+H]^+$.

Step D: tert-butyl ((3S,6S,9S,10aR)-9-((3,3-difluoropropyl)amino)-5-oxo-3-((S)-6-phenyl-4-azaspiro[2.4]heptane-4-carbonyl)decahydropyrrolo[1,2-a]azocin-6-yl)carbamate

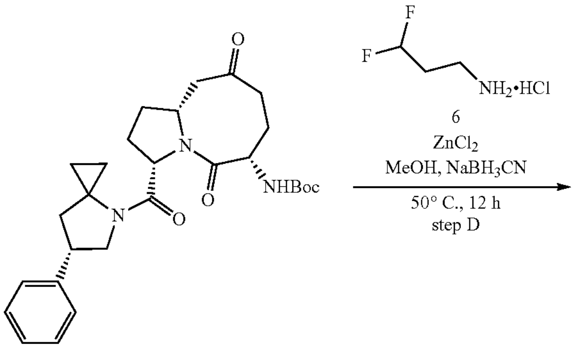

5

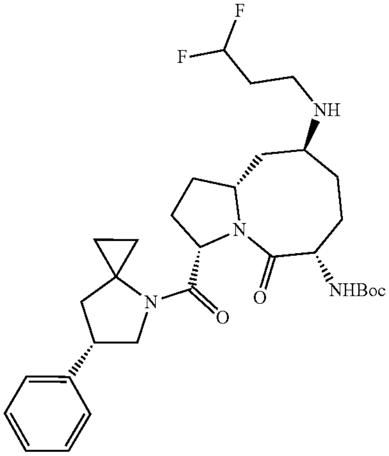

7

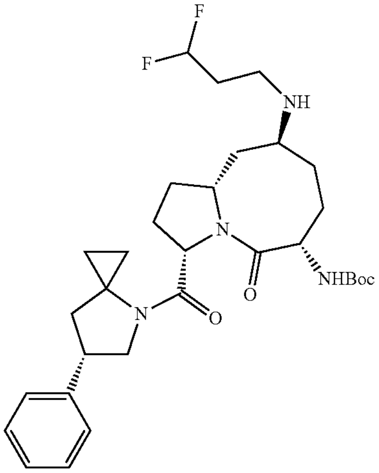

7

To a solution of tert-butyl ((3S,6S,10aR)-5,9-dioxo-3-((S)-6-phenyl-4-azaspiro[2.4]heptane-4-carbonyl)decahydropyrrolo[1,2-a]azocin-6-yl)carbamate (5, 3 g, 6.06 mmol, 1 eq.) in MeOH (60 mL) was added 3,3-difluoropropan-1-amine hydrochloride (2, 1.19 g, 9.09 mmol, 1.5 eq.), and $ZnCl_2$ (8.3 g, 60.6 mmol, 10 eq.) and the resulting solution was stirred for 2 hr at 50° C. under the atmosphere of $N_2$. Then $NaBH_3CN$ (3.81 g, 60.6 mmol, 10 eq.) was added portion wise every 30 mins (2 eq. (762 mg each time) added 5 times). The solution was stirred at 50° C. for additional 12 hr, then cooled to room temperature and used in the next step without further purification. LCMS (ESI): m/z=575 $[M+H]^+$.

Step E: tert-butyl ((3S,6S,9S,10aR)-9-((3,3-difluoropropyl)(methyl)amino)-5-oxo-3-((S)-6-phenyl-4-azaspiro[2.4]heptane-4-carbonyl)decahydropyrrolo[1,2-a]azocin-6-yl)carbamate

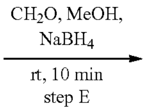

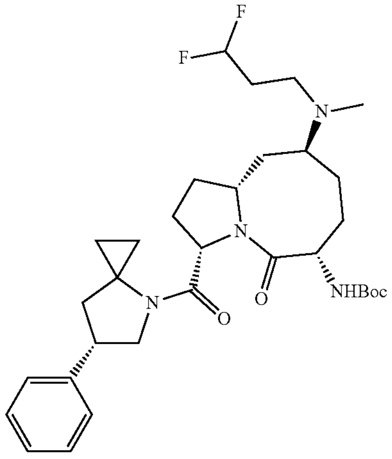

8

To the above mixture (step A) was added 40% formaldehyde aqueous (3 mL) at room temperature, the resulting mixture was stirred for 30 min, then $NaBH_4$ (1.15 g, 30.3 mmol, 5 eq.) was added in portions, and the mixture was stirred for additional 30 min. The reaction mixture was cooled down to 0° C., quenched by $NH_4Cl$ (sat. aq), diluted with $H_2O$ (200 mL), then extracted with EtOAc (100 mL×3), and the combined organic layers were washed with brine (20 mL), dried over $Na_2SO_4$, then concentrated to dryness under reduced pressure, the crude product was purified by C18 column (MeCN:$H_2O$ (0.1% ammonium hydroxide)=5%-70%) to afford tert-butyl ((3S,6S,9S,10aR)-9-((3,3-difluoropropyl)(methyl)amino)-5-oxo-3-((S)-6-phenyl-4-azaspiro[2.4]heptane-4-carbonyl)decahydropyrrolo[1,2-a]azocin-6-yl)carbamate (8, 3 g, 5.10 mmol, 84% yield two steps) as a white solid. LCMS (ESI): m/z=589 $[M+H]^+$.

Step F: (3S,6S,9S,10aR)-6-amino-9-((3,3-difluoropropyl)(methyl)amino)-3-((S)-6-phenyl-4-azaspiro[2.4]heptane-4-carbonyl)octahydropyrrolo[1,2-a]azocin-5(1H)-one

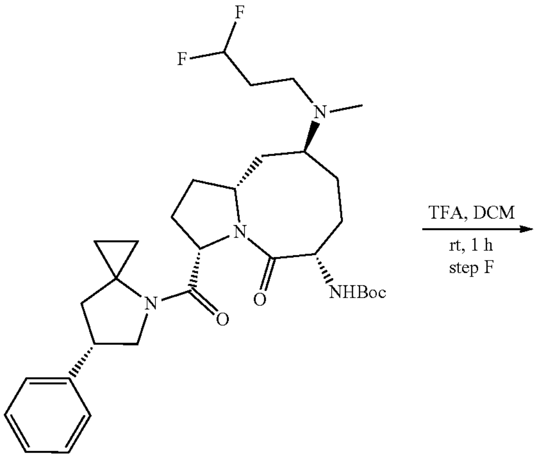

8

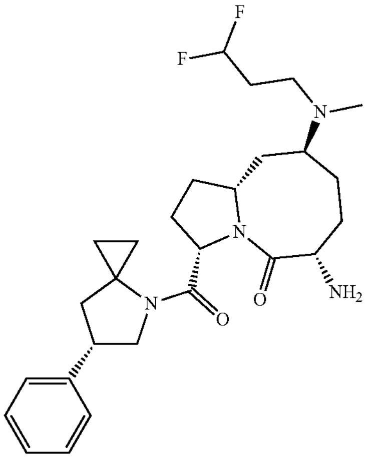

9

To a solution of tert-butyl ((3S,6S,9S,10aR)-9-((3,3-difluoropropyl)(methyl)amino)-5-oxo-3-((S)-6-phenyl-4-azaspiro[2.4]heptane-4-carbonyl)decahydropyrrolo[1,2-a]azocin-6-yl)carbamate (8, 20 mg, 0.034 mmol) in DCM (2 mL) was added TFA (2 mL). The resulting mixture was stirred for 1 h at room temperature. The resulting mixture was concentrated to dryness under reduced pressure to afford crude product (3S,6S,9S,10aR)-6-amino-9-((3,3-difluoropropyl)(methyl)amino)-3-((S)-6-phenyl-4-azaspiro[2.4]heptane-4-carbonyl)octahydropyrrolo[1,2-a]azocin-5(1H)-one (9, 20 mg, TFA salt) as a yellow oil which was used to the next step without further purification. LCMS (ESI): m/z=489 $[M+H]^+$.

Step G: benzyl (((R)-(2-(((3S,6S,9S,10aR)-9-((3,3-difluoropropyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)(phenoxy)phosphoryl)-L-alaninate
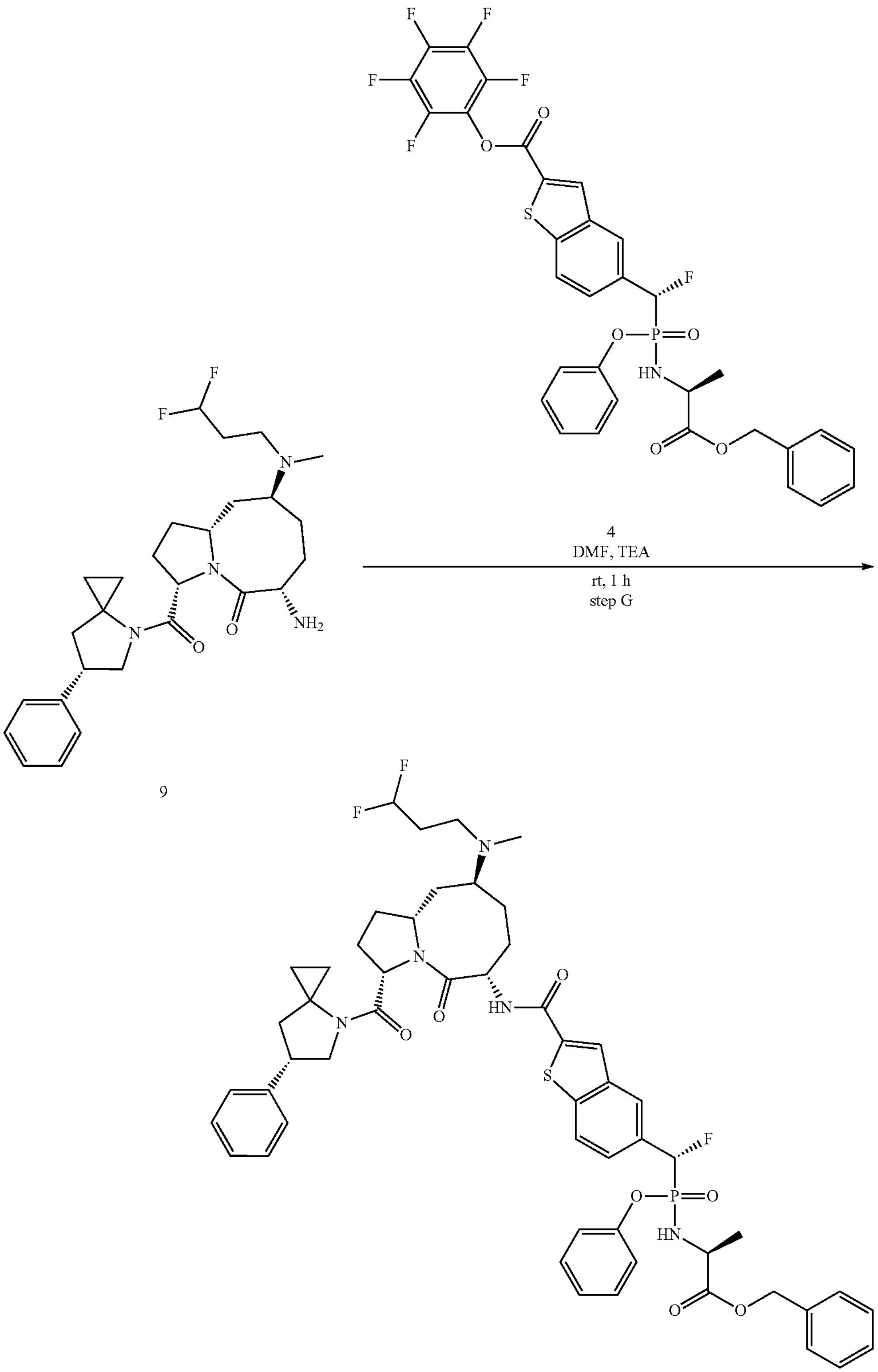
9

To a solution of (3S,6S,9S,10aR)-6-amino-9-((3,3-difluoropropyl)(methyl)amino)-3-((S)-6-phenyl-4-azaspiro[2.4]heptane-4-carbonyl)octahydropyrrolo[1,2-a]azocin-5(1H)-one (9, 20 mg, TFA salt) in DMF (2 mL) was added TEA (6.9 mg, 0.068 mmol, 2 eq.), perfluorophenyl 5-((1R)—((((S)-1-(benzyloxy)-1-oxopropan-2-yl)amino)(phenoxy)phosphoryl)fluoromethyl)benzo[b]thiophene-2-carboxylate (4, 23.6 mg, 0.034 mmol, 1 eq.). The resulting mixture was stirred for 1 hr at room temperature and the crude product was purified by Prep-HPLC to afford benzyl (((R)-(2-(((3S,6S,9S,10aR)-9-((3,3-difluoropropyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)(phenoxy)phosphoryl)-L-alaninate (Compound C52, 21 mg) as a white solid. LCMS (ESI): m/z=998 $[M+H]^+$. $^1$H NMR (400 MHz, DMSO-$d_6$) δ (ppm) 8.79 (M, 1H), 8.28 (s, 1H), 8.10-8.02 (m, 2H), 7.60 (t, J=7.5 Hz, 1H), 7.39-7.11 (m, 16H), 6.37-6.05 (m, 3H), 5.09-4.90 (m, 2H), 4.84-4.72 (m, 1H), 4.50 (t, J=8.5 Hz, 1H), 4.38-4.27 (m, 1H), 4.16-4.06 (m, 1H), 3.97-3.83 (m, 1H), 3.75 (t, J=9.7 Hz, 1H), 3.60-3.49 (m, 1H), 3.06-2.94 (m, 1H), 2.47-2.33 (m, 2H), 2.25-2.19 (m, 1H), 2.16-2.11 (m, 4H), 2.07-1.93 (m, 5H), 1.89-1.54 (m, 8H), 1.22-1.15 (m, 3H), 0.55-0.41 (m, 2H). $^{19}$F NMR (377 MHz, DMSO-$d_6$) δ (ppm) −115.74-−116.43 (m), −194.66-−196.64 (m). $^{31}$P NMR (162 MHz, DMSO-$d_6$) δ (ppm) 17.26 (d, J=82.3 Hz), 17.15 (d, J=86.2 Hz).

Synthesis of ((R)-fluoro(2-(((3S,6S,9S,10aR)-9-(((1s,3R)-3-fluorocyclobutyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)phosphonic acid (Compound A21)

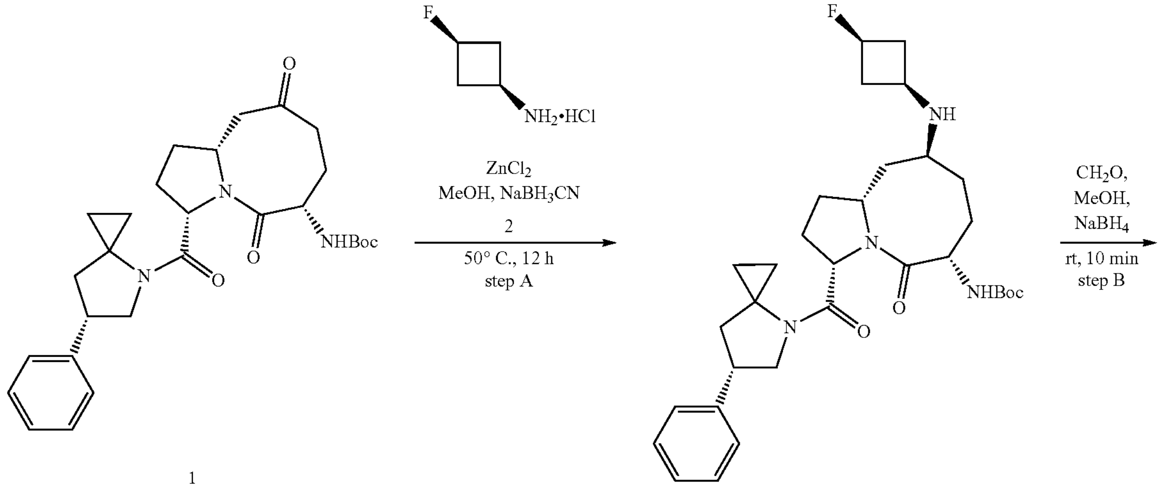

1

3

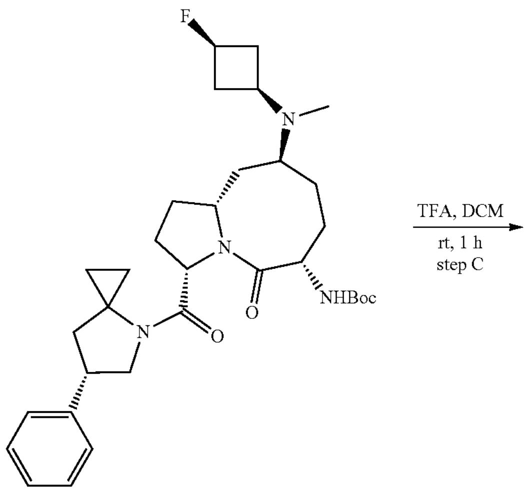

4

-continued
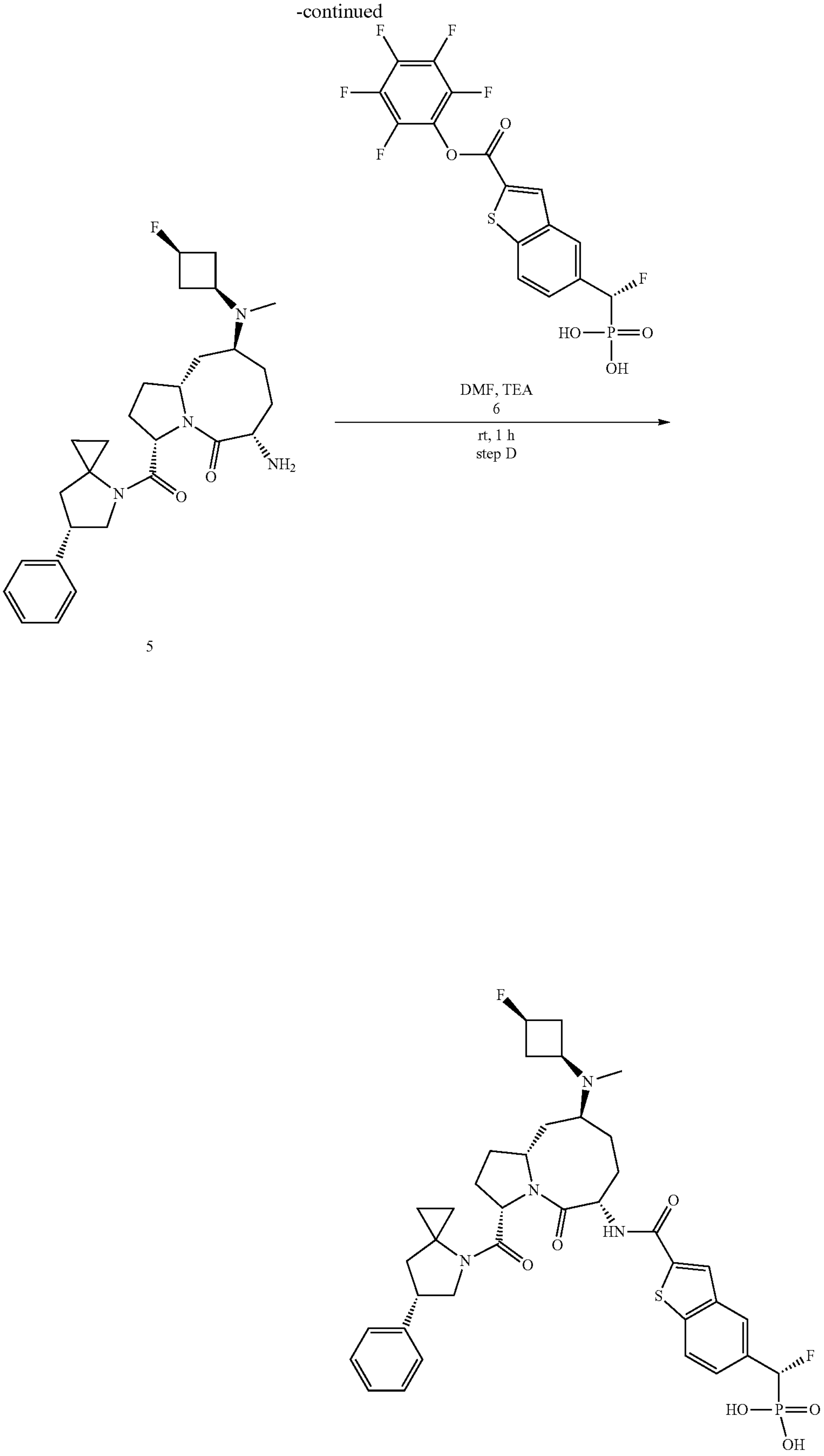
5

Step A: tert-butyl ((3S,6S,9S,10aR)-9-(((1s,3R)-3-fluorocyclobutyl)amino)-5-oxo-3-((S)-6-phenyl-4-azaspiro[2.4]heptane-4-carbonyl)decahydropyrrolo[1,2-a]azocin-6-yl)carbamate Step B: tert-butyl ((3S,6S,9S,10aR)-9-(((1s,3R)-3-fluorocyclobutyl)(methyl)amino)-5-oxo-3-((S)-6-phenyl-4-azaspiro[2.4]heptane-4-carbonyl)decahydropyrrolo[1,2-a]azocin-6-yl)carbamate

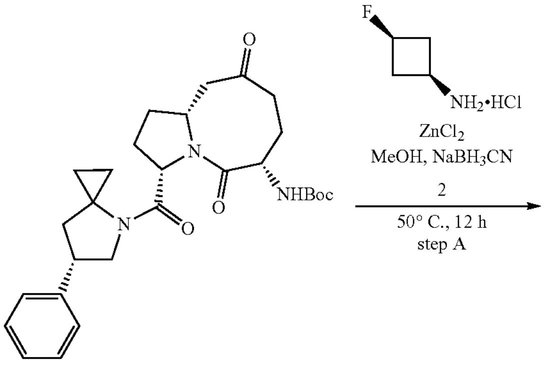

1

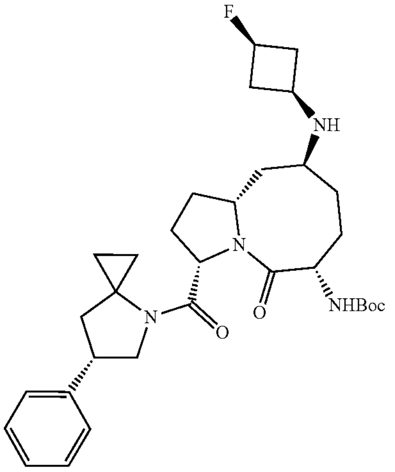

3

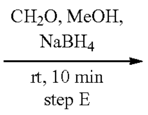

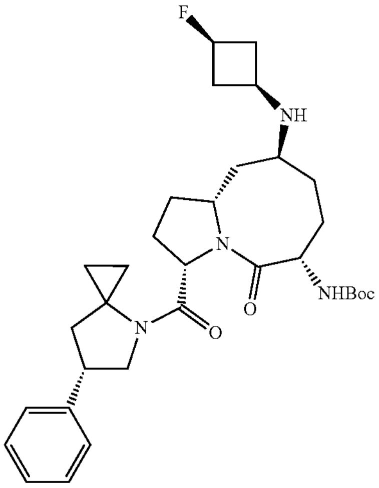

3

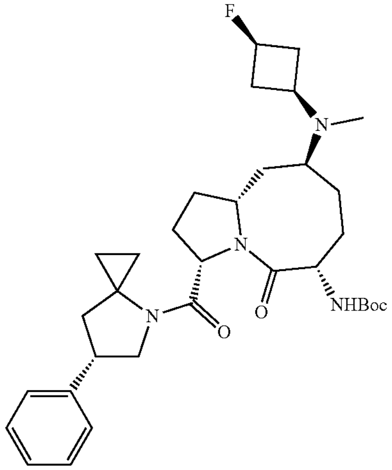

4

To a solution of tert-butyl ((3S,6S,10aR)-5,9-dioxo-3-((S)-6-phenyl-4-azaspiro[2.4]heptane-4-carbonyl)decahydropyrrolo[1,2-a]azocin-6-yl)carbamate (1, 3 g, 6.06 mmol, 1 eq.) in MeOH (60 mL) was added (1s,3s)-3-fluorocyclobutan-1-amine hydrochloride (2, 1.14 g, 9.09 mmol, 1.5 eq.), $ZnCl_2$ (8.3 g, 60.6 mmol, 10 eq.), the resulting mixture was stirred for 2 hr. at 50° C. under the atmosphere of $N_2$. Then $NaBH_3CN$ (3.81 g, 60.6 mmol, 10 eq.) was added portion wise every 30 mins (2 eq. (762 mg each time) added 5 times). The solution was stirred for 12 hr at 50° C., then cooled to room temperature. The solution was used to next step without further workup. LCMS (ESI): m/z=569 $[M+H]^+$.

To the above mixture (step A) was added 40% formaldehyde aqueous (3 mL) at room temperature, the mixture was stirred for 30 min, then $NaBH_4$ (1.15 g, 30.3 mmol, 5 eq.) was added in portions and the mixture was stirred for another 30 min. The reaction was quenched by $NH_4Cl$ (sat. aq), diluted with $H_2O$ (200 mL), then extracted with EtOAc (100 mL×3), the organic layers were combined and washed with brine (20 mL), dried over $Na_2SO_4$, filtered, then concentrated to dryness under reduced pressure. The crude product was purified by C18 column (MeCN:$H_2O$ (0.1% ammonium hydroxide)=5%-70%) to afford tert-butyl ((3S,6S,9S,10aR)-9-(((1s,3R)-3-fluorocyclobutyl)(methyl)amino)-5-oxo-3-((S)-6-phenyl-4-azaspiro[2.4]heptane-4-carbonyl)decahydropyrrolo[1,2-a]azocin-6-yl)carbamate (4, 3 g, 5.15 mmol, 85% yield two steps) as a white solid. LCMS (ESI): m/z=583 $[M+H]^+$.

Step C: (3S,6S,9S,10aR)-6-amino-9-(((1s,3R)-3-fluorocyclobutyl)(methyl)amino)-3-((S)-6-phenyl-4-azaspiro[2.4]heptane-4-carbonyl)octahydropyrrolo[1,2-a]azocin-5(1H)-one

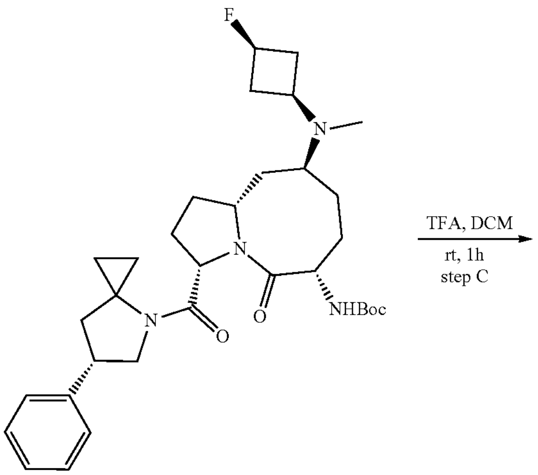

4

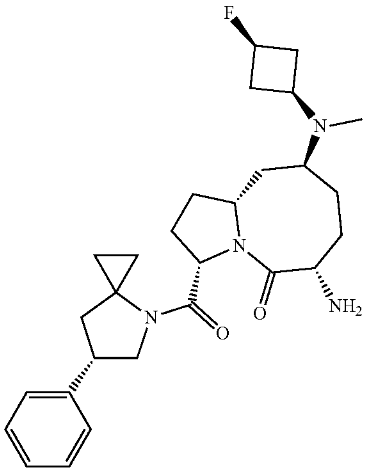

5

To a solution of tert-butyl ((3S,6S,9S,10aR)-9-(((1s,3R)-3-fluorocyclobutyl)(methyl)amino)-5-oxo-3-((S)-6-phenyl-4-azaspiro[2.4]heptane-4-carbonyl)decahydropyrrolo[1,2-a]azocin-6-yl)carbamate (4, 20 mg, 0.034 mmol) in DCM (2 mL) was added TFA (2 mL). The resulting mixture was stirred for 1 h at room temperature. The resulting mixture was concentrated to dryness under reduced pressure to afford crude product (3S,6S,9S,10aR)-6-amino-9-(((1s,3R)-3-fluorocyclobutyl)(methyl)amino)-3-((S)-6-phenyl-4-azaspiro[2.4]heptane-4-carbonyl)octahydropyrrolo[1,2-a]azocin-5(1H)-one (5, 20 mg, TFA salt) as a yellow oil which was used to the next step without further purification. LCMS (ESI): m/z=483 $[M+H]^+$.

Step D: ((R)-fluoro(2-(((3S,6S,9S,10aR)-9-(((1s,3R)-3-fluorocyclobutyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)phosphonic acid

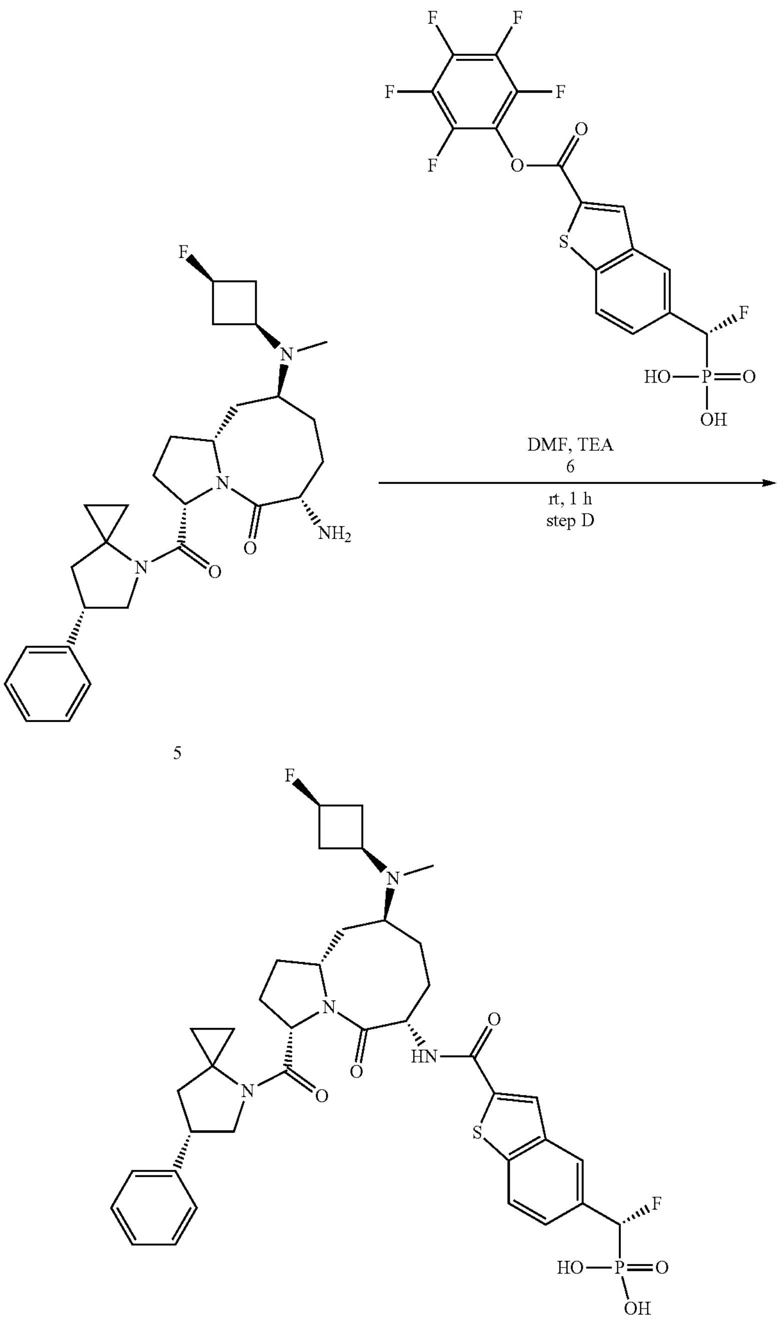 [SMILES: CN([C@H]1CC[C@H](N)C(=O)N2[C@H](CC[C@H]2C(=O)N2C[C@H](c3ccccc3)CC23CC3)C1)[C@H]1C[C@@H](F)C1 ; O=C(Oc1c(F)c(F)c(F)c(F)c1F)c1cc2cc([C@H](F)P(=O)(O)O)ccc2s1 ; CN([C@H]1CC[C@H](NC(=O)c2cc3cc([C@H](F)P(=O)(O)O)ccc3s2)C(=O)N2[C@H](CC[C@H]2C(=O)N2C[C@H](c3ccccc3)CC23CC3)C1)[C@H]1C[C@@H](F)C1]

5

To a solution of (3S,6S,9S,10aR)-6-amino-9-(((1s,3R)-3-fluorocyclobutyl)(methyl)amino)-3-((S)-6-phenyl-4-azaspiro[2.4]heptane-4-carbonyl)octahydropyrrolo[1,2-a]azocin-5(1H)-one (5, 20 mg, TFA salt) in DMF (2 mL) was added TEA (6.9 mg, 0.068 mmol, 2 eq.), (R)-(fluoro(2-((perfluorophenoxy)carbonyl)benzo[b]thiophen-5-yl)methyl)phosphonic acid (6, 15.6 mg, 0.034 mmol, 1 eq.). The resulting mixture was stirred for 1 h at room temperature. The crude product was purified by Prep-HPLC to afford ((R)-fluoro(2-(((3S,6S,9S,10aR)-9-(((1s,3R)-3-fluorocyclobutyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)phosphonic acid (Compound A21, 6 mg) as a white solid. LCMS (ESI): m/z=755 $[M+H]^+$. 1H NMR (400 MHz, $CD_3OD-d_4$) δ (ppm) 8.08-8.01 (m, 2H), 7.88 (d, J=8.4 Hz, 1H), 7.66 (d, J=8.4 Hz, 1H), 7.37-7.26 (m, 4H), 7.24-7.17 (m, 1H), 5.65 (dd, J=45.2, 8.4 Hz, 1H), 4.79-4.68 (m, 2H), 4.66-4.58 (m, 1H), 4.52-4.40 (m, 1H), 4.07-3.99 (m, 1H), 3.96-3.89 (m, 1H), 3.86-3.73 (m, 1H), 3.61-3.49 (m, 1H), 3.00-2.86 (m, 1H), 2.81-2.68 (m, 1H), 2.65-2.06 (m, 11H), 2.03-1.60 (m, 9H), 0.59-0.44 (m, 2H). $^{19}F$ NMR (376 MHz, $CD_3OD-d_4$) δ (ppm) −169.82 (s), −195.37-−196.18 (m). $^{31}P$ NMR (162 MHz, $CD_3OD-d_4$) δ (ppm) 9.80 (d, J=76.8 Hz).

Synthesis of (3,3-difluorocyclobutyl)methyl (((R)-fluoro(2-(((3S,6S,9S,10aR)-9-(((1s,3R)-3-fluorocyclobutyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate (Compound C66)
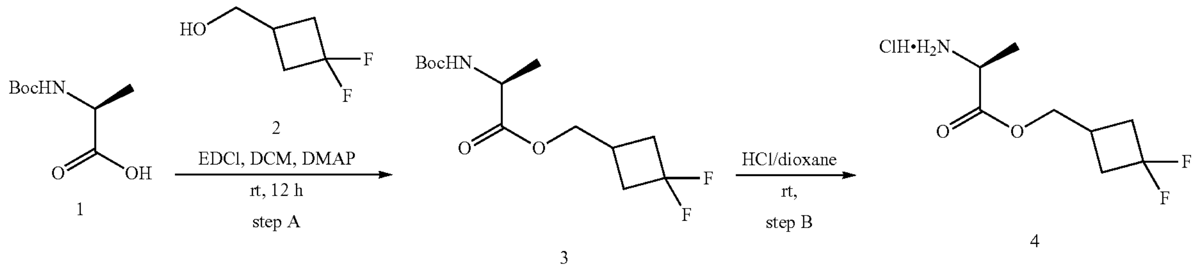
1 2 3 4
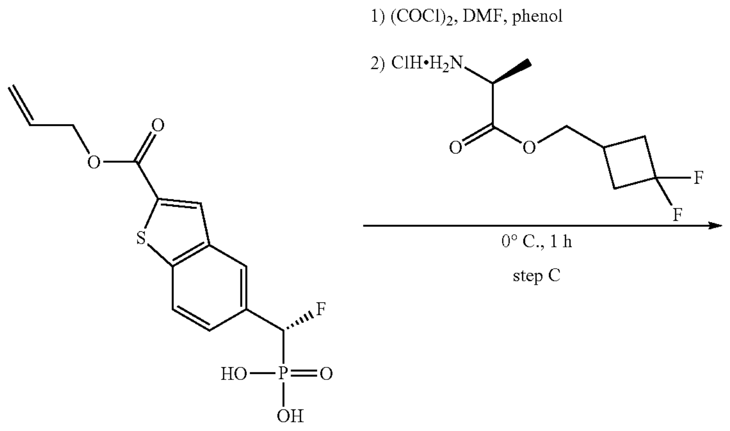
5
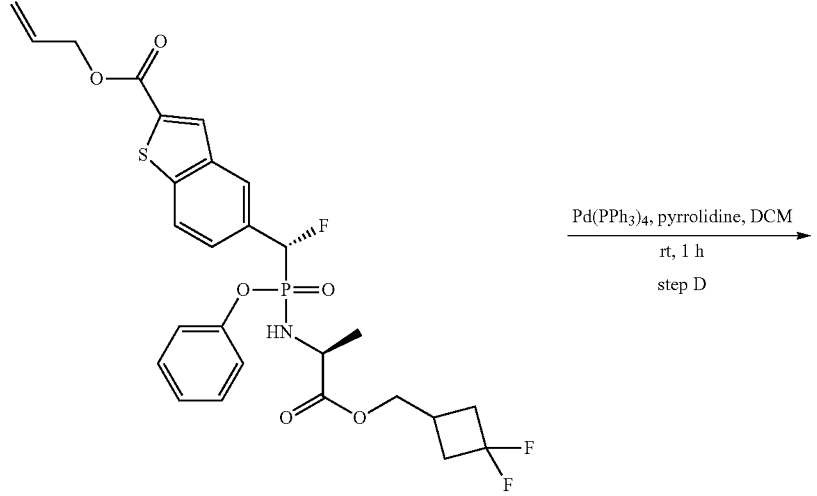
6

-continued
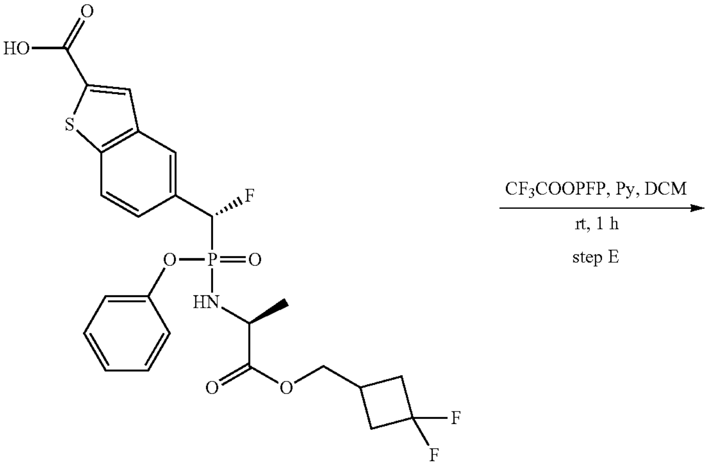
7
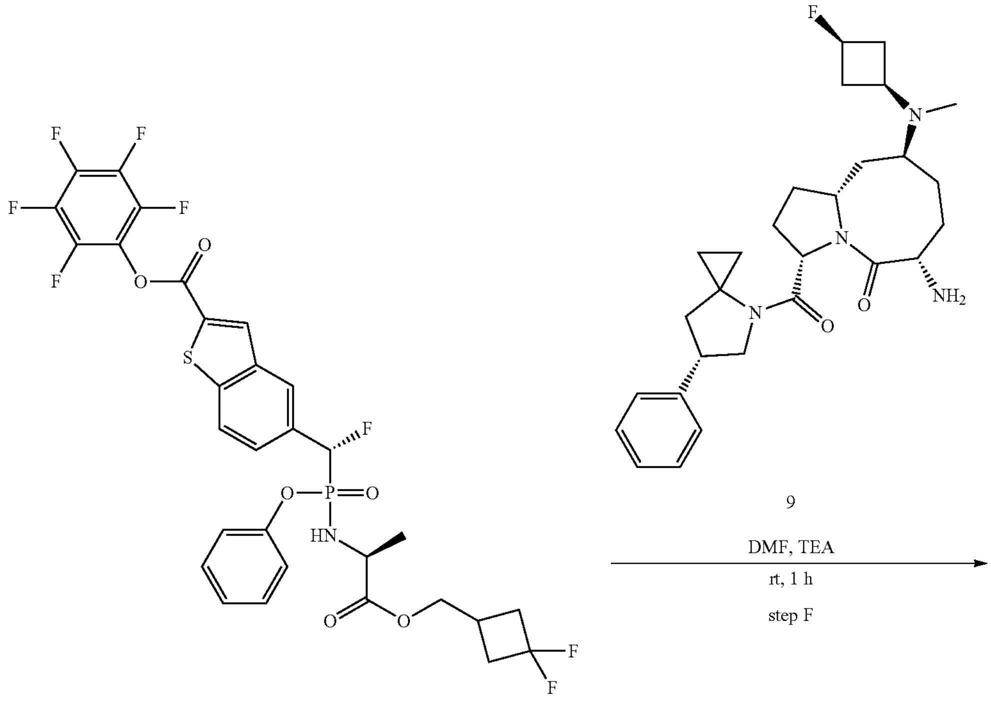
9
8

-continued

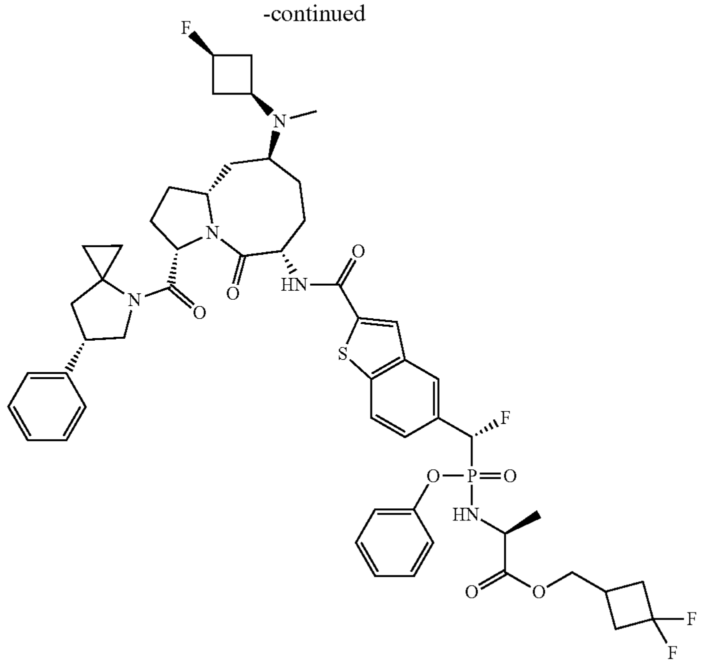

Step A: (3,3-difluorocyclobutyl)methyl (tert-butoxycarbonyl)-L-alaninate

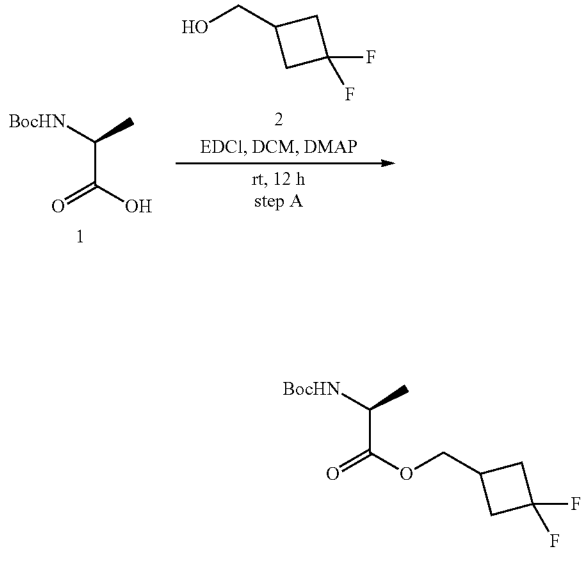

3

To a solution of (tert-butoxycarbonyl)-L-alanine (1, 2 g, 10.58 mmol, 1 eq.) in DCM (20 mL) was added (3,3-difluorocyclobutyl)methanol (2, 1.29 g, 10.58 mmol, 1 eq.), DMAP (1.42 g, 11.64 mmol, 1.1 eq.), and EDCI (2.23 g, 11.64 mmol, 1.1 eq.), The solution was stirred for 12 h at room temperature then $H_2O$ (20 mL) was added to the solution, then extracted with DCM (20 mL×2), the organic layers were combined and washed with brine (20 mL), dried over $Na_2SO_4$, filtered and concentrated to dryness under reduced pressure. The crude product was purified by silica gel column to afford (3,3-difluorocyclobutyl)methyl (tert-butoxycarbonyl)-L-alaninate (3, 2.5 g, 8.5 mmol, 80.6% yield) as a colorless oil. LCMS (ESI): m/z=294 $[M+H]^+$.

Step B: (3,3-difluorocyclobutyl)methyl L-alaninate hydrochloride

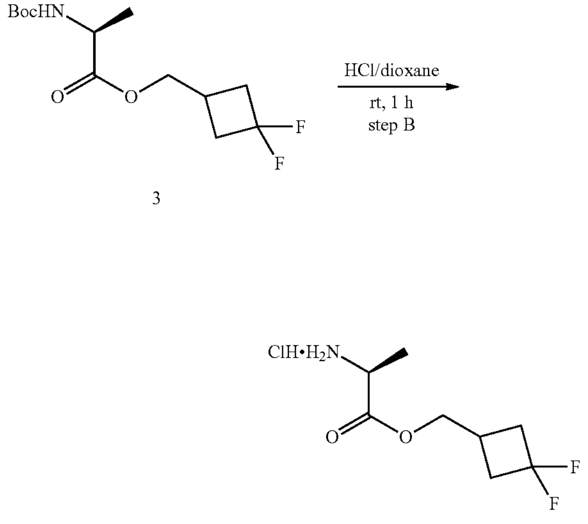

4

To a solution of (3,3-difluorocyclobutyl)methyl (tert-butoxycarbonyl)-L-alaninate (2, 2.5 g, 8.5 mmol) in dioxane (5 mL) was added 4M HCl in dioxane (10 mL). The resulting mixture was stirred for 1 h at room temperature then concentrated under vacuum to afford (3,3-difluorocyclobutyl)methyl L-alaninate hydrochloride (4, 1.95 g, 8.5 mmol 100% yield) as a white solid. LCMS (ESI): m/z=194 $[M+H]^+$.

Step C: allyl 5-((1R)—((((S)-1-((3,3-difluorocyclobutyl)methoxy)-1-oxopropan-2-yl)amino)(phenoxy)phosphoryl)fluoromethyl)benzo[b]thiophene-2-carboxylate

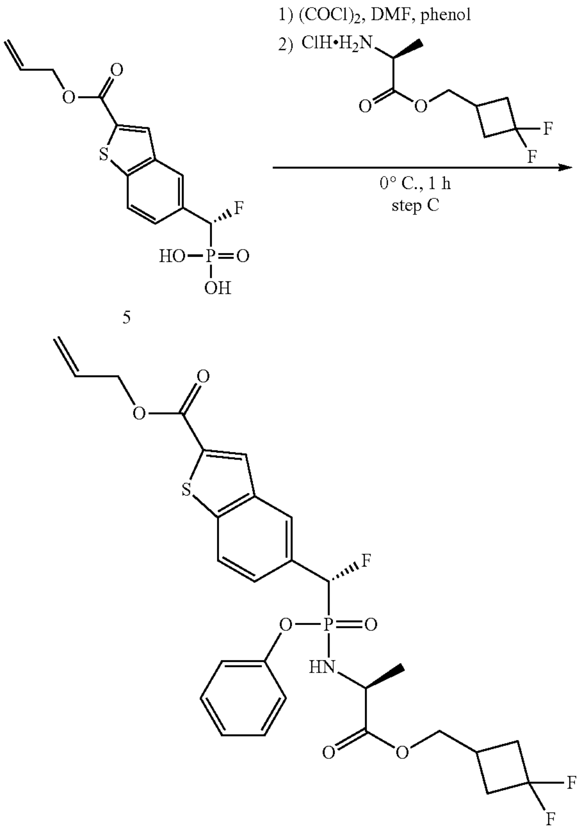

5

6

To a solution of (R)-((2-((allyloxy)carbonyl)benzo[b]thiophen-5-yl)fluoromethyl)phosphonic acid (5, 1.3 g, 3.94 mmol, 1 eq.) in DCM (20 mL) was added DMF (1 drop) and oxalyl chloride (2.5 g, 19.7 mmol, 5 eq). The resulting mixture was stirred for 1 h at room temperature, then oxalyl chloride was removed under reduced pressure. The residue was redissolved in DCM (20 mL) and cooled to 0° C. and phenol (285 mg, 3.94 mmol, 1 eq) was added to the solution followed by the dropwise addition of TEA (2 g, 19.7 mmol, 5 eq.). The mixture was stirred for 1 h at 0° C. then (3,3-difluorocyclobutyl)methyl L-alaninate hydrochloride (4, 1.80 g, 7.88 mmol, 2 eq.) was added to the solution, then stirred for 10 mins and quenched by adding $H_2O$ (50 mL), then extracted with DCM (50 mL×2), the organic layers were combined and washed with brine (30 mL), then dried over $Na_2SO_4$, filtered, and concentrated to dryness under reduced pressure. The crude product was purified by silica gel chromatography column to afford allyl 5-((1R)—((((S)-1-((3,3-difluorocyclobutyl)methoxy)-1-oxopropan-2-yl)amino)(phenoxy)phosphoryl)fluoromethyl)benzo[b]thiophene-2-carboxylate (6, 800 mg, 1.38 mmol, 35% yield) as a colorless oil. LCMS (ESI): m/z=582 $[M+H]^+$.

Step D: 5-((1R)—((((S)-1-((3,3-difluorocyclobutyl)methoxy)-1-oxopropan-2-yl)amino)(phenoxy)phosphoryl)fluoromethyl)benzo[b]thiophene-2-carboxylic acid

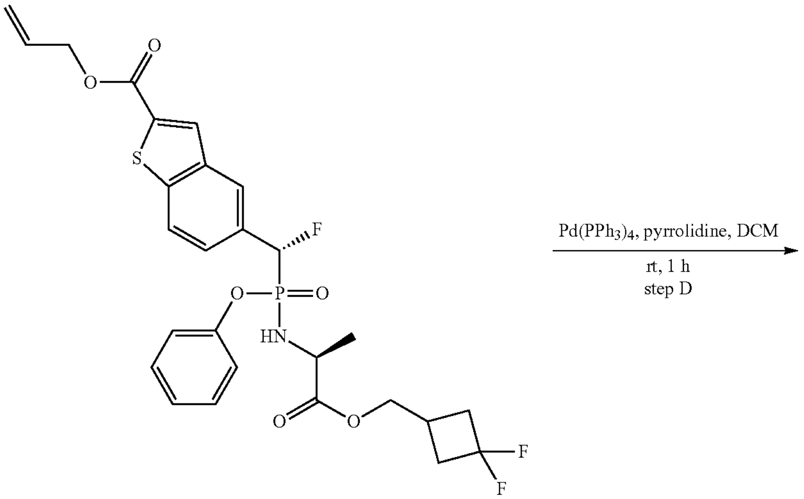

6

-continued

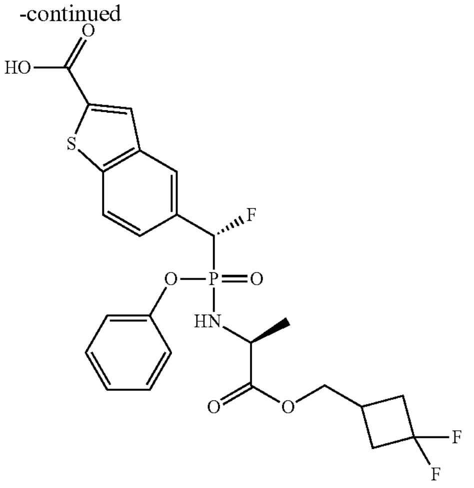

7

To a solution of allyl 5-((1R)—((((S)-1-((3,3-difluorocyclobutyl)methoxy)-1-oxopropan-2-yl)amino)(phenoxy)phosphoryl)fluoromethyl)benzo[b]thiophene-2-carboxylate (6, 800 mg, 1.38 mmol, 1 eq.) in DCM (10 mL) was added $Pd(PPh_3)_4$ (165 mg, 0.14 mmol, 0.1 eq.) and pyrrolidine (98 mg, 1.38 mmol, 1 eq.). The resulting mixture was stirred for 1 hr at room temperature under the atmosphere of $N_2$. The pH was adjusted to pH=3 with 1M HCl (aq.), then extracted with DCM (20 mL×2), the organic layers were combined and washed with brine (20 mL) dried over $Na_2SO_4$, filtered and concentrated to dryness under reduced pressure to afford crude product 5-((1R)—((((S)-1-((3,3-difluorocyclobutyl)methoxy)-1-oxopropan-2-yl)amino)(phenoxy)phosphoryl)fluoromethyl)benzo[b]thiophene-2-carboxylic acid (7, 700 mg, 1.29 mmol, 93% yield) as a yellow solid. LCMS (ESI): m/z=542 $[M+H]^+$.

Step E: perfluorophenyl 5-((1R)—((((S)-1-((3,3-difluorocyclobutyl)methoxy)-1-oxopropan-2-yl)amino)(phenoxy)phosphoryl)fluoromethyl)benzo[b]thiophene-2-carboxylate

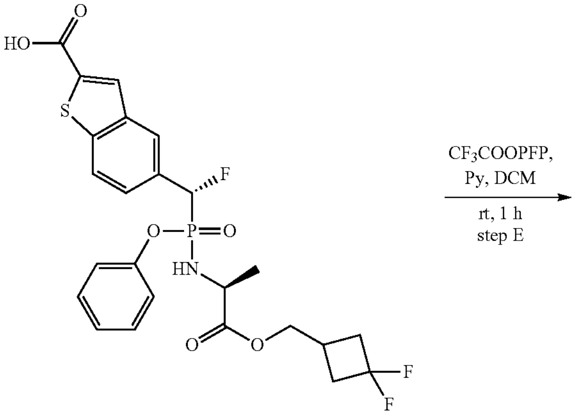

7

-continued

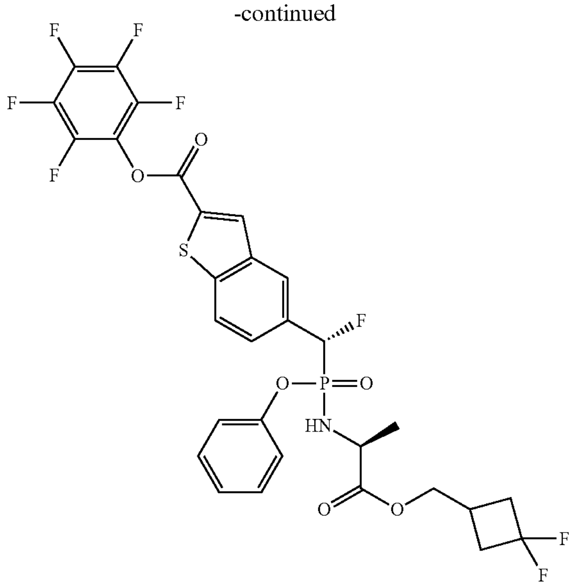

8

To a solution of 5-((1R)—((((S)-1-((3,3-difluorocyclobutyl)methoxy)-1-oxopropan-2-yl)amino)(phenoxy)phosphoryl)fluoromethyl)benzo[b]thiophene-2-carboxylic acid (7, 700 mg, 1.29 mmol, 1 eq.) in DCM (10 mL) was added pyridine (306 mg, 3.87 mmol, 3 eq.) and perfluorophenyl 2,2,2-trifluoroacetate (722 mg, 2.58 mmol, 2 eq.). The resulting mixture was stirred for 1 h at room temperature, then $H_2O$ (20 mL) was added to the solution which was then extracted with DCM (20 mL×2). The organic layers were combined and washed with brine, dried over $Na_2SO_4$, then concentrated under vacuum. The crude product was purified by silica gel column chromatography to afford perfluorophenyl 5-((1R)—((((S)-1-((3,3-difluorocyclobutyl)methoxy)-1-oxopropan-2-yl)amino)(phenoxy)phosphoryl)fluoromethyl)benzo[b]thiophene-2-carboxylate (8, 700 mg, 0.99 mmol, 77% yield) as a white solid. LCMS (ESI): m/z=708 $[M+H]^+$.

Step F: (3,3-difluorocyclobutyl)methyl (((R)-fluoro(2-(((3S,6S,9S,10aR)-9-(((1s,3R)-3-fluorocyclobutyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate

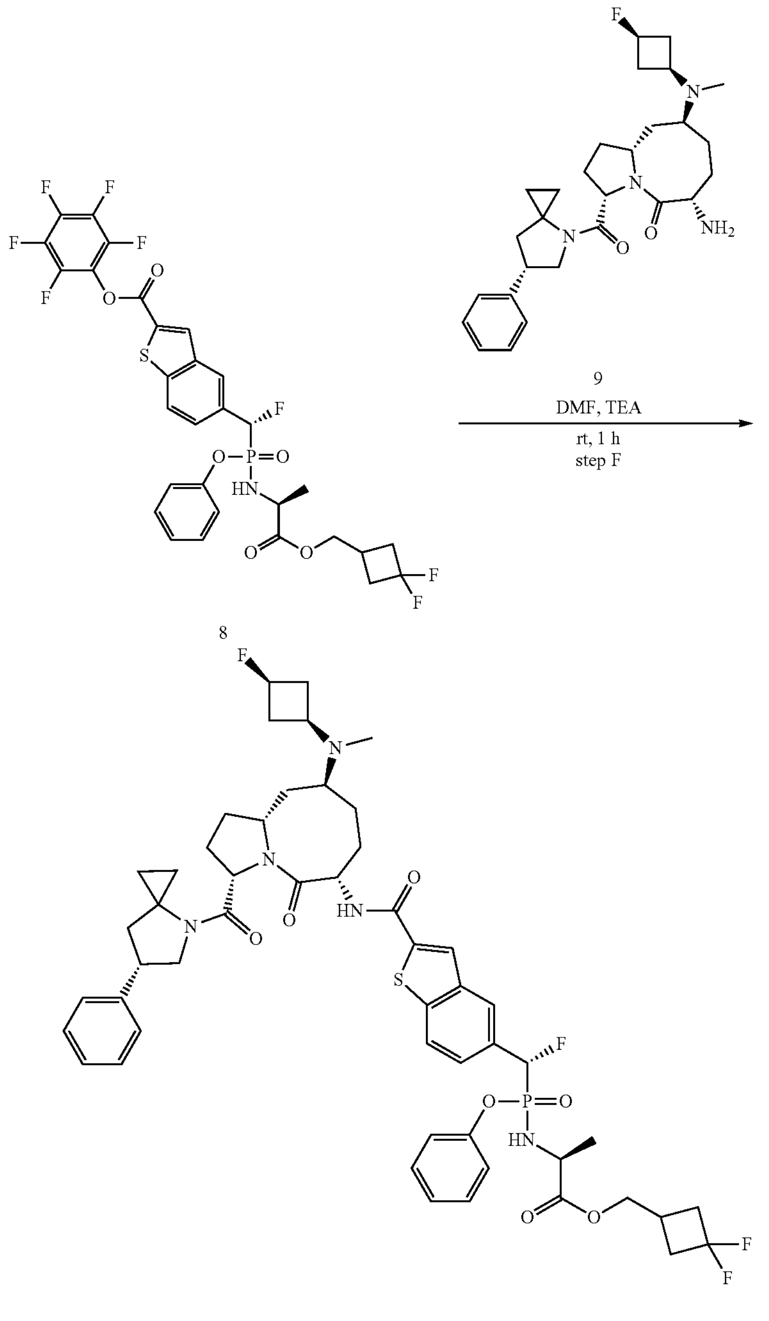

To a solution of perfluorophenyl 5-((1R)—((((S)-1-((3,3-difluorocyclobutyl)methoxy)-1-oxopropan-2-yl)amino)(phenoxy)phosphoryl)fluoromethyl)benzo[b]thiophene-2-carboxylate (8, 20 mg, 0.028 mml, 1 eq.) in DMF (3 mL) was added (3S,6S,9S,10aR)-6-amino-9-(((1s,3R)-3-fluorocyclobutyl)(methyl)amino)-3-((S)-6-phenyl-4-azaspiro[2.4]heptane-4-carbonyl)octahydropyrrolo[1,2-a]azocin-5(1H)-one (9, 14 mg, 0.029 mmol, 1 eq.), TEA (5.7 mg, 0.056 mmol, 2 eq). The resulting mixture was stirred for 1 h at room temperature. The crude product was purified by Prep-HPLC to afford (3,3-difluorocyclobutyl)methyl (((R)-fluoro(2-(((3S,6S,9S,10aR)-9-(((1s,3R)-3-fluorocyclobutyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate (Compound C66, 18 mg, 0.018 mmol, 64% yield) as a white solid. LCMS (ESI): m/z=1006 $[M+H]^+$. $^1H$ NMR (400 MHz, DMSO-d6) δ (ppm) 8.89-8.71 (m, 1H), 8.27 (s, 1H), 8.12-7.99 (m, 2H), 7.65-7.56 (m, 1H), 7.39-7.27 (m, 6H), 7.24-7.13 (m, 4H), 6.31-6.21 (m, 1H), 6.18-6.10 (m, 1H), 4.90-4.66 (m, 2H), 4.52-4.43 (m, 1H), 4.33-4.24 (m, 1H), 4.15-3.70 (m, 5H), 3.59-3.48 (m, 1H), 3.06-2.93 (m, 1H), 2.63-2.53 (m, 3H), 2.49-1.45 (m, 24H), 1.15 (d, J=7.0 Hz, 3H), 0.60-0.36 (m, 2H). $^{19}F$ NMR (377

MHz, DMSO-d6) δ (ppm) −80.84−−82.82 (m), −91.58−−93.03 (m), −165.27 (s), −194.62 (d, J=82.8 Hz), −196.26 (d, J=86.1 Hz). $^{31}$P NMR (162 MHz, DMSO-d6) δ (ppm) 17.25 (d, J=83.1 Hz), 17.12 (d, J=86.1 Hz).

Synthesis of ((S)-(2-(((3S,6S,9S,10aR)-9-(ethyl((1s, 3R)-3-fluorocyclobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)phosphonic acid (Compound A34) and propyl (((S)-(2-(((3S,6S,9S, 10aR)-9-(ethyl((1s,3R)-3-fluorocyclobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)(phenoxy)phosphoryl)-L-alaninate (Compound C56)

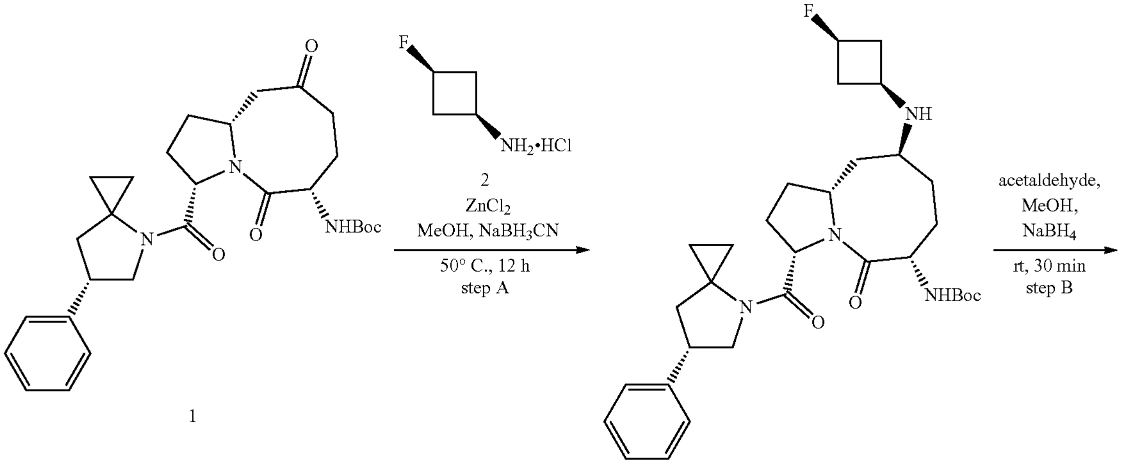

1

3

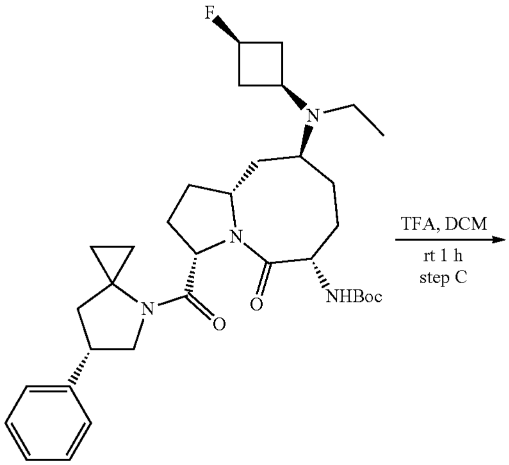

4

-continued

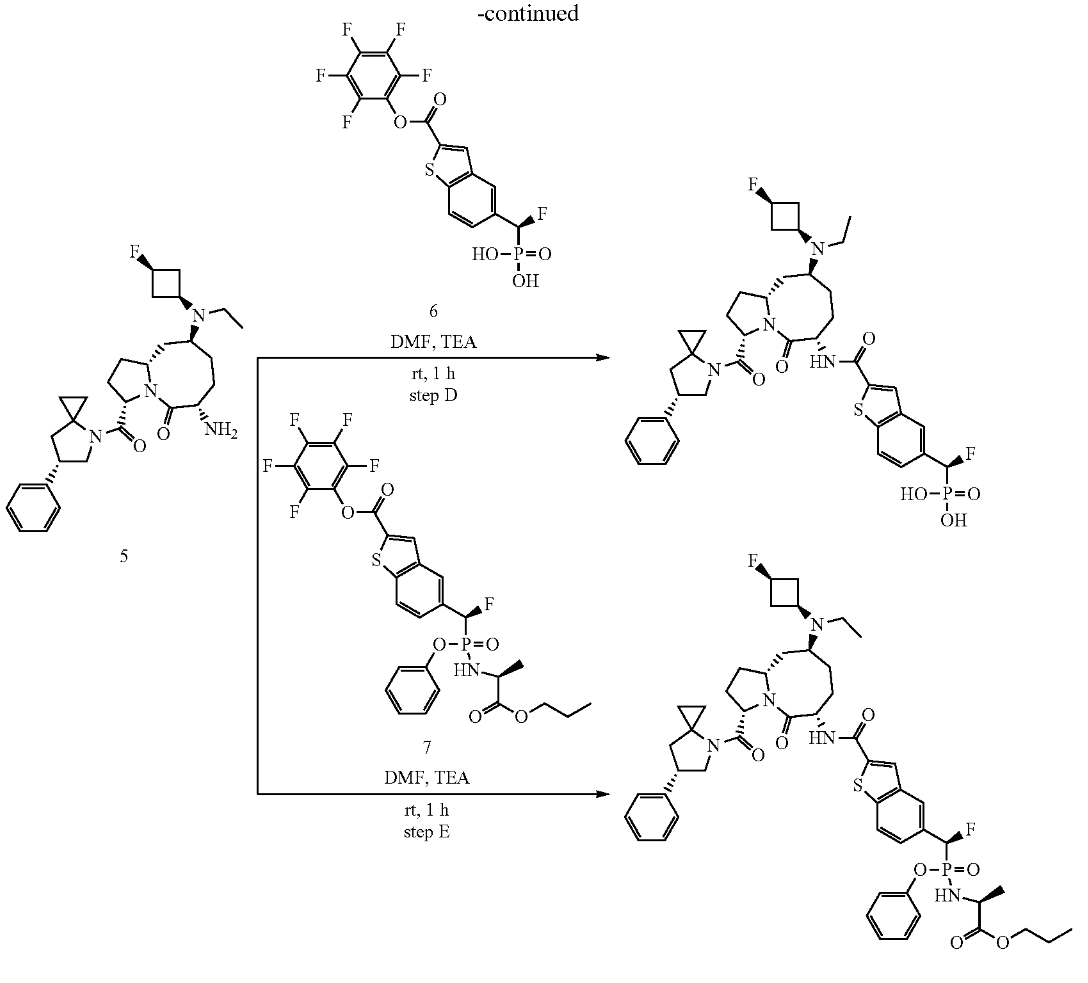

Step A: tert-butyl ((3S,6S,9S,10aR)-9-(((1s,3R)-3-fluorocyclobutyl)amino)-5-oxo-3-((S)-6-phenyl-4-azaspiro[2.4]heptane-4-carbonyl)decahydropyrrolo[1,2-a]azocin-6-yl)carbamate

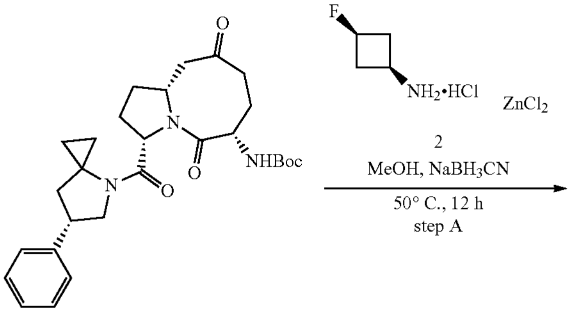

1

-continued

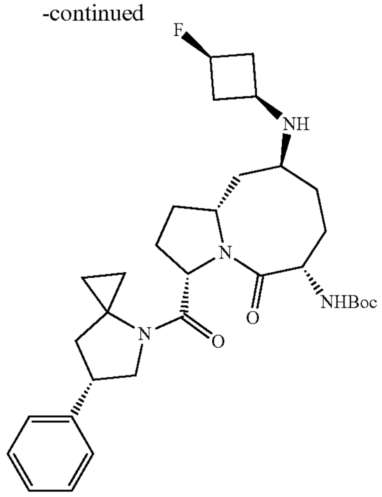

3

To a solution of tert-butyl ((3S,6S,10aR)-5,9-dioxo-3-((S)-6-phenyl-4-azaspiro[2.4]heptane-4-carbonyl)decahydropyrrolo[1,2-a]azocin-6-yl)carbamate (1, 3 g, 6.06 mmol, 1 eq.) in MeOH (60 mL) was added (1s,3s)-3-fluorocyclobutan-1-amine hydrochloride (2, 1.14 g, 9.09 mmol, 1.5 eq.), $ZnCl_2$ (8.3 g, 60.6 mmol, 10 eq.) and the resulting mixture was stirred for 2 hr at 50° C. under the atmosphere of $N_2$.

Then $NaBH_3CN$ (3.81 g, 60.6 mmol, 10 eq.) was added portion wise every 30 mins (2 eq. (762 mg each time) added 5 times). The solution was stirred for 12 hr at 50° C. then cooled to room temperature. The solution was used to next step without further workup. LCMS (ESI): m/z=569 $[M+H]^+$.

Step B: tert-butyl ((3S,6S,9S,10aR)-9-(ethyl((1s,3R)-3-fluorocyclobutyl)amino)-5-oxo-3-((S)-6-phenyl-4-azaspiro[2.4]heptane-4-carbonyl)decahydropyrrolo[1,2-a]azocin-6-yl)carbamate

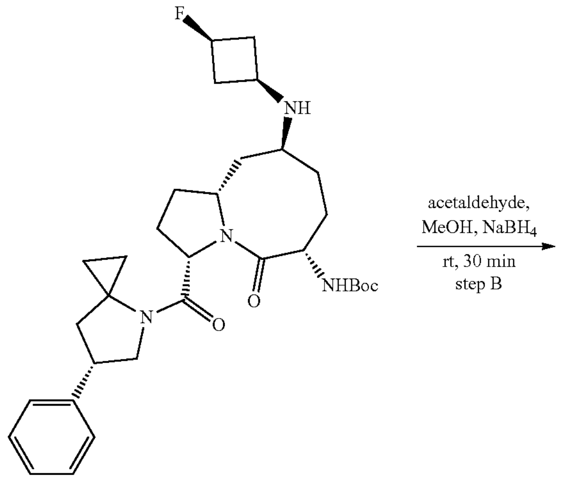

3

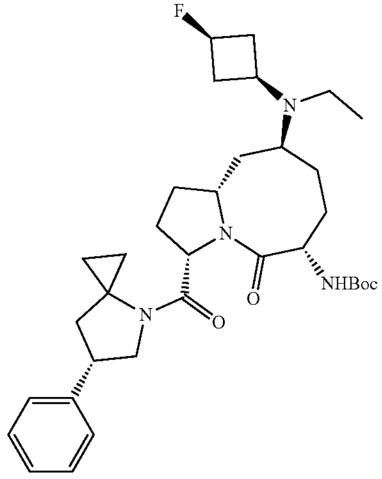

4

To the above mixture (step A) was added acetaldehyde (800 mg, 18.18 mmol, 3 eq.) at room temperature, the mixture was stirred for 30 min, then $NaBH_4$ (1.15 g, 30.3 mmol, 5 eq.) was added in portions, the mixture was stirred for another 30 min, LCMS show that the reaction was completed. The reaction was quenched by $NH_4Cl$ (sat. aq), diluted with $H_2O$ (200 mL) and extracted with EtOAc (100 mL×3), the organic solution was dried over $Na_2SO_4$, filtered, then concentrated under vacuum. The crude product was purified by C18 column (MeCN:$H_2O$ (0.1% ammonium hydroxide)=5%-70%) to afford tert-butyl ((3S,6S,9S,10aR)-9-(((1s,3R)-3-fluorocyclobutyl)(methyl)amino)-5-oxo-3-((S)-6-phenyl-4-azaspiro[2.4]heptane-4-carbonyl)decahydropyrrolo[1,2-a]azocin-6-yl)carbamate (4, 3 g, 5.03 mmol, 83% yield two steps) as a white solid. LCMS (ESI): m/z=597 $[M+H]^+$.

Step C: (3S,6S,9S,10aR)-6-amino-9-(ethyl((1s,3R)-3-fluorocyclobutyl)amino)-3-((S)-6-phenyl-4-azaspiro[2.4]heptane-4-carbonyl)octahydropyrrolo[1,2-a]azocin-5(1H)-one

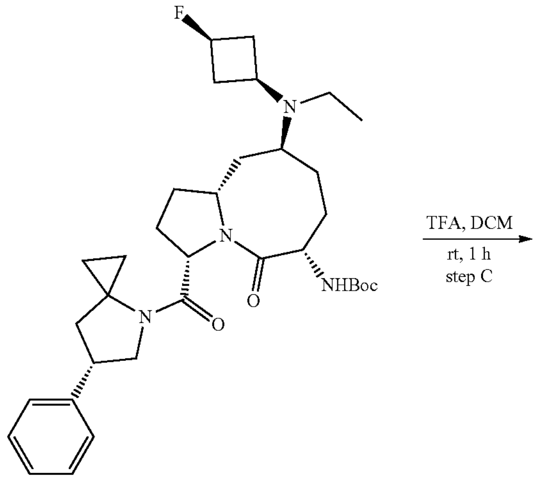

4

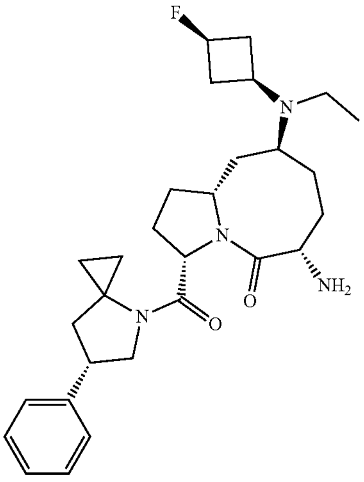

5

To a solution of tert-butyl ((3S,6S,9S,10aR)-9-(ethyl((1s,3R)-3-fluorocyclobutyl)amino)-5-oxo-3-((S)-6-phenyl-4-azaspiro[2.4]heptane-4-carbonyl)decahydropyrrolo[1,2-a]azocin-6-yl)carbamate (4, 20 mg, 0.034 mmol) in DCM (2 mL) was added TFA (2 mL). The resulting mixture was stirred for 1 h at room temperature then concentrated to dryness under reduced pressure to afford crude product (3S,6S,9S,10aR)-6-amino-9-(ethyl((1s,3R)-3-fluorocyclobutyl)amino)-3-((S)-6-phenyl-4-azaspiro[2.4]heptane-4-carbonyl)octahydropyrrolo[1,2-a]azocin-5(1H)-one (5, 20 mg, TFA salt) as a yellow oil which was used to the next step without further purification. LCMS (ESI): m/z=497 $[M+H]^+$.

Step D: ((S)-(2-(((3S,6S,9S,10aR)-9-(ethyl((1s,3R)-3-fluorocyclobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)phosphonic acid

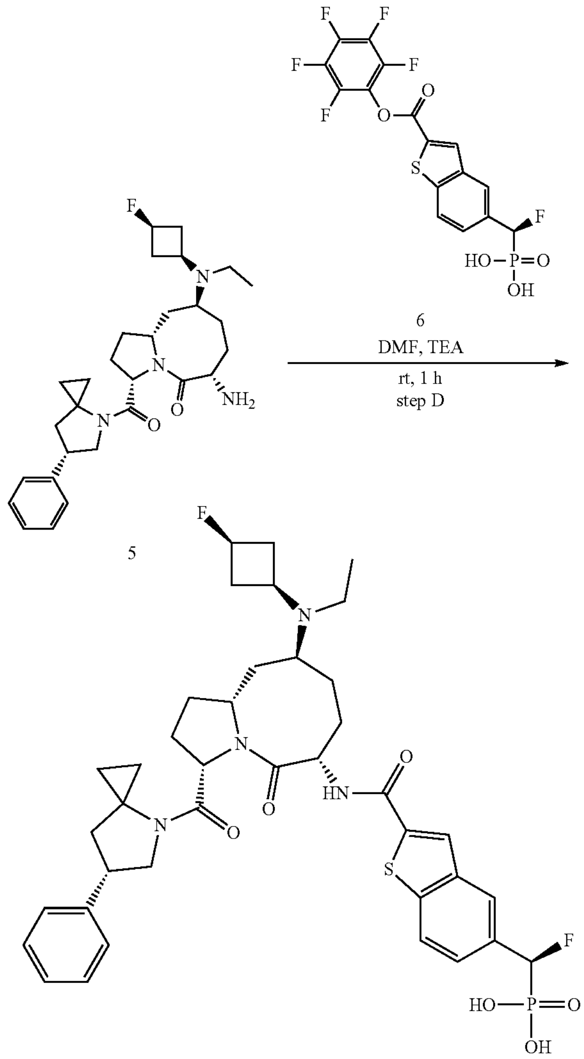

To a solution of (3S,6S,9S,10aR)-6-amino-9-(ethyl((1s,3R)-3-fluorocyclobutyl)amino)-3-((S)-6-phenyl-4-azaspiro[2.4]heptane-4-carbonyl)octahydropyrrolo[1,2-a]azocin-5(1H)-one (5, 20 mg, TFA salt) in DMF (2 mL) was added TEA (6.8 mg, 0.067 mmol, 2 eq.), (S)-(fluoro(2-((perfluorophenoxy)carbonyl)benzo[b]thiophen-5-yl)methyl)phosphonic acid (6, 15.3 mg, 0.034 mmol, 1 eq.). The resulting mixture was stirred for 1 h at room temperature then purified by Prep-HPLC to afford ((S)-(2-(((3S,6S,9S,10aR)-9-(ethyl((1s,3R)-3-fluorocyclobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)phosphonic acid (Compound A34, 13 mg) as a white solid. LCMS (ESI): m/z=769 $[M+H]^+$. $^1H$ NMR (400 MHz, $CD_3OD$-$d_4$) δ (ppm) 8.09-8.02 (m, 2H), 7.87 (d, J=8.4 Hz, 1H), 7.62 (d, J=8.5 Hz, 1H), 7.38-7.25 (m, 4H), 7.23-7.16 (m, 1H), 5.76-5.52 (m, 1H), 4.77-4.37 (m, 4H), 4.09-3.85 (m, 2H), 3.79-3.64 (m, 1H), 3.62-3.49 (m, 1H), 3.08-1.54 (m, 21H), 1.33-1.20 (m, 3H), 0.52 (s, 2H). $^{31}P$ NMR (162 MHz, $CD_3OD$-$d_4$) δ (ppm) 9.79 (d, J=75.4 Hz). $^{19}F$ NMR (376 MHz, $CD_3OD$-$d_4$) δ (ppm) −169.78-−170.16 (m), −196.02 (d, J=75.9 Hz).

Step E: propyl (((S)-(2-(((3S,6S,9S,10aR)-9-(ethyl((1s,3R)-3-fluorocyclobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)(phenoxy)phosphoryl)-L-alaninate

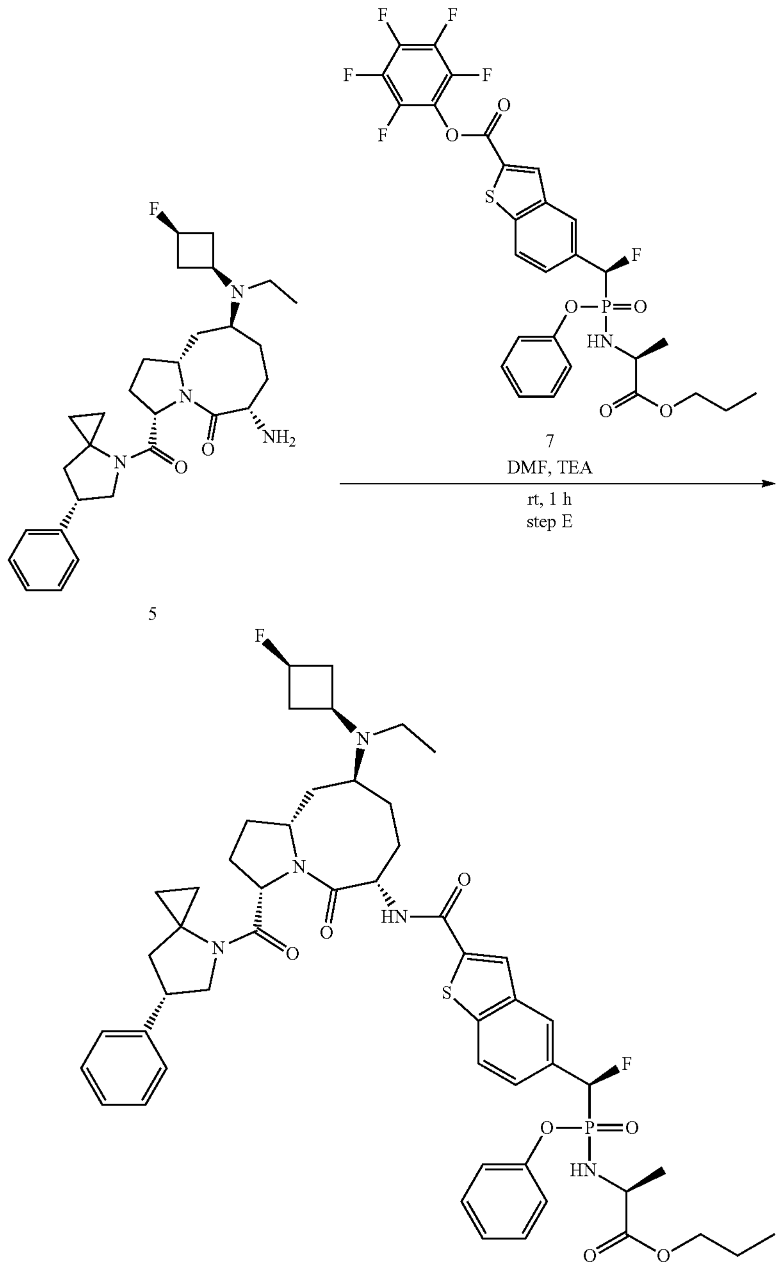

To a solution of (3S,6S,9S,10aR)-6-amino-9-(ethyl((1s,3R)-3-fluorocyclobutyl)amino)-3-((S)-6-phenyl-4-azaspiro[2.4]heptane-4-carbonyl)octahydropyrrolo[1,2-a]azocin-5(1H)-one (5, 20 mg, TFA salt) in DMF (2 mL) was added TEA (6.8 mg, 0.067 mmol, 2 eq.), perfluorophenyl 5-((1S)-fluoro((((S)-1-oxo-1-propoxypropan-2-yl)amino)(phenoxy)phosphoryl)methyl)benzo[b]thiophene-2-carboxylate (7, 21.6 mg, 0.034 mmol, 1 eq.). The resulting mixture was stirred for 1 h at room temperature then crude product was purified by Prep-HPLC to afford propyl (((S)-(2-(((3S,6S,9S,10aR)-9-(ethyl((1s,3R)-3-fluorocyclobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)(phenoxy)phosphoryl)-L-alaninate. (Compound C56, 15 mg) as a white solid. LCMS (ESI): m/z=958 $[M+H]^+$. $^1$H NMR (400 MHz, DMSO-$d_6$) δ (ppm) 8.84-8.73 (m, 1H), 8.31-8.23 (m, 1H), 8.11-8.01 (m, 2H), 7.64-7.56 (m, 1H), 7.41-7.28 (m, 6H), 7.23-7.11 (m, 4H), 6.29-6.08 (m, 2H), 4.88-4.66 (m, 2H), 4.47 (t, J=8.5 Hz, 1H), 4.33-4.23 (m, 1H), 4.17-4.09 (m, 1H), 3.94-3.69 (m, 4H), 3.60-3.48 (m, 1H), 3.09-2.98 (m, 1H), 2.74-2.66 (m, 1H), 2.61-2.53 (m, 1H), 2.45-2.38 (m, 1H), 2.37-1.89 (m, 10H), 1.88-1.37 (m, 11H), 1.18-1.16 (m, 1H), 1.00-0.93 (m, 4H), 0.83-0.78 (m, 3H), 0.55-0.41 (m, 2H). $^{19}$F NMR (377 MHz, DMSO-$d_6$) −165.89 (s), −194.18 (d, J=82.6 Hz), −196.07 (d, J=86.6 Hz). $^{31}$P NMR (162 MHz, DMSO-d6) δ (ppm) 17.32 (d, J=86.6 Hz), 16.94 (d, J=82.5 Hz).

Synthesis of ((R)-fluoro(2-(((3S,6S,9S,10aR)-9-(methyl((3-methyloxetan-3-yl)methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)phosphonic acid (Compound A56) and cyclobutyl ((R)-((R)-fluoro(2-(((3S,6S,9S,10aR)-9-(methyl((3-methyloxetan-3-yl)methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate (Compound C172)

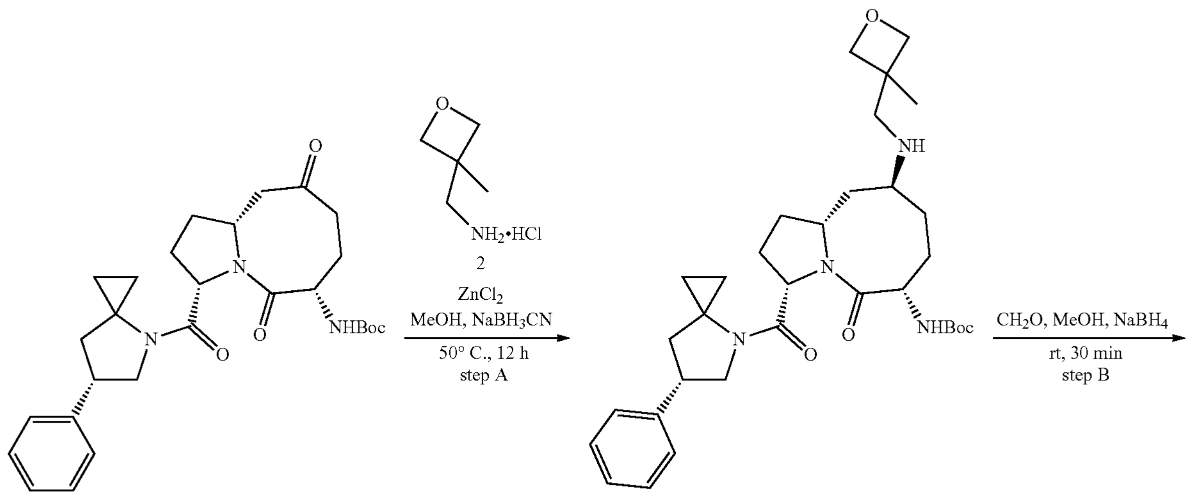

1

3

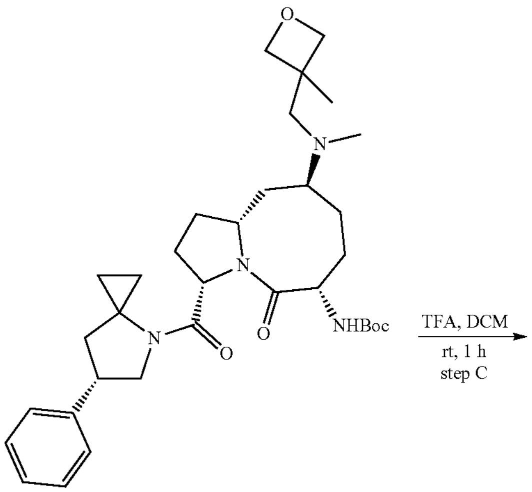

4

-continued
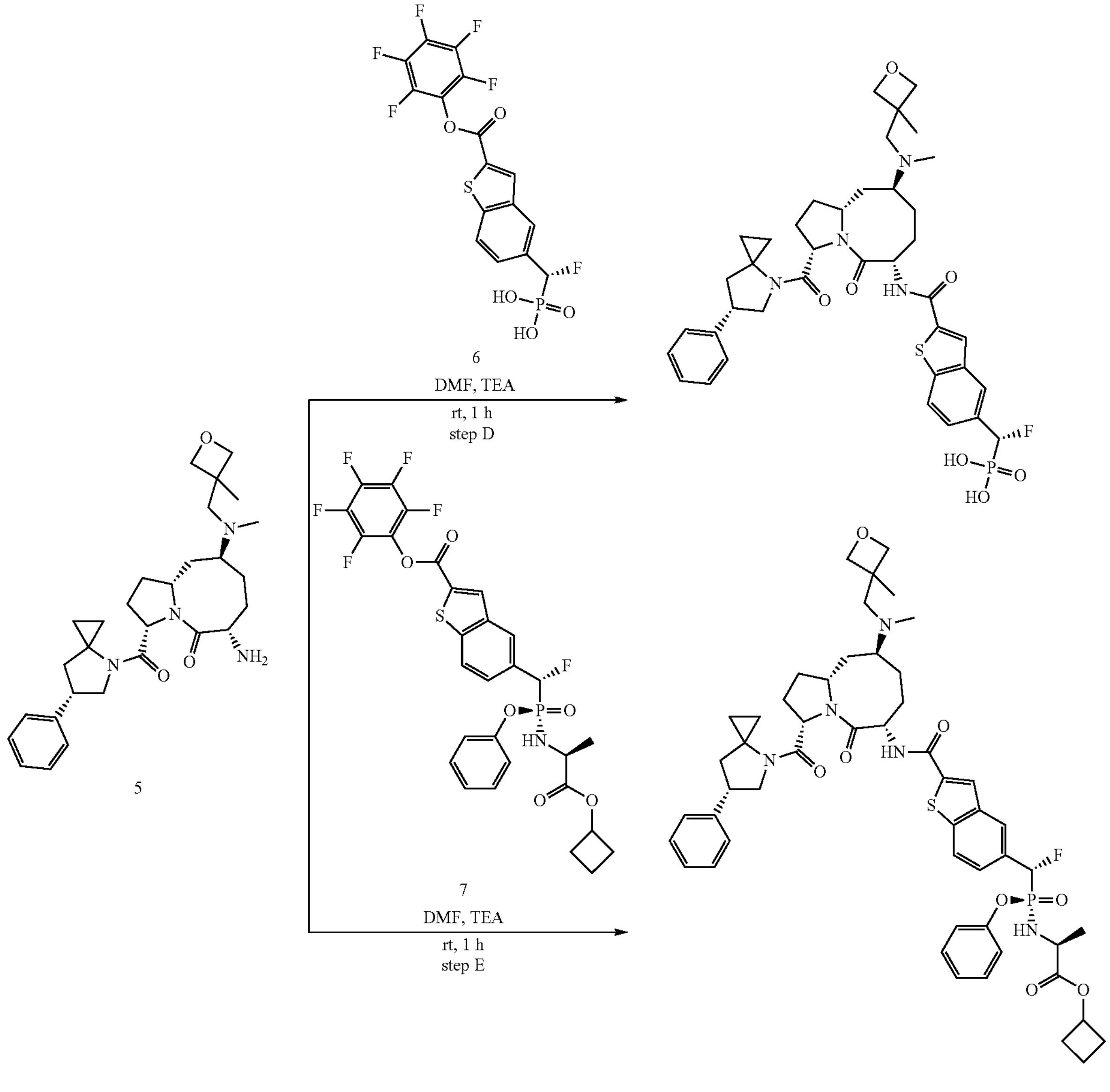

Step A: tert-butyl ((3S,6S,9S,10aR)-9-(((3-methyloxetan-3-yl)methyl)amino)-5-oxo-3-((S)-6-phenyl-4-azaspiro[2.4]heptane-4-carbonyl)decahydropyrrolo[1,2-a]azocin-6-yl)carbamate

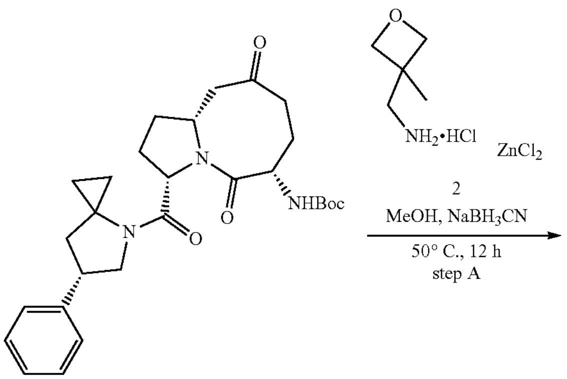

1

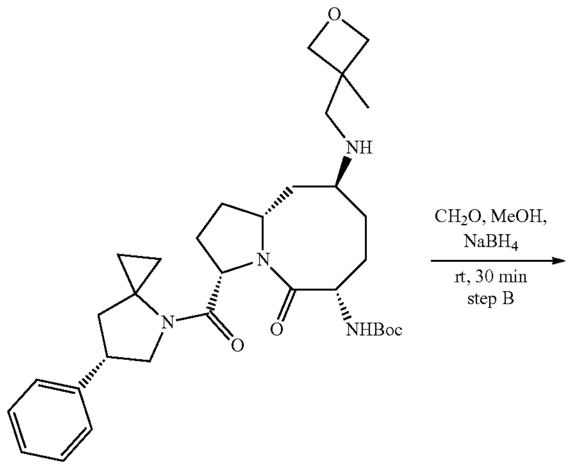

3

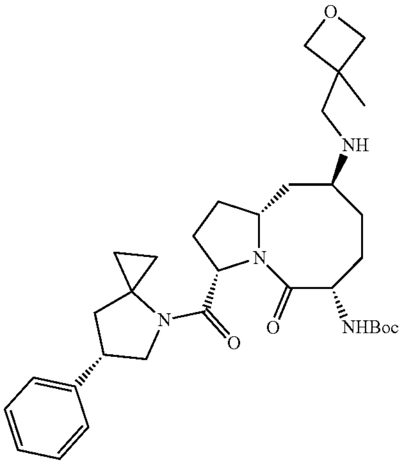

3

To a solution of tert-butyl ((3S,6S,10aR)-5,9-dioxo-3-((S)-6-phenyl-4-azaspiro[2.4]heptane-4-carbonyl)decahydropyrrolo[1,2-a]azocin-6-yl)carbamate (1, 1 g, 2.02 mmol, 1 eq.) in MeOH (20 mL) was added (3-methyloxetan-3-yl) methanamine hydrochloride (2, 417 mg, 3.03 mmol, 1.5 eq.), $ZnCl_2$ (2.77 g, 20.2 mmol, 10 eq.), the resulting mixture was stirred for 2 hr. at 50° C. under the atmosphere of $N_2$. Then $NaBH_3CN$ (1.27 g, 20.2 mmol, 10 eq.) was added portion wise every 30 mins (2 eq. (254 mg each time) added 5 times). The mixture was stirred for 12 hr. at 50° C., LCMS show that the reaction was completed, then cooled to room temperature, The solution was used to next step without further workup. LCMS (ESI): m/z=581 [M+H]$^+$.

Step B: tert-butyl ((3S,6S,9S,10aR)-9-(methyl((3-methyloxetan-3-yl)methyl)amino)-5-oxo-3-((S)-6-phenyl-4-azaspiro[2.4]heptane-4-carbonyl)decahydropyrrolo[1,2-a]azocin-6-yl)carbamate

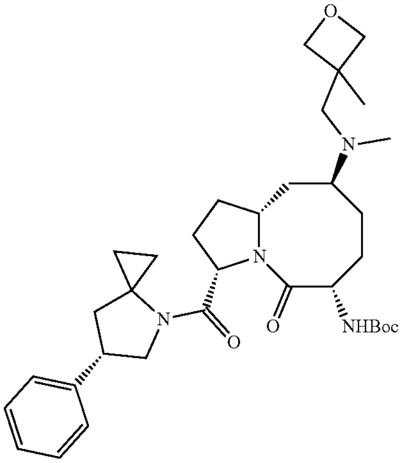

4

To the above mixture (step A) was added 40% Formaldehyde (3 mL) at room temperature, the mixture was stirred for 30 min, then $NaBH_4$ (383 mg, 10.1 mmol, 5 eq.) was added in portions, the mixture was stirred for another 30 min, LCMS show that the reaction was completed. The reaction was quenched by $NH_4Cl$ (sat. aq), diluted with $H_2O$ (100 mL) and extracted with EtOAc (50 mL×3), the organic solution was dried over $Na_2SO_4$, then concentrated under vacuum, the crude product was purified by C18 column ($MeCN:H_2O$ (0.1% ammonium hydroxide)=5%-70%) to afford tert-butyl ((3S,6S,9S,10aR)-9-(methyl((3-methyloxetan-3-yl)methyl)amino)-5-oxo-3-((S)-6-phenyl-4-azaspiro[2.4]heptane-4-carbonyl)decahydropyrrolo[1,2-a]azocin-6-yl)carbamate (4, 3 g, 5.04 mmol, 83% yield two steps) as a white solid. LCMS (ESI): m/z=595 [M+H]$^+$.

Step C: (3S,6S,9S,10aR)-6-amino-9-(methyl((3-methyloxetan-3-yl)methyl)amino)-3-((S)-6-phenyl-4-azaspiro[2.4]heptane-4-carbonyl)octahydropyrrolo[1,2-a]azocin-5(1H)-one

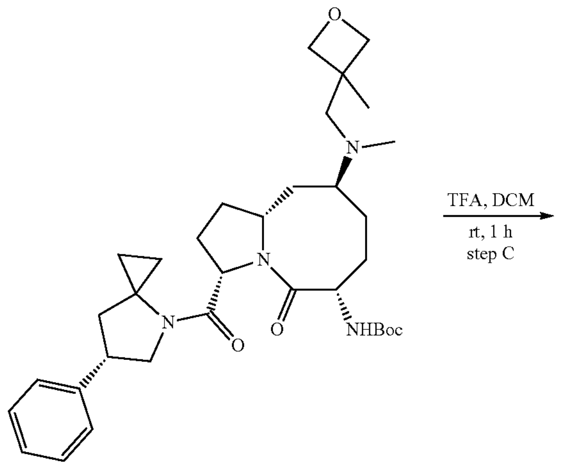

4

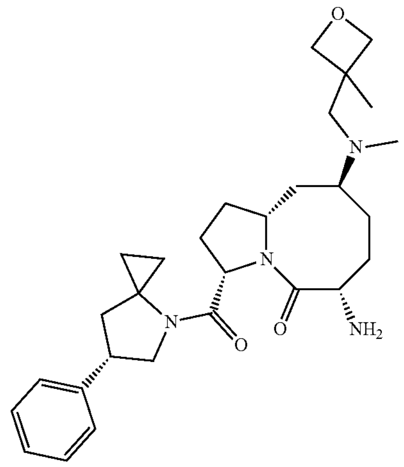

5

To a solution of tert-butyl ((3S,6S,9S,10aR)-9-(methyl((3-methyloxetan-3-yl)methyl)amino)-5-oxo-3-((S)-6-phenyl-4-azaspiro[2.4]heptane-4-carbonyl)decahydropyrrolo[1,2-a]azocin-6-yl)carbamate (4, 20 mg, 0.034 mmol) in DCM (2 mL) was added TFA (2 mL). The resulting mixture was stirred for 1 h at room temperature, then concentrated to dryness under reduced pressure to afford crude product (3S,6S,9S,10aR)-6-amino-9-(methyl((3-methyloxetan-3-yl)methyl)amino)-3-((S)-6-phenyl-4-azaspiro[2.4]heptane-4-carbonyl)octahydropyrrolo[1,2-a]azocin-5(1H)-one (5, 20 mg, TFA salt) as a yellow oil which was used to the next step without further purification. LCMS (ESI): m/z=495 $[M+H]^+$.

Step D: ((R)-fluoro(2-(((3S,6S,9S,10aR)-9-(methyl((3-methyloxetan-3-yl)methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)phosphonic acid

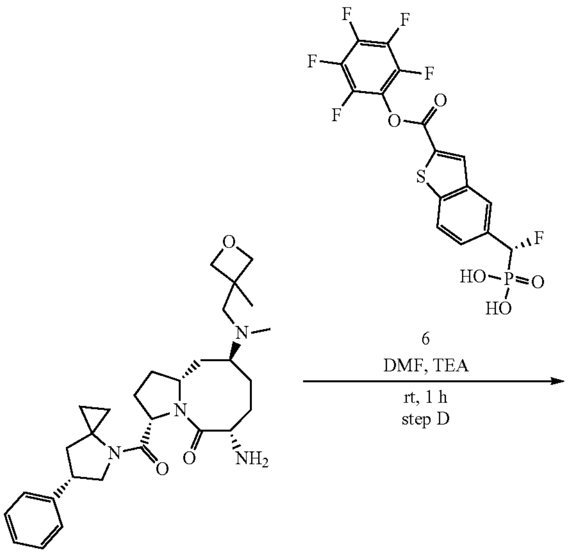

6

5

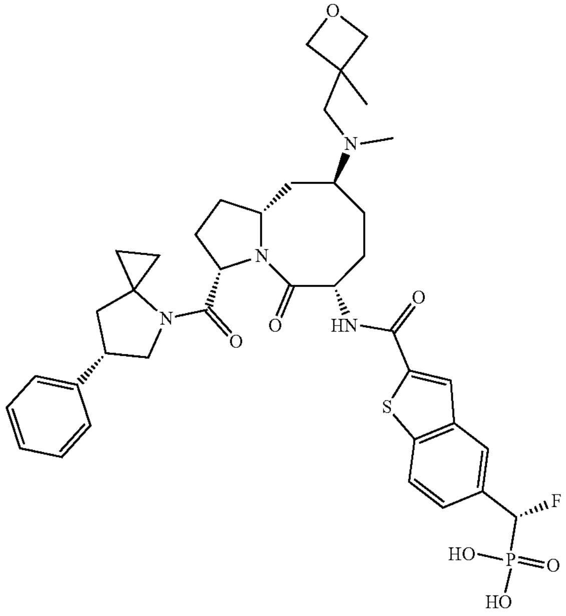

To a solution of (3S,6S,9S,10aR)-6-amino-9-(methyl((3-methyloxetan-3-yl)methyl)amino)-3-((S)-6-phenyl-4-azaspiro[2.4]heptane-4-carbonyl)octahydropyrrolo[1,2-a]azocin-5(1H)-one (5, 20 mg, TFA salt) in DMF (2 mL) was added TEA (6.8 mg, 0.067 mmol, 2 eq.), (R)-(fluoro(2-((perfluorophenoxy)carbonyl)benzo[b]thiophen-5-yl)methyl)phosphonic acid (6, 15.3 mg, 0.034 mmol, 1 eq.). The resulting mixture was stirred for 1 h at room temperature then was purified by Prep-HPLC to afford ((R)-fluoro(2-(((3S,6S,9S,10aR)-9-(methyl((3-methyloxetan-3-yl)methyl)amino)-5-oxo-3-((S)-6-phenyl-4-azaspiro[2.4]heptane-4-carbonyl)decahydropyrrolo[1,2-a]azocin-6-yl)

carbamoyl)benzo[b]thiophen-5-yl)methyl)phosphonic acid (Compound A56, 20 mg) as a white solid. LCMS (ESI): m/z=767 $[M+H]^+$. $^1H$ NMR (400 MHz, $CD_3OD-d_4$) δ (ppm) 8.09-7.99 (m, 2H), 7.88 (d, J=8.5 Hz, 1H), 7.65 (d, J=8.5 Hz, 1H), 7.36-7.26 (m, 4H), 7.23-7.18 (m, 1H), 5.64 (dd, J=45.3, 8.3 Hz, 1H), 4.75-4.67 (m, 1H), 4.63-4.54 (m, 3H), 4.44-4.30 (m, 3H), 4.06-3.87 (m, 2H), 3.61-3.46 (m, 2H), 3.26-3.07 (m, 2H), 2.55 (s, 3H), 2.48-2.39 (m, 1H), 2.30 (t, J=11.4 Hz, 1H), 2.22-1.92 (m, 7H), 1.92-1.75 (m, 4H), 1.66-1.59 (m, 1H), 1.52 (s, 3H), 0.57-0.44 (m, 2H). $^{19}F$ NMR (377 MHz, $CD_3OD-d_4$) δ (ppm) −195.52-−195.88 (m). $^{31}P$ NMR (162 MHz, $CD_3OD-d_4$) δ (ppm) 9.71 (d, J=76.3 Hz).

Step E: cyclobutyl ((R)-((R)-fluoro(2-(((3S,6S,9S,10aR)-9-(methyl((3-methyloxetan-3-yl)methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate

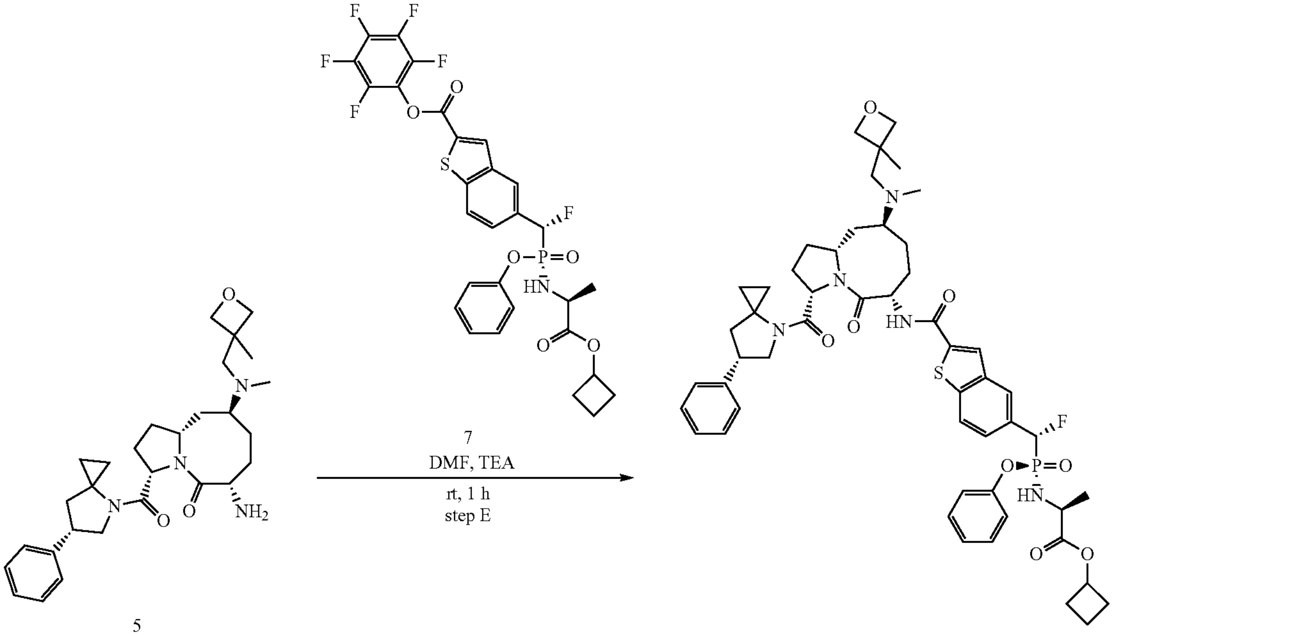 [SMILES: CN(CC1(C)COC1)[C@H]1CC[C@H](N)C(=O)N2[C@H](CC[C@H]2C(=O)N2C[C@H](c3ccccc3)CC23CC3)C1 ; C[C@H](N[P@](=O)(Oc1ccccc1)[C@@H](F)c1ccc2sc(C(=O)Oc3c(F)c(F)c(F)c(F)c3F)cc2c1)C(=O)OC1CCC1 ; C[C@H](N[P@](=O)(Oc1ccccc1)[C@@H](F)c1ccc2sc(C(=O)N[C@H]3CC[C@H](N(C)CC4(C)COC4)C[C@H]4CC[C@@H](C(=O)N5C[C@H](c6ccccc6)CC56CC6)N4C3=O)cc2c1)C(=O)OC1CCC1]

5

To a solution of (3S,6S,9S,10aR)-6-amino-9-(methyl((3-methyloxetan-3-yl)methyl)amino)-3-((S)-6-phenyl-4-azaspiro[2.4]heptane-4-carbonyl)octahydropyrrolo[1,2-a]azocin-5(1H)-one (5, 30 mg, TFA salt) in DMF (2 mL) was added TEA (10.2 mg, 0.1 mmol, 2 eq.), perfluorophenyl 5-((R)-((R)—(((S)-1-cyclobutoxy-1-oxopropan-2-yl)amino)(phenoxy)phosphoryl)fluoromethyl)benzo[b]thiophene-2-carboxylate (7, 33.15 mg, 0.051 mmol, 1 eq.). The resulting mixture was stirred for 1 h at room temperature then purified by Prep-HPLC to afford cyclobutyl ((R)-((R)-fluoro(2-(((3S,6S,9S,10aR)-9-(methyl((3-methyloxetan-3-yl)methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate (Compound C172, 15 mg) as a white solid. LCMS (ESI): m/z=968 $[M+H]^+$. $^1H$ NMR (400 MHz, DMSO-$d_6$) δ (ppm) 8.77 (d, J=7.7 Hz, 1H), 8.27 (s, 1H), 8.10-7.99 (m, 2H), 7.61 (d, J=8.6 Hz, 1H), 7.40-7.27 (m, 6H), 7.23-7.12 (m, 4H), 6.27-6.04 (m, 2H), 4.81-4.65 (m, 2H), 4.52-4.43 (m, 1H), 4.40 (d, J=5.4 Hz, 1H), 4.36 (d, J=5.4 Hz, 1H), 4.32-4.24 (m, 1H), 4.19 (d, J=5.4 Hz, 1H), 4.14-4.05 (m, 2H), 3.84-3.67 (m, 2H), 3.59-3.48 (m, 1H), 2.88-2.78 (m, 1H), 2.58-2.52 (m, 1H), 2.39-2.31 (m, 1H), 2.22-1.50 (m, 23H), 1.28 (s, 3H), 1.11 (d, J=7.0 Hz, 3H), 0.54-0.38 (m, 2H). $^{19}F$ NMR (376 MHz, DMSO-$d_6$) δ (ppm) −194.33 (d, J=82.8 Hz). $^{31}P$ NMR (162 MHz, DMSO-$d_6$) δ (ppm) 17.28 (d, J=82.9 Hz).

Synthesis of ((S)-fluoro(2-(((3S,6S,9S,10aR)-9-(methyl((1s,3R)-3-(trifluoromethyl)cyclobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)phosphonic acid (Compound A65) and propyl ((S)-((S)-fluoro(2-(((3S,6S,9S,10aR)-9-(methyl((1s,3R)-3-(trifluoromethyl)cyclobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate (Compound C210)

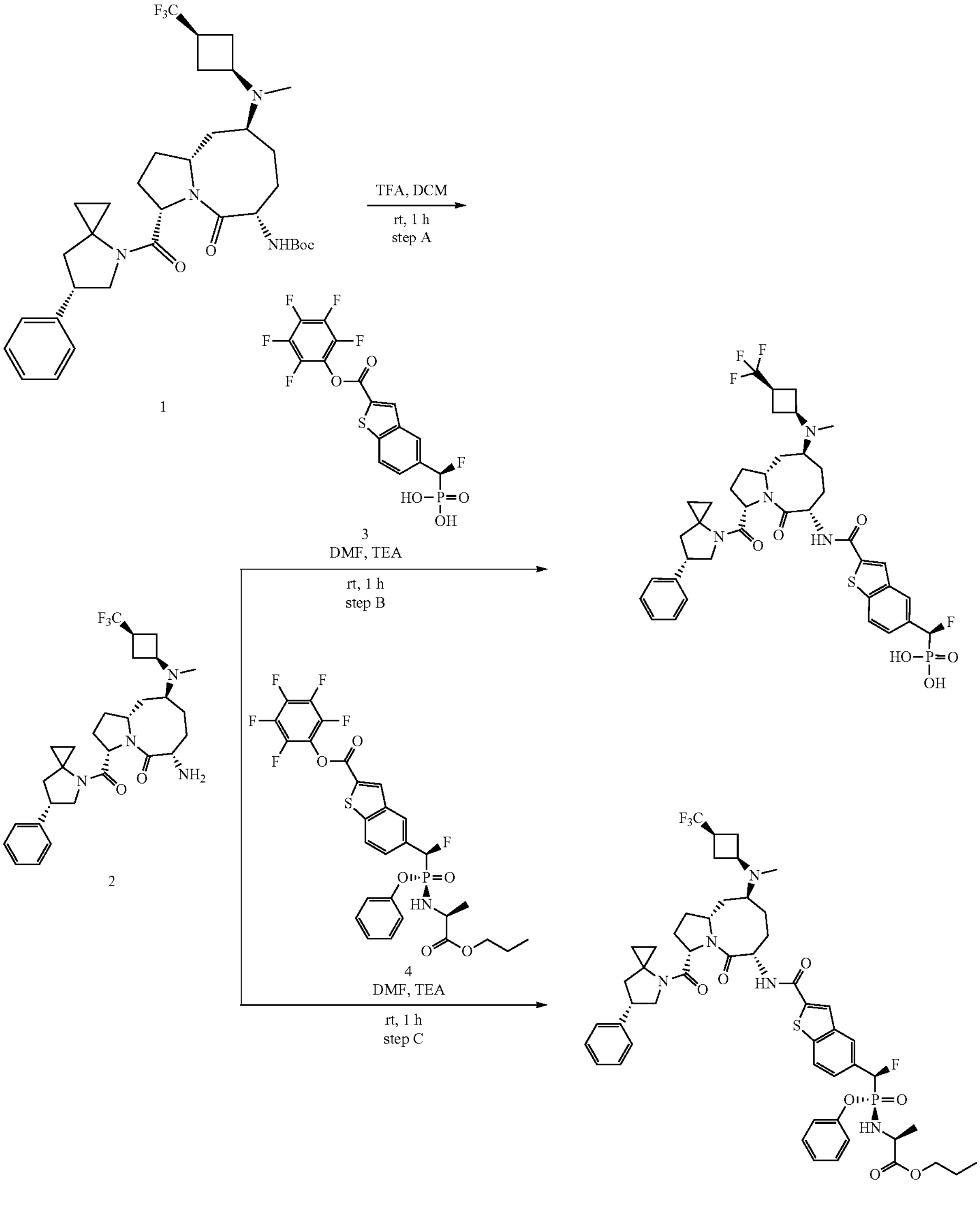

Step A: (3S,6S,9S,10aR)-6-amino-9-(methyl((1s,3R)-3-(trifluoromethyl)cyclobutyl)amino)-3-((S)-6-phenyl-4-azaspiro[2.4]heptane-4-carbonyl)octahydropyrrolo[1,2-a]azocin-5(1H)-one

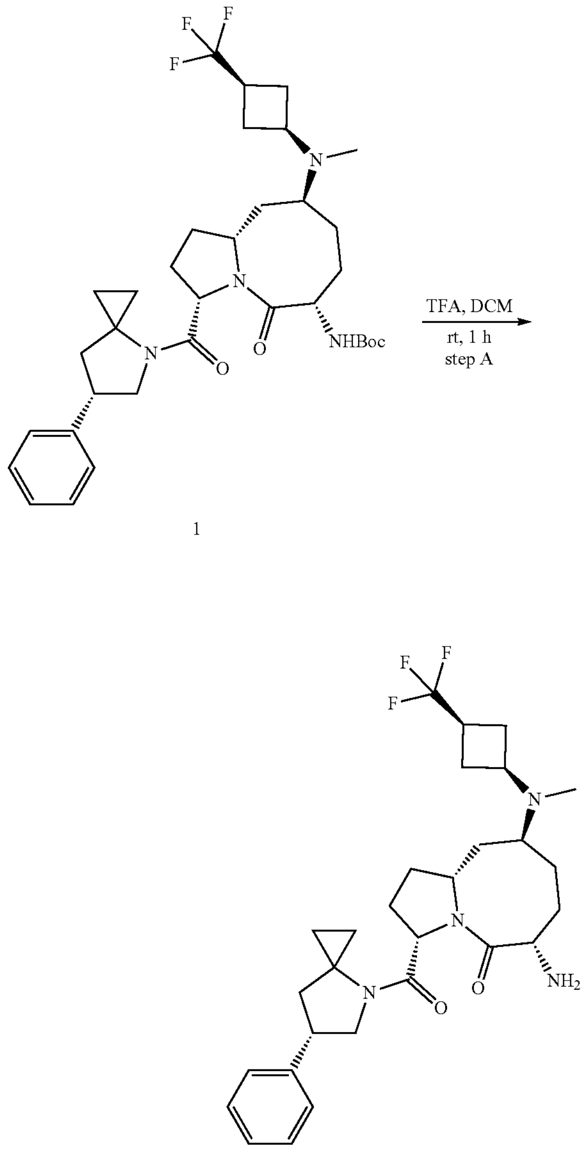

1

2

To a solution of tert-butyl ((3S,6S,9S,10aR)-9-(methyl((1s,3R)-3-(trifluoromethyl)cyclobutyl)amino)-5-oxo-3-((S)-6-phenyl-4-azaspiro[2.4]heptane-4-carbonyl)decahydropyrrolo[1,2-a]azocin-6-yl)carbamate (1, 30 mg, 0.047 mmol) in DCM (2 mL) was added TFA (2 mL). The resulting mixture was stirred for 1 h at room temperature and the resulting mixture was concentrated to dryness under reduced pressure to afford crude product (3S,6S,9S,10aR)-6-amino-9-(methyl((1s,3R)-3-(trifluoromethyl)cyclobutyl)amino)-3-((S)-6-phenyl-4-azaspiro[2.4]heptane-4-carbonyl)octahydropyrrolo[1,2-a]azocin-5(1H)-one (2, 30 mg, TFA salt) as a yellow oil which was used to the next step without further purification. LCMS (ESI): m/z=533 $[M+H]^+$.

Step B: ((S)-fluoro(2-(((3S,6S,9S,10aR)-9-(methyl((1s,3R)-3-(trifluoromethyl)cyclobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)phosphonic acid

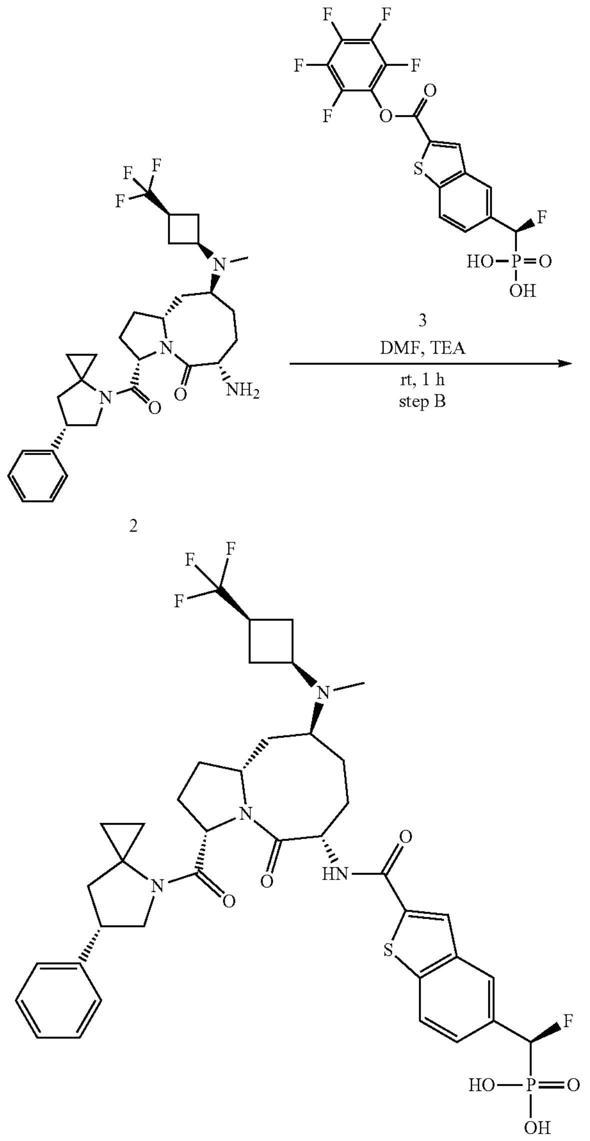

2

3

To a solution of (3S,6S,9S,10aR)-6-amino-9-(methyl((1s,3R)-3-(trifluoromethyl)cyclobutyl)amino)-3-((S)-6-phenyl-4-azaspiro[2.4]heptane-4-carbonyl)octahydropyrrolo[1,2-a]azocin-5(1H)-one (2, 30 mg, TFA salt) in DMF (2 mL) was added TEA (9.6 mg, 0.095 mmol, 2 eq.), (S)-(fluoro(2-((perfluorophenoxy)carbonyl)benzo[b]thiophen-5-yl)methyl)phosphonic acid (3, 21.6 mg, 0.047 mmol, 1 eq.). The resulting mixture was stirred for 1 h at room temperature then purified by Prep-HPLC to afford ((S)-fluoro(2-(((3S,6S,9S,10aR)-9-(methyl((1s,3R)-3-(trifluoromethyl)cyclobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)phosphonic acid (Compound A65, 23 mg) as a white solid. LCMS (ESI):

m/z=805 $[M+H]^+$. 1H NMR (400 MHz, $CD_3OD-d_4$) δ (ppm) 8.08 (d, J=8.7 Hz, 2H), 7.89 (d, J=8.4 Hz, 1H), 7.61 (d, J=8.4 Hz, 1H), 7.36-7.15 (m, 5H), 5.79-5.50 (m, 1H), 4.71-4.50 (m, 2H), 4.48-4.31 (m, 1H), 4.10-3.65 (m, 4H), 3.57-3.46 (m, 1H), 2.99-2.50 (m, 6H), 2.45-1.55 (m, 16H), 0.60-0.35 (m, 2H). $^{19}F$ NMR (376 MHz, $CD_3OD-d_4$) δ (ppm) −74.43 (s), −196.02 (d, J=76.0 Hz). $^{31}P$ NMR (162 MHz, $CD_3OD-d_4$) δ (ppm) 9.65 (d, J=76.0 Hz).

Step C: propyl ((S)-((S)-fluoro(2-(((3S,6S,9S,10aR)-9-(methyl((1s,3R)-3-(trifluoromethyl)cyclobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate To a solution of (3S,6S,9S,10aR)-6-amino-9-(methyl((1s,3R)-3-(trifluoromethyl)cyclobutyl)amino)-3-((S)-6-phenyl-4-azaspiro[2.4]heptane-4-carbonyl)octahydropyrrolo[1,2-a]azocin-5(1H)-one (2, 30 mg, TFA salt) in DMF (2 mL) was added TEA (9.6 mg, 0.095 mmol, 2 eq.), (perfluorophenyl 5-((S)-fluoro((S)-(((S)-1-oxo-1-propoxypropan-2-yl)amino)(phenoxy)phosphoryl)methyl)benzo[b]thiophene-2-carboxylate (4, 30.6 mg, 0.047 mmol, 1 eq.). The resulting mixture was stirred for 1 h at room temperature, then the crude product was purified by Prep-HPLC to afford propyl ((S)-((S)-fluoro(2-(((3S,6S,9S,10aR)-9-(methyl((1s,3R)-3-(trifluoromethyl)cyclobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)

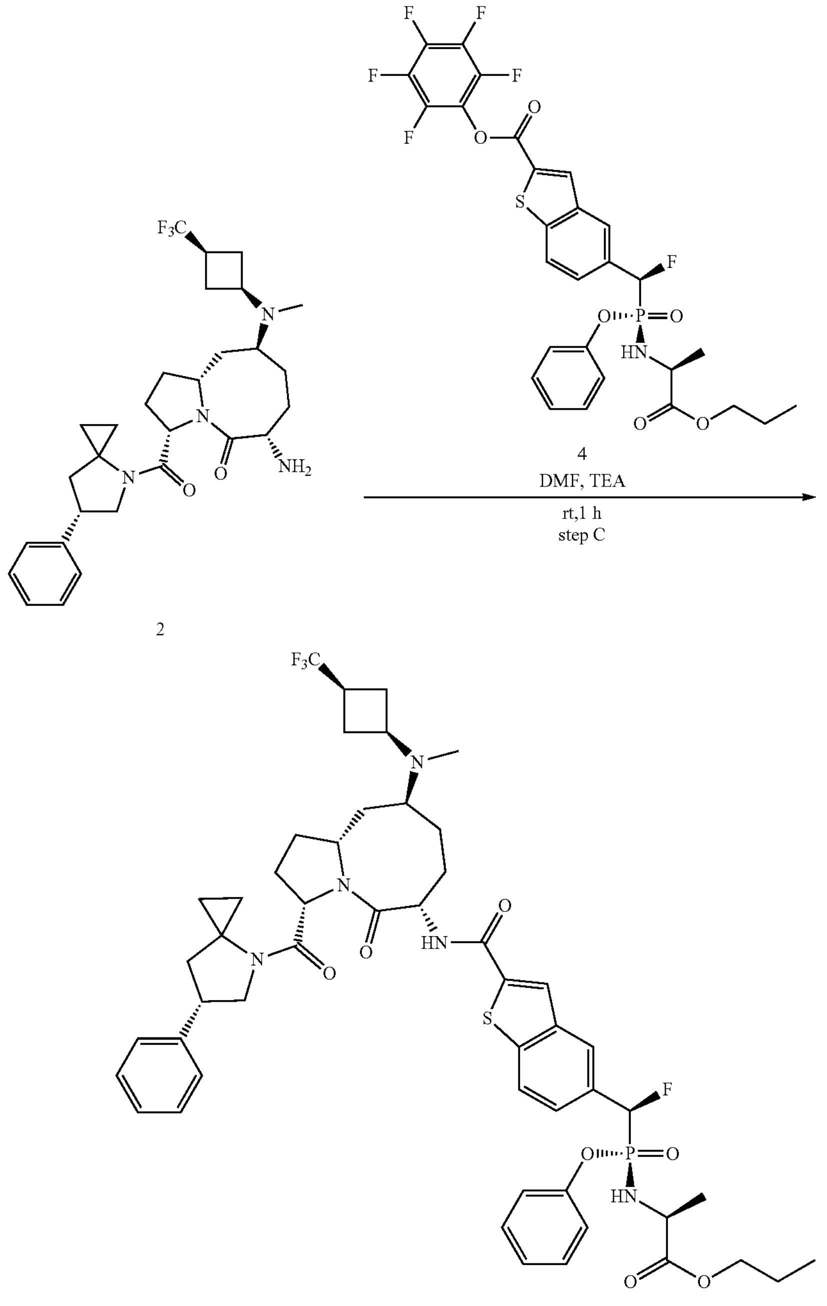

(phenoxy)phosphoryl)-L-alaninate (Compound C210, 13 mg) as a white solid. LCMS (ESI): m/z=994 $[M+H]^+$. 1H NMR (400 MHz, DMSO-$d_6$) δ (ppm) 8.77 (d, J=7.6 Hz, 1H), 8.28 (s, 1H), 8.13-7.99 (m, 2H), 7.61 (d, J=8.5 Hz, 1H), 7.39-7.26 (m, 6H), 7.24-7.13 (m, 4H), 6.24-6.06 (m, 2H), 4.78-4.64 (m, 1H), 4.48 (t, J=8.6 Hz, 1H), 4.36-4.23 (m, 1H), 4.11 (t, J=8.6 Hz, 1H), 3.96-3.85 (m, 2H), 3.77-3.63 (m, 2H), 3.59-3.46 (m, 1H), 3.07-2.90 (m, 2H), 2.84-2.69 (m, 1H), 2.38-2.17 (m, 3H), 2.14-2.03 (m, 3H), 2.02-1.90 (m, 6H), 1.86-1.44 (m, 11H), 0.94 (d, J=7.1 Hz, 3H), 0.81 (t, J=7.4 Hz, 3H), 0.54-0.37 (m, 2H). $^{19}F$ NMR (376 MHz, DMSO-$d_6$) δ (ppm) −71.26 (s), −194.18 (d, J=82.9 Hz). $^{31}P$ NMR (162 MHz, DMSO-$d_6$) δ (ppm) 16.94 (d, J=82.8 Hz).

Synthesis of ((R)-(2-(((3S,6S,9S,10aR)-9-(((1s,3R)-3-cyanocyclobutyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)phosphonic acid (Compound A37)

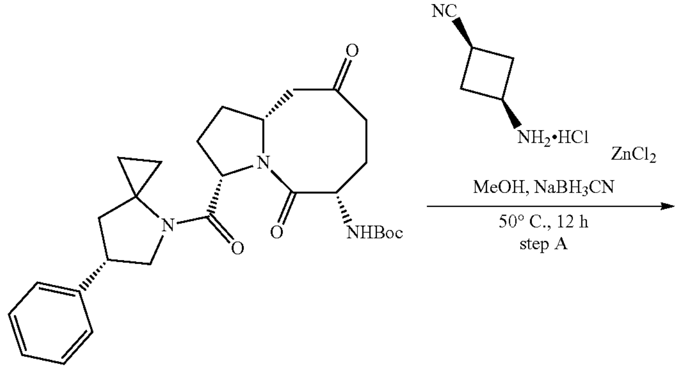

1

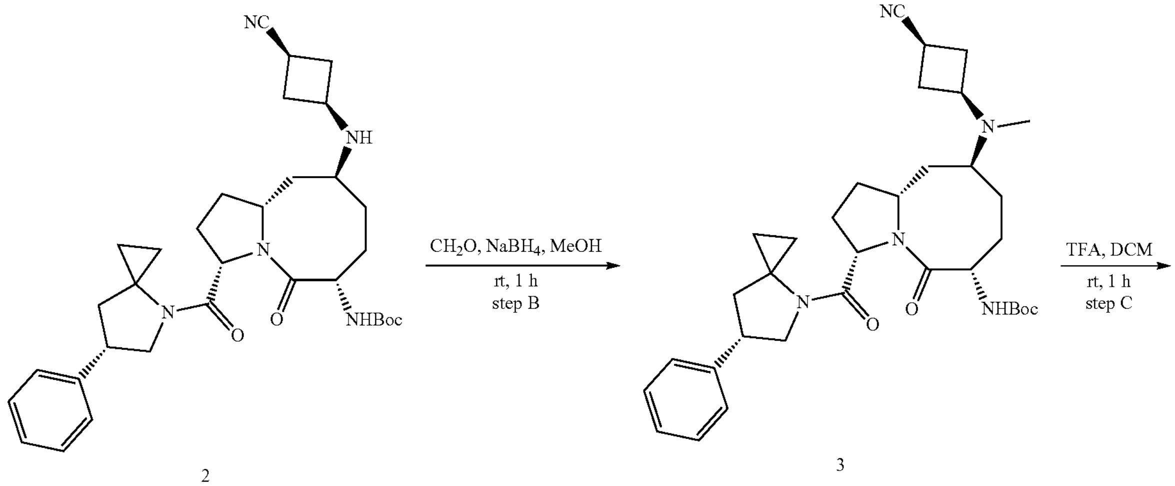

2

3

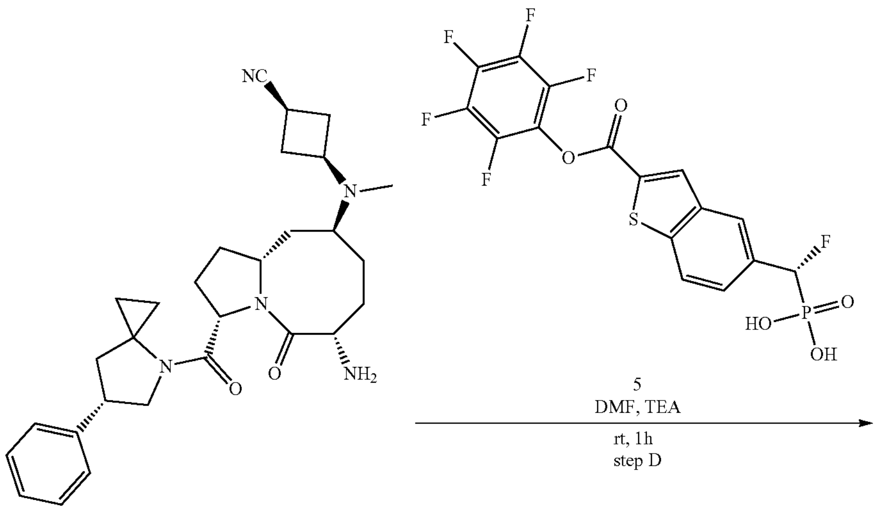

4

-continued

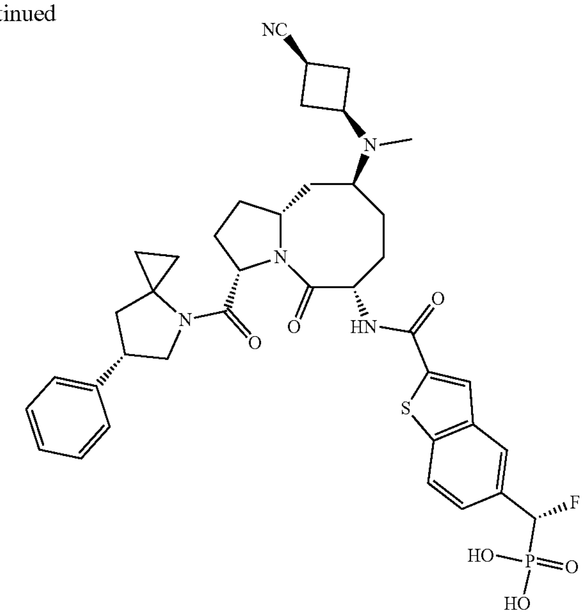

Step A: tert-butyl ((3S,6S,9S,10aR)-9-(((1s,3R)-3-cyanocyclobutyl)amino)-5-oxo-3-((S)-6-phenyl-4-azaspiro[2.4]heptane-4-carbonyl)decahydropyrrolo[1,2-a]azocin-6-yl)carbamate

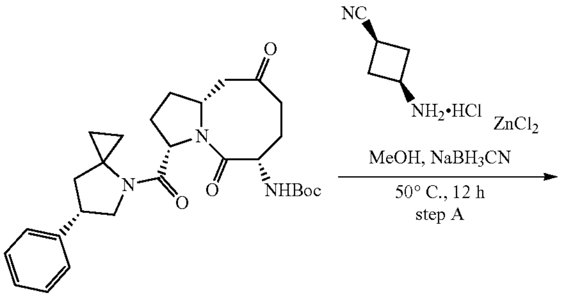

1

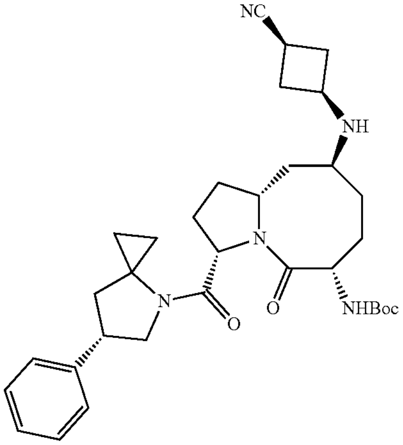

2

To a solution of tert-butyl ((3S,6S,10aR)-5,9-dioxo-3-((S)-6-phenyl-4-azaspiro[2.4]heptane-4-carbonyl)decahydropyrrolo[1,2-a]azocin-6-yl)carbamate (1, 1 g, 2.02 mmol, 1 eq.) in MeOH (20 mL) was added (1s,3s)-3-aminocyclobutane-1-carbonitrile hydrochloride (400 mg, 3.03 mml, 1.5 eq.), $ZnCl_2$ (2.75 g, 20.2 mmol, 10 eq.). The resulting mixture was stirred for 1 h at 50° C., then $NaBH_3CN$ (1.27 g, 20.2 mmol, 10 eq.) was added portion wise every 30 mins (2 eq. (254 mg each time) added 5 times). The mixture was stirred for 12 h at 50° C., then cooled to room temperature, and used to the next step directly without further workup. LCMS (ESI): m/z=576 $[M+H]^+$.

Step B: tert-butyl ((3S,6S,9S,10aR)-9-(((1s,3R)-3-cyanocyclobutyl)(methyl)amino)-5-oxo-3-((S)-6-phenyl-4-azaspiro[2.4]heptane-4-carbonyl)decahydropyrrolo[1,2-a]azocin-6-yl)carbamate

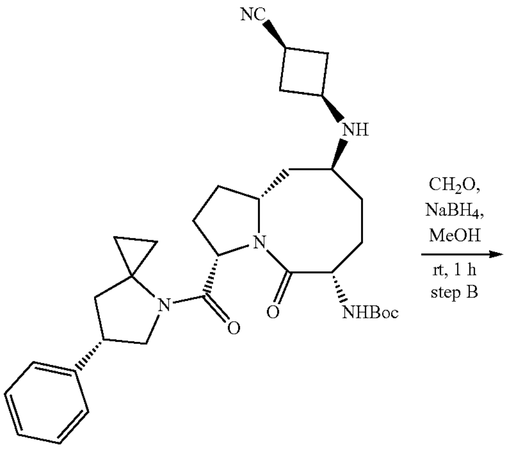

2

-continued

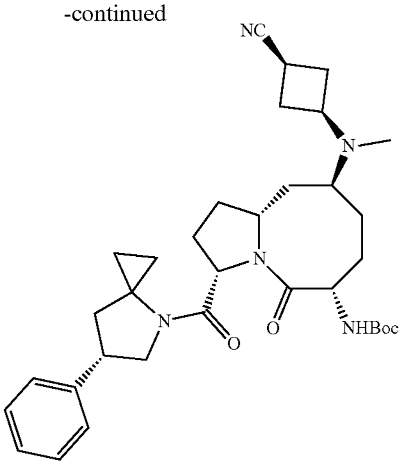

3

-continued

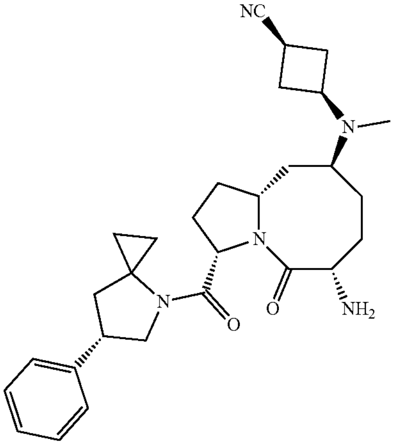

4

To the above mixture (step A) was added 40% formaldehyde (1 mL) at room temperature, the mixture was stirred for 10 min, then $NaBH_4$ (764 mg, 20.2 mmol, 10 eq.) was added to the mixture, stirred for another 1 hr. The reaction was quenched by $NH_4Cl$ (sat. aq), diluted with $H_2O$ (100 mL), then extracted with EtOAc (50 mL×3), the organic solution was dried over $Na_2SO_4$, then concentrated under reduced pressure, the crude product was purified by C18 column (MeCN:$H_2O$ (0.1% ammonium hydroxide)=5%-70%) to afford tert-butyl ((3S,6S,9S,10aR)-9-(((1s,3R)-3-cyanocyclobutyl)(methyl)amino)-5-oxo-3-((S)-6-phenyl-4-azaspiro[2.4]heptane-4-carbonyl)decahydropyrrolo[1,2-a]azocin-6-yl)carbamate (3, 1.1 g, 1.87 mmol, 92% yield, two steps) as a white solid. LCMS (ESI): m/z=590 $[M+H]^+$.

Step C: (1R,3s)-3-(((3S,6S,9S,10aR)-6-amino-5-oxo-3-((S)-6-phenyl-4-azaspiro[2.4]heptane-4-carbonyl)decahydropyrrolo[1,2-a]azocin-9-yl)(methyl)amino)cyclobutane-1-carbonitrile

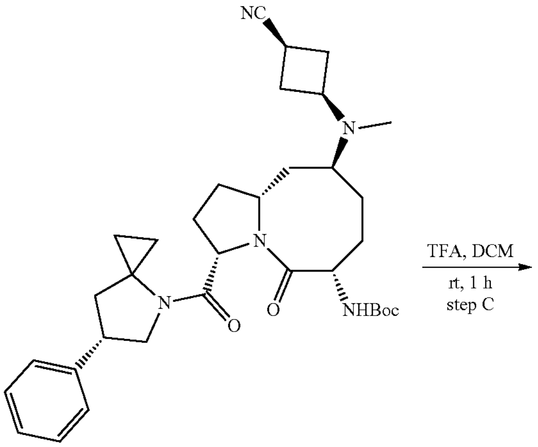

3

To a solution of tert-butyl ((3S,6S,9S,10aR)-9-(((1s,3R)-3-cyanocyclobutyl)(methyl)amino)-5-oxo-3-((S)-6-phenyl-4-azaspiro[2.4]heptane-4-carbonyl)decahydropyrrolo[1,2-a]azocin-6-yl)carbamate (3, 30 mg, 0.051 mmol) in DCM (2 mL) was added TFA (2 mL), The resulting mixture was stirred for 1 h at room temperature, and the resulting mixture was concentrated to dryness under reduced pressure to afford crude product (1R,3s)-3-(((3S,6S,9S,10aR)-6-amino-5-oxo-3-((S)-6-phenyl-4-azaspiro[2.4]heptane-4-carbonyl)decahydropyrrolo[1,2-a]azocin-9-yl)(methyl)amino)cyclobutane-1-carbonitrile (4, 30 mg, TFA salt) as a yellow oil which used in the next step without further purification. LCMS (ESI): m/z=490 $[M+H]^+$.

Step D: ((R)-(2-(((3S,6S,9S,10aR)-9-(((1s,3R)-3-cyanocyclobutyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)phosphonic acid

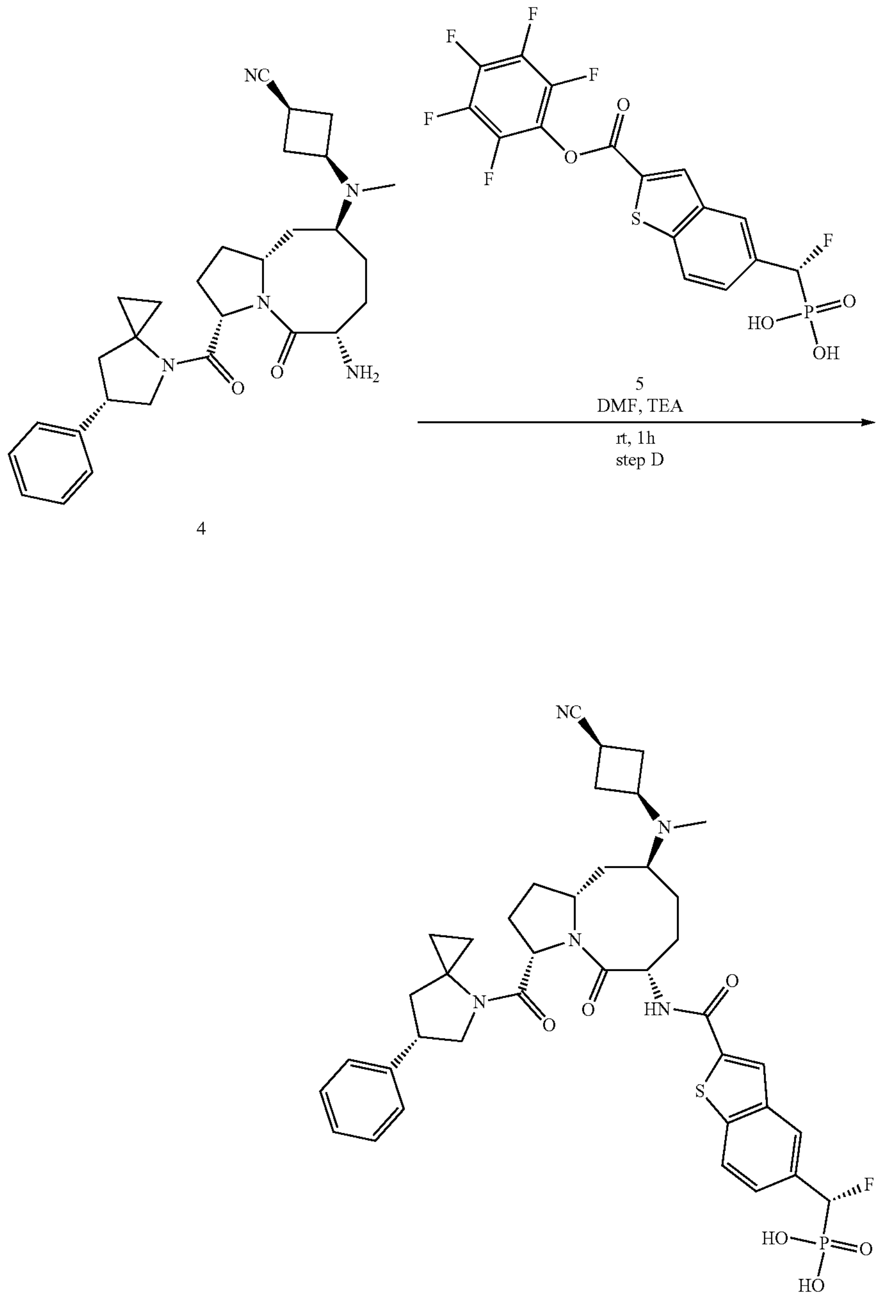

To a solution of (1R,3s)-3-(((3S,6S,9S,10aR)-6-amino-5-oxo-3-((S)-6-phenyl-4-azaspiro[2.4]heptane-4-carbonyl)decahydropyrrolo[1,2-a]azocin-9-yl)(methyl)amino)cyclobutane-1-carbonitrile (4, 30 mg, TFA salt) in DMF (2 mL) was added TEA (10.3 mg, 0.102 mmol, 2 eq.), (R)-(fluoro(2-((perfluorophenoxy)carbonyl)benzo[b]thiophen-5-yl)methyl)phosphonic acid (5, 23.2 mg, 0.051 mmol, 1 eq). The resulting mixture was stirred for 1 h at room temperature. The crude product was purified by Prep-HPLC to afford propyl ((R)-(2-(((3S,6S,9S,10aR)-9-(((1s,3R)-3-cyanocyclobutyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)phosphonic acid (Compound A37, 11 mg, 0.015 mmol) as a white solid. LCMS (ESI): m/z=762 $[M+H]^+$. 1H NMR (400 MHz, $CD_3OD-d_4$) δ (ppm) 8.15-8.08 (m, 1H), 8.07-8.01 (m, 1H), 8.00-7.92 (m, 1H), 7.66-7.54 (m, 1H), 7.42-7.15 (m, 5H), 6.06-5.68 (m, 1H), 4.91-4.80 (m, 1H), 4.73-4.63 (m, 1H), 4.62-4.50 (m, 1H), 4.20-3.79 (m, 4H), 3.69-3.47 (m, 1H), 3.24-3.10 (m, 1H), 3.01-2.73 (m, 3H), 2.73-2.66 (m, 3H), 2.58-2.45 (m, 1H), 2.43-1.62 (m, 13H), 0.67-0.53 (m, 2H). $^{19}F$ NMR (377 MHz, $CD_3OD-d_4$) δ (ppm) −199.44 (d, J=82.9 Hz). $^{31}P$ NMR (162 MHz, $CD_3OD-d_4$) δ (ppm) 13.11 (d, J=85.9 Hz).

Synthesis of propyl (((R)-(2-(((3S,6S,9S,10aR)-9-(((1s,3R)-3-cyanocyclobutyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)(2,2,2-trifluoroethoxy)phosphoryl)-L-alaninate (Compound C110)
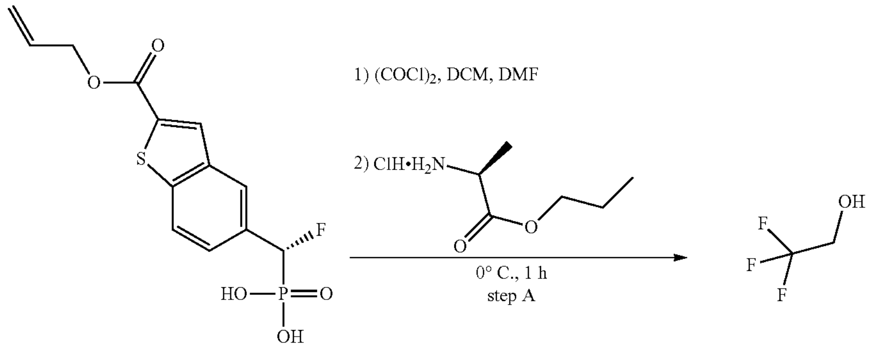
1
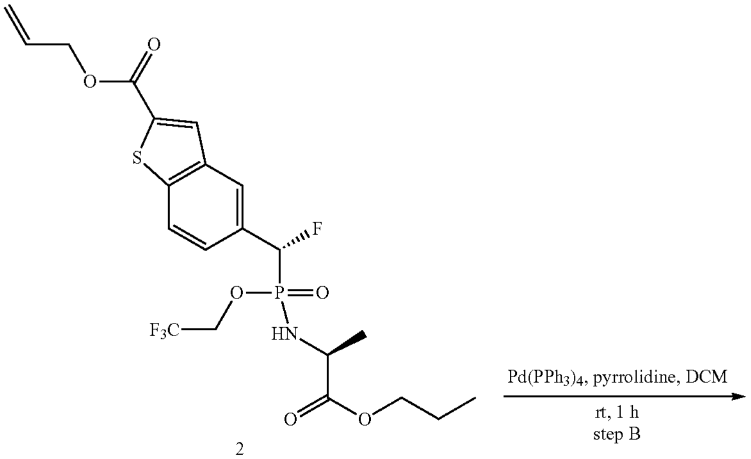
2
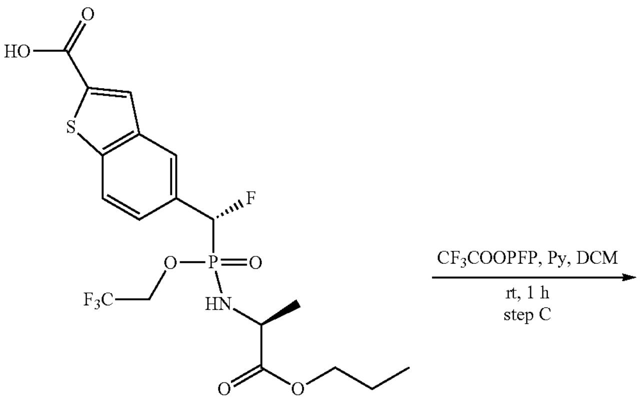
3

-continued
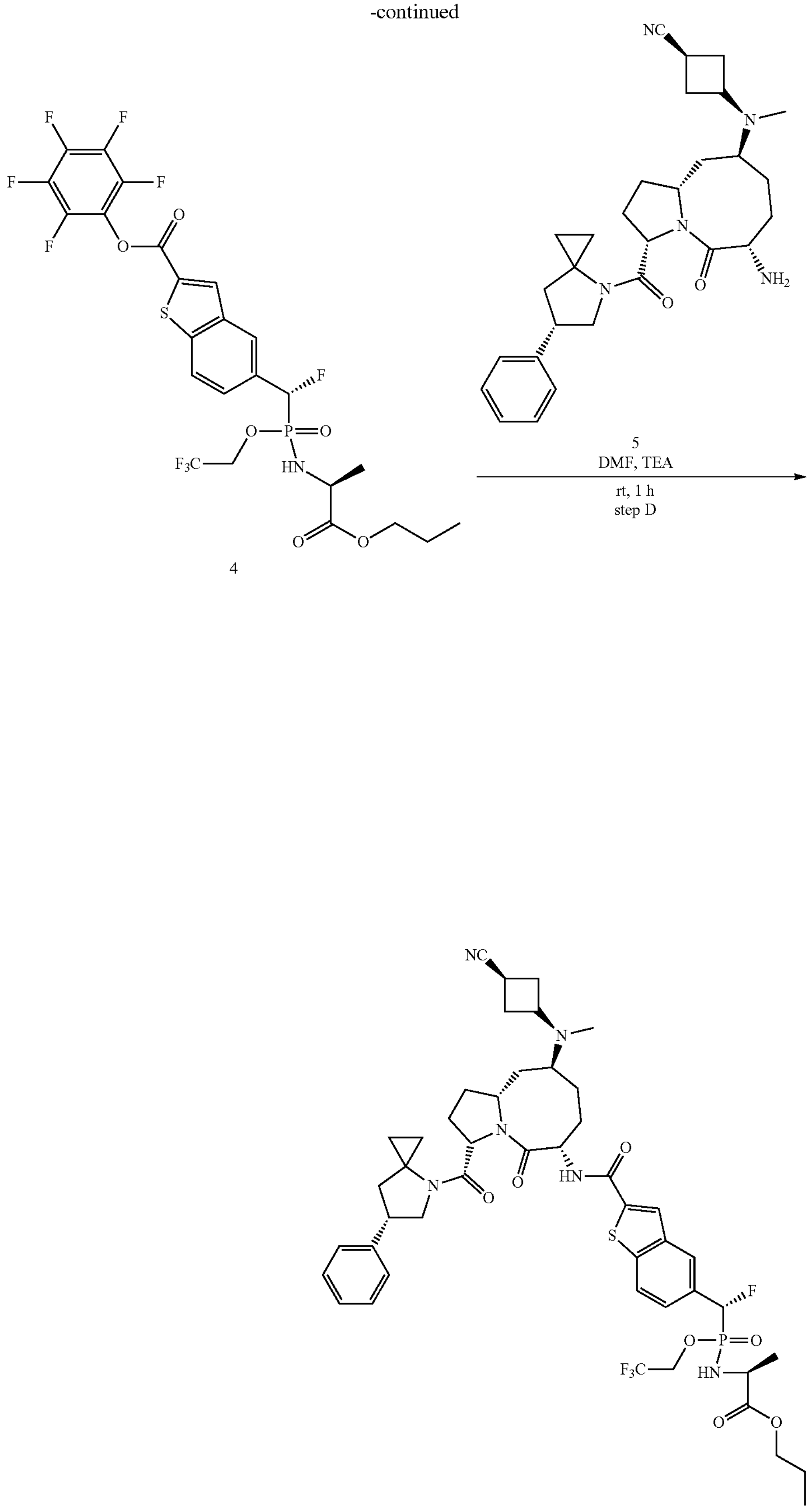
4

Step A: allyl 5-((1R)-fluoro((((S)-1-oxo-1-propoxypropan-2-yl)amino)(2,2,2-trifluoroethoxy)phosphoryl)methyl)benzo[b]thiophene-2-carboxylate

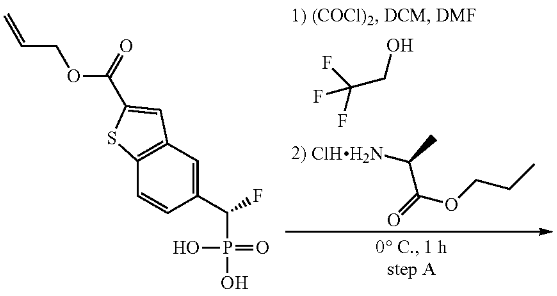

1

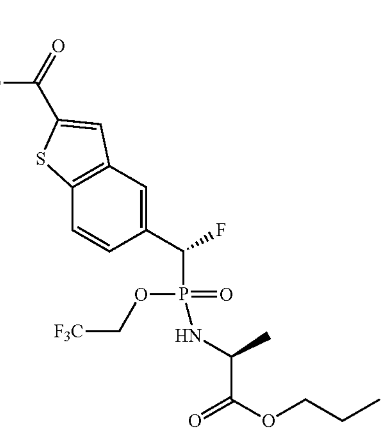

2

To a solution of (R)-((2-((allyloxy)carbonyl)benzo[b]thiophen-5-yl)fluoromethyl)phosphonic acid (1, 2.6 g, 7.88 mmol, 1 eq.) in DCM (40 mL) was added DMF (1 drop) and oxalyl chloride (5 g, 39.4 mmol, 5 eq). The resulting mixture was stirred for 1 h at room temperature, then dried under reduced pressure. The residue was dissolved in DCM (40 mL) and cooled to 0° C., 2,2,2-trifluoroethan-1-ol (788 mg, 7.88 mmol, 1 eq) was added to the solution, then TEA (4 g, 39.4 mmol, 5 eq.) was added dropwise to the solution, the mixture was stirred for 1 h at 0° C. and propyl L-alaninate hydrochloride (2.64 g, 15.76 mmol, 2 eq.) was added to the solution, then stirred for 10 min. The reaction was quenched by adding $H_2O$ (50 mL), then extracted with DCM (50 mL×2), the organic layers were combined and washed with brine, then dried over $Na_2SO_4$, concentrated to dryness under reduced pressure The crude product was purified by silica gel column chromatography to afford allyl 5-((1R)-fluoro((((S)-1-oxo-1-propoxypropan-2-yl)amino)(2,2,2-trifluoroethoxy)phosphoryl)methyl)benzo[b]thiophene-2-carboxylate (2, 7.72 g, 3.28 mmol, 41.6% yield) as a colorless oil. LCMS (ESI): m/z=526 $[M+H]^+$.

Step B: 5-((1R)-fluoro((((S)-1-oxo-1-propoxypropan-2-yl)amino)(2,2,2-trifluoroethoxy)phosphoryl)methyl)benzo[b]thiophene-2-carboxylic acid

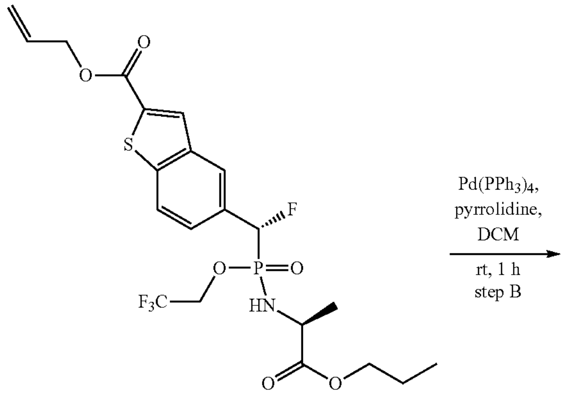

2

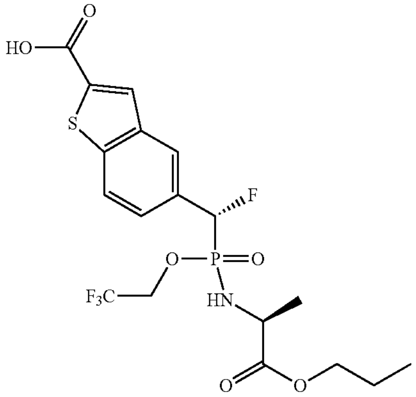

3

To a solution of allyl 5-((1R)-fluoro((((S)-1-oxo-1-propoxypropan-2-yl)amino)(2,2,2-trifluoroethoxy)phosphoryl)methyl)benzo[b]thiophene-2-carboxylate (2, 860 mg, 1.64 mmol, 1 eq.) in DCM (10 mL) was added $Pd(PPh_3)_4$ (184 mg, 0.16 mmol, 0.1 eq.), pyrrolidine (116 mg, 1.64 mmol, 1 eq.). The resulting mixture was stirred for 1 h at room temperature under the atmosphere of $N_2$, The pH was adjusted to pH=3 with 1M HCl (aq.), then extracted with DCM (20 mL×2), the organic layers were combined and washed with brine (20 mL) dried over $Na_2SO_4$, The resulting mixture was concentrated to dryness under reduced pressure to afford crude product 5-((1R)-fluoro((((S)-1-oxo-1-propoxypropan-2-yl)amino)(2,2,2-trifluoroethoxy)phosphoryl)methyl)benzo[b]thiophene-2-carboxylic acid (3, 650 mg, 1.34 mmol, 81.7% yield) as a yellow solid. LCMS (ESI): m/z=486 $[M+H]^+$.

Step C: perfluorophenyl 5-((1R)-fluoro((((S)-1-oxo-1-propoxypropan-2-yl)amino)(2,2,2-trifluoroethoxy)phosphoryl)methyl)benzo[b]thiophene-2-carboxylate

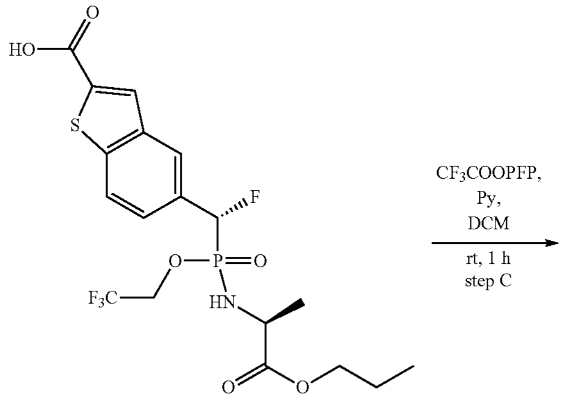

3

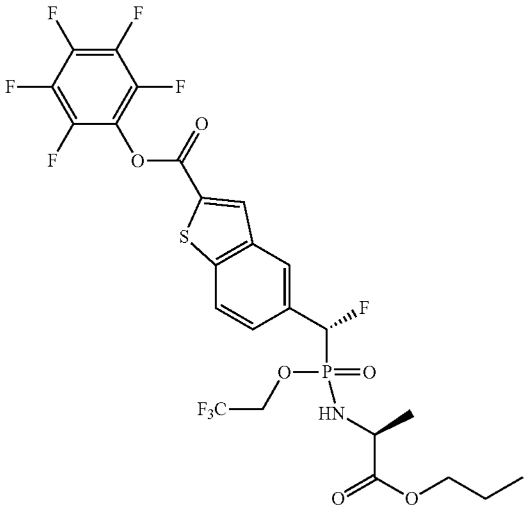

4

To a solution of 5-((1R)-fluoro((((S)-1-oxo-1-propoxypropan-2-yl)amino)(2,2,2-trifluoroethoxy)phosphoryl)methyl)benzo[b]thiophene-2-carboxylic acid (3, 650 mg, 1.34 mmol, 1 eq.) in DCM (10 mL) was added pyridine (317 mg, 4.02 mmol, 3 eq.), perfluorophenyl 2,2,2-trifluoroacetate (750 mg, 2.68 mmol, 2 eq.). The resulting mixture was stirred for 1 hr at room temperature, then. $H_2O$ (20 mL) was added to the solution, then extracted with DCM (30 mL×3), the organic layers were combined and washed with brine (30 mL), dried over $Na_2SO_4$, then concentrated under vacuum. The crude product was purified by silica gel column chromatography to afford perfluorophenyl 5-((1R)-fluoro((((S)-1-oxo-1-propoxypropan-2-yl)amino)(2,2,2-trifluoroethoxy)phosphoryl)methyl)benzo[b]thiophene-2-carboxylate (4, 600 mg, 0.92 mmol, 67% yield) as a white solid. LCMS (ESI): m/z=652 $[M+H]^+$.

Step D: propyl (((R)-(2-(((3S,6S,9S,10aR)-9-(((1s,3R)-3-cyanocyclobutyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)(2,2,2-trifluoroethoxy)phosphoryl)-L-alaninate To a solution of perfluorophenyl 5-((1R)-fluoro((((S)-1-oxo-1-propoxypropan-2-yl)amino)(2,2,2-trifluoroethoxy)phosphoryl)methyl)benzo[b]thiophene-2-carboxylate (4, 30 mg, 0.046 mml, 1 eq.) in DMF (3 mL) was added (1R,3s)-3-(((3S,6S,9S,10aR)-6-amino-5-oxo-3-((S)-6-phenyl-4-azaspiro[2.4]heptane-4-carbonyl)decahydropyrrolo[1,2-a]

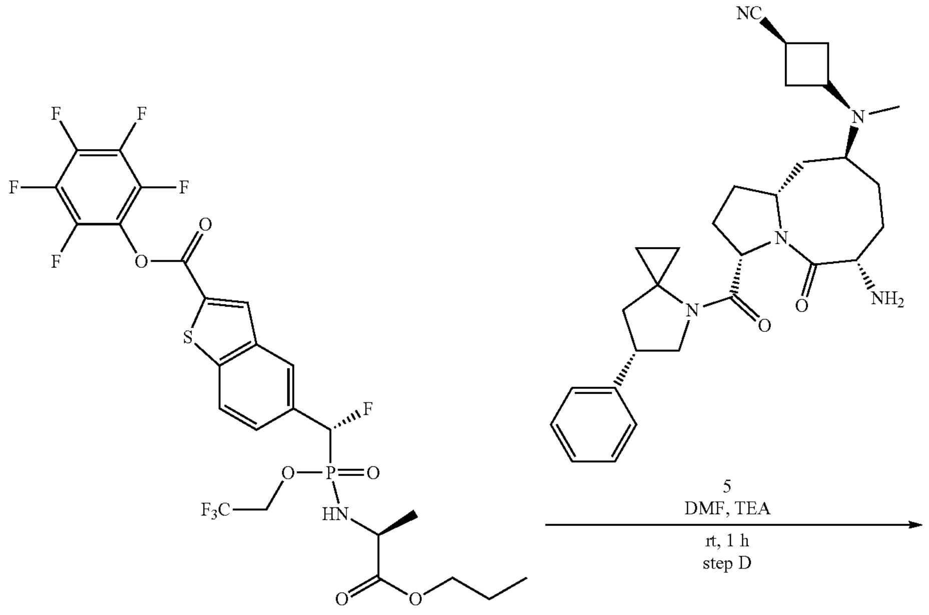

4

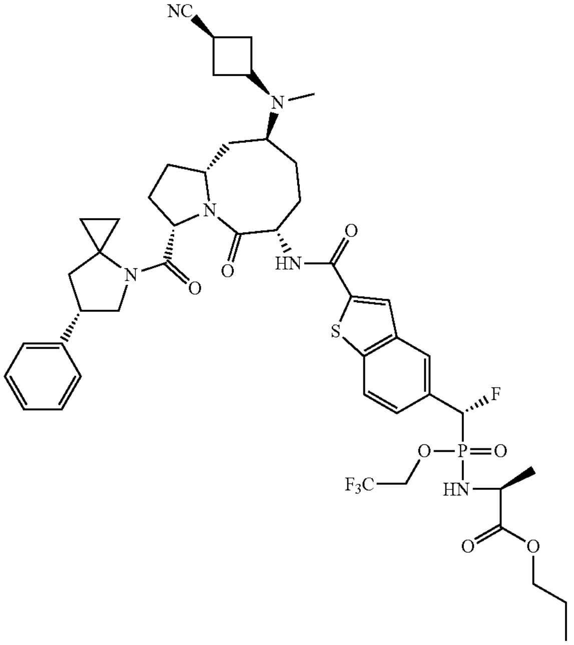

azocin-9-yl)(methyl)amino)cyclobutane-1-carbonitrile (5, 22.5 mg, 0.046 mmol, 1 eq.), TEA (14 mg, 0.138 mmol, 3 eq). The resulting mixture was stirred for 1 hr at room temperature, then the crude product was purified by Prep-HPLC to afford propyl (((R)-(2-(((3S,6S,9S,10aR)-9-(((1s, 3R)-3-cyanocyclobutyl)(methyl)amino)-5-oxo-3-((S)-6-phenyl-4-azaspiro[2.4]heptane-4-carbonyl) decahydropyrrolo[1,2-a]azocin-6-yl)carbamoyl)benzo[b] thiophen-5-yl)fluoromethyl)(2,2,2-trifluoroethoxy) phosphoryl)-L-alaninate (Compound C110, 16 mg, 0.017 mmol) as a white solid. LCMS (ESI): m/z=957 [M+H]$^+$. $^1$H NMR (400 MHz, DMSO-$d_6$) δ (ppm) 9.94-9.42 (m, 1H), 8.99-8.71 (m, 1H), 8.33-8.16 (m, 1H), 8.14-7.93 (m, 2H), 7.67-7.47 (m, 1H), 7.42-7.27 (m, 4H), 7.26-7.14 (m, 1H), 6.38-5.86 (m, 2H), 4.86-4.75 (m, 1H), 4.66-4.47 (m, 4H), 4.20-4.09 (m, 2H), 4.04-3.89 (m, 4H), 3.87-3.77 (m, 2H), 3.75-3.62 (m, 2H), 3.59-3.51 (m, 1H), 3.27-3.13 (m, 1H), 2.74-2.62 (m, 2H), 2.61-2.53 (m, 4H), 2.49-2.42 (m, 1H), 2.29-2.19 (m, 1H), 2.15-1.97 (m, 5H), 1.90-1.74 (m, 4H), 1.60-1.45 (m, 3H), 1.32-1.16 (m, 3H), 0.91-0.77 (m, 3H), 0.66-0.38 (m, 2H). $^{19}$F NMR (377 MHz, DMSO-$d_6$) δ (ppm) −72.97-−75.39 (m), −193.72-−197.54 (m). $^{31}$P NMR (162 MHz, DMSO-$d_6$) δ (ppm) 22.10-20.38 (m).

Synthesis of ((S)-(2-(((3S,6S,9S,10aR)-9-(((S)-3,3-difluorocyclopentyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b] thiophen-5-yl)fluoromethyl)phosphonic acid (Compound A36) and propyl (((S)-(2-(((3S,6S,9S,10aR)-9-(((S)-3,3-difluorocyclopentyl)(methyl) amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl) (2,2,2-trifluoroethoxy)phosphoryl)-L-alaninate (Compound C95)

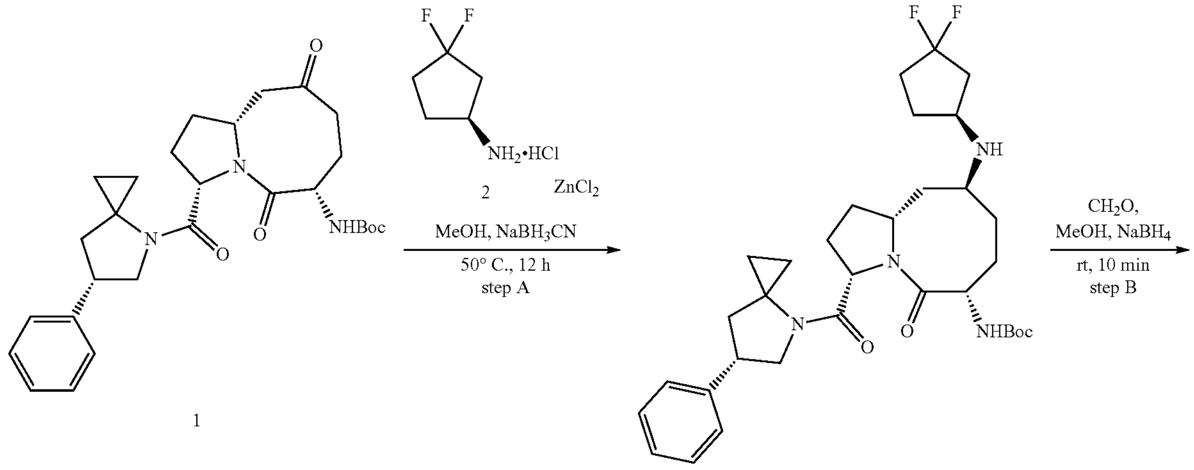

1

3

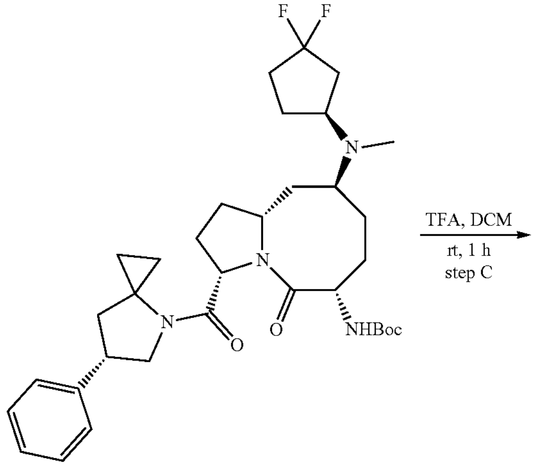

4

-continued
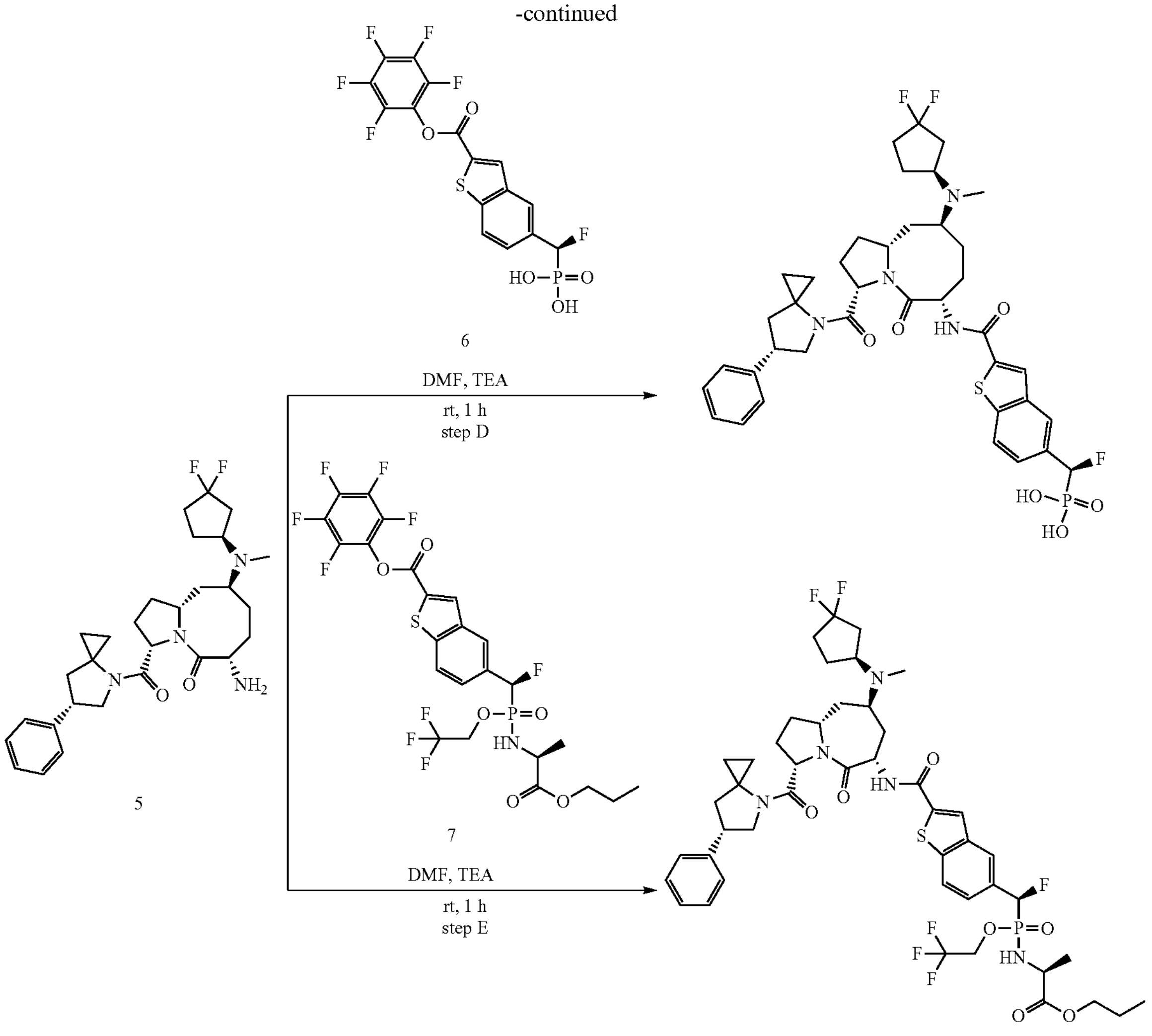
6
5
7
345
Step A: tert-butyl ((3S,6S,9S,10aR)-9-(((S)-3,3-difluorocyclopentyl)amino)-5-oxo-3-((S)-6-phenyl-4-azaspiro[2.4]heptane-4-carbonyl)decahydropyrrolo[1,2-a]azocin-6-yl)carbamate
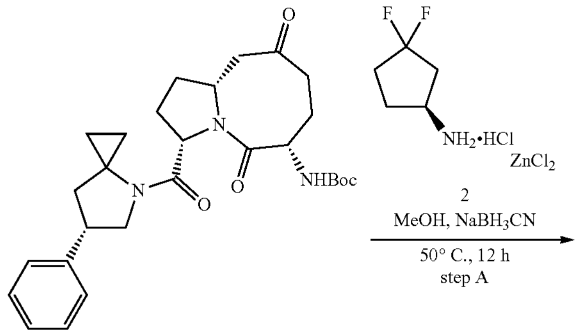
1
-continued
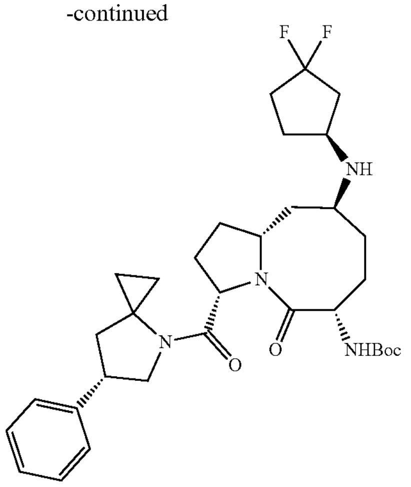
3
To a solution of tert-butyl ((3S,6S,10aR)-5,9-dioxo-3-((R)-6-phenyl-4-azaspiro[2.4]heptane-4-carbonyl)decahydropyrrolo[1,2-a]azocin-6-yl)carbamate (1, 1 g, 2.02 mmol, 1 eq.) in MeOH (20 mL) was added (1s,3s)-3-(trifluoromethyl)cyclobutan-1-amine hydrochloride (2, 477 mg, 3.03 mmol, 1.5 eq.), $ZnCl_2$ (2.77 g, 20.2 mmol, 10 eq.), the resulting mixture was stirred for 2 hr. at 50° C. under the atmosphere of $N_2$. Then $NaBH_3CN$ (1.27 g, 20.2 mmol, 10 eq.) was added portion wise every 30 mins (2 eq. (254 mg each time) added 5 times). The mixture was stirred for 12 hr at 50° C., then cooled to room temperature and used to next step without further workup. LCMS (ESI): m/z=601 $[M+H]^+$.

Step B: tert-butyl ((3S,6S,9S,10aR)-9-(((S)-3,3-difluorocyclopentyl)(methyl)amino)-5-oxo-3-((S)-6-phenyl-4-azaspiro[2.4]heptane-4-carbonyl)decahydropyrrolo[1,2-a]azocin-6-yl)carbamate

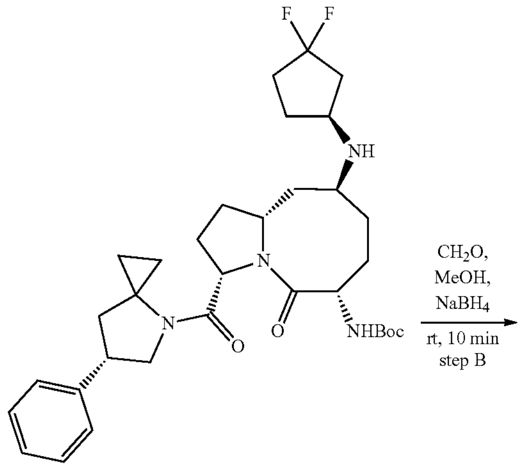

3

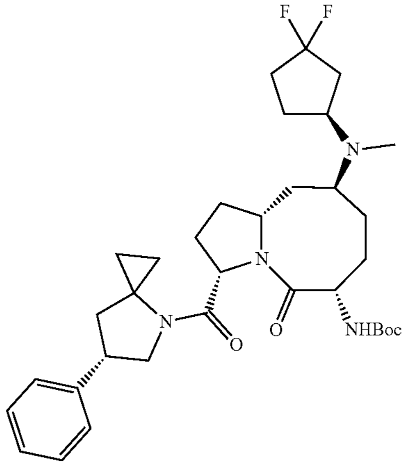

4

To the above mixture (step A) was added 40% formaldehyde aqueous (3 mL) at room temperature, the mixture was stirred for 30 min, then $NaBH_4$ (383 mg, 10.1 mmol, 5 eq.) was added in portions, the mixture was stirred for another 30 min. The reaction was quenched by $NH_4Cl$ (sat. aq), diluted with $H_2O$ (80 mL), then extracted with EtOAc (40 mL×3), the organic layers were combined and washed with brine (20 mL), dried over $Na_2SO_4$, then concentrated to dryness under reduced pressure. The crude product was purified by C18 column ($MeCN:H_2O$ (0.1% ammonium hydroxide)=5%-

70%) to afford tert-butyl ((3S,6S,9S,10aR)-9-(((S)-3,3-difluorocyclopentyl)(methyl)amino)-5-oxo-3-((S)-6-phenyl-4-azaspiro[2.4]heptane-4-carbonyl)decahydropyrrolo[1,2-a]azocin-6-yl)carbamate (4, 700 mg, 1.14 mmol, 56.4% yield two steps) as a white solid. LCMS (ESI): m/z=615 $[M+H]^+$.

Step C: (3S,6S,9S,10aR)-6-amino-9-(((S)-3,3-difluorocyclopentyl)(methyl)amino)-3-((S)-6-phenyl-4-azaspiro[2.4]heptane-4-carbonyl)octahydropyrrolo[1,2-a]azocin-5(1H)-one

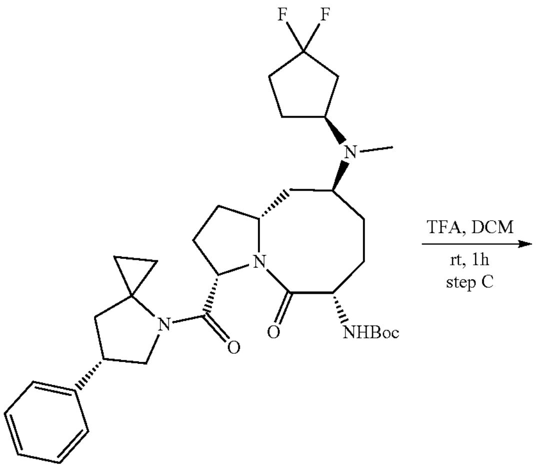

4

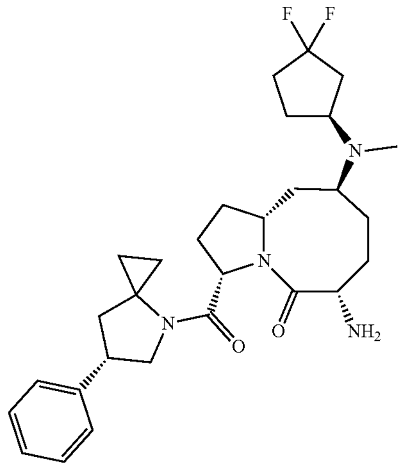

5

To a solution of tert-butyl ((3S,6S,9S,10aR)-9-(((S)-3,3-difluorocyclopentyl)(methyl)amino)-5-oxo-3-((S)-6-phenyl-4-azaspiro[2.4]heptane-4-carbonyl)decahydropyrrolo[1,2-a]azocin-6-yl)carbamate (4, 30 mg, 0.047 mmol) in DCM (2 mL) was added TFA (2 mL). The resulting mixture was stirred for 1 h at room temperature then the resulting mixture was concentrated to dryness under reduced pressure to afford crude product (3S,6S,9S,10aR)-6-amino-9-(((S)-3,3-difluorocyclopentyl)(methyl)amino)-3-((S)-6-phenyl-4-azaspiro[2.4]heptane-4-carbonyl)octahydropyrrolo[1,2-a]azocin-5(1H)-one (5, 30 mg, TFA salt) as a yellow oil which was used to the next step without further purification. LCMS (ESI): m/z=515 $[M+H]^+$.

Step D: ((S)-(2-(((3S,6S,9S,10aR)-9-(((S)-3,3-difluorocyclopentyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)phosphonic acid

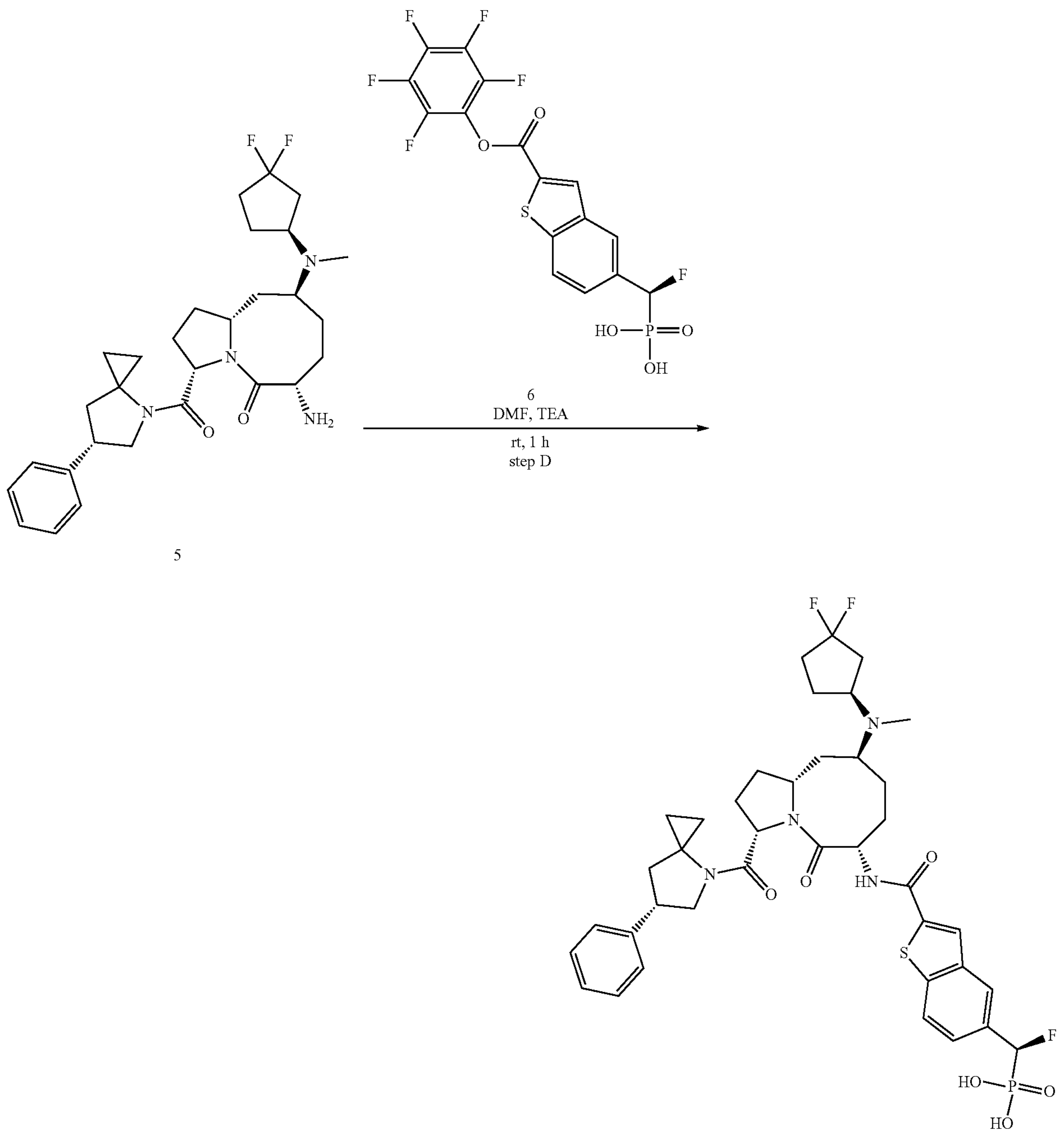 [SMILES: CN([C@H]1CC[C@H](N)C(=O)N2[C@H](CC[C@H]2C(=O)N2C[C@H](c3ccccc3)CC23CC3)C1)[C@H]1CCC(F)(F)C1 ; O=C(Oc1c(F)c(F)c(F)c(F)c1F)c1cc2cc([C@@H](F)P(=O)(O)O)ccc2s1 ; CN([C@H]1CC[C@H](NC(=O)c2cc3cc([C@@H](F)P(=O)(O)O)ccc3s2)C(=O)N2[C@H](CC[C@H]2C(=O)N2C[C@H](c3ccccc3)CC23CC3)C1)[C@H]1CCC(F)(F)C1]

To a solution of (3S,6S,9S,10aR)-6-amino-9-(((S)-3,3-difluorocyclopentyl)(methyl)amino)-3-((S)-6-phenyl-4-azaspiro[2.4]heptane-4-carbonyl)octahydropyrrolo[1,2-a]azocin-5(1H)-one (5, 30 mg, TFA salt) in DMF (2 mL) was added TEA (9.9 mg, 0.098 mmol, 2 eq.), (S)-(fluoro(2-((perfluorophenoxy)carbonyl)benzo[b]thiophen-5-yl)methyl)phosphonic acid (6, 22.3 mg, 0.049 mmol, 1 eq.). The resulting mixture was stirred for 1 h at room temperature, LCMS show that the reaction was completed. The crude product was purified by Prep-HPLC to afford ((S)-(2-(((3S,6S,9S,10aR)-9-(((S)-3,3-difluorocyclopentyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)phosphonic acid (Compound A36, 8 mg) as a white solid. LCMS (ESI): m/z=787 $[M+H]^+$. $^1$H NMR (400 MHz, $CD_3OD-d_4$) δ (ppm) 8.09 (d, J=5.4 Hz, 1H), 8.03 (s, 1H), 7.98-7.89 (m, 1H), 7.58 (d, J=8.4 Hz, 1H), 7.38-7.25 (m, 4H), 7.24-7.17 (m, 1H), 5.93-5.71 (m, 1H), 4.71-4.54 (m, 2H), 4.39-4.03 (m, 2H), 3.98-3.83 (m, 2H), 3.67-3.32 (m, 2H), 2.84-2.76 (m, 3H), 2.55-1.85 (m, 19H), 1.73-1.58 (m, 1H), 0.62-0.43 (m, 2H). $^{19}$F NMR (376 MHz, $CD_3OD-d_4$) δ (ppm) −89.99 (d, J=12.3 Hz), −90.74-92.79 (m), −199.39 (dd, J=85.6, 5.4 Hz). $^{31}$P NMR (162 MHz, $CD_3OD-d_4$) δ (ppm) 13.07 (d, J=85.3 Hz).

Step E: propyl (((S)-(2-(((3S,6S,9S,10aR)-9-(((S)-3,3-difluorocyclopentyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)(2,2,2-trifluoroethoxy)phosphoryl)-L-alaninate
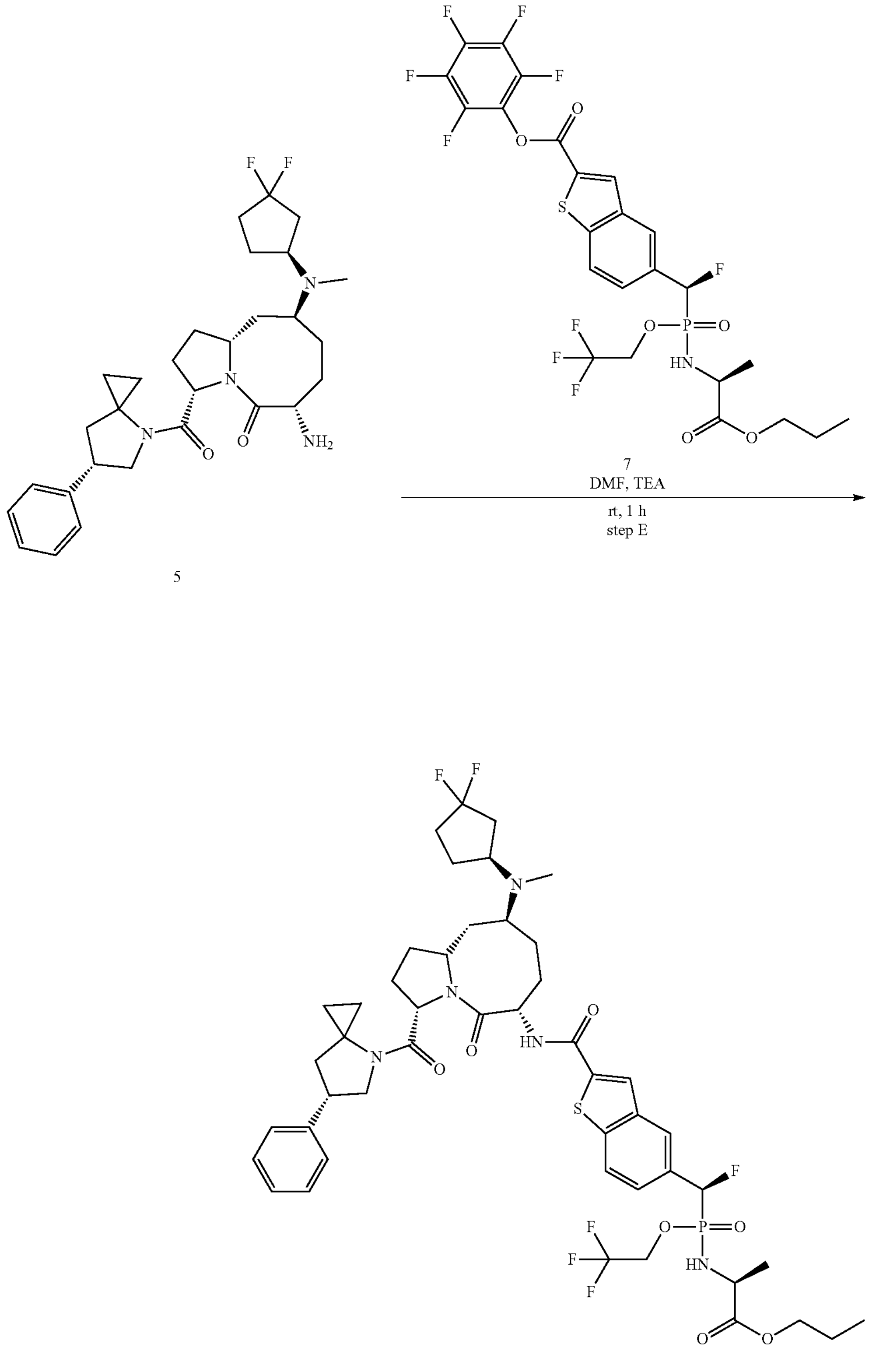

To a solution of (3S,6S,9S,10aR)-6-amino-9-(((S)-3,3-difluorocyclopentyl)(methyl)amino)-3-((S)-6-phenyl-4-azaspiro[2.4]heptane-4-carbonyl)octahydropyrrolo[1,2-a]azocin-5(1H)-one (5, 30 mg, TFA salt) in DMF (2 mL) was added TEA (9.9 mg, 0.098 mmol, 2 eq.), perfluorophenyl 5-((1S)-fluoro((((S)-1-oxo-1-propoxypropan-2-yl)amino)(2,2,2-trifluoroethoxy)phosphoryl)methyl)benzo[b]thiophene-2-carboxylate (7, 31.8 mg, 0.049 mmol, 1 eq.). The resulting mixture was stirred for 1 h at room temperature. The crude product was purified by Prep-HPLC to afford propyl (((S)-(2-(((3S,6S,9S,10aR)-9-(((S)-3,3-difluorocyclopentyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)(2,2,2-trifluoroethoxy)phosphoryl)-L-alaninate (Compound C95, 11 mg) as a white solid. LCMS (ESI): m/z=982 $[M+H]^+$. $^1$H NMR (400 MHz, DMSO-$d_6$) δ (ppm) 8.85-8.71 (m, 1H), 8.31-8.22 (m, 1H), 8.11-7.94 (m, 2H), 7.56-7.46 (m, 1H), 7.37-7.28 (m, 4H), 7.24-7.15 (m, 1H), 6.28-5.90 (m, 2H), 4.79-4.68 (m, 1H), 4.66-4.41 (m, 3H), 4.35-4.25 (m, 1H), 4.14-3.62 (m, 5H), 3.58-3.47 (m, 1H), 3.11-2.93 (m, 2H), 2.72-2.58 (m, 1H), 2.40-2.32 (m, 1H), 2.25-2.06 (m, 6H), 2.02-1.68 (m, 12H), 1.64-1.48 (m, 5H), 1.30-1.00 (m, 3H), 0.89-0.81 (m, 3H), 0.52-0.38 (m, 2H). $^{19}$F NMR (376 MHz, DMSO-$d_6$) δ (ppm) −72.10--76.44 (m), −83.74--88.46 (m), −196.13 (dd, J=663.5, 84.9 Hz). $^{31}$P NMR (162 MHz, DMSO-$d_6$) δ (ppm) 21.33 (d, J=83.6 Hz), δ (ppm) 20.98 (d, J=86.2 Hz).

Synthesis of ((S)-(2-(((3S,6S,9S,10aR)-9-(((1s,3R)-3-cyanocyclobutyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)phosphonic acid (Compound A40)

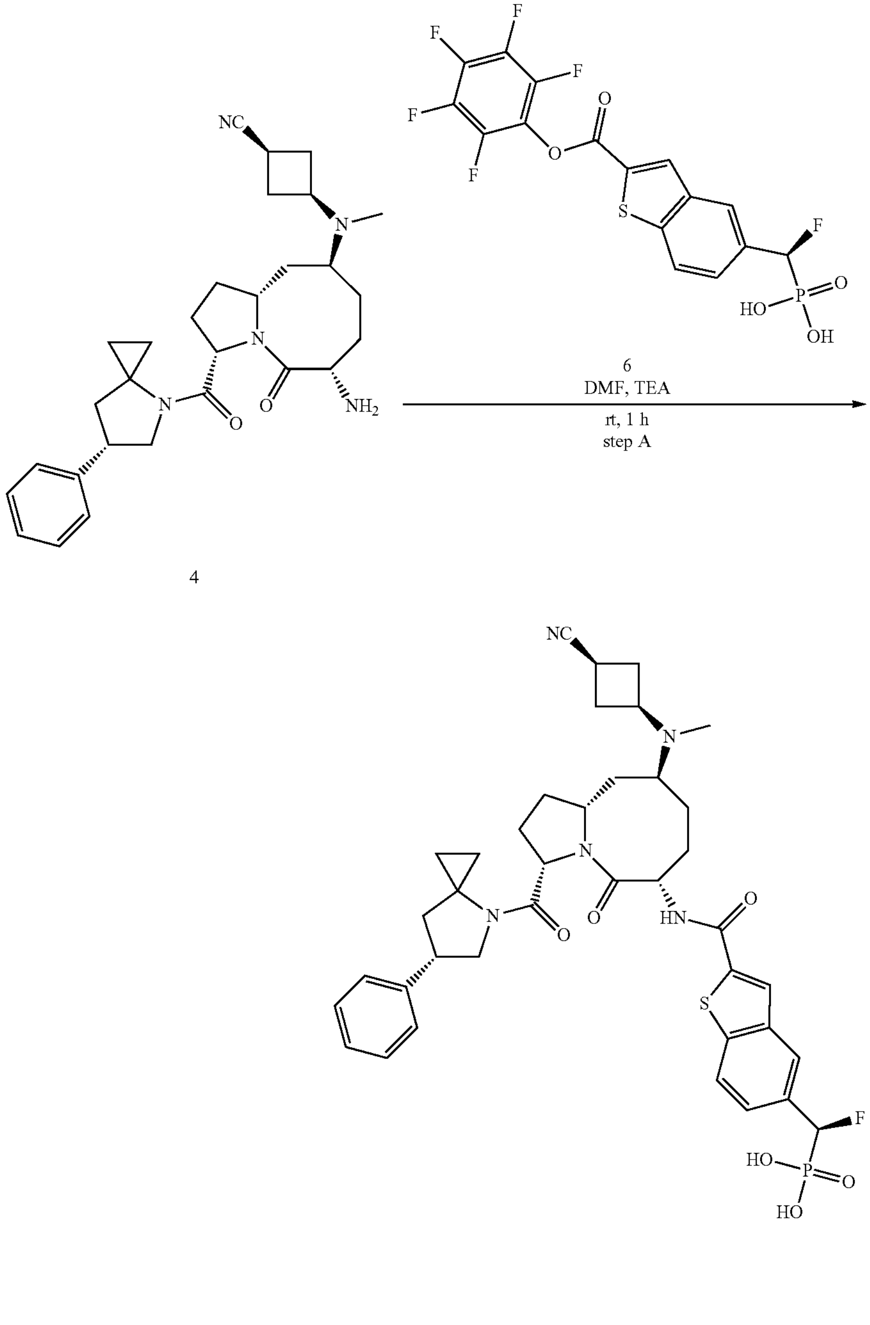

4

Step A: ((S)-(2-(((3S,6S,9S,10aR)-9-(((1s,3R)-3-cyanocyclobutyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)phosphonic acid

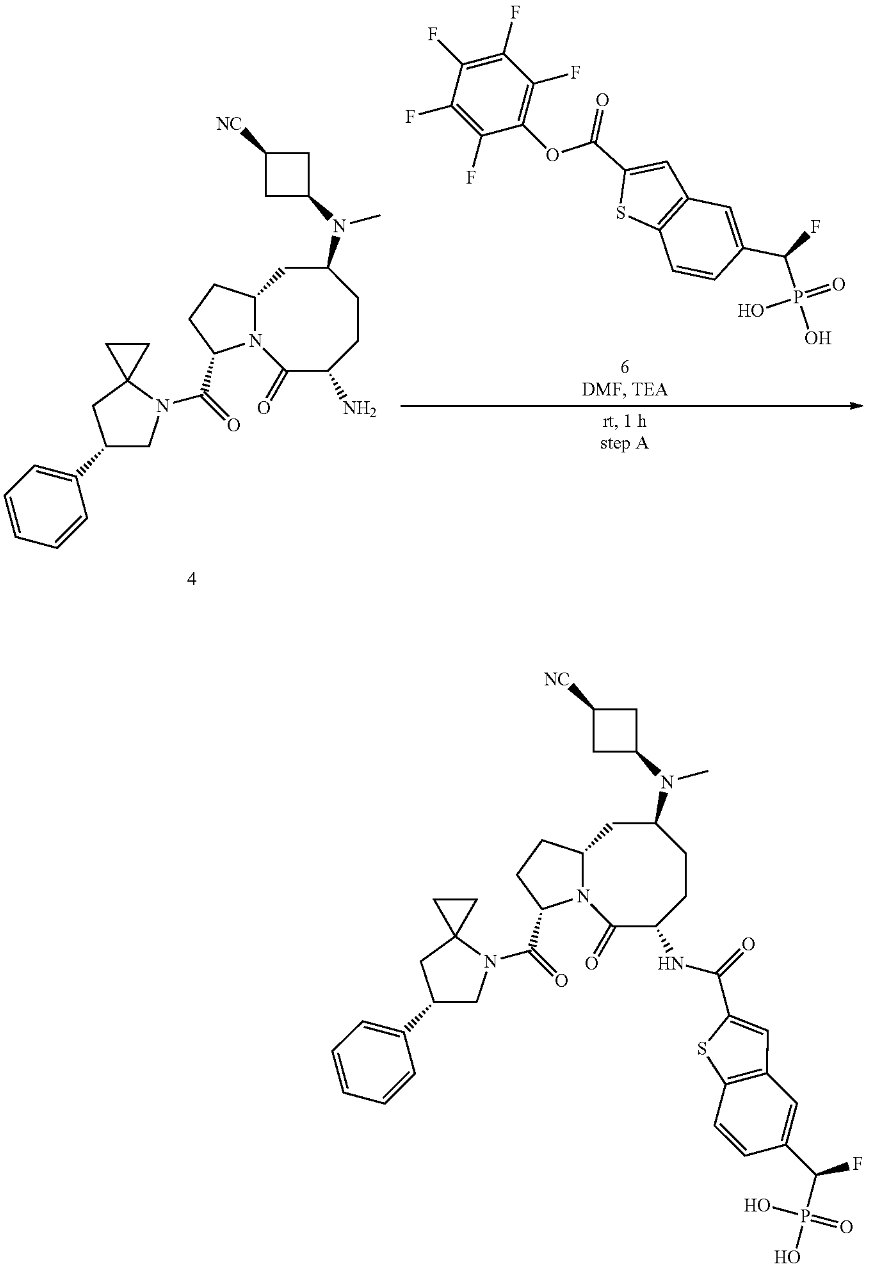 [SMILES: CN([C@H]1CC[C@H](N)C(=O)N2[C@H](CC[C@H]2C(=O)N2C[C@H](c3ccccc3)CC23CC3)C1)[C@H]1C[C@@H](C#N)C1 ; O=C(Oc1c(F)c(F)c(F)c(F)c1F)c1cc2cc([C@@H](F)P(=O)(O)O)ccc2s1 ; CN([C@H]1CC[C@H](NC(=O)c2cc3cc([C@@H](F)P(=O)(O)O)ccc3s2)C(=O)N2[C@H](CC[C@H]2C(=O)N2C[C@H](c3ccccc3)CC23CC3)C1)[C@H]1C[C@@H](C#N)C1]

4

To a solution of (1R,3s)-3-(((3S,6S,9S,10aR)-6-amino-5-oxo-3-((S)-6-phenyl-4-azaspiro[2.4]heptane-4-carbonyl)decahydropyrrolo[1,2-a]azocin-9-yl)(methyl)amino)cyclobutane-1-carbonitrile (4, 30 mg, TFA salt) in DMF (2 mL) was added TEA (10.3 mg, 0.102 mmol, 2 eq.), (S)-(fluoro(2-((perfluorophenoxy)carbonyl)benzo[b]thiophen-5-yl)methyl)phosphonic acid (6, 23.2 mg, 0.051 mmol, 1 eq). The resulting mixture was stirred for 1 h at room temperature, LCMS show that the reaction was completed. The crude product was purified by Prep-HPLC to afford ((S)-(2-(((3S,6S,9S,10aR)-9-(((1s,3R)-3-cyanocyclobutyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)phosphonic acid (Compound A40, 16 mg, 0.021 mmol) as a white solid. LCMS (ESI): m/z=762 $[M+H]^+$. 1H NMR (400 MHz, $CD_3OD-d_4$) δ (ppm) 8.04 (s, 2H), 7.86 (d, J=8.4 Hz, 1H), 7.63 (d, J=8.6 Hz, 1H), 7.40-7.26 (m, 4H), 7.23-7.16 (m, 1H), 5.75-5.52 (m, 1H), 4.78-4.71 (m, 2H), 4.64-4.52 (m, 2H), 4.46-4.35 (m, 1H), 4.12-3.88 (m, 2H), 3.65-3.52 (m, 1H), 3.02-2.86 (m, 1H), 2.70-2.57 (m, 1H), 2.55-2.15 (m, 8H), 2.11 (s, 3H), 2.02-1.93 (m, 3H), 1.88-1.79 (m, 2H), 1.78-1.61 (m, 4H), 0.57-0.46 (m, 2H). $^{19}F$ NMR (377 MHz, $CD_3OD-d_4$) δ (ppm) −195.94 (d, J=76.2 Hz). $^{31}P$ NMR (162 MHz, $CD_3OD-d_4$) δ (ppm) 9.91 (d, J=76.2 Hz).

Synthesis of cyclobutyl (((S)-(2-(((3S,6S,9S,10aR)-9-(((1s,3R)-3-cyanocyclobutyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)(phenoxy)phosphoryl)-L-alaninate (Compound C112)
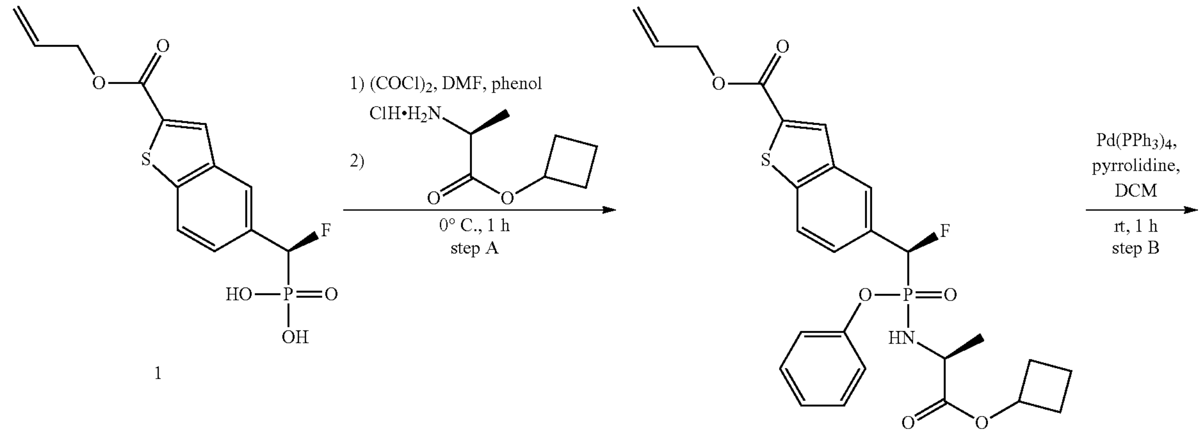
1
2
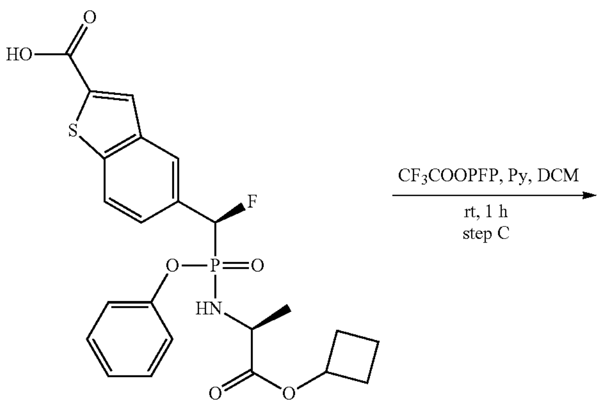
3

-continued
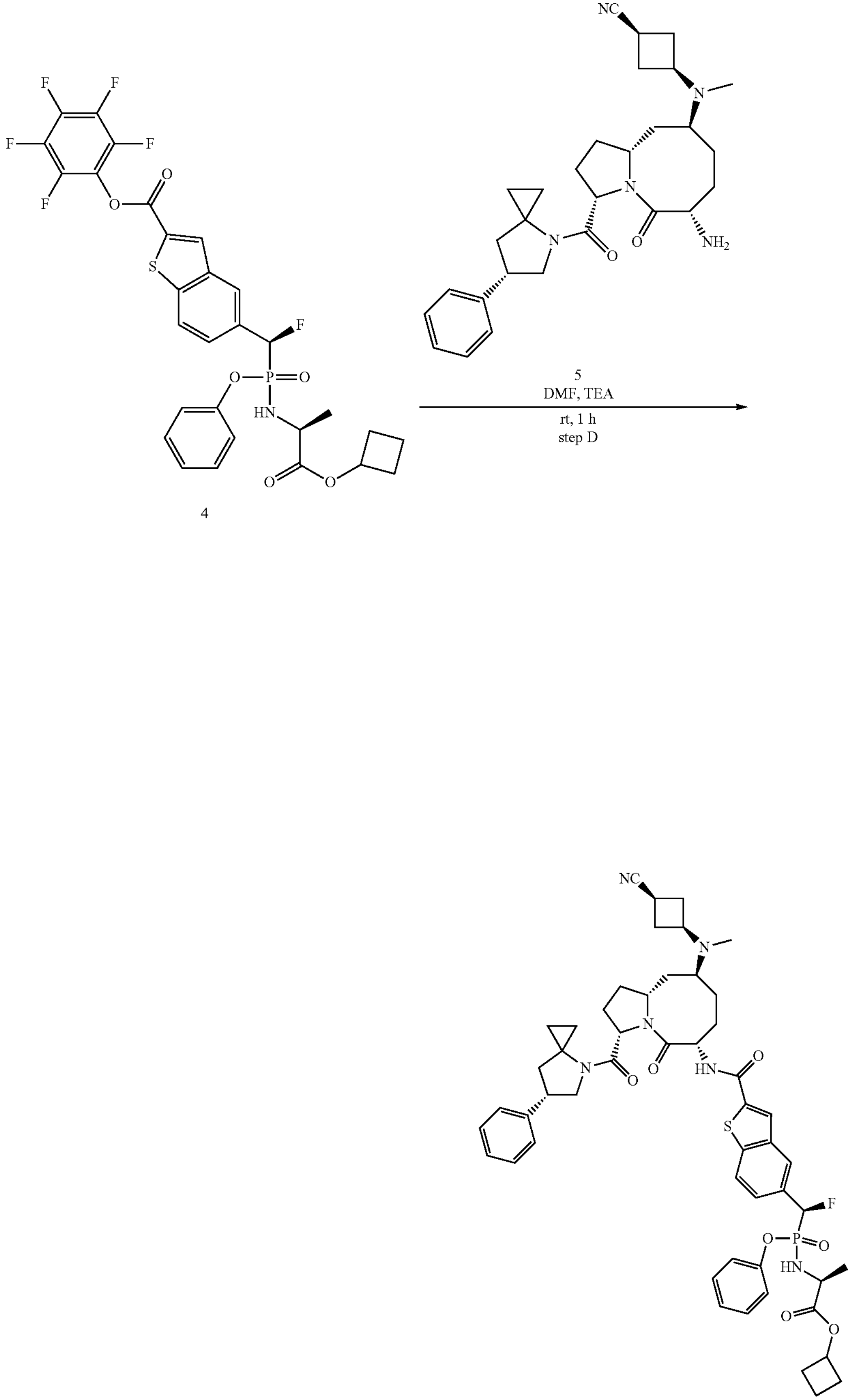
4

Step A: allyl 5-((1S)—((((S)-1-cyclobutoxy-1-oxopropan-2-yl)amino)(phenoxy)phosphoryl)fluoromethyl)benzo[b]thiophene-2-carboxylate

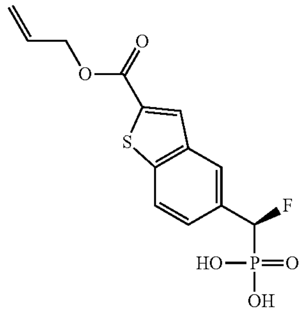

1

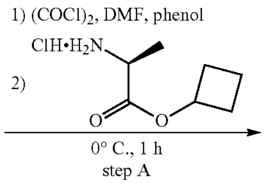

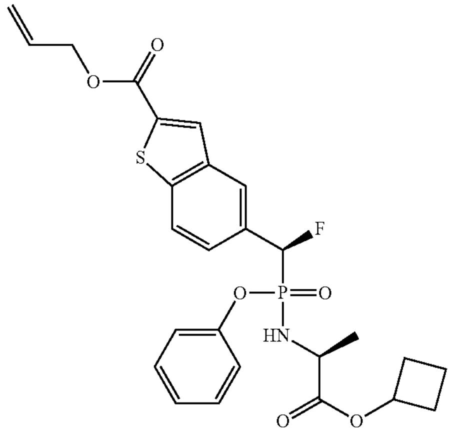

2

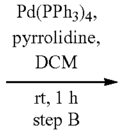

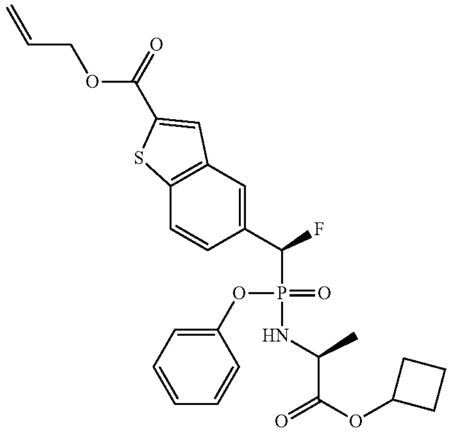

2

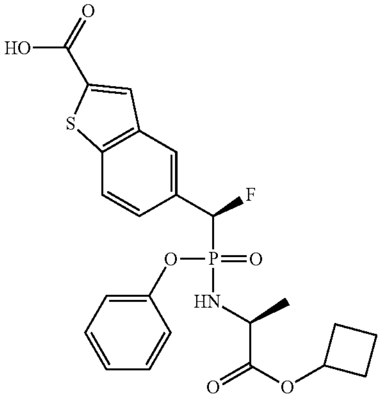

3

To a solution of (S)-((2-((allyloxy)carbonyl)benzo[b]thiophen-5-yl)fluoromethyl)phosphonic acid (1, 1.3 g, 3.94 mmol, 1 eq.) in DCM (20 mL) was added DMF (1 drop) and oxalyl chloride (2.5 g, 19.7 mmol, 5 eq). The resulting mixture was stirred for 1 h at room temperature, then DCM was removed by reduced pressure. The residue was dissolved in DCM (20 mL) and cooled to 0° C., phenol (285 mg, 3.94 mmol, 1 eq) was added to the solution and TEA (2 g, 19.7 mmol, 5 eq.) was added dropwise then the mixture was stirred for 1 h at 0° C. Then cyclobutyl L-alaninate hydrochloride (4, 1.41 g, 7.88 mmol, 2 eq.) was added to the solution, then $H_2O$ (50 mL) was added to the solution, then extracted with DCM (50 mL×2). The organic layers were combined and washed with brine, then dried over $Na_2SO_4$, concentrated to dryness under reduced pressure The crude product was purified by silica gel column chromatography to afford allyl 5-((1S)—((((S)-1-cyclobutoxy-1-oxopropan-2-yl)amino)(phenoxy)phosphoryl)fluoromethyl)benzo[b]thiophene-2-carboxylate (2, 800 mg, 1.51 mmol, 38% yield) as a colorless oil. LCMS (ESI): m/z=532 $[M+H]^+$.

Step B: 5-((1S)—((((S)-1-cyclobutoxy-1-oxopropan-2-yl)amino)(phenoxy)phosphoryl)fluoromethyl)benzo[b]thiophene-2-carboxylic acid To a solution of allyl 5-((1S)—((((S)-1-cyclobutoxy-1-oxopropan-2-yl)amino)(phenoxy)phosphoryl)fluoromethyl)benzo[b]thiophene-2-carboxylate (2, 800 mg, 1.51 mmol, 1 eq.) in DCM (10 mL) was added $Pd(PPh_3)_4$ (173 mg, 0.15 mmol, 0.1 eq.) and pyrrolidine (107 mg, 1.51 mmol, 1 eq.). The resulting mixture was stirred for 1 h at room temperature under the atmosphere of $N_2$, then adjusted pH=3 with 1M HCl (aq.) extracted with DCM (20 mL×2). The organic layers were combined and washed with brine (20 mL) dried over $Na_2SO_4$, The resulting mixture was concentrated to dryness under reduced pressure to afford crude product 5-((1S)—((((S)-1-cyclobutoxy-1-oxopropan-2-yl)amino)(phenoxy)phosphoryl)fluoromethyl)benzo[b]thiophene-2-carboxylic acid (3, 650 mg, 1.32 mmol, 88% yield) as a yellow solid. LCMS (ESI): m/z=492 $[M+H]^+$.

Step C: perfluorophenyl 5-((1S)—((((S)-1-cyclobutoxy-1-oxopropan-2-yl)amino)(phenoxy)phosphoryl) fluoromethyl)benzo[b]thiophene-2-carboxylate

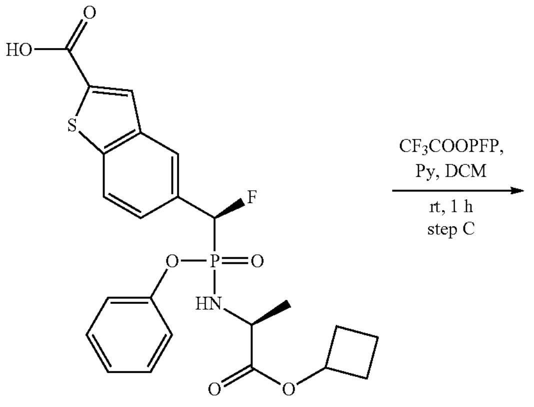

3

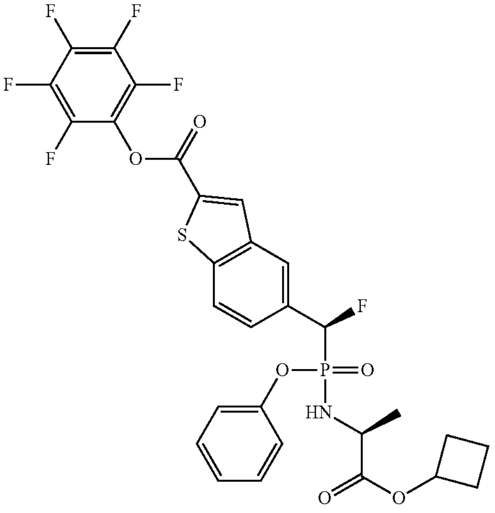

4

To a solution of 5-((1S)—((((S)-1-cyclobutoxy-1-oxopropan-2-yl)amino)(phenoxy)phosphoryl)fluoromethyl)benzo[b]thiophene-2-carboxylic acid (3, 650 mg, 1.32 mmol, 1 eq.) in DCM (10 mL) was added pyridine (106 mg, 1.32 mmol, 3 eq.), perfluorophenyl 2,2,2-trifluoroacetate (741 mg, 2.64 mmol, 2 eq.). The resulting mixture was stirred for 1 h at room temperature, then the reaction was quenched by adding $H_2O$ (20 mL), then extracted with DCM (20 mL×2), the organic layers were combined and washed with brine (20 mL), dried over $Na_2SO_4$, then concentrated to dryness under reduced pressure. The crude product was purified by silica gel column chromatography to afford perfluorophenyl 5-((1S)—((((S)-1-cyclobutoxy-1-oxopropan-2-yl)amino)(phenoxy)phosphoryl)fluoromethyl)benzo[b]thiophene-2-carboxylate (4, 620 mg, 0.942 mmol, 71% yield) as a white solid. LCMS (ESI): m/z=658 [M+H]$^+$.

Step D: cyclobutyl (((S)-(2-(((3S,6S,9S,10aR)-9-(((1s,3R)-3-cyanocyclobutyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)(phenoxy)phosphoryl)-L-alaninate

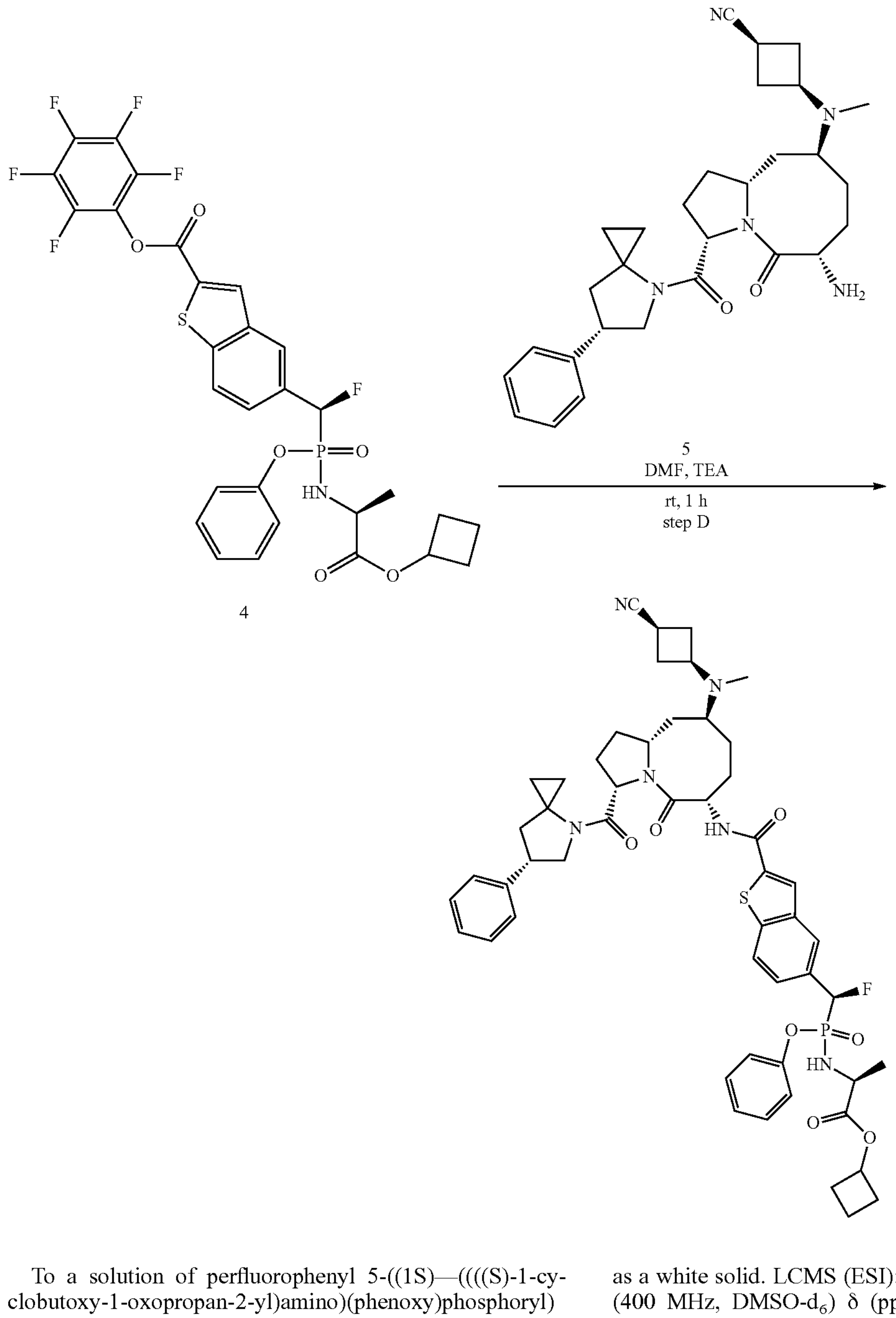

4

To a solution of perfluorophenyl 5-((1S)—((((S)-1-cyclobutoxy-1-oxopropan-2-yl)amino)(phenoxy)phosphoryl)fluoromethyl)benzo[b]thiophene-2-carboxylate (4, 20 mg, 0.030 mml, 1 eq.) in DMF (3 mL) was added (1R,3s)-3-(((3S,6S,9S,10aR)-6-amino-5-oxo-3-((S)-6-phenyl-4-azaspiro[2.4]heptane-4-carbonyl)decahydropyrrolo[1,2-a]azocin-9-yl)(methyl)amino)cyclobutane-1-carbonitrile (5, 15 mg, 0.030 mmol, 1 eq.), TEA (6.1 mg, 0.061 mmol, 2 eq). Procedure for 5 is described in syntheses of Compound A37 and Compound C110. The resulting mixture was stirred for 1 h at room temperature, then the crude product was purified by Prep-HPLC to afford cyclobutyl (((S)-(2-(((3S,6S,9S,10aR)-9-(((1s,3R)-3-cyanocyclobutyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)(phenoxy)phosphoryl)-L-alaninate (Compound C112, 13 mg, 0.014 mmol, 69% yield) as a white solid. LCMS (ESI): m/z=963 $[M+H]^+$. $^1$H NMR (400 MHz, DMSO-$d_6$) δ (ppm) 8.80 (t, J=7.1 Hz, 1H), 8.30-8.24 (m, 1H), 8.10-8.03 (m, 2H), 7.63-7.57 (m, 1H), 7.40-7.27 (m, 6H), 7.24-7.10 (m, 4H), 6.34-6.00 (m, 2H), 4.87-4.65 (m, 2H), 4.47 (t, J=8.4 Hz, 1H), 4.33-4.25 (m, 1H), 4.12 (t, J=8.5 Hz, 1H), 3.88-3.48 (m, 3H), 3.07-2.89 (m, 3H), 2.38-2.29 (m, 2H), 2.26-2.11 (m, 5H), 2.05-1.47 (m, 20H), 1.20-0.87 (m, 3H), 0.55-0.42 (m, 2H). $^{19}$F NMR (377 MHz, DMSO-$d_6$) δ (ppm) −194.13 (d, J=82.6 Hz), −195.92 (d, J=87.3 Hz). $^{31}$P NMR (162 MHz, DMSO-$d_6$) δ (ppm) 17.29 (d, J=86.7 Hz), 16.94 (d, J=82.5 Hz).

Synthesis of ((S)-fluoro(2-(((3S,6S,9S,10aR)-9-(methyl(4,4,4-trifluorobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)phosphonic acid (Compound A38) and propyl (((S)-fluoro(2-(((3S,6S,9S,10aR)-9-(methyl(4,4,4-trifluorobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(2,2,2-trifluoroethoxy)phosphoryl)-L-alaninate (Compound C87)

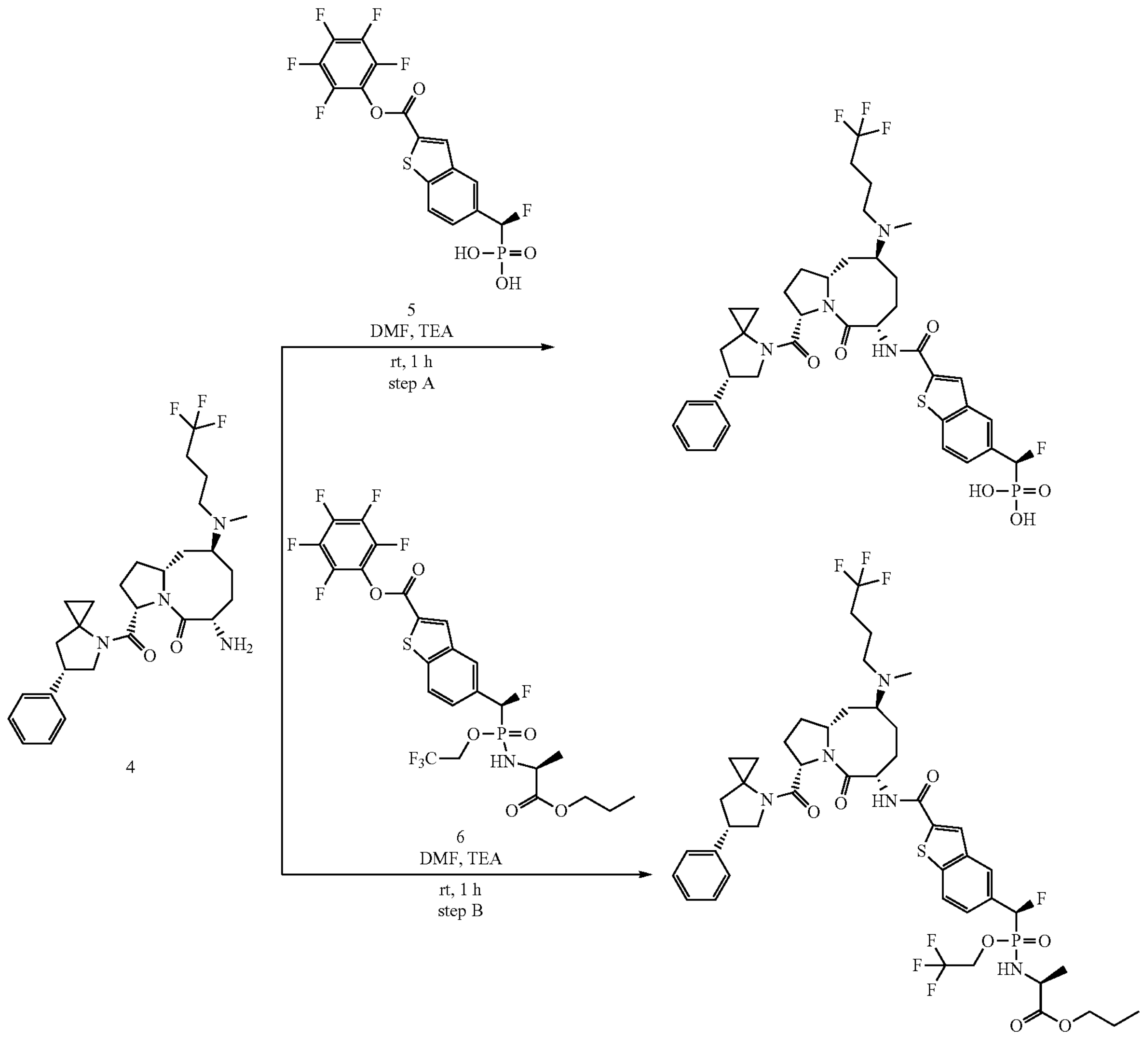

Step A: ((S)-fluoro(2-(((3S,6S,9S,10aR)-9-(methyl(4,4,4-trifluorobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)phosphonic acid

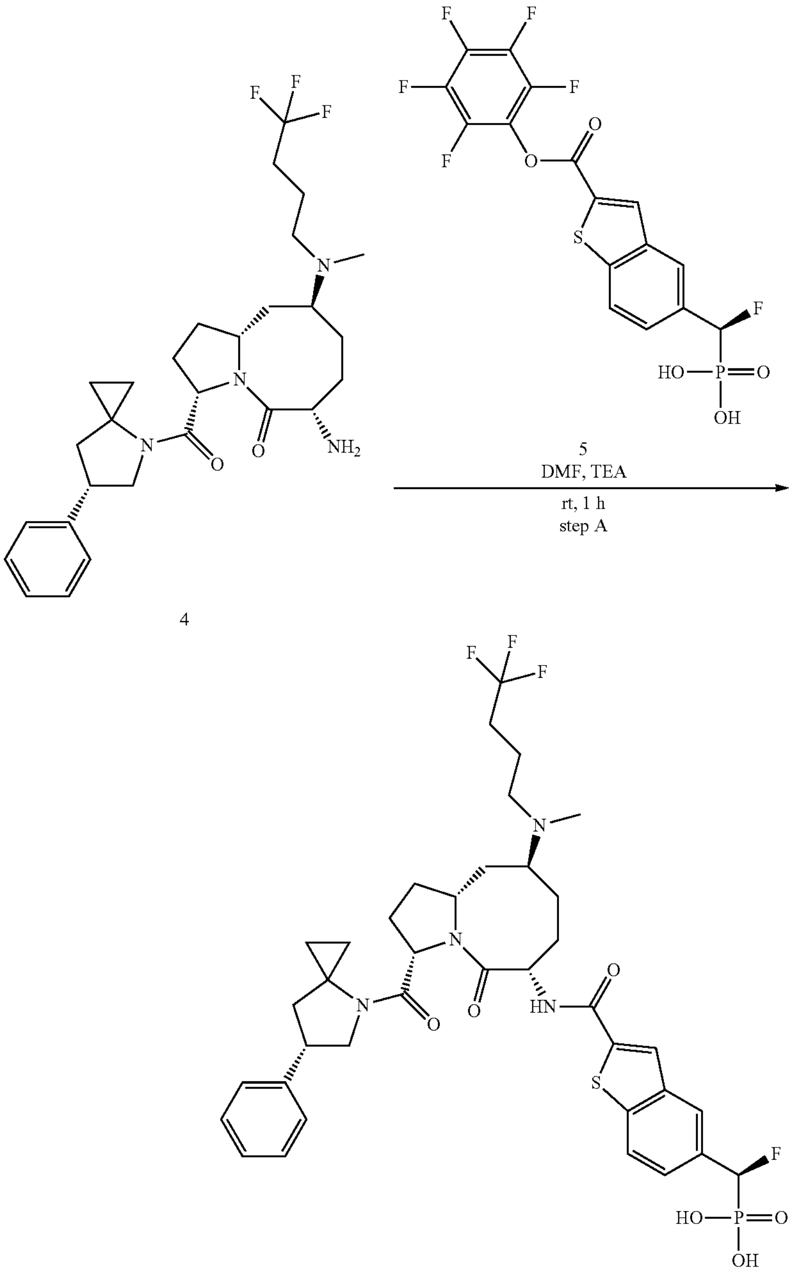

4

Procedure for 4 is described in the synthesis of Compound A3 and Compound C135. To a solution of (3S,6S,9S,10aR)-6-amino-9-(methyl(4,4,4-trifluorobutyl)amino)-3-((S)-6-phenyl-4-azaspiro[2.4]heptane-4-carbonyl)octahydropyrrolo[1,2-a]azocin-5(1H)-one (4, 20 mg, TFA salt) in DMF (2 mL) was added TEA (6.5 mg, 0.065 mmol, 2 eq.), (S)-(fluoro(2-((perfluorophenoxy)carbonyl)benzo[b]thiophen-5-yl)methyl)phosphonic acid (5, 14.67 mg, 0.032 mmol, 1 eq). The resulting mixture was stirred for 1 h at room temperature, then the crude product was purified by Prep-HPLC to afford ((S)-fluoro(2-(((3S,6S,9S,10aR)-9-(methyl(4,4,4-trifluorobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)phosphonic acid (Compound A38, 17 mg, 0.021 mmol) as a white solid. LCMS (ESI): m/z=793 $[M+H]^+$. 1H NMR (400 MHz, DMSO-$d_6$) δ (ppm) 9.72-9.32 (m, 1H), 8.91-8.69 (m, 1H), 8.25 (s, 1H), 8.08-7.94 (m, 2H), 7.53 (d, J=8.5 Hz, 1H), 7.38-7.28 (m, 4H), 7.25-7.20 (m, 1H), 5.81 (dd, J=44.3, 7.9 Hz, 1H), 4.81 (s, 1H), 4.60-4.50 (m, 2H), 4.17-4.09 (m, 1H), 3.90-3.69 (m, 2H), 3.63-3.51 (m, 1H), 3.23-3.00 (m, 2H), 2.79-2.68 (m, 3H), 2.41-1.75 (m, 17H), 1.58-1.49 (m, 1H), 0.57-0.42 (m, 2H). $^{19}F$ NMR (376 MHz, DMSO $d_6$) δ (ppm) −64.73 (d, J=58.3 Hz), −194.65 (dd, J=82.9, 16.4 Hz). $^{31}P$ NMR (162 MHz, DMSO-$d_6$) δ (ppm) 10.87 (d, J=80.8 Hz).

Step B: propyl (((S)-fluoro(2-(((3S,6S,9S,10aR)-9-(methyl(4,4,4-trifluorobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(2,2,2-trifluoroethoxy)phosphoryl)-L-alaninate Procedure for 6 is described in the synthesis of Compound C64. To a solution of perfluorophenyl 5-((1S)-fluoro((((S)-1-oxo-1-propoxypropan-2-yl)amino)(2,2,2-trifluoroethoxy)phosphoryl)methyl)benzo[b]thiophene-2-carboxylate (6, 15 mg, 0.023 mml, 1 eq.) in DMF (3 mL) was added (3S,6S,9S,10aR)-6-amino-9-(methyl(4,4,4-trifluorobutyl)amino)-

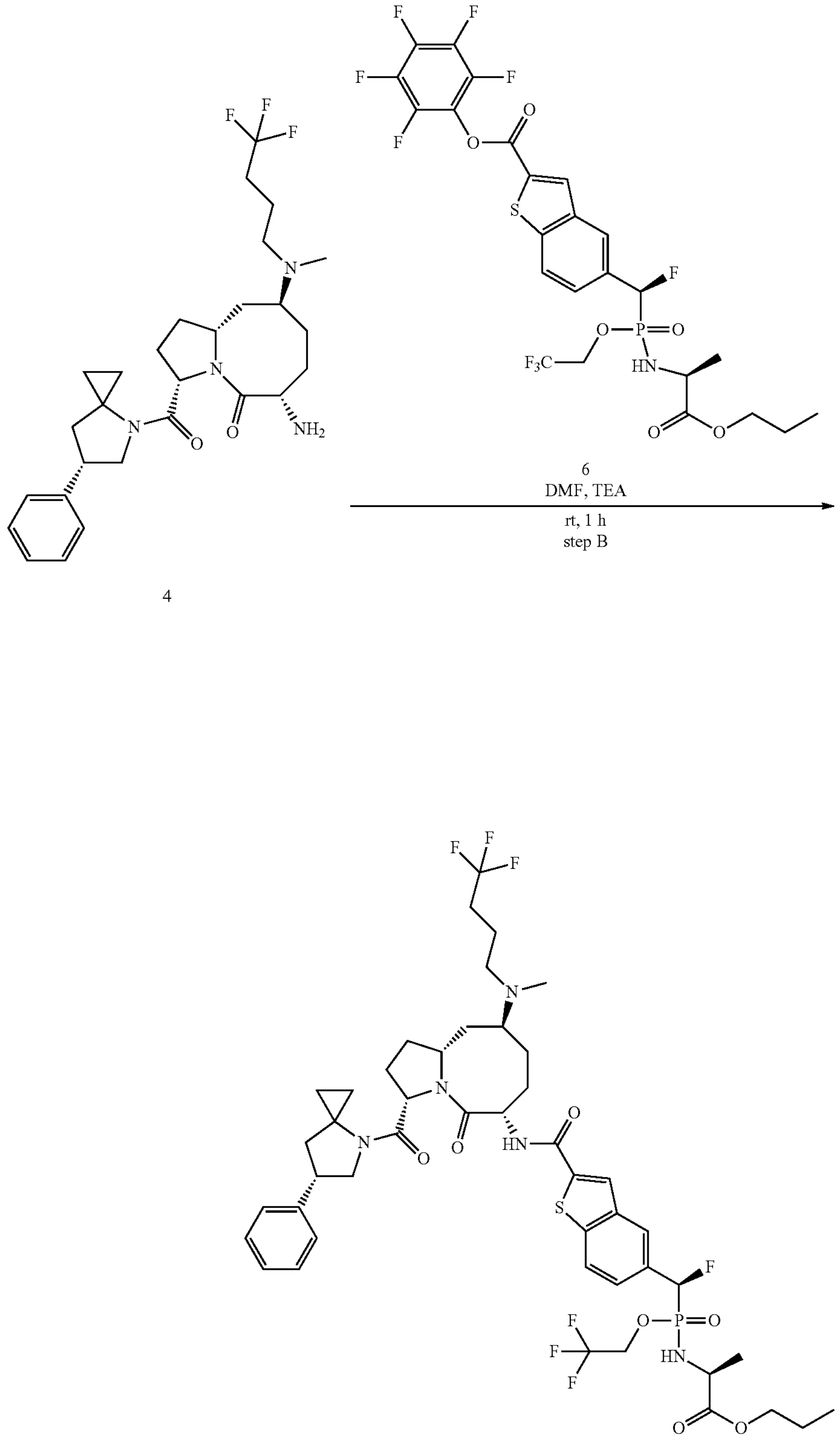

4

3-((S)-6-phenyl-4-azaspiro[2.4]heptane-4-carbonyl)octahydropyrrolo[1,2-a]azocin-5(1H)-one (4, 14 mg, 0.023 mmol, 1 eq.), TEA (14 mg, 0.138 mmol, 6 eq). The resulting mixture was stirred for 1 h at room temperature, then the crude product was purified by Prep-HPLC to afford propyl (((S)-fluoro(2-(((3S,6S,9S,10aR)-9-(methyl(4,4,4-trifluorobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(2,2,2-trifluoroethoxy)phosphoryl)-L-alaninate (Compound C87, 7 mg, 0.007 mmol) as a white solid. LCMS (ESI): m/z=988 $[M+H]^+$. $^1$H NMR (400 MHz, DMSO-$d_6$) δ (ppm) 8.84-8.72 (m, 1H), 8.26 (s, 1H), 8.11-8.02 (m, 1H), 7.98 (d, J=9.6 Hz, 1H), 7.58-7.46 (m, 1H), 7.39-7.26 (m, 4H), 7.24-7.19 (m, 1H), 6.27-5.92 (m, 2H), 4.84-4.73 (m, 1H), 4.65-4.42 (m, 3H), 4.36-4.26 (m, 1H), 4.16-4.06 (m, 1H), 4.05-3.93 (m, 2H), 3.84-3.63 (m, 2H), 3.58-3.49 (m, 1H), 3.01-2.89 (m, 1H), 2.47-2.43 (m, 1H), 2.35-2.20 (m, 4H), 2.16-2.08 (m, 4H), 2.04-1.94 (m, 3H), 1.90-1.48 (m, 13H), 1.31-1.02 (m, 3H), 0.89-0.80 (m, 3H), 0.54-0.39 (m, 2H). $^{19}$F NMR (376 MHz, DMSO-$d_6$) δ (ppm) −64.56 (s), −73.67 (d, J=22.0 Hz), −195.22 (d, J=83.8 Hz), −197.00 (d, J=86.1 Hz). $^{31}$P NMR (162 MHz, DMSO-$d_6$) δ (ppm) 21.32 (d, J=83.8 Hz), 20.98 (d, J=86.2 Hz).

Synthesis of propyl (((R)-fluoro(2-(((3S,6S,9S,10aR)-9-(((1s,3R)-3-fluorocyclobutyl)(methyl)amino)-5-oxo-3-(4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate (Compound C85) and ((R)-fluoro(2-(((3S,6S,9S,10aR)-9-(((1s,3R)-3-fluorocyclobutyl)(methyl)amino)-5-oxo-3-(4-azaspiro[2.4]heptane-4-carbonyl)decahydropyrrolo[1,2-a]azocin-6-yl)carbamoyl)benzo[b]thiophen-5-yl)methyl)phosphonic acid (Compound A39)

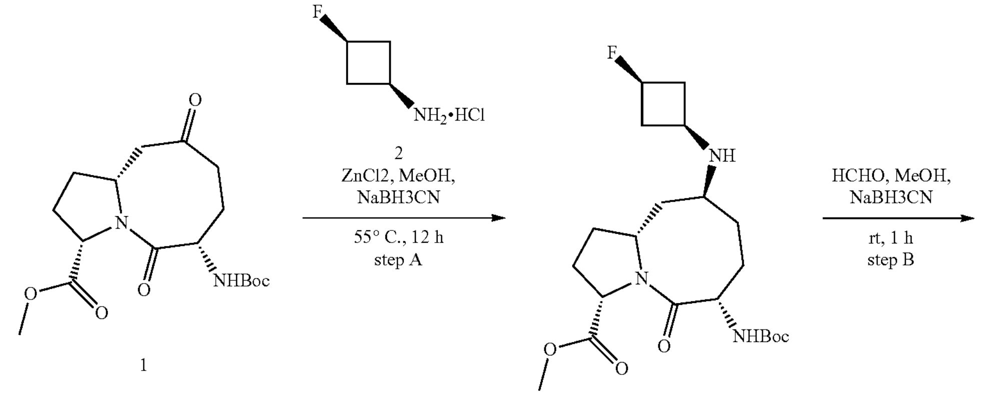

1

3

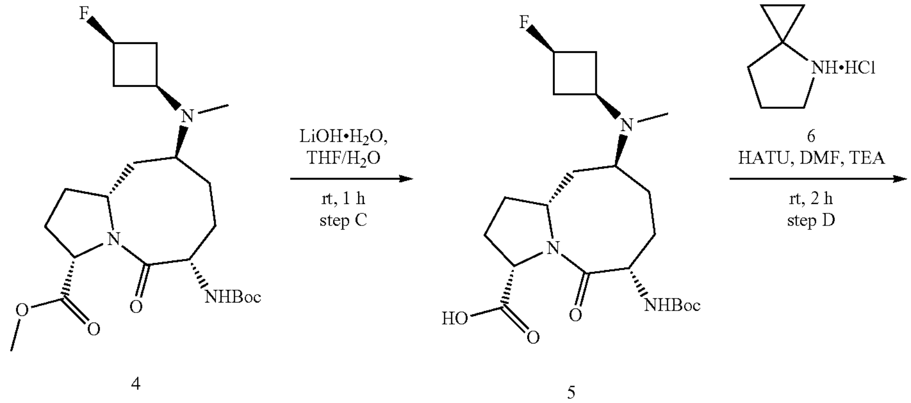

4

5

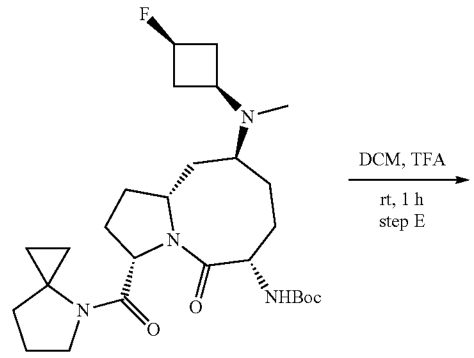

7

-continued
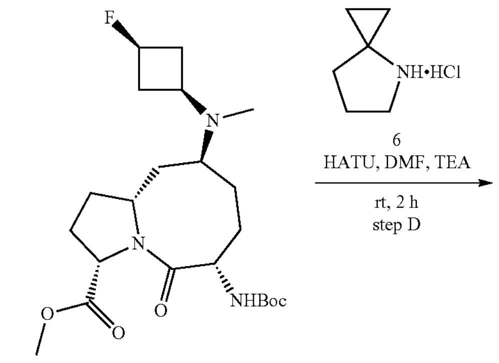
4
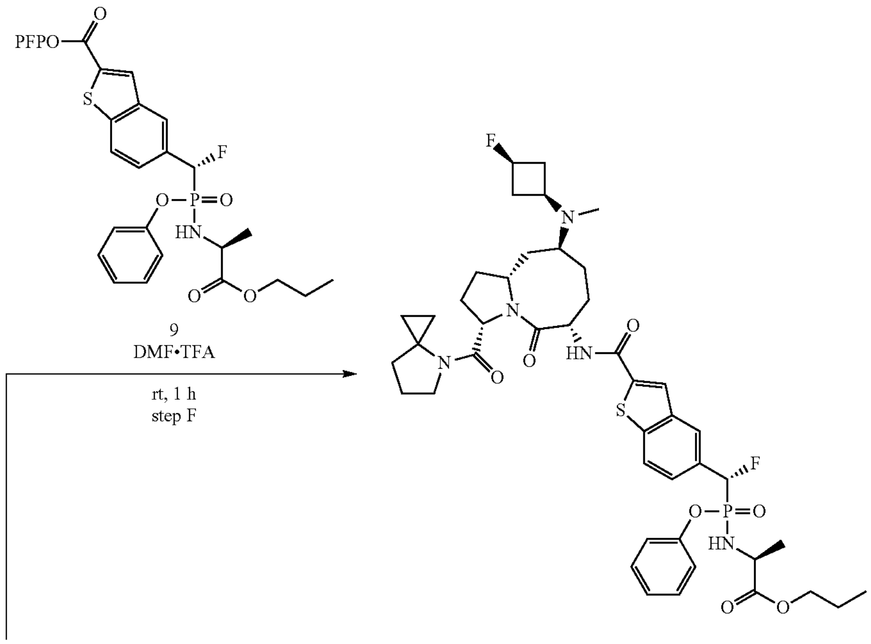

-continued

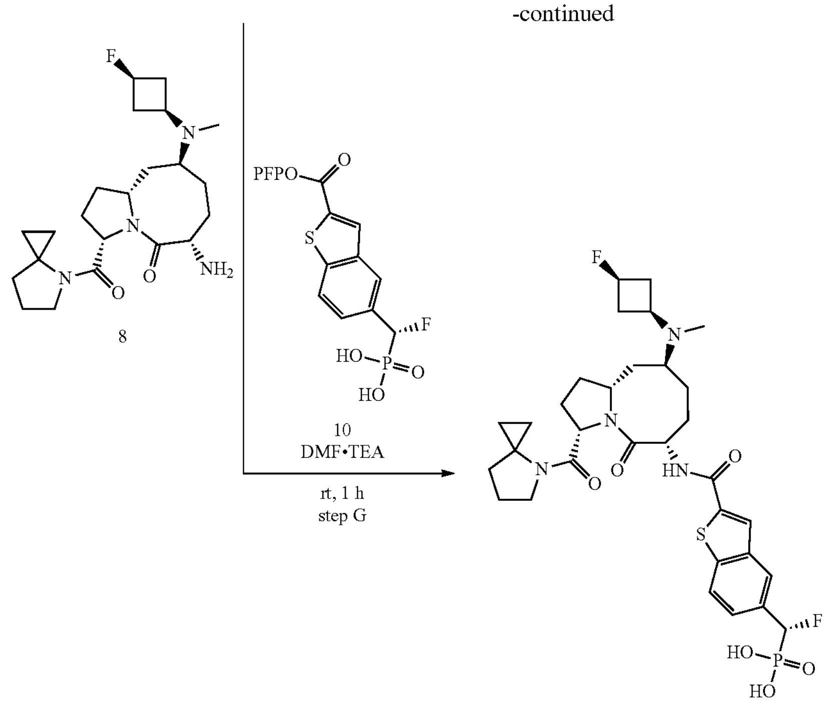

Step A: methyl (3S,6S,9S,10aR)-6-((tert-butoxycarbonyl)amino)-9-(((1s,3R)-3-fluorocyclobutyl)amino)-5-oxodecahydropyrrolo[1,2-a]azocine-3-carboxylate

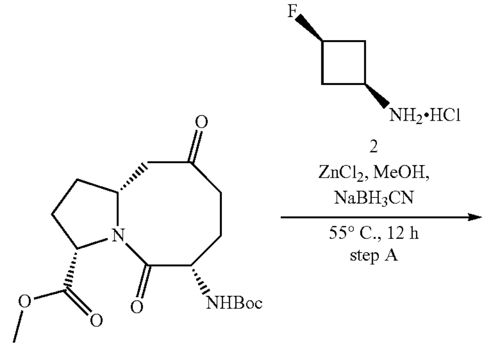

1

To a solution of methyl (3S,6S,10aR)-6-((tert-butoxycarbonyl)amino)-5,9-dioxodecahydropyrrolo[1,2-a]azocine-3-carboxylate (1, 1 g, 2.82 mmol, 1.0 eq.) and (1s,3s)-3-fluorocyclobutan-1-amine hydrochloride (2, 635 mg, 5.08 mmol, 1.8 eq.) in MeOH (10 mL) was added $ZnCl_2$ (1.89 g, 14.1 mmol, 5.0 eq.). The resulting mixture was stirred at 55° C. for 1 hr under $N_2$, then $NaBH_3CN$ (1.78 g, 28.2 mmol, 10.0 eq.) was added portion wise every 30 mins (2 eq. (356 mg each time) added 5 times) and then the resulting mixture was stirred at 55° C. for 12 h under $N_2$. The reaction mixture was cooled to room temperature then used to next step directly without further purification. LCMS (ESI): m/z=428 $[M+H]^+$.

Step B: methyl (3S,6S,9S,10aR)-6-((tert-butoxycarbonyl)amino)-9-(((1s,3R)-3-fluorocyclobutyl)(methyl)amino)-5-oxodecahydropyrrolo[1,2-a]azocine-3-carboxylate

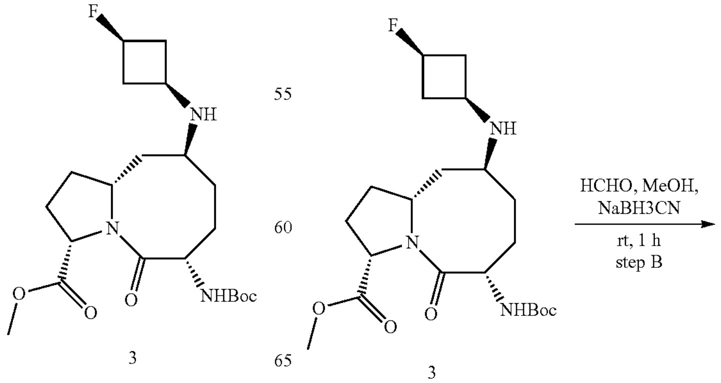

3

3

-continued

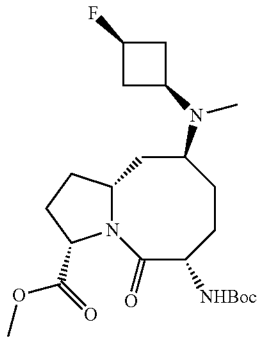

4

-continued

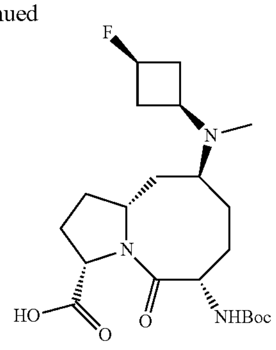

5

To a mixture of methyl (3S,6S,9S,10aR)-6-((tert-butoxycarbonyl)amino)-9-(((1s,3R)-3-fluorocyclobutyl)amino)-5-oxodecahydropyrrolo[1,2-a]azocine-3-carboxylate (3, step A above, crude.) were added HCHO (2 mL, 30 wt % in water) and $NaBH_3CN$ (355 mg, 5.64 mmol, 2.0 eq.). The resulting mixture was stirred at 55° C. for 30 min under $N_2$ then the reaction was quenched by $NH_4Cl$ (sat. aq), diluted with $H_2O$ (50 mL), then extracted with EtOAc (30 mL×3). The organic layers were combined and washed with brine (10 mL), dried over $Na_2SO_4$, then concentrated to dryness under reduced pressure. The crude product was purified by reverse phase chromatography using a 40 g C18 cartridge eluting with a gradient of 5-80% MeCN in water (with 0.1% $NH_3H_2O$) to afford methyl (3S,6S,9S,10aR)-6-((tert-butoxycarbonyl)amino)-9-(((1s,3R)-3-fluorocyclobutyl)(methyl)amino)-5-oxodecahydropyrrolo[1,2-a]azocine-3-carboxylate (4, 0.6 g, 1.36 mmol, 48% over 2 steps). LCMS (ESI): m/z=442 $[M+H]^+$.

Step C: (3S,6S,9S,10aR)-6-((tert-butoxycarbonyl)amino)-9-(((1s,3R)-3-fluorocyclobutyl)(methyl)amino)-5-oxodecahydropyrrolo[1,2-a]azocine-3-carboxylic acid

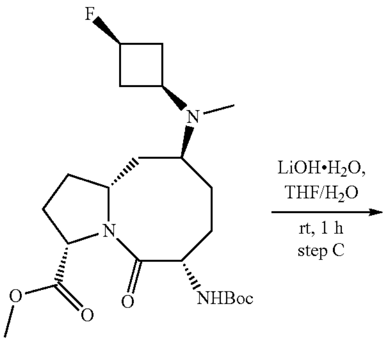

4

To a solution of methyl (3S,6S,9S,10aR)-6-((tert-butoxycarbonyl)amino)-9-(((1s,3R)-3-fluorocyclobutyl)(methyl)amino)-5-oxodecahydropyrrolo[1,2-a]azocine-3-carboxylate (4, 600 mg, 1.36 mmol, 1 eq) in a 3:1 mixture of THF/$H_2O$ (12 mL) was added lithium hydroxide monohydrate (171.1 mg, 4.08 mmol, 3 eq.), and the resulting mixture was stirred at room temperature for 1 h, then the reaction mixture was adjusted pH=3 with 1M HCl (aq.), then extracted with EtOAc (15 mL*3). The combined organic layers were washed with brine (10 mL), dried over anhydrous $Na_2SO_4$, filtered and concentrated under reduced pressure to give (3S,6S,9S,10aR)-6-((tert-butoxycarbonyl)amino)-9-(((1s,3R)-3-fluorocyclobutyl)(methyl)amino)-5-oxodecahydropyrrolo[1,2-a]azocine-3-carboxylic acid (5, 500 mg, 1.17 mmol, 86%) as a white solid. LCMS (ESI): m/z=428 $[M+H]^+$.

Step D: tert-butyl ((3S,6S,9S,10aR)-9-(((1s,3R)-3-fluorocyclobutyl)(methyl)amino)-5-oxo-3-(4-azaspiro[2.4]heptane-4-carbonyl)decahydropyrrolo[1,2-a]azocin-6-yl)carbamate

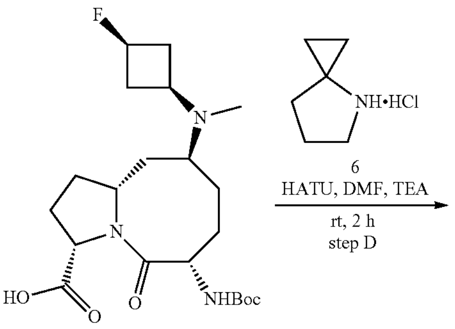

5

-continued

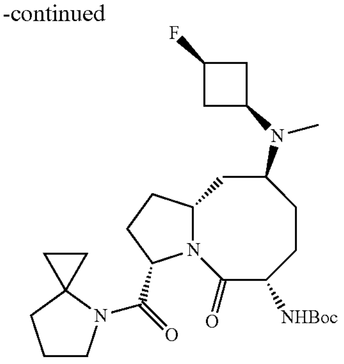

7

To a solution of (3S,6S,9S,10aR)-6-((tert-butoxycarbonyl)amino)-9-(((1s,3R)-3-fluorocyclobutyl)(methyl)amino)-5-oxodecahydropyrrolo[1,2-a]azocine-3-carboxylic acid (5, 100 mg, 0.234 mmol, 1 eq) in DMF (3 mL) were added TEA (70.9 mg, 0.702 mmol, 3 eq.), HATU (97.8 mg, 0.257 mmol, 1.1 eq.) and 4-azaspiro[2.4]heptane hydrochloride (6, 34.4 mg, 0.257 mmol, 1.1 eq.), and the resulting mixture was stirred at room temperature for 2 h. LCMS indicated the complete consumption of the starting material. The reaction mixture was purified by reverse phase chromatography using a C18 column eluting with 20-70% $CH_3CN$ in water (0.1% TFA) to give tert-butyl ((3S,6S,9S,10aR)-9-(((1s,3R)-3-fluorocyclobutyl)(methyl)amino)-5-oxo-3-(4-azaspiro[2.4]heptane-4-carbonyl)decahydropyrrolo[1,2-a]azocin-6-yl)carbamate (7, 105 mg, 0.207 mmol, 88.5%) as a white solid. LCMS (ESI): m/z=507 $[M+H]^+$.

Step E: (3S,6S,9S,10aR)-6-amino-9-(((1s,3R)-3-fluorocyclobutyl)(methyl)amino)-3-(4-azaspiro[2.4]heptane-4-carbonyl)octahydropyrrolo[1,2-a]azocin-5(1H)-one

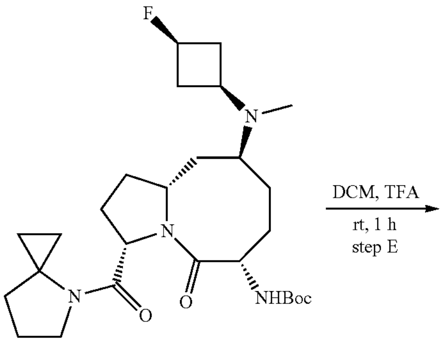

7

-continued

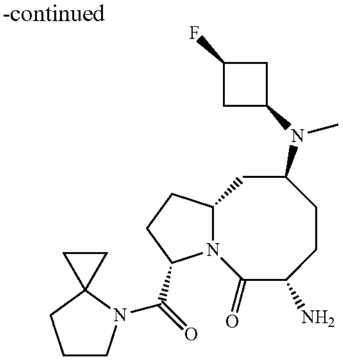

8

To a solution of tert-butyl ((3S,6S,9S,10aR)-9-(((1s,3R)-3-fluorocyclobutyl)(methyl)amino)-5-oxo-3-(4-azaspiro[2.4]heptane-4-carbonyl)decahydropyrrolo[1,2-a]azocin-6-yl)carbamate (7, 80 mg, 0.158 mmol, 1 eq.) in DCM (2 mL) was added TFA (2 mL), The resulting mixture was stirred for 1 h at room temperature, LCMS show that the reaction was completed. The resulting mixture was concentrated to dryness under reduced pressure to afford crude product (3S,6S,9S,10aR)-6-amino-9-(((1s,3R)-3-fluorocyclobutyl)(methyl)amino)-3-(4-azaspiro[2.4]heptane-4-carbonyl)octahydropyrrolo[1,2-a]azocin-5(1H)-one (8, 80 mg, TFA salt) as a yellow oil which used in the next step without further purification. LCMS (ESI): m/z=407 $[M+H]^+$.

Step F: propyl (((R)-fluoro(2-(((3S,6S,9S,10aR)-9-(((1s,3R)-3-fluorocyclobutyl)(methyl)amino)-5-oxo-3-(4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate

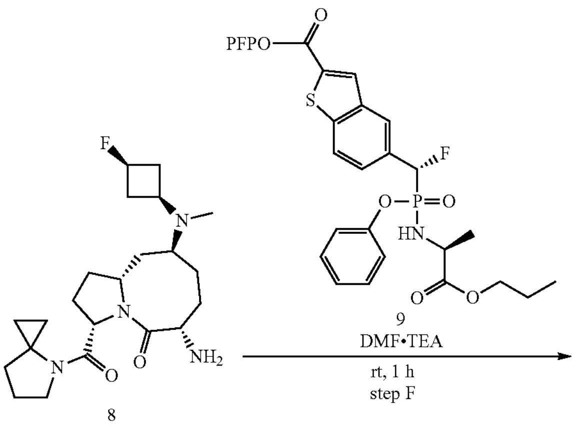

8

-continued

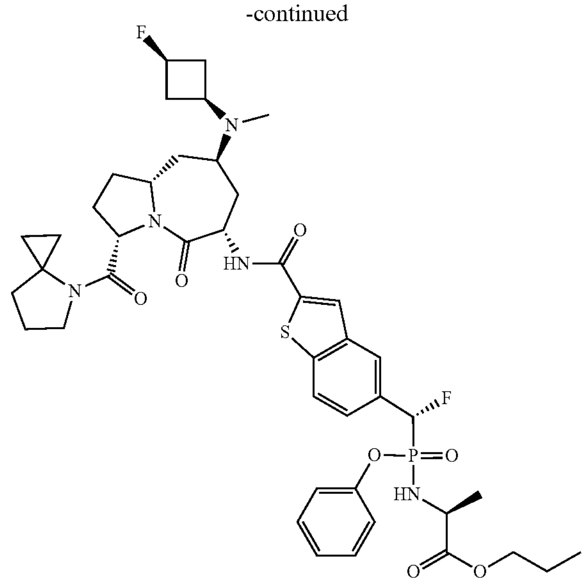

To a solution of (3S,6S,9S,10aR)-6-amino-9-(((1s,3R)-3-fluorocyclobutyl)(methyl)amino)-3-(4-azaspiro[2.4]heptane-4-carbonyl)octahydropyrrolo[1,2-a]azocin-5(1H)-one (8, 40 mg, TFA salt) in DMF (2 mL) was added TEA (23.9 mg, 0.228 mmol, 3 eq.), perfluorophenyl 5-((1R)-fluoro((((S)-1-oxo-1-propoxypropan-2-yl)amino)(phenoxy)phosphoryl)methyl)benzo[b]thiophene-2-carboxylate (9, 50 mg, 0.076 mmol, 1 eq.). The resulting mixture was stirred for 1 h at room temperature, then the crude product was purified by Prep-HPLC to give propyl (((R)-fluoro(2-(((3S,6S,9S,10aR)-9-(((1s,3R)-3-fluorocyclobutyl)(methyl)amino)-5-oxo-3-(4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate (Compound C85, 9 mg, 0.0103 mmol, 13.5%) as a white solid. LCMS (ESI): m/z=868.5 $[M+H]^+$. $^1H$ NMR (400 MHz, DMSO-$d_6$) δ (ppm) 8.84-8.71 (m, 1H), 8.27 (s, 1H), 8.10-8.03 (m, 2H), 7.61 (d, J=8.1 Hz, 1H), 7.36 (t, J=7.8 Hz, 2H), 7.21-7.11 (m, 3H), 6.27-6.06 (m, 2H), 4.90-4.65 (m, 2H), 4.45 (t, J=8.5 Hz, 1H), 4.33-4.23 (m, 1H), 3.97-3.73 (m, 4H), 3.64-3.54 (m, 1H), 2.97 (s, 1H), 2.65-2.55 (m, 1H), 2.41-2.24 (m, 2H), 2.13-1.92 (m, 6H), 1.91-1.37 (m, 17H), 1.17-1.09 (m, 3H), 0.86-0.75 (m, 3H), 0.46-0.35 (m, 2H). $^{19}F$ NMR (377 MHz, DMSO-$d_6$) δ (ppm) −165.30 (s), −194.33 (d, J=82.9 Hz), −196.33 (d, J=86.1 Hz). $^{31}P$ NMR (162 MHz, DMSO-$d_6$) δ (ppm) 17.32 (d, J=82.6 Hz), 17.07 (d, J=86.5 Hz).

Step G: ((R)-fluoro(2-(((3S,6S,9S,10aR)-9-(((1s,3R)-3-fluorocyclobutyl)(methyl)amino)-5-oxo-3-(4-azaspiro[2.4]heptane-4-carbonyl)decahydropyrrolo[1,2-a]azocin-6-yl)carbamoyl)benzo[b]thiophen-5-yl)methyl)phosphonic acid

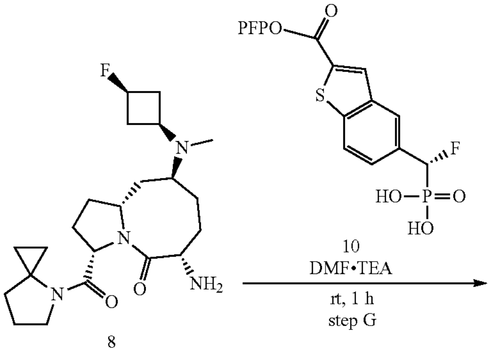

8

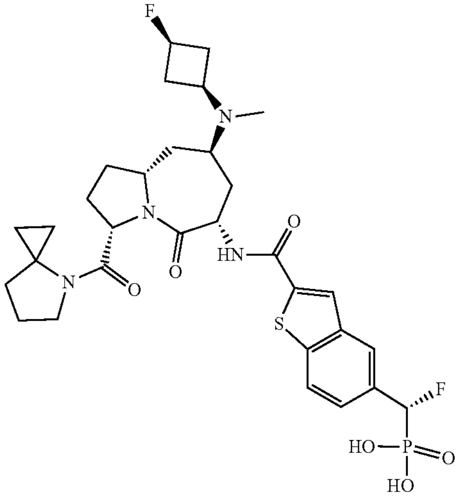

To a solution of (3S,6S,9S,10aR)-6-amino-9-(((1s,3R)-3-fluorocyclobutyl)(methyl)amino)-3-(4-azaspiro[2.4]heptane-4-carbonyl)octahydropyrrolo[1,2-a]azocin-5(1H)-one (8, 40 mg, TFA salt) in DMF (2 mL) was added TEA (23.9 mg, 0.228 mmol, 3 eq.), (R)-(fluoro(2-((perfluorophenoxy)carbonyl)benzo[b]thiophen-5-yl)methyl)phosphonic acid (10, 34 mg, 0.076 mmol, 1 eq). The resulting mixture was stirred for 1 h at room temperature then the crude product was purified by Prep-HPLC to afford ((R)-fluoro(2-(((3S,6S,9S,10aR)-9-(((1s,3R)-3-fluorocyclobutyl)(methyl)amino)-5-oxo-3-(4-azaspiro[2.4]heptane-4-carbonyl)decahydropyrrolo[1,2-a]azocin-6-yl)carbamoyl)benzo[b]thiophen-5-yl)methyl)phosphonic acid (Compound A39, 26.7 mg, 0.039 mmol, 51.3%) as a white solid. LCMS (ESI): m/z=679.4 $[M+H]^+$. $^1H$ NMR (400 MHz, $CD_3OD$-$d_4$) δ (ppm) 8.04 (d, J=10.2 Hz, 2H), 7.94 (d, J=8.5 Hz, 1H), 7.60 (d, J=8.3 Hz, 1H), 5.80 (dd, J=44.6, 8.0 Hz, 1H), 4.83-4.74 (m, 2H), 4.72-4.49 (m, 2H), 4.13-3.81 (m, 2H), 3.69-3.43 (m, 2H), 3.00-2.74 (m, 2H), 2.67 (s, 3H), 2.52-2.41 (m, 2H), 2.30-2.13 (m, 3H), 2.06-1.69 (m, 13H), 0.56-0.45 (m, 2H). $^{19}F$ NMR (376 MHz, $CD_3OD$-$d_4$) δ (ppm) −169.68 (s), −198.76 (d, J=83.9 Hz). $^{31}P$ NMR (162 MHz, $CD_3OD$-$d_4$) δ (ppm) 12.46 (d, J=83.5 Hz). (TFA salt).

Synthesis of propyl (((S)-(2-(((3S,6S,9S,10aR)-9-(ethyl((1r,3S)-3-(trifluoromethoxy)cyclobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)(phenoxy)phosphoryl)-L-alaninate (Compound C119) and ((S)-(2-(((3S,6S,9S,10aR)-9-(ethyl((1s,3R)-3-(trifluoromethoxy)cyclobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)phosphonic acid (Compound A47)

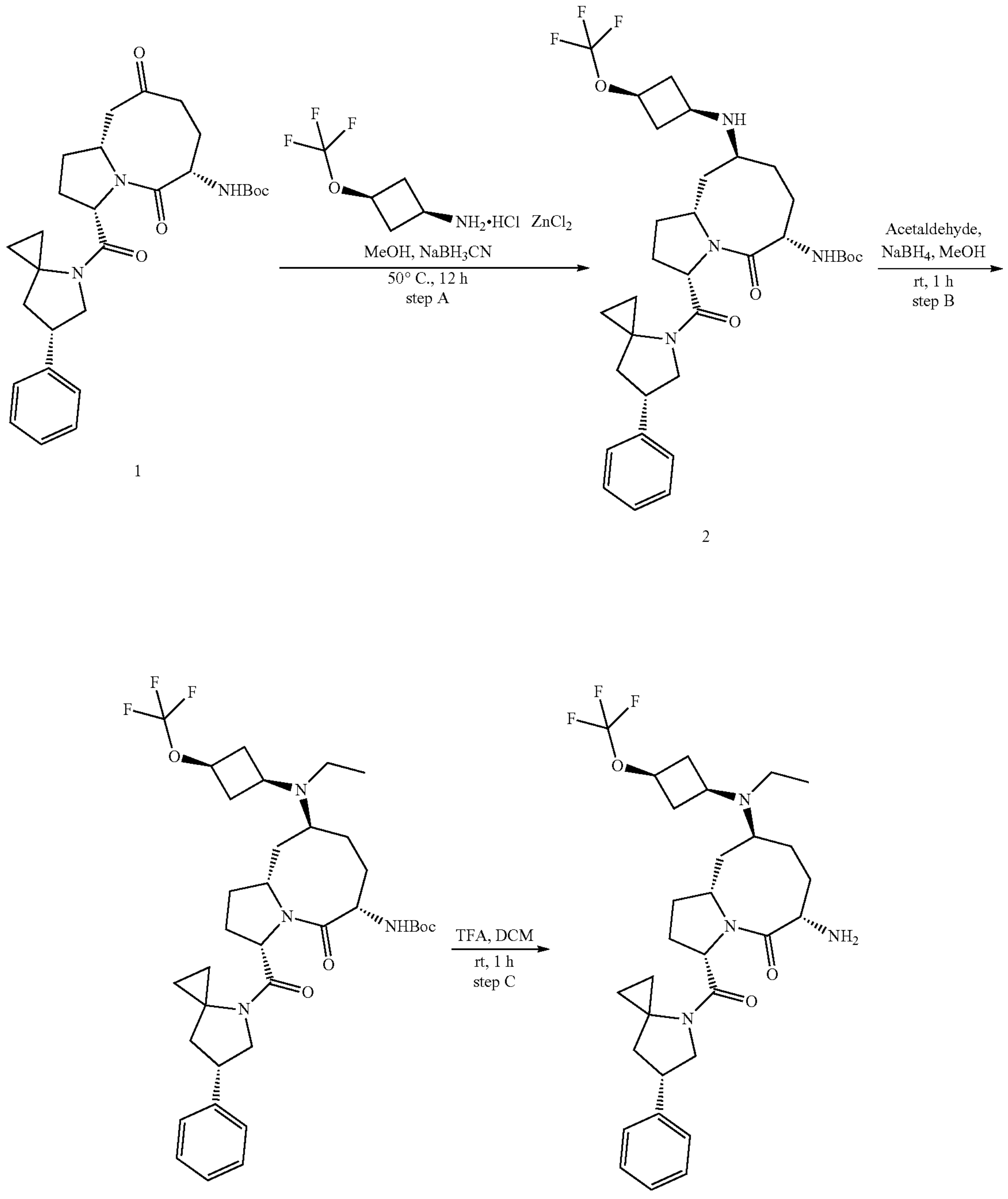

1

2

3

4

-continued
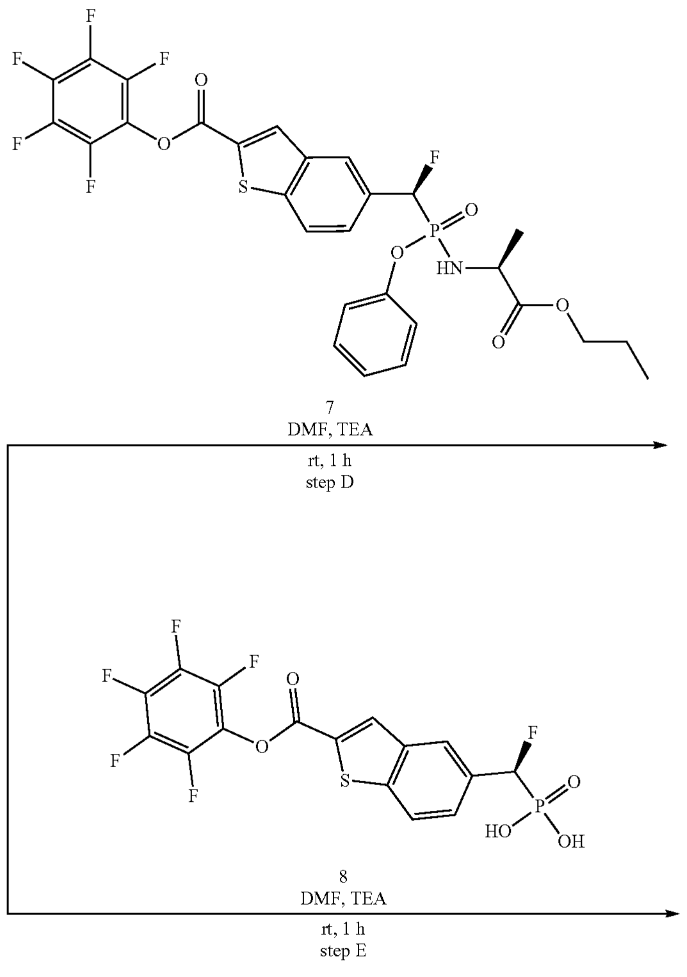

-continued
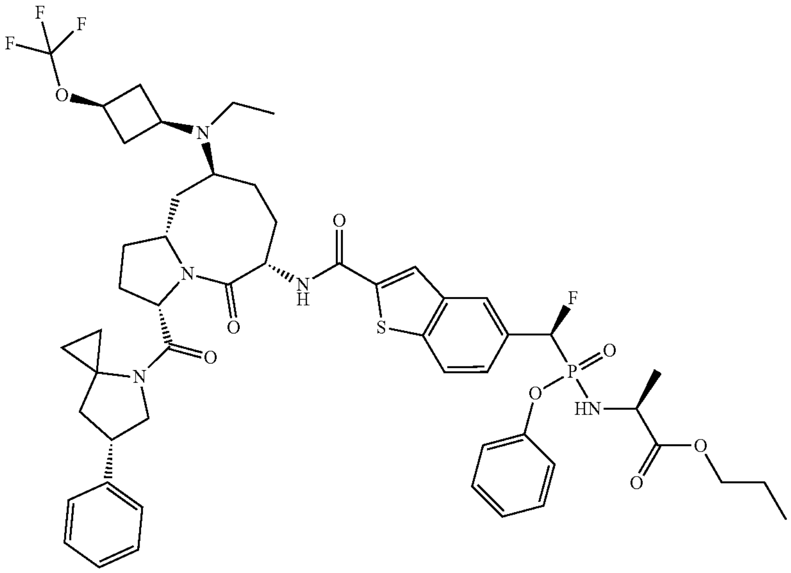
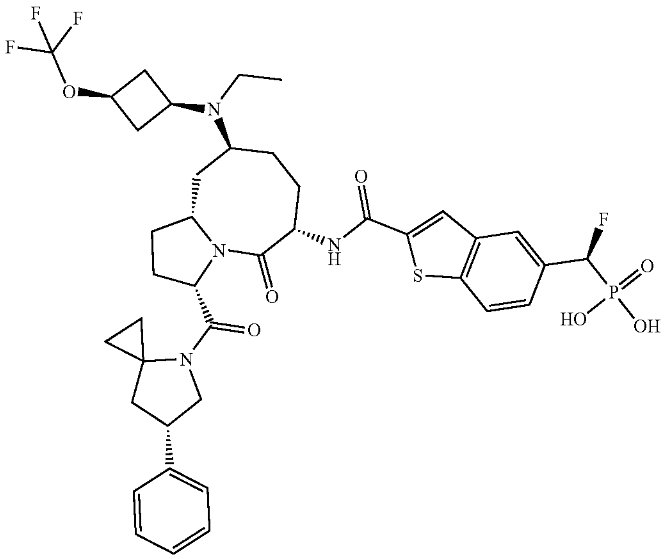

Step A: tert-butyl ((3S,6S,9S,10aR)-5-oxo-3-((S)-6-phenyl-4-azaspiro[2.4]heptane-4-carbonyl)-9-(((1s,3R)-3-(trifluoromethoxy)cyclobutyl)amino)decahydropyrrolo[1,2-a]azocin-6-yl)carbamate

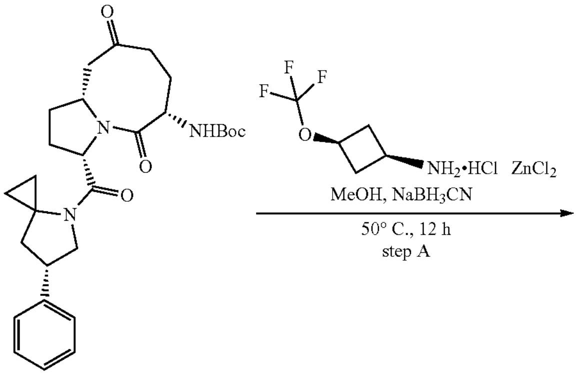

1

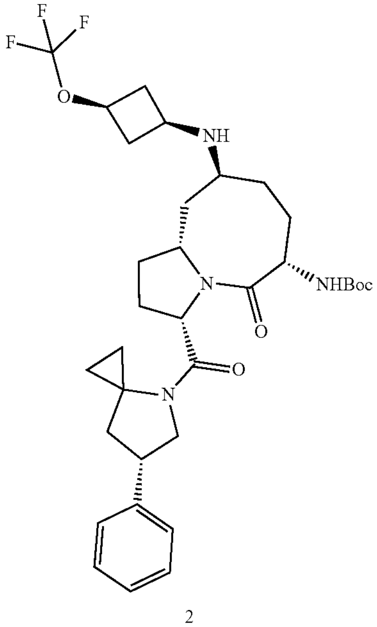

2

To a solution of tert-butyl ((3S,6S,10aR)-5,9-dioxo-3-((S)-6-phenyl-4-azaspiro[2.4]heptane-4-carbonyl)decahydropyrrolo[1,2-a]azocin-6-yl)carbamate (1, 1 g, 2.02 mmol, 1 eq.) in MeOH (20 mL) was added (1s,3s)-3-(trifluoromethoxy)cyclobutan-1-amine hydrochloride (579 mg, 3.03 mml, 1.5 eq.), $ZnCl_2$ (2.75 g, 20.2 mmol, 10 eq.). The resulting mixture was stirred for 1 h at 50° C., then $NaBH_3CN$ (1.27 g, 20.2 mmol, 10 eq.) was added portion wise every 30 mins (2 eq. (254 mg each time) added 5 times). The mixture was stirred for 12 h at 50° C., then cooled to room temperature, and used to the next step directly without further workup. LCMS (ESI): m/z=635 $[M+H]^+$.

Step B: tert-butyl ((3S,6S,9S,10aR)-9-(ethyl((1s,3R)-3-(trifluoromethoxy)cyclobutyl)amino)-5-oxo-3-((S)-6-phenyl-4-azaspiro[2.4]heptane-4-carbonyl)decahydropyrrolo[1,2-a]azocin-6-yl)carbamate

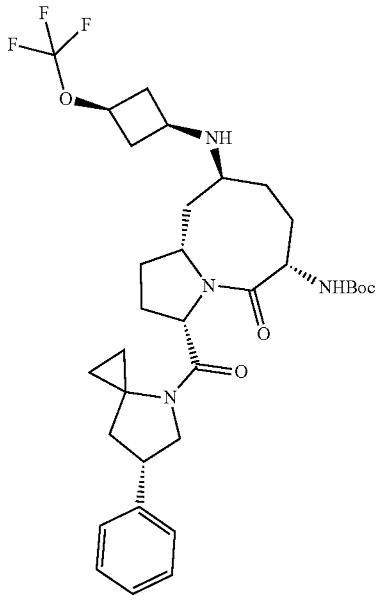

2

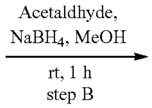

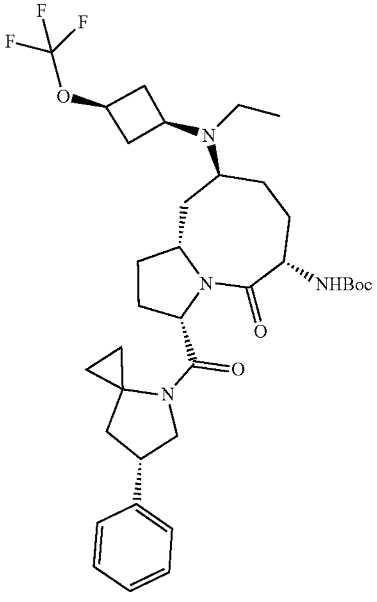

3

To the above mixture (step A) was added acetaldehyde (1 mL) at room temperature, the mixture was stirred for 10 min, then $NaBH_4$ (767 mg, 20.2 mmol, 10 eq.) was added to the mixture and stirred for another 10 min. The reaction was quenched by $NH_4Cl$ (sat. aq), diluted with $H_2O$ (100 mL), then extracted with EtOAc (50 mL×3). The organic layers were combined and washed with brine (30 mL), dried over $Na_2SO_4$, then concentrated under reduced pressure. The crude product was purified by C18 column (ACN:$H_2O$ (0.1% ammonium hydroxide)=5%-70%) to afford tert-butyl ((3S,6S,9S,10aR)-9-(ethyl((1s,3R)-3-(trifluoromethoxy)cyclobutyl)amino)-5-oxo-3-((S)-6-phenyl-4-azaspiro[2.4]heptane-4-carbonyl)decahydropyrrolo[1,2-a]azocin-6-yl)carbamate (3, 470 mg, 0.709 mmol, 35.1% yield, two steps) as a white solid. LCMS (ESI): m/z=663 $[M+H]^+$.

Step C: (3S,6S,9S,10aR)-6-amino-9-(ethyl((1s,3R)-3-(trifluoromethoxy)cyclobutyl)amino)-3-((S)-6-phenyl-4-azaspiro[2.4]heptane-4-carbonyl)octahydropyrrolo[1,2-a]azocin-5(1H)-one

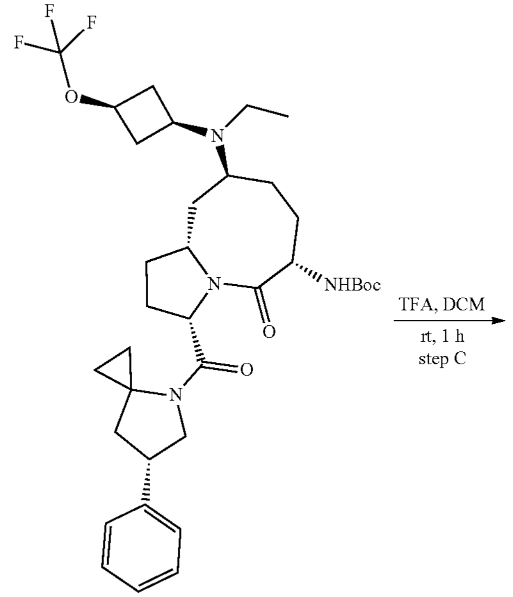

3

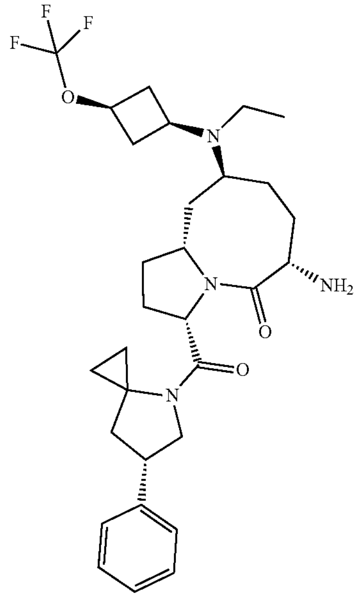

4

To a solution of tert-butyl ((3S,6S,9S,10aR)-9-(ethyl((1s,3R)-3-(trifluoromethoxy)cyclobutyl)amino)-5-oxo-3-((S)-6-phenyl-4-azaspiro[2.4]heptane-4-carbonyl)decahydropyrrolo[1,2-a]azocin-6-yl)carbamate (3, 120 mg, 0.181 mmol) in DCM (2 mL) was added TFA (2 mL) and the resulting mixture was stirred for 1 h at room temperature, then the resulting mixture was concentrated to dryness under reduced pressure to afford crude product (3S,6S,9S,10aR)-6-amino-9-(ethyl((1s,3R)-3-(trifluoromethoxy)cyclobutyl)amino)-3-((S)-6-phenyl-4-azaspiro[2.4]heptane-4-carbonyl)octahydropyrrolo[1,2-a]azocin-5(1H)-one (4, 30 mg, TFA salt) as a yellow oil which used in the next step without further purification. LCMS (ESI): m/z=563 [M+H]$^+$.

Step D: propyl (((S)-(2-(((3S,6S,9S,10aR)-9-(ethyl ((1s,3R)-3-(trifluoromethoxy)cyclobutyl)amino)-5-oxo-3-((S)-6-phenyl-4-azaspiro[2.4]heptane-4-carbonyl)decahydropyrrolo[1,2-a]azocin-6-yl) carbamoyl)benzo[b]thiophen-5-yl)fluoromethyl) (phenoxy)phosphoryl)-L-alaninate

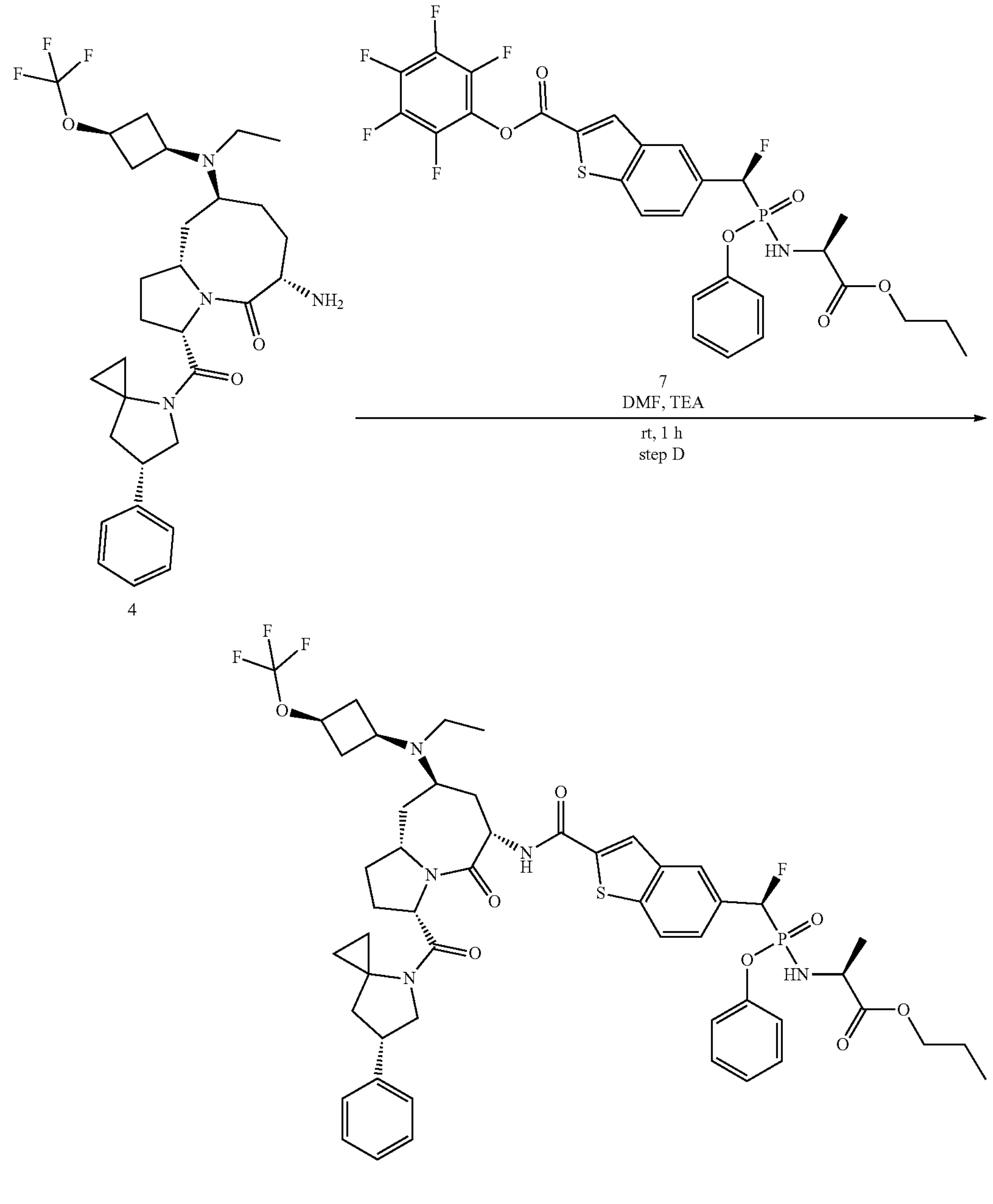

4

To a solution of (3S,6S,9S,10aR)-6-amino-9-(ethyl((1s,3R)-3-(trifluoromethoxy)cyclobutyl)amino)-3-((S)-6-phenyl-4-azaspiro[2.4]heptane-4-carbonyl)octahydropyrrolo[1,2-a]azocin-5(1H)-one (4, 30 mg, TFA salt) in DMF (2 mL) was added TEA (13.7 mg, 0.135 mmol, 3 eq.), perfluorophenyl 5-((1S)-fluoro((((S)-1-oxo-1-propoxypropan-2-yl)amino)(phenoxy)phosphoryl)methyl)benzo[b]thiophene-2-carboxylate (7, 29 mg, 0.045 mmol, 1 eq). The resulting mixture was stirred for 1 h at room temperature, then the crude product was purified by Prep-HPLC to afford propyl (((S)-(2-(((3S,6S,9S,10aR)-9-(ethyl((1s,3R)-3-(trifluoromethoxy)cyclobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)(phenoxy)phosphoryl)-L-alaninate (Compound C119, 26 mg, 0.025 mmol, 55.5%) as a white solid. LCMS (ESI): m/z=1024.8 $[M+H]^+$. 1H NMR (400 MHz, DMSO-$d_6$) δ (ppm) 8.89-8.68 (m, 1H), 8.27 (d, J=3.8 Hz, 1H), 8.13-8.00 (m, 2H), 7.60 (t, J=7.5 Hz, 1H), 7.40-7.26 (m, 6H), 7.24-7.08 (m, 4H), 6.34-6.04 (m, 2H), 4.77-4.62 (m, 1H), 4.57-4.41 (m, 2H), 4.34-4.22 (m, 1H), 4.12 (t, J=8.4 Hz, 1H), 3.96-3.66 (m, 4H), 3.60-3.47 (m, 1H), 3.11-2.98 (m, 1H), 2.92-2.79 (m, 1H), 2.60-2.54 (m, 1H), 2.47-2.40 (m, 1H), 2.34-1.41 (m, 21H), 1.17 (d, J=7.2 Hz, 1H), 1.01-0.92 (m, 4H), 0.81 (t, J=7.4 Hz, 3H), 0.53-0.33 (m, 2H). $^{19}F$ NMR (376 MHz, DMSO-$d_6$) δ (ppm) −57.62 (s), −194.20 (d, J=82.7 Hz), −196.08 (d, J=86.9 Hz). $^{31}P$ NMR (162 MHz, DMSO-$d_6$) δ (ppm) 16.94 (d, J=82.4 Hz), 17.32 (d, J=87.0 Hz).

Step E: ((S)-(2-(((3S,6S,9S,10aR)-9-(ethyl((1s,3R)-3-(trifluoromethoxy)cyclobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)phosphonic acid

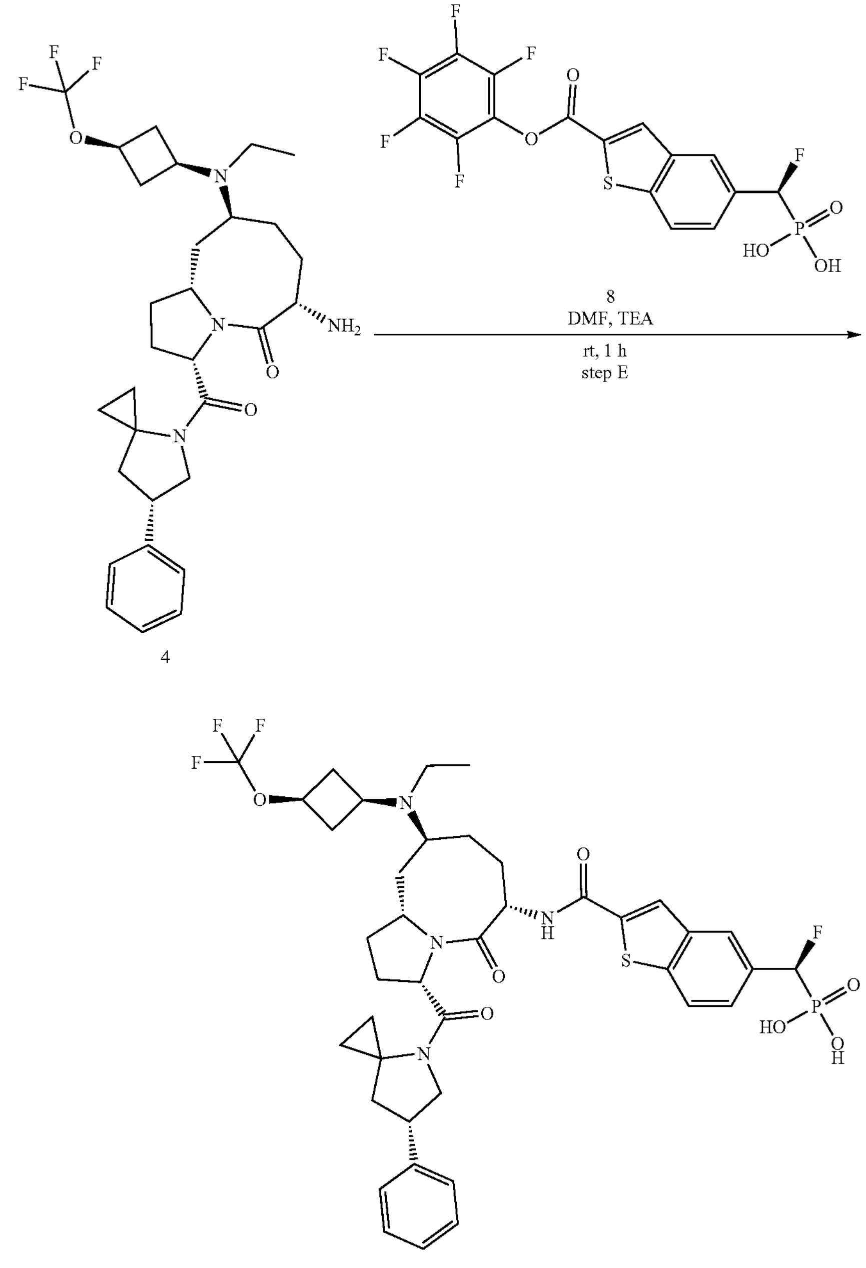

To a solution of (3S,6S,9S,10aR)-6-amino-9-(ethyl((1s,3R)-3-(trifluoromethoxy)cyclobutyl)amino)-3-((S)-6-phenyl-4-azaspiro[2.4]heptane-4-carbonyl)octahydropyrrolo[1,2-a]azocin-5(1H)-one (4, 30 mg, TFA salt) in DMF (2 mL) was added TEA (13.7 mg, 0.135 mmol, 3 eq.), (S)-(fluoro(2-((perfluorophenoxy)carbonyl)benzo[b]thiophen-5-yl)methyl)phosphonic acid (8, 20 mg, 0.045 mmol, 1 eq.). The resulting mixture was stirred for 1 h at room temperature then the crude product was purified by Prep-HPLC to afford ((S)-(2-(((3S,6S,9S,10aR)-9-(ethyl((1s,3R)-3-(trifluoromethoxy)cyclobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)phosphonic acid (Compound A47, 9.4 mg, 0.011 mmol, 24.4%) as a white solid. LCMS (ESI): m/z=835.3 $[M+H]^+$. 1H NMR (400 MHz, $CD_3OD-d_4$) δ (ppm) 8.08 (s, 1H), 8.07 (s, 1H), 7.95 (d, J=8.5 Hz, 1H), 7.62 (d, J=8.4 Hz, 1H), 7.45-7.36 (m, 2H), 7.36-7.28 (m, 2H), 7.28-7.19 (m, 1H), 5.80 (dd, J=44.6, 8.0 Hz, 1H), 4.86-4.77 (m, 2H), 4.75-4.48 (m, 3H), 4.19-3.90 (m, 3H), 3.84-3.53 (m, 2H), 3.28-2.93 (m, 3H), 2.91-2.81 (m, 1H), 2.75-2.60 (m, 1H), 2.57-2.48 (m, 1H), 2.46-2.35 (m, 1H), 2.35-2.18 (m, 4H), 2.17-1.72 (m, 7H), 1.70-1.58 (m, 1H), 1.51-1.34 (m, 3H), 0.71-0.41 (m, 2H). $^{19}F$ NMR (377 MHz, $CD_3OD-d_4$) δ (ppm) −61.29 (s), −198.41 (d, J=82.6 Hz). $^{31}P$ NMR (162 MHz, $CD_3OD-d_4$) δ (ppm) 12.06 (d, J=82.0 Hz).

Synthesis of propyl (((S)-(2-(((3S,6S,9S,10aR)-9-(ethyl(4,4,4-trifluorobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)(phenoxy)phosphoryl)-L-alaninate (Compound C101) and ((S)-(2-(((3S,6S,9S,10aR)-9-(ethyl(4,4,4-trifluorobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)phosphonic acid (Compound A44)

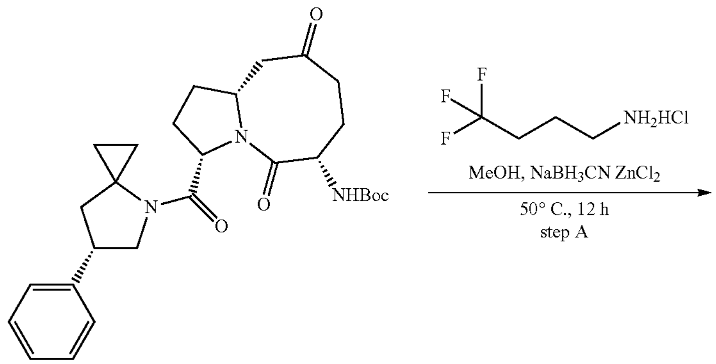

1

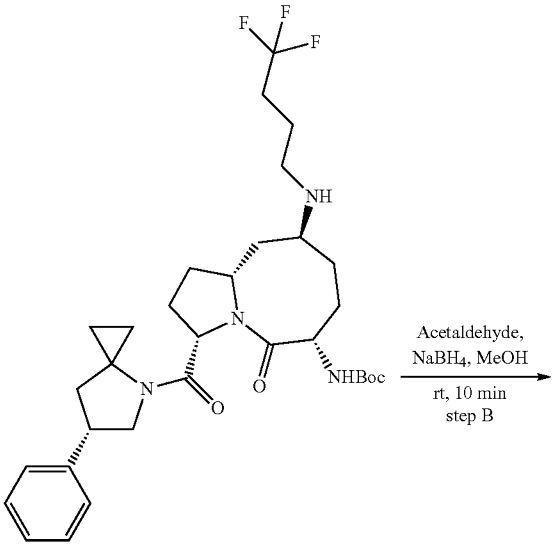

2

-continued
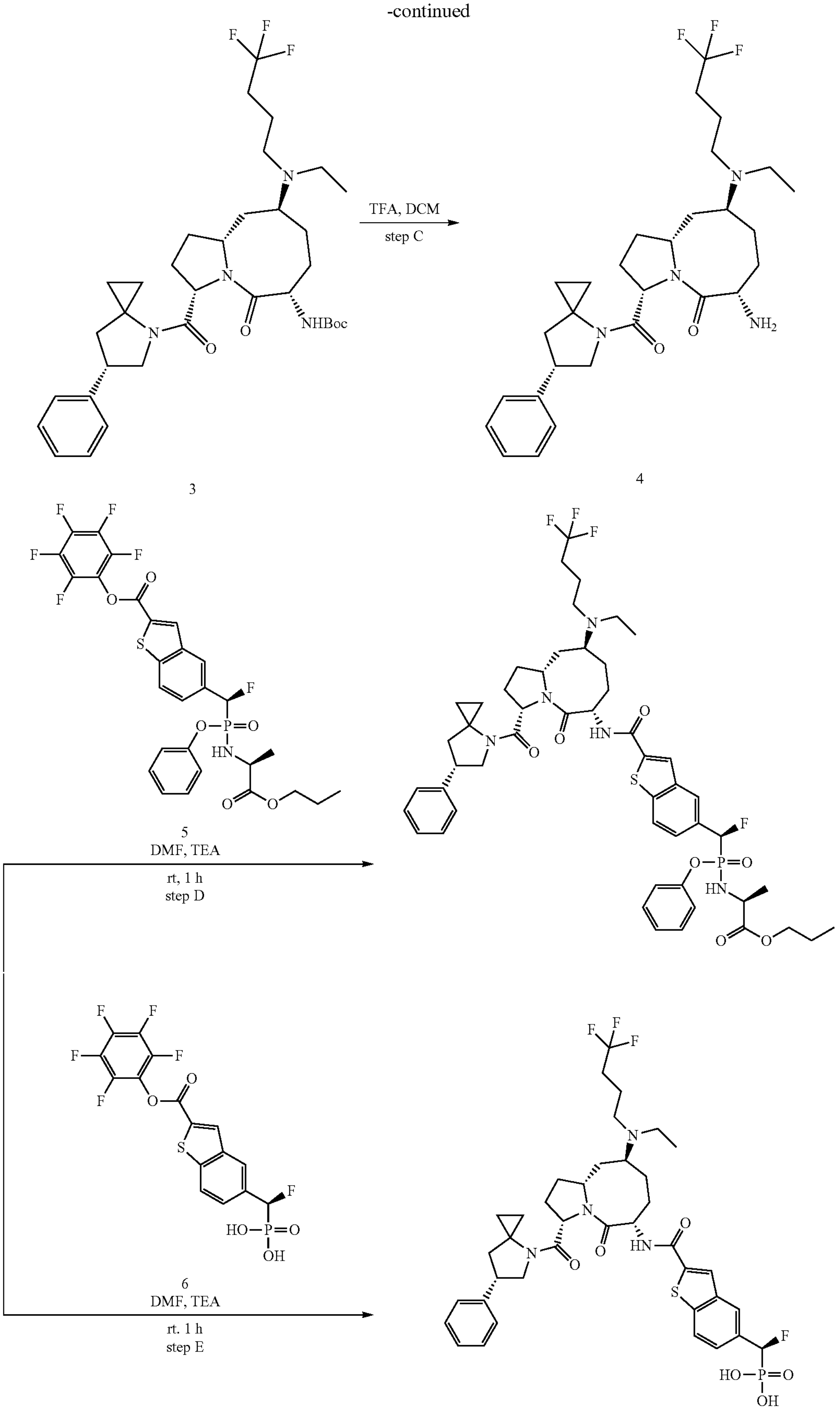

Step A: tert-butyl ((3S,6S,9S,10aR)-5-oxo-3-((S)-6-phenyl-4-azaspiro[2.4]heptane-4-carbonyl)-9-((4,4,4-trifluorobutyl)amino)decahydropyrrolo[1,2-a]azocin-6-yl)carbamate

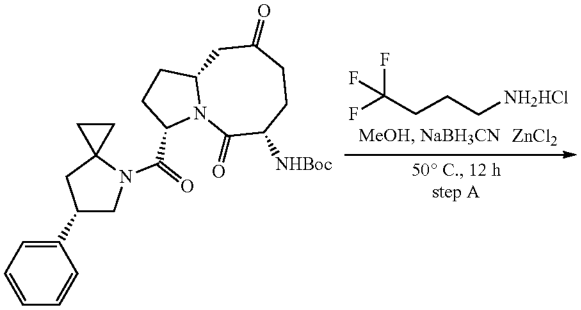

1

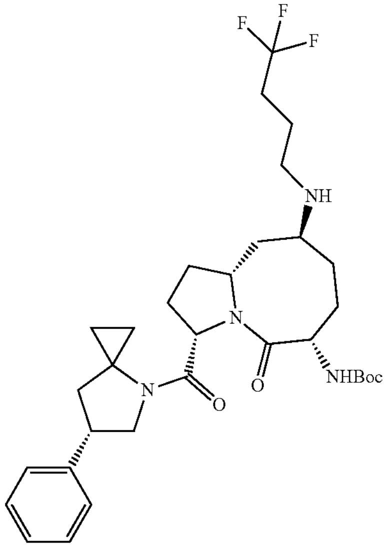

2

To a solution of tert-butyl ((3S,6S,10aR)-5,9-dioxo-3-((S)-6-phenyl-4-azaspiro[2.4]heptane-4-carbonyl)decahydropyrrolo[1,2-a]azocin-6-yl)carbamate (1, 1 g, 2.02 mmol, 1 eq.) in MeOH (20 mL) was added 4,4,4-trifluorobutan-1-amine hydrochloride (494 mg, 3.03 mml, 1.5 eq.), $ZnCl_2$ (2.75 g, 20.2 mmol, 10 eq.). The mixture was stirred for 1 h at 50° C., then $NaBH_3CN$ (1.27 g, 20.2 mmol, 10 eq.) was added portion wise every 30 mins (2 eq. (254 mg each time) added 5 times). The mixture was stirred for 12 h at 50° C., then cooled to room temperature and used directly in the next step without further workup. LCMS (ESI): m/z=607 $[M+H]^+$.

Step B: tert-butyl ((3S,6S,9S,10aR)-9-(ethyl(4,4,4-trifluorobutyl)amino)-5-oxo-3-((S)-6-phenyl-4-azaspiro[2.4]heptane-4-carbonyl)decahydropyrrolo[1,2-a]azocin-6-yl)carbamate

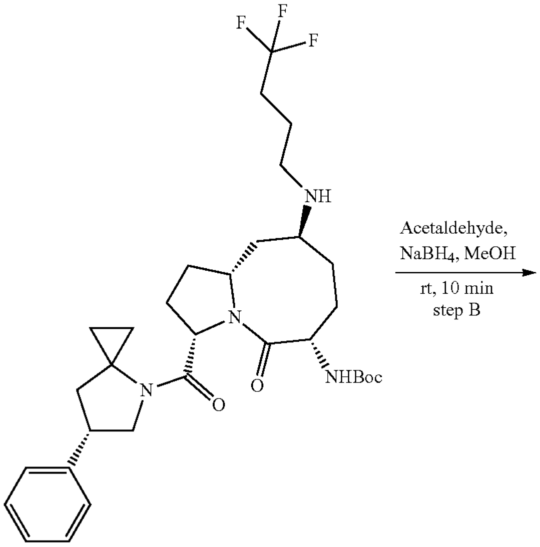

2

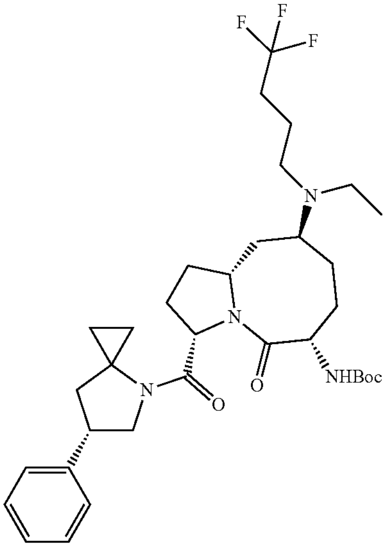

3

To the above mixture (step A) was added 40% acetaldehyde (1 mL) at room temperature, and stirred for 10 min, then $NaBH_4$ (767 mg, 20.2 mmol, 10 eq.) was added to the mixture, stirred for additional 10 min, then the reaction was quenched by $NH_4Cl$ (sat. aq), diluted with $H_2O$ (100 mL), then extracted with EtOAc (50 mL×3). The organic layers were combined and washed with brine (20 mL), dried over $Na_2SO_4$, then concentrated to dryness under reduced pressure. The crude product was purified by C18 column ($MeCN:H_2O$ (0.1% ammonium hydroxide)=5%-70%) to afford tert-butyl ((3S,6S,9S,10aR)-9-(ethyl(4,4,4-trifluorobutyl)amino)-5-oxo-3-((S)-6-phenyl-4-azaspiro[2.4]heptane-4-carbonyl)decahydropyrrolo[1,2-a]azocin-6-yl)carbamate (3, 650 mg, 1.02 mmol, 50.5% yield, two steps) as a white solid. LCMS (ESI): m/z=635 $[M+H]^+$.

Step C: (3S,6S,9S,10aR)-6-amino-9-(ethyl(4,4,4-trifluorobutyl)amino)-3-((S)-6-phenyl-4-azaspiro[2.4]heptane-4-carbonyl)octahydropyrrolo[1,2-a]azocin-5(1H)-one

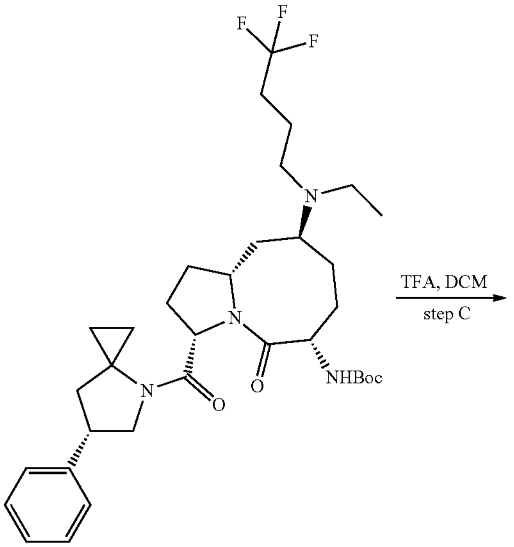

3

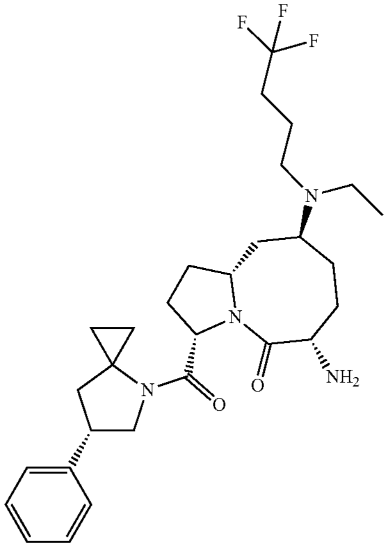

4

To a solution of tert-butyl ((3S,6S,9S,10aR)-9-(methyl(4,4,4-trifluorobutyl)amino)-5-oxo-3-((S)-6-phenyl-4-azaspiro[2.4]heptane-4-carbonyl)decahydropyrrolo[1,2-a]azocin-6-yl)carbamate (3, 120 mg, 0.188 mmol, 1 eq.) in DCM (2 mL) was added TFA (2 mL) and the resulting mixture was stirred for 1 h at room temperature. The resulting mixture was concentrated to dryness under reduced pressure to afford crude product (3S,6S,9S,10aR)-6-amino-9-(ethyl(4,4,4-trifluorobutyl)amino)-3-((S)-6-phenyl-4-azaspiro[2.4]heptane-4-carbonyl)octahydropyrrolo[1,2-a]azocin-5(1H)-one (4, 120 mg, TFA salt) as a yellow oil which used in the next step without further purification. LCMS (ESI): m/z=535 $[M+H]^+$.

Step D: propyl (((S)-(2-(((3S,6S,9S,10aR)-9-(ethyl(4,4,4-trifluorobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)(phenoxy)phosphoryl)-L-alaninate To a solution of (3S,6S,9S,10aR)-6-amino-9-(ethyl(4,4,4-trifluorobutyl)amino)-3-((S)-6-phenyl-4-azaspiro[2.4]heptane-4-carbonyl)octahydropyrrolo[1,2-a]azocin-5(1H)-one (4, 30 mg, TFA salt) in DMF (2 mL) was added TEA (14.3 mg, 0.141 mmol, 3 eq.), perfluorophenyl 5-((1S)-fluoro

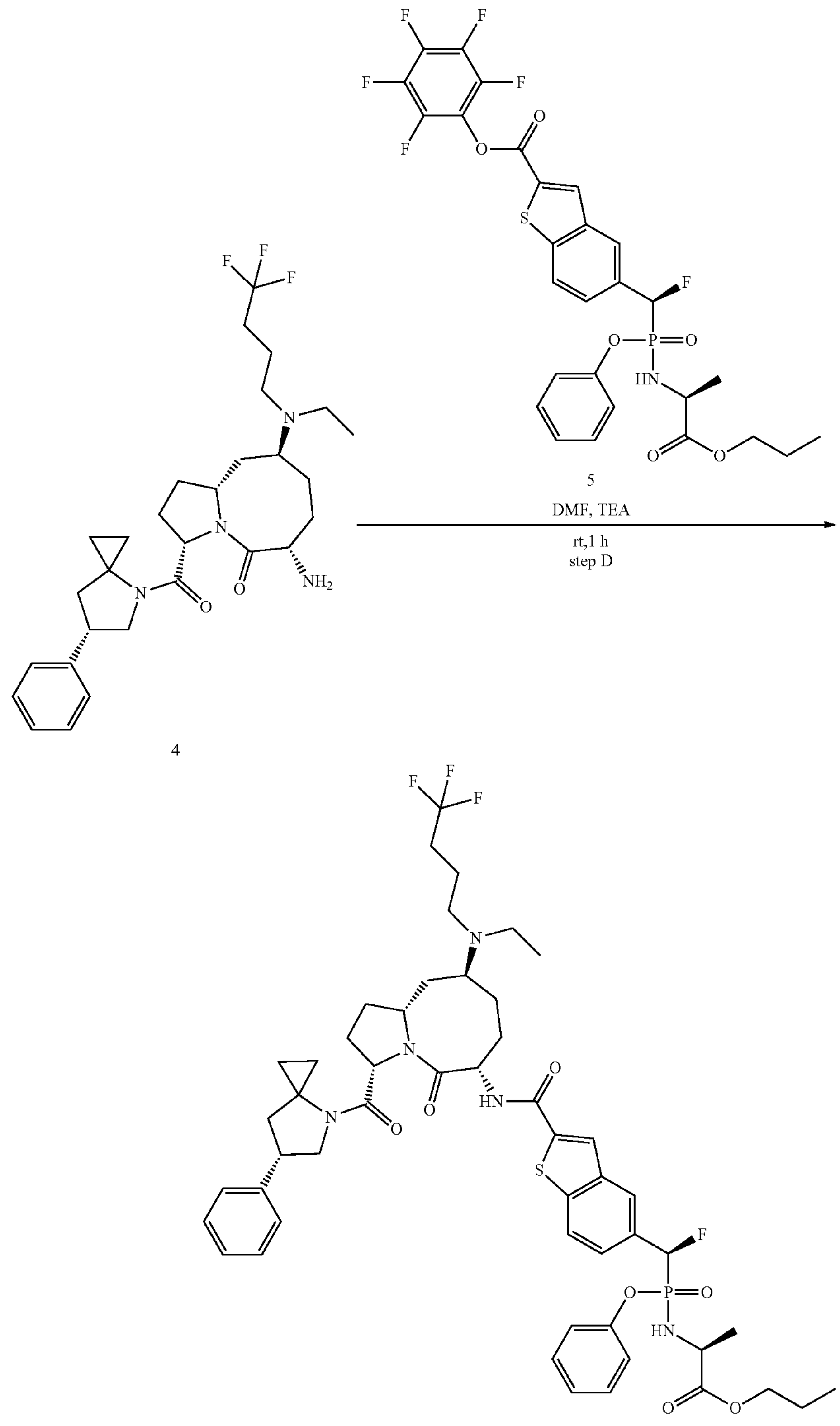

((((S)-1-oxo-1-propoxypropan-2-yl)amino)(phenoxy)phosphoryl)methyl)benzo[b]thiophene-2-carboxylate (5, 30 mg, 0.046 mmol, 1 eq). The resulting mixture was stirred for 1 h at room temperature, LCMS show that the reaction was completed. The crude product was purified by Prep-HPLC to afford propyl (((S)-(2-(((3S,6S,9S,10aR)-9-(ethyl(4,4,4-trifluorobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)(phenoxy)phosphoryl)-L-alaninate (Compound C101, 25 mg, 0.025 mmol, 54.3%) as a white solid. LCMS (ESI): m/z=996.6 $[M+H]^+$. 1H NMR (400 MHz, DMSO-$d_6$) δ (ppm) 8.83-8.74 (m, 1H), 8.29-8.24 (m, 1H), 8.11-8.01 (m, 2H), 7.65-7.55 (m, 1H), 7.39-7.27 (m, 6H), 7.24-7.11 (m, 4H), 6.31-6.08 (m, 2H), 4.78-4.67 (m, 1H), 4.51-4.43 (m, 1H), 4.35-4.25 (m, 1H), 4.16-4.06 (m, 1H), 3.95-3.65 (m, 4H), 3.58-3.48 (m, 1H), 3.07-2.96 (m, 1H), 2.48-2.16 (m, 8H), 2.15-2.08 (m, 1H), 2.04-1.92 (m, 3H), 1.85-1.43 (m, 12H), 1.20-0.92 (m, 6H), 0.84-0.77 (m, 3H), 0.53-0.38 (m, 2H). $^{19}F$ NMR (376 MHz, DMSO $d_6$) δ (ppm) −64.51 (d, J=2.7 Hz), −194.17 (d, J=83.3 Hz), −196.05 (d, J=87.0 Hz). $^{31}P$ NMR (162 MHz, DMSO-$d_6$) δ (ppm) 17.33 (d, J=86.5 Hz), 16.94 (d, J=82.4 Hz).

Step E: ((S)-(2-(((3S,6S,9S,10aR)-9-(ethyl(4,4,4-trifluorobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)phosphonic acid

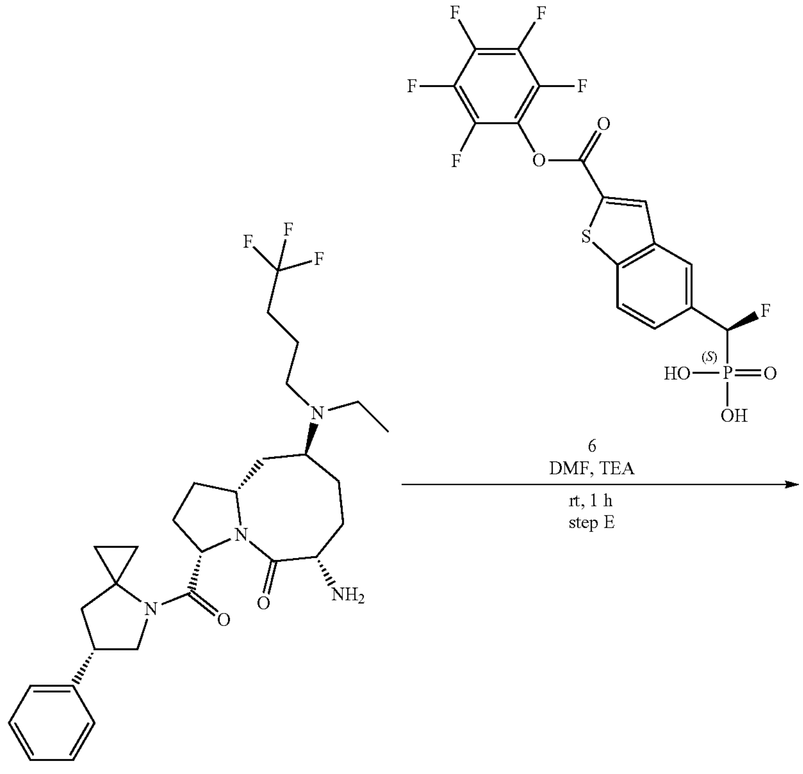

4

-continued

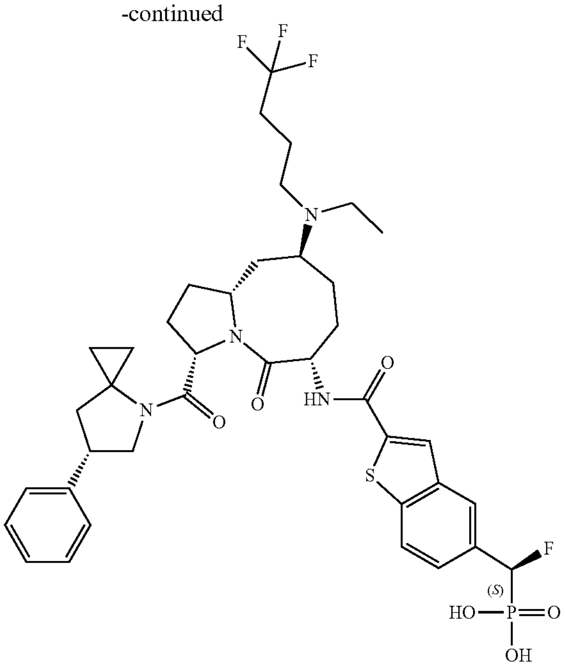

To a solution of (3S,6S,9S,10aR)-6-amino-9-(ethyl(4,4,4-trifluorobutyl)amino)-3-((S)-6-phenyl-4-azaspiro[2.4]heptane-4-carbonyl)octahydropyrrolo[1,2-a]azocin-5(1H)-one (4, 30 mg, TFA salt) in DMF (2 mL) was added TEA (14.3 mg, 0.141 mmol, 3 eq.), (S)-(fluoro(2-((perfluorophenoxy)carbonyl)benzo[b]thiophen-5-yl)methyl)phosphonic acid (6, 21 mg, 0.046 mmol, 1 eq). The resulting mixture was stirred for 1 h at room temperature, then the crude product was purified by Prep-HPLC to afford propyl ((S)-(2-(((3S,6S,9S,10aR)-9-(ethyl(4,4,4-trifluorobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)phosphonic acid (Compound A44, 10 mg, 0.012 mmol, 26.1%) as a white solid. LCMS (ESI): m/z=807.3 $[M+H]^+$. $^1H$ NMR (400 MHz, DMSO-$d_6$) δ (ppm) 8.97 (s, 1H), 8.86-8.78 (m, 1H), 8.24 (d, J=4.2 Hz, 1H), 8.03 (d, J=8.5 Hz, 1H), 7.98 (s, 1H), 7.53 (d, J=8.6 Hz, 1H), 7.38-7.28 (m, 4H), 7.26-7.19 (m, 1H), 5.93-5.73 (m, 1H), 4.86-4.78 (m, 1H), 4.59-4.50 (m, 2H), 4.17-4.10 (m, 1H), 3.88-3.72 (m, 2H), 3.56-3.51 (m, 1H), 3.22-3.06 (m, 4H), 2.49-2.30 (m, 3H), 2.26-2.19 (m, 1H), 2.14-1.73 (m, 13H), 1.58-1.48 (m, 1H), 1.34-1.24 (m, 3H), 0.58-0.41 (m, 2H). $^{19}F$ NMR (376 MHz, DMSO-$d_6$) δ (ppm) −64.75 (s), −194.71 (d, J=81.7 Hz). $^{31}P$ NMR (162 MHz, DMSO-$d_6$) δ (ppm) 10.95 (d, J=80.8 Hz).

Synthesis of ((R)-(2-(((3S,6S,9S,10aR)-9-(((1s,3R)-3-(difluoromethyl)cyclobutyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)phosphonic acid (Compound A35) and propyl ((S)-((R)-(2-(((3S,6S,9S,10aR)-9-(((1s,3R)-3-(difluoromethyl)cyclobutyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)(phenoxy)phosphoryl)-L-alaninate (Compound C71)

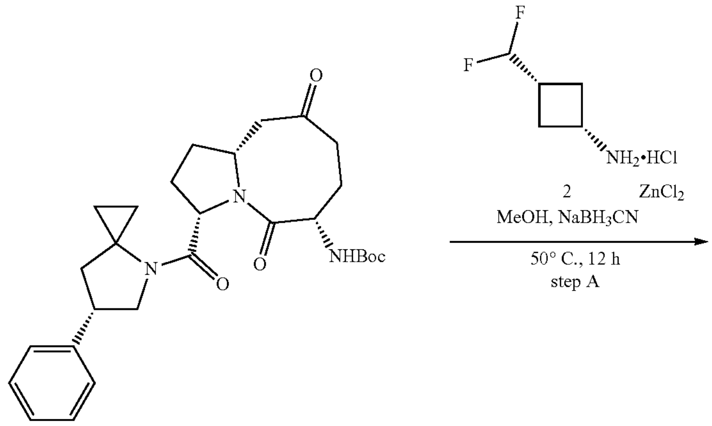

1

-continued
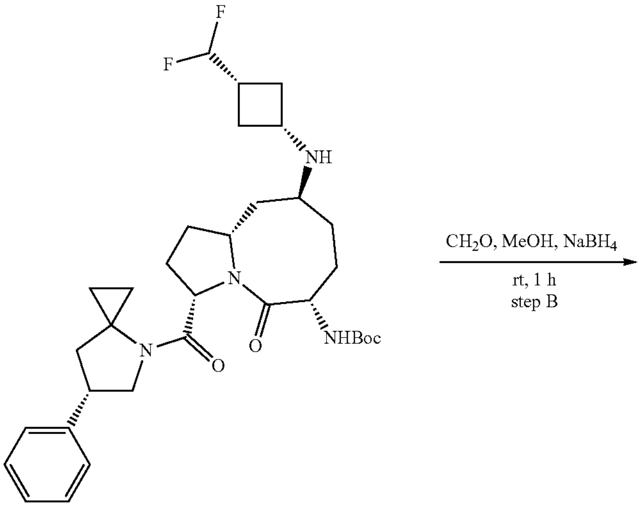
3
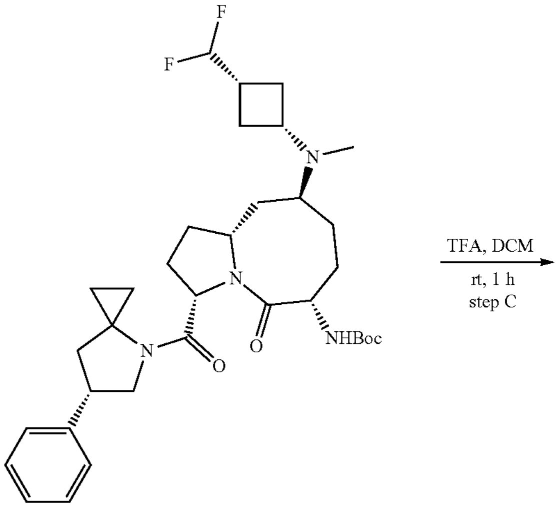
4

-continued
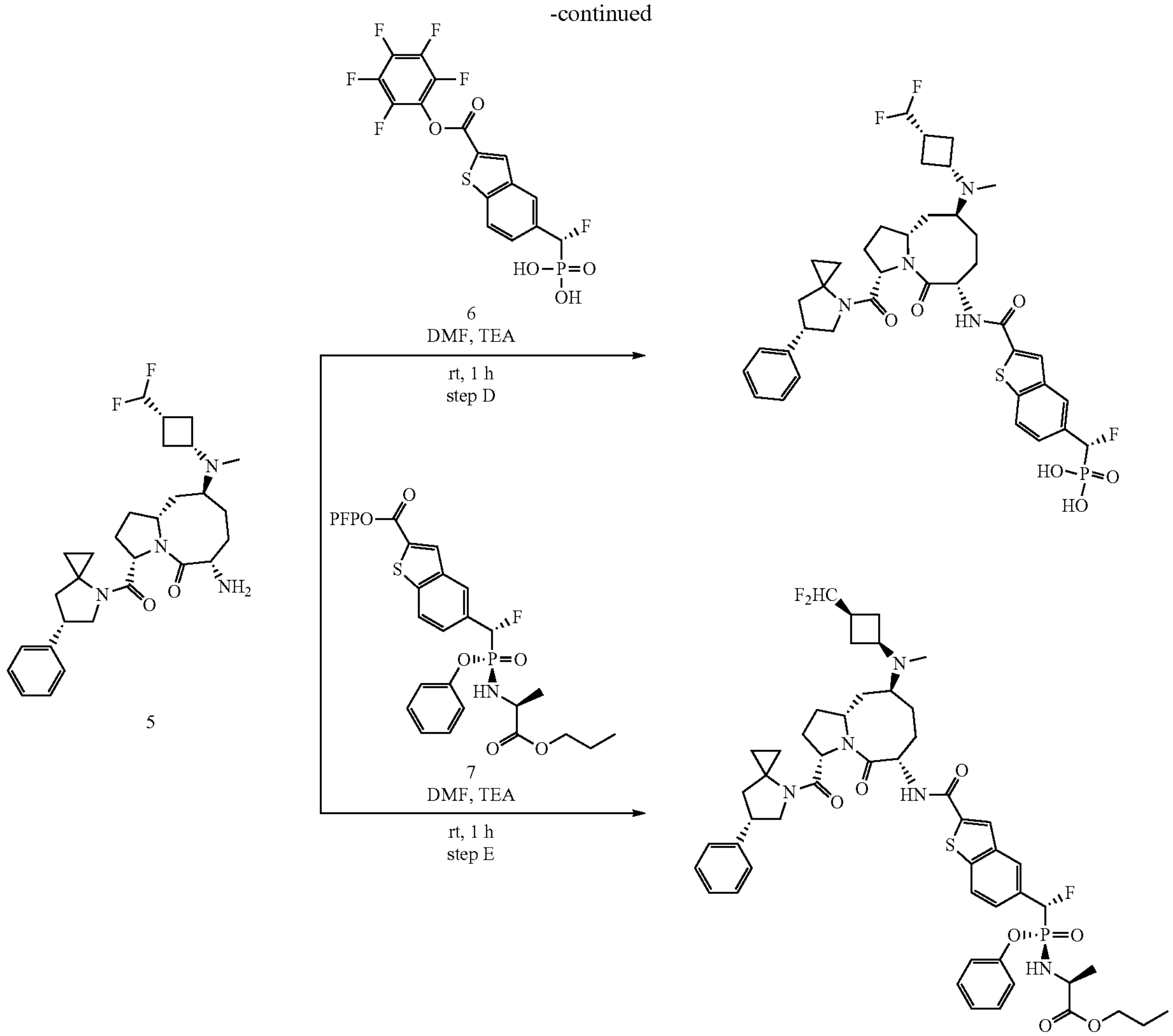
5
Step A: tert-butyl ((3S,6S,9S,10aR)-9-(((1s,3R)-3-(difluoromethyl)cyclobutyl)amino)-5-oxo-3-((S)-6-phenyl-4-azaspiro[2.4]heptane-4-carbonyl)decahydropyrrolo[1,2-a]azocin-6-yl)carbamate
-continued
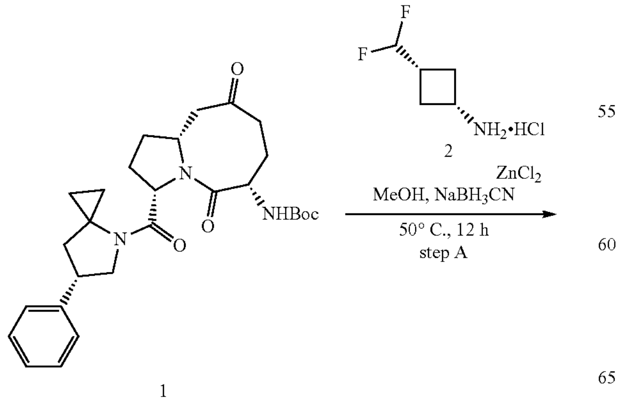
1
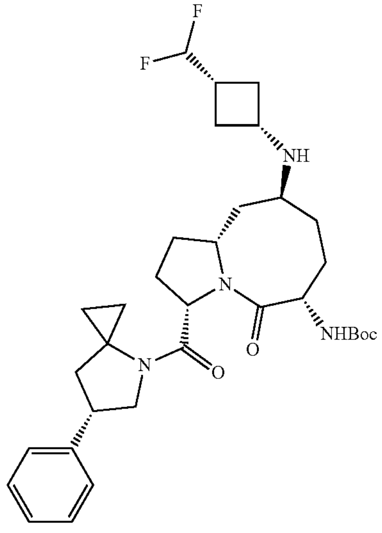
3

To a solution of tert-butyl ((3S,6S,10aR)-5,9-dioxo-3-((R)-6-phenyl-4-azaspiro[2.4]heptane-4-carbonyl)decahydropyrrolo[1,2-a]azocin-6-yl)carbamate (1, 3 g, 6.06 mmol, 1 eq.) in MeOH (60 mL) was added (1s,3s)-3-(trifluoromethyl)cyclobutan-1-amine hydrochloride (2, 1.43 g, 9.09 mmol, 1.5 eq.), $ZnCl_2$ (8.3 g, 60.6 mmol, 10 eq.), the solution was stirred for 2 hr at 50° C. under the atmosphere of $N_2$. Then $NaBH_3CN$ (3.81 g, 60.6 mmol, 10 eq.) was added portion wise every 30 mins (2 eq. (762 mg each time) added 5 times). The solution was stirred for 12 hr at 50° C., then cooled to room temperature and was used to next step without further workup. LCMS (ESI): m/z=601 $[M+H]^+$.

Step B: tert-butyl ((3S,6S,9S,10aR)-9-(((1s,3R)-3-(difluoromethyl)cyclobutyl)(methyl)amino)-5-oxo-3-((S)-6-phenyl-4-azaspiro[2.4]heptane-4-carbonyl)decahydropyrrolo[1,2-a]azocin-6-yl)carbamate Step C: (3S,6S,9S,10aR)-6-amino-9-(((1s,3R)-3-(difluoromethyl)cyclobutyl)(methyl)amino)-3-((S)-6-phenyl-4-azaspiro[2.4]heptane-4-carbonyl)octahydropyrrolo[1,2-a]azocin-5(1H)-one

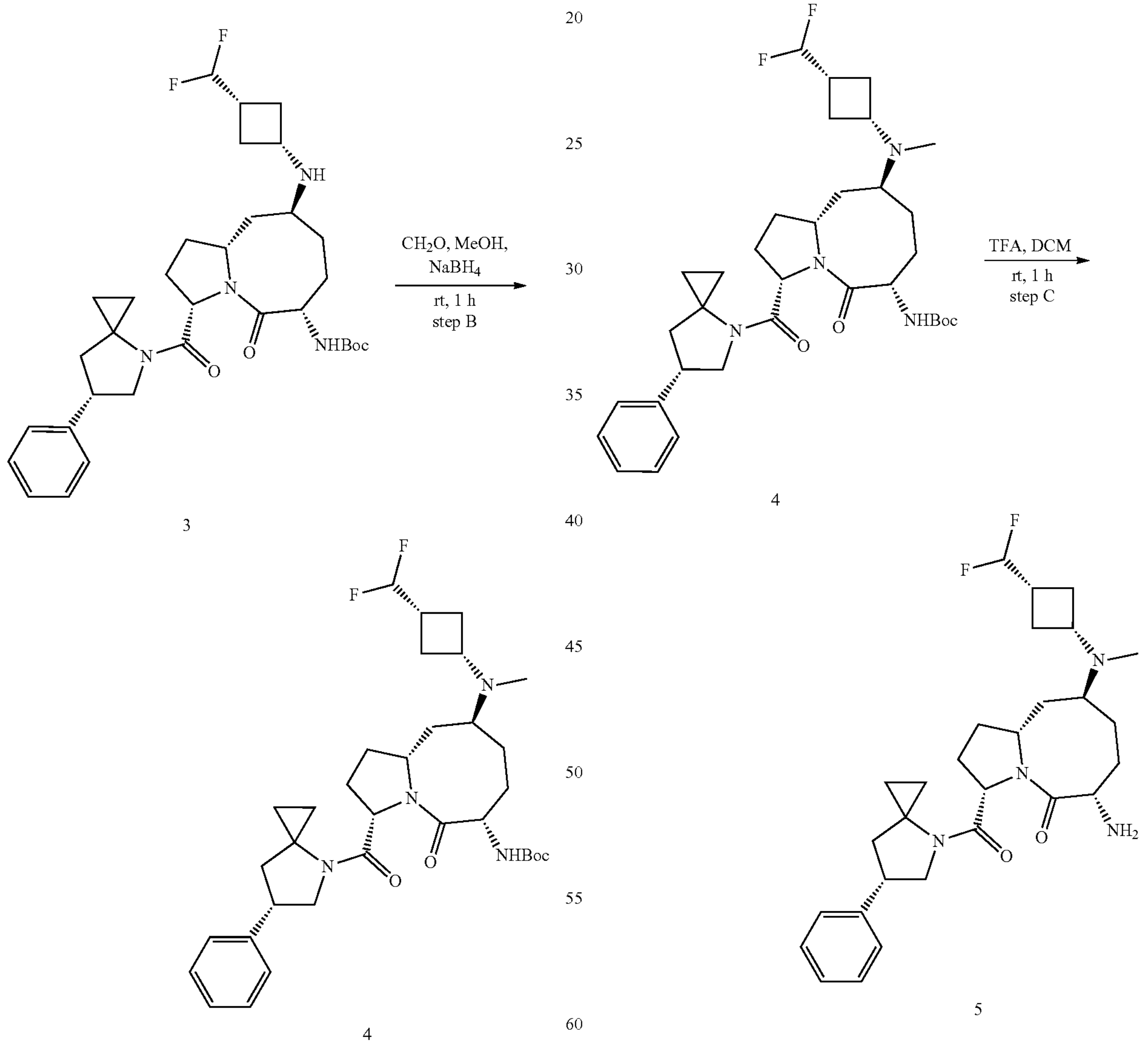

3 4 4 5

To the above mixture (step A) was added 40% formaldehyde aqueous (3 mL) at room temperature, the mixture was stirred for 30 min, then $NaBH_4$ (1.15 g, 30.3 mmol, 5 eq.) was added in portions, the mixture was stirred for another 30 min, then reaction was quenched by $NH_4Cl$ (sat. aq), diluted with $H_2O$ (200 mL), then extracted with EtOAc (80 mL×3). The organic layers were combined and washed with brine (20 mL), dried over $Na_2SO_4$, then concentrated to dryness under reduced pressure. The crude product was purified by C18 column (MeCN:$H_2O$ (0.1% ammonium hydroxide)=5%-70%) to afford tert-butyl ((3S,6S,9S,10aR)-9-(((1s,3R)-3-(difluoromethyl)cyclobutyl)(methyl)amino)-5-oxo-3-((S)-6-phenyl-4-azaspiro[2.4]heptane-4-carbonyl)decahydropyrrolo[1,2-a]azocin-6-yl)carbamate (4, 3 g, 4.86 mmol, 78.9% yield two steps) as a white solid. LCMS (ESI): m/z=615 $[M+H]^+$.

To a solution of tert-butyl ((3S,6S,9S,10aR)-9-(((1s,3R)-3-(difluoromethyl)cyclobutyl)(methyl)amino)-5-oxo-3-((S)-6-phenyl-4-azaspiro[2.4]heptane-4-carbonyl)decahydropyrrolo[1,2-a]azocin-6-yl)carbamate (4, 30 mg, 0.047 mmol) in DCM (2 mL) was added TFA (2 mL). The resulting mixture was stirred for 1 h at room temperature, then the resulting mixture was concentrated to dryness under reduced pressure to afford crude product (3S,6S,9S,10aR)-6-amino-9-(((1s,3R)-3-(difluoromethyl)cyclobutyl)(methyl)amino)-3-((S)-6-phenyl-4-azaspiro[2.4]heptane-4-carbonyl)octahydropyrrolo[1,2-a]azocin-5(1H)-one (5, 30 mg, TFA salt) as a yellow oil which was used to the next step without further purification. LCMS (ESI): m/z=515 $[M+H]^+$.

Step D: ((R)-(2-(((3S,6S,9S,10aR)-9-(((1s,3R)-3-(difluoromethyl)cyclobutyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)phosphonic acid To a solution of (3S,6S,9S,10aR)-6-amino-9-(((1s,3R)-3-(difluoromethyl)cyclobutyl)(methyl)amino)-3-((S)-6-phenyl-4-azaspiro[2.4]heptane-4-carbonyl)octahydropyrrolo[1,2-a]azocin-5(1H)-one (5, 30 mg, TFA salt) in DMF (2 mL) was added TEA (9.9 mg, 0.098 mmol, 2 eq.), (R)-(fluoro(2-((perfluorophenoxy)carbonyl)benzo[b]thiophen-5-yl)methyl)phosphonic acid (6, 21.3 mg, 0.049 mmol, 1 eq.). The resulting mixture was stirred for 1 h at room temperature, then the crude product was purified by Prep-HPLC to afford ((R)-(2-(((3S,6S,9S,10aR)-9-(((1s,3R)-3-(difluoromethyl)cyclobutyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)phosphonic acid (Compound A35, 17 mg) as a

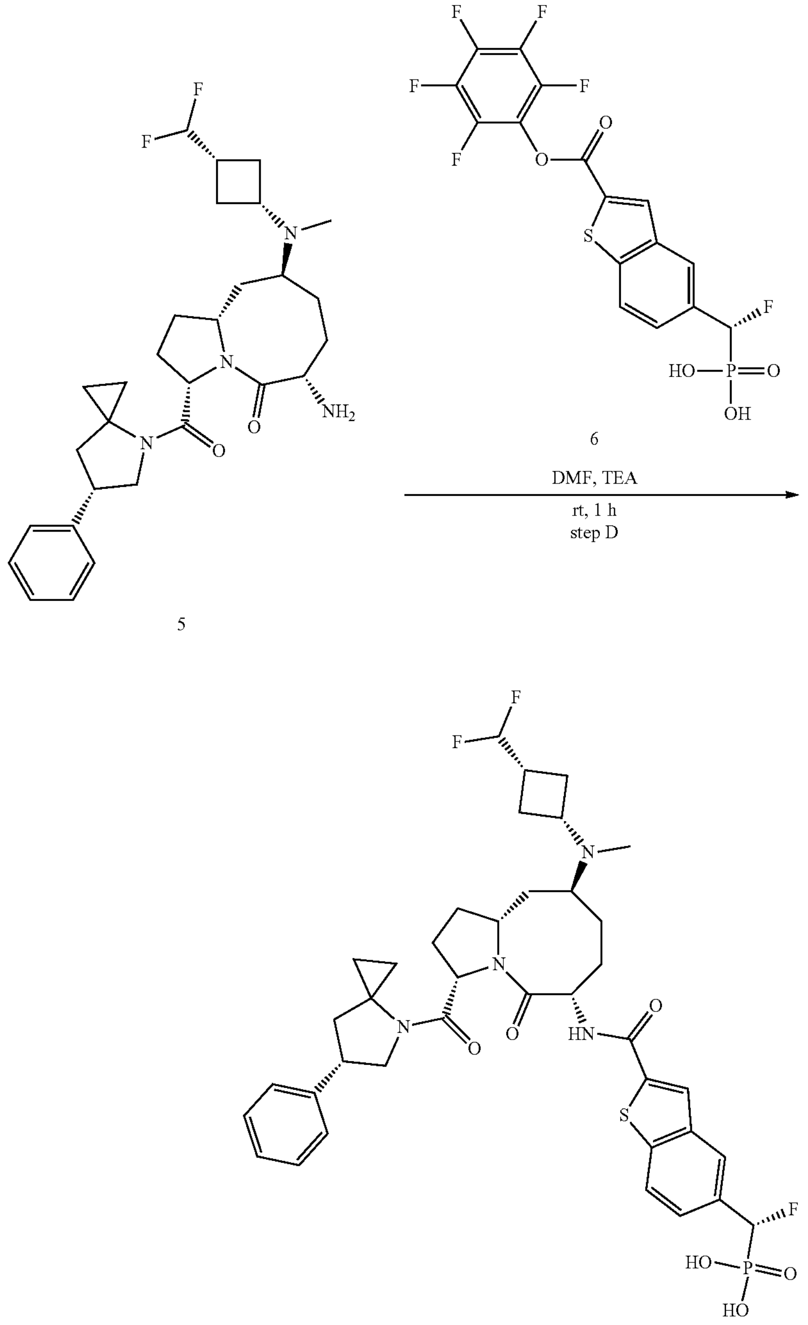 [SMILES: CN([C@H]1CC[C@H](N)C(=O)N2[C@H](CC[C@H]2C(=O)N2C[C@H](c3ccccc3)CC23CC3)C1)[C@H]1C[C@@H](C(F)F)C1 ; O=C(Oc1c(F)c(F)c(F)c(F)c1F)c1cc2cc([C@H](F)P(=O)(O)O)ccc2s1 ; CN([C@H]1CC[C@H](NC(=O)c2cc3cc([C@H](F)P(=O)(O)O)ccc3s2)C(=O)N2[C@H](CC[C@H]2C(=O)N2C[C@H](c3ccccc3)CC23CC3)C1)[C@H]1C[C@@H](C(F)F)C1]

5

6 white solid. LCMS (ESI): m/z=787 $[M+H]^+$. 1H NMR (400 MHz, DMSO-$d_6$) δ (ppm) 9.74-9.31 (m, 1H), 8.89-8.69 (m, 1H), 8.29-8.20 (m, 1H), 8.08-7.94 (m, 2H), 7.57-7.49 (m, 1H), 7.38-7.28 (m, 4H), 7.26-7.21 (m, 1H), 6.23-5.74 (m, 2H), 4.85-4.75 (m, 1H), 4.62-4.46 (m, 2H), 4.20-4.07 (m, 1H), 3.87-3.74 (m, 2H), 3.60-3.49 (m, 2H), 2.62-2.53 (m, 3H), 2.47-1.49 (m, 19H), 0.61-0.40 (m, 2H). $^{19}F$ NMR (376 MHz, DMSO-$d_6$) δ (ppm)-122.05--122.83 (m), −194.81--195.03 (m). $^{31}P$ NMR (162 MHz, DMSO-$d_6$) δ (ppm) 11.22-10.71 (m).

Step E: propyl ((S)-((R)-(2-(((3S,6S,9S,10aR)-9-(((1s,3R)-3-(difluoromethyl)cyclobutyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)(phenoxy)phosphoryl)-L-alaninate

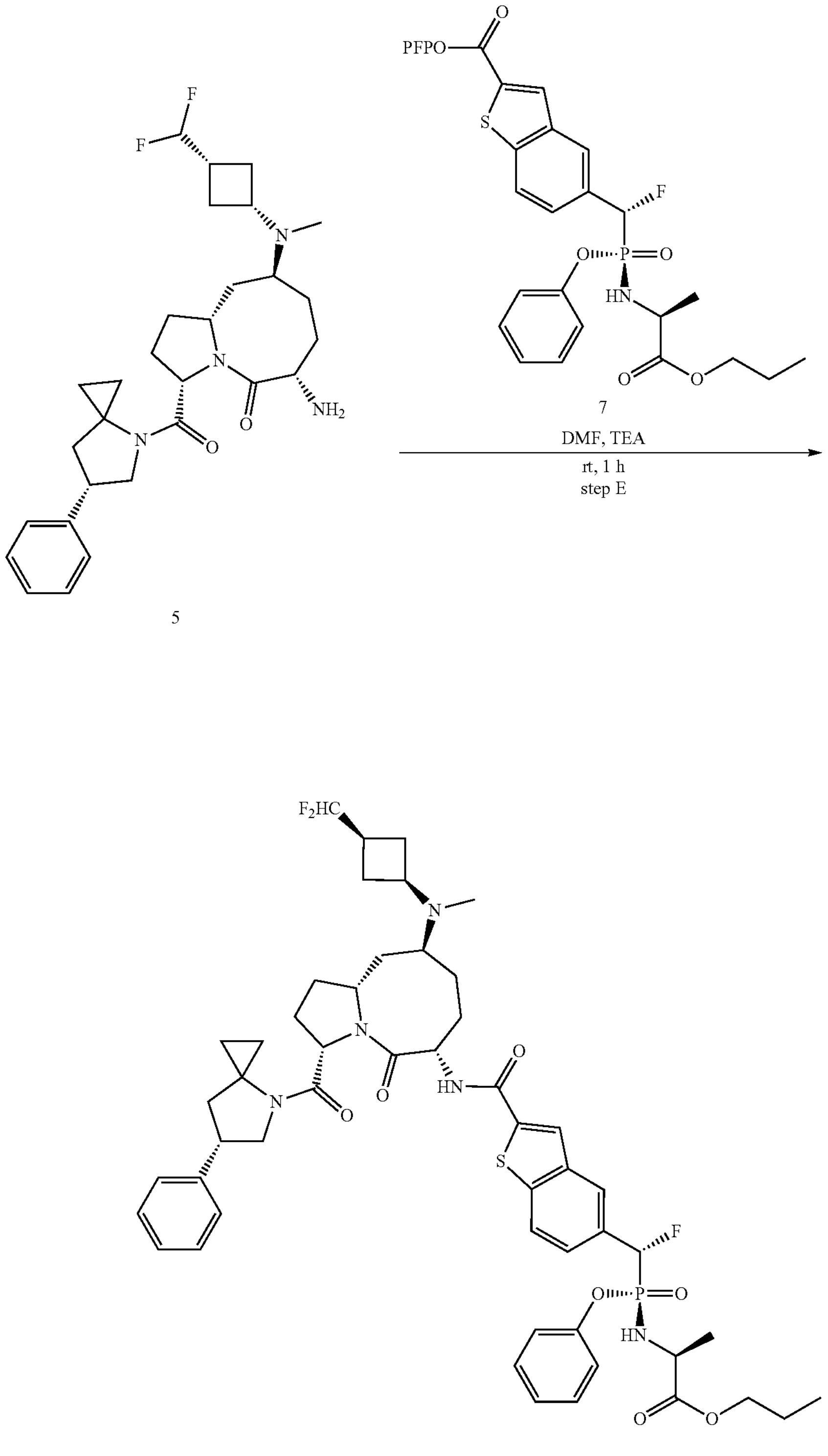

5

7

To a solution of (3S,6S,9S,10aR)-6-amino-9-(((1s,3R)-3-(difluoromethyl)cyclobutyl)(methyl)amino)-3-((S)-6-phenyl-4-azaspiro[2.4]heptane-4-carbonyl)octahydropyrrolo[1,2-a]azocin-5(1H)-one (5, 30 mg, TFA salt) in DMF (2 mL) was added TEA (9.9 mg, 0.098 mmol, 2 eq.), perfluorophenyl 5-((R)-fluoro((S)-(((S)-1-oxo-1-propoxypropan-2-yl)amino)(phenoxy)phosphoryl)methyl)benzo[b]thiophene-2-carboxylate (7, 31.5 mg, 0.049 mmol, 1 eq.). The resulting mixture was stirred for 1 h at room temperature. The crude product was purified by Prep-HPLC to afford propyl ((S)-((R)-(2-(((3S,6S,9S,10aR)-9-(((1s,3R)-3-(difluoromethyl)cyclobutyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)(phenoxy)phosphoryl)-L-alaninate (Compound C71, 17 mg) as a white solid. LCMS (ESI): m/z=976 $[M+H]^+$. $^1$H NMR (400 MHz, DMSO-$d_6$) δ (ppm) 8.81 (d, J=7.4 Hz, 1H), 8.27 (s, 1H), 8.11-8.04 (m, 2H), 7.60 (d, J=8.5 Hz, 1H), 7.39-7.27 (m, 6H), 7.25-7.14 (m, 4H), 6.29-5.82 (m, 3H), 4.81-4.66 (m, 1H), 4.50 (t, J=8.5 Hz, 1H), 4.43-4.29 (m, 1H), 4.13 (t, J=8.6 Hz, 1H), 3.99-3.88 (m, 2H), 3.83-3.68 (m, 2H), 3.60-3.46 (m, 1H), 3.41-3.33 (m, 2H), 2.44-1.44 (m, 24H), 1.13 (d, J=7.1 Hz, 3H), 0.83 (t, J=7.4 Hz, 3H), 0.56-0.39 (m, 2H). $^{19}$F NMR (376 MHz, DMSO-$d_6$) δ (ppm) −121.32 (s), −196.32 (d, J=85.8 Hz). $^{31}$P NMR (162 MHz, DMSO-$d_6$) δ (ppm) 17.08 (d, J=86.2 Hz).

Synthesis of propyl (((R)-fluoro(2-(((3S,6S,9S,10aR)-9-(methyl((R)-tetrahydrofuran-3-yl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate (Compound C24) and ((R)-fluoro(2-(((3S,6S,9S,10aR)-9-(methyl((R)-tetrahydrofuran-3-yl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)phosphonic acid (Compound A19)

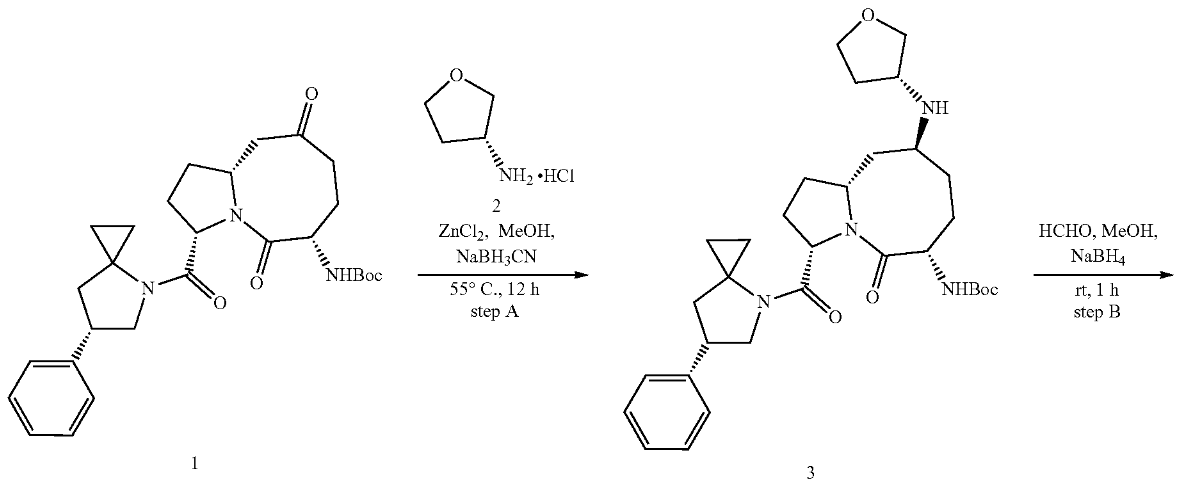

1

3

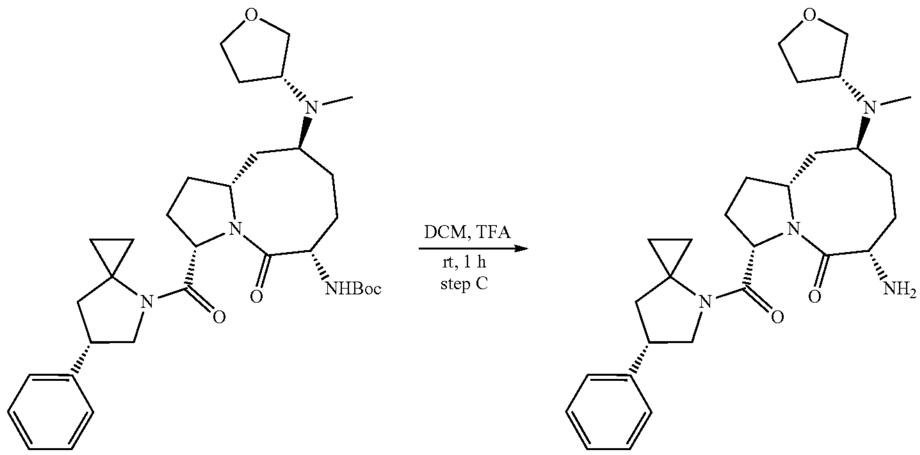

4

5

-continued
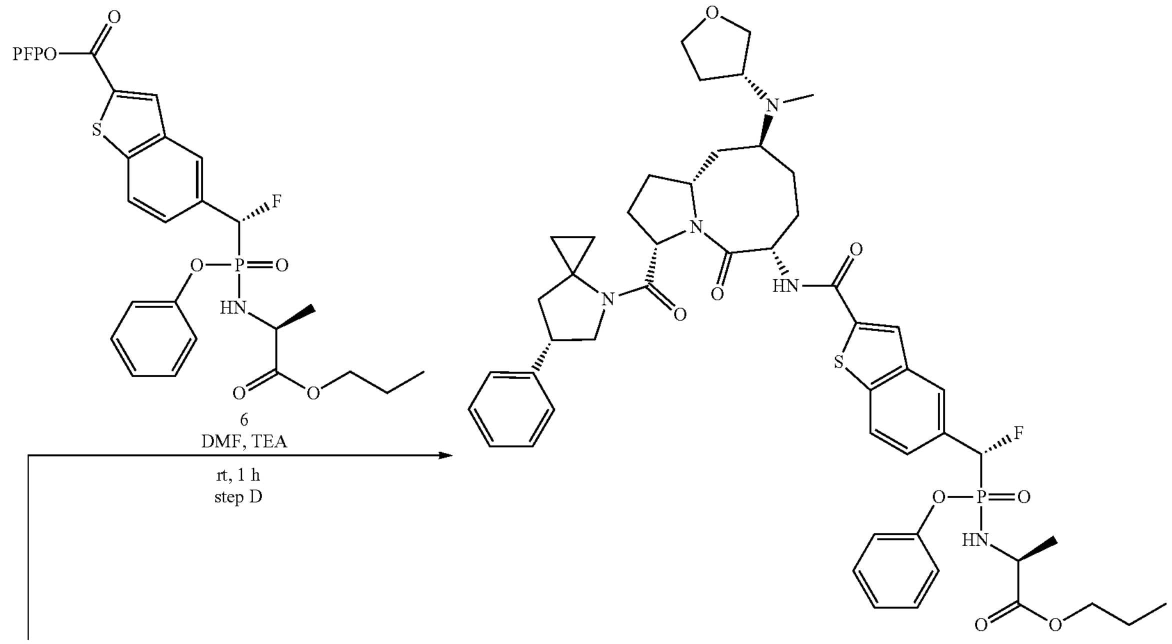
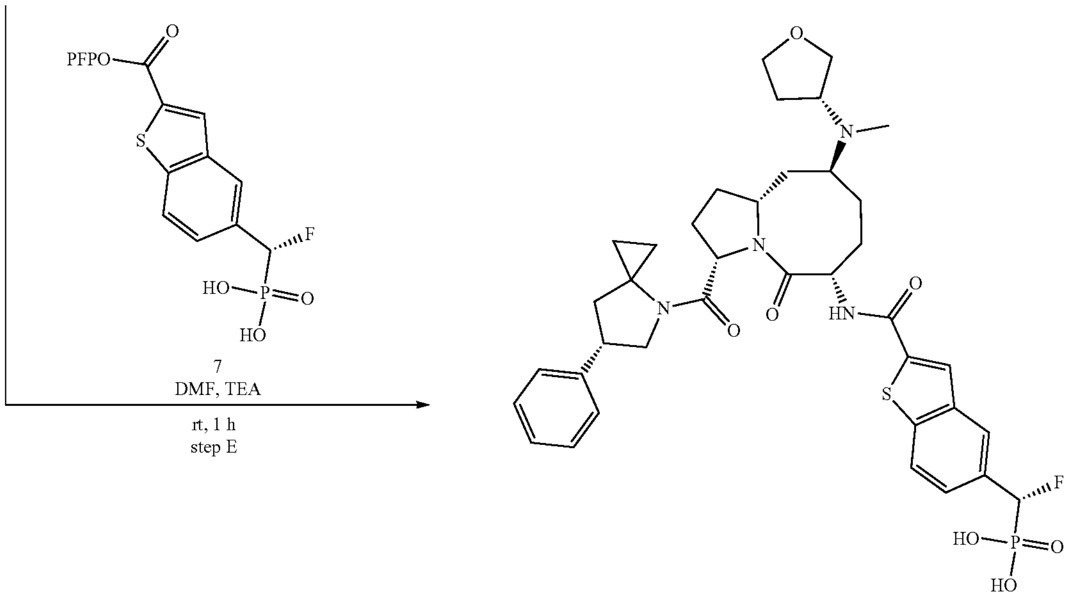

Step A: tert-butyl ((3S,6S,9S,10aR)-5-oxo-3-((S)-6-phenyl-4-azaspiro[2.4]heptane-4-carbonyl)-9-(((R)-tetrahydrofuran-3-yl)amino)decahydropyrrolo[1,2-a]azocin-6-yl)carbamate

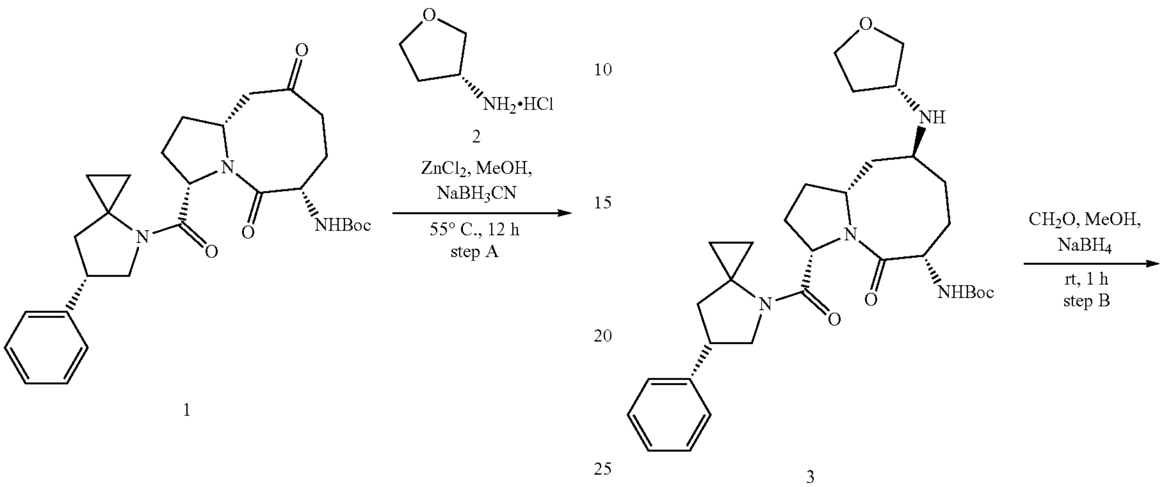

1

2

3

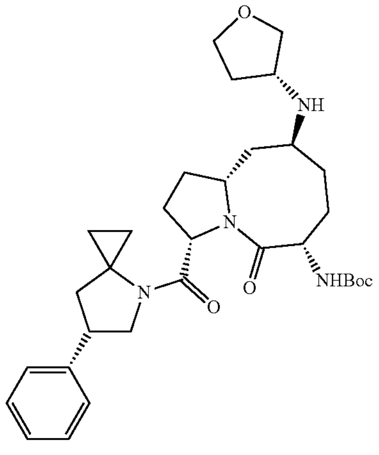

3

To a solution of tert-butyl ((3S,6S,10aR)-5,9-dioxo-3-((S)-6-phenyl-4-azaspiro[2.4]heptane-4-carbonyl)decahydropyrrolo[1,2-a]azocin-6-yl)carbamate (1, 1 g, 2.02 mmol, 1 eq.) in MeOH (20 mL) was added (R)-tetrahydrofuran-3-amine hydrochloride (2, 372.7 mg, 3.03 mmol, 1.5 eq.), $ZnCl_2$ (2.75 g, 20.2 mmol, 10 eq.). The resulting mixture was stirred for 1 h at 50° C., then $NaBH_3CN$ (1.27 g, 20.2 mmol, 10 eq.) was added portion wise every 30 mins (2 eq. (254 mg each time) added 5 times). The mixture was stirred for 12 h at 50° C., LCMS show that the reaction was completed. Then cooled to room temperature, the mixture was used to the next step directly without further workup. LCMS (ESI): m/z=567 $[M+H]^+$.

Step B: tert-butyl ((3S,6S,9S,10aR)-9-(methyl((R)-tetrahydrofuran-3-yl)amino)-5-oxo-3-((S)-6-phenyl-4-azaspiro[2.4]heptane-4-carbonyl)decahydropyrrolo[1,2-a]azocin-6-yl)carbamate

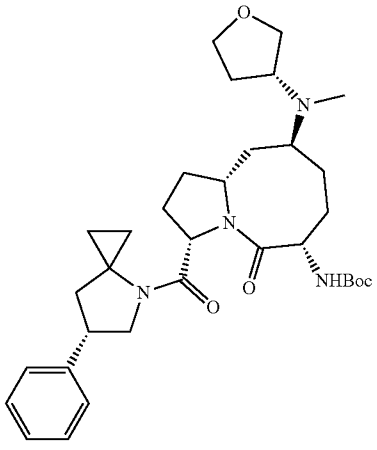

4

To a above mixture (step A) was added 40% formaldehyde (1 mL) at room temperature, then the mixture was stirred for 10 min, then $NaBH_4$ (767 mg, 20.2 mmol, 10 eq.) was added to the mixture, stirred for another 10 min, LCMS show that the reaction was completed, the reaction was quenched by $NH_4Cl$ (sat. aq), diluted with $H_2O$ (80 mL), then extracted with EtOAc (40 mL×3), the organic layers were combined and washed with brine (20 mL), dried over $Na_2SO_4$, filtered, then concentrated to dryness under reduced pressure. The crude product was purified by C18 column (MeCN:$H_2O$ (0.1% ammonium hydroxide)=5%-70%) to afford tert-butyl ((3S,6S,9S,10aR)-9-(methyl((R)-tetrahydrofuran-3-yl)amino)-5-oxo-3-((S)-6-phenyl-4-azaspiro[2.4]heptane-4-carbonyl)decahydropyrrolo[1,2-a]azocin-6-yl)carbamate (4, 480 mg, 0.826 mmol, 40.9% yield, two steps) as a white solid. LCMS (ESI): m/z=581 $[M+H]^+$.

Step C: (3S,6S,9S,10aR)-6-amino-9-(methyl((R)-tetrahydrofuran-3-yl)amino)-3-((S)-6-phenyl-4-azaspiro[2.4]heptane-4-carbonyl)octahydropyrrolo[1,2-a]azocin-5(1H)-one

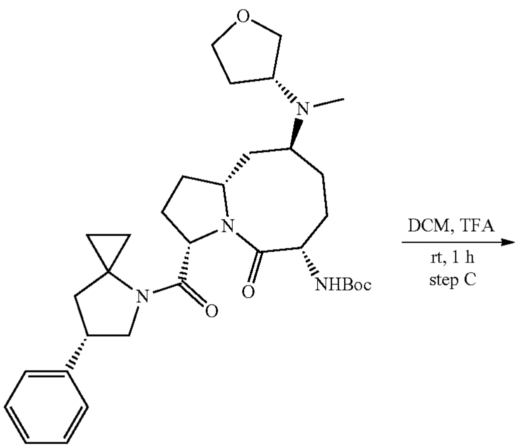

4

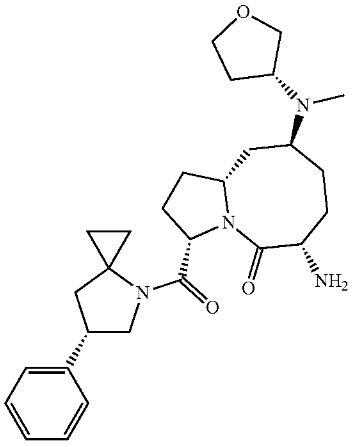

5

To a solution of tert-butyl ((3S,6S,9S,10aR)-9-(methyl((R)-tetrahydrofuran-3-yl)amino)-5-oxo-3-((S)-6-phenyl-4-azaspiro[2.4]heptane-4-carbonyl)decahydropyrrolo[1,2-a]azocin-6-yl)carbamate (4, 40 mg, 0.069 mmol, 1 eq.) in DCM (2 mL) was added TFA (2 mL), The resulting mixture was stirred for 1 hr at room temperature. The resulting mixture was concentrated to dryness under reduced pressure to afford crude product (3S,6S,9S,10aR)-6-amino-9-(methyl((R)-tetrahydrofuran-3-yl)amino)-3-((S)-6-phenyl-4-azaspiro[2.4]heptane-4-carbonyl)octahydropyrrolo[1,2-a]azocin-5(1H)-one (5, 40 mg, TFA salt) as a yellow oil which used in the next step without further purification. LCMS (ESI): m/z=481 [M+H]$^+$.

Step D: propyl (((R)-fluoro(2-(((3S,6S,9S,10aR)-9-(methyl((R)-tetrahydrofuran-3-yl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate To a solution of (3S,6S,9S,10aR)-6-amino-9-(methyl((R)-tetrahydrofuran-3-yl)amino)-3-((S)-6-phenyl-4-azaspiro[2.4]heptane-4-carbonyl)octahydropyrrolo[1,2-a]azocin-5(1H)-one (5, 20 mg, TFA salt) in DMF (2 mL) was added TEA (10.4 mg, 0.103 mmol, 3 eq.), perfluorophenyl 5-((1R)-fluoro((((S)-1-oxo-1l-propoxypropan-2-yl)amino)(phe

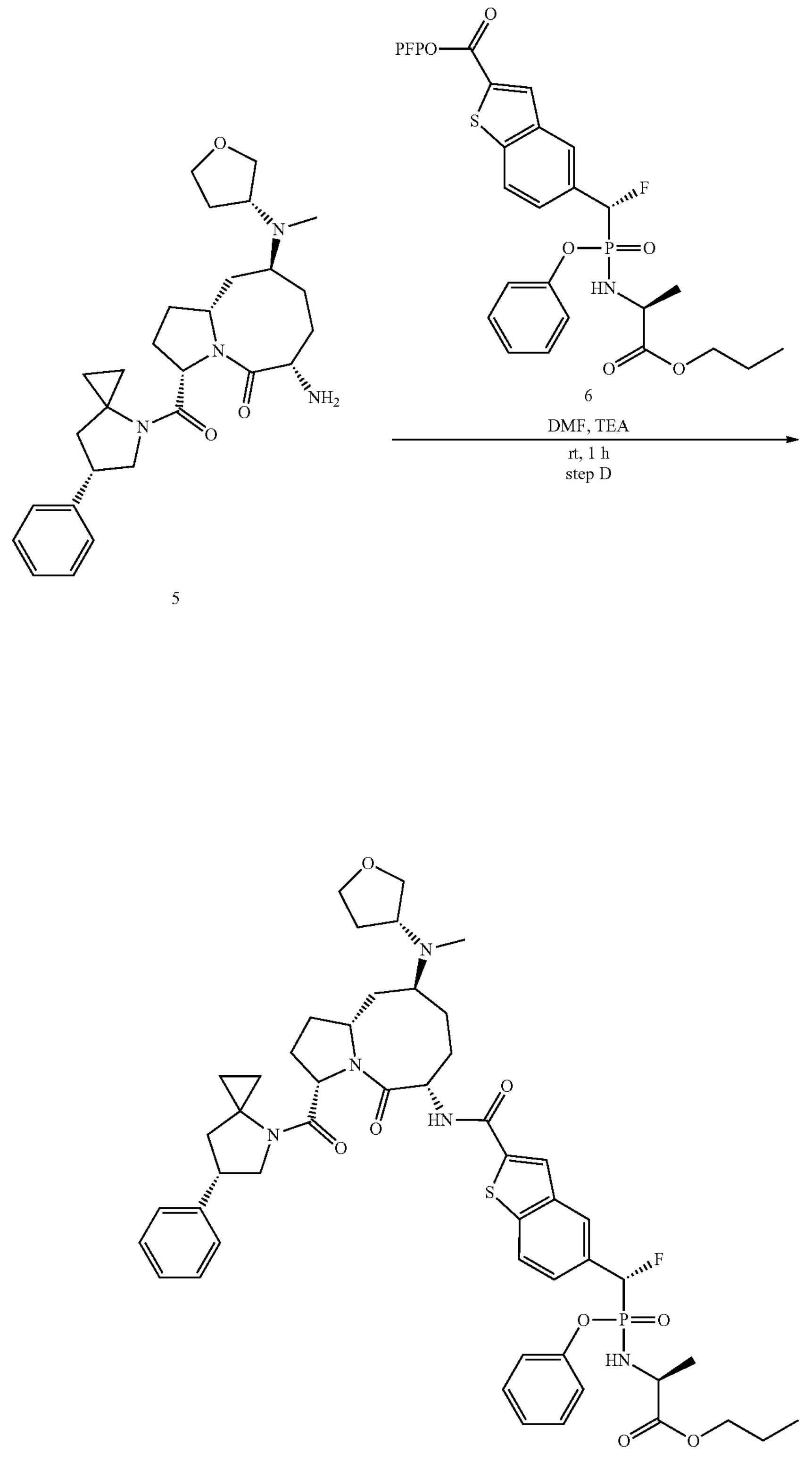

5

6 noxy)phosphoryl)methyl)benzo[b]thiophene-2-carboxylate (6, 22.2 mg, 0.034 mmol, 1 eq). The resulting mixture was stirred for 1 h at room temperature, then the crude product was purified by Prep-HPLC to afford propyl (((R)-fluoro(2-(((3S,6S,9S,10aR)-9-(methyl((R)-tetrahydrofuran-3-yl) amino)-5-oxo-3-((S)-6-phenyl-4-azaspiro[2.4]heptane-4-carbonyl)decahydropyrrolo[1,2-a]azocin-6-yl)carbamoyl) benzo[b]thiophen-5-yl)methyl)(phenoxy)phosphoryl)-L-alaninate (Compound C24, 21 mg, 0.022 mmol, 64.7%) as a white solid. LCMS (ESI): m/z=942.6 $[M+H]^+$. $^1$H NMR (400 MHz, DMSO-$d_6$) δ (ppm) 8.83-8.73 (m, 1H), 8.27 (s, 1H), 8.09-8.02 (m, 2H), 7.64-7.56 (m, 1H), 7.38-7.26 (m, 6H), 7.24-7.13 (m, 4H), 6.28-6.05 (m, 2H), 4.77-4.66 (m, 1H), 4.47 (t, J=8.6 Hz, 1H), 4.34-4.23 (m, 1H), 4.12 (t, J=8.5 Hz, 1H), 3.98-3.89 (m, 1H), 3.86-3.60 (m, 6H), 3.59-3.47 (m, 2H), 3.17-3.06 (m, 1H), 2.99-2.87 (m, 1H), 2.40-2.30 (m, 1H), 2.23 (t, J=11.5 Hz, 1H), 2.16-2.09 (m, 2H), 2.07 (s, 3H), 2.03-1.87 (m, 4H), 1.85-1.48 (m, 9H), 1.47-1.36 (m, 1H), 1.17-1.09 (m, 3H), 0.85-0.75 (m, 3H), 0.54-0.41 (m, 2H). $^{19}$F NMR (376 MHz, DMSO-$d_6$) δ (ppm) −194.29 (d, J=82.5 Hz), −196.30 (d, J=85.9 Hz). $^{31}$P NMR (162 MHz, DMSO-$d_6$) δ (ppm) 17.32 (d, J=82.5 Hz), 17.08 (d, J=86.2 Hz).

Step E: ((R)-fluoro(2-(((3S,6S,9S,10aR)-9-(methyl ((R)-tetrahydrofuran-3-yl)amino)-5-oxo-3-((S)-6-phenyl-4-azaspiro[2.4]heptane-4-carbonyl)decahydropyrrolo[1,2-a]azocin-6-yl)carbamoyl)benzo[b] thiophen-5-yl)methyl)phosphonic acid

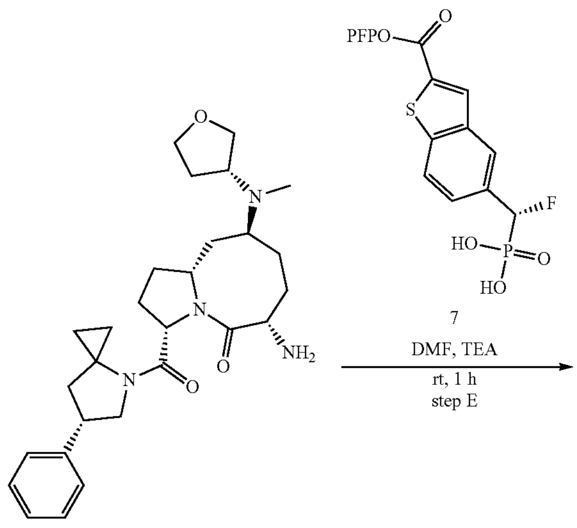

5

-continued

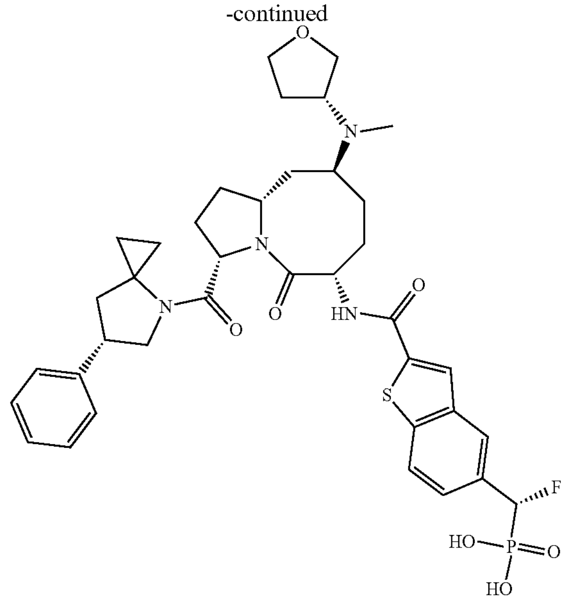

To a solution of (3S,6S,9S,10aR)-6-amino-9-(methyl((R)-tetrahydrofuran-3-yl)amino)-3-((S)-6-phenyl-4-azaspiro [2.4]heptane-4-carbonyl)octahydropyrrolo[1,2-a]azocin-5 (1H)-one (5, 20 mg, TFA salt) in DMF (2 mL) was added TEA (10.4 mg, 0.103 mmol, 3 eq.), (R)-(fluoro(2-((perfluorophenoxy)carbonyl)benzo[b]thiophen-5-yl)methyl)phosphonic acid (7, 15.4 mg, 0.034 mmol, 1 eq). The resulting mixture was stirred for 1 h at room temperature, then the crude product was purified by Prep-HPLC to afford ((R)-fluoro(2-(((3S,6S,9S,10aR)-9-(methyl((R)-tetrahydrofuran-3-yl)amino)-5-oxo-3-((S)-6-phenyl-4-azaspiro[2.4]heptane-4-carbonyl)decahydropyrrolo[1,2-a]azocin-6-yl)carbamoyl) benzo[b]thiophen-5-yl)methyl)phosphonic acid (Compound A19, 16 mg, 0.021 mmol, 61.7%) as a white solid. LCMS (ESI): m/z=753.2 $[M+H]^+$. 1H NMR (400 MHz, DMSO-$d_6$) δ (ppm) 9.77-9.44 (m, 1H), 8.90-8.68 (m, 1H), 8.25 (s, 1H), 8.02 (d, J=8.4 Hz, 1H), 7.97 (s, 1H), 7.53 (d, J=8.5 Hz, 1H), 7.39-7.28 (m, 4H), 7.26-7.20 (m, 1H), 5.81 (dd, J=44.3, 7.9 Hz, 1H), 4.87-4.75 (m, 1H), 4.61-4.45 (m, 2H), 4.18-4.10 (m, 2H), 3.99-3.93 (m, 1H), 3.85-3.80 (m, 1H), 3.74-3.64 (m, 3H), 3.58-3.52 (m, 1H), 2.74-2.62 (m, 3H), 2.48-2.40 (m, 1H), 2.38-2.17 (m, 3H), 2.15-1.90 (m, 8H), 1.89-1.63 (m, 4H), 1.57-1.47 (m, 1H), 0.65-0.41 (m, 2H). $^{19}$F NMR (377 MHz, DMSO-$d_6$) δ (ppm) −194.82 (d, J=80.3 Hz). $^{31}$P NMR (162 MHz, DMSO-$d_6$) δ (ppm) 10.87 (d, J=81.0 Hz).

Synthesis of ((S)-fluoro(2-(((3S,6S,9S,10aR)-9-(methyl(((R)-oxetan-2-yl)methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)phosphonic acid (Compound A31) and propyl (((S)-fluoro(2-(((3S,6S,9S,10aR)-9-(methyl(((R)-oxetan-2-yl)methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate (Compound C51)

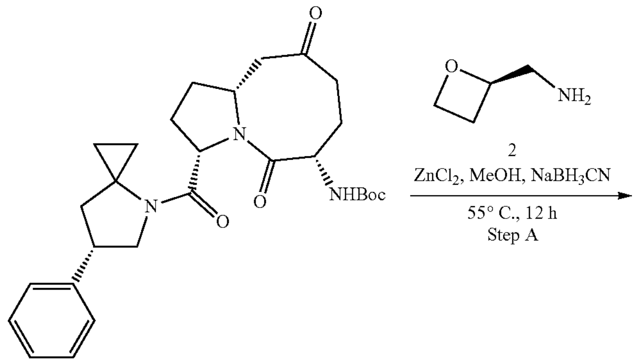

1

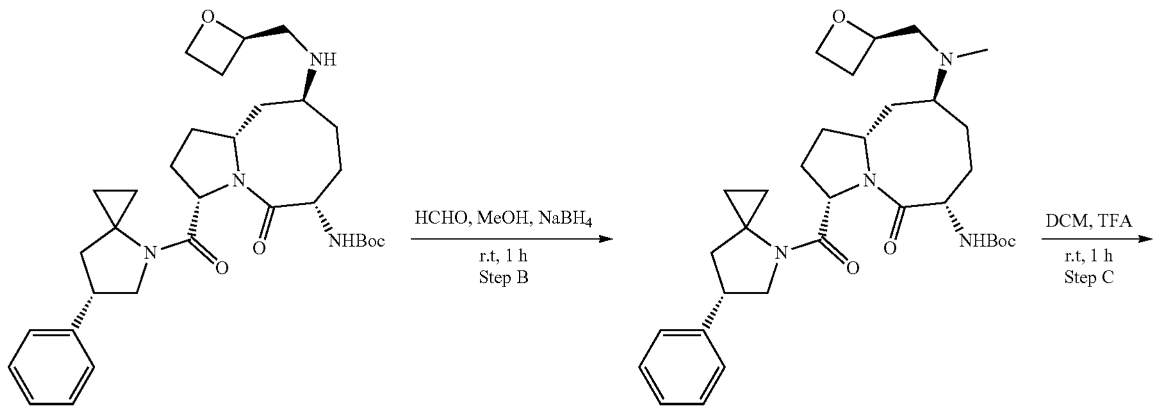

3

4

-continued
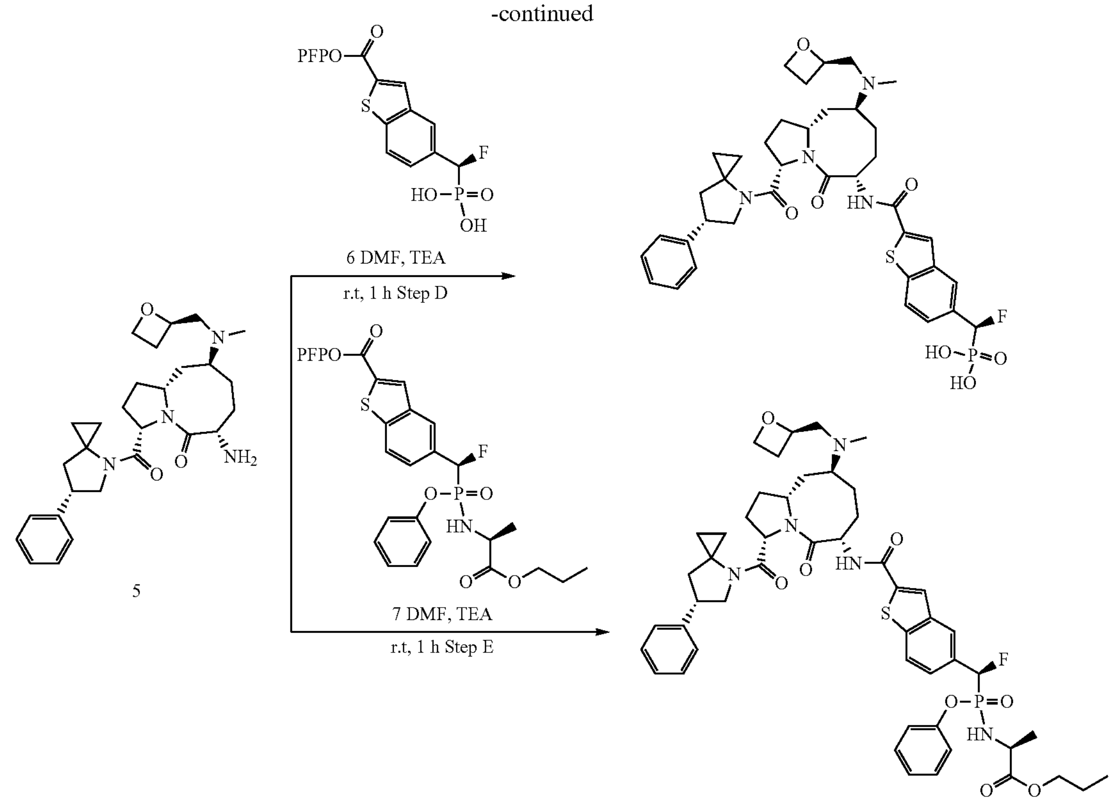
5
Step A: tert-butyl ((3S,6S,9S,10aR)-9-((((R)-oxetan-2-yl)methyl)amino)-5-oxo-3-((S)-6-phenyl-4-azaspiro[2.4]heptane-4-carbonyl)decahydropyrrolo[1,2-a]azocin-6-yl)carbamate
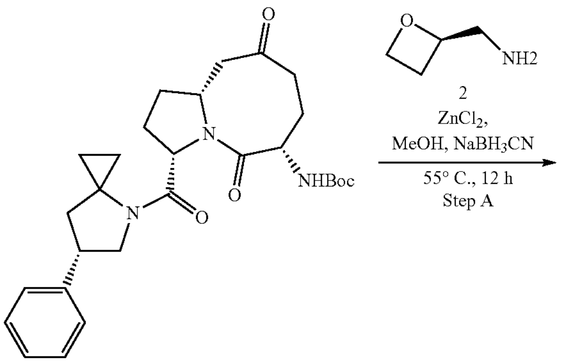
1
-continued
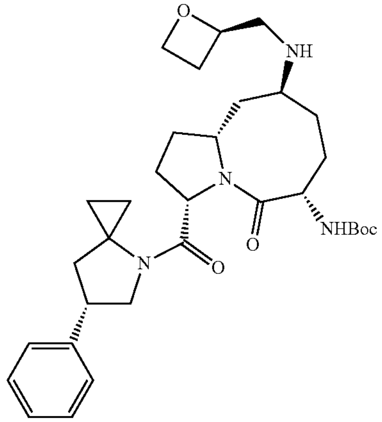
3
To a solution of tert-butyl ((3S,6S,10aR)-5,9-dioxo-3-((S)-6-phenyl-4-azaspiro[2.4]heptane-4-carbonyl)decahydropyrrolo[1,2-a]azocin-6-yl)carbamate (1, 150 mg, 302.65 mol, 1 eq.) in MeOH (10 mL) was added (R)-oxetan-2-ylmethanamine (2, 39.55 mg, 453.98 mol, 1.5 eq), $ZnCl_2$ (412.45 mg, 3.03 mmol, 10 eq.). The solution was stirred for 2 h at 55° C. under the atmosphere of $N_2$, then $NaBH_3CN$ (190 mg, 3.02 mmol, 10 eq.) was added portion wise every 10 mins (2 eq. (38 mg each time) added 5 times. The mixture was stirred for 12 hr at 55° C., then the reaction mixture was cooled to room temperature, then was used to next step without further workup. LCMS (ESI): m/z=567 $[M+H]^+$.

Step B: tert-butyl ((3S,6S,9S,10aR)-9-(methyl(((R)-oxetan-2-yl)methyl)amino)-5-oxo-3-((S)-6-phenyl-4-azaspiro[2.4]heptane-4-carbonyl)decahydropyrrolo[1,2-a]azocin-6-yl)carbamate

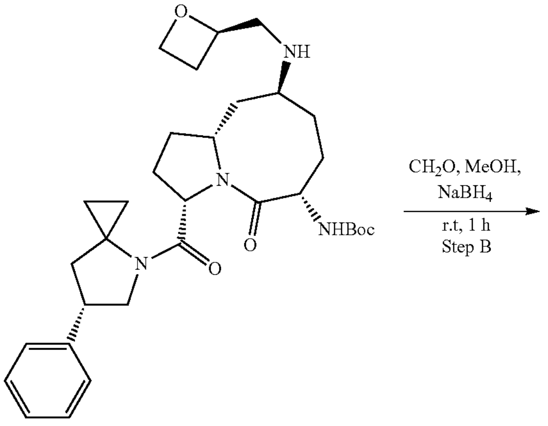

3

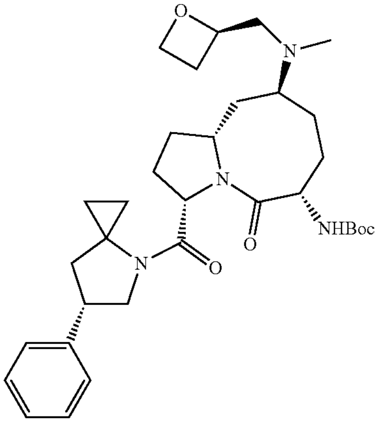

4

To the above solution (Step A) was added 40% formaldehyde (0.5 mL) at room temperature, then $NaBH_4$ (23 mg, 605.3 mol, 2 eq.), and the mixture was stirred 1 h. LCMS indicated the reaction was completed. Sat. aq. $NH_4Cl$ (20 mL) was added and the mixture was extracted with EtOAc (20 mL×3) and the combined organics was washed with brine, dried ($Na_2SO_4$), filtered, and concentrated. The crude product was purified by C18 column eluting with (MeCN: $H_2O$ (0.1% ammonium hydroxide)=5%-70%) to afford tert-butyl ((3S,6S,9S,10aR)-9-(methyl(((R)-oxetan-2-yl)methyl)amino)-5-oxo-3-((S)-6-phenyl-4-azaspiro[2.4]heptane-4-carbonyl)decahydropyrrolo[1,2-a]azocin-6-yl)carbamate (4, 129 mg, 222.1 mol, 70.7% yield two steps) as a white solid. LCMS (ESI): m/z=581 $[M+H]^+$.

Step C: (3S,6S,9S,10aR)-6-amino-9-(methyl(((R)-oxetan-2-yl)methyl)amino)-3-((S)-6-phenyl-4-azaspiro[2.4]heptane-4-carbonyl)octahydropyrrolo[1,2-a]azocin-5(1H)-one

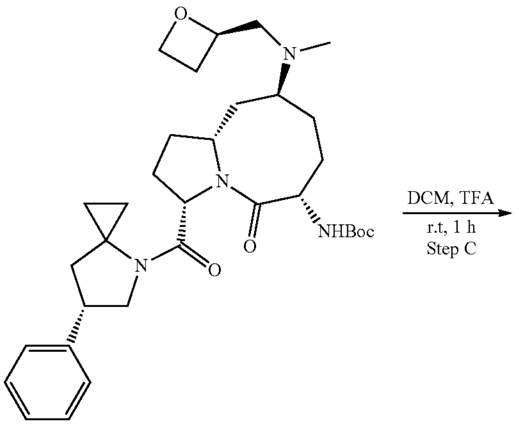

4

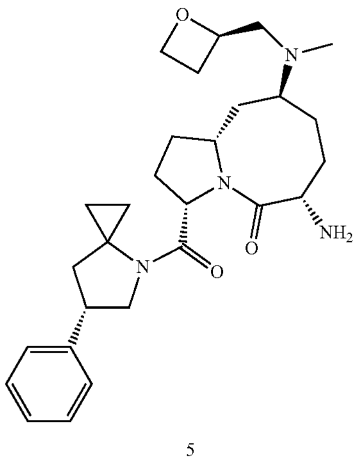

5

To a solution of tert-butyl ((3S,6S,9S,10aR)-9-(methyl(((R)-oxetan-2-yl)methyl)amino)-5-oxo-3-((S)-6-phenyl-4-azaspiro[2.4]heptane-4-carbonyl)decahydropyrrolo[1,2-a]azocin-6-yl)carbamate (4, 180 mg, 154.97 mol, 1 eq.) in DCM (3 mL) was added TFA (1 mL). The resulting mixture was stirred for 1 h at room temperature then concentrated to dryness under reduced pressure to afford crude product (3S,6S,9S,10aR)-6-amino-9-(methyl(((R)-oxetan-2-yl)methyl)amino)-3-((S)-6-phenyl-4-azaspiro[2.4]heptane-4-carbonyl)octahydropyrrolo[1,2-a]azocin-5(1H)-one (5, 180 mg, TFA salt) as a yellow oil. LCMS (ESI): m/z=481 $[M+H]^+$.

Step D: ((S)-fluoro(2-(((3S,6S,9S,10aR)-9-(methyl(((R)-oxetan-2-yl)methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)phosphonic acid

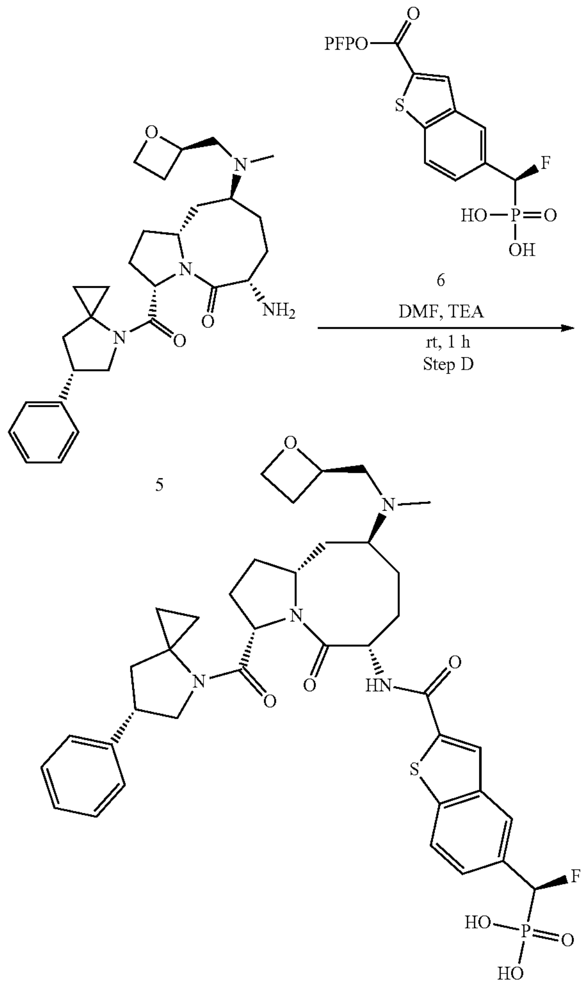

To a solution of (3S,6S,9S,10aR)-6-amino-9-(methyl(((R)-oxetan-2-yl)methyl)amino)-3-((S)-6-phenyl-4-azaspiro[2.4]heptane-4-carbonyl)octahydropyrrolo[1,2-a]azocin-5(1H)-one (5, 45 mg, TFA salt) in DMF (2 mL) were added TEA (23.29 mg. 230.14 mol, 3 eq.) and (S)-(fluoro(2-((perfluorophenoxy)carbonyl)benzo[b]thiophen-5-yl)methyl)phosphonic acid (6, 35 mg, 76.71 mol, 1 eq.), and the resulting mixture was stirred at room temperature for 1 hr, then the crude product was purified by Prep-HPLC to afford ((S)-fluoro(2-(((3S,6S,9S,10aR)-9-(methyl(((R)-oxetan-2-yl)methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)phosphonic acid (Compound A31, 18 mg, 23.90 mol) as a white solid. LCMS (ESI): m/z=753.3 (M+H)+. $^{1}$H NMR (400 MHz, DMSO-$d_6$) δ (ppm) 8.88-8.65 (m, 1H), 8.24 (s, 1H), 8.01 (d, J=8.5 Hz, 1H), 7.97 (s, 1H), 7.52 (d, J=8.5 Hz, 1H), 7.38-7.16 (m, 5H), 5.77 (dd, J=44.6, 7.7 Hz, 1H), 5.26-5.03 (m, 1H), 4.83-4.74 (m, 1H), 4.65-4.42 (m, 4H), 4.16-4.11 (m, 1H), 3.76-3.71 (m, 2H), 3.55-3.51 (m, 2H), 3.28-3.20 (m, 1H), 2.83-2.61 (m, 4H), 2.48-2.32 (m, 2H), 2.29-2.18 (m, 1H), 2.15-1.66 (m, 11H), 1.61-1.53 (m, 1H), 0.60-0.44 (m, 2H). $^{19}$F NMR (376 MHz, DMSO-$d_6$) δ (ppm) −194.52 (d, J=80.3 Hz). $^{31}$P NMR (162 MHz, DMSO-$d_6$) δ (ppm) 10.73 (d, J=79.4 Hz).

Step E: propyl (((S)-fluoro(2-(((3S,6S,9S,10aR)-9-(methyl(((R)-oxetan-2-yl)methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate

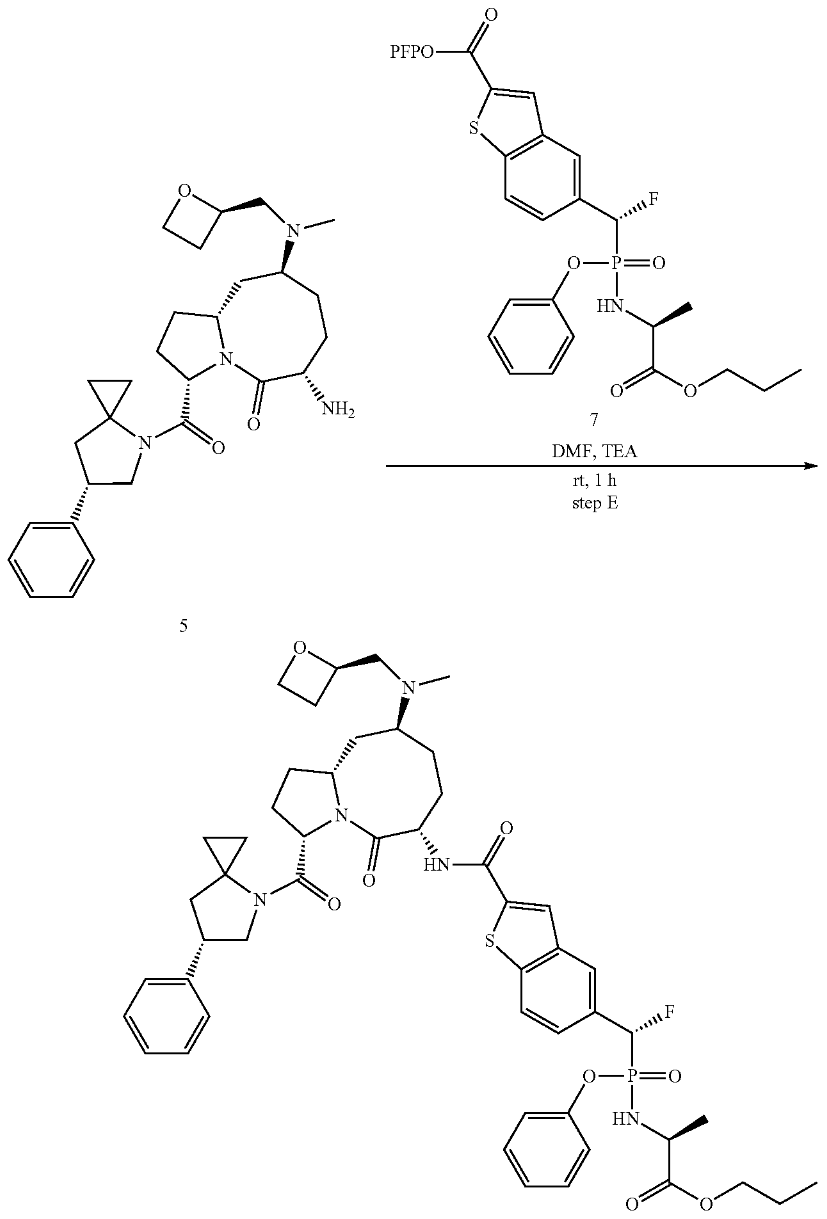

To a solution of (3S,6S,9S,10aR)-6-amino-9-(methyl(((R)-oxetan-2-yl)methyl)amino)-3-((S)-6-phenyl-4-azaspiro[2.4]heptane-4-carbonyl)octahydropyrrolo[1,2-a]azocin-5(1H)-one (5, 45 mg, TFA salt) in DMF (2 mL) were added TEA (23.51 mg. 232.37 mol, 3 eq.) and perfluorophenyl 5-((1S)-fluoro((((S)-1-oxo-1-propoxypropan-2-yl)amino)(phenoxy)phosphoryl)methyl)benzo[b]thiophene-2-carboxylate (7, 50 mg, 77.46 mol, 1 eq.), and the resulting mixture was stirred at room temperature for 1 hr. The crude product was purified by Prep-HPLC to afford propyl (((S)-fluoro(2-(((3S,6S,9S,10aR)-9-(methyl(((R)-oxetan-2-yl)methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate (Compound C51, 25 mg, 26.54 mol, 34.3%) as a white solid. LCMS (ESI): m/z=942.5 $(M+H)^+$. $^1H$ NMR (400 MHz, DMSO-$d_6$) δ (ppm) 8.80-8.68 (m, 1H), 8.30-8.22 (m, 1H), 8.12-7.99 (m, 2H), 7.65-7.55 (m, 1H), 7.40-7.26 (m, 6H), 7.23-7.10 (m, 4H), 6.30-6.07 (m, 2H), 4.85-4.67 (m, 2H), 4.53-4.42 (m, 2H), 4.41-4.34 (m, 1H), 4.33-4.25 (m, 1H), 4.16-4.06 (m, 1H), 3.96-3.63 (m, 4H), 3.58-3.47 (m, 1H), 2.96-2.84 (m, 1H), 2.73-2.52 (m, 3H), 2.41-2.21 (m, 3H), 2.20-2.08 (m, 4H), 2.04-1.92 (m, 3H), 1.90-1.61 (m, 6H), 1.59-1.40 (m, 4H), 1.19-0.92 (m, 3H), 0.81 (t, J=7.4 Hz, 3H), 0.55-0.39 (m, 2H). $^{19}F$ NMR (377 MHz, DMSO-$d_6$) δ (ppm) −194.14 (d, J=82.5 Hz), −196.07 (d, J=86.8 Hz). $^{31}P$ NMR (162 MHz, DMSO-$d_6$) δ (ppm) 17.32 (d, J=86.6 Hz), 16.94 (d, J=82.5 Hz).

Synthesis of ((R)-fluoro(2-(((3S,6S,9S,10aR)-9-(methyl(oxetan-3-yl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)phosphonic acid (Compound A13) and propyl ((R)-((S)-fluoro(2-(((3S,6S,9S,10aR)-9-(methyl(oxetan-3-yl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate (Compound C30)

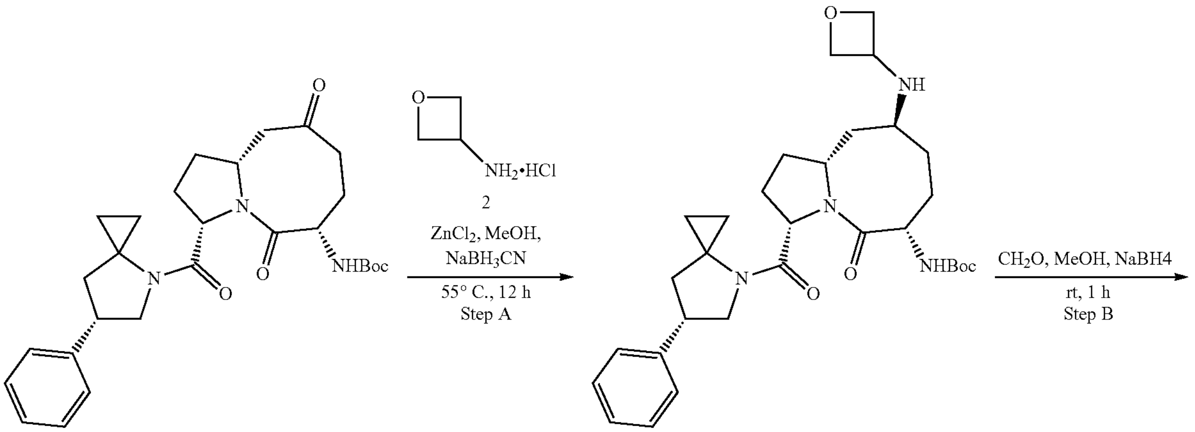

1

3

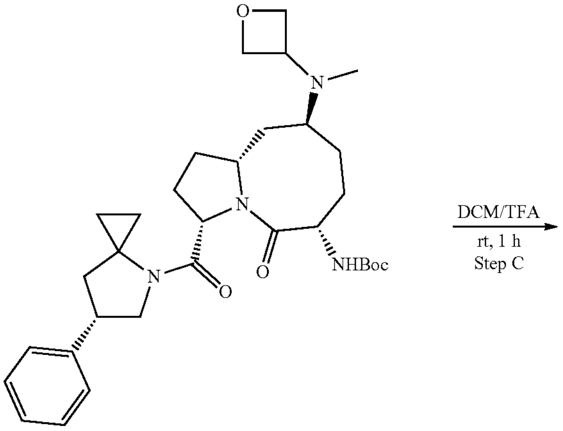

4

-continued

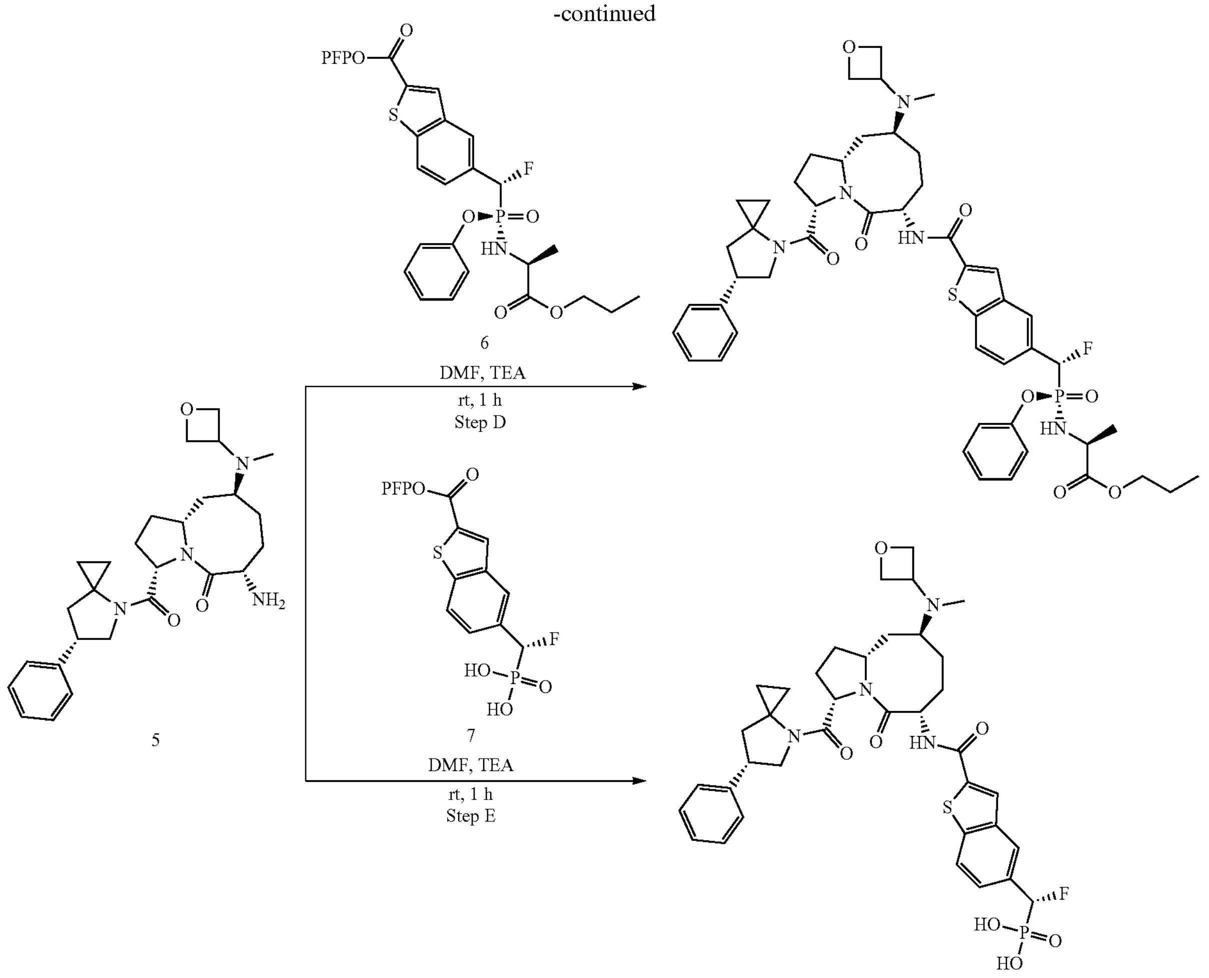

Step A: tert-butyl ((3S,6S,9S,10aR)-9-(oxetan-3-ylamino)-5-oxo-3-((R)-6-phenyl-4-azaspiro[2.4]heptane-4-carbonyl)decahydropyrrolo[1,2-a]azocin-6-yl)carbamate

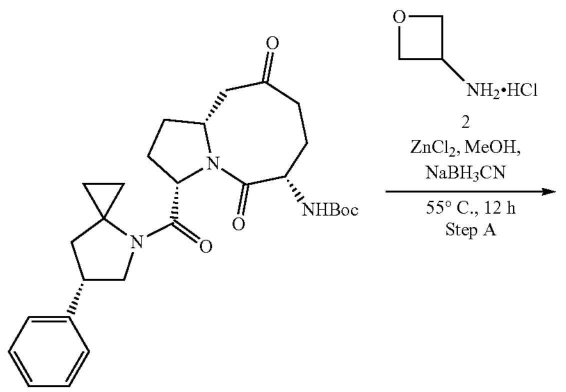

1

-continued

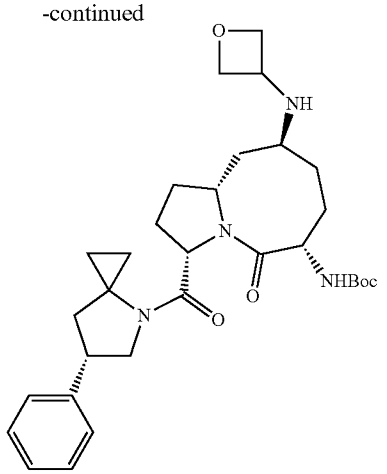

2

To a solution of tert-butyl ((3S,6S,10aR)-5,9-dioxo-3-((R)-6-phenyl-4-azaspiro[2.4]heptane-4-carbonyl)decahydropyrrolo[1,2-a]azocin-6-yl)carbamate (1, 2 g, 4.04 mmol, 1 eq.) in MeOH (40 mL) was added oxetan-3-amine hydrochloride (2, 663.13 mg, 6.05 mmol, 1.5 eq), $ZnCl_2$ (5.50 g, 40.35 mmol, 10 eq.). The resulting mixture was stirred for 2 h at 55° C. under the atmosphere of $N_2$, then $NaBH_3CN$ (2.54 g, 40.4 mmol, 10 eq) was added portion wise every 30 mins (2 eq. (508 mg each time) added 5 times). The solution was stirred for 12 h at 55° C., then the reaction mixture was cooled to room temperature, then was used to next step without further workup. LCMS (ESI): m/z=553 $[M+H]^+$.

Step B: tert-butyl ((3S,6S,9S,10aR)-9-(methyl (oxetan-3-yl)amino)-5-oxo-3-((R)-6-phenyl-4-azaspiro[2.4]heptane-4-carbonyl)decahydropyrrolo [1,2-a]azocin-6-yl)carbamate

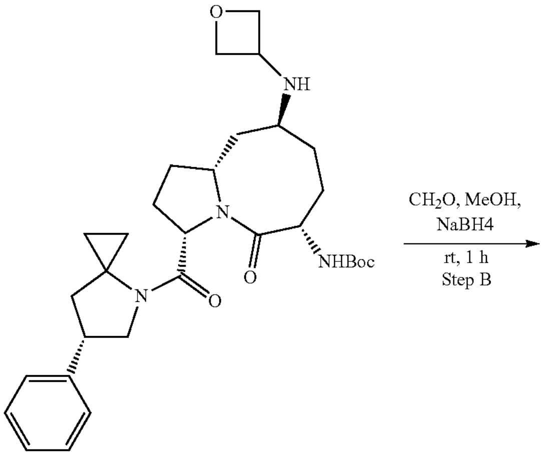

3

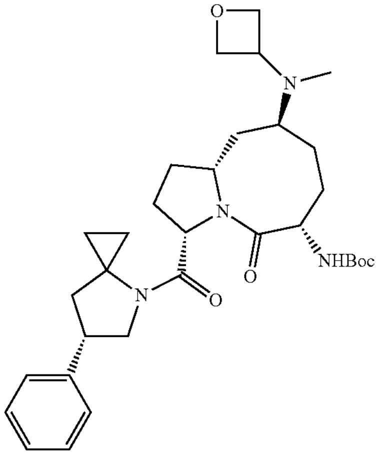

4

To the above solution (Step A) was added 40% formaldehyde (3 mL) at room temperature, and the solution was stirred for 30 min, then $NaBH_4$ (764 mg, 20.2 mmol, 5 eq.) in several portions, the mixture was stirred for additional 30 mins, the reaction was quenched by $NH_4Cl$ (sat. aq), diluted with $H_2O$ (150 mL), extracted with EtOAc (60 mL×3), the organic solution was dried over $Na_2SO_4$, then concentrated under vacuum, filtered, and the crude product was purified by C18 column (MeCN:$H_2O$ (0.1% ammonium hydroxide)=5%-70%) to afford tert-butyl ((3S,6S,9S,10aR)-9-(methyl (oxetan-3-yl)amino)-5-oxo-3-((R)-6-phenyl-4-azaspiro[2.4]heptane-4-carbonyl)decahydropyrrolo[1,2-a]azocin-6-yl) carbamate (4, 1.8 g, 3.17 mmol, 78.6% yield two steps) as a white solid. LCMS (ESI): m/z=567 $[M+H]^+$.

Step C: (3S,6S,9S,10aR)-6-amino-9-(methyl (oxetan-3-yl)amino)-3-((R)-6-phenyl-4-azaspiro[2.4] heptane-4-carbonyl)octahydropyrrolo[1,2-a]azocin-5 (1H)-one

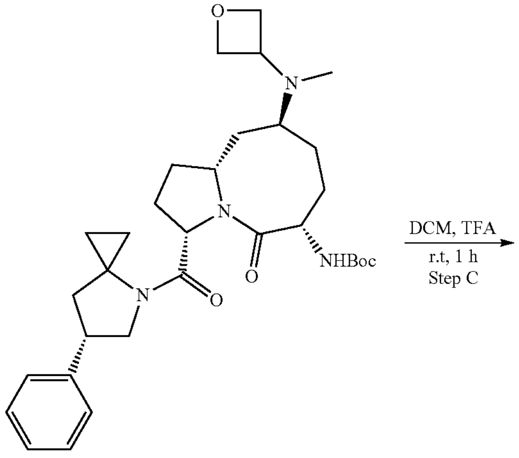

4

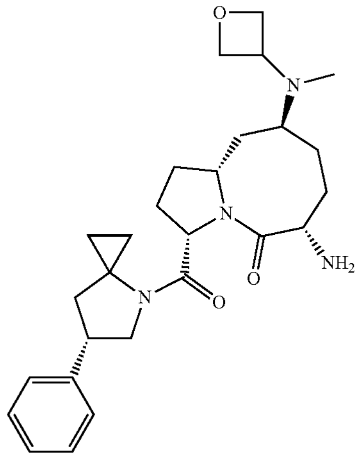

5

To a solution of tert-butyl ((3S,6S,9S,10aR)-9-(methyl (oxetan-3-yl)amino)-5-oxo-3-((R)-6-phenyl-4-azaspiro[2.4] heptane-4-carbonyl)decahydropyrrolo[1,2-a]azocin-6-yl) carbamate (4, 1.8 g, 3.17 mmol, 1 eq.) in DCM (18 mL) was added TFA (6 mL). The resulting mixture was stirred for 1 hr at room temperature. The resulting mixture was concentrated to dryness under reduced pressure to afford crude product (3S,6S,9S,10aR)-6-amino-9-(methyl(oxetan-3-yl) amino)-3-((R)-6-phenyl-4-azaspiro[2.4]heptane-4-carbonyl)octahydropyrrolo[1,2-a]azocin-5(1H)-one (5, 1.8 g, TFA salt) as a yellow oil. LCMS (ESI): m/z=467 $[M+H]^+$.

Step D: propyl ((R)-((S)-fluoro(2-(((3S,6S,9S,10aR)-9-(methyl(oxetan-3-yl)amino)-5-oxo-3-((R)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate

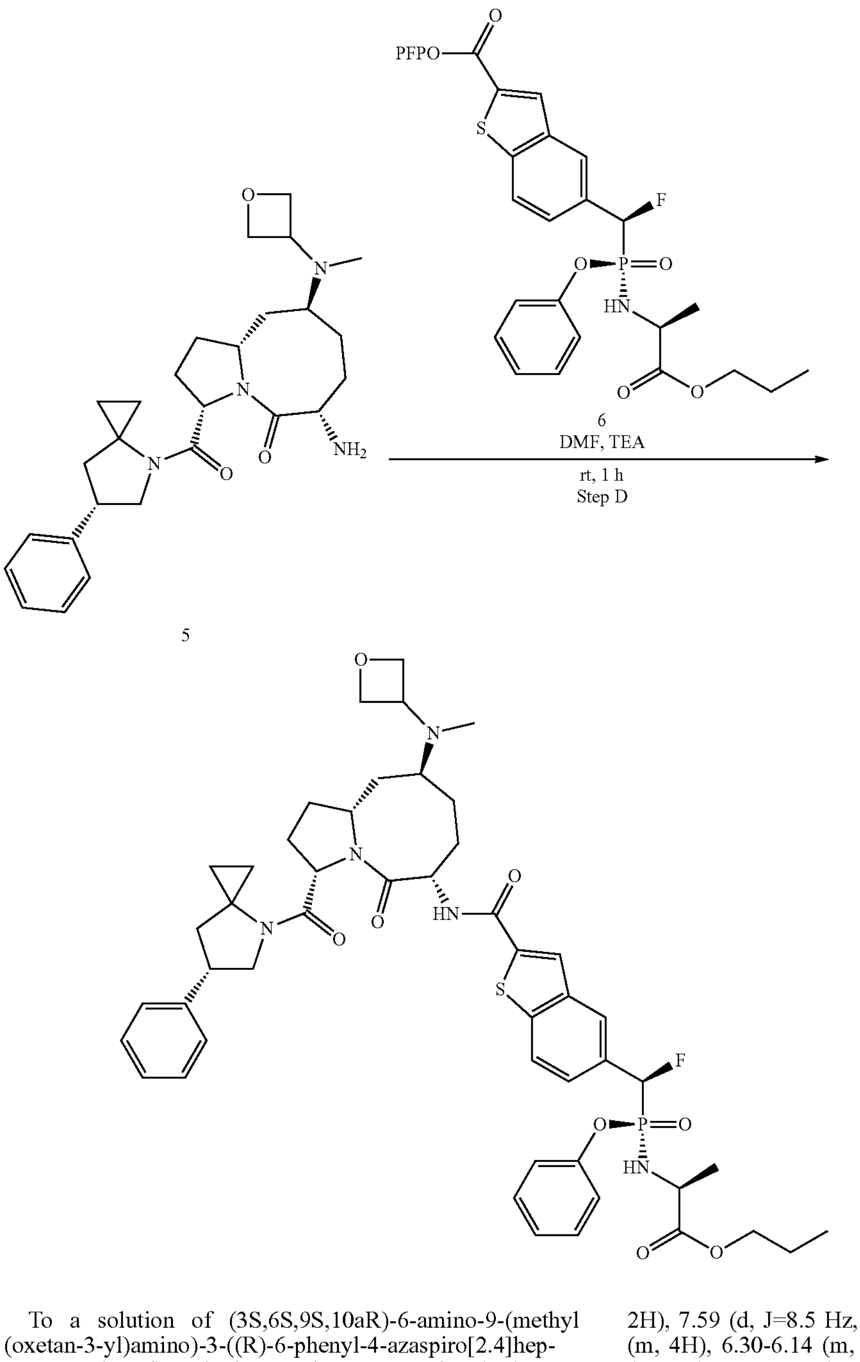

To a solution of (3S,6S,9S,10aR)-6-amino-9-(methyl(oxetan-3-yl)amino)-3-((R)-6-phenyl-4-azaspiro[2.4]heptane-4-carbonyl)octahydropyrrolo[1,2-a]azocin-5(1H)-one (5, 50 mg, TFA salt) in DMF (2 mL) were added TEA (25.75 mg. 0.255 mmol, 3 eq.) and perfluorophenyl 5-((S)-fluoro((R)-(((S)-1-oxo-1-propoxypropan-2-yl)amino)(phenoxy)phosphoryl)methyl)benzo[b]thiophene-2-carboxylate (6, 55 mg, 0.085 mmol, 1 eq.), and the resulting mixture was stirred at room temperature for 1 hr. The crude product was purified by Prep-HPLC to afford propyl ((R)-((S)-fluoro(2-(((3S,6S,9S,10aR)-9-(methyl(oxetan-3-yl)amino)-5-oxo-3-((R)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate (Compound C30, 41 mg, 0.044 mmol, 51.8%) as a white solid. LCMS (ESI): m/z=928.5 $[M+H]^+$. 1H NMR (400 MHz, DMSO-$d_6$) δ (ppm) 8.78 (d, J=7.6 Hz, 1H), 8.26 (s, 1H), 8.08-8.02 (m, 2H), 7.59 (d, J=8.5 Hz, 1H), 7.38-7.27 (m, 6H), 7.23-7.09 (m, 4H), 6.30-6.14 (m, 2H), 4.76-4.65 (m, 1H), 4.58-4.50 (m, 2H), 4.49-4.39 (m, 2H), 4.37-4.33 (m, 1H), 4.32-4.24 (m, 1H), 4.15-4.07 (m, 1H), 3.95-3.81 (m, 3H), 3.79-3.67 (m, 2H), 3.60-3.47 (m, 1H), 2.88-2.78 (m, 1H), 2.42-2.31 (m, 1H), 2.28-2.18 (m, 1H), 2.16-2.07 (m, 1H), 2.04-1.90 (m, 6H), 1.84-1.55 (m, 7H), 1.54-1.40 (m, 3H), 1.17 (d, J=7.1 Hz, 3H), 0.81 (t, J=7.4 Hz, 3H), 0.60-0.38 (m, 2H). $^{19}F$ NMR (376 MHz, DMSO-$d_6$) δ (ppm) −196.08 (d, J=86.6 Hz). $^{31}P$ NMR (162 MHz, DMSO-$d_6$) δ (ppm) 17.32 (d, J=87.4 Hz).

Step E: ((R)-fluoro(2-(((3S,6S,9S,10aR)-9-(methyl(oxetan-3-yl)amino)-5-oxo-3-((R)-6-phenyl-4-azaspiro[2.4]heptane-4-carbonyl)decahydropyrrolo[1,2-a]azocin-6-yl)carbamoyl)benzo[b]thiophen-5-yl)methyl)phosphonic acid

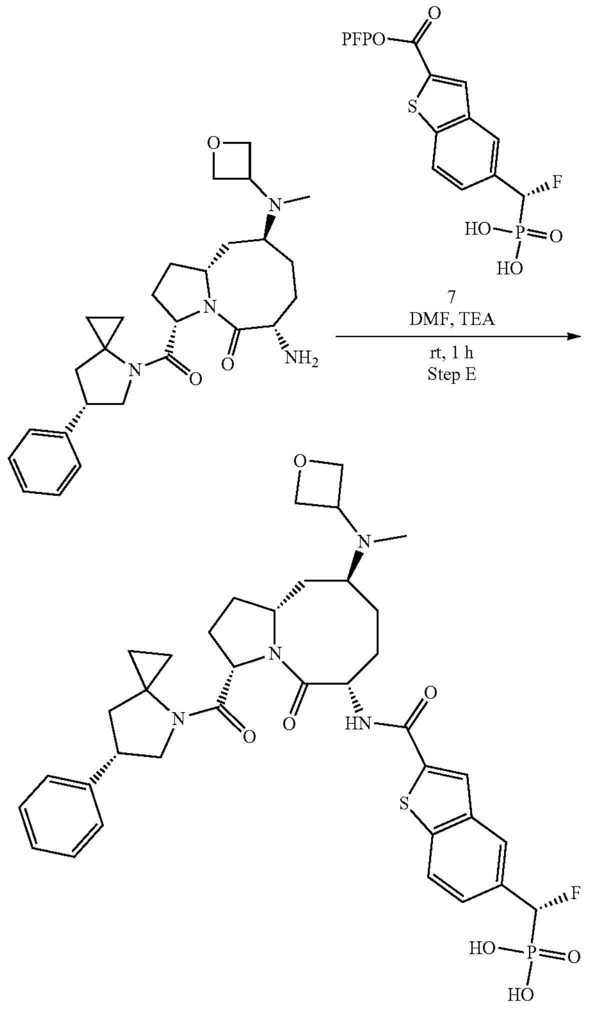

To a solution of (3S,6S,9S,10aR)-6-amino-9-(methyl(oxetan-3-yl)amino)-3-((R)-6-phenyl-4-azaspiro[12.4]heptane-4-carbonyl)octahydropyrrolo[1,2-a]azocin-5(1H)-one (5, 50 mg, TFA salt) in DMF (2 mL) were added TEA (25.75 mg. 0.255 mmol, 3 eq.) and (R)-(fluoro(2-((perfluorophenoxy)carbonyl)benzo[b]thiophen-5-yl)methyl)phosphonic acid (7, 40 mg, 0.088 mmol, 1 eq.), and the resulting mixture was stirred at room temperature for 1 h. The crude product was purified by Prep-HPLC to afford ((R)-fluoro(2-(((3S,6S,9S,10aR)-9-(methyl(oxetan-3-yl)amino)-5-oxo-3-((R)-6-phenyl-4-azaspiro[2.4]heptane-4-carbonyl)decahydropyrrolo[[1,2-a]azocin-6-yl)carbamoyl)benzo(b]thiophen-5-yl)methyl)phosphonic acid (Compound A13, 36 mg, 0.048 mmol, 54.5%) as a white solid. LCMS (ESI): m/z=739.6 $[M+H]^+$. $^1$H NMR (400 MHz, DMSO-$d_6$) δ (ppm) 10.85-10.19 (m, 1H), 8.87-8.68 (m, 1H), 8.24 (s, 1H), 8.03 (d, J=8.5 Hz, 1H), 7.97 (s, 1H), 7.53 (d, J=8.6 Hz, 1H), 7.38-7.30 (m, 4H), 7.25-7.21 (m, 1H), 5.83 (dd, J=44.4, 8.0 Hz, 1H), 4.92-4.50 (m, 8H), 4.18-4.09 (m, 1H), 3.74-3.68 (m, 1H), 3.60-3.52 (m, 2H), 2.60 (s, 3H), 2.48-2.41 (m, 1H), 2.28-2.21 (m, 1H), 2.16-1.70 (m, 11H), 1.57-1.51 (m, 1H), 0.61-0.48 (m, 2H). $^{19}$F NMR (377 MHz, DMSO-$d_6$) δ (ppm) −194.91 (d, J=80.8 Hz). $^{31}$P NMR (162 MHz, DMSO-$d_6$) δ (ppm) 10.92 (d, J=80.9 Hz).

Synthesis of ((R)-fluoro(2-(((3S,6S,9S,10aR)-9-(methyl(((R)-oxetan-2-yl)methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)phosphonic acid (Compound A17) and propyl (((1R)-fluoro(2-(((3S,6S,9S,10aR)-9-(methyl(((R)-oxetan-2-yl)methyl)amino)-5-oxo-3-((S)-6-phenyl-4-azaspiro[2.4]heptane-4-carbonyl)decahydropyrrolo[1,2-a]azocin-6-yl)carbamoyl)-2,3-dihydrobenzo[b]thiophen-5-yl)methyl)(phenoxy)phosphoryl)-L-alaninate (Compound C20)

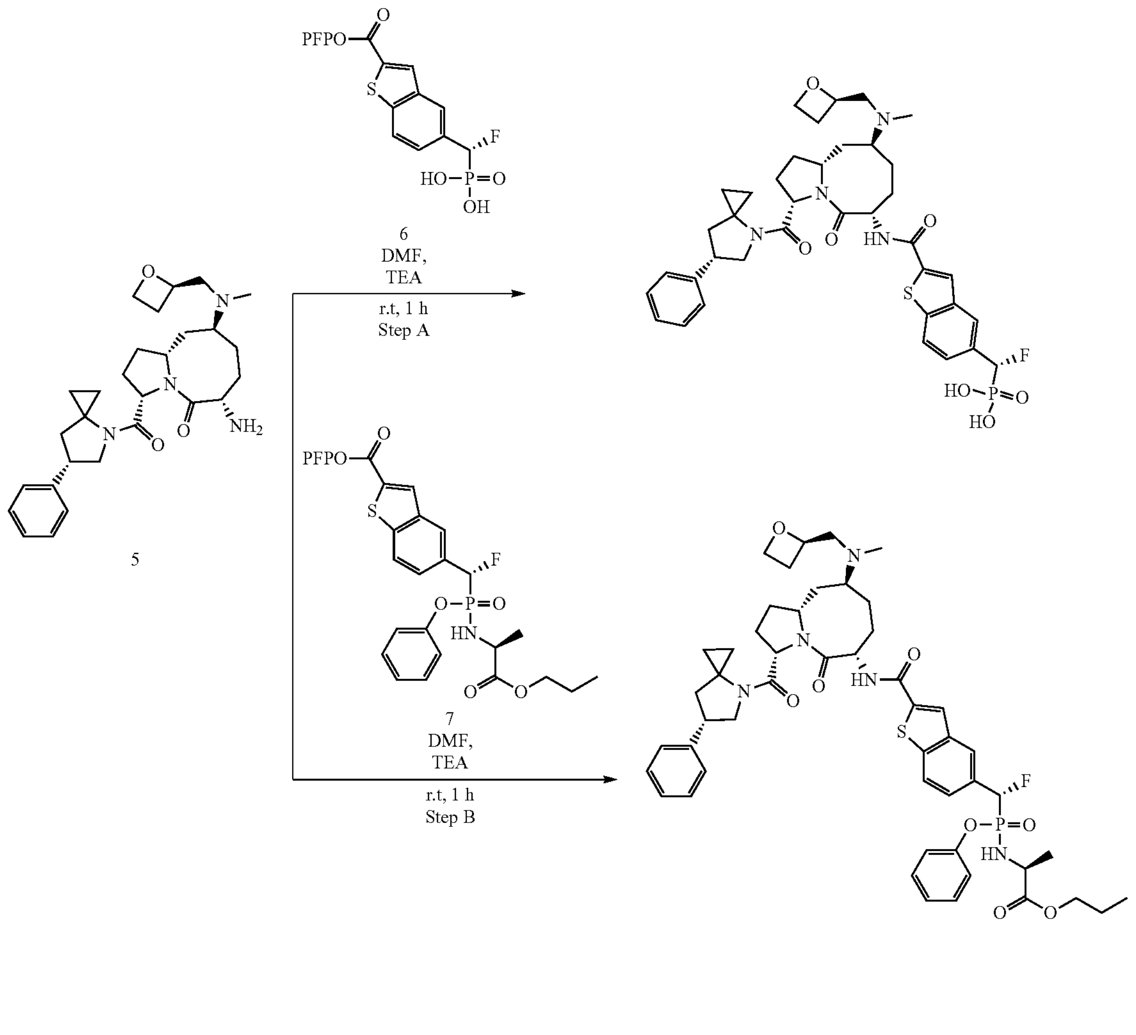

Step A: ((R)-fluoro(2-(((3S,6S,9S,10aR)-9-(methyl(((R)-oxetan-2-yl)methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)phosphonic acid

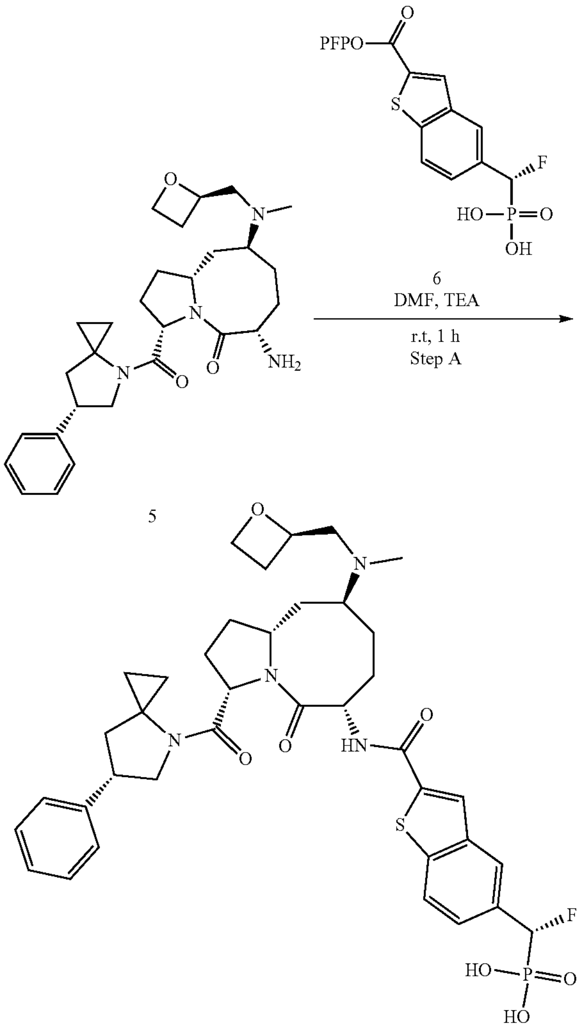

To a solution of (3S,6S,9S,10aR)-6-amino-9-(methyl(((R)-oxetan-2-yl)methyl)amino)-3-((S)-6-phenyl-4-azaspiro[2.4]heptane-4-carbonyl)octahydropyrrolo[1,2-a]azocin-5(1H)-one (5, 45 mg, TFA salt) in DMF (2 mL) were added TEA (23.29 mg. 230.14 mol, 3 eq.) and (R)-(fluoro(2-((perfluorophenoxy)carbonyl)benzo[b]thiophen-5-yl)methyl)phosphonic acid (6, 35 mg, 76.71 mol, 1 eq.), and the resulting mixture was stirred at room temperature for 1 h. The crude product was purified by Prep-HPLC to afford ((R)-fluoro(2-(((3S,6S,9S,10aR)-9-(methyl(((R)-oxetan-2-yl)methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)phosphonic acid (Compound A17, 11.7 mg, 15.54 mol, 20.2%) as a white solid. LCMS (ESI): m/z=753.2 $[M+H]^+$. $^1H$ NMR (400 MHz, DMSO-$d_6$) δ (ppm) 9.44 (d, J=48.2 Hz, 1H), 8.77 (d, J=15.4 Hz, 1H), 8.25 (s, 1H), 8.04-7.89 (m, 2H), 7.52 (d, J=8.5 Hz, 1H), 7.39-7.20 (m, 5H), 5.78 (dd, J=44.4, 7.9 Hz, 1H), 5.14 (d, J=40.9 Hz, 1H), 4.84-4.73 (m, 1H), 4.58-4.52 (m, 2H), 4.14 (s, 1H), 3.73 (d, J=12.7 Hz, 2H), 3.57-3.50 (m, 2H), 3.35-3.26 (m, 1H), 3.20 (s, 1H), 2.79-2.63 (m, 4H), 2.48-2.15 (m, 4H), 2.13-1.71 (m, 11H), 1.63-1.55 (m, 1H), 0.53 (s, 2H). (TFA salt). $^{19}F$ NMR (377 MHz, DMSO-$d_6$) δ (ppm) −36.21-−36.91 (m). $^{31}P$ NMR (162 MHz, DMSO-$d_6$) δ (ppm) 10.78 (d, J=80.1 Hz).

Step B: propyl (((R)-fluoro(2-(((3S,6S,9S,10aR)-9-(methyl(((R)-oxetan-2-yl)methyl)amino)-5-oxo-3-((S)-6-phenyl-4-azaspiro[2.4]heptane-4-carbonyl) decahydropyrrolo[1,2-a]azocin-6-yl)carbamoyl) benzo[b]thiophen-5-yl)methyl)(phenoxy) phosphoryl)-L-alaninate

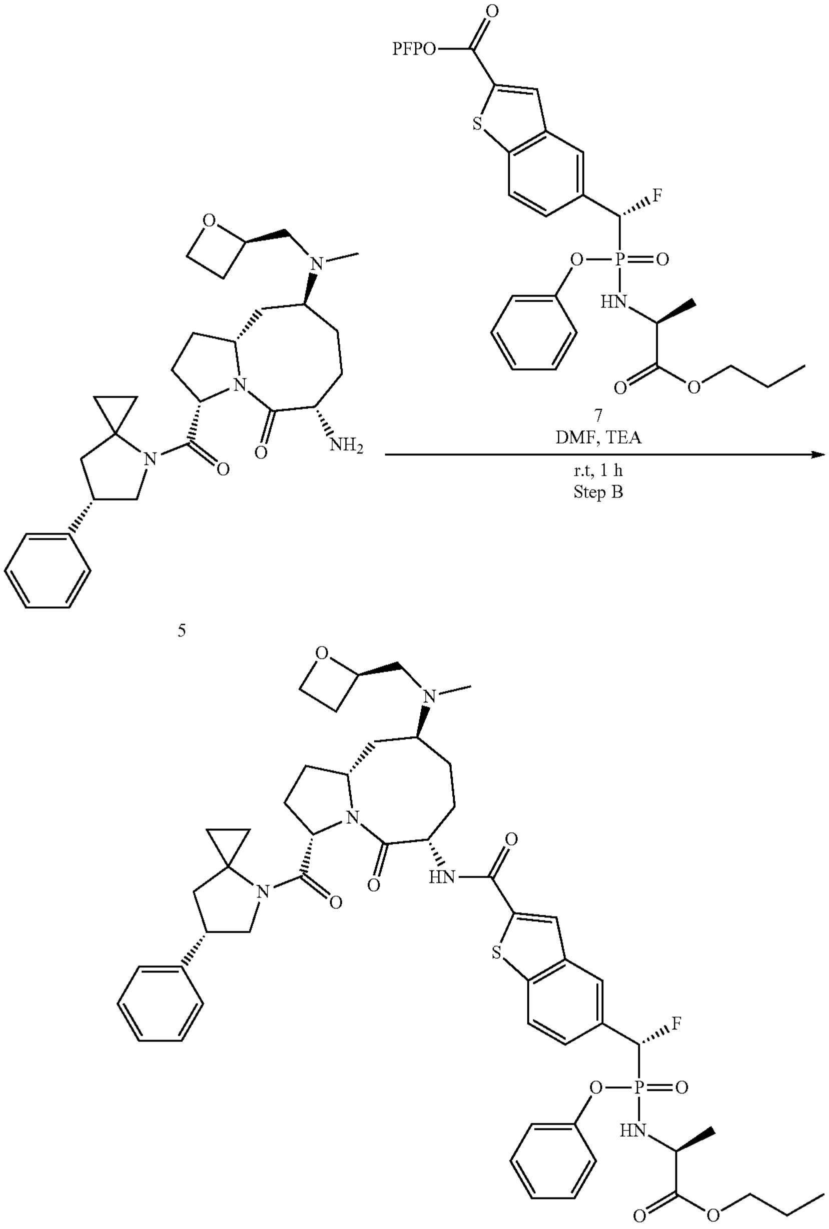

7

5

Procedure for 5 is described in the synthesis of Compound A31 and Compound C51. To a solution of (3S,6S,9S,10aR)-6-amino-9-(methyl(((R)-oxetan-2-yl)methyl)amino)-3-((S)-6-phenyl-4-azaspiro[12.4]heptane-4-carbonyl)octahydropyrrolo[1,2-a]azocin-5(1H)-one (5, 45 mg, TFA salt) in DMF (2 mL) were added TEA (23.51 mg. 232.37 mol, 3 eq.) and perfluorophenyl 5-((1R)-fluoro((((S)-1-oxo-1-propoxypropan-2-yl)amino)(phenoxy)phosphoryl)methyl)benzo[b] thiophene-2-carboxylate (7, 50 mg, 77.46 μmol, 1 eq.), and the resulting mixture was stirred at room temperature for 1 hr. LCMS indicated the complete consumption of the starting material. The crude product was purified by Prep-HPLC to afford propyl (((R)-fluoro(2-(((3S,6S,9S,10aR)-9-(methyl (((R)-oxetan-2-yl)methyl)amino)-5-oxo-3-((S)-6-phenyl-4-azaspiro[2.4]heptane-4-carbonyl)decahydropyrrolo[1,2-a] azocin-6-yl)carbamoyl)benzo[b]thiophen-5-yl)methyl) (phenoxy)phosphoryl)-L-alaninate (Compound C20, 26.6 mg, 28.23 mol, 36.4%) as a white solid. LCMS (ESI): m/z 943.0 $[M+H]^+$. $^1$H NMR (400 MHz, DMSO-do) δ (ppm) 8.83-8.69 (m, 1H), 8.27 (s, 1H), 8.09-8.02 (m, 2H), 7.65-7.58 (m, 1H), 7.40-7.26 (m, 6H), 7.24-7.13 (m, 4H), 6.29-5.99 (m, 2H), 4.86-4.67 (m, 2H), 4.54-4.41 (m, 2H), 4.40-4.34 (m, 1H), 4.33-4.25 (m, 1H), 4.12 (t, J=8.5 Hz, 1H), 4.00-3.88 (m, 1H), 3.87-3.68 (m, 3H), 3.59-3.48 (m, 1H), 2.93-2.87 (m, 1H), 2.70-2.51 (m, 3H), 2.40-2.19 (m, 3H), 2.16 (s, 3H), 2.14-2.08 (m, 1H), 2.04-1.92 (m, 3H), 1.90-1.62 (m, 6H), 1.61-1.36 (m, 4H), 1.18-1.07 (m, 3H), 0.86-0.73 (m, 3H), 0.54-0.40 (m, 2H). $^{19}$F NMR (377 MHz, DMSO-$d_6$) δ (ppm) −194.27 (d, J=82.7 Hz), −196.29 (d, J=86.0 Hz). $^{31}$P NMR (162 MHz, DMSO-$d_6$) δ (ppm) 17.32 (d, J=82.8 Hz), 17.07 (d, J=86.1 Hz).

Synthesis of ((R)-fluoro(2-(((3S,6S,9S,10aR)-9-(methyl(((S)-oxetan-2-yl)methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)phosphonic acid (Compound A15) and propyl (((R)-fluoro(2-(((3S,6S,9S,10aR)-9-(methyl(((S)-oxetan-2-yl)methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate (Compound C18)

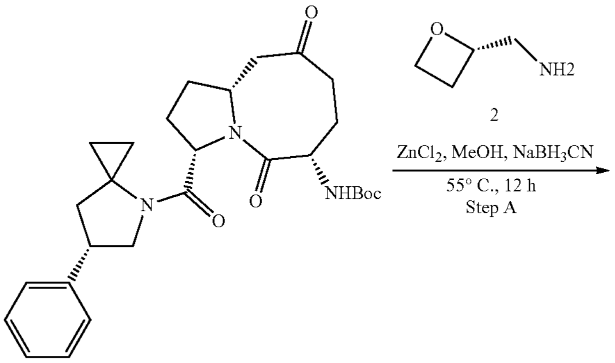

1

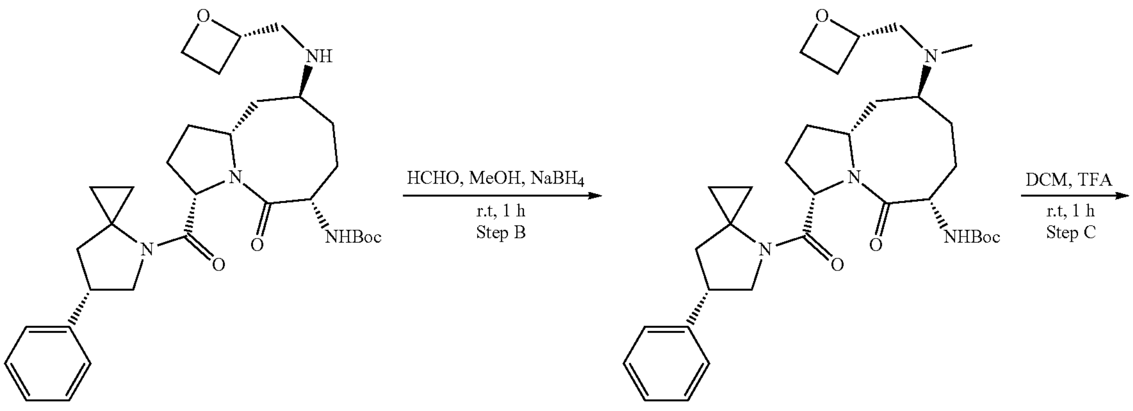

3

4

-continued

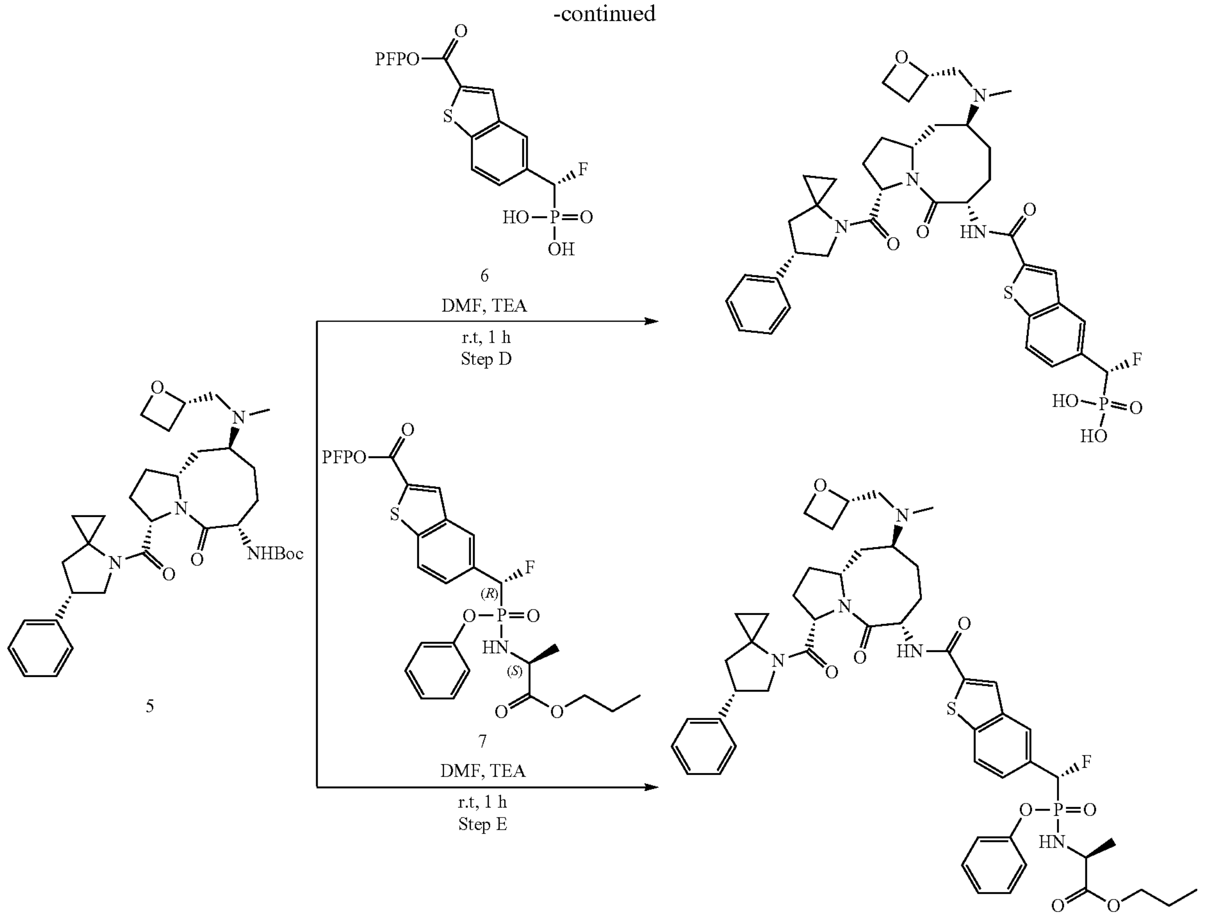

Step A: tert-butyl ((3S,6S,9S,10aR)-9-((((S)-oxetan-2-yl)methyl)amino)-5-oxo-3-((R)-6-phenyl-4-azaspiro[2.4]heptane-4-carbonyl)decahydropyrrolo[1,2-a]azocin-6-yl)carbamate

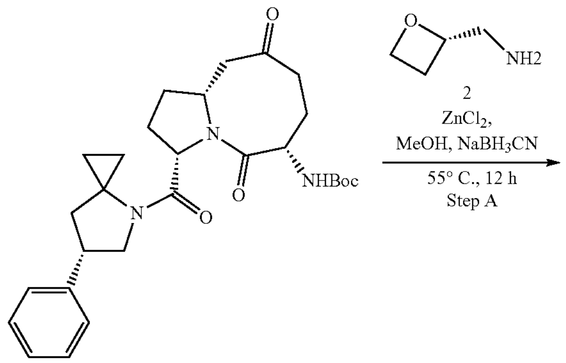

1

-continued

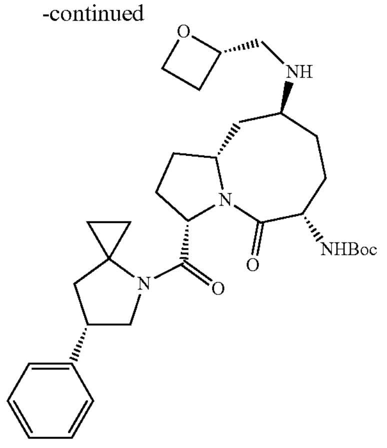

3

To a solution of tert-butyl ((3S,6S,10aR)-5,9-dioxo-3-((R)-6-phenyl-4-azaspiro[2.4]heptane-4-carbonyl)decahydropyrrolo[1,2-a]azocin-6-yl)carbamate (1, 150 mg, 302.65 mol, 1 eq.) in MeOH (5 mL) was added (S)-oxetan-2-ylmethanamine (2, 39.55 mg, 453.98 mol, 1.5 eq), $ZnCl_2$ (412.45 mg, 3.03 mmol, 10 eq.). The resulting mixture was stirred for 2 h at 55° C. under the atmosphere of $N_2$, then $NaBH_3CN$ (190 mg, 3.03 mmol, 2 eq) was added portion wise every 10 mins (2 eq. (38 mg each time) added 5 times). The solution was stirred for 12 h at 55° C., then the reaction mixture was cooled to room temperature, then was used to next step without further workup. LCMS (ESI): m/z=567 $[M+H]^+$.

Step B: tert-butyl ((3S,6S,9S,10aR)-9-(methyl(((S)-oxetan-2-yl)methyl)amino)-5-oxo-3-((R)-6-phenyl-4-azaspiro[2.4]heptane-4-carbonyl)decahydropyrrolo[1,2-a]azocin-6-yl)carbamate

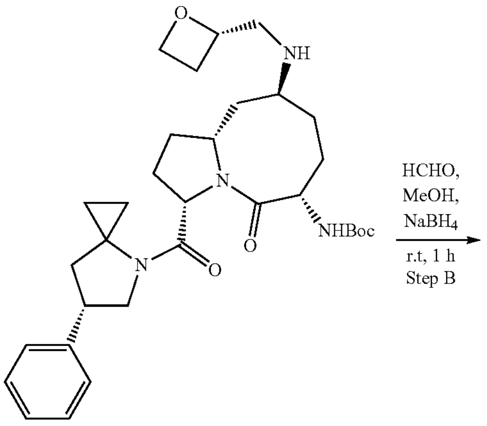

3

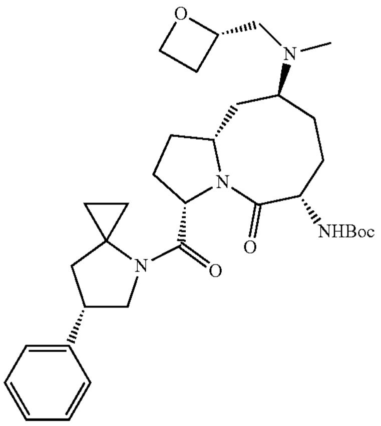

4

To the above solution (Step A) was added 40% formaldehyde (0.5 mL) at room temperature, and the solution was stirred for 30 min, then $NaBH_4$ (57.25 mg, 1.51 mmol, 5 eq) was added in one portion, the mixture was stirred for another 30 mins, then the reaction was quenched by $NH_4Cl$ (sat. aq), diluted with $H_2O$ (20 mL), then extracted with EtOAc (10 mL×3), the organic solution was dried over $Na_2SO_4$, filtered, then concentrated under vacuum. The crude product was purified by C18 column ($MeCN:H_2O$ (0.1% ammonium hydroxide)=5%-70%) to afford tert-butyl ((3S,6S,9S,10aR)-9-(methyl(((S)-oxetan-2-yl)methyl)amino)-5-oxo-3-((R)-6-phenyl-4-azaspiro[2.4]heptane-4-carbonyl)decahydropyrrolo[1,2-a]azocin-6-yl)carbamate (4, 120 mg, 206.6 mol, 68.2% yield two steps) as a white solid. LCMS (ESI): m/z=581 $[M+H]^+$.

Step C: (3S,6S,9S,10aR)-6-amino-9-(methyl(((S)-oxetan-2-yl)methyl)amino)-3-((R)-6-phenyl-4-azaspiro[2.4]heptane-4-carbonyl)octahydropyrrolo[1,2-a]azocin-5(1H)-one

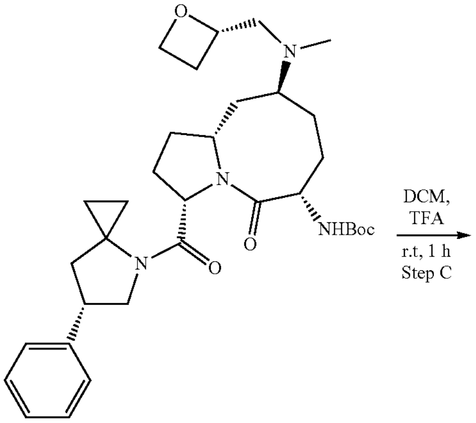

4

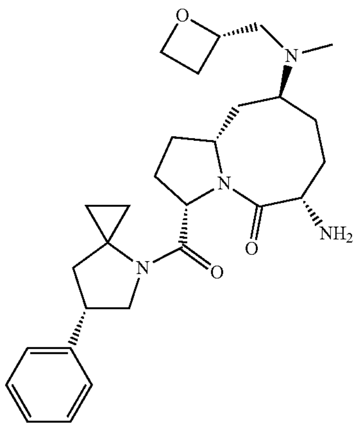

5

To a solution of tert-butyl ((3S,6S,9S,10aR)-9-(methyl(((S)-oxetan-2-yl)methyl)amino)-5-oxo-3-((R)-6-phenyl-4-azaspiro[2.4]heptane-4-carbonyl)decahydropyrrolo[1,2-a]azocin-6-yl)carbamate (4, 90 mg, 154.97 mol, 1 eq.) in DCM (3 mL) was added TFA (1 mL). The resulting mixture was stirred for 1 h at room temperature. The resulting mixture was concentrated to dryness under reduced pressure to afford crude product (3S,6S,9S,10aR)-6-amino-9-(methyl(((S)-oxetan-2-yl)methyl)amino)-3-((R)-6-phenyl-4-azaspiro[2.4]heptane-4-carbonyl)octahydropyrrolo[1,2-a]azocin-5(1H)-one (5, 90 mg, TFA salt) as a yellow oil. LCMS (ESI): m/z=481 [M+H]$^+$.

Step D: ((R)-fluoro(2-(((3S,6S,9S,10aR)-9-(methyl(((S)-oxetan-2-yl)methyl)amino)-5-oxo-3-((R)-6-phenyl-4-azaspiro[2.4]heptane-4-carbonyl)decahydropyrrolo[1,2-a]azocin-6-yl)carbamoyl)benzo[b]thiophen-5-yl)methyl)phosphonic acid

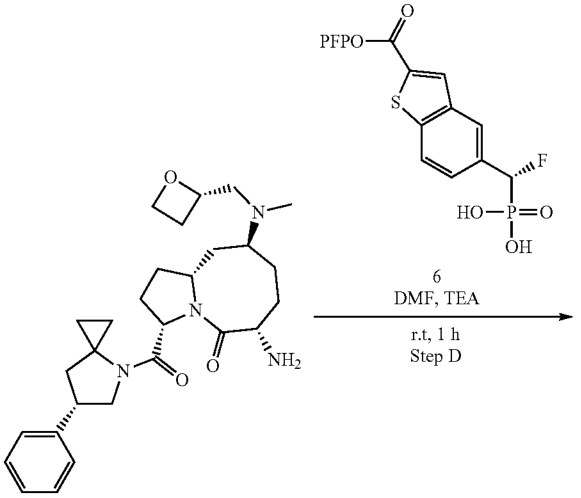

5

-continued

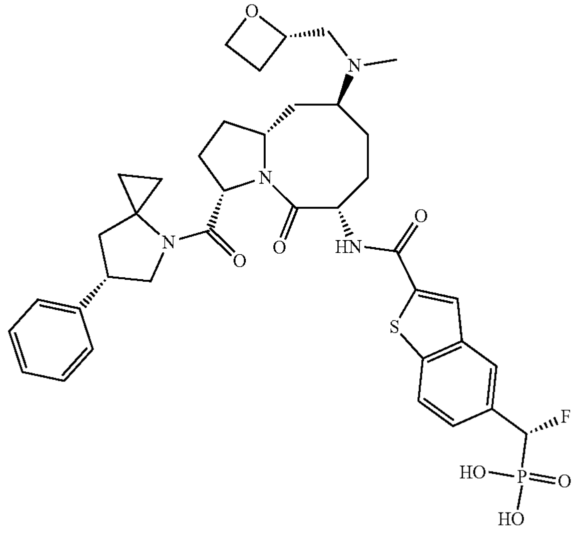

To a solution of (3S,6S,9S,10aR)-6-amino-9-(methyl(((S)-oxetan-2-yl)methyl)amino)-3-((R)-6-phenyl-4-azaspiro[2.4]heptane-4-carbonyl)octahydropyrrolo[1,2-a]azocin-5(1H)-one (5, 45 mg, TFA salt) in DMF (2 mL) were added TEA (23.29 mg. 230.14 mol, 3 eq.) and (R)-(fluoro(2-((perfluorophenoxy)carbonyl)benzo[b]thiophen-5-yl)methyl)phosphonic acid (6, 35 mg, 76.71 mol, 1 eq.), and the resulting mixture was stirred at room temperature for 1 h. The crude product was purified by Prep-HPLC to afford ((R)-fluoro(2-(((3S,6S,9S,10aR)-9-(methyl(((S)-oxetan-2-yl)methyl)amino)-5-oxo-3-((R)-6-phenyl-4-azaspiro[2.4]heptane-4-carbonyl)decahydropyrrolo[1,2-a]azocin-6-yl)carbamoyl)benzo[b]thiophen-5-yl)methyl)phosphonic acid (Compound A15, 22.8 mg, 30.28 mol, 39.4%) as a white solid. LCMS (ESI): m/z=753.3 [M+H]$^+$. $^1$H NMR (400 MHz, DMSO-$d_6$) δ (ppm) 9.61-9.30 (m, 1H), 8.86-8.69 (m, 1H), 8.29-8.22 (m, 1H), 8.06-7.93 (m, 2H), 7.53 (d, J=8.5 Hz, 1H), 7.40-7.29 (m, 4H), 7.23 (t, J=7.0 Hz, 1H), 5.81 (dd, J=44.4, 8.0 Hz, 1H), 5.21-5.06 (m, 1H), 4.84-4.75 (m, 1H), 4.62-4.51 (m, 3H), 4.15-4.09 (m, 1H), 3.78-3.66 (m, 2H), 3.60-3.48 (m, 2H), 3.38-3.16 (m, 1H), 2.83-2.64 (m, 4H), 2.49-1.70 (m, 15H), 1.63-1.53 (m, 1H), 0.57-0.43 (m, 2H). (TFA salt). $^{19}$F NMR (376 MHz, DMSO-$d_6$) δ (ppm) −194.80 (d, J=80.8 Hz). $^{31}$P NMR (162 MHz, DMSO-$d_6$) δ (ppm) 10.86 (d, J=80.8 Hz).

Step E: propyl (((R)-fluoro(2-(((3S,6S,9S,10aR)-9-(methyl(((S)-oxetan-2-yl)methyl)amino)-5-oxo-3-((R)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate

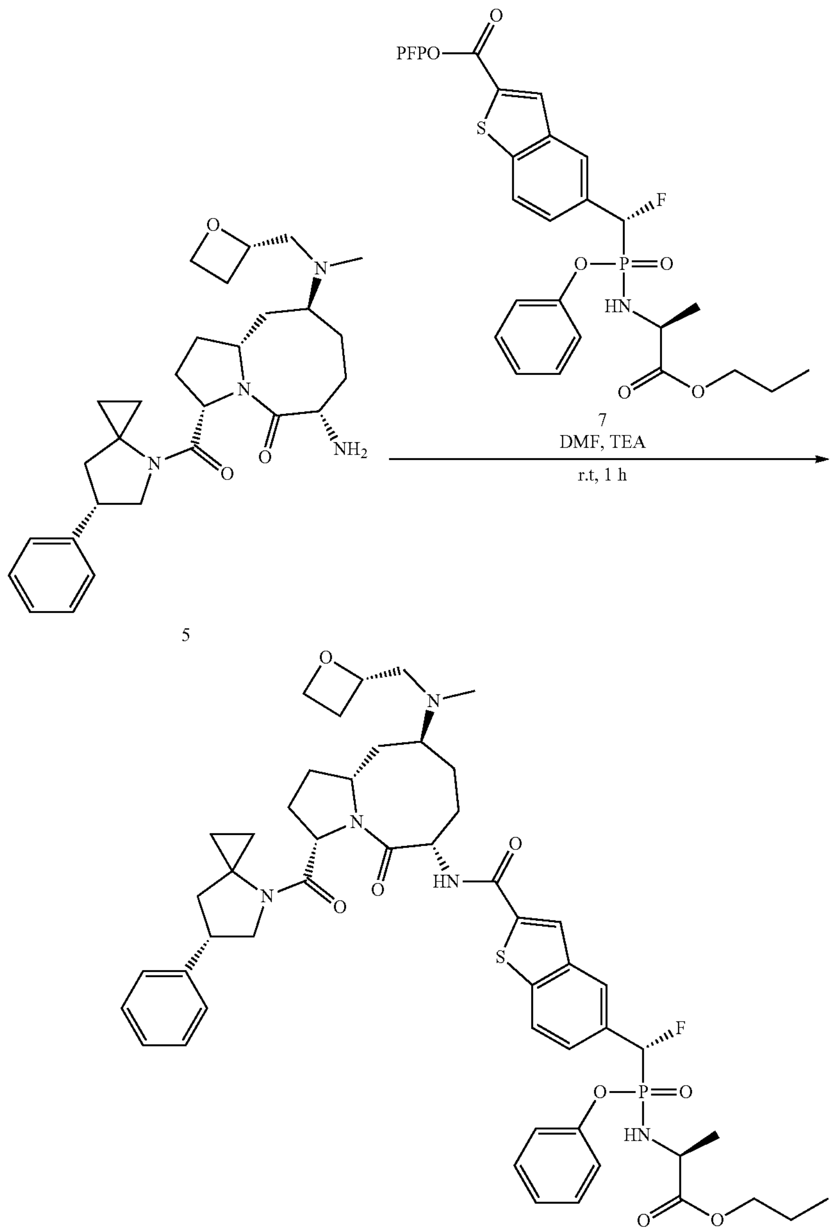

5

To a solution of (3S,6S,9S,10aR)-6-amino-9-(methyl(((S)-oxetan-2-yl)methyl)amino)-3-((R)-6-phenyl-4-azaspiro[2.4]heptane-4-carbonyl)octahydropyrrolo[1,2-a]azocin-5(1H)-one (5, 45 mg, TFA salt) in DMF (2 mL) were added TEA (23.51 mg. 232.37 mol, 3 eq.) and perfluorophenyl 5-((1R)-fluoro((((S)-1-oxo-1-propoxypropan-2-yl)amino)(phenoxy)phosphoryl)methyl)benzo[b]thiophene-2-carboxylate (7, 50 mg, 77.46 mol, 1 eq.), and the resulting mixture was stirred at room temperature for 1 h. The crude product was purified by Prep-HPLC to afford propyl (((R)-fluoro(2-(((3S,6S,9S,10aR)-9-(methyl(((S)-oxetan-2-yl)methyl)amino)-5-oxo-3-((R)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate (Compound C18, 7.2 mg, 7.64 mol, 9.8%) as a white solid. LCMS (ESI): m/z=943.0 $[M+H]^+$. $^1H$ NMR (400 MHz, DMSO-$d_6$) δ (ppm) 8.79-8.68 (m, 1H), 8.27 (s, 1H), 8.11-8.01 (m, 2H), 7.64-7.55 (m, 1H), 7.39-7.25 (m, 6H), 7.23-7.09 (m, 4H), 6.26-6.01 (m, 2H), 4.83-4.70 (m, 2H), 4.54-4.42 (m, 2H), 4.41-4.25 (m, 2H), 4.15-4.08 (m, 1H), 3.96-3.69 (m, 4H), 3.59-3.49 (m, 1H), 2.95-2.84 (m, 1H), 2.70-2.55 (m, 2H), 2.42-1.35 (m, 21H), 1.13 (d, J=7.1 Hz, 3H), 0.84-0.71 (m, 3H), 0.57-0.41 (m, 2H). $^{19}F$ NMR (376 MHz, DMSO-$d_6$) δ (ppm) −194.25 (d, J=83.0 Hz), −196.30 (d, J=85.7 Hz). $^{31}P$ NMR (162 MHz, DMSO-$d_6$) δ (ppm) 17.32 (d, J=82.8 Hz), 17.07 (d, J=85.3 Hz).

Synthesis of ((S)-fluoro(2-(((3S,6S,9S,10aR)-9-morpholino-5-oxo-3-((R)-6-(pyridin-3-yl)-4-azaspiro[2.4]heptane-4-carbonyl)decahydropyrrolo[1,2-a]azocin-6-yl)carbamoyl)benzo[b]thiophen-5-yl)methyl)phosphonic acid (Compound A10) and propyl ((S)-((S)-fluoro(2-(((3S,6S,9S,10aR)-9-morpholino-5-oxo-3-((R)-6-(pyridin-3-yl)-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate (Compound C43)

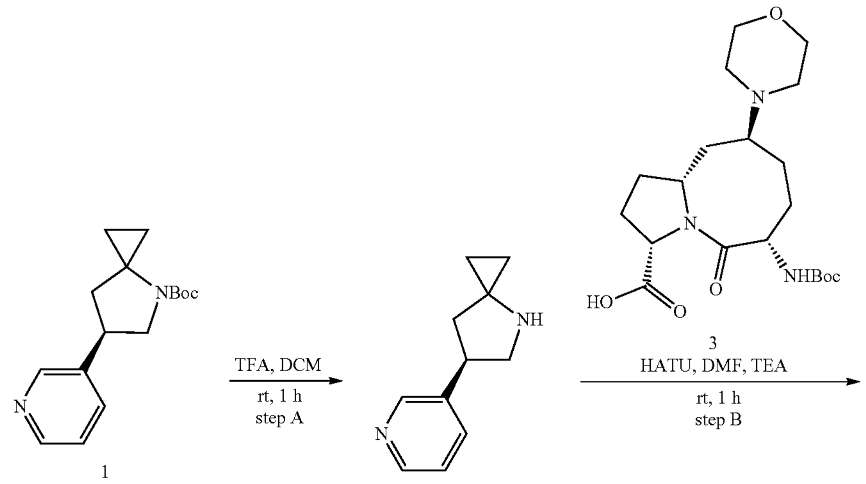

1 2 3

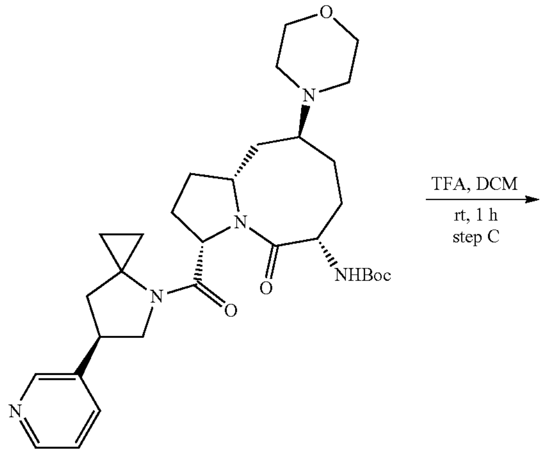

4

-continued
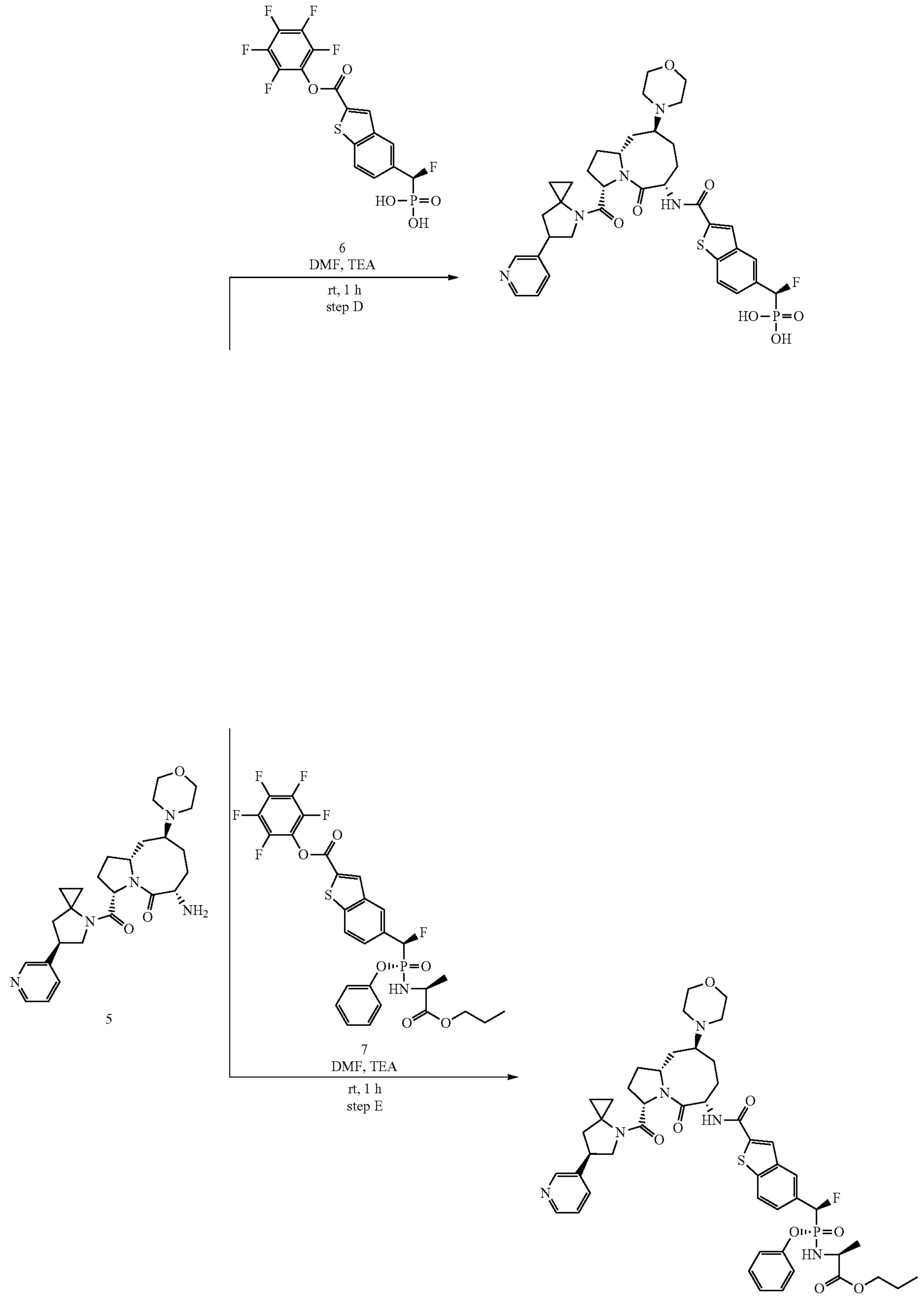

Step A: (R)-6-(pyridin-3-yl)-4-azaspiro[2.4]heptane

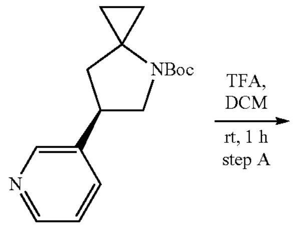

1 2

To a solution of tert-butyl (R)-6-(pyridin-3-yl)-4-azaspiro[2.4]heptane-4-carboxylate (1, 1 g, 3.65 mmol, 1 eq.) in DCM (10 mL) was added TFA (10 mL), The resulting mixture was stirred for 1 h at room temperature. The resulting mixture was concentrated to dryness under reduced pressure to afford crude product (R)-6-(pyridin-3-yl)-4-azaspiro[2.4]heptane (2, 1.0 g, TFA salt) as a yellow oil which was used to the next step without further purification. LCMS (ESI): m/z=175 $[M+H]^+$.

Step B: tert-butyl ((3S,6S,9S,10aR)-9-morpholino-5-oxo-3-((R)-6-(pyridin-3-yl)-4-azaspiro[2.4]heptane-4-carbonyl)decahydropyrrolo[1,2-a]azocin-6-yl)carbamate

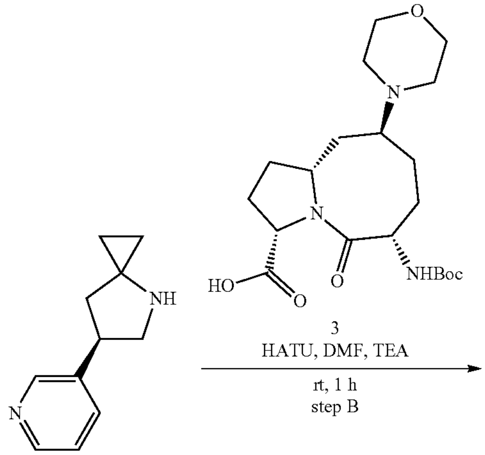

2

-continued

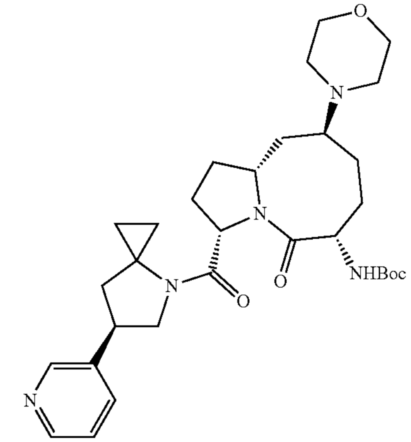

4

To a solution of (3S,6S,9S,10aR)-6-((tert-butoxycarbonyl)amino)-9-morpholino-5-oxodecahydropyrrolo[1,2-a]azocine-3-carboxylic acid (3, 1.5 g, 3.65 mmol, 1 eq.) in DMF (10 mL) was added HATU (1.39 g, 3.65 mmol, 1 eq.), TEA (737 mg, 7.30 mmol, 2 eq). The solution was stirred for 10 min, then (R)-6-(pyridin-3-yl)-4-azaspiro[2.4]heptane (2, 1.0 g, TFA salt) was added to the solution, The resulting mixture was stirred for 1 h at room temperature. The crude product was purified by C18 column to afford tert-butyl ((3S,6S,9S,10aR)-9-morpholino-5-oxo-3-((R)-6-(pyridin-3-yl)-4-azaspiro[2.4]heptane-4-carbonyl)decahydropyrrolo[1,2-a]azocin-6-yl)carbamate (4, 1.7 g, 3.0 mmol, 82.1% yield, two steps) as a white solid. LCMS (ESI): m/z=468 $[M+H]^+$.

Step C: (3S,6S,9S,10aR)-6-amino-9-morpholino-3-((R)-6-(pyridin-3-yl)-4-azaspiro[2.4]heptane-4-carbonyl)octahydropyrrolo[1,2-a]azocin-5(1H)-one

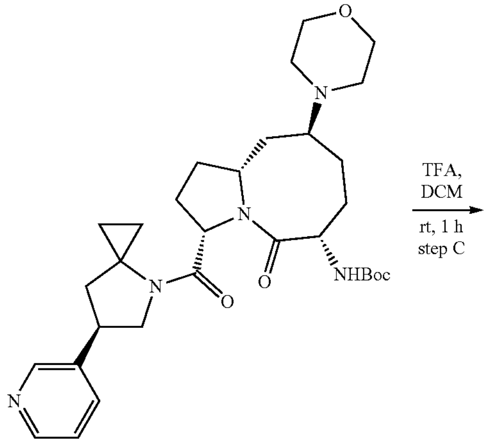

4

-continued

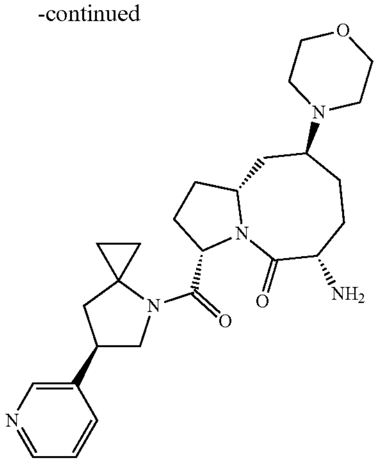

5

To a solution of tert-butyl ((3S,6S,9S,10aR)-9-morpholino-5-oxo-3-((R)-6-(pyridin-3-yl)-4-azaspiro[2.4]heptane-4-carbonyl)decahydropyrrolo[1,2-a]azocin-6-yl)carbamate (4, 20 mg, 0.035 mmol) in DCM (2 mL) was added TFA (1 mL) and the resulting mixture was stirred for 1 h at room temperature. The resulting mixture was concentrated to dryness under reduced pressure to afford crude product (3S,6S,9S,10aR)-6-amino-9-morpholino-3-((R)-6-(pyridin-3-yl)-4-azaspiro[2.4]heptane-4-carbonyl)octahydropyrrolo[1,2-a]azocin-5(1H)-one (5, 20 mg, TFA salt) as a yellow oil which was used to the next step without further purification. LCMS (ESI): m/z=568 [M+H]$^+$.

Step D: ((S)-fluoro(2-(((3S,6S,9S,10aR)-9-morpholino-5-oxo-3-((R)-6-(pyridin-3-yl)-4-azaspiro[2.4]heptane-4-carbonyl)decahydropyrrolo[1,2-a]azocin-6-yl)carbamoyl)benzo[b]thiophen-5-yl)methyl)phosphonic acid

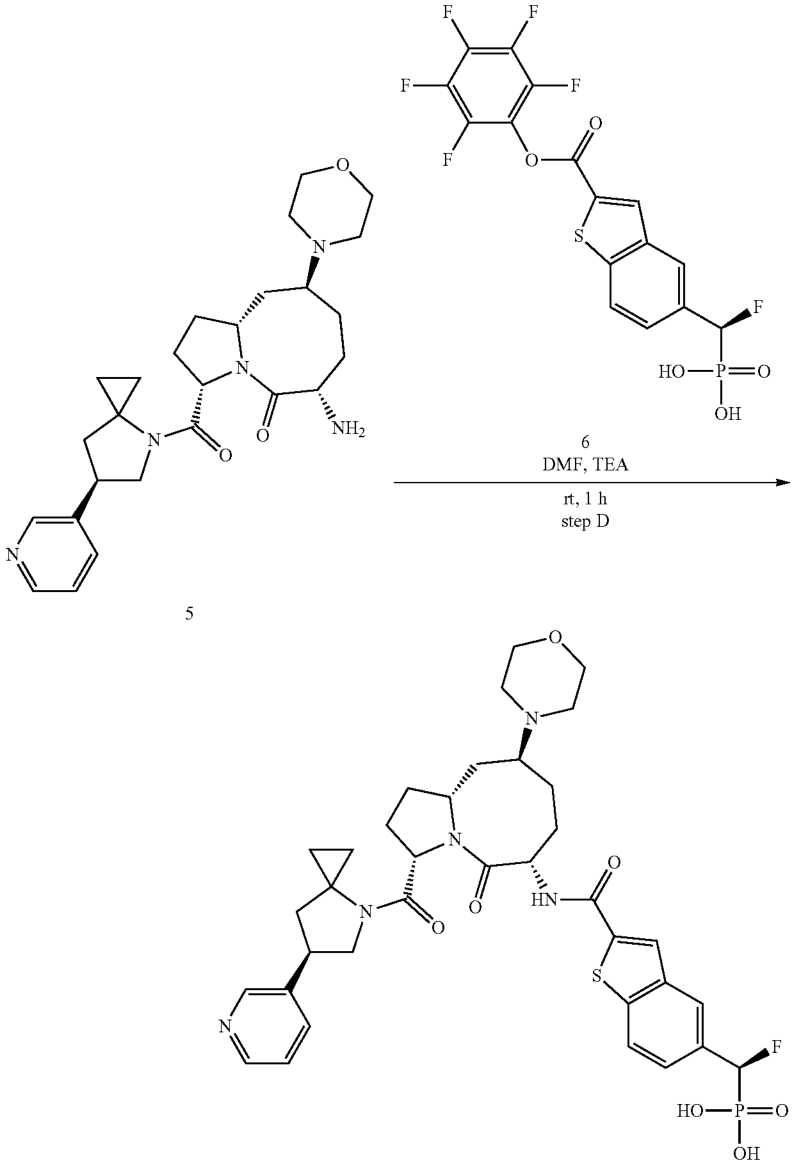

5

To a solution of (3S,6S,9S,10aR)-6-amino-9-morpholino-3-((R)-6-(pyridin-3-yl)-4-azaspiro[2.4]heptane-4-carbonyl) octahydropyrrolo[1,2-a]azocin-5(1H)-one (5, 20 mg, TFA salt) was added TEA (7.1 mg, 0.07 mmol, 2 eq.), (S)-(fluoro (2-((perfluorophenoxy)carbonyl)benzo[b]thiophen-5-yl) methyl)phosphonic acid (6, 16.1 mg, 0.035 mml, 1 eq.). The resulting mixture was stirred for 1 h at room temperature. The crude product was purified by Prep-HPLC to afford ((S)-fluoro(2-(((3S,6S,9S,10aR)-9-morpholino-5-oxo-3-((R)-6-(pyridin-3-yl)-4-azaspiro[2.4]heptane-4-carbonyl) decahydropyrrolo[1,2-a]azocin-6-yl)carbamoyl)benzo[b] thiophen-5-yl)methyl)phosphonic acid (Compound A10, 10 mg, 0.014 mmol) as a white solid. LCMS (ESI): m/z=740 $[M+H]^+$. $^1H$ NMR (400 MHz, DMSO-$d_6$) δ (ppm) 8.82-8.74 (m, 1H), 8.61 (s, 1H), 8.51-8.43 (m, 1H), 8.24 (s, 1H), 8.06-7.95 (m, 2H), 7.89-7.81 (m, 1H), 7.57-7.49 (m, 1H), 7.43-7.35 (m, 1H), 5.91-5.74 (m, 1H), 4.85-4.78 (m, 1H), 4.56 (t, J=8.5 Hz, 2H), 4.19-4.11 (m, 2H), 4.06-4.01 (m, 2H), 3.84-3.78 (m, 2H), 3.73-3.69 (m, 1H), 3.62-3.55 (m, 2H), 3.28-3.22 (m, 2H), 3.15-3.08 (m, 1H), 2.25-1.95 (m, 9H), 1.87-1.61 (m, 5H), 0.56-0.44 (m, 2H). $^{19}F$ NMR (377 MHz, DMSO-$d_6$) δ (ppm) −194.71 (d, J=81.3 Hz). $^{31}P$ NMR (162 MHz, DMSO-$d_6$) δ (ppm) 10.92 (d, J=81.1 Hz).

Step E: propyl ((S)-((S)-fluoro(2-(((3S,6S,9S,10aR)-9-morpholino-5-oxo-3-((R)-6-(pyridin-3-yl)-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate

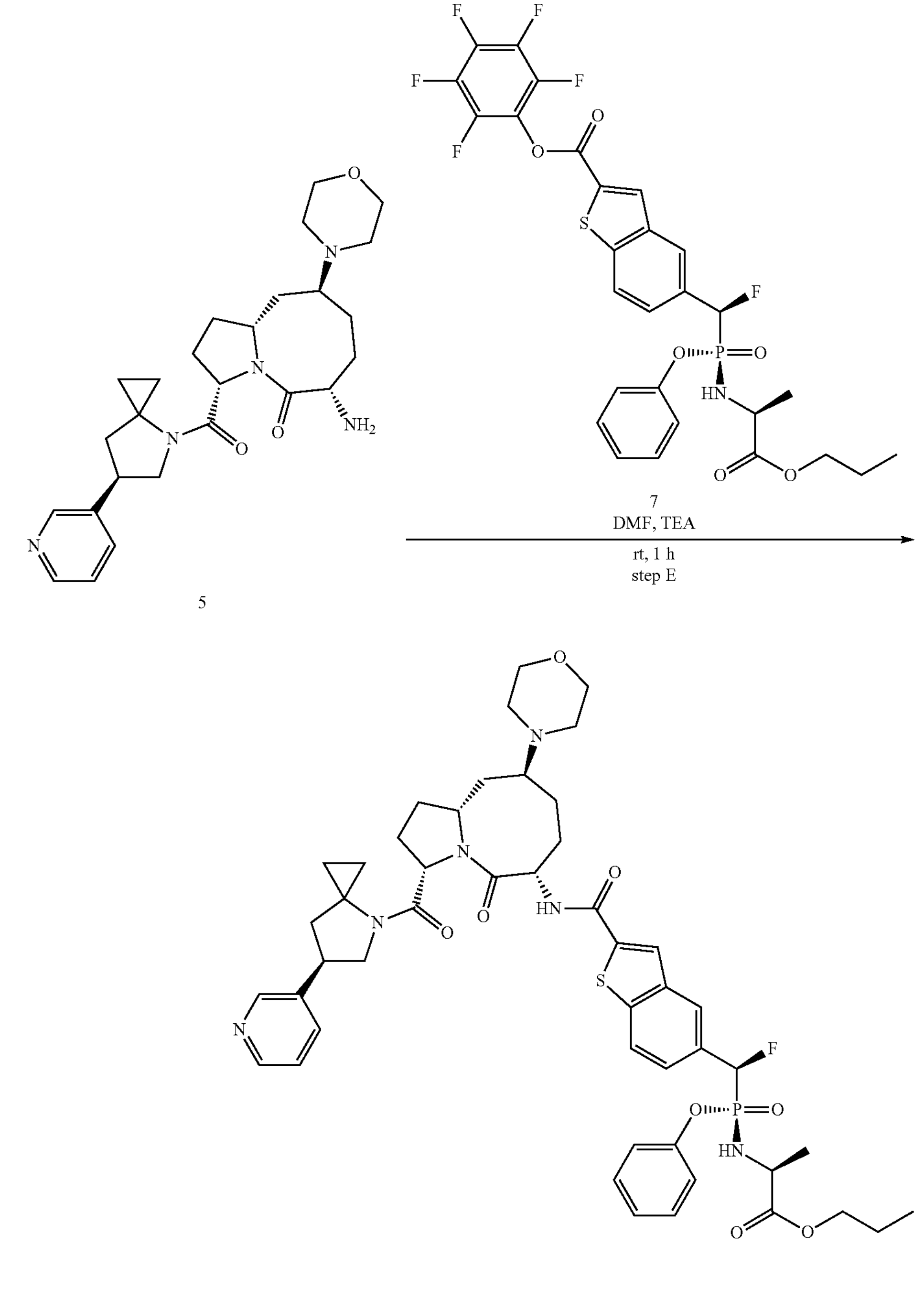

To a solution of (3S,6S,9S,10aR)-6-amino-9-morpholino-3-((R)-6-(pyridin-3-yl)-4-azaspiro[2.4]heptane-4-carbonyl) octahydropyrrolo[1,2-a]azocin-5(1H)-one (5, 20 mg, TFA salt) was added TEA (7.1 mg, 0.07 mmol, 2 eq.), perfluorophenyl 5-((S)-fluoro((S)-(((S)-1-oxo-1-propoxypropan-2-yl)amino)(phenoxy)phosphoryl)methyl)benzo[b]thiophene-2-carboxylate (7, 22.5 mg, 0.035 mml, 1 eq.). The resulting mixture was stirred for 1 h at room temperature. The crude product was purified by Prep-HPLC to afford propyl ((S)-((S)-fluoro(2-(((3S,6S,9S,10aR)-9-morpholino-5-oxo-3-((R)-6-(pyridin-3-yl)-4-azaspiro[2.4]heptane-4-carbonyl) decahydropyrrolo[1,2-a]azocin-6-yl)carbamoyl)benzo[b] thiophen-5-yl)methyl)(phenoxy)phosphoryl)-L-alaninate (Compound C43, 15 mg, 0.016 mmol, 57% yield) as a white solid. LCMS (ESI): m/z=929 $[M+H]^+$. $^{1}$H NMR (400 MHz, DMSO-$d_6$) δ (ppm) 8.79-8.65 (m, 1H), 8.63-8.51 (m, 1H), 8.46-8.38 (m, 1H), 8.28 (s, 1H), 8.14-7.99 (m, 2H), 7.82-7.73 (m, 1H), 7.65-7.56 (m, 1H), 7.41-7.29 (m, 3H), 7.24-7.14 (m, 3H), 6.25-6.03 (m, 2H), 5.04-4.87 (m, 1H), 4.56-4.44 (m, 1H), 4.37-4.24 (m, 1H), 4.20-4.06 (m, 1H), 3.98-3.85 (m, 2H), 3.84-3.49 (m, 7H), 2.80-2.69 (m, 1H), 2.48-1.57 (m, 18H), 1.54-1.42 (m, 2H), 0.98-0.89 (m, 3H), 0.85-0.74 (m, 3H), 0.56-0.37 (m, 2H). $^{19}$F NMR (376 MHz, DMSO-$d_6$) δ (ppm) −194.13 (d, J=82.5 Hz). $^{31}$P NMR (162 MHz, DMSO-$d_6$) δ (ppm) 16.93 (d, J=82.5 Hz).

Synthesis of propyl (((R)-fluoro(2-(((3S,6S,9S,10aR)-9-(((1s,3R)-3-fluorocyclobutyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-D-alaninate (Compound C84)

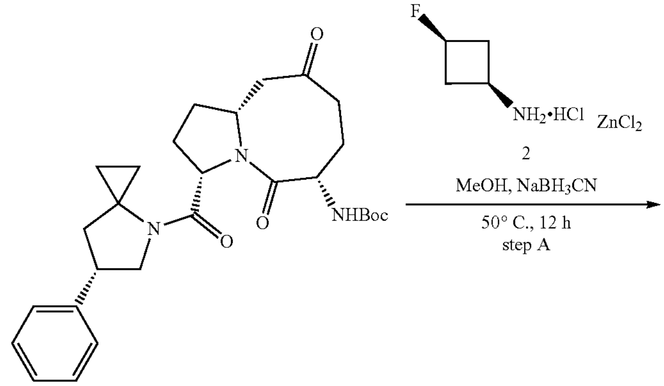

1

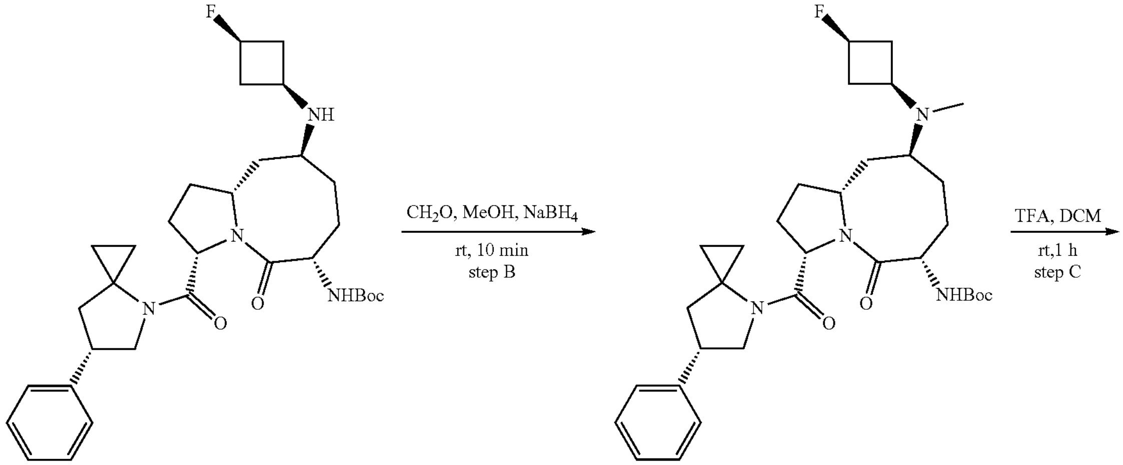

3

4

-continued
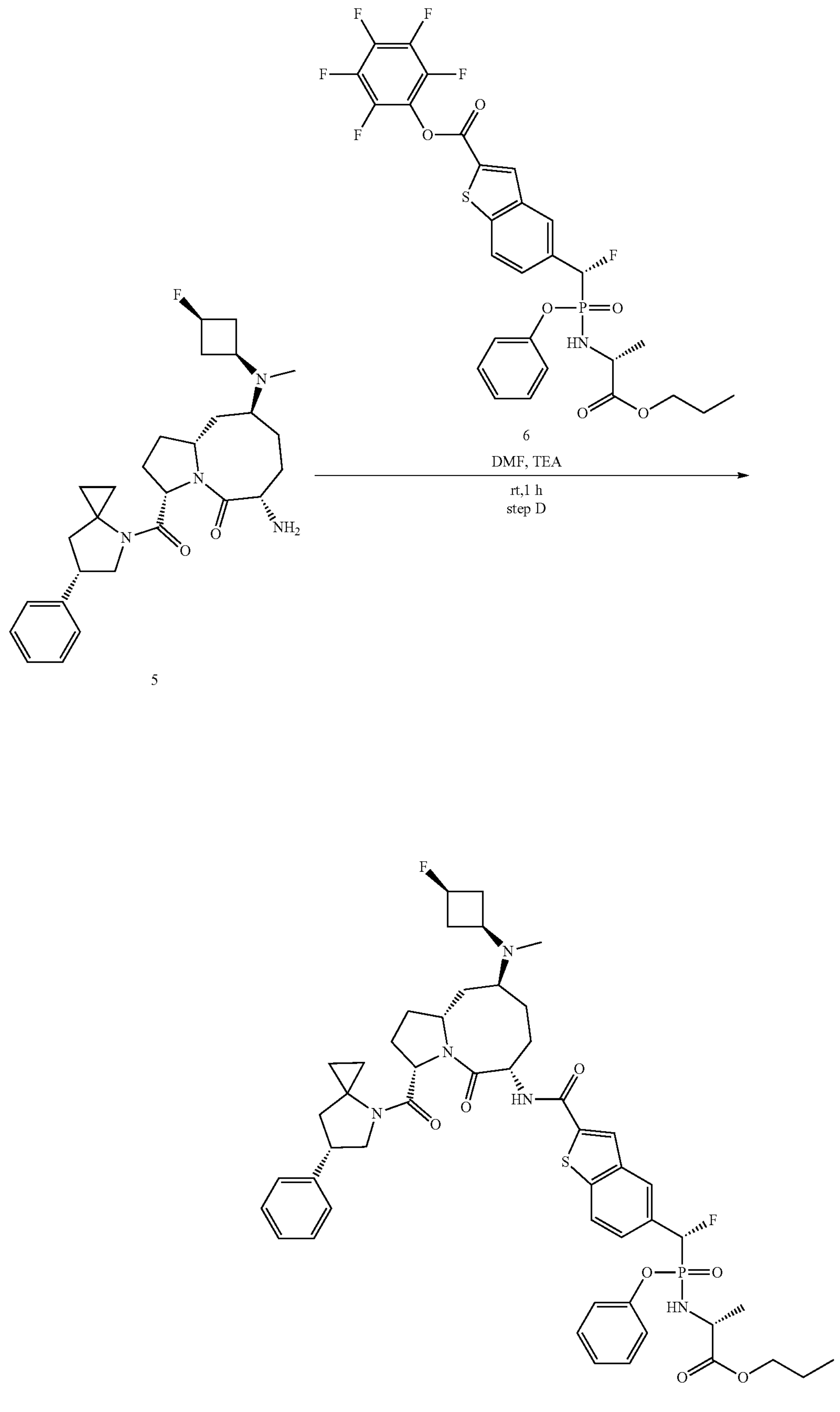

Step A: tert-butyl ((3S,6S,9S,10aR)-9-(((1s,3R)-3-fluorocyclobutyl)amino)-5-oxo-3-((S)-6-phenyl-4-azaspiro[2.4]heptane-4-carbonyl)decahydropyrrolo[1,2-a]azocin-6-yl)carbamate Step B: tert-butyl ((3S,6S,9S,10aR)-9-(((1s,3R)-3-fluorocyclobutyl)(methyl)amino)-5-oxo-3-((S)-6-phenyl-4-azaspiro[2.4]heptane-4-carbonyl)decahydropyrrolo[1,2-a]azocin-6-yl)carbamate

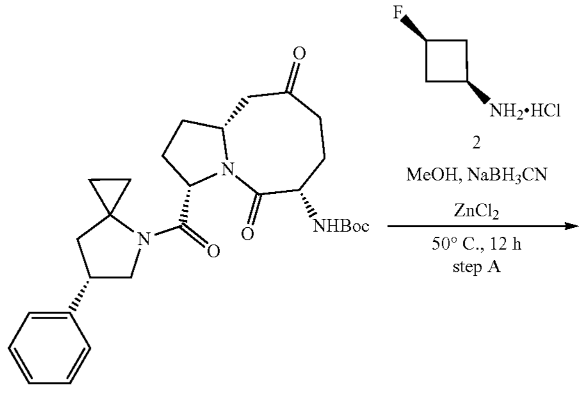

1

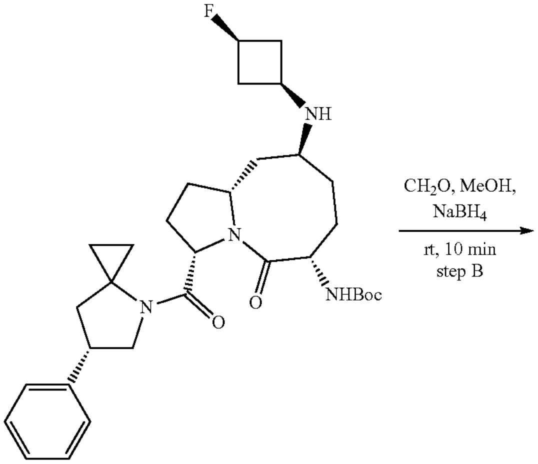

3

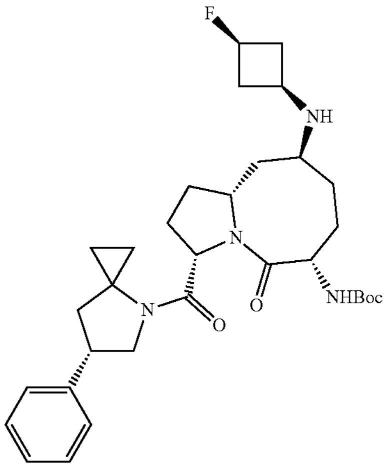

3

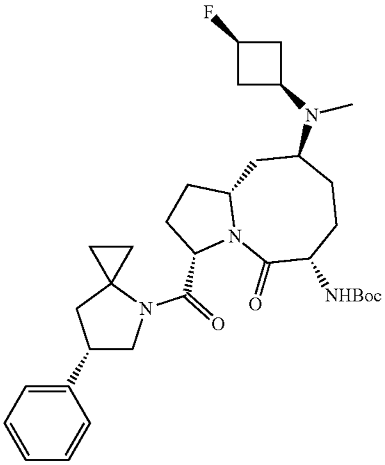

4

To a solution of tert-butyl ((3S,6S,10aR)-5,9-dioxo-3-((S)-6-phenyl-4-azaspiro[2.4]heptane-4-carbonyl)decahydropyrrolo[1,2-a]azocin-6-yl)carbamate (1, 3 g, 6.06 mmol, 1 eq.) in MeOH (60 mL) was added (1s,3s)-3-fluorocyclobutan-1-amine hydrochloride (2, 1.14 g, 9.09 mmol, 1.5 eq.), $ZnCl_2$ (8.3 g, 60.6 mmol, 10 eq.), the solution was stirred for 2 hr at 50° C. under the atmosphere of $N_2$. Then $NaBH_3CN$ (3.81 g, 60.6 mmol, 10 eq.) was added portion wise every 30 mins (2 eq. (762 mg each time) added 5 times). The resulting mixture was stirred for 12 hr at 50° C., then cooled to room temperature, The solution was used to next step without further workup. LCMS (ESI): m/z=569 $[M+H]^+$.

To the above mixture (step A) was added 40% formaldehyde aqueous (3 mL) at room temperature, the mixture was stirred for 30 min, then $NaBH_4$ (1.15 g, 30.3 mmol, 5 eq.) was added in portions, the mixture was stirred for another 30 mins. The reaction was quenched by $NH_4Cl$ (sat. aq), diluted with $H_2O$ (200 mL) and extracted with EtOAc (100 mL×3), the organic solution was dried over $Na_2SO_4$, then concentrated under vacuum, the crude product was purified by C18 column (MeCN:$H_2O$ (0.1% ammonium hydroxide)=5%-70%) to afford tert-butyl ((3S,6S,9S,10aR)-9-(((1s,3R)-3-fluorocyclobutyl)(methyl)amino)-5-oxo-3-((S)-6-phenyl-4-azaspiro[2.4]heptane-4-carbonyl)decahydropyrrolo[1,2-a]azocin-6-yl)carbamate (4, 3 g, 5.15 mmol, 85% yield two steps) as a white solid. LCMS (ESI): m/z=583 $[M+H]^+$.

Step C: (3S,6S,9S,10aR)-6-amino-9-(((1s,3R)-3-fluorocyclobutyl)(methyl)amino)-3-((S)-6-phenyl-4-azaspiro[2.4]heptane-4-carbonyl)octahydropyrrolo[1,2-a]azocin-5(1H)-one

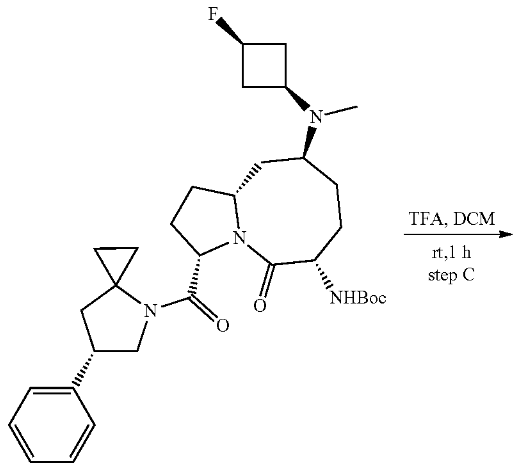

4

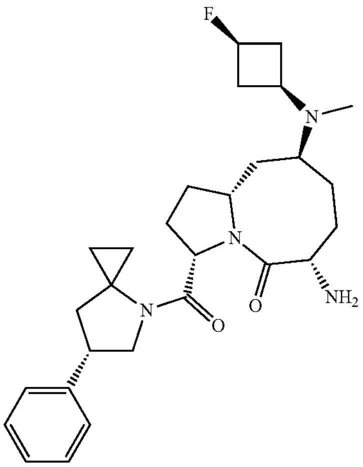

5

To a solution of tert-butyl((3S,6S,9S,10aR)-9-(((1s,3R)-3-fluorocyclobutyl)(methyl)amino)-5-oxo-3-((S)-6-phenyl-4-azaspiro[2.4]heptane-4-carbonyl)decahydropyrrolo[1,2-a]azocin-6-yl)carbamate (4, 20 mg, 0.034 mmol) in DCM (2 mL) was added TFA (2 mL). The resulting mixture was stirred for 1 h at room temperature. The resulting mixture was concentrated to dryness under reduced pressure to afford crude product (3S,6S,9S,10aR)-6-amino-9-(((1s,3R)-3-fluorocyclobutyl)(methyl)amino)-3-((S)-6-phenyl-4-azaspiro[2.4]heptane-4-carbonyl)octahydropyrrolo[1,2-a]azocin-5(1H)-one (5, 20 mg, TFA salt) as a yellow oil which was used to the next step without further purification. LCMS (ESI): m/z=483 $[M+H]^+$.

Step D: propyl (((R)-fluoro(2-(((3S,6S,9S,10aR)-9-(((1s,3R)-3-fluorocyclobutyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-D-alaninate To a solution of (3S,6S,9S,10aR)-6-amino-9-(((1s,3R)-3-fluorocyclobutyl)(methyl)amino)-3-((S)-6-phenyl-4-azaspiro[2.4]heptane-4-carbonyl)octahydropyrrolo[1,2-a]azocin-5(1H)-one (5, 20 mg, TFA salt) in DMF (2 mL) was added TEA (6.9 mg, 0.068 mmol, 2 eq.), perfluorophenyl 5-((1R)-fluoro((((R)-1-oxo-1-propoxypropan-2-yl)amino)

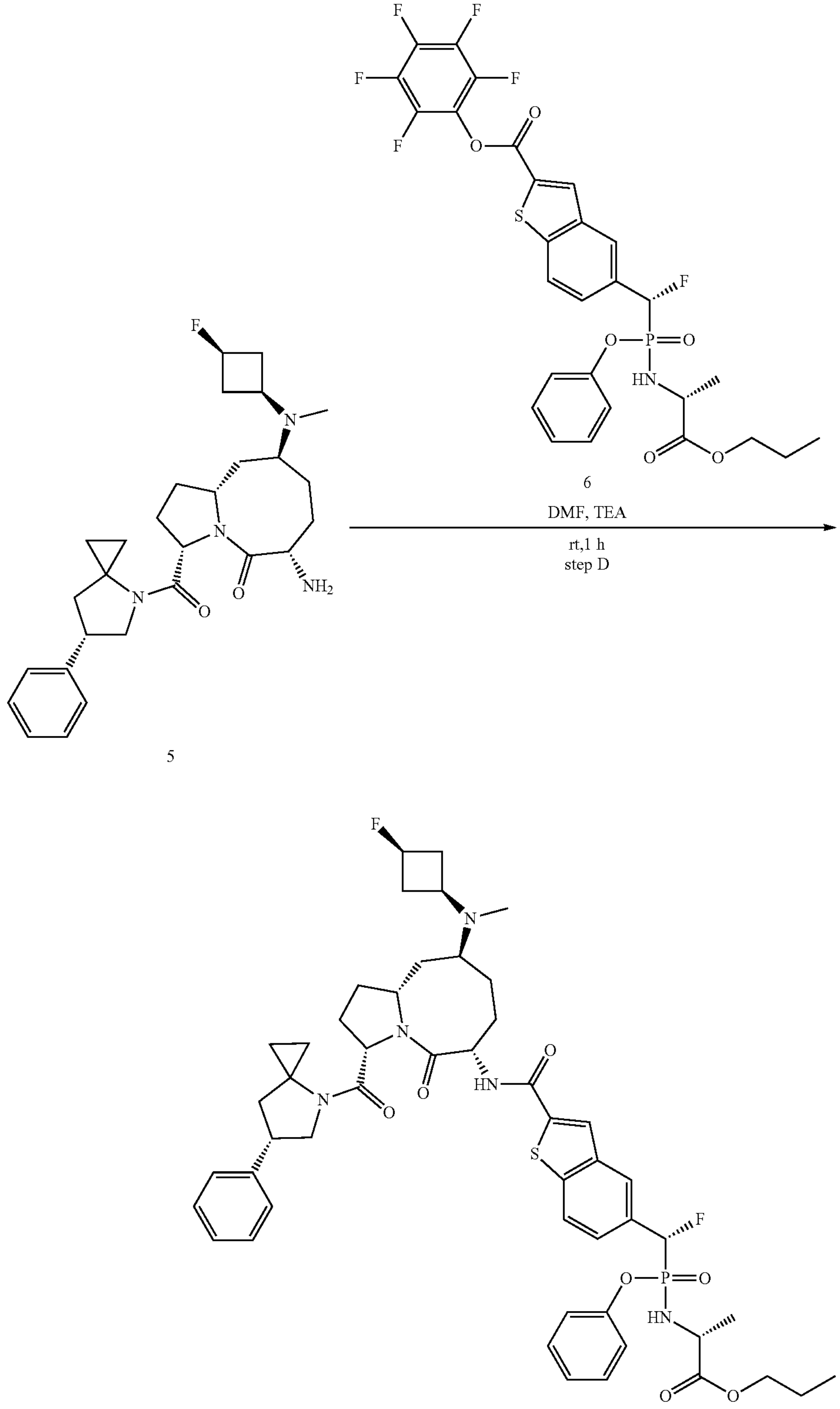

(phenoxy)phosphoryl)methyl)benzo[b]thiophene-2-carboxylate (7, 22.2 mg, 0.034 mmol, 1 eq.). The resulting mixture was stirred for 1 h at room temperature, LCMS shows that the reaction was completed. The crude product was purified by Prep-HPLC to afford propyl (((R)-fluoro(2-(((3S,6S,9S,10aR)-9-(((1s,3R)-3-fluorocyclobutyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-D-alaninate (Compound C84, 21 mg) as a white solid. LCMS (ESI): m/z=944 $[M+H]^+$. 1H NMR (400 MHz, DMSO-$d_6$) δ (ppm) 8.85-8.73 (m, 1H), 8.27 (d, J=4.2 Hz, 1H), 8.11-8.01 (m, 2H), 7.64-7.54 (m, 1H), 7.40-7.27 (m, 6H), 7.24-7.11 (m, 4H), 6.30-6.08 (m, 2H), 4.91-4.65 (m, 2H), 4.52-4.41 (m, 1H), 4.29 (s, 1H), 4.17-4.07 (m, 1H), 3.96-3.67 (m, 4H), 3.59-3.46 (m, 1H), 3.05-2.93 (m, 1H), 2.64-2.54 (m, 1H), 2.44-2.30 (m, 2H), 2.27-2.03 (m, 3H), 2.02-1.92 (m, 6H), 1.89-1.75 (m, 3H), 1.74-1.43 (m, 8H), 1.19-0.94 (m, 3H), 0.84-0.74 (m, 3H), 0.55-0.40 (m, 2H). $^{19}F$ NMR (376 MHz, DMSO-$d_6$) δ (ppm) −165.28 (s), −194.23 (d, J=82.5 Hz), −196.21 (d, J=86.3 Hz). $^{31}P$ NMR (162 MHz, DMSO-$d_6$) δ (ppm) 17.36 (d, J=86.2 Hz), 16.87 (d, J=82.3 Hz).

Synthesis of propyl (((R)-(2-(((3S,6S,9S,10aR)-9-(ethyl(4,4,4-trifluorobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)(phenoxy)phosphoryl)-L-alaninate (Compound C100) and ((R)-(2-(((3S,6S,9S,10aR)-9-(ethyl(4,4,4-trifluorobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)phosphonic acid (Compound A43)

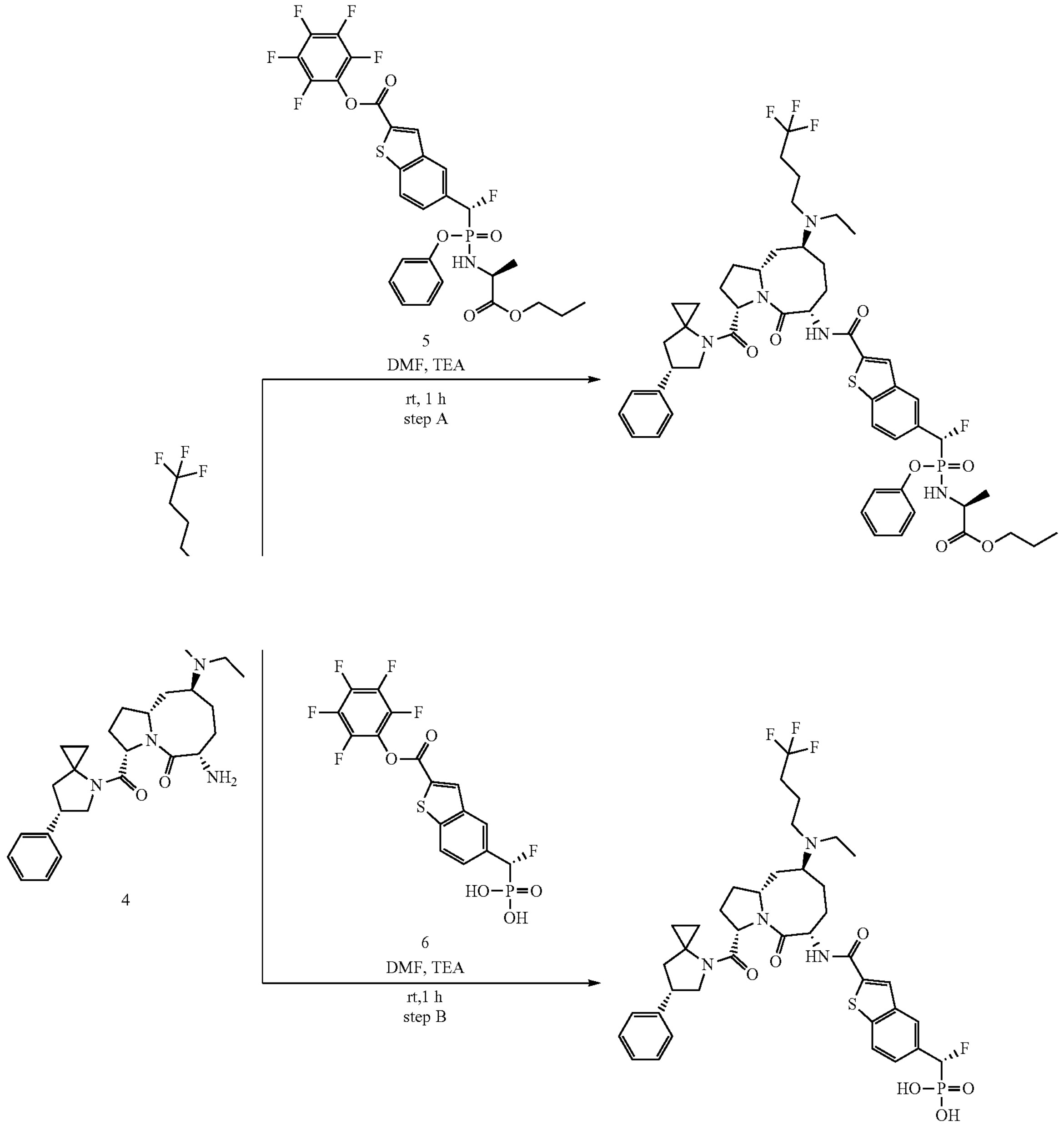

5
4
6

Step A: propyl (((R)-(2-(((3S,6S,9S,10aR)-9-(ethyl (4,4,4-trifluorobutyl)amino)-5-oxo-3-((S)-6-phenyl-4-azaspiro[2.4]heptane-4-carbonyl)decahydropyrrolo [1,2-a]azocin-6-yl)carbamoyl)benzo[b]thiophen-5-yl)fluoromethyl)(phenoxy)phosphoryl)-L-alaninate
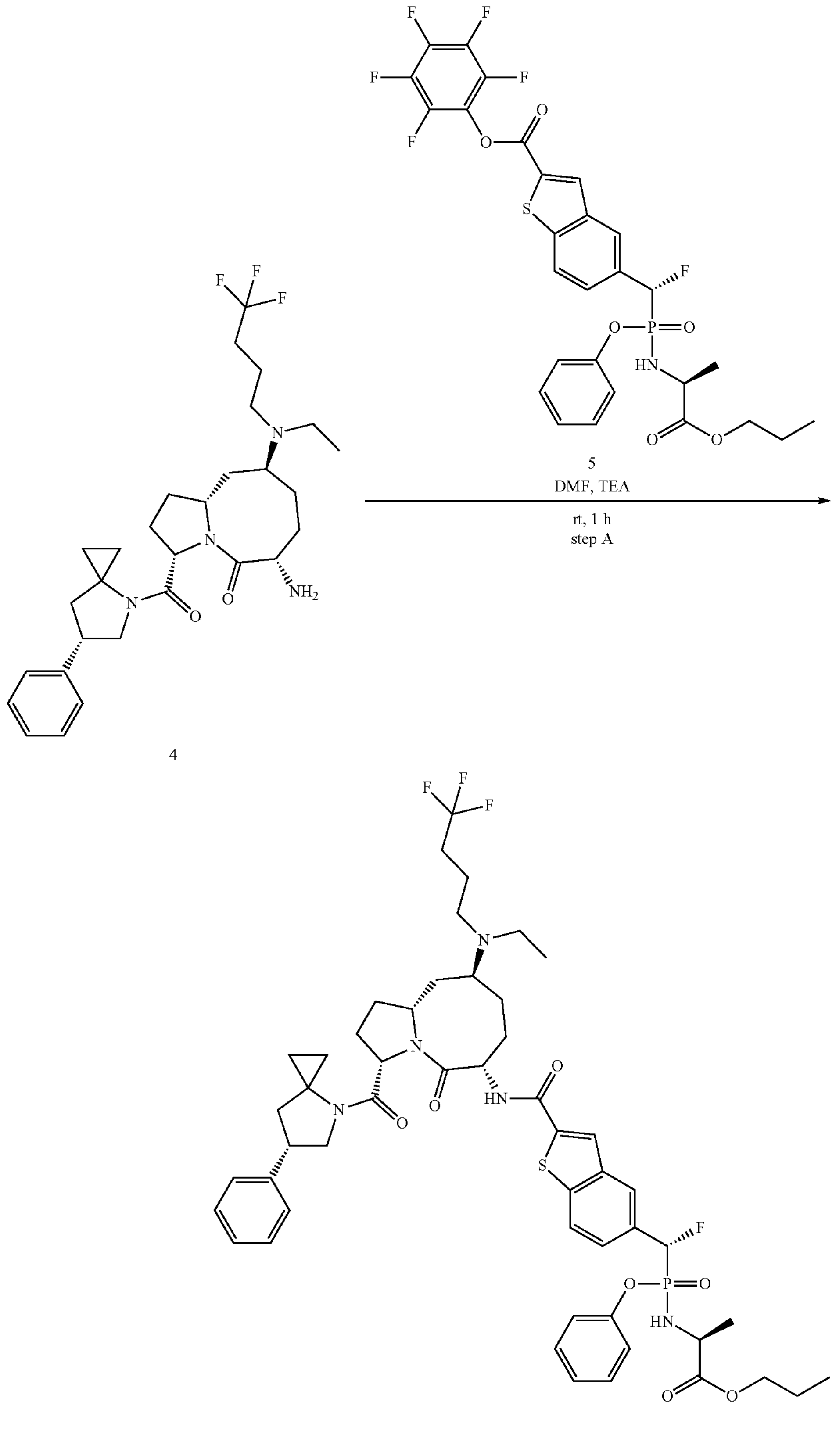

To a solution of (3S,6S,9S,10aR)-6-amino-9-(ethyl(4,4,4-trifluorobutyl)amino)-3-((S)-6-phenyl-4-azaspiro[2.4]heptane-4-carbonyl)octahydropyrrolo[1,2-a]azocin-5(1H)-one (4, 30 mg, TFA salt) in DMF (2 mL) was added TEA (14.3 mg, 0.141 mmol, 3 eq.), perfluorophenyl 5-((1R)-fluoro((((S)-1-oxo-1-propoxypropan-2-yl)amino)(phenoxy)phosphoryl)methyl)benzo[b]thiophene-2-carboxylate (5, 30 mg, 0.046 mmol, 1 eq). The resulting mixture was stirred for 1 h at room temperature. The crude product was purified by Prep-HPLC to afford propyl (((R)-(2-(((3S,6S,9S,10aR)-9-(ethyl(4,4,4-trifluorobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)(phenoxy)phosphoryl)-L-alaninate (Compound C100, 35 mg, 0.035 mmol, 76.1%) as a white solid. LCMS (ESI): m/z=996.6 $[M+H]^+$. $^1H$ NMR (400 MHz, DMSO-$d_6$) δ (ppm) 8.82-8.75 (m, 1H), 8.27 (s, 1H), 8.09-8.03 (m, 2H), 7.63-7.57 (m, 1H), 7.38-7.27 (m, 6H), 7.24-7.14 (m, 4H), 6.30-6.04 (m, 2H), 4.78-4.67 (m, 1H), 4.50-4.42 (m, 1H), 4.33-4.25 (m, 1H), 4.16-4.06 (m, 1H), 3.95-3.67 (m, 4H), 3.58-3.48 (m, 1H), 3.07-2.97 (m, 1H), 2.48-2.09 (m, 9H), 2.04-1.92 (m, 3H), 1.84-1.39 (m, 12H), 1.16-1.08 (m, 3H), 0.96 (t, J=7.0 Hz, 3H), 0.86-0.74 (m, 3H), 0.53-0.38 (m, 2H). $^{19}F$ NMR (377 MHz, DMSO-$d_6$) δ (ppm) −64.51 (s), −194.30 (d, J=83.0 Hz), −196.31 (d, J=85.8 Hz). $^{31}P$ NMR (162 MHz, DMSO-$d_6$) δ (ppm) 17.32 (d, J=82.6 Hz), 17.07 (d, J=86.1 Hz). (freebase).

Step B: ((R)-(2-(((3S,6S,9S,10aR)-9-(ethyl(4,4,4-trifluorobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)phosphonic acid

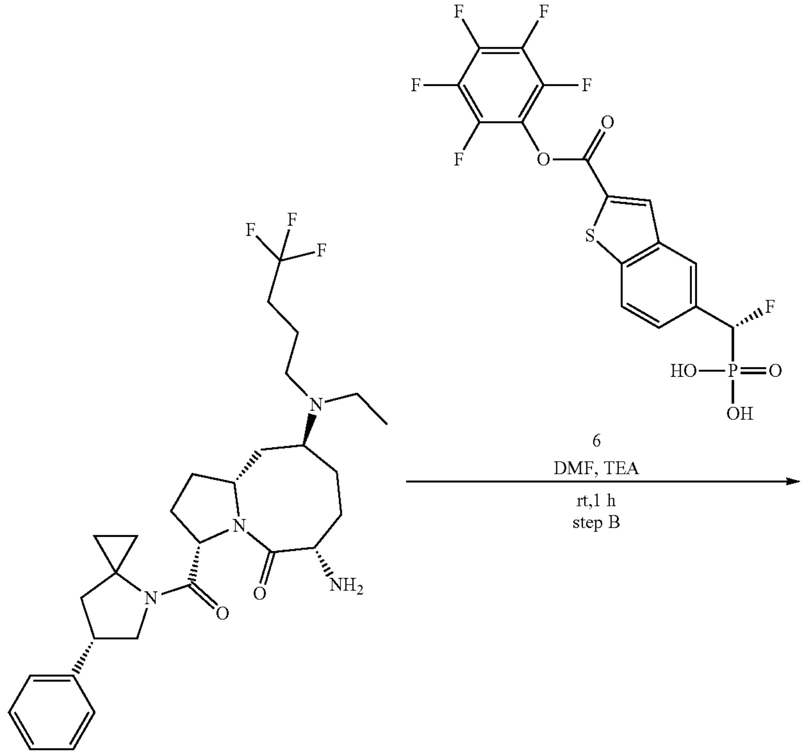

4

-continued

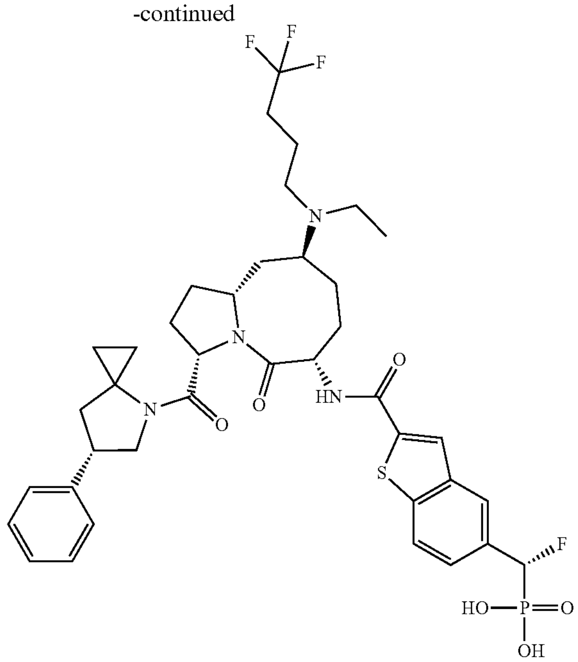

Procedure for 4 is described in the synthesis of Compound C101 and Compound A44. To a solution of (3S,6S,9S,10aR)-6-amino-9-(ethyl(4,4,4-trifluorobutyl)amino)-3-((S)-6-phenyl-4-azaspiro[2.4]heptane-4-carbonyl)octahydropyrrolo[1,2-a]azocin-5(1H)-one (4, 30 mg, TFA salt) in DMF (2 mL) was added TEA (14.3 mg, 0.141 mmol, 3 eq.), (R)-(fluoro(2-((perfluorophenoxy)carbonyl)benzo[b]thiophen-5-yl)methyl)phosphonic acid (6, 21 mg, 0.046 mmol, 1 eq). The resulting mixture was stirred for 1 h at room temperature. The crude product was purified by Prep-HPLC to afford propyl ((R)-(2-(((3S,6S,9S,10aR)-9-(ethyl(4,4,4-trifluorobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)phosphonic acid (Compound A43, 23 mg, 0.028 mmol, 60.9%) as a white solid. LCMS (ESI): m/z=807.7 $[M+H]^+$. $^1H$ NMR (400 MHz, DMSO-$d_6$) δ (ppm) 9.03-8.86 (m, 1H), 8.86-8.72 (m, 1H), 8.30-8.16 (m, 1H), 8.07-7.89 (m, 2H), 7.58-7.47 (m, 1H), 7.39-7.27 (m, 4H), 7.26-7.20 (m, 1H), 5.93-5.57 (m, 1H), 4.94-4.73 (m, 1H), 4.62-4.42 (m, 2H), 4.19-4.04 (m, 1H), 3.90-3.70 (m, 2H), 3.59-3.47 (m, 2H), 3.45-3.17 (m, 3H), 2.48-2.15 (m, 4H), 2.14-1.71 (m, 13H), 1.59-1.44 (m, 1H), 1.36-1.20 (m, 3H), 0.61-0.38 (m, 2H). $^{19}F$ NMR (377 MHz, DMSO-$d_6$) δ (ppm) −64.75 (s), −194.80 (d, J=80.6 Hz). $^{31}P$ NMR (162 MHz, DMSO-$d_6$) δ (ppm) 10.86 (d, J=80.8 Hz). (TFA salt).

Synthesis of propyl (((R)-(2-(((3S,6S,9S,10aR)-9-(ethyl((1s,3R)-3-(trifluoromethoxy)cyclobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)(phenoxy)phosphoryl)-L-alaninate (Compound C99) and ((R)-(2-(((3S,6S,9S,10aR)-9-(ethyl((1s,3R)-3-(trifluoromethoxy)cyclobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)phosphonic acid (Compound A42)

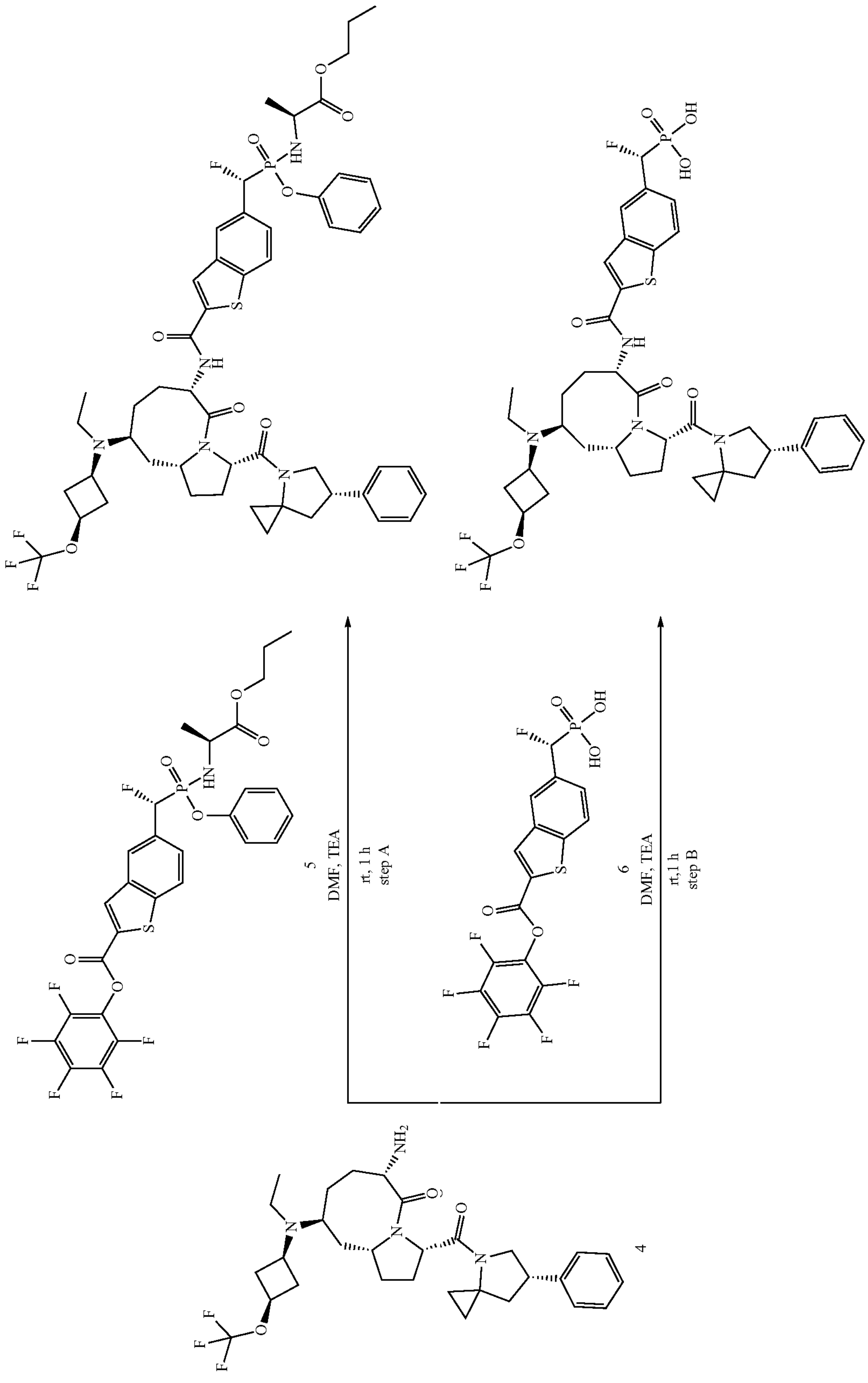
4

Step A: propyl (((R)-(2-(((3S,6S,9S,10aR)-9-(ethyl((1s,3R)-3-(trifluoromethoxy)cyclobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)(phenoxy)phosphoryl)-L-alaninate

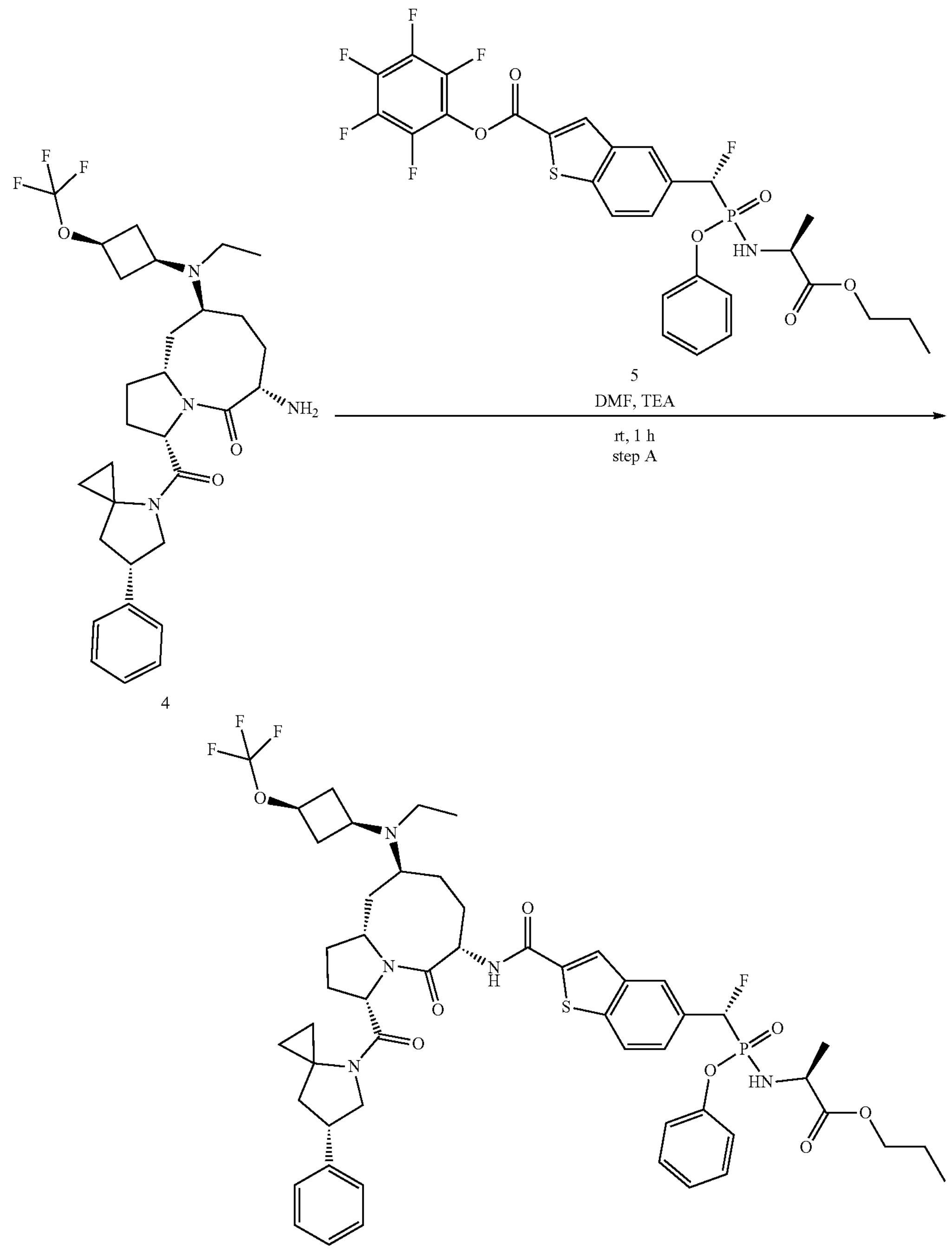

Procedure for 4 is described in the syntheses of Compound C119 and Compound A47. To a solution of (3S,6S,9S,10aR)-6-amino-9-(ethyl((1s,3R)-3-(trifluoromethoxy)cyclobutyl)amino)-3-((S)-6-phenyl-4-azaspiro[12.4]heptane-4-carbonyl)octahydropyrrolo[1,2-a]azocin-5(1H)-one (4, 30 mg, TFA salt) in DMF (2 mL) was added TEA (13.7 mg, 0.135 mmol, 3 eq.), perfluorophenyl 5-((1R)-fluoro((((S)-1-oxo-1-propoxypropan-2-yl)amino)(phenoxy)phosphoryl)methyl)benzo[b]thiophene-2-carboxylate (5, 29 mg, 0.045 mmol, 1 eq). The resulting mixture was stirred for 1 h at room temperature, LCMS show that the reaction was completed. The crude product was purified by Prep-HPLC to afford propyl (((R)-(2-(((3S,6S,9S,10aR)-9-(ethyl((1s,3R)-3-(trifluoromethoxy)cyclobutyl)amino)-5-oxo-3-((S)-6-phenyl-4-azaspiro[2.4]heptane-4-carbonyl)decahydropyrrolo[1,2-a]azocin-6-yl)carbamoyl)benzo[1b]thiophen-5-yl)fluoromethyl)(phenoxy)phosphoryl)-L-alaninate (Compound C99, 23 mg, 0.022 mmol, 48.9%) as a white solid. LCMS (ESI): m/z=1024.7 $[M+H]^+$. $^1H$ NMR (400 MHz, DMSO-$d_6$) δ (ppm) 8.85-8.76 (1, 1H), 8.27 (s, 1H), 8.06 (d, J=4.8 Hz, 2H), 7.60 (d, J=7.2 Hz, 1H), 7.39-7.27 (m, 6H), 7.23-7.13 (1, 4H), 6.28-6.06 (m, 2H), 4.76-4.65 (m, 1H), 4.54-4.43 (m, 2H), 4.34-4.23 (m, 1H), 4.13 (t, J=8.7 Hz, 1H), 3.97-3.89 (m, 1H), 3.85-3.70 (m, 3H), 3.59-3.49 (m, 1H), 3.08-2.99 (m, 1H), 2.89-2.79 (m, 1H), 2.63-2.53 (m, 1H), 2.37-1.90 (m, 10H), 1.88-1.38 (m, 11H), 1.13 (d, J=7.0 Hz, 3H), 0.97 (t, J=7.1 Hz, 3H), 0.85-0.74 (m, 3H), 0.52-0.39 (m, 2H). $^{19}$F NMR (377 MHz, DMSO-d) δ (ppm) −57.60 (s), −194.29 (d, J=83.1 Hz), −196.31 (d, J=86.0 Hz). $^{31}$P NMR (162 MHz, DMSO-$d_6$) δ (ppm) 17.32 (d, J=82.5 Hz), 17.07 (d, J=86.0 Hz).

Step B: ((R)-(2-(((3S,6S,9S,10aR)-9-(ethyl((1s,3R)-3-(trifluoromethoxy)cyclobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)phosphonic acid To a solution of (3S,6S,9S,10aR)-6-amino-9-(ethyl((1s,3R)-3-(trifluoromethoxy)cyclobutyl)amino)-3-((S)-6-phenyl-4-azaspiro[2.4]heptane-4-carbonyl)octahydropyrrolo[1,2-a]azocin-5(1H)-one (4, 30 mg, TFA salt) in DMF (2 mL) was added TEA (13.7 mg, 0.135 mmol, 3 eq.), (R)-(fluoro(2-((perfluorophenoxy)carbonyl)benzo[b]thiophen-5-yl)methyl)phosphonic acid (6, 20 mg, 0.045 mmol, 1 eq.). The resulting mixture was stirred for 1 h at room temperature. The crude product was purified by Prep-HPLC to ((R)-(2-(((3S,6S,9S,10aR)-9-(ethyl((1s,3R)-3-(trifluoromethoxy)cyclobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)phosphonic acid (Compound A42, 20 mg, 0.024 mmol, 54.5%) as a white solid. LCMS (ESI): m/z=835.4 $[M+H]^+$. $^1$H NMR (400 MHz, $CD_3OD$-$d_4$) δ (ppm) 8.05 (d, J=9.8 Hz, 2H), 7.93 (d, J=8.5 Hz, 1H), 7.60 (d, J=8.6 Hz, 1H), 7.38-7.27 (m, 4H), 7.21 (t, J=7.3 Hz, 1H), 5.79 (dd, J=44.8, 8.0 Hz, 1H),

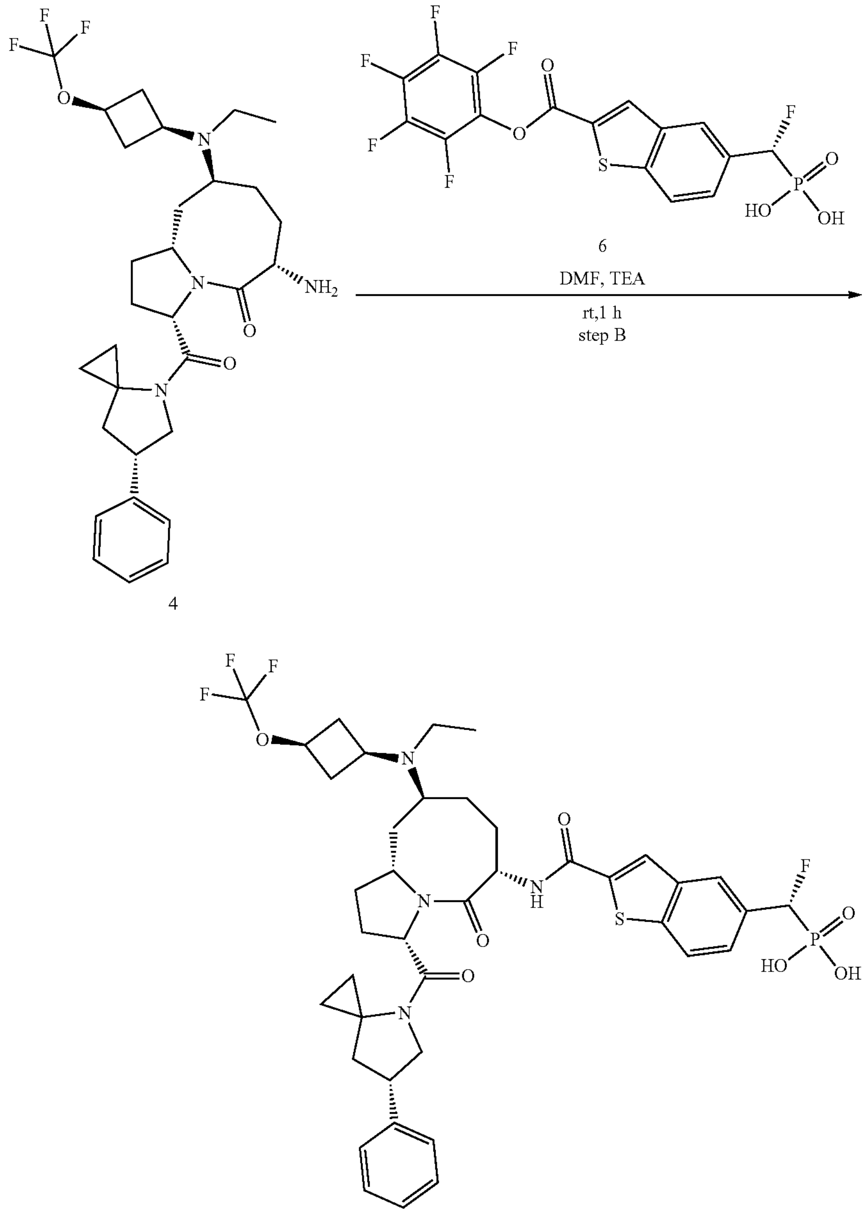

4.70-4.47 (m, 4H), 4.11-3.90 (m, 3H), 3.82-3.51 (m, 3H), 3.13 (s, 1H), 2.88-2.81 (m, 1H), 2.70-2.42 (m, 3H), 2.39-2.14 (m, 6H), 2.11-1.84 (m, 8H), 1.38-1.35 (m, 3H), 0.61-0.48 (m, 2H). $^{19}F$ NMR (377 MHz, $CD_3OD-d_4$) δ (ppm) −61.29 (s), −198.66 (d, J=83.0 Hz). $^{31}P$ NMR (162 MHz, $CD_3OD-d_4$) δ (ppm) 12.31 (d, J=84.2 Hz). (TFA salt).

Synthesis of propyl ((R)-((R)-fluoro(2-(((3S,6S,9S,10aR)-9-(methyl(oxetan-3-yl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate (Compound C37) and ((R)-fluoro(2-(((3S,6S,9S,10aR)-9-(methyl(oxetan-3-yl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)phosphonic acid (Compound A13)

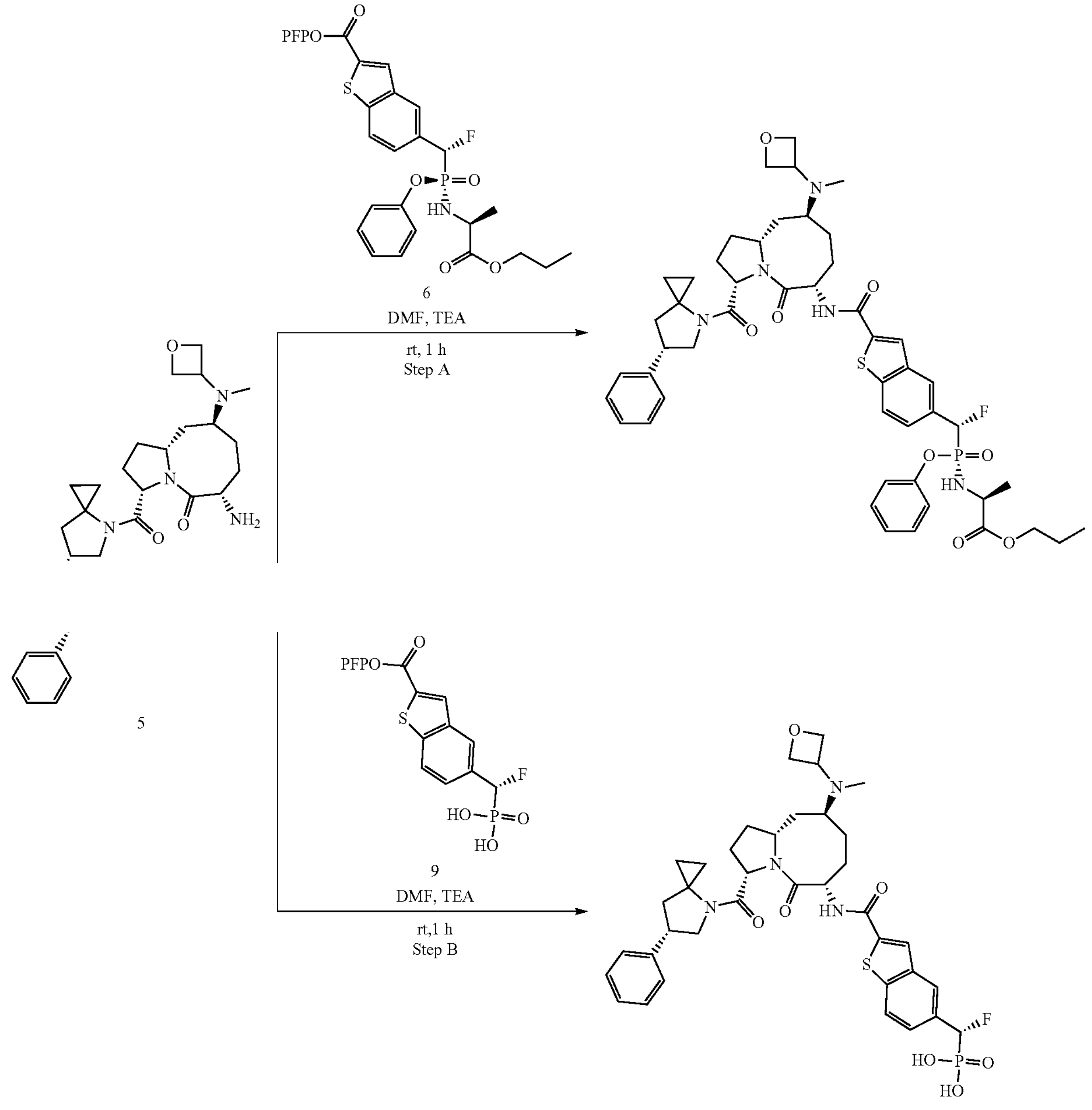

Step A: propyl ((R)-((R)-fluoro(2-(((3S,6S,9S,10aR)-9-(methyl(oxetan-3-yl)amino)-5-oxo-3-((R)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate Procedure for 5 is described in the syntheses of Compound A16 and Compound C30. To a solution of (3S,6S,9S,10aR)-6-amino-9-(methyl(oxetan-3-yl)amino)-3-((R)-6-phenyl-4-azaspiro[2.4]heptane-4-carbonyl) octahydropyrrolo[1,2-a]azocin-5(1H)-one (5, 50 mg, TFA salt) in DMF (2 mL) were added TEA (25.75 mg. 0.255

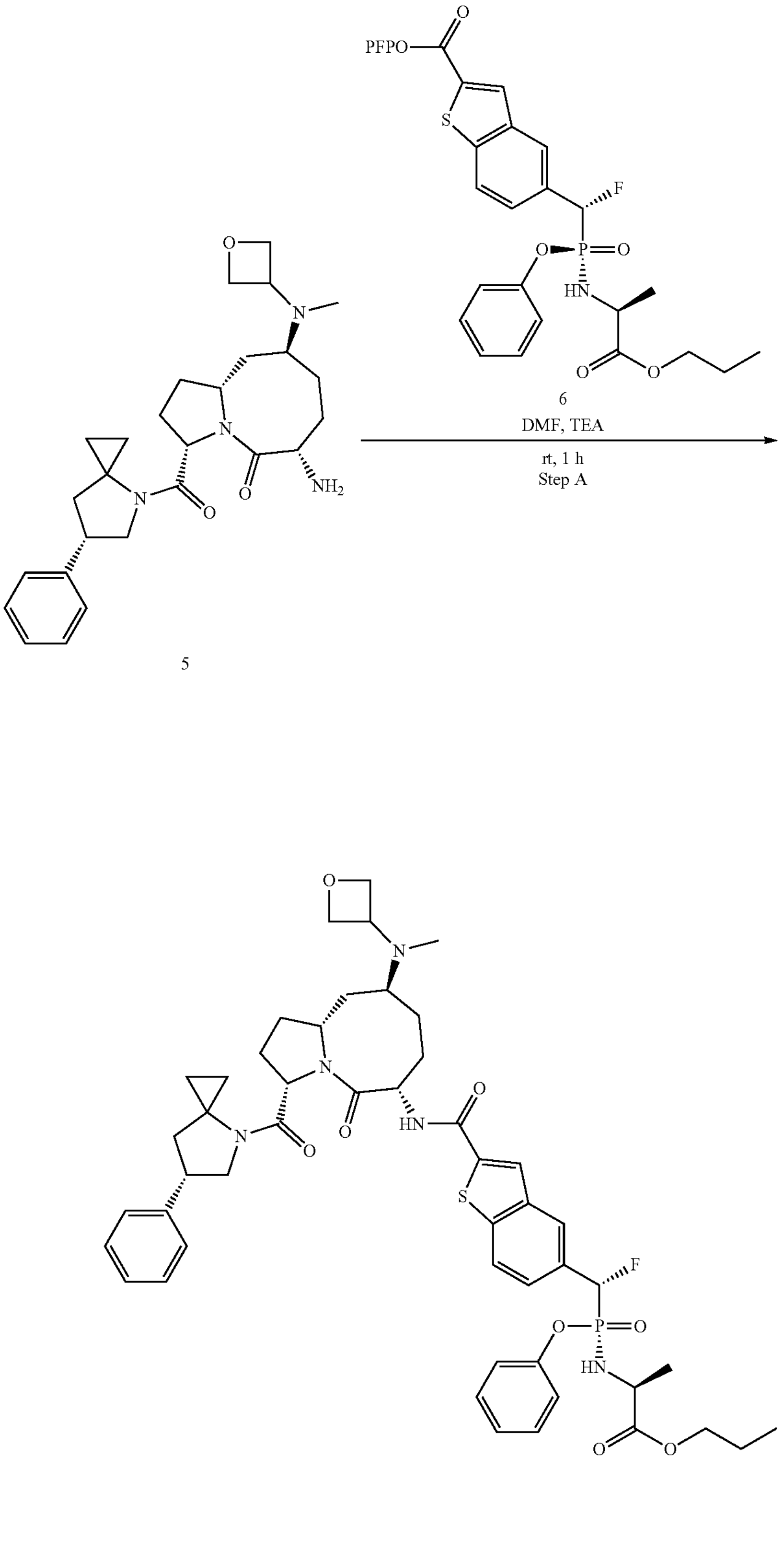

mmol, 3 eq.) and perfluorophenyl 5-((R)-fluoro((R)-(((S)-1-oxo-1-propoxypropan-2-yl)amino)(phenoxy)phosphoryl)methyl)benzo[b]thiophene-2-carboxylate (6, 55 mg, 0.085 mmol, 1 eq.), and the resulting mixture was stirred at room temperature for 1 h. The crude product was purified by Prep-HPLC to afford propyl ((R)-((R)-fluoro(2-(((3S,6S,9S,10aR)-9-(methyl(oxetan-3-yl)amino)-5-oxo-3-((R)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate (Compound C37, 46 mg, 0.049 mmol, 57.6%) as a white solid. LCMS (ESI): m/z=928.5 $[M+H]^+$. $^1H$ NMR (400 MHz, DMSO-$d_6$) δ (ppm) 8.81-8.74 (m, 1H), 8.27 (s, 1H), 8.09-8.02 (m, 2H), 7.64-7.58 (m, 1H), 7.40-7.12 (m, 10H), 6.27-6.03 (m, 2H), 4.80-4.63 (m, 1H), 4.59-4.23 (m, 6H), 4.18-4.04 (m, 1H), 3.89-3.66 (m, 5H), 3.59-3.48 (m, 1H), 2.88-2.76 (m, 1H), 2.41-2.29 (m, 1H), 2.27-2.16 (m, 1H), 2.15-2.07 (m, 1H), 2.06-1.86 (m, 6H), 1.85-1.34 (m, 10H), 1.17-1.08 (m, 3H), 0.82-0.73 (m, 3H), 0.57-0.42 (m, 2H). $^{19}F$ NMR (376 MHz, DMSO-$d_6$) δ (ppm) −194.21-194.43 (m). $^{31}P$ NMR (162 MHz, DMSO-$d_6$) δ (ppm) 17.58-17.07 (m).

Step B: ((R)-fluoro(2-(((3S,6S,9S,10aR)-9-(methyl(oxetan-3-yl)amino)-5-oxo-3-((R)-6-phenyl-4-azaspiro[2.4]heptane-4-carbonyl)decahydropyrrolo[1,2-a]azocin-6-yl)carbamoyl)benzo[b]thiophen-5-yl)methyl)phosphonic acid

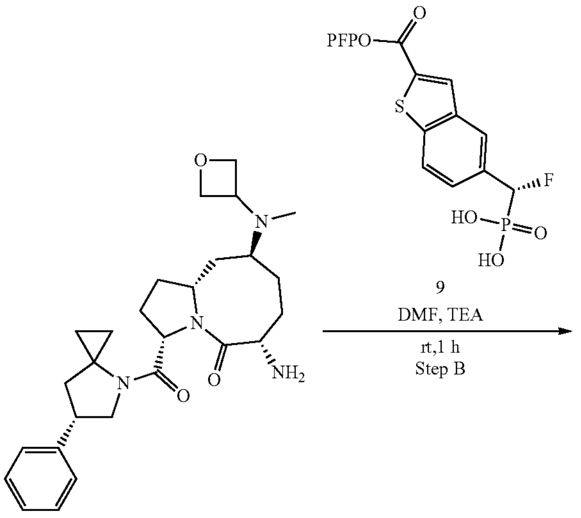

-continued

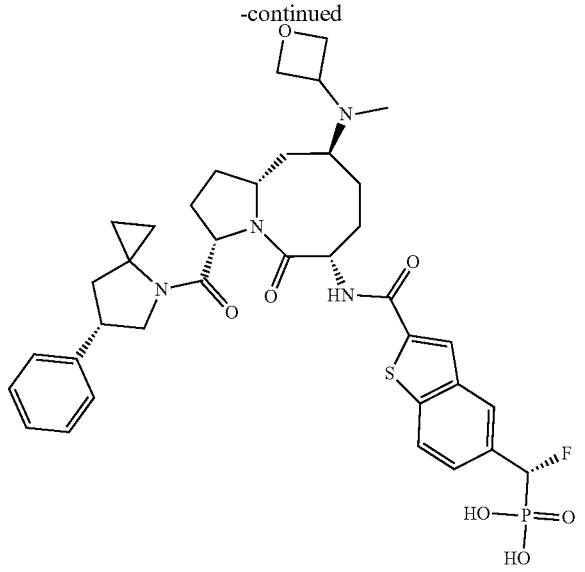

To a solution of (3S,6S,9S,10aR)-6-amino-9-(methyl(oxetan-3-yl)amino)-3-((R)-6-phenyl-4-azaspiro[2.4]heptane-4-carbonyl)octahydropyrrolo[1,2-a]azocin-5(1H)-one (5, 50 mg, TFA salt) in DMF (2 mL) were added TEA (25.75 mg. 0.255 mmol, 3 eq.) and (R)-(fluoro(2-((perfluorophenoxy)carbonyl)benzo[b]thiophen-5-yl)methyl)phosphonic acid (9, 40 mg, 0.088 mmol, 1 eq.), and the resulting mixture was stirred at room temperature for 1 h. The crude product was purified by Prep-HPLC to afford ((R)-fluoro(2-(((3S,6S,9S,10aR)-9-(methyl(oxetan-3-yl)amino)-5-oxo-3-((R)-6-phenyl-4-azaspiro[2.4]heptane-4-carbonyl)decahydropyrrolo[1,2-a]azocin-6-yl)carbamoyl)benzo[b]thiophen-5-yl)methyl)phosphonic acid (Compound A13, 36 mg, 0.048 mmol, 54.5%) as a white solid. LCMS (ESI): m/z=739.6 $[M+H]^+$. $^1H$ NMR (400 MHz, DMSO-$d_6$) δ (ppm) 10.85-10.19 (m, 1H), 8.87-8.68 (m, 1H), 8.24 (s, 1H), 8.03 (d, J=8.5 Hz, 1H), 7.97 (s, 1H), 7.53 (d, J=8.6 Hz, 1H), 7.38-7.30 (m, 4H), 7.25-7.21 (m, 1H), 5.83 (dd, J=44.4, 8.0 Hz, 1H), 4.92-4.50 (m, 8H), 4.18-4.09 (m, 1H), 3.74-3.68 (m, 1H), 3.60-3.52 (m, 2H), 2.60 (s, 3H), 2.48-2.41 (m, 1H), 2.28-2.21 (m, 1H), 2.16-1.70 (m, 11H), 1.57-1.51 (m, 1H), 0.61-0.48 (m, 2H). $^{19}F$ NMR (377 MHz, DMSO-$d_6$) δ (ppm) −194.91 (d, J=80.8 Hz). $^{31}P$ NMR (162 MHz, DMSO-$d_6$) δ (ppm) 10.92 (d, J=80.9 Hz).

The following compounds in Table 1A, Table 1B, and Table 1C were prepared according to the representative procedures described above, using the appropriate starting materials and modifications.

TABLE 1A

| No. | Name | Structure | NMR and LCMS |
|---|---|---|---|
| A1 | ((S)-fluoro(2-(((3S,6S,9S,10aR)-9-(((1s,3R)-3-fluoro-cyclobutyl)(methyl)amino)-5-oxo-3-((S)-6-phenyl-4-azaspiro[2.4]heptane-4-carbonyl)decahydro-pyrrolo[1,2-a]azocin-6-yl)carbamoyl)benzo[b]thiophen-5-yl)methyl)phosphonic acid | 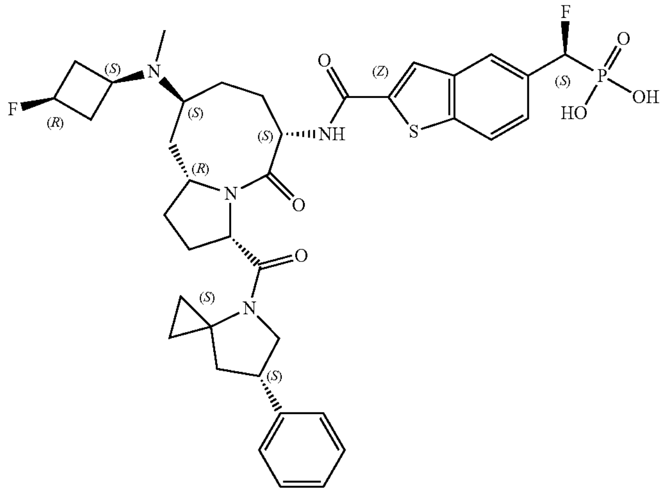 | $^1$H NMR (400 MHz, MeOD-d4) δ (ppm) 8.12-8.02 (m, 2H), 7.89 (d, J = 8.4 Hz, 1H), 7.61 (d, J = 8.3 Hz, 1H), 7.33-7.17 (m, 5H), 5.67 (dd, J = 45.2, 8.3 Hz, 1H), 4.78-4.52 (m, 3H), 4.44-4.36 (m, 1H), 4.01-3.75 (m, 3H), 3.56-3.46 (m, 1H), 3.01-2.84 (m, 1H), 2.77-1.55 (m, 21H), 0.55-0.39 (m, 2H); 755.2 [M + H]$^+$. |
| A2 | ((R)-fluoro(2-(((3S,6S,9S,10aR)-9-(methyl((1s,3R)-3-(trifluoromethyl)cyclobutyl)amino)-5-oxo-3-((S)-6-phenyl-4-azaspiro[2.4]heptane-4-carbonyl)decahydro-pyrrolo[1,2-a]azocin-6-yl)carbamoyl)benzo[b]thiophen-5-yl)methyl)phosphonic acid | 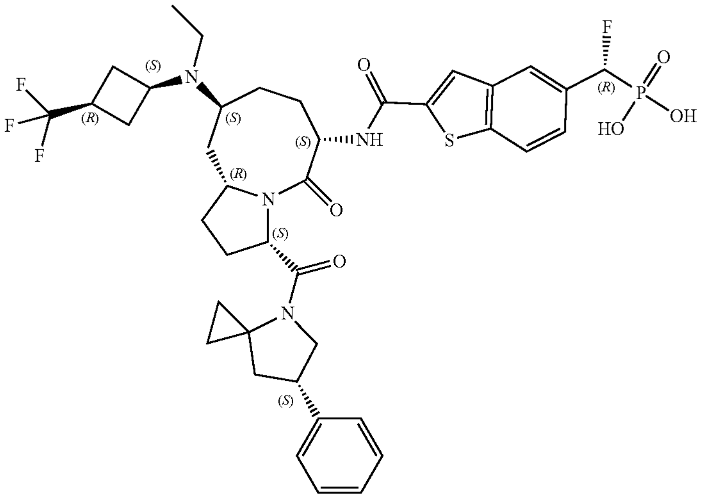 | $^1$H NMR (400 MHz, DMSO-d6) δ (ppm) 8.98-8.82 (m, 1H), 8.77-8.68 (m, 1H), 8.27-8.19 (m, 1H), 8.08-7.92 (m, 2H), 7.65-7.25 (m, 2H), 6.85-6.65 (m, 2H), 5.65 (dd, J = 44.8, 8.1 Hz, 1H), 5.14-4.88 (m, 3H), 4.40-4.28 (m, 1H), 3.58-3.46 (m, 1H), 3.41-3.29 (m, 1H), 2.32-2.07 (m, 4H), 2.02-1.53 (m, 9H), 1.52-1.40 (m, 3H), 1.38-1.14 (m, 1H), 1.08-0.80 (m, 2H), 0.78-0.55 (m, 2H); 805.3 [M + H]$^+$. |
| A3 | ((R)-fluoro(2-(((3S,6S,9S,10aR)-9-(methyl(4,4,4-trifluorobutyl)amino)-5-oxo-3-((S)-6-phenyl-4-azaspiro[2.4]heptane-4-carbonyl)decahydro-pyrrolo[1,2-a]azocin-6-yl)carbamoyl)benzo[b]thiophen-5-yl)methyl)phosphonic acid | 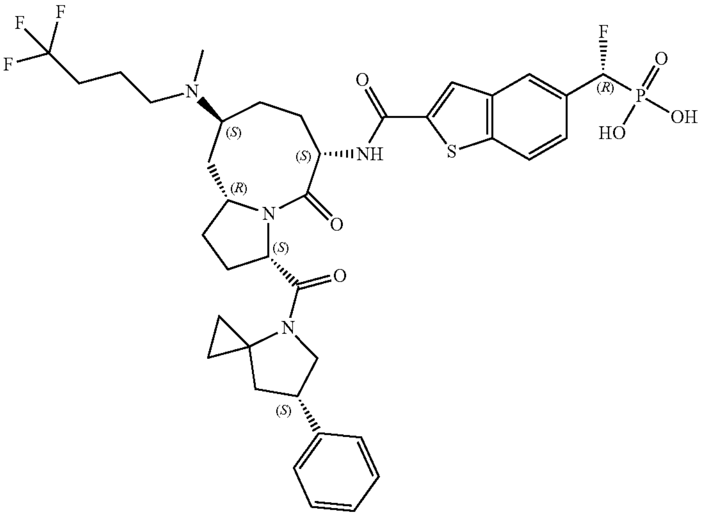 | 1H NMR (400 MHz, MeOD-d4) δ (ppm) 8.09 (s, 1H), 8.05 (s, 1H), 7.94 (d, J = 8.5 Hz, 1H), 7.70 (d, J = 8.6 Hz, 1H), 7.38-7.26 (m, 4H), 7.25-7.18 (m, 1H), 5.68 (dd, J = 45.3, 8.1 Hz, 1H), 4.64-4.47 (m, 2H), 4.38-4.21 (m, 1H), 4.07-3.80 (m, 2H), 3.77-3.63 (m, 1H), 3.58-3.47 (m, 1H), 3.14-2.94 (m, 2H), 2.73-2.60 (m, 3H), 2.50-2.36 (m, 1H), 2.20-1.77 (m, 10H), 1.91-1.78 (m, 3H), 1.76-1.50 (m, 4H), 0.60-0.36 (m, 2H); 793.2 [M + H]$^+$. |

TABLE 1A-continued

| No. | Name | Structure | NMR and LCMS |
|---|---|---|---|
| A4 | ((R)-fluoro(2-(((3S,6S,9S,10aR)-9-(methyl((1s,3R)-3-(trifluoro-methoxy)cyclobutyl)amino)-5-oxo-3-((S)-6-phenyl-4-azaspiro[2.4]heptane-4-carbonyl)decahydro-pyrrolo[1,2-a]azocin-6-yl)carbamoyl)benzo[b]thiophen-5-yl)methyl)phosphonic acid | 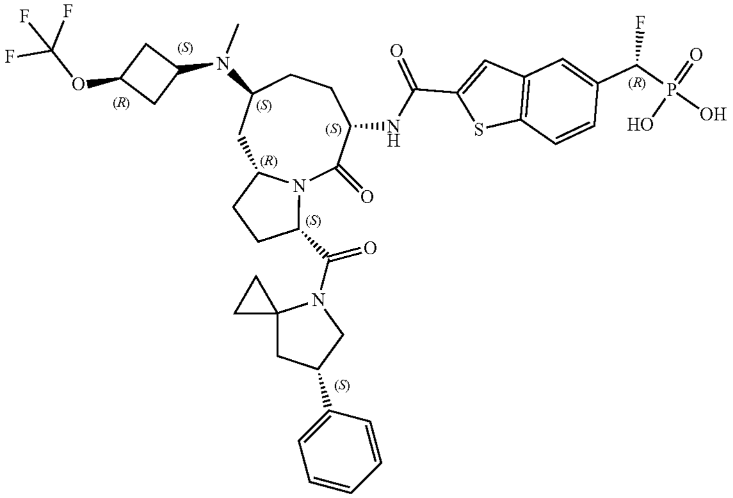 | 1H NMR (400 MHz, MeOD-d4) δ (ppm) 8.09-8.02 (m, 2H), 7.91 (d, J = 8.5 Hz, 1H), 7.69 (d, J = 8.5 Hz, 1H), 7.38-7.27 (m, 4H), 7.25-7.18 (m, 1H), 5.68 (dd, J = 45.3, 8.3 Hz, 1H), 4.71-4.64 (m, 1H), 4.63-4.49 (m, 2H), 4.45-4.35 (m, 1H), 4.08-3.85 (m, 2H), 3.70-3.47 (m, 2H), 3.28-3.12 (m, 1H), 2.98-2.83 (m, 1H), 2.79-2.64 (m, 1H), 2.63-2.51 (m, 1H), 2.47-1.59 (m, 18H), 0.60-0.40 (m, 2H); 821.2 [M + H]$^+$. |
| A5 | ((S)-fluoro(2-(((3S,6S,9S,10aR)-9-(methyl((1s,3R)-3-(trifluoro-methoxy)cyclo-butyl)amino)-5-oxo-3-((S)-6-phenyl-4-azaspiro[2.4]heptane-4-carbonyl)decahydro-pyrrolo[1,2-a]azocin-6-yl)carbamoyl)benzo[b]thiophen-5-yl)methyl)phosphonic acid | 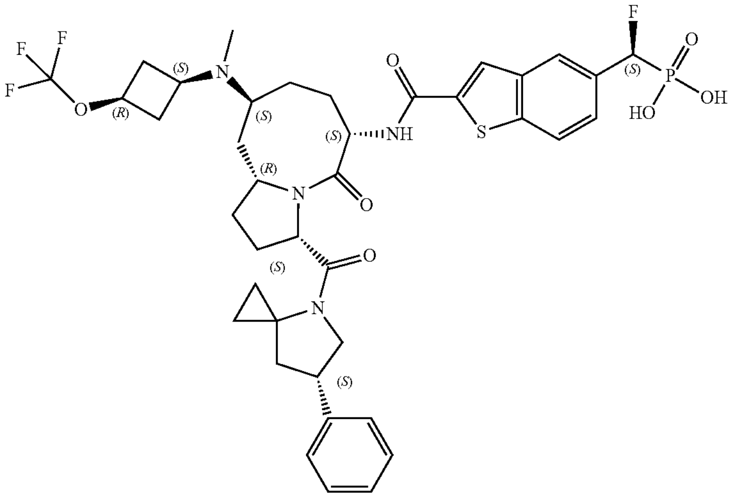 | 1H NMR (400 MHz, MeOD-d4) δ (ppm) 8.12-8.03 (m, 1H), 7.89 (d, J = 8.4 Hz, 1H), 7.60 (d, J = 8.4 Hz, 1H), 7.36-7.23 (m, 4H), 7.22-7.16 (m, 1H), 5.69 (dd, J = 45.2, 8.4 Hz, 1H), 4.71-4.31 (m, 4H), 4.14-3.78 (m, 3H), 3.56-3.43 (m, 2H), 2.82-2.67 (m, 2H), 2.65-1.52 (m, 19H), 0.56-0.38 (m, 2H); 821.3 [M + H]$^+$. |
| A6 | ((R)-(2-(((3S,6S,9S,10aR)-3-((6S,7R)-7-cyano-6-phenyl-4-azaspiro[2.4]heptane-4-carbonyl)-9-morpholino-5-oxodecahydro-pyrrolo[1,2-a]azocin-6-yl)carbamoyl)benzo[b]thiophen-5-yl)fluoromethyl)phosphonic acid | 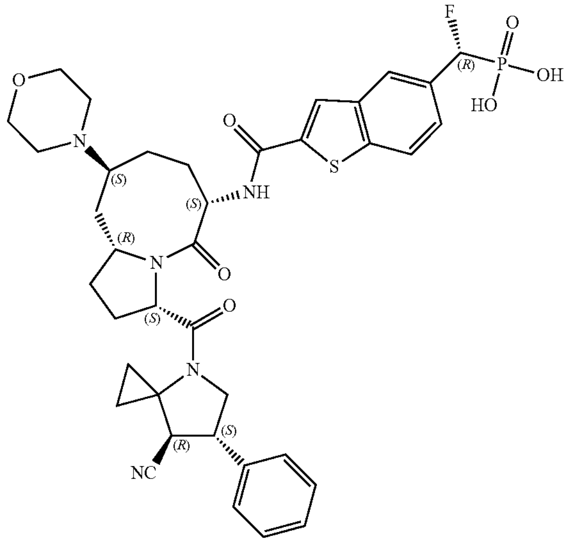 | $^1$H NMR (400 MHz, MeOD) δ 8.08 (s, 1H), 8.01 (s, 1H), 7.94-7.92 (m, 1H), 7.45-7.27 (m, 5H), 5.77-5.58 (m, 1H), 4.62-4.57 (m, 1H), 4.51-4.32 (m, 2H), 4.15-4.05 (m, 1H), 3.87-3.75 (m, 5H), 3.74-3.67 (m, 2H), 3.10 3.00 (m, 1H), 2.90-2.80 (m, 4H), 2.41-2.24 (m, 2H), 2.22-2.09 (m, 1H), 2.04-1.90 (m, 4H), 1.87-1.67 (m, 3H), 1.53-1.43 (m, 1H), 1.35-1.25 (m, 1H), 0.99-0.89 (m, 1H), 0.75-0.64 (m, 1H); 764.1 [M + H]$^+$. |

TABLE 1A-continued

| No. | Name | Structure | NMR and LCMS |
|---|---|---|---|
| A7 | ((R)-fluoro(2-(((3S,6S,9S,10aR)-9-morpholino-5-oxo-3-((R)-6-(pyridin-3-yl)-4-azaspiro[2.4]heptane-4-carbonyl)decahydro-pyrrolo[1,2-a]azocin-6-yl)carbamoyl)benzo[b]thiophen-5-yl)methyl)phosphonic acid | 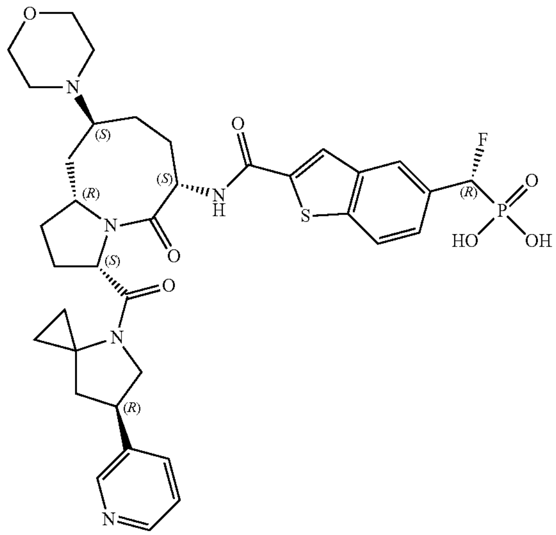 | 1H NMR (400 MHz, DMSO-d6) δ (ppm) 8.68-8.57 (m, 1H), 8.57-8.51 (m, 1H), 8.45-8.38 (m, 1H), 8.21 (s, 1H), 8.04-7.91 (m, 2H), 7.81-7.71 (m, 1H), 7.61-7.52 (m, 1H), 7.35-7.26 (m, 1H), 5.58 (dd, J = 45.4, 8.1 Hz, 1H), 4.49-4.40 (m, 2H), 4.17-4.04 (m, 3H), 3.78-3.73 (m, 3H), 3.58-3.50 (m, 2H), 3.21-3.13 (m, 1H), 2.91-2.68 (m, 4H), 2.21-1.56 (m, 12H), 1.49-1.17 (m, 2H), 0.54-0.31 (m, 2H); 740.4 [M + H]+. |
| A8 | ((R)-(2-(((3S,6S,9S,10aR)-3-((R)-6-(4-(dimethyl-amino)pyridin-3-yl)-4-azaspiro[2.4]heptane-4-carbonyl)-9-morpholino-5-oxodecahydro-pyrrolo[1,2-a]azocin-6-yl)carbamoyl)benzo[b]thiophen-5-yl)fluoromethyl)phosphonic acid | 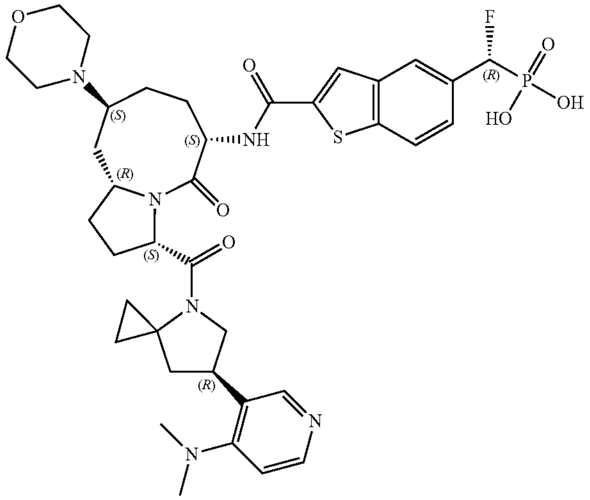 | 1H NMR (400 MHz, DMSO-d6) δ (ppm) 8.71 (d, J = 7.3 Hz, 1H), 8.37 (s, 1H), 8.27-8.21 (m, 2H), 8.03 (d, J = 8.5 Hz, 1H), 7.98 (s, 1H), 7.54 (d, J = 8.6 Hz, 1H), 7.11 (d, J = 7.1 Hz, 1H), 5.92-5.60 (m, 1H), 4.84-4.77 (m, 1H), 4.59-4.51 (m, 2H), 4.13-3.99 (m, 4H), 3.93-3.85 (m, 2H), 3.82-3.62 (m, 6H), 3.17 (s, 6H), 2.46-2.38 (m, 1H), 2.28-2.16 (m, 2H), 2.15-1.98 (m, 5H), 1.96-1.75 (m, 5H), 1.74-1.66 (m, 1H), 0.58-0.46 (m, 2H); 783.5 [M + H]+. |
| A9 | ((R)-fluoro(2-(((3S,6S,9S,10aR)-9-morpholino-5-oxo-3-((S)-6-(pyridin-3-yl)-4-azaspiro[2.4]heptane-4-carbonyl)decahydro-pyrrolo[1,2-a]azocin-6-yl)carbamoyl)benzo[b]thiophen-5-yl)methyl)phosphonic acid | 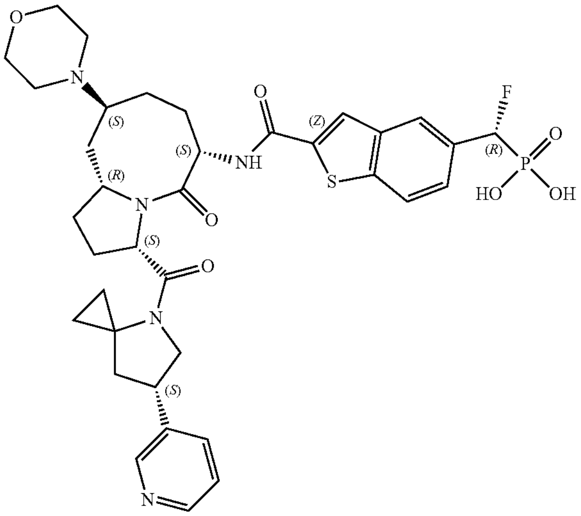 | 1H NMR (400 MHz, DMSO-d6) δ (ppm) 8.68-8.59 (m, 1H), 8.59-8.53 (m, 1H), 8.47-8.39 (m, 1H), 8.25-8.11 (m, 1H), 8.05-7.87 (m, 2H), 7.83-7.68 (m, 1H), 7.62-7.51 (m, 1H), 7.41-7.28 (m, 1H), 5.58 (dd, J = 45.2, 8.1 Hz, 1H), 4.55-4.48 (m, 1H), 4.43-4.28 (m, 2H), 4.15-4.07 (m, 1H), 3.81 (s, 4H), 3.60-3.47 (m, 3H), 3.25-3.16 (m, 1H), 2.82 (s, 3H), 2.40-2.21 (m, 2H), 2.13-1.13 (m, 12H), 0.46 (s, 2H); 740.5 [M + H]+. |

TABLE 1A-continued

| No. | Name | Structure | NMR and LCMS |
|---|---|---|---|
| A10 | ((S)-fluoro(2-(((3S,6S,9S,10aR)-9-morpholino-5-oxo-3-((R)-6-(pyridin-3-yl)-4-azaspiro[2.4]heptane-4-carbonyl)decahydropyrrolo[1,2-a]azocin-6-yl)carbamoyl)benzo[b]thiophen-5-yl)methyl)phosphonic acid | 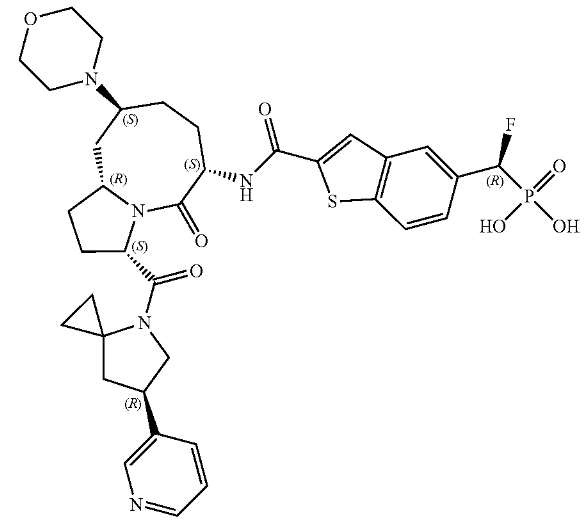 | 1H NMR (400 MHz, DMSO-d6) δ (ppm) 8.68-8.34 (m, 3H), 8.25-7.87 (m, 3H), 7.78-7.23 (m, 3H), 5.58 (dd, J = 45.4, 8.0 Hz, 1H), 4.55-4.38 (m, 2H), 4.22-3.99 (m, 3H), 3.88-3.67 (m, 4H), 3.56-3.46 (m, 1H), 3.28-3.15 (m, 1H), 2.94-2.63 (m, 4H), 2.42-1.13 (m, 14H), 0.51-0.23 (m, 2H); 740.4 [M + H]+. |
| A11 | ((R)-(2-(((3S,6S,9S,10aR)-3-((6S,7R)-7-cyano-6-(pyridin-3-yl)-4-azaspiro[2.4]heptane-4-carbonyl)-9-morpholino-5-oxodecahydro-pyrrolo[1,2-a]azocin-6-yl)carbamoyl)benzo[b]thiophen-5-yl)fluoromethyl)phosphonic acid | 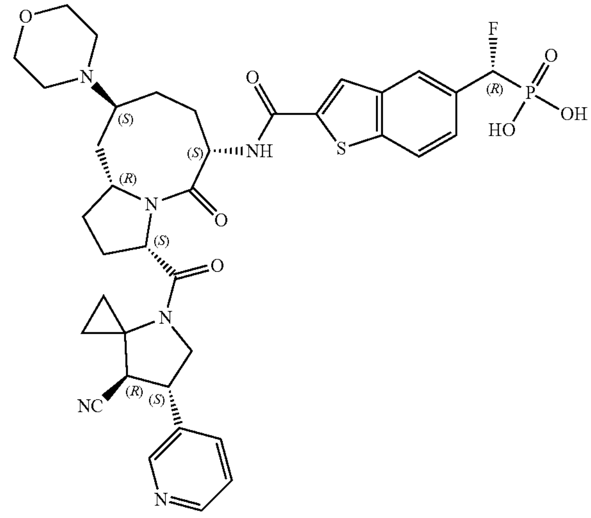 | 1H NMR (400 MHz, DMSO-d6) δ (ppm) 8.69-8.49 (m, 3H), 8.24-8.11 (m, 1H), 8.01-7.83 (m, 3H), 7.59-7.54 (m, 1H), 7.44-7.38 (m, 1H), 5.58 (dd, J = 45.2, 8.0 Hz, 1H), 4.56-4.25 (m, 3H), 4.15-4.00 (m, 2H), 3.83-3.67 (m, 6H), 3.11-3.01 (m, 1H), 2.96-2.63 (m, 4H), 2.37-2.13 (m, 2H), 2.02-1.54 (m, 8H), 1.52-1.12 (m, 2H), 0.85-0.58 (m, 2H); 765.3 [M + H]+. |
| A12 | ((S)-(2-(((3S,6S,9S,10aR)-3-((R)-6-(4-(dimethyl-amino)pyridin-3-yl)-4-azaspiro[2.4]heptane-4-carbonyl)-9-morpholino-5-oxodecahydro-pyrrolo[1,2-a]azocin-6-yl)carbamoyl)benzo[b]thiophen-5-yl)fluoromethyl)phosphonic acid | 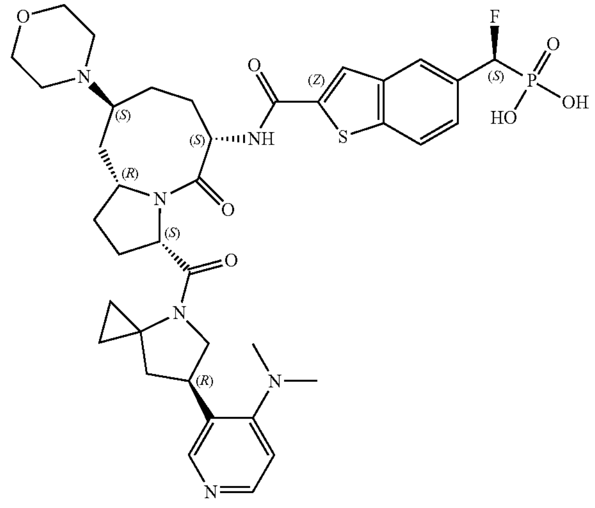 | 1H NMR (400 MHz, DMSO-d6) δ (ppm) 9.46-8.51 (m, 1H), 8.46-7.66 (m, 4H), 7.62-7.25 (m, 1H), 7.22-6.54 (m, 1H), 5.85-5.44 (m, 1H), 5.05-4.58 (m, 1H), 4.51-4.25 (m, 2H), 4.16-3.79 (m, 4H), 3.53-3.11 (m, 8H), 2.76-2.64 (m, 6H), 2.38-2.13 (m, 3H), 2.12-1.83 (m, 7H), 1.78-1.55 (m, 4H), 0.55-0.29 (m, 2H); 783.4 [M + H]+. |

TABLE 1A-continued

| No. | Name | Structure | NMR and LCMS |
| --- | --- | --- | --- |
| A13 | ((R)-fluoro(2-(((3S,6S,9S,10aR)-9-(methyl(oxetan-3-yl)amino)-5-oxo-3-((S)-6-phenyl-4-azaspiro[2.4]heptane-4-carbonyl)decahydro-pyrrolo[1,2-a]azocin-6-yl)carbamoyl)benzo[b]thiophen-5-yl)methyl)phosphonic acid | 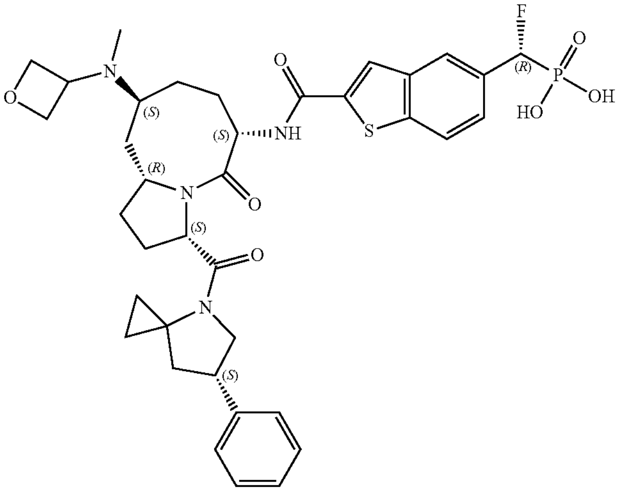 | 1H NMR (400 MHz, DMSO-d6) δ (ppm) 10.38 (s, 1H), 8.87-8.68 (m, 1H), 8.24 (s, 1H), 8.03 (d, J = 8.5 Hz, 1H), 7.97 (s, 1H), 7.53 (d, J = 8.6 Hz, 1H), 7.38-7.30 (m, 4H), 7.25-7.21 (m, 1H), 5.83 (dd, J = 44.4, 8.0 Hz, 1H), 4.92-4.50 (m, 8H), 4.18-4.09 (m, 1H), 3.74-3.68 (m, 1H), 3.60-3.52 (m, 2H), 2.60 (s, 3H), 2.48-2.41 (m, 1H), 2.28-2.21 (m, 1H), 2.16-1.70 (m, 11H), 1.57-1.51 (m, 1H), 0.61-0.48 (m, 2H); 739.6 $[M + H]^+$. |
| A14 | ((R)-fluoro(2-(((3S,6S,9S,10aR)-9-(methyl(oxetan-3-ylmethyl)amino)-5-oxo-3-((S)-6-phenyl-4-azaspiro[2.4]heptane-4-carbonyl)decahydro-pyrrolo[1,2-a]azocin-6-yl)carbamoyl)benzo[b]thiophen-5-yl)methyl)phosphonic acid | 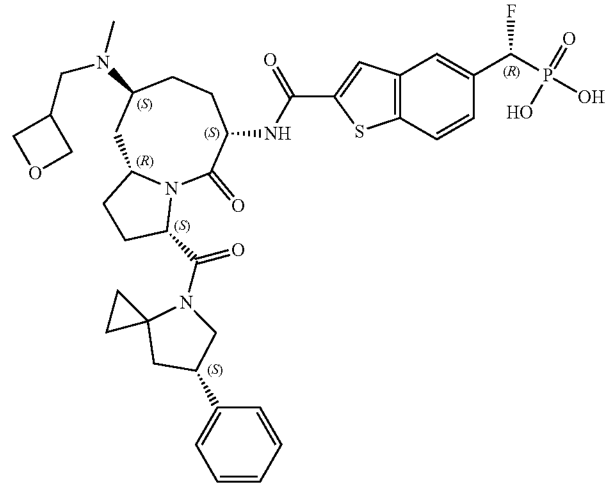 | 1H NMR (400 MHz, DMSO-d6) δ (ppm) 9.73-9.33 (m, 1H), 8.84-8.68 (m, 1H), 8.29-8.16 (m, 1H), 8.06-7.90 (m, 2H), 7.58-7.45 (m, 1H), 7.39-7.19 (m, 5H), 5.79 (dd, J = 44.4, 7.9 Hz, 1H), 4.83-4.76 (m, 1H), 4.69-4.66 (m, 1H), 4.58-4.50 (m, 2H), 4.41-4.30 (m, 2H), 4.15-4.10 (m, 1H), 3.79-3.66 (m, 3H), 3.55-3.44 (m, 3H), 3.12-3.00 (m, 1H), 2.74-2.53 (m, 3H), 2.32-1.46 (m, 14H), 0.61-0.40 (m, 2H); 753.5 $[M + H]^+$. |
| A15 | ((R)-fluoro(2-(((3S,6S,9S,10aR)-9-(methyl(((S)-oxetan-2-yl)methyl)amino)-5-oxo-3-((S)-6-phenyl-4-azaspiro[2.4]heptane-4-carbonyl)decahydro-pyrrolo[1,2-a]azocin-6-yl)carbamoyl)benzo[b]thiophen-5-yl)methyl)phosphonic acid | 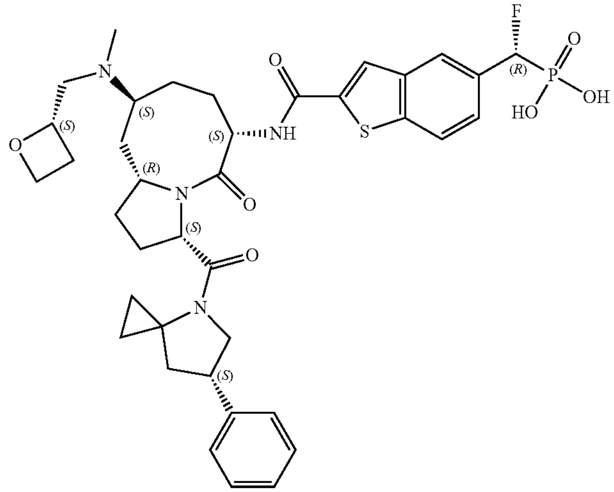 | 1H NMR (400 MHz, DMSO-d6) δ (ppm) 9.61-9.30 (m, 1H), 8.86-8.69 (m, 1H), 8.29-8.22 (m, 1H), 8.06-7.93 (m, 2H), 7.53 (d, J = 8.5 Hz, 1H), 7.40-7.29 (m, 4H), 7.23 (t, J = 7.0 Hz, 1H), 5.81 (dd, J = 44.4, 8.0 Hz, 1H), 5.21-5.06 (m, 1H), 4.84-4.75 (m, 1H), 4.62-4.51 (m, 3H), 4.15-4.09 (m, 1H), 3.78-3.66 (m, 2H), 3.60-3.48 (m, 2H), 3.38-3.16 (m, 1H), 2.83-2.64 (m, 4H), 2.49-1.70 (m, 15H), 1.63-1.53 (m, 1H), 0.57-0.43 (m, 2H); 753.3 $[M + H]^+$. |

TABLE 1A-continued

| No. | Name | Structure | NMR and LCMS |
|---|---|---|---|
| A16 | ((S)-fluoro(2-(((3S,6S,9S,10aR)-9-(methyl(oxetan-3-yl)amino)-5-oxo-3-((S)-6-phenyl-4-azaspiro[2.4]heptane-4-carbonyl)decahydro-pyrrolo[1,2-a]azocin-6-yl)carbamoyl)benzo[b]thiophen-5-yl)methyl)phosphonic acid | 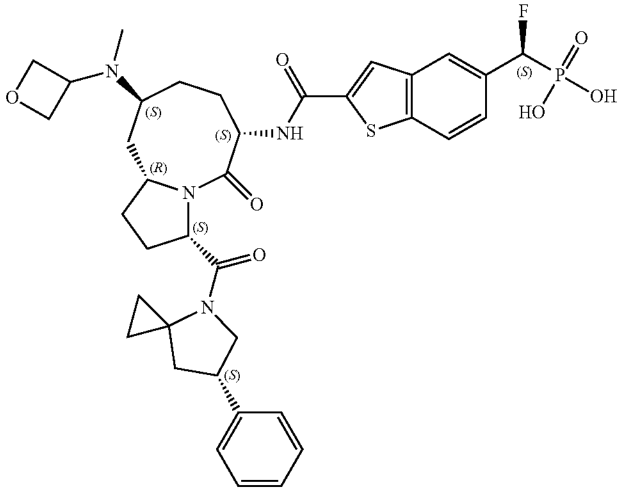 | 1H NMR (400 MHz, DMSO-d6) δ (ppm) 8.84-8.68 (m, 1H), 8.24 (s, 1H), 8.03-7.84 (m, 2H), 7.57-7.13 (m, 6H), 5.59 (dd, J = 44.9, 8.4 Hz, 1H), 4.81-4.42 (m, 6H), 4.39-4.27 (m, 1H), 4.24-4.00 (m, 2H), 3.77-3.65 (m, 1H), 3.56-3.46 (m, 1H), 3.24-3.03 (m, 1H), 2.44-1.44 (m, 17H), 0.55-0.36 (m, 2H); 739.7 $[M + H]^+$. |
| A17 | ((R)-fluoro(2-(((3S,6S,9S,10aR)-9-(methyl(((R)-oxetan-2-yl)methyl)amino)-5-oxo-3-((S)-6-phenyl-4-azaspiro[2.4]heptane-4-carbonyl)decahydro-pyrrolo[1,2-a]azocin-6-yl)carbamoyl)benzo[b]thiophen-5-yl)methyl)phosphonic acid | 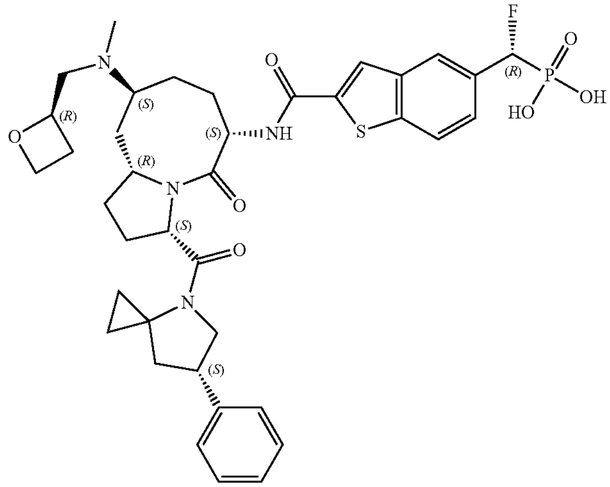 | 1H NMR (400 MHz, DMSO-d6) δ (ppm) 9.59-9.23 (m, 1H), 8.86-8.63 (m, 1H), 8.25 (s, 1H), 8.04-7.89 (m, 2H), 7.52 (d, J = 8.5 Hz, 1H), 7.39-7.20 (m, 5H), 5.78 (dd, J = 44.4, 7.9 Hz, 1H), 5.26-5.04 (m, 1H), 4.84-4.73 (m, 1H), 4.64-4.46 (m, 4H), 4.17-4.08 (m, 1H), 3.77-3.68 (m, 2H), 3.57-3.50 (m, 2H), 3.34-3.22 (m, 1H), 2.82-2.64 (m, 4H), 2.48-2.15 (m, 4H), 2.13-1.71 (m, 11H), 1.63-1.55 (m, 1H), 0.60-0.43 (m, 2H); 753.2 $[M + H]^+$. |
| A18 | ((R)-fluoro(2-(((3S,6S,9S,10aR)-9-(methyl((S)-tetrahydro-furan-3-yl)amino)-5-oxo-3-((S)-6-phenyl-4-azaspiro[2.4]heptane-4-carbonyl)decahydro-pyrrolo[1,2-a]azocin-6-yl)carbamoyl)benzo[b]thiophen-5-yl)methyl)phosphonic acid | 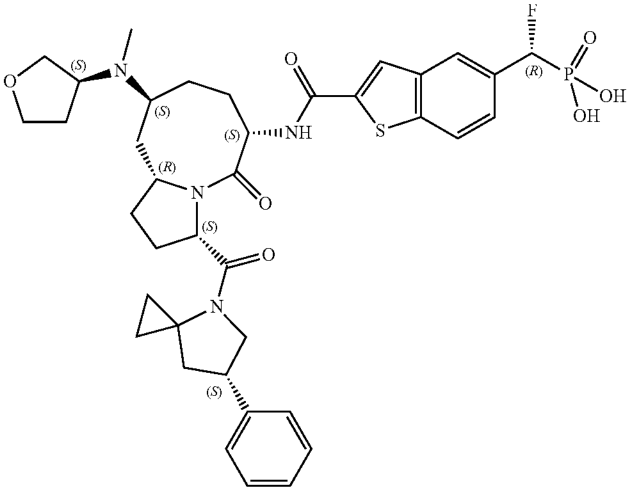 | 1H NMR (400 MHz, DMSO-d6) δ (ppm) 8.90-8.61 (m, 1H), 8.24 (s, 1H), 8.08-7.88 (m, 2H), 7.61-7.44 (m, 1H), 7.41-7.14 (m, 5H), 6.00-5.62 (m, 1H), 4.89-4.71 (m, 1H), 4.64-4.45 (m, 2H), 4.21-4.04 (m, 2H), 3.93-3.84 (m, 2H), 3.77-3.67 (m, 2H), 3.58-3.50 (m, 2H), 2.77-2.57 (m, 3H), 2.47-2.40 (m, 1H), 2.34-1.92 (m, 11H), 1.87-1.46 (m, 5H), 0.62-0.43 (m, 2H); 753.2 $[M + H]^+$. |

TABLE 1A-continued

| No. | Name | Structure | NMR and LCMS |
| --- | --- | --- | --- |
| A19 | ((R)-fluoro(2-(((3S,6S,9S,10aR)-9-(methyl((R)-tetrahydrofuran-3-yl)amino)-5-oxo-3-((S)-6-phenyl-4-azaspiro[2.4]heptane-4-carbonyl)decahydro-pyrrolo[1,2-a]azocin-6-yl)carbamoyl)benzo[b]thiophen-5-yl)methyl)phosphonic acid | 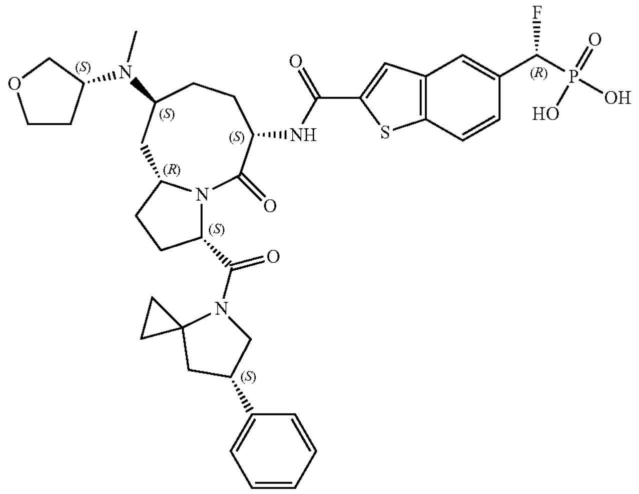 | 1H NMR (400 MHz, DMSO-d6) δ (ppm) 9.77-9.44 (m, 1H), 8.90-8.68 (m, 1H), 8.25 (s, 1H), 8.02 (d, J = 8.4 Hz, 1H), 7.97 (s, 1H), 7.53 (d, J = 8.5 Hz, 1H), 7.39-7.28 (m, 4H), 7.26-7.20 (m, 1H), 5.81 (dd, J = 44.3, 7.9 Hz, 1H), 4.87-4.75 (m, 1H), 4.61-4.45 (m, 2H), 4.18-4.10 (m, 2H), 3.99-3.93 (m, 1H), 3.85-3.80 (m, 1H), 3.77-3.63 (m, 4H), 3.58-3.52 (m, 1H), 2.74-2.62 (m, 3H), 2.48-2.40 (m, 1H), 2.35-2.17 (m, 3H), 2.17-1.91 (m, 8H), 1.86-1.69 (m, 3H), 1.57-1.47 (m, 1H), 0.65-0.41 (m, 2H); 753.2 [M + H]$^+$. |
| A20 | ((R)-(2-(((3S,6S,9S,10aR)-9-((3,3-difluoropropyl)(methyl)amino)-5-oxo-3-((S)-6-phenyl-4-azaspiro[2.4]heptane-4-carbonyl)deca-hydropyrrolo[1,2-a]azocin-6-yl)carbamoyl)benzo[b]thiophen-5-yl)fluoromethyl)phosphonic acid | 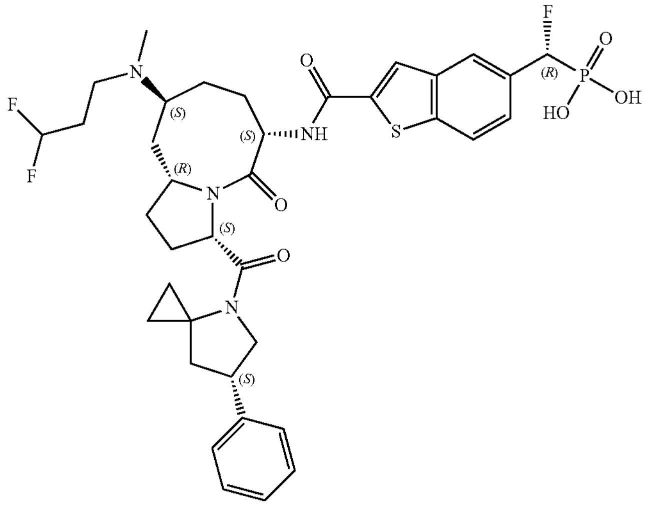 | 1H NMR (400 MHz, DMSO-d6) δ (ppm) 8.87-8.67 (m, 1H), 8.24 (s, 1H), 8.03 (d, J = 8.4 Hz, 1H), 7.98 (s, 1H), 7.53 (d, J = 8.4 Hz, 1H), 7.38-7.29 (m, 4H), 7.26-7.19 (m, 1H), 6.40-6.03 (m, 1H), 5.83 (dd, J = 44.3, 8.0 Hz, 1H), 4.81 (s, 1H), 4.60-4.50 (m, 2H), 4.17-4.09 (m, 1H), 3.85-3.70 (m, 2H), 3.57-3.51 (m, 1H), 3.35-3.19 (m, 2H), 2.80-2.69 (m, 3H), 2.49-2.42 (m, 1H), 2.39-1.70 (m, 14H), 1.56 (s, 1H), 0.59-0.42 (m, 2H); 761.5 [M + H]$^+$. |
| A21 | ((R)-fluoro(2-(((3S,6S,9S,10aR)-9-(((1s,3R)-3-fluoro-cyclobutyl)(methyl)amino)-5-oxo-3-((S)-6-phenyl-4-azaspiro[2.4]heptane-4-carbonyl)deca-hydropyrrolo[1,2-a]azocin-6-yl)carbamoyl)benzo[b]thiophen-5-yl)methyl)phosphonic acid | 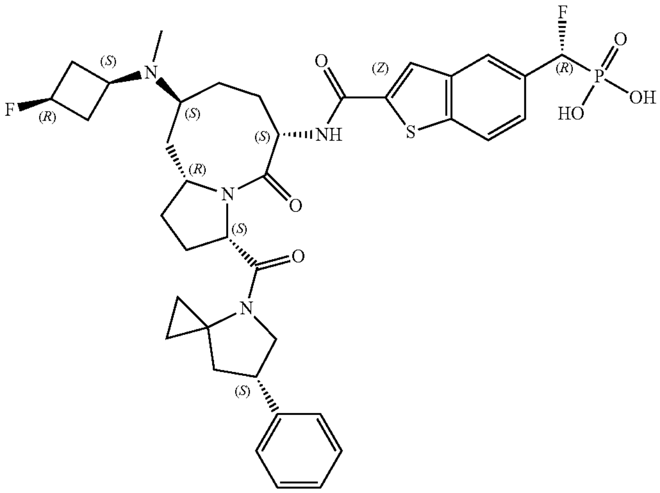 | 1H NMR (400 MHz, MeOD-d4) δ (ppm) 8.08-8.01 (m, 2H), 7.88 (d, J = 8.4 Hz, 1H), 7.66 (d, J = 8.4 Hz, 1H), 7.37-7.26 (m, 4H), 7.24-7.17 (m, 1H), 5.65 (dd, J = 45.2, 8.4 Hz, 1H), 4.79-4.68 (m, 2H), 4.66-4.58 (m, 1H), 4.52-4.40 (m, 1H), 4.07-3.99 (m, 1H), 3.96-3.89 (m, 1H), 3.86-3.73 (m, 1H), 3.61-3.49 (m, 1H), 3.00-2.86 (m, 1H), 2.81-2.68 (m, 1H), 2.65-2.06 (m, 11H), 2.03-1.60 (m, 9H), 0.59-0.44 (m, 2H); [M + H]$^+$. |

TABLE 1A-continued

| No. | Name | Structure | NMR and LCMS |
|---|---|---|---|
| A22 | ((R)-fluoro(2-(((3S,6S,9S,10aR)-9-(((1r,3S)-3-fluoro-cyclobutyl)(methyl)amino)-5-oxo-3-((S)-6-phenyl-4-azaspiro[2.4]heptane-4-carbonyl)deca-hydropyrrolo[1,2-a]azocin-6-yl)carbamoyl)benzo[b]thiophen-5-yl)methyl)phosphonic acid | 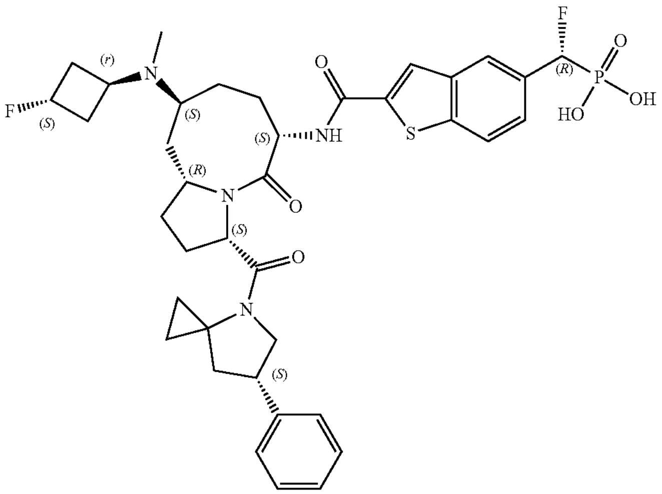 | 1H NMR (400 MHz, DMSO-d6) δ (ppm) 8.90-8.56 (m, 1H), 8.23 (s, 1H), 8.04-7.87 (m, 2H), 7.67-7.43 (m, 1H), 7.37-7.19 (m, 5H), 5.77-5.57 (m, 1H), 5.36-5.09 (m, 1H), 4.55-4.41 (m, 2H), 4.15-4.02 (m, 2H), 3.77-3.66 (m, 2H), 3.56-3.45 (m, 2H), 2.96-2.60 (m, 3H), 2.46-2.13 (m, 5H), 2.12-1.42 (m, 13H), 0.63-0.40 (m, 2H); 755.3 $[M + H]^+$. |
| A23 | 2,2,2-trifluoroacetic acid compound with ((R)-(2-(((3S,6S,9S,10aR)-9-((3,3-difluorocyclo-butyl)(methyl)amino)-5-oxo-3-((S)-6-phenyl-4-azaspiro[2.4]heptane-4-carbonyl)deca-hydropyrrolo[1,2-a]azocin-6-yl)carbamoyl)benzo[b]thiophen-5-yl)fluoromethyl)phosphonic acid | 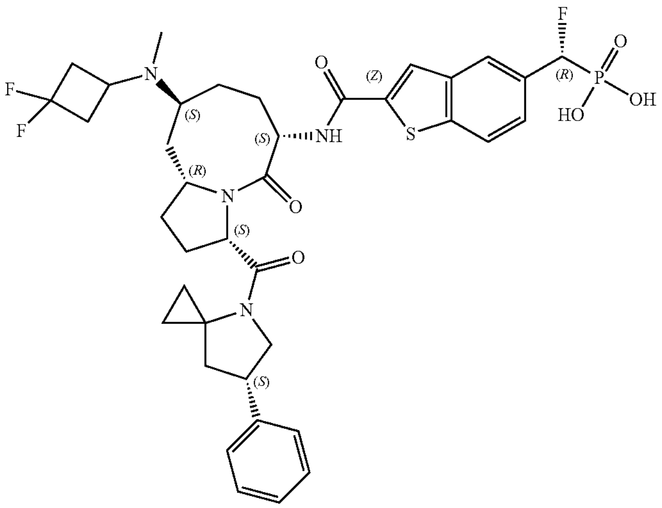 | 1H NMR (400 MHz, DMSO-d6) δ (ppm) 10.48-9.56 (m, 1H), 8.78 (s, 1H), 8.24 (s, 1H), 8.05-7.95 (m, 2H), 7.53 (d, J = 8.5 Hz, 1H), 7.38-7.29 (m, 4H), 7.23 (t, J = 7.0 Hz, 1H), 5.76 (dd, J = 44.6, 7.0 Hz, 1H), 4.84-4.74 (m, 1H), 4.60-4.45 (m, 2H), 4.18-4.10 (m, 1H), 3.73-3.71 (m, 5H), 3.02-2.89 (m, 2H), 2.63 (s, 3H), 2.48-2.43 (m, 1H), 2.35-2.16 (m, 2H), 2.13-1.75 (m, 11H), 1.57-1.51 (m, 1H), 0.61-0.48 (m, 2H); 773.3 $[M + H]^+$. |
| A24 | ((S)-fluoro(2-(((3S,6S,9S,10aR)-9-(methyl(((S)-oxetan-2-yl)methyl)amino)-5-oxo-3-((S)-6-phenyl-4-azaspiro[2.4]heptane-4-carbonyl)deca-hydropyrrolo[1,2-a]azocin-6-yl)carbamoyl)benzo[b]thiophen-5-yl)methyl)phosphonic acid | 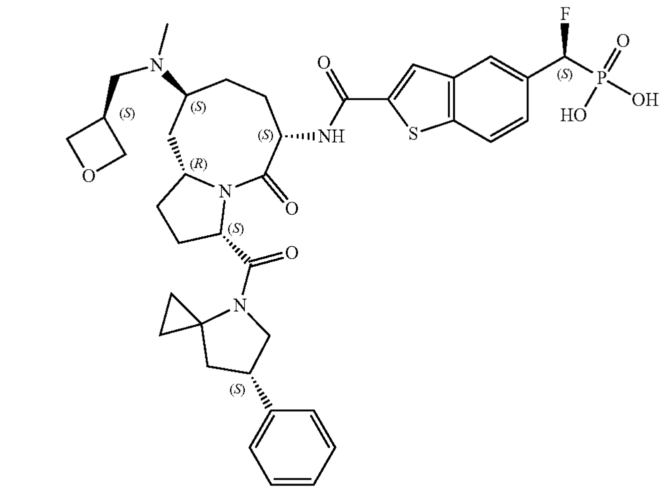 | 1H NMR (400 MHz, DMSO-d6) δ (ppm) 9.67-9.28 (m, 1H), 8.86-8.70 (m, 1H), 8.25 (s, 1H), 8.06-7.93 (m, 2H), 7.52 (d, J = 8.5 Hz, 1H), 7.38-7.27 (m, 4H), 7.26-7.19 (m, 1H), 5.78 (dd, J = 44.4, 8.0 Hz, 1H), 5.26-5.04 (m, 1H), 4.82-4.74 (m, 1H), 4.58-4.45 (m, 3H), 4.19-4.05 (m, 1H), 3.78-3.67 (m, 2H), 3.59-3.49 (m, 2H), 3.38-3.17 (m, 1H), 2.84-2.61 (m, 4H), 2.47-2.18 (m, 3H), 2.17-1.42 (m, 13H), 0.58-0.45 (m, 2H); 753.3 $[M + H]^+$. |

TABLE 1A-continued

| No. | Name | Structure | NMR and LCMS |
| --- | --- | --- | --- |
| A25 | ((S)-(2-(((3S,6S,9S,10aR)-9-((3,3-difluorocyclo-butyl)(methyl)amino)-5-oxo-3-((S)-6-phenyl-4-azaspiro[2.4]heptane-4-carbonyl)deca-hydropyrrolo[1,2-a]azocin-6-yl)carbamoyl)benzo[b]thiophen-5-yl)fluoromethyl)phosphonic acid | 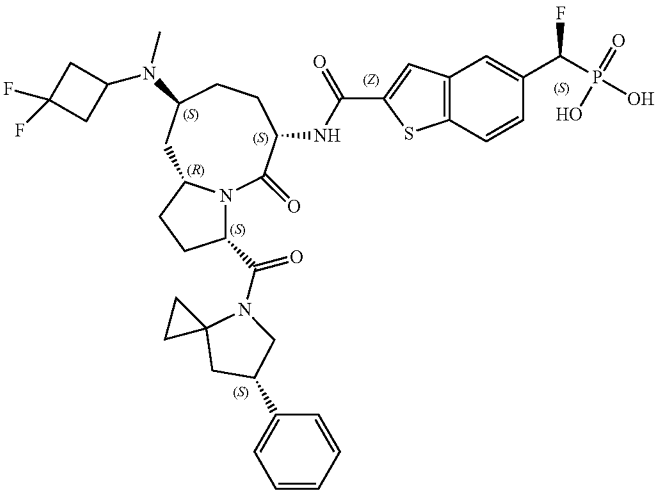 | 1H NMR (400 MHz, DMSO-d6) δ (ppm) 10.06 (d, J = 176.4 Hz, 1H), 8.77 (s, 1H), 8.24 (s, 1H), 8.06-7.94 (m, 2H), 7.53 (d, J = 8.5 Hz, 1H), 7.38-7.29 (m, 4H), 7.27-7.20 (m, 1H), 5.81 (dd, J = 44.3, 8.0 Hz, 1H), 4.85-4.75 (m, 1H), 4.58-4.46 (m, 2H), 4.14 (s, 1H), 3.82-3.68 (m, 2H), 3.64-3.49 (m, 2H), 3.15-2.83 (m, 4H), 2.62 (s, 3H), 2.49-2.41 (m, 1H), 2.27-2.21 (m, 1H), 2.12-1.62 (m, 11H), 1.58-1.49 (m, 1H), 0.60-0.47 (m, 2H); 773.2 [M + H]+. |
| A26 | ((S)-fluoro(2-(((3S,6S,9S,10aR)-9-(methyl((R)-tetrahydro-furan-3-yl)amino)-5-oxo-3-((S)-6-phenyl-4-azaspiro[2.4]heptane-4-carbonyl)deca-hydropyrrolo[1,2-a]azocin-6-yl)carbamoyl)benzo[b]thiophen-5-yl)methyl)phosphonic acid | 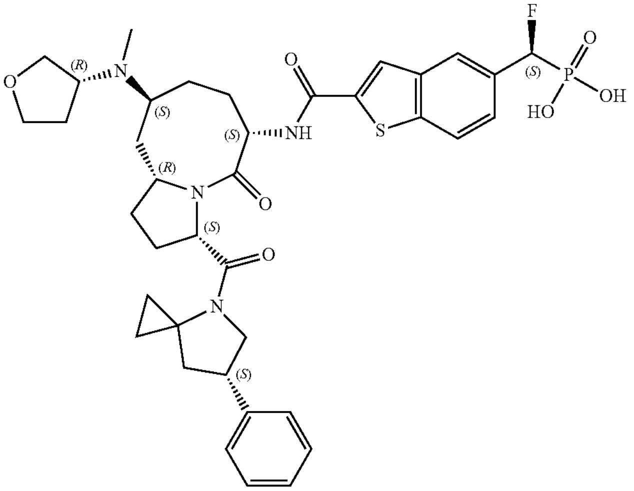 | 1H NMR (400 MHz, DMSO-d6) δ (ppm) 8.72 (s, 1H), 8.22 (s, 1H), 8.03-7.85 (m, 2H), 7.57-7.43 (m, 1H), 7.38-7.25 (m, 4H), 7.23-7.17 (m, 1H), 5.67-5.42 (m, 1H), 4.63-4.19 (m, 3H), 4.13-4.04 (m, 1H), 3.93-3.74 (m, 4H), 3.71-3.62 (m, 3H), 2.43-1.57 (m, 19H), 1.54-1.48 (m, 1H), 0.56-0.37 (m, 2H); 753.3 [M + H]+. |
| A27 | ((R)-fluoro(2-(((3S,6S,9S,10aR)-3-((S)-6-(3-fluoro-phenyl)-4-azaspiro[2.4]heptane-4-carbonyl)-9-(methyl(oxetan-3-yl)amino)-5-oxodecahydro-pyrrolo[1,2-a]azocin-6-yl)carbamoyl)benzo[b]thiophen-5-yl)methyl)phosphonic acid | 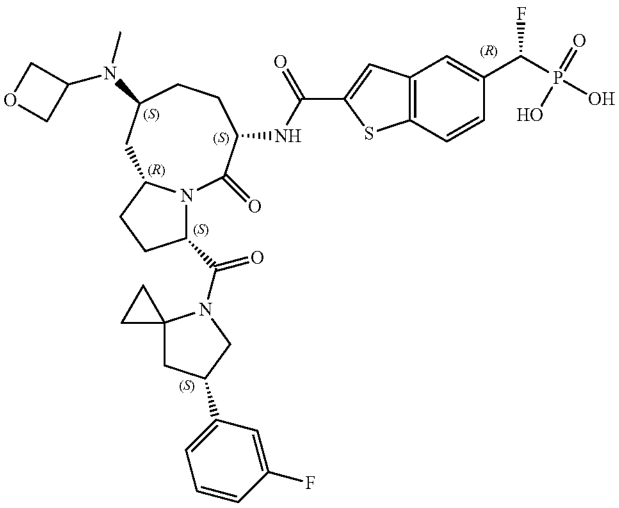 | 1H NMR (400 MHz, DMSO-d6) δ (ppm) 10.80-10.14 (m, 1H), 8.89-8.62 (m, 1H), 8.27-8.17 (m, 1H), 8.03 (s, 1H), 7.97 (s, 1H), 7.53 (d, J = 8.6 Hz, 1H), 7.40-7.33 (m, 1H), 7.25-7.18 (m, 2H), 7.09-7.03 (m, 1H), 5.83 (dd, J = 44.3, 8.0 Hz, 1H), 4.89-4.50 (m, 8H), 4.17-4.09 (m, 1H), 3.75-3.69 (m, 1H), 3.59-3.56 (m, 1H), 2.60 (s, 3H), 2.48-2.40 (m, 1H), 2.26-1.52 (m, 14H), 0.61-0.40 (m, 2H); 757.4 [M + H]+. |

TABLE 1A-continued

| No. | Name | Structure | NMR and LCMS |
|---|---|---|---|
| A28 | ((S)-fluoro(2-(((3S,6S,9S,10aR)-9-(methyl((S)-tetrahydro-furan-3-yl)amino)-5-oxo-3-((S)-6-phenyl-4-azaspiro[2.4]heptane-4-carbonyl)deca-hydropyrrolo[1,2-a]azocin-6-yl)carbamoyl)benzo[b]thiophen-5-yl)methyl)phosphonic acid | 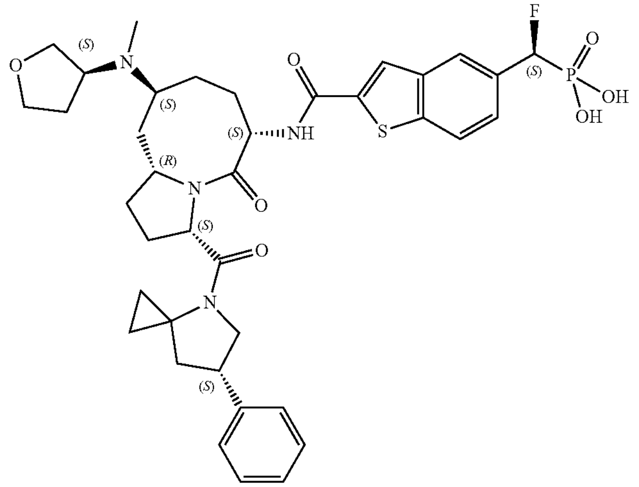 | 1H NMR (400 MHz, DMSO-d6) δ (ppm) 10.01-9.49 (m, 1H), 8.90-8.65 (m, 1H), 8.24 (s, 1H), 8.06-7.92 (m, 2H), 7.53 (d, J = 8.5 Hz, 1H), 7.39-7.27 (m, 4H), 7.26-7.20 (m, 1H), 5.80 (dd, J = 44.4, 8.0 Hz, 1H), 4.85-4.75 (m, 1H), 4.62-4.48 (m, 2H), 4.18-4.02 (m, 2H), 3.93-3.85 (m, 2H), 3.77-3.63 (m, 2H), 3.62-3.40 (m, 2H), 2.76-2.60 (m, 3H), 2.49-2.41 (m, 1H), 2.35-1.46 (m, 16H), 0.62-0.42 (m, 2H); 753.2 $[M + H]^+$. |
| A29 | ((S)-(2-(((3S,5S,9S,10aR)-9-((3,3-difluoropropyl)(methyl)amino)-5-oxo-3-((S)-6-phenyl-4-azaspiro[2.4]heptane-4-carbonyl)deca-hydropyrrolo[1,2-a]azocin-6-yl)carbamoyl)benzo[b]thiophen-5-yl)fluoromethyl)phosphonic acid | 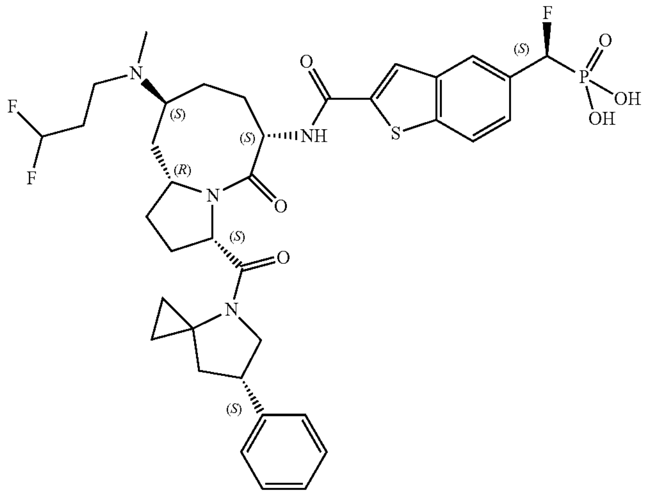 | 1H NMR (400 MHz, DMSO-d6) 1H NMR (400 MHz, DMSO-d6) δ (ppm) 8.85-8.61 (m, 1H), 8.29-8.17 (m, 1H), 8.02-7.92 (m, 2H), 7.60-7.41 (m, 1H), 7.37-7.26 (m, 4H), 7.21 (t, J = 7.0 Hz, 1H), 6.38-5.93 (m, 1H), 5.74-5.47 (m, 1H), 4.73-4.32 (m, 4H), 4.13-4.03 (m, 1H), 3.76-3.64 (m, 1H), 3.54-3.46 (m, 1H), 3.05 (2, 2H), 2.69-2.54 (m, 3H), 2.47-2.14 (m, 4H), 2.06-1.66 (m, 11H), 1.59-1.51 (m, 1H), 0.51-0.36 (m, 2H); 761.4 $[M + H]^+$. |
| A30 | ((R)-fluoro(2-(((3S,6S,9S,10aR)-9-(((1s,3R)-3-fluorocyclo-butyl)(methyl)amino)-5-oxo-3-((R)-6-(pyridin-3-yl)-4-azaspiro[2.4]heptane-4-carbonyl)deca-hydropyrrolo[1,2-a]azocin-6-yl)carbamoyl)benzo[b]thiophen-5-yl)methyl)phosphonic acid. | 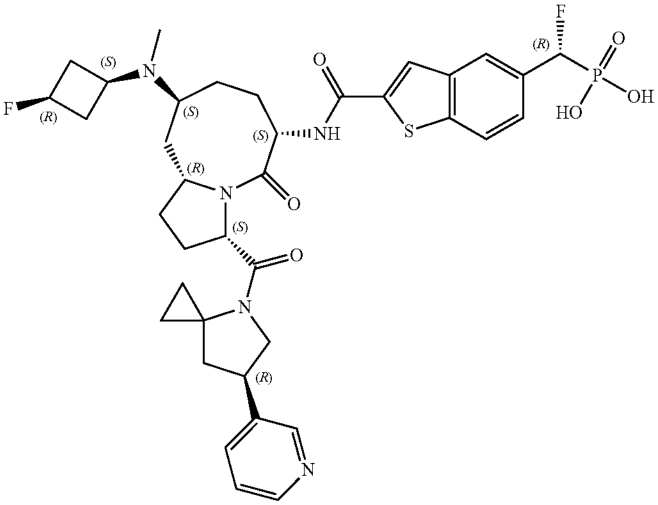 | 1H NMR (400 MHz, DMSO-d6) δ (ppm) 8.93-8.43 (m, 3H), 8.30-8.05 (m, 2H), 8.05-7.94 (m, 2H), 7.69-7.48 (m, 2H), 5.84 (dd, J = 44.3, 8.0 Hz, 1H), 5.02-4.75 (m, 2H), 4.61-4.48 (m, 2H), 4.24-4.11 (m, 1H), 3.90-3.74 (m, 2H), 3.73-3.62 (m, 1H), 3.45-3.00 (m, 1H), 2.80-2.62 (m, 2H), 2.62-2.54 (m, 3H), 2.50-2.36 (m, 3H), 2.27-1.59 (m, 13H), 0.63-0.35 (m, 2H); 756.6 $[M + H]^+$. |

TABLE 1A-continued

| No. | Name | Structure | NMR and LCMS |
|---|---|---|---|
| A31 | ((S)-fluoro(2-(((3S,6S,9S,10aR)-9-(methyl(((R)-oxetan-2-yl)methyl)amino)-5-oxo-3-((S)-6-phenyl-4-azaspiro[2.4]heptane-4-carbonyl)deca-hydropyrrolo[1,2-a]azocin-6-yl)carbamoyl)benzo[b]thiophen-5-yl)methyl)phosphonic acid | 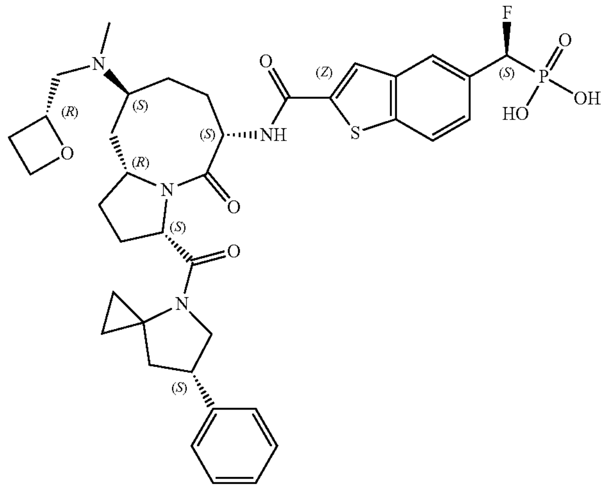 | 1H NMR (400 MHz, DMSO-d6) δ (ppm) 8.88-8.65 (m, 1H), 8.24 (s, 1H), 8.07-7.92 (m, 2H), 7.52 (d, J = 8.5 Hz, 1H), 7.38-7.16 (m, 5H), 5.77 (dd, J = 44.6, 7.7 Hz, 1H), 5.26-5.03 (m, 1H), 4.83-4.74 (m, 1H), 4.65-4.42 (m, 4H), 4.16-4.11 (m, 1H), 3.76-3.71 (m, 2H), 3.55-3.51 (m, 2H), 3.28-3.20 (m, 1H), 2.83-2.61 (m, 4H), 2.48-2.32 (m, 2H), 2.29-2.18 (m, 1H), 2.15-1.66 (m, 11H), 1.61-1.53 (m, 1H), 0.60-0.44 (m, 2H); 753.3 [M + H]+. |
| A32 | ((R)-(2-(((3S,6S,9S,10aR)-9-(((S)-3,3-difluoro-cyclopentyl)(methyl)amino)-5-oxo-3-((S)-6-phenyl-4-azaspiro[2.4]heptane-4-carbonyl)deca-hydropyrrolo[1,2-a]azocin-6-yl)carbamoyl)benzo[b]thiophen-5-yl)fluoromethyl)phosphonic acid | 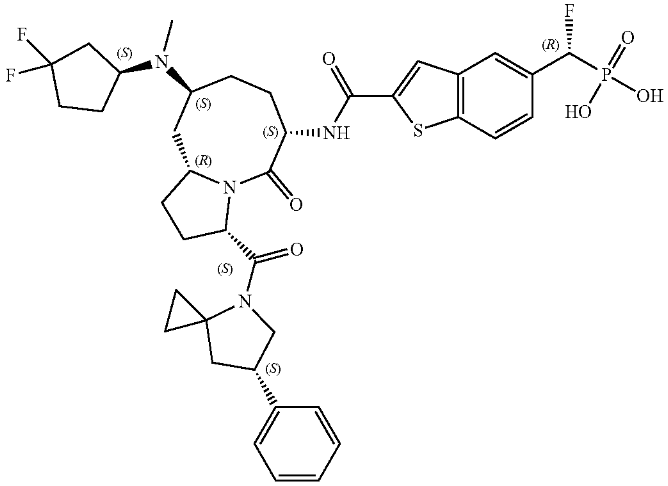 | 1H NMR (400 MHz, DMSO-d6) δ (ppm) 8.82-8.64 (m, 1H), 8.25-8.19 (m, 1H), 8.04-7.90 (m, 2H), 7.60-7.49 (m, 1H), 7.38-7.26 (m, 4H), 7.25-7.12 (m, 1H), 5.79-5.52 (m, 1H), 4.57-4.40 (m, 2H), 4.14-4.04 (m, 2H), 3.76-3.68 (m, 2H), 3.56-3.47 (m, 2H), 2.66-2.55 (m, 3H), 2.48-2.16 (m, 5H), 2.16-1.85 (m, 9H), 1.85-1.64 (m, 5H), 1.64-1.52 (m, 1H), 0.60-0.38 (m, 2H); 787.4 [M + H]+. |
| A33 | ((R)-(2-(((3S,6S,9S,10aR)-9-(ethyl((1s,3R)-3-fluorocyclo-butyl)amino)-5-oxo-3-((S)-6-phenyl-4-azaspiro[2.4]heptane-4-carbonyl)deca-hydropyrrolo[1,2-a]azocin-6-yl)carbamoyl)benzo[b]thiophen-5-yl)fluoromethyl)phosphonic acid | 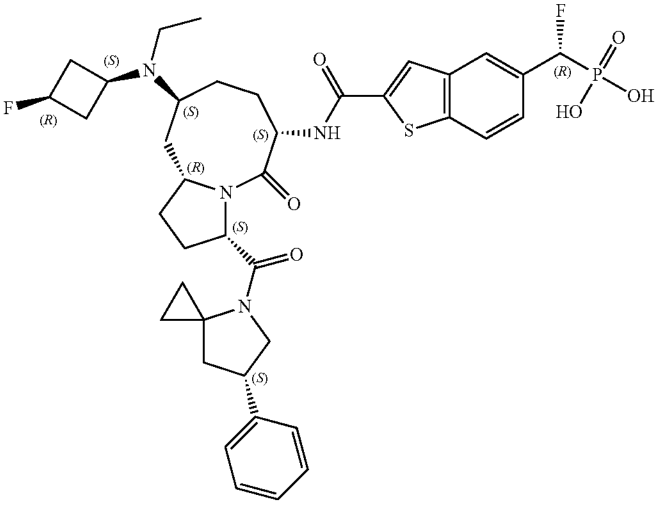 | 1H NMR (400 MHz, DMSO-d6) δ (ppm) 9.65-9.12 (m, 1H), 8.90-8.71 (m, 1H), 8.30-8.22 (m, 1H), 8.03-7.91 (m, 2H), 7.55-7.47 (m, 1H), 7.38-7.20 (m, 5H), 5.86-5.63 (m, 1H), 5.00-4.72 (m, 2H), 4.59-4.45 (m, 2H), 4.20-4.09 (m, 1H), 3.77-3.72 (m, 1H), 3.57-3.53 (m, 1H), 3.24-3.15 (m, 1H), 3.09-3.03 (m, 1H), 2.89-2.53 (m, 4H), 2.46-1.50 (m, 16H), 1.32-1.21 (m, 3H), 0.61-0.42 (m, 2H); 769.3 [M + H]+. |

TABLE 1A-continued

| No. | Name | Structure | NMR and LCMS |
| --- | --- | --- | --- |
| A34 | ((S)-(2-(((3S,6S,9S,10aR)-9-(ethyl((1s,3R)-3-fluorocyclobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)phosphonic acid | 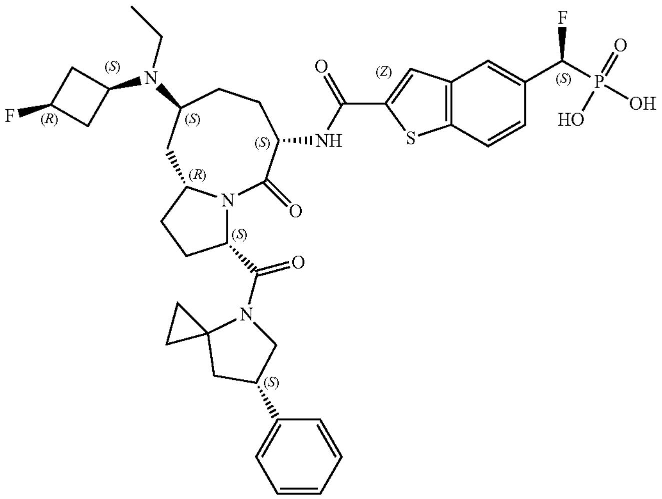 | 1H NMR (400 MHz, MeOD-d4) δ (ppm) 8.06 (s, 2H), 7.89 (d, J = 8.5 Hz, 1H), 7.61 (d, J = 8.4 Hz, 1H), 7.36-7.25 (m, 4H), 7.24-7.16 (m, 1H), 5.69 (dd, J = 45.1, 8.3 Hz, 1H), 4.84-4.73 (m, 1H), 4.69 (d, J = 11.6 Hz, 1H), 4.65-4.58 (m, 1H), 4.52-4.40 (m, 1H), 4.07-3.83 (m, 3H), 3.62-3.43 (m, 2H), 3.24-3.01 (m, 2H), 3.00-2.38 (m, 5H), 2.35-1.72 (m, 12H), 1.59 (s, 1H), 1.36 (s, 3H), 0.59-0.45 (m, 2H); 769.4 $[M + H]^+$. |
| A35 | ((R)-(2-(((3S,6S,9S,10aR)-9-(((1s,3R)-3-(difluoromethyl)cyclobutyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)phosphonic acid | 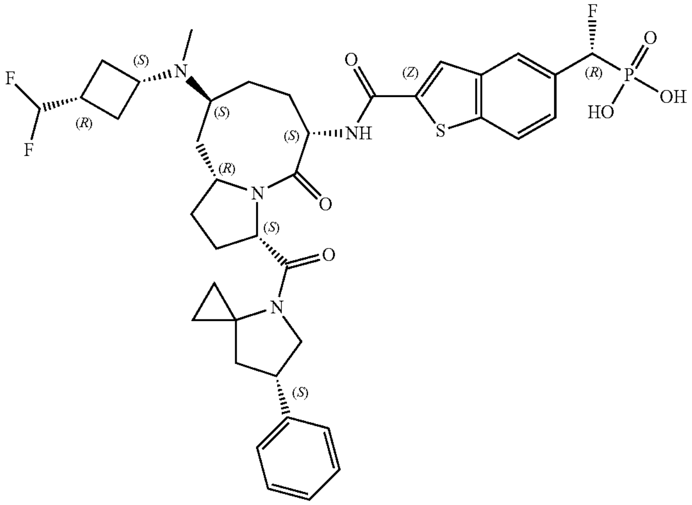 | 1H NMR (400 MHz, DMSO-d6) δ (ppm) 9.74-9.31 (m, 1H), 8.89-8.69 (m, 1H), 8.29-8.20 (m, 1H), 8.08-7.94 (m, 2H), 7.57-7.49 (m, 1H), 7.38-7.28 (m, 4H), 7.26-7.21 (m, 1H), 6.22-5.90 (m, 1H), 5.83 (dd, J = 44.4, 8.1 Hz, 1H), 4.85-4.75 (m, 1H), 4.62-4.46 (m, 2H), 4.20-4.07 (m, 1H), 3.87-3.74 (m, 2H), 3.60-3.49 (m, 2H), 2.62-2.53 (m, 3H), 2.47-1.49 (m, 19H), 0.61-0.40 (m, 2H); 787.4 $[M + H]^+$. |
| A36 | ((S)-(2-(((3S,6S,9S,10aR)-9-(((S)-3,3-difluorocyclopentyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)phosphonic acid | 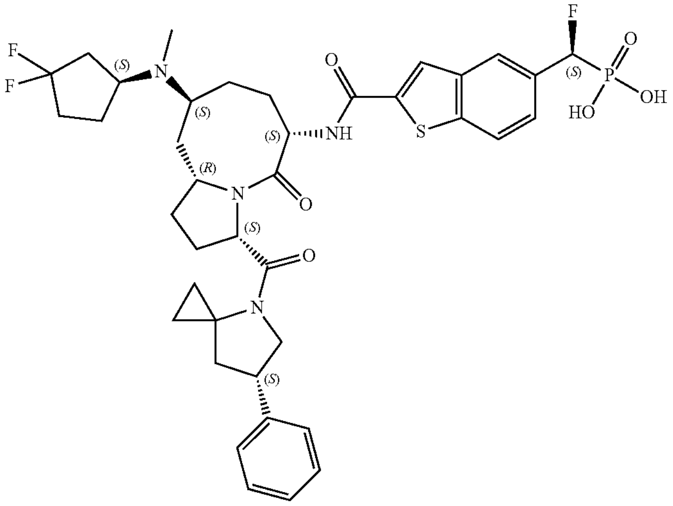 | 1H NMR (400 MHz, MeOD-d4) δ (ppm) 8.09 (d, J = 5.4 Hz, 1H), 8.03 (s, 1H), 7.98-7.89 (m, 1H), 7.58 (d, J = 8.4 Hz, 1H), 7.38-7.25 (m, 4H), 7.24-7.17 (m, 1H), 5.93-5.71 (m, 1H), 4.71-4.54 (m, 2H), 4.39-4.03 (m, 2H), 3.98-3.83 (m, 2H), 3.67-3.32 (m, 2H), 2.84-2.76 (m, 3H), 2.55-1.85 (m, 19H), 1.73-1.58 (m, 1H), 0.62-0.43 (m, 2H); 787.3 $[M + H]^+$. |

TABLE 1A-continued

| No. | Name | Structure | NMR and LCMS |
|---|---|---|---|
| A37 | ((R)-(2-(((3S,6S,9S,10aR)-9-(((1s,3R)-3-cyanocyclobutyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)phosphonic acid | 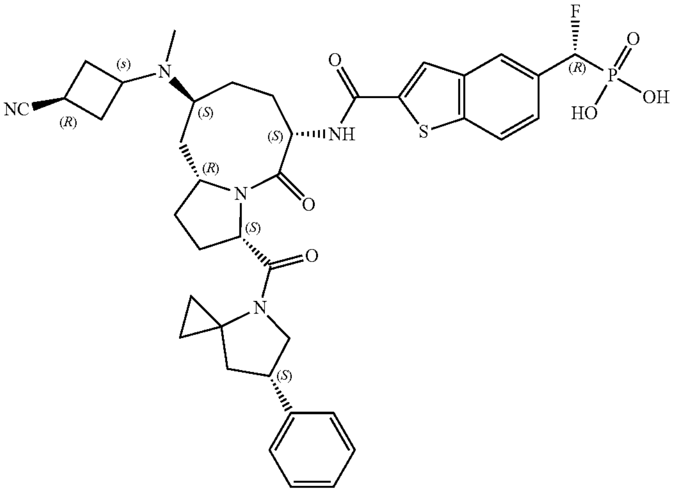 | 1H NMR (400 MHz, MeOD-d4) δ (ppm) 8.16-8.08 (m, 1H), 8.08-8.01 (m, 1H), 8.01-7.92 (m, 1H), 7.65-7.54 (m, 1H), 7.45-7.16 (m, 5H), 6.00-5.69 (m, 1H), 4.90-4.81 (m, 1H), 4.75-4.64 (m, 1H), 4.64-4.53 (m, 1H), 4.20-3.80 (m, 4H), 3.67-3.47 (m, 1H), 3.24-3.12 (m, 1H), 3.03-2.62 (m, 7H), 2.60-2.45 (m, 1H), 2.39-2.19 (m, 5H), 2.15-1.89 (m, 6H), 1.87-1.59 (m, 2H), 0.68-0.50 (m, 2H); 762.3 $[M + H]^+$. |
| A38 | ((S)-fluoro(2-(((3S,6S,9S,10aR)-9-(methyl(4,4,4-trifluorobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)phosphonic acid | 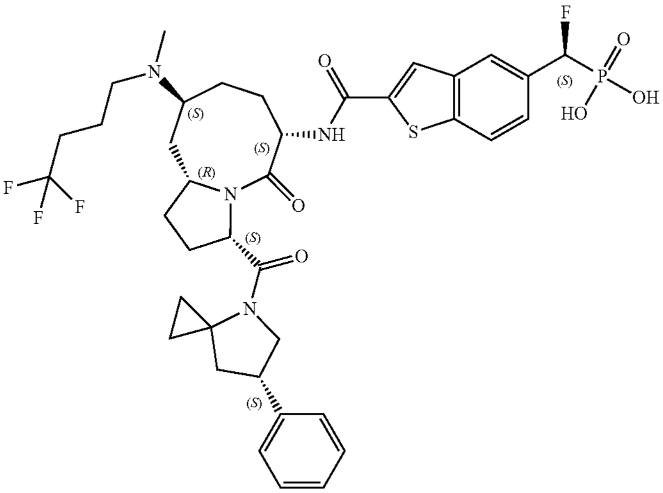 | 1H NMR (400 MHz, DMSO-d6) δ (ppm) 9.72-9.32 (m, 1H), 8.91-8.69 (m, 1H), 8.25 (s, 1H), 8.08-7.94 (m, 2H), 7.53 (d, J = 8.5 Hz, 1H), 7.38-7.28 (m, 4H), 7.25-7.20 (m, 1H), 5.81 (dd, J = 44.3, 7.9 Hz, 1H), 4.81 (s, 1H), 4.60-4.50 (m, 2H), 4.17-4.09 (m, 1H), 3.90-3.69 (m, 2H), 3.63-3.51 (m, 1H), 3.23-3.00 (m, 2H), 2.79-2.68 (m, 3H), 2.41-1.75 (m, 17H), 1.58-1.49 (m, 1H), 0.57-0.42 (m, 2H); 793.3 $[M + H]^+$. |
| A39 | ((R)-fluoro(2-(((3S,6S,9S,10aR)-9-(((1s,3R)-3-fluorocyclobutyl)(methyl)amino)-5-oxo-3-(4-azaspiro[2.4]heptane-4-carbonyl)decahydropyrrolo[1,2-a]azocin-6-yl)carbamoyl)benzo[b]thiophen-5-yl)methyl)phosphonic acid | 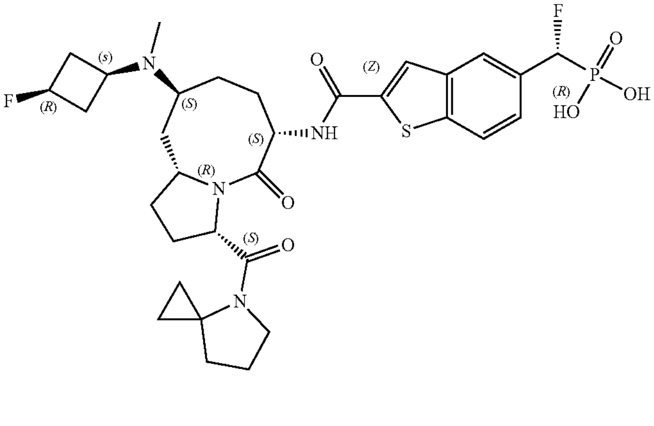 | 1H NMR (400 MHz, MeOD-d4) δ (ppm) 8.04 (d, J = 10.2 Hz, 2H), 7.94 (d, J = 8.5 Hz, 1H), 7.60 (d, J = 8.3 Hz, 1H), 5.80 (dd, J = 44.6, 8.0 Hz, 1H), 4.83-4.74 (m, 2H), 4.72-4.49 (m, 2H), 4.13-3.81 (m, 2H), 3.69-3.43 (m, 2H), 3.00-2.74 (m, 2H), 2.67 (s, 3H), 2.52-2.41 (m, 2H), 2.30-2.13 (m, 3H), 2.06-1.69 (m, 13H), 0.56-0.45 (m, 2H); 679.4 $[M + H]^+$. |

TABLE 1A-continued

| No. | Name | Structure | NMR and LCMS |
|---|---|---|---|
| A40 | ((S)-(2-(((3S,6S,9S,10aR)-9-(((1s,3R)-3-cyanocyclobutyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)phosphonic acid | 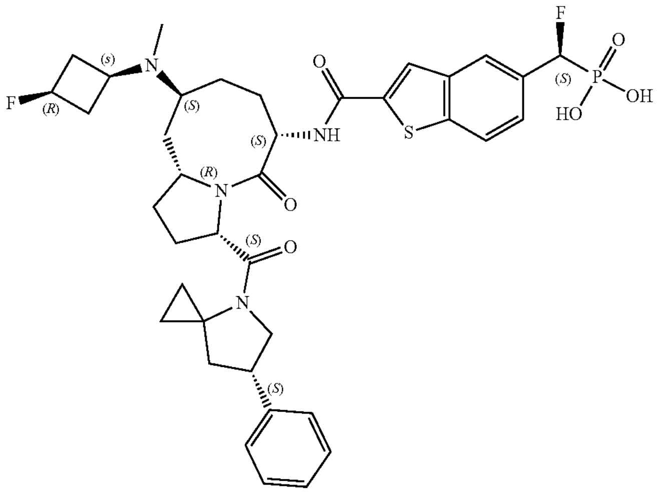 | 1H NMR (400 MHz, MeOD-d4) δ (ppm) 8.04 (s, 2H), 7.86 (d, J = 8.4 Hz, 1H), 7.63 (d, J = 8.6 Hz, 1H), 7.40-7.26 (m, 4H), 7.23-7.16 (m, 1H), 5.64 (dd, J = 45.2, 8.4 Hz, 1H), 4.78-4.71 (m, 2H), 4.64-4.52 (m, 2H), 4.46-4.35 (m, 1H), 4.12-3.88 (m, 2H), 3.65-3.52 (m, 1H), 3.02-2.86 (m, 1H), 2.70-2.57 (m, 1H), 2.55-2.15 (m, 8H), 2.11 (s, 3H), 2.02-1.93 (m, 3H), 1.88-1.79 (m, 2H), 1.78-1.61 (m, 4H), 0.57-0.46 (m, 2H); 762.4 [M + H]+. |
| A41 | 2,2,2-trifluoroacetic acid compound with ((R)-(2-(((3S,6S,9S,10aR)-9-(ethyl((3-methyloxetan-3-yl)methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)phosphonic acid | 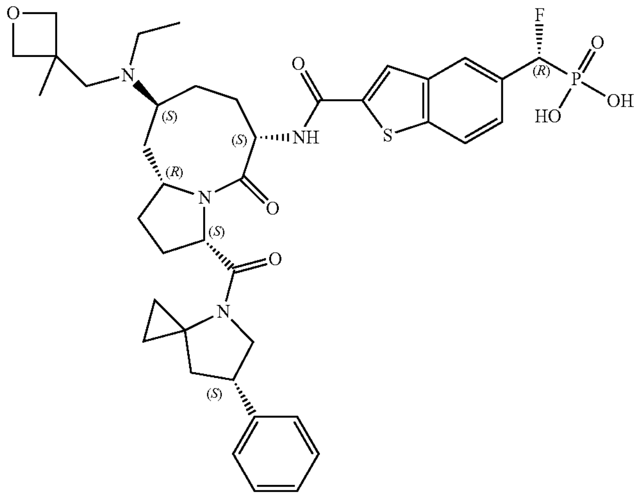 | 1H NMR (400 MHz, DMSO-d6) δ (ppm) 8.86-8.76 (m, 1H), 8.66-8.37 (m, 1H), 8.28-8.21 (m, 1H), 8.06-7.94 (m, 2H), 7.53 (d, J = 8.5 Hz, 1H), 7.39-7.27 (m, 4H), 7.26-7.20 (m, 1H), 5.82 (dd, J = 44.3, 8.0 Hz, 1H), 4.86-4.78 (m, 1H), 4.57-4.34 (m, 4H), 4.30-4.20 (m, 2H), 4.16-4.09 (m, 1H), 3.91-3.79 (m, 1H), 3.78-3.71 (m, 1H), 3.61-3.49 (m, 2H), 3.42-3.33 (m, 1H), 3.25-3.15 (m, 1H), 3.06-2.87 (m, 1H), 2.49-1.55 (m, 14H), 1.51 (s, 3H), 1.31 (t, J = 6.9 Hz, 3H), 0.58-0.45 (m, 2H); 781.4 [M + H]+. |
| A42 | ((R)-(2-(((3S,6S,9S,10aR)-9-(ethyl((1s,3R)-3-(trifluoromethoxy)cyclobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)phosphonic acid | 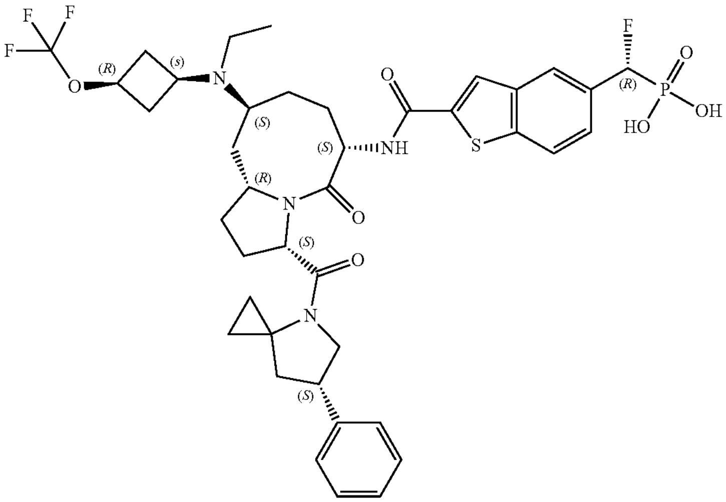 | 1H NMR (400 MHz, MeOD-d4) δ (ppm) 8.05 (d, J = 9.8 Hz, 2H), 7.93 (d, J = 8.5 Hz, 1H), 7.60 (d, J = 8.6 Hz, 1H), 7.38-7.27 (m, 4H), 7.21 (t, J = 7.3 Hz, 1H), 5.79 (dd, J = 44.8, 8.0 Hz, 1H), 4.70-4.47 (m, 4H), 4.11-3.90 (m, 3H), 3.82-3.51 (m, 3H), 3.13 (s, 1H), 2.88-2.81 (m, 1H), 2.70-2.42 (m, 3H), 2.39-2.14 (m, 6H), 2.11-1.84 (m, 8H), 1.38-1.35 (m, 3H), 0.61-0.48 (m, 2H); 835.4 [M + H]+. |

TABLE 1A-continued

| No. | Name | Structure | NMR and LCMS |
|---|---|---|---|
| A43 | ((R)-(2-(((3S,6S,9S,10aR)-9-(ethyl(4,4,4-trifluorobutyl)amino)-5-oxo-3-((S)-6-phenyl-4-azaspiro[2.4]heptane-4-carbonyl)deca-hydropyrrolo[1,2-a]azocin-6-yl)carbamoyl)benzo[b]thiophen-5-yl)fluoromethyl)phosphonic acid | 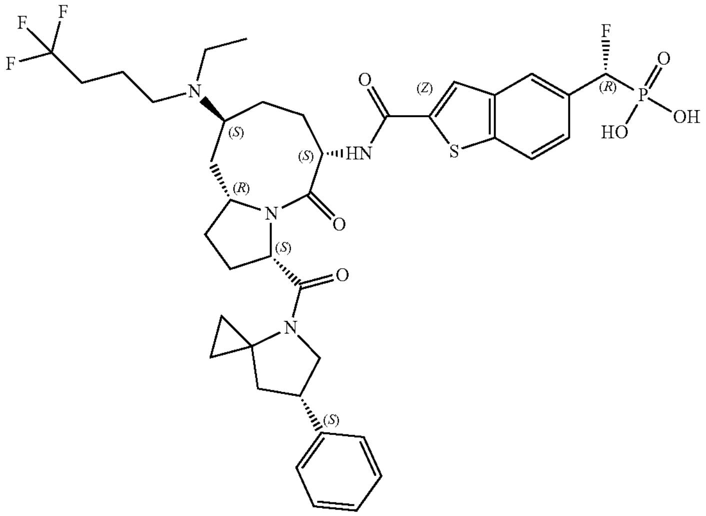 | 1H NMR (400 MHz, DMSO-d6) δ (ppm) 9.03-8.86 (m, 1H), 8.86-8.72 (m, 1H), 8.30-8.16 (m, 1H), 8.07-7.89 (m, 2H), 7.58-7.47 (m, 1H), 7.39-7.27 (m, 4H), 7.26-7.20 (m, 1H), 5.80 (dd, J = 44.4, 8.0 Hz, 1H), 4.94-4.73 (m, 1H), 4.62-4.42 (m, 2H), 4.19-4.04 (m, 1H), 3.90-3.70 (m, 2H), 3.59-3.47 (m, 2H), 3.45-3.17 (m, 3H), 2.48-2.15 (m, 4H), 2.14-1.71 (m, 13H), 1.59-1.44 (m, 1H), 1.36-1.20 (m, 3H), 0.61-0.38 (m, 2H); 807.7 [M + H]$^+$. |
| A44 | ((S)-(2-(((3S,6S,9S,10aR)-9-(ethyl(4,4,4-trifluorobutyl)amino)-5-oxo-3-((S)-6-phenyl-4-azaspiro[2.4]heptane-4-carbonyl)deca-hydropyrrolo[1,2-a]azocin-6-yl)carbamoyl)benzo[b]thiophen-5-yl)fluoromethyl)phosphonic acid | 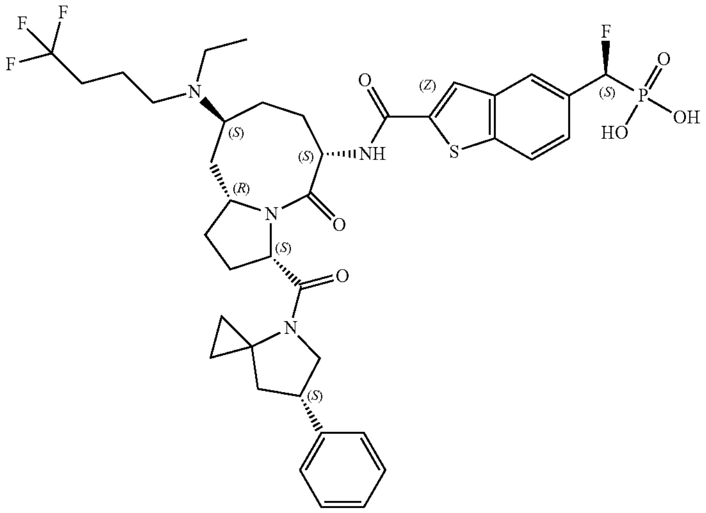 | 1H NMR (400 MHz, DMSO-d6) δ (ppm) 8.97 (s, 1H), 8.86-8.78 (m, 1H), 8.24 (d, J = 4.2 Hz, 1H), 8.03 (d, J = 8.5 Hz, 1H), 7.98 (s, 1H), 7.53 (d, J = 8.6 Hz, 1H), 7.38-7.28 (m, 4H), 7.26-7.19 (m, 1H), 5.83 (dd, J = 44.3, 8.0 Hz, 1H), 4.86-4.78 (m, 1H), 4.59-4.50 (m, 2H), 4.17-4.10 (m, 1H), 3.88-3.72 (m, 2H), 3.56-3.51 (m, 1H), 3.22-3.06 (m, 4H), 2.49-2.30 (m, 3H), 2.26-2.19 (m, 1H), 2.14-1.73 (m, 13H), 1.58-1.48 (m, 1H), 1.34-1.24 (m, 3H), 0.58-0.41 (m, 2H); 807.3 [M + H]$^+$. |
| A45 | ((R)-(2-(((3S,6S,9S,10aR)-9-(ethyl((1s,3R)-3-(trifluoromethyl)cyclobutyl)amino)-5-oxo-3-((S)-6-phenyl-4-azaspiro[2.4]heptane-4-carbonyl)deca-hydropyrrolo[1,2-a]azocin-6-yl)carbamoyl)benzo[b]thiophen-5-yl)fluoromethyl)phosphonic acid | 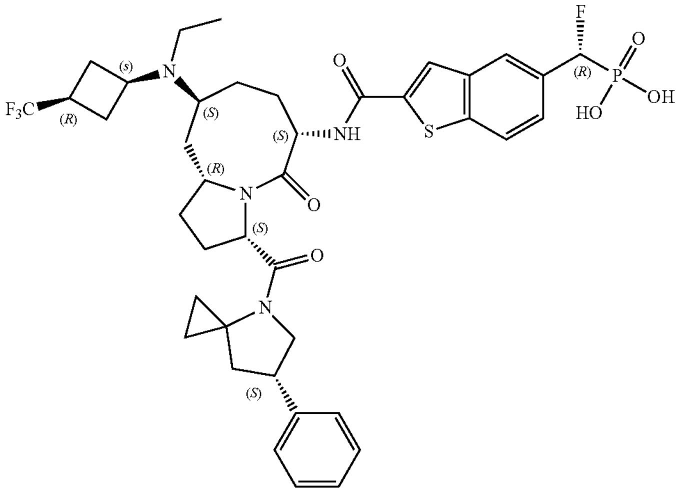 | 1H NMR (400 MHz, DMSO-d6) δ (ppm) 8.86-8.72 (m, 1H), 8.30-8.16 (m, 1H), 8.03-7.92 (m, 2H), 7.57-7.48 (m, 1H), 7.40-7.20 (m, 5H), 5.76 (dd, J = 44.6, 7.7 Hz, 1H), 4.88-4.73 (m, 1H), 4.65-4.43 (m, 2H), 4.21-4.07 (m, 1H), 4.03-3.90 (m, 1H), 3.87-3.68 (m, 3H), 3.60-3.48 (m, 2H), 3.21-3.12 (m, 1H), 2.78-2.60 (m, 1H), 2.50-1.50 (m, 17H), 1.35-1.14 (m, 3H), 0.66-0.34 (m, 2H); 819.4 [M + H]$^+$. |

TABLE 1A-continued

| No. | Name | Structure | NMR and LCMS |
| --- | --- | --- | --- |
| A46 | ((S)-(2-(((3S,6S,9S,10aR)-9-(ethyl((1r,3S)-3-(trifluoromethyl)cyclobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)phosphonic acid | 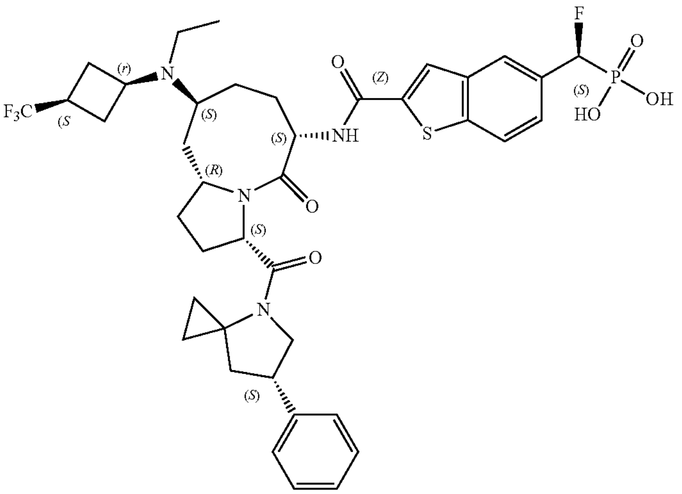 | 1H NMR (400 MHz, DMSO-d6) δ (ppm) 8.89-8.73 (m, 1H), 8.30-8.20 (m, 1H), 8.05-7.93 (m, 2H), 7.56-7.48 (m, 1H), 7.39-7.19 (m, 5H), 5.80 (dd, J = 44.3, 8.0 Hz, 1H), 4.85-4.71 (m, 1H), 4.62-4.44 (m, 2H), 4.20-4.08 (m, 1H), 4.02-3.62 (m, 4H), 3.60-3.49 (m, 1H), 3.24-3.02 (m, 2H), 2.74-2.52 (m, 2H), 2.45-1.51 (m, 16H), 1.31-1.19 (m, 3H), 0.58-0.41 (m, 2H); 819.4 [M + H]+. |
| A47 | ((S)-(2-(((3S,6S,9S,10aR)-9-(ethyl((1s,3R)-3-(trifluoromethoxy)cyclobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)phosphonic acid | 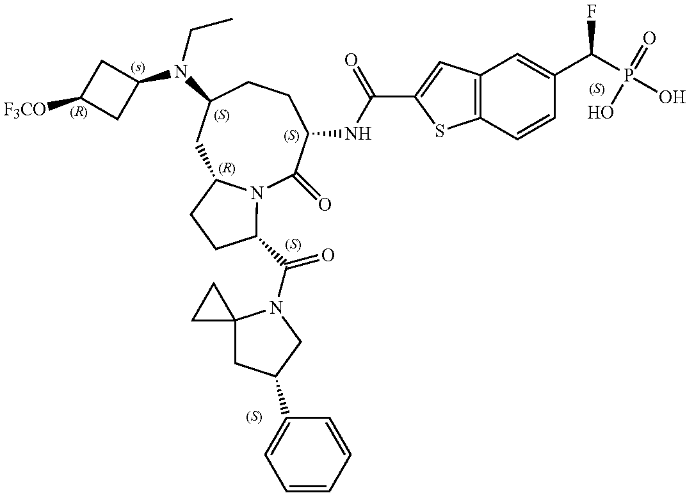 | 1H NMR (400 MHz, MeOD-d4) δ (ppm) 8.19-8.02 (m, 2H), 7.95 (d, J = 8.5 Hz, 1H), 7.62 (d, J = 8.4 Hz, 1H), 7.45-7.36 (m, 2H), 7.36-7.28 (m, 2H), 7.28-7.19 (m, 1H), 5.80 (dd, J = 44.6, 8.0 Hz, 1H), 4.86-4.77 (m, 2H), 4.75-4.48 (m, 3H), 4.19-3.88 (m, 3H), 3.84-3.53 (m, 2H), 3.29-3.09 (m, 2H), 3.06-2.93 (m, 1H), 2.92-2.79 (m, 1H), 2.72-2.58 (m, 1H), 2.57-2.47 (m, 1H), 2.42-2.16 (m, 5H), 2.15-1.90 (m, 6H), 1.89-1.71 (m, 1H), 1.69-1.58 (m, 1H), 1.51-1.34 (m, 3H), 0.71-0.41 (m, 2H); 8.35.3 [M + H]+. |

TABLE 1A-continued

| No. | Name | Structure | NMR and LCMS |
|---|---|---|---|
| A48 | ((R)-fluoro(2-(((3S,6S,9S,10aR)-9-(methyl(((1s,3R)-3-(trifluoromethyl)cyclobutyl)methyl)amino)-5-oxo-3-((S)-6-phenyl-4-azaspiro[2.4]heptane-4-carbonyl)deca-hydropyrrolo[1,2-a]azocin-6-yl)carbamoyl)benzo[b]thiophen-5-yl)methyl)phosphonic acid | 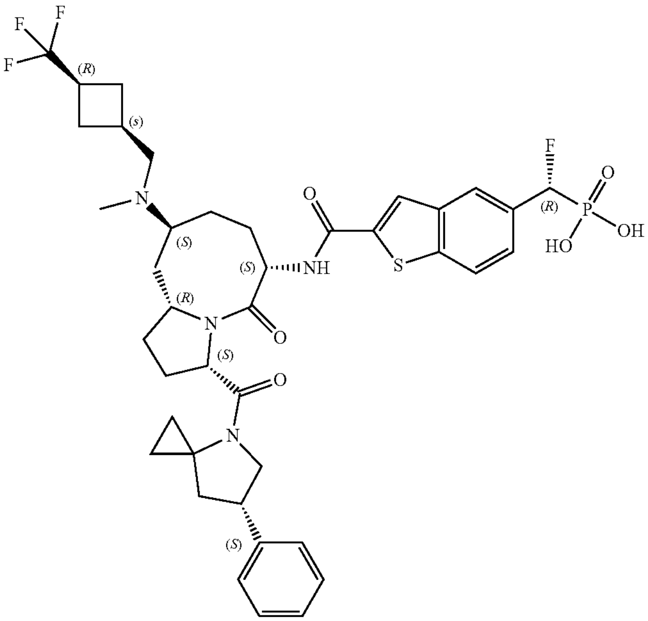 | 1H NMR (400 MHz, DMSO-d6) δ (ppm) 8.77 (dd, J = 32.3, 7.1 Hz, 1H), 8.31-8.19 (m, 1H), 8.03 (d, J = 8.4 Hz, 1H), 7.98 (s, 1H), 7.53 (d, J = 8.6 Hz, 1H), 7.42-7.17 (m, 5H), 5.83 (dd, J = 44.4, 8.1 Hz, 1H), 4.86-4.73 (m, 1H), 4.60-4.46 (m, 2H), 4.13 (t, J = 8.3 Hz, 1H), 3.79-3.69 (m, 2H), 3.58-3.52 (m, 1H), 3.27-2.95 (m, 4H), 2.84-2.57 (m, 4H), 2.42-1.64 (m, 16H), 1.63-1.51 (m, 1H), 0.54 (s, 2H); 819.5 $[M + H]^+$. |
| A49 | ((R)-fluoro(2-(((3S,6S,9S,10aR)-9-(methyl(((1s,3R)-3-(trifluoromethyl)cyclobutyl)methyl)amino)-5-oxo-3-((S)-6-phenyl-4-azaspiro[2.4]heptane-4-carbonyl)deca-hydropyrrolo[1,2-a]azocin-6-yl)carbamoyl)benzo[b]thiophen-5-yl)methyl)phosphonic acid | 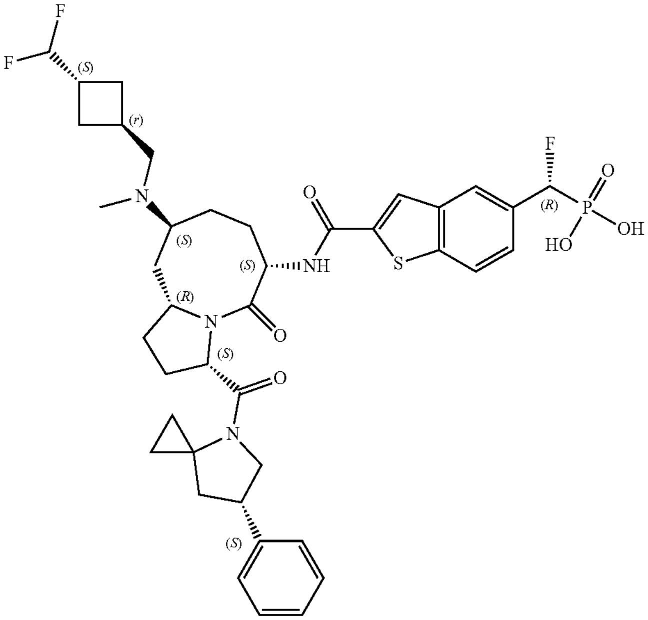 | 1H NMR (400 MHz, MeOD-d4) δ (ppm) 8.13-8.09 (m, 1H), 8.08-7.96 (m, 2H), 7.96-7.92 (m, 1H), 7.63-7.26 (m, 4H), 7.37-7.56 (m, 1H), 7.23-7.17 (m, 1H), 6.15-5.95 (m, 1H), 5.93-5.79 (m, 1H), 4.89-4.79 (m, 1H), 4.74-4.51 (m, 2H), 4.12-3.87 (m, 3H), 3.68-3.36 (m, 2H), 3.27-3.18 (m, 1H), 2.92-2.69 (m, 5H), 2.57-2.44 (m, 1H), 2.38-1.91 (m, 15H), 1.72-1.57 (m, 1H), 0.63-0.47 (m, 2H); 801.5 $[M + H]^+$. |

TABLE 1A-continued

| No. | Name | Structure | NMR and LCMS |
|---|---|---|---|
| A50 | ((R)-fluoro(2-(((3S,6S,9S,10aR)-9-(methyl(2-(1-(trifluoromethyl)cyclopropyl)ethyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)phosphonic acid | 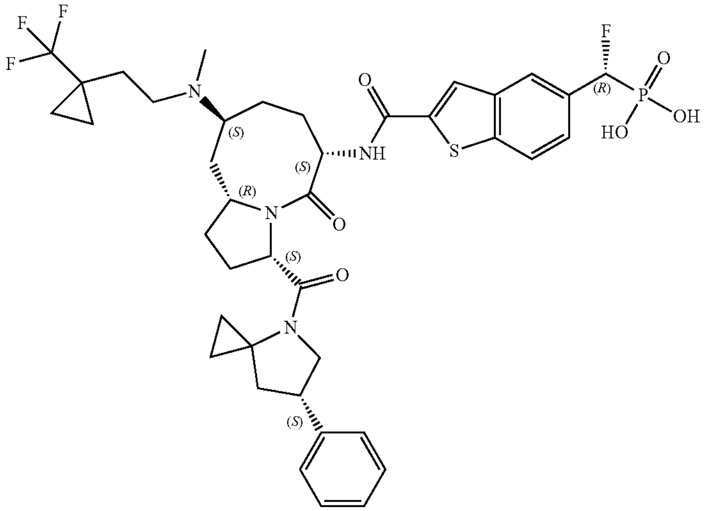 | 1H NMR (400 MHz, MeOD-d4) δ (ppm) 8.11-8.07 (m, 1H), 8.05 (s, 1H), 7.99-7.92 (m, 1H), 7.63 (d, J = 8.1 Hz, 1H), 7.40-7.27 (m, 4H), 7.26-7.20 (m, 1H), 5.81 (dd, J = 44.6, 7.7 Hz, 1H), 4.82-4.70 (m, 1H), 4.70-4.59 (m, 1H), 4.58-4.44 (m, 1H), 4.13-3.86 (m, 3H), 3.67-3.35 (m, 2H), 3.30-3.17 (m, 1H), 2.90-2.69 (m, 3H), 2.57-2.44 (m, 1H), 2.39-2.27 (m, 1H), 2.26-1.76 (m, 13H), 1.71-1.62 (m, 1H), 1.14-1.02 (m, 2H), 0.93-0.82 (m, 2H), 0.62-0.47 (m, 2H); 819.3 [M + H]+. |
| A51 | ((R)-fluoro(2-(((3S,6S,9S,10aR)-9-(methyl((1s,3R)-3-(trifluoromethoxy)cyclobutyl)amino)-5-oxo-3-(4-azaspiro[2.4]heptane-4-carbonyl)decahydropyrrolo[1,2-a]azocin-6-yl)carbamoyl)benzo[b]thiophen-5-yl)methyl)phosphonic acid | 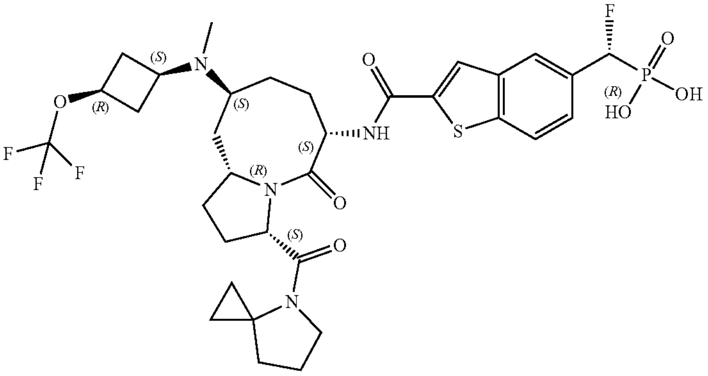 | 1H NMR (400 MHz, MeOD-d4) δ (ppm) 8.13-7.97 (m, 2H), 7.96-7.78 (m, 1H), 7.68-7.50 (m, 1H), 5.66 (dd, J = 45.2, 8.4 Hz, 1H), 4.71-4.59 (m, 2H), 4.58-4.48 (m, 1H), 4.48-4.33 (m, 1H), 3.98-3.84 (m, 1H), 3.83-3.67 (m, 1H), 3.66-3.56 (m, 1H), 3.52-3.36 (m, 1H), 3.01-2.88 (m, 1H), 2.84-2.70 (m, 1H), 2.68-2.37 (m, 6H), 2.29-2.08 (m, 1H), 2.05-1.66 (m, 14H), 0.64-0.28 (m, 2H); 745.5 [M + H]+. |
| A52 | ((R)-fluoro(2-(((3S,6S,9S,10aR)-9-(methyl(3-(trifluoromethoxy)propyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)phosphonic acid | 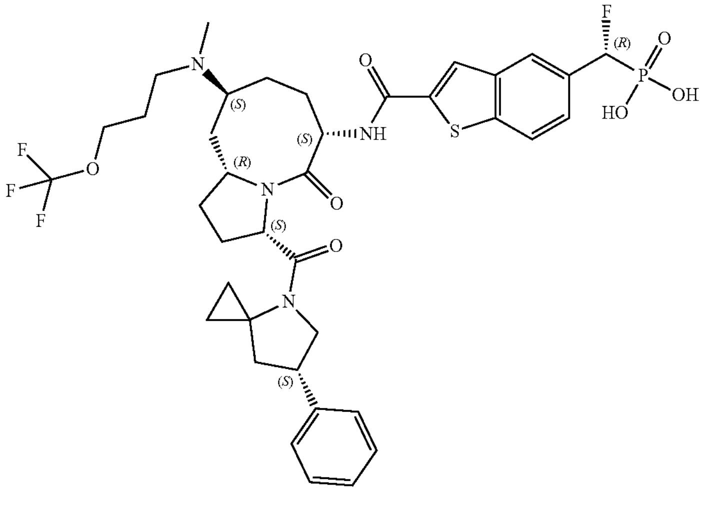 | 1H NMR (400 MHz, DMSO-d6) δ (ppm) 10.87-9.92 (m, 1H), 8.73 (s, 1H), 8.23 (s, 1H), 8.09-7.72 (m, 2H), 7.63-7.41 (m, 1H), 7.39-7.10 (m, 5H), 5.63 (dd, J = 45.1, 7.8 Hz, 1H), 4.82-4.60 (m, 1H), 4.56-4.35 (m, 2H), 4.20-4.01 (m, 3H), 3.79-3.60 (m, 2H), 3.55-3.47 (m, 1H), 3.22-2.95 (m, 2H), 2.84-2.53 (m, 3H), 2.45-2.37 (m, 1H), 2.24-1.63 (m, 14H), 1.58-1.49 (m, 1H), 0.57-0.29 (m, 2H); 809.5 [M + H]+. |

TABLE 1A-continued

| No. | Name | Structure | NMR and LCMS |
| --- | --- | --- | --- |
| A53 | ((R)-fluoro(2-(((3S,6S,9S,10aR)-9-(methyl((S)-4,4,4-trifluoro-3-methoxybutyl)amino)-5-oxo-3-((S)-6-phenyl-4-azaspiro[2.4]heptane-4-carbonyl)deca-hydropyrrolo[1,2-a]azocin-6-yl)carbamoyl)benzo[b]thiophen-5-yl)methyl)phosphonic acid | 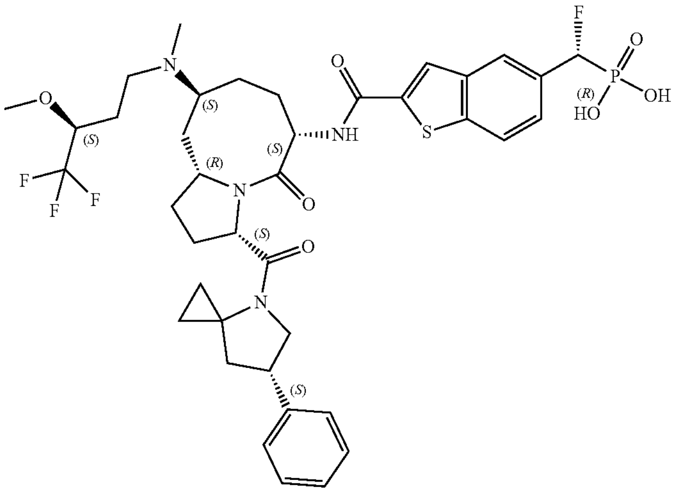 | 1H NMR (400 MHz, MeOD-d4) δ (ppm) 8.03-7.89 (m, 2H), 7.86-7.75 (m, 1H), 7.51 (d, J = 8.4 Hz, 1H), 7.32-7.01 (m, 5H), 5.69 (dd, J = 44.7, 8.0 Hz, 1H), 4.71-4.62 (m, 1H), 4.59-4.48 (m, 1H), 4.46-4.34 (m, 1H), 4.01-3.67 (m, 4H), 3.56-3.25 (m, 5H), 3.10-2.83 (m, 1H), 2.80-2.60 (m, 3H), 2.46-2.32 (m, 1H), 2.26-1.72 (m, 14H), 1.62-1.46 (m, 1H), 0.54-0.23 (m, 2H); 823.4 [M + H]+. |
| A54 | ((R)-fluoro(2-(((3S,6S,9S,10aR)-9-morpholino-5-oxo-3-((S)-6-phenyl-4-azaspiro[2.4]heptane-4-carbonyl)deca-hydropyrrolo[1,2-a]azocin-6-yl)carbamoyl)benzo[b]thiophen-5-yl)methyl)phosphonic acid | 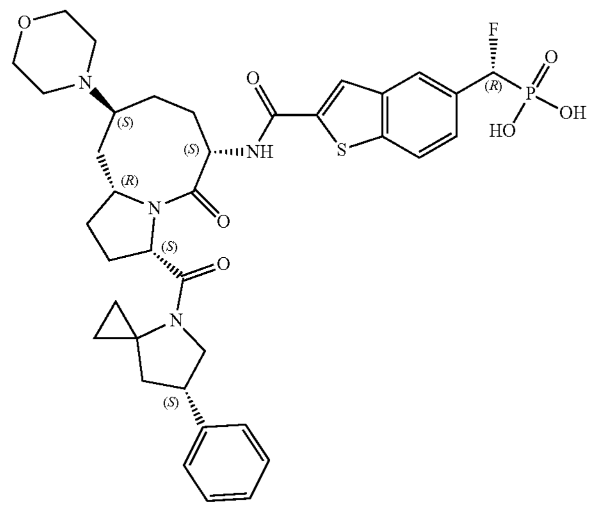 | 1H NMR (400 MHz, DMSO-d6) δ (ppm) 8.82-8.70 (m, 1H), 8.25-8.20 (m, 1H), 8.06-7.91 (m, 2H), 7.56-7.49 (m, 1H), 7.38-7.26 (m, 4H), 7.26-7.19 (m, 1H), 5.77 (dd, J = 44.5, 8.1 Hz, 1H), 4.82-4.71 (m, 1H), 4.57-4.41 (m, 2H), 4.16-4.09 (m, 1H), 4.04-3.87 (m, 2H), 3.74-3.48 (m, 5H), 3.23-3.06 (m, 4H), 2.35-1.95 (m, 8H), 1.93-1.48 (m, 6H), 0.58-0.40 (m, 2H); 739.4 [M + H]+. |
| A55 | ((R)-(2-(((3S,6S,9S,10aR)-9-(((R)-3,3-difluoro-cyclopentyl)(methyl)amino)-5-oxo-3-((S)-6-phenyl-4-azaspiro[2.4]heptane-4-carbonyl)deca-hydropyrrolo[1,2-a]azocin-6-yl)carbamoyl)benzo[b]thiophen-5-yl)fluoromethyl)phosphonic acid | 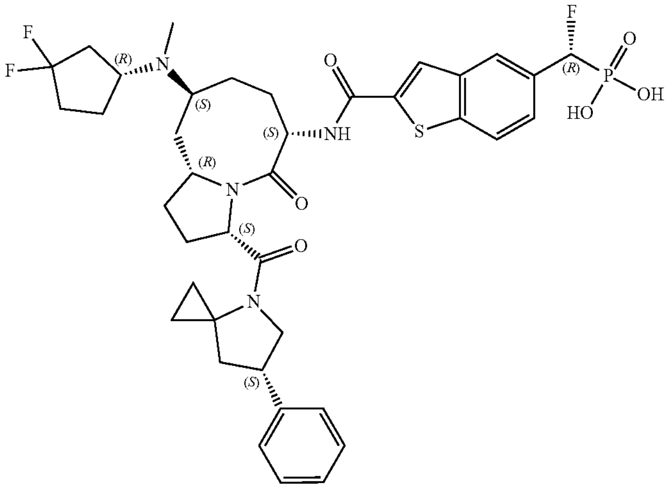 | 1H NMR (400 MHz, DMSO-d6) δ (ppm) 8.86-8.64 (m, 1H), 8.23 (s, 1H), 8.04-7.92 (m, 2H), 7.53 (d, J = 8.4 Hz, 1H), 7.37-7.28 (m, 4H), 7.25-7.18 (m, 1H), 5.72 (dd, J = 44.7, 7.5 Hz, 1H), 4.87-4.71 (m, 1H), 4.60-4.46 (m, 2H), 4.18-4.01 (m, 2H), 3.84-3.71 (m, 2H), 3.58-3.50 (m, 1H), 2.65 (s, 3H), 2.48-2.20 (m, 5H), 2.15-1.62 (m, 14H), 1.57-1.48 (m, 1H), 0.59-0.44 (m, 2H); 787.3 [M + H]+. |

TABLE 1A-continued

| No. | Name | Structure | NMR and LCMS |
|---|---|---|---|
| A56 | ((R)-fluoro(2-(((3S,6S,9S,10aR)-9-(methyl((3-methyl-oxetan-3-yl)methyl)amino)-5-oxo-3-((S)-6-phenyl-4-azaspiro[2.4]heptane-4-carbonyl)deca-hydropyrrolo[1,2-a]azocin-6-yl)carbamoyl)benzo[b]thiophen-5-yl)methyl)phosphonic acid | 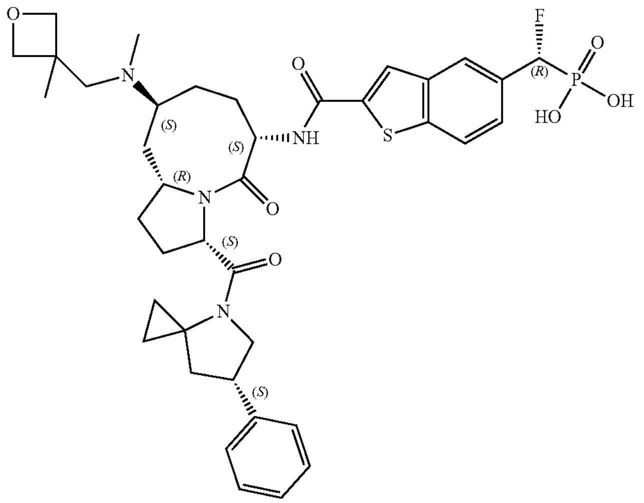 | 1H NMR (400 MHz, MeOD-d4) δ (ppm) 8.09-7.99 (m, 2H), 7.88 (d, J = 8.5 Hz, 1H), 7.65 (d, J = 8.5 Hz, 1H), 7.36-7.26 (m, 4H), 7.23-7.18 (m, 1H), 5.64 (dd, J = 45.3, 8.3 Hz, 1H), 4.75-4.67 (m, 1H), 4.63-4.54 (m, 3H), 4.44-4.30 (m, 3H), 4.06-3.87 (m, 2H), 3.61-3.46 (m, 2H), 3.26-3.07 (m, 2H), 2.55 (s, 3H), 2.48-2.39 (m, 1H), 2.30 (t, J = 11.4 Hz, 1H), 2.22-1.92 (m, 7H), 1.92-1.75 (m, 4H), 1.66-1.59 (m, 1H), 1.52 (s, 3H), 0.57-0.44 (m, 2H); 767.4 [M + H]$^+$. |
| A57 | ((S)-fluoro(2-(((3S,6S,9S,10aR)-9-(methyl((1R,3S)-3-(trifluoro-methoxy)cyclo-pentyl)amino)-5-oxo-3-((S)-6-phenyl-4-azaspiro[2.4]heptane-4-carbonyl)deca-hydropyrrolo[1,2-a]azocin-6-yl)carbamoyl)benzo[b]thiophen-5-yl)methyl)phosphonic acid | 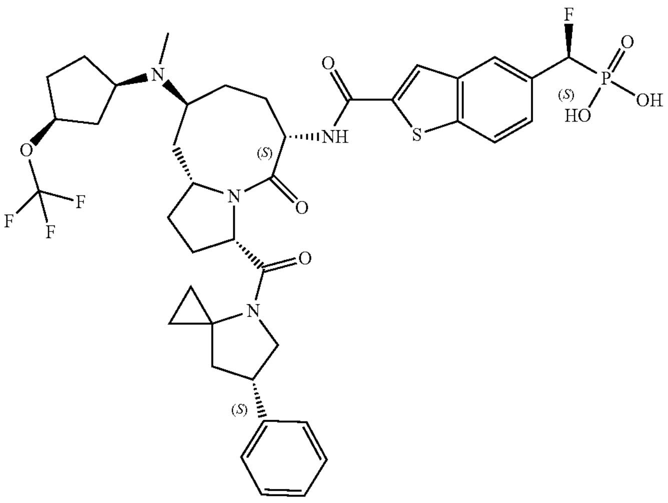 | 1H NMR (400 MHz, MeOD-d4) δ (ppm) 8.11-8.04 (m, 2H), 7.95 (d, J = 8.5 Hz, 1H), 7.62 (d, J = 8.3 Hz, 1H), 7.41-7.19 (m, 5H), 5.79 (dd, J = 44.7, 8.2 Hz, 1H), 4.80-4.42 (m, 3H), 4.26-3.51 (m, 5H), 2.83-1.61 (m, 24H), 0.61-0.48 (m, 2H); 835.2 [M + H]$^+$. |
| A58 | (difluoro(2-(((3S,6S,9S,10aR)-9-(methyl((1s,3R)-3-(trifluoro-methoxy)cyclo-butyl)amino)-5-oxo-3-((S)-6-phenyl-4-azaspiro[2.4]heptane-4-carbonyl)deca-hydropyrrolo[1,2-a]azocin-6-yl)carbamoyl)benzo[b]thiophen-5-yl)methyl)phosphonic acid | 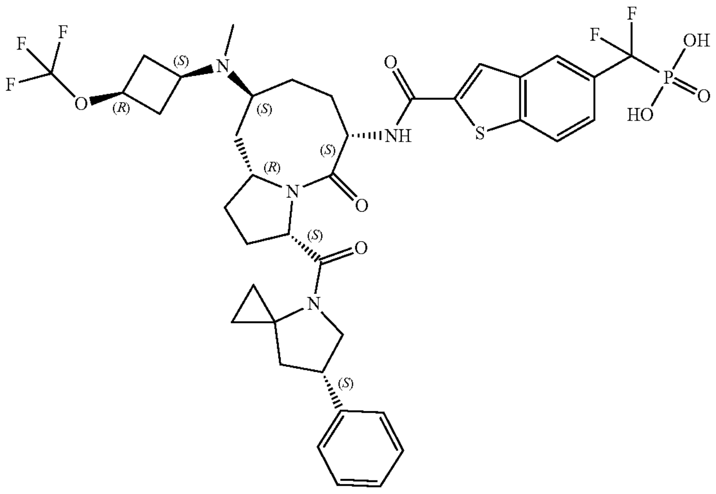 | 1H NMR (400 MHz, DMSO-d6) δ (ppm) 8.86 (s, 1H), 8.45-8.26 (m, 1H), 8.21-8.07 (m, 1H), 8.01 (d, J = 8.5 Hz, 1H), 7.71-7.56 (m, 1H), 7.37-7.13 (m, 5H), 4.71-4.26 (m, 4H), 4.10-4.00 (m, 1H), 3.73-3.67 (m, 1H), 3.52-3.43 (m, 2H), 3.42-3.27 (m, 2H), 3.10-2.92 (m, 1H), 2.83-2.56 (m, 3H), 2.43-2.29 (m, 3H), 2.22-2.14 (m, 1H), 2.07-1.31 (m, 12H), 0.60-0.32 (m, 2H), 839.5 [M + H]$^+$. |

TABLE 1A-continued

| No. | Name | Structure | NMR and LCMS |
|---|---|---|---|
| A59 | ((R)-fluoro(2-(((3S,6S,9S,10aR)-9-(methyl((1s,3R)-3-(trifluoro-methoxy)cyclo-butyl)amino)-5-oxo-3-((R)-6-(pyridin-3-yl)-4-azaspiro[2.4]heptane-4-carbonyl)deca-hydropyrrolo[1,2-a]azocin-6-yl)carbamoyl)benzo[b]thiophen-5-yl)methyl)phosphonic acid | 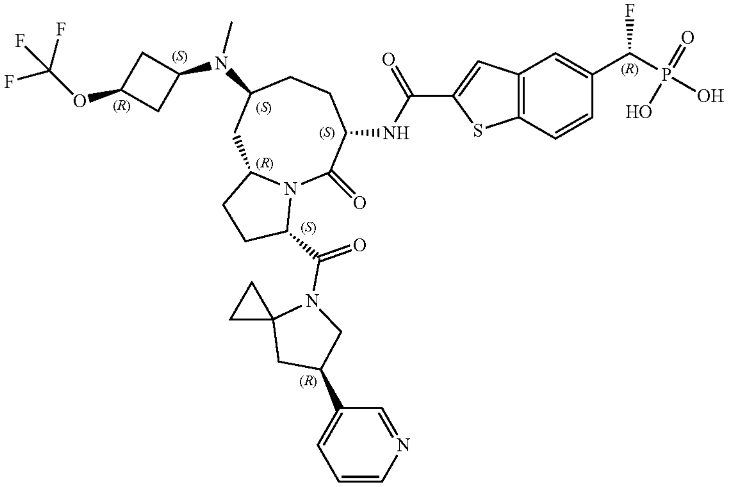 | 1H NMR (400 MHz, DMSO-d6) δ (ppm) 10.20-9.46 (m, 1H), 8.91-8.48 (m, 3H), 8.24 (s, 1H), 8.05-7.92 (m, 3H), 7.54 (d, J = 8.6 Hz, 2H), 5.83 (dd, J = 44.3, 8.0 Hz, 1H), 4.85-4.77 (m, 1H), 4.70-4.65 (m, 1H), 4.61-4.53 (m, 2H), 4.20-4.16 (m, 2H), 3.84-3.82 (m, 2H), 2.86-2.56 (m, 6H), 2.49-2.40 (m, 2H), 2.28-1.56 (m, 14H), 0.62-0.42 (m, 2H); 822.3 $[M + H]^+$. |
| A60 | ((R)-fluoro(2-(((3S,6S,9S,10aR)-9-(methyl((1s,3R)-3-(trifluoro-methoxy)cyclo-butyl)amino)-5-oxo-3-((S)-6-(pyridin-3-yl)-4-azaspiro[2.4]heptane-4-carbonyl)deca-hydropyrrolo[1,2-a]azocin-6-yl)carbamoyl)benzo[b]thiophen-5-yl)methyl)phosphonic acid | 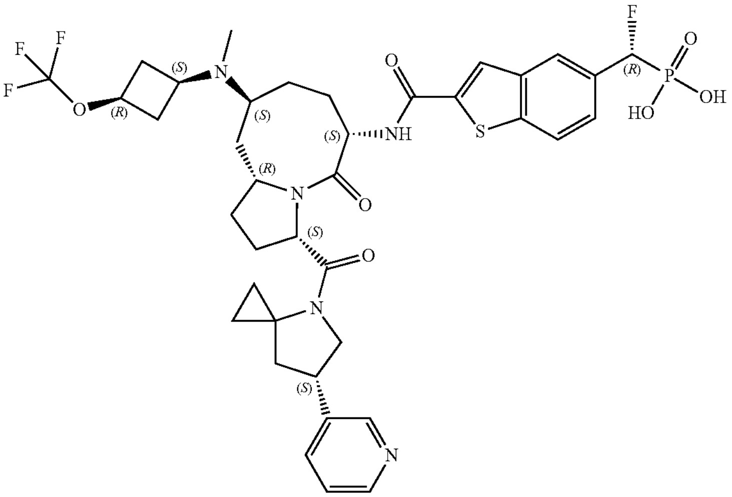 | 1H NMR (400 MHz, DMSO-d6) δ (ppm) 9.86-9.43 (m, 1H), 8.92-8.71 (m, 1H), 8.65 (s, 1H), 8.57-8.48 (m, 1H), 8.28-8.20 (m, 1H), 8.07-7.90 (m, 1H), 7.57-7.44 (m, 2H), 5.84 (dd, J = 44.3, 8.1 Hz, 1H), 4.86-4.75 (m, 1H), 4.70-4.36 (m, 5H), 3.68-3.67 (m, 2H), 2.83-2.74 (m, 1H), 2.70-2.54 (m, 5H), 2.46-2.27 (m, 3H), 2.16-1.51 (m, 13H), 0.59-0.44 (m, 2H); 822.4 $[M + H]^+$. |

TABLE 1A-continued

| No. | Name | Structure | NMR and LCMS |
|---|---|---|---|
| A61 | ((R)-fluoro(2-(((3S,6S,9S,10aR)-3-((6S,7S)-7-methoxy-6-phenyl-4-azaspiro[2.4]heptane-4-carbonyl)-9-(methyl((1s,3R)-3-(trifluoro-methoxy)cyclo-butyl)amino)-5-oxodecahydro-pyrrolo[1,2-a]azocin-6-yl)carbamoyl)benzo[b]thiophen-5-yl)methyl)phosphonic acid | 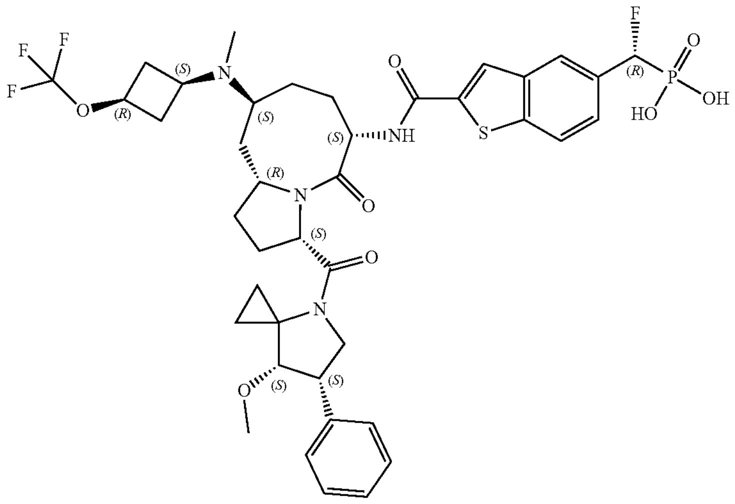 | 1H NMR (400 MHz, MeOD-d4) δ (ppm) 8.13-8.02 (m, 2H), 7.96-7.88 (m, 1H), 7.71-7.60 (m, 1H), 7.45-7.25 (m, 5H), 5.72 (dd, J = 44.8, 7.7 Hz, 1H), 4.81-4.36 (m, 5H), 4.05-3.95 (m, 1H), 3.78-3.58 (m, 2H), 3.51-3.39 (m, 1H), 3.08 (s, 3H), 2.89-2.79 (m, 1H), 2.73-2.63 (m, 3H), 2.57-2.44 (m, 2H), 2.32-2.16 (m, 3H), 2.08-1.98 (m, 3H), 1.94-1.89 (m, 1H), 1.61-1.52 (m, 1H), 1.41-1.27 (m, 5H), 0.97-0.85 (m, 2H), 0.75-0.63 (m, 1H); 851.4 [M + H]$^+$. |
| | | Absolute stereochemistry of cis-3-OMe-4-Ph pyrrolidine arbitrarily assigned | |
| A62 | ((R)-fluoro(2-(((3S,6S,9S,10aR)-3-((6R,7R)-7-methoxy-6-phenyl-4-azaspiro[2.4]heptane-4-carbonyl)-9-(methyl((1s,3R)-3-(trifluoro-methoxy)cyclo-butyl)amino)-5-oxodecahydro-pyrrolo[1,2-a]azocin-6-yl)carbamoyl)benzo[b]thiophen-5-yl)methyl)phosphonic acid | 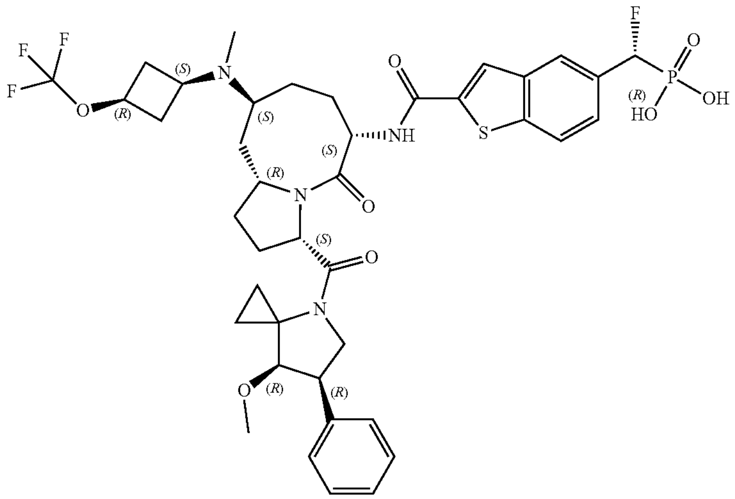 | 1H NMR (400 MHz, DMSO-d6) δ (ppm) 9.68-8.64 (m, 1H), 8.25 (s, 1H), 8.05-7.89 (m, 2H), 7.60-7.46 (m, 1H), 7.42-7.17 (m, 5H), 5.87-5.54 (m, 1H), 4.85-4.44 (m, 4H), 4.17-3.98 (m, 3H), 3.68-3.65 (m, 2H), 3.02 (s, 3H), 2.75-2.52 (m, 5H), 2.47-2.31 (m, 2H), 2.22-1.22 (m, 13H), 0.88-0.58 (m, 2H); 851.1 [M + H]$^+$. |
| | | Absolute stereochemistry of cis-3-OMe-4-Ph pyrrolidine arbitrarily assigned | |
| A63 | ((R)-fluoro(2-(((3S,6S,9S,10aR)-9-(methyl((S)-3,3,3-trifluoro-2-methoxypropyl)amino)-5-oxo-3-((S)-6-phenyl-4-azaspiro[2.4]heptane-4-carbonyl)deca-hydropyrrolo[1,2-a]azocin-6-yl)carbamoyl)benzo[b]thiophen-5-yl)methyl)phosphonic acid | 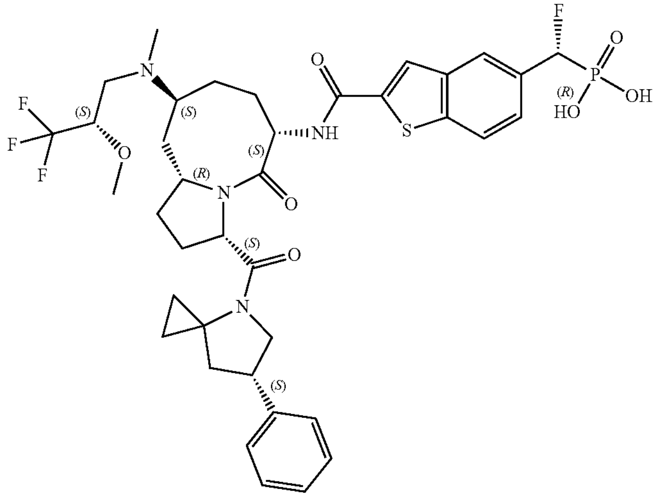 | 1H NMR (400 MHz, MeOD-d4) δ (ppm) 8.10-8.06 (m, 1H), 8.05 (s, 1H), 7.95 (d, J = 8.5 Hz, 1H), 7.65 (d, J = 8.5 Hz, 1H), 7.37 (d, J = 7.3 Hz, 2H), 7.32 (t, J = 7.6 Hz, 2H), 7.23 (t, J = 7.2 Hz, 1H), 5.78 (dd, J = 44.8, 8.1 Hz, 1H), 5.25-4.91 (m, 1H), 4.78 (d, J = 10.8 Hz, 1H), 4.70-4.63 (m, 1H), 4.59-4.49 (m, 1H), 4.12-3.85 (m, 3H), 3.74 (s, 3H), 3.65-3.52 (m, 1H), 3.38 (s, 1H), 2.92 (s, 3H), 2.58-2.44 (m, 1H), 2.34 (t, J = 11.5 Hz, 1H), 2.27-1.80 (m, 12H), 1.74-1.61 (m, 1H), 0.64-0.45 (m, 2H); 809.2 |

TABLE 1A-continued

| No. | Name | Structure | NMR and LCMS |
| --- | --- | --- | --- |
| | | | [M + H]+. |
| A64 | ((R)-fluoro(2-(((3S,6S,9S,10aR)-9-(methyl(2-(trifluoro-methoxy)ethyl)amino)-5-oxo-3-((S)-6-phenyl-4-azaspiro[2.4]heptane-4-carbonyl)deca-hydropyrrolo[1,2-a]azocin-6-yl)carbamoyl)benzo[b]thiophen-5-yl)methyl)phosphonic acid | 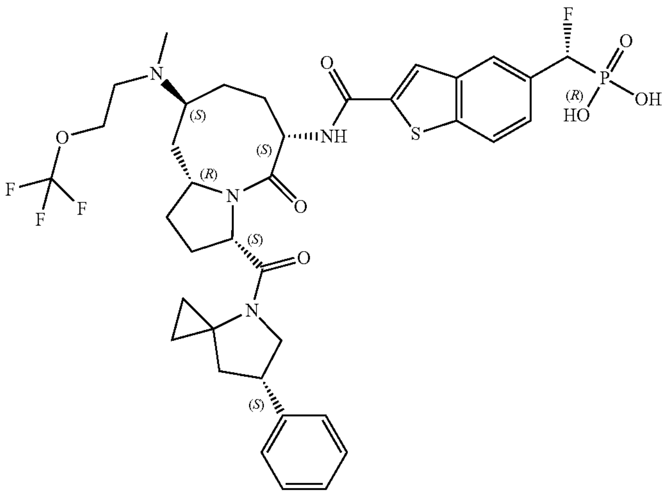 | 1H NMR (400 MHz, DMSO-d6) δ (ppm) 8.84-8.60 (m, 1H), 8.34-8.11 (m, 1H), 8.05-7.86 (m, 2H), 7.59-7.45 (m, 1H), 7.37-7.19 (m, 5H), 5.70 (dd, J = 44.6, 7.8 Hz, 1H), 4.83-4.67 (m, 1H), 4.58-4.34 (m, 4H), 4.15-4.08 (m, 1H), 3.76-3.70 (m, 1H), 3.57-3.49 (m, 2H), 3.18-3.03 (m, 1H). 2.81-2.55 (m, 3H), 2.45-2.35 (m, 1H), 2.26-2.18 (m, 1H), 2.12-1.68 (m, 12H), 1.60-1.54 (m, 1H), 0.55-0.41 (m, 2H); 795.3 [M + H]+. |
| A65 | ((S)-fluoro(2-(((3S,6S,9S,10aR)-9-(methyl((1s,3R)-3-(trifluoromethyl)cyclobutyl)amino)-5-oxo-3-((S)-6-phenyl-4-azaspiro[2.4]heptane-4-carbonyl)deca-hydropyrrolo[1,2-a]azocin-6-yl)carbamoyl)benzo[b]thiophen-5-yl)methyl)phosphonic acid | 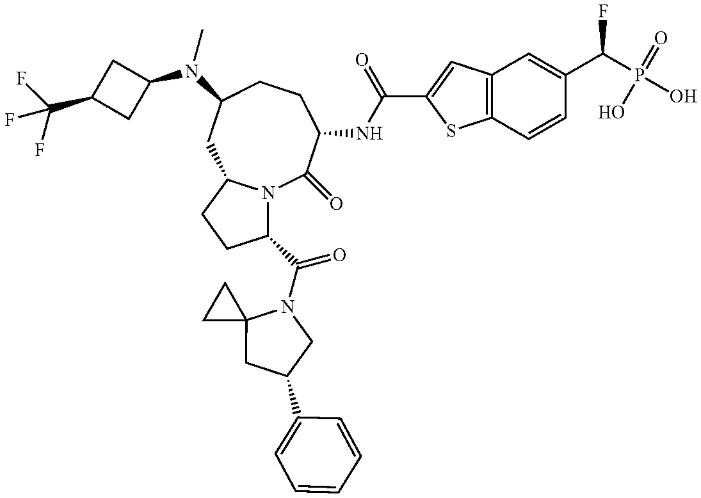 [SMILES: CN([C@H]1CC[C@H](NC(=O)c2cc3cc([C@@H](F)P(=O)(O)O)ccc3s2)C(=O)N2[C@H](CC[C@H]2C(=O)N2C[C@H](c3ccccc3)CC23CC3)C1)[C@H]1C[C@@H](C(F)(F)F)C1] | 1H NMR (400 MHz, $CD_3OD$-d4) δ (ppm) 8.08 (d, J = 8.7 Hz, 2H), 7.89 (d, J = 8.4 Hz, 1H), 7.61 (d, J = 8.4 Hz, 1H), 7.36-7.15 (m, 5H), 5.79-5.50 (m, 1H), 4.71-4.50 (m, 2H), 4.48-4.31 (m, 1H), 4.10-3.65 (m, 4H), 3.57-3.46 (m, 1H), 2.99-2.50 (m, 6H), 2.45-1.55 (m, 16H), 0.60-0.35 (m, 2H); 805 [M + H]+. |

TABLE 1B

| No. | Name | Structure | NMR and LCMS |
| --- | --- | --- | --- |
| B1 | (((S)-fluoro(2-(((3S,6S,9S,10aR)-9-(((1s,3R)-3-fluorocyclobutyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(hydroxy)phosphoryl)-L-alanine | 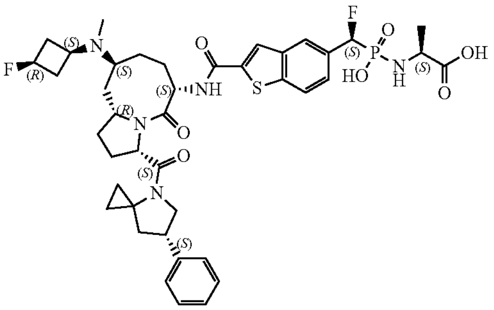 | 1H NMR (400 MHz, MeOD-d4) δ (ppm) 8.05 (s, 2H), 7.86 (d, J = 8.4 Hz, 1H), 7.60 (d, J = 8.5 Hz, 1H), 7.36 - 7.26 (m, 4H), 7.20 (t, J = 7.0 Hz, 1H), 7.17 - 6.74 (m, 1H), 5.66 (dd, J = 45.3, 7.0 Hz, 1H), 4.79 - 4.55 (m, 3H), 4.48 - 4.39 (m, 1H), 4.00 (t, J = 8.7 Hz, 1H), 3.94 - 3.75 (m, 3H), 3.59 - 3.48 (m, 1H), 3.39 - 3.32 (m, 1H), 3.01 - 2.90 (m, 1H), 2.80 - 2.70 (m, 1H), 2.69 - 2.57 (m, 1H), 2.55 (s, 3H), 2.50 - 2.37 (m, 2H), 2.31 (t, J = 11.5 Hz, 1H), 2.22 - 2.11 (m, 2H), 2.06 (d, J = 12.0 Hz, 1H), 2.01 - 1.69 (m, 8H), 1.64 - 1.56 (m, 1H), 1.32 (d, J = 7.0 Hz, 3H), 0.57 - 0.43 (m, 2H); 826.5 $[M + H]^+$. |
| B2 | (((R)-fluoro(2-(((3S,6S,9S,10aR)-9-(methyl((1s,3R)-3-(trifluoromethoxy)cyclobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(hydroxy)phosphoryl)-L-alanine | 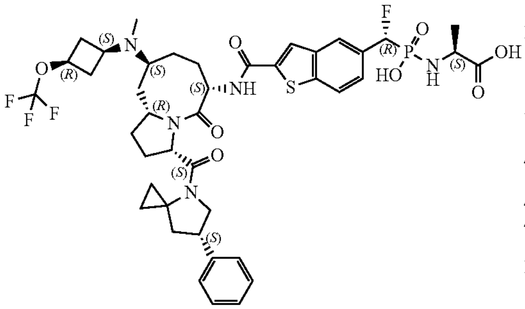 | 1H NMR (400 MHz, MeOD-d4) δ (ppm) 8.03 (d, J = 16.1 Hz, 2H), 7.82 (d, J = 8.5 Hz, 1H), 7.63 (d, J = 8.5 Hz, 1H), 7.37 - 7.26 (m, 4H), 7.22 - 7.15 (m, 1H), 5.61 (dd, J = 45.3, 7.2 Hz, 1H), 4.75 (d, J = 10.3 Hz, 1H), 4.59 (t, J = 8.7 Hz, 1H), 4.50 - 4.43 (m, 1H), 4.41 - 4.34 (m, 1H), 4.04 (t, J = 8.7 Hz, 1H), 3.91 (t, J = 9.8 Hz, 1H), 3.74 - 3.64 (m, 1H), 3.60 - 3.50 (m, 1H), 3.29 - 3.22 (m, 1H), 2.87 - 2.76 (m, 1H), 2.74 - 2.64 (m, 1H), 2.60 - 2.50 (m, 1H), 2.44 - 2.25 (m, 4H), 2.22 - 2.05 (m, 6H), 2.02 - 1.91 (m, 3H), 1.88 - 1.58 (m, 6H), 1.30 (d, J = 6.9 Hz, 3H), 0.54 - 0.43 (m, 2H); 892.4 $[M + H]^+$. |
| B3 | (((S)-fluoro(2-(((3S,6S,9S,10aR)-9-(methyl((1s,3R)-3-(trifluoromethoxy)cyclobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(hydroxy)phosphoryl)-L-alanine | 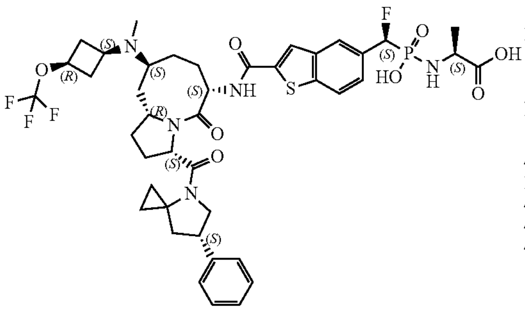 | 1H NMR (400 MHz, DMSO-d6) δ (ppm) 8.76 (s, 1H), 8.21 (s, 1H), 7.92 (d, J = 8.0 Hz, 2H), 7.53 (d, J = 8.5 Hz, 1H), 7.38 - 7.28 (m, 4H), 7.22 (t, J = 7.0 Hz, 2H), 5.63 (dd, J = 45.6, 7.3 Hz, 1H), 4.71 (s, 1H), 4.61 - 4.45 (m, 2H), 4.35 (s, 1H), 4.12 (t, J = 8.4 Hz, 1H), 3.74 (t, J = 9.9 Hz, 1H), 3.58 - 3.42 (m, 3H), |

TABLE 1B-continued

| No. | Name | Structure | NMR and LCMS |
|---|---|---|---|
| | | | 2.78 – 2.65 (m, 1H), 2.42 – 1.49 (m, 20H), 1.10 (d, J = 6.8 Hz, 3H), 0.56 – 0.39 (m, 2H); 892.5 [M + H]+. |
| B4 | (((R)-fluoro(2-(((3S,6S,9S, 10aR)-9-(methyl((1s,3R)-3-(trifluoromethyl) cyclobutyl)amino)-5-oxo-3-((S)-6-phenyl-4-azaspiro[2.4]heptane-4-carbonyl)decahydropyrrolo [1,2-a]azocin-6-yl)carbamoyl)benzo [b]thiophen-5-yl)methyl)(hydroxy) phosphoryl)-L-alanine | 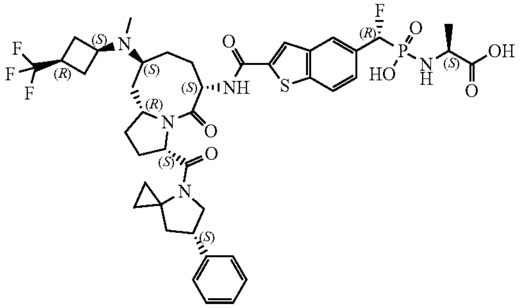 | 1H NMR (400 MHz, DMSO-d6) δ (ppm) 8.79 (s, 1H), 8.22 (s, 1H), 7.92 (d, J = 8.5 Hz, 2H), 7.56 (d, J = 8.5 Hz, 1H), 7.36 – 7.28 (m, 4H), 7.26 – 6.95 (m, 2H), 5.64 (dd, J = 45.7, 7.4 Hz, 1H), 4.70 (s, 1H), 4.58 – 4.33 (m, 2H), 4.14 – 4.05 (m, 1H), 3.81 3.38 (m, 5H), 2.96 – 2.78 (m, 1H), 2.46-1.48 (m, 21H), 1.09 (d, J = 6.8 Hz, 3H), 0.56 – 0.39 (m, 2H); 876.4 [M + H]+. |
| B5 | ((S)-((R)-fluoro(2-(((3S,6S, 9S,10aR)-9-(methyl(4,4,4-trifluorobutyl)amino)-5-oxo-3-((S)-6-phenyl-4-azaspiro[2.4]heptane-4-carbonyl)decahydropyrrolo [1,2-a]azocin-6-yl)carbamoyl) benzo[b]thiophen-5-yl)methyl)(hydroxy) phosphoryl)-L-alanine | 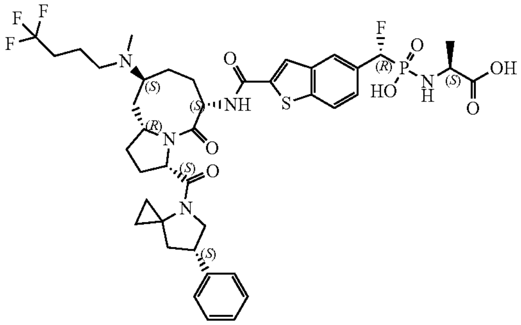 | 1H NMR (400 MHz, DMSO-d6) δ (ppm) 8.85 – 8.63 (m, 1H), 8.27 – 8.10 (m, 1H), 7.96 – 7.86 (m, 2H), 7.54 (d, J = 8.5 Hz, 1H), 7.40 – 7.27 (m, 4H), 7.25 – 7.14 (m, 1H), 5.62 (dd, J = 45.7, 7.6 Hz, 1H), 4.85 – 4.66 (m, 1H), 4.54 – 4.27 (m, 2H), 4.19 – 4.00 (m, 1H), 3.77 – 3.67 (m, 1H), 3.60 – 3.48 (m, 1H), 3.44 – 3.39 (m, 2H), 3.24 – 3.15 (m, 2H), 2.42 – 2.17 (m, 6H), 2.13 – 1.46 (m, 15H), 1.22 – 0.94 (m, 3H), 0.57 – 0.29 (m, 2H); 864.4 [M + H]+. |
| B6 | (((R)-(2-(((3S,6S,9S,10a R)-9-((3,3-difluoropropyl) (methyl)amino)-5-oxo-3-((S)-6-phenyl-4-azaspiro[2.4]heptane-4-carbonyl)decahydropyrrolo [1,2-a]azocin-6-yl) carbamoyl)benzo[b] thiophen-5-yl) fluoromethyl)(hydroxy) phosphoryl)-L-alanine | 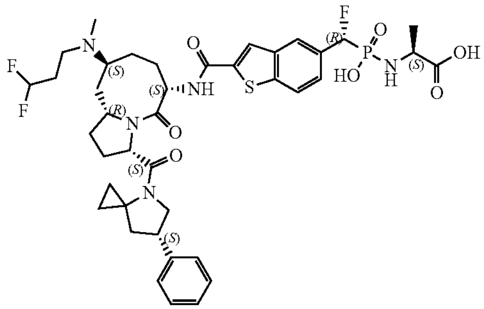 | 1H NMR (400 MHz, DMSO-d6) δ (ppm) 8.70 (d, J = 7.4 Hz, 1H), 8.20 (s, 1H), 7.92 (d, J = 8.1 Hz, 2H), 7.54 (d, J = 8.5 Hz, 1H), 7.38 – 7.28 (m, 4H), 7.22 (t, J = 7.1 Hz, 1H), 6.10 (t, J = 57.2 Hz, 1H), 5.61 (dd, J = 45.7, 7.6 Hz, 1H), 4.81 – 4.69 (m, 1H), 4.49 (t, J = 8.3 Hz, 1H), 4.34 (s, 1H), 4.10 (t, J = 8.6 Hz, 1H), 3.74 (t, J = 9.8 Hz, 1H), 3.58 – 3.37 (m, 2H), 3.28 – 2.98 (m, 2H), 2.45 – 2.30 (m, 2H), 2.29 – 2.15 (m, 3H), 2.14 – 2.05 (m, 2H), 2.04 – 1.93 (m, 4H), 1.92 – 1.35 (m, 9H), 1.06 (d, J = 6.8 Hz, 3H), 0.53 – |

TABLE 1B-continued

| No. | Name | Structure | NMR and LCMS |
| --- | --- | --- | --- |
| | | | 0.41 (m, 2H); 832.5 [M + H]+. |
| B7 | (((R)-fluoro(2-(((3S,6S,9S,10aR)-9-(((1s,3R)-3-fluorocyclobutyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(hydroxy)phosphoryl)-L-alanine | 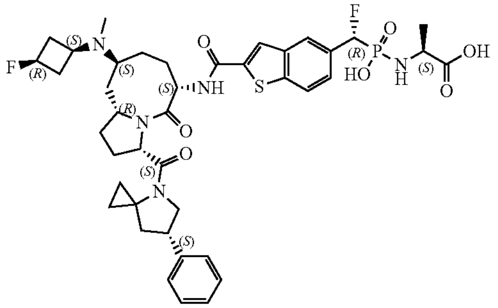 | 1H NMR (400 MHz, DMSO-d6) δ (ppm) 8.77 (s, 1H), 8.22 (s, 1H), 7.92 (d, J = 7.7 Hz, 2H), 7.56 (d, J = 8.2 Hz, 1H), 7.33 (dd, J = 12.2, 7.3 Hz, 4H), 7.22 (t, J = 7.0 Hz, 1H), 7.14 (t, J = 7.3 Hz, 1H), 6.76 (t, J = 7.2 Hz, 1H), 5.63 (dd, J = 45.7, 7.4 Hz, 1H), 4.99 - 4.64 (m, 2H), 4.57 - 4.33 (m, 2H), 4.16 - 4.06 (m, 1H), 3.74 (t, 1H), 3.61 - 3.45 (m, 2H), 2.80 - 2.56 (m, 2H), 2.47 - 1.39 (m, 21H), 1.09 (d, J = 6.7 Hz, 3H), 0.57 - 0.42 (m, 2H); 826.5 [M + H]+. |
| B8 | (((S)-(2-(((3S,6S,9S,10aR)-9-(ethyl((1s,3R)-3-fluorocyclobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)(hydroxy)phosphoryl)-L-alanine | 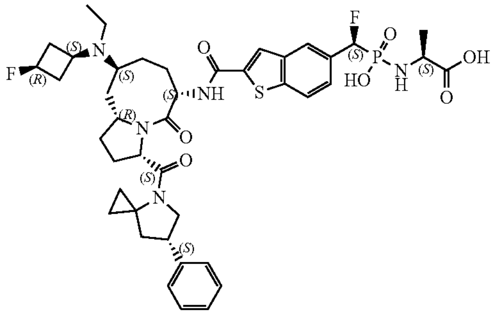 | 1H NMR (400 MHz, MeOD-d4) δ (ppm) 8.82 (s, 1H), 8.23 (s, 1H), 8.05 - 7.80 (m, 2H), 7.54 (d, J = 8.5 Hz, 1H), 7.38 - 7.26 (m, 4H), 7.25 - 7.19 (m, 1H), 5.64 (dd, J = 45.4, 7.3 Hz, 1H), 4.97 - 4.62 (m, 2H), 4.57 - 4.30 (m, 2H), 4.17 - 4.06 (m, 1H), 3.77 - 3.71 (m, 1H), 3.53 - 3.46 (m, 2H), 3.04 - 2.91 (m, 1H), 2.85 - 2.55 (m, 3H), 2.43 - 2.36 (m, 1H), 2.27 - 2.20 (m, 1H), 2.16 - 1.62 (m, 11H), 1.59 - 1.51 (m, 1H), 1.35 - 1.01 (m, 6H), 0.60 - 0.39 (m, 2H); 840.4 [M + H]+. |
| B9 | (((R)-fluoro(2-(((3S,6S,9S,10aR)-9-(methyl((3-methyloxetan-3-yl)methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(hydroxy)phosphoryl)-L-alanine | 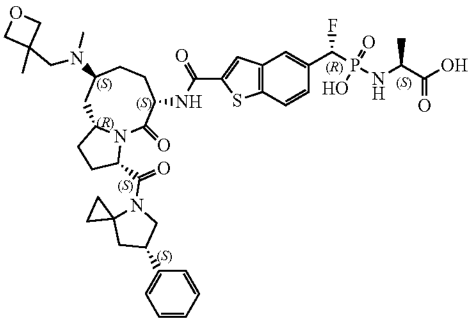 | 1H NMR (400 MHz, DMSO-d6) δ (ppm) 8.72 (d, J = 7.2 Hz, 1H), 8.20 (s, 1H), 7.93 (d, J = 8.1 Hz, 2H), 7.54 (d, J = 8.6 Hz, 1H), 7.39 - 7.27 (m, 4H), 7.26 - 7.08 (m, 2H), 5.72 - 5.63 (dd, J = 45.7, 7.6 Hz, 1H), 4.80 - 4.71 (m, 1H), 4.55 - 4.47 (m, 1H), 4.44 - 4.36 (m, 2H), 4.25 - 4.15 (m, 2H), 4.12 - 4.05 (m, 1H), 3.76 - 3.71 (m, 1H), 3.55 - 3.47 (m, 1H), 3.46 - 3.27 (m, 6H), 2.49 - 1.26 (m, 21H), 1.14 - 1.02 (m, 3H), 0.55 - 0.41 (m, 2H); 838.5 [M + H]+. |

TABLE 1B-continued

| No. | Name | Structure | NMR and LCMS |
| --- | --- | --- | --- |
| B10 | (((S)-fluoro(2-(((3S,6S,9S,10aR)-9-(methyl((1s,3R)-3-(trifluoromethyl)cyclobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(hydroxy)phosphoryl)-L-alanine | 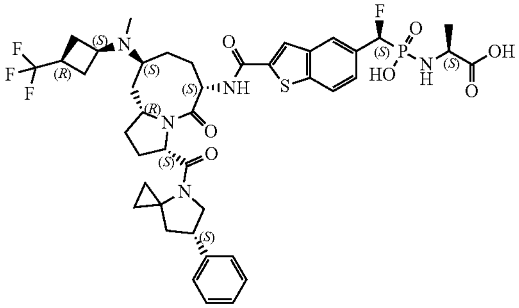 | 1H NMR (400 MHz, DMSO-d6) δ (ppm) 8.78 (s, 1H), 8.23 (s, 1H), 7.93 (d, J = 8.9 Hz, 2H), 7.53 (d, J = 8.5 Hz, 1H), 7.37 - 7.28 (m, 4H), 7.24 - 7.00 (m, 2H), 5.63 (dd, J = 45.5, 7.4 Hz, 1H), 4.72 (s, 1H), 4.58 - 4.28 (m, 2H), 4.17 - 4.06 (m, 1H), 3.81 - 3.39 (m, 5H), 2.96 - 2.78 (m, 1H), 2.45 - 1.45 (m, 21H), 1.10 (d, J = 6.8 Hz, 3H), 0.58 - 0.36 (m, 2H); 876.4 [M + H]$^+$. |
| B11 | (((R)-(2-(((3S,6S,9S,10aR)-9-(((1s,3R)-3-cyanocyclobutyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)(hydroxy)phosphoryl)-L-alanine | 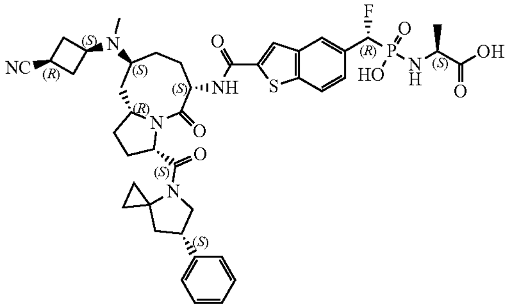 | 1H NMR (400 MHz, DMSO-d6) δ (ppm) 8.78 (s, 1H), 8.21 (s, 1H), 7.92 (d, J = 8.6 Hz, 2H), 7.56 (d, J = 8.5 Hz, 1H), 7.38 - 7.28 (m, 4H), 7.26 - 7.02 (m, 2H), 5.64 (dd, J = 45.7, 7.5 Hz, 1H), 4.70 (s, 1H), 4.57 - 4.32 (m, 2H), 4.12 (t, J = 8.3 Hz, 1H), 3.78 - 3.70 (m, 1H), 3.59 - 3.44 (m, 2H), 3.28 - 3.22 (m, 1H), 3.11 - 3.00 (m, 1H), 2.69 - 2.58 (m, 1H), 2.50 - 1.39 (m, 21H), 1.15 - 1.02 (m, 3H), 0.59 - 0.42 (m, 2H); 833.6 [M + H]$^+$. |
| B12 | (((S)-(2-(((3S,6S,9S,10aR)-9-(((S)-3,3-difluorocyclopentyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)(hydroxy)phosphoryl)-L-alanine | 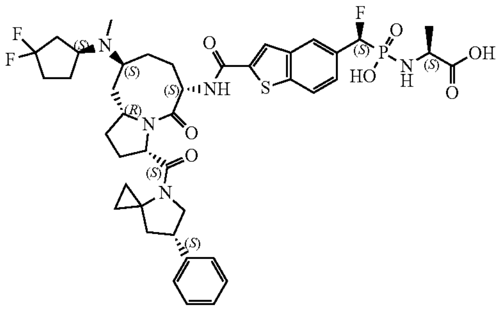 | 1H NMR (400 MHz, DMSO-d6) δ (ppm) 8.85 - 8.61 (m, 1H), 8.22 (s, 1H), 8.05 - 7.83 (m, 2H), 7.53 (d, J = 8.5 Hz, 1H), 7.37 - 7.27 (m, 4H), 7.23 - 7.19 (m, 1H), 5.65 (dd, J = 45.5, 7.3 Hz, 1H), 4.76 - 4.44 (m, 2H), 4.42 - 4.28 (m, 1H), 4.14 - 4.03 (m, 1H), 3.82 - 3.41 (m, 5H), 2.50 - 1.38 (m, 23H), 1.12 (d, J = 6.8 Hz, 3H), 0.57 - 0.35 (m, 2H); 858.4 [M + H]$^+$. |

TABLE 1B-continued

| No. | Name | Structure | NMR and LCMS |
|---|---|---|---|
| B13 | ((R)-((S)-fluoro(2-(((3S,6S,9S,10a R)-9-(((1s,3R)-3-fluorocyclobutyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-6-yl)methyl)(hydroxy)phosphoryl)-L-alanine | 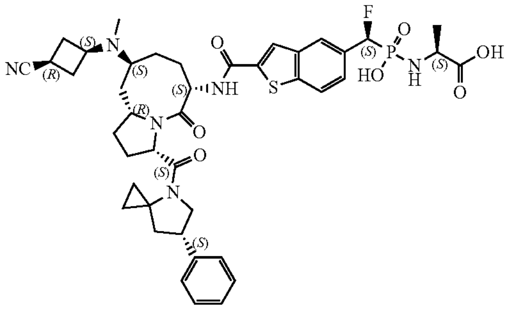 | 1H NMR (400 MHz, MeOD-d4) δ (ppm) 8.05 (s, 2H), 7.86 (d, J = 8.4 Hz, 1H), 7.60 (d, J = 8.5 Hz, 1H), 7.36 − 7.26 (m, 4H), 7.20 (t, J = 7.0 Hz, 1H), 7.17 − 6.74 (m, 1H), 5.66 (dd, J = 45.3, 7.0 Hz, 1H), 4.79 − 4.55 (m, 3H), 4.48 − 4.39 (m, 1H), 4.00 (t, J = 8.7 Hz, 1H), 3.94 − 3.75 (m, 3H), 3.59 − 3.48 (m, 1H), 3.39 − 3.32 (m, 1H), 3.01 − 2.90 (m, 1H), 2.80 − 2.70 (m, 1H), 2.69 − 2.57 (m, 1H), 2.55 (s, 3H), 2.50 − 2.37 (m, 2H), 2.31 (t, J = 11.5 Hz, 1H), 2.22 − 2.11 (m, 2H), 2.06 (d, J = 12.0 Hz, 1H), 2.01 − 1.69 (m, 8H), 1.64 − 1.56 (m, 1H), 1.32 (d, J = 7.0 Hz, 3H), 0.57 − 0.43 (m, 3H); 833.7 [M + H]+. |
| B14 | (((S)-fluoro(2-(((3S,6S,9S,10aR)-9-(methyl(4,4,4-trifluorobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(hydroxy)phosphoryl)-L-alanine | 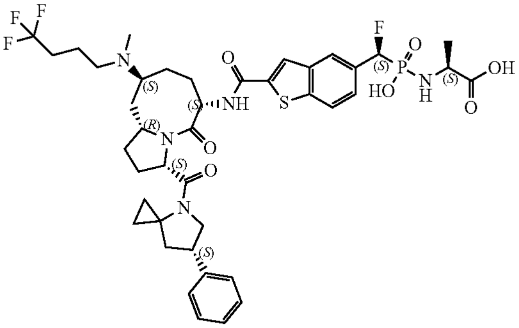 | 1H NMR (400 MHz, MeOD-d4) δ (ppm) 8.11 − 8.04 (m, 2H), 7.90 (d, J = 8.5 Hz, 1H), 7.61 (d, J = 8.5 Hz, 1H), 7.39 − 7.28 (m, 4H), 7.26 − 7.20 (m, 1H), 5.67 (dd, J = 45.3, 7.0 Hz, 1H), 4.71 − 4.58 (m, 2H), 4.46 − 4.35 (m, 1H), 4.06 − 3.76 (m, 4H), 3.61 − 3.52 (m, 1H), 3.21 − 3.11 (m, 2H), 2.78 (s, 3H), 2.52 − 2.41 (m, 1H), 2.37 − 2.27 (m, 3H), 2.20 − 1.81 (m, 13H), 1.66 − 1.57 (m, 1H), 1.33 (d, J = 7.0 Hz, 3H), 0.58 − 0.39 (m, 2H); 864.6 [M + H]+. |
| B15 | (((R)-fluoro(2(((3S,6S,9S,10aR)-9-(((1s,3R)-3-fluorocyclobutyl)(methyl)amino)-5-oxo-3-(4-azaspiro[2.4]heptane-4-carbonyl)decahydropyrrolo[1,2-a]azocin-6-yl)carbamoyl)benzo[b]thiophen-5-yl)methyl)(hydroxy)phosphoryl)-L-alanine | 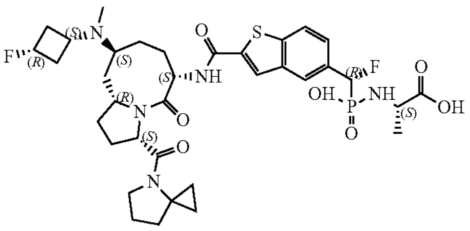 | 1H NMR (400 MHz, MeOD-d4) δ (ppm) 8.07 − 7.98 (m, 2H), 7.82 (d, J = 8.5 Hz, 1H), 7.64 (d, J = 8.5 Hz, 1H), 5.61 (dd, J = 45.3, 7.2 Hz, 1H), 4.79 − 4.55 (m, 3H), 4.43 − 4.35 (m, 1H), 4.00 − 3.92 (m, 1H), 3.75 − 3.56 (m, 2H), 3.27 − 3.21 (m, 1H), 2.73 2.59 (m, 2H), 2.56 2.46 (m, 1H), 2.42 2.33 (m, 1H), 2.27 − 2.11 (m, 3H), 2.07 (s, 3H), 2.02 − 1.60 (m, 14H), 1.30 (d, J = 6.9 Hz, 3H), 0.51 − 0.39 (m, 2H); 750.6 [M + H]+. |

TABLE 1B-continued

| No. | Name | Structure | NMR and LCMS |
| --- | --- | --- | --- |
| B16 | (((S)-(2-(((3S,6S,9S,10aR)-9-(ethyl((1s,3R)-3-(trifluoromethoxy)cyclobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)(hydroxy)phosphoryl)-L-alanine | 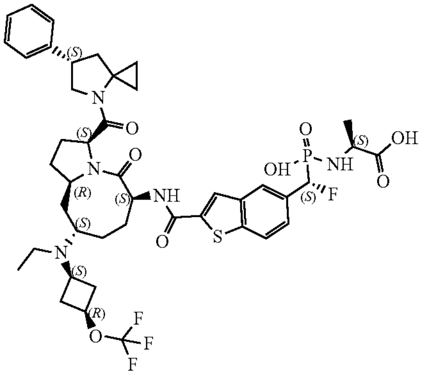 | 1H NMR (400 MHz, MeOD-d4) δ (ppm) 8.05 (d, J = 3.1 Hz, 2H), 7.86 (d, J = 8.4 Hz, 1H), 7.60 (d, J = 8.4 Hz, 1H), 7.37 - 7.25 (m, 4H), 7.20 (t, J = 7.1 Hz, 1H), 5.65 (dd, J = 45.3, 7.0 Hz, 1H), 4.68 - 4.52 (m, 3H), 4.48 - 4.38 (m, 1H), 4.01 (t, J = 8.8 Hz, 1H), 3.93 - 3.73 (m, 3H), 3.59 - 3.48 (m, 2H), 3.17 - 3.07 (m, 1H), 3.06 - 2.95 (m, 2H), 2.84 - 2.54 (m, 3H), 2.48 - 2.39 (m, 1H), 2.32 (t, J = 11.5 Hz, 1H), 2.23 - 2.11 (m, 2H), 2.07 - 1.81 (m, 8H), 1.78 - 1.67 (m, 1H), 1.62 - 1.54 (m, 1H), 1.36 - 1.24 (m, 6H), 0.58 - 0.42 (m, 2H); 906.4 $[M + H]^+$. |
| B17 | (((S)-(2-(((3S,6S,9S,10aR)-9-(ethyl(4,4,4-trifluorobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)(hydroxy)phosphoryl)-L-alanine | 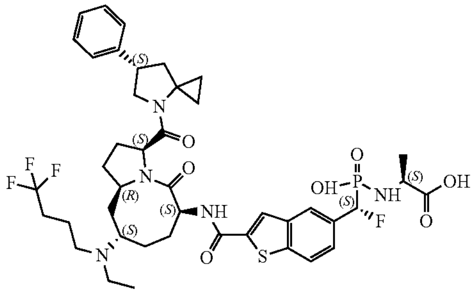 | 1H NMR (400 MHz, MeOD-d4) δ (ppm) 8.06 - 8.00 (m, 2H), 7.81 (d, J = 8.5 Hz, 1H), 7.61 (d, J = 8.5 Hz, 1H), 7.39 - 7.34 (m, 2H), 7.29 (t, J = 7.6 Hz, 2H), 7.22 - 7.17 (m, 1H), 5.61 (dd, J = 45.4, 7.2 Hz, 1H), 4.78 - 4.72 (m, 1H), 4.59 (t, J = 8.7 Hz, 1H), 4.45 - 4.34 (m, 1H), 4.07 - 3.91 (m, 2H), 3.71 - 3.50 (m, 2H), 3.25 - 3.17 (m, 1H), 2.61 - 2.09 (m, 12H), 2.04 - 1.73 (m, 9H), 1.65 - 1.55 (m, 2H), 1.32 (d, J = 6.9 Hz, 3H), 1.07 (t, J = 7.1 Hz, 3H), 0.54 - 0.43 (m, 2H); 878.6 $[M + H]^+$. |
| B18 | ((S)-((R)-(2-(((3S,6S,9S,10aR)-9-(((1s,3R)-3-(difluoromethyl)cyclobutyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)(hydroxy)phosphoryl)-L-alanine | 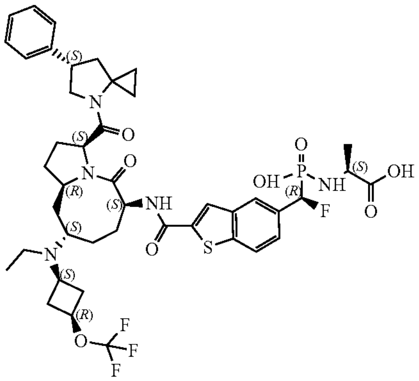 | 1H NMR (400 MHz, MeOD-d4) δ (ppm) 8.10 - 7.99 (m, 2H), 7.89 (d, J = 8.8 Hz, 1H), 7.66 (d, J = 9.8 Hz, 1H), 7.34 - 7.25 (m, 4H), 7.19 (t, J = 7.0 Hz, 1H), 6.07 - 5.58 (m, 2H), 4.64 4.54 (m, 2H), 4.44 - 4.35 (m, 1H), 3.98 (t, J = 8.7 Hz, 1H), 3.91 - 3.65 (m, 4H), 3.55 - 3.45 (m, 1H), 2.62 - 2.05 (m, 13H), 1.99 - 1.66 (m, 9H), 1.62 - 1.55 (m, 1H), 1.33 (d, J = 7.0 Hz, 3H), 0.55 - 0.40 (m, 2H); 858.6 $[M + H]^+$. |

TABLE 1B-continued

| No. | Name | Structure | NMR and LCMS |
|---|---|---|---|
| B19 | (((R)-fluoro(2-(((3S,6S,9S,10aR)-9-(methyl((R)-tetrahydrofuran-3-yl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(hydroxy)phosphoryl)-L-alanine | 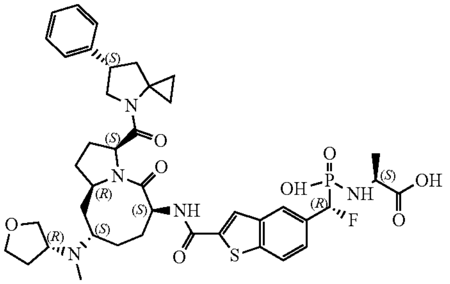 | 1H NMR (400 MHz, MeOD-d4) δ (ppm) 7.92 (s, 1H), 7.86 (s, 1H), 7.77 (d, J = 8.5 Hz, 1H), 7.53 (d, J = 8.5 Hz, 1H), 7.22 - 7.12 (m, 4H), 7.09 - 7.03 (m, 1H), 5.52 (dd, J = 45.3, 7.0 Hz, 1H), 4.45 (t, J = 8.3 Hz, 1H), 4.27 (d, J = 11.7 Hz, 1H), 4.14 - 3.99 (m, 2H), 3.94 3.84 (m, 3H), 3.79 3.66 (m, 3H), 3.61 - 3.51 (m, 2H), 3.45 - 3.36 (m, 1H), 2.53 (s, 3H), 2.37 - 2.26 (m, 2H), 2.17 (t, J = 11.5 Hz, 1H), 2.09 - 1.68 (m, 9H), 1.64 - 1.51 (m, 2H), 1.49 1.41 (m, 1H), 1.37 1.27 (m, 1H), 1.21 (d, J = 7.0 Hz, 3H), 0.41 - 0.31 (m, 2H); 824.6 [M + H]+. |
| B20 | (((S)-fluoro(2-(((3S,6S,9S,10aR)-9-(methyl(((R)-oxetan-2-yl)methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(hydroxy)phosphoryl)-L-alanine | 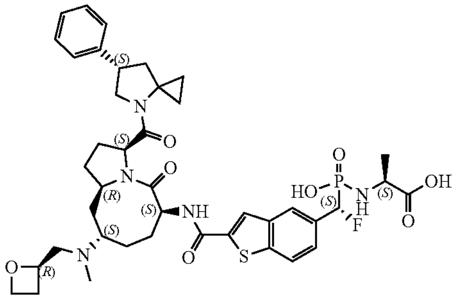 | 1H NMR (400 MHz, MeOD-d4) δ (ppm) 8.05 (d, J = 6.0 Hz, 2H), 7.84 (d, J = 8.4 Hz, 1H), 7.60 (d, J = 8.5 Hz, 1H), 7.36 - 7.25 (m, 4H), 7.23 - 7.16 (m, 1H), 5.62 (dd, J = 45.4, 7.1 Hz, 1H), 5.23 - 5.10 (m, 1H), 4.72 - 4.52 (m, 4H), 4.42 - 4.33 (m, 1H), 4.06 - 3.86 (m, 2H), 3.74 - 3.65 (m, 1H), 3.60 - 3.47 (m, 2H), 3.27 - 3.18 (m, 1H), 3.11 - 3.01 (m, 1H), 2.84 - 2.71 (m, 1H), 2.55 (s, 3H), 2.47 - 2.36 (m, 2H), 2.33 - 1.93 (m, 8H), 1.91 - 1.60 (m, 6H), 1.31 (d, J = 7.0 Hz, 3H), 0.54 - 0.40 (m, 2H); 824.3 [M + H]+. |
| B21 | (((S)-fluoro(2-(((3S,6S,9S,10aR)-9-(methyl(oxetan-3-yl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(hydroxy)phosphoryl)-L-alanine | 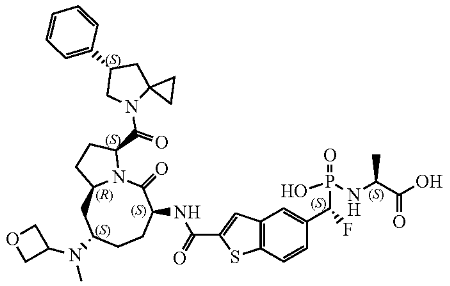 | 1H NMR (400 MHz, MeOD-d4) δ (ppm) 8.06 - 8.01 (m, 2H), 7.85 - 7.80 (m, 1H), 7.62 (d, J = 8.3 Hz, 1H), 7.38 - 7.27 (m, 4H), 7.20 (t, J = 7.2 Hz, 1H), 5.61 (dd, J = 45.4, 7.1 Hz, 1H), 4.81 - 4.71 (m, 4H), 4.66 - 4.55 (m, 3H), 4.45 - 4.36 (m, 1H), 4.04 (t, J = 8.7 Hz, 1H), 3.99 - 3.89 (m, 2H), 3.71 - 3.64 (m, 1H), 3.61 - 3.50 (m, 1H), 3.14 - 3.04 (m, 1H), 2.44 - 2.32 (m, 2H), 2.28 - 2.10 (m, 6H), 2.01 - 1.93 (m, 3H), 1.89 - 1.72 (m, 4H), 1.69 - 1.61 (m, |

| No. | Name | Structure | NMR and LCMS |
|---|---|---|---|
| | | | 2H), 1.31 (d, J = 6.8 Hz, 3H), 0.55 - 0.47 (m, 2H); 810.4 [M + H]+. |
| B22 | (((R)-fluoro(2-(((3S,6S,9S,10aR)-9-(methyl(((R)-oxetan-2-yl)methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(hydroxy)phosphoryl)-L-alanine | 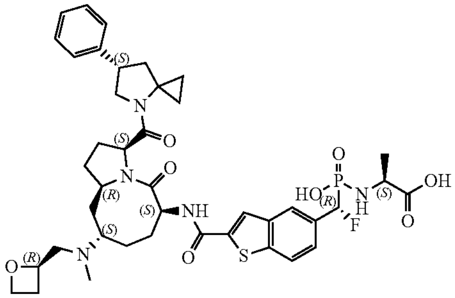 | 1H NMR (400 MHz, MeOD-d4) δ (ppm) 8.08 - 7.99 (m, 2H), 7.88 - 7.79 (m, 1H), 7.67 - 7.61 (m, 1H), 7.39 - 7.26 (m, 4H), 7.20 (t, J = 7.2 Hz, 1H), 5.63 (dd, J = 45.3, 7.3 Hz, 1H), 5.19 - 5.10 (m, 1H), 4.73 - 4.53 (m, 4H), 4.46 - 4.35 (m, 1H), 4.04 (t, J = 8.7 Hz, 1H), 3.97 - 3.87 (m, 1H), 3.78 - 3.68 (m, 1H), 3.59 - 3.46 (m, 2H), 3.23 - 3.11 (m, 1H), 3.09 - 3.00 (m, 1H), 2.84 - 2.71 (m, 1H), 2.49 - 2.39 (m, 2H), 2.33 (t, J = 11.5 Hz, 1H), 2.28 - 2.21 (m, 1H), 2.20 - 1.93 (m, 7H), 1.93 - 1.77 (m, 5H), 1.75 - 1.61 (m, 2H), 1.36 - 1.24 (m, 3H), 0.57 - 0.45 (m, 2H); 824.4 [M + H]+. |
| B23 | (((R)-fluoro(2-(((3S,6S,9S,10aR)-9-(methyl(((S)-oxetan-2-yl)methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(hydroxy)phosphoryl)-L-alanine | 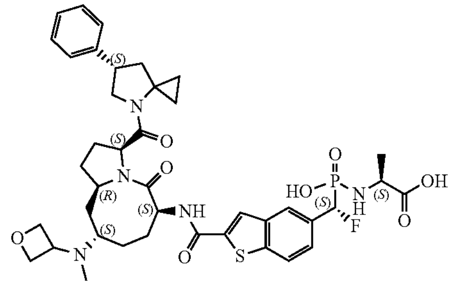 | 1H NMR (400 MHz, MeOD-d4) δ (ppm) 8.07 - 8.04 (m, 1H), 8.03 - 7.99 (m, 1H), 7.87 - 7.83 (m, 1H), 7.66 - 7.60 (m, 1H), 7.36 - 7.25 (m, 4H), 7.22 - 7.18 (m, 1H), 5.64 (dd, J = 45.3, 7.3 Hz, 1H), 5.22 - 5.14 (m, 1H), 4.71 - 4.62 (m, 2H), 4.62 - 4.53 (m, 2H), 4.43 - 4.34 (m, 1H), 4.06 - 3.99 (m, 1H), 3.95 - 3.87 (m, 1H), 3.80 - 3.70 (m, 1H), 3.63 - 3.47 (m, 2H), 3.30 - 3.24 (m, 1H), 3.15 - 3.07 (m, 1H), 2.84 - 2.73 (m, 1H), 2.48 - 2.37 (m, 2H), 2.36 - 2.28 (m, 1H), 2.25 - 2.13 (m, 2H), 2.10 - 1.92 (m, 5H), 1.91 - 1.78 (m, 3H), 1.75 - 1.60 (m, 2H), 1.35 - 1.24 (m, 3H), 0.58 - 0.41 (m, 2H); 824.4 [M + H]+. |

TABLE 1B-continued

| No. | Name | Structure | NMR and LCMS |
|---|---|---|---|
| B24 | (((S)-fluoro(2-(((3S,6S,9S,10a R)-9-morpholino-5-oxo-3-((R)-6-(pyridin-3-yl)-4-azaspiro[2.4]heptane-4-carbonyl)decahydropyrrolo [1,2-a]azocin-6-yl)carbamoyl)benzo [b]thiophen-5-yl) methyl)(hydroxy) phosphoryl)-L-alanine | 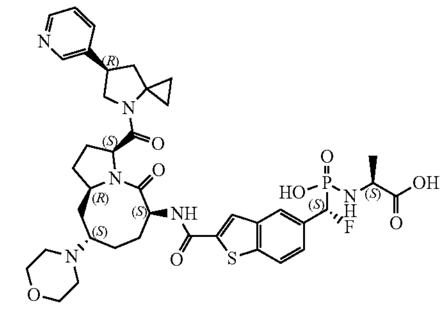 | 1H NMR (400 MHz, MeOD-d4) δ (ppm) 8.59 - 8.52 (m, 1H), 8.44 - 8.36 (m, 1H), 8.14 - 8.07 (m, 2H), 7.91 (t, J = 7.5 Hz, 2H), 7.63 - 7.55 (m, 1H), 7.42 - 7.35 (m, 1H), 5.68 (dd, J = 45.2, 6.6 Hz, 1H), 4.63 - 4.55 (m, 1H), 4.49 - 4.31 (m, 1H), 4.18 - 3.97 (m, 3H), 3.91 - 3.76 (m, 5H), 3.69 - 3.59 (m, 1H), 3.12 - 3.03 (m, 1H), 2.98 - 2.73 (m, 4H), 2.50 - 2.38 (m, 1H), 2.30 - 2.10 (m, 4H), 2.07 - 1.65 (m, 7H), 1.50 - 1.35 (m, 4H), 1.28 - 1.09 (m, 1H), 0.58 - 0.44 (m, 2H); 811.6 $[M + H]^+$. |
| B25 | (((R)-fluoro(2-(((3S,6S,9S, 10aR)-9-(((1s,3R)-3-fluorocyclobutyl)(methyl) amino)-5-oxo-3-((S)-6-phenyl-4-azaspiro[2.4] heptane-4-carbonyl) decahydropyrrolo[1,2-a]azocin-6-yl)carbamoyl) benzo[b]thiophen-5-yl)methyl)(hydroxy) phosphoryl)-D-alanine | 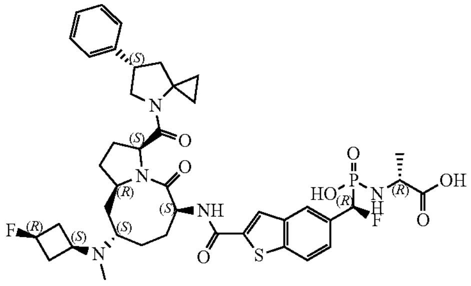 | 1H NMR (400 MHz, MeOD-d4) δ (ppm) 8.02 (d, J = 10.9 Hz, 2H), 7.82 (d, J = 8.5 Hz, 1H), 7.64 (d, J = 8.5 Hz, 1H), 7.39 - 7.26 (m, 4H), 7.20 (t, J = 7.2 Hz, 1H), 5.61 (dd, J = 45.4, 7.2 Hz, 1H), 4.78 - 4.64 (m, 2H), 4.60 (t, J = 8.7 Hz, 1H), 4.44 - 4.35 (m, 1H), 4.04 (t, J = 8.7 Hz, 1H), 3.93 (t, J = 9.8 Hz, 1H), 3.76 - 3.66 (m, 1H), 3.61 - 3.51 (m, 1H), 2.80 - 2.62 (m, 2H), 2.60 - 2.49 (m, 1H), 2.46 - 2.23 (m, 4H), 2.22 - 2.05 (m, 6H), 2.02 - 1.92 (m, 3H), 1.87 - 1.74 (m, 2H), 1.73 - 1.58 (m, 3H), 1.31 (d, J = 8.2 Hz, 3H), 0.55 - 0.46 (m, 2H); 827.5 $[M + H]^+$. |
| B26 | (((R)-(2-(((3S,6S,9S,10a R)-9-(ethyl(4,4,4-trifluorobutyl)amino)-5-oxo-3-((S)-6-phenyl-4-azaspiro[2.4]heptane-4-carbonyl)decahydropyrrolo [1,2-a]azocin-6-yl) carbamoyl)benzo[b] thiophen-5-yl)fluoromethyl) (hydroxy)phosphoryl)-L-alanine | 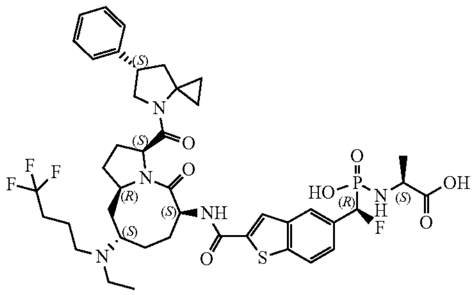 | 1H NMR (400 MHz, MeOD-d4) δ (ppm) 8.06 - 8.00 (m, 2H), 7.86 - 7.80 (m, 1H), 7.64 (d, J = 8.5 Hz, 1H), 7.38 - 7.26 (m, 4H), 7.20 (t, J = 7.2 Hz, 1H), 5.62 (dd, J = 45.3, 7.2 Hz, 1H), 4.73 (d, J = 10.6 Hz, 1H), 4.59 (t, J = 8.7 Hz, 1H), 4.43 - 4.34 (m, 1H), 4.04 (t, J = 8.7 Hz, 1H), 3.94 (t, J = 9.7 Hz, 1H), 3.75 - 3.67 (m, 1H), 3.59 - 3.49 (m, 1H), 3.40 - 3.32 (m, 1H), 2.73 - 2.50 (m, 4H), 2.49 - 2.31 (m, 2H), 2.29 - 2.11 (m, 5H), 2.06 - 1.91 (m, 4H), 1.87 - |

TABLE 1B-continued

| No. | Name | Structure | NMR and LCMS |
|---|---|---|---|
| | | | 1.74 (m, 5H), 1.69 – 1.59 (m, 2H), 1.31 (d, J = 6.9 Hz, 3H), 1.12 (t, J = 7.0 Hz, 3H), 0.53 – 0.45 (m, 2H); 878.4 [M + H]+. |
| B27 | (((R)-(2-(((3S,6S,9S,10aR)-9-(ethyl((1s,3R)-3-(trifluoromethoxy)cyclobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)(hydroxy)phosphoryl)-L-alanine | 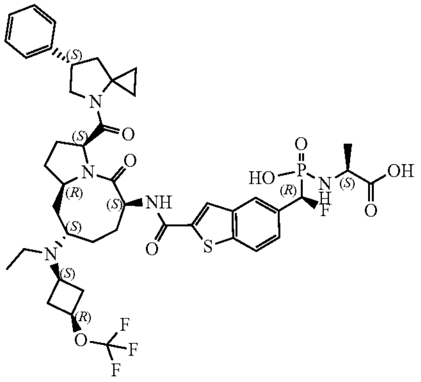 | 1H NMR (400 MHz, MeOD-d4) δ (ppm) 8.08 – 7.99 (m, 2H), 7.88 – 7.81 (m, 1H), 7.63 (d, J = 8.5 Hz, 1H), 7.38 – 7.26 (m, 4H), 7.22 – 7.17 (m, 1H), 5.65 (dd, J = 45.3, 7.2 Hz, 1H), 4.73 – 4.57 (m, 2H), 4.55 – 4.48 (m, 1H), 4.46 – 4.38 (m, 1H), 4.09 – 3.97 (m, 1H), 3.96 – 3.86 (m, 1H), 3.79 – 3.67 (m, 1H), 3.67 – 3.50 (m, 2H), 3.39 – 3.32 (m, 1H), 3.01 – 2.78 (m, 3H), 2.76 – 2.55 (m, 2H), 2.49 – 2.29 (m, 3H), 2.25 – 2.12 (m, 2H), 2.08 – 1.92 (m, 5H), 1.88 – 1.69 (m, 4H), 1.59 (s, 1H), 1.31 (d, J = 6.9 Hz, 3H), 1.27 – 1.21 (m, 3H), 0.50 (s, 2H); 906.4 [M + H]+. |
| B28 | (((R)-fluoro(2-(((3S,6S,9S,10aR)-9-(methyl(oxetan-3-yl)amino)-5-oxo-3-((S)-6-phenyl-4-azaspiro[ 2.4]heptane-4-carbonyl)decahdropyrrolo[1,2-a]azocin-6-yl)carbamoyl)benzo[b]thiophen-5-yl)methyl)(hydroxy)phosphoryl)-L-alanine | 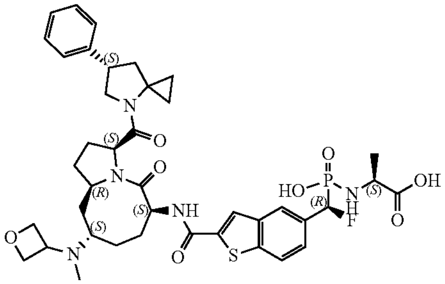 | 1H NMR (400 MHz, MeOD-d4) δ (ppm) 8.02 (d, J = 11.3 Hz, 2H), 7.82 (d, J = 8.5 Hz, 1H), 7.63 (d, J = 8.5 Hz, 1H), 7.36 (d, J = 7.3 Hz, 2H), 7.32 – 7.26 (m, 2H), 7.23 – 7.17 (m, 1H), 5.61 (dd, J = 45.3, 7.2 Hz, 1H), 4.79 – 4.70 (m, 3H), 4.65 – 4.56 (m, 3H), 4.43 – 4.34 (m, 1H), 4.07 – 4.01 (m, 1H), 3.98 – 3.88 (m, 2H), 3.74 – 3.65 (m, 1H), 3.63 – 3.52 (m, 1H), 3.12 – 3.04 (m, 1H), 2.46 – 2.13 (m, 5H), 2.10 (s, 3H), 2.03 – 1.91 (m, 3H), 1.87 – 1.70 (m, 4H), 1.69 – 1.59 (m, 2H), 1.30 (d, J = 6.9 Hz, 3H), 0.55 – 0.47 (m, 2H); 810.7 [M + H]+. |

TABLE 1C

| No. | Name | Structure |
|---|---|---|
| C1 | propyl (((R)-(2-(((3S,6S,9S,10aR)-9-((3,3-difluoropropyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)(phenoxy)phosphoryl)-L-alaninate | 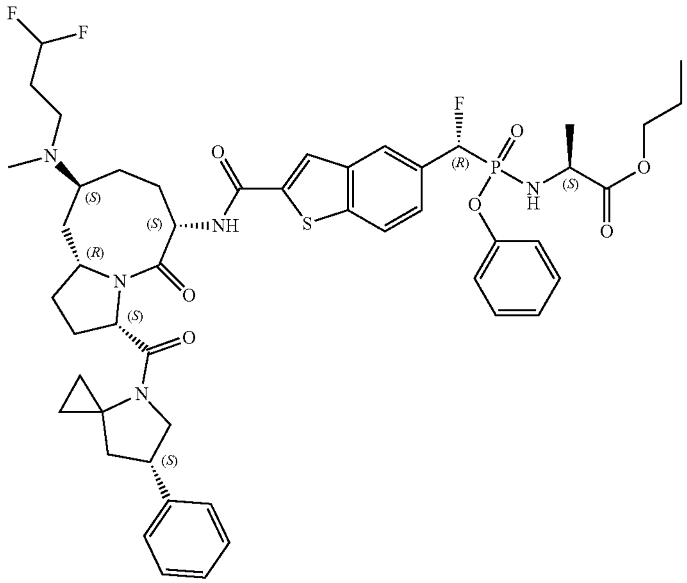 |
| C2 | propyl (((1R)-(2-(((3S,6S,9S,10aR)-9-((3,3-difluorocyclobutyl)(methyl)amino)-5-oxo-3-((S)-6-phenyl-4-azaspiro[2.4]heptane-4-carbonyl)decahydropyrrolo[1,2-a]azocin-6-yl)carbamoyl)-2,3-dihydrobenzo[b]thiophen-5-yl)fluoromethyl)(phenoxy)phosphoryl)-L-alaninate | 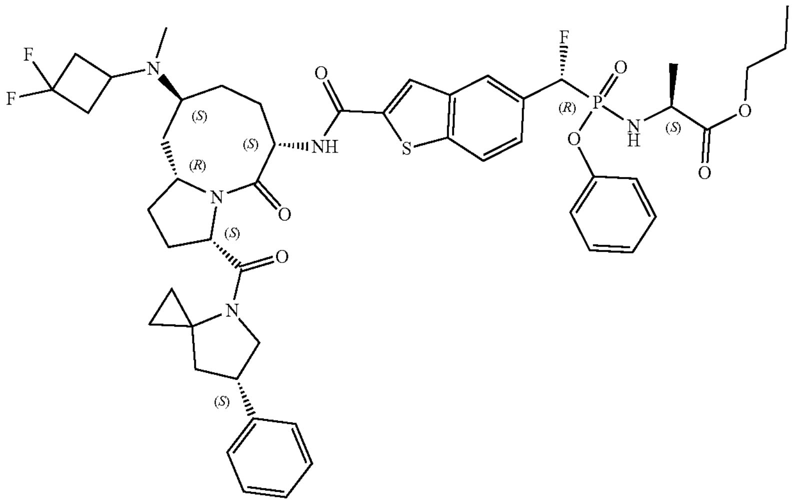 |
| C3 | propyl (((1S)-(2-(((3S,6S,9S,10aR)-9-((3,3-difluorocyclobutyl)(methyl)amino)-5-oxo-3-((S)-6-phenyl-4-azaspiro[2.4]heptane-4-carbonyl)decahydropyrrolo[1,2-a]azocin-6-yl)carbamoyl)-2,3-dihydrobenzo[b]thiophen-5-yl)fluoromethyl)(phenoxy)phosphoryl)-L-alaninate | 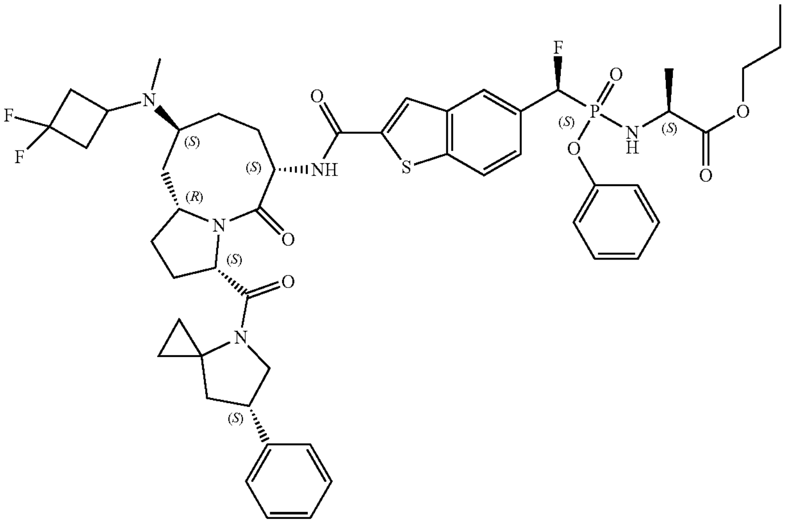 |

TABLE 1C-continued

| | | |
|---|---|---|
| C4 | propyl ((R)-((1R)-fluoro(2-(((3S,6S,9S,10aR)-9-(methyl((1s,3R)-3-(trifluoromethyl)cyclobutyl)amino)-5-oxo-3-((S)-6-phenyl-4-azaspiro[2.4]heptane-4-carbonyl)decahydropyrrolo[1,2-a]azocin-6-yl)carbamoyl)-2,3-dihydrobenzo[b]thiophen-5-yl)methyl)(phenoxy)phosphoryl)-L-alaninate | 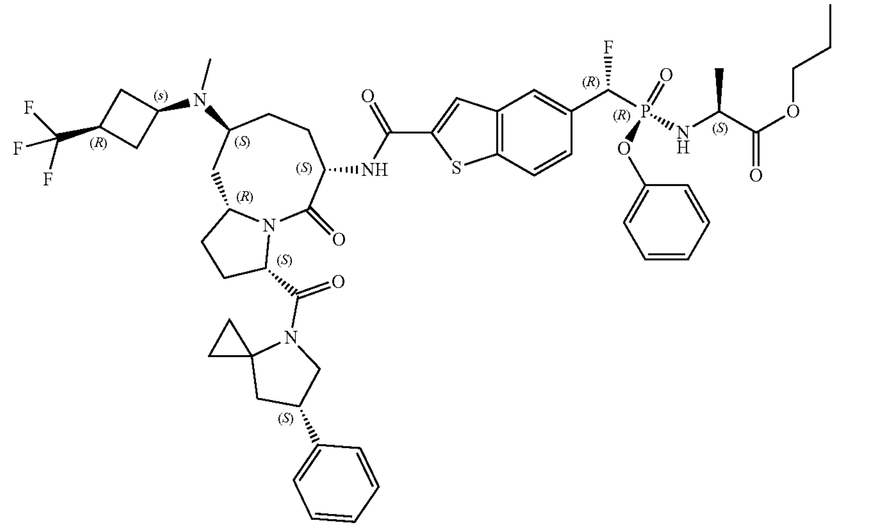 |
| C5 | propyl ((R)-((1R)-fluoro(2-(((3S,6S,9S,10aR)-9-(methyl((1s,3R)-3-(trifluoromethoxy)cyclobutyl)amino)-5-oxo-3-((S)-6-phenyl-4-azaspiro [2.4]heptane-4-carbonyl)decahydropyrrolo[1,2-a]azocin-6-yl)carbamoyl)-2,3-dihydrobenzo[b]thiophen-5-yl)methyl)(phenoxy)phosphoryl)-L-alaninate | 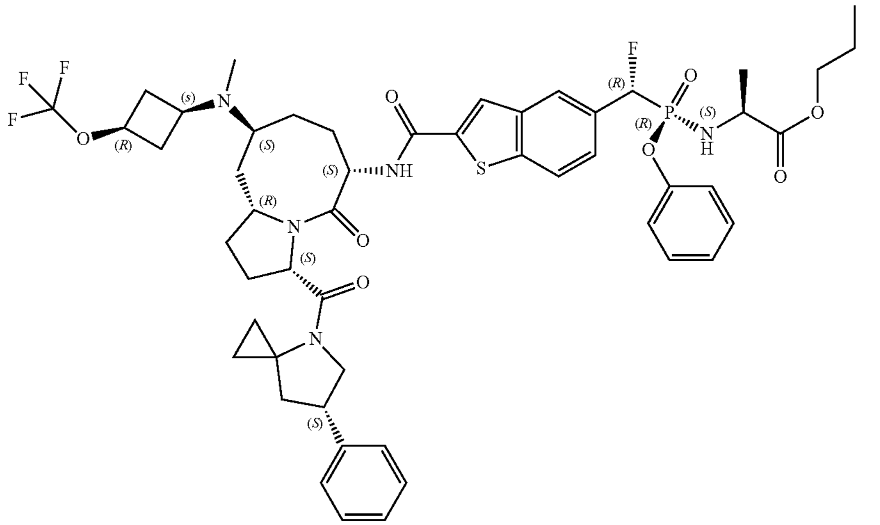 |
| C6 | propyl ((S)-((1R)-fluoro(2-(((3S,6S,9S,10aR)-9-(methyl((1s,3R)-3-(trifluoromethoxy)cyclobutyl)amino)-5-oxo-3-((S)-6-phenyl-4-azaspiro[2.4]heptane-4-carbonyl)decahydropyrrolo[1,2-a]azocin-6-yl)carbamoyl)-2,3-dihydrobenzo[b]thiophen-5-yl)methyl)(phenoxy)phosphoryl)-L-alaninate | 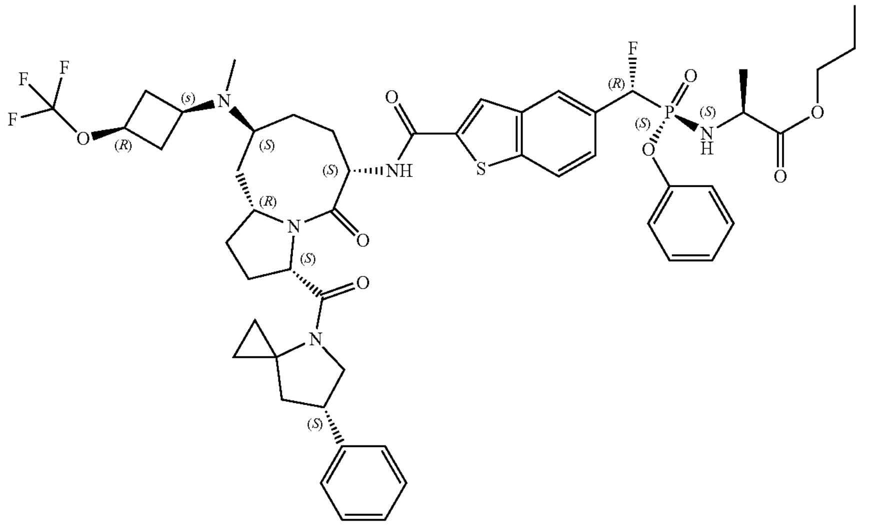 |

TABLE 1C-continued

| | | |
|---|---|---|
| C7 | propyl ((R)-((S)-fluoro(2-(((3S,6S,9S,10aR)-9-(methyl((1s,3R)-3-(trifluoromethoxy)cyclobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate | 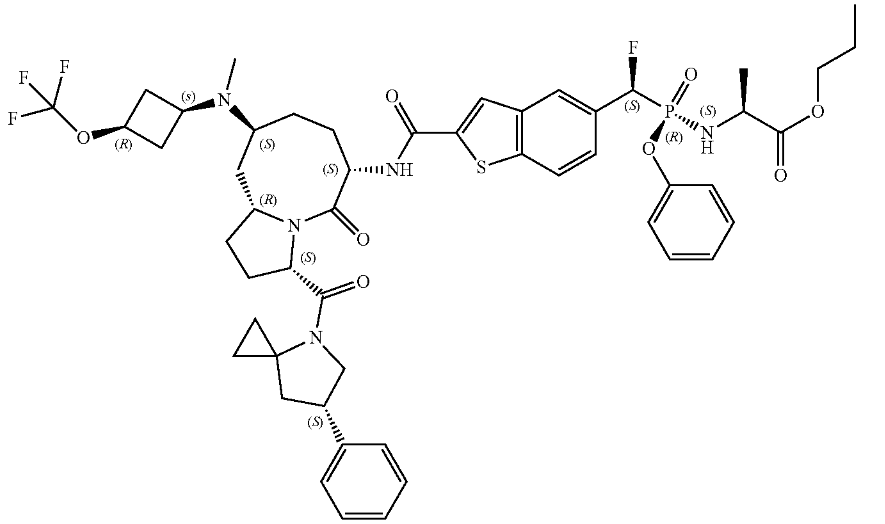 |
| C8 | propyl ((S)-((R)-fluoro(2-(((3S,6S,9S,10aR)-9-(methyl(4,4,4-trifluorobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate | 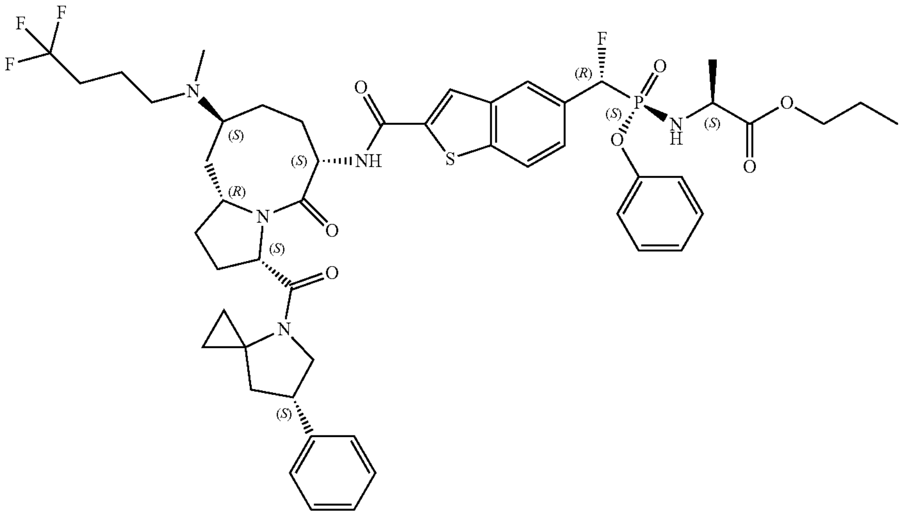 |
| C9 | propyl (((1S)-(2-(((3S,6S,9S,10aR)-9-((3,3-difluoropropyl)(methyl)amino)-5-oxo-3-((S)-6-phenyl-4-azaspiro[2.4]heptane-4-carbonyl)decahydropyrrolo[1,2-a]azocin-6-yl)carbamoyl)-2,3-dihydrobenzo[b]thiophen-5-yl)fluoromethyl)(phenoxy)phosphoryl)-L-alaninate | 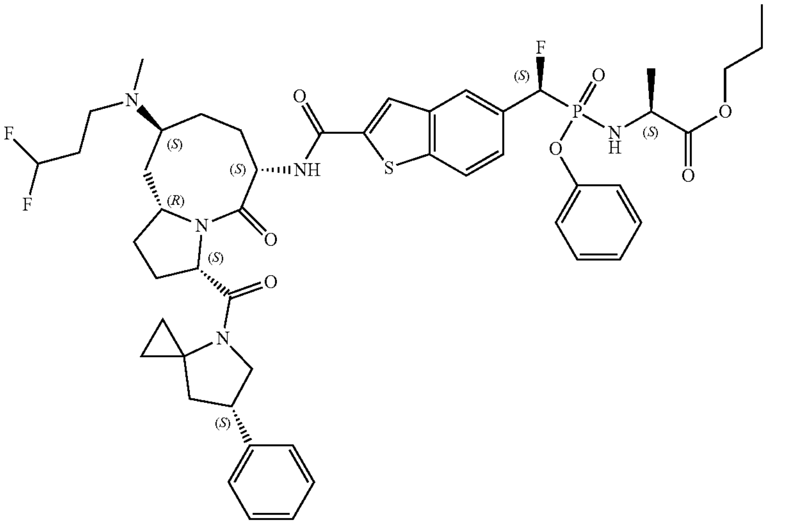 |

TABLE 1C-continued

| | | |
|---|---|---|
| C10 | propyl ((S)-((R)-fluoro(2-(((3S,6S,9S,10aR)-9-(methyl((1s,3R)-3-(trifluoromethyl)cyclobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate | 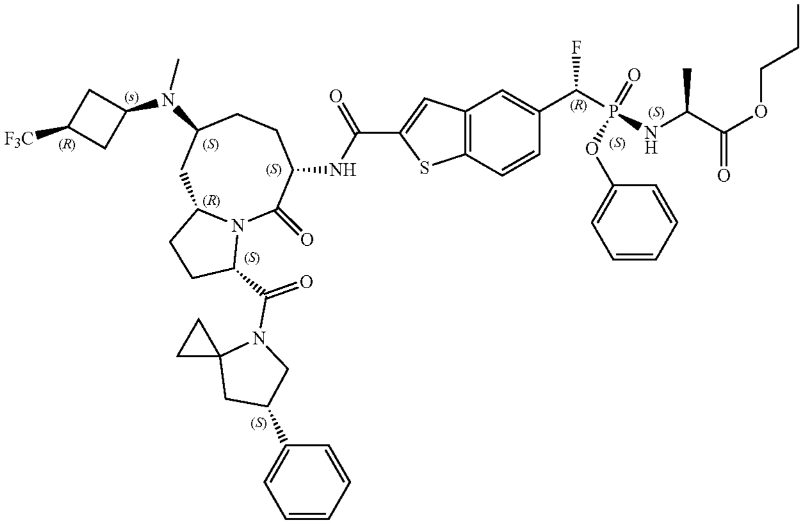 |
| C11 | propyl ((S)-((R)-(2-(((3S,6S,9S,10aR)-9-((3,3-difluoropropyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)(phenoxy)phosphoryl)-L-alaninate | 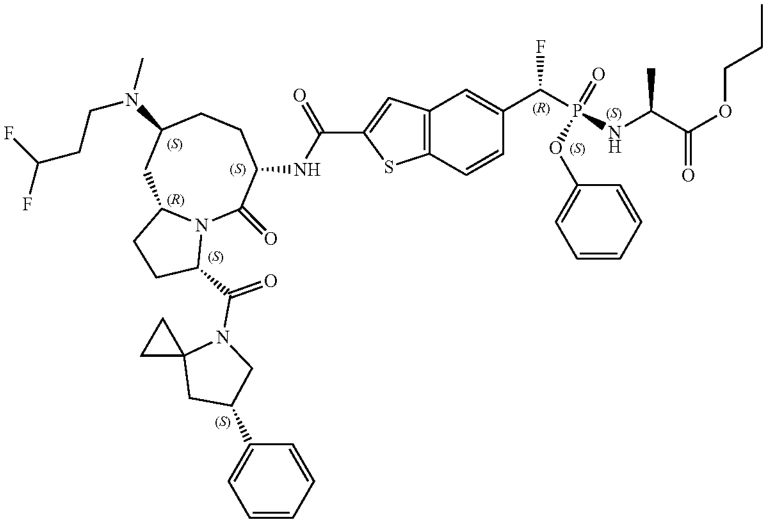 |
| C12 | propyl ((R)-((R)-(2-(((3S,6S,9S,10aR)-9-((3,3-difluoropropyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)(phenoxy)phosphoryl)-L-alaninate | 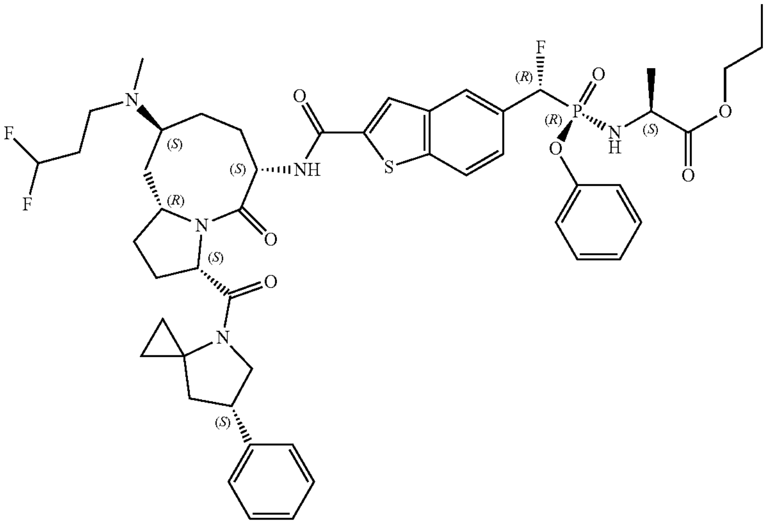 |

TABLE 1C-continued

| | | |
|---|---|---|
| C13 | propyl (((R)-fluoro(2-(((3S,6S,9S,10aR)-9-(methyl((1s,3R)-3-(trifluoromethyl)cyclobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate | 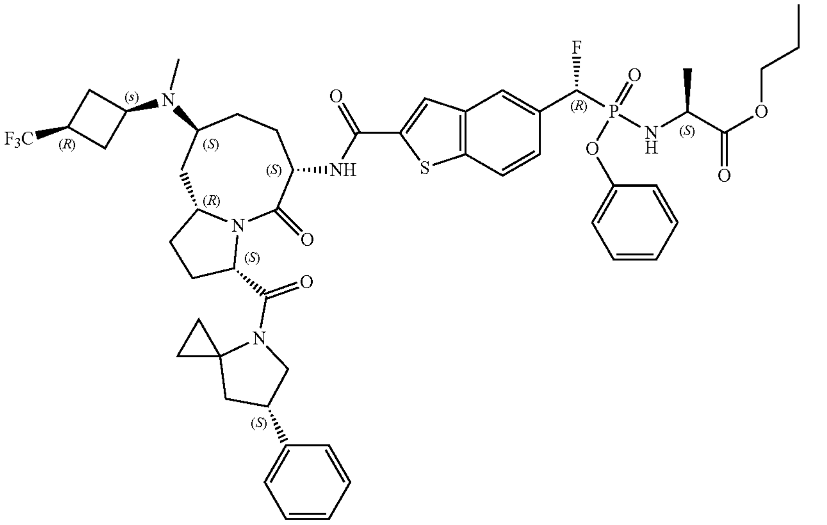 |
| C14 | cyclobutyl ((S)-((S)-fluoro(2-(((3S,6S,9S,10aR)-9-(((1s,3R)-3-fluorocyclobutyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate | 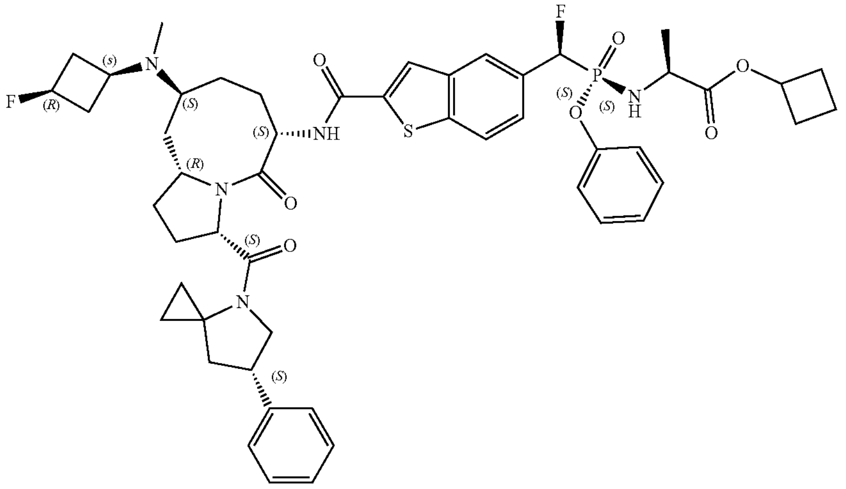 Phosphorus absolute stereochemistry arbitrarily assigned |
| C15 | cyclobutyl ((R)-((S)-fluoro(2-(((3S,6S,9S,10aR)-9-(((1s,3R)-3-fluorocyclobutyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate | 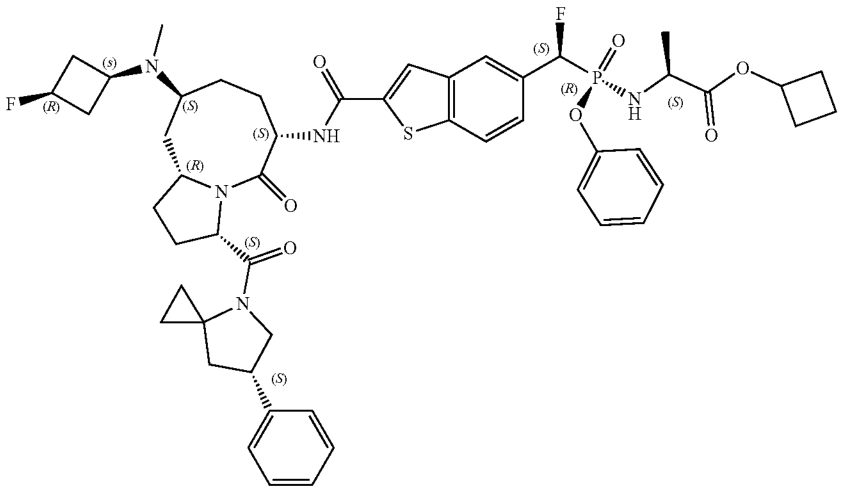 Phosphorus absolute stereochemistry arbitrarily assigned |

TABLE 1C-continued

| | | |
|---|---|---|
| C16 | propyl (((R)-fluoro(2-(((3S,6S,9S,10aR)-9-(((1r,3S)-3-fluorocyclobutyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate | 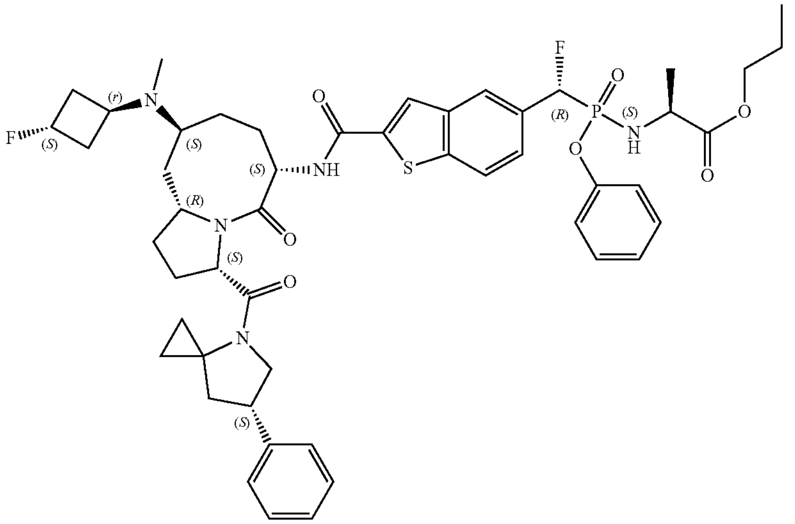 |
| C17 | propyl ((S)-((S)-fluoro(2-(((3S,6S,9S,10aR)-9-(((1s,3R)-3-fluorocyclobutyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate | 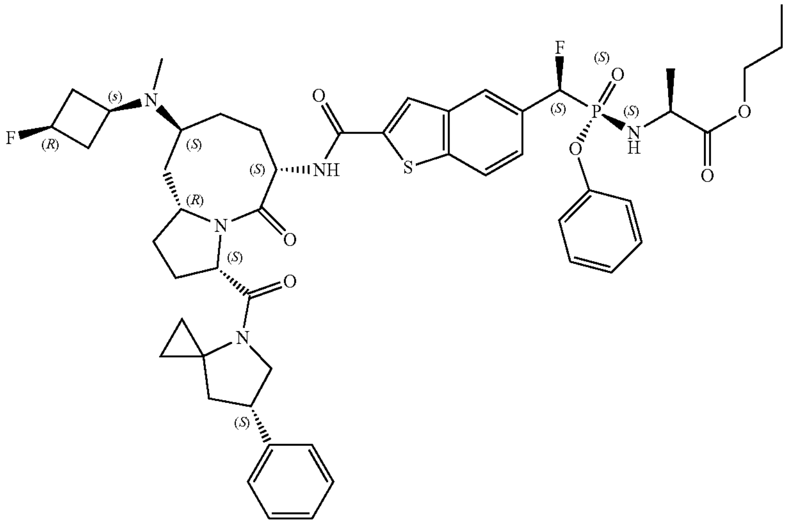 |
| C18 | propyl (((R)-fluoro(2-(((3S,6S,9S,10aR)-9-(methyl(((S)-oxetan-2-yl)methyl)amino)-5-oxo-3-((S)-6-phenyl-4-azaspiro [2.4] heptane-4-carbonyl)decahydropyrrolo[1,2-a]azocin-6-yl)carbamoyl)benzo[b]thiophen-5-yl)methyl)(phenoxy)phosphoryl)-L-alaninate | 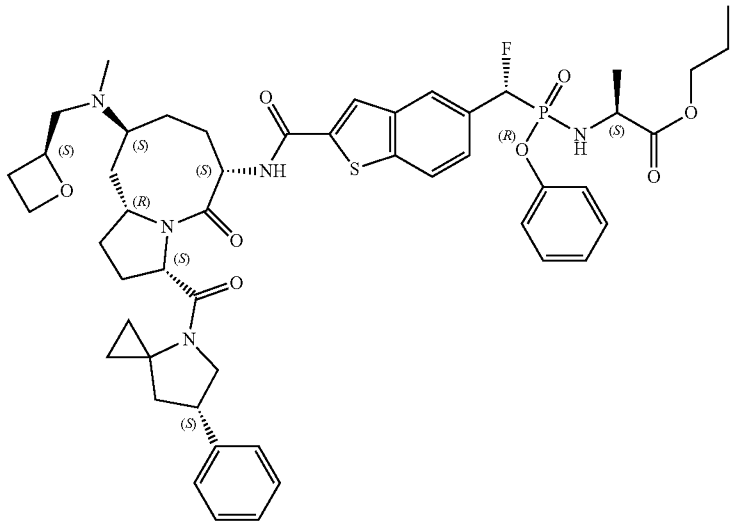 |

TABLE 1C-continued

| | | |
|---|---|---|
| C19 | propyl ((R)-((1R)-fluoro(2-(((3S,6S,9S,10aR)-9-(((1s,3R)-3-fluorocyclobutyl)(methyl)amino)-5-oxo-3-((S)-6-phenyl-4-azaspiro[2.4]heptane-4-carbonyl)decahydropyrrolo[1,2-a]azocin-6-yl)carbamoyl)-2,3-dihydrobenzo[b]thiophen-5-yl)methyl)(phenoxy)phosphoryl)-L-alaninate | 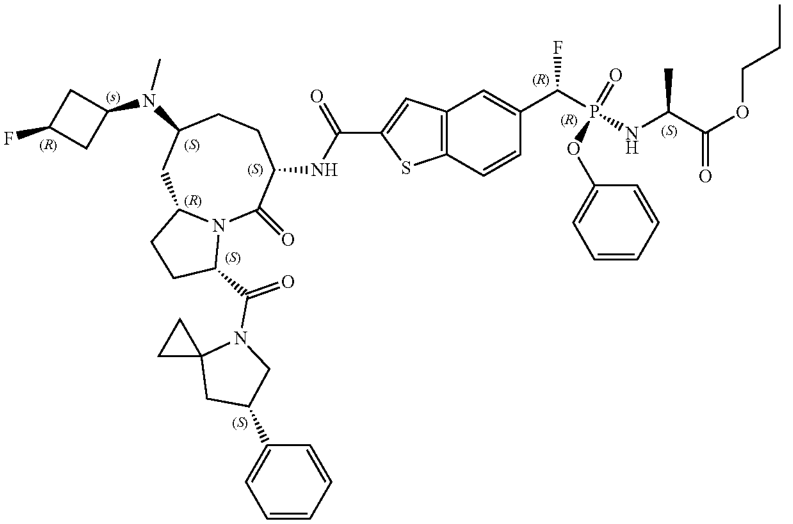 |
| C20 | propyl (((1R)-fluoro(2-(((3S,6S,9S,10aR)-9-(methyl(((R)-oxetan-2-yl)methyl)amino)-5-oxo-3-((S)-6-phenyl-4-azaspiro[2.4]heptane-4-carbonyl)decahydropyrrolo[1,2-a]azocin-6-yl)carbamoyl)-2,3-dihydrobenzo[b]thiophen-5-yl)methyl)(phenoxy)phosphoryl)-L-alaninate | 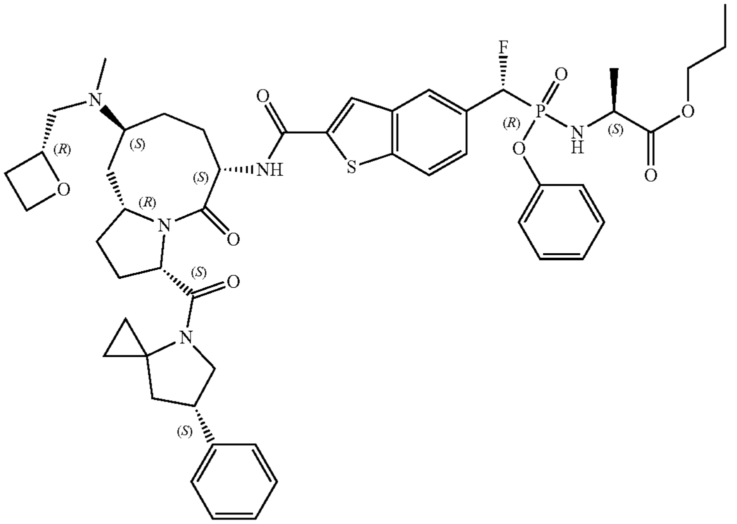 |
| C21 | propyl (((1S)-fluoro(2-(((3S,6S,9S,10aR)-9-(methyl(((S)-oxetan-2-yl)methyl)amino)-5-oxo-3-((S)-6-phenyl-4-azaspiro[2.4]heptane-4-carbonyl)decahydropyrrolo[1,2-a]azocin-6-yl)carbamoyl)-2,3-dihydrobenzo[b]thiophen-5-yl)methyl)(phenoxy)phosphoryl)-L-alaninate | 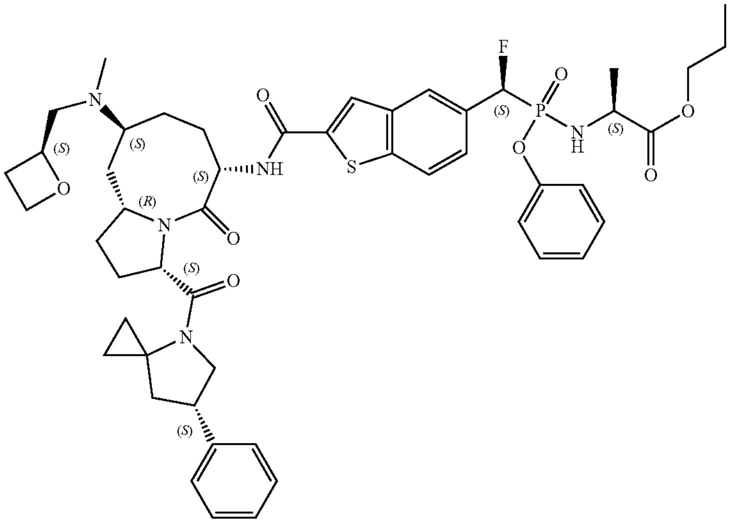 |

TABLE 1C-continued

| | | |
|---|---|---|
| C22 | propyl (((1S)-fluoro(2-(((3S,6S,9S,10aR)-9-(methyl((R)-tetrahydrofuran-3-yl)amino)-5-oxo-3-((S)-6-phenyl-4-azaspiro [2.4] heptane-4-carbonyl) decahydropyrrolo [1,2-a]azocin-6-yl)carbamoyl)-2,3-dihydrobenzo[b] thiophen-5-yl)methyl) (phenoxy) phosphoryl)-L-alaninate | 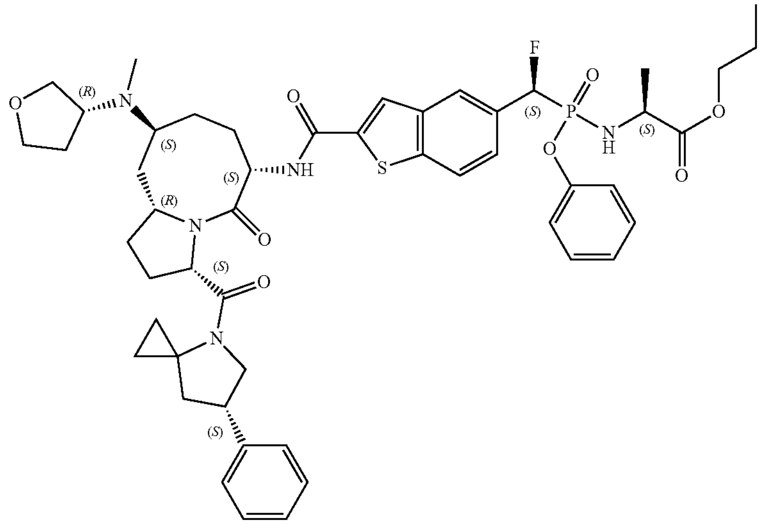 |
| C23 | propyl ((S)-((R)-fluoro(2-(((3S,6S,9S,10aR)-9-(((1s,3R)-3-fluorocyclobutyl) (methyl)amino)-5-oxo-3-((S)-6-phenyl-4-azaspiro [2.4] heptane-4-carbonyl) decahydropyrrolo [1,2-a]azocin-6-yl)carbamoyl) benzo [b]thiophen-5-yl)methyl) (phenoxy) phosphoryl)-L-alaninate | 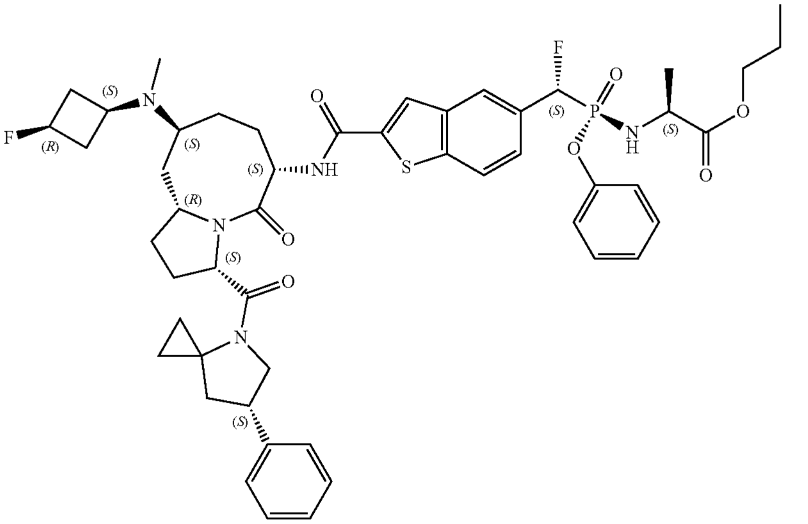 |
| C24 | propyl (((R)-fluoro(2-(((3S,6S,9S,10aR)-9-(methyl((R)-tetrahydrofuran-3-yl)amino)-5-oxo-3-((S)-6-phenyl-4-azaspiro[2.4] heptane-4-carbonyl) decahydropyrrolo [1,2-a]azocin-6-yl)carbamoyl) benzo [b]thiophen-5-yl)methyl) (phenoxy) phosphoryl)-L-alaninate | 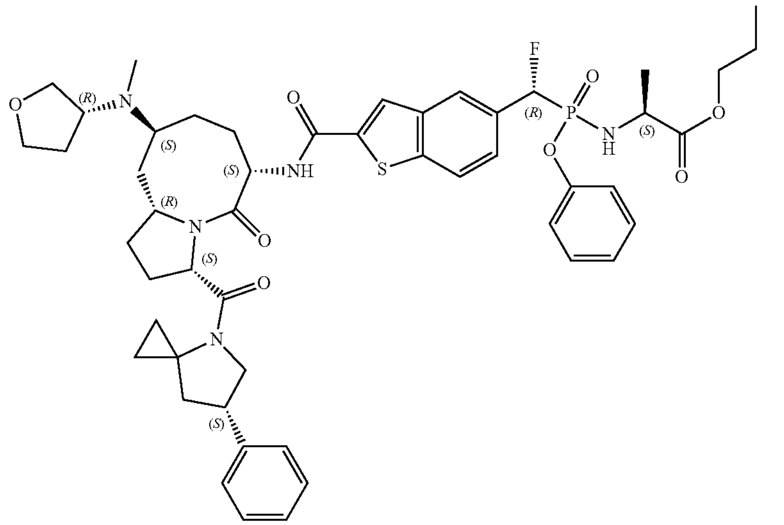 |

TABLE 1C-continued

| | | |
|---|---|---|
| C25 | propyl ((R)-((S)-fluoro(2-(((3S,6S,9S,10aR)-9-(((1s,3R)-3-fluorocyclobutyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate | 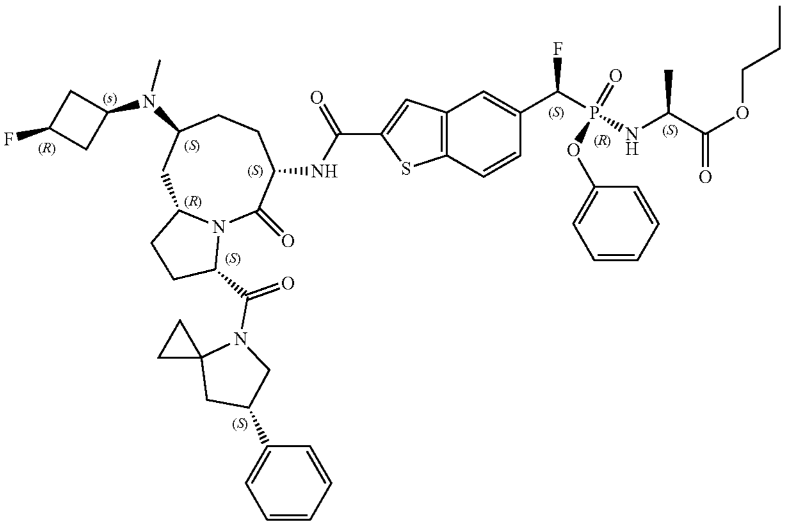 |
| C26 | propyl (((R)-fluoro(2-(((3S,6S,9S,10aR)-9-(methyl(oxetan-3-ylmethyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate | 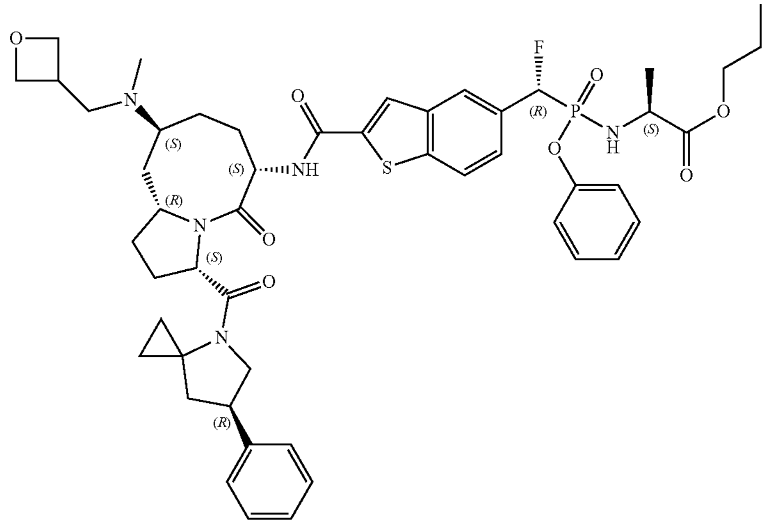 |
| C27 | propyl (((S)-fluoro(2-(((3S,6S,9S,10aR)-9-(methyl((S)-tetrahydrofuran-3-yl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate | 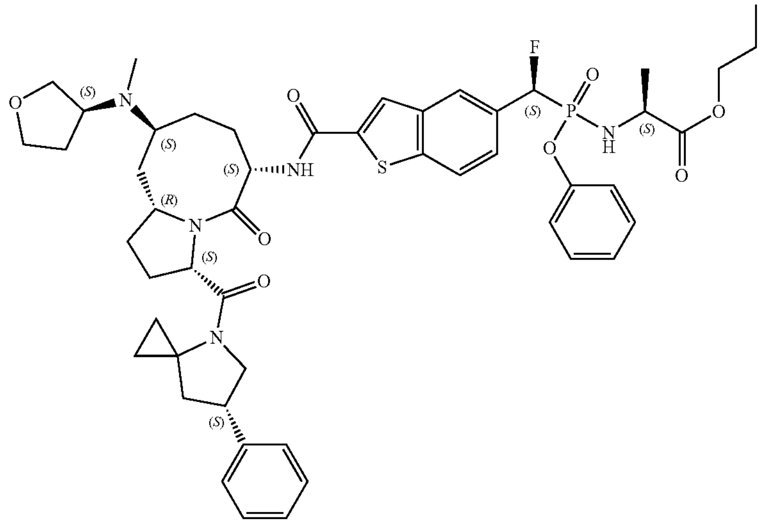 |

TABLE 1C-continued

| | | |
|---|---|---|
| C28 | propyl (((R)-fluoro(2-(((3S,6S,9S,10aR)-9-(((1s,3R)-3-fluorocyclobutyl)(methyl)amino)-5-oxo-3-((R)-6-(pyridin-3-yl)-4-azaspiro [2.4] heptane-4-carbonyl) decahydropyrrolo [1,2-a]azocin-6-yl)carbamoyl) benzo [b]thiophen-5-yl)methyl) (phenoxy) phosphoryl)-L-alaninate | 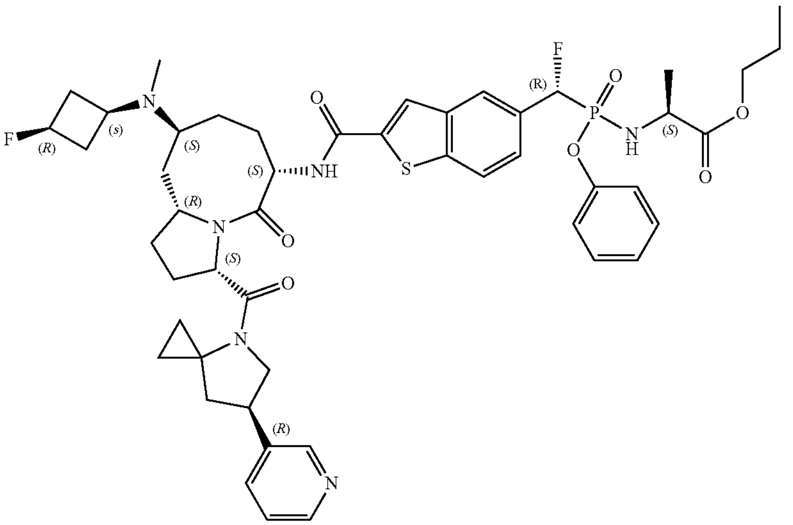 |
| C29 | propyl ((S)-((R)-fluoro(2-(((3S,6S,9S,10aR)-9-morpholino-5-oxo-3-((R)-6-(pyridin-3-yl)-4-azaspiro[2.4] heptane-4-carbonyl) decahydropyrrolo [1,2-a]azocin-6-yl)carbamoyl) benzo [b]thiophen-5-yl)methyl) (phenoxy) phosphoryl)-L-alaninate | 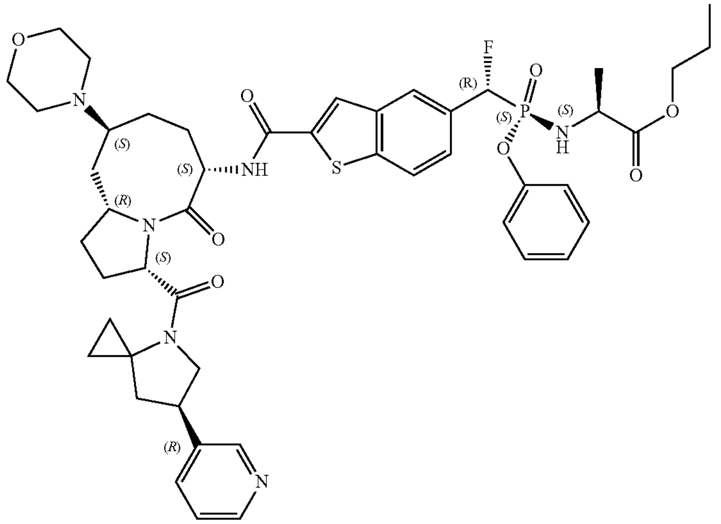 |
| C30 | propyl ((R)-((S)-fluoro(2-(((3S,6S,9S,10aR)-9-(methyl(oxetan-3-yl)amino)-5-oxo-3-((S)-6-phenyl-4-azaspiro[2.4] heptane-4-carbonyl) decahydropyrrolo [1,2-a]azocin-6-yl)carbamoyl) benzo [b]thiophen-5-yl)methyl) (phenoxy) phosphoryl)-L-alaninate | 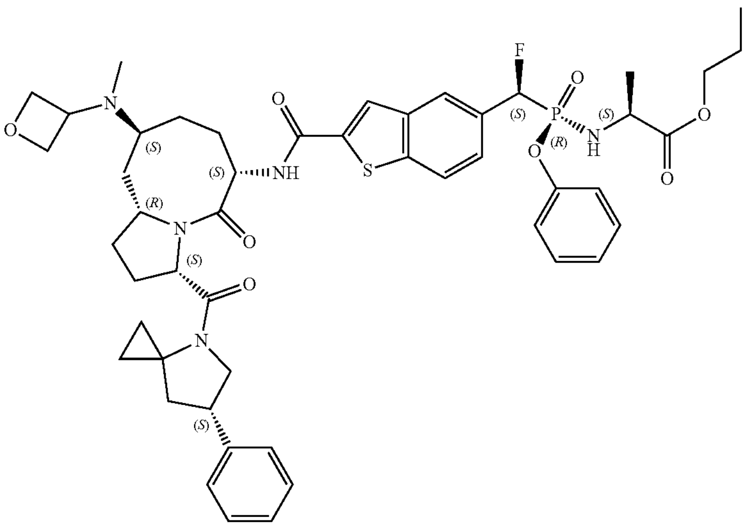 |

TABLE 1C-continued

| | | |
|---|---|---|
| C31 | propyl ((S)-((R)-(2-(((3S,6S,9S,10aR)-3-((R)-6-(4-(dimethylamino)pyridin-3-yl)-4-azaspiro[2.4]heptane-4-carbonyl)-9-morpholino-5-oxodecahydropyrrolo[1,2-a]azocin-6-yl)carbamoyl)benzo[b]thiophen-5-yl)fluoromethyl)(phenoxy)phosphoryl)-L-alaninate | 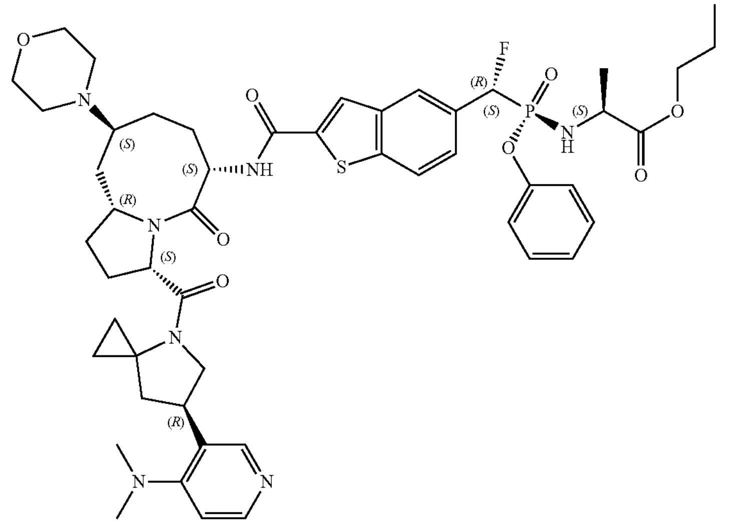 |
| C32 | propyl (((R)-fluoro(2-(((3S,6S,9S,10aR)-9-(methyl((S)-tetrahydrofuran-3-yl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate | 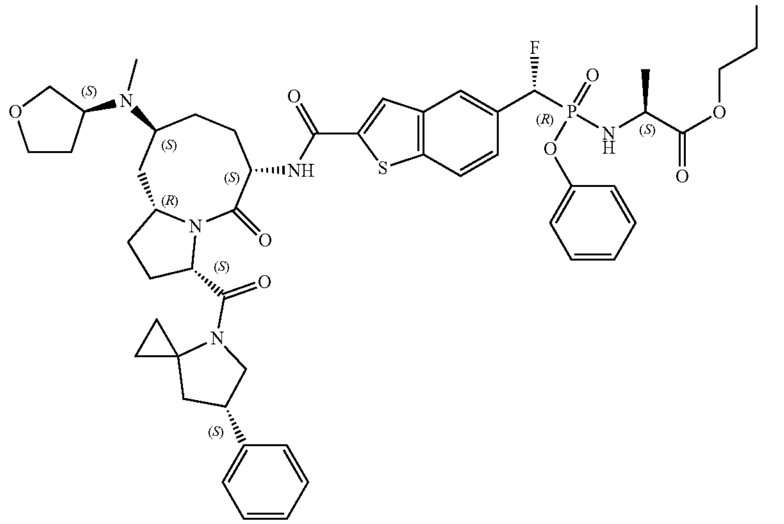 |
| C33 | propyl ((R)-((S)-fluoro(2-(((3S,6S,9S,10aR)-9-morpholino-5-oxo-3-((R)-6-(pyridin-3-yl)-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate | 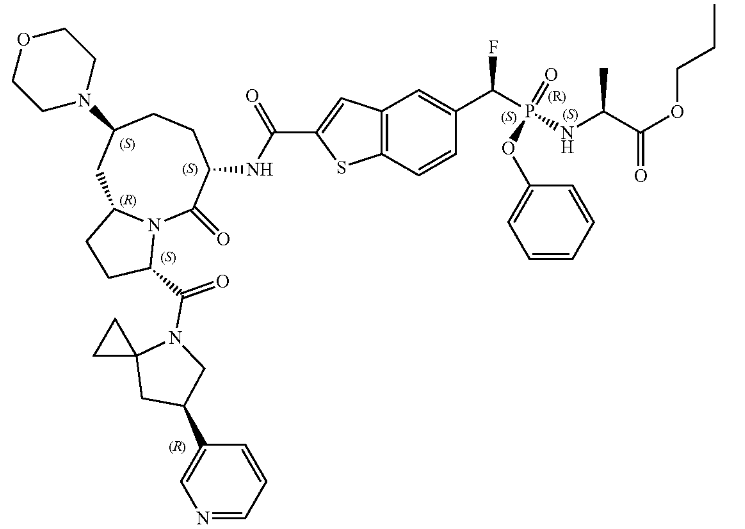 |

TABLE 1C-continued

| | | |
|---|---|---|
| C34 | propyl ((S)-((R)-fluoro(2-(((3S,6S,9S,10aR)-9-(methyl(oxetan-3-yl)amino)-5-oxo-3-((S)-6-phenyl-4-azaspiro [2.4] heptane-4-carbonyl) decahydropyrrolo [1,2-a]azocin-6-yl)carbamoyl) benzo [b]thiophen-5-yl)methyl) (phenoxy) phosphoryl)-L-alaninate | 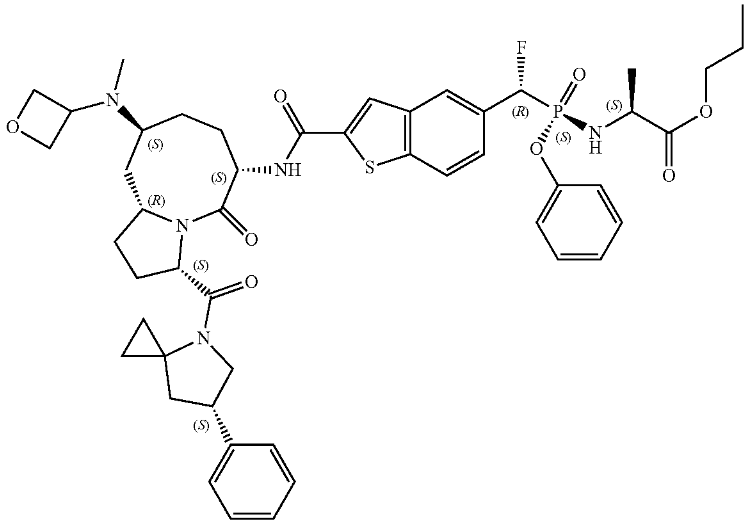 |
| C35 | propyl ((S)-((S)-fluoro(2-(((3S,6S,9S,10aR)-9-(methyl(oxetan-3-yl)amino)-5-oxo-3-((S)-6-phenyl-4-azaspiro[2.4] heptane-4-carbonyl) decahydropyrrolo [1,2-a]azocin-6-yl)carbamoyl) benzo [b]thiophen-5-yl)methyl) (phenoxy) phosphoryl)-L-alaninate | 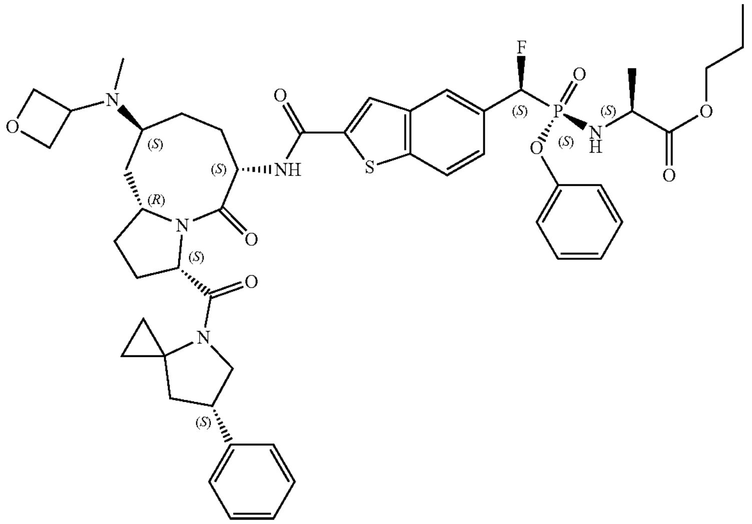 |
| C36 | propyl (((R)-fluoro(2-(((3S,6S,9S,10aR)-3-((S)-6-(3-fluorophenyl)-4-azaspiro [2.4] heptane-4-carbonyl)-9-(methyl(oxetan-3-yl)amino)-5-oxodecahydropyrrolo [1,2-a]azocin-6-yl)carbamoyl) benzo [b]thiophen-5-yl)methyl) (phenoxy) phosphoryl)-L-alaninate | 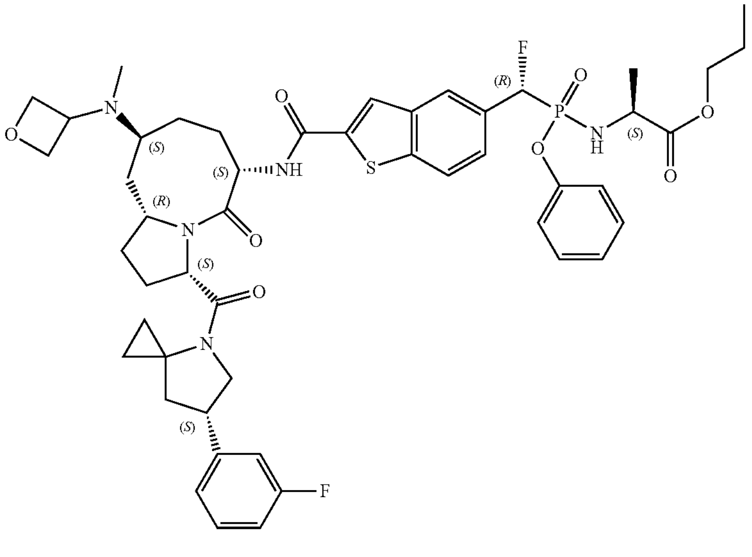 |

TABLE 1C-continued

| | | |
|---|---|---|
| C37 | propyl ((R)-((R)-fluoro(2-(((3S,6S,9S,10aR)-9-(methyl(oxetan-3-yl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate | 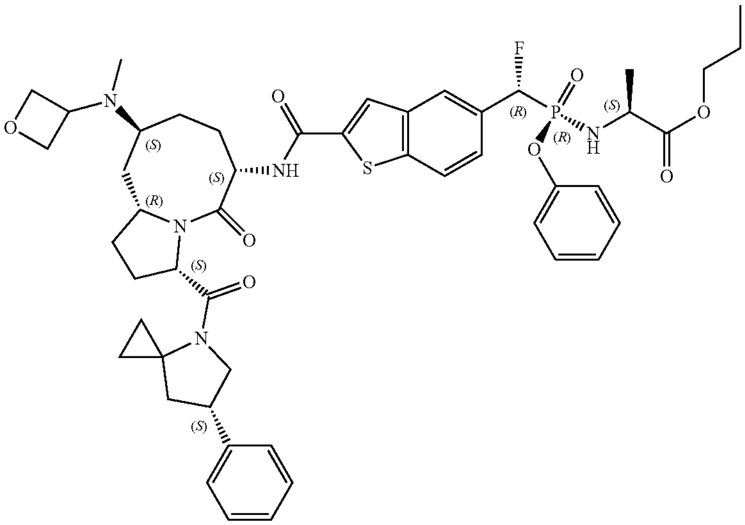 |
| C38 | propyl (((R)-(2-(((3S,6S,9S,10aR)-3-((6S,7R)-7-cyano-6-phenyl-4-azaspiro [2.4]heptane-4-carbonyl)-9-morpholino-5-oxodecahydropyrrolo[1,2-a]azocin-6-yl)carbamoyl)benzo[b]thiophen-5-yl)fluoromethyl)(phenoxy)phosphoryl)-L-alaninate | 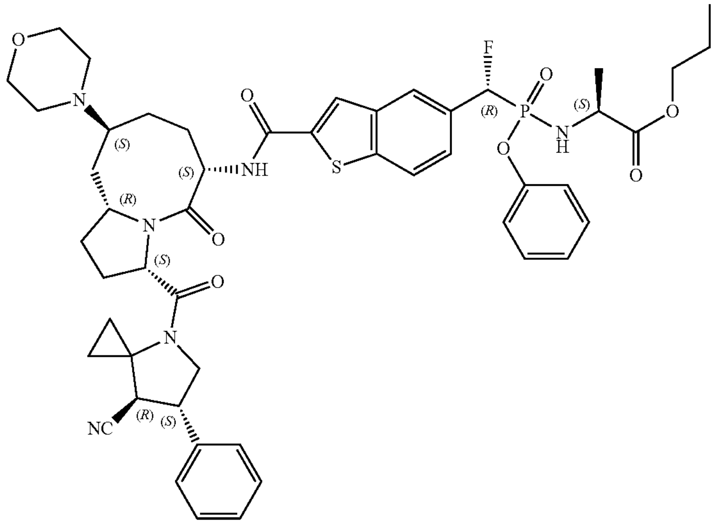 |
| C39 | propyl (((R)-fluoro(2-(((3S,6S,9S,10aR)-9-morpholino-5-oxo-3-((R)-6-(pyridin-3-yl)-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate | 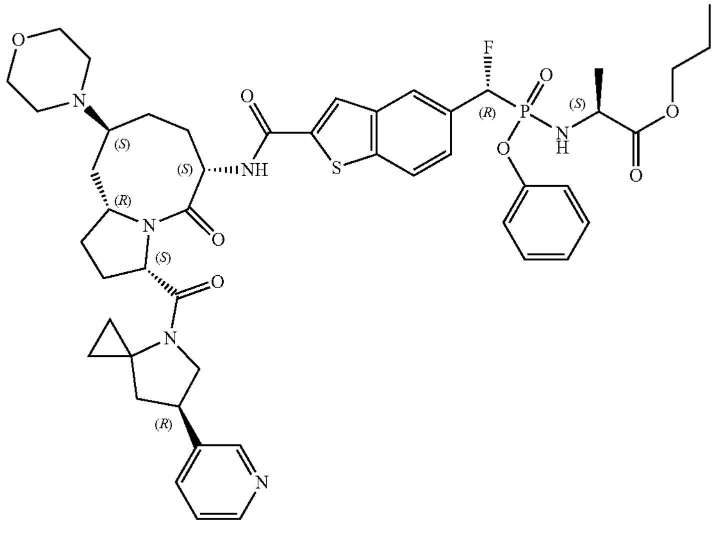 |

TABLE 1C-continued

| | | |
|---|---|---|
| C40 | propyl ((R)-((R)-fluoro(2-(((3S,6S,9S,10aR)-9-morpholino-5-oxo-3-((R)-6-(pyridin-3-yl)-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate | 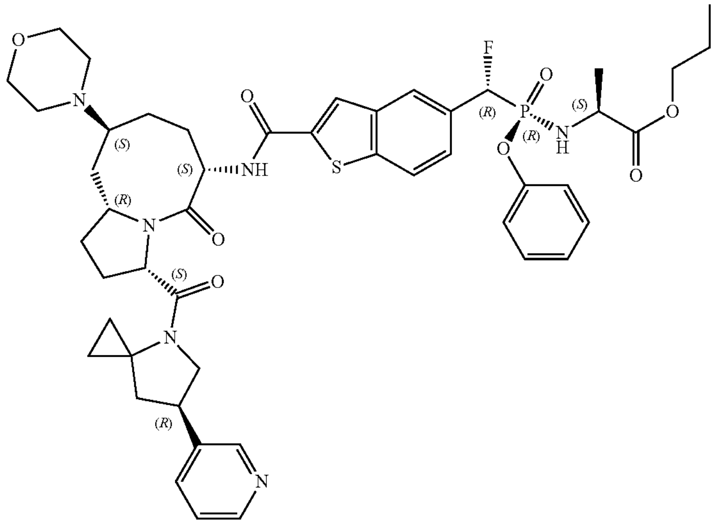 |
| C41 | propyl ((R)-((R)-fluoro(2-(((3S,6S,9S,10aR)-9-morpholino-5-oxo-3-((S)-6-(pyridin-3-yl)-4-azaspiro [2.4]heptane-4-carbonyl)decahydropyrrolo[1,2-a]azocin-6-yl)carbamoyl)benzo[b]thiophen-5-yl)methyl)(phenoxy)phosphoryl)-L-alaninate | 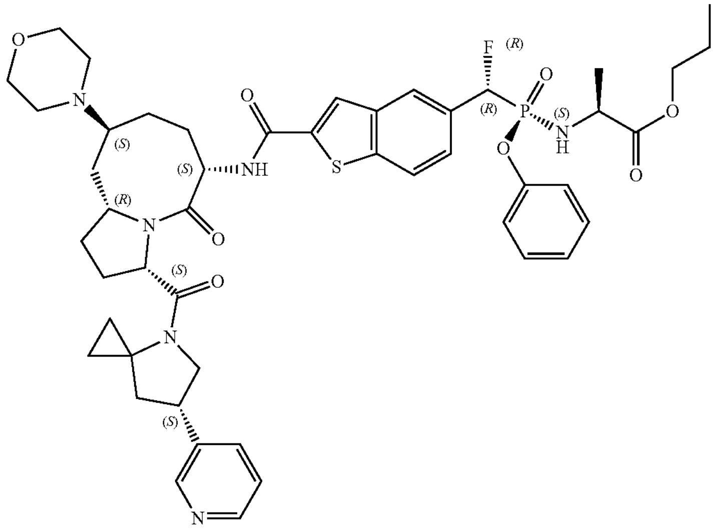 |
| C42 | propyl ((S)-((R)-fluoro(2-(((3S,6S,9S,10aR)-9-morpholino-5-oxo-3-((S)-6-(pyridin-3-yl)-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate | 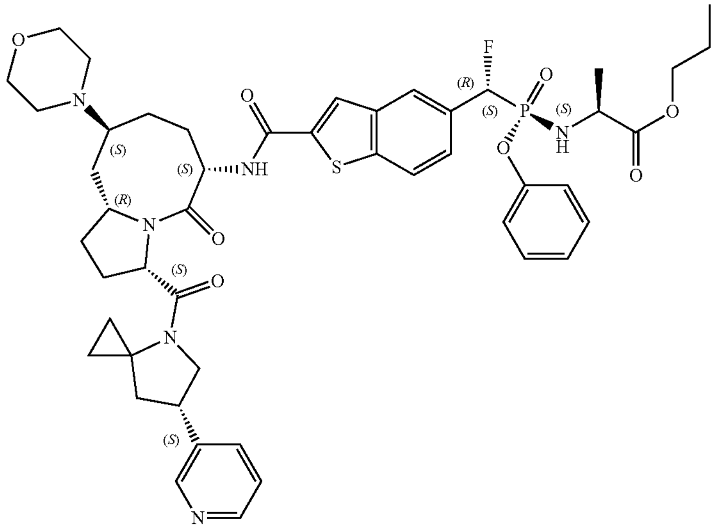 |

TABLE 1C-continued

| | | |
|---|---|---|
| C43 | propyl ((S)-((S)-fluoro(2-(((3S,6S,9S,10aR)-9-morpholino-5-oxo-3-((R)-6-(pyridin-3-yl)-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate | 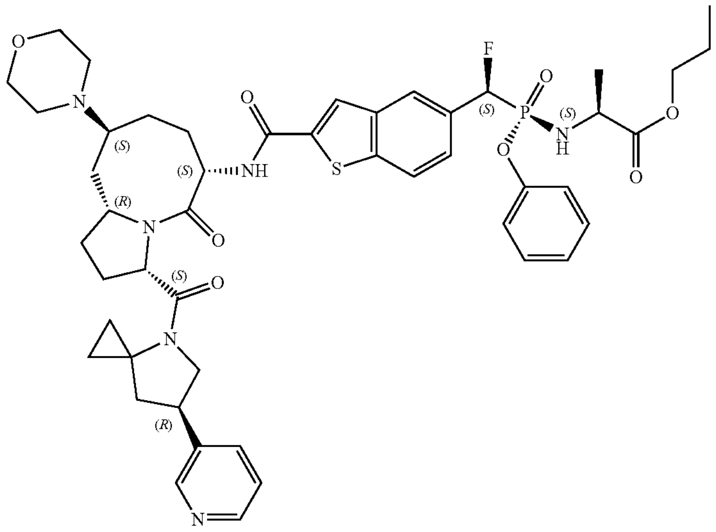 |
| C44 | propyl ((R)-((R)-(2-(((3S,6S,9S,10aR)-3-((6S,7R)-7-cyano-6-(pyridin-3-yl)-4-azaspiro[2.4]heptane-4-carbonyl)-9-morpholino-5-oxodecahydropyrrolo[1,2-a]azocin-6-yl)carbamoyl)benzo[b]thiophen-5-yl)fluoromethyl)(phenoxy)phosphoryl)-L-alaninate | 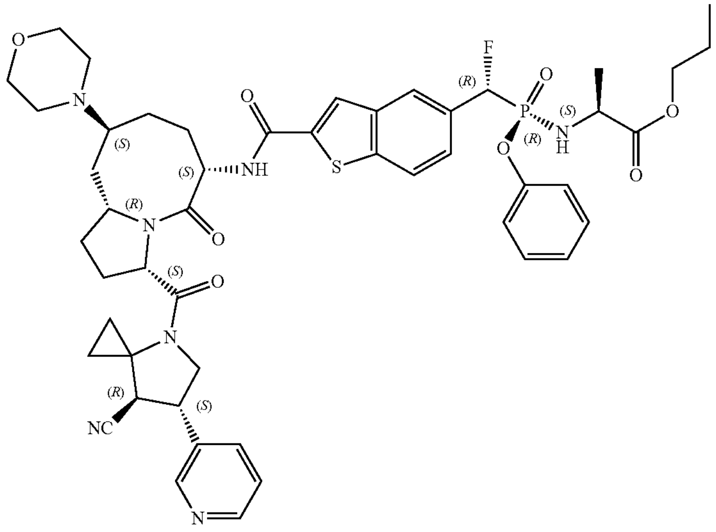 |
| C45 | propyl ((S)-((R)-(2-(((3S,6S,9S,10aR)-3-((6S,7R)-7-cyano-6-(pyridin-3-yl)-4-azaspiro[2.4]heptane-4-carbonyl)-9-morpholino-5-oxodecahydropyrrolo[1,2-a]azocin-6-yl)carbamoyl)benzo[b]thiophen-5-yl)fluoromethyl)(phenoxy)phosphoryl)-L-alaninate | 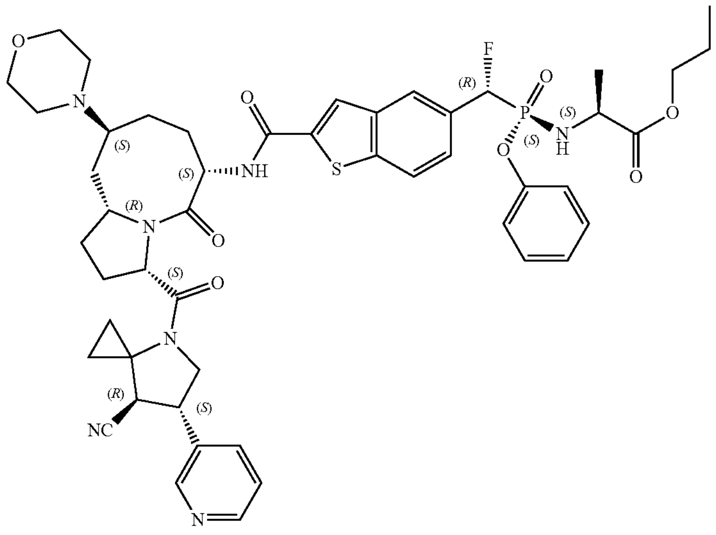 |

TABLE 1C-continued

| | | |
|---|---|---|
| C46 | propyl ((R)-((R)-(2-(((3S,6S,9S,10aR)-3-((R)-6-(4-(dimethylamino)pyridin-3-yl)-4-azaspiro[2.4]heptane-4-carbonyl)-9-morpholino-5-oxodecahydropyrrolo[1,2-a]azocin-6-yl)carbamoyl)benzo[b]thiophen-5-yl)fluoromethyl)(phenoxy)phosphoryl)-L-alaninate | 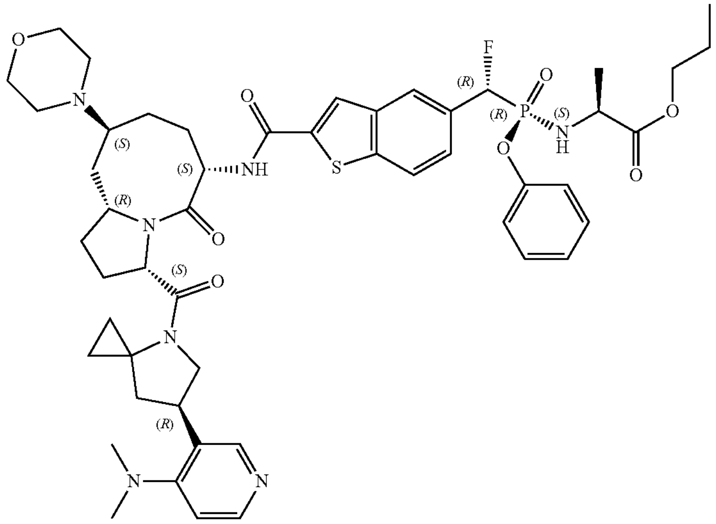 |
| C47 | propyl ((R)-((S)-(2-(((3S,6S,9S,10aR)-3-((R)-6-(4-(dimethylamino)pyridin-3-yl)-4-azaspiro[2.4]heptane-4-carbonyl)-9-morpholino-5-oxodecahydropyrrolo[1,2-a]azocin-6-yl)carbamoyl)benzo[b]thiophen-5-yl)fluoromethyl)(phenoxy)phosphoryl)-L-alaninate | 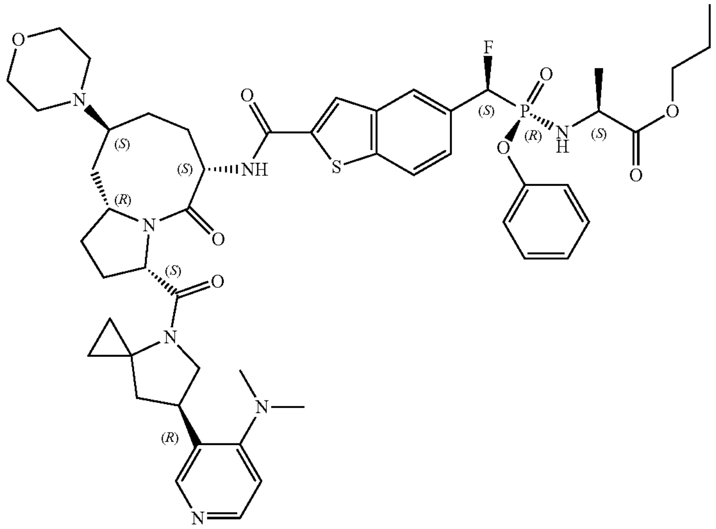 |
| C48 | propyl ((S)-((S)-(2-(((3S,6S,9S,10aR)-3-((R)-6-(4-(dimethylamino)pyridin-3-yl)-4-azaspiro[2.4]heptane-4-carbonyl)-9-morpholino-5-oxodecahydropyrrolo[1,2-a]azocin-6-yl)carbamoyl)benzo[b]thiophen-5-yl)fluoromethyl)(phenoxy)phosphoryl)-L-alaninate | 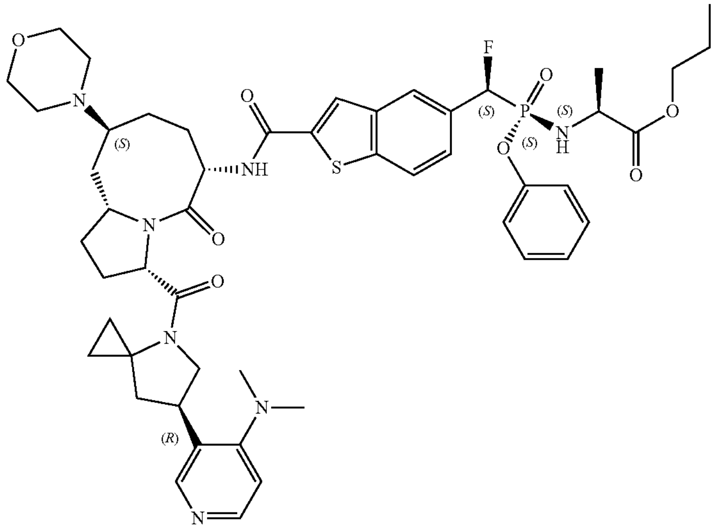 |

TABLE 1C-continued

| | | |
|---|---|---|
| C49 | isopropyl ((S)-((R)-fluoro(2-(((3S,6S,9S,10aR)-9-morpholino-5-oxo-3-((R)-6-(pyridin-3-yl)-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate | 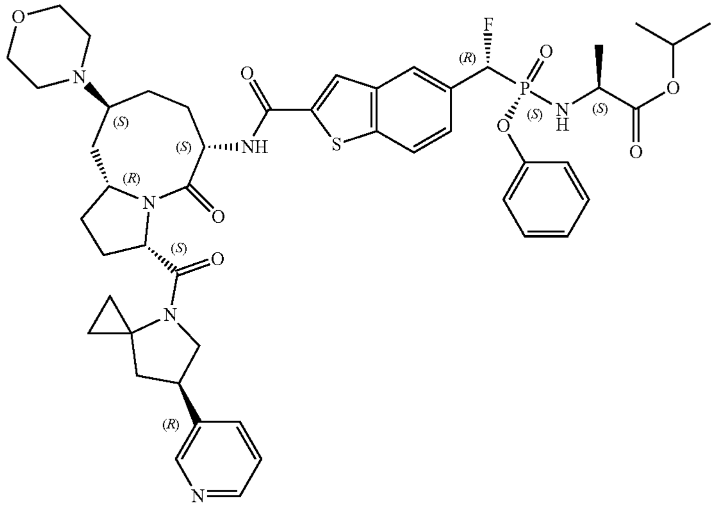<br>Phosphorus absolute stereochemistry arbitrarily assigned |
| C50 | isopropyl ((R)-((R)-fluoro(2-(((3S,6S,9S,10aR)-9-morpholino-5-oxo-3-((R)-6-(pyridin-3-yl)-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate | 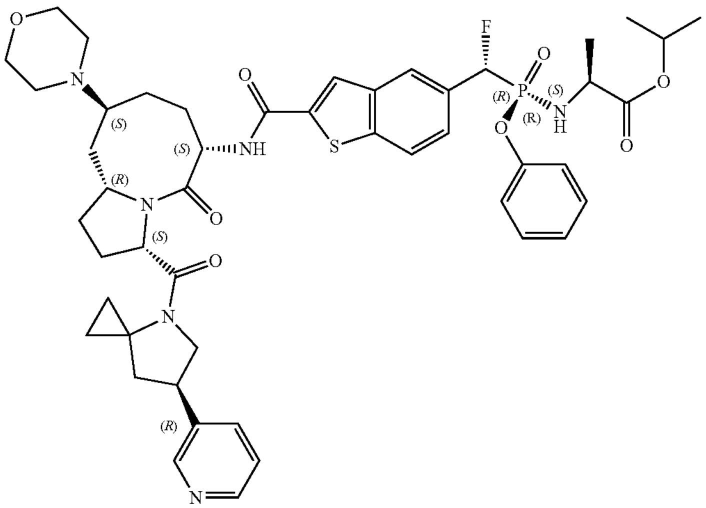<br>Phosphorus absolute stereochemistry arbitrarily assigned |
| C51 | propyl (((S)-fluoro(2-(((3S,6S,9S,10aR)-9-(methyl(((R)-oxetan-2-yl)methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate | 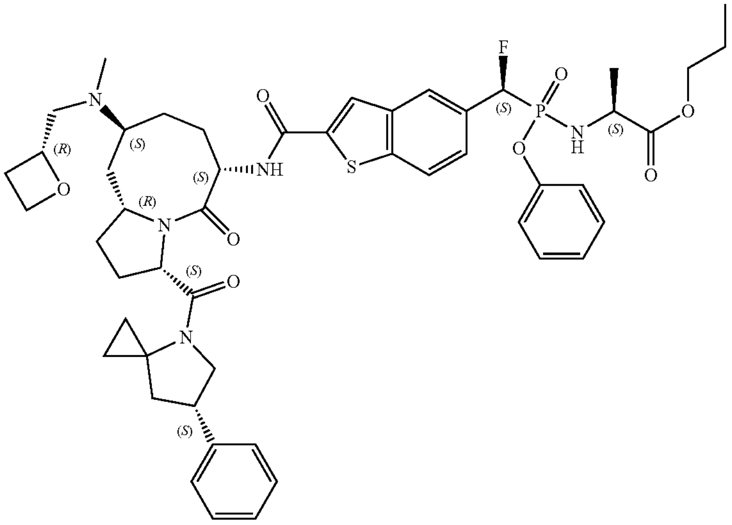 |

TABLE 1C-continued

| | | |
|---|---|---|
| C52 | benzyl (((R)-(2-(((3S,6S,9S,10aR)-9-((3,3-difluoropropyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)(phenoxy)phosphoryl)-L-alaninate | 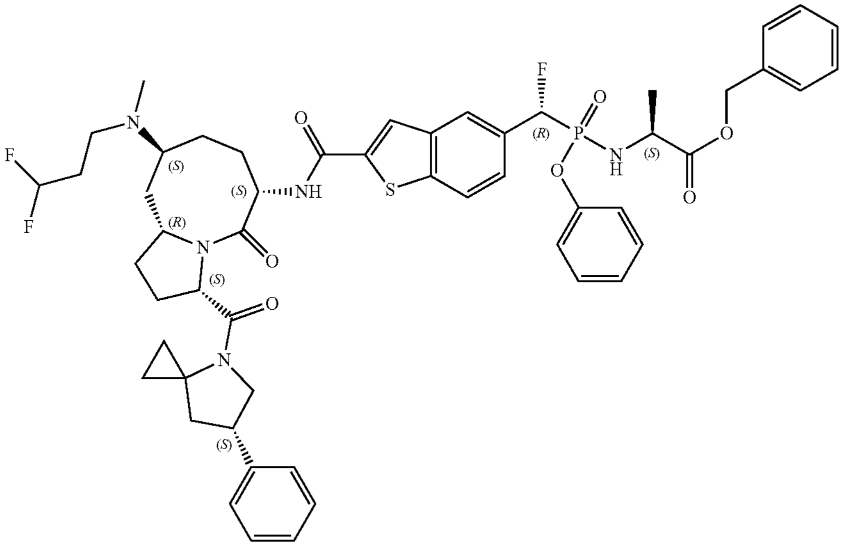 |
| C53 | propyl (2S)-2-((((R)-(2-(((3S,6S,9S,10aR)-9-((3,3-difluoropropyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)(phenoxy)phosphoryl)amino)butanoate. | 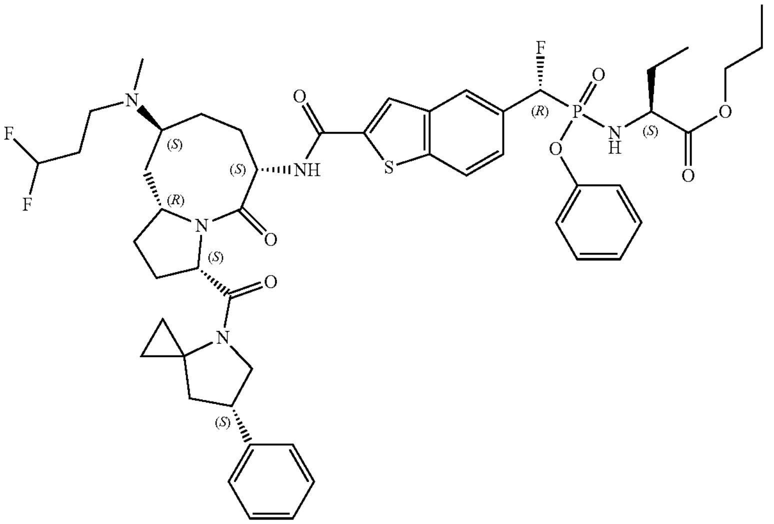 |
| C54 | 2-methoxyethyl (((R)-(2-(((3S,6S,9S,10aR)-9-((3,3-difluoropropyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)(phenoxy)phosphoryl)-L-alaninate | 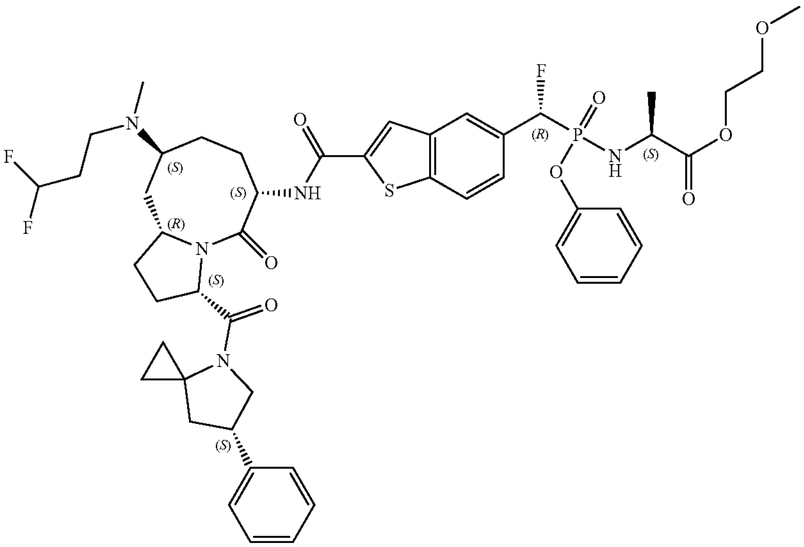 |

TABLE 1C-continued

| | | |
|---|---|---|
| C55 | propyl (((R)-(2-(((3S,6S,9S,10aR)-9-(ethyl((1s,3R)-3-fluorocyclobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)(phenoxy)phosphoryl)-L-alaninate | 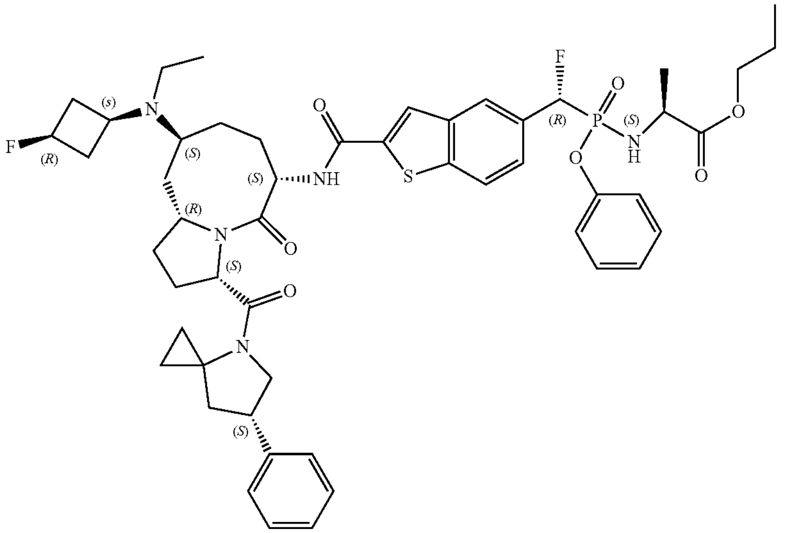 |
| C56 | propyl (((S)-(2-(((3S,6S,9S,10aR)-9-(ethyl((1s,3R)-3-fluorocyclobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)(phenoxy)phosphoryl)-L-alaninate | 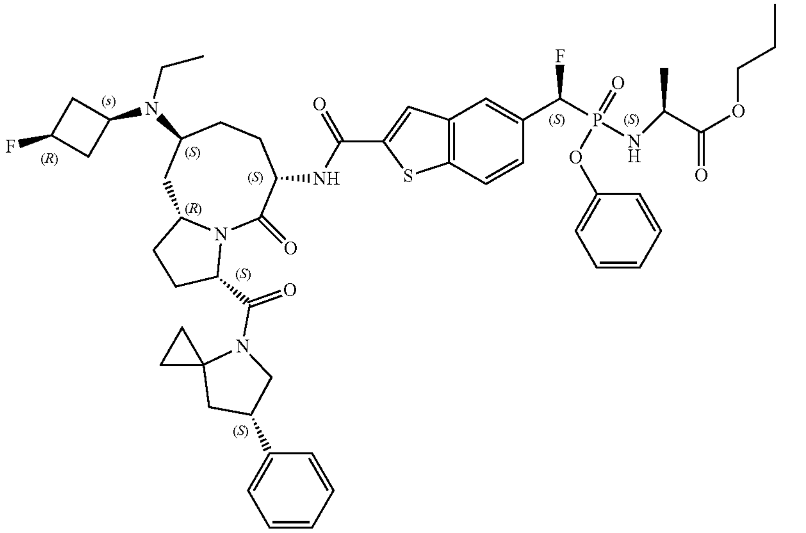 |
| C57 | isopropyl (((R)-(2-(((3S,6S,9S,10aR)-9-((3,3-difluoropropyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)(phenoxy)phosphoryl)-L-alaninate | 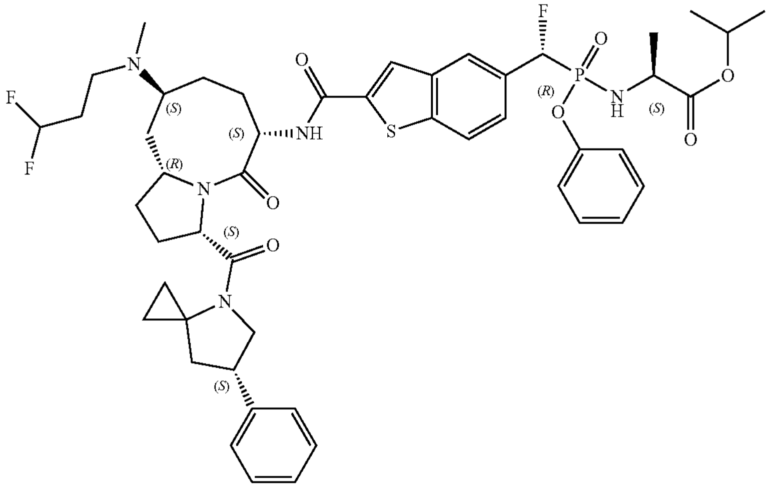 |

TABLE 1C-continued

| | | |
|---|---|---|
| C58 | ethyl (((R)-(2-(((3S,6S,9S,10aR)-9-((3,3-difluoropropyl)(methyl)amino)-5-oxo-3-((S)-6-phenyl-4-azaspiro [2.4] heptane-4-carbonyl) decahydropyrrolo [1,2-a]azocin-6-yl)carbamoyl) benzo [b]thiophen-5-yl)fluoromethyl) (phenoxy) phosphoryl)-L-alaninate | 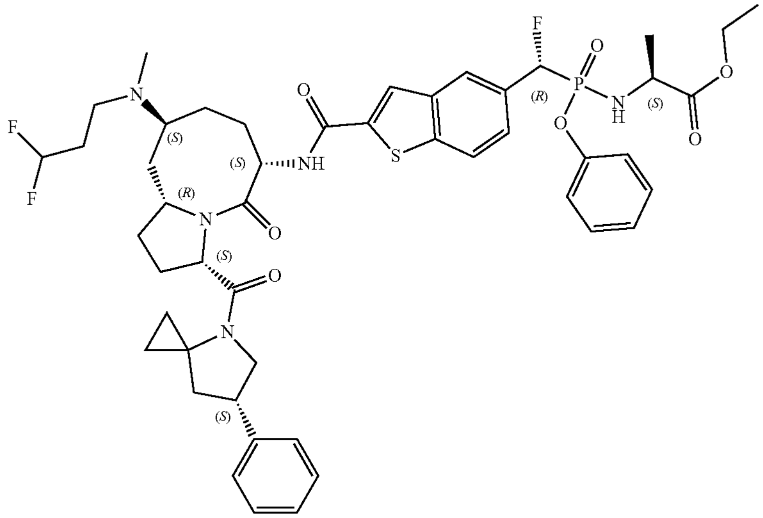 |
| C59 | propyl ((R)-((R)-fluoro(2-(((3S,6S,9S,10aR)-9-(methyl((R)-tetrahydrofuran-3-yl)amino)-5-oxo-3-((S)-6-phenyl-4-azaspiro[2.4] heptane-4-carbonyl) decahydropyrrolo [1,2-a]azocin-6-yl)carbamoyl) benzo [b]thiophen-5-yl)methyl) (phenoxy) phosphoryl)-L-alaninate | 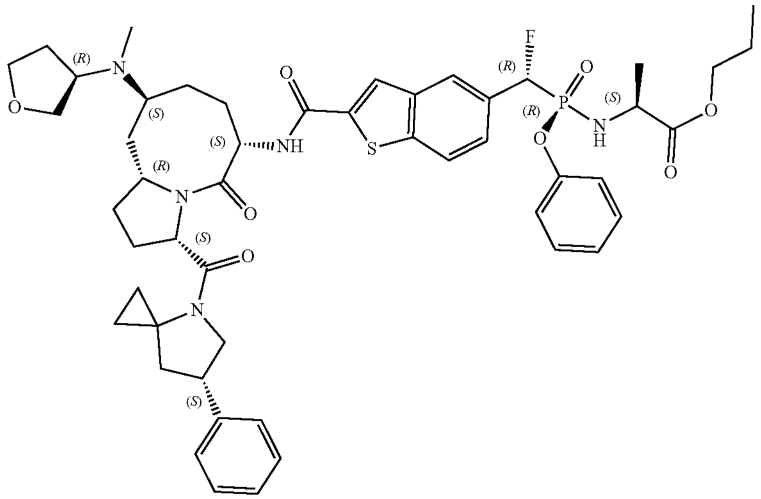 |
| C60 | propyl ((S)-((R)-fluoro(2-(((3S,6S,9S,10aR)-9-(methyl((R)-tetrahydrofuran-3-yl)amino)-5-oxo-3-((S)-6-phenyl-4-azaspiro[2.4] heptane-4-carbonyl) decahydropyrrolo [1,2-a]azocin-6-yl)carbamoyl) benzo [b]thiophen-5-yl)methyl) (phenoxy) phosphoryl)-L-alaninate | 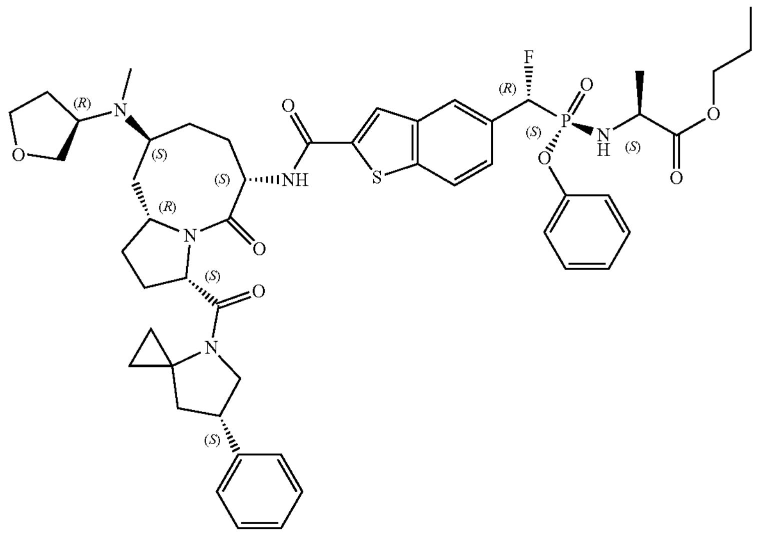 |

TABLE 1C-continued

| | | |
|---|---|---|
| C61 | cyclobutyl (((R)-fluoro(2-(((3S,6S,9S,10aR)-9-(((1s,3R)-3-fluorocyclobutyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate | 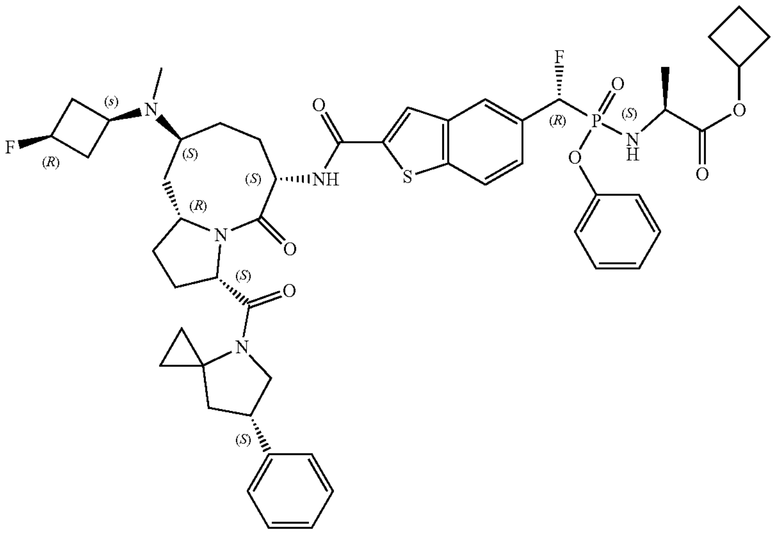 |
| C62 | cyclobutyl (((S)-fluoro(2-(((3S,6S,9S,10aR)-9-(((1s,3R)-3-fluorocyclobutyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate | 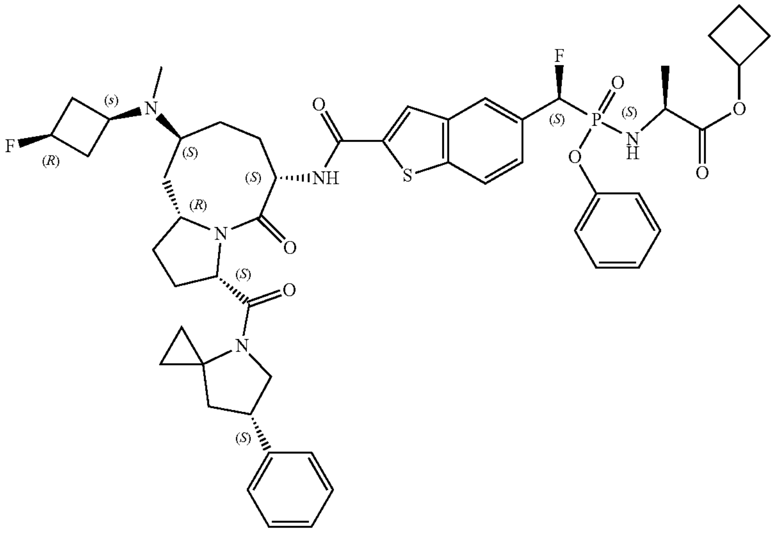 |
| C63 | propyl (((R)-fluoro(2-(((3S,6S,9S,10aR)-9-(((1s,3R)-3-fluorocyclobutyl)(methyl)amino)-5-oxo-3-((S)-6-phenyl-4-azaspiro [2.4]heptane-4-carbonyl)decahydropyrrolo[1,2-a]azocin-6-yl)carbamoyl)benzo[b]thiophen-5-yl)methyl)(2,2,2-trifluoroethoxy)phosphoryl)-L-alaninate | 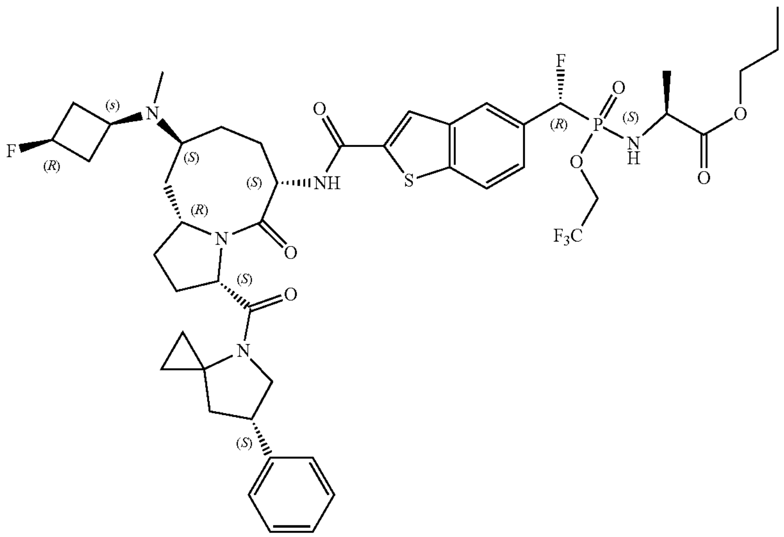 |

TABLE 1C-continued

| | | |
|---|---|---|
| C64 | propyl (((R)-fluoro(2-(((3S,6S,9S,10aR)-9-(((1s,3R)-3-fluorocyclobutyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(2,2,2-trifluoroethoxy)phosphoryl)-L-alaninate | 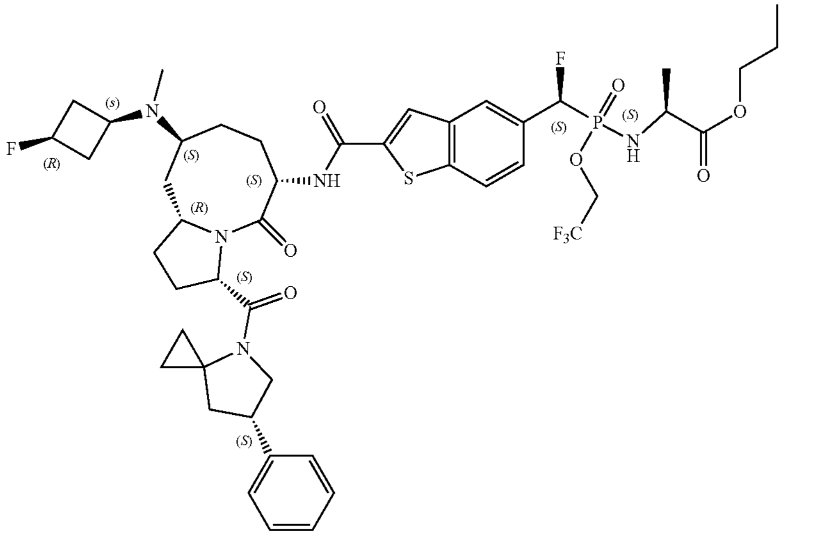 |
| C65 | propyl (((R)-(2-(((3S,6S,9S,10aR)-9-(((1s,3R)-3-cyanocyclobutyl)(methyl)amino)-5-oxo-3-((S)-6-phenyl-4-azaspiro [2.4]heptane-4-carbonyl)decahydropyrrolo[1,2-a]azocin-6-yl)carbamoyl)benzo[b]thiophen-5-yl)fluoromethyl)(phenoxy)phosphoryl)-L-alaninate | 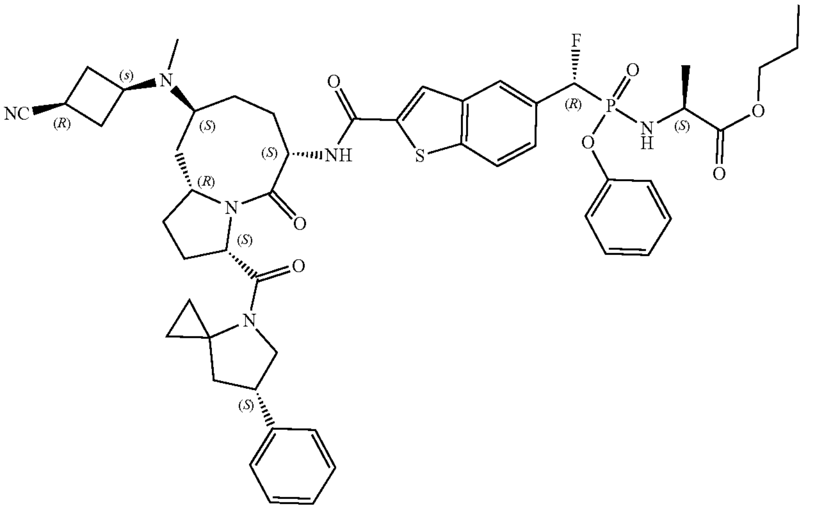 |
| C66 | (3,3-difluorocyclobutyl)methyl (((R)-fluoro(2-(((3S,6S,9S,10aR)-9-(((1s,3R)-3-fluorocyclobutyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate | 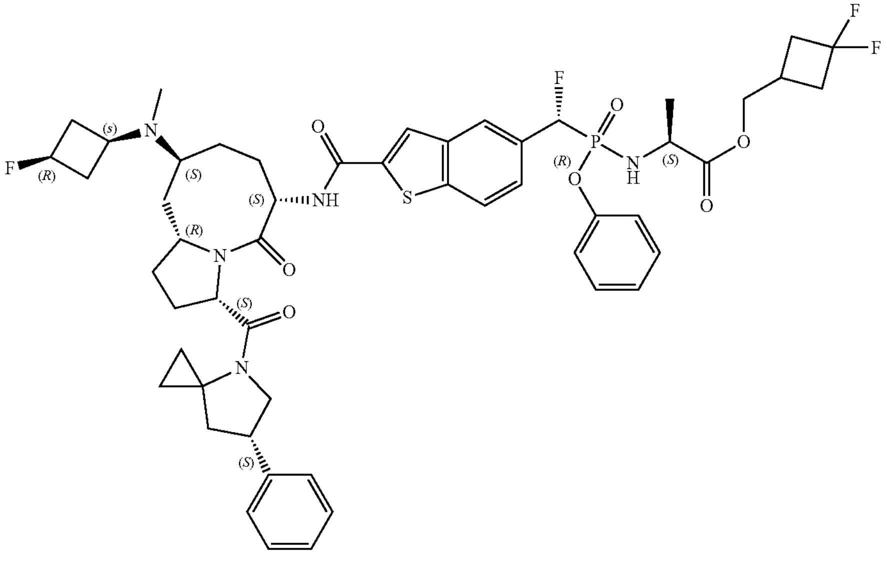 |

TABLE 1C-continued

| | | |
|---|---|---|
| C67 | (3,3-difluorocyclobutyl) methyl (((S)-fluoro(2-(((3S,6S,9S,10aR)-9-(((1s,3R)-3-fluorocyclobutyl) (methyl)amino)-5-oxo-3-((S)-6-phenyl-4-azaspiro[2.4] heptane-4-carbonyl) decahydropyrrolo [1,2-a]azocin-6-yl)carbamoyl) benzo [b]thiophen-5-yl)methyl) (phenoxy) phosphoryl)-L-alaninate | 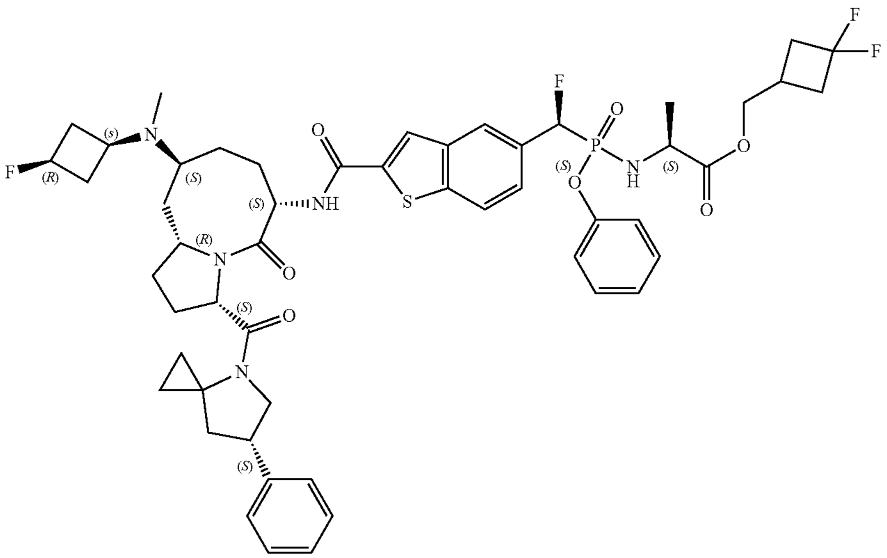 |
| C68 | isopropyl (((R)-fluoro(2-(((3S,6S,9S,10aR)-9-(((1s,3R)-3-fluorocyclobutyl) (methyl)amino)-5-oxo-3-((S)-6-phenyl-4-azaspiro[2.4] heptane-4-carbonyl) decahydropyrrolo [1,2-a]azocin-6-yl)carbamoyl) benzo [b]thiophen-5-yl)methyl) (phenoxy) phosphoryl)-L-alaninate | 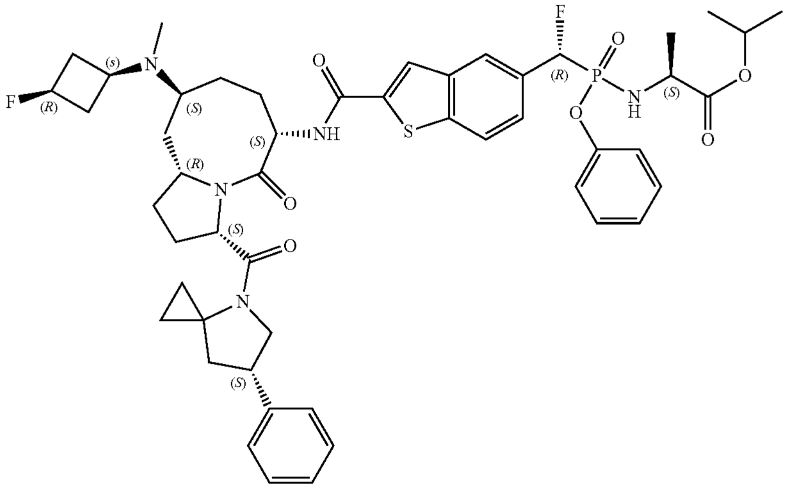 |
| C69 | isopropyl (((S)-fluoro(2-(((3S,6S,9S,10aR)-9-(((1s,3R)-3-fluorocyclobutyl) (methyl)amino)-5-oxo-3-((S)-6-phenyl-4-azaspiro[2.4] heptane-4-carbonyl) decahydropyrrolo [1,2-a]azocin-6-yl)carbamoyl) benzo [b]thiophen-5-yl)methyl) (phenoxy) phosphoryl)-L-alaninate | 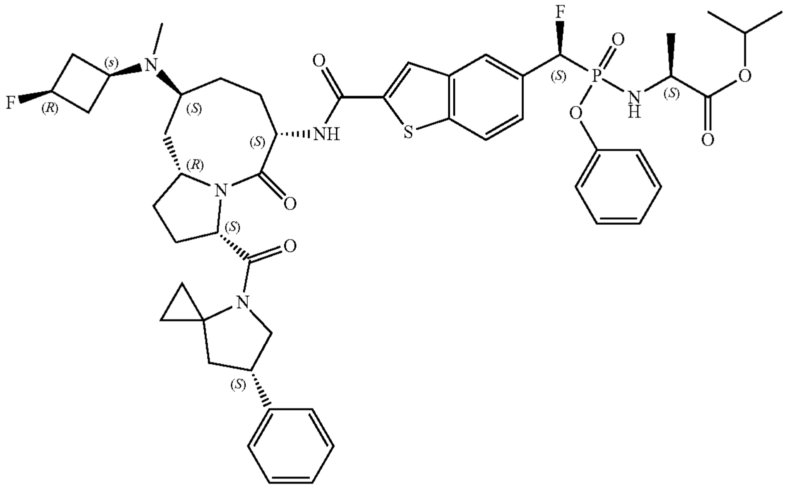 |

TABLE 1C-continued

| | | |
|---|---|---|
| C70 | propyl ((R)-((R)-(2-(((3S,6S,9S,10aR)-9-(((1s,3R)-3-(difluoromethyl) cyclobutyl)(methyl) amino)-5-oxo-3-((S)-6-phenyl-4-azaspiro[2.4] heptane-4-carbonyl) decahydropyrrolo [1,2-a]azocin-6-yl)carbamoyl) benzo [b]thiophen-5-yl)fluoromethyl) (phenoxy) phosphoryl)-L-alaninate | 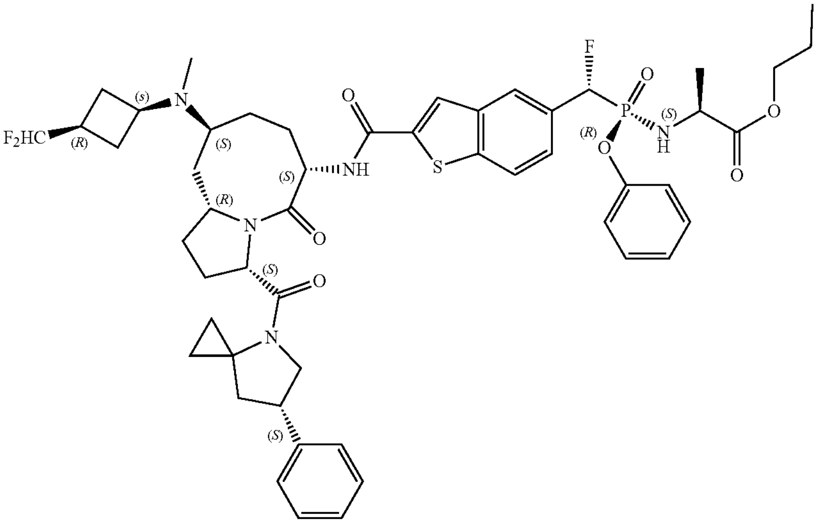 |
| C71 | propyl ((S)-((R)-(2-(((3S,6S,9S,10aR)-9-(((1s,3R)-3-(difluoromethyl) cyclobutyl)(methyl) amino)-5-oxo-3-((S)-6-phenyl-4-azaspiro[2.4] heptane-4-carbonyl) decahydropyrrolo [1,2-a]azocin-6-yl)carbamoyl) benzo [b]thiophen-5-yl)fluoromethyl) (phenoxy) phosphoryl)-L-alaninate | 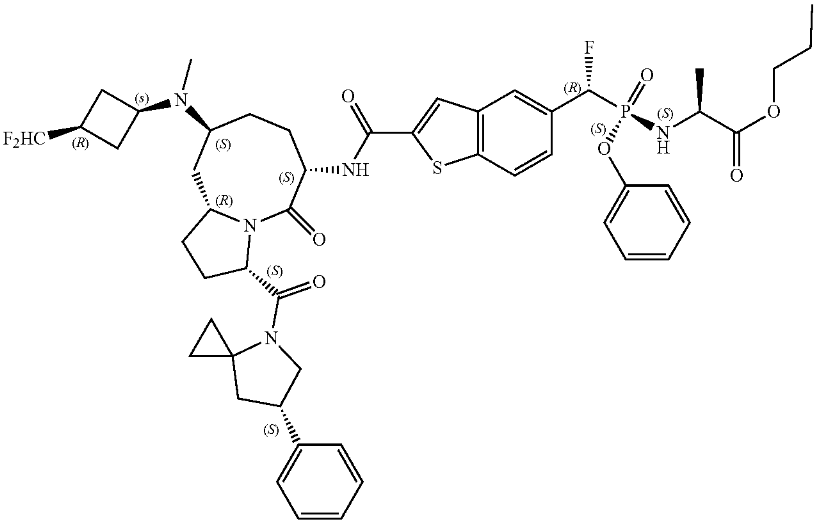 |
| C72 | (1r,3S)-3-fluorocyclobutyl (((S)-fluoro(2-(((3S,6S,9S,10aR)-9-(((1s,3R)-3-fluorocyclobutyl) (methyl)amino)-5-oxo-3-((S)-6-phenyl-4-azaspiro [2.4] heptane-4-carbonyl) decahydropyrrolo [1,2-a]azocin-6-yl)carbamoyl) benzo [b]thiophen-5-yl)methyl) (phenoxy) phosphoryl)-L-alaninate | 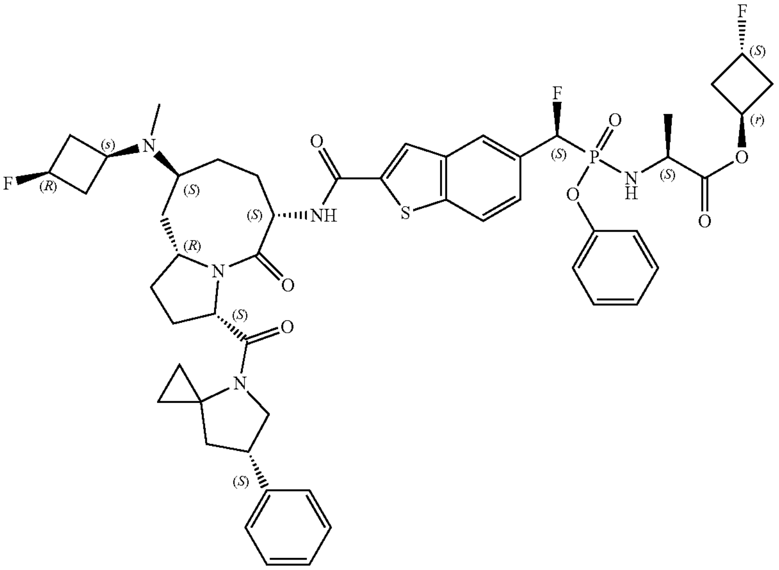 |

TABLE 1C-continued

| | | |
|---|---|---|
| C73 | (1r,3S)-3-fluorocyclobutyl (((R)-fluoro(2-(((3S,6S,9S,10aR)-9-(((1s,3R)-3-fluorocyclobutyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate | 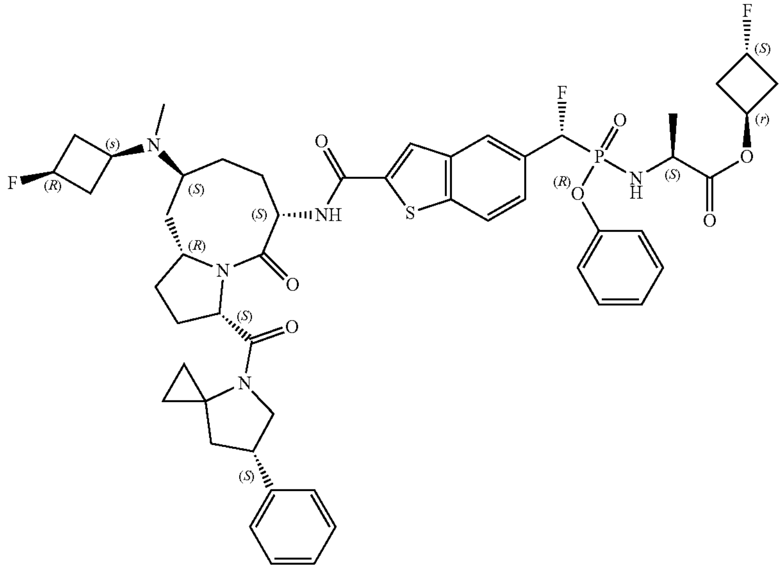 |
| C74 | 2-ethylbutyl (((R)-fluoro(2-(((3S,6S,9S,10aR)-9-(((1s,3R)-3-fluorocyclobutyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate | 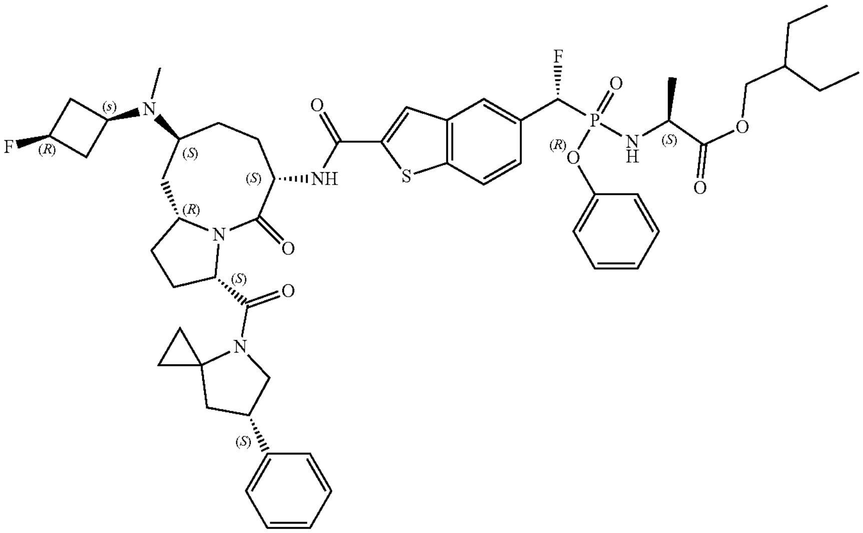 |
| C75 | neopentyl (((R)-fluoro(2-(((3S,6S,9S,10aR)-9-(((1s,3R)-3-fluorocyclobutyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate | 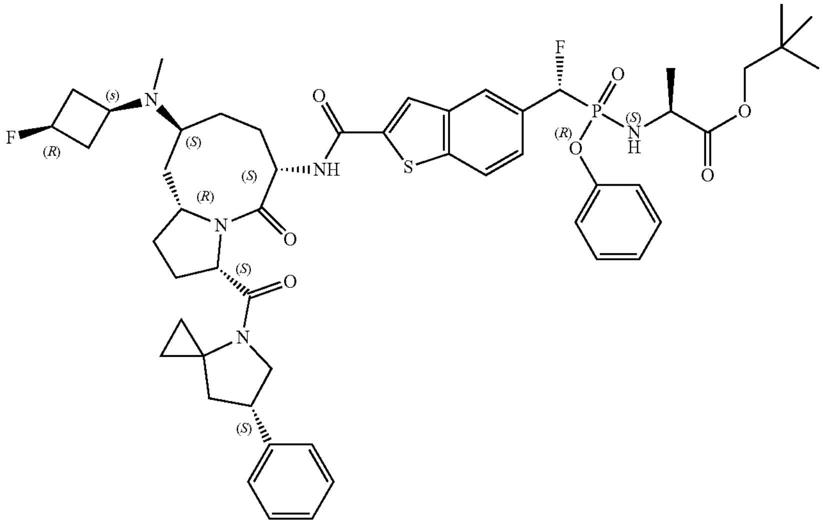 |

TABLE 1C-continued

| | | |
|---|---|---|
| C76 | (1s,3R)-3-fluorocyclobutyl (((S)-fluoro(2-(((3S,6S,9S,10aR)-9-(((1s,3R)-3-fluorocyclobutyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate | 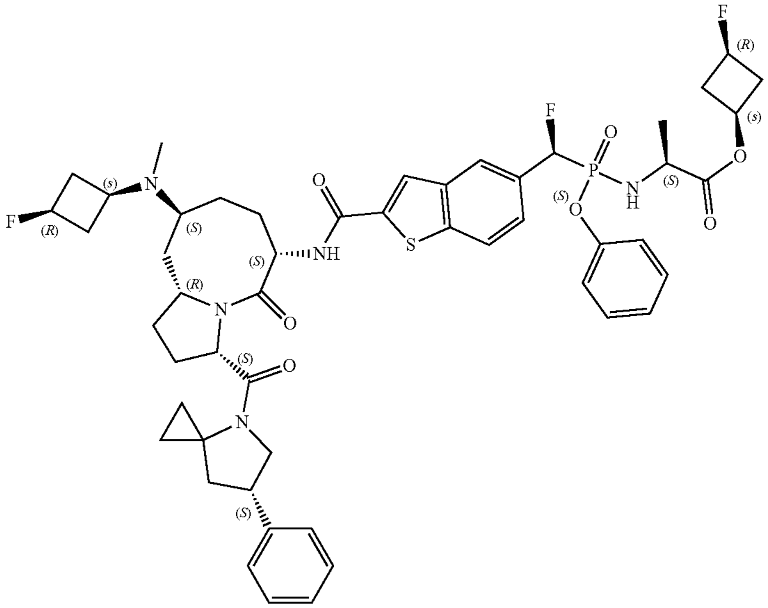 |
| C77 | (1s,3R)-3-fluorocyclobutyl (((R)-fluoro(2-(((3S,6S,9S,10aR)-9-(((1s,3R)-3-fluorocyclobutyl)(methyl)amino)-5-oxo-3-((S)-6-phenyl-4-azaspiro [2.4]heptane-4-carbonyl)decahydropyrrolo[1,2-a]azocin-6-yl)carbamoyl)benzo[b]thiophen-5-yl)methyl)(phenoxy)phosphoryl)-L-alaninate | 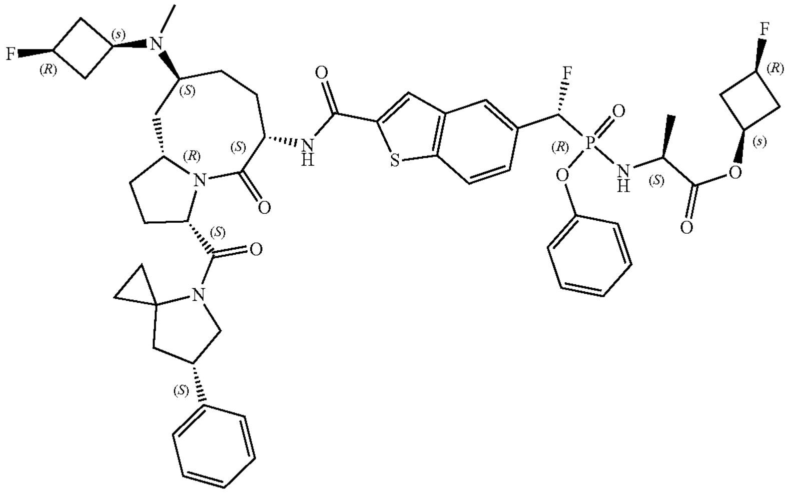 |

TABLE 1C-continued

| | | |
|---|---|---|
| C78 | isopropyl ((R)-ethoxy((S)-fluoro(2-(((3S,6S,9S,10aR)-9-(((1s,3R)-3-fluorocyclobutyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)phosphoryl)-L-alaninate | 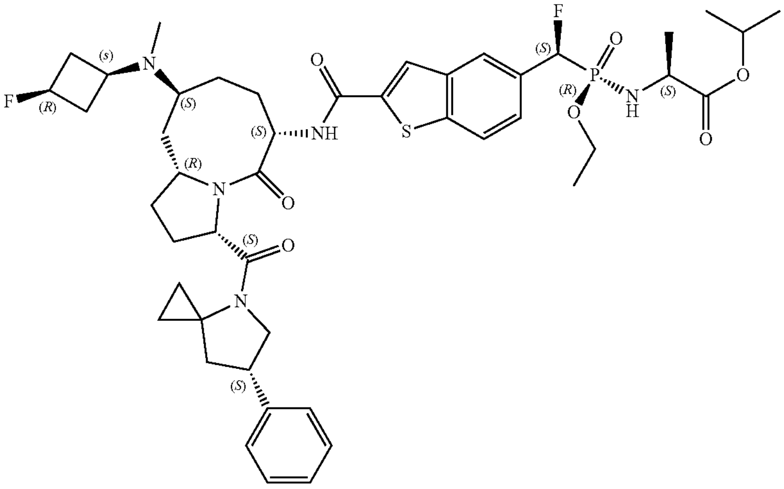 Phosphorus absolute stereochemistry arbitrarily assigned |
| C79 | 2-ethylbutyl (((S)-fluoro(2-(((3S,6S,9S,10aR)-9-(((1s,3R)-3-fluorocyclobutyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate | 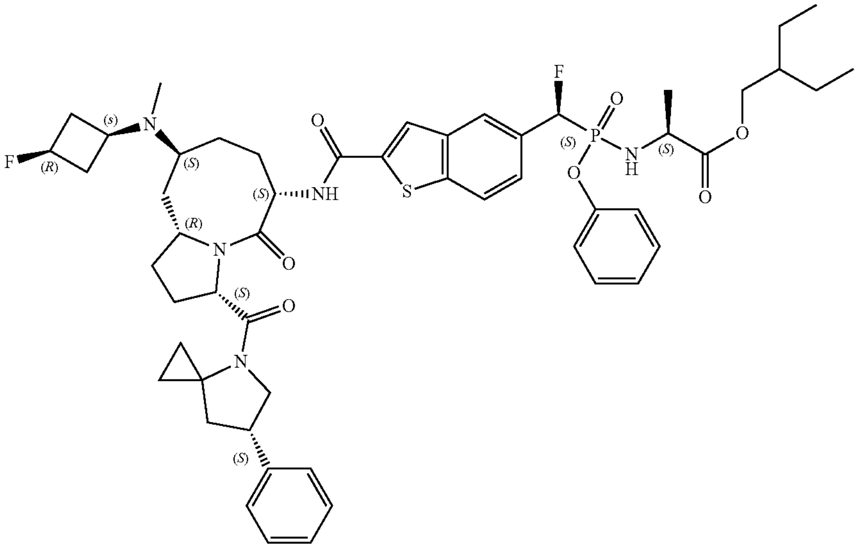 |
| C80 | neopentyl (((S)-fluoro(2-(((3S,6S,9S,10aR)-9-(((1s,3R)-3-fluorocyclobutyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate | 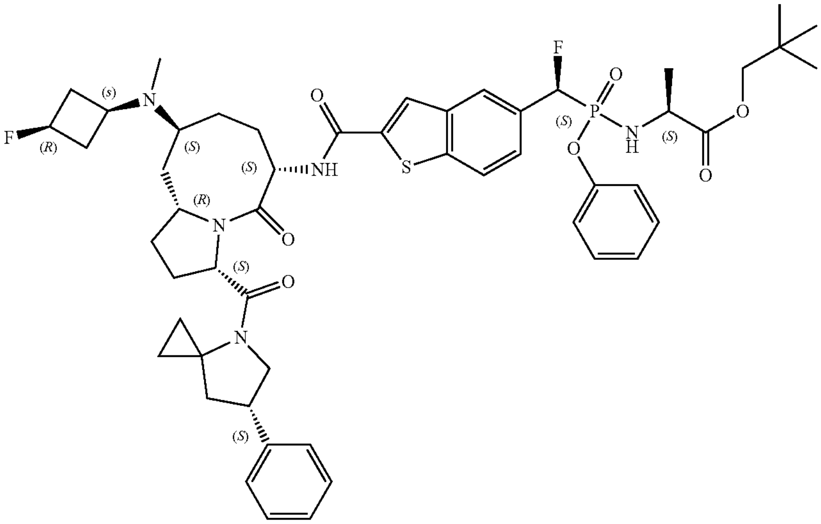 |

TABLE 1C-continued

| | | |
|---|---|---|
| C81 | propyl (((S)-fluoro(2-(((3S,6S,9S,10aR)-9-(((1s,3R)-3-fluorocyclobutyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-D-alaninate | 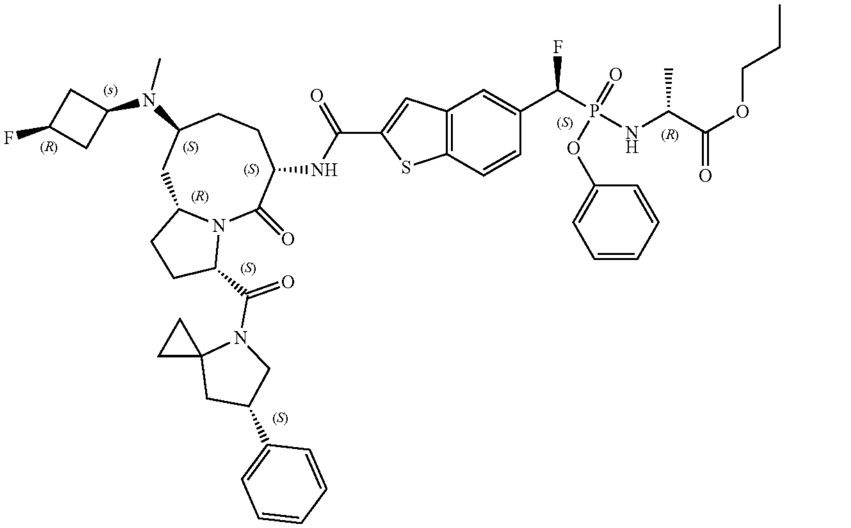 |
| C82 | propyl ((R)-((R)-fluoro(2-(((3S,6S,9S,10aR)-9-(methyl(4,4,4-trifluorobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate | 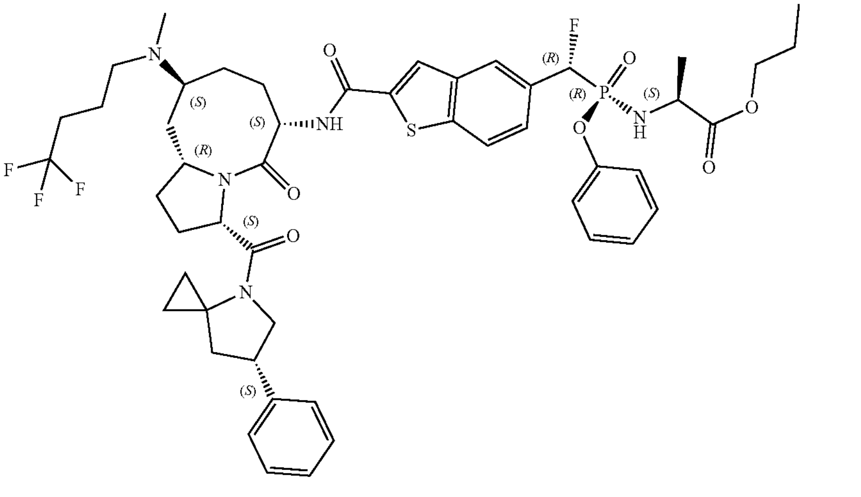 |

TABLE 1C-continued

| | | |
|---|---|---|
| C83 | isopropyl ((S)-ethoxy((S)-fluoro(2-(((3S,6S,9S,10aR)-9-(((1s,3R)-3-fluorocyclobutyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)phosphoryl)-L-alaninate | 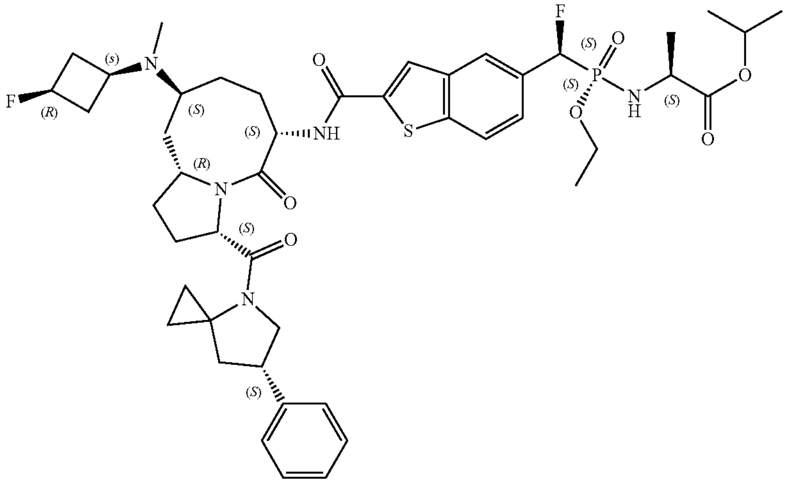 Phosphorus absolute stereochemistry arbitrarily assigned |
| C84 | propyl (((R)-fluoro(2-(((3S,6S,9S,10aR)-9-(((1s,3R)-3-fluorocyclobutyl)(methyl)amino)-5-oxo-3-((S)-6-phenyl-4-azaspiro [2.4]heptane-4-carbonyl)decahydropyrrolo[1,2-a]azocin-6-yl)carbamoyl)benzo[b]thiophen-5-yl)methyl)(phenoxy)phosphoryl)-D-alaninate | 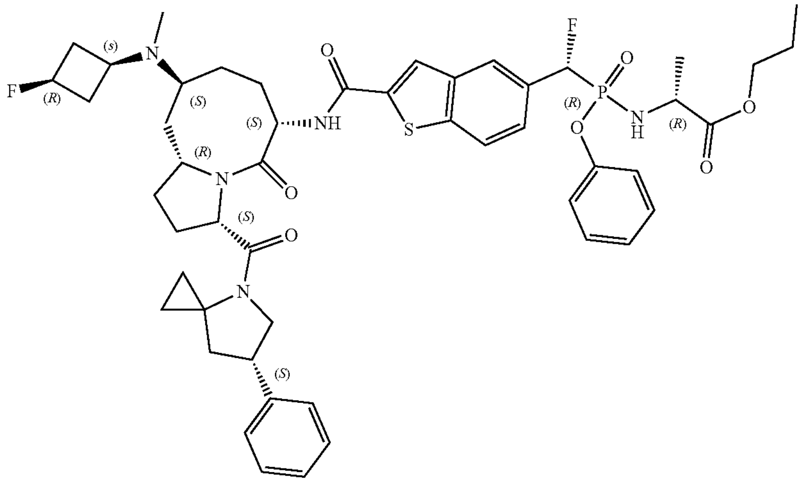 |
| C85 | propyl (((R)-fluoro(2-(((3S,6S,9S,10aR)-9-(((1s,3R)-3-fluorocyclobutyl)(methyl)amino)-5-oxo-3-(4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate | 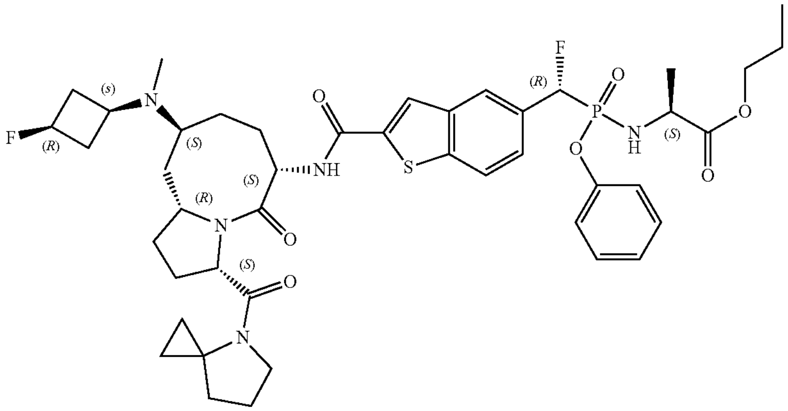 |

TABLE 1C-continued

| | | |
|---|---|---|
| C86 | isopropyl ((R)-ethoxy((R)-fluoro(2-(((3S,6S,9S,10aR)-9-(((1s,3R)-3-fluorocyclobutyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)phosphoryl)-L-alaninate | 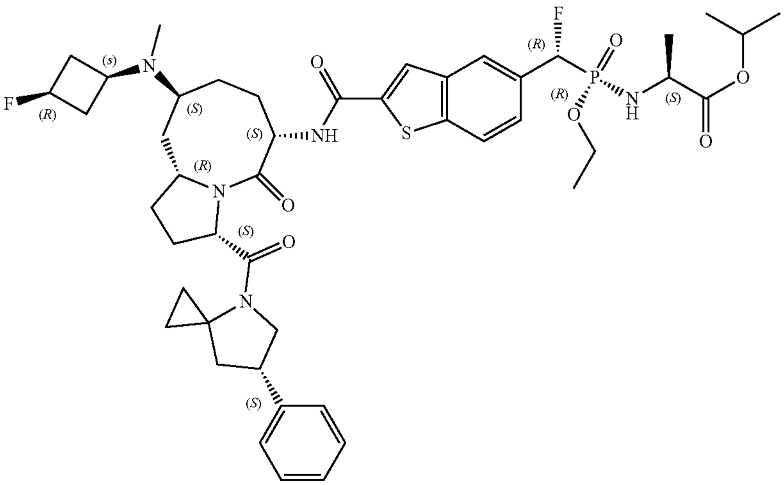 Phosphorus absolute stereochemistry arbitrarily assigned |
| C87 | propyl (((S)-fluoro(2-(((3S,6S,9S,10aR)-9-(methyl(4,4,4-trifluorobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(2,2,2-trifluoroethoxy)phosphoryl)-L-alaninate | 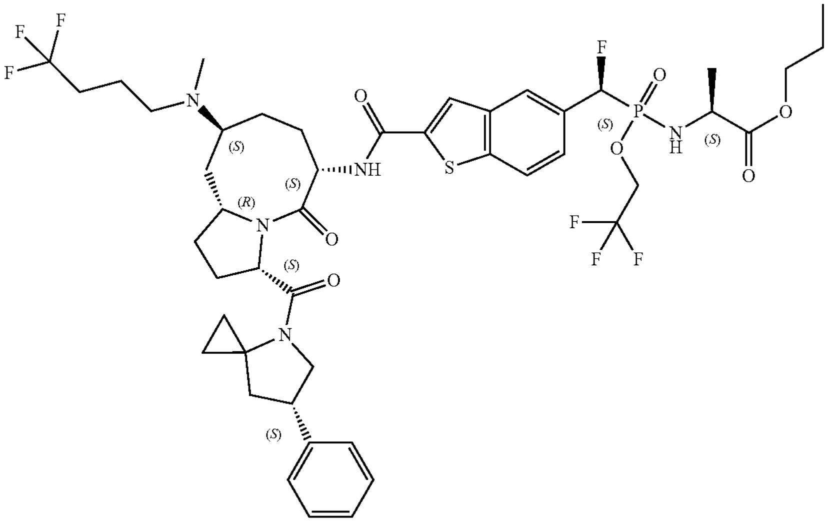 |
| C88 | propyl (((R)-fluoro(2-(((3S,6S,9S,10aR)-9-(((1s,3R)-3-fluorocyclobutyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(propoxy)phosphoryl)-L-alaninate | 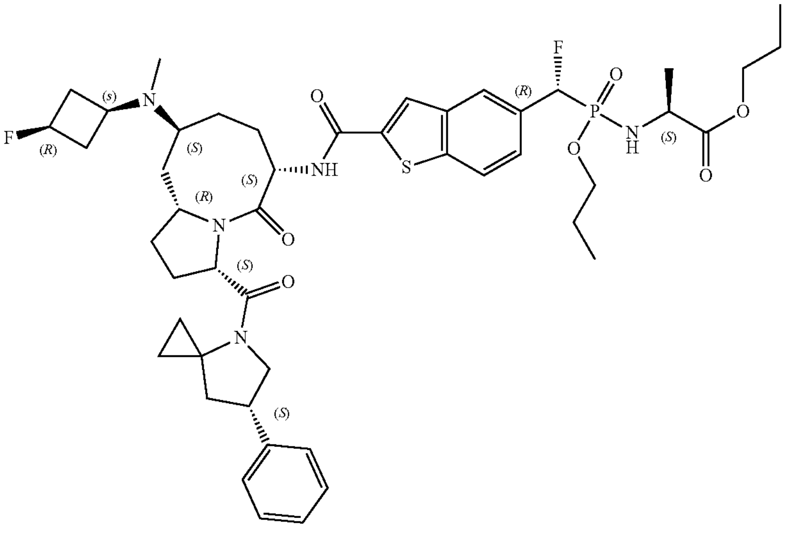 |

TABLE 1C-continued

| | | |
|---|---|---|
| C89 | cyclobutyl (((S)-fluoro(2-(((3S,6S,9S,10aR)-9-(((1s,3R)-3-fluorocyclobutyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(2,2,2-trifluoroethoxy)phosphoryl)-L-alaninate | 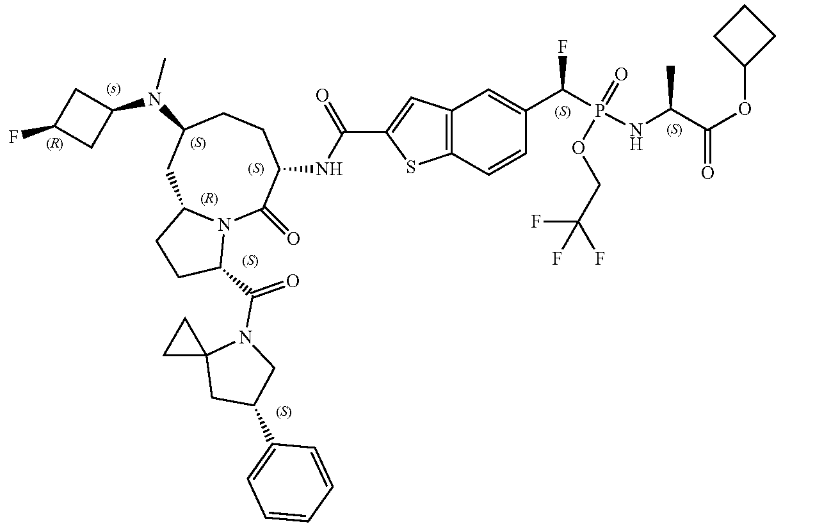 |
| C90 | propyl (((R)-(2-(((3S,6S,9S,10aR)-9-(((S)-3,3-difluorocyclopentyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)(2,2,2-trifluoroethoxy)phosphoryl)-L-alaninate | 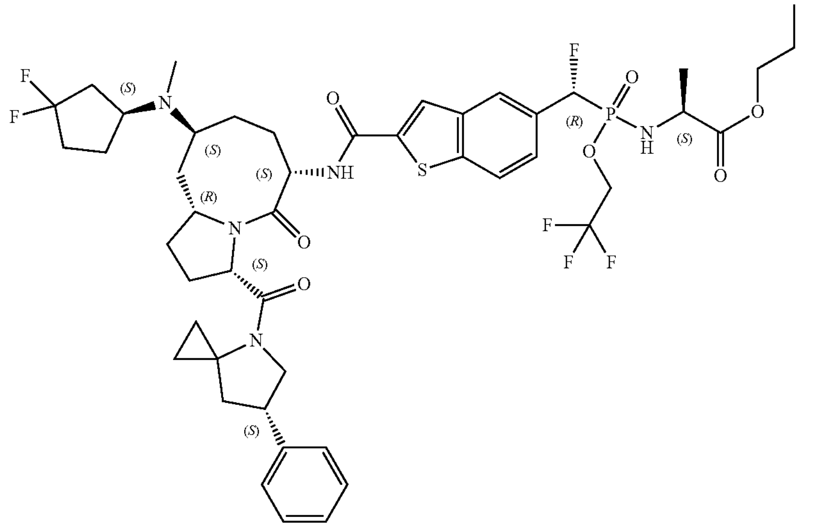 |
| C91 | propyl (((R)-fluoro(2-(((3S,6S,9S,10aR)-9-(methyl(4,4,4-trifluorobutyl)amino)-5-oxo-3-((S)-6-phenyl-4-azaspiro [2.4]heptane-4-carbonyl)decahydropyrrolo[1,2-a]azocin-6-yl)carbamoyl)benzo[b]thiophen-5-yl)methyl)(2,2,2-trifluoroethoxy)phosphoryl)-L-alaninate | 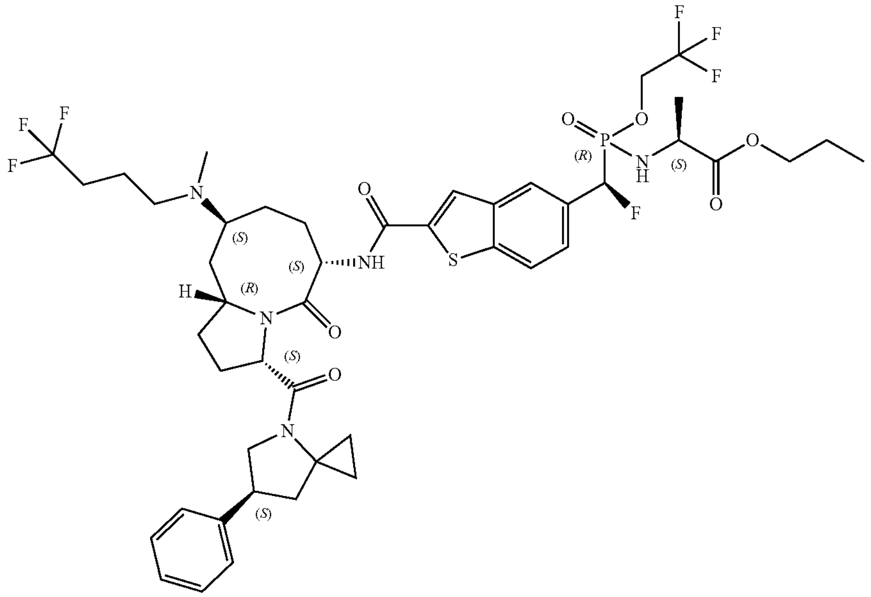 |

| | | |
|---|---|---|
| C92 | propyl (cyclopropoxy((R)-fluoro(2-(((3S,6S,9S,10aR)-9-(((1s,3R)-3-fluorocyclobutyl) (methyl)amino)-5-oxo-3-((S)-6-phenyl-4-azaspiro [2.4] heptane-4-carbonyl) decahydropyrrolo [1,2-a]azocin-6-yl)carbamoyl) benzo [b]thiophen-5-yl)methyl) phosphoryl)-L-alaninate | 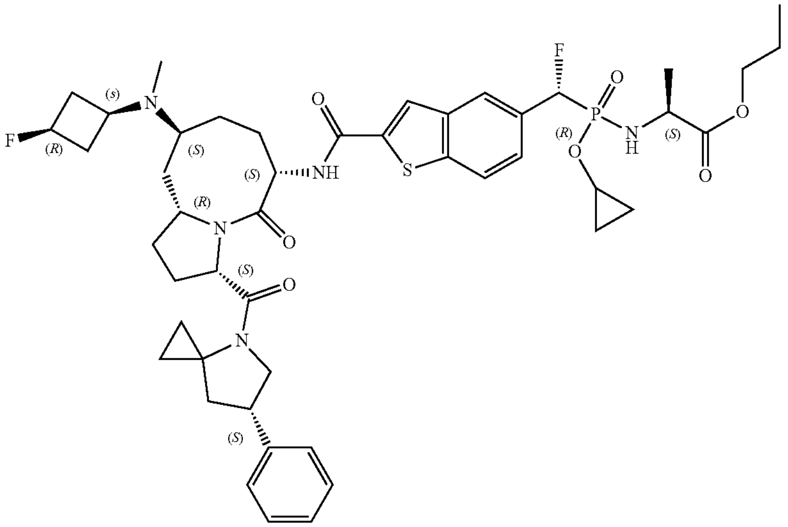 |
| C93 | isopropyl ((S)-ethoxy((R)-fluoro(2-(((3S,6S,9S,10aR)-9-(((1s,3R)-3-fluorocyclobutyl) (methyl)amino)-5-oxo-3-((S)-6-phenyl-4-azaspiro[2.4] heptane-4-carbonyl) decahydropyrrolo [1,2-a]azocin-6-yl)carbamoyl) benzo [b]thiophen-5-yl)methyl) phosphoryl)-L-alaninate | 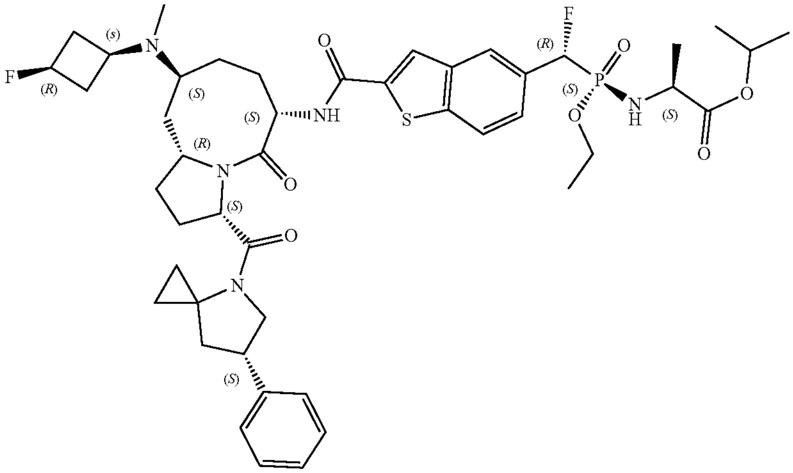 Phosphorus absolute stereochemistry arbitrarily assigned |
| C94 | isopropyl (((R)-fluoro(2-(((3S,6S,9S,10aR)-9-(((1s,3R)-3-fluorocyclobutyl) (methyl)amino)-5-oxo-3-((S)-6-phenyl-4-azaspiro[2.4] heptane-4-carbonyl) decahydropyrrolo [1,2-a]azocin-6-yl)carbamoyl) benzo [b]thiophen-5-yl)methyl)(2,2,2-trifluoroethoxy) phosphoryl)-L-alaninate | 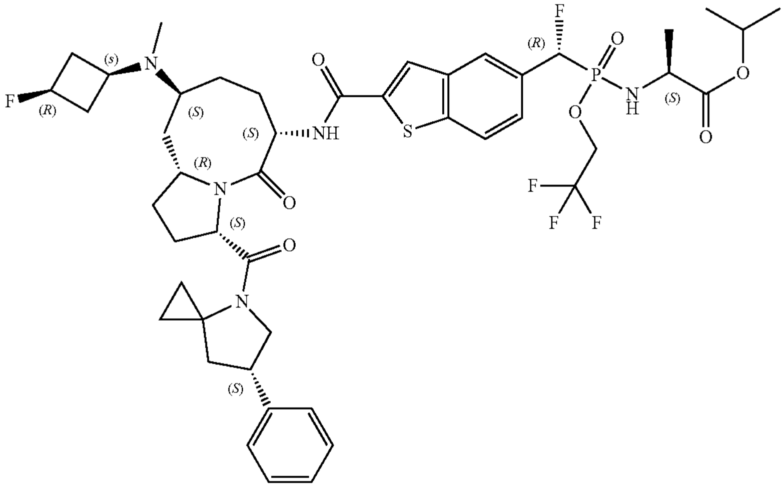 |

TABLE 1C-continued

| | | |
|---|---|---|
| C95 | propyl (((S)-(2-(((3S,6S,9S,10aR)-9-(((S)-3,3-difluorocyclopentyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)(2,2,2-trifluoroethoxy)phosphoryl)-L-alaninate | 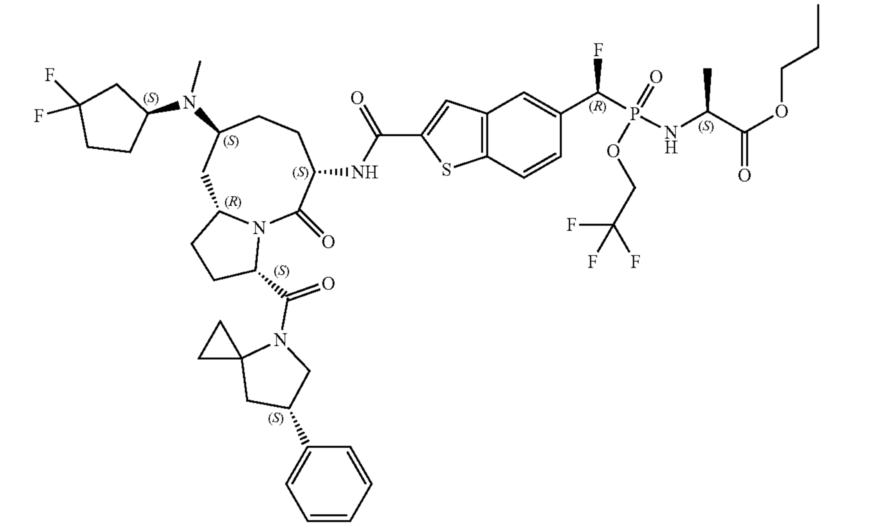 |
| C96 | propyl (((R)-fluoro(2-(((3S,6S,9S,10aR)-9-(methyl((1s,3R)-3-(trifluoromethoxy)cyclobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(2,2,2-trifluoroethoxy)phosphoryl)-L-alaninate | 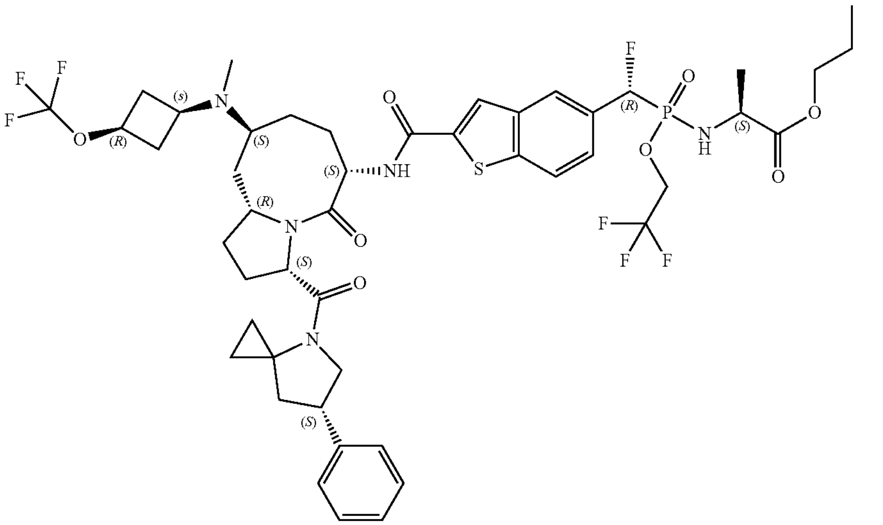 |
| C97 | propyl (((S)-fluoro(2-(((3S,6S,9S,10aR)-9-(methyl((1s,3R)-3-(trifluoromethoxy)cyclobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(2,2,2-trifluoroethoxy)phosphoryl)-L-alaninate | 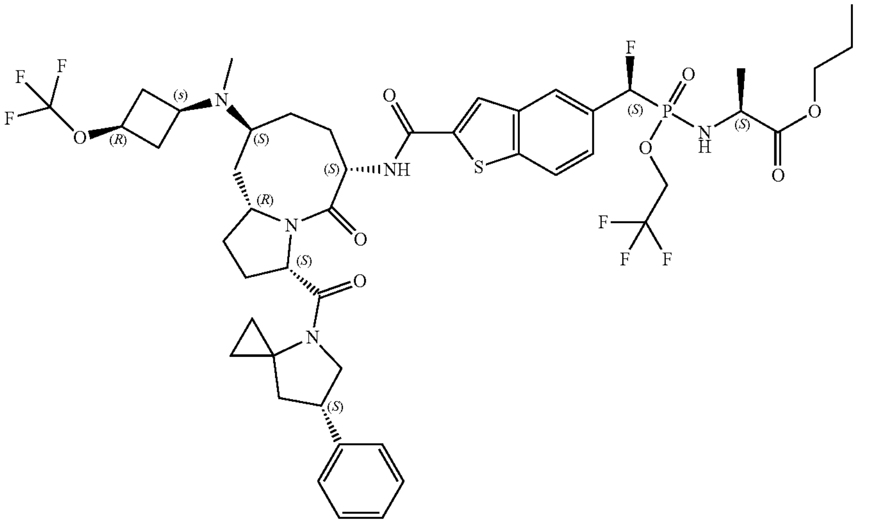 |

TABLE 1C-continued

| | | |
|---|---|---|
| C98 | propyl (((R)-(2-(((3S,6S,9S,10aR)-9-(ethyl((3-methyloxetan-3-yl)methyl)amino)-5-oxo-3-((S)-6-phenyl-4-azaspiro[2.4] heptane-4-carbonyl) decahydropyrrolo [1,2-a]azocin-6-yl)carbamoyl) benzo [b]thiophen-5-yl)fluoromethyl) (phenoxy) phosphoryl)-L-alaninate | 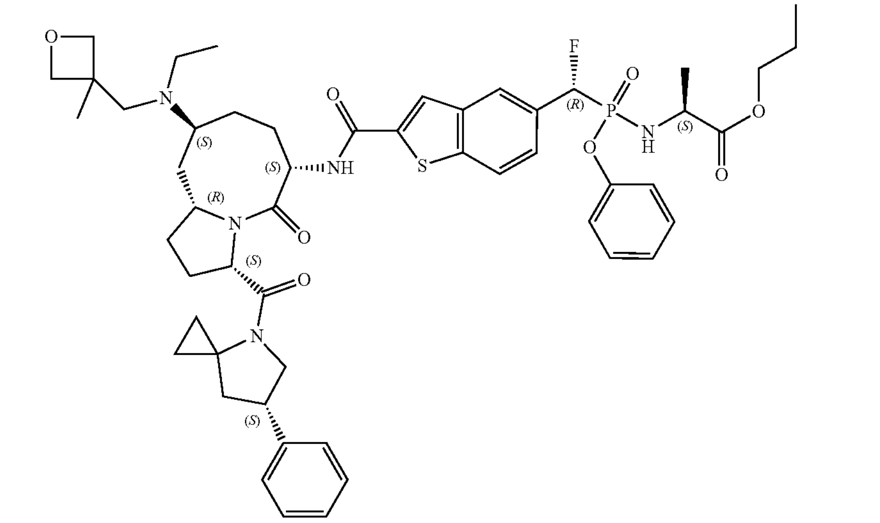 |
| C99 | propyl (((R)-(2-(((3S,6S,9S,10aR)-9-(ethyl((1s,3R)-3-(trifluoromethoxy) cyclobutyl)amino)-5-oxo-3-((S)-6-phenyl-4-azaspiro [2.4] heptane-4-carbonyl) decahydropyrrolo [1,2-a]azocin-6-yl)carbamoyl) benzo [b]thiophen-5-yl)fluoromethyl) (phenoxy) phosphoryl)-L-alaninate | 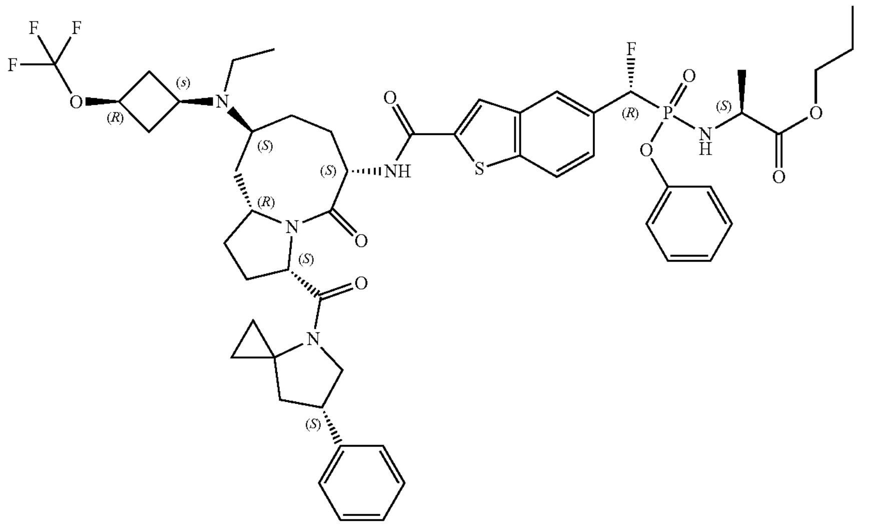 |
| C100 | propyl (((R)-(2-(((3S,6S,9S,10aR)-9-(ethyl(4,4,4-trifluorobutyl) amino)-5-oxo-3-((S)-6-phenyl-4-azaspiro[2.4] heptane-4-carbonyl) decahydropyrrolo [1,2-a]azocin-6-yl)carbamoyl) benzo [b]thiophen-5-yl)fluoromethyl) (phenoxy) phosphoryl)-L-alaninate | 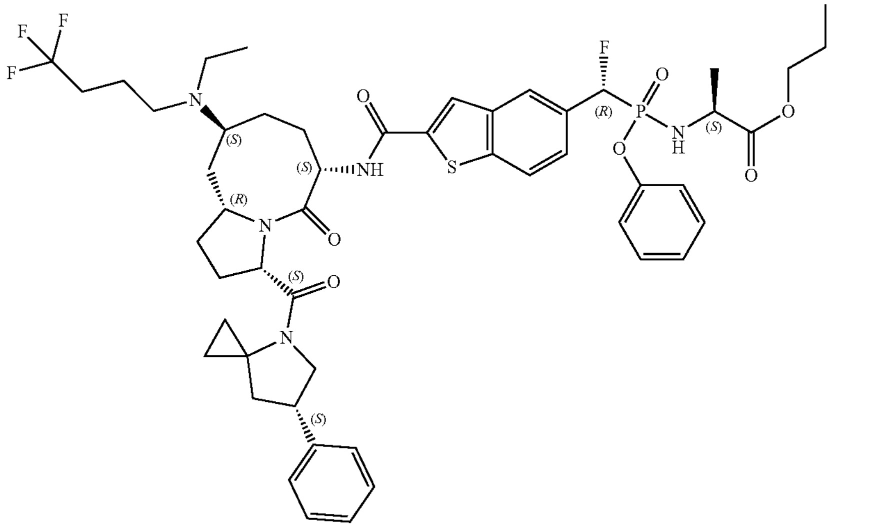 |

TABLE 1C-continued

| | | |
|---|---|---|
| C101 | propyl (((S)-(2-(((3S,6S,9S,10aR)-9-(ethyl(4,4,4-trifluorobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)(phenoxy)phosphoryl)-L-alaninate | 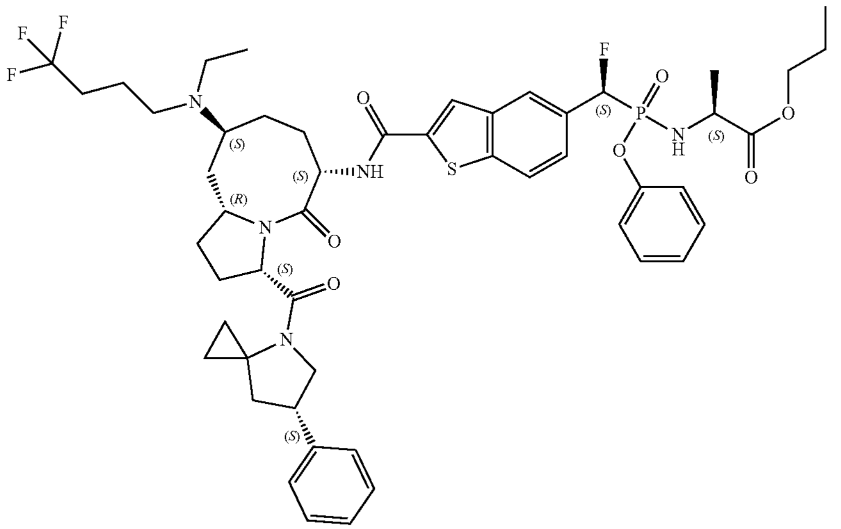 |
| C102 | cyclobutyl (((R)-fluoro(2-(((3S,6S,9S,10aR)-9-(((1s,3R)-3-fluorocyclobutyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(2,2,2-trifluoroethoxy)phosphoryl)-L-alaninate | 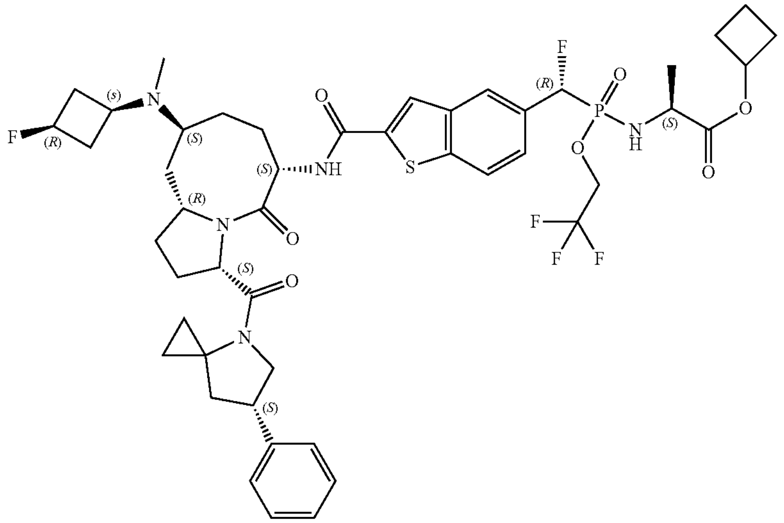 |
| C103 | isopropyl (((S)-fluoro(2-(((3S,6S,9S,10aR)-9-(((1s,3R)-3-fluorocyclobutyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(2,2,2-trifluoroethoxy)phosphoryl)-L-alaninate | 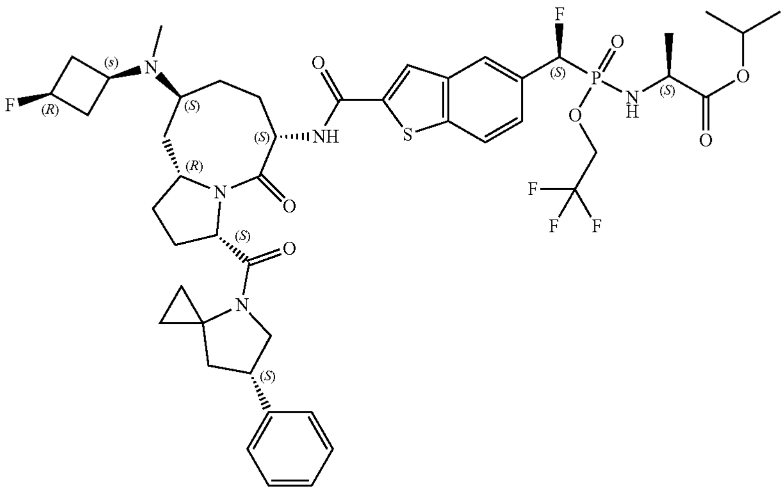 |

TABLE 1C-continued

| | | |
|---|---|---|
| C104 | isobutyl (((R)-fluoro(2-(((3S,6S,9S,10aR)-9-(((1s,3R)-3-fluorocyclobutyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate | 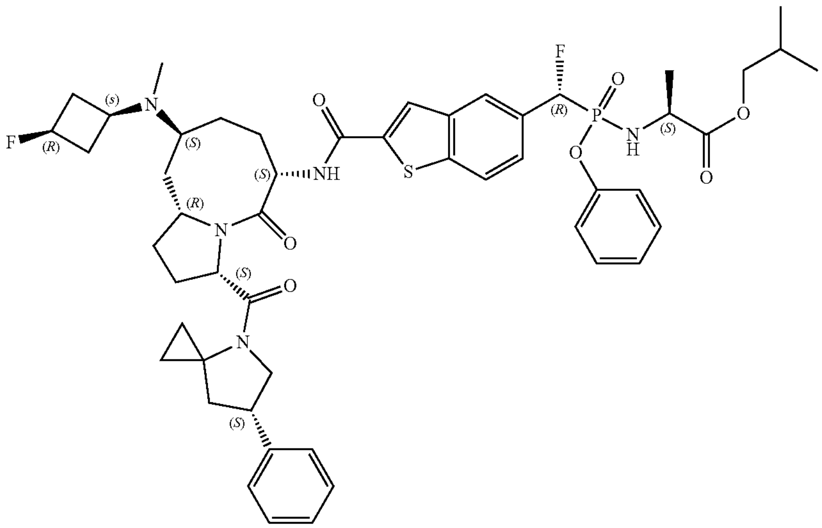 |
| C105 | isobutyl (((S)-fluoro(2-(((3S,6S,9S,10aR)-9-(((1s,3R)-3-fluorocyclobutyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate | 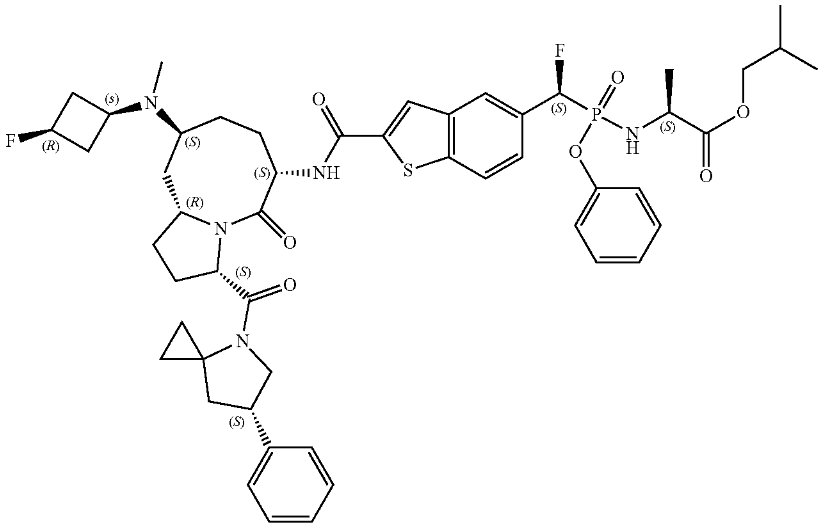 |
| C106 | cyclobutyl (ethoxy((R)-fluoro(2-(((3S,6S,9S,10aR)-9-(((1s,3R)-3-fluorocyclobutyl)(methyl)amino)-5-oxo-3-((S)-6-phenyl-4-azaspiro [2.4]heptane-4-carbonyl)decahydropyrrolo[1,2-a]azocin-6-yl)carbamoyl)benzo[b]thiophen-5-yl)methyl)phosphoryl)-L-alaninate | 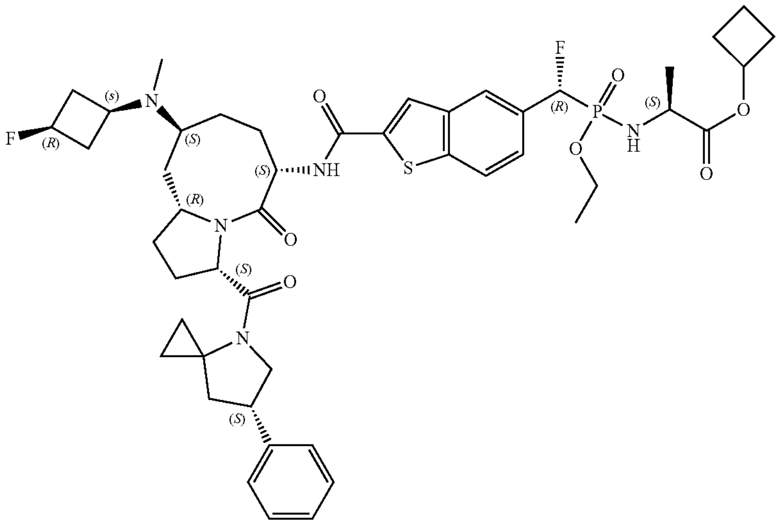 |

TABLE 1C-continued

| | | |
|---|---|---|
| C107 | cyclobutyl (ethoxy((S)-fluoro(2-(((3S,6S,9S,10aR)-9-(((1s,3R)-3-fluorocyclobutyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)phosphoryl)-L-alaninate | 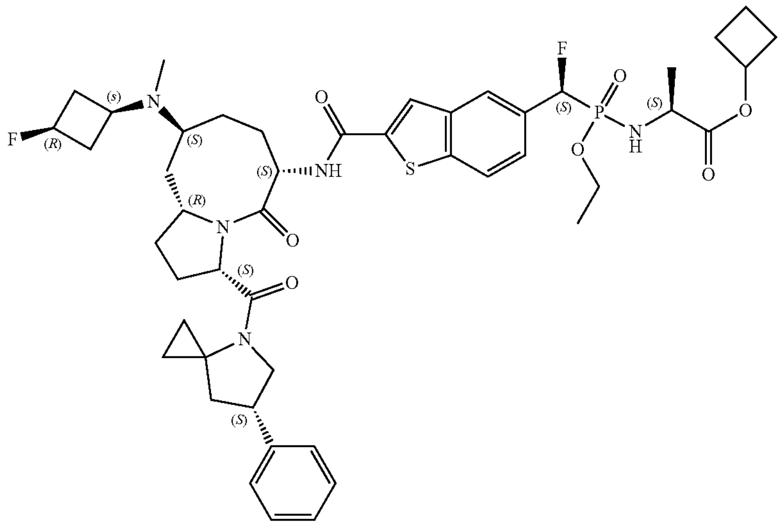 |
| C108 | propyl (((R)-(2-(((3S,6S,9S,10aR)-9-(ethyl((1s,3R)-3-(trifluoromethyl)cyclobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)(phenoxy)phosphoryl)-L-alaninate | 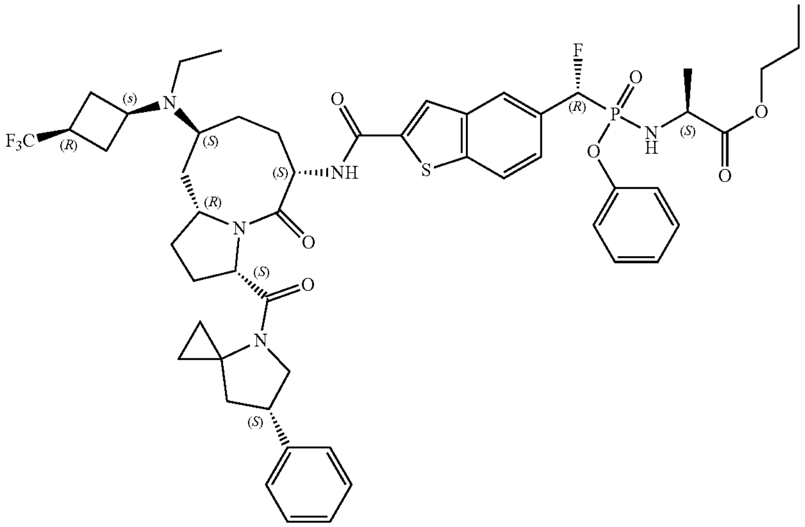 |
| C109 | propyl (((S)-(2-(((3S,6S,9S,10aR)-9-(ethyl((1s,3R)-3-(trifluoromethyl)cyclobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)(phenoxy)phosphoryl)-L-alaninate | 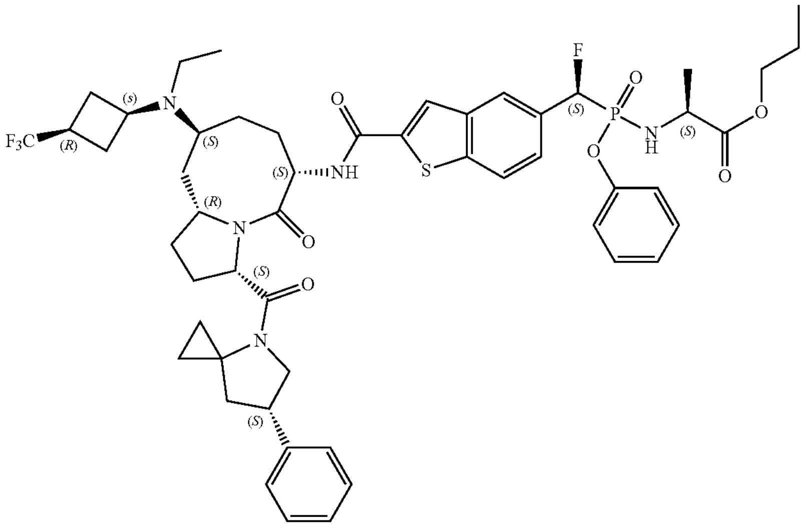 |

TABLE 1C-continued

| | | |
|---|---|---|
| C110 | propyl (((R)-(2-(((3S,6S,9S,10aR)-9-(((1s,3R)-3-cyanocyclobutyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)(2,2,2-trifluoroethoxy)phosphoryl)-L-alaninate | 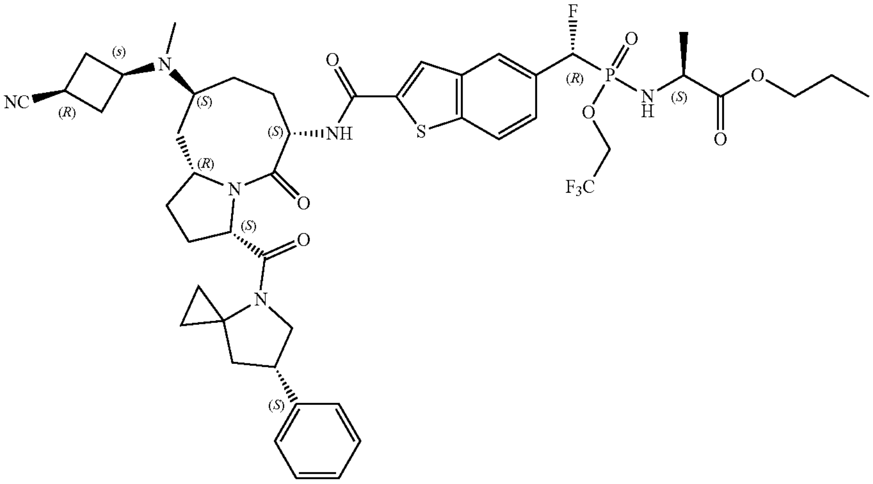 |
| C111 | cyclobutyl (((R)-(2-(((3S,6S,9S,10aR)-9-(((1s,3R)-3-cyanocyclobutyl)(methyl)amino)-5-oxo-3-((S)-6-phenyl-4-azaspiro [2.4]heptane-4-carbonyl)decahydropyrrolo[1,2-a]azocin-6-yl)carbamoyl)benzo[b]thiophen-5-yl)fluoromethyl)(phenoxy)phosphoryl)-L-alaninate | 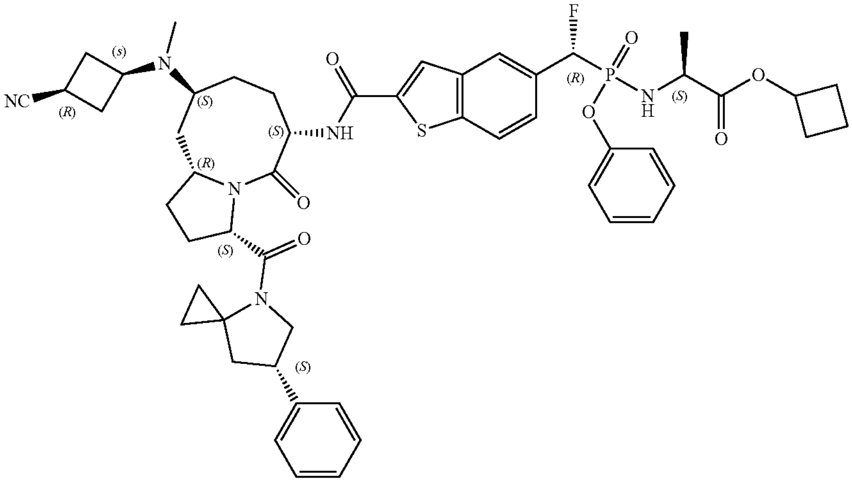 |
| C112 | cyclobutyl (((S)-(2-(((3S,6S,9S,10aR)-9-(((1s,3R)-3-cyanocyclobutyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)(phenoxy)phosphoryl)-L-alaninate | 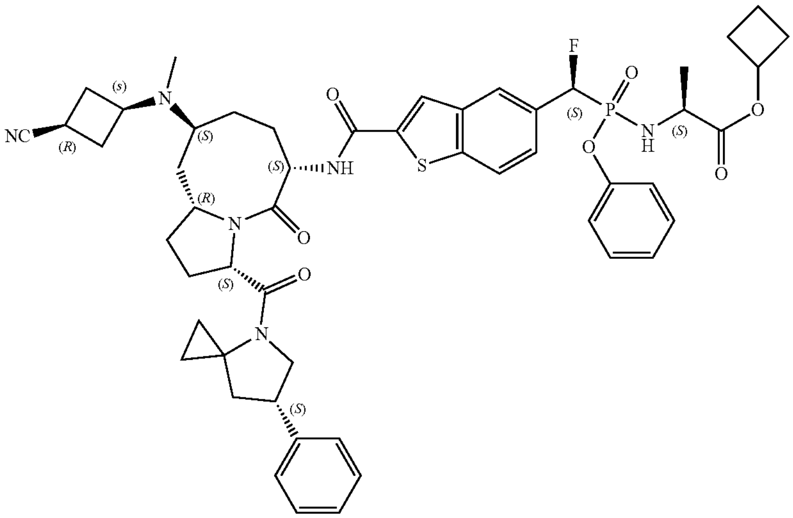 |

TABLE 1C-continued

| | | |
|---|---|---|
| C113 | cyclobutyl (((R)-fluoro(2-(((3S,6S,9S,10aR)-9-(methyl((1s,3R)-3-(trifluoromethyl)cyclobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate | 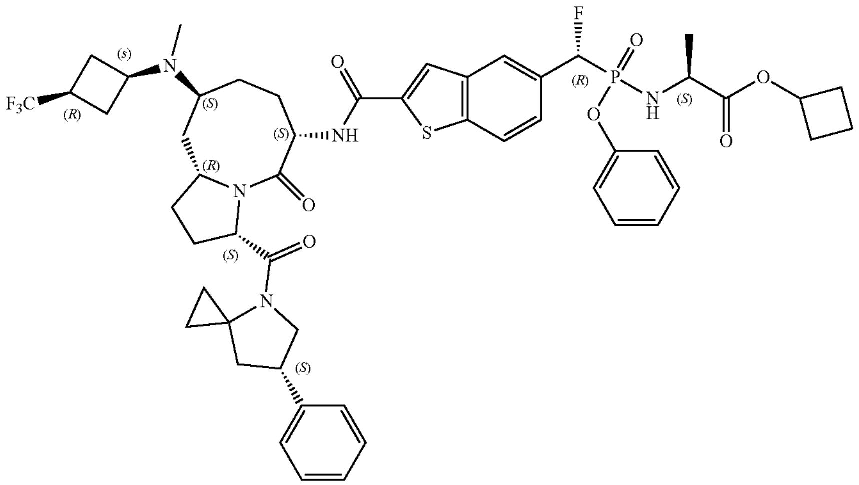 |
| C114 | propyl (((R)-fluoro(2-(((3S,6S,9S,10aR)-9-(methyl((1s,3R)-3-(trifluoromethyl)cyclobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(2,2,2-trifluoroethoxy)phosphoryl)-L-alaninate | 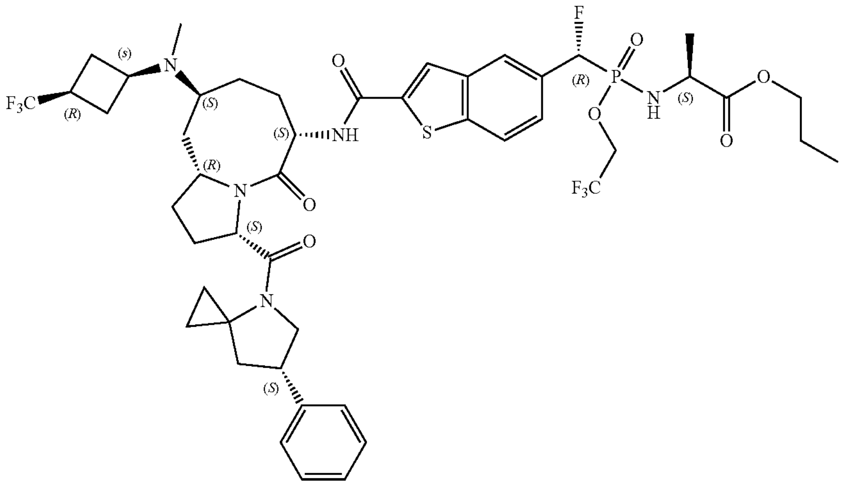 |
| C115 | propyl ((S)-((S)-fluoro(2-(((3S,6S,9S,10aR)-9-(methyl(4,4,4-trifluorobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate | 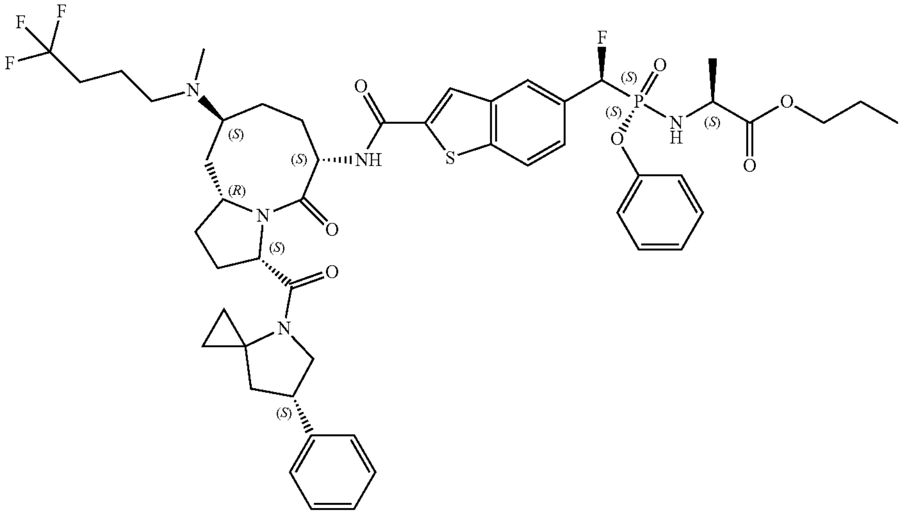 |

TABLE 1C-continued

| | | |
|---|---|---|
| C116 | propyl (cyclopropoxy((R)-fluoro(2-(((3S,6S,9S,10aR)-9-(methyl((1s,3R)-3-(trifluoromethoxy) cyclobutyl)amino)-5-oxo-3-((S)-6-phenyl-4-azaspiro[2.4] heptane-4-carbonyl) decahydropyrrolo [1,2-a]azocin-6-yl)carbamoyl) benzo [b]thiophen-5-yl)methyl) phosphoryl)-L-alaninate | 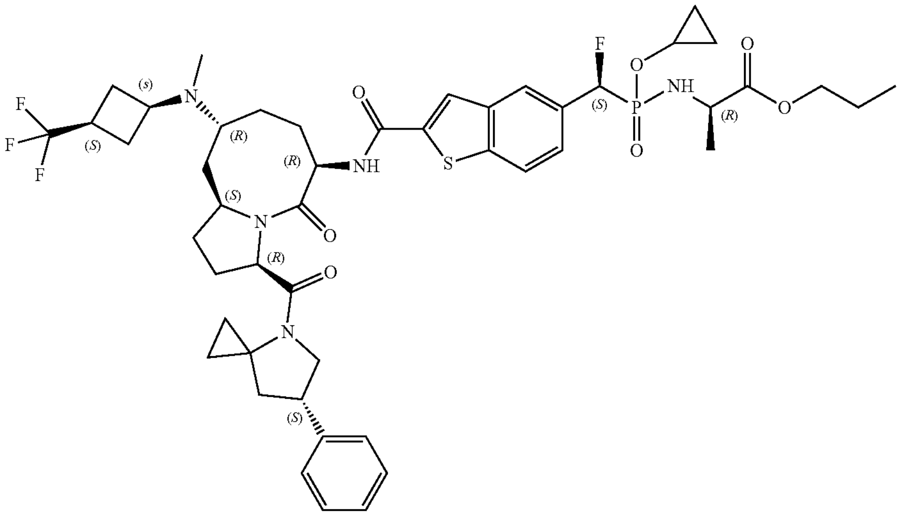 |
| C117 | propyl (cyclopropoxy((R)-fluoro(2-(((3S,6S,9S,10aR)-9-(methyl((1s,3R)-3-(trifluoromethyl) cyclobutyl)amino)-5-oxo-3-((S)-6-phenyl-4-azaspiro[2.4] heptane-4-carbonyl) decahydropyrrolo [1,2-a]azocin-6-yl)carbamoyl) benzo [b]thiophen-5-yl)methyl) phosphoryl)-L-alaninate | 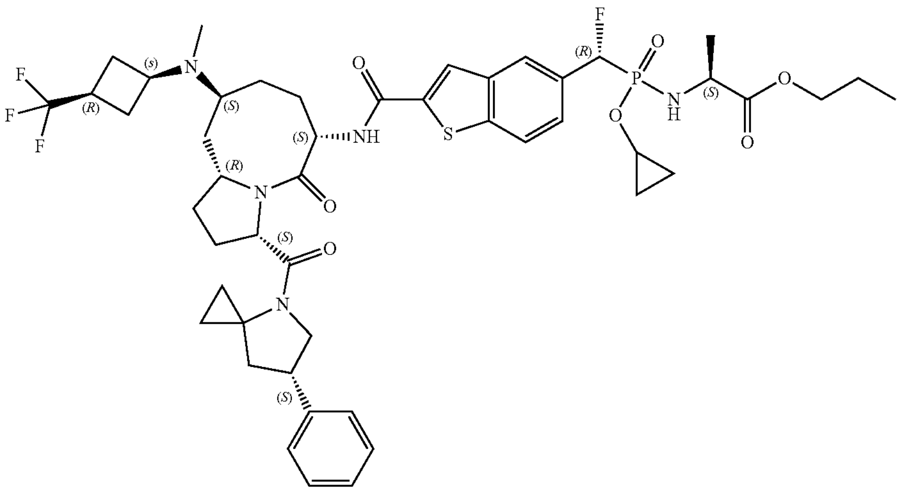 |
| C118 | isopropyl (((S)-fluoro(2-(((3S,6S,9S,10aR)-9-(methyl((1s,3R)-3-(trifluoromethoxy) cyclobutyl)amino)-5-oxo-3-((S)-6-phenyl-4-azaspiro[2.4] heptane-4-carbonyl) decahydropyrrolo [1,2-a]azocin-6-yl)carbamoyl) benzo [b]thiophen-5-yl)methyl) (phenoxy) phosphoryl)-L-alaninate | 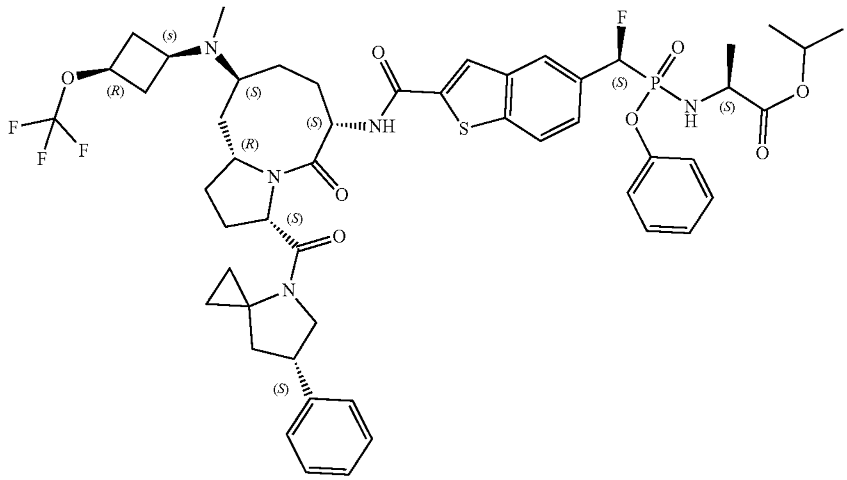 |

TABLE 1C-continued

| | | |
|---|---|---|
| C119 | propyl (((S)-(2-(((3S,6S,9S,10aR)-9-(ethyl((1s,3R)-3-(trifluoromethoxy)cyclobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)(phenoxy)phosphoryl)-L-alaninate | 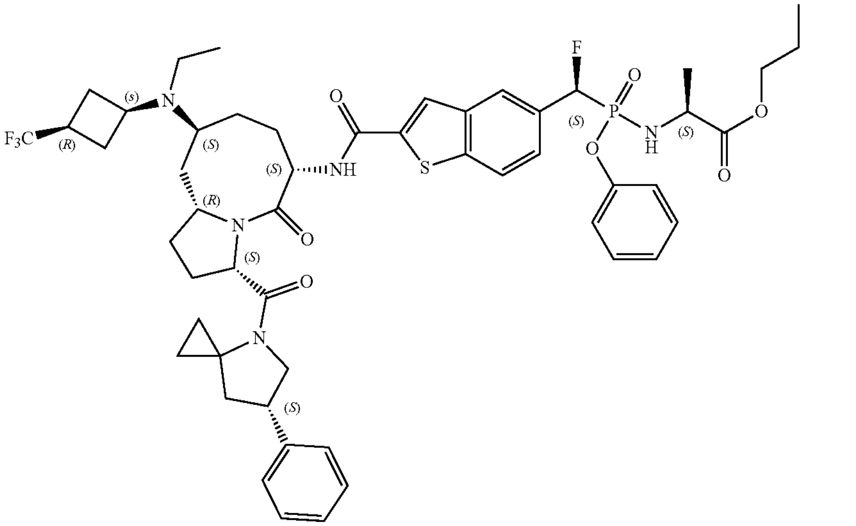 |
| C120 | propyl ((R)-((S)-fluoro(2-(((3S,6S,9S,10aR)-9-(methyl(4,4,4-trifluorobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate | 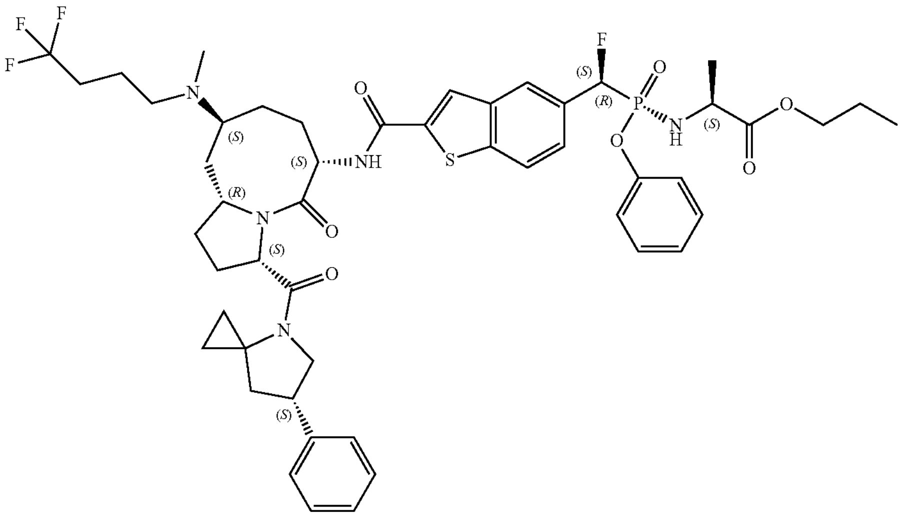 |
| C121 | isopropyl (((R)-fluoro(2-(((3S,6S,9S,10aR)-9-(methyl((1s,3R)-3-(trifluoromethoxy)cyclobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate 2,2,2-trifluoroacetate | 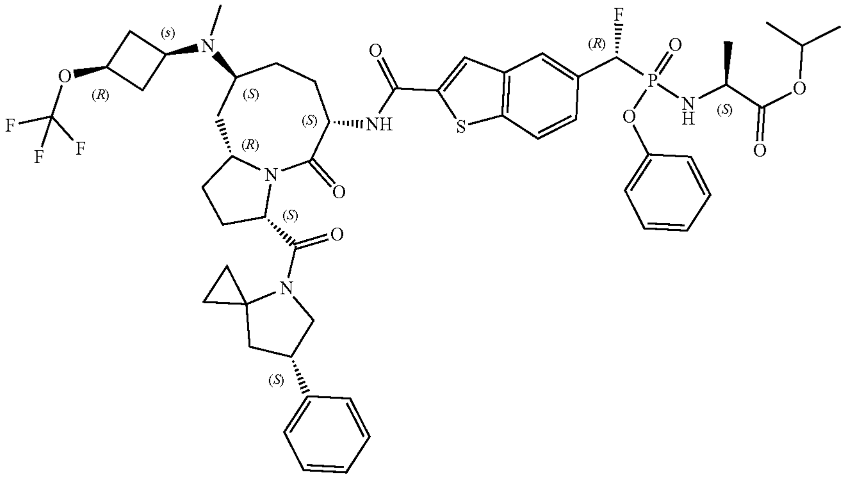 |

TABLE 1C-continued

| | | |
|---|---|---|
| C122 | isobutyl (cyclopropoxy((R)-fluoro(2-(((3S,6S,9S,10aR)-9-(methyl((1s,3R)-3-(trifluoromethoxy) cyclobutyl)amino)-5-oxo-3-((S)-6-phenyl-4-azaspiro [2.4] heptane-4-carbonyl) decahydropyrrolo [1,2-a]azocin-6-yl)carbamoyl) benzo [b]thiophen-5-yl)methyl) phosphoryl)-L-alaninate | 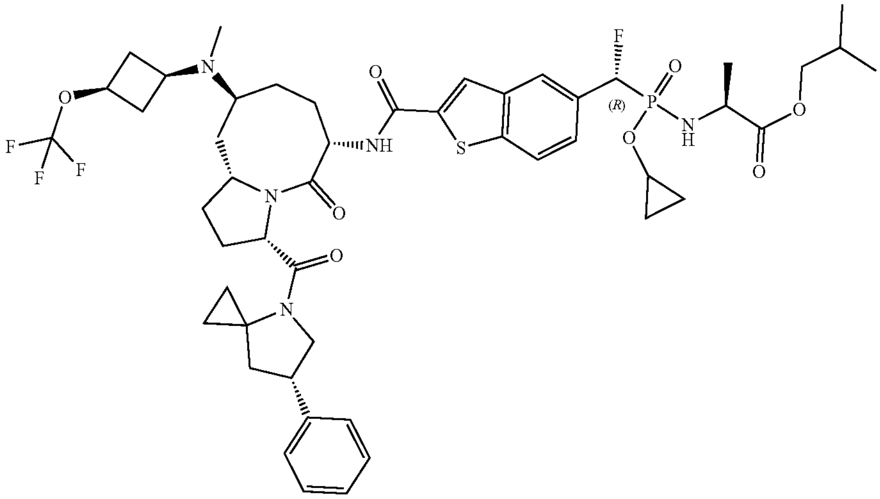 |
| C123 | cyclobutyl (ethoxy((R)-fluoro(2-(((3S,6S,9S,10aR)-9-(methyl((1s,3R)-3.(trifluoromethoxy) cyclobutyl)amino)-5-oxo-3-((S)-6-phenyl-4-azaspiro[2.4] heptane-4-carbonyl) decahydropyrrolo [1,2-a]azocin-6-yl)carbamoyl) benzo [b]thiophen-5-yl)methyl) phosphoryl)-L-alaninate | 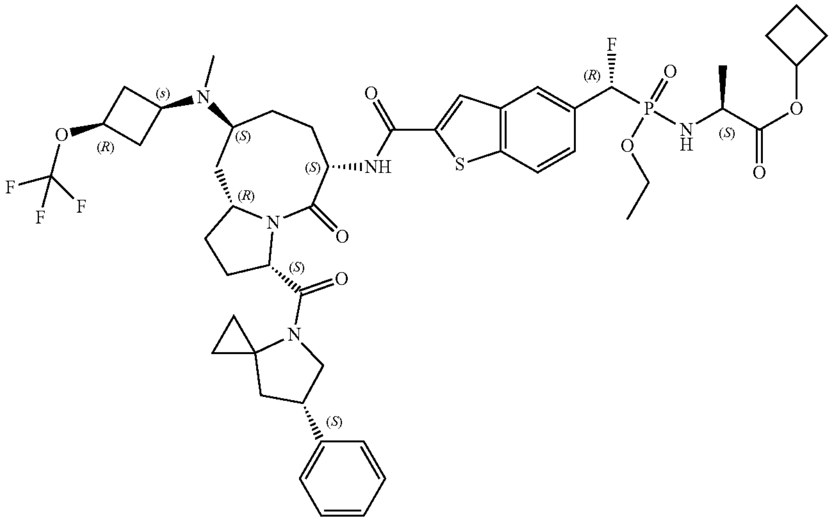 |

TABLE 1C-continued

| | | |
|---|---|---|
| C124 | cyclobutyl ((S)-((R)-fluoro(2-(((3S,6S,9S,10aR)-9-(methyl((1s,3R)-3-(trifluoromethoxy)cyclobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate | 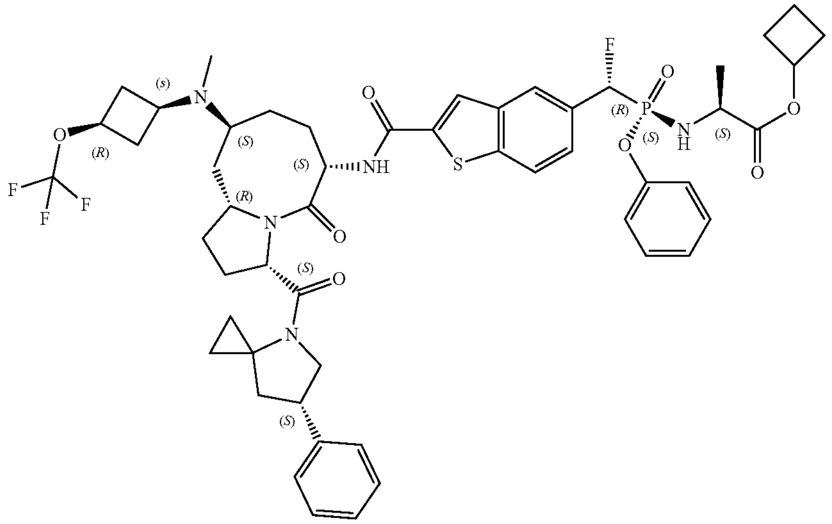 Phosphorus absolute stereochemistry arbitrarily assigned |
| C125 | cyclobutyl ((R)-((R)-fluoro(2-(((3S,6S,9S,10aR)-9-(methyl((1s,3R)-3-(trifluoromethoxy)cyclobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate | 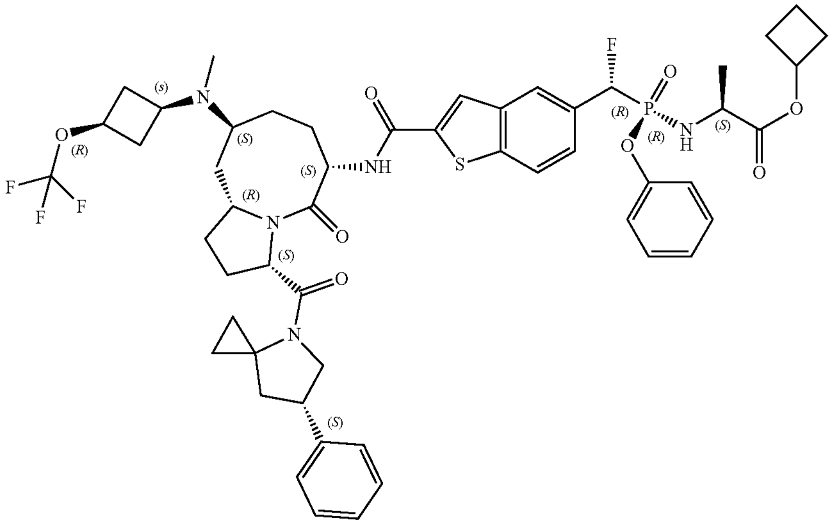 Phosphorus absolute stereochemistry arbitrarily assigned |

TABLE 1C-continued

| | | |
|---|---|---|
| C126 | propyl N-(((R)-fluoro(2-(((3S,6S,9S,10aR)-9-(methyl((1s,3R)-3.(trifluoromethoxy)cyclobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-O-methyl-L-serinate | 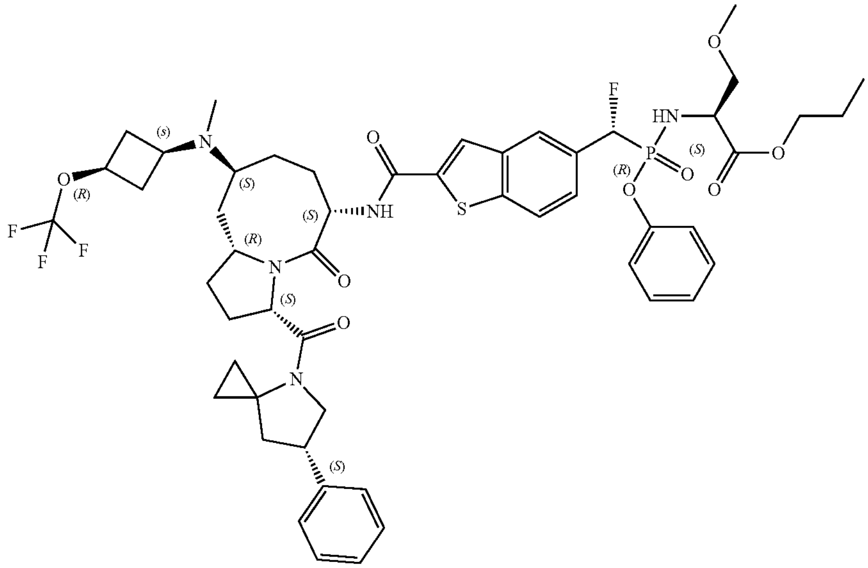 |
| C127 | propyl 2-((((R)-fluoro(2-(((3S,6S,9S,10aR)-9-(methyl((1s,3R)-3-(trifluoromethoxy)cyclobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)amino)-2-methylpropanoate | 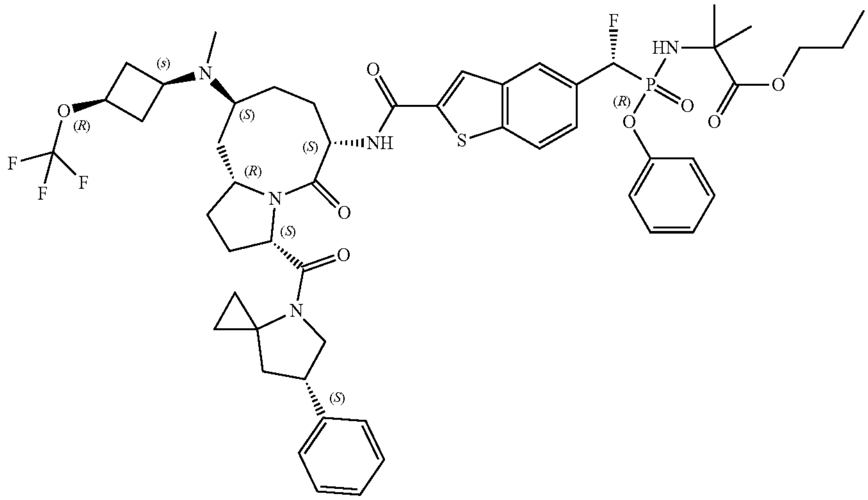 |

TABLE 1C-continued

| | | |
|---|---|---|
| C128 | propyl (((R)-fluoro(2-(((3S,6S,9S,10aR)-9-(methyl((1s,3R)-3-(trifluoromethoxy)cyclobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-phenylalaninate | 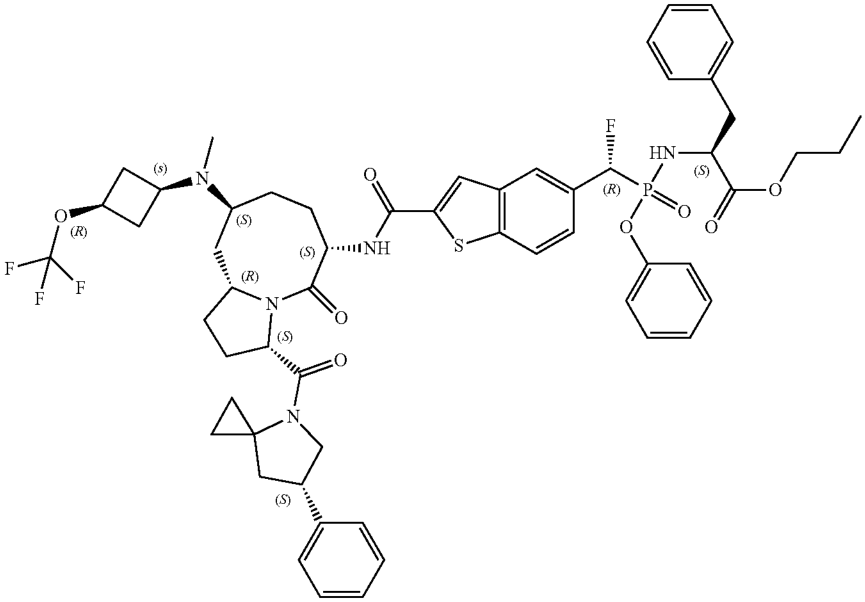 |
| C129 | isobutyl (((R)-fluoro(2-(((3S,6S,9S,10aR)-9-(methyl(((1s,3R)-3-(trifluoromethyl)cyclobutyl)methyl)amino)-5-oxo-3-((S)-6-phenyl-4-azaspiro [2.4]heptane-4-carbonyl)decahydropyrrolo[1,2-a]azocin-6-yl)carbamoyl)benzo[b]thiophen-5-yl)methyl)(phenoxy)phosphoryl)-L-alaninate | 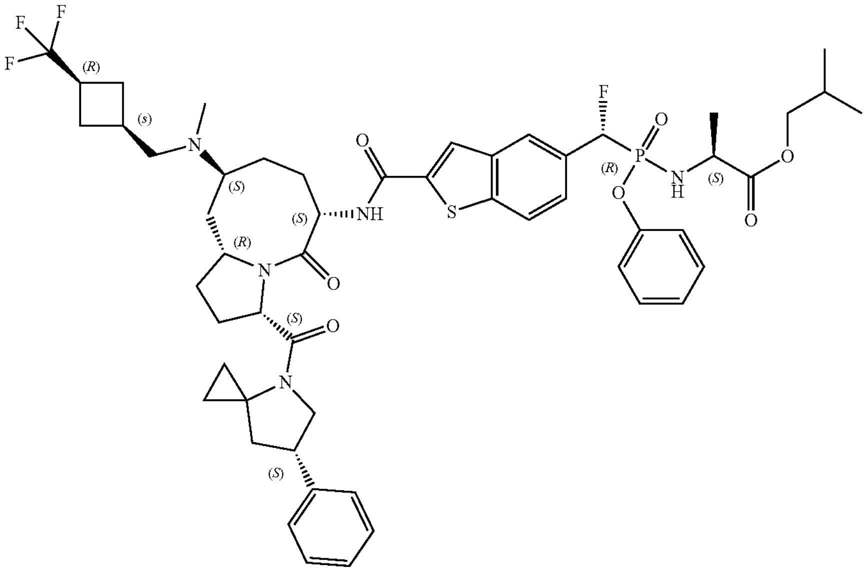 |

TABLE 1C-continued

| | | |
|---|---|---|
| C130 | isobutyl (((R)-(2-(((3S,6S,9S,10aR)-9-((((1r,3S)-3-(difluoromethyl)cyclobutyl)methyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)(phenoxy)phosphoryl)-L-alaninate | 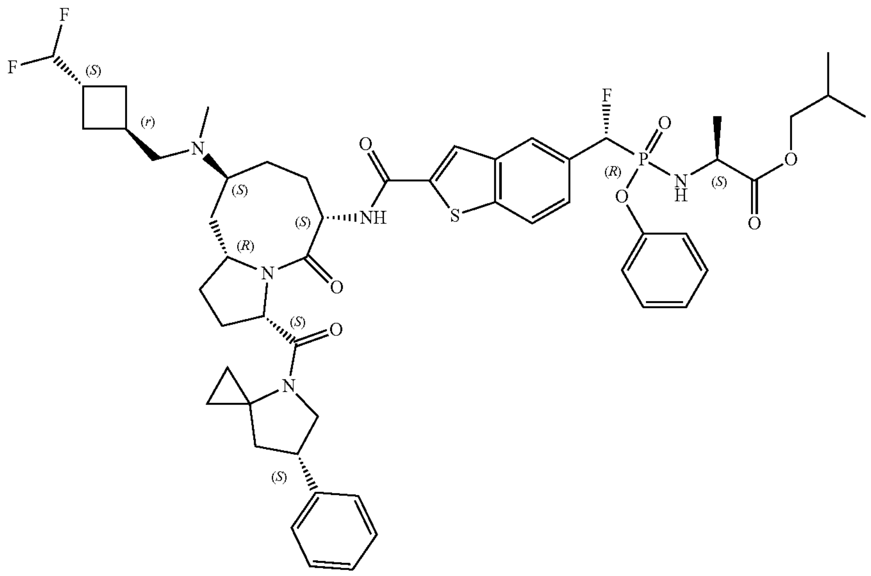 |
| C131 | isobutyl (((R)-fluoro(2-(((3S,6S,9S,10aR)-9-(methyl(2-(1-(trifluoromethyl)cyclopropyl)ethyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate | 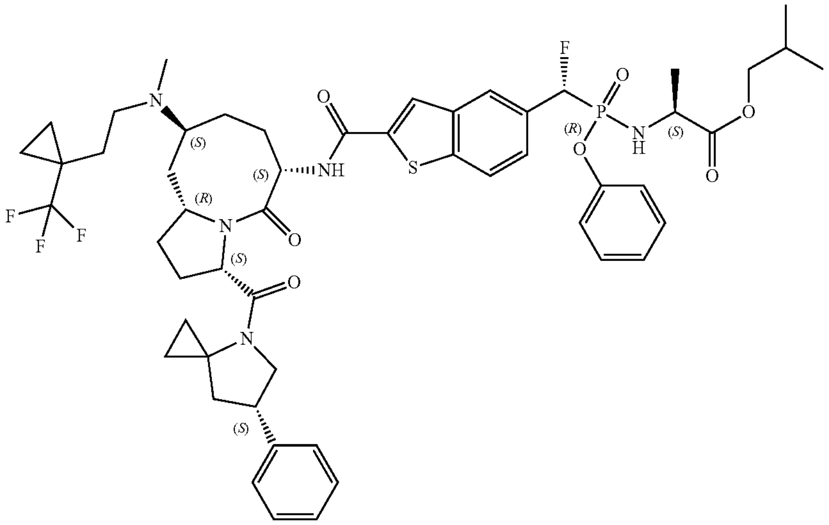 |
| C132 | isobutyl (((R)-fluoro(2-(((3S,6S,9S,10aR)-9-(methyl((1s,3R)-3-(trifluoromethoxy)cyclobutyl)amino)-5-oxo-3-(4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate | 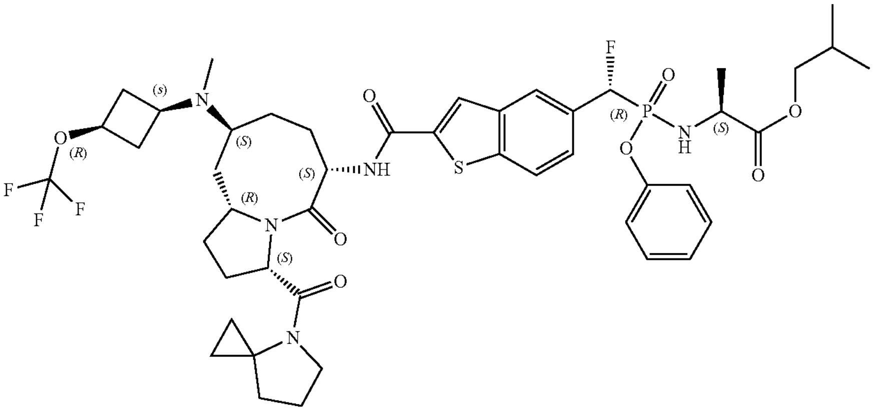 |

TABLE 1C-continued

| | | |
|---|---|---|
| C133 | isobutyl (((R)-fluoro(2-(((3S,6S,9S,10aR)-9-(methyl(3-(trifluoromethoxy) propyl)amino)-5-oxo-3-((S)-6-phenyl-4-azaspiro [2.4] heptane-4-carbonyl) decahydropyrrolo [1,2-a]azocin-6-yl)carbamoyl) benzo [b]thiophen-5-yl)methyl) (phenoxy) phosphoryl)-L-alaninate | 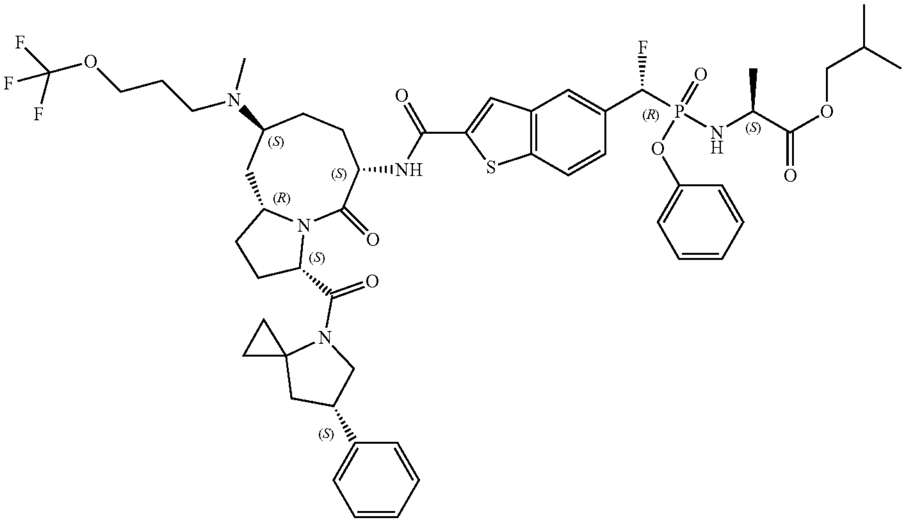 |
| C134 | isobutyl ((R)-((R)-fluoro(2-(((3S,6S,9S,10aR)-9-(methyl((1s,3R)-3-(trifluoromethyl) cyclobutyl)amino)-5-oxo-3-((S)-6-phenyl-4-azaspiro[2.4] heptane-4-carbonyl) decahydropyrrolo [1,2-a]azocin-6-yl)carbamoyl) benzo [b]thiophen-5-yl)methyl) (phenoxy) phosphoryl)-L-alaninate | 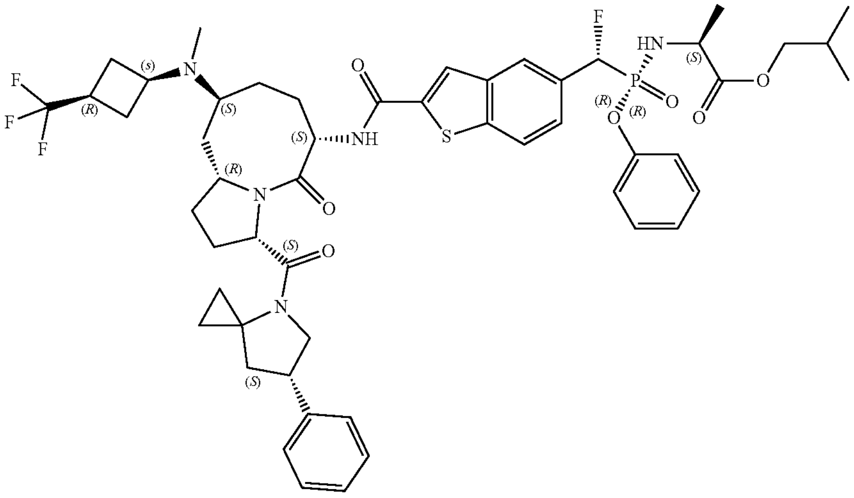 Phosphorus absolute stereochemistry arbitrarily assigned |
| C135 | isobutyl ((S)-((R)-fluoro(2-(((3S,6S,9S,10aR)-9-(methyl(4,4,4-trifluorobutyl) amino)-5-oxo-3-((S)-6-phenyl-4-azaspiro [2.4] heptane-4-carbonyl) decahydropyrrolo [1,2-a]azocin-6-yl)carbamoyl) benzo [b]thiophen-5-yl)methyl) (phenoxy) phosphoryl)-L-alaninate | 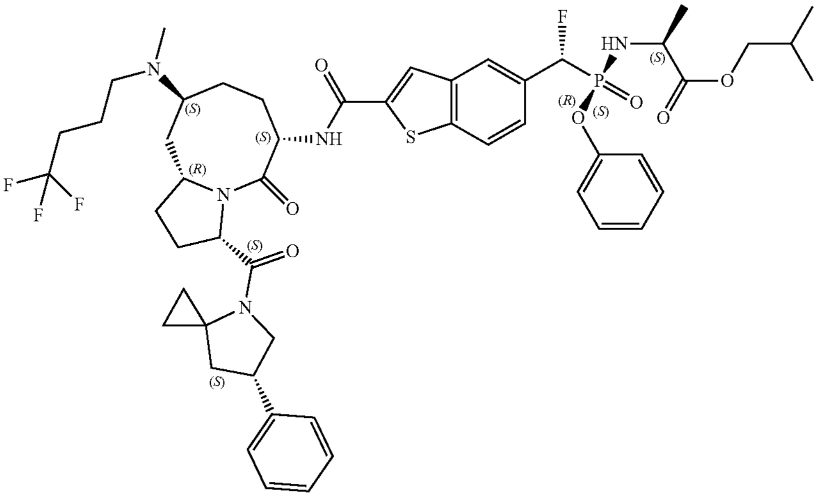 Phosphorus absolute stereochemistry arbitrarily assigned |

TABLE 1C-continued

| | | |
|---|---|---|
| C136 | isobutyl ((R)-((R)-fluoro(2-(((3S,6S,9S,10aR)-9-(methyl(4,4,4-trifluorobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate | 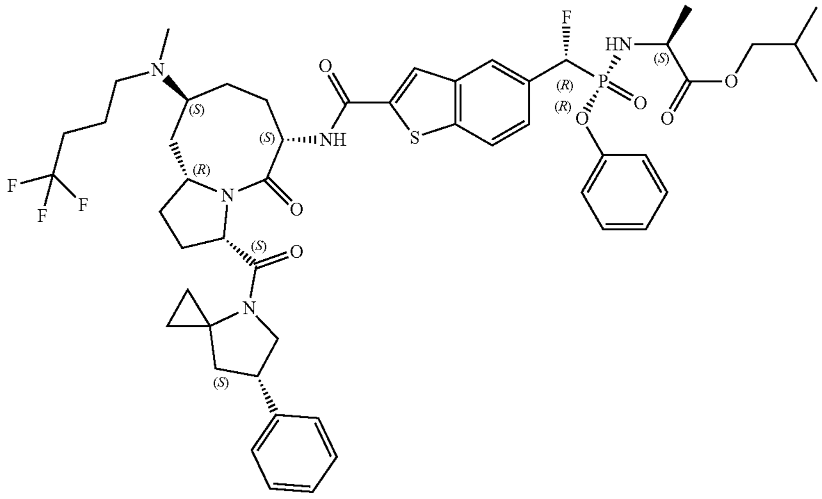<br>Phosphorus absolute stereochemistry arbitrarily assigned |
| C137 | propyl (((R)-fluoro(2-(((3S,6S,9S,10aR)-9-(methyl((S)-4,4,4-trifluoro-3-methoxybutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate | 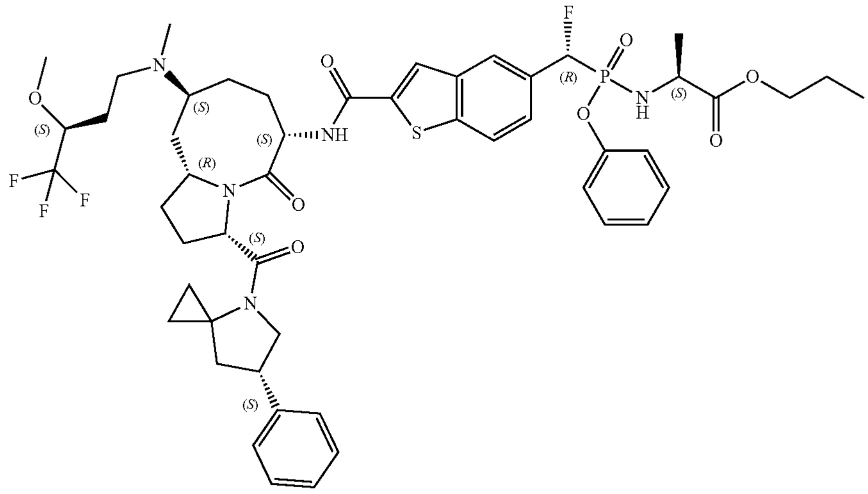 |
| C138 | propyl (((R)-(2-(((3S,6S,9S,10aR)-9-((((1r,3S)-3-(difluoromethyl)cyclobutyl)methyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)(phenoxy)phosphoryl)-L-alaninate | 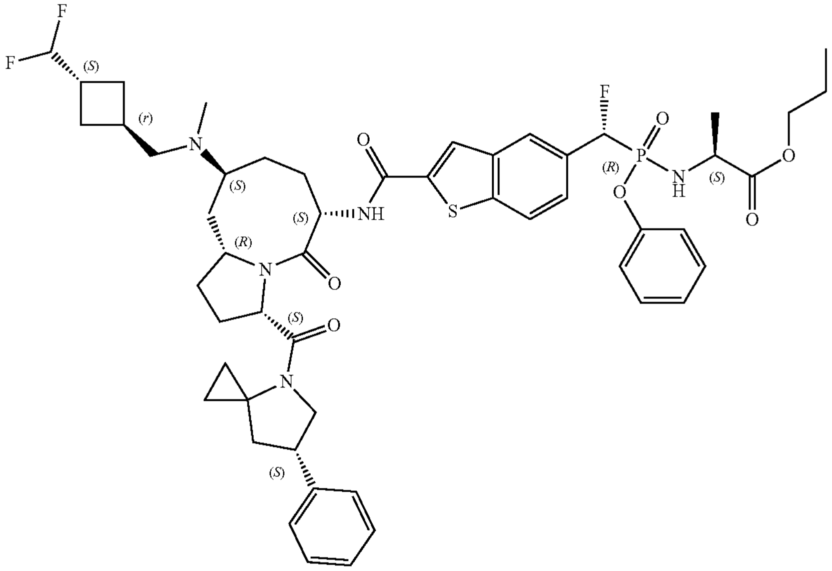 |

TABLE 1C-continued

| | | |
|---|---|---|
| C139 | propyl (((R)-fluoro(2-(((3S,6S,9S,10aR)-9-(methyl(2-(1-(trifluoromethyl)cyclopropyl)ethyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate | 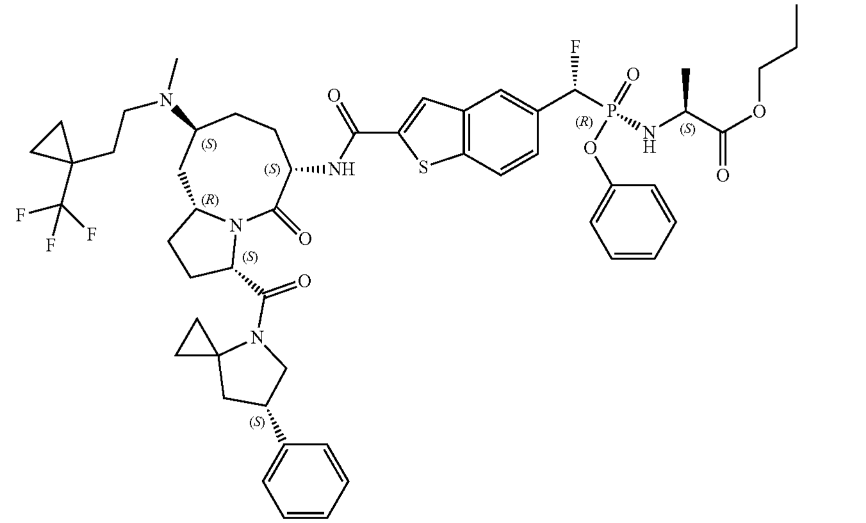 |
| C140 | propyl ((R)-((R)-fluoro(2-(((3S,6S,9S,10aR)-9-(methyl(3-(trifluoromethoxy)propyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate | 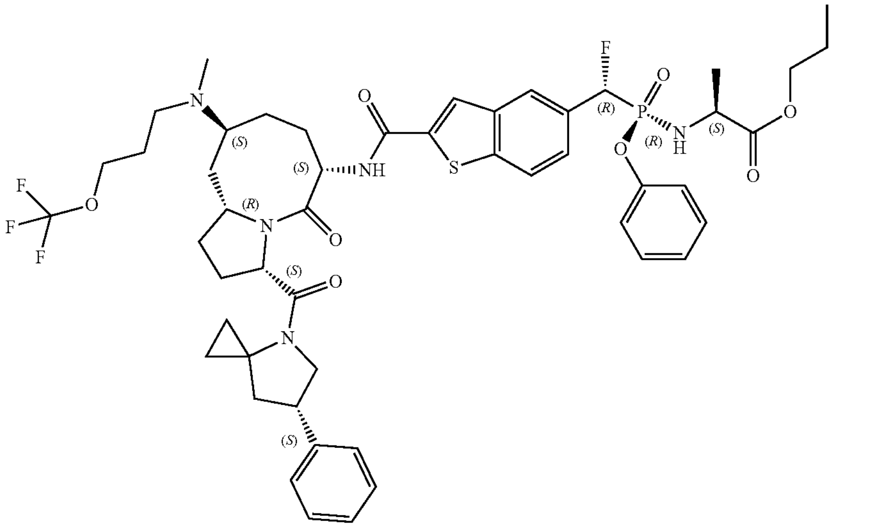 |
| C141 | propyl ((S)-((R)-fluoro(2-(((3S,6S,9S,10aR)-9-(methyl(3-(trifluoromethoxy)propyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate | 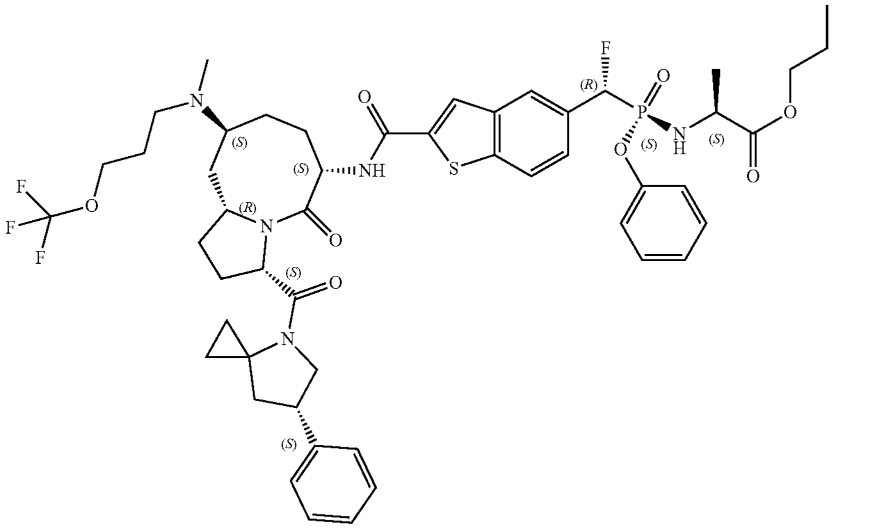 |

TABLE 1C-continued

| | | |
|---|---|---|
| C142 | propyl (((R)-(2-(((3S,6S,9S,10aR)-9-(((R)-3,3-difluorocyclopentyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)(phenoxy)phosphoryl)-L-alaninate | 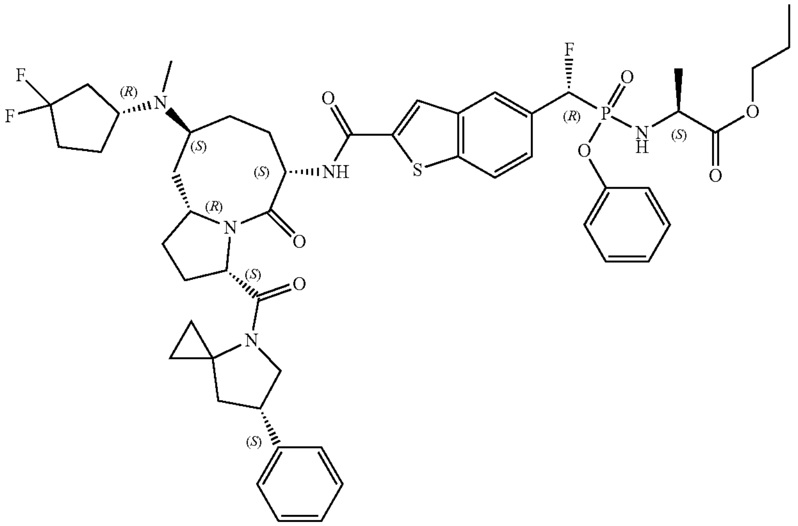 |
| C143 | propyl (((R)-(2-(((3S,6S,9S,10aR)-9-(((S)-3,3-difluorocyclopentyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)(phenoxy)phosphoryl)-L-alaninate | 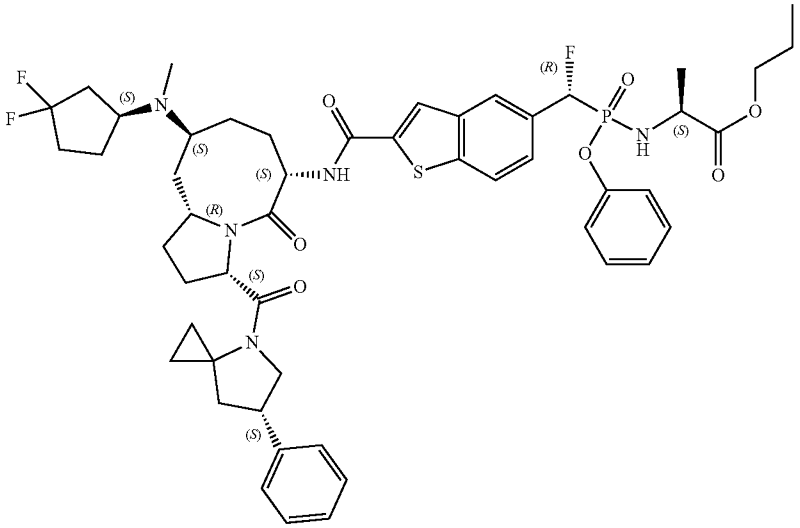 |
| C144 | propyl (((R)-fluoro(2-(((3S,6S,9S,10aR)-9-(methyl(4,4,4-trifluorobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate | 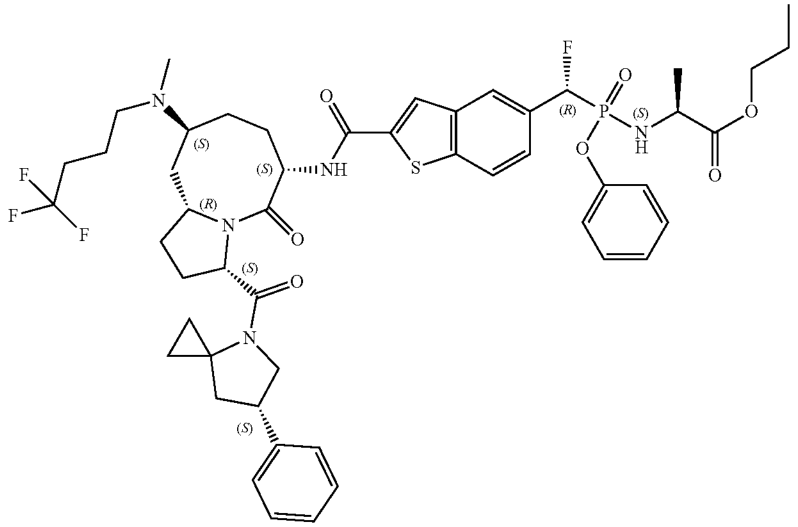 |

TABLE 1C-continued

| | | |
|---|---|---|
| C145 | propyl ((S)-((R)-fluoro(2-(((3S,6S,9S,10aR)-9-morpholino-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate | 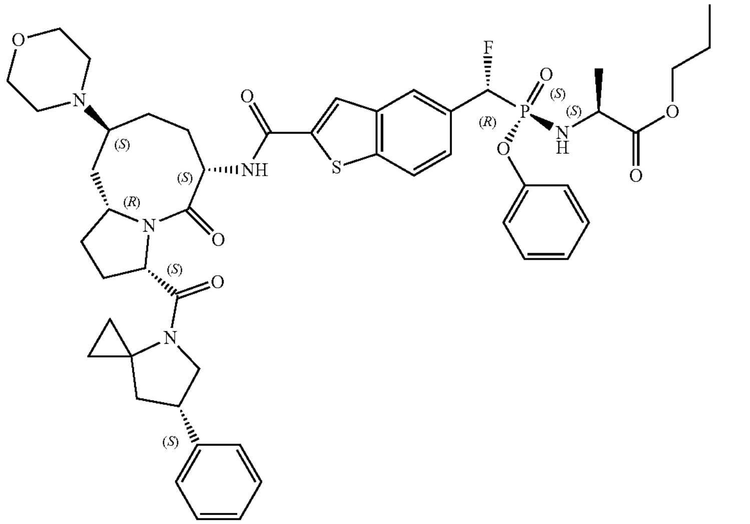 |
| C146 | propyl (((R)-fluoro(2-(((3S,6S,9S,10aR)-9-(methyl((3-methyloxetan-3-yl)methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate | 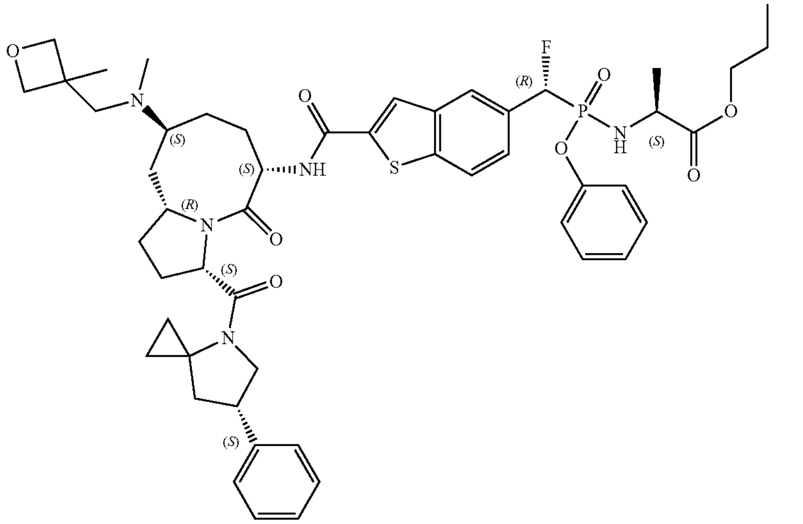 |
| C147 | propyl (((R)-fluoro(2-(((3S,6S,9S,10aR)-9-(methyl(oxetan-3-yl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate | 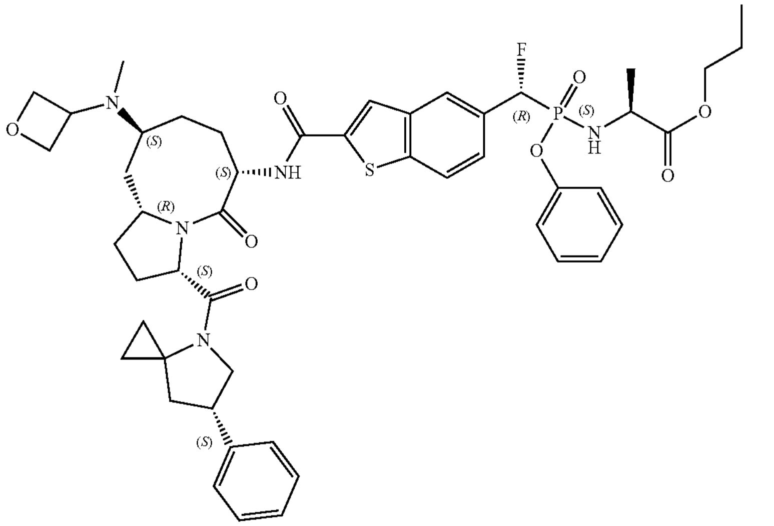 |

TABLE 1C-continued

| | | |
|---|---|---|
| C148 | isobutyl (((R)-(2-(((3S,6S,9S,10aR)-9-((3,3-difluoropropyl)(methyl)amino)-5-oxo-3-((S)-6-phenyl-4-azaspiro [2.4]heptane-4-carbonyl)decahydropyrrolo[1,2-a]azocin-6-yl)carbamoyl)benzo[b]thiophen-5-yl)fluoromethyl)(phenoxy)phosphoryl)-L-alaninate | 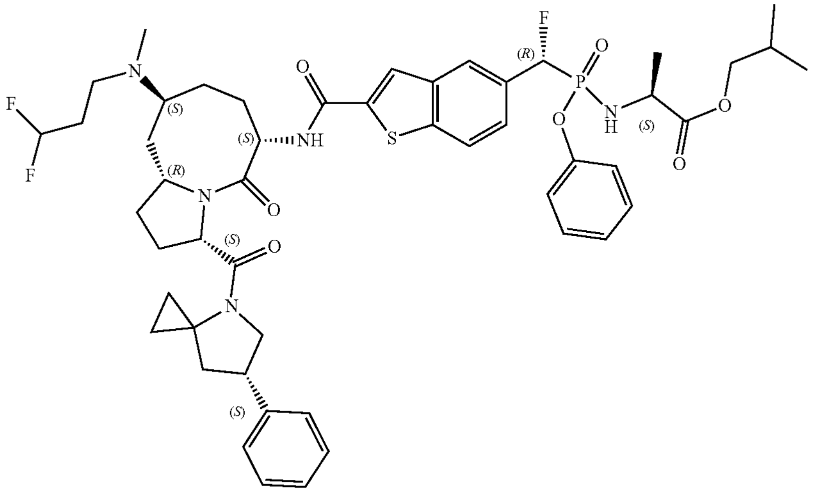 |
| C149 | propyl N-(((R)-(2-(((3S,6S,9S,10aR)-9-((3,3-difluoropropyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)(phenoxy)phosphoryl)-O-methyl-L-serinate | 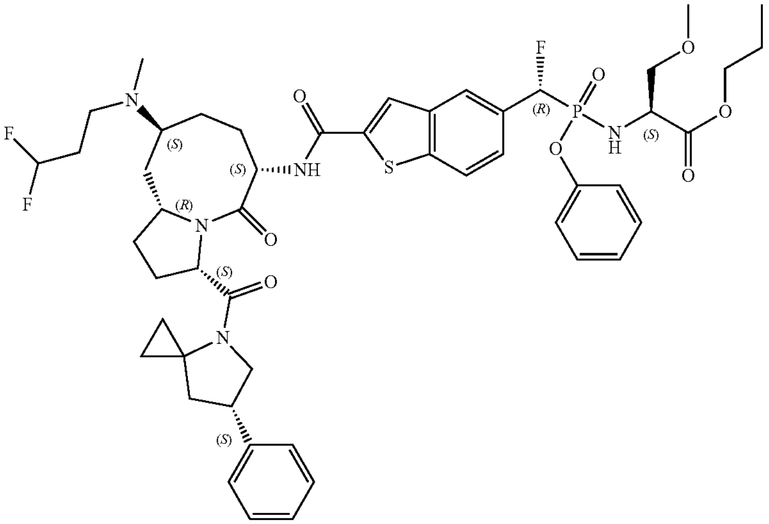 |
| C150 | propyl 2-((((R)-(2-(((3S,6S,9S,10aR)-9-((3,3-difluoropropyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)(phenoxy)phosphoryl)amino)-2-methylpropanoate | 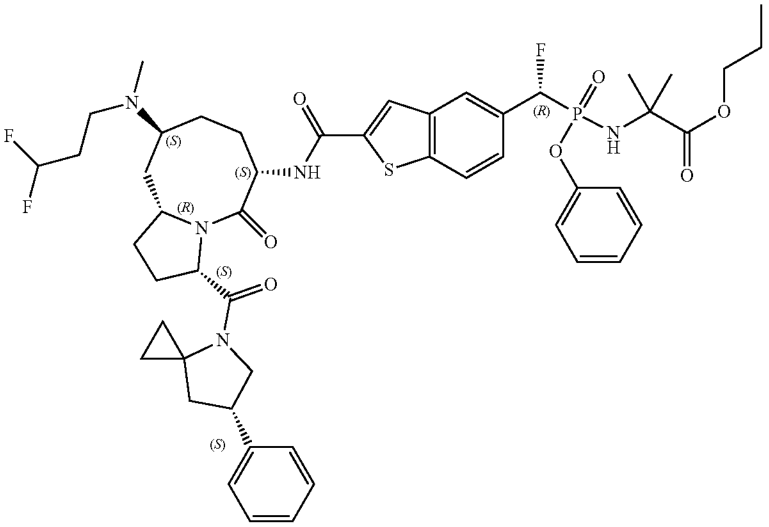 |

TABLE 1C-continued

| | | |
|---|---|---|
| C151 | isopropyl (S)-2-(((S)-((R)-(2-(((3S,6S,9S,10aR)-9-((3,3-difluoropropyl)(methyl)amino)-5-oxo-3-((S)-6-phenyl-4-azaspiro [2.4] heptane-4-carbonyl) decahydropyrrolo [1,2-a]azocin-6-yl)carbamoyl) benzo [b]thiophen-5-yl)fluoromethyl) (phenoxy) phosphoryl) amino) butanoate | 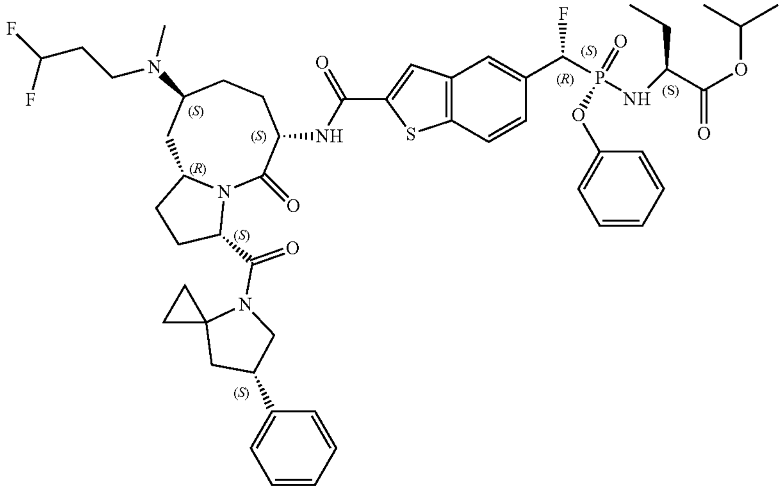 |
| C152 | propyl ((difluoro(2-(((3S,6S,9S,10aR)-9-(methyl((1s,3R)-3-(trifluoromethoxy) cyclobutyl)amino)-5-oxo-3-((S)-6-phenyl-4-azaspiro[2.4] heptane-4-carbonyl) decahydropyrrolo [1,2-a]azocin-6-yl)carbamoyl) benzo [b]thiophen-5-yl)methyl) (phenoxy) phosphoryl) prolinate | 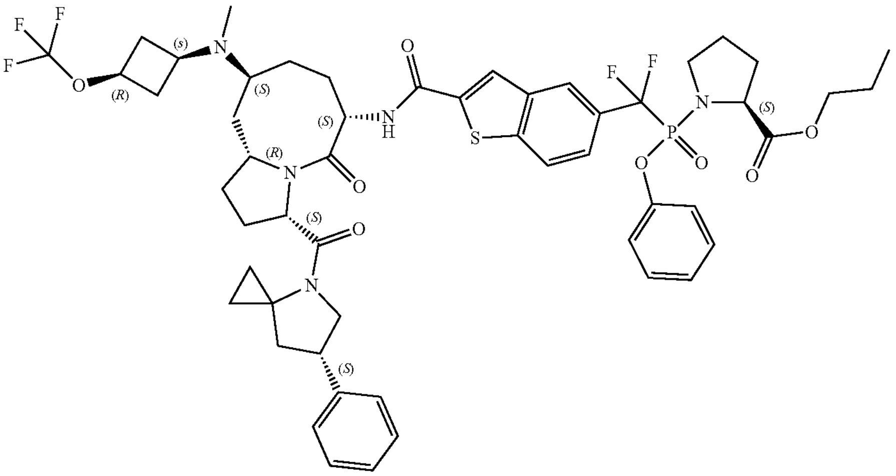 |
| C153 | propyl 1-(ethoxy((R)-fluoro(2-(((3S,6S,9S,10aR)-9-(methyl((1s,3R)-3-(trifluoromethoxy) cyclobutyl)amino)-5-oxo-3-((S)-6-phenyl-4-azaspiro [2.4] heptane-4-carbonyl) decahydropyrrolo [1,2-a]azocin-6-yl)carbamoyl) benzo [b]thiophen-5-yl)methyl) phosphoryl)-3,3-difluoropyrrolidine-2-carboxylate | 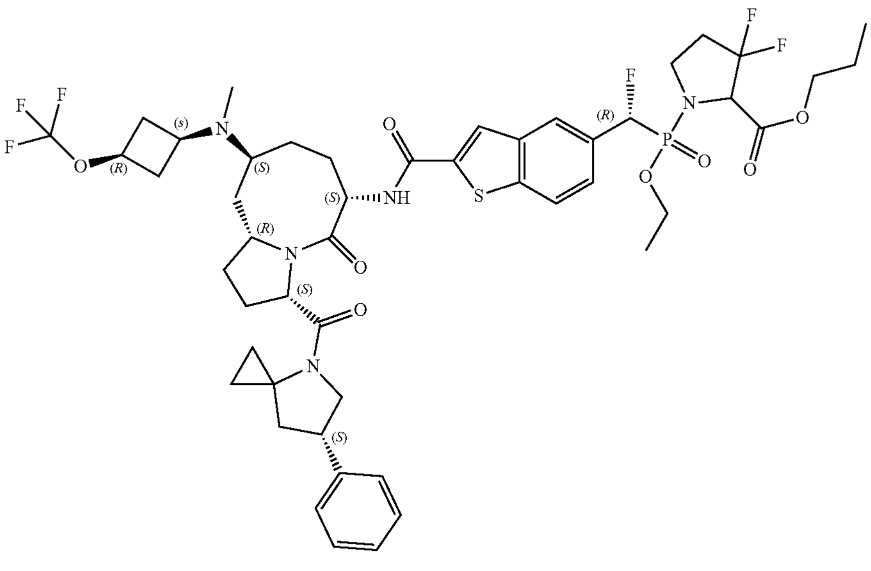 |

TABLE 1C-continued

| | | |
|---|---|---|
| C154 | propyl ((difluoro(2-(((3S,6S,9S,10aR)-9-(methyl((1s,3R)-3-(trifluoromethoxy) cyclobutyl)amino)-5-oxo-3-((S)-6-phenyl-4-azaspiro[2.4] heptane-4-carbonyl) decahydropyrrolo [1,2-a]azocin-6-yl)carbamoyl) benzo [b]thiophen-5-yl)methyl) (phenoxy) phosphoryl)-L-alaninate | 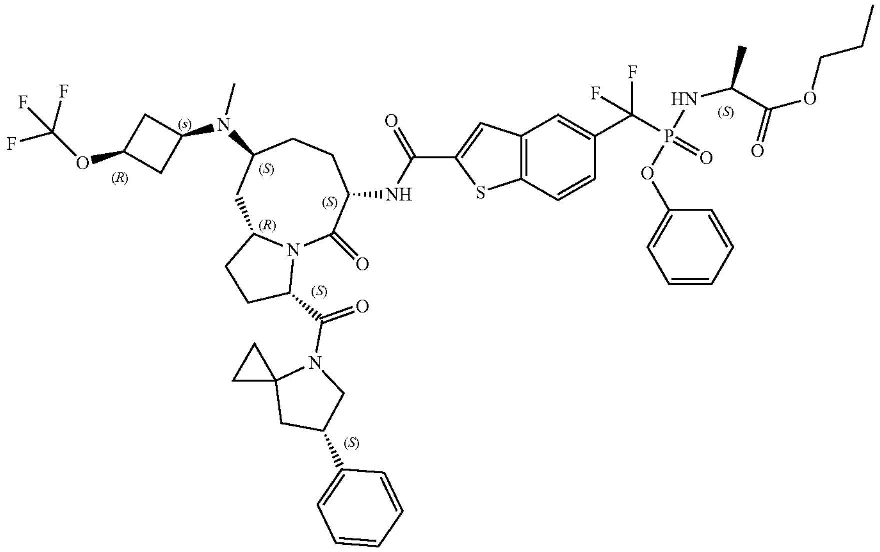 |
| C155 | dipropyl 2,2'-((((R)-fluoro(2-(((3S,6S,9S,10aR)-9-(methyl((1s,3R)-3-(trifluoromethoxy) cyclobutyl)amino)-5-oxo-3-((S)-6-phenyl-4-azaspiro[2.4] heptane-4-carbonyl) decahydropyrrolo [1,2-a]azocin-6-yl)carbamoyl) benzo [b]thiophen-5-yl)methyl) phosphoryl) bis(azanediyl)) (2S,2'S)-dipropionate | 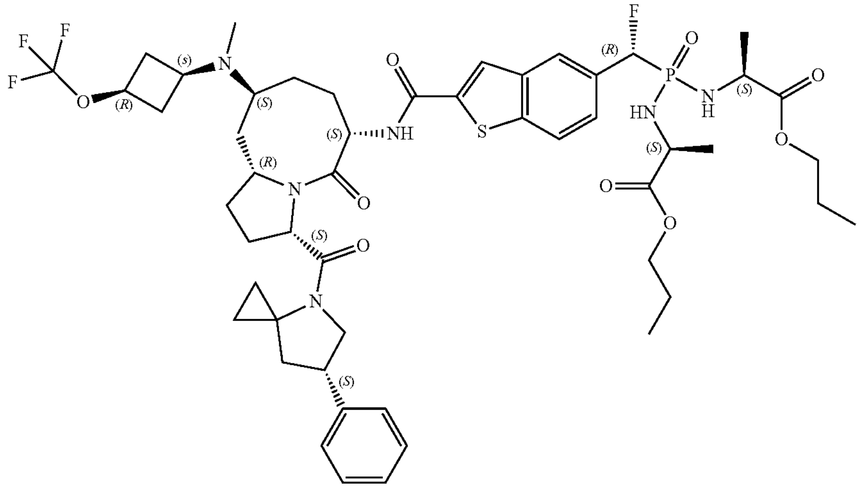 |
| C156 | isobutyl (cyclopropoxy((S)-fluoro(2-(((3S,6S,9S,10aR)-9-(methyl((1s,3R)-3-(trifluoromethoxy) cyclobutyl)amino)-5-oxo-3-((S)-6-phenyl-4-azaspiro[2.4] heptane-4-carbonyl) decahydropyrrolo [1,2-a]azocin-6-yl)carbamoyl) benzo [b]thiophen-5-yl)methyl) phosphoryl)-L-alaninate | 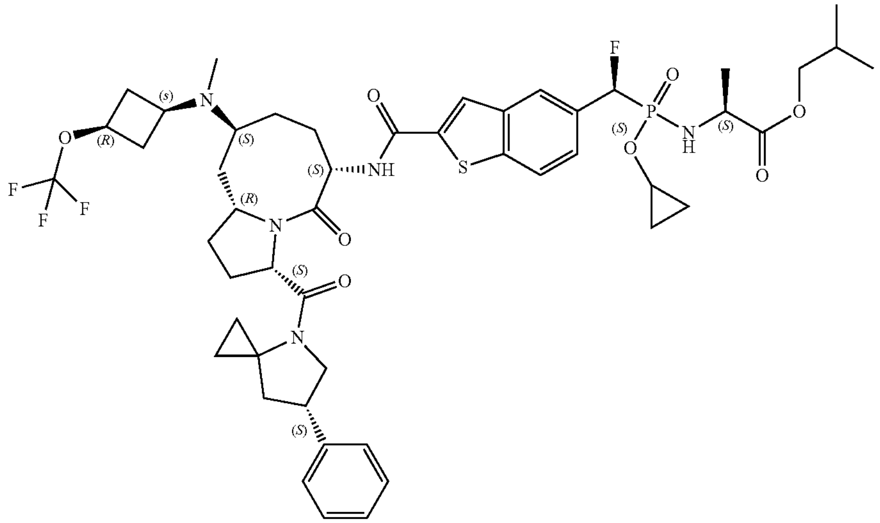 |

TABLE 1C-continued

| | | |
|---|---|---|
| C157 | propyl 1-((((R)-fluoro(2-(((3S,6S,9S,10aR)-9-(((1s,3R)-3-fluorocyclobutyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)amino)cyclopropane-1-carboxylate | 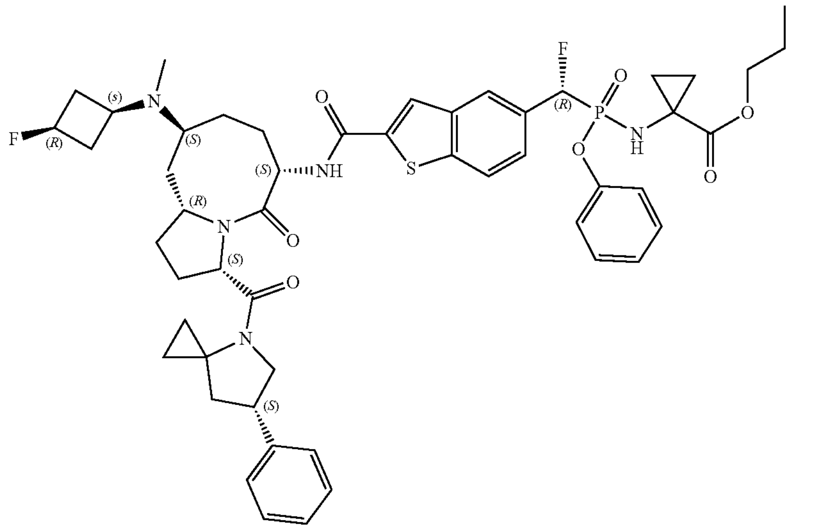 |
| C158 | isobutyl (((R)-fluoro(2-(((3S,6S,9S,10aR)-9-(methyl((1R,3S)-3-(trifluoromethoxy)cyclopentyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate | 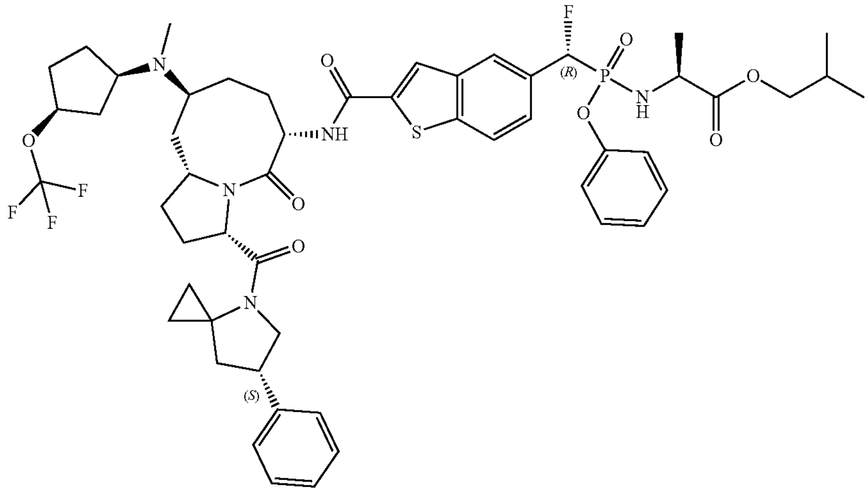 |
| C159 | isobutyl (((S)-fluoro(2-(((3S,6S,9S,10aR)-9-(methyl((1R,3S)-3-(trifluoromethoxy)cyclopentyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate | 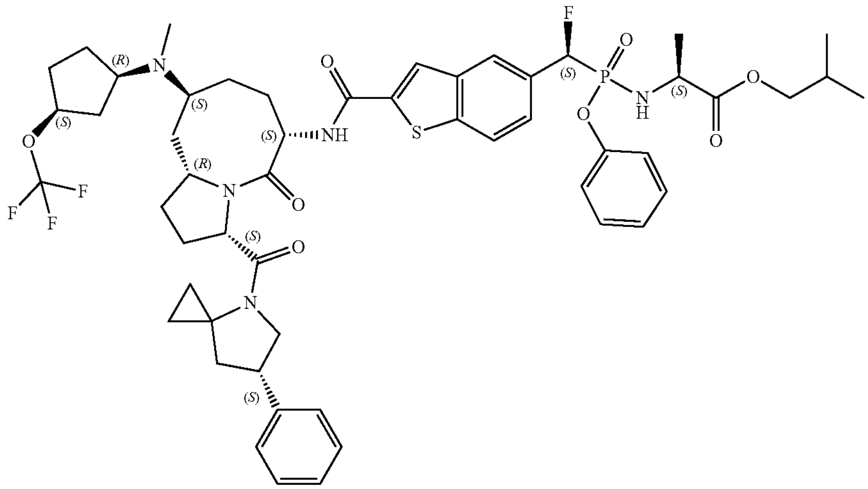 |

TABLE 1C-continued

| | | |
|---|---|---|
| C160 | propyl (((S)-fluoro(2-(((3S,6S,9S,10aR)-9-(methyl((1R,3S)-3-(trifluoromethoxy)cyclopentyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate | 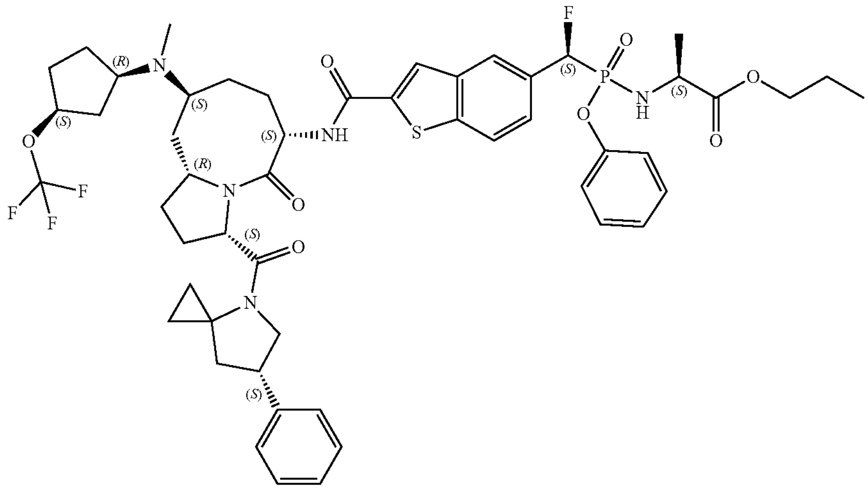 |
| C161 | (1-fluorocyclobutyl)methyl (((S)-fluoro(2-(((3S,6S,9S,10aR)-9-(((1s,3R)-3-fluorocyclobutyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate | 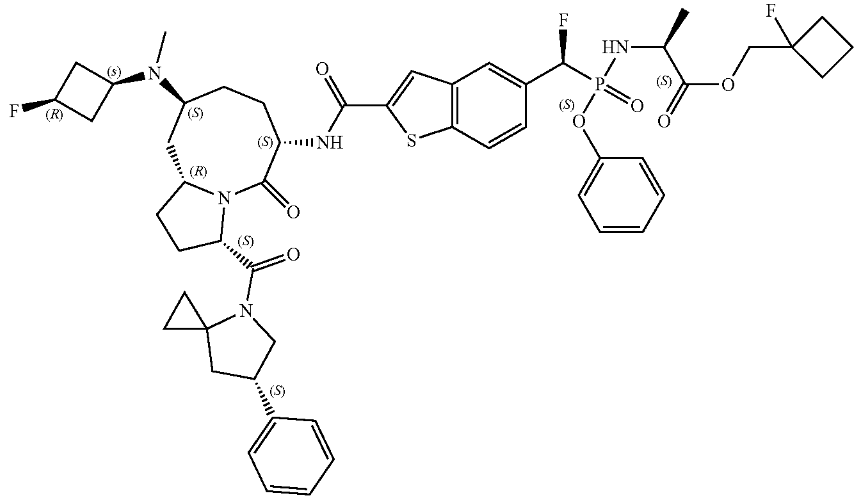 |
| C162 | propyl (((R)-fluoro(2-(((3S,6S,9S,10aR)-9-(((1s,3R)-3-fluorocyclobutyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(3,3,3-trifluoropropoxy)phosphoryl)-L-alaninate | 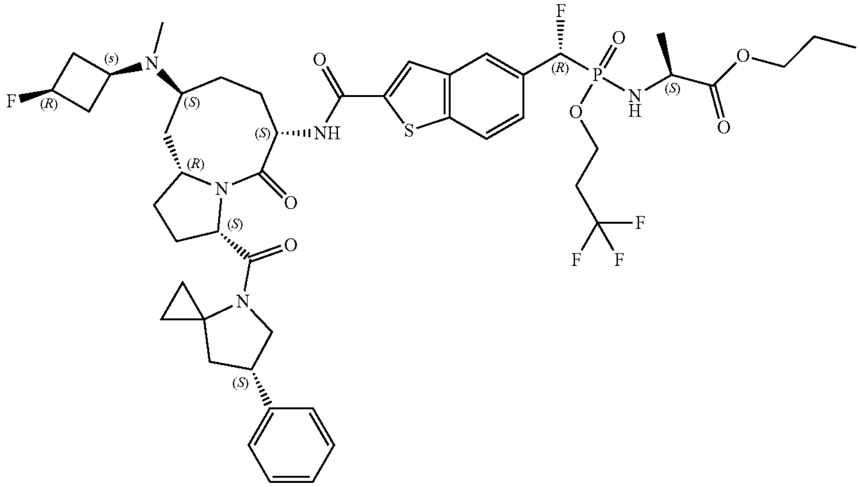 |

TABLE 1C-continued

| | | |
|---|---|---|
| C163 | propyl (((R)-fluoro(2-(((3S,6S,9S,10aR)-9-(methyl((1s,3R)-3-(trifluoromethoxy)cyclobutyl)amino)-5-oxo-3-((R)-6-(pyridin-3-yl)-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate | 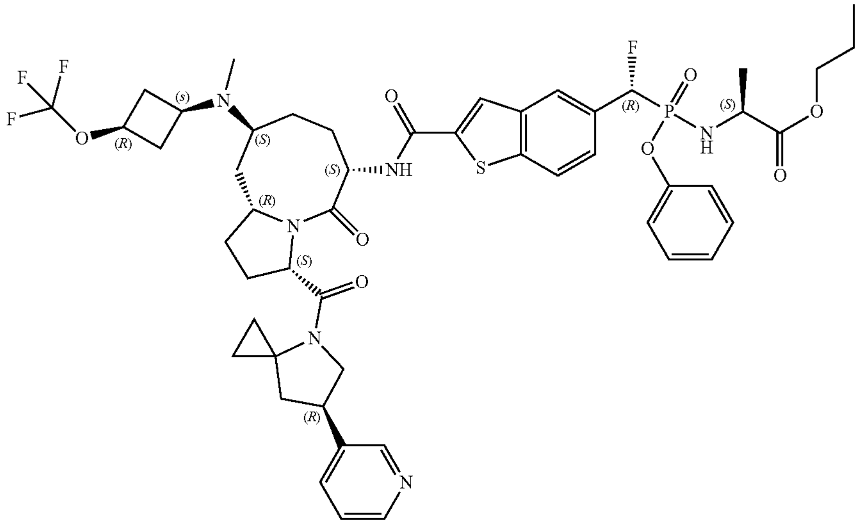 |
| C164 | propyl (((R)-fluoro(2-(((3S,6S,9S,10aR)-9-(methyl((1s,3R)-3-(trifluoromethoxy)cyclobutyl)amino)-5-oxo-3-((S)-6-(pyridin-3-yl)-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate | 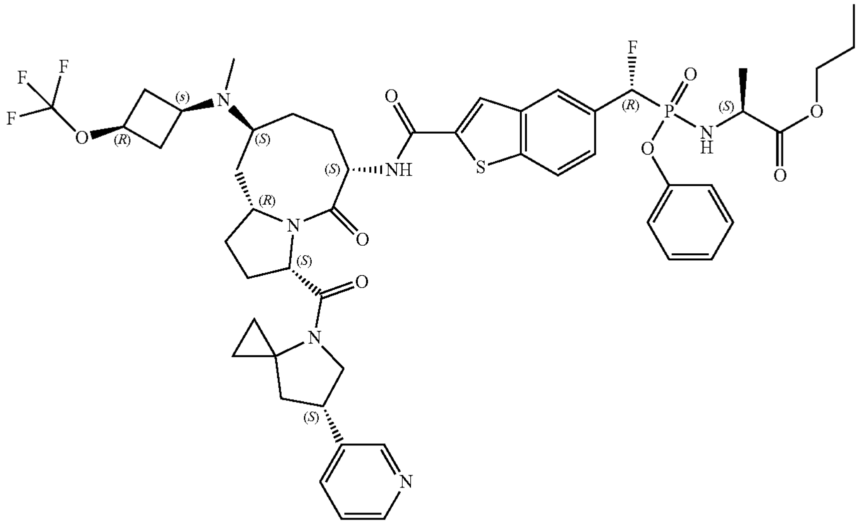 |
| C165 | propyl (((R)-fluoro(2-(((3S,6S,9S,10aR)-3-((6S,7S)-7-methoxy-6-phenyl-4-azaspiro[2.4]heptane-4-carbonyl)-9-(methyl((1s,3R)-3-(trifluoromethoxy)cyclobutyl)amino)-5-oxodecahydropyrrolo[1,2-a]azocin-6-yl)carbamoyl)benzo[b]thiophen-5-yl)methyl)(phenoxy)phosphoryl)-L-alaninate | 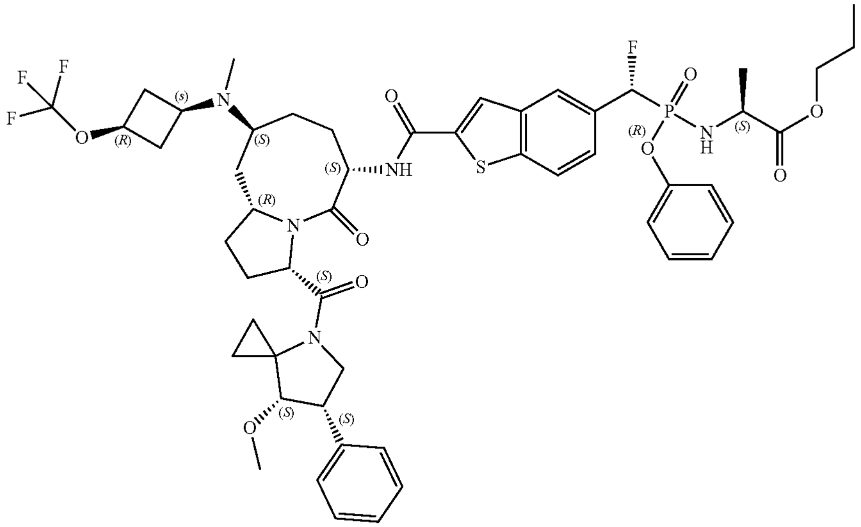<br>Absolute stereochemistry of cis-3-OMe-4-Ph pyrrolidine arbitrarily assigned |

TABLE 1C-continued

| | | |
|---|---|---|
| C166 | propyl (((R)-fluoro(2-(((3S,6S,9S,10aR)-3-((6R,7R)-7-methoxy-6-phenyl-4-azaspiro[2.4]heptane-4-carbonyl)-9-(methyl((1s,3R)-3-(trifluoromethoxy)cyclobutyl)amino)-5-oxodecahydropyrrolo[1,2-a]azocin-6-yl)carbamoyl)benzo[b]thiophen-5-yl)methyl)(phenoxy)phosphoryl)-L-alaninate | 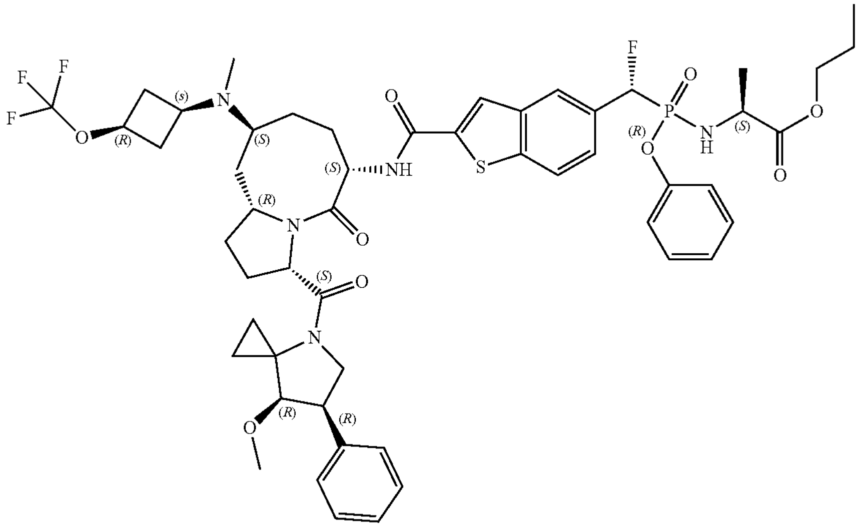<br>Absolute stereochemistry of cis-3-OMe-4-Ph pyrrolidine arbitrarily assigned |
| C167 | propyl (((R)-fluoro(2-(((3S,6S,9S,10aR)-9-(methyl((S)-3,3,3-trifluoro-2-methoxypropyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate | 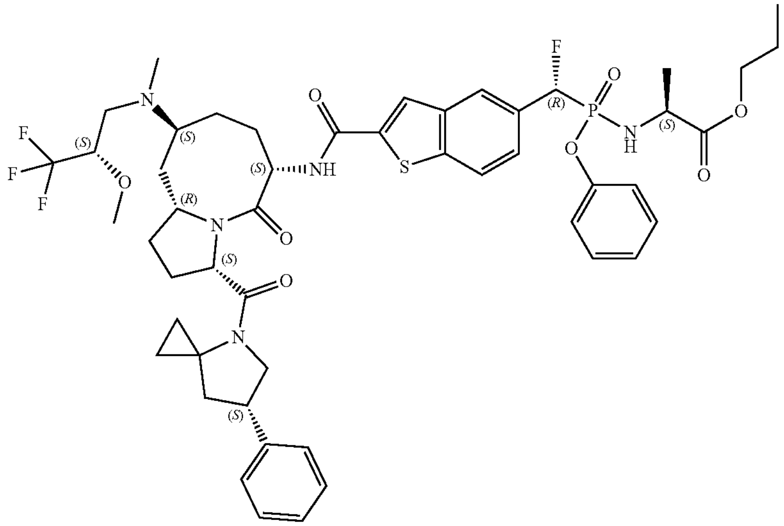 |
| C168 | propyl ((R)-((R)-fluoro(2-(((3S,6S,9S,10aR)-9-(methyl(2-(trifluoromethoxy)ethyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate | 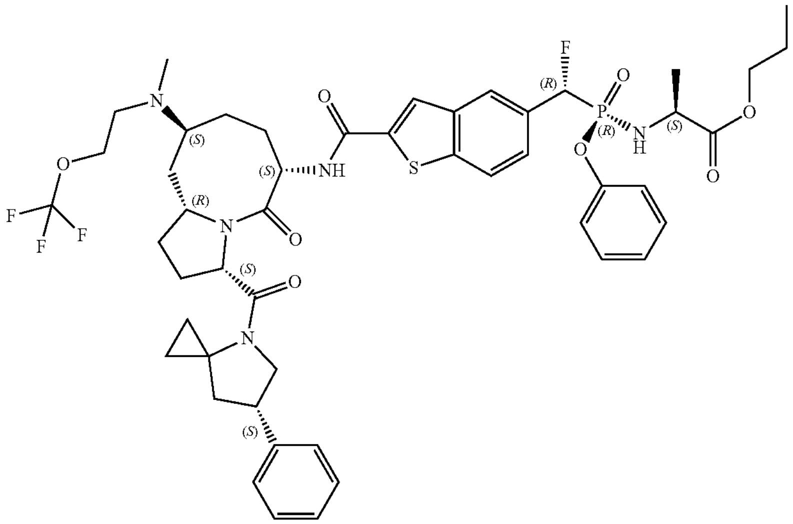 |

TABLE 1C-continued

| | | |
|---|---|---|
| C169 | propyl ((S)-((R)-fluoro(2-(((3S,6S,9S,10aR)-9-(methyl(2-(trifluoromethoxy)ethyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate | 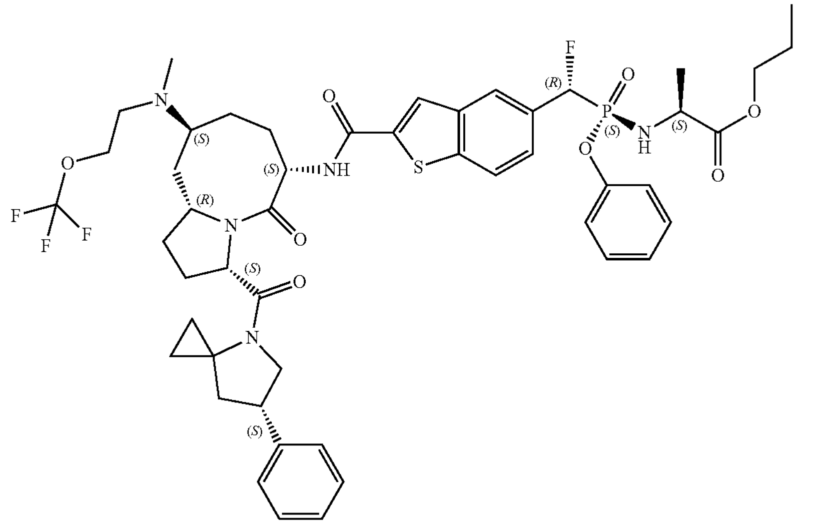 |
| C170 | propyl (((R)-fluoro(2-(((3S,6S,9S,10aR)-9-(((1s,3R)-3-fluorocyclobutyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(2-oxopyrrolidin-1-yl)phosphoryl)-L-alaninate | 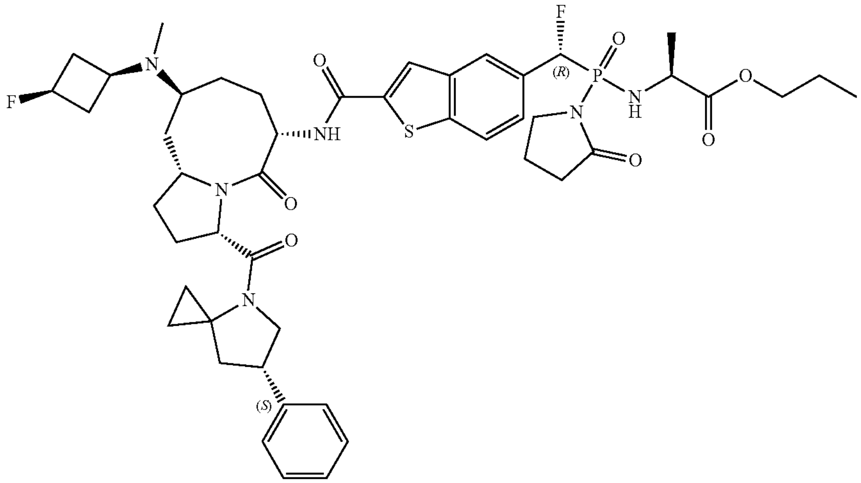 |
| C172 | cyclobutyl ((R)-((R)-fluoro(2-(((3S,6S,9S,10aR)-9-(methyl((3-methyloxetan-3-yl)methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate | 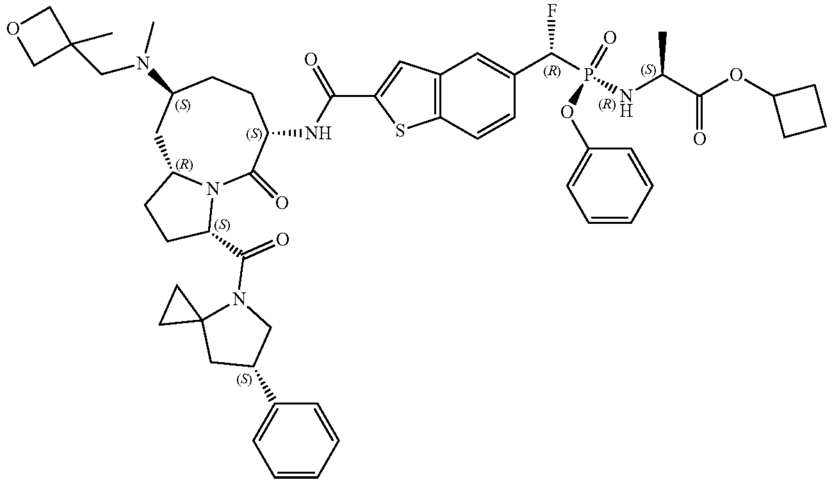 Phosphorus absolute stereochemistry arbitrarily assigned |

TABLE 1C-continued

| | | |
|---|---|---|
| C173 | propyl ((S)-((R)-fluoro(2-(((3S,6S,9S,10aR)-9-(methyl((3-methyloxetan-3-yl)methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(2,2,2-trifluoroethoxy)phosphoryl)-L-alaninate | 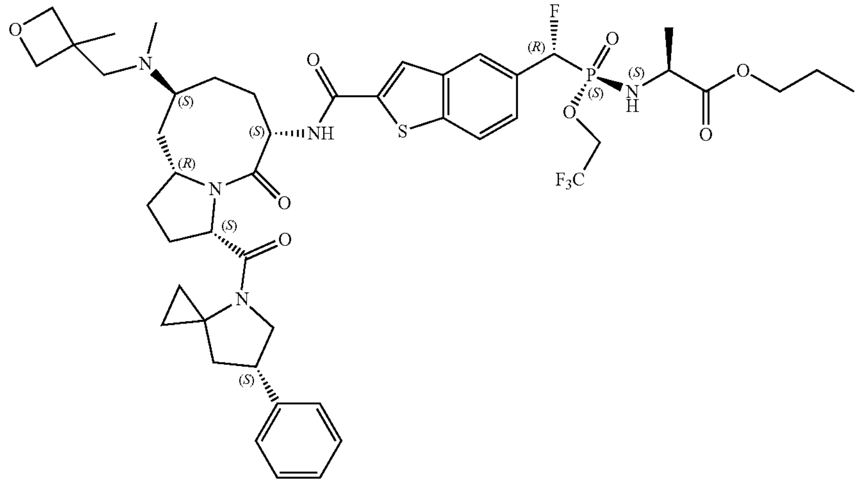<br>Phosphorus absolute stereochemistry arbitrarily assigned |
| C174 | ((S)-tetrahydrofuran-3-yl)methyl (((R)-fluoro(2-(((3S,6S,9S,10aR)-9-(methyl((1s,3R)-3-(trifluoromethyl)cyclobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate | 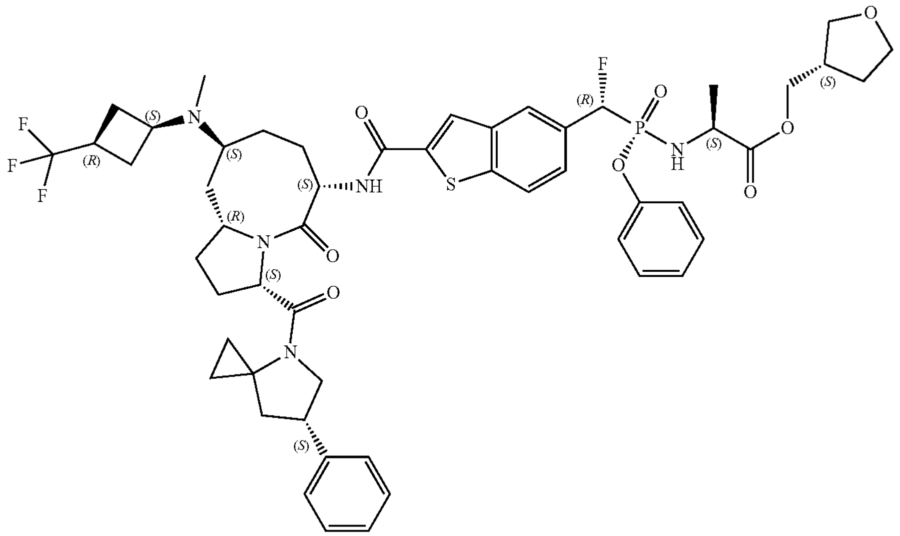 |
| C175 | propyl ((R)-((R)-fluoro(2-(((3S,6S,9S,10aR)-9-(methyl((1s,3R)-3-(trifluoromethyl)cyclobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(2,2,2-trifluoroethoxy)phosphoryl)-L-alaninate | 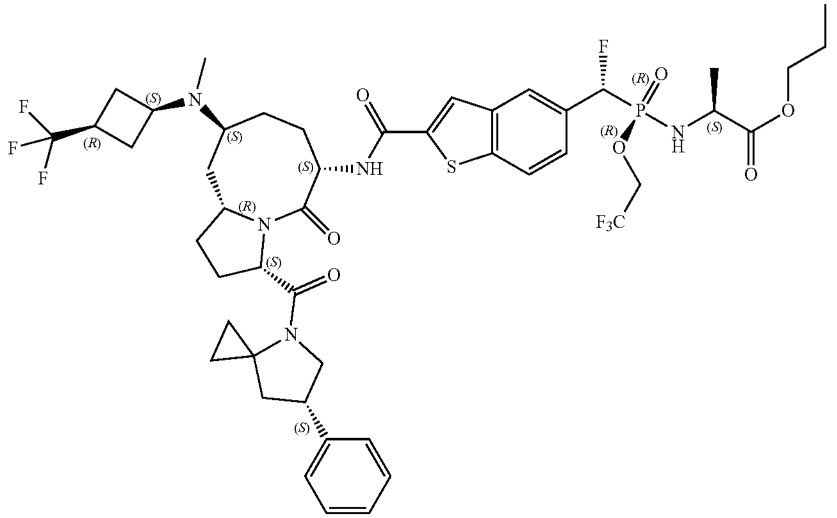<br>Phosphorus absolute stereochemistry arbitrarily assigned |

TABLE 1C-continued

| | | |
|---|---|---|
| C176 | isopropyl ((R)-ethoxy((R)-fluoro(2-(((3S,6S,9S,10aR)-9-(methyl((1s,3R)-3-(trifluoromethyl)cyclobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)phosphoryl)-L-alaninate | 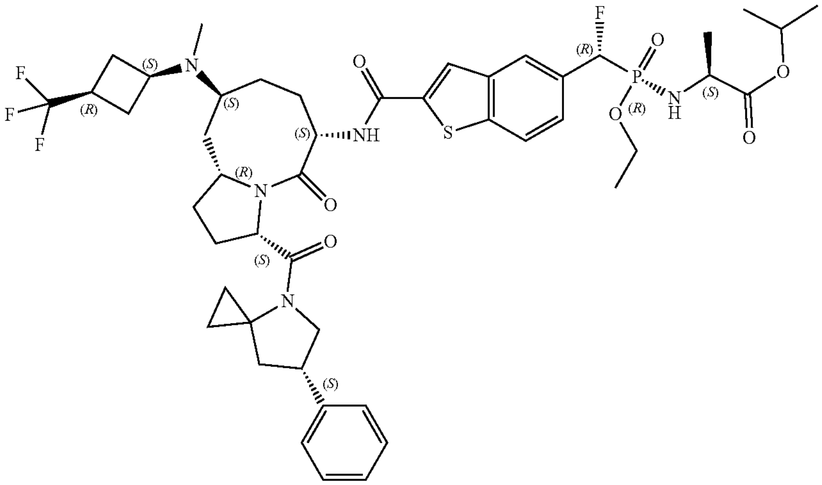 Phosphorus absolute stereochemistry arbitrarily assigned |
| C177 | isopropyl ((S)-ethoxy((R)-fluoro(2-(((3S,6S,9S,10aR)-9-(methyl(4,4,4-trifluorobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)phosphoryl)-L-alaninate | 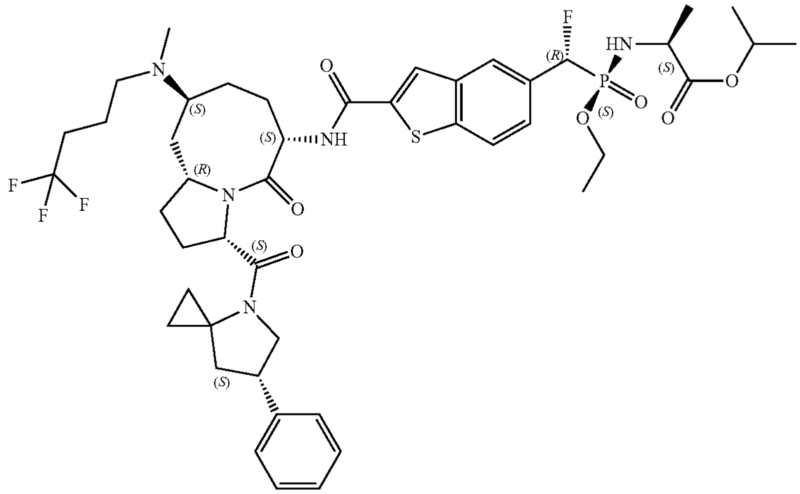 Phosphorus absolute stereochemistry arbitrarily assigned |
| C178 | propyl (ethoxy((R)-(2-(((3S,6S,9S,10aR)-9-(ethyl((1s,3R)-3-fluorocyclobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)phosphoryl)-L-alaninate | 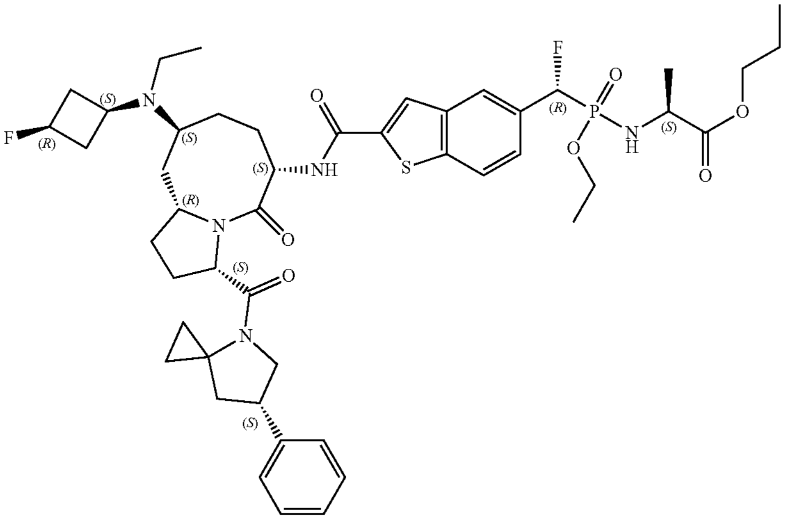 |

TABLE 1C-continued

| | | |
|---|---|---|
| C179 | 2-morpholinoethyl (((R)-(2-(((3S,6S,9S,10aR)-9-((3,3-difluoropropyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)(phenoxy)phosphoryl)-L-alaninate | 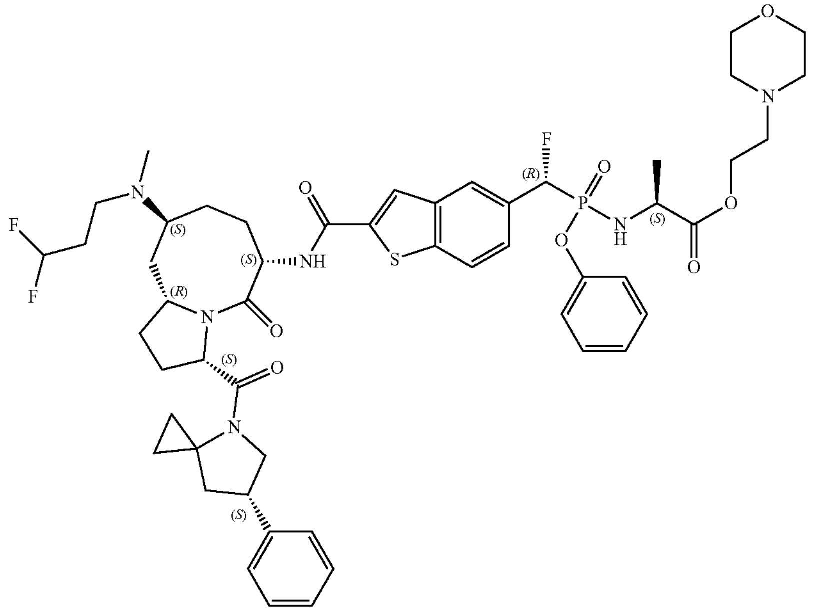 |
| C180 | neopentyl (((R)-(2-(((3S,6S,9S,10aR)-9-((3,3-difluoropropyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)(phenoxy)phosphoryl)-L-alaninate | 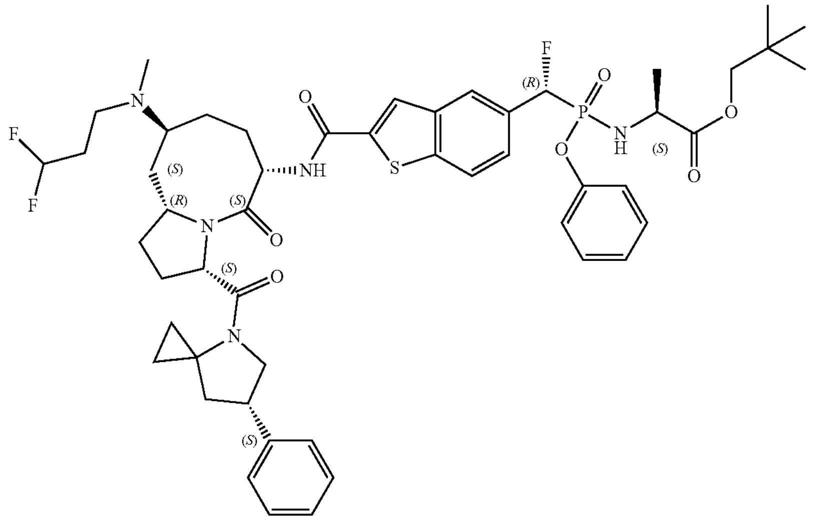 |
| C181 | propyl ((R)-((R)-(2-(((3S,6S,9S,10aR)-9-((3,3-difluoropropyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)fluoromethyl)(phenoxy)phosphoryl)-L-prolinate | 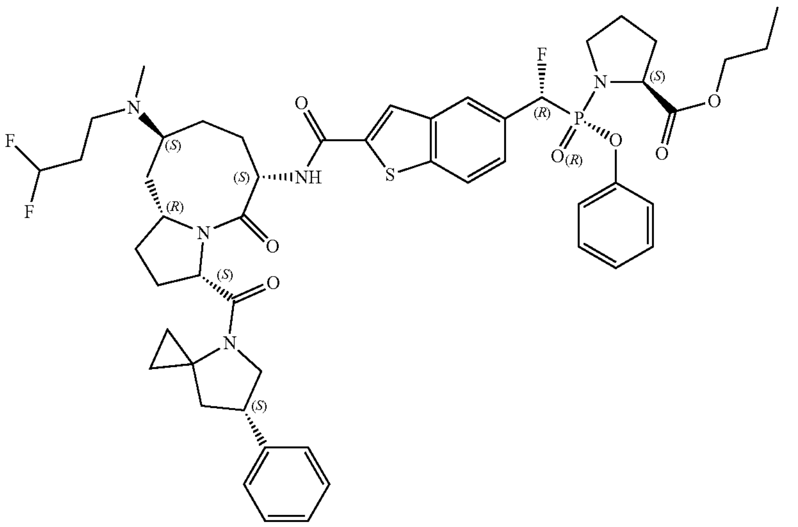 |

TABLE 1C-continued

| | | |
|---|---|---|
| C182 | 2-methoxy-2-methylpropyl (((R)-fluoro(2-(((3S,6S,9S,10aR)-9-(((1s,3R)-3-fluorocyclobutyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate | 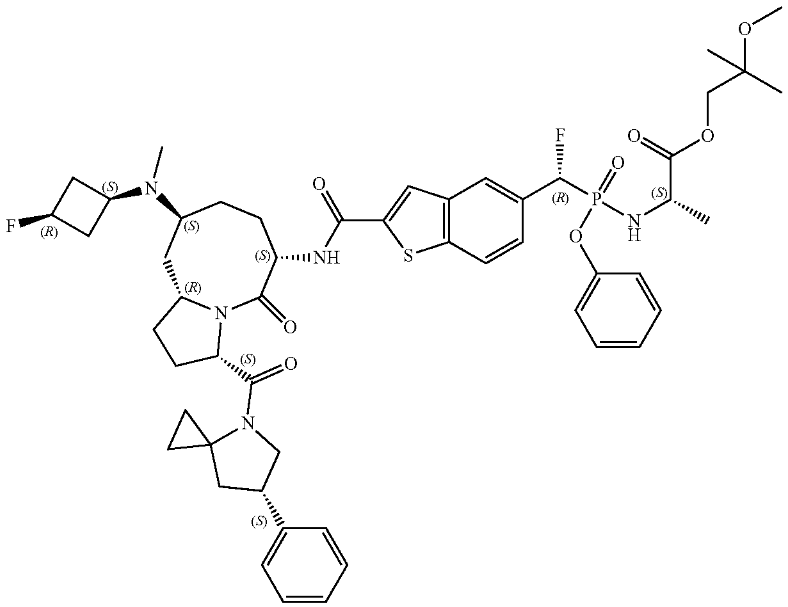 |
| C183 | 6,6-difluorospiro[3.3]heptan-2-yl (((R)-fluoro(2-(((3S,6S,9S,10aR)-9-(((1s,3R)-3-fluorocyclobutyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate | 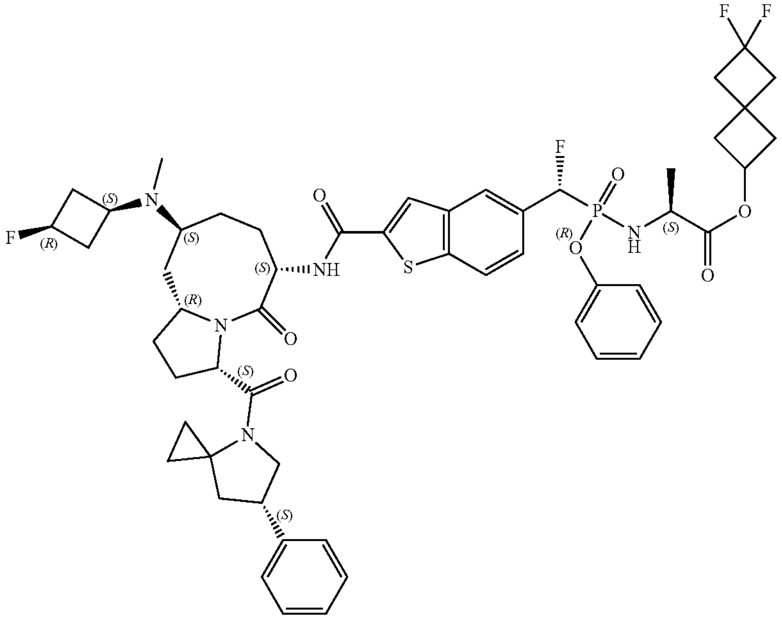 |

TABLE 1C-continued

| | | |
|---|---|---|
| C184 | ((R)-tetrahydrofuran-3-yl)methyl (((R)-fluoro(2-(((3S,6S,9S,10aR)-9-(((1s,3R)-3-fluorocyclobutyl)(methyl)amino)-5-oxo-3-((S)-6-phenyl-4-azaspiro [2.4] heptane-4-carbonyl) decahydropyrrolo [1,2-a]azocin-6-yl)carbamoyl) benzo [b]thiophen-5-yl)methyl) (phenoxy) phosphoryl)-L-alaninate | 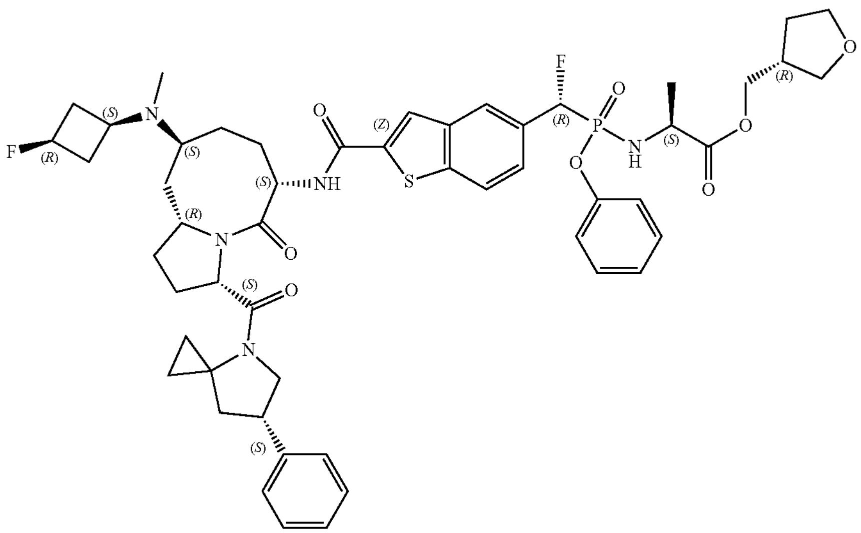 |
| C185 | ((S)-tetrahydrofuran-3-yl)methyl (((R)-fluoro(2-(((3S,6S,9S,10aR)-9-(((1s,3R)-3-fluorocyclobutyl)(methyl)amino)-5-oxo-3-((S)-6-phenyl-4-azaspiro[2.4] heptane-4-carbonyl) decahydropyrrolo [1,2-a]azocin-6-yl)carbamoyl) benzo [b]thiophen-5-yl)methyl) (phenoxy) phosphoryl)-L-alaninate | 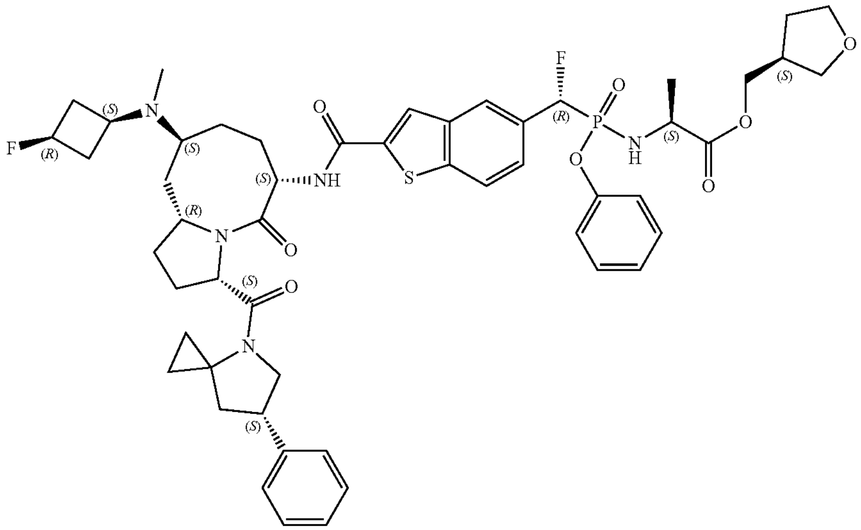 |
| C186 | (tetrahydro-2H-pyran-4-yl)methyl (((R)-fluoro(2-(((3S,6S,9S,10aR)-9-(((1s,3R)-3-fluorocyclobutyl)(methyl)amino)-5-oxo-3-((S)-6-phenyl-4-azaspiro[2.4] heptane-4-carbonyl) decahydropyrrolo [1,2-a]azocin-6-yl)carbamoyl) benzo [b]thiophen-5-yl)methyl) (phenoxy) phosphoryl)-L-alaninate | 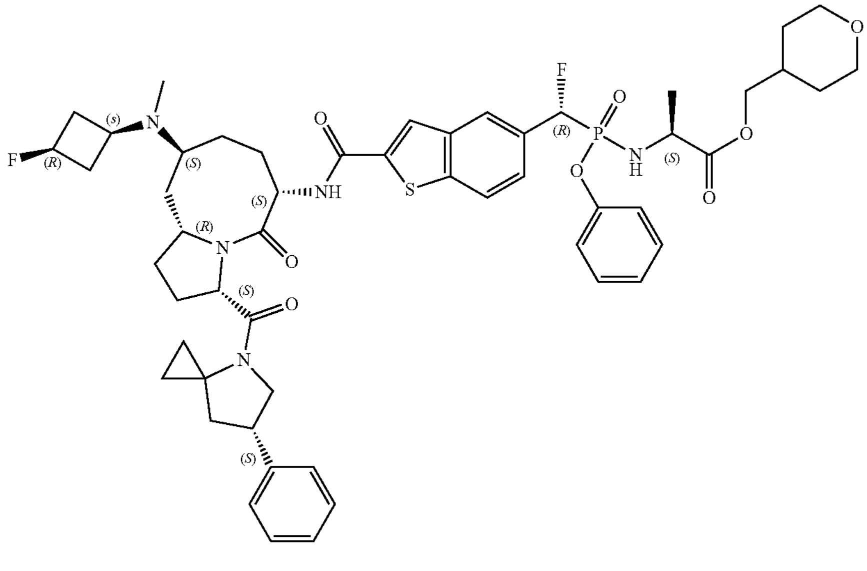 |

TABLE 1C-continued

| | | |
|---|---|---|
| C187 | isobutyl (2S)-2-((((R)-fluoro(2-(((3S,6S,9S,10aR)-9-(((1s,3R)-3-fluorocyclobutyl)(methyl)amino)-5-oxo-3-((S)-6-phenyl-4-azaspiro [2.4]heptane-4-carbonyl)decahydropyrrolo[1,2-a]azocin-6-yl)carbamoyl)benzo[b]thiophen-5-yl)methyl)(phenoxy)phosphoryl)amino)butanoate | 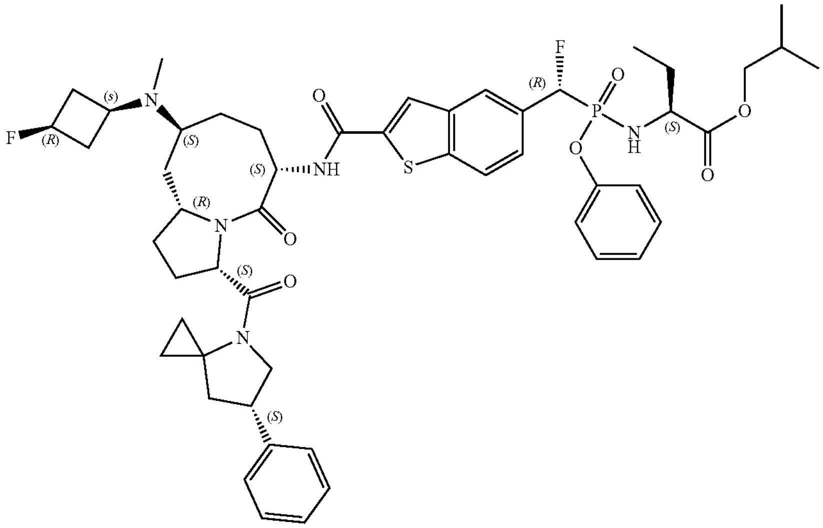 |
| C188 | isopentyl (((R)-fluoro(2-(((3S,6S,9S,10aR)-9-(((1s,3R)-3-fluorocyclobutyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate | 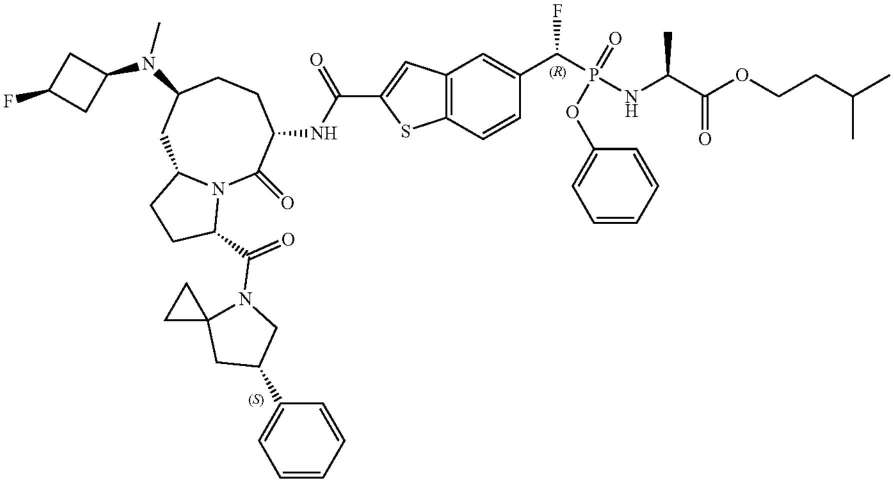 |
| C189 | propyl (2S)-2-((((R)-fluoro(2-(((3S,6S,9S,10aR)-9-(((1s,3R)-3-fluorocyclobutyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)amino)pentanoate | 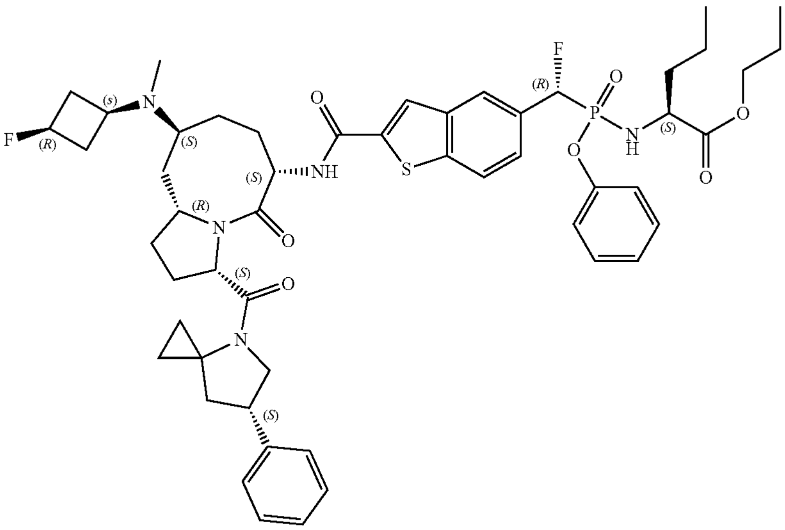 |

TABLE 1C-continued

| | | |
|---|---|---|
| C190 | propyl ((cyclohexyloxy) ((R)-fluoro(2- (((3S,6S,9S,10aR)- 9-(((1s,3R)-3- fluorocyclobutyl) (methyl)amino)-5- oxo-3-((S)-6- phenyl-4- azaspiro[2.4] heptane-4- carbonyl) decahydropyrrolo [1,2- a]azocin-6- yl)carbamoyl) benzo [b]thiophen-5- yl)methyl) phosphoryl)- L-alaninate | 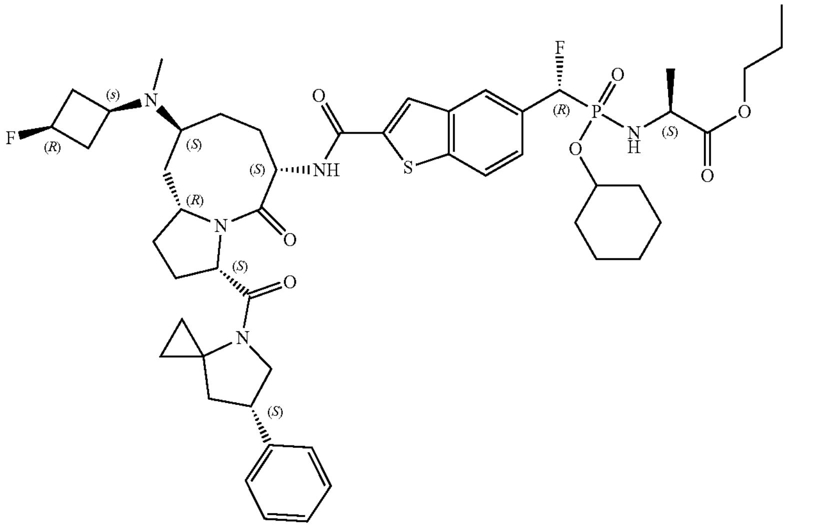 |
| C191 | propyl ((cyclopentyloxy) ((R)-fluoro(2- (((3S,6S,9S,10aR)- 9-(((1s,3R)-3- fluorocyclobutyl) (methyl)amino)-5- oxo-3-((S)-6- phenyl-4- azaspiro[2.4] heptane-4- carbonyl) decahydropyrrolo [1,2- a]azocin-6- yl)carbamoyl) benzo [b]thiophen-5- yl)methyl) phosphoryl)- L-alaninate | 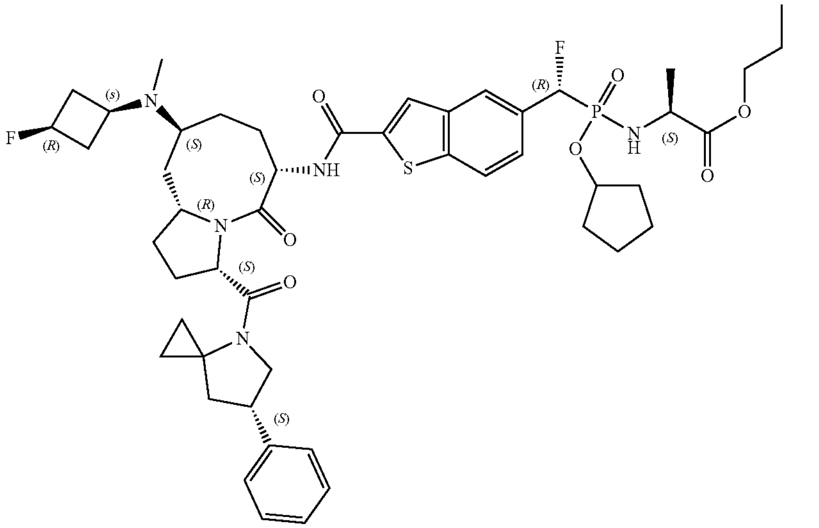 |
| C192 | propyl (((R)- fluoro(2- (((3S,6S,9S,10aR)- 9-(((1s,3R)-3- fluorocyclobutyl) (methyl)amino)-5- oxo-3-((S)-6- phenyl-4- azaspiro[2.4] heptane-4- carbonyl) decahydropyrrolo [1,2- a]azocin-6- yl)carbamoyl) benzo [b]thiophen-5- yl)methyl) (isopropoxy) phosphoryl)- L-alaninate | 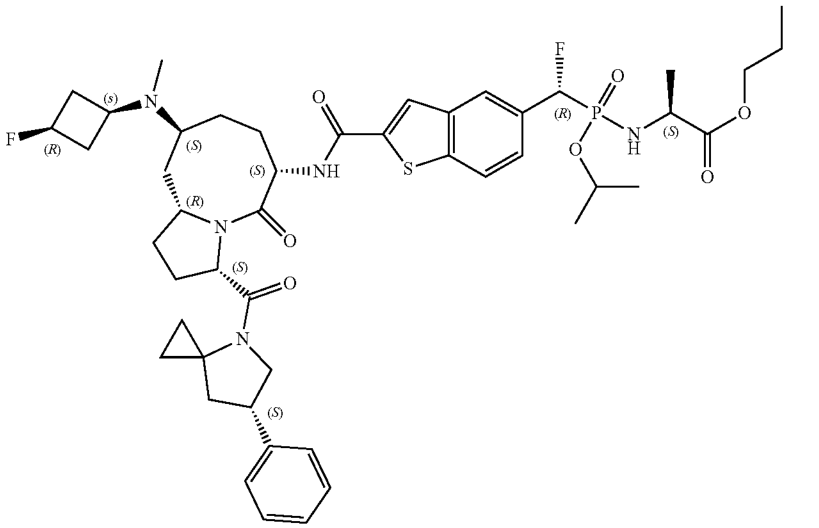 |

TABLE 1C-continued

| | | |
|---|---|---|
| C193 | neopentyl (((R)-fluoro(2-(((3S,6S,9S,10aR)-9-(((1s,3R)-3-fluorocyclobutyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(2,2,2-trifluoroethoxy)phosphoryl)-L-alaninate | 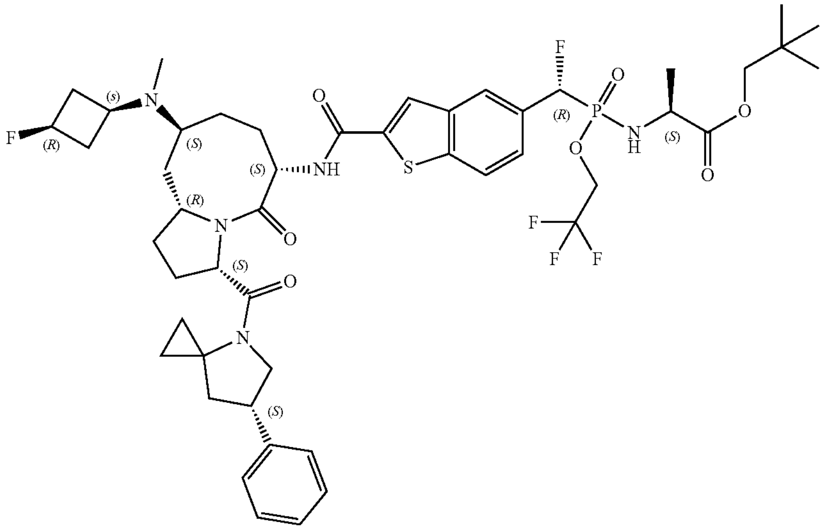 |
| C194 | propyl (((R)-fluoro(2-(((3S,6S,9S,10aR)-9-(((1s,3R)-3-fluorocyclobutyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(2-methoxyethoxy)phosphoryl)-L-alaninate | 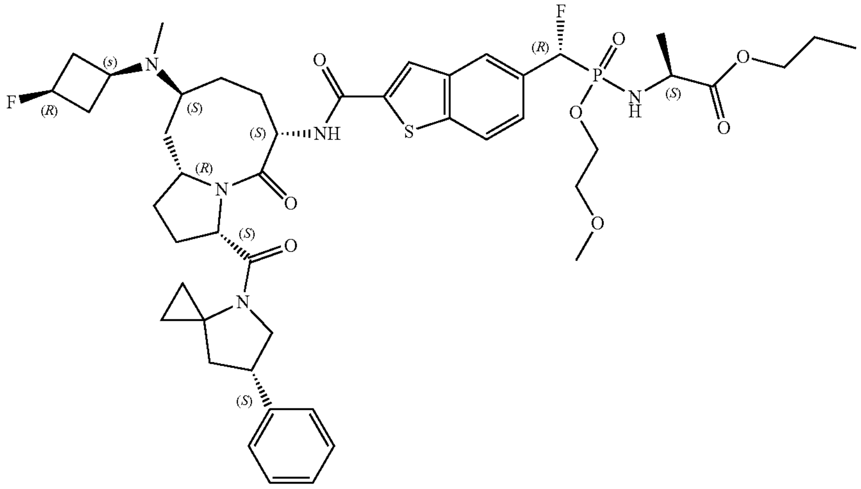 |
| C195 | spiro[3.3]heptan-2-yl (((R)-fluoro(2-(((3S,6S,9S,10aR)-9-(((1s,3R)-3-fluorocyclobutyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate | 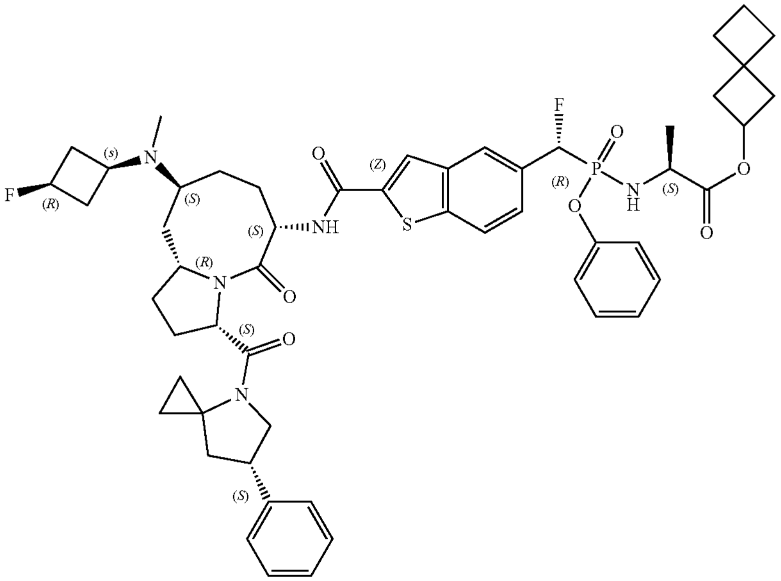 |

TABLE 1C-continued

| | | |
|---|---|---|
| C196 | propyl (((R)-fluoro(2-(((3S,6S,9S,10aR)-9-(((1s,3R)-3-fluorocyclobutyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-valinate | 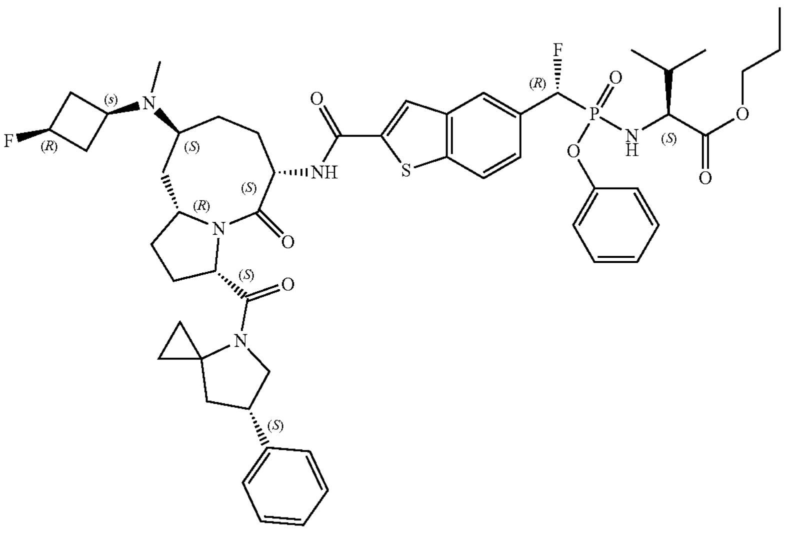 |
| C197 | (R)-tetrahydrofuran-3-yl (((R)-fluoro(2-(((3S,6S,9S,10aR)-9-(((1s,3R)-3-fluorocyclobutyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate | 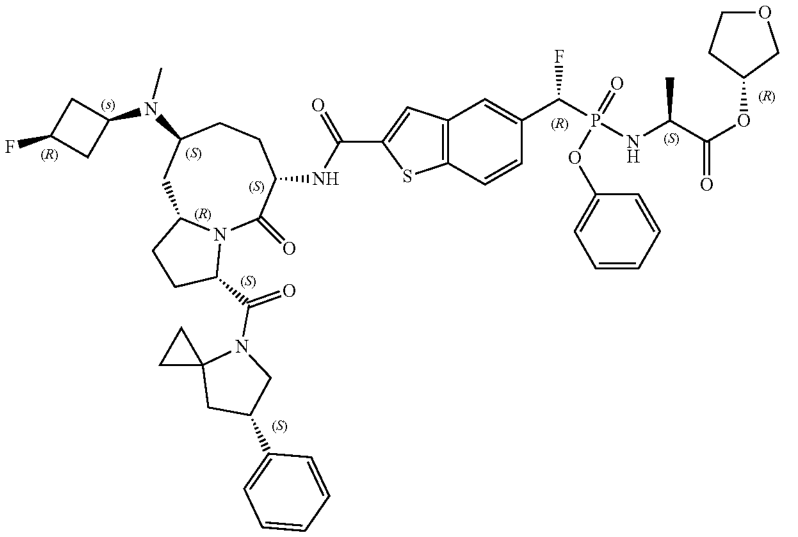 |
| C198 | (S)-tetrahydrofuran-3-yl (((R)-fluoro(2-(((3S,6S,9S,10aR)-9-(((1s,3R)-3-fluorocyclobutyl)(methyl)amino)-5-oxo-3-((S)-6-phenyl-4-azaspiro [2.4]heptane-4-carbonyl)decahydropyrrolo[1,2-a]azocin-6-yl)carbamoyl)benzo[b]thiophen-5-yl)methyl)(phenoxy)phosphoryl)-L-alaninate | 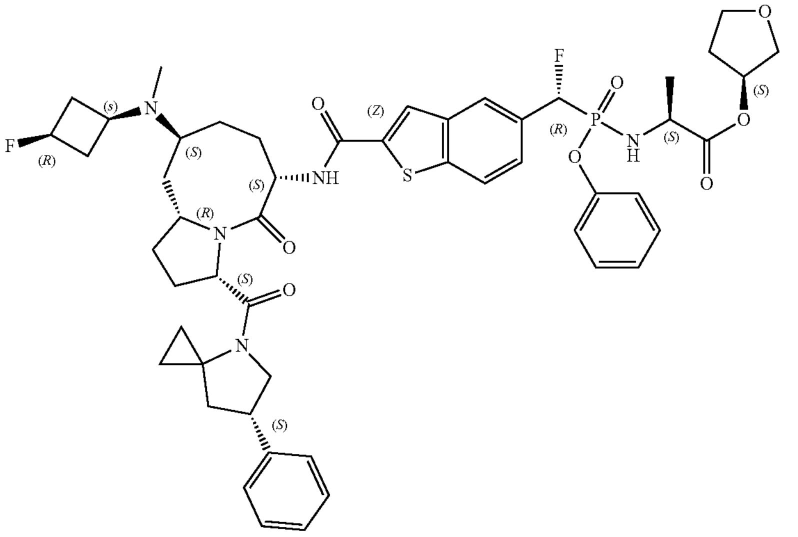 |

TABLE 1C-continued

| | | |
|---|---|---|
| C199 | 2-fluoro-2-methylpropyl (((S)-fluoro(2-(((3S,6S,9S,10aR)-9-(((1s,3R)-3-fluorocyclobutyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate | 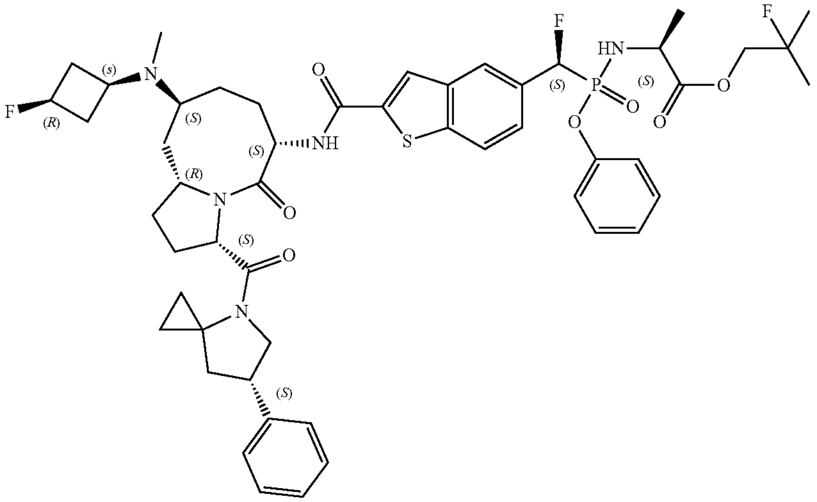 |
| C200 | ((R)-tetrahydrofuran-3-yl)methyl (((S)-fluoro(2-(((3S,6S,9S,10aR)-9-(((1s,3R)-3-fluorocyclobutyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate | 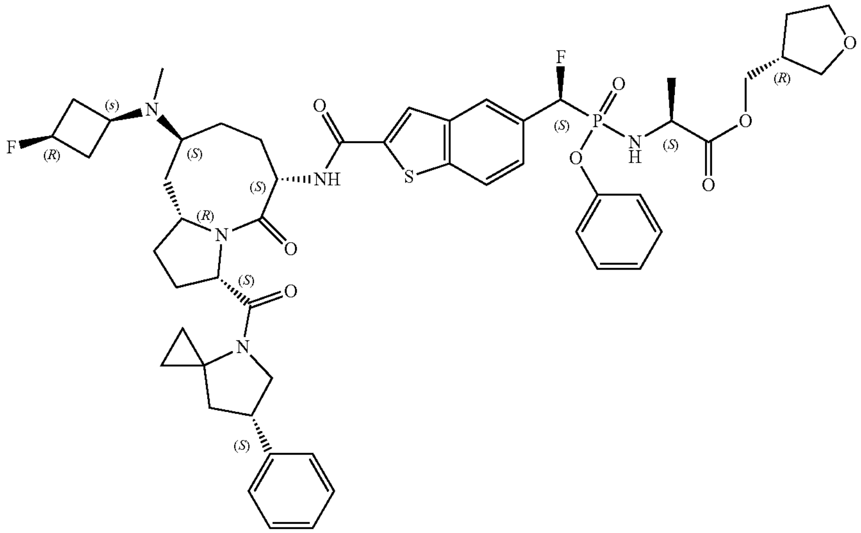 |
| C201 | ((S)-tetrahydrofuran-3-yl)methyl (((S)-fluoro(2-(((3S,6S,9S,10aR)-9-(((1s,3R)-3-fluorocyclobutyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate | 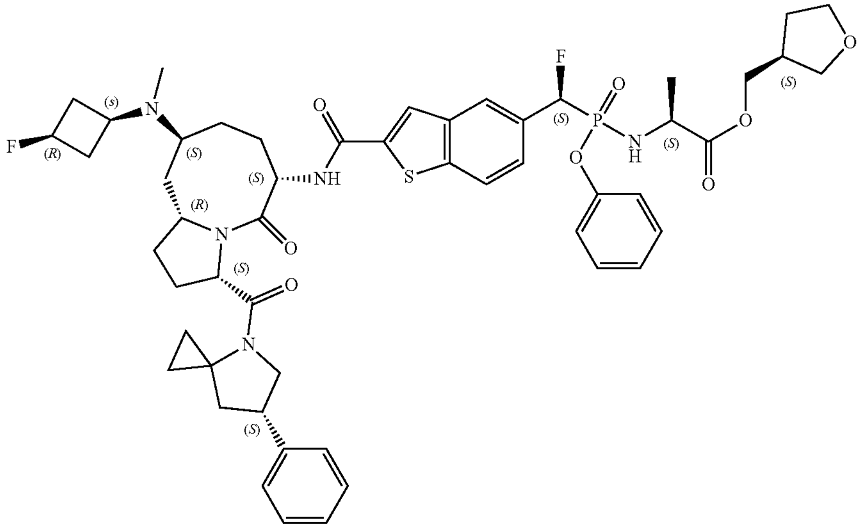 |

TABLE 1C-continued

| | | |
|---|---|---|
| C202 | (tetrahydro-2H-pyran-4-yl)methyl (((S)-fluoro(2-(((3S,6S,9S,10aR)-9-(((1s,3R)-3-fluorocyclobutyl)(methyl)amino)-5-oxo-3-((S)-6-phenyl-4-azaspiro [2.4] heptane-4-carbonyl) decahydropyrrolo [1,2-a]azocin-6-yl)carbamoyl) benzo [b]thiophen-5-yl)methyl) (phenoxy) phosphoryl)-L-alaninate | 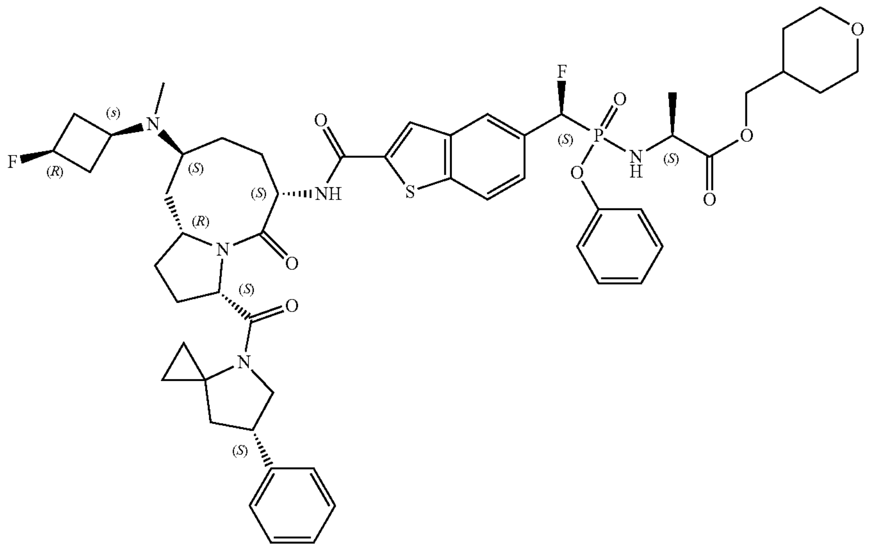 |
| C203 | propyl (2S)-4,4-difluoro-1-(((R)-fluoro(2-(((3S,6S,9S,10aR)-9-(methyl((1s,3R)-3-(trifluoromethoxy) cyclobutyl)amino)-5-oxo-3-((S)-6-phenyl-4-azaspiro[2.4] heptane-4-carbonyl) decahydropyrrolo [1,2-a]azocin-6-yl)carbamoyl) benzo [b]thiophen-5-yl)methyl) (phenoxy) phosphoryl) pyrrolidine-2-carboxylate | 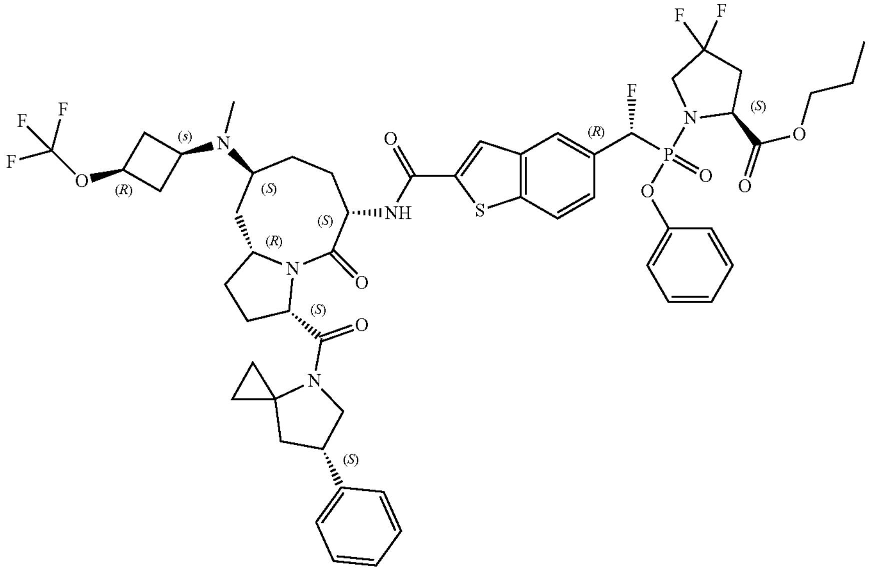 |
| C204 | propyl N-(((R)-fluoro(2-(((3S,6S,9S,10aR)-9-(methyl((1s,3R)-3-(trifluoromethoxy) cyclobutyl)amino)-5-oxo-3-((S)-6-phenyl-4-azaspiro[2.4] heptane-4-carbonyl) decahydropyrrolo [1,2-a]azocin-6-yl)carbamoyl) benzo [b]thiophen-5-yl)methyl)(2,2,2-trifluoroethoxy) phosphoryl)-N-methyl-L-alaninate | 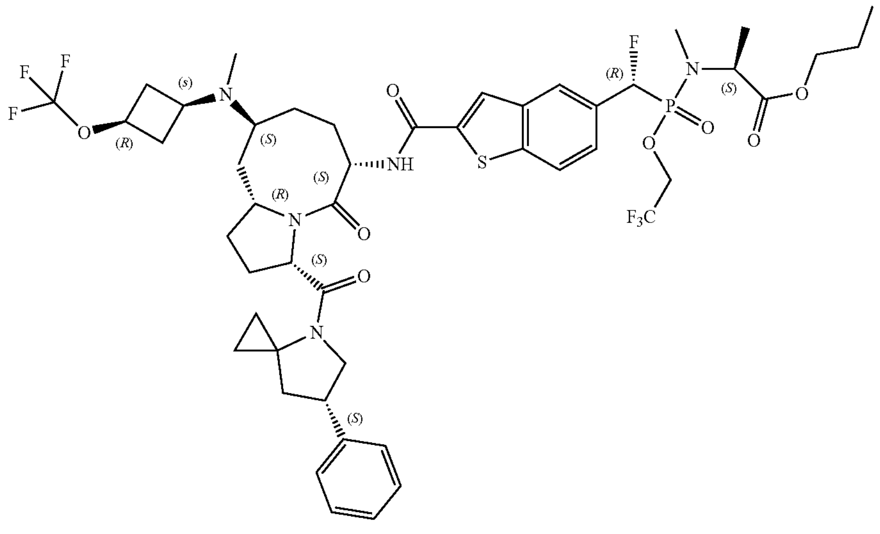 |

TABLE 1C-continued

| | | |
|---|---|---|
| C205 | 2-ethylbutyl (ethoxy((R)-fluoro(2-(((3S,6S,9S,10aR)-9-(methyl((1s,3R)-3-(trifluoromethoxy) cyclobutyl)amino)-5-oxo-3-((S)-6-phenyl-4-azaspiro[2.4] heptane-4-carbonyl) decahydropyrrolo [1,2-a]azocin-6-yl)carbamoyl) benzo [b]thiophen-5-yl)methyl) phosphoryl)-L-alaninate | 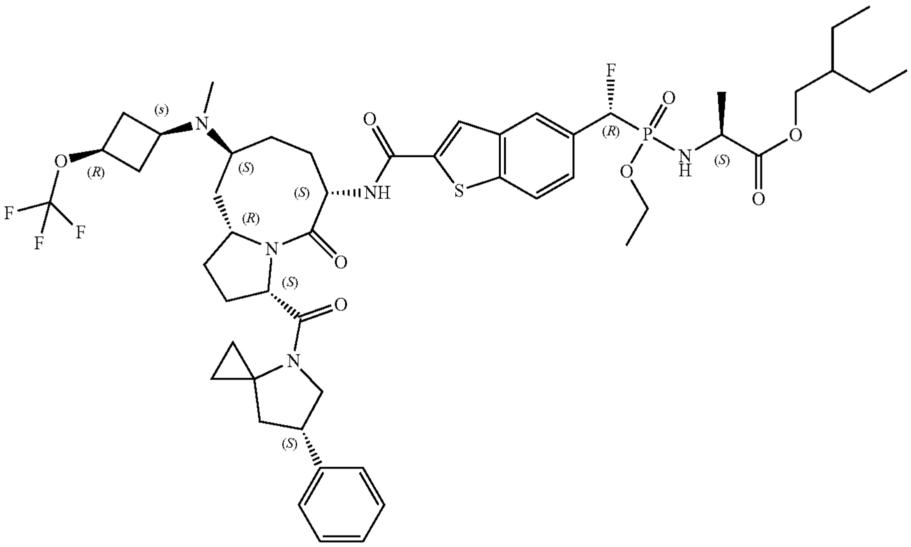 |
| C206 | propyl N-(ethoxy((R)-fluoro(2-(((3S,6S,9S,10aR)-9-(methyl((1s,3R)-3-(trifluoromethoxy) cyclobutyl)amino)-5-oxo-3-((S)-6-phenyl-4-azaspiro[2.4] heptane-4-carbonyl) decahydropyrrolo [1,2-a]azocin-6-yl)carbamoyl) benzo [b]thiophen-5-yl)methyl) phosphoryl)-N-methyl-L-alaninate | 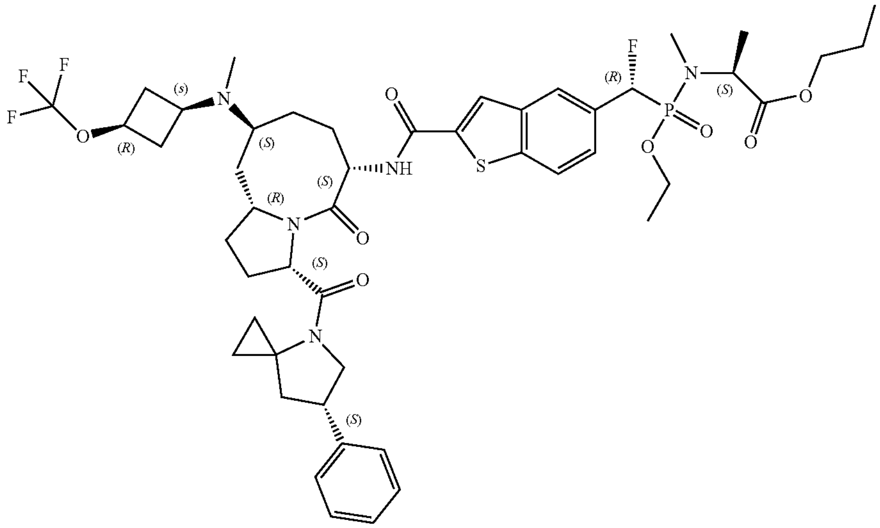 |
| C207 | propyl (ethoxy((R)-fluoro(2-(((3S,6S,9S,10aR)-9-(methyl((1s,3R)-3-(trifluoromethoxy) cyclobutyl)amino)-5-oxo-3-((S)-6-phenyl-4-azaspiro[2.4] heptane-4-carbonyl) decahydropyrrolo [1,2-a]azocin-6-yl)carbamoyl) benzo [b]thiophen-5-yl)methyl) phosphoryl)-L-prolinate | 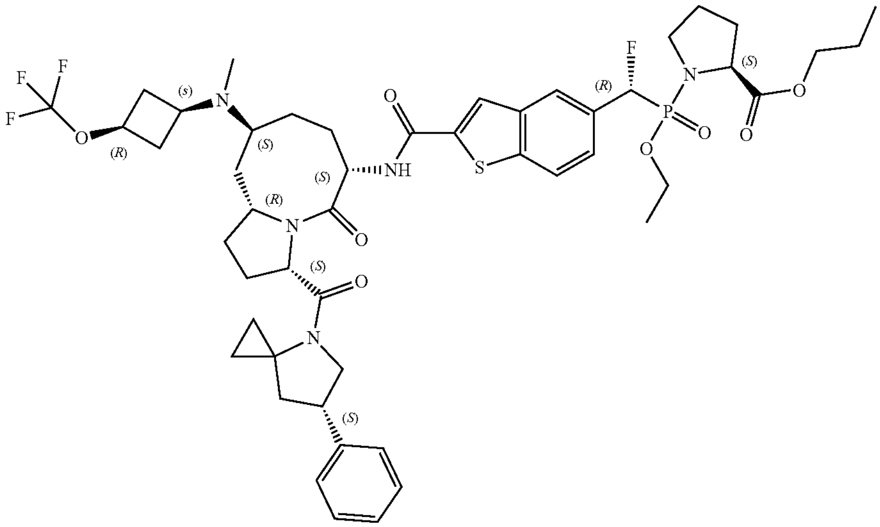 |

TABLE 1C-continued

| | | |
|---|---|---|
| C208 | spiro[3.4]octan-2-yl (((R)-fluoro(2-(((3S,6S,9S,10aR)-9-(((1s,3R)-3-fluorocyclobutyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate | 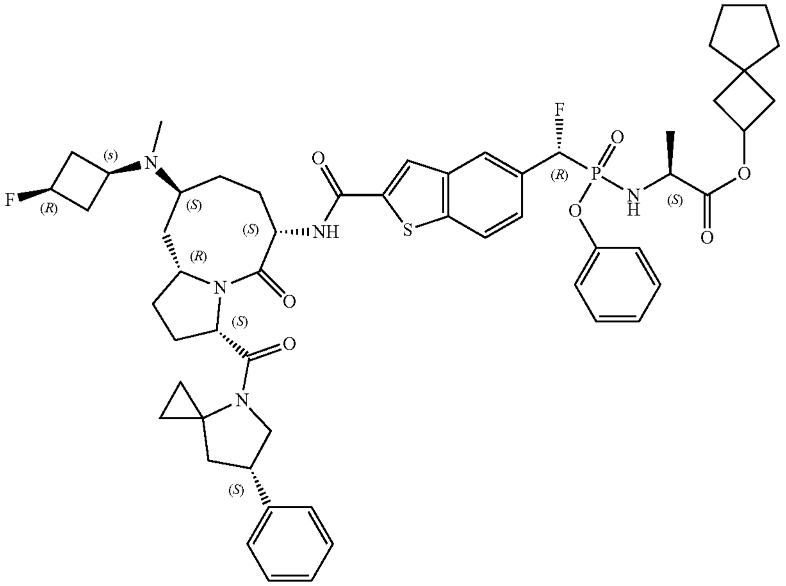 |
| C209 | spiro[2.3]hexan-5-yl (((R)-fluoro(2-(((3S,6S,9S,10aR)-9-(((1s,3R)-3-fluorocyclobutyl)(methyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate | 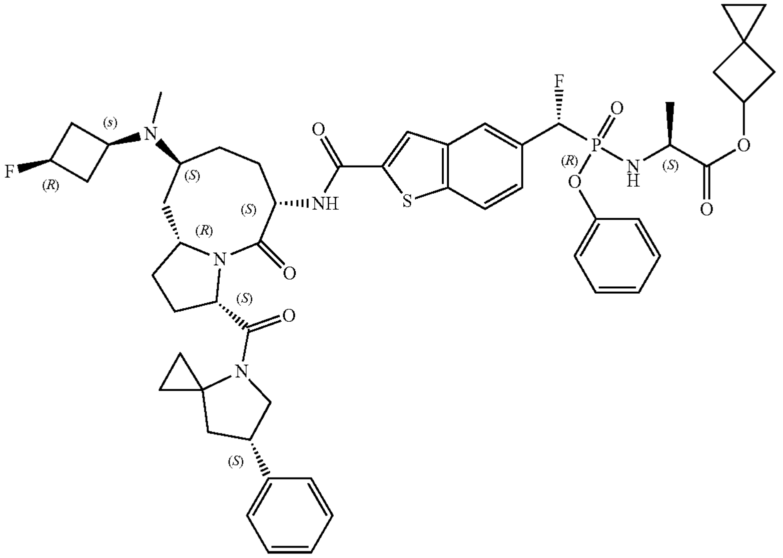 |

| | | |
|---|---|---|
| C210 | propyl ((S)-((S)-fluoro(2-(((3S,6S,9S,10aR)-9-(methyl((1s,3R)-3-(trifluoromethyl)cyclobutyl)amino)-5-oxo-3-((S)-6-phenyl-4-azaspiro[2.4]heptane-4-carbonyl)decahydropyrrolo[1,2-a]azocin-6-yl)carbamoyl)benzo[b]thiophen-5-yl)methyl)(phenoxy)phosphoryl)-L-alaninate | 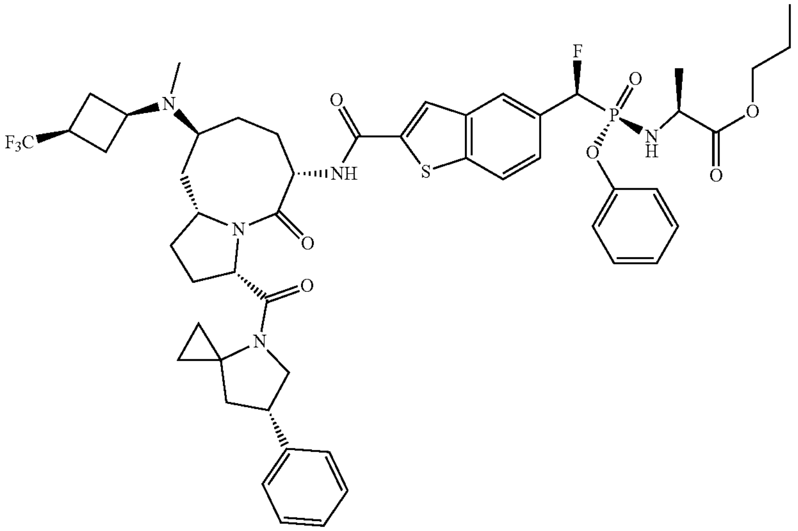 [SMILES: CCCOC(=O)[C@H](C)N[P@@](=O)(Oc1ccccc1)[C@H](F)c1ccc2sc(C(=O)N[C@H]3CC[C@H](N(C)[C@H]4C[C@@H](C(F)(F)F)C4)C[C@H]4CC[C@@H](C(=O)N5C[C@H](c6ccccc6)CC56CC6)N4C3=O)cc2c1] |
| C211 | propyl 2-((((1R)-fluoro(2-(((3R,6R,9R,10aS)-9-(methyl((1s,3S)-3-(trifluoromethoxy)cyclobutyl)amino)-5-oxo-3-((R)-6-phenyl-4-azaspiro[2.4]heptane-4-carbonyl)decahydropyrrolo[1,2-a]azocin-6-yl)carbamoyl)-2,3-dihydrobenzo[b]thiophen-5-yl)methyl)(isobutoxy)phosphoryl)amino)-2-methylpropanoate | 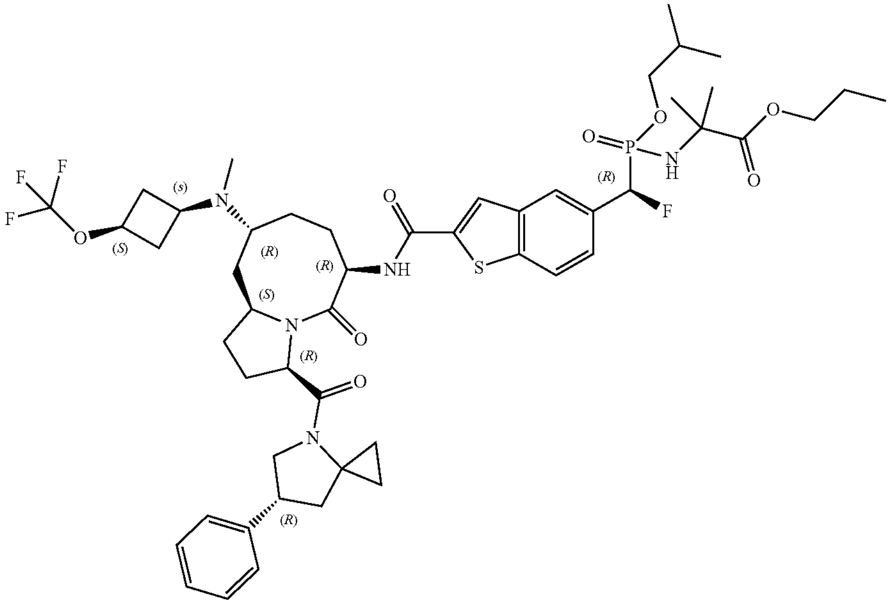 |
| C212 | propyl 2-((((1R)-fluoro(2-(((3S,6S,9S,10aR)-9-(methyl((1s,3R)-3-(trifluoromethoxy)cyclobutyl)amino)-5-oxo-3-((S)-6-phenyl-4-azaspiro[2.4]heptane-4-carbonyl)decahydropyrrolo[1,2-a]azocin-6-yl)carbamoyl)-2,3-dihydrobenzo[b]thiophen-5-yl)methyl)(isopropoxy)phosphoryl)amino)-2-methylpropanoate | 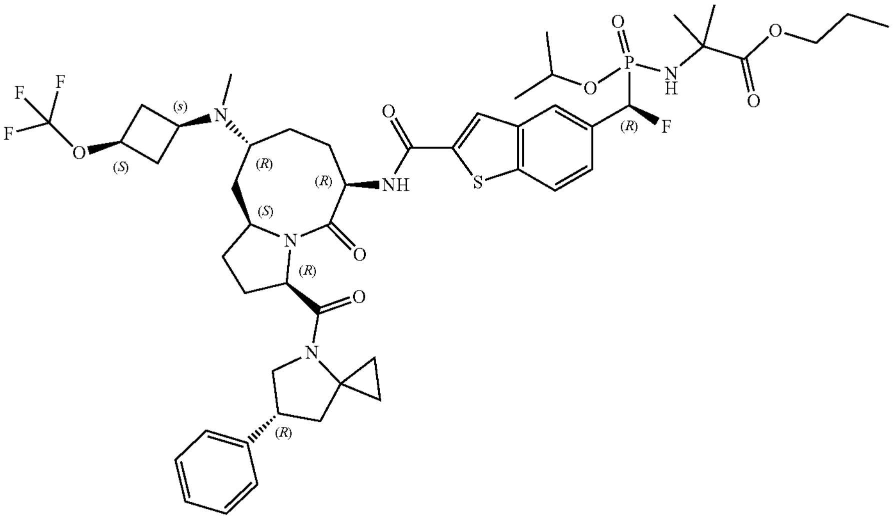 |

TABLE 1C-continued

| | | |
|---|---|---|
| C213 | propyl 2-((butoxy((1S)-fluoro(2-(((3S,6S,9S,10aR)-9-(methyl((1s,3R)-3-(trifluoromethoxy)cyclobutyl)amino)-5-oxo-3-((S)-6-phenyl-4-azaspiro[2.4]heptane-4-carbonyl)decahydropyrrolo[1,2-a]azocin-6-yl)carbamoyl)-2,3-dihydrobenzo[b]thiophen-5-yl)methyl)phosphoryl)amino)-2-methylpropanoate | 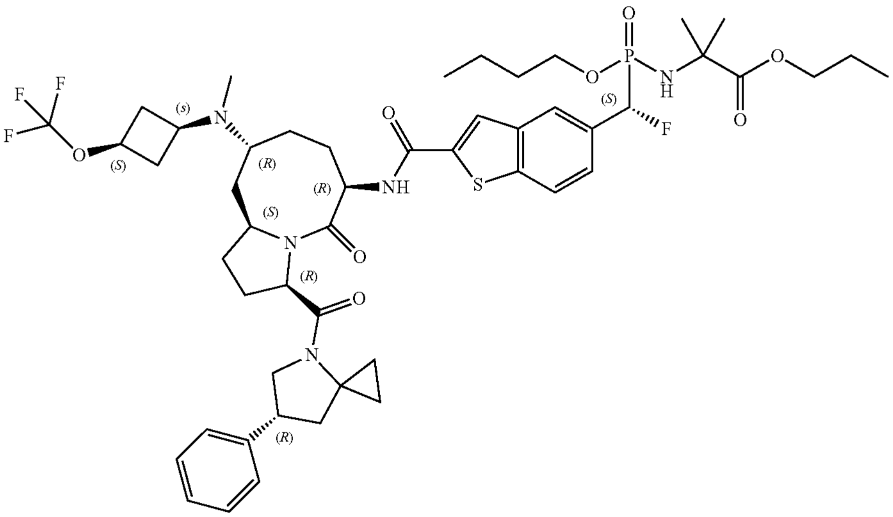 |
| C214 | propyl 2-((((1R)-fluoro(2-(((3S,6S,9S,10aR)-9-(methyl((1s,3R)-3-(trifluoromethoxy)cyclobutyl)amino)-5-oxo-3-((S)-6-phenyl-4-azaspiro[2.4]heptane-4-carbonyl)decahydropyrrolo[1,2-a]azocin-6-yl)carbamoyl)-2,3-dihydrobenzo[b]thiophen-5-yl)methyl)(propoxy)phosphoryl)amino)-2-methylpropanoate | 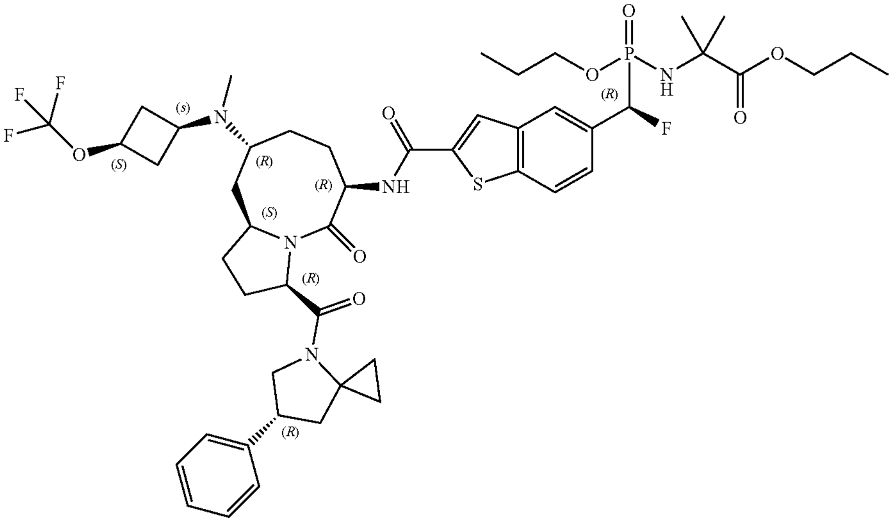 |
| C215 | propyl 2-((ethoxy((1R)-fluoro(2-(((3S,6S,9S,10aR)-9-(methyl((1s,3R)-3.(trifluoromethoxy)cyclobutyl)amino)-5-oxo-3-((S)-6-phenyl-4-azaspiro[2.4]heptane-4-carbonyl)decahydropyrrolo[1,2-a]azocin-6-yl)carbamoyl)-2,3-dihydrobenzo[b]thiophen-5-yl)methyl)phosphoryl)amino)-2-methylpropanoate | 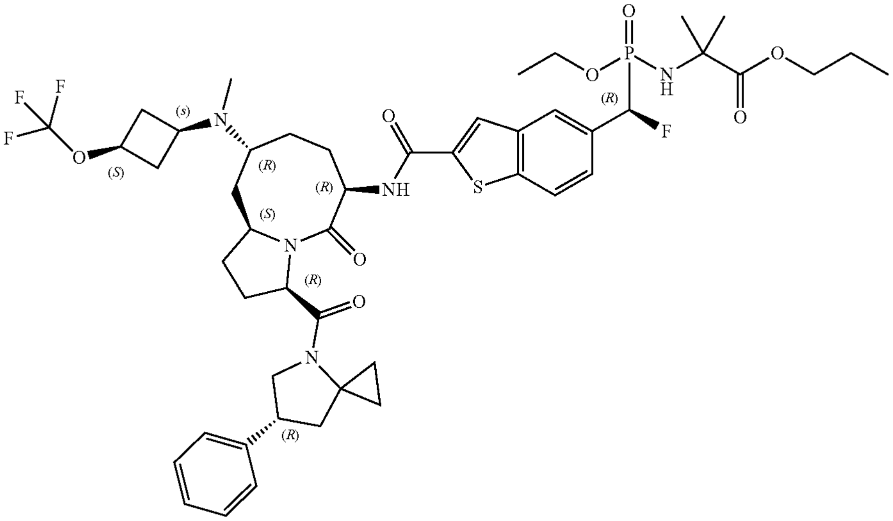 |

TABLE 1C-continued

| No. | NMR and LCMS |
| --- | --- |
| C1 | 1H NMR (400 MHz, DMSO-d6) δ (ppm) 8.85-8.69 (m, 1H), 8.27 (s, 1H), 8.12-7.97 (m, 2H), 7.65-7.52 (m, 1H), 7.39-7.12 (m, 10H), 6.27-5.87 (m, 3H), 4.84-4.71 (m, 1H), 4.54-4.40 (m, 1H), 4.36-4.23 (m, 1H), 4.16-4.05 (m, 1H), 4.00-3.68 (m, 4H), 3.62-3.44 (m, 1H), 3.04-2.91 (m, 1H), 2.48-1.34 (m, 23H), 1.17-1.05 (m, 3H), 0.85-0.75 (m, 3H), 0.52-0.41 (m, 2H); 950.5 $[M + H]^+$. |
| C2 | 1H NMR (400 MHz, DMSO-d6) δ (ppm) 8.86-8.71 (m, 1H), 8.27 (s, 1H), 8.12-8.01 (m, 2H), 7.65-7.56 (m, 1H), 7.40-7.28 (m, 6H), 7.21-7.08 (m, 4H), 6.29-6.06 (m, 2H), 4.76-4.66 (m, 1H), 4.48 (t, J = 8.6 Hz, 1H), 4.35-4.26 (m, 1H), 4.12 (t, J = 8.5 Hz, 1H), 3.96-3.89 (m, 1H), 3.85-3.67 (m, 3H), 3.58-3.49 (m, 1H), 3.06-2.89 (m, 2H), 2.77 (s, 1H), 2.58 (s, 2H), 2.41-2.20 (m, 3H), 2.12-2.06 (m, 1H), 2.03-1.89 (m, 6H), 1.88-1.76 (m, 2H), 1.74-1.40 (m, 8H), 1.16-1.08 (m, 3H), 0.85-0.75 (m, 3H), 0.59-0.39 (m, 2H); |

TABLE 1C-continued

| | |
|---|---|
| C3 | 963.0 $[M + H]^+$ . 1H NMR (400 MHz, DMSO-d6) δ (ppm) 10.20-9.71 (m, 1H), 8.91-8.72 (m, 1H), 8.32-8.20 (m, 1H), 8.13-8.01 (m, 2H), 7.66-7.55 (m, 1H), 7.39-7.28 (m, 6H), 7.25-7.10 (m, 4H), 6.31-6.06 (m, 2H), 4.85-4.77 (m, 1H), 4.62-4.47 (m, 2H), 4.22-4.01 (m, 1H), 3.89-3.76 (m, 5H), 3.65-3.50 (m, 2H), 3.23-2.83 (m, 4H), 2.69-2.60 (m, 3H), 2.48-2.40 (m, 1H), 2.32-2.16 (m, 2H), 2.12-1.97 (m, 5H), 1.95-1.59 (m, 5H), 1.57-1.40 (m, 3H), 1.20-0.91 (m, 3H), 0.81 (t, J = 7.4 Hz, 3H), 0.63-0.44 (m, 2H); 962.8 $[M + H]^+$ . |
| C4 | 1H NMR (400 MHz, DMSO-d6) δ (ppm) 8.85-8.70 (m, 1H), 8.27 (s, 1H), 8.09-8.03 (m, 2H), 7.61 (d, J = 8.5 Hz, 1H), 7.39-7.26 (m, 6H), 7.24-7.12 (m, 4H), 6.27-6.04 (m, 2H), 4.77-4.64 (m, 1H), 4.52-4.43 (m, 1H), 4.35-4.23 (m, 1H), 4.16-4.06 (m, 1H), 3.88-3.68 (m, 4H), 3.60-3.48 (m, 1H), 3.08-2.90 (m, 2H), 2.84-2.70 (m, 1H), 2.39-2.18 (m, 3H), 2.15-2.04 (m, 3H), 2.02-1.90 (m, 6H), 1.89-1.48 (m, 9H), 1.46-1.36 (m, 2H), 1.13 (d, J = 7.1 Hz, 3H), 0.78 (t, J = 7.4 Hz, 3H), 0.53-0.38 (m, 2H); 994.3 $[M + H]^+$ . |

TABLE 1C-continued

| | |
|---|---|
| C5 | 1H NMR (400 MHz, DMSO-d6) δ (ppm) 8.79 (d, J = 7.7 Hz, 1H), 8.27 (s, 1H), 8.10-8.01 (m, 2H), 7.61 (d, J = 8.6 Hz, 1H), 7.38-7.27 (m, 6H), 7.24-7.13 (m, 4H), 6.26-6.06 (m, 2H), 4.71 (t, J = 8.8 Hz, 1H), 4.57-4.44 (m, 2H), 4.34-4.24 (m, 1H), 4.12 (t, J = 8.6 Hz, 1H), 3.88-3.70 (m, 4H), 3.59-3.49 (m, 1H), 3.05-2.94 (m, 1H), 2.71-2.58 (m, 2H), 2.45-2.30 (m, 2H), 2.23 (t, J = 11.6 Hz, 1H), 2.18-2.08 (m, 2H), 2.01-1.91 (m, 6H), 1.90-1.49 (m, 9H), 1.46-1.36 (m, 2H), 1.13 (d, J = 7.1 Hz, 3H), 0.78 (t, J = 7.4 Hz, 3H), 0.53-0.39 (m, 2H); 1010.8 $[M + H]^+$. |
| C6 | 1H NMR (400 MHz, DMSO-d6) δ (ppm) 8.80 (d, J = 7.7 Hz, 1H), 8.27 (s, 1H), 8.12-8.03 (m, 2H), 7.60 (d, J = 8.6 Hz, 1H), 7.39-7.27 (m, 6H), 7.24-7.15 (m, 4H), 6.27-6.11 (m, 2H), 4.71 (t, J = 8.9 Hz, 1H), 4.57-4.44 (m, 2H), 4.35-4.24 (m, 1H), 4.12 (t, J = 8.6 Hz, 1H), 3.99-3.88 (m, 2H), 3.82-3.69 (m, 2H), 3.60-3.48 (m, 1H), 3.07-2.96 (m, 1H), 2.72-2.58 (m, 2H), 2.46-2.30 (m, 2H), 2.23 (t, J = 11.6 Hz, 1H), 2.17-2.08 (m, 2H), 2.03-1.91 (m, 6H), 1.91-1.45 (m, 11H), 1.13 (d, J = 7.1 Hz, 3H), 0.83 (t, J = 7.4 Hz, 3H), 0.57-0.36 (m, 2H); 1011.3 $[M + H]^+$. |

TABLE 1C-continued

| | |
|---|---|
| C7 | 1H NMR (400 MHz, DMSO-d6) δ (ppm) 8.85-8.74 (m, 1H), 8.31-8.23 (m, 1H), 8.09-8.00 (m, 2H), 7.66-7.55 (m, 1H), 7.39-7.09 (m, 10H), 6.32-6.12 (m, 2H), 4.76-4.65 (m, 1H), 4.58-4.43 (m, 2H), 4.33-4.23 (m, 1H), 4.16-4.08 (m, 1H), 3.96-3.82 (m, 3H), 3.79-3.69 (m, 1H), 3.60-3.49 (m, 1H), 3.06-2.94 (m, 1H), 2.73-2.57 (m, 2H), 2.44-2.11 (m, 5H), 1.99-1.42 (m, 17H), 1.21-1.12 (m, 3H), 0.85-0.76 (m, 3H), 0.54-0.35 (m, 2H); 1010.7 $[M + H]^+$ . |
| C8 | 1H NMR (400 MHz, DMSO-d6) δ (ppm) 8.78 (d, J = 7.5 Hz, 1H), 8.27 (s, 1H), 8.12-8.01 (m, 2H), 7.60 (d, J = 8.6 Hz, 1H), 7.40-7.26 (m, 6H), 7.24-7.15 (m, 4H), 6.28-6.10 (m, 2H), 4.85-4.72 (m, 1H), 4.47 (t, J = 8.6 Hz, 1H), 4.36-4.24 (m, 1H), 4.16-4.05 (m, 1H), 3.99-3.88 (m, 2H), 3.82-3.68 (m, 2H), 3.59-3.47 (m, 1H), 3.00-2.88 (m, 1H), 2.47-2.08 (m, 10H), 2.02-1.47 (m, 15H), 1.13 (d, J = 7.1 Hz, 3H), 0.83 (t, J = 7.4 Hz, 3H), 0.55-0.38 (m, 2H); 982.5 $[M + H]^+$ . |

TABLE 1C-continued

| | |
|---|---|
| C9 | 1H NMR (400 MHz, DMSO-d6) δ (ppm) 8.92-8.67 (m, 1H), 8.32-8.23 (m, 1H), 8.13-8.02 (m, 2H), 7.64-7.56 (m, 1H), 7.42-7.26 (m, 6H), 7.25-7.05 (m, 4H), 6.34-5.98 (m, 3H), 4.93-4.71 (m, 1H), 4.64-4.35 (m, 2H), 4.19-4.07 (m, 1H), 4.01-3.79 (m, 3H), 3.77-3.62 (m, 2H), 3.59-3.46 (m, 1H), 3.24-3.04 (m, 1H), 2.89-2.55 (m, 3H), 2.46-1.63 (m, 16H), 1.61-1.39 (m, 3H), 1.20-0.90 (m, 3H), 0.86-0.72 (m, 3H), 0.58-0.39 (m, 2H); 950.9 $[M+H]^+$. |
| C10 | 1H NMR (400 MHz, DMSO-d6) δ (ppm) 8.79 (d, J = 7.6 Hz, 1H), 8.27 (s, 1H), 8.11-8.00 (m, 2H), 7.60 (d, J = 8.5 Hz, 1H), 7.41-7.26 (m, 6H), 7.24-7.13 (m, 4H), 6.28-6.09 (m, 2H), 4.71 (t, J = 8.6 Hz, 1H), 4.48 (t, J = 8.5 Hz, 1H), 4.34-4.23 (m, 1H), 4.12 (t, J = 8.6 Hz, 1H), 3.99-3.88 (m, 2H), 3.82-3.69 (m, 2H), 3.59-3.48 (m, 1H), 3.08-2.89 (m, 2H), 2.86-2.65 (m, 1H), 2.40-2.17 (m, 3H), 2.15-2.03 (m, 3H), 2.02-1.90 (m, 6H), 1.84-1.44 (m, 11H), 1.13 (d, J = 7.1 Hz, 3H), 0.83 (t, J = 7.4 Hz, 3H), 0.53-0.36 (m, 2H); 994.6 $[M+H]^+$. |

TABLE 1C-continued

| | |
|---|---|
| C11 | 1H NMR (400 MHz, DMSO-d6) δ (ppm) 8.77 (d, J = 7.7 Hz, 1H), 8.27 (s, 1H), 8.11-8.02 (m, 2H), 7.60 (d, J = 8.5 Hz, 1H), 7.39-7.26 (m, 6H), 7.24-7.14 (m, 4H), 6.27-5.91 (m, 3H), 4.84-4.71 (m, 1H), 4.53-4.43 (m, 1H), 4.36-4.26 (m, 1H), 4.17-4.05 (m, 1H), 3.99-3.87 (m, 2H), 3.83-3.68 (m, 2H), 3.59-3.47 (m, 1H), 3.05-2.94 (m, 1H), 2.57-2.51 (m, 1H), 2.46-2.32 (m, 2H), 2.26-2.17 (m, 1H), 2.16-2.08 (m, 4H), 2.05-1.45 (m, 15H), 1.14 (d, J = 7.1 Hz, 3H), 0.83 (t, J = 7.4 Hz, 3H), 0.54-0.39 (m, 2H); 950.6 $[M + H]^+$ . |
| C12 | 1H NMR (400 MHz, DMSO-d6) δ (ppm) 8.81-8.70 (m, 1H), 8.27 (s, 1H), 8.10-8.02 (m, 2H), 7.61 (d, J = 8.5 Hz, 1H), 7.39-7.26 (m, 6H), 7.24-7.12 (m, 4H), 6.26-5.91 (m, 3H), 4.82-4.72 (m, 1H), 4.53-4.43 (m, 1H), 4.35-4.26 (m, 1H), 4.15-4.07 (m, 1H), 3.91-3.69 (m, 4H), 3.59-3.48 (m, 1H), 3.04-2.93 (m, 1H), 2.57-2.51 (m, 1H), 2.46-2.31 (m, 2H), 2.26-2.17 (m, 1H), 2.16-2.08 (m, 4H), 2.07-1.89 (m, 5H), 1.89-1.62 (m, 6H), 1.61-1.50 (m, 2H), 1.47-1.36 (m, 2H), 1.19-1.08 (m, 3H), 0.82-0.74 (m, 3H), 0.54-0.37 (m, 2H); 950.4 $[M + H]^+$ . |

TABLE 1C-continued

| | | |
|---|---|---|
| C13 | | 1H NMR (400 MHz, DMSO-d6) δ (ppm) 8.90-8.69 (m, 1H), 8.27 (s, 1H), 8.10-8.02 (m, 1H), 7.60 (d, J = 8.7 Hz, 1H), 7.38-7.28 (m, 6H), 7.23-7.11 (m, 4H), 6.29-6.07 (m, 2H), 4.79-4.63 (m, 1H), 4.54-4.44 (m, 1H), 4.37-4.23 (m, 1H), 4.17-4.07 (m, 1H), 3.98-3.89 (m, 1H), 3.86-3.71 (m, 3H), 3.59-3.47 (m, 1H), 3.12-2.88 (m, 2H), 2.87-2.71 (m, 1H), 2.38-2.21 (m, 3H), 2.17-2.05 (m, 3H), 2.03-1.88 (m, 6H), 1.85-1.39 (m, 11H), 1.13 (d, J = 7.0 Hz, 3H), 0.84-0.75 (m, 3H), 0.55-0.37 (m, 2H); 994.9 $[M + H]^+$ . |
| C14 | | 1H NMR (400 MHz, DMSO-d6) δ (ppm) 8.79 (d, J = 7.6 Hz, 1H), 8.28 (s, 1H), 8.11-8.03 (m, 2H), 7.61 (d, J = 8.6 Hz, 1H), 7.40-7.27 (m, 6H), 7.24-7.15 (m, 4H), 6.23-6.06 (m, 2H), 4.91-4.66 (m, 3H), 4.52-4.43 (m, 1H), 4.33-4.24 (m, 1H), 4.16-4.07 (m, 1H), 3.78-3.49 (m, 3H), 3.04-2.94 (m, 1H), 2.62-2.56 (m, 1H), 2.44-2.30 (m, 2H), 2.27-2.12 (m, 5H), 2.02-1.93 (m, 6H), 1.91-1.51 (m, 14H), 0.92 (d, J = 7.1 Hz, 3H), 0.55-0.41 (m, 2H); 956.4 $[M + H]^+$ . |

TABLE 1C-continued

| | | |
|---|---|---|
| C15 | | 1H NMR (400 MHz, DMSO-d6) δ (ppm) 8.91-8.76 (m, 1H), 8.33-8.25 (m, 1H), 8.12-8.02 (m, 2H), 7.66-7.54 (m, 1H), 7.40-7.28 (m, 6H), 7.25-7.11 (m, 4H), 6.34-6.12 (m, 2H), 4.93-4.65 (m, 3H), 4.55-4.43 (m, 1H), 4.35-4.24 (m, 1H), 4.20-4.07 (m, 1H), 3.91-3.70 (m, 2H), 3.61-3.49 (m, 1H), 3.08-2.92 (m, 1H), 2.70-2.57 (m, 1H), 2.46-2.31 (m, 2H), 2.30-2.08 (m, 5H), 2.04-1.49 (m, 20H), 1.22-1.08 (m, 3H), 0.60-0.36 (m, 2H); 956.5 $[M + H]^+$ . |
| C16 | | 1H NMR (400 MHz, DMSO-d6) δ (ppm) 8.85-8.75 (m, 1H), 8.27 (s, 1H), 8.10-8.02 (m, 2H), 7.64-7.57 (m, 1H), 7.38-7.28 (m, 6H), 7.23-7.14 (m, 4H), 6.29-6.18 (m, 1H), 6.15-6.06 (m, 1H), 5.20-4.98 (m, 1H), 4.79-4.62 (m, 1H), 4.53-4.42 (m, 1H), 4.37-4.23 (m, 1H), 4.16-4.07 (m, 1H), 3.98-3.89 (m, 1H), 3.84-3.68 (m, 3H), 3.57-3.49 (m, 1H), 3.14-2.94 (m, 1H), 2.40-2.29 (m, 2H), 2.27-2.19 (m, 2H), 2.15-2.08 (m, 2H), 2.07-1.87 (m, 7H), 1.87-1.63 (m, 5H), 1.62-1.45 (m, 5H), 1.44-1.37 (m, 1H), 1.16-1.08 (m, 3H), 0.85-0.76 (m, 3H), 0.54-0.41 (m, 2H); 944.5 $[M + H]^+$ . |

TABLE 1C-continued

| | |
|---|---|
| C17 | 1H NMR (400 MHz, DMSO-d6) δ (ppm) 8.80 (d, J = 7.5 Hz, 1H), 8.29 (s, 1H), 8.14-8.02 (m, 2H), 7.62 (d, J = 8.4 Hz, 1H), 7.41-7.27 (m, 6H), 7.25-7.13 (m, 4H), 6.24-6.07 (m, 2H), 4.89-4.68 (m, 2H), 4.48 (t, J = 8.4 Hz, 1H), 4.33-4.24 (m, 1H), 4.12 (t, J = 8.5 Hz, 1H), 3.97-3.86 (m, 2H), 3.78-3.65 (m, 2H), 3.59-3.49 (m, 1H), 3.06-2.92 (m, 1H), 2.64-2.56 (m, 1H), 2.44-2.31 (m, 2H), 2.24-1.46 (m, 21H), 0.95 (d, J = 7.1 Hz, 3H), 0.81 (t, J = 7.3 Hz, 3H), 0.56-0.36 (m, 2H); 944.8 $[M + H]^+$ . |
| C18 | 1H NMR (400 MHz, DMSO-d6) δ (ppm) 8.81-8.73 (m, 1H), 8.27 (s, 1H), 8.09-8.04 (m, 2H), 7.64-7.57 (m, 1H), 7.38-7.29 (m, 6H), 7.22-7.12 (m, 4H), 6.27-6.17 (m, 1H), 6.16-6.04 (m, 1H), 4.85-4.69 (m, 2H), 4.51-4.44 (m, 2H), 4.39-4.25 (m, 2H), 4.15-4.08 (m, 1H), 3.97-3.89 (m, 1H), 3.86-3.70 (m, 3H), 3.59-3.47 (m, 1H), 2.95-2.84 (m, 1H), 2.68-2.56 (m, 2H), 2.34-2.12 (m, 7H), 2.03-1.93 (m, 3H), 1.91-1.63 (m, 7H), 1.57-1.39 (m, 4H), 1.13 (d, J = 7.0 Hz, 3H), 0.86-0.76 (m, 3H), 0.53-0.41 (m, 2H); 943.0 $[M + H]^+$ . |

TABLE 1C-continued

| | |
|---|---|
| C19 | 1H NMR (400 MHz, DMSO-d6) δ (ppm) 8.79 (d, J = 7.8 Hz, 1H), 8.27 (s, 1H), 8.08-8.03 (m, 2H), 7.60 (d, J = 8.6 Hz, 1H), 7.38-7.29 (m, 6H), 7.23-7.13 (m, 4H), 6.25-6.04 (m, 2H), 4.90-4.68 (m, 2H), 4.47 (t, J = 8.8 Hz, 1H), 4.36-4.24 (m, 1H), 4.12 (t, J = 8.5 Hz, 1H), 3.86-3.68 (m, 4H), 3.60-3.49 (m, 1H), 3.04-2.96 (m, 1H), 2.64-2.55 (m, 1H), 2.43-2.30 (m, 2H), 2.29-2.17 (m, 1H), 2.15-1.76 (m, 12H), 1.73-1.50 (m, 6H), 1.46-1.34 (m, 2H), 1.13 (d, J = 7.1 Hz, 3H), 0.77 (t, J = 7.4 Hz, 3H), 0.53-0.42 (m, 2H); 944.5 $[M + H]^+$ . |
| C20 | 1H NMR (400 MHz, DMSO-d6) δ (ppm) 8.79-8.71 (m, 1H), 8.27 (s, 1H), 8.10-8.03 (m, 2H), 7.63-7.57 (m, 1H), 7.40-7.25 (m, 6H), 7.24-7.12 (m, 4H), 6.28-6.06 (m, 2H), 4.84-4.70 (m, 2H), 4.52-4.42 (m, 2H), 4.40-4.34 (m, 1H), 4.33-4.25 (m, 1H), 4.12 (t, J = 8.6 Hz, 1H), 3.98-3.89 (m, 1H), 3.89-3.68 (m, 3H), 3.59-3.48 (m, 1H), 2.95-2.84 (m, 1H), 2.69-2.52 (m, 3H), 2.40-2.19 (m, 3H), 2.18-2.08 (m, 4H), 2.04-1.93 (m, 3H), 1.91-1.62 (m, 6H), 1.61-1.37 (m, 4H), 1.17-1.08 (m, 3H), 0.85-0.75 (m, 3H), 0.55-0.41 (m, 2H); 943.0 $[M + H]^+$ . |

TABLE 1C-continued

| | |
|---|---|
| C21 | 1H NMR (400 MHz, DMSO-d6) δ (ppm) 8.78-8.71 (m, 1H), 8.31-8.24 (m, 1H), 8.11-8.03 (m, 2H), 7.65-7.56 (m, 1H), 7.38-7.27 (m, 6H), 7.22-7.10 (m, 4H), 6.29-6.10 (m, 2H), 4.84-4.72 (m, 2H), 4.52-4.43 (m, 2H), 4.41-4.34 (m, 1H), 4.30 (s, 1H), 4.11 (t, J = 8.5 Hz, 1H), 3.94-3.85 (m, 2H), 3.77-3.63 (m, 2H), 3.59-3.47 (m, 1H), 2.90 (s, 1H), 2.71-2.58 (m, 2H), 2.40-2.18 (m, 4H), 2.16 (s, 3H), 2.03-1.92 (m, 3H), 1.90-1.61 (m, 7H), 1.58-1.43 (m, 4H), 1.17 (d, J = 7.1 Hz, 1H), 0.94 (d, J = 7.1 Hz, 2H), 0.84-0.78 (m, 3H), 0.55-0.41 (m, 2H); 942.5 [M+ H]+ |
| C22 | 1H NMR (400 MHz, DMSO-d6) δ (ppm) 8.82-8.73 (m, 1H), 8.31-8.24 (m, 1H), 8.12-8.02 (m, 2H), 7.64-7.56 (m, 1H), 7.40-7.27 (m, 6H), 7.24-7.11 (m, 4H), 6.32-6.07 (m, 2H), 4.78-4.67 (m, 1H), 4.47 (t, J = 8.6 Hz, 1H), 4.33-4.23 (m, 1H), 4.11 (t, J = 8.6 Hz, 1H), 3.95-3.86 (m, 2H), 3.85-3.59 (m, 5H), 3.58-3.47 (m, 2H), 3.18-3.06 (m, 1H), 3.00-2.88 (m, 1H), 2.41-2.30 (m, 1H), 2.22 (t, J = 11.5 Hz, 1H), 2.17-2.09 (m, 2H), 2.07 (s, 3H), 2.03-1.88 (m, 4H), 1.87-1.53 (m, 8H), 1.52-1.42 (m, 2H), 1.20-0.92 (m, 3H), 0.85-0.76 m, 3H), 0.54-0.41 (m, 2H); 942.8 $[M + H]^+$ . |

TABLE 1C-continued

| | | |
|---|---|---|
| C23 | | 1H NMR (400 MHz, DMSO-d6) δ (ppm) 8.81 (d, J = 7.6 Hz, 1H), 8.28 (s, 1H), 8.11-8.03 (m, 2H), 7.60 (d, J = 8.4 Hz, 1H), 7.39-7.15 (m, 10H), 6.28-6.11 (m, 2H), 4.90-4.67 (m, 2H), 4.48 (t, J = 8.4 Hz, 1H), 4.34-4.24 (m, 1H), 4.16-4.07 (m, 1H), 3.99-3.88 (m, 2H), 3.83-3.70 (m, 2H), 3.60-3.48 (m, 1H), 3.05-2.95 (m, 1H), 2.65-2.55 (m, 1H), 2.45-2.29 (m, 2H), 2.23 (t, J = 12.0 Hz, 1H), 2.18-1.92 (m, 8H), 1.91-1.62 (m, 6H), 1.62-1.44 (m, 6H), 1.14 (d, J = 7.2 Hz, 3H), 0.83 (t, J = 7.4 Hz, 3H), 0.55-0.41 (m, 2H); 944.4 $[M + H]^+$. |
| C24 | | 1H NMR (400 MHz, DMSO-d6) δ (ppm) 8.83-8.73 (m, 1H), 8.27 (s, 1H), 8.09-8.02 (m, 2H), 7.64-7.56 (m, 1H), 7.38-7.26 (m, 6H), 7.24-7.13 (m, 4H), 6.28-6.05 (m, 2H), 4.77-4.66 (m, 1H), 4.47 (t, J = 8.6 Hz, 1H), 4.34-4.23 (m, 1H), 4.12 (t, J = 8.5 Hz, 1H), 3.98-3.89 (m, 1H), 3.86-3.60 (m, 6H), 3.59-3.47 (m, 2H), 3.17-3.06 (m, 1H), 2.99-2.87 (m, 1H), 2.40-2.30 (m, 1H), 2.23 (t, J = 11.5 Hz, 1H), 2.16-2.09 (m, 2H), 2.07 (s, 3H), 2.03-1.87 (m, 4H), 1.85-1.48 (m, 9H), 1.47-1.36 (m, 1H), 1.17-1.09 (m, 3H), 0.85-0.75 (m, 3H), 0.54-0.41 (m, 2H); 942.6 $[M + H]^+$. |

TABLE 1C-continued

| | | |
|---|---|---|
| C25 | | 1H NMR (400 MHz, DMSO-d6) δ (ppm) 10.05-9.43 (m, 1H), 8.94-8.75 (m, 1H), 8.32-8.21 (m, 1H), 8.11-7.98 (m, 2H), 7.60 (d, J = 8.7 Hz, 1H), 7.39-7.25 (m, 6H), 7.24-7.09 (m, 4H), 6.32-6.14 (m, 2H), 5.04-4.75 (m, 2H), 4.64-4.44 (m, 2H), 4.22-4.06 (m, 1H), 3.97-3.82 (m, 3H), 3.79-3.69 (m, 2H), 3.56-3.53 (m, 2H), 3.36-2.99 (m, 1H), 2.84-2.62 (m, 2H), 2.61-2.55 (m, 3H), 2.48-2.31 (m, 2H), 2.26-1.43 (m, 15H), 1.17 (d, J = 7.0 Hz, 3H), 0.81 (t, J = 7.4 Hz, 3H), 0.63-0.44 (m, 2H); 944.6 $[M + H]^+$ . |
| C26 | | 1H NMR (400 MHz, DMSO-d6) δ (ppm) 9.12-8.72 (m, 1H), 8.37-8.21 (m, 1H), 8.16-8.00 (m, 2H), 7.62 (d, J = 8.6 Hz, 1H), 7.44-7.10 (m, 10H), 6.30-6.05 (m, 2H), 4.89-4.77 (m, 1H), 4.67-4.37 (m, 3H), 4.31-4.01 (m, 4H), 3.98-3.78 (m, 6H), 3.58-3.51 (m, 3H), 3.11-2.68 (m, 4H), 2.41-1.70 (m, 12H), 1.66-1.34 (m, 3H), 1.14 (d, J = 7.1 Hz, 3H), 0.90-0.71 (m, 3H), 0.62-0.39 (m, 2H); 942.6 $[M + H]^+$ . |

TABLE 1C-continued

| | |
|---|---|
| C27 | 1H NMR (400 MHz, DMSO-d6) δ (ppm) 8.86-8.65 (m, 1H), 8.36-8.22 (m, 1H), 8.14-8.00 (m, 2H), 7.60 (t, J = 7.7 Hz, 1H), 7.45-7.25 (m, 6H), 7.25-7.07 (m, 4H), 6.37-5.96 (m, 2H), 4.81-4.61 (m, 1H), 4.47 (t, J = 8.5 Hz, 1H), 4.37-4.22 (m, 1H), 4.12 (t, J = 8.4 Hz, 1H), 4.01-3.85 (m, 3H), 3.78-3.64 (m, 4H), 3.59-3.46 (m, 1H), 3.24-2.92 (m, 2H), 2.44-1.33 (m, 22H), 1.19-0.91 (m, 3H), 0.81 (t, J = 7.4 Hz, 3H), 0.58-0.36 (m, 2H); 942.6 $[M + H]^+$ . |
| C28 | 1H NMR (400 MHz, DMSO-d6) δ (ppm) 8.87-8.74 (m, 1H), 8.61-8.53 (m, 1H), 8.47-8.38 (m, 1H), 8.29-8.24 (m, 1H), 8.11-8.01 (m, 2H), 7.81-7.73 (m, 1H), 7.63-7.55 (m, 1H), 7.39-7.27 (m, 3H), 7.22-7.11 (m, 3H), 6.30-6.05 (m, 2H), 4.90-4.65 (m, 2H), 4.54-4.43 (m, 1H), 4.36-4.24 (m, 1H), 4.19-4.08 (m, 1H), 3.97-3.87 (m, 1H), 3.86-3.69 (m, 3H), 3.64-3.49 (m, 1H), 3.13-2.92 (m, 1H), 2.65-2.56 (m, 1H), 2.45-2.30 (m, 2H), 2.23-1.35 (m, 21H), 1.18-1.08 (m, 3H), 0.89-0.71 (m, 3H), 0.54-0.37 (m, 2H); 945.6 $[M + H]^+$ . |

TABLE 1C-continued

| | | |
|---|---|---|
| C29 | | 1H NMR (400 MHz, DMSO-d6) δ (ppm) 8.75 (d, J = 7.1 Hz, 1H), 8.58 (s, 1H), 8.43 (d, J = 4.0 Hz, 1H), 8.28 (s, 1H), 8.13-8.02 (m, 2H), 7.78 (d, J = 7.6 Hz, 1H), 7.60 (d, J = 8.4 Hz, 1H), 7.43-7.27 (m, 3H), 7.19 (d, J = 7.6 Hz, 3H), 6.31-6.10 (m, 2H), 5.01-4.90 (m, 1H), 4.55-4.47 (m, 1H), 4.36-4.27 (m, 1H), 4.17-4.09 (m, 1H), 3.97-3.89 (m, 2H), 3.83-3.73 (m, 2H), 3.65-3.53 (m, 5H), 2.86-2.76 (m, 1H), 2.46-2.31 (m, 4H), 2.25-1.57 (m, 14H), 1.56-1.45 (m, 2H), 1.14 (d, J = 6.9 Hz, 3H), 0.83 (t, J = 7.3 Hz, 3H), 0.56-0.35 (m, 2H); 929.2 $[M + H]^+$ . |
| C30 | | 1H NMR (400 MHz, DMSO-d6) δ (ppm) 8.78 (d, J = 7.6 Hz, 1H), 8.26 (s, 1H), 8.11-7.96 (m, 2H), 7.63-7.56 (m, 1H), 7.40-7.26 (m, 6H), 7.25-7.08 (m, 4H), 6.31-6.13 (m, 2H), 4.77-4.66 (m, 1H), 4.58-4.50 (m, 2H), 4.49-4.38 (m, 2H), 4.38-4.25 (m, 2H), 4.11 (t, J = 8.6 Hz, 1H), 3.94-3.83 (m, 3H), 3.78-3.69 (m, 2H), 3.60-3.48 (m, 1H), 2.87-2.78 (m, 1H), 2.42-2.30 (m, 1H), 2.22 (t, J = 11.5 Hz, 1H), 2.16-2.07 (m, 1H), 2.05-1.91 (m, 6H), 1.86-1.44 (m, 10H), 1.17 (d, J = 7.1 Hz, 3H), 0.85-0.75 (m, 3H), 0.56-0.42 (m, 2H); 928.5 $[M + H]^+$ . |

TABLE 1C-continued

| | |
|---|---|
| C31 | 1H NMR (400 MHz, DMSO-d6) δ (ppm) 8.85-8.69 (m, 1H), 8.42 (s, 1H), 8.29 (s, 1H), 8.24-8.18 (m, 1H), 8.10-8.04 (m, 2H), 7.63-7.56 (m, 1H), 7.40-7.32 (m, 2H), 7.23-7.14 (m, 3H), 6.96-6.89 (m, 1H), 6.29-6.08 (m, 2H), 5.03-4.93 (m, 1H), 4.52-4.43 (m, 1H), 4.36-4.23 (m, 1H), 4.18-4.08 (m, 1H), 4.00-3.87 (m, 2H), 3.86-3.68 (m, 3H), 3.59 (s, 4H), 2.74 (s, 7H), 2.48-2.22 (m, 5H), 2.19-2.09 (m, 2H), 2.07-1.60 (m, 11H), 1.56-1.43 (m, 2H), 1.18-1.07 (m, 3H), 0.88-0.78 (m, 3H), 0.55-0.43(m, 2H); 972.5 $[M + H]^+$ . |
| C32 | 1H NMR (400 MHz, DMSO-d6) δ (ppm) 8.86-8.66 (m, 1H), 8.26 (s, 1H), 8.10-8.00 (m, 2H), 7.64-7.56 (m, 1H), 7.41-7.11 (m, 10H), 6.29-6.02 (m, 2H), 4.79-4.64 (m, 1H), 4.52-4.40 (m, 1H), 4.33-4.21 (m, 1H), 4.15-4.04 (m, 1H), 3.97-3.49 (m, 8H), 3.15-2.97 (m, 2H), 2.38-1.36 (m, 22H), 1.19-1.05 (m, 3H), 0.88-0.73 (m, 3H), 0.56-0.36 (m, 2H); 942.5 $[M + H]^+$ . |

TABLE 1C-continued

| | |
|---|---|
| C33 | 1H NMR (400 MHz, DMSO-d6) δ (ppm) 8.78-8.69 (m, 1H), 8.60-8.55 (m, 1H), 8.46-8.37 (m, 1H), 8.31-8.21 (m, 1H), 8.09-8.00 (m, 2H), 7.83-7.72 (m, 1H), 7.65-7.53 (m, 1H), 7.39-7.28 (m, 3H), 7.20-7.09 (m, 3H), 6.32-6.13 (m, 2H), 5.06-4.84 (m, 1H), 4.57-4.43 (m, 1H), 4.38-4.24 (m, 1H), 4.19-4.06 (m, 1H), 3.96-3.75 (m, 4H), 3.63-3.52 (m, 5H), 2.82-2.64 (m, 1H), 2.44-2.29 (m, 4H), 2.23-1.58 (m, 14H), 1.51-1.41 (m, 2H), 1.20-1.12 (m, 3H), 0.85-0.76 (m, 3H), 0.55-0.38 (m, 2H); 929.4 $[M + H]^+$ . |
| C34 | 1H NMR (400 MHz, DMSO-d6) δ (ppm) 8.79 (d, J = 7.7 Hz, 1H), 8.27 (s, 1H), 8.10-8.03 (m, 2H), 7.60 (d, J = 8.6 Hz, 1H), 7.39-7.27 (m, 6H), 7.24-7.14 (m, 4H), 6.28-6.11 (m, 2H), 4.78-4.64 (m, 1H), 4.59-4.50 (m, 2H), 4.50-4.38 (m, 2H), 4.38-4.33 (m, 1H), 4.33-4.25 (m, 1H), 4.16-4.06 (m, 1H), 3.99-3.88 (m, 2H), 3.83-3.65 (m, 3H), 3.60-3.48 (m, 1H), 2.90-2.76 (m, 1H), 2.42-2.30 (m, 1H), 2.28-2.18 (m, 1H), 2.15-2.07 (m, 1H), 2.05-1.89 (m, 6H), 1.87-1.56 (m, 7H), 1.55-1.44 (m, 3H), 1.13 (d, J = 7.1 Hz, 3H), 0.83 (t, J = 7.2 Hz, 3H), 0.59-0.40 (m, 2H); 928.4 $[M + H]^+$ . |

TABLE 1C-continued

| | | |
|---|---|---|
| C35 | | 1H NMR (400 MHz, DMSO-d6) δ (ppm) 8.77 (d, J = 7.7 Hz, 1H), 8.27 (s, 1H), 8.11-8.03 (m, 2H), 7.61 (d, J = 8.5 Hz, 1H), 7.39-7.27 (m, 6H), 7.24-7.15 (m, 4H), 6.23-6.07 (m, 2H), 4.74-4.64 (m, 1H), 4.57-4.50 (m, 2H), 4.50-4.38 (m, 2H), 4.37-4.26 (m, 2H), 4.16-4.07 (m, 1H), 3.97-3.86 (m, 2H), 3.79-3.64 (m, 3H), 3.60-3.48 (m, 1H), 2.88-2.79 (m, 1H), 2.40-2.29 (m, 1H), 2.27-2.17 (m, 1H), 2.14-2.07 (m, 1H), 2.03-1.91 (m, 6H), 1.85-1.46 (m, 10H), 0.94 (d, J = 7.1 Hz, 3H), 0.81 (t, J = 7.4 Hz, 3H), 0.56-0.42 (m, 2H); 929.0 $[M + H]^+$. |
| C36 | | 1H NMR (400 MHz, DMSO-d6) δ (ppm) 8.83-8.72 (m, 1H), 8.30-8.22 (m, 1H), 8.10-8.02 (m, 2H), 7.63-7.56 (m, 1H), 7.38-7.31 (m, 3H), 7.23-7.12 (m, 5H), 7.07-7.00 (m, 1H), 6.29-6.17 (m, 1H), 6.14-6.06 (m, 1H), 4.76-4.66 (m, 1H), 4.57-4.27 (m, 6H), 4.18-4.08 (m, 1H), 3.99-3.87 (m, 1H), 3.86-3.69 (m, 4H), 3.62-3.52 (m, 1H), 2.90-2.75 (m, 1H), 2.41-2.32 (m, 1H), 2.25-2.17 (m, 1H), 2.12-1.91 (m, 7H), 1.84-1.38 (m, 10H), 1.13 (d, J = 7.1 Hz, 3H), 0.85-0.75 (m, 3H), 0.57-0.40 (m, 2H); 946.6 $[M + H]^+$. |

TABLE 1C-continued

| | |
|---|---|
| C37 | 1H NMR (400 MHz, DMSO-d6) δ (ppm) 8.81-8.74 (m, 1H), 8.27 (s, 1H), 8.09-8.02 (m, 2H), 7.64-7.58 (m, 1H), 7.40-7.12 (m, 10H), 6.27-6.03 (m, 2H), 4.80-4.63 (m, 1H), 4.59-4.23 (m, 6H), 4.18-4.04 (m, 1H), 3.89-3.66 (m, 5H), 3.59-3.48 (m, 1H), 2.88-2.76 (m, 1H), 2.41-2.29 (m, 1H), 2.27-2.16 (m, 1H), 2.15-2.07 (m, 1H), 2.06-1.86 (m, 6H), 1.85-1.34 (m, 10H), 1.17-1.08 (m, 3H), 0.82-0.73 (m, 3H), 0.57-0.42 (m, 2H); 928.5 $[M + H]^+$ . |
| C38 | 1H NMR (400 MHz, MeOD) 8 8.13-8.02 (m, 2H), 7.97-7.94 (m, 1H), 7.66-7.61 (m, 1H), 7.43-7.27 (m, 7H), 7.25-7.12 (m, 3H), 6.19-5.95 (m, 1H), 5.04-4.93 (m, 1H), 4.66-4.62 (m, 1H), 4.55-4.38 (m, 2H), 4.00-3.78 (m, 4H), 3.75-3.69 (m, 5H), 2.95-2.85 (m, 1H), 2.67-2.49 (m, 4H), 2.40-2.25 (m, 2H), 2.21-1.93 (m, 5H), 1.90-1.82 (m, 3H), 1.78-1.65 (m, 1H), 1.62-1.46 (m, 2H), 1.37-1.26 (m, 2H), 1.23-1.21 (m, 3H), 1.00-0.92 (m, 1H), 0.90-0.84 (m, 3H), 0.76-0.65 (m, 1H); 953.2 $[M + H]^+$ . |

TABLE 1C-continued

| | | |
|---|---|---|
| C39 | | 1H NMR (400 MHz, DMSO-d6) δ (ppm) 8.84-8.72 (m, 1H), 8.62-8.55 (m, 1H), 8.47-8.40 (m, 1H), 8.31-8.24 (m, 1H), 8.11-8.03 (m, 2H), 7.82-7.75 (m, 1H), 7.66-7.56 (m, 1H), 7.39-7.30 (m, 3H), 7.22-7.13 (m, 3H), 6.29-6.05 (m, 2H), 4.97-4.80 (m, 1H), 4.57-4.49 (m, 1H), 4.18-4.10 (m, 1H), 3.97-3.54 (m, 9H), 3.36-3.29 (m, 5H), 2.26-1.34 (m, 16H), 1.13 (d, J = 7.1 Hz, 3H), 0.87-0.73 (m, 3H), 0.57-0.40 (m, 2H); 929.7 [M+ H]+ |
| C40 | | 1H NMR (400 MHz, DMSO-d6) δ (ppm) 8.74 (d, J = 7.5 Hz, 1H), 8.58 (d, J = 2.0 Hz, 1H), 8.43 (dd, J = 4.7, 1.5 Hz, 1H), 8.28 (s, 1H), 8.12-7.97 (m, 2H), 7.78 (d, J = 8.0 Hz, 1H), 7.61 (d, J = 8.7 Hz, 1H), 7.42-7.27 (m, 3H), 7.24-7.09 (m, 3H), 6.29 6.04 (m, 2H), 5.03-4.88 (m, 1H), 4.58-4.43 (m, 1H), 4.40-4.25 (m, 1H), 4.21-4.07 (m, 1H), 3.89-3.72 (m, 4H), 3.63-3.51 (m, 7H), 2.82-2.69 (m, 1H), 2.46-2.29 (m, 4H), 2.12-1.97 (m, 4H), 1.81-1.59 (m, 8H), 1.45-1.36 (m, 2H), 1.13 (d, J = 7.1 Hz, 3H), 0.78 (t, J = 7.4 Hz, 3H), 0.61-0.33 (m, 2H); 930.0 $[M + H]^+$ . |

TABLE 1C-continued

| | |
|---|---|
| C41 | 1H NMR (400 MHz, DMSO-d6) δ (ppm) 8.79-8.66 (m, 1H), 8.61-8.51 (m, 1H), 8.49-8.40 (m, 1H), 8.29 (s, 1H), 8.14-7.99 (m, 2H), 7.82-7.73 (m, 1H), 7.66-7.55 (m, 1H), 7.42-7.27 (m, 3H), 7.22-7.06 (m, 3H), 6.32-6.01 (m, 2H), 5.09-4.81 (m, 1H), 4.65-4.21 (m, 3H), 3.93-3.69 (m, 3H), 3.68-3.44 (m, 6H), 2.82-2.68 (m, 1H), 2.48-2.22 (m, 6H), 2.10-1.55 (m, 12H), 1.47-1.34 (m, 2H), 1.18-0.99 (m, 3H), 0.83-0.69 (m, 3H), 0.49 (s, 2H); 930.6 $[M + H]^+$ . |
| C42 | 1H NMR (400 MHz, DMSO-d6) δ (ppm) 8.80-8.71 (m, 1H), 8.61-8.54 (m, 1H), 8.48-8.42 (m, 1H), 8.31-8.26 (m, 1H), 8.10-8.04 (m, 2H), 7.82-7.74 (m, 1H), 7.64-7.57 (m, 1H), 7.41-7.31 (m, 3H), 7.22-7.14 (m, 3H), 6.29-6.10 (m, 2H), 5.04-4.89 (m, 1H), 4.60-4.49 (m, 1H), 4.48-4.36 (m, 1H), 4.35-4.22 (m, 1H), 4.01-3.86 (m, 2H), 3.84-3.71 (m, 1H), 3.66-3.49 (m, 6H), 2.84-2.70 (m, 1H), 2.49-2.42 (m, 2H), 2.42-2.23 (m, 4H), 2.12-1.45 (m, 15H), 1.19-1.08 (m, 3H), 0.89-0.76 (m, 3H), 0.55-0.41 (m, 2H); 929.6 $[M + H]^+$ . |

TABLE 1C-continued

| | |
|---|---|
| C43 | 1H NMR (400 MHz, DMSO-d6) δ (ppm) 8.79-8.65 (m, 1H), 8.63 8.51 (m, 1H), 8.46-8.38 (m, 1H), 8.28 (s, 1H), 8.14-7.99 (m, 2H), 7.82-7.73 (m, 1H), 7.65-7.56 (m, 1H), 7.41-7.29 (m, 3H), 7.24 7.14 (m, 3H), 6.25-6.03 (m, 2H), 5.04-4.87 (m, 1H), 4.56-4.44 (m, 1H), 4.37-4.24 (m, 1H), 4.20-4.06 (m, 1H), 3.98-3.85 (m, 2H), 3.84-3.49 (m, 7H), 2.80-2.69 (m, 1H), 2.48-1.57 (m, 18H), 1.54-1.42 (m, 2H), 0.98-0.89 (m, 3H), 0.85-0.74 (m, 3H), 0.56-0.37 (m, 2H); 929.8 $[M + H]^+$ . |
| C44 | 1H NMR (400 MHz, DMSO-d6) δ (ppm) 8.80-8.73 (m, 1H), 8.72-8.67 (m, 1H), 8.56-8.50 (m, 1H), 8.29 (s, 1H), 8.09-8.03 (m, 2H), 7.95-7.89 (m, 1H), 7.64-7.59 (m, 1H), 7.46-7.40 (m, 1H), 7.38-7.33 (m, 2H), 7.19-7.13 (m, 3H), 6.26-6.06 (m, 2H), 5.00-4.92 (m, 1H), 4.55-4.41 (m, 2H), 4.35-4.28 (m, 1H), 4.08-4.02 (m, 1H), 3.86-3.73 (m, 5H), 3.61-3.55 (m, 4H), 2.77-2.71 (m, 1H), 2.46-2.16 (m, 6H), 2.03-1.66 (m, 10H), 1.46-1.37 (m, 2H), 1.16-1.09 (m, 3H), 0.84-0.76 (m, 4H), 0.72-0.65 (m, 1H); 954.8 $[M + H]^+$ . |

TABLE 1C-continued

| | |
|---|---|
| C45 | 1H NMR (400 MHz, DMSO-d6) δ (ppm) 8.78 (d, J = 7.6 Hz, 1H), 8.72-8.67 (m, 1H), 8.57-8.51 (m, 1H), 8.29 (s, 1H), 8.11-8.04 (m, 2H), 7.95-7.90 (m, 1H), 7.60 (d, J = 8.6 Hz, 1H), 7.46-7.40 (m, 1H), 7.39-7.33 (m, 2H), 7.22-7.14 (m, 3H), 6.28-6.11 (m, 2H), 5.01-4.90 (m, 1H), 4.56-4.49 (m, 1H), 4.48-4.40 (m, 1H), 4.36-4.26 (m, 1H), 4.06 (d, J = 9.3 Hz, 1H), 4.00-3.88 (m, 2H), 3.85-3.71 (m, 3H), 3.65-3.51 (m, 4H), 2.80-2.70 (m, 1H), 2.48-2.33 (m, 4H), 2.33-2.16 (m, 2H), 2.04-1.91 (m, 3H), 1.89-1.60 (m, 7H), 1.56-1.46 (m, 2H), 1.14 (d, J = 7.1 Hz, 3H), 0.86-0.78 (m, 4H), 0.73-0.64 (m, 1H); 954.6 $[M + H]^+$ . |
| C46 | 1H NMR (400 MHz, DMSO-d6) δ (ppm) 8.80-8.70 (m, 1H), 8.42 (s, 1H), 8.29 (s, 1H), 8.24-8.18 (m, 1H), 8.08-8.03 (m, 2H), 7.64-7.56 (m, 1H), 7.41-7.32 (m, 2H), 7.21-7.11 (m, 3H), 6.97-6.90 (m, 1H), 6.30-6.03 (m, 2H), 5.04-4.91 (m, 1H), 4.56-4.44 (m, 1H), 4.36-4.23 (m, 1H), 4.18-4.07 (m, 1H), 3.87-3.69 (m, 5H), 3.59 (s, 4H), 2,84-2.70 (m, 7H), 2.49-2.23 (m, 5H), 2.20-1.57 (m, 13H), 1.49-1.33 (m, 2H), 1.12 (d, J = 7.1 Hz, 3H), 0.78 (t, J = 7.2 Hz, 3H), 0.57-0.43 (m, 2H); 972.6 $[M + H]^+$ . |

TABLE 1C-continued

| | |
|---|---|
| C47 | 1H NMR (400 MHz, DMSO-d6) δ (ppm) 8.81-8.70 (m, 1H), 8.42 (s, 1H), 8.28 (s, 1H), 8.23-8.19 (m, 1H), 8.08-8.02 (m, 2H), 7.62-7.56 (m, 1H), 7.38-7.31 (m, 2H), 7.19-7.09 (m, 3H), 6.95-6.90 (m, 1H), 6.30-6.13 (m, 2H), 5.01-4.93 (m, 1H), 4.52-4.44 (m, 1H), 4.34-4.25 (m, 1H), 4.17-4.08 (m, 1H), 3.95-3.72 (m, 5H), 3.63-3.52 (m, 4H), 2.74 (s, 6H), 2.48-2.25 (m, 6H), 2.19-2.10 (m, 2H), 2.08-1.87 (m, 5H), 1.81-1.58 (m, 6H), 1.52-1.41 (m, 2H), 1.20-1.12 (m, 3H), 0.81 (t, J = 7.4 Hz, 3H), 0.53-0.44 (m, 2H); 972.5 $[M + H]^+$ . |
| C48 | 1H NMR (400 MHz, DMSO-d6) δ (ppm) 8.75 (d, J = 7.2 Hz, 1H), 8.42 (s, 1H), 8.29 (s, 1H), 8.21 (d, J = 5.2 Hz, 1H), 8.12-8.04 (m, 2H), 7.61 (d, J = 8.4 Hz, 1H), 7.42-7.31 (m, 2H), 7.27-7.14 (m, 3H), 6.93 (d, J = 5.2 Hz, 1H), 6.25-6.03 (m, 2H), 5.04-4.90 (m, 1H), 4.53-4.44 (m, 1H), 4.36-4.25 (m, 1H), 4.18-4.07 (m, 1H), 3.96-3.86 (m, 2H), 3.84-3.54 (m, 7H), 2.84-2.65 (m, 7H), 2.49-1.43 (m, 20H), 0.94 (d, J = 6.8 Hz, 3H), 0.81 (t, J = 6.8 Hz, 3H), 0.56-0.42 (m, 2H); 972.5 $[M + H]^+$ . |

TABLE 1C-continued

| | | |
|---|---|---|
| C49 | | 1H NMR (400 MHz, DMSO-d6) δ (ppm) 8.81-8.68 (m, 1H), 8.62-8.54 (m, 1H), 8.46-8.36 (m, 1H), 8.28 (s, 1H), 8.12-8.00 (m, 2H), 7.83-7.74 (m, 1H), 7.65-7.55 (m, 1H), 7.42-7.27 (m, 3H), 7.24-7.11 (m, 3H), 6.28-6.08 (m, 2H), 5.04-4.91 (m, 1H), 4.90-4.74 (m, 1H), 4.58-4.42 (m, 1H), 4.38-4.24 (m, 1H), 4.20-4.07 (m, 1H), 3.89-3.65 (m, 2H), 3.64-3.46 (m, 5H), 2.82-2.61 (m, 1H), 2.46-2.43 (m, 1H), 2.42-2.30 (m, 3H), 2.25-1.53 (m, 14H), 1.15-1.08 (m, 9H), 0.60-0.33 (m, 2H); 929.6 $[M + H]^+$ . |
| C50 | | 1H NMR (400 MHz, DMSO-d6) δ (ppm) 8.76-8.70 (m, 1H), 8.60-8.56 (m, 1H), 8.45-8.40 (m, 1H), 8.27 (s, 1H), 8.08-8.03 (m, 2H), 7.81-7.76 (m, 1H), 7.63-7.58 (m, 1H), 7.38-7.30 (m, 3H), 7.19-7.12 (m, 3H), 6.27-6.04 (m, 2H), 5.00-4.91 (m, 1H), 4.77-4.70 (m, 1H), 4.54 4.46 (m, 1H), 4.35-4.26 (m, 1H), 4.18-4.11 (m, 1H), 3.83-3.73 (m, 2H), 3.62-3.52 (m, 5H), 2.79-2.69 (m, 1H), 2.45-2.32 (m, 4H), 2.22-1.91 (m, 7H), 1.87-1.58 (m, 7H), 1.14-1.07 (m, 6H), 1.02 (d, J = 6.2 Hz, 3H), 0.53-0.41 (m, 2H); 929.6 $[M + H]^+$ . |

TABLE 1C-continued

| | |
|---|---|
| C51 | 1H NMR (400 MHz, DMSO-d6) δ (ppm) 8.80-8.68 (m, 1H), 8.27 (d, J = 3.6 Hz, 1H), 8.12-7.99 (m, 2H), 7.65-7.55 (m, 1H), 7.40-7.26 (m, 6H), 7.23-7.10 (m, 4H), 6.30-6.07 (m, 2H), 4.85-4.67 (m, 2H), 4.53-4.42 (m, 2H), 4.41-4.34 (m, 1H), 4.33-4.25 (m, 1H), 4.16-4.06 (m, 1H), 3.96-3.63 (m, 4H), 3.58-3.47 (m, 1H), 2.96-2.84 (m, 1H), 2.73-2.52 (m, 3H), 2.41-2.21 (m, 3H), 2.20-2.08 (m, 4H), 2.04-1.92 (m, 3H), 1.90-1.61 (m, 6H), 1.59-1.40 (m, 4H), 1.19-0.92 (m, 3H), 0.81 (t, J = 7.4 Hz, 3H), 0.55-0.39 (m, 2H); 942.5 $[M + H]^+$ . |
| C52 | 1H NMR (400 MHz, DMSO-d6) δ (ppm) 8.79 (M, 1H), 8.28 (s, 1H), 8.10-8.02 (m, 2H), 7.60 (t, J = 7.5 Hz, 1H), 7.39-7.11 (m, 16H), 6.37-6.05 (m, 3H), 5.09-4.90 (m, 2H), 4.84-4.72 (m, 1H), 4.50 (t, J = 8.5 Hz, 1H), 4.38-4.27 (m, 1H), 4.16-4.06 (m, 1H), 3.97-3.83 (m, 1H), 3.75 (t, J = 9.7 Hz, 1H), 3.60-3.49 (m, 1H), 3.06-2.94 (m, 1H), 2.47-2.33 (m, 2H), 2.25-2.19 (m, 1H), 2.16-2.11 (m, 4H), 2.07-1.93 (m, 5H), 1.89-1.54 (m, 8H), 1.22-1.15 (m, 3H), 0.55-0.41 (m, 2H); 998.6 $[M + H]^+$ . |

TABLE 1C-continued

| | | |
|---|---|---|
| C53 | | 1H NMR (400 MHz, DMSO-d6) δ (ppm) 9.86-9.38 (m, 1H), 8.91-8.74 (m, 1H), 8.31-8.23 (m, 1H), 8.11-8.03 (m, 2H), 7.61 (d, J = 8.5 Hz, 1H), 7.39 7.27 (m, 6H), 7.24-7.11 (m, 4H), 6.39-5.95 (m, 3H), 4.87-4.76 (m, 1H), 4.63-4.47 (m, 2H), 4.17-4.08 (m, 1H), 3.98-3.89 (m, 1H), 3.79-3.68 (m, 3H), 3.60-3.56 (m, 2H), 3.35-3.12 (m, 2H), 2.82-2.68 (m, 3H), 2.48-1.68 (m, 15H), 1.61-1.35 (m, 5H), 0.84 (t, J = 7.4 Hz, 1H), 0.79-0.72 (m, 3H), 0.63 (t, J = 7.4 Hz, 2H), 0.57-0.43 (m, 2H); 964.5 $[M + H]^+$. |
| C54 | | 1H NMR (400 MHz, DMSO-d6) δ (ppm) 8.81-8.71 (m, 1H), 8.27 (s, 1H), 8.07 (d, J = 7.5 Hz, 2H), 7.60 (d, J = 8.5 Hz, 1H), 7.38-7.28 (m, 6H), 7.23-7.12 (m, 4H), 6.29-5.93 (m, 3H), 4.78 (d, J = 7.6 Hz, 1H), 4.53-4.43 (m, 1H), 4.31 (s, 1H), 4.15-3.96 (m, 3H), 3.92-3.69 (m, 2H), 3.57-3.49 (m, 1H), 3.47-3.37 (m, 2H), 3.21 (d, J = 5.6 Hz, 3H), 2.99 (s, 1H), 2.44-2.32 (m, 2H), 2.26-2.18 (m, 1H), 2.16-1.51 (m, 18H), 1.18-1.10 (m, 3H), 0.52-0.40 (m, 2H); 966.5 $[M + H]^+$. |

TABLE 1C-continued

| | |
|---|---|
| C55 | 1H NMR (400 MHz, DMSO-d6) δ (ppm) 8.92-8.67 (m, 1H), 8.28 (s, 1H), 8.14-7.96 (m, 2H), 7.68-7.54 (m, 1H), 7.43-7.27 (m, 6H), 7.25-7.10 (m, 4H), 6.32-6.06 (m, 2H), 4.90-4.60 (m, 2H), 4.48 (t, J = 8.5 Hz, 1H), 4.36-4.22 (m, 1H), 4.12 (t, J = 8.4 Hz, 1H), 3.99-3.69 (m, 4H), 3.63-3.46 (m, 1H), 3.10-2.96 (m, 1H), 2.77-2.62 (m, 1H), 2.60-2.53 (m, 1H), 2.47-1.32 (m, 21H), 1.13 (d, J = 7.0 Hz, 3H), 0.98 (t, J = 6.9 Hz, 3H), 0.88-0.72 (m, 3H), 0.60-0.35 (m, 2H); 958.5 $[M + H]^+$ . |
| C56 | 1H NMR (400 MHz, DMSO-d6) δ (ppm) 8.84-8.73 (m, 1H), 8.27 (d, J = 3.7 Hz, 1H), 8.11-8.01 (m, 2H), 7.60 (t, J = 7.6 Hz, 1H), 7.41-7.28 (m, 6H), 7.23-7.11 (m, 4H), 6.29-6.08 (m, 2H), 4.88-4.66 (m, 2H), 4.47 (t, J = 8.5 Hz, 1H), 4.33-4.23 (m, 1H), 4.12 (t, J = 8.5 Hz, 1H), 3.94-3.69 (m, 4H), 3.60-3.48 (m, 1H), 3.09-2.98 (m, 1H), 2.74-2.66 (m, 1H), 2.61-2.53 (m, 1H), 2.47-1.92 (m, 11H), 1.89-1.62 (m, 6H), 1.60-1.43 (m, 4H), 1.17 (d, J = 7.1 Hz, 1H), 1.03-0.90 (m, 5H), 0.81 (t, J = 7.4 Hz, 3H), 0.55-0.41 (m, 2H); 958.6 $[M + H]^+$ . |

TABLE 1C-continued

| | | |
|---|---|---|
| C57 | | 1H NMR (400 MHz, DMSO-d6) δ (ppm) 8.84-8.70 (m, 1H), 8.27 (s, 1H), 8.11-7.98 (m, 2H), 7.61 (d, J = 8.4 Hz, 1H), 7.44-7.06 (m, 10H), 6.31-5.89 (m, 3H), 4.91-4.64 (m, 2H), 4.56-4.41 (m, 1H), 4.38-4.25 (m, 1H), 4.14-4.01 (m, 1H), 3.84-3.64 (m, 2H), 3.60-3.43 (m, 1H), 2.99 (s, 1H), 2.44-2.27 (m, 2H), 2.24-1.49 (m, 18H), 1.20-0.94 (m, 9H), 0.55-0.35 (m, 2H); 950.6 $[M + H]^+$ . |
| C58 | | 1H NMR (400 MHz, DMSO-d6) δ 8.81-8.72 (m, 1H), 8.27 (s, 1H), 8.11-8.03 (m, 2H), 7.66-7.57 (m, 1H), 7.38-7.28 (m, 6H), 7.23-7.13 (m, 4H), 6.26-5.93 (m, 3H), 4.83-4.71 (m, 1H), 4.54-4.43 (m, 1H), 4.38-4.26 (m, 1H), 4.16-4.07 (m, 1H), 4.06-3.97 (m, 1H), 3.95-3.69 (m, 3H), 3.59-3.48 (m, 1H), 3.09-2.89 (m, 1H), 2.44-2.32 (m, 2H), 2.25-1.53 (m, 19H), 1.15-1.01 (m, 6H), 0.54-0.40 (m, 2H); 936.7 $[M + H]^+$ . |
| C59 | | 1H NMR (400 MHz, DMSO-d6) δ (ppm) 8.78 (d, J = 7.7 Hz, 1H), 8.27 (s, 1H), 8.11-8.01 (m, 2H), 7.61 (d, J = 8.6 Hz, 1H), 7.39-7.13 (m, 10H), 6.27-6.04 (m, 2H), 4.79-4.66 (m, 1H), 4.52-4.39 (m, 1H), 4.34-4.21 (m, 1H), 4.18-4.05 (m, 1H), 3.87-3.48 (m, 9H), 3.19-3.05 (m, 1H), 2.99-2.85 (m, 1H), 2.40-2.30 (m, 1H), 2.28-2.19 (m, 1H), 2.15-1.52 (m, 17H), 1.47-1.35 (m, 2H), 1.18-1.08 (m, 3H), 0.82-0.70 (m, 3H), 0.55-0.38 (m, 2H); 942.6 $[M + H]^+$ . |

TABLE 1C-continued

| | |
|---|---|
| C60 | 1H NMR (400 MHz, DMSO-d6) δ (ppm) 8.80 (d, J = 7.3 Hz, 1H), 8.27 (s, 1H), 8.15-8.00 (m, 2H), 7.60 (d, J = 8.5 Hz, 1H), 7.40-7.27 (m, 6H), 7.24-7.12 (m, 4H), 6.29-6.09 (m, 2H), 4.80-4.66 (m, 1H), 4.47 (t, J = 8.4 Hz, 1H), 4.36-4.23 (m, 1H), 4.11 (t, J = 8.4 Hz, 1H), 3.99-3.88 (m, 2H), 3.82-3.58 (m, 5H), 3.57-3.49 (m, 2H), 3.20-3.07 (m, 1H), 3.03-2.88 (m, 1H), 2.40-2.30 (m, 1H), 2.22 (t, J = 11.4 Hz, 1H), 2.16-2.05 (m, 5H), 2.03-1.88 (m, 4H), 1.88-1.48 (m, 10H), 1.14 (d, J = 6.9 Hz, 3H), 0.83 (t, J = 7.4 Hz, 3H), 0.57-0.39 (m, 2H); 942.8 $[M + H]^+$ . |
| C61 | 1H NMR (400 MHz, DMSO-d6) δ (ppm) 10.02-9.32 (m, 1H), 8.99-8.73 (m, 1H), 8.33-8.23 (m, 1H), 8.12-8.02 (m, 2H), 7.66-7.55 (m, 1H), 7.41-7.27 (m, 6H), 7.25-7.11 (m, 4H), 6.28-6.05 (m, 2H), 4.99-4.71 (m, 3H), 4.61-4.47 (m, 2H), 4.21-4.07 (m, 1H), 3.80-3.71 (m, 2H), 3.61-3.49 (m, 2H), 3.44-2.97 (m, 1H), 2.78-2.55 (m, 5H), 2.49-1.44 (m, 22H), 1.20-1.03 (m, 3H), 0.63-0.41 (m, 2H); 957 $[M + H]^+$ . |

TABLE 1C-continued

| | |
|---|---|
| C62 | 1H NMR (400 MHz, DMSO-d6) δ (ppm) 8.87-8.74 (m, 1H), 8.33-8.23 (m, 1H), 8.09-8.01 (m, 2H), 7.63-7.55 (m, 1H), 7.38-7.27 (m, 6H), 7.24-7.10 (m, 4H), 6.31-6.13 (m, 2H), 4.93-4.66 (m, 3H), 4.52-4.39 (m, 1H), 4.34-4.22 (m, 1H), 4.18-4.05 (m, 1H), 3.89-3.68 (m, 2H), 3.62-3.46 (m, 1H), 3.07-2.92 (m, 1H), 2.66-2.54 (m, 1H), 2.41-1.49 (m, 27H), 1.20-1.08 (m, 3H), 0.56-0.38 (m, 2H); 956.6 $[M + H]^+$ . |
| C63 | 1H NMR (400 MHz, DMSO-d6) δ (ppm) 8.81 (d, J = 7.7 Hz, 1H), 8.29-8.25 (m, 1H), 8.06 (d, J = 8.4 Hz, 1H), 7.99 (s, 1H), 7.51 (d, J = 8.5 Hz, 1H), 7.37-7.28 (m, 4H), 7.24-7.18 (m, 1H), 6.26-6.01 (m, 2H), 4.91-4.56 (m, 4H), 4.51-4.43 (m, 1H), 4.34-4.24 (m, 1H), 4.16-4.08 (m, 1H), 4.05-3.92 (m, 2H), 3.78-3.61 (m, 2H), 3.59-3.48 (m, 1H), 3.06-2.95 (m, 1H), 2.64-2.55 (m, 1H), 2.43-2.30 (m, 2H), 2.27-2.19 (m, 1H), 2.17-1.45 (m, 20H), 1.27-1.18 (m, 3H), 0.90-0.81 (m, 3H), 0.55-0.41 (m, 2H); 950.6 $[M + H]^+$ . |

TABLE 1C-continued

| | |
|---|---|
| C64 | 1H NMR (400 MHz, DMSO-d6) δ (ppm) 8.86-8.75 (m, 1H), 8.30-8.22 (m, 1H), 8.10-8.02 (m, 1H), 8.01-7.95 (m, 1H), 7.56-7.47 (m, 1H), 7.37-7.27 (m, 4H), 7.24-7.18 (m, 1H), 6.27-5.91 (m, 2H), 4.92-4.68 (m, 2H), 4.66-4.42 (m, 3H), 4.36-4.24 (m, 1H), 4.16-4.08 (m, 1H), 4.05-3.93 (m, 2H), 3.84-3.50 (m, 3H), 3.08-2.93 (m, 1H), 2.64-2.56 (m, 1H), 2.44-2.31 (m, 2H), 2.30-1.45 (m, 21H), 1.31-1.01 (m, 3H), 0.89-0.82 (m, 3H), 0.58-0.39 (m, 2H); 950.7 $[M + H]^+$ . |
| C65 | 1H NMR (400 MHz, DMSO-d6) δ (ppm) 8.86-8.75 (m, 1H), 8.27 (s, 1H), 8.10-8.02 (m, 2H), 7.60 (d, J = 8.0 Hz, 1H), 7.39-7.27 (m, 6H), 7.24-7.13 (m, 4H), 6.28-6.18 (m, 1H), 6.15-6.05 (m, 1H), 4.71 (m, 1H), 4.48 (m, 1H), 4.34-4.23 (m, 1H), 4.12 (m = 8.6 Hz, 1H), 3.98-3.89 (m, 1H), 3.87-3.70 (m, 3H), 3.60-3.49 (m, 1H), 3.07-2.90 (m, 3H), 2.40-2.28 (m, 2H), 2.26-2.10 (m, 3H), 2.05-1.91 (m, 7H), 1.90-1.34 (m, 11H), 1.13 (d, J = 7.1 Hz, 3H), 0.86-0.75 (m, 3H), 0.55-0.42 (m, 2H); 951.0 [M+ H]+ |

TABLE 1C-continued

| | | |
|---|---|---|
| C66 | | 1H NMR (400 MHz, DMSO-d6) δ (ppm) 8.89-8.71 (m, 1H), 8.27 (s, 1H), 8.12-7.99 (m, 2H), 7.65-7.56 (m, 1H), 7.39-7.27 (m, 6H), 7.24-7.13 (m, 4H), 6.31-6.21 (m, 1H), 6.18-6.10 (m, 1H), 4.90-4.66 (m, 2H), 4.52-4.43 (m, 1H), 4.33-4.24 (m, 1H), 4.15-3.70 (m, 5H), 3.59-3.48 (m, 1H), 3.06-2.93 (m, 1H), 2.63-2.53 (m, 3H), 2.49-1.45 (m, 24H), 1.15 (d, J = 7.0 Hz, 3H), 0.60-0.36 (m, 2H); 1006.7 $[M + H]^+$ . |
| C67 | | 1H NMR (400 MHz, DMSO-d6) δ (ppm) 8.85-8.74 (m, 1H), 8.30-8.23 (m, 1H), 8.08-8.00 (m, 2H), 7.63-7.54 (m, 1H), 7.40-7.26 (m, 6H), 7.24-7.10 (m, 4H), 6.30-6.14 (m, 2H), 4.90-4.67 (m, 2H), 4.52-4.42 (m, 1H), 4.34-4.21 (m, 1H), 4.15-3.84 (m, 4H), 3.78-3.67 (m, 1H), 3.58-3.45 (m, 1H), 3.09-2.94 (m, 1H), 2.66-2.50 (m, 3H), 2.43-1.48 (m, 24H), 1.22-1.13 (m, 3H), 0.56-0.38 (m, 2H); 1007.7 $[M + H]^+$ . |
| C68 | | 1H NMR (400 MHz, DMSO-d6) δ (ppm) 8.87-8.74 (m, 1H), 8.27 (s, 1H), 8.11-8.03 (m, 2H), 7.60 (d, J = 8.5 Hz, 1H), 7.39 7.27 (m, 6H), 7.24-7.12 (m, 4H), 6.32-5.99 (m, 2H), 4.92-4.63 (m, 3H), 4.53-4.41 (m, 1H), 4.35-4.24 (m, 1H), 4.17-4.07 (m, 1H), 3.85-3.67 (m, 2H), 3.60-3.47 (m, 1H), 3.06-2.95 (m, 1H), 2.64-2.55 (m, 1H), 2.46-1.41 (m, 21H), 1.16-0.98 (m, 9H), 0.57-0.40 (m, 2H); 944.7 $[M + H]^+$ . |

TABLE 1C-continued

| | |
|---|---|
| C69 | 1H NMR (400 MHz, DMSO-d6) δ (ppm) 8.90-8.71 (m, 1H), 8.34-8.20 (m, 1H), 8.10-8.03 (m, 2H), 7.63-7.57 (m, 1H), 7.40-7.27 (m, 6H), 7.23-7.09 (m, 4H), 6.32-6.04 (m, 2H), 4.91-4.67 (m, 3H), 4.47 (t, J = 8.5 Hz, 1H), 4.34-4.25 (m, 1H), 4.12 (t, J = 8.6 Hz, 1H), 3.88-3.49 (m, 3H), 3.08-2.94 (m, 1H), 2.65-2.57 (m, 1H), 2.45-2.29 (m, 2H), 2.23 (t, J = 11.6 Hz, 1H), 2.17-2.10 (m, 1H), 2.03-1.94 (m, 5H), 1.89-1.46 (m, 9H), 1.20-1.04 (m, 7H), 0.91 (d, J = 7.1 Hz, 2H), 0.56-0.39 (m, 2H); 944.7 $[M + H]^+$. |
| C70 | 1H NMR (400 MHz, DMSO-d6) δ (ppm) 8.78 (d, J = 7.7 Hz, 1H), 8.27 (s, 1H), 8.16 (s, 1H), 8.11-7.92 (m, 2H), 7.60 (d, J = 8.5 Hz, 1H), 7.40 7.09 (m, 10H), 6.30-5.79 (m, 3H), 4.77-4.65 (m, 1H), 4.53-4.41 (m, 1H), 4.34-4.24 (m, 1H), 4.16-4.02 (m, 1H), 3.89-3.64 (m, 4H), 3.60-3.50 (m, 1H), 3.10-2.94 (m, 2H), 2.38-2.09 (m, 5H), 2.03-1.86 (m, 8H), 1.85-1.51 (m, 9H), 1.47-1.35 (m, 2H), 1.13 (d, J = 7.1 Hz, 3H), 0.78 (m, 3H), 0.55-0.34 (m, 2H); 976.4 $[M + H]^+$. |
| C71 | 1H NMR (400 MHz, DMSO-d6) δ (ppm) 8.81 (d, J = 7.4 Hz, 1H), 8.27 (s, 1H), 8.11-8.04 (m, 2H), 7.60 (d, J = 8.5 Hz, 1H), 7.39-7.27 (m, 6H), 7.25-7.14 (m, 4H), 6.29-5.82 (m, 3H), 4.81-4.66 (m, 1H), 4.50 (t, J = 8.5 Hz, 1H), 4.43-4.29 (m, 1H), 4.13 (t, J = 8.6 Hz, 1H), 3.99-3.88 (m, 2H), 3.83-3.68 (m, 2H), 3.60-3.46 (m, 1H), 3.41-3.33 (m, 2H), 2.44-1.44 (m, 24H), 1.13 (d, J = 7.1 Hz, 3H), 0.83 (m, 3H), 0.56-0.39 (m, 2H); 976.6 $[M + H]^+$. |

TABLE 1C-continued

| | | |
|---|---|---|
| C72 | | 1H NMR (400 MHz, DMSO-d6) δ (ppm) 9.86-9.42 (m, 1H), 8.93-8.75 (m, 1H), 8.31-8.24 (m, 1H), 8.13-8.03 (m, 2H), 7.64-7.57 (m, 1H), 7.43-7.09 (m, 10H), 6.32 6.07 (m, 2H), 5.27-4.76 (m, 4H), 4.61-4.48 (m, 2H), 4.21-4.08 (m, 1H), 3.93-3.68 (m, 4H), 3.43-3.07 (m, 1H), 2.83-2.56 (m, 5H), 2.50-1.48 (m, 20H), 1.21-0.90 (m, 3H), 0.64-0.43 (m, 2H); 974.5 $[M + H]^+$ . |
| C73 | | 1H NMR (400 MHz, DMSO-d6) δ (ppm) 9.92-9.51 (m, 1H), 8.97-8.72 (m, 1H), 8.30-8.21 (m, 1H), 8.12-7.98 (m, 2H), 7.61 (d, J = 8.3 Hz, 1H), 7.40-7.27 (m, 6H), 7.24-7.09 (m, 4H), 6.28-6.09 (m, 2H), 5.01-4.77 (m, 2H), 4.62-4.47 (m, 2H), 4.21-4.09 (m, 1H), 3.96-3.89 (m, 1H), 3.87-3.63 (m, 4H), 3.58-3.53 (m, 1H), 3.46-3.03 (m, 1H), 2.82-2.71 (m, 1H), 2.67-2.57 (m, 3H), 2.32-1.71 (m, 12H), 1.70-1.50 (m, 2H), 1.45-1.20 (m, 5H), 1.17-1.10 (m, 3H), 0.85-0.73 (m, 6H), 0.62-0.46 (m, 2H); 974.9 $[M + H]^+$ . |

TABLE 1C-continued

| | | |
|---|---|---|
| C74 | | 1H NMR (400 MHz, DMSO-d6) δ (ppm) 9.69 (d, J = 120.2 Hz, 1H), 8.97-8.72 (m, 1H), 8.27 (d, J = 4.2 Hz, 1H), 8.07 (d, J = 3.3 Hz, 2H), 7.61 (d, J = 8.3 Hz, 1H), 7.40-7.27 (m, 6H), 7.24-7.09 (m, 4H), 6.28-6.09 (m, 2H), 4.82 (s, 2H), 4.52 (s, 2H), 4.21-4.09 (m, 1H), 3.96-3.89 (m, 1H), 3.87-3.63 (m, 4H), 3.54 (d, J = 7.3 Hz, 1H), 3.46-3.03 (m, 1H), 2.75 (s, 1H), 2.67-2.57 (m, 3H), 2.32-1.71 (m, 12H), 1.70-1.50 (m, 2H), 1.45-1.20 (m, 5H), 1.14 (d, J = 6.3 Hz, 3H), 0.85-0.73 (m, 6H), 0.51 (s, 2H); 987.1 $[M + H]^+$ . |
| C75 | | 1H NMR (400 MHz, DMSO-d6) δ (ppm) 9.86-9.44 (m, 1H), 8.97-8.75 (m, 1H), 8.35-8.23 (m, 1H), 8.07 (d, J = 6.1 Hz, 2H), 7.68-7.55 (m, 1H), 7.43-7.03 (m, 10H), 6.33-6.04 (m, 2H), 5.07-4.71 (m, 2H), 4.67-4.46 (m, 2H), 4.29-4.06 (m, 1H), 3.85-3.78 (m, 1H), 3.77-3.72 (m, 1H), 3.71-3.64 (m, 1H), 3.62-3.47 (m, 2H), 3.45-3.00 (m, 1H), 2.82-2.71 (m, 1H), 2.63-2.54 (m, 3H), 2.47-1.30 (m, 18H), 1.25-1.12 (m, 3H), 0.95-0.74 (m, 9H), 0.64-0.43 (m, 2H); 972.5 $[M + H]^+$ . |

TABLE 1C-continued

| | | |
|---|---|---|
| C76 | | 1H NMR (400 MHz, DMSO-d6) δ (ppm) 8.85-8.71 (m, 1H), 8.31-8.23 (m, 1H), 8.14-8.00 (m, 2H), 7.61 (d, J = 8.4 Hz, 1H), 7.40-7.26 (m, 6H), 7.23-7.10 (m, 4H), 6.32-6.05 (m, 2H), 4.91-4.80 (m, 1H), 4.77-4.64 (m, 2H), 4.53-4.37 (m, 2H), 4.34-4.23 (m, 1H), 4.17-4.05 (m, 1H), 3.97-3.62 (m, 2H), 3.59-3.48 (m, 1H), 3.06-2.96 (m, 1H), 2.89-2.68 (m, 2H), 2.64-2.56 (m, 1H), 2.45-1.42 (m, 23H), 1.22-1.15 (m, 1H), 0.99-0.90 (m, 2H), 0.56-0.36 (m, 2H); 974.9 $[M + H]^+$. |
| C77 | | 1H NMR (400 MHz, DMSO-d6) δ (ppm) 8.80 (s, 1H), 8.27 (d, J = 3.6 Hz, 1H), 8.11-8.02 (m, 2H), 7.61 (d, J = 8.9 Hz, 1H), 7.40-7.26 (m, 6H), 7.24-7.12 (m, 4H), 6.34-6.07 (m, 2H), 4.96-4.64 (m, 3H), 4.57-4.23 (m, 3H), 4.19-4.05 (m, 1H), 3.95-3.66 (m, 2H), 3.59-3.49 (m, 1H), 3.10-2.52 (m, 5H), 2.42-1.50 (m, 22H), 1.20-1.08 (m, 3H), 0.58-0.38 (m, 2H); 974.6 $[M + H]^+$. |

TABLE 1C-continued

| | | |
|---|---|---|
| C78 | | 1H NMR (400 MHz, DMSO-d6) δ (ppm) 8.78 (d, J = 7.6 Hz, 1H), 8.26 (s, 1H), 8.12-7.90 (m, 2H), 7.52 (d, J = 8.5 Hz, 1H), 7.37-7.27 (m, 4H), 7.24-7.17 (m, 1H), 5.87 (dd, J = 44.3, 6.5 Hz, 1H), 5.58-5.38 (m, 1H), 4.89-4.85 (m, 1H), 4.73-4.69 (m, 1H), 4.52-4.41 (m, 1H), 4.34-4.23 (m, 1H), 4.15-4.01 (m, 3H), 3.79-3.67 (m, 1H), 3.59-3.46 (m, 2H), 3.07-2.94 (m, 1H), 2.63-2.55 (m, 1H), 2.43-1.48 (m, 22H), 1.25 (t, J = 7.0 Hz, 3H), 1.20-1.11 (m, 6H), 0.97 (d, J = 7.2 Hz, 3H), 0.56-0.40 (m, 2H); 986.7 $[M + H]^+$ . |
| C79 | | 1H NMR (400 MHz, DMSO-d6) δ (ppm) 9.90-9.47 (m, 1H), 8.92-8.74 (m, 1H), 8.30-8.23 (m, 1H), 8.11-8.03 (m, 2H), 7.60 (t, J = 8.2 Hz, 1H), 7.40-7.27 (m, 6H), 7.26-7.10 (m, 4H), 6.30-6.06 (m, 2H), 5.05-4.76 (m, 2H), 4.62-4.47 (m, 2H), 4.20-4.07 (m, 1H), 3.96-3.67 (m, 5H), 3.58-3.53 (m, 1.5H), 3.13 3.00 (m, 0.5H), 2.83-2.55 (m, 5H), 2.49-2.34 (m, 2H), 2.30-1.48 (m, 14H), 1.45-1.33 (m, 1H), 1.30-1.20 (m, 4H), 1.19-0.92 (m, 3H), 0.85-0.72 (m, 6H), 0.62-0.43 (m, 2H); 986.6 $[M + H]^+$ . |

TABLE 1C-continued

| | |
|---|---|
| C80 | 1H NMR (400 MHz, DMSO-d6) δ (ppm) 9.82-9.43 (m, 1H), 8.95-8.74 (m, 1H), 8.30-8.25 (m, 1H), 8.17-8.03 (m, 2H), 7.71-7.56 (m, 1H), 7.39-7.28 (m, 6H), 7.23-7.06 (m, 4H), 6.31-6.07 (m, 2H), 5.03-4.73 (m, 2H), 4.65-4.47 (m, 2H), 4.21-4.11 (m, 1H), 3.83-3.69 (m, 4H), 3.63-3.52 (m, 2H), 3.43 3.02 (m, 1H), 2.82-2.62 (m, 2H), 2.61-2.55 (m, 3H), 2.49-1.45 (m, 16H), 1.23-0.95 (m, 3H), 0.83 (s, 8H), 0.64-0.44 (m, 2H); 973.0 $[M + H]^+$ . |
| C81 | 1H NMR (400 MHz, DMSO-d6) δ (ppm) 8.80 (d, J = 7.5 Hz, 1H), 8.27 (s, 1H), 8.11-7.99 (m, 2H), 7.60 (d, J = 8.7 Hz, 1H), 7.43-7.26 (m, 6H), 7.23-7.08 (m, 4H), 6.29-6.04 (m, 2H), 4.94-4.66 (m, 2H), 4.53-4.41 (m, 1H), 4.29 (s, 1H), 4.19-4.04 (m, 1H), 3.99-3.87 (m, 1H), 3.86-3.67 (m, 3H), 3.60-3.46 (m, 1H), 3.00 (s, 1H), 2.69-2.57 (m, 1H), 2.33 (s, 2H), 2.27-1.48 (m, 20H), 1.45-1.33 (m, 1H), 1.18-1.07 (m, 3H), 0.88-0.70 (m, 3H), 0.57-0.40 (m, 2H); 944.6 $[M + H]^+$ . |

TABLE 1C-continued

| | |
|---|---|
| C82 | 1H NMR (400 MHz, DMSO-d6) δ (ppm) 8.77 (d, J = 7.6 Hz, 1H), 8.27 (s, 1H), 8.10-8.00 (m, 2H), 7.61 (d, J = 8.5 Hz, 1H), 7.40-7.26 (m, 6H), 7.24-7.11 (m, 4H), 6.26-6.04 (m, 2H), 4.85-4.71 (m, 1H), 4.52-4.42 (m, 1H), 4.35-4.25 (m, 1H), 4.17-4.06 (m, 1H), 3.87-3.67 (m, 4H), 3.57-3.48 (m, 1H), 2.99-2.87 (m, 1H), 2.46-2.42 (m, 1H), 2.33-1.55 (m, 22H), 1.46-1.36 (m, 2H), 1.13 (d, J = 7.1 Hz, 3H), 0.83-0.70 (m, 3H), 0.53-0.37 (m, 2H); 982.5 $[M + H]^+$ . |
| C83 | 1H NMR (400 MHz, DMSO-d6) δ (ppm) 8.79 (d, J = 7.7 Hz, 1H), 8.25 (s, 1H), 8.01 (d, J = 8.4 Hz, 1H), 7.96 (s, 1H), 7.51 (d, J = 8.5 Hz, 1H), 7.36-7.28 (m, 4H), 7.24-7.18 (m, 1H), 6.01 (dd, J = 44.1, 7.0 Hz, 1H), 5.68-5.56 (m, 1H), 4.95-4.65 (m, 3H), 4.54-4.43 (m, 1H), 4.33-4.24 (m, 1H), 4.15-4.08 (m, 1H), 4.00-3.89 (m, 2H), 3.77-3.66 (m, 2H), 3.58-3.49 (m, 1H), 3.06-2.94 (m, 1H), 2.63-2.55 (m, 1H), 2.44-2.29 (m, 2H), 2.26-2.19 (m, 1H), 2.17-1.89 (m, 9H), 1.88-1.76 (m, 3H), 1.74-1.49 (m, 6H), 1.25 (d, J = 7.1 Hz, 3H), 1.19-1.10 (m, 9H), 0.54-0.42 (m, 2H); 896.6 $[M + H]^+$ . |

TABLE 1C-continued

| | | |
|---|---|---|
| C84 | | 1H NMR (400 MHz, DMSO-d6) δ (ppm) 8.85-8.73 (m, 1H), 8.27 (d, J = 4.2 Hz, 1H), 8.11-8.01 (m, 2H), 7.64-7.54 (m, 1H), 7.40-7.27 (m, 6H), 7.24-7.11 (m, 4H), 6.30-6.08 (m, 2H), 4.91-4.65 (m, 2H), 4.52-4.41 (m, 1H), 4.29 (s, 1H), 4.17-4.07 (m, 1H), 3.96-3.67 (m, 4H), 3.59-3.46 (m, 1H), 3.05-2.93 (m, 1H), 2.64-2.54 (m, 1H), 2.44-2.30 (m, 2H), 2.27-2.03 (m, 3H), 2.02-1.92 (m, 6H), 1.89-1.75 (m, 3H), 1.74-1.43 (m, 8H), 1.19-0.94 (m, 3H), 0.84-0.74 (m, 3H), 0.55-0.40 (m, 2H); 944.6 $[M + H]^+$ . |
| C85 | | 1H NMR (400 MHz, DMSO-d6) δ (ppm) 8.84-8.71 (m, 1H), 8.27 (s, 1H), 8.10-8.03 (m, 2H), 7.61 (d, J = 8.1 Hz, 1H), 7.36 (t, J = 7.8 Hz, 2H), 7.21-7.11 (m, 3H), 6.27-6.06 (m, 2H), 4.90-4.65 (m, 2H), 4.45 (t, J = 8.5 Hz, 1H), 4.33-4.23 (m, 1H), 3.97-3.73 (m, 4H), 3.64-3.54 (m, 1H), 2.97 (s, 1H), 2.65-2.55 (m, 1H), 2.41-2.24 (m, 2H), 2.13-1.92 (m, 6H), 1.91-1.37 (m, 17H), 1.17-1.09 (m, 3H), 0.86-0.75 (m, 3H), 0.46-0.35 (m, 2H); 868.5 $[M + H]^+$ . |

TABLE 1C-continued

| | | |
|---|---|---|
| C86 | | 1H NMR (400 MHz, DMSO-d6) δ (ppm) 8.89-8.66 (m, 1H), 8.25 (s, 1H), 8.09-7.89 (m, 2H), 7.53 (d, J = 8.5 Hz, 1H), 7.38-7.27 (m, 4H), 7.25-7.18 (m, 1H), 6.06-5.82 (m, 1H), 5.64-5.47 (m, 1H), 4.91-4.63 (m, 3H), 4.55-4.41 (m, 1H), 4.37-4.22 (m, 1H), 4.17-4.06 (m, 1H), 4.03-3.90 (m, 2H), 3.80-3.65 (m, 2H), 3.59-3.48 (m, 1H), 3.06-2.92 (m, 1H), 2.63-2.55 (m, 1H), 2.49-1.46 (m, 21H), 1.26-1.06 (m, 12H), 0.59-0.38 (m, 2H); 896.7 $[M + H]^+$ . |
| C87 | | 1H NMR (400 MHz, DMSO-d6) δ (ppm) 8.84-8.72 (m, 1H), 8.26 (s, 1H), 8.11-8.02 (m, 1H), 7.98 (d, J = 9.6 Hz, 1H), 7.58-7.46 (m, 1H), 7.39-7.26 (m, 4H), 7.24-7.19 (m, 1H), 6.27-5.92 (m, 2H), 4.84-4.73 (m, 1H), 4.65-4.42 (m, 3H), 4.36-4.26 (m, 1H), 4.16-4.06 (m, 1H), 4.05-3.93 (m, 2H), 3.84-3.63 (m, 2H), 3.58-3.49 (m, 1H), 3.01-2.89 (m, 1H), 2.47-2.43 (m, 1H), 2.35-2.20 (m, 4H), 2.16-2.08 (m, 4H), 2.04-1.94 (m, 3H), 1.90-1.48 (m, 13H), 1.31-1.02 (m, 3H), 0.89-0.80 (m, 3H), 0.54 0.39 (m, 2H); 988.5 $[M + H]^+$ . |

TABLE 1C-continued

| | |
|---|---|
| C88 | 1H NMR (400 MHz, DMSO-d6) δ (ppm) 8.79 (d, J = 7.7 Hz, 1H), 8.25 (d, J = 3.0 Hz, 1H), 8.08-7.95 (m, 2H), 7.56-7.48 (m, 1H), 7.38-7.17 (m, 5H), 6.07-5.88 (m, 1H), 5.69-5.53 (m, 1H), 4.90-4.67 (m, 2H), 4.53-4.41 (m, 1H), 4.34-4.23 (m, 1H), 4.16-4.08 (m, 1H), 4.05-3.81 (m, 4H), 3.80-3.47 (m, 3H), 3.05-2.93 (m, 1H), 2.65-2.55 (m, 1H), 2.46-1.46 (m, 25H), 1.29-1.17 (m, 3H), 0.93-0.73 (m, 6H), 0.57-0.36 (m, 2H); 910.5 $[M+H]^+$. |
| C89 | 1H NMR (400 MHz, DMSO-d6) δ (ppm) 8.81 (m 7.5 Hz, 1H), 8.27 (s, 1H), 8.10-7.93 (m, 2H), 7.51 (m, 1H), 7.39-7.26 (m, 4H), 7.25-7.16 (m, 1H), 6.28-5.89 (m, 2H), 4.96-4.39 (m, 6H), 4.35-4.22 (m, 1H), 4.17-4.06 (m, 1H), 3.85-3.48 (m, 3H), 3.00 (s, 1H), 2.67-2.56 (m, 1H), 2.45-1.39 (m, 27H), 1.30-0.98 (m, 3H), 0.55-0.40 (m, 2H); 962.5 $[M+H]^+$. |
| C90 | 1H NMR (400 MHz, DMSO-d6) δ (ppm) 8.82-8.74 (m, 1H), 8.30-8.23 (m, 1H), 8.09-7.97 (m, 2H), 7.56-7.47 (m, 1H), 7.39-7.27 (m, 4H), 7.24-7.18 (m, 1H), 6.24-5.88 (m, 2H), 4.78-4.69 (m, 1H), 4.64-4.41 (m, 3H), 4.37-4.24 (m, 1H), 4.15-3.50 (m, 6H), 3.12-2.95 (m, 2H), 2.72-2.57 (m, 1H), 2.42-2.28 (m, 1H), 2.25-2.05 (m, 6H), 2.02-1.67 (m, 12H), 1.64-1.42 (m, 5H), 1.28-1.17 (m, 3H), 0.90-0.76 (m, 3H), 0.52-0.38 (m, 2H); 982.5 $[M+H]^+$. |

TABLE 1C-continued

| | |
|---|---|
| C91 | 1H NMR (400 MHz, DMSO-d6) δ (ppm) 8.88-8.68 (m, 1H), 8.34-8.19 (m, 1H), 8.11-7.95 (m, 2H), 7.58-7.46 (m, 1H), 7.38-7.17 (m, 5H), 6.24-5.93 (m, 2H), 4.86-4.70 (m, 1H), 4.66-4.43 (m, 3H), 4.35-4.25 (m, 1H), 4.15-3.50 (m, 6H), 3.01-2.87 (m, 1H), 2.44-2.20 (m, 6H), 2.14-2.10 (m, 3H), 2.05-1.92 (m, 3H), 1.88-1.44 (m, 13H), 1.28-1.20 (m, 3H), 0.89-0.77 (m, 3H), 0.54-0.37 (m, 2H); 988.7 $[M + H]^+$. |
| C92 | 1H NMR (400 MHz, DMSO-d6) δ (ppm) 9.04-8.72 (m, 1H), 8.25 (s, 1H), 8.07-7.95 (m, 2H), 7.51 (d, J = 8.2 Hz, 1H), 7.38-7.28 (m, 4H), 7.25-7.19 (m, 1H), 6.06-5.55 (m, 2H), 5.05-4.71 (m, 2H), 4.64-4.23 (m, 2H), 4.20-4.10 (m, 1H), 4.01-3.52 (m, 7H), 3.15-2.90 (m, 1H), 2.84-2.55 (m, 4H), 2.39-1.40 (m, 19H), 1.31-1.19 (m, 3H), 0.88-0.78 (m, 3H), 0.78-0.63 (m, 2H), 0.62-0.44 (m, 4H); 908.7 $[M + H]^+$. |
| C93 | 1H NMR (400 MHz, DMSO-d6) δ (ppm) 8.89-8.70 (m, 1H), 8.26 (s, 1H), 8.10-7.90 (m, 2H), 7.59-7.45 (m, 1H), 7.40-7.17 (m, 5H), 6.07-5.84 (m, 1H), 5.71-5.54 (m, 1H), 4.93-4.66 (m, 3H), 4.56-4.42 (m, 1H), 4.34-4.23 (m, 1H), 4.17-4.00 (m, 3H), 3.78-3.69 (m, 1H), 3.58-3.50 (m, 2H), 3.05-2.97 (m, 1H), 2.63-2.56 (m, 1H), 2.43-2.31 (m, 2H), 2.27-2.19 (m, 1H), 2.17-1.46 (m, 18H), 1.28-1.11 (m, 12H), 0.59-0.38 (m, 2H); 896.7 $[M + H]^+$. |

TABLE 1C-continued

| | |
|---|---|
| C94 | 1H NMR (400 MHz, DMSO-d6) δ (ppm) 9.65-9.40 (m, 1H), 8.85 (m, 1H), 8.31-8.22 (m, 1H), 8.12-7.94 (m, 2H), 7.53 (d, J = 8.6 Hz, 1H), 7.39-7.28 (m, 4H), 7.25-7.19 (m, 1H), 6.27-5.91 (m, 2H), 5.08-4.77 (m, 3H), 4.71-4.40 (m, 4H), 4.23-4.04 (m, 1H), 3.95-3.68 (m, 2H), 3.66-3.48 (m, 2H), 3.46-2.99 (m, 1H), 2.83-2.65 (m, 2H), 2.64-2.54 (m, 3H), 2.47-2.38 (m, 2H), 2.34-1.48 (m, 14H), 1.29-1.06 (m, 9H), 0.66-0.43 (m, 2H); 950.1 $[M + H]^+$ . |
| C95 | 1H NMR (400 MHz, DMSO-d6) δ (ppm) 8.85-8.71 (m, 1H), 8.31-8.22 (m, 1H), 8.11-7.94 (m, 2H), 7.56-7.46 (m, 1H), 7.37-7.28 (m, 4H), 7.24-7.15 (m, 1H), 6.28-5.90 (m, 2H), 4.79-4.68 (m, 1H), 4.66-4.41 (m, 3H), 4.35-4.25 (m, 1H), 4.14-3.62 (m, 5H), 3.58-3.47 (m, 1H), 3.11-2.93 (m, 2H), 2.72-2.58 (m, 1H), 2.40-2.32 (m, 1H), 2.25-2.06 (m, 6H), 2.02-1.68 (m, 12H), 1.64-1.48 (m, 5H), 1.30-1.00 (m, 3H), 0.89-0.81 (m, 3H), 0.52-0.38 (m, 2H); 982.5 $[M + H]^+$ . |
| C96 | 1H NMR (400 MHz, DMSO-d6) δ (ppm) 8.98-8.58 (m, 1H), 8.38-8.14 (m, 1H), 8.13-7.83 (m, 2H), 7.60-7.47 (m, 1H), 7.41-7.07 (m, 5H), 6.27-5.89 (m, 2H), 4.87-4.40 (m, 5H), 4.36-4.24 (m, 1H), 4.20-3.46 (m, 6H), 3.06-2.91 (m, 1H), 2.75-2.57 (m, 2H), 2.48-1.42 (m, 22H), 1.34-1.13 (m, 3H), 0.95-0.70 (m, 3H), 0.59-0.29 (m, 2H); 982.5 $[M + H]^+$ . |

TABLE 1C-continued

| | |
|---|---|
| C97 | 1H NMR (400 MHz, DMSO-d6) δ (ppm) 8.88-8.62 (m, 1H), 8.37-8.12 (m, 1H), 8.11-7.82 (m, 2H), 7.59-7.43 (m, 1H), 7.40-7.08 (m, 5H), 6.33-5.82 (m, 2H), 4.81-4.34 (m, 5H), 4.34-4.20 (m, 1H), 4.17-4.07 (m, 1H), 4.05-3.88 (m, 2H), 3.86-3.47 (m, 3H), 3.07-2.89 (m, 1H), 2.75-2.57 (m, 2H), 2.46-2.08 (m, 5H), 2.05-1.39 (m, 17H), 1.32-0.98 (m, 3H), 0.93-0.72 (m, 3H), 0.60-0.29 (m, 2H); 1016.9 $[M + H]^+$ . |
| C98 | 1H NMR (400 MHz, DMSO-d6) δ (ppm) 8.85-8.74 (m, 1H), 8.27 (s, 1H), 8.11-8.01 (m, 2H), 7.65-7.57 (m, 1H), 7.42-7.26 (m, 6H), 7.24-7.11 (m, 4H), 6.30-6.04 (m, 2H), 4.78-4.65 (m, 1H), 4.50-4.38 (m, 3H), 4.34-4.25 (m, 1H), 4.21-4.16 (m, 1H), 4.15-4.06 (m, 2H), 3.99-3.89 (m, 1H), 3.87-3.67 (m, 3H), 3.59-3.48 (m, 1H), 2.93-2.81 (m, 1H), 2.48-2.43 (m, 1H), 2.41-2.31 (m, 2H), 2.29-2.16 (m, 2H), 2.14-1.36 (m, 15H), 1.29 (s, 3H), 1.18-1.09 (m, 3H), 0.94 (t, J = 6.9 Hz, 3H), 0.85-0.75 (m, 3H), 0.53-0.42 (m, 2H); 970.4 $[M + H]^+$ . |

TABLE 1C-continued

| | |
|---|---|
| C99 | 1H NMR (400 MHz, DMSO-d6) δ (ppm) 8.85-8.76 (m, 1H), 8.27 (s, 1H), 8.06 (d, J = 4.8 Hz, 2H), 7.60 (d, J = 7.2 Hz, 1H), 7.39-7.27 (m, 6H), 7.23-7.13 (m, 4H), 6.28-6.06 (m, 2H), 4.76-4.65 (m, 1H), 4.54-4.43 (m, 2H), 4.34-4.23 (m, 1H), 4.13 (t, J = 8.7 Hz, 1H), 3.97-3.89 (m, 1H), 3.85-3.70 (m, 3H), 3.59-3.49 (m, 1H), 3.08-2.99 (m, 1H), 2.89-2.79 (m, 1H), 2.63-2.53 (m, 1H), 2.37-1.90 (m, 10H), 1.88-1.38 (m, 11H), 1.13 (d, J = 7.0 Hz, 3H), 0.97 (t, J = 7.1 Hz, 3H), 0.85-0.74 (m, 3H), 0.52-0.39 (m, 2H); 1024.7 $[M + H]^+$ . |
| C100 | 1H NMR (400 MHz, DMSO-d6) δ (ppm) 8.82-8.75 (m, 1H), 8.27 (s, 1H), 8.09-8.03 (m, 2H), 7.63-7.57 (m, 1H), 7.38-7.27 (m, 6H), 7.24-7.14 (m, 4H), 6.30-6.04 (m, 2H), 4.78-4.67 (m, 1H), 4.50-4.42 (m, 1H), 4.33-4.25 (m, 1H), 4.16-4.06 (m, 1H), 3.95-3.67 (m, 4H), 3.58-3.48 (m, 1H), 3.07-2.97 (m, 1H), 2.48-2.09 (m, 9H), 2.04-1.92 (m, 3H), 1.84-1.39 (m, 12H), 1.16-1.08 (m, 3H), 0.96 (t, J = 7.0 Hz, 3H), 0.86-0.74 (m, 3H), 0.53-0.38 (m, 2H); 996.6 $[M + H]^+$ . |

TABLE 1C-continued

| | | |
|---|---|---|
| C101 | | 1H NMR (400 MHz, DMSO-d6) δ (ppm) 8.83-8.74 (m, 1H), 8.29-8.24 (m, 1H), 8.11-8.01 (m, 2H), 7.65-7.55 (m, 1H), 7.39-7.27 (m, 6H), 7.24-7.11 (m, 4H), 6.31-6.08 (m, 2H), 4.78-4.67 (m, 1H), 4.51-4.43 (m, 1H), 4.35-4.25 (m, 1H), 4.16-4.06 (m, 1H), 3.95-3.65 (m, 4H), 3.58-3.48 (m, 1H), 3.07-2.96 (m, 1H), 2.48-2.16 (m, 8H), 2.15-2.08 (m, 1H), 2.04-1.92 (m, 3H), 1.85-1.43 (m, 12H), 1.20-0.92 (m, 6H), 0.84-0.77 (m, 3H), 0.53-0.38 (m, 2H); 996.6 $[M + H]^+$ . |
| C102 | | 1H NMR (400 MHz, DMSO-d6) δ (ppm) 8.85-8.76 (m, 1H), 8.29-8.22 (m, 1H), 8.08-8.03 (m, 1H), 8.00-7.98 (m, 1H), 7.55-7.49 (m, 1H), 7.37-7.27 (m, 4H), 7.24-7.18 (m, 1H), 6.23-5.93 (m, 2H), 4.94-4.44 (m, 6H), 4.33-4.25 (m, 1H), 4.12 (t, J = 8.8 Hz, 1H), 3.83-3.47 (m, 3H), 3.05-2.90 (m, 1H), 2.65-2.55 (m, 1H), 2.41-2.30 (m, 2H), 2.28-2.10 (m, 4H), 2.05-1.47 (m, 21H), 1.26-1.17 (m, 3H), 0.55-0.40 (m, 2H); 962.5 $[M + H]^+$ . |

TABLE 1C-continued

| | |
|---|---|
| C103 | 1H NMR (400 MHz, DMSO-d6) δ (ppm) 9.06-8.65 (m, 1H), 8.26 (s, 1H), 8.12-7.96 (m, 2H), 7.56-7.49 (m, 1H), 7.39-7.27 (m, 4H), 7.25-7.19 (m, 1H), 6.29-5.89 (m, 2H), 5.02-4.71 (m, 3H), 4.68-4.34 (m, 4H), 4.21-4.07 (m, 1H), 3.93-3.75 (m, 1H), 3.74-3.48 (m, 3H), 2.84-2.54 (m, 5H), 2.33-1.51 (m, 17H), 1.31-1.24 (m, 1H), 1.20-1.10 (m, 6H), 1.09-0.96 (m, 2H), 0.64-0.42 (m, 2H); 950.5 [M+ H]+ |
| C104 | 1H NMR (400 MHz, DMSO-d6) δ (ppm) 9.88-9.41 (m, 1H), 8.95-8.74 (m, 1H), 8.27 (d, J = 5.1 Hz, 1H), 8.13-7.97 (m, 2H), 7.61 (d, J = 8.3 Hz, 1H), 7.41-7.26 (m, 6H), 7.25-7.13 (m, 4H), 6.29-6.08 (m, 2H), 5.04-4.73 (m, 2H), 4.64-4.41 (m, 2H), 4.23-4.03 (m, 1H), 3.90-3.64 (m, 4H), 3.62-3.02 (m, 3H), 2.81-2.54 (m, 5H), 2.49-1.46 (m, 17H), 1.21-1.04 (m, 3H), 0.90-0.70 (m, 6H), 0.63-0.40 (m, 2H); 958.7 $[M + H]^+$ . |
| C105 | 1H NMR (400 MHz, DMSO-d6) δ (ppm) 9.86-9.40 (m, 1H), 8.96-8.70 (m, 1H), 8.31-8.20 (m, 1H), 8.14-7.97 (m, 2H), 7.68-7.50 (m, 1H), 7.44-7.06 (m, 10H), 6.30-6.08 (m, 2H), 5.00-4.78 (m, 2H), 4.62-4.47 (m, 2H), 4.21-4.07 (m, 1H), 3.80-3.67 (m, 4H), 3.67-2.93 (m, 3H), 2.81-2.54 (m, 5H), 2.49-1.50 (m, 17H), 1.23-0.90 (m, 3H), 0.89-0.72 (m, 6H), 0.64-0.41 (m, 2H); 958.6 $[M + H]^+$ . |

TABLE 1C-continued

| | |
|---|---|
| C106 | 1H NMR (400 MHz, DMSO-d6) δ (ppm) 10.00-9.43 (m, 1H), 8.95-8.76 (m, 1H), 8.31-8.22 (m, 1H), 8.08-7.94 (m, 2H), 7.56-7.48 (m, 1H), 7.39-7.28 (m, 4H), 7.27-7.18 (m, 1H), 6.09-5.60 (m, 2H), 5.05-4.74 (m, 4H), 4.66-4.49 (m, 2H), 4.22-3.92 (m, 4H), 3.85-3.73 (m, 1H), 3.61-3.54 (m, 1H), 3.44-2.98 (m, 1H), 2.84-2.63 (m, 2H), 2.64-2.55 (m, 3H), 2.47-2.39 (m, 1H), 2.34-1.51 (m, 21H), 1.29-1.17 (m, 6H), 0.64-0.44 (m, 2H); 908.5 $[M + H]^+$. |
| C107 | 1H NMR (400 MHz, DMSO-d6) δ (ppm) 10.13-9.39 (m, 1H), 8.95-8.72 (m, 1H), 8.31-8.22 (m, 1H), 8.12-7.93 (m, 2H), 7.52 (t, J = 7.9 Hz, 1H), 7.40-7.30 (m, 4H), 7.27-7.18 (m, 1H), 6.11-5.48 (m, 2H), 5.02-4.77 (m, 3H), 4.62-4.48 (m, 2H), 4.22-4.05 (m,2H), 4.00-3.90 (m, 1H), 3.85-3.74 (m, 2H), 3.65-3.53 (m, 2H), 3.45-2.97 (m, 1H), 2.80-2.60 (m, 2H), 2.60-2.53 (m, 3H), 2.49-1.46 (m, 22H), 1.31-0.93 (m, 6H), 0.68-0.41 (m, 1H); 908.6 $[M + H]^+$. |

TABLE 1C-continued

| | | |
|---|---|---|
| C108 | | 1H NMR (400 MHz, DMSO-d6) δ (ppm) 9.73-9.14 (m, 1H), 8.92-8.77 (m, 1H), 8.27 (s, 1H), 8.13-8.02 (m, 2H), 7.62 (d, J = 8.3 Hz, 1H), 7.39-7.09 (m, 10H), 6.29-6.07 (m, 2H), 4.83-4.76 (m, 1H), 4.59-4.50 (m, 2H), 4.20-4.10 (m, 1H), 3.98-3.91 (m, 1H), 3.84-3.75 (m, 2H), 3.60-3.47 (m, 1H), 3.22-2.88 (m, 4H), 2.76-2.53 (m, 2H), 2.47-1.02 (m, 26H), 0.86-0.72 (m, 3H), 0.61-0.38 (m, 2H); 1009.4 $[M + H]^+$ . |
| C109 | | 1H NMR (400 MHz, DMSO-d6) δ (ppm) 8.93-8.79 (m, 1H), 8.33-8.20 (m, 1H), 8.13-8.01 (m, 2H), 7.67-7.56 (m, 1H), 7.39-7.09 (m, 10H), 6.30-6.08 (m, 2H), 4.86-4.73 (m, 1H), 4.61-4.47 (m, 2H), 4.20-4.07 (m, 1H), 4.01-3.80 (m, 4H), 3.79-3.65 (m, 2H), 3.63-3.45 (m, 1H), 3.21-3.10 (m, 1H), 3.08-2.84 (m, 2H), 2.77-2.54 (m, 2H), 2.46-0.92 (m, 24H), 0.85-0.76 (m, 3H), 0.62-0.36 (m, 2H); 1008.5 $[M + H]^+$ . |

TABLE 1C-continued

| | | |
|---|---|---|
| C110 | | 1H NMR (400 MHz, DMSO-d6) δ (ppm) 9.94-9.42 (m, 1H), 8.99-8.71 (m, 1H), 8.33-8.16 (m, 1H), 8.14-7.93 (m, 2H), 7.67-7.47 (m, 1H), 7.42-7.27 (m, 4H), 7.26-7.14 (m, 1H), 6.38-5.86 (m, 2H), 4.86-4.75 (m, 1H), 4.66-4.47 (m, 4H), 4.20-4.09 (m, 2H), 4.04-3.89 (m, 4H), 3.87-3.77 (m, 2H), 3.75-3.62 (m, 2H), 3.59-3.51 (m, 1H), 3.27-3.13 (m, 1H), 2.74-2.62 (m, 2H), 2.61-2.53 (m, 4H), 2.49-2.42 (m, 1H), 2.29-2.19 (m, 1H), 2.15-1.97 (m, 5H), 1.90-1.74 (m, 4H), 1.60-1.45 (m, 3H), 1.32-1.16 (m, 3H), 0.91-0.77 (m, 3H), 0.66-0.38 (m, 2H); 957.5 $[M + H]^+$ . |
| C111 | | 1H NMR (400 MHz, DMSO-d6) δ (ppm) 8.88-8.72 (m, 1H), 8.34-8.23 (m, 1H), 8.12-7.99 (m, 2H), 7.67-7.56 (m, 1H), 7.41-7.26 (m, 6H), 7.25-7.07 (m, 4H), 6.31-6.03 (m, 2H), 4.93-4.65 (m, 2H), 4.56-4.40 (m, 1H), 4.36-4.21 (m, 1H), 4.19-4.07 (m, 1H), 3.88-3.65 (m, 2H), 3.61-3.46 (m, 1H), 3.10-2.87 (m, 3H), 2.41-1.39 (m, 27H), 1.21-1.03 (m, 3H), 0.62-0.37 (m, 2H); 964.4 $[M + H]^+$ . |

TABLE 1C-continued

| | | |
|---|---|---|
| C112 | | 1H NMR (400 MHz, DMSO-d6) δ (ppm) 8.80 (t, J = 7.1 Hz, 1H), 8.30-8.24 (m, 1H), 8.10-8.03 (m, 2H), 7.63-7.57 (m, 1H), 7.40-7.27 (m, 6H), 7.24-7.10 (m, 4H), 6.34-6.00 (m, 2H), 4.87-4.65 (m, 2H), 4.47 (t, J = 8.4 Hz, 1H), 4.33-4.25 (m, 1H), 4.12 (t, J = 8.5 Hz, 1H), 3.88-3.48 (m, 3H), 3.07-2.89 (m, 3H), 2.38-2.29 (m, 2H), 2.26-2.11 (m, 5H), 2.05-1.47 (m, 20H), 1.20-0.87 (m, 3H), 0.55-0.42 (m, 2H); 963.6 $[M + H]^+$ . |
| C113 | | 1H NMR (400 MHz, DMSO-d6) δ (ppm) 8.85-8.74 (m, 1H), 8.27 (s, 1H), 8.09-8.02 (m, 2H), 7.63-7.56 (m, 1H), 7.39-7.27 (m, 6H), 7.24-7.12 (m, 4H), 6.28-6.05 (m, 2H), 4.88-4.67 (m, 2H), 4.51-4.44 (m, 1H), 4.34-4.25 (m, 1H), 4.16-4.07 (m, 1H), 3.86-3.68 (m, 2H), 3.59-3.48 (m, 1H), 3.06-2.94 (m, 2H), 2.84-2.70 (m, 1H), 2.32-1.49 (m, 27H), 1.18-1.08 (m, 3H), 0.52-0.38 (m, 2H); 1006.7 $[M + H]^+$ . |

TABLE 1C-continued

| | |
|---|---|
| C114 | 1H NMR (400 MHz, DMSO-d6) δ (ppm) 8.80 (d, J = 7.7 Hz, 1H), 8.27 (d, J = 3.9 Hz, 1H), 8.09-8.03 (m, 1H), 8.00 (s, 1H), 7.58-7.47 (m, 1H), 7.38-7.26 (m, 4H), 7.24-7.18 (m, 1H), 6.24-5.92 (m, 2H), 4.77-4.42 (m, 4H), 4.35-4.24 (m, 1H), 4.18-4.06 (m, 1H), 4.04-3.62 (m, 4H), 3.59-3.49 (m, 1H), 3.08-2.89 (m, 2H), 2.84-2.70 (m, 1H), 2.39-2.18 (m, 3H), 2.16-2.04 (m, 3H), 2.03-1.89 (m, 6H), 1.87-1.44 (m, 11H), 1.29-1.19 (m, 3H), 0.90-0.76 (m, 3H), 0.54-0.33 (m, 2H); 1000.6 $[M + H]^+$. |
| C115 | 1H NMR (400 MHz, DMSO-d6) δ (ppm) 8.96-8.68 (m, 1H), 8.28 (s, 1H), 8.15-8.03 (m, 2H), 7.62 (d, J = 8.4 Hz, 1H), 7.42-7.27 (m, 6H), 7.24-7.15 (m, 4H), 6.28-6.04 (m, 2H), 4.88-4.74 (m, 1H), 4.61-4.43 (m, 2H), 4.18-4.07 (m, 1H), 3.97-3.85 (m, 2H), 3.76-3.66 (m, 2H), 3.59-3.48 (m, 1H), 3.22-2.93 (m, 2H), 2.80-2.55 (m, 3H), 2.47-2.42 (m, 1H), 2.41-2.29 (m, 2H), 2.26-2.18 (m, 1H), 2.15-1.68 (m, 14H), 1.59-1.52 (m, 1H), 1.52-1.44 (m, 2H), 0.94 (d, J = 7.0 Hz, 3H), 0.81 (t, J = 7.4 Hz, 3H), 0.58-0.42 (m, 2H); 982.5 $[M + H]^+$. |

TABLE 1C-continued

| | |
|---|---|
| C116 | 1H NMR (400 MHz, DMSO-d6) δ (ppm) 8.85-8.71 (m, 1H), 8.29-8.18 (m, 1H), 8.07-7.91 (m, 2H), 7.50 (d, J = 8.6 Hz, 1H), 7.41-7.27 (m, 4H), 7.25-7.18 (m, 1H), 6.10-5.61 (m, 2H), 4.79-4.63 (m, 1H), 4.58-4.42 (m, 2H), 4.36-4.24 (m, 1H), 4.12 (t, J = 8.5 Hz, 1H), 4.05-3.94 (m, 1H), 3.92-3.85 (m, 1H), 3.84-3.70 (m, 2H), 3.61-3.48 (m, 1H), 3.05-2.94 (m, 1H), 2.73-2.58 (m, 2H), 2.46-2.29 (m, 2H), 2.27-2.18 (m, 1H), 2.17-2.09 (m, 2H), 2.03-1.40 (m, 18H), 1.29-1.16 (m, 3H), 0.89-0.55 (m, 7H), 0.53-0.39 (m, 2H); 975.3 $[M + H]^+$ . |
| C117 | 1H NMR (400 MHz, DMSO-d6) δ (ppm) 8.82-8.73 (m, 1H), 8.28-8.21 (m, 1H), 8.06-7.92 (m, 2H), 7.50 (d, J = 8.4 Hz, 1H), 7.39-7.26 (m, 4H), 7.25-7.18 (m, 1H), 6.08-5.61 (m, 2H), 4.76-4.64 (m, 1H), 4.48 (t, J = 8.5 Hz, 1H), 4.35-4.21 (m, 1H), 4.12 (t, J = 8.5 Hz, 1H), 4.04-3.94 (m, 1H), 3.92-3.85 (m, 1H), 3.84-3.70 (m, 2H), 3.61-3.47 (m, 1H), 3.10-2.89 (m, 2H), 2.85-2.69 (m, 1H), 2.42-2.16 (m, 3H), 2.13-2.03 (m, 3H), 2.02-1.90 (m, 6H), 1.87-1.41 (m, 11H), 1.30-1.18 (m, 3H), 0.92-0.56 (m, 7H), 0.52-0.36 (m, 2H); 958.5 $[M + H]^+$ . |

TABLE 1C-continued

| | |
|---|---|
| C118 | 1H NMR (400 MHz, DMSO-d6) δ (ppm) 8.94-8.71 (m, 1H), 8.32-8.22 (m, 1H), 8.11-8.01 (m, 2H), 7.64-7.56 (m, 1H), 7.41-7.27 (m, 6H), 7.24-7.10 (m, 4H), 6.30-6.04 (m, 2H), 4.89-4.69 (m, 2H), 4.61-4.25 (m, 3H), 4.16-4.08 (m, 1H), 3.84-3.51 (m, 3H), 2.80-2.60 (m, 2H), 2.44-1.50 (m, 20H), 1.21-1.02 (m, 8H), 0.96-0.86 (m, 2H), 0.55-0.41 (m, 2H); 1011.2 $[M + H]^+$ . |
| C119 | 1H NMR (400 MHz, DMSO-d6) δ (ppm) 8.89-8.68 (m, 1H), 8.27 (d, J = 3.8 Hz, 1H), 8.13-8.00 (m, 2H), 7.60 (t, J = 7.5 Hz, 1H), 7.40-7.26 (m, 6H), 7.24-7.08 (m, 4H), 6.34-6.04 (m, 2H), 4.77-4.62 (m, 1H), 4.57-4.41 (m, 2H), 4.34-4.22 (m, 1H), 4.12 (t, J = 8.4 Hz, 1H), 3.96-3.66 (m, 4H), 3.60-3.47 (m, 1H), 3.11-2.98 (m, 1H), 2.92-2.79 (m, 1H), 2.60-2.54 (m, 1H), 2.47-2.40 (m, 1H), 2.34-1.41 (m, 21H), 1.17 (d, J = 7.2 Hz, 1H), 1.01-0.92 (m, 4H), 0.81 (t, J = 7.4 Hz, 3H), 0.53-0.33 (m, 2H); 1024.8 $[M + H]^+$ . |

TABLE 1C-continued

| | |
|---|---|
| C120 | 1H NMR (400 MHz, DMSO-d6) δ (ppm) 8.77 (d, J = 7.6 Hz, 1H), 8.26 (s, 1H), 8.09-8.00 (m, 2H), 7.59 (d, J = 8.5 Hz, 1H), 7.38-7.27 (m, 6H), 7.24-7.11 (m, 4H), 6.31-6.13 (m, 2H), 4.85-4.71 (m, 1H), 4.47 (t, J = 8.5 Hz, 1H), 4.36-4.25 (m, 1H), 4.16-4.07 (m, 1H), 3.95-3.82 (m, 3H), 3.73 (t, J = 9.8 Hz, 1H), 3.58-3.48 (m, 1H), 3.03-2.86 (m, 1H), 2.47-2.07 (m, 10H), 2.02-1.44 (m, 15H), 1.17 (d, J = 7.1 Hz, 3H), 0.81 (t, J = 7.4 Hz, 3H), 0.53-0.39 (m, 2H); 982.5 $[M + H]^+$ . |
| C121 | 1H NMR (400 MHz, DMSO-d6) δ (ppm) 10.01-9.50 (m, 1H), 8.95-8.75 (m, 1H), 8.30-8.25 (m, 1H), 8.12-8.04 (m, 2H), 7.62 (d, J = 8.5 Hz, 1H), 7.41 7.27 (m, 6H), 7.25-7.12 (m, 4H), 6.31-6.02 (m, 2H), 4.88-4.48 (m, 5H), 4.21-4.08 (m, 1H), 3.76-3.73 (m, 1H), 3.67-3.60 (m, 1H), 3.57-3.50 (m, 1H), 3.19-3.04 (m, 0.5H), 2.85-2.75 (m, 1H), 2.74-2.63 (m, 1.5H), 2.62-2.57 (m, 3H), 2.57-2.51 (m, 1H), 2.50-2.40 (m, 2H), 2.29-1.71 (m, 12H), 1.70-1.47 (m, 2H), 1.15-1.01 (m, 9H), 0.61 z-0.43 (m, 2H); 1010.6 [M+ H]+ |

TABLE 1C-continued

| | |
|---|---|
| C122 | 1H NMR (400 MHz, DMSO-d6) δ (ppm) 8.87-8.72 (m, 1H), 8.28-8.19 (m, 1H), 8.08-7.91 (m, 2H), 7.54-7.46 (m, 1H), 7.38-7.27 (m, 4H), 7.25-7.16 (m, 1H), 6.07-5.59 (m, 2H), 4.80-4.63 (m, 1H), 4.59-4.41 (m, 2H), 4.35-4.23 (m, 1H), 4.17-4.05 (m, 1H), 3.99-3.49 (m, 6H), 3.07-2.92 (m, 1H), 2.68-2.62 (m, 1H), 2.45-1.46 (m, 22H), 1.29-1.18 (m, 3H), 0.88-0.56 (m, 10H), 0.53-0.35 (m, 2H); 989.2 $[M+H]^+$. |
| C123 | 1H NMR (400 MHz, DMSO-d6) δ (ppm) 8.83-8.73 (m, 1H), 8.29-8.19 (m, 1H), 8.06-7.94 (m, 2H), 7.54-7.46 (m, 1H), 7.36-7.28 (m, 4H), 7.24-7.16 (m, 1H), 6.07-5.85 (m, 1H), 5.70-5.49 (m, 1H), 4.92-4.66 (m, 2H), 4.57-4.44 (m, 2H), 4.30 (d, J = 5.3 Hz, 1H), 4.15-3.94 (m, 3H), 3.76-3.49 (m, 3H), 3.06-2.93 (m, 1H), 2.65 (s, 2H), 2.45-2.12 (m, 7H), 2.03-1.48 (m, 19H), 1.26-1.15 (m, 6H), 0.53-0.39 (m, 2H); 974.6 $[M+H]^+$. |

TABLE 1C-continued

| | |
|---|---|
| C124 | 1H NMR (400 MHz, DMSO-d6) δ (ppm) 8.88-8.72 (m, 1H), 8.32-8.21 (m, 1H), 8.11-8.01 (m, 2H), 7.65-7.53 (m, 1H), 7.45-7.25 (m, 6H), 7.25-7.06 (m, 4H), 6.38-5.99 (m, 2H), 4.94-4.79 (m, 1H), 4.77-4.63 (m, 1H), 4.60-4.39 (m, 2H), 4.35-4.21 (m, 1H), 4.17-4.04 (m, 1H), 3.83-3.65 (m, 2H), 3.60-3.44 (m, 1H), 3.08-2.92 (m, 1H), 2.73-2.56 (m, 2H), 2.47-2.30 (m, 2H), 2.27-2.09 (m, 5H), 2.01-1.50 (m, 19H), 1.16-1.06 (m, 3H), 0.57-0.34 (m, 2H); 1022.4 $[M + H]^+$ . |
| C125 | 1H NMR (400 MHz, DMSO-d6) δ (ppm) 8.80 (d, J = 7.7 Hz, 1H), 8.27 (s, 1H), 8.11-8.01 (m, 2H), 7.61 (d, J = 8.6 Hz, 1H), 7.41-7.10 (m, 10H), 6.26-6.05 (m, 2H), 4.80-4.63 (m, 2H), 4.58-4.42 (m, 2H), 4.35-4.23 (m, 1H), 4.19-4.06 (m, 1H), 3.85-3.69 (m, 2H), 3.61-3.47 (m, 1H), 3.06-2.93 (m, 1H), 2.72-2.58 (m, 2H), 2.47-2.29 (m, 2H), 2.28-2.07 (m, 5H), 2.03-1.92 (m, 6H), 1.91-1.75 (m, 5H), 1.74-1.44 (m, 8H), 1.12 (d, J = 7.1 Hz, 3H), 0.57-0.37 (m, 2H); 1022.5 $[M + H]^+$ . |

TABLE 1C-continued

| | |
|---|---|
| C126 | 1H NMR (400 MHz, DMSO-d6) δ (ppm) 8.86-8.78 (m, 1H), 8.29 (s, 1H), 8.12-8.04 (m, 2H), 7.65-7.58 (m, 1H), 7.41-7.30 (m, 6H), 7.26-7.14 (m, 4H), 6.32-6.04 (m, 2H), 4.79-4.68 (m, 1H), 4.60-4.45 (m, 2H), 4.37-4.26 (m, 1H), 4.19-4.09 (m, 1H), 4.04-3.68 (m, 4H), 3.62-3.49 (m, 1H), 3.42-3.37 (m, 1H), 3.20-3.10 (m, 3H), 3.07-2.98 (m, 1H), 2.73-2.61 (m, 2H), 2.47-2.32 (m, 3H), 2.30-2.21 (m, 1H), 2.20-2.11 (m, 2H), 2.04-1.95 (m, 6H), 1.91-1.32 (m, 11H), 0.89-0.71 (m, 3H), 0.57-0.41 (m, 2H); 1041.2 $[M + H]^+$ . |
| C127 | 1H NMR (400 MHz, DMSO-d6) δ (ppm) 8.76 (d, J = 7.7 Hz, 1H), 8.26 (s, 1H), 8.11-7.98 (m, 2H), 7.62-7.53 (m, 1H), 7.37-7.26 (m, 6H), 7.24-7.12 (m, 4H), 6.21-5.97 (m, 1H), 5.95-5.78 (m, 1H), 4.71 (t, J = 8.6 Hz, 1H), 4.57-4.41 (m, 2H), 4.37-4.21 (m, 1H), 4.12 (t, J = 8.6 Hz, 1H), 3.95-3.81 (m, 2H), 3.73 (t, J = 9.9 Hz, 1H), 3.60-3.47 (m, 1H), 3.06-2.95 (m, 1H), 2.72-2.58 (m, 2H), 2.45-2.10 (m, 5H), 2.05-1.40 (m, 18H), 1.26-1.17 (m, 5H), 0.84-0.77 (m, 3H), 0.55-0.38 (m, 2H); 1024.6 [M+ H]+ |

TABLE 1C-continued

| | | |
|---|---|---|
| C128 | | 1H NMR (400 MHz, DMSO-d6) δ (ppm) 8.89-8.69 (m, 1H), 8.25 (s, 1H), 8.13-7.92 (m, 2H), 7.60-7.45 (m, 1H), 7.39-7.12 (m, 11H), 7.11-6.92 (m, 4H), 6.40-5.95 (m, 2H), 4.77-4.66 (m, 1H), 4.59-4.42 (m, 2H), 4.35-4.23 (m, 1H), 4.18-4.07 (m, 1H), 3.99-3.86 (m, 1H), 3.85-3.78 (m, 1H), 3.76-3.46 (m, 3H), 3.06-2.94 (m, 1H), 2.91-2.77 (m, 1H), 2.75-2.63 (m, 2H), 2.44-2.28 (m, 2H), 2.27-2.06 (m, 3H), 1.92-1.17 (m, 18H), 0.74-0.58 (m, 3H), 0.53-0.37 (m, 2H); 1086.9 $[M + H]^+$ . |
| C129 | | 1H NMR (400 MHz, DMSO-d6) δ (ppm) 8.82-8.70 (m, 1H), 8.33-8.21 (m, 1H), 8.10-8.01 (m, 2H), 7.65-7.55 (m, 1H), 7.37-7.28 (m, 6H), 7.24-7.14 (m, 4H), 6.26-6.05 (m, 2H), 4.83-4.66 (m, 1H), 4.52-4.40 (m, 1H), 4.34-4.22 (m, 1H), 4.17-4.06 (m, 1H), 3.84-3.63 (m, 3H), 3.60-3.47 (m, 2H), 3.05-2.89 (m, 2H), 2.47-2.16 (m, 8H), 2.12-2.07 (m, 3H), 2.04-1.93 (m, 3H), 1.86-1.53 (m, 11H), 1.18-1.07 (m, 3H), 0.84-0.71 (m, 6H), 0.55-0.44 (m, 2H); 1023.0 $[M + H]^+$ . |

TABLE 1C-continued

| | |
|---|---|
| C130 | 1H NMR (400 MHz, DMSO-d6) δ (ppm) 8.80-8.69 (m, 1H), 8.27 (s, 1H), 8.09-8.00 (m, 2H), 7.63-7.54 (m, 1H), 7.39-7.26 (m, 6H), 7.24-7.12 (m, 4H), 6.27-5.95 (m, 3H), 4.80-4.68 (m, 1H), 4.47 (t, J = 8.5 Hz, 1H), 4.34-4.23 (m, 1H), 4.11 (t, J = 8.6 Hz, 1H), 3.83-3.46 (m, 6H), 3.00-2.90 (m, 1H), 2.70-2.59 (m, 1H), 2.38-2.31 (m, 2H), 2.26-2.18 (m, 1H), 2.15-2.07 (m, 4H), 2.05-1.92 (m, 5H), 1.85-1.63 (m, 10H), 1.60-1.52 (m, 2H), 1.19-1.07 (m, 3H), 0.86-0.71 (m, 6H), 0.54-0.40 (m, 2H); 1004.7 $[M + H]^+$ . |
| C131 | 1H NMR (400 MHz, DMSO-d6) δ (ppm) 8.81-8.71 (m, 1H), 8.31-8.21 (m, 1H), 8.10-8.01 (m, 2H), 7.65-7.55 (m, 1H), 7.41-7.26 (m, 6H), 7.25-7.09 (m, 4H), 6.29-6.04 (m, 2H), 4.84-4.68 (m, 1H), 4.54-4.41 (m, 1H), 4.36-4.21 (m, 1H), 4.16-4.06 (m, 1H), 3.89-3.62 (m, 3H), 3.61-3.48 (m, 2H), 3.00-2.86 (m, 1H), 2.41-2.29 (m, 2H), 2.27-2.17 (m, 1H), 2.15-2.06 (m, 4H), 2.05-1.47 (m, 15H), 1.17-1.08 (m, 3H), 0.90-0.83 (m, 2H), 0.81-0.70 (m, 8H), 0.56-0.36 (m, 2H); 1022.4 $[M + H]^+$ . |

TABLE 1C-continued

| | |
|---|---|
| C132 | 1H NMR (400 MHz, DMSO-d6) δ (ppm) 8.82-8.68 (m, 1H), 8.26 (s, 1H), 8.12-7.95 (m, 2H), 7.60 (d, J = 8.0 Hz, 1H), 7.35 (t, J = 7.9 Hz, 2H), 7.17 (t, J = 8.7 Hz, 3H), 6.29-6.18 (m, 1H), 6.15-6.05 (m, 1H), 4.70 (t, J = 8.5 Hz, 1H), 4.55-4.39 (m, 2H), 4.36-4.20 (m, 1H), 3.90-3.53 (m, 5H), 3.03-2.90 (m, 1H), 2.70-2.56 (m, 2H), 2.42-2.34 (m, 1H), 2.31-2.24 (m, 1H), 2.14-2.05 (m, 1H), 1.99-1.51 (m, 20H), 1.20-1.08 (m, 3H), 0.88-0.75 (m, 6H), 0.44-0.29 (m, 2H); 948.4 $[M + H]^+$ . |
| C133 | 1H NMR (400 MHz, DMSO-d6) δ (ppm) 8.81-8.70 (m, 1H), 8.27 (s, 1H), 8.13-7.99 (m, 2H), 7.60 (d, J = 7.7 Hz, 1H), 7.41-7.10 (m, 10H), 6.30-6.04 (m, 2H), 4.86-4.67 (m, 1H), 4.55-4.41 (m, 1H), 4.37-4.23 (m, 1H), 4.20-4.02 (m, 3H), 3.86-3.49 (m, 5H), 3.03-2.86 (m, 1H), 2.48-1.48 (m, 22H), 1.21-1.07 (m, 3H), 0.86-0.74 (m, 6H), 0.57-0.38 (m, 2H); 1012.5 $[M + H]^+$ . |

TABLE 1C-continued

| | |
|---|---|
| C134 | 1H NMR (400 MHz, DMSO-d6) δ (ppm) 8.78 (d, J = 7.4 Hz, 1H), 8.27 (s, 1H), 8.09-8.00 (m, 2H), 7.60 (d, J = 8.7 Hz, 1H), 7.40-7.25 (m, 6H), 7.23-7.12 (m, 4H), 6.27-6.03 (m, 2H), 4.76-4.62 (m, 1H), 4.47 (t, J = 8.6 Hz, 1H), 4.35-4.23 (m, 1H), 4.12 (t, J = 8.8 Hz, 1H), 3.89-3.62 (m, 3H), 3.60-3.48 (m, 2H), 3.06-2.92 (m, 2H), 2.87-2.70 (m, 1H), 2.37-2.15 (m, 3H), 2.15-1.91 (m, 9H), 1.85-1.45 (m, 10H), 1.13 (d, J = 7.1 Hz, 3H), 0.77 (d, J = 6.7 Hz, 6H), 0.55-0.36 (m, 2H); 1008.4 $[M + H]^+$ . |
| C135 | 1H NMR (400 MHz, DMSO-d6) δ (ppm) 8.85-8.67 (m, 1H), 8.34-8.18 (m, 1H), 8.12-7.99 (m, 2H), 7.68-7.53 (m, 1H), 7.39-7.14 (m, 10H), 6.32-6.07 (m, 2H), 4.89-4.69 (m, 1H), 4.56-4.40 (m, 1H), 4.36-4.21 (m, 1H), 4.16-4.04 (m, 1H), 3.85-3.67 (m, 4H), 3.58-3.44 (m, 1H), 3.01-2.85 (m, 1H), 2.46-2.17 (m, 7H), 2.14-2.08 (m, 3H), 2.05-1.95 (m, 3H), 1.87-1.52 (m, 11H), 1.19-1.07 (m, 3H), 0.89-0.75 (m, 6H), 0.54-0.37 (m, 2H); 996.4 $[M + H]^+$ . |

TABLE 1C-continued

| | |
|---|---|
| C136 | 1H NMR (400 MHz, DMSO-d6) δ (ppm) 8.77 (d, J = 7.8 Hz, 1H), 8.27 (s, 1H), 8.10-8.00 (m, 2H), 7.60 (d, J = 8.4 Hz, 1H), 7.40-7.25 (m, 6H), 7.24-7.11 (m, 4H), 6.27-6.02 (m, 2H), 4.86-4.72 (m, 1H), 4.47 (t, J = 8.6 Hz, 1H), 4.36-4.25 (m, 1H), 4.16-4.05 (m, 1H), 3.90-3.45 (m, 5H), 3.01-2.87 (m, 1H), 2.44-2.17 (m, 6H), 2.12 (s, 3H), 2.10-1.90 (m, 4H), 1.87-1.51 (m, 11H), 1.13 (d, J = 7.1 Hz, 3H), 0.77 (d, J = 6.7 Hz, 6H), 0.53-0.40 (m, 2H); 996.5 $[M + H]^+$ . |
| C137 | 1H NMR (400 MHz, DMSO-d6) δ (ppm) 8.82-8.74 (m, 1H), 8.28 (s, 1H), 8.10-8.01 (m, 2H), 7.64-7.55 (m, 1H), 7.40-7.27 (m, 6H), 7.24-7.13 (m, 4H), 6.27-6.05 (m, 2H), 4.80-4.72 (m, 1H), 4.50-4.41 (m, 1H), 4.36-4.27 (m, 1H), 4.14-4.07 (m, 1H), 3.97-3.67 (m, 5H), 3.58-3.46 (m, 4H), 3.01-2.91 (m, 1H), 2.46-2.31 (m, 2H), 2.26-1.64 (m, 16H), 1.60-1.37 (m, 5H), 1.16-1.09 (m, 3H), 0.87-0.74 (m, 3H), 0.52-0.39 (m, 2H); 996.5 $[M + H]^+$ . |

TABLE 1C-continued

| | | |
|---|---|---|
| C138 | | 1H NMR (400 MHz, DMSO-d6) δ (ppm) 8.80-8.71 (m, 1H), 8.26 (s, 1H), 8.11-8.00 (m, 2H), 7.60 (d, J = 8.5 Hz, 1H), 7.39-7.27 (m, 6H), 7.23-7.12 (m, 4H), 6.25-5.93 (m, 3H), 4.82-4.69 (m, 1H), 4.47 (t, J = 8.4 Hz, 1H), 4.35-4.23 (m, 1H), 4.11 (t, J = 8.6 Hz, 1H), 3.97-3.67 (m, 4H), 3.59-3.46 (m, 1H), 3.01-2.79 (m, 1H), 2.75-2.57 (m, 1H), 2.37-1.34 (m, 26H), 1.13 (d, J = 7.1 Hz, 3H), 0.84-0.75 (m, 3H), 0.54-0.43 (m, 2H); 990.4 $[M + H]^+$ . |
| C139 | | 1H NMR (400 MHz, DMSO-d6) δ (ppm) 8.80-8.72 (m, 1H), 8.27 (s, 1H), 8.09-8.02 (m, 2H), 7.64-7.56 (m, 1H), 7.41-7.26 (m, 6H), 7.25-7.11 (m, 4H), 6.29-6.05 (m, 2H), 4.83-4.68 (m, 1H), 4.51-4.39 (m, 1H), 4.35-4.24 (m, 1H), 4.15-4.06 (m, 1H), 3.99-3.87 (m, 1H), 3.87-3.67 (m, 3H), 3.60-3.47 (m, 1H), 3.02-2.87 (m, 1H), 2.61-2.51 (m, 1H), 2.42-2.30 (m, 2H), 2.27-2.17 (m, 1H), 2.15-2.06 (m, 4H), 2.03-1.91 (m, 3H), 1.89-1.62 (m, 8H), 1.60-1.47 (m, 3H), 1.47-1.36 (m, 1H), 1.17-1.09 (m, 3H), 0.90-0.71 (m, 7H), 0.56-0.40 (m, 2H); 1008.6 $[M + H]^+$ . |

TABLE 1C-continued

| | |
|---|---|
| C140 | 1H NMR (400 MHz, DMSO-d6) δ (ppm) 8.82-8.69 (m, 1H), 8.27 (s, 1H), 8.12-8.00 (m, 2H), 7.61 (d, J = 8.6 Hz, 1H), 7.40-7.12 (m, 10H), 6.31-5.99 (m, 2H), 4.87-4.66 (m, 1H), 4.55-4.40 (m, 1H), 4.37-4.23 (m, 1H), 4.20-3.99 (m, 3H), 3.92-3.64 (m, 4H), 3.58-3.47 (m, 1H), 3.02-2.89 (m, 1H), 2.49-2.43 (m, 1H), 2.41-2.30 (m, 2H), 2.26-2.18 (m, 1H), 2.17-2.06 (m, 4H), 2.05-1.93 (m, 3H), 1.89-1.51 (m, 10H), 1.47-1.36 (m, 2H), 1.13 (d, J = 7.1 Hz, 3H), 0.83-0.71 (m, 3H), 0.62-0.33 (m, 2H); 998.3 $[M + H]^+$ . |
| C141 | 1H NMR (400 MHz, DMSO-d6) δ (ppm) 8.86-8.66 (m, 1H), 8.27 (s, 1H), 8.17-7.95 (m, 2H), 7.60 (d, J = 8.3 Hz, 1H), 7.40-7.26 (m, 6H), 7.24-7.14 (m, 4H), 6.39-6.05 (m, 2H), 4.84-4.69 (m, 1H), 4.58-4.40 (m, 1H), 4.37-4.24 (m, 1H), 4.22-4.01 (m, 3H), 4.01-3.85 (m, 2H), 3.81-3.65 (m, 2H), 3.64-3.42 (m, 1H), 3.05-2.83 (m, 1H), 2.48-2.41 (m, 1H), 2.41-2.30 (m, 2H), 2.27-2.17 (m, 1H), 2.16-2.05 (m, 4H), 2.04-1.92 (m, 3H), 1.90-1.62 (m, 8H), 1.60-1.46 (m, 4H), 1.13 (d, J = 7.0 Hz, 3H), 0.83 (t, J = 7.4 Hz, 3H), 0.58-0.39 (m, 2H); 998.3 $[M + H]^+$ . |

TABLE 1C-continued

| | | |
|---|---|---|
| C142 | | 1H NMR (400 MHz, DMSO-d6) δ (ppm) 8.82-8.75 (m, 1H), 8.26 (s, 1H), 8.09-8.03 (m, 2H), 7.60 (d, J = 7.3 Hz, 1H), 7.40-7.26 (m, 6H), 7.22-7.11 (m, 4H), 6.27-6.18 (m, 1H), 6.15-6.05 (m, 1H), 4.76-4.68 (m, 1H), 4.48 (t, J = 8.4 Hz, 1H), 4.34-4.24 (m, 1H), 4.12 (t, J = 8.6 Hz, 1H), 3.97-3.90 (m, 1H), 3.85-3.70 (m, 3H), 3.59-3.49 (m, 1H), 3.12-2.93 (m, 2H), 2.39-2.32 (m, 1H), 2.26-2.18 (m, 2H), 2.16-1.93 (m, 11H), 1.88-1.81 (m, 1H), 1.76-1.37 (m, 10H), 1.13 (d, J = 7.0 Hz, 3H), 0.85-0.75 (m, 3H), 0.53-0.41 (m, 2H); 976.5 $[M + H]^+$ . |
| C143 | | 1H NMR (400 MHz, DMSO-d6) δ (ppm) 8.96-8.69 (m, 1H), 8.39-8.19 (m, 1H), 8.14-8.00 (m, 2H), 7.67-7.55 (m, 1H), 7.41-7.28 (m, 6H), 7.24-7.10 (m, 4H), 6.30-6.04 (m, 2H), 4.90-4.73 (m, 1H), 4.63-4.42 (m, 2H), 4.21-4.06 (m, 1H), 3.99-3.85 (m, 2H), 3.78-3.71 (m, 2H), 3.58-3.52 (m, 3H), 2.75-2.60 (m, 3H), 2.48-2.40 (m, 1H), 2.40-2.15 (m, 5H), 2.15-1.59 (m, 13H), 1.59-1.30 (m, 3H), 1.20-1.06 (m, 3H), 0.87-0.72 (m, 3H), 0.60-0.37 (m, 2H); 976.6 $[M + H]^+$ . |

TABLE 1C-continued

| | |
|---|---|
| C144 | 1H NMR (400 MHz, DMSO-d6) δ (ppm) 8.84-8.73 (m, 1H), 8.31-8.23 (m, 1H), 8.11-8.01 (m, 2H), 7.65-7.55 (m, 1H), 7.39-7.12 (m, 10H), 6.31-6.03 (m, 2H), 4.84-4.72 (m, 1H), 4.53-4.41 (m, 1H), 4.39-4.27 (m, 1H), 4.16-4.05 (m, 1H), 3.99-3.68 (m, 4H), 3.58-3.49 (m, 1H), 3.16-2.84 (m, 1H), 2.47-1.31 (m, 25H), 1.19-1.06 (m, 3H), 0.87-0.73 (m, 3H), 0.54-0.38 (m, 2H); 983.6 $[M + H]^+$ . |
| C145 | 1H NMR (400 MHz, DMSO-d6) δ (ppm) 8.74 (d, J = 7.2 Hz, 1H), 8.28 (s, 1H), 8.11-8.02 (m, 2H), 7.60 (d, J = 8.5 Hz, 1H), 7.41 7.30 (m, 6H), 7.24-7.16 (m, 4H), 6.28-6.11 (m, 2H), 4.99-4.91 (m, 1H), 4.49 (t, J = 8.2 Hz, 1H), 4.37-4.25 (m, 1H), 4.19-4.08 (m, 1H), 4.00-3.88 (m, 2H), 3.82-3.72 (m, 2H), 3.64-3.50 (m, 5H), 2.85-2.72 (m, 1H), 2.44-2.33 (m, 3H), 2.26-2.20 (m, 1H), 2.12-1.50 (m, 16H), 1.13 (d, J = 7.0 Hz, 3H), 0.83 (t, J = 7.4 Hz, 3H), 0.56-0.40 (m, 2H); 928.6 $[M + H]^+$ . |
| C146 | 1H NMR (400 MHz, DMSO-d6) δ (ppm) 8.83-8.69 (m, 1H), 8.27 (s, 1H), 8.13-7.97 (m, 2H), 7.67-7.50 (m, 1H), 7.44-7.05 (m, 10H), 6.30-6.01 (m, 2H), 4.81-4.69 (m, 1H), 4.55-4.04 (m, 7H), 3.98-3.66 (m, 4H), 3.56-3.50 (m, 1H), 2.88-2.79 (m, 1H), 2.40-2.31 (m, 1H), 2.24-2.17 (m, 1H), 2.12-1.35 (m, 18H), 1.28 (s, 3H), 1.26-1.20 (m, 1H), 1.18-1.07 (m, 3H), 0.85-0.74 (m, 3H), 0.56-0.35 (m, 2H); 956.5 $[M + H]^+$ . |

TABLE 1C-continued

| | |
|---|---|
| C147 | 1H NMR (400 MHz, DMSO-d6) δ (ppm) 8.81-8.74 (m, 1H), 8.27 (s, 1H), 8.10-8.02 (m, 2H), 7.65-7.56 (m, 1H), 7.40-7.26 (m, 6H), 7.24-7.12 (m, 4H), 6.28-6.05 (m, 2H), 4.78-4.64 (m, 1H), 4.59-4.50 (m, 2H), 4.49-4.38 (m, 2H), 4.38-4.33 (m, 1H), 4.33-4.24 (m, 1H), 4.17-4.06 (m, 1H), 3.99-3.86 (m, 1H), 3.85-3.68 (m, 4H), 3.59-3.49 (m, 1H), 2.89-2.76 (m, 1H), 2.40-2.30 (m, 1H), 2.27-2.16 (m, 1H), 2.15-2.07 (m, 1H), 2.04-1.99 (m, 1H), 1.96 (s, 4H), 1.86-1.68 (m, 3H), 1.65-1.55 (m, 3H), 1.54-1.37 (m, 3H), 1.23 (s, 2H), 1.18-1.08 (m, 3H), 0.87-0.82 (m, 1H), 0.81-0.74 (m, 2H), 0.57-0.42 (m, 2H); 928.6 $[M + H]^+$. |
| C148 | 1H NMR (400 MHz, DMSO-d6) δ (ppm) 8.93-8.74 (m, 1H), 8.32-8.23 (m, 1H), 8.11-8.02 (m, 2H), 7.65-7.57 (m, 1H), 7.38-7.28 (m, 6H), 7.24-7.14 (m, 4H), 6.39-6.04 (m, 3H), 4.87-4.76 (m, 1H), 4.61-4.50 (m, 2H), 4.18-4.10 (m, 1H), 3.79-3.72 (m, 3H), 3.58-3.54 (m, 2H), 3.39-3.06 (m, 3H), 2.83-2.68 (m, 3H), 2.45-1.64 (m, 16H), 1.62-1.50 (m, 1H), 1.18-1.10 (m, 3H), 0.84-0.76 (m, 6H), 0.58-0.44 (m, 2H); 964.9 $[M + H]^+$. |

TABLE 1C-continued

| | |
|---|---|
| C149 | 1H NMR (400 MHz, DMSO-d6) δ (ppm) 8.83-8.64 (m, 1H), 8.30-8.21 (m, 1H), 8.14-7.93 (m, 2H), 7.64-7.52 (m, 1H), 7.42-7.26 (m, 6H), 7.24-7.07 (m, 4H), 6.53-5.89 (m, 3H), 4.84-4.67 (m, 1H), 4.53-4.43 (m, 1H), 4.37-4.26 (m, 1H), 4.19-4.06 (m, 1H), 4.03-3.63 (m, 4H), 3.60-3.45 (m, 1H), 3.43-3.35 (m, 1H), 3.26-3.18 (m, 1H), 3.18-3.06 (m, 3H), 3.02-2.97 (m, 1H), 2.47-2.31 (m, 3H), 2.26-2.18 (m, 1H), 2.17-2.07 (m, 4H), 2.05-1.92 (m, 5H), 1.89-1.62 (m, 6H), 1.61-1.41 (m, 3H), 1.40-1.32 (m, 1H), 1.29-1.18 (m, 1H), 0.89-0.70 (m, 3H), 0.54-0.37 (m, 2H); 980.9 $[M + H]^+$ . |
| C150 | 1H NMR (400 MHz, DMSO-d6) δ (ppm) 8.73 (d, J = 7.5 Hz, 1H), 8.26 (s, 1H), 8.10-8.00 (m, 2H), 7.63-7.54 (m, 1H), 7.37-7.27 (m, 6H), 7.24-7.12 (m, 4H), 6.24-5.83 (m, 3H), 4.84-4.69 (m, 1H), 4.52-4.43 (m, 1H), 4.37-4.25 (m, 1H), 4.16-4.05 (m, 1H), 3.95-3.83 (m, 2H), 3.78-3.67 (m, 1H), 3.59-3.47 (m, 1H), 3.06-2.92 (m, 1H), 2.45-2.31 (m, 2H), 2.29-1.40 (m, 21H), 1.32-1.20 (m, 6H), 0.84-0.78 (m, 3H), 0.55-0.38 (m, 2H); 964.6 $[M + H]^+$ . |

TABLE 1C-continued

| | | |
|---|---|---|
| C151 | | 1H NMR (400 MHz, DMSO-d6) δ (ppm) 8.83-8.72 (m, 1H), 8.26 (s, 1H), 8.11-8.01 (m, 2H), 7.60 (d, J = 8.5 Hz, 1H), 7.38-7.27 (m, 6H), 7.24-7.12 (m, 4H), 6.24-5.93 (m, 3H), 4.89-4.66 (m, 2H), 4.54-4.44 (m, 1H), 4.38-4.26 (m, 1H), 4.16-4.06 (m, 1H), 3.76-3.50 (m, 3H), 3.31-3.28 (m, 1H), 3.05-2.91 (m, 1H), 2.45-2.32 (m, 2H), 2.24-1.37 (m, 21H), 1.15-1.12 (m, 3H), 1.08 (d, J = 6.2 Hz, 1H), 0.96 (d, J = 6.2 Hz, 1H), 0.87-0.73 (m, 2H), 0.65-0.60 (m, 1H), 0.53-0.39 (m, 2H); 964.6 $[M + H]^+$ . |
| C152 | | 1H NMR (400 MHz, DMSO-d6) δ (ppm) 10.02-9.48 (m, 1H), 9.02-8.80 (m, 1H), 8.32 (s, 1H), 8.27-8.18 (m, 2H), 7.73-7.65 (m, 1H), 7.45-7.15 (m, 9H), 7.10 (d, J = 8.2 Hz, 1H), 4.87-4.76 (m, 1H), 4.75-4.46 (m, 3H), 4.38-4.15 (m, 1H), 3.97-3.59 (m, 6H), 3.33-3.02 (m, 3H), 2.85-2.54 (m, 6H), 2.47-2.42 (m, 1H), 2.32-1.42 (m, 20H), 0.81 (t, J = 7.4 Hz, 3H), 0.63-0.41 (m, 2H); 1055.0 $[M + H]^+$ . |

TABLE 1C-continued

| | |
|---|---|
| C153 | 1H NMR (400 MHz, DMSO-d6) δ (ppm) 9.75-9.45 (m, 1H), 8.98-8.71 (m, 1H), 8.30-8.20 (m, 1H), 8.12-8.05 (m, 1H), 8.05-7.99 (m, 1H), 7.59-7.48 (m, 1H), 7.39-7.27 (m, 4H), 7.25-7.19 (m, 1H), 6.41-6.19 (m, 1H), 4.87-4.74 (m, 1H), 4.68-4.48 (m, 3H), 4.19-4.05 (m, 4H), 4.03-3.89 (m, 1H), 3.81-3.52 (m, 5H), 3.21-3.10 (m, 1H), 2.85-2.75 (m, 1H), 2.68-2.56 (m, 4H), 2.43-1.75 (m, 14H), 1.65-1.44 (m, 4H), 1.32-1.15 (m, 6H), 0.91-0.84 (m, 3H), 0.61-0.41 (m, 2H); 1025.1 [M+ H]+ |
| C154 | 1H NMR (400 MHz, DMSO-d6) δ (ppm) 9.72-9.45 (m, 1H), 9.02-8.78 (m, 1H), 8.36-8.27 (m, 1H), 8.23-8.14 (m, 2H), 7.67 (d, J = 8.7 Hz, 1H), 7.39-7.30 (m, 6H), 7.24-7.11 (m, 4H), 6.86-6.75 (m, 1H), 4.89-4.75 (m, 1H), 4.73-4.46 (m, 3H), 4.22-4.07 (m, 1H), 3.97-3.72 (m, 4H), 3.66-3.49 (m, 2H), 2.85-2.55 (m, 6H), 2.46-2.41 (m, 1H), 2.25-1.77 (m, 11H), 1.66-1.14 (m, 9H), 0.86-0.78 (m, 3H), 0.62-0.41 (m, 2H); 1028.7 $[M + H]^+$ . |

TABLE 1C-continued

| | |
|---|---|
| C155 | 1H NMR (400 MHz, DMSO-d6) δ (ppm) 8.80 (d, J = 7.8 Hz, 1H), 8.24 (s, 1H), 8.04-7.91 (m, 2H), 7.51 (d, J = 8.5 Hz, 1H), 7.39-7.26 (m, 4H), 7.24-7.16 (m, 1H), 5.99-5.76 (m, 1H), 5.05-4.93 (m, 1H), 4.89-4.79 (m, 1H), 4.75-4.66 (m, 1H), 4.58-4.43 (m, 2H), 4.34-4.24 (m, 1H), 4.19-4.08 (m, 1H), 4.01-3.81 (m, 4H), 3.78-3.70 (m, 1H), 3.64-3.49 (m, 2H), 3.06-2.91 (m, 1H), 2.72-2.56 (m, 2H), 2.44-2.33 (m, 2H), 2.25-2.10 (m, 3H), 2.03-1.43 (m, 20H), 1.30-1.23 (m, 3H), 1.18 (d, J = 7.2 Hz, 3H), 0.90-0.79 (m, 6H), 0.54-0.39 (m, 2H); 1048.4 $[M + H]^+$ . |
| C156 | 1H NMR (400 MHz, DMSO-d6) δ (ppm) 8.87-8.70 (m, 1H), 8.32-8.20 (m, 1H), 8.08-7.98 (m, 1H), 7.98-7.92 (m, 1H), 7.55-7.44 (m, 1H), 7.38-7.26 (m, 4H), 7.24-7.17 (m, 1H), 6.11-5.60 (m, 2H), 4.78-4.64 (m, 1H), 4.59-4.42 (m, 2H), 4.36-4.23 (m, 1H), 4.17-4.06 (m, 1H), 4.02-3.86 (m, 1H), 3.86-3.60 (m, 4H), 3.59-3.46 (m, 1H), 3.08-2.92 (m, 1H), 2.74-2.57 (m, 2H), 2.47-2.29 (m, 2H), 2.28-2.18 (m, 1H), 2.17-2.08 (m, 2H), 2.05-1.92 (m, 6H), 1.90-1.45 (m, 10H), 1.32-0.97 (m, 3H), 0.89-0.82 (m, 6H), 0.81-0.62 (m, 2H), 0.61-0.53 (m, 2H), 0.54-0.35 (m, 2H); 988.4 $[M + H]^+$ . |

TABLE 1C-continued

| | |
|---|---|
| C157 | 1H NMR (400 MHz, DMSO-d6) δ (ppm) 9.68-9.40 (m, 1H), 8.96-8.66 (m, 1H), 8.34-8.24 (m, 1H), 8.10-7.98 (m, 2H), 7.63-7.50 (m, 1H), 7.40-7.25 (m, 6H), 7.25-7.11 (m, 4H), 6.67-6.52 (m, 1H), 6.26-6.03 (m, 1H), 5.05-4.76 (m, 2H), 4.65-4.45 (m, 2H), 4.25-4.06 (m, 1H), 3.90-3.72 (m, 5H), 3.68-3.59 (m, 3H), 2.85-2.53 (m, 6H), 2.45-1.34 (m, 17H), 0.97-0.85 (m, 1H), 0.85-0.75 (m, 3H), 0.75-0.44 (m, 3H); 957.4 $[M + H]^+$ . |
| C158 | 1H NMR (400 MHz, DMSO-d6) δ (ppm) 8.95-8.68 (m, 1H), 8.27 (s, 1H), 8.10-7.98 (m, 2H), 7.61 (d, J = 8.5 Hz, 1H), 7.41-7.25 (m, 6H), 7.23-7.09 (m, 4H), 6.27-6.02 (m, 2H), 4.95-4.63 (m, 2H), 4.60-4.27 (m, 2H), 4.19-4.04 (m, 1H), 3.80-3.52 (m, 5H), 2.78-2.57 (m, 2H), 2.40-1.37 (m, 24H), 1.17-1.08 (m, 3H), 0.84-0.71 (m, 6H), 0.55-0.38 (m, 2H); 1038.5 $[M + H]^+$ . |

TABLE 1C-continued

| | |
|---|---|
| C159 | 1H NMR (400 MHz, DMSO-d6) δ (ppm) 8.85-8.69 (m, 1H), 8.32-8.20 (m, 1H), 8.13-8.00 (m, 2H), 7.66-7.54 (m, 1H), 7.42-7.25 (m, 6H), 7.24-7.10 (m, 4H), 6.31-6.06 (m, 2H), 4.84-4.66 (m, 2H), 4.54-4.40 (m, 1H), 4.35-4.20 (m, 1H), 4.18-4.05 (m, 1H), 3.92-3.66 (m, 4H), 3.58-3.48 (m, 1H), 3.19-2.97 (m, 1H), 2.91-2.72 (m, 1H), 2.64-2.52 (m, 1H), 2.39-2.30 (m, 1H), 2.26-2.18 (m, 1H), 2.16-1.47 (m, 21H), 1.21-1.15 (m, 1H), 1.02-0.92 (m, 2H), 0.85-0.76 (m, 6H), 0.56-0.32 (m, 2H); 1038.3 $[M + H]^+$ . |
| C160 | 1H NMR (400 MHz, DMSO-d6) δ (ppm) 8.82-8.72 (m, 1H), 8.29-8.23 (m, 1H), 8.10-8.01 (m, 2H), 7.60 (t, J = 7.7 Hz, 1H), 7.40-7.27 (m, 6H), 7.24-7.10 (m, 4H), 6.30-6.06 (m, 2H), 4.82-4.68 (m, 2H), 4.47 (t, J = 8.6 Hz, 1H), 4.33-4.23 (m, 1H), 4.11 (t, J = 8.6 Hz, 1H), 3.97-3.65 (m, 4H), 3.58-3.46 (m, 1H), 3.13-3.01 (m, 1H), 2.87-2.76 (m, 1H), 2.61-2.53 (m, 1H), 2.39-2.28 (m, 1H), 2.22 (t, J = 11.5 Hz, 1H), 2.16-2.03 (m, 4H), 2.02-1.93 (m, 3H), 1.91-1.78 (m, 4H), 1.75-1.43 (m, 11H), 1.20-0.91 (m, 3H), 0.81 (t, J = 7.4 Hz, 3H), 0.52-0.39 (m, 2H); 1024.6 [M+ H]+ |

TABLE 1C-continued

| | |
|---|---|
| C161 | 1H NMR (400 MHz, DMSO) δ 8.87-8.72 (m, 1H), 8.35-8.20 (m, 1H), 8.12-8.00 (m, 2H), 7.66-7.55 (m, 1H), 7.42-7.27 (m, 6H), 7.25-7.07 (m, 4H), 6.32-6.06 (m, 2H), 4.91-4.63 (m, 2H), 4.54-4.41 (m, 1H), 4.54-4.40 (m, 1H), 4.35-4.06 (m, 4H), 4.02-3.68 (m, 2H), 3.63-3.38 (m, 1H), 3.09-2.90 (m, 1H), 2.64-2.55 (m, 1H), 2.44-1.91 (m, 16H), 1.88-1.45 (m, 11H), 1.22-0.95 (m, 3H), 0.59-0.37 (m, 2H); 988.4 $[M + H]^+$ . |
| C162 | 1H NMR (400 MHz, DMSO-d6) δ (ppm) 8.81 (d, J = 7.6 Hz, 1H), 8.30-8.21 (m, 1H), 8.03 (t, J = 8.1 Hz, 1H), 7.97 (s, 1H), 7.56-7.46 (m, 1H), 7.38-7.26 (m, 4H), 7.25-7.17 (m, 1H), 6.09-5.90 (m, 1H), 5.86-5.69 (m, 1H), 4.91-4.65 (m, 2H), 4.47 (t, J = 8.6 Hz, 1H), 4.33-4.07 (m, 4H), 4.04-3.50 (m, 5H), 3.07-2.93 (m, 1H), 2.73-2.56 (m, 3H), 2.46-1.41 (m, 23H), 1.30-1.18 (m, 3H), 0.89-0.78 (m, 3H), 0.60-0.36 (m, 2H); 965.0 $[M + H]^+$ . |
| C163 | 1H NMR (400 MHz, DMSO-d6) δ (ppm) 10.13-9.47 (m, 1H), 8.95-8.71 (m, 1H), 8.73-8.46 (m, 2H), 8.26 (s, 1H), 8.10-7.88 (m, 3H), 7.68-7.46 (m, 2H), 7.40-7.25 (m, 2H), 7.23-7.06 (m, 3H), 6.30-6.05 (m, 2H), 4.86-4.48 (m, 4H), 4.25-4.10 (m, 1H), 3.97-3.89 (m, 1H), 3.86-3.75 (m, 5H), 2.85-2.55 (m, 6H), 2.48-2.36 (m, 2H), 2.25-1.38 (m, 16H), 1.13 (d, J = 6.9 Hz, 3H), 0.86-0.72 (m, 3H), 0.59-0.43 (m, 2H); 1011.5 [M+ H]+ |

TABLE 1C-continued

| | |
|---|---|
| C164 | 1H NMR (400 MHz, DMSO-d6) δ (ppm) 9.97-9.42 (m, 1H), 8.98-8.72 (m, 1H), 8.71-8.51 (m, 2H), 8.35-8.21 (m, 1H), 8.14-7.88 (m, 3H), 7.65-7.47 (m, 2H), 7.40-7.28 (m, 2H), 7.22-7.09 (m, 3H), 6.31-6.05 (m, 2H), 4.87-4.75 (m, 1H), 4.72-4.34 (m, 4H), 3.97-3.90 (m, 1H), 3.85-3.77 (m, 3H), 3.64-3.62 (m, 2H), 2.85-2.53 (m, 6H), 2.48-2.26 (m, 3H), 2.23-1.36 (m, 15H), 1.14 (d, J = 7.1 Hz, 3H), 0.87-0.74 (m, 3H), 0.60-0.43 (m, 2H); 1011.5 [M+ H]+ |
| C165 | 1H NMR (400 MHz, DMSO-d6) δ (ppm) 9.69-9.43 (m, 1H), 8.95-8.68 (m, 1H), 8.32-8.23 (m, 1H), 8.13-8.01 (m, 2H), 7.67-7.56 (m, 1H), 7.39-7.27 (m, 6H), 7.27-7.13 (m, 4H), 6.26-6.05 (m, 2H), 4.87-4.77 (m, 1H), 4.73-4.48 (m, 3H), 4.42-4.23 (m, 1H), 3.98-3.74 (m, 4H), 3.70-3.56 (m, 2H), 3.54-3.46 (m, 1H), 3.06-2.99 (m, 3H), 2.86-2.55 (m, 6H), 2.47-2.41 (m, 1H), 2.25-1.98 (m, 5H), 1.93-1.36 (m, 9H), 1.27-1.21 (m, 1H), 1.16-1.09 (m, 3H), 0.93-0.74 (m, 4H), 0.72-0.61 (m, 1H); 1040.6 $[M + H]^+$ . |

TABLE 1C-continued

| | |
|---|---|
| C166 | 1H NMR (400 MHz, DMSO-d6) δ (ppm) 9.74-9.44 (m, 1H), 8.96-8.74 (m, 1H), 8.32-8.22 (m, 1H), 8.11-8.03 (m, 2H), 7.66-7.58 (m, 1H), 7.39-7.27 (m, 6H), 7.25-7.13 (m, 4H), 6.29-6.05 (m, 2H), 4.89-4.78 (m, 1H), 4.73-4.46 (m, 3H), 4.18-3.99 (m, 2H), 3.96-3.89 (m, 1H), 3.86-3.64 (m, 4H), 3.54-3.49 (m, 1H), 3.06-3.00 (m, 3H), 2.85-2.55 (m, 6H), 2.47-2.40 (m, 1H), 2.22-1.22 (m, 15H), 1.14 (d, J = 7.1 Hz, 3H), 0.88-0.62 (m, 5H); 1040.5 $[M + H]^+$ . |
| C167 | 1H NMR (400 MHz, DMSO-d6) δ (ppm) 9.86-9.31 (m, 1H), 8.92-8.71 (m, 1H), 8.28 (s, 1H), 8.08 (d, J = 4.1 Hz, 2H), 7.62 (d, J = 8.6 Hz, 1H), 7.42-7.15 (m, 10H), 6.30-5.99 (m, 2H), 4.90-4.74 (m, 1H), 4.67-4.44 (m, 2H), 4.14 (t, J = 8.3 Hz, 1H), 3.99-3.89 (m, 1H), 3.88-3.71 (m, H), 3.47-3.30 (m, 3H), 3.28-3.11 (m, 1H), 2.92 (s, 1H), 2.77 (s, 2H), 2.35-1.56 (m, 16H), 1.54-1.46 (m, 1H), 1.46-1.38 (m, 1H), 1.14 (d, J = 7.1 Hz, 3H), 0.88-0.72 (m, 3H), 0.60-0.43 (m, 2H); 998.4 $[M + H]^+$ . |

TABLE 1C-continued

| | | |
|---|---|---|
| C168 | | 1H NMR (400 MHz, DMSO-d6) δ (ppm) 9.79-9.43 (m, 1H), 8.90-8.71 (m, 1H), 8.34-8.21 (m, 1H), 8.15-8.00 (m, 2H), 7.72-7.53 (m, 1H), 7.42-7.27 (m, 6H), 7.26-7.09 (m, 4H), 6.29-6.04 (m, 2H), 4.88-4.38 (m, 5H), 4.20-4.07 (m, 1H), 3.90-3.78 (m, 3H), 3.78-3.70 (m, 3H), 3.57-3.55 (m, 1H), 3.42-3.31 (m, 1H), 2.90-2.70 (m, 3H), 2.28-1.30 (m, 16H), 1.18-1.08 (m, 3H), 0.83-0.71 (m, 3H), 0.64-0.41 (m, 2H); 984.7 $[M + H]^+$ . |
| C169 | | 1H NMR (400 MHz, DMSO-d6) δ (ppm) 9.77-9.48 (m, 1H), 8.92-8.73 (m, 1H), 8.38-8.20 (m, 1H), 8.17-7.97 (m, 2H), 7.68-7.53 (m, 1H), 7.44 7.26 (m, 6H), 7.26-7.10 (m, 4H), 6.30-6.09 (m, 2H), 4.88-4.43 (m, 5H), 4.16-4.11 (m, 1H), 3.97-3.89 (m, 3H), 3.77-3.71 (m, 2H), 3.57-3.36 (m, 3H), 2.92-2.69 (m, 3H), 2.28-2.19 (m, 1H), 2.10-2.01 (m, 4H), 1.95-1.89 (m, 3H), 1.85-1.75 (m, 3H), 1.72-1.65 (m, 2H), 1.61-1.47 (m, 3H), 1.18-1.05 (m, 3H), 0.86-0.77 (m, 3H), 0.64-0.38 (m, 2H); 984.7 $[M + H]^+$ . |

TABLE 1C-continued

| | | |
|---|---|---|
| C170 | | 1H NMR (400 MHz, DMSO-d6) δ (ppm) 8.88-8.72 (m, 1H), 8.29-8.21 (m, 1H), 8.14-7.91 (m, 2H), 7.61-7.42 (m, 1H), 7.38-7.26 (m, 4H), 7.25-7.15 (m, 1H), 6.34-6.13 (m, 1H), 6.00-5.57 (m, 1H), 4.92-4.66 (m, 2H), 4.54-4.42 (m, 1H), 4.38-4.22 (m, 1H), 4.18-4.07 (m, 1H), 4.05-3.51 (m, 6H), 3.24-2.91 (m, 2H), 2.67-2.56 (m, 1H), 2.46-1.50 (m, 27H), 1.25-1.16 (m, 3H), 0.90-0.72 (m, 3H), 0.56-0.37 (m, 2H); 935.3 $[M + H]^+$ . |
| C172 | | 1H NMR (400 MHz, DMSO-d6) δ (ppm) 8.77 (d, J = 7.7 Hz, 1H), 8.27 (s, 1H), 8.10-7.99 (m, 2H), 7.61 (d, J = 8.6 Hz, 1H), 7.40-7.27 (m, 6H), 7.23-7.12 (m, 4H), 6.27-6.04 (m, 2H), 4.81-4.65 (m, 2H), 4.52-4.43 (m, 1H), 4.40 (d, J = 5.4 Hz, 1H), 4.36 (d, J = 5.4 Hz, 1H), 4.32-4.24 (m, 1H), 4.19 (d, J = 5.4 Hz, 1H), 4.14-4.05 (m, 2H), 3.84-3.67 (m, 2H), 3.59-3.48 (m, 1H), 2.88-2.78 (m, 1H), 2.58-2.52 (m, 1H), 2.39-2.31 (m, 1H), 2.22-1.50 (m, 23H), 1.28 (s, 3H), 1.11 (d, J = 7.0 Hz, 3H), 0.54-0.38 (m, 2H); 968.7 $[M + H]^+$ . |

TABLE 1C-continued

| | |
|---|---|
| C173 | 1H NMR (400 MHz, DMSO-d6) δ (ppm) 8.86-8.71 (m, 1H), 8.31-8.21 (m, 1H), 8.08-7.95 (m, 2H), 7.58-7.47 (m, 1H), 7.41-7.17 (m, 5H), 6.22-5.93 (m, 2H), 4.84-4.69 (m, 1H), 4.65-4.24 (m, 6H), 4.21-4.16 (m, 1H), 4.14-4.06 (m, 2H), 3.94-3.68 (m, 4H), 3.59-3.47 (m, 1H), 2.90-2.78 (m, 1H), 2.60-2.51 (m, 1H), 2.41-1.40 (m, 20H), 1.34-1.17 (m, 6H), 0.85-0.78 (m, 3H), 0.54-0.39 (m, 2H); 962.4 $[M + H]^+$. |
| C174 | 1H NMR (400 MHz, DMSO-d6) δ (ppm) 8.78 (d, J = 7.1 Hz, 1H), 8.27 (s, 1H), 8.10-8.00 (m, 2H), 7.60 (d, J = 8.3 Hz, 1H), 7.40-7.26 (m, 6H), 7.23-7.12 (m, 4H), 6.29-6.07 (m, 2H), 4.76-4.66 (m, 1H), 4.48 (t, J = 8.4 Hz, 1H), 4.34-4.22 (m, 1H), 4.12 (t, J = 8.6 Hz, 1H), 3.98-3.84 (m, 1H), 3.81-3.49 (m, 7H), 3.07-2.92 (m, 2H), 2.83-2.69 (m, 1H), 2.40-2.19 (m, 4H), 2.14-2.03 (m, 3H), 2.02-1.90 (m, 6H), 1.88-1.33 (m, 12H), 1.17-1.05 (m, 3H), 0.52-0.37 (m, 2H); 1036.6 $[M + H]^+$. |

TABLE 1C-continued

| | |
|---|---|
| C175 | 1H NMR (400 MHz, DMSO-d6) δ (ppm) 8.80 (d, J = 7.6 Hz, 1H), 8.27 (s, 1H), 8.06 (d, J = 8.4 Hz, 1H), 8.00 (s, 1H), 7.52 (d, J = 8.5 Hz, 1H), 7.37-7.27 (m, 4H), 7.24-7.18 (m, 1H), 6.26-6.03 (m, 2H), 4.76-4.55 (m, 3H), 4.48 (t, J = 8.5 Hz, 1H), 4.33-4.24 (m, 1H), 4.15-4.07 (m, 1H), 4.06-3.94 (m, 2H), 3.78-3.61 (m, 2H), 3.58-3.49 (m, 1H), 3.08-2.92 (m, 2H), 2.84-2.71 (m, 1H), 2.37-2.19 (m, 3H), 2.11-1.51 (m, 20H), 1.23 (d, J = 7.2 Hz, 3H), 0.86 (t, J = 7.4 Hz, 3H), 0.52 0.39 (m, 2H); 1000.4 $[M + H]^+$ . |
| C176 | 1H NMR (400 MHz, DMSO-d6) δ (ppm) 8.78 (d, J = 7.6 Hz, 1H), 8.26 (s, 1H), 8.03 (d, J = 8.4 Hz, 1H), 7.98 (s, 1H), 7.51 (d, J = 8.5 Hz, 1H), 7.37-7.27 (m, 4H), 7.24-7.18 (m, 1H), 6.05-5.89 (m, 1H), 5.68-5.59 (m, 1H), 4.93-4.82 (m, 1H), 4.76-4.65 (m, 1H), 4.53-4.43 (m, 1H), 4.35-4.23 (m, 1H), 4.16-3.99 (m, 3H), 3.79-3.68 (m, 1H), 3.60-3.48 (m, 2H), 3.09-2.91 (m, 2H), 2.84-2.69 (m, 1H), 2.39-2.18 (m, 3H), 2.14-2.04 (m, 3H), 2.02-1.90 (m, 6H), 1.89-1.64 (m, 5H), 1.64-1.44 (m, 4H), 1.23 (t, J = 7.1 Hz, 3H), 1.20-1.14 (m, 9H), 0.53-0.38 (m, 2H); 946.4 $[M + H]^+$ . |

TABLE 1C-continued

| | |
|---|---|
| C177 | 1H NMR (400 MHz, DMSO-d6) δ (ppm) 8.76 (d, J = 7.6 Hz, 1H), 8.25 (s, 1H), 8.06-7.94 (m, 2H), 7.53 (d, J = 8.5 Hz, 1H), 7.39-7.17 (m, 5H), 5.94 (dd, J = 44.0, 6.6 Hz, 1H), 5.60-5.49 (m, 1H), 4.87-4.72 (m, 2H), 4.47 (t, J = 8.5 Hz, 1H), 4.36-4.25 (m, 1H), 4.11 (t, J = 8.6 Hz, 1H), 4.03-3.92 (m, 2H), 3.78-3.63 (m, 2H), 3.59-3.47 (m, 1H), 2.94 (s, 1H), 2.44-1.52 (m, 23H), 1.25-1.13 (m, 9H), 1.09 (d, J = 6.3 Hz, 3H), 0.55-0.39 (m, 2H); 934.9 $[M+H]^+$. |
| C178 | 1H NMR (400 MHz, DMSO-d6) δ (ppm) 8.79 (d, J = 7.7 Hz, 1H), 8.25 (s, 1H), 8.09-7.92 (m, 2H), 7.53 (d, J = 8.5 Hz, 1H), 7.37-7.27 (m, 4H), 7.24-7.17 (m, 1H), 6.05-5.82 (m, 1H), 5.65-5.51 (m, 1H), 4.89-4.62 (m, 2H), 4.53-4.41 (m, 1H), 4.35-4.21 (m, 1H), 4.18-4.08 (m, 1H), 4.05-3.66 (m, 6H), 3.59-3.49 (m, 1H), 3.11-2.97 (m, 1H), 2.76-2.65 (m, 1H), 2.59-2.52 (m, 1H), 2.44-1.43 (m, 21H), 1.27-1.16 (m, 6H), 1.03-0.93 (m, 3H), 0.86-0.78 (m, 3H), 0.56-0.39 (m, 2H); 910.6 $[M+H]^+$. |

TABLE 1C-continued

| | | |
|---|---|---|
| C179 | | 1H NMR (400 MHz, DMSO-d6) δ (ppm) 9.67-9.42 (m, 1H), 8.92-8.66 (m, 1H), 8.27 (s, 1H), 8.15-7.98 (m, 2H), 7.61 (d, J = 8.2 Hz, 1H), 7.41-7.28 (m, 6H), 7.25-7.11 (m, 4H), 6.47-5.94 (m, 3H), 4.87-4.69 (m, 1H), 4.65-4.43 (m, 2H), 4.33-3.51 (m, 13H), 3.29-2.99 (m, 6H), 2.81-2.69 (m, 3H), 2.39-1.74 (m, 15H), 1.61-1.51 (m, 1H), 1.23-1.12 (m, 3H), 0.60-0.39 (m, 2H); 1021.5 $[M + H]^+$ . |
| C180 | | 1H NMR (400 MHz, DMSO-d6) δ (ppm) 9.78-9.39 (m, 1H), 8.92-8.72 (m, 1H), 8.35-8.00 (m, 3H), 7.61 (d, J = 8.6 Hz, 1H), 7.38-7.27 (m, 6H), 7.25-7.12 (m, 4H), 6.38-6.00 (m, 3H), 4.81 (s, 1H), 4.60-4.50 (m, 2H), 4.18-4.08 (m, 1H), 3.87-3.66 (m, 4H), 3.60-3.51 (m, 2H), 3.31 3.09 (m, 2H), 2.85-2.66 (m, 1H), 2.48-1.49 (m, 16H), 1.21-1.13 (m, 3H), 0.88-0.74 (m, 9H), 0.56-0.44 (m, 2H); 979.0 $[M + H]^+$ . |
| C181 | | 1H NMR (400 MHz, DMSO-d6) δ (ppm) 9.84-9.20 (m, 1H), 8.89-8.71 (m, 1H), 8.30-8.25 (m, 1H), 8.13-8.09 (m, 2H), 7.62 (d, J = 8.6 Hz, 1H), 7.42-7.29 (m, 6H), 7.25-7.17 (m, 4H), 6.50-6.36 (m, 1H), 6.34-6.01 (m, 1H), 4.87-4.78 (m, 1H), 4.60-4.50 (m, 2H), 4.17-4.11 (m, 1H), 4.02-3.88 (m, 4H), 3.78-3.73 (m, 1H), 3.60-3.46 (m, 2H), 3.39-3.10 (m, 3H), 2.83-2.68 (m, 3H), 2.45-1.74 (m, 19H), 1.63-1.42 (m, 3H), 0.81 (t, J = 7.4 Hz, 3H), 0.49 (s, 2H); 977.8 $[M + H]^+$ . |

TABLE 1C-continued

| | |
|---|---|
| C182 | 1H NMR (400 MHz, DMSO-d6) δ (ppm) 8.87-8.71 (m, 1H), 8.27 (s, 1H), 8.14-7.96 (m, 2H), 7.60 (d, J = 8.6 Hz, 1H), 7.40-7.25 (m, 6H), 7.24-7.12 (m, 4H), 6.33-6.09 (m, 2H), 4.90-4.66 (m, 2H), 4.47 (t, J = 8.5 Hz, 1H), 4.35-4.22 (m, 1H), 4.12 (t, J = 8.6 Hz, 1H), 4.02-3.67 (m, 4H), 3.61-3.45 (m, 1H), 3.11-2.95 (m, 4H), 2.64-2.55 (m, 1H), 2.40-1.49 (m, 21H), 1.19-1.13 (m, 3H), 1.09-1.01 (m, 6H), 0.55-0.39 (m, 2H); 989.0 $[M+H]^+$. |
| C183 | 1H NMR (400 MHz, DMSO-d6) δ (ppm) 9.82-9.44 (m, 1H), 8.96-8.74 (m, 1H), 8.27 (m, 1H), 8.12-8.00 (m, 2H), 7.67-7.57 (m, 1H), 7.43-7.28 (m, 6H), 7.26-7.11 (m, 4H), 6.31-6.03 (m, 2H), 5.04-4.75 (m, 3H), 4.65-4.48 (m, 3H), 4.21-4.08 (m, 1H), 3.81-3.69 (m, 2H), 3.60-3.50 (m, 1H), 2.81-2.72 (m, 1H), 2.68-2.52 (m, 8H), 2.47-1.49 (m, 20H), 1.11 (d, J = 7.1 Hz, 3H), 0.67-0.41 (m, 2H); 1032.4 $[M+H]^+$. |
| C184 | 1H NMR (400 MHz, DMSO-d6) δ (ppm) 8.86-8.75 (m, 1H), 8.27 (s, 1H), 8.12-7.98 (m, 2H), 7.60 (d, J = 7.5 Hz, 1H), 7.40-7.10 (m, 10H), 6.32-6.05 (m, 2H), 4.92-4.64 (m, 2H), 4.55-4.41 (m, 1H), 4.37-4.21 (m, 1H), 4.17-4.05 (m, 1H), 4.03-3.46 (m, 8H), 3.03-2.95 (m, 1H), 2.64-2.55 (m, 1H), 2.45-1.31 (m, 25H), 1.19-1.07 (m, 3H), 0.57-0.39 (m, 2H); 986.6 $[M+H]^+$. |

TABLE 1C-continued

| | | |
|---|---|---|
| C185 | | 1H NMR (400 MHz, DMSO-d6) δ (ppm) 8.84-8.74 (m, 1H), 8.27 (s, 1H), 8.11-8.01 (m, 2H), 7.65-7.55 (m, 1H), 7.42-7.26 (m, 6H), 7.25-7.10 (m, 4H), 6.30-6.06 (m, 2H), 4.90-4.66 (m, 2H), 4.47 (t, J = 8.6 Hz, 1H), 4.35-4.22 (m, 1H), 4.12 (t, J = 8.6 Hz, 1H), 4.01-3.51 (m, 8H), 3.39-3.33 (m, 1H), 3.05-2.95 (m, 1H), 2.65-2.55 (m, 1H), 2.41-1.39 (m, 24H), 1.13 (d, J = 7.1 Hz, 3H), 0.58-0.37 (m, 2H); 987.1 $[M + H]^+$. |
| C186 | | 1H NMR (400 MHz, DMSO-d6) δ (ppm) 9.87-9.47 (m, 1H), 8.95-8.77 (m, 1H), 8.37-8.23 (m, 1H), 8.13-8.03 (m, 2H), 7.61 (d, J = 8.6 Hz, 1H), 7.45-7.27 (m, 6H), 7.25-7.12 (m, 4H), 6.27-6.08 (m, 2H), 5.02-4.79 (m, 2H), 4.62-4.50 (m, 2H), 4.22-4.09 (m, 2H), 3.87-3.79 (m, 3H), 3.71-3.50 (m, 5H), 3.43-3.01 (m, 3H), 2.82-2.64 (m, 2H), 2.64-2.55 (m, 3H), 2.48-2.40 (m, 2H), 2.31-1.50 (m, 14H), 1.48-1.37 (m, 2H), 1.19-1.04 (m, 5H), 0.65-0.44 (m, 2H); 500.9 $[M/2 + H]^+$. |

TABLE 1C-continued

| | |
|---|---|
| C187 | 1H NMR (400 MHz, DMSO-d6) δ (ppm) 9.77-9.41 (m, 1H), 9.01-8.67 (m, 1H), 8.32-8.18 (m, 1H), 8.13-7.96 (m, 2H), 7.67-7.54 (m, 1H), 7.39-7.28 (m, 6H), 7.24-7.11 (m, 4H), 6.28-5.92 (m, 2H), 5.09-4.71 (m, 2H), 4.66-4.45 (m, 2H), 4.22-4.07 (m, 1H), 3.87-3.66 (m, 3H), 3.62-3.52 (m, 3H), 2.82-2.63 (m, 2H), 2.63-2.55 (m, 3H), 2.48-2.41 (m, 2H), 2.34-1.71 (m, 13H), 1.70-1.36 (m, 5H), 0.87-0.82 (m, 2H), 0.80-0.69 (m, 5H), 0.67-0.60 (m, 2H), 0.59-0.44 (m, 2H); 972.6 $[M+H]^+$. |
| C188 | 1H NMR (400 MHz, DMSO-d6) δ (ppm) 8.91-8.74 (m, 1H), 8.29 (s, 1H), 8.18-8.03 (m, 2H), 7.62 (d, J = 6.7 Hz, 1H), 7.46-7.27 (m, 6H), 7.27-7.13 (m, 4H), 6.30-6.19 (m, 1H), 6.19-6.05 (m, 1H), 4.95-4.67 (m, 2H), 4.49 (t, J = 8.5 Hz, 1H), 4.40-4.23 (m, 1H), 4.14 (t, J = 8.5 Hz, 1H), 4.07-3.67 (m, 4H), 3.64-3.51 (m, 1H), 3.10-2.95 (m, 1H), 2.68-2.57 (m, 1H), 2.45-2.32 (m, 2H), 2.25 (t, J = 11.5 Hz, 1H), 2.20-2.06 (m, 2H), 2.05-1.95 (m, 6H), 1.91-1.51 (m, 10H), 1.43-1.30 (m, 2H), 1.19-1.12 (m, 3H), 0.94-0.74 (m, 7H), 0.60-0.37 (m, 2H); 972.6 $[M+H]^+$. |

TABLE 1C-continued

| | | |
|---|---|---|
| C189 | | 1H NMR (400 MHz, DMSO-d6) δ (ppm) 9.71-9.44 (m, 1H), 8.96-8.76 (m, 1H), 8.32-8.24 (m, 1H), 8.10-8.03 (m, 2H), 7.61 (d, J = 8.2 Hz, 1H), 7.41-7.29 (m, 6H), 7.25-7.09 (m, 4H), 6.30-5.96 (m, 2H), 5.03-4.78 (m, 2H), 4.61-4.49 (m, 2H), 4.22-4.13 (m, 2H), 3.96-3.91 (m, 1H), 3.78-3.72 (m, 2H), 3.65-3.54 (m, 2H), 3.12-2.71 (m, 1H), 2.63-2.55 (m, 3H), 2.50-1.81 (m, 14H), 1.81-0.95 (m, 10H), 0.88-0.65 (m, 6H), 0.63-0.46 (m, 2H); 972.6 $[M + H]^+$ . |
| C190 | | 1H NMR (400 MHz, DMSO-d6) δ (ppm) 8.78 (d, J = 7.6 Hz, 1H), 8.25 (s, 1H), 8.07-7.90 (m, 2H), 7.52 (d, J = 8.7 Hz, 1H), 7.37-7.26 (m, 4H), 7.23-7.18 (m, 1H), 5.97-5.73 (m, 1H), 5.52-5.38 (m, 1H), 4.89-4.66 (m, 2H), 4.53-4.38 (m, 2H), 4.33-4.23 (m, 1H), 4.16-4.06 (m, 1H), 4.03-3.92 (m, 2H), 3.78-3.68 (m, 1H), 3.65-3.50 (m, 2H), 3.05-2.94 (m, 1H), 2.62-2.57 (m, 1H), 2.44-1.35 (m, 33H), 1.08-0.97 (m, 3H), 0.90-0.82 (m, 3H), 0.55-0.38 (m, 2H); 950.8 $[M + H]^+$ . |

TABLE 1C-continued

| | |
|---|---|
| C191 | 1H NMR (400 MHz, DMSO-d6) δ (ppm) 8.80 (d, J = 7.7 Hz, 1H), 8.25 (d, J = 2.8 Hz, 1H), 8.06-7.99 (m, 1H), 7.95 (s, 1H), 7.49 (d, J = 8.6 Hz, 1H), 7.37-7.26 (m, 4H), 7.24-7.14 (m, 1H), 6.02-5.80 (m, 1H), 5.64-5.48 (m, 1H), 4.97-4.66 (m, 3H), 4.51-4.43 (m, 1H), 4.34-4.24 (m, 1H), 4.14-4.08 (m, 1H), 4.02-3.47 (m, 5H), 3.04-2.95 (m, 1H), 2.65-2.55 (m, 1H), 2.44-1.45 (m, 31H), 1.30-1.18 (m, 3H), 0.92-0.81 (m, 3H), 0.56-0.38 (m, 2H); 936.9 $[M + H]^+$. |
| C192 | 1H NMR (400 MHz, DMSO-d6) δ (ppm) 8.79 (d, J = 7.7 Hz, 1H), 8.25 (s, 1H), 8.08-7.89 (m, 2H), 7.52 (d, J = 8.6 Hz, 1H), 7.37-7.26 (m, 4H), 7.24-7.17 (m, 1H), 6.02-5.76 (m, 1H), 5.61-5.43 (m, 1H), 4.90-4.66 (m, 2H), 4.63-4.53 (m, 1H), 4.51-4.42 (m, 1H), 4.35-4.22 (m, 1H), 4.18-4.05 (m, 1H), 3.95-3.48 (m, 5H), 3.06-2.93 (m, 1H), 2.65-2.56 (m, 1H), 2.44-1.41 (m, 23H), 1.29-1.13 (m, 9H), 0.89-0.75 (m, 3H), 0.56-0.37 (m, 2H); 910.7 $[M + H]^+$. |

TABLE 1C-continued

| | | |
|---|---|---|
| C193 | | 1H NMR (400 MHz, DMSO-d6) δ (ppm) 9.76-9.42 (m, 1H), 8.98-8.75 (m, 1H), 8.31-8.21 (m, 1H), 8.09-7.96 (m, 2H), 7.53 (d, J = 8.3 Hz, 1H), 7.39-7.27 (m, 4H), 7.26-7.19 (m, 1H), 6.22-5.95 (m, 2H), 4.97-4.78 (m, 2H), 4.60-4.48 (m, 4H), 4.19-4.11 (m, 1H), 3.89-3.69 (m, 4H), 3.63-3.49 (m, 3H), 3.45-2.99 (m, 1H), 2.81-2.72 (m, 1H), 2.66-2.55 (m, 4H), 2.46-2.41 (m, 1H), 2.29-1.51 (m, 14H), 1.30-1.24 (m, 3H), 0.88-0.80 (m, 9H), 0.63-0.44 (m, 2H); 978.9 $[M + H]^+$. |
| C194 | | 1H NMR (400 MHz, DMSO-d6) δ (ppm) 8.80 (d, J = 7.6 Hz, 1H), 8.35-8.19 (m, 1H), 8.08-7.91 (m, 2H), 7.59-7.47 (m, 1H), 7.39-7.16 (m, 5H), 6.13-5.86 (m, 1H), 5.77-5.50 (m, 1H), 4.93-4.65 (m, 2H), 4.47 (t, J = 8.5 Hz, 1H), 4.35-4.23 (m, 1H), 4.16-3.46 (m, 10H), 3.29-3.21 (m, 3H), 3.06-2.93 (m, 1H), 2.63-2.56 (m, 1H), 2.43-1.44 (m, 23H), 1.28-1.18 (m, 3H), 0.90-0.76 (m, 3H), 0.58-0.38 (m, 2H); 926.8 $[M + H]^+$. |

TABLE 1C-continued

| | |
|---|---|
| C195 | 1H NMR (400 MHz, DMSO-d6) δ (ppm) 10.07-9.41 (m, 1H), 8.98-8.73 (m, 1H), 8.31-8.23 (m, 1H), 8.11-8.03 (m, 2H), 7.61 (d, J = 8.3 Hz, 1H), 7.40-7.28 (m, 6H), 7.25-7.10 (m, 4H), 6.31-6.04 (m, 2H), 5.05-4.90 (m, 1H), 4.88-4.76 (m, 2H), 4.75-4.65 (m, 1H), 4.64-4.47 (m, 3H), 4.23-4.06 (m, 2H), 3.75-3.70 (m, 1H), 3.56-3.50 (m, 1H), 3.45-3.02 (m, 1H), 2.81-2.62 (m, 2H), 2.62-2.55 (m, 3H), 2.48-2.41 (m, 1H), 2.39-2.17 (m, 4H), 2.16-1.49 (m, 20H), 1.17-0.88 (m, 3H), 0.64-0.45 (m, 2H); 996.5 $[M + H]^+$. |
| C196 | 1H NMR (400 MHz, DMSO-d6) δ (ppm) 9.93-9.45 (m, 1H), 8.95-8.76 (m, 1H), 8.31-8.24 (m, 1H), 8.12-8.02 (m, 2H), 7.61 (d, J = 8.5 Hz, 1H), 7.40-7.06 (m, 10H), 6.25-5.87 (m, 2H), 4.99-4.78 (m, 2H), 4.58-4.46 (m, 2H), 4.16-4.10 (m, 2H), 3.94-3.89 (m, 1H), 3.79-3.74 (m, 1H), 3.70-3.62 (m, 1H), 3.57-3.51 (m, 1H), 3.44-3.33 (m, 1H), 3.09-2.73 (m, 1H), 2.70-2.56 (m, 4H), 2.48-1.43 (m, 19H), 1.33-1.21 (m, 1H), 0.88-0.78 (m, 5H), 0.73-0.68 (m, 1H), 0.65-0.47 (m, 5H); 972.6 $[M + H]^+$. |

TABLE 1C-continued

| | | |
|---|---|---|
| C197 | | 1H NMR (400 MHz, DMSO-d6) δ (ppm) 8.85-8.72 (m, 1H), 8.31-8.24 (m, 1H), 8.10-8.01 (m, 2H), 7.60 (d, J = 8.6 Hz, 1H), 7.40-7.27 (m, 6H), 7.25-7.10 (m, 4H), 6.30-6.19 (m, 1H), 6.18-6.09 (m, 1H), 5.20-5.03 (m, 1H), 4.90-4.65 (m, 2H), 4.52-4.44 (m, 1H), 4.34-4.24 (m, 1H), 4.16-4.07 (m, 1H), 3.88-3.63 (m, 5H), 3.58-3.42 (m, 2H), 3.06-2.96 (m, 1H), 2.66-2.51 (m, 2H), 2.43-2.29 (m, 2H), 2.27-2.20 (m, 1H), 2.16-1.51 (m, 19H), 1.19-1.07 (m, 3H), 0.58-0.39 (m, 2H); 972.5 $[M + H]^+$ . |
| C198 | | 1H NMR (400 MHz, DMSO-d6) δ (ppm) 8.83-8.75 (m, 1H), 8.27 (s, 1H), 8.11-7.96 (m, 2H), 7.60 (d, J = 8.2 Hz, 1H), 7.40-7.10 (m, 10H), 6.34-6.04 (m, 2H), 5.19-5.01 (m, 1H), 4.90-4.66 (m, 2H), 4.54-4.44 (m, 1H), 4.35-4.24 (m, 1H), 4.12 (t, J = 8.5 Hz, 1H), 3.82-3.48 (m, 7H), 3.05-2.93 (m, 1H), 2.63-2.56 (m, 1H), 2.42-2.30 (m, 2H), 2.27-2.20 (m, 1H), 2.16-1.48 (m, 20H), 1.17-1.04 (m, 3H), 0.55-0.40 (m, 2H); 972.8 $[M + H]^+$ . |

TABLE 1C-continued

| | |
|---|---|
| C199 | 1H NMR (400 MHz, DMSO-d6) δ (ppm) 8.85-8.73 (m, 1H), 8.27 (d, J = 4.6 Hz, 1H), 8.11-8.02 (m, 2H), 7.60 (t, J = 7.7 Hz, 1H), 7.39-7.27 (m, 6H), 7.23-7.11 (m, 4H), 6.35-6.07 (m, 2H), 4.90-4.66 (m, 2H), 4.47 (t, J = 8.6 Hz, 1H), 4.34-4.24 (m, 1H), 4.16-3.69 (m, 5H), 3.60-3.47 (m, 1H), 3.05-2.95 (m, 1H), 2.64-2.55 (m, 1H), 2.41-2.31 (m, 2H), 2.23 (t, J = 11.6 Hz, 1H), 2.16-2.10 (m, 1H), 2.03-1.91 (m, 7H), 1.89-1.61 (m, 6H), 1.60-1.51 (m, 3H), 1.35-1.14 (m, 9H), 0.99 (d, J = 7.1 Hz, 1H), 0.54-0.40 (m, 2H); 976.3 $[M + H]^+$ . |
| C200 | 1H NMR (400 MHz, DMSO-d6) δ (ppm) 8.84-8.73 (m, 1H), 8.31-8.23 (m, 1H), 8.11-8.03 (m, 2H), 7.63-7.56 (m, 1H), 7.38-7.27 (m, 6H), 7.23-7.14 (m, 4H), 6.24-6.06 (m, 2H), 4.90-4.66 (m, 2H), 4.52-4.40 (m, 1H), 4.36-4.22 (m, 1H), 4.18-4.06 (m, 1H), 3.92-3.84 (m, 2H), 3.78-3.51 (m, 6H), 3.06-2.94 (m, 1H), 2.65-2.56 (m, 1H), 2.44-1.42 (m, 25H), 1.22-1.11 (m, 1H), 0.97-0.93 (m, 2H), 0.55-0.39 (m, 2H); 987.8 $[M + H]^+$ . |

TABLE 1C-continued

| | |
|---|---|
| C201 | 1H NMR (400 MHz, DMSO-d6) δ (ppm) 8.79 (t, J = 6.8 Hz, 1H), 8.31-8.23 (m, 1H), 8.12-8.00 (m, 2H), 7.65-7.54 (m, 1H), 7.43-7.26 (m, 6H), 7.24-7.07 (m, 4H), 6.31-6.07 (m, 2H), 4.92-4.63 (m, 2H), 4.47 (t, J = 8.6 Hz, 1H), 4.35-4.24 (m, 1H), 4.12 (t, J = 8.5 Hz, 1H), 3.99-3.48 (m, 8H), 3.37-3.33 (m, 1H), 3.04-2.95 (m, 1H), 2.63-2.54 (m, 1H), 2.42-1.43 (m, 24H), 1.22-0.91 (m, 3H), 0.57-0.37 (m, 2H); 987.1 $[M + H]^+$ . |
| C202 | 1H NMR (400 MHz, DMSO-d6) δ (ppm) 8.86-8.71 (m, 1H), 8.30-8.25 (m, 1H), 8.14-7.99 (m, 2H), 7.68-7.50 (m, 1H), 7.42-7.08 (m, 10H), 6.33-6.02 (m, 2H), 4.94-4.59 (m, 2H), 4.54-4.39 (m, 1H), 4.35-4.21 (m, 1H), 4.18-4.03 (m, 1H), 3.94-3.64 (m, 6H), 3.60-3.47 (m, 1H), 3.25-3.14 (m, 2H), 3.06-2.92 (m, 1H), 2.64-2.56 (m, 1H), 2.45-1.32 (m, 24H), 1.22-0.91 (m, 5H), 0.60-0.35 (m, 2H); 1000.6 $[M + H]^+$ . |
| C203 | 1H NMR (400 MHz, DMSO-d6) δ (ppm) 9.70-9.41 (m, 1H), 8.98-8.71 (m, 1H), 8.35-8.23 (m, 1H), 8.17-8.03 (m, 2H), 7.62 (d, 1H), 7.48-7.11 (m, 10H), 6.63-6.43 (m, 1H), 4.88-4.75 (m, 1H), 4.74-4.44 (m, 3H), 4.43-4.30 (m, 1H), 4.25-3.87 (m, 4H), 3.84 3.46 (m, 5H), 3.18-3.05 (m, 1H), 2.83-2.62 (m, 4H), 2.34-1.69 (m, 13H), 1.56-1.41 (m, 3H), 1.33-1.13 (m, 4H), 0.85-0.73 (m, 3H), 0.65-0.38 (m, 2H); 1072.7 $[M + H]^+$ . |

TABLE 1C-continued

| | |
|---|---|
| C204 | 1H NMR (400 MHz, DMSO-d6) δ (ppm) 8.91-8.65 (m, 1H), 8.26 (s, 1H), 8.14-7.90 (m, 2H), 7.54 (d, J = 8.6 Hz, 1H), 7.38-7.15 (m, 5H), 6.42-6.17 (m, 1H), 4.77-4.40 (m, 5H), 4.39-4.20 (m, 2H), 4.19-4.04 (m, 1H), 3.97-3.82 (m, 2H), 3.80-3.65 (m, 1H), 3.61-3.44 (m, 1H), 3.06-2.93 (m, 1H), 2.72-2.52 (m, 5H), 2.44-2.10 (m, 5H), 2.01-1.44 (m, 17H), 1.31-1.23 (m, 3H), 0.85-0.76 (m, 3H), 0.58-0.31 (m, 2H); 1030.4 $[M + H]^+$ . |
| C205 | 1H NMR (400 MHz, DMSO-d6) δ (ppm) 10.09-9.53 (m, 1H), 8.98-8.72 (m, 1H), 8.32-8.20 (m, 1H), 8.12-7.95 (m, 2H), 7.60-7.49 (m, 1H), 7.42-7.29 (m, 4H), 7.26-7.17 (m, 1H), 6.08-5.86 (m, 1H), 5.73-5.56 (m, 1H), 4.90-4.45 (m, 5H), 4.26-3.85 (m, 6H), 3.80-3.71 (m, 3H), 2.81-2.72 (m, 1H), 2.63-2.56 (m, 3H), 2.37-1.70 (m, 14H), 1.69-1.33 (m, 4H), 1.30-1.17 (m, 10H), 0.88-0.76 (m, 6H), 0.62-0.43 (m, 2H); 1004.6 $[M + H]^+$ . |

TABLE 1C-continued

| | |
|---|---|
| C206 | 1H NMR (400 MHz, DMSO-d6) δ (ppm) 9.91-9.42 (m, 1H), 8.92-8.71 (m, 1H), 8.31-8.19 (m, 1H), 8.13-7.96 (m, 2H), 7.64-7.48 (m, 1H), 7.39-7.27 (m, 4H), 7.26-7.19 (m, 1H), 6.29-6.01 (m, 1H), 4.87-4.76 (m, 1H), 4.72-4.46 (m, 3H), 4.35-3.87 (m, 6H), 3.81-3.48 (m, 6H), 2.85-2.75 (m, 1H), 2.73-2.65 (m, 1H), 2.63-2.52 (m, 6H), 2.47-2.43 (m, 1H), 2.28-1.49 (m, 15H), 1.34-1.11 (m, 6H), 0.92-0.81 (m, 3H), 0.65-0.39 (m, 2H); 976.8 $[M + H]^+$ . |
| C207 | 1H NMR (400 MHz, DMSO-d6) δ (ppm) 9.77-9.36 (m, 1H), 8.95-8.67 (m, 1H), 8.30-8.19 (m, 1H), 8.10-7.97 (m, 2H), 7.61-7.49 (m, 1H), 7.45-7.06 (m, 5H), 6.30-6.06 (m, 1H), 4.85-4.75 (m, 1H), 4.71-4.41 (m, 3H), 4.39-4.27 (m, 1H), 4.23-4.07 (m, 1H), 4.01 (t, J = 6.5 Hz, 2H), 3.96-3.84 (m, 2H), 3.83-3.71 (m, 1H), 3.65-3.41 (m, 7H), 3.20-3.14 (m, 1H), 2.99-2.91 (m, 1H), 2.84-2.74 (m, 1H), 2.68-2.58 (m, 3H), 2.30-1.46 (m, 19H), 1.16 (t, J = 7.0 Hz, 3H), 0.89 (t, J = 7.4 Hz, 3H), 0.59-0.36 (m, 2H); 988.8 [M+ H]+ |

TABLE 1C-continued

| | |
|---|---|
| C208 | 1H NMR (400 MHz, DMSO-d6) δ (ppm) 10.09-9.39 (m, 1H), 8.98-8.75 (m, 1H), 8.32-8.24 (m, 1H), 8.12-8.02 (m, 2H), 7.66-7.58 (m, 1H), 7.40-7.28 (m, 6H), 7.25-7.14 (m, 4H), 6.29-6.05 (m, 2H), 4.95-4.81 (m, 2H), 4.59-4.52 (m, 2H), 4.20-4.10 (m, 1H), 3.83-3.47 (m, 5H), 3.45-3.02 (m, 1H), 2.84-2.53 (m, 6H), 2.48-2.43 (m, 1H), 2.31-1.40 (m, 26H), 1.18-1.05 (m, 3H), 0.67-0.39 (m, 2H); 1011.0 [M+ H]+ |
| C209 | 1H NMR (400 MHz, DMSO-d6) δ (ppm) 8.85-8.72 (m, 1H), 8.27 (s, 1H), 8.11-7.99 (m, 2H), 7.66-7.57 (m, 1H), 7.41-7.11 (m, 10H), 6.27-6.05 (m, 2H), 4.95-4.66 (m, 3H), 4.51-4.42 (m, 1H), 4.35-4.23 (m, 1H), 4.18-4.05 (m, 1H), 3.86-3.67 (m, 2H), 3.60-3.48 (m, 1H), 3.06-2.93 (m, 1H), 2.43-1.48 (m, 26H), 1.19-1.05 (m, 3H), 0.57-0.27 (m, 6H); 982.5 $[M + H]^+$ . |
| C210 | 1H NMR (400 MHz, DMSO-d6) δ (ppm) 8.77 (d, J = 7.6 Hz, 1H), 8.28 (s, 1H), 8.13-7.99 (m, 2H), 7.61 (d, J = 8.5 Hz, 1H), 7.39-7.26 (m, 6H), 7.24-7.13 (m, 4H), 6.24-6.06 (m, 2H), 4.78-4.64 (m, 1H), 4.48 (t, J = 8.6 Hz, 1H), 4.36-4.23 (m, 1H), 4.11 (t, J = 8.6 Hz, 1H), 3.96-3.85 (m, 2H), 3.77-3.63 (m, 2H), 3.59-3.46 (m, 1H), 3.07-2.90 (m, 2H), 2.84-2.69 (m, 1H), 2.38-2.17 (m, 3H), 2.14-2.03 (m, 3H), 2.02-1.90 (m, 6H), 1.86-1.44 (m, 11H), 0.94 (d, J = 7.1 Hz, 3H), 0.81 (t, J = 7.4 Hz, 3H), 0.54-0.37 (m, 2H); 994 $[M + H]^+$ . |

TABLE 1C-continued

| | |
|---|---|
| C211 | 1H NMR (400 MHz, DMSO) δ 8.82-8.71 (m, 1H), 8.24 (s, 1H), 8.02 (d, J = 8.4 Hz, 1H), 7.95 (s, 1H), 7.50 (d, J = 8.5 Hz, 1H), 7.36-7.26 (m, 4H), 7.24-7.18 (m, 1H), 5.98-5.82 (m, 1H), 5.37-5.25 (m, 1H), 4.75-4.64 (m, 1H), 4.57-4.43 (m, 2H), 4.35-4.22 (m, 1H), 4.16-4.06 (m, 1H), 4.01-3.94 (m, 2H), 3.78-3.66 (m, 3H), 3.59-3.49 (m, 1H), 3.04-2.93 (m, 1H), 2.70-2.59 (m, 2H), 2.44-2.30 (m, 2H), 2.26-2.19 (m, 1H), 2.18-2.08 (m, 2H), 2.03-1.91 (m, 6H), 1.90-1.50 (m, 12H), 1.36-1.30 (m, 3H), 1.27-1.23 (m, 3H), 0.91-0.85 (m, 3H), 0.84-0.78 (m, 6H), 0.53-0.38 (m, 2H); 1004.7 $[M + H]^+$ . |
| C212 | 1H NMR (400 MHz, DMSO) δ 8.87-8.66 (m, 1H), 8.25 (s, 1H), 8.08-7.88 (m, 2H), 7.50 (d, J = 8.5 Hz, 1H), 7.40-7.17 (m, 5H), 5.99-5.73 (m, 1H), 5.30-5.16 (m, 1H), 4.76-4.63 (m, 2H), 4.57-4.42 (m, 2H), 4.34-4.25 (m, 1H), 4.15-4.07 (m, 1H), 4.02-3.90 (m, 2H), 3.81-3.66 (m, 1H), 3.57-3.45 (m, 1H), 3.04-2.93 (m, 1H), 2.72-2.59 (m, 2H), 2.45-2.29 (m, 2H), 2.24-2.07 (m, 3H), 2.02-1.92 (m, 6H), 1.89-1.48 (m, 11H), 1.34-1.10 (m, 12H), 0.92-0.81 (m, 3H), 0.54-0.36 (m, 2H); 990.9 [M+ H]+ |

TABLE 1C-continued

| | |
|---|---|
| C213 | 1H NMR (400 MHz, DMSO) δ 8.76 (m, 1H), 8.24 (s, 1H), 8.02 (d, J = 8.4 Hz, 1H), 7.94 (s, 1H), 7.49 (d, J = 8.5 Hz, 1H), 7.39-7.25 (m, 4H), 7.25-7.16 (m, 1H), 6.00-5.79 (m, 1H), 5.42-5.25 (m, 1H), 4.77-4.64 (m, 1H), 4.61-4.41 (m, 2H), 4.35-4.25 (m, 1H), 4.17-4.08 (m, 1H), 4.02-3.86 (m, 4H), 3.82-3.65 (m, 1H), 3.58-3.48 (m, 1H), 3.07-2.94 (m, 1H), 2.73-2.55 (m, 2H), 2.45-2.29 (m, 2H), 2.28-2.19 (m, 1H), 2.17-2.09 (m, 2H), 2.05. 1.92 (m, 6H), 1.90-1.66 (m, 5H), 1.62-1.44 (m, 8H), 1.36-1.20 (m, 8H), 0.93-0.85 (m, 3H), 0.84-0.77 (m, 3H), 0.54-0.37 (m, 2H); 1004 [M+ H]+ |
| C214 | 1H NMR (400 MHz, DMSO) § 8.79-8.72 (m, 1H), 8.24 (s, 1H), 8.02 (d, J = 8.4 Hz, 1H), 7.95 (s, 1H), 7.49 (d, J = 8.4 Hz, 1H), 7.36-7.27 (m, 4H), 7.23-7.18 (m, 1H), 5.98-5.81 (m, 1H), 5.37-5.26 (m, 1H), 4.76-4.66 (m, 1H), 4.57-4.44 (m, 2H), 4.33-4.23 (m, 1H), 4.16-4.07 (m, 1H), 4.00-3.85 (m, 4H), 3.76-3.68 (m, 1H), 3.58-3.49 (m, 1H), 3.06-2.92 (m, 1H), 2.70-2.59 (m, 2H), 2.45-2.30 (m, 2H), 2.27-2.19 (m, 1H), 2.18-2.10 (m, 2H), 2.02-1.92 (m, 6H), 1.91-1.61 (m, 6H), 1.60-1.50 (m, 7H), 1.37-1.30 (m, 3H), 1.26-1.21 (m, 3H), 0.91-0.79 (m, 6H), 0.52-0.40 (m, 2H); 990.9 $[M + H]^+$ . |

TABLE 1C-continued

| | |
|---|---|
| C215 | 1H NMR (400 MHz, DMSO) & 8.79-8.70 (m, 1H), 8.27-8.21 (m, 1H), 8.06-7.99 (d, J = 8.4 Hz, 1H), 7.95 (s, 1H), 7.53-7.44 (d, J = 8.5 Hz, 1H), 7.38-7.27 (m, 4H), 7.21 (m, 1H), 5.98-5.77 (m, 1H), 5.39-5.30 (m, 1H), 4.75-4.66 (m, 1H), 4.59-4.43 (m, 2H), 4.37-4.23 (m, 1H), 4.18-4.08 (m, 1H), 4.07-3.93 (m, 4H), 3.73 (m, 1H), 3.58-3.50 (m, 1H), 3.05-2.95 (m, 1H), 2.70-2.58 (m, 2H), 2.48-2.45 (m, 1H), 2.45-2.38 (m, 1H), 2.36-2.30 (m, 1H), 2.27-2.19 (m, 1H), 2.18-2.08 (m, 2H), 2.02-1.92 (m, 6H), 1.88-1.63 (m, 5H), 1.60-1.51 (m, 5H), 1.35-1.27 (m, 3H), 1.24-1.14 (m, 6H), 0.91-0.85 (m, 3H), 0.53-0.40 (m, 2H); 976.8 $[M + H]^+$ . |

Example 2: SH2 Scan Assay

SH2 domain-tagged T7 phage strains were prepared in an *E. coli* host derived from the BL21 strain. *E. coli* were grown to log-phase and infected with T7 phage and incubated with shaking at 32° C. until lysis. The lysates were centrifuged and filtered to remove cell debris. The remaining SH2 domains were produced in HEK-293 cells and subsequently tagged with DNA for qPCR detection. Streptavidin-coated magnetic beads were treated with biotinylated small molecule ligands for 30 minutes at room temperature to generate affinity resins for SH2 domain assays. The liganded beads were blocked with excess biotin and washed with blocking buffer (SeaBlock (Pierce), 1% BSA, 0.05% Tween 20, 1 mM DTT) to remove unbound ligand and to reduce non-specific binding. Binding reactions were assembled by combining SH2 domains, liganded affinity beads, and test compounds in 1× binding buffer (10 mM HEPES, 50 mM NaCl, 1 mM EDTA, 0.01% Tween 20, 6 mM DTT). Test compounds were prepared as 111× stocks in 100% DMSO. Kds were determined using an 11-point 3-fold compound dilution series with three DMSO control points. All compounds for Kd measurements were distributed by acoustic transfer (non-contact dispensing) in 100% DMSO. The compounds were then diluted directly into the assays such that the final concentration of DMSO was 0.9%. All reactions were performed in polypropylene 384-well plate. Each was a final volume of 0.02 ml. The assay plates were incubated at room temperature with shaking for 1 hour and the affinity beads were washed with wash buffer (10 mM HEPES, 50 mM NaCl, 1 mM EDTA, 0.01% Tween 20). The beads were then re-suspended in elution buffer (10 mM HEPES, 50 mM NaCl, 1 mM EDTA, 0.01% Tween 20, 20 mM sodium phenyl phosphate) and incubated at room temperature with shaking for 30 minutes. The SH2 domain concentration in the eluates was measured by qPCR.

Results are shown in Table 2 for STAT1, STAT2, STAT3, STAT4, STAT5a, and STAT5b Kds, where 5 nM≤A<50 nM, 50 nM≤B<100 nM, 100 nM≤C<500 nM, 500 nM≤D<1000 nM, 1000 nM≤E<5000 nM (E* indicates only that the Kd was determined to be >1000 nM), 5000 nM≤F<10000 nM, and G>10000 nM; NT=not tested.

TABLE 2

| | (STAT1/2/3/4/5a/5b) | | | | | |
|---|---|---|---|---|---|---|
| No. | STAT1 | STAT2 | STAT3 | STAT4 | STAT5a | STAT5b |
| A1 | F | E | F | F | C | C |
| A2 | F | C | E | F | E | C |
| A3 | G | E | F | F | D | C |
| A4 | F | C | E | E | C | C |
| A5 | F | E | F | G | D | D |
| A6 | E | C | D | F | A | A |
| A7 | E* | D | D | E* | A | B |
| A8 | A | C | A | C | A | A |
| A9 | D | E* | D | E* | NT | A |
| A10 | E* | E* | E* | E* | C | C |
| A11 | E* | C | E* | E* | A | A |
| A12 | B | D | A | E* | B | A |
| A13 | E* | E* | E* | E* | A | B |
| A14 | E* | D | E* | E* | C | B |
| A15 | E* | E* | E* | E* | C | C |

TABLE 2-continued

| (STAT1/2/3/4/5a/5b) | | | | | | |
|---|---|---|---|---|---|---|
| No. | STAT1 | STAT2 | STAT3 | STAT4 | STAT5a | STAT5b |
| A16 | E* | D | E* | E* | B | C |
| A17 | E* | E* | E* | E* | C | C |
| A18 | E* | C | E* | E* | A | A |
| A19 | E* | C | E* | D | B | B |
| A20 | E* | E* | E* | E* | C | C |
| A21 | G | D | E | F | C | C |
| A22 | E* | D | E* | E* | C | B |
| A23 | E* | D | E* | E* | B | B |
| A24 | E* | E* | D | E* | D | D |
| A25 | E* | D | E* | E* | B | C |
| A26 | E* | E* | F* | E* | C | C |
| A27 | E* | E* | E* | E* | C | C |
| A28 | E* | E* | E* | E* | C | C |
| A29 | E* | E* | E* | E* | D | E* |
| A30 | E* | C | E* | E* | C | C |
| A31 | E* | E* | C | E* | E* | E* |
| A32 | D | E* | E* | E* | C | B |
| A33 | E* | D | E* | E* | C | B |
| A34 | E* | E* | E* | E* | C | C |
| A35 | E* | C | E* | E* | C | C |
| A36 | E* | E* | E* | E* | D | D |
| A37 | E* | E* | E* | E* | B | B |
| A38 | E* | E* | E* | E* | E* | E* |
| A39 | E* | E* | E* | E* | E* | E* |
| A40 | E* | E* | E* | E* | C | C |
| A41 | E* | E* | E* | E* | B | B |
| A42 | E* | D | E* | E* | C | C |
| A43 | E* | E* | E* | E* | C | C |
| A44 | E* | E* | E* | E* | D | D |
| A45 | E* | D | E* | E* | C | C |
| A46 | E* | E* | E* | E* | C | E* |
| A47 | E* | E* | E* | E* | C | C |
| A48 | E* | E* | E* | E* | B | C |
| A49 | E* | E* | E* | E* | C | C |
| A50 | E* | E* | E* | E* | E* | E* |
| A51 | E* | E* | E* | E* | E* | E* |
| A52 | E* | E* | E* | E* | C | D |
| A53 | E* | E* | E* | E* | D | E* |
| A54 | E* | D | E* | E* | B | B |
| A55 | E* | C | E* | E* | B | B |
| A56 | E* | E* | D | E* | B | C |
| A57 | E* | E* | E* | E* | C | C |
| A58 | E* | D | E* | E* | C | C |
| A59 | E* | C | C | E* | C | C |
| A60 | E* | E* | E* | E* | D | D |
| A61 | E* | E* | E* | E* | E* | E* |
| A62 | E* | E* | E* | E* | D | C |
| A63 | E* | E* | E* | E* | C | D |
| A64 | E* | E* | E* | E* | C | C |
| A65 | — | D | D | D | C | C |
| B1 | E* | E* | E* | E* | E* | E* |
| B2 | F | E | G | G | E | E |
| B3 | G | F | G | G | E | E |
| B4 | G | E | G | G | E | E |
| B5 | G | F | G | G | E | E |
| B6 | F | E | G | G | E | E |
| B7 | E* | E* | E* | E* | D | D |
| B8 | G | G | G | G | E | E |
| B9 | E* | E* | E* | E* | C | D |
| B10 | G | E | G | G | G | F |
| B11 | G | E | G | G | C | D |
| B12 | G | F | G | G | E | F |
| B13 | G | G | G | G | G | G |
| B14 | E* | E* | E* | E* | E* | E* |
| B15 | E* | E* | E* | E* | E* | E* |
| B16 | E* | E* | E* | E* | E* | E* |
| B17 | E* | E* | E* | E* | E* | E* |
| B18 | E* | E* | E* | E* | D | D |
| B19 | E* | E* | E* | E* | C | C |
| B20 | E* | E* | E* | E* | E* | E* |
| B21 | E* | E* | E* | E* | E* | E* |
| B22 | E* | E* | E* | E* | E* | E* |
| B23 | E* | E* | E* | E* | E* | E* |
| B24 | E* | E* | E* | E* | D | E* |
| B25 | E* | E* | E* | E* | E* | E* |
| B26 | E* | E* | E* | E* | E* | E* |

TABLE 2-continued

| (STAT1/2/3/4/5a/5b) | | | | | | |
|---|---|---|---|---|---|---|
| No. | STAT1 | STAT2 | STAT3 | STAT4 | STAT5a | STAT5b |
| B27 | E* | E* | E* | E* | E* | E* |
| B28 | E* | E* | E* | E* | E* | E* |

Results are shown in Table 3 for STAT6 Kd, where A<0.1 nM; 0.1 nM≤B<0.5 nM; 0.5 nM≤C<1 nM; 1 nM≤D<5 nM; and E≥5 nM.

TABLE 3

| (STAT6) | |
|---|---|
| No. | STAT6 |
| A1 | B |
| A2 | B |
| A3 | A |
| A4 | A |
| A5 | A |
| A6 | A |
| A7 | A |
| A8 | A |
| A9 | B |
| A10 | D |
| A11 | A |
| A12 | B |
| A13 | A |
| A14 | A |
| A15 | B |
| A16 | B |
| A17 | B |
| A18 | A |
| A19 | A |
| A20 | A |
| A21 | A |
| A22 | A |
| A23 | A |
| A24 | C |
| A25 | A |
| A26 | C |
| A27 | B |
| A28 | B |
| A29 | B |
| A30 | A |
| A31 | C |
| A32 | A |
| A33 | A |
| A34 | B |
| A35 | A |
| A36 | A |
| A37 | A |
| A38 | A |
| A39 | B |
| A40 | A |
| A41 | B |
| A42 | A |
| A43 | A |
| A44 | A |
| A45 | B |
| A46 | B |
| A47 | A |
| A48 | A |
| A49 | A |
| A50 | A |
| A51 | B |
| A52 | A |
| A53 | A |
| A54 | B |
| A55 | A |
| A56 | B |
| A57 | A |
| A58 | A |
| A59 | A |
| A60 | A |
| A61 | A |

TABLE 3-continued (STAT6)

| No. | STAT6 |
|---|---|
| A62 | B |
| A63 | B |
| A64 | B |
| A65 | A |
| B1 | C |
| B2 | B |
| B3 | B |
| B4 | B |
| B5 | B |
| B6 | B |
| B7 | B |
| B8 | D |
| B9 | C |
| B10 | D |
| B11 | B |
| B12 | C |
| B13 | E |
| B14 | B |
| B15 | E |
| B16 | B |
| B17 | D |
| B18 | B |
| B19 | B |
| B20 | E |
| B21 | E |
| B22 | D |
| B23 | D |
| B24 | D |
| B25 | C |
| B26 | D |
| B27 | B |
| B28 | E |

Example 3: MSD-pSTAT-PBMC Assay

Materials: Cryopreserved Peripheral Blood Mononuclear Cells (PBMC) are from STEM CELL. Recombinant Human IL-4 is from Peprotech. Rabbit monoclonal Anti-pY641-STAT6 antibody, and lysis buffer are from Cell Signaling Technology (CST). Mouse monoclonal anti-STAT6 antibody is from BioLegend. Assay plates, blocker, and anti-rabbit secondary antibody are from Meso Scale Discovery (MSD).

Assay Method: Cryopreserved PBMCs were thawed out and allowed to recover overnight in IMDM+10% heat-inactivated FBS prior to plating 30,000 (STAT6) cells per well in 96-well U-bottom tissue culture plates. Cells were treated with compound for 3 hrs or 20 hrs, then stimulated with 1 ng/mL IL-4 (STAT6) for 10 min. Cells were then spun down and washed with ice-cold PBS prior to lysing the cell pellet with 1× lysis buffer (CST) with 1×HALT protease and phosphatase inhibitor cocktail (Thermo). Lysates were freeze-thawed and then transferred to and incubated overnight at 4° C. with shaking in QuickPlex 96-well high bind assay plates (MSD) pre-coated overnight with 30 µL per well of 2 µg/mL mouse monoclonal anti-STAT6 antibody (STAT6) in 1×PBS, and pre-blocked for 1 hour with 3% Blocker-A (MSD). Captured protein in the assay plates were then washed and probed with 25 µL per well of 0.18 µg/ml rabbit monoclonal Anti-pY641-STAT6 antibody (STAT6) in 1% Blocker-A for 1 hour at room temperature with shaking, then washed and probed with 25 ul per well of 1 ug/ml Sulfo-TAG Labeled Goat Anti-Rabbit Antibody (MSD) in 1% Blocker-A for 1 hour at room temperature with shaking. Assay plates were then washed and 150 µL of 1× Read Buffer-T (MSD) was added to each well prior to reading on an SQ120 MSD Plate Reader. Assay signal from each sample was subtracted by the signal from unstimulated control wells and normalized to DMSO control wells. $IC_{50}$ values were calculated using Graph Pad Prism Dose-Response Nonlinear Regression with variable slope. Results are shown in Table 4. For pSTAT6: A<1 nM; 1 nM≤B<5 nM; 5 nM≤C<10 nM; 10 nM≤D<50 nM; and E≥50 nM.

TABLE 4

(pSTAT6)

| No. | pSTAT6 |
|---|---|
| C1 | B |
| C2 | B |
| C3 | B |
| C4 | A |
| C5 | A |
| C6 | A |
| C7 | A |
| C8 | A |
| C9 | B |
| C10 | A |
| C11 | B |
| C12 | B |
| C13 | A |
| C14 | B |
| C15 | B |
| C16 | B |
| C17 | A |
| C18 | B |
| C19 | A |
| C20 | B |
| C21 | D |
| C22 | C |
| C23 | A |
| C24 | B |
| C25 | A |
| C26 | B |
| C27 | C |
| C28 | B |
| C29 | C |
| C30 | D |
| C31 | D |
| C32 | B |
| C33 | D |
| C34 | B |
| C35 | D |
| C36 | C |
| C37 | B |
| C38 | B |
| C39 | C |
| C40 | B |
| C41 | C |
| C42 | D |
| C43 | E |
| C44 | D |
| C45 | D |
| C46 | D |
| C47 | D |
| C48 | E |
| C49 | D |
| C50 | B |
| C51 | D |
| C52 | B |
| C53 | A |
| C54 | A |
| C55 | B |
| C56 | B |
| C57 | B |
| C59 | B |
| C60 | B |
| C61 | A |
| C62 | B |
| C63 | A |
| C64 | A |
| C65 | A |
| C66 | A |
| C67 | B |
| C68 | A |

TABLE 4-continued

| (pSTAT6) | |
|---|---|
| No. | pSTAT6 |
| C69 | B |
| C70 | A |
| C71 | A |
| C72 | B |
| C73 | A |
| C74 | A |
| C75 | A |
| C76 | B |
| C77 | B |
| C78 | B |
| C79 | B |
| C80 | B |
| C81 | B |
| C82 | A |
| C83 | A |
| C84 | A |
| C85 | B |
| C86 | B |
| C87 | B |
| C88 | B |
| C89 | A |
| C90 | A |
| C91 | A |
| C92 | A |
| C93 | A |
| C94 | A |
| C95 | B |
| C105 | A |
| C106 | A |
| C107 | A |
| C108 | B |
| C109 | C |
| C110 | A |
| C111 | A |
| C112 | B |
| C113 | B |
| C114 | A |
| C115 | B |
| C116 | A |
| C117 | B |
| C118 | A |
| C119 | B |
| C120 | B |
| C121 | A |
| C122 | A |
| C123 | A |
| C124 | A |
| C125 | A |
| C126 | A |
| C127 | A |
| C128 | A |
| C129 | B |
| C130 | B |
| C131 | B |
| C132 | A |
| C133 | A |
| C134 | B |
| C135 | A |
| C136 | A |
| C137 | A |
| C138 | B |
| C139 | B |
| C140 | A |
| C141 | A |
| C142 | B |
| C143 | A |
| C144 | A |
| C145 | C |
| C146 | B |
| C147 | B |
| C148 | A |
| C149 | B |
| C150 | B |
| C151 | B |
| C152 | E |
| C153 | E |

TABLE 4-continued

| (pSTAT6) | |
|---|---|
| No. | pSTAT6 |
| C154 | B |
| C155 | A |
| C156 | A |
| C157 | B |
| C158 | B |
| C159 | B |
| C160 | A |
| C161 | B |
| C162 | A |
| C167 | B |
| C168 | D |
| C169 | C |
| C170 | A |
| C172 | B |
| C173 | A |
| C174 | B |
| C175 | A |
| C176 | A |
| C177 | A |
| C178 | B |
| C179 | B |
| C180 | A |
| C181 | C |
| C182 | A |
| C183 | B |
| C184 | B |
| C185 | A |
| C186 | A |
| C187 | B |
| C188 | A |
| C189 | A |
| C190 | C |
| C191 | B |
| C192 | B |
| C193 | B |
| C194 | A |
| C195 | A |
| C196 | B |
| C197 | A |
| C198 | A |
| C199 | B |
| C200 | B |
| C201 | B |
| C202 | B |
| C203 | B |
| C204 | C |
| C205 | A |
| C206 | E |
| C207 | E |
| C208 | A |
| C209 | A |
| C210 | B |
| C211 | C |
| C212 | B |
| C213 | B |
| C214 | B |
| C215 | B |

Example 4: Flow Cytometry-pSTAT6-Whole Blood Assay

Materials: Recombinant canine IL-4 is from Novus Biologics. PE anti-STAT6 Phospho (Tyr641) Antibody and Human TruStain FcX are from BioLegend. BD Phosflow Lyse/Fix Buffer 5× and BD Phosflow Perm Buffer III are from BD Biosciences.

Assay Method: Whole blood is serially collected into $K_2$EDTA tubes from beagle dogs via the cephalic or saphenous vein at various times pre- and post-dosing (P.O.) and stored on wet ice until the following protocol can be performed. 25 µL of each whole blood sample is stimulated with 1 ng/mL IL-4 for 15 min. Each sample then receives 500 μL of 1× Lyse/Fix Buffer, which is prepared by adding 4 volumes of water to 1 volume of 5× Lyse/Fix Buffer, and is incubated at 37° C. for 10 min. Samples are then spun down and washed with PBS prior to addition of 200 μL Perm Buffer III and incubation on ice for 30 min. Samples are then spun down and washed twice with PBS. Each sample is then stained with 50 μL of PBS containing 5 μL of Human TruStain FcX and incubated on ice for 15 min. Each sample then receives 50 μL of PBS containing 5 μL of PE anti-STAT6 Phospho (Tyr641) Antibody and is incubated at room temperature in the dark for 30 min. Samples are spun down and washed with PBS prior to final resuspension in 100 μL of PBS. Samples are analyzed on a flow cytometer capable of detecting signal from the PE fluorophore. Cells expressing pSTAT6 signal are determined by gating relative to a sample-matched unstimulated (no IL-4) control. Inhibition of pSTAT6 is determined by subtracting the percentage of pSTAT6 positive cells in each sample divided by the percentage of pSTAT6 positive cells in the animal-matched pre-dose control sample from 100. Additional normalization to a vehicle-matched control may be applied, such that the average inhibition of vehicle control samples at each individual timepoint is equal to 0%.

Example 5: PBMC PK Assay

Assay Method: Up to 5 mL whole blood is serially collected into $K_2EDTA$ tubes from beagle dogs via the cephalic or saphenous vein at various times pre- and post-dosing (P.O.) and stored on wet ice until the following protocol can be performed. Each whole blood sample is diluted with 10 volumes of RBC Lysis Buffer and incubated on ice for 10 min with mixing. Samples are quenched with ice-cold PBS, spun down at 4° C., and washed again with ice-cold PBS prior to resuspension in 1 mL ice-cold PBS. PBMC counts are determined, and samples are spun down at 4° C. Supernatants are removed from each cell pellet and a normalized volume of 70% methanol containing 1% formic acid is added to each sample based on the lowest cell count within the experiment, such that the sample with the lowest cell count is resuspended in 100 μL of the 70% methanol/1% formic acid solution. Samples are vortexed for 1-2 min and stored as a mixture at −80° C. until LC-MS/MS analysis can be performed. Upon LC-MS/MS analysis, samples are spun down and, once pelleted, 20-30 μL of supernatant is added to 200 μL of acetonitrile containing 1% formic acid and 40 ng/mL diclofenac internal standard. The samples are vortexed for 1 minute, spun down, and 100 μL is transferred to a new plate. The samples are then injected for LC-MS/MS analysis. The amount of analyte (parent drug) in each sample is determined by comparing the detected peak counts normalized to the internal standard to a standard curve generated from known amounts of analyte. Intracellular PBMC concentrations are determined by calculating the mass of analyte detected in each cell pellet divided by the volume of cells within that pellet, assuming an individual cell volume of 2E-13 L. PBMC PK averages are calculated by averaging the intracellular PBMC PK concentrations at individual timepoints collected over a 24-hour period. PBMC PK AUCs are determined by multiplying the PBMC PK average by 24 to approximate the area under the curve over a full 24-hour period.

Example 6: CD23 Expression and TARC Production

Assay Method: Frozen human PBMCs are thawed and rested overnight at 37° C., 5% $CO_2$. The following day 50,000 cells are plated in 96-well dishes, dosed with diluting concentrations of test article (1,000-10,000 nM top concentration; 1:3-1:5 dilution) and stimulated with 10 ng/mL IL-4 and 10 μg/mL anti-IFN-γ or 1 ng/mL IL-13. For assessment of the induction of CD23 surface expression, cells are collected after 4 days of incubation at 37° C., 5% $CO_2$ and evaluated by flow cytometry to determine the CD23 mean fluorescence intensity on CD23 positive cells. For assessment of TARC production, supernatants are collected after 4 days of incubation at 37° C., 5% $CO_2$ and amounts of TARC protein are measured by electrochemiluminescence (Meso Scale discovery).

What is claimed is:

1. A compound of Formula (I), (I)

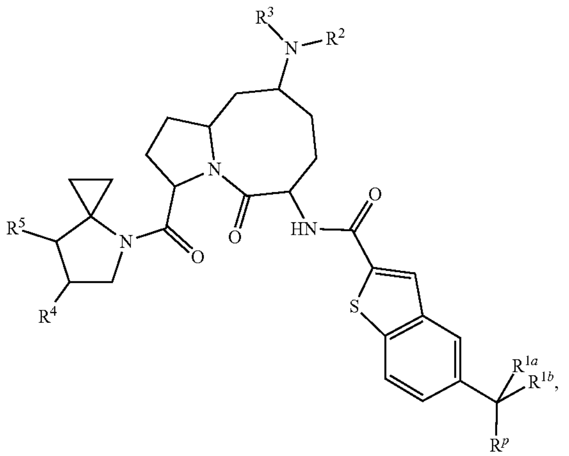

or a pharmaceutically acceptable salt thereof, wherein:

$R^{1a}$ and $R^{1b}$ are each independently H or halogen;

$R^2$ is H, $(C_1-C_6)$alkyl, or $(C_3-C_6)$cycloalkyl;

$R^3$ is $(C_1-C_6)$alkyl, halo$(C_1-C_6)$alkyl, $(C_3-C_6)$cycloalkyl, 3- to 7-membered heterocyclyl, —$(C_1-C_6)$alkylene-$(C_3-C_6)$cycloalkyl, or —$(C_1-C_6)$alkylene-(3- to 7-membered heterocyclyl), wherein $(C_1-C_6)$alkyl, $(C_3-C_6)$cycloalkyl, $(C_3-C_6)$cycloalkyl of —$(C_1-C_6)$alkylene-$(C_3-C_6)$cycloalkyl, or (3- to 7-membered heterocyclyl) of —$(C_1-C_6)$alkylene-(3- to 7-membered heterocyclyl) is each substituted with 0, 1, 2, 3, 4, or 5 substituents each independently selected from the group consisting of $(C_1-C_6)$alkyl, $(C_1-C_6)$alkoxy, cyano, halogen, halo$(C_1-C_6)$alkyl, and halo$(C_1-C_6)$alkoxy;

$R^4$ is H, $(C_6-C_{10})$aryl, or 5- to 10-membered heteroaryl, wherein $(C_6-C_{10})$aryl or 5- to 10-membered heteroaryl is each substituted with 0, 1, 2, or 3 substituents each independently selected from the group consisting of halogen, cyano, $(C_1-C_6)$alkyl, $(C_1-C_6)$alkoxy, halo$(C_1-C_6)$alkyl, halo$(C_1-C_6)$alkoxy, and —$NR^{4a}R^{4b}$, wherein: each $R^{4a}$ and $R^{4b}$ is independently H or $(C_1-C_6)$alkyl;

$R^5$ is H;

$R^P$ is;

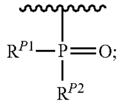

$R^{P1}$ and $R^{P2}$ are each independently —OH, —$OR^{Pa}$, N-linked amino acid, N-linked amino acid ester, or

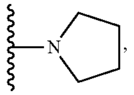

wherein

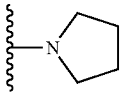 [SMILES: *N1CCCC1]

is substituted with 0, 1, 2, or 3 substituents each independently selected from the group consisting of halo, oxo, COOH, and —C(O)$OR^{PE}$;

each $R^{Pa}$ is independently ($C_1$-$C_6$)alkyl, halo($C_1$-$C_6$)alkyl, ($C_6$-$C_{10}$)aryl, or ($C_3$-$C_6$)cycloalkyl, wherein ($C_1$-$C_6$)alkyl is substituted with 0, 1, 2, or 3 substituents each independently selected from the group consisting of halo and ($C_1$-$C_6$)alkoxy; and each $R^{PE}$ is independently ($C_1$-$C_6$)alkyl, halo($C_1$-$C_6$)alkyl, —($C_1$-$C_6$)alkylene-($C_1$-$C_6$)alkoxy, ($C_3$-$C_6$)cycloalkyl, ($C_5$-$C_8$)spirocycloalkyl, —($C_1$-$C_6$)alkylene-($C_6$-$C_{10}$)aryl, —($C_1$-$C_6$)alkylene-($C_3$-$C_7$)cycloalkyl, 3- to 7-membered heterocyclyl, or —($C_1$-$C_6$)alkylene-(3- to 7-membered heterocyclyl), wherein ($C_1$-$C_6$)alkyl, ($C_3$-$C_6$)cycloalkyl, ($C_5$-$C_8$)spirocycloalkyl, or ($C_3$-$C_7$) cycloalkyl of —($C_1$-$C_6$)alkylene-($C_3$-$C_7$)cycloalkyl is each substituted with 0, 1, 2, or 3 independently selected halogen.

2. The compound of claim 1, or a pharmaceutically acceptable salt thereof, wherein $R^{P1}$ is —$OR^{Pa}$ and $R^{P2}$ is N-linked amino acid ester, wherein:

N-linked amino acid ester is —$NR^{Paa1}CR^{Paa2}R^{Paa3}C(O)OR^{Paa4}$;

$R^{Paa1}$ is H or ($C_1$-$C_6$)alkyl;

$R^{Paa2}$ is H or ($C_1$-$C_6$)alkyl, and $R^{Paa3}$ is H, ($C_1$-$C_6$)alkyl, —($C_1$-$C_6$)alkylene-($C_1$-$C_6$)alkoxy, or —($C_1$-$C_6$)alkylene-($C_6$-$C_{10}$)aryl; or $R^{Paa2}$ and $R^{Paa3}$, together with the carbon atom to which they are attached, form ($C_3$-$C_6$)cycloalkyl; and $R^{Paa4}$ is ($C_1$-$C_6$)alkyl, halo($C_1$-$C_6$)alkyl, —($C_1$-$C_6$)alkylene-($C_1$-$C_6$)alkoxy, ($C_3$-$C_6$)cycloalkyl, ($C_5$-$C_8$)spirocycloalkyl, —($C_1$-$C_6$)alkylene-($C_6$-$C_{10}$)aryl, —($C_1$-$C_6$)alkylene-($C_3$-$C_7$)cycloalkyl, 3- to 7-membered heterocyclyl, or —($C_1$-$C_6$)alkylene-(3- to 7-membered heterocyclyl), wherein ($C_1$-$C_6$)alkyl, ($C_3$-$C_6$)cycloalkyl, ($C_5$-$C_8$)spirocycloalkyl, or ($C_3$-$C_7$)cycloalkyl of —($C_1$-$C_6$)alkylene-($C_3$-$C_7$)cycloalkyl is each substituted with 0, 1, 2, or 3 independently selected halogen.

3. The compound of claim 1, wherein the compound is selected from the group consisting of:

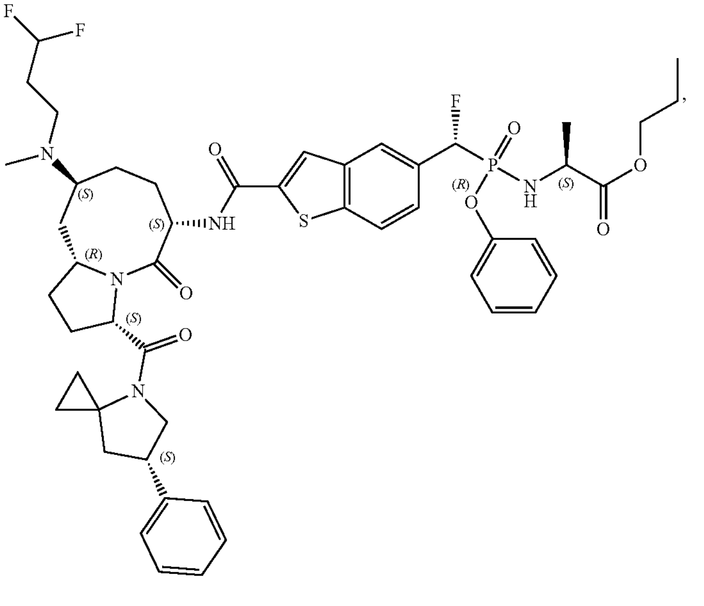

-continued
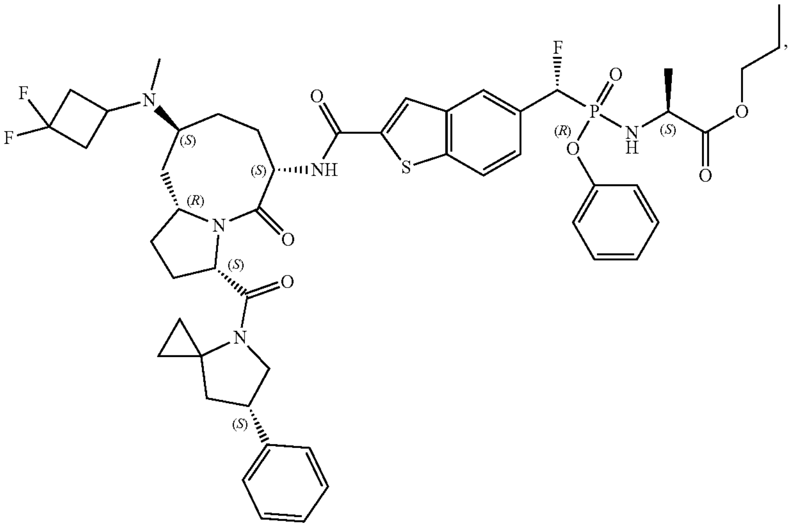
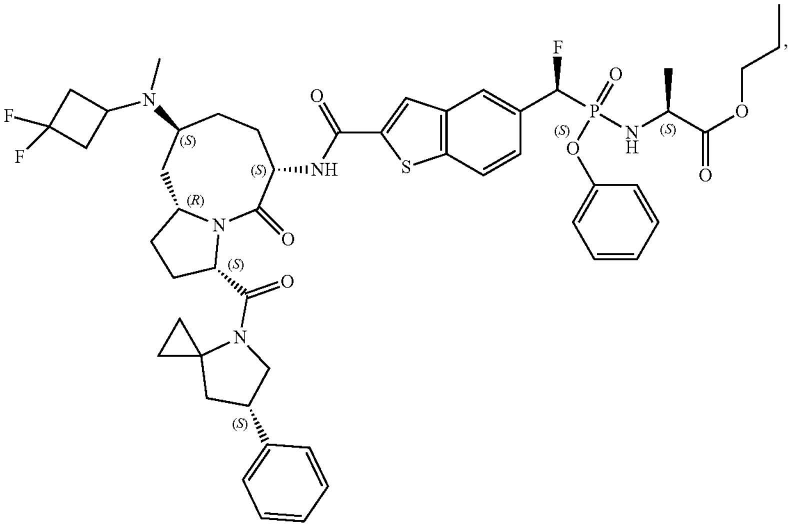
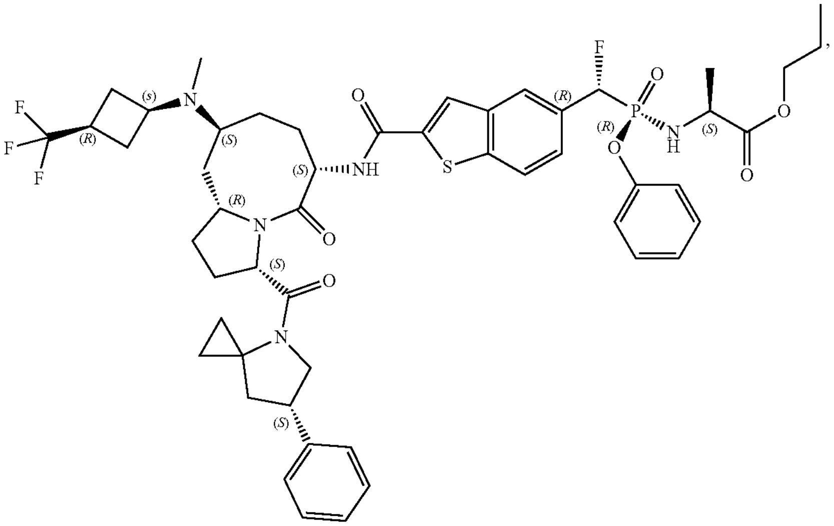

-continued
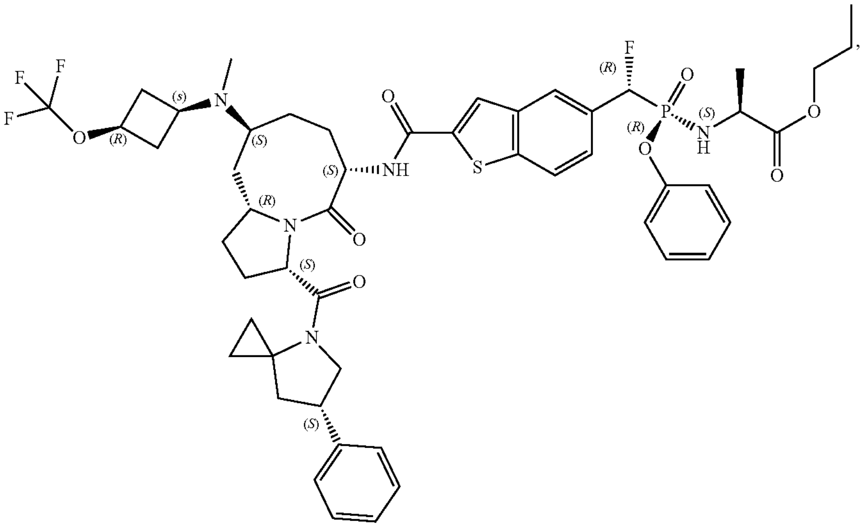
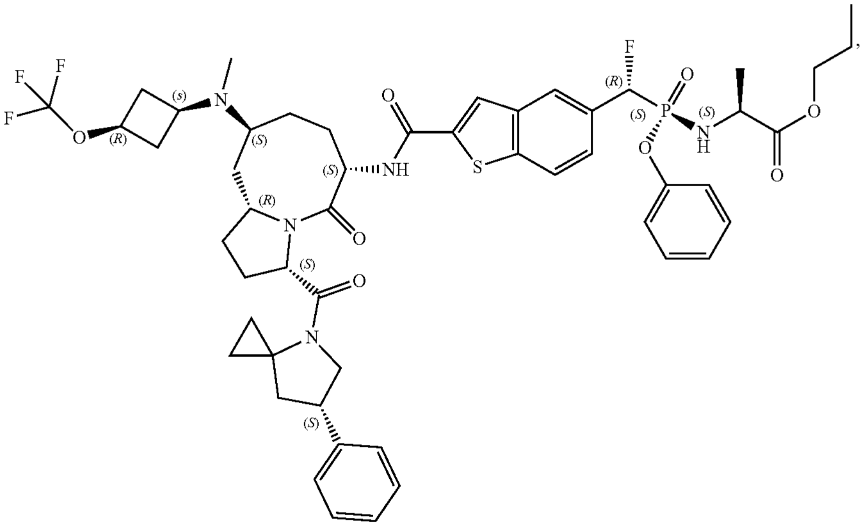
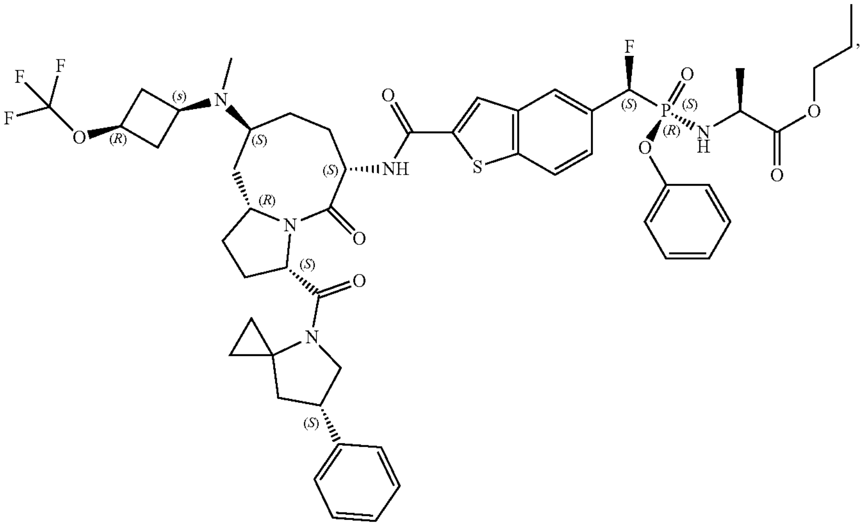

-continued
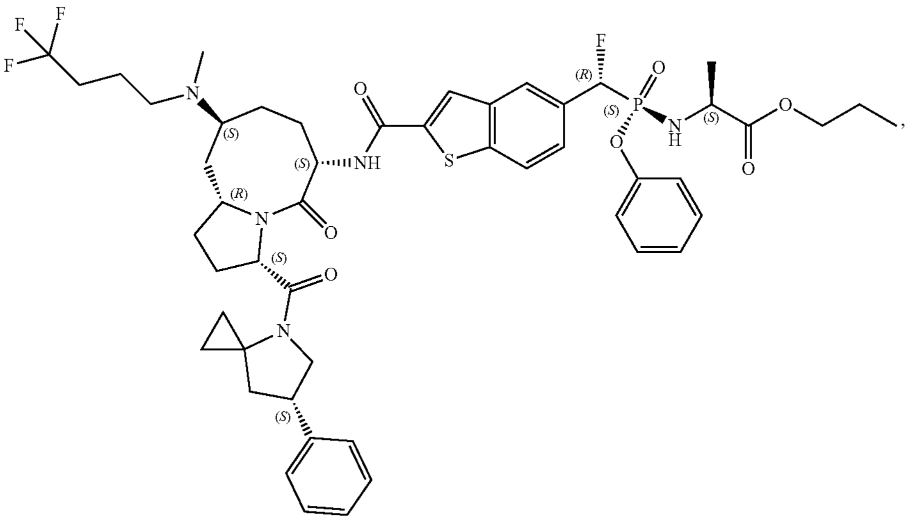
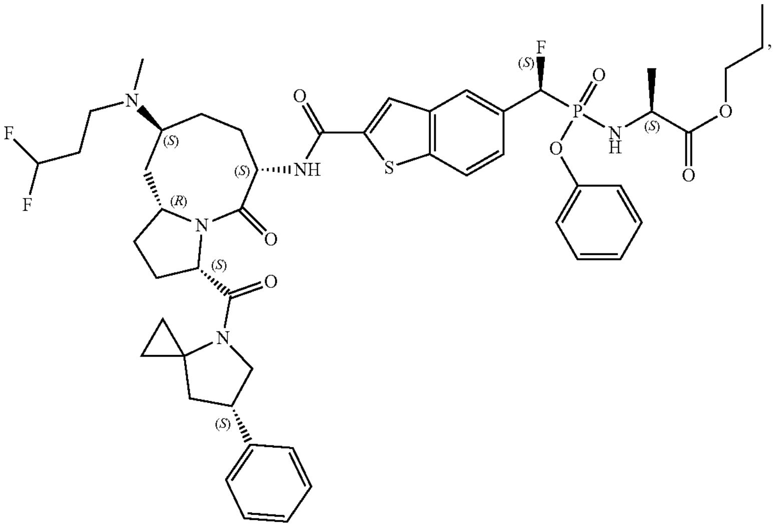
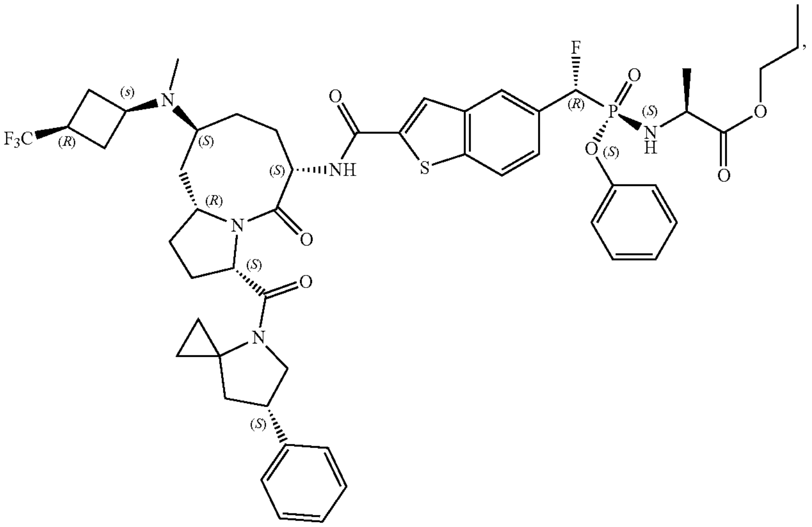

-continued
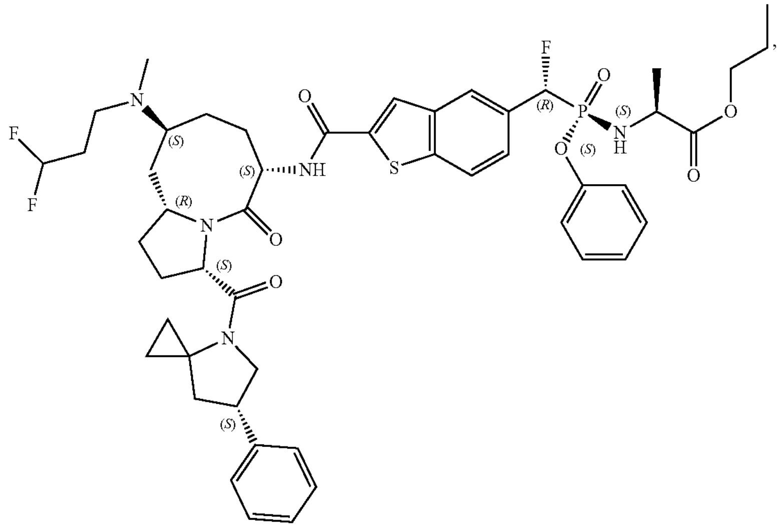
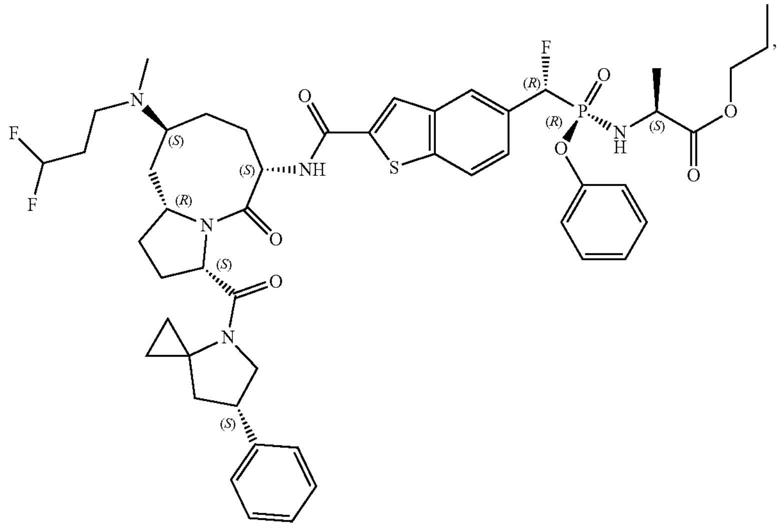
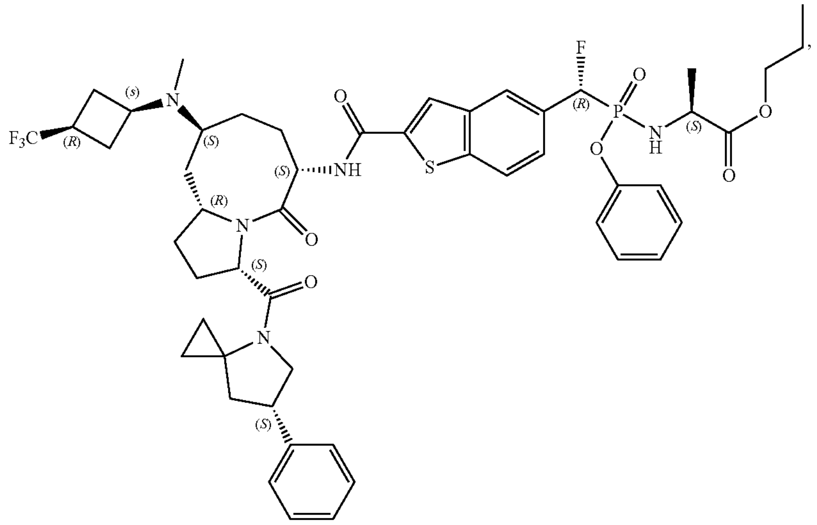

-continued
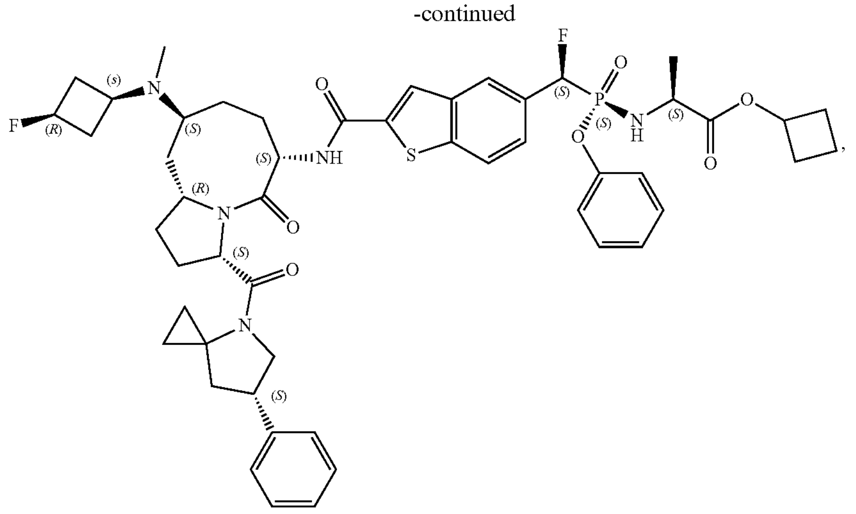
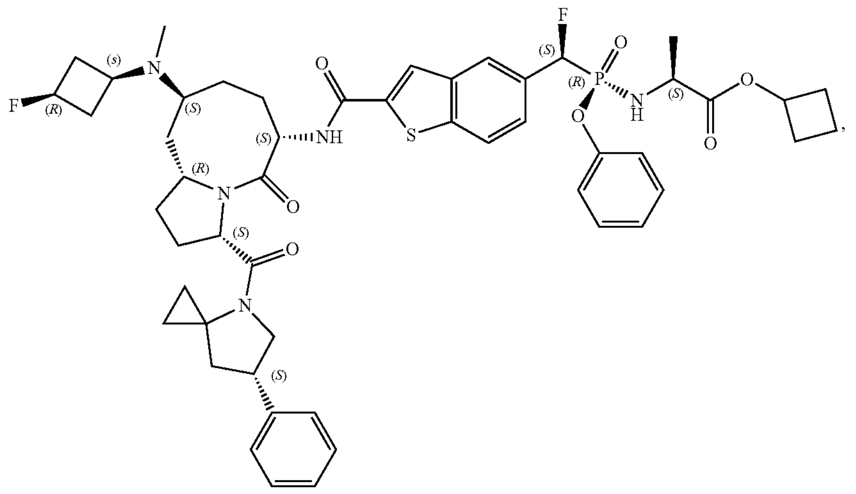
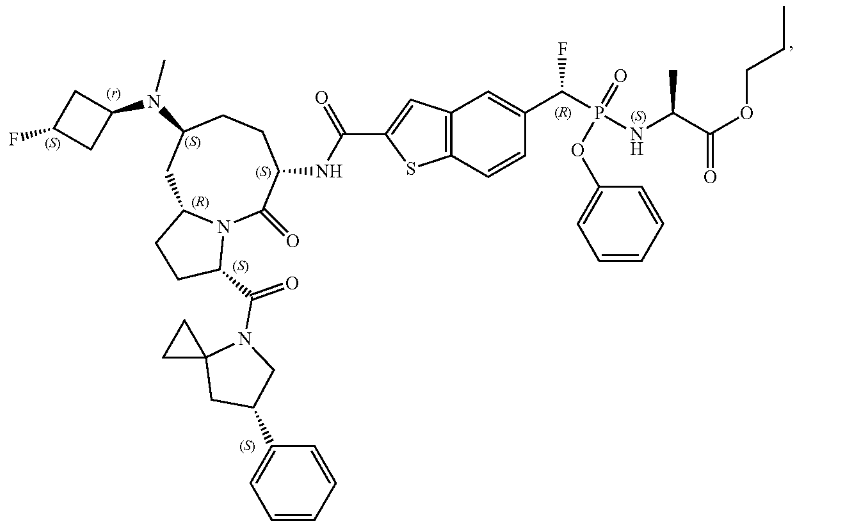

-continued
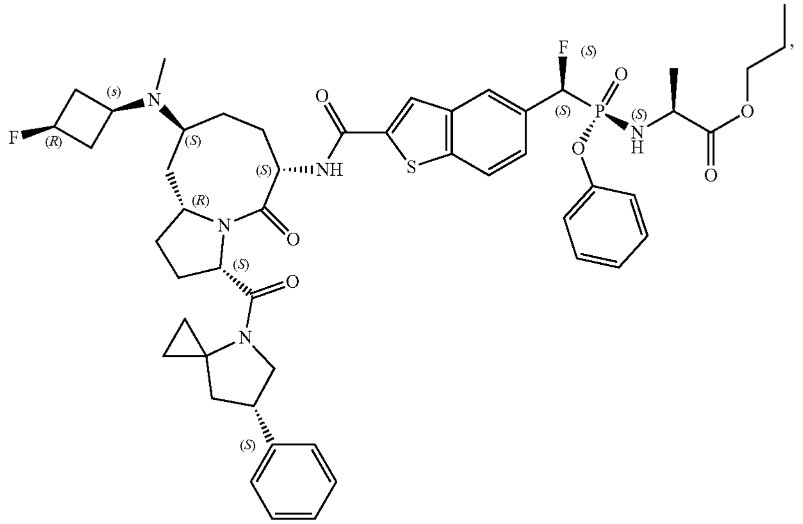
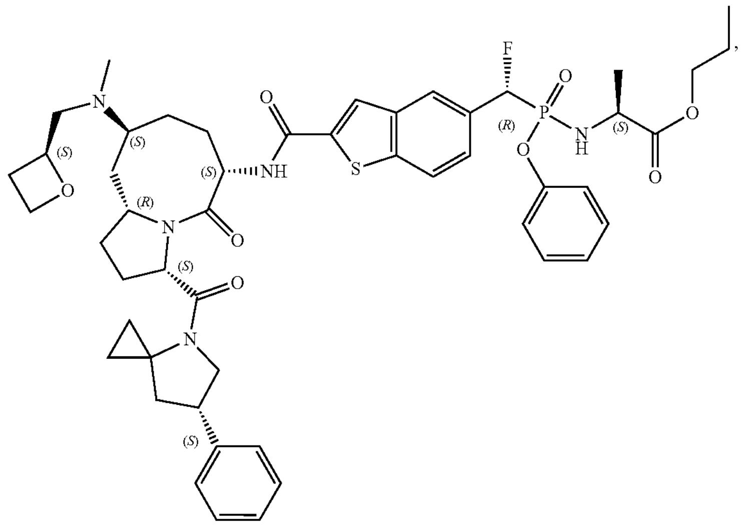
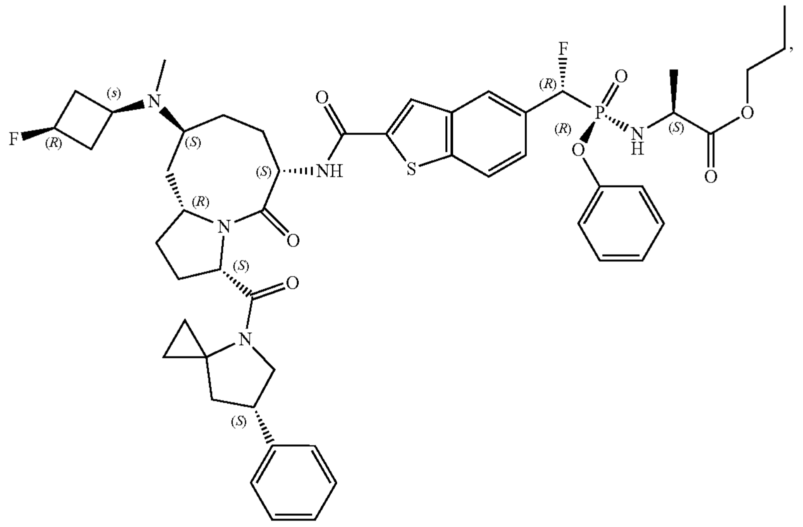

-continued
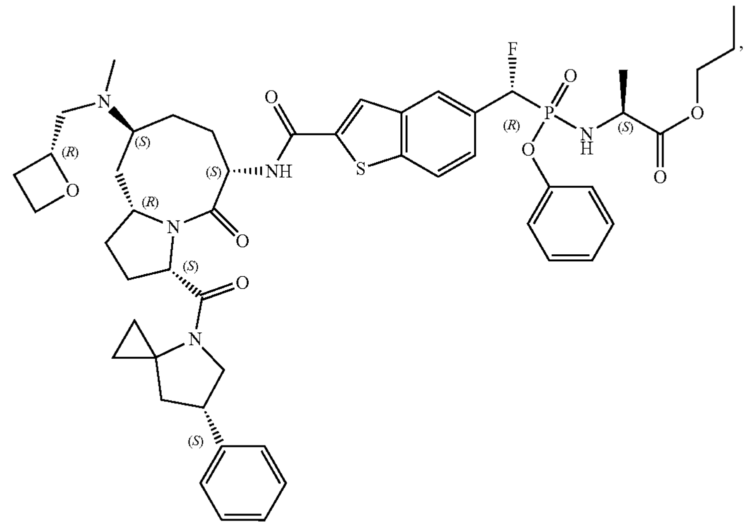
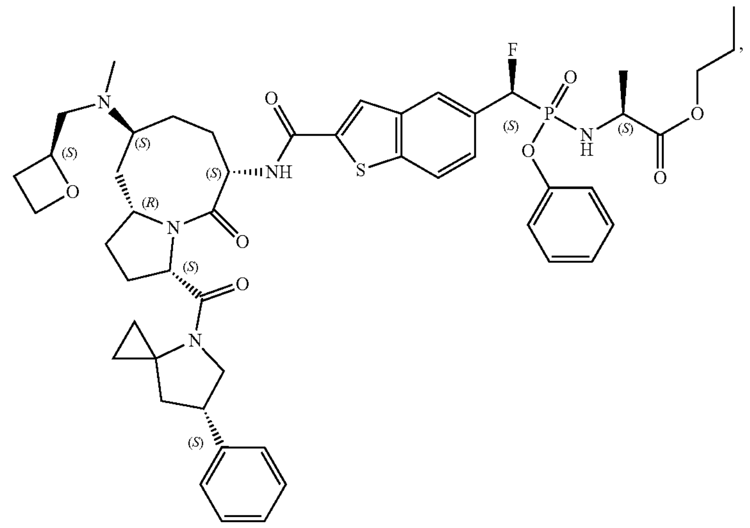
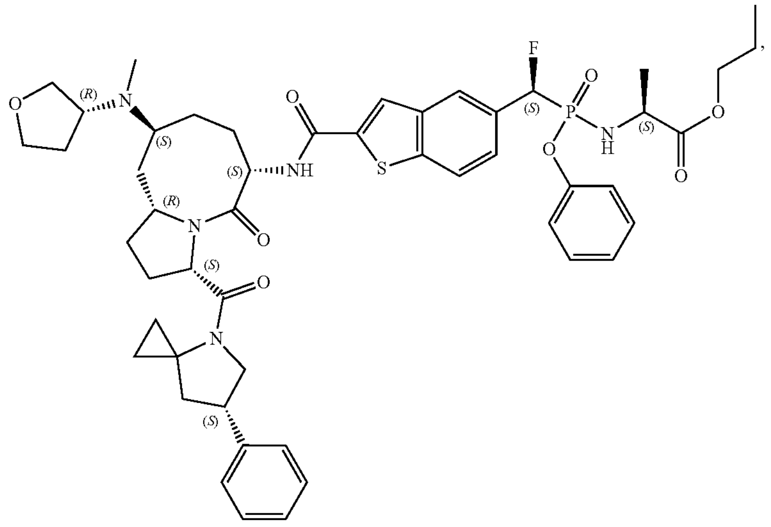

-continued
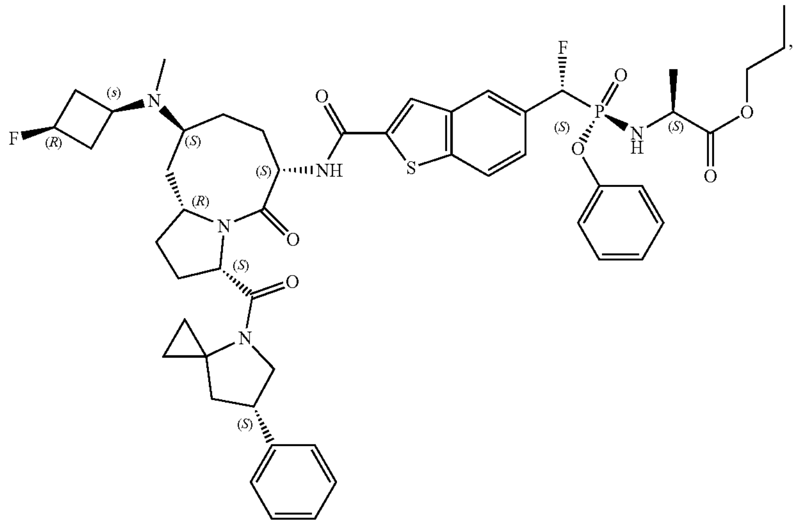
,
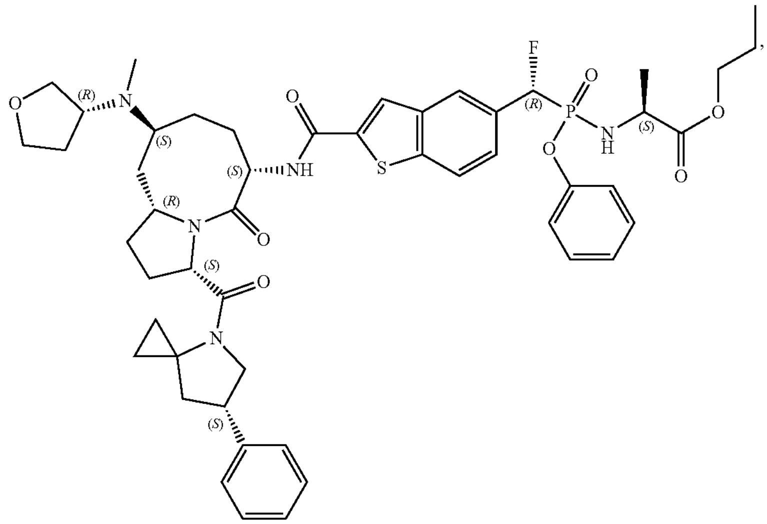
,
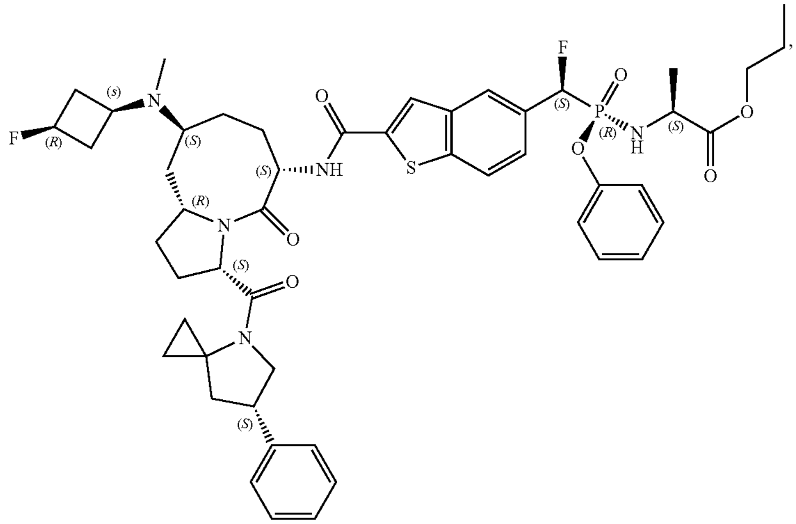
,

-continued
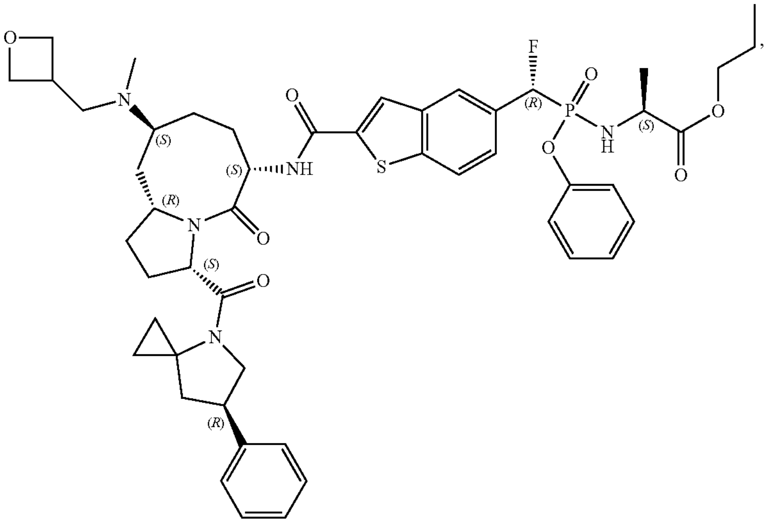
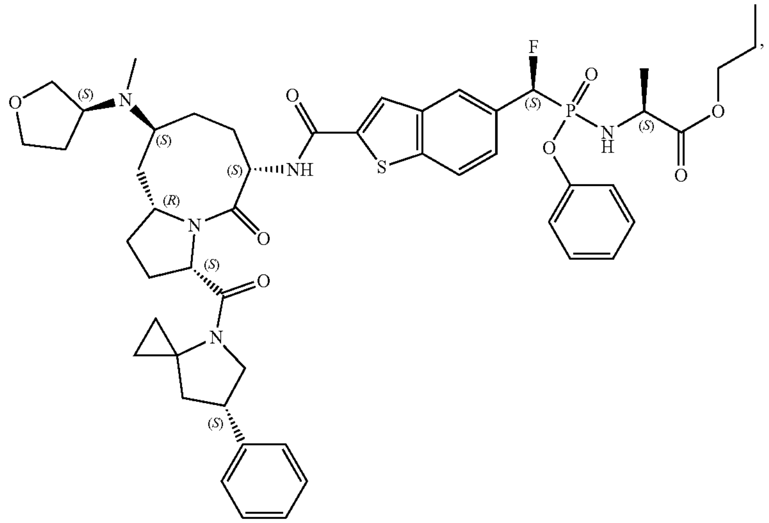
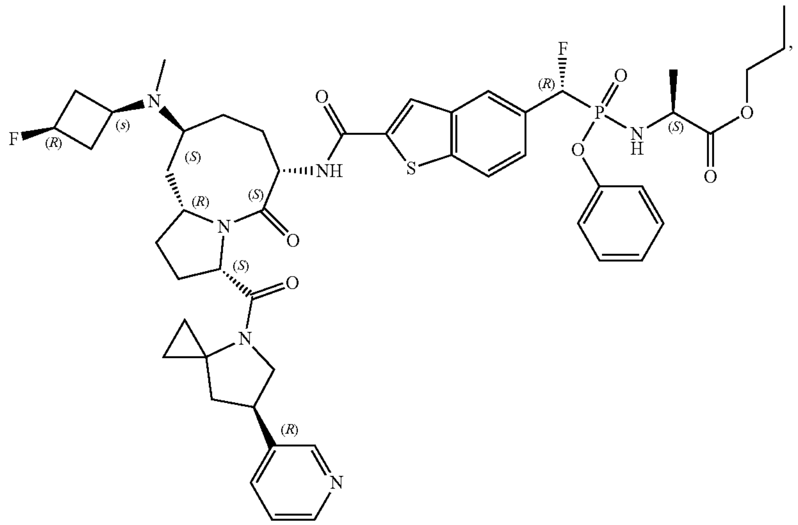

-continued
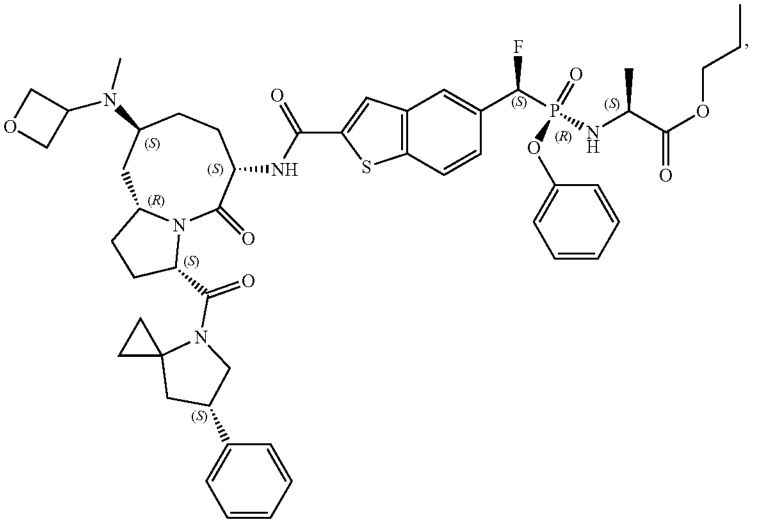
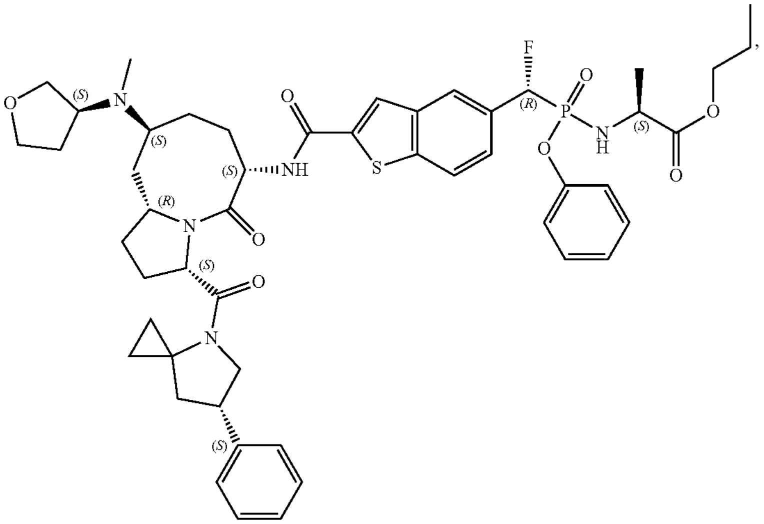
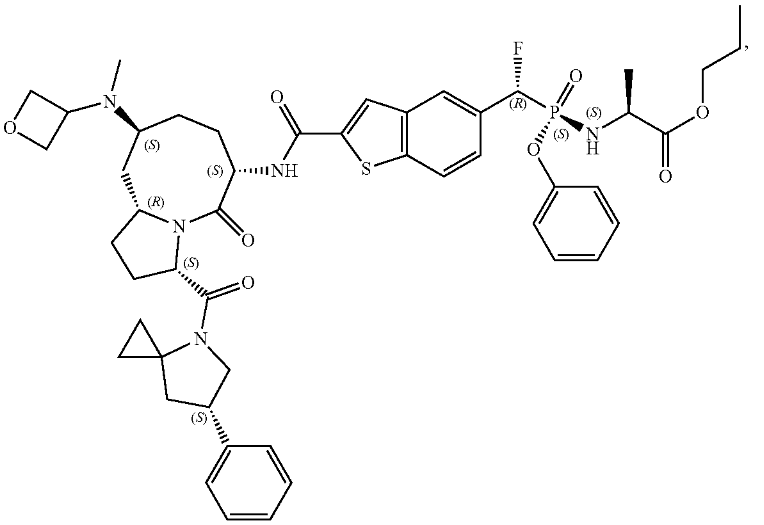

-continued
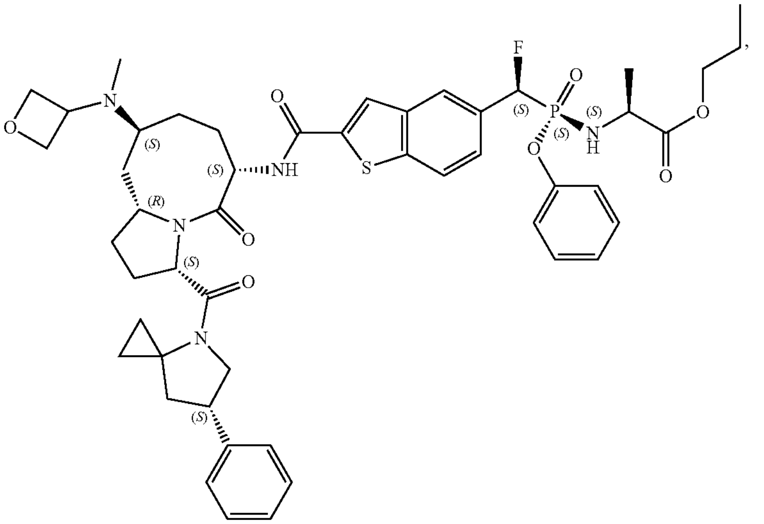
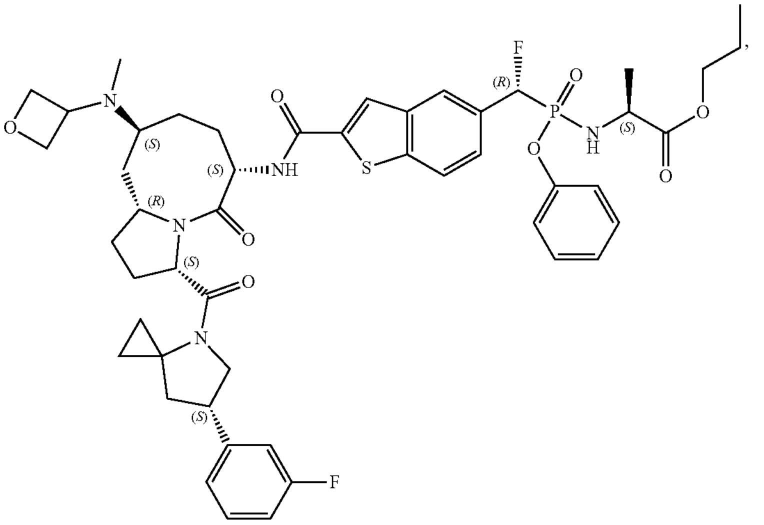
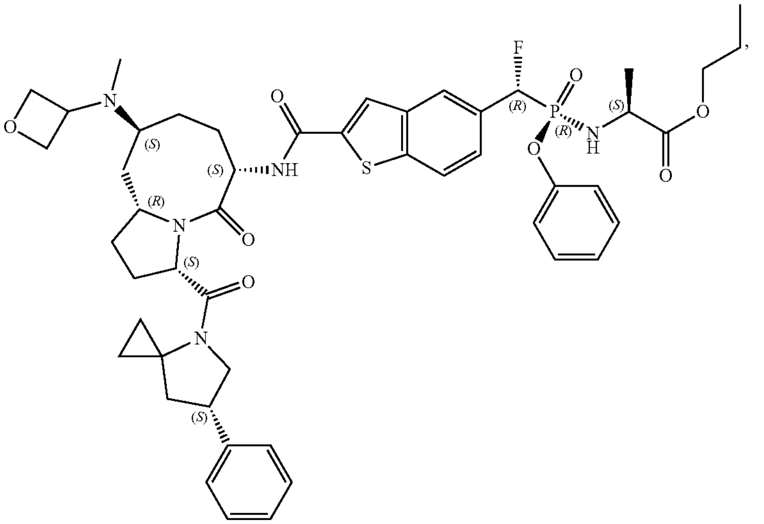

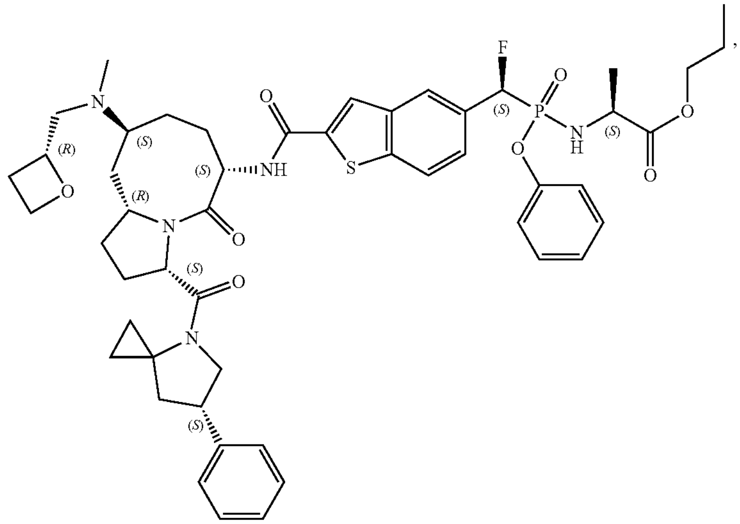,
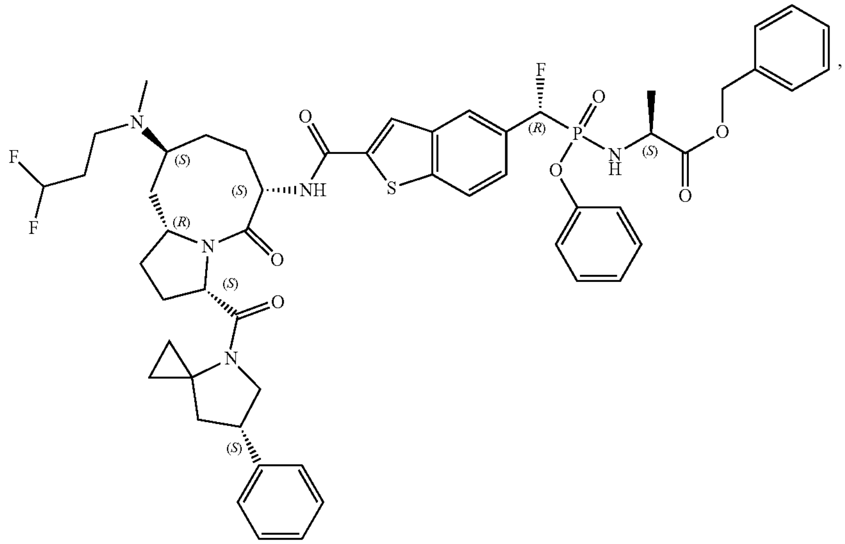,
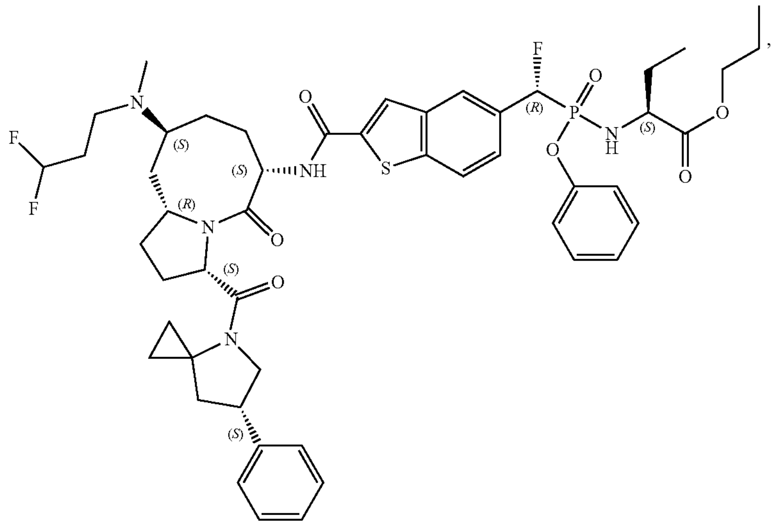,

-continued
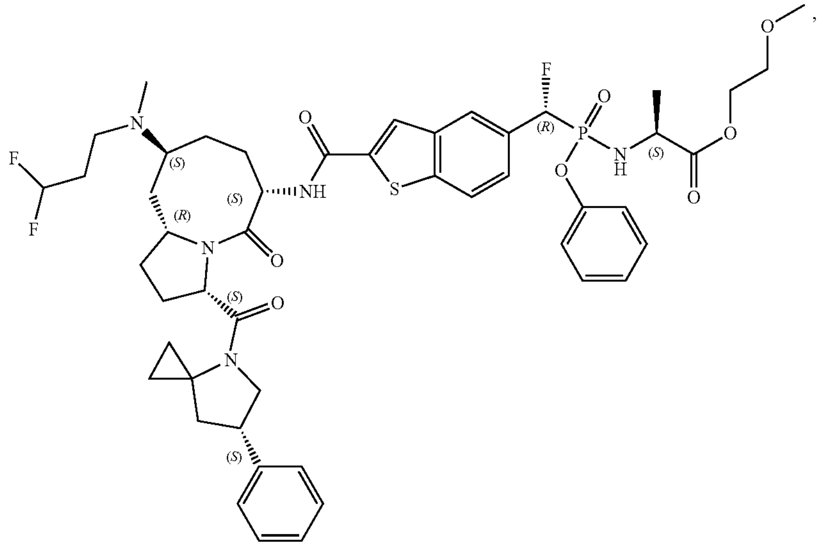
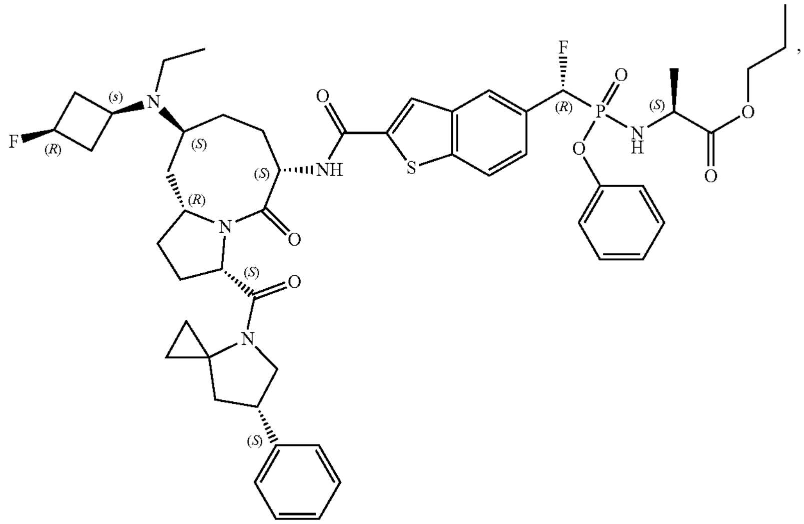
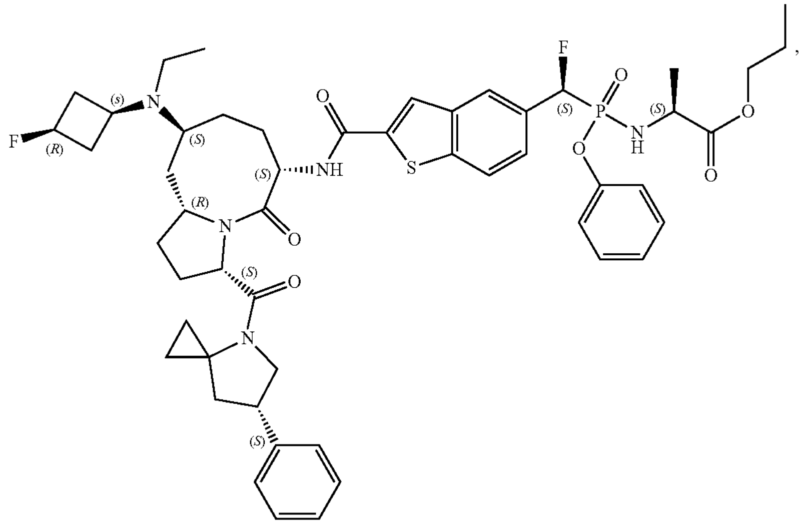

-continued
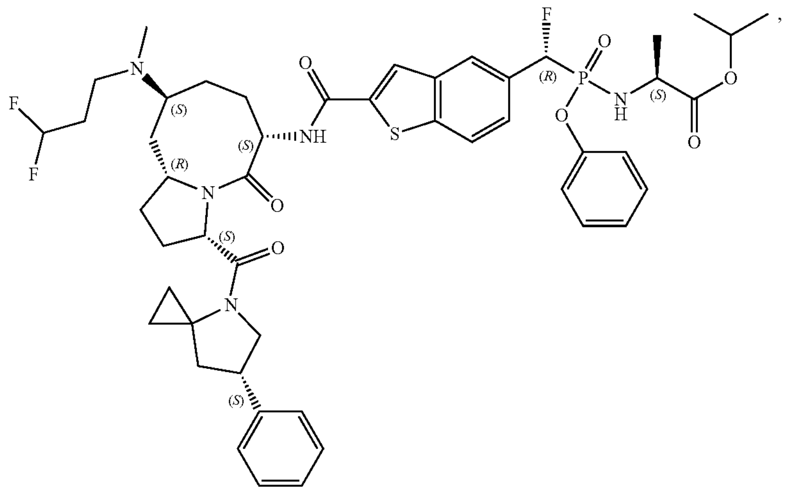
,
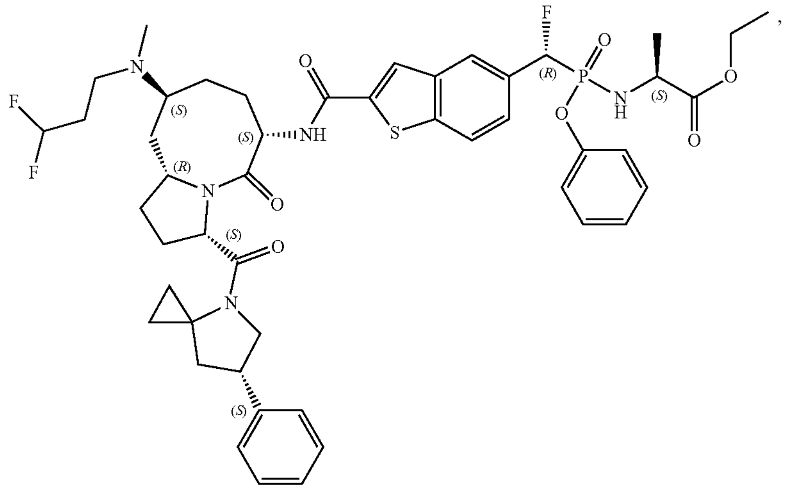
,
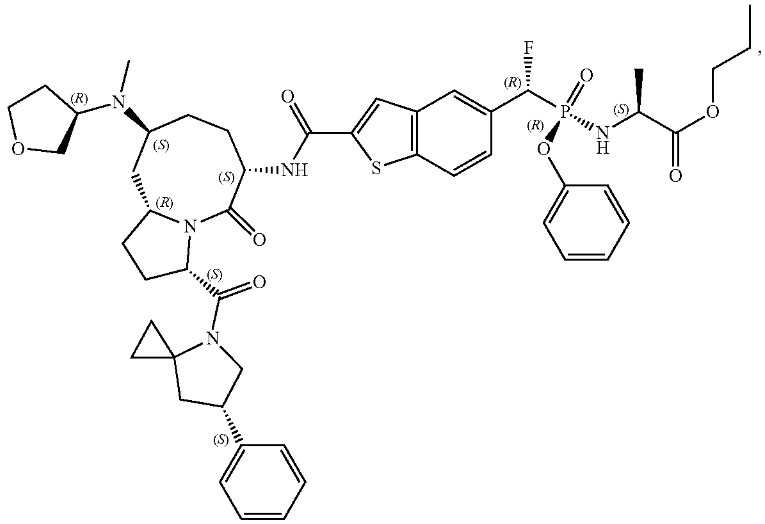
,

-continued
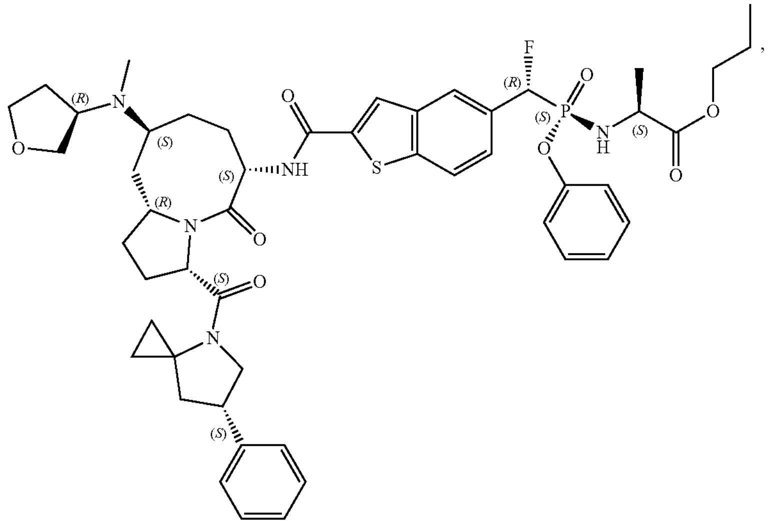
,
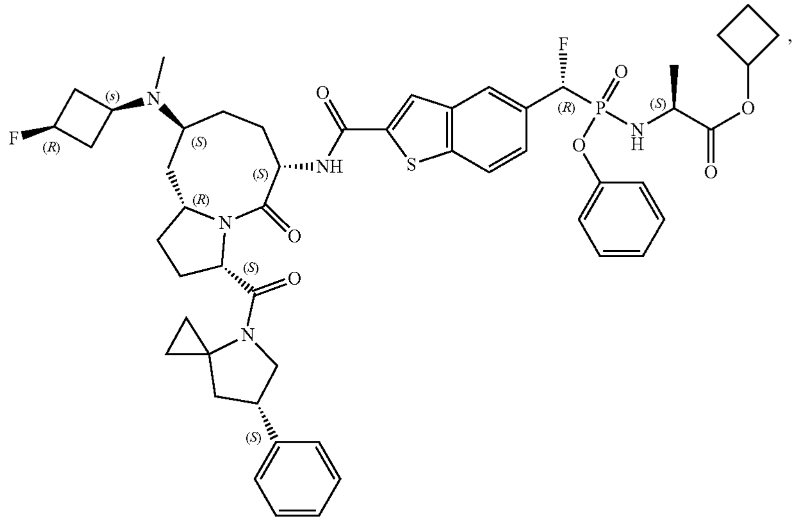
,
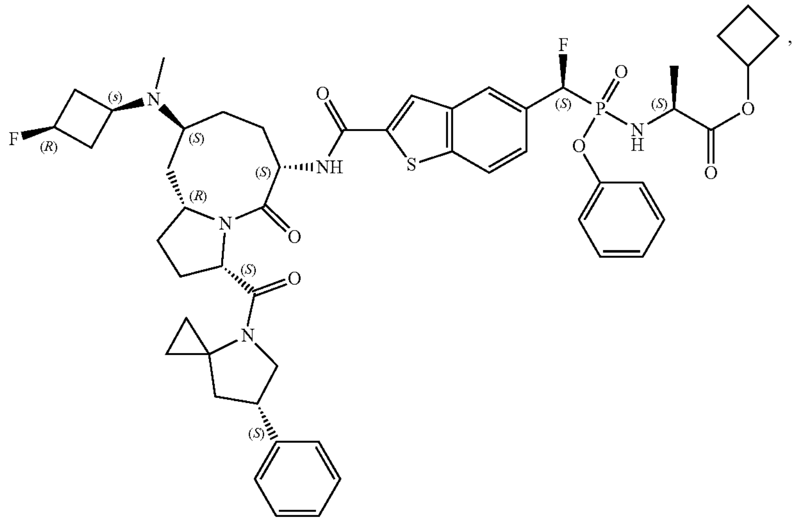
,

-continued
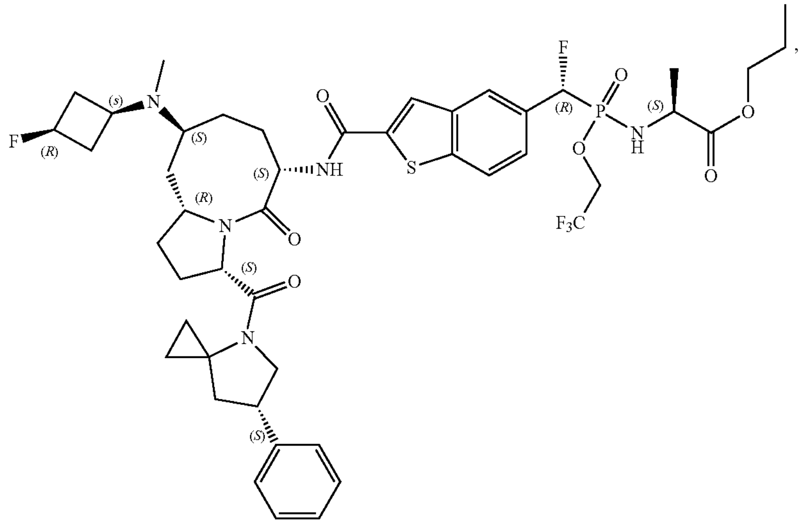
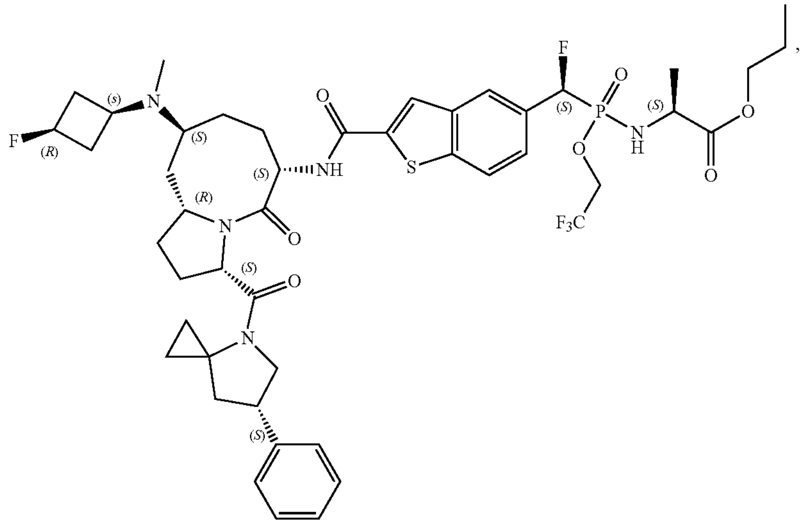
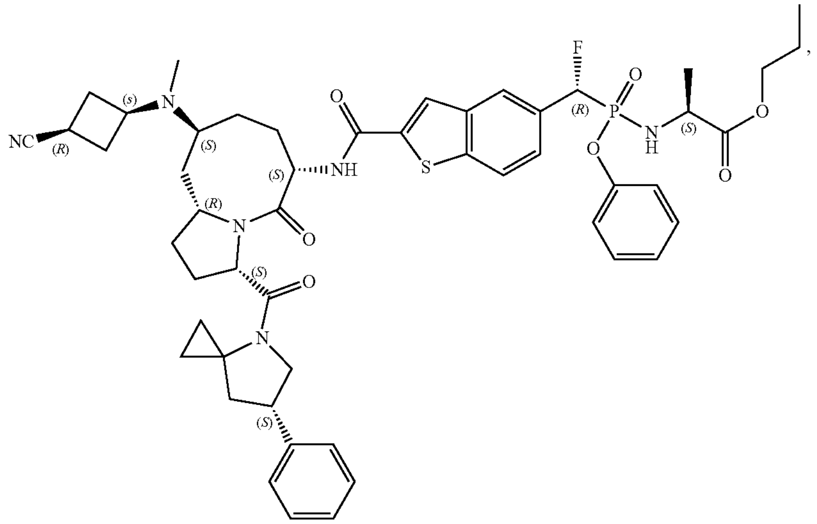

-continued
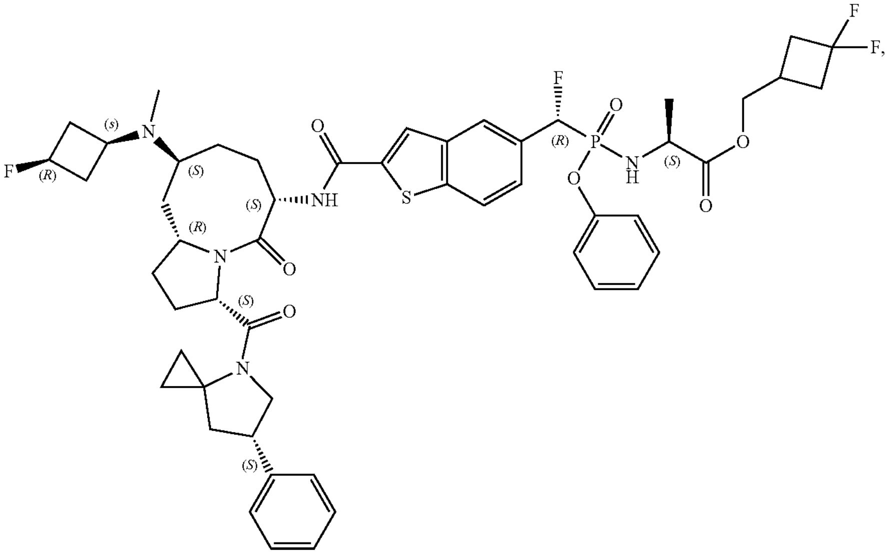
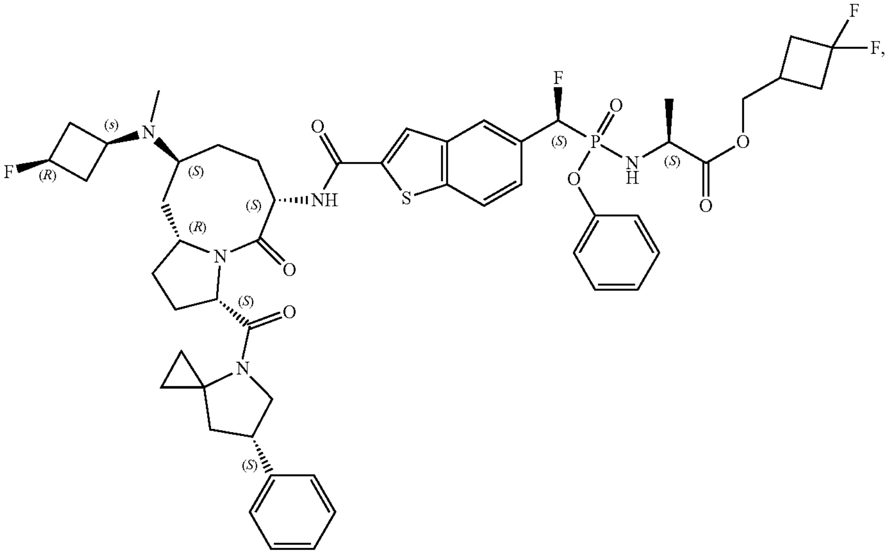
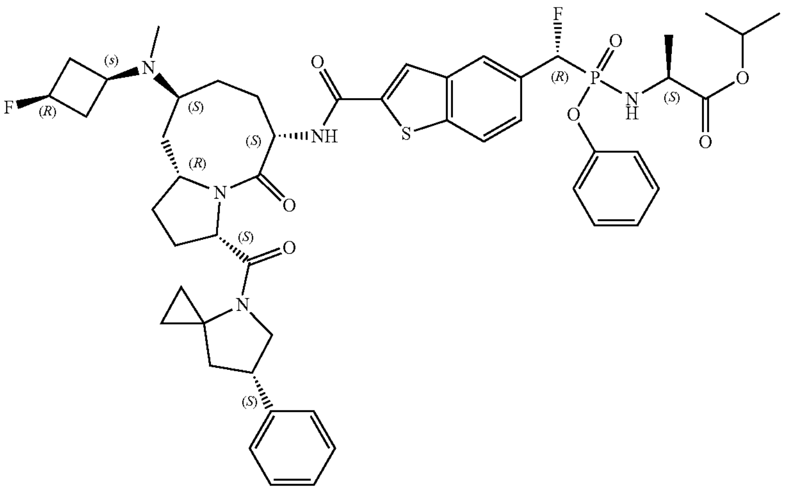
,

-continued
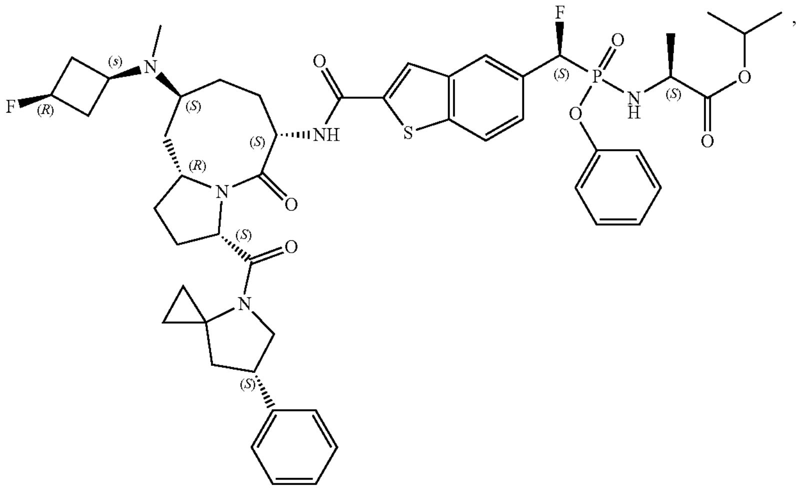
,
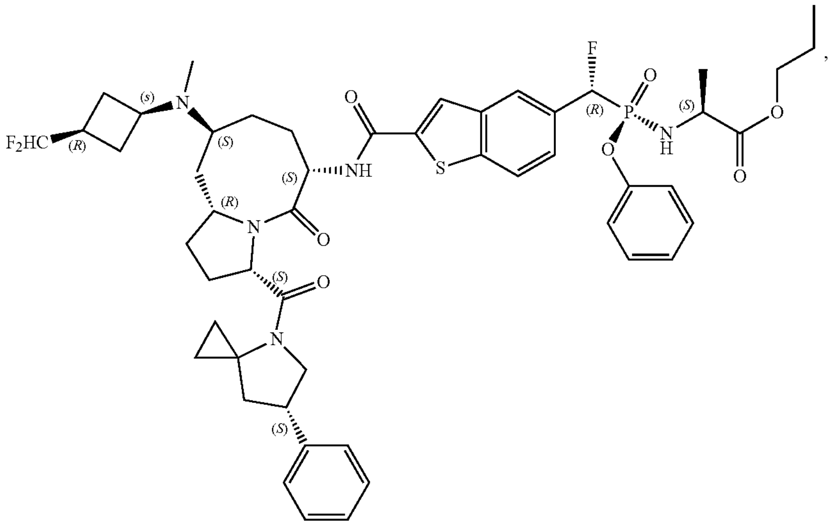
,
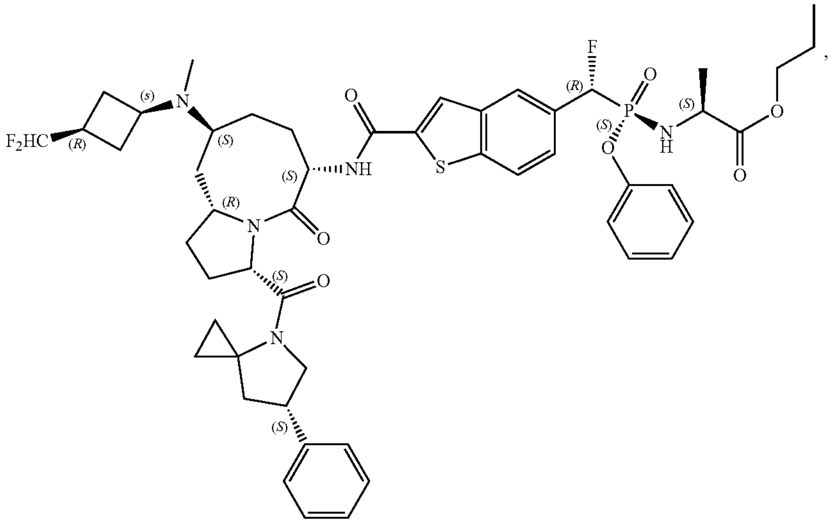
,

-continued
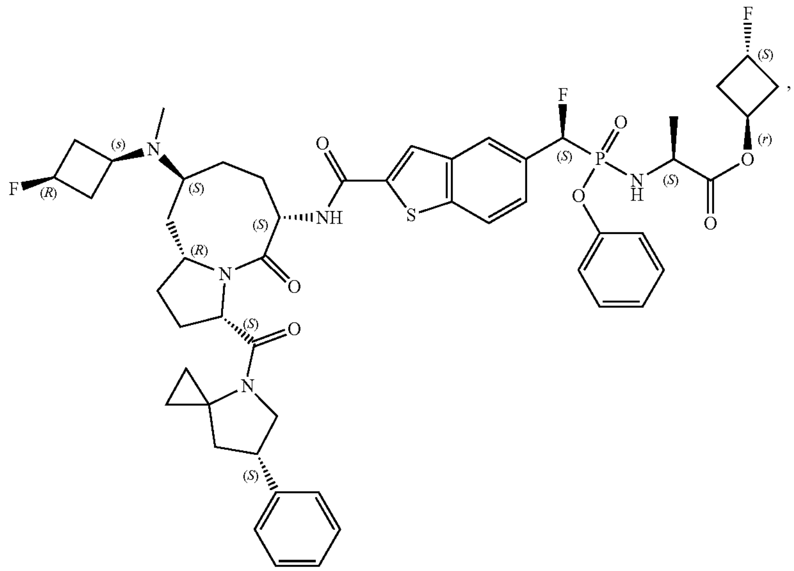
,
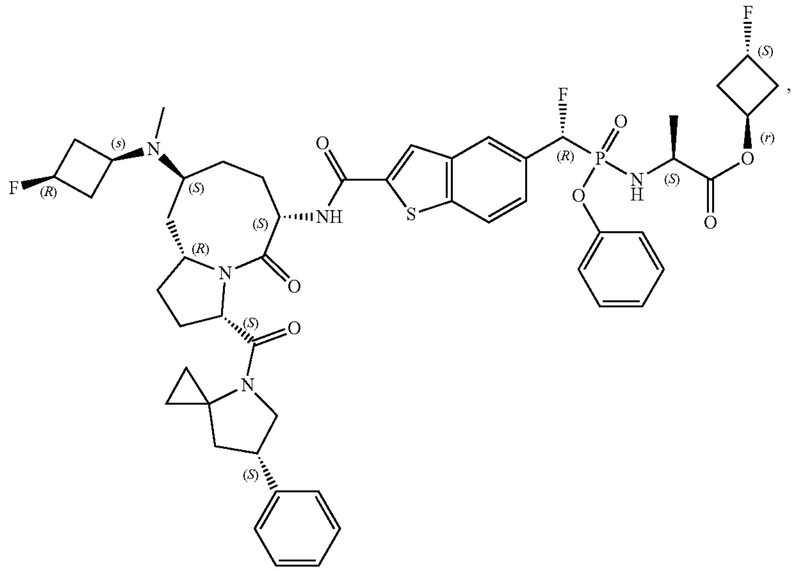
,
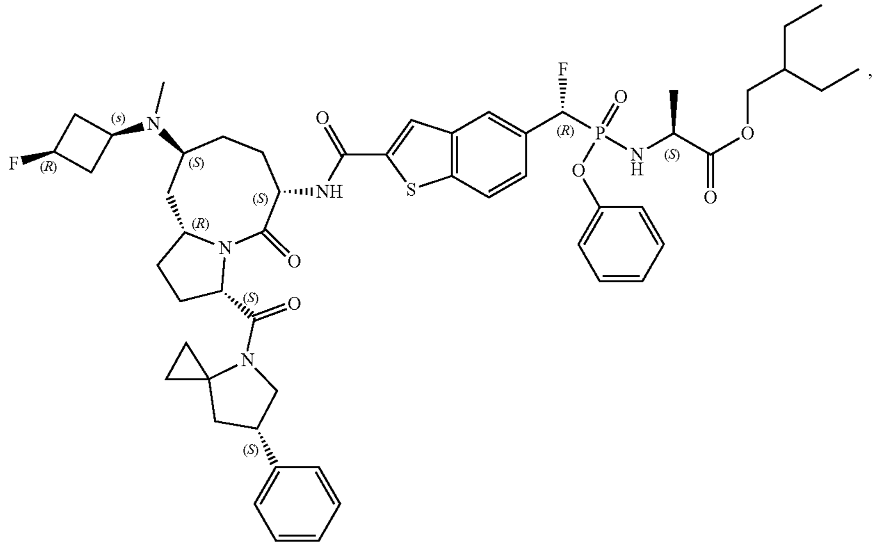
,

-continued
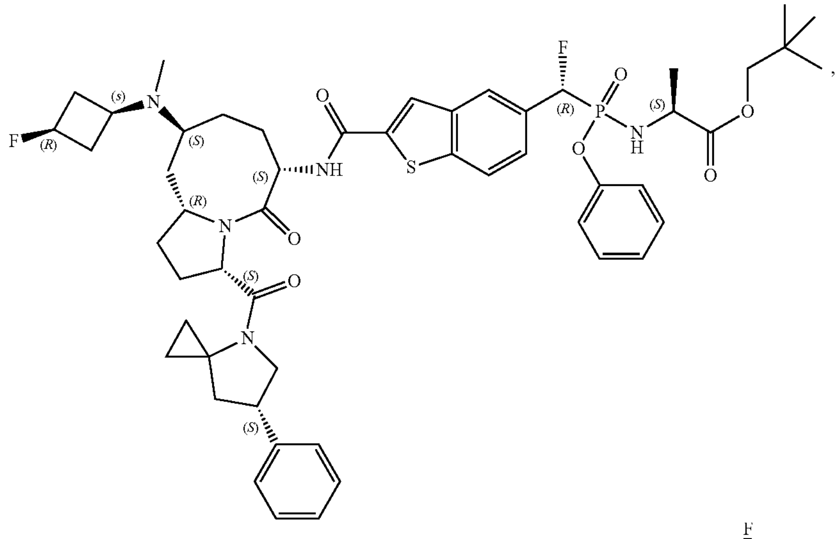
,
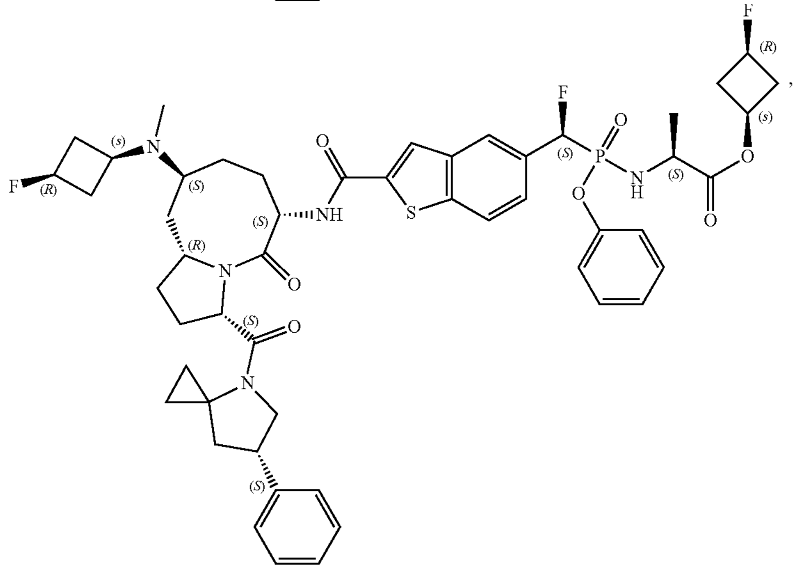
,
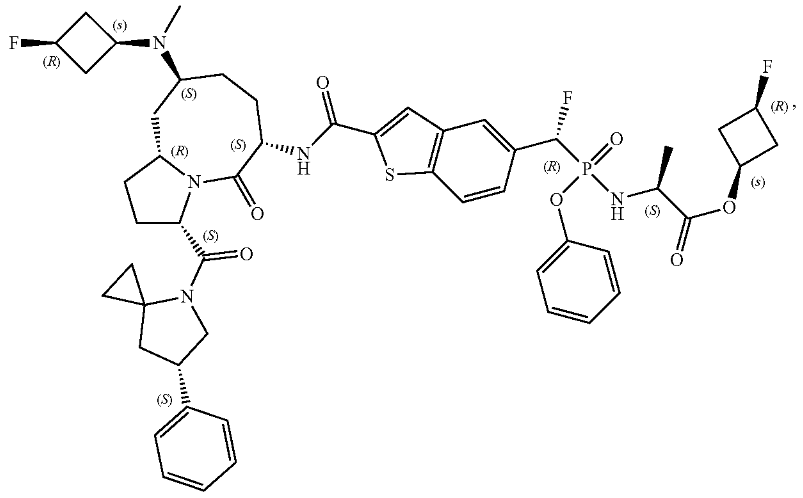
,

-continued
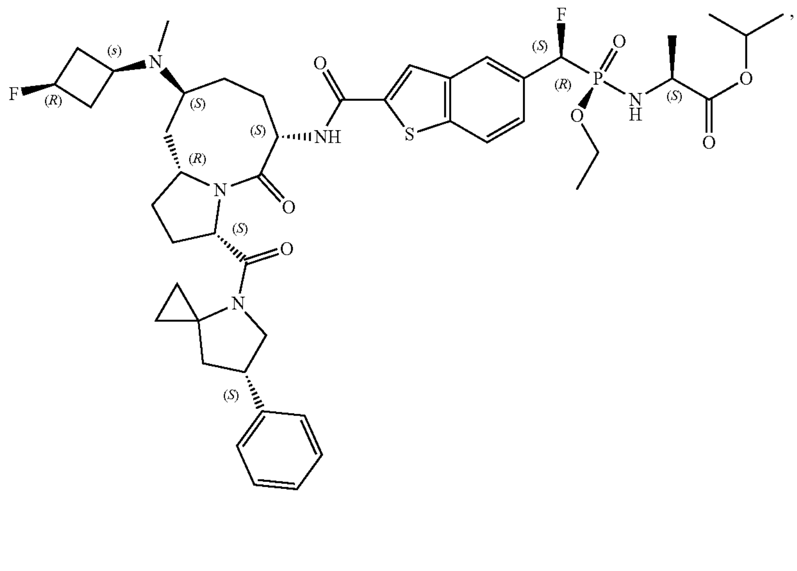
,
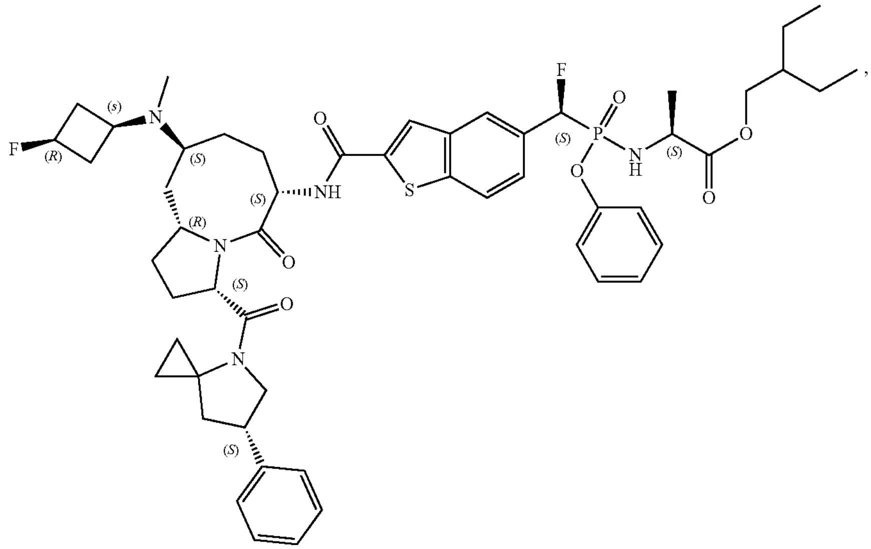
,
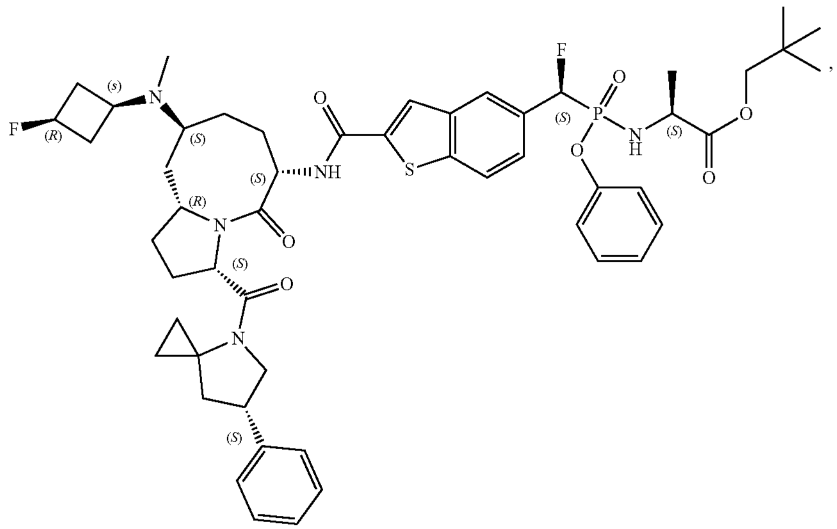
,

-continued
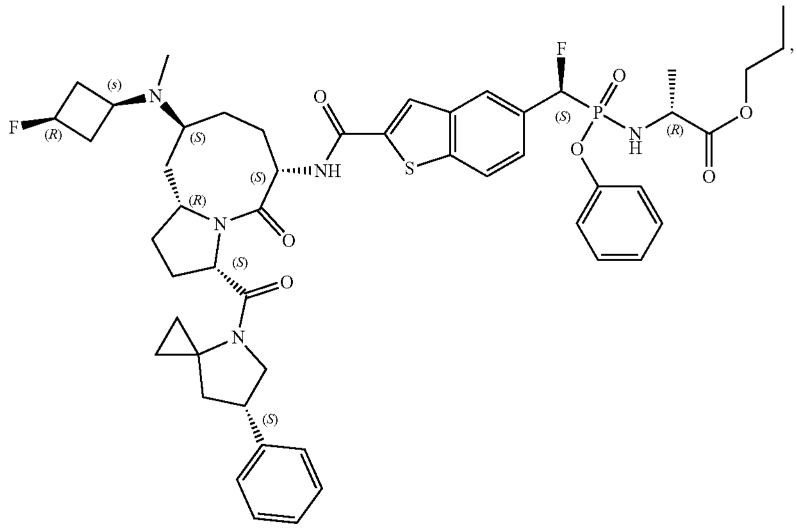
,
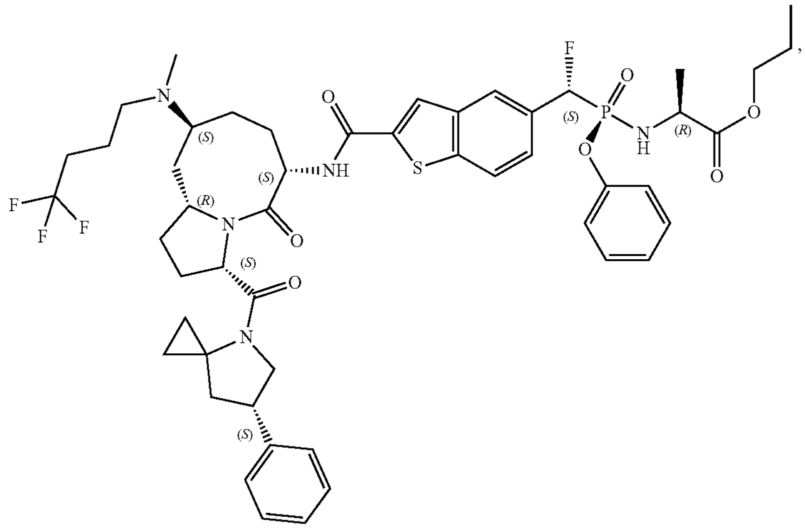
,
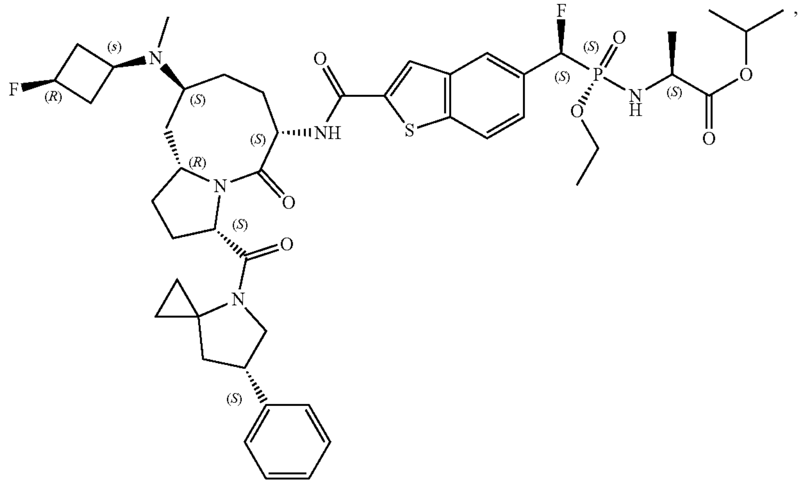
,

-continued
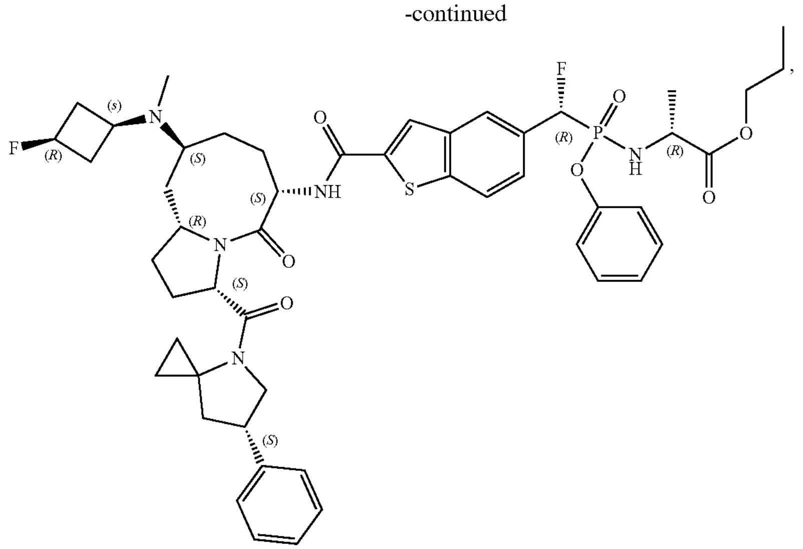
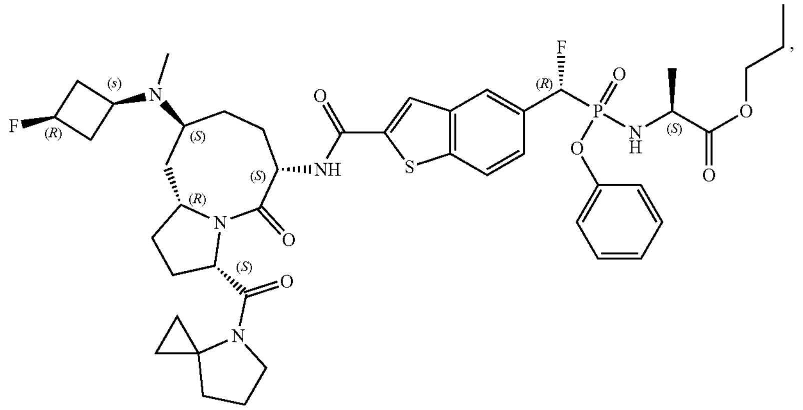
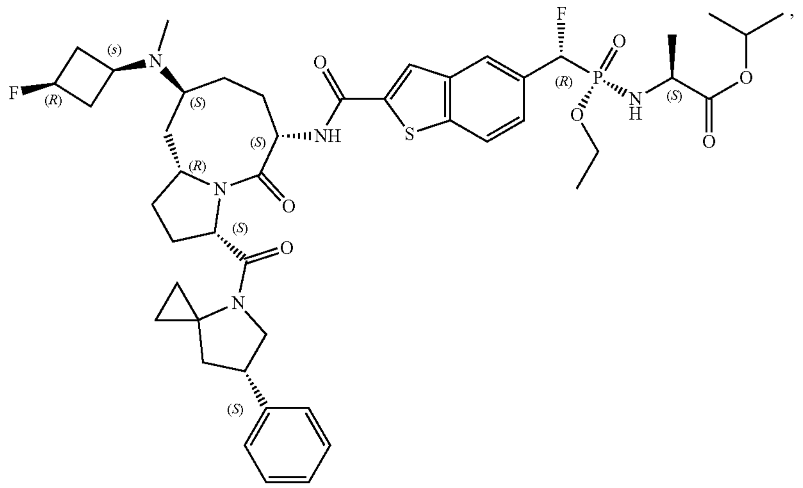

-continued
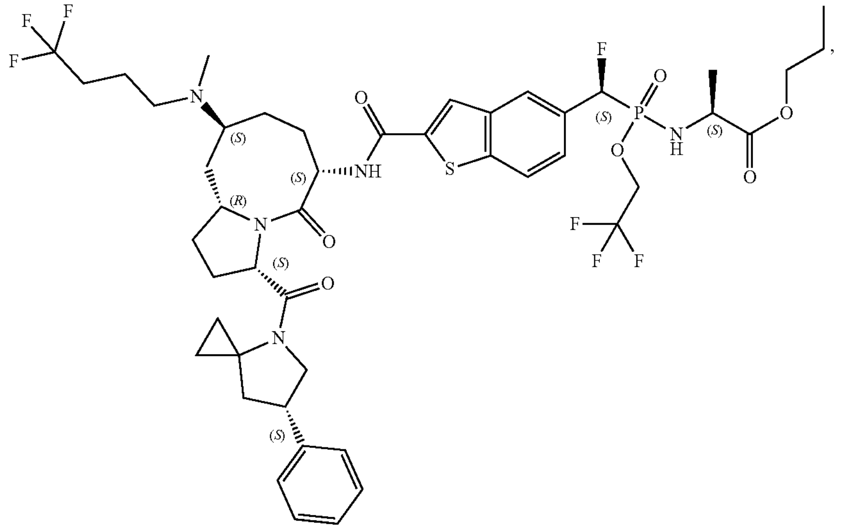
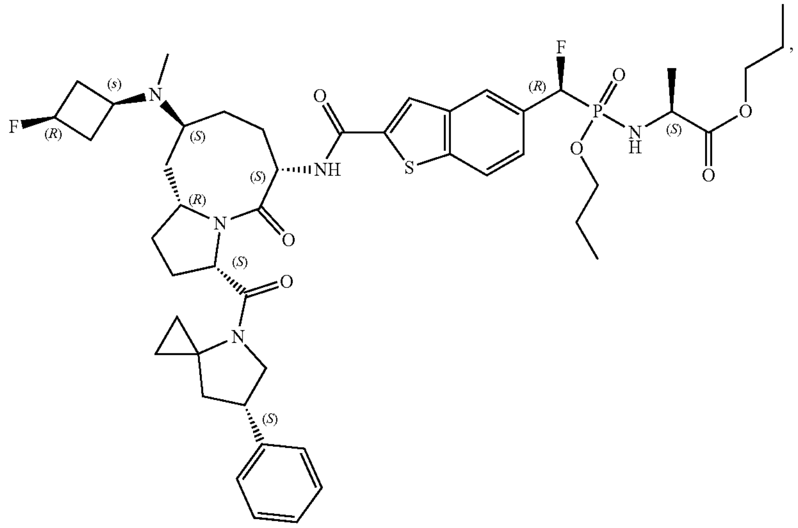
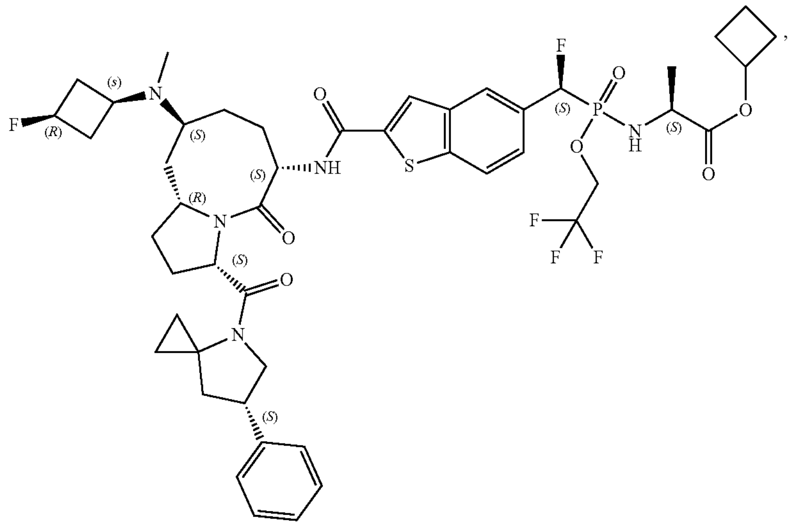

-continued
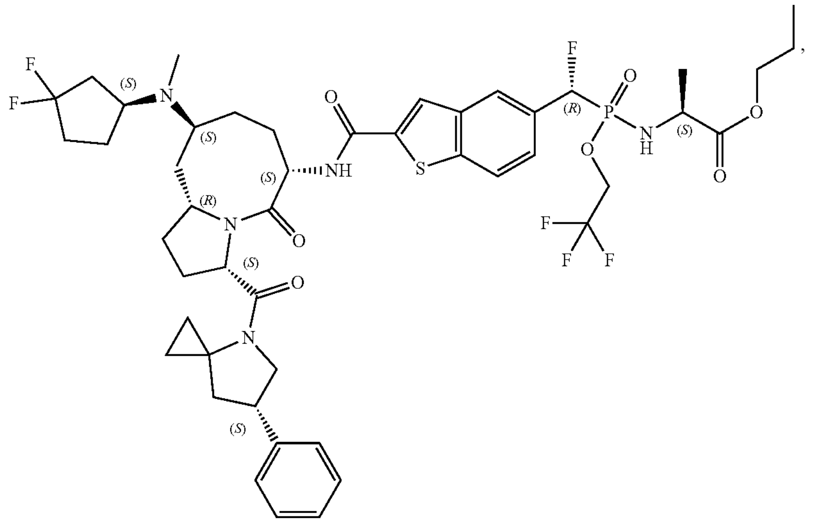
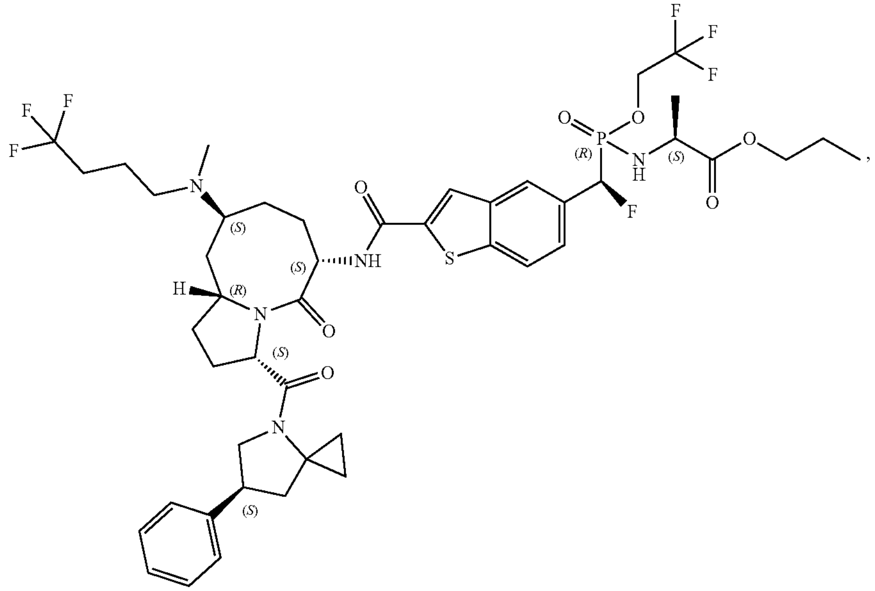
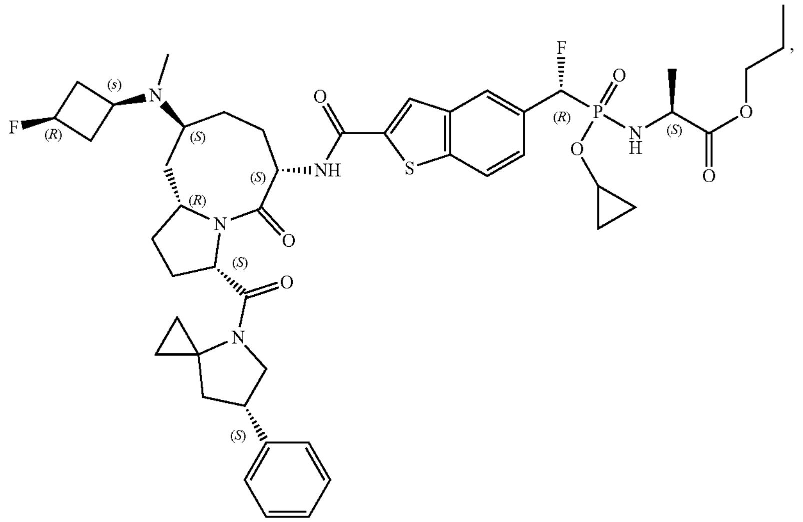

-continued
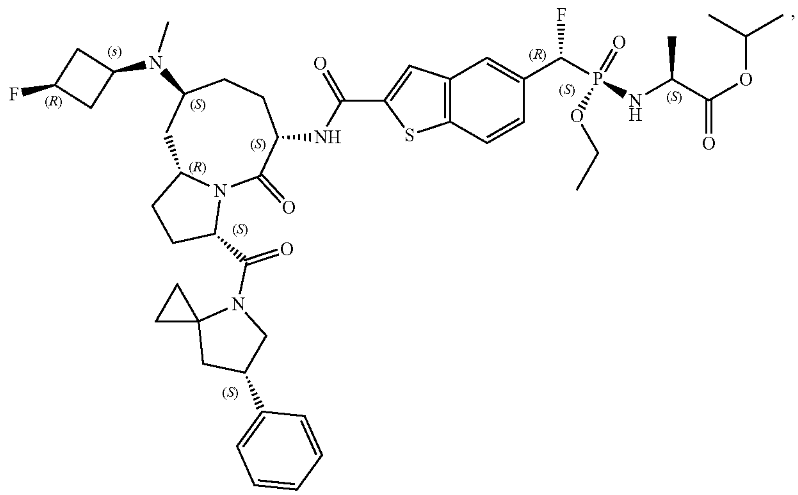
,
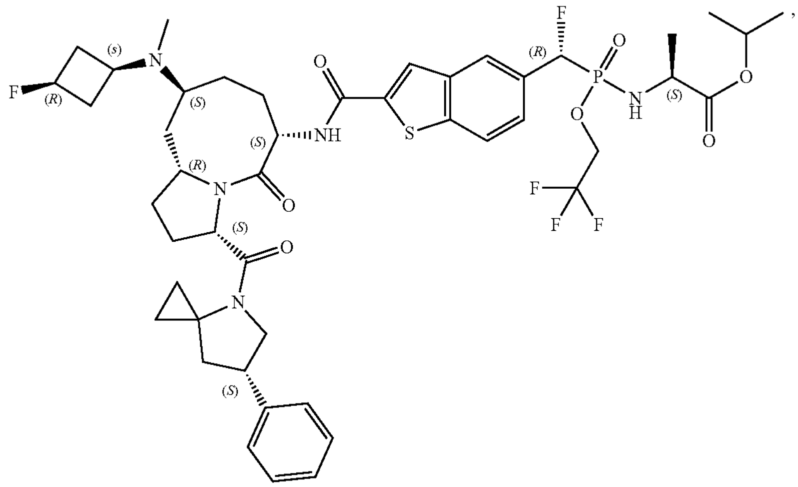
,
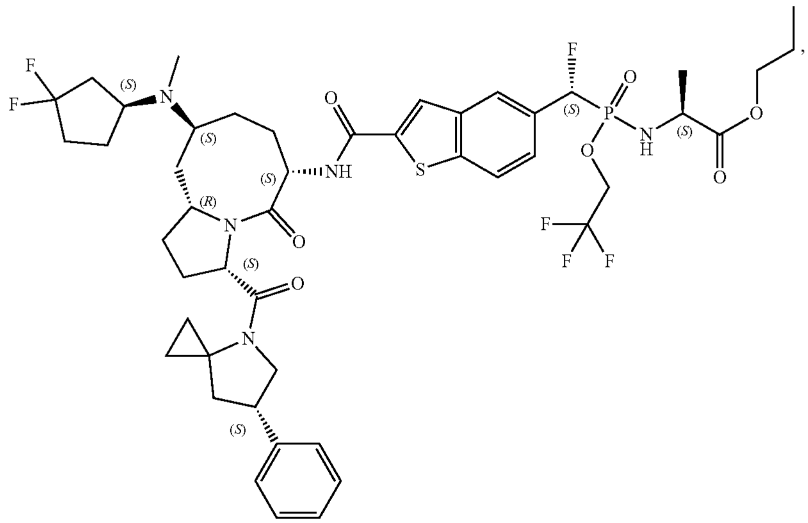
,

-continued
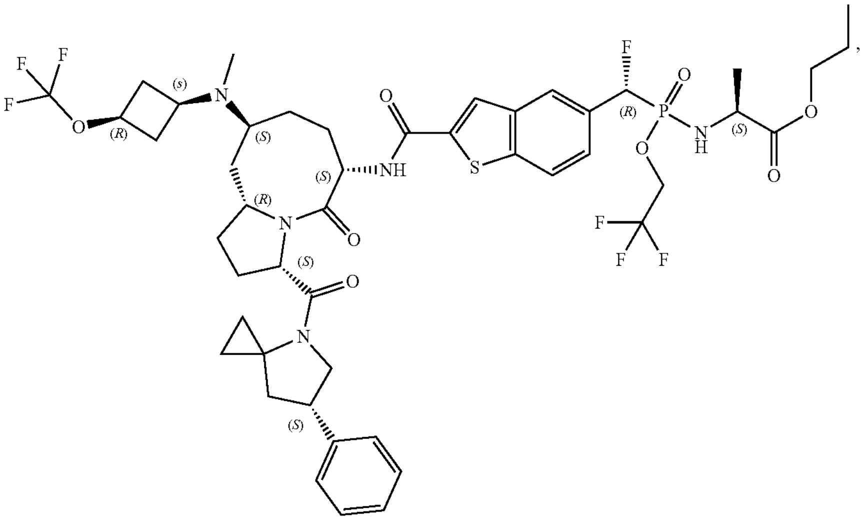
,
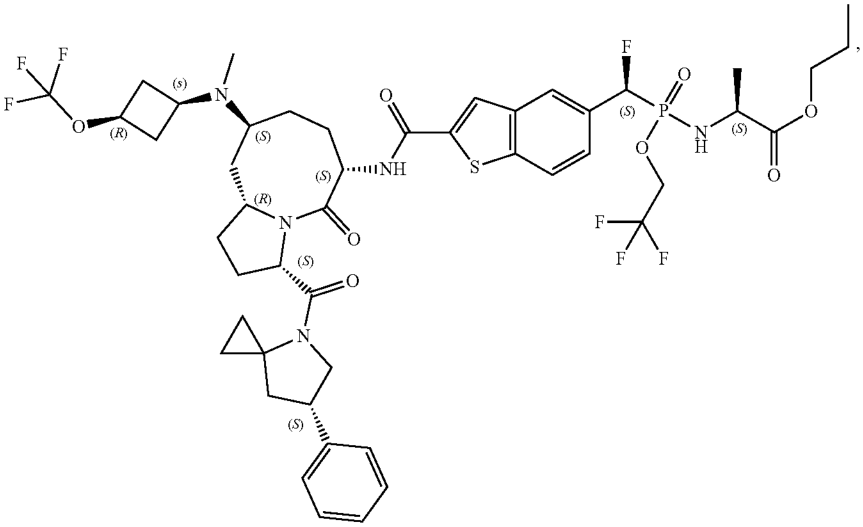
,
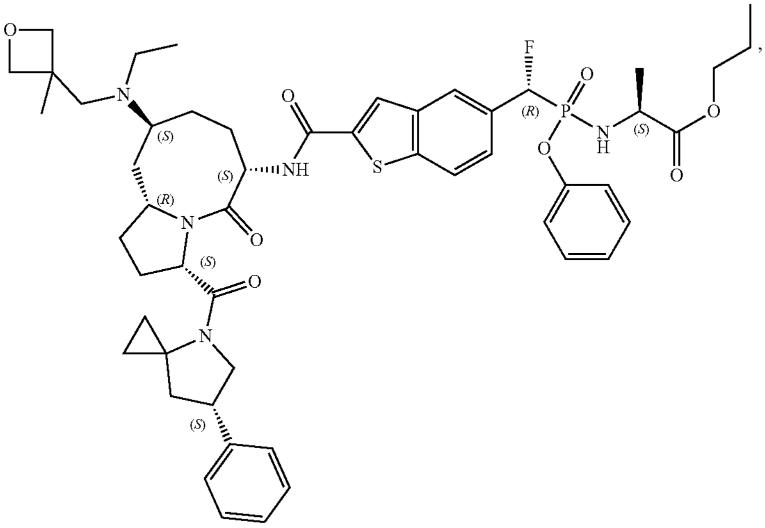
,

-continued
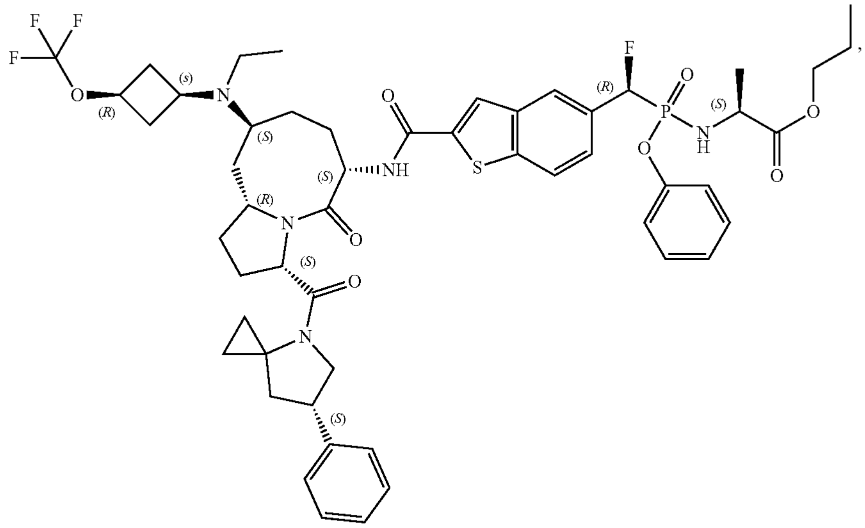
,
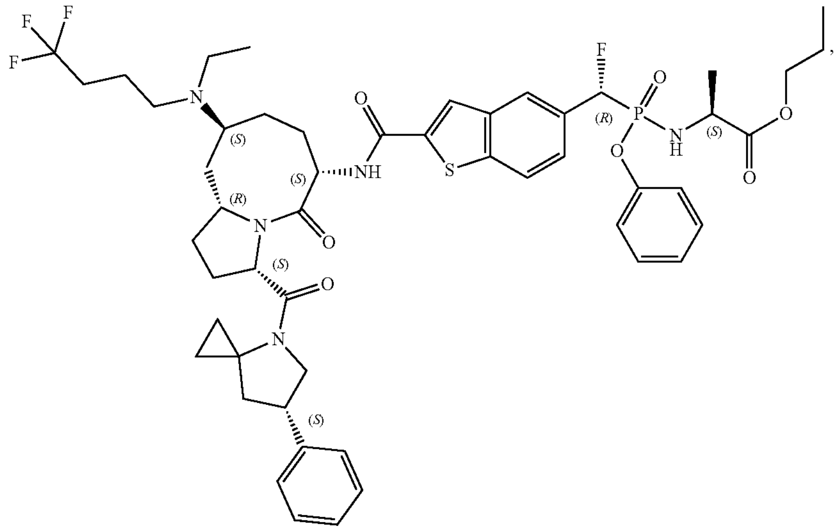
,
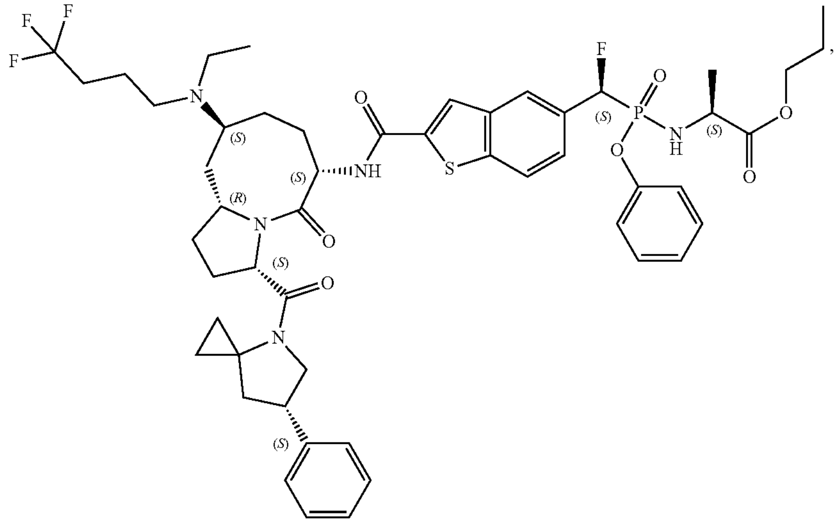
,

-continued
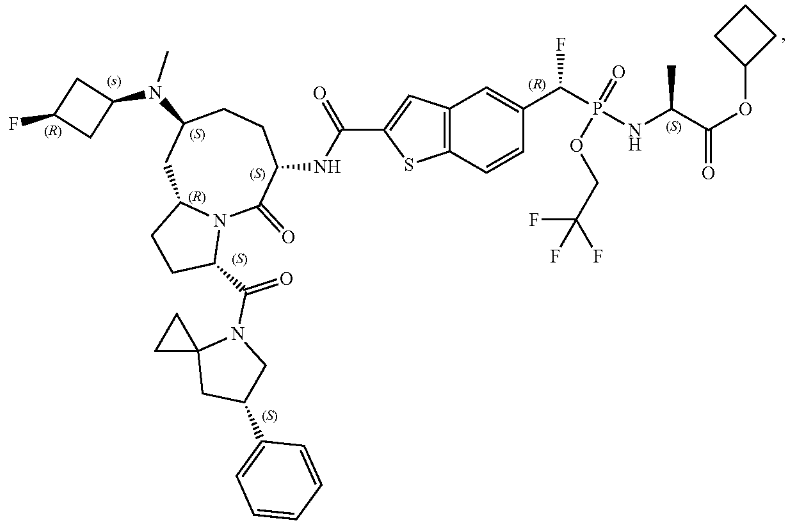
,
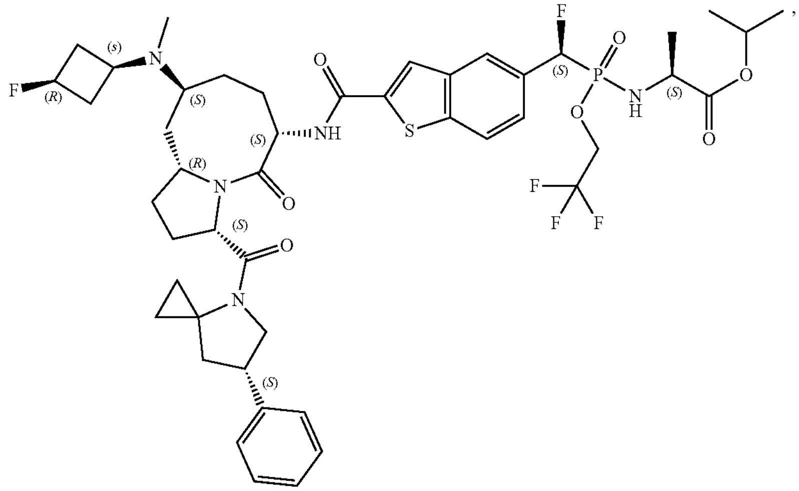
,
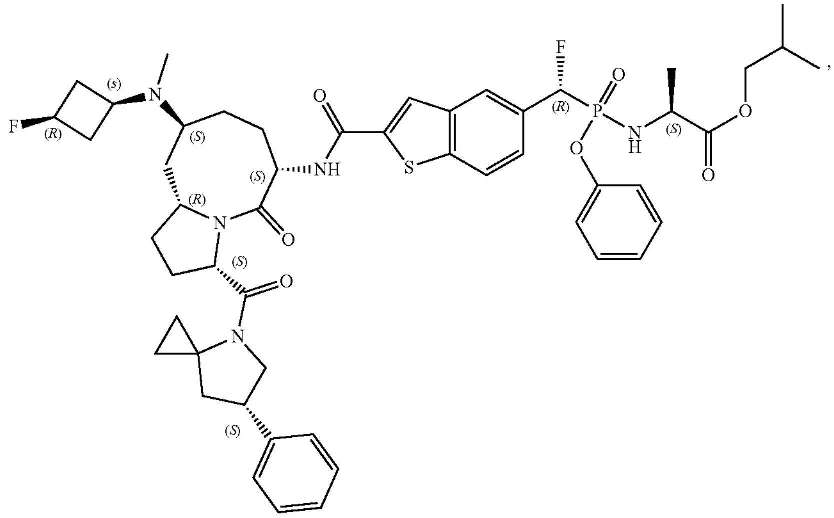
,

-continued
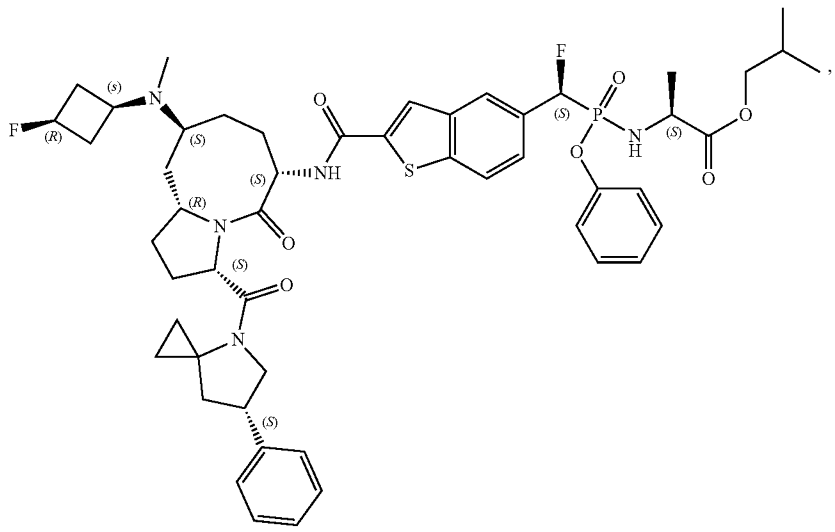
,
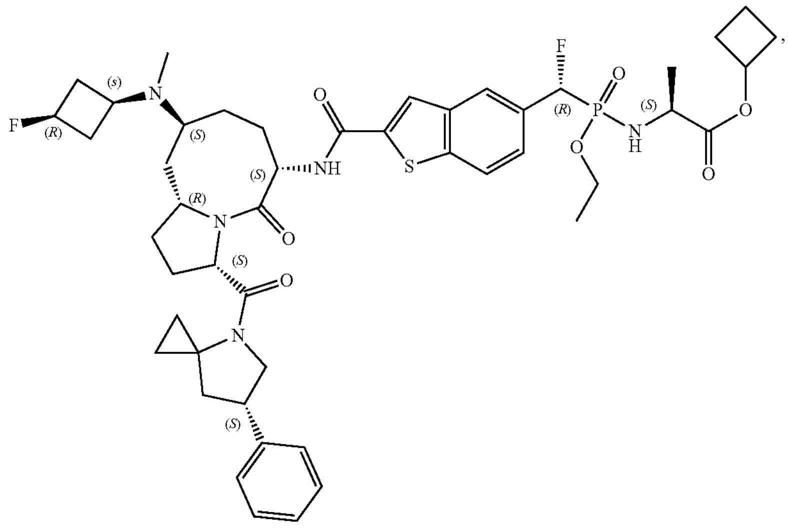
,
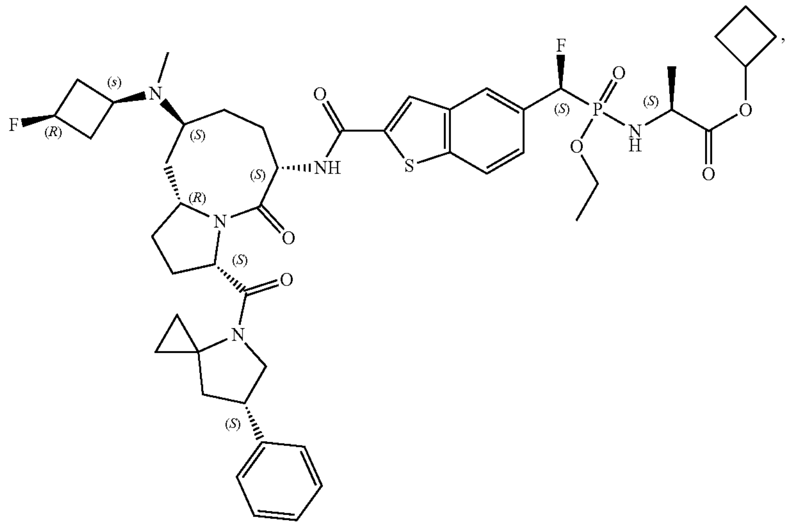
,

-continued
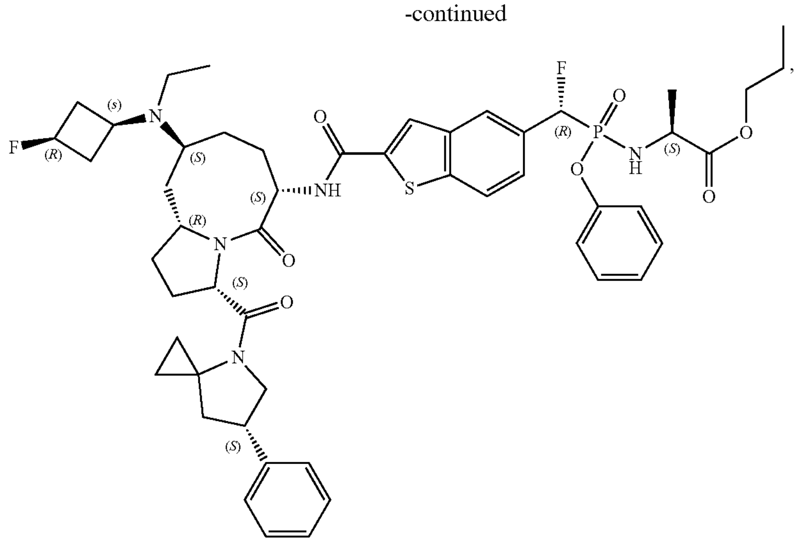
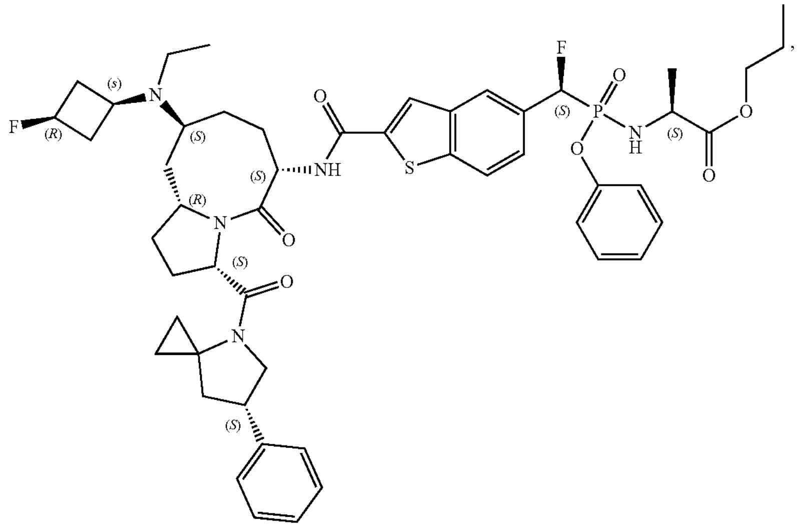
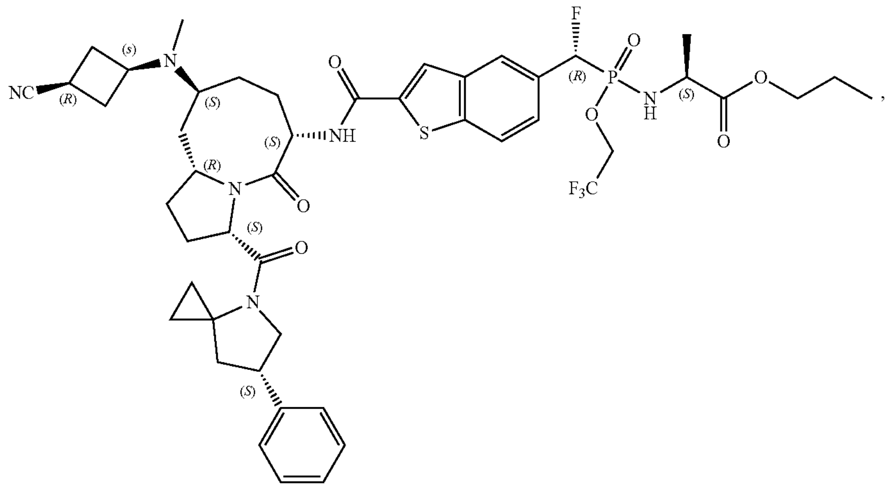

-continued
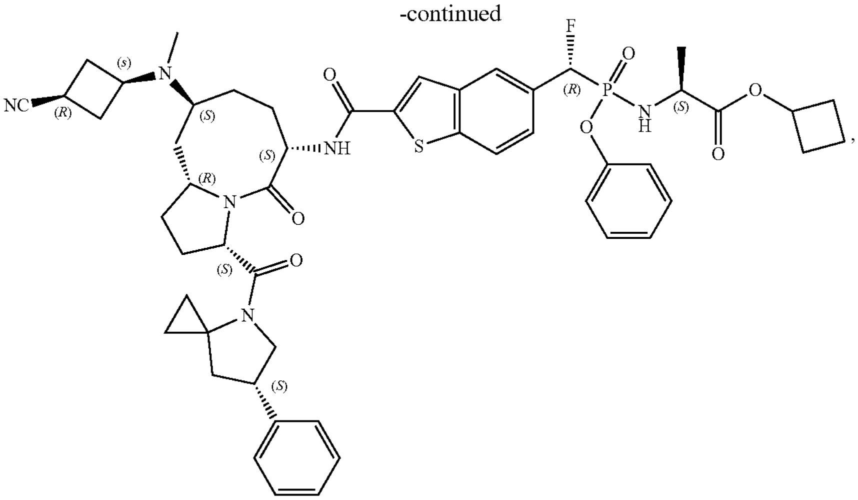
,
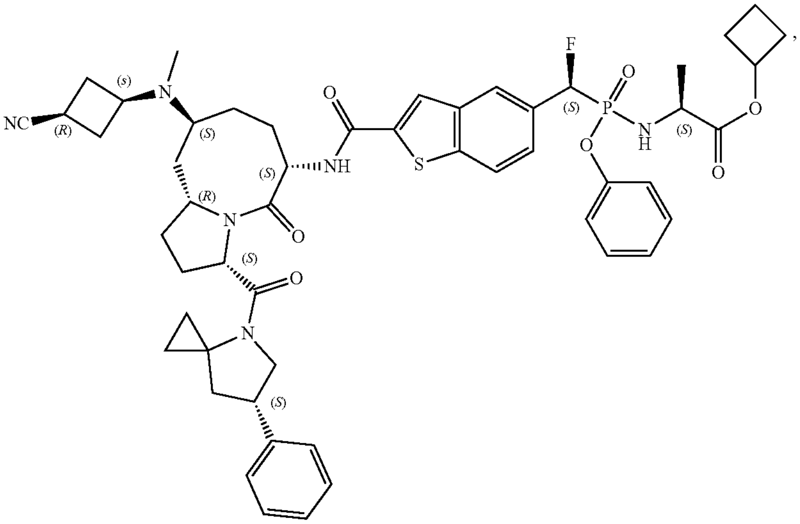
,
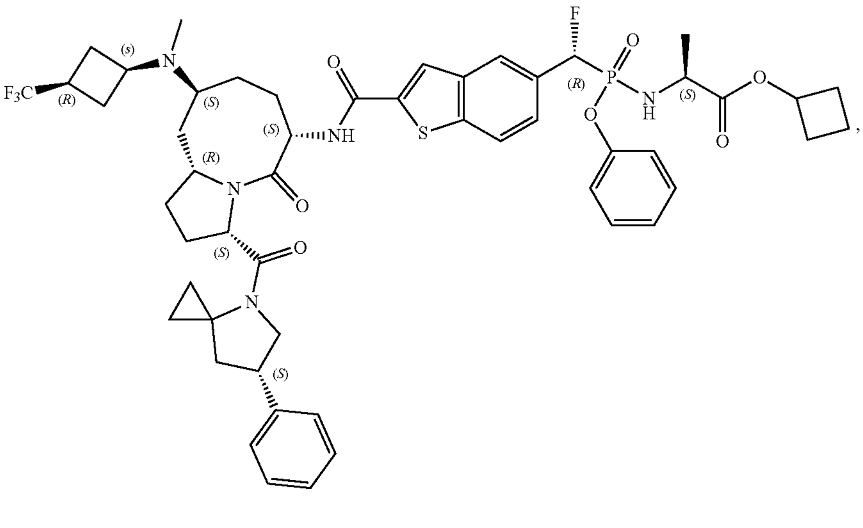
,

-continued
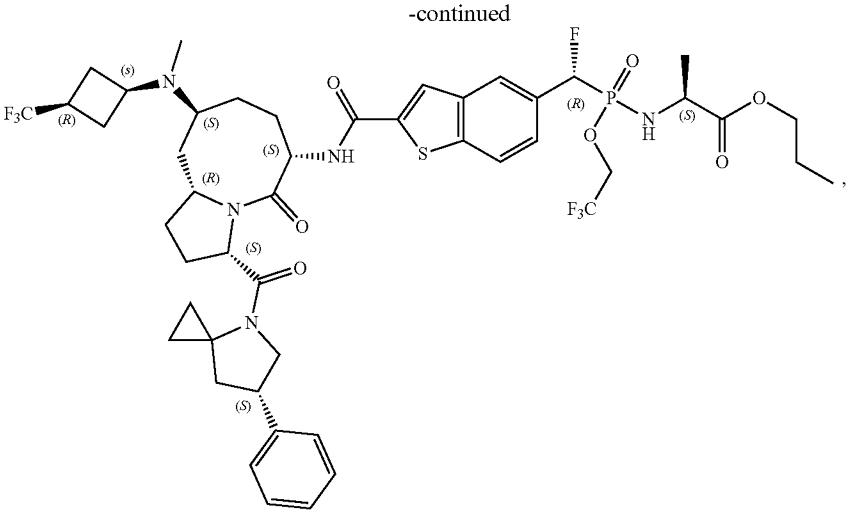
,
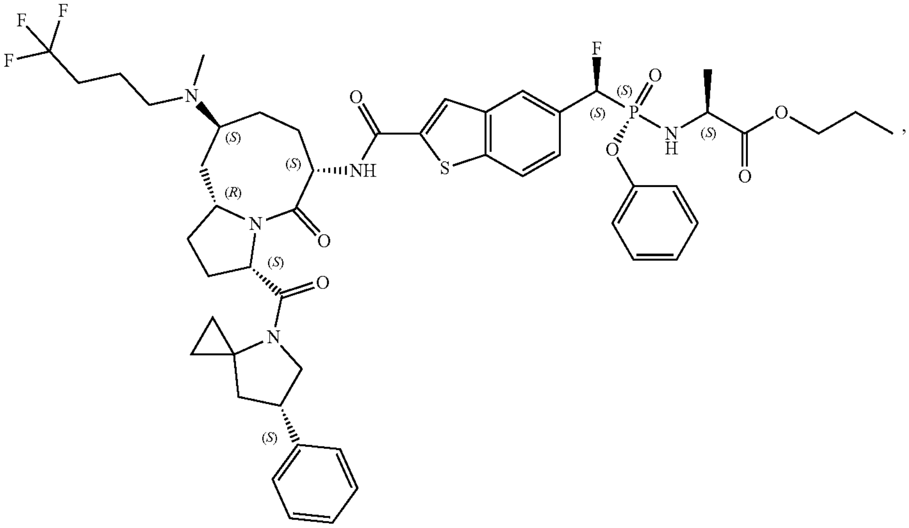
,
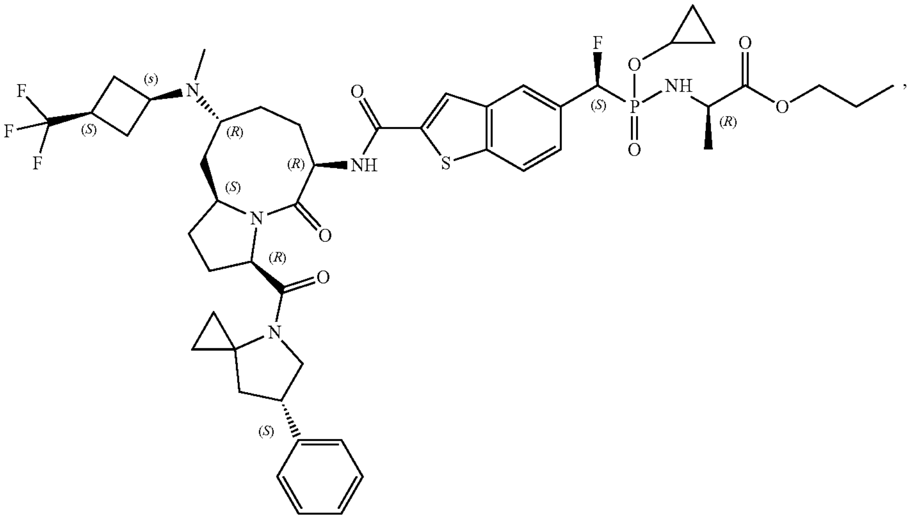
,

-continued
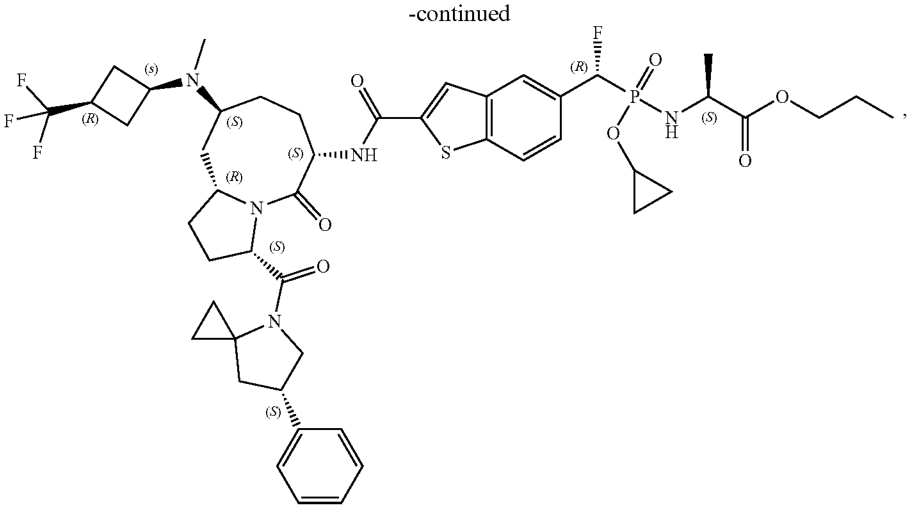
,
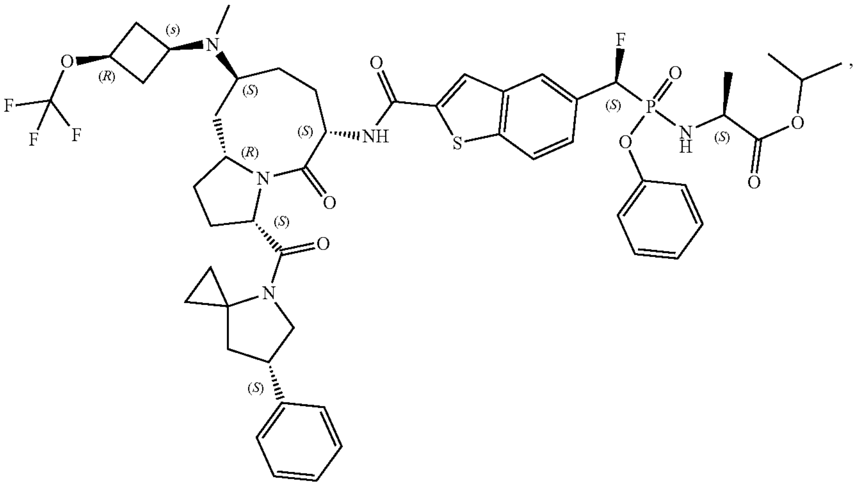
,
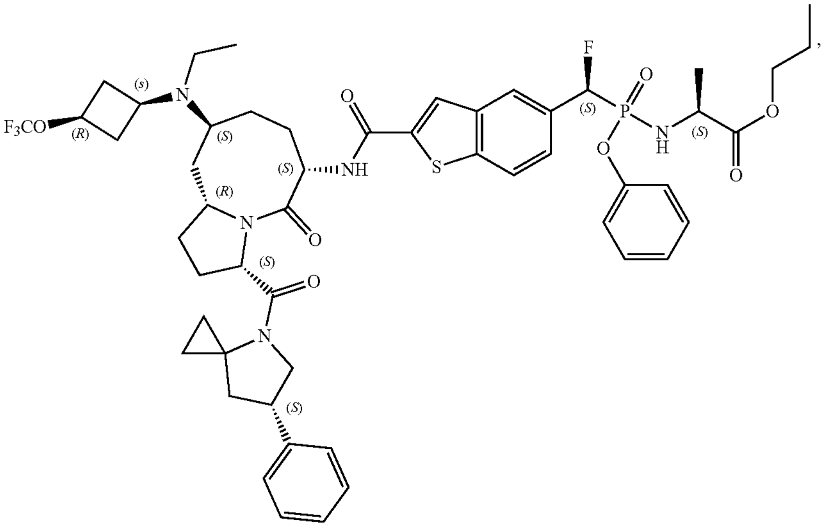
,

-continued
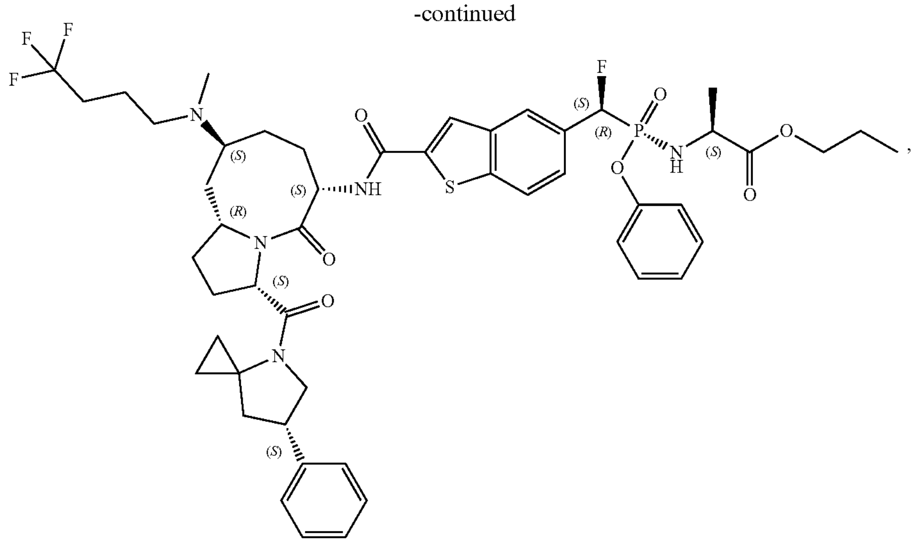
,
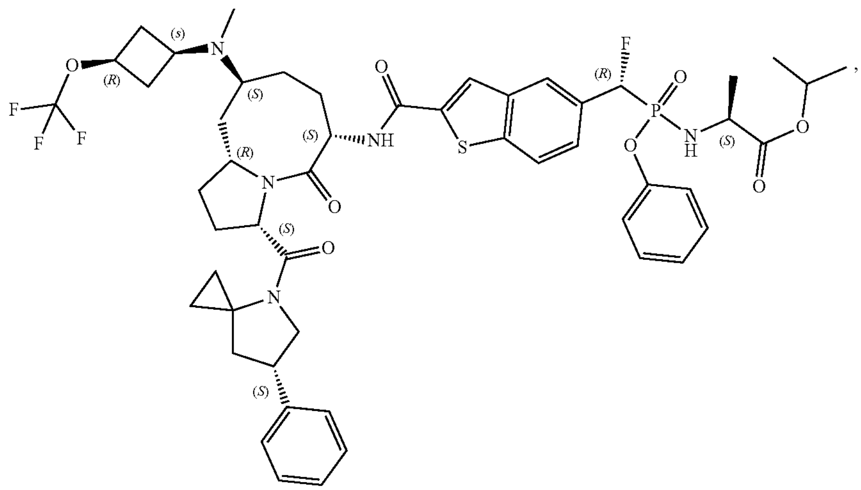
,
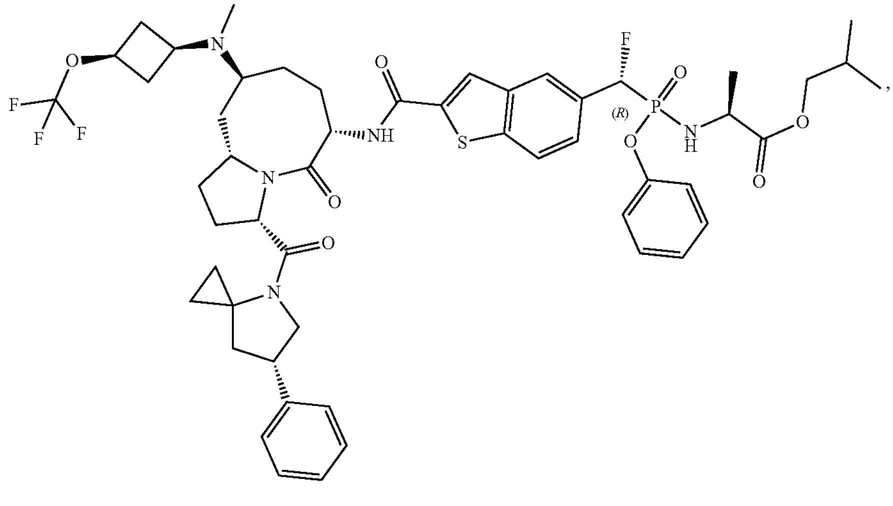
,

-continued
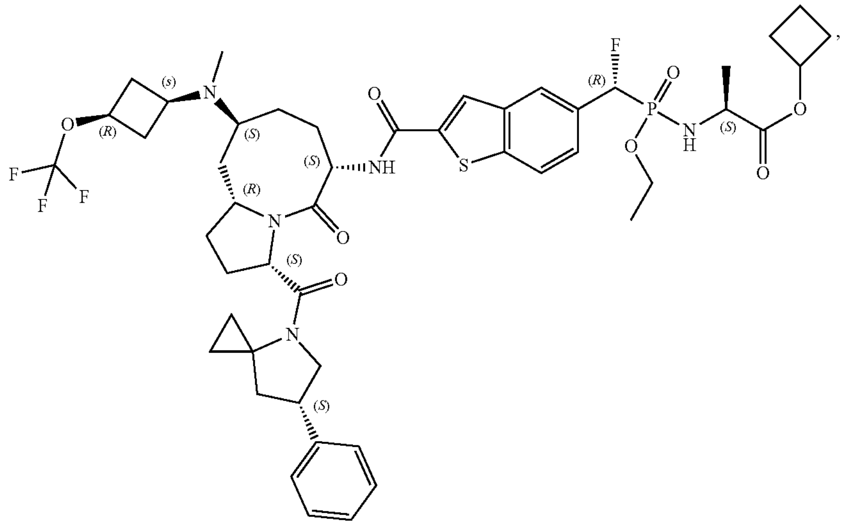
,
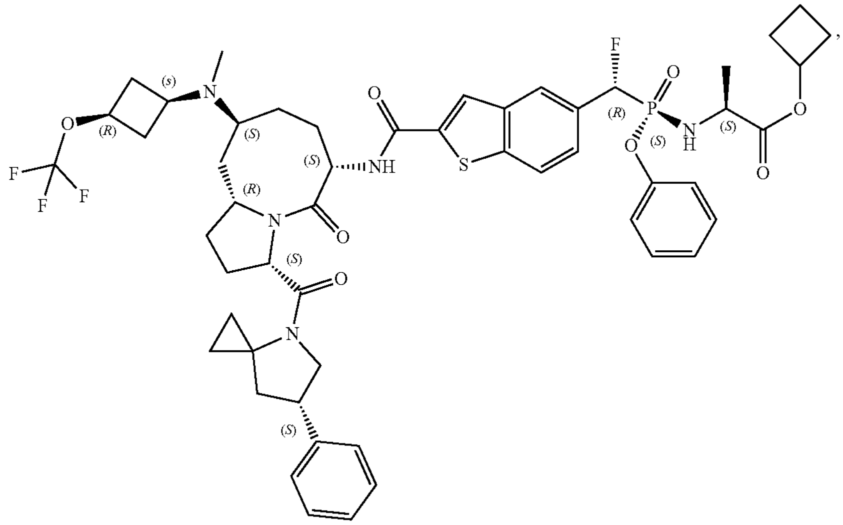
,
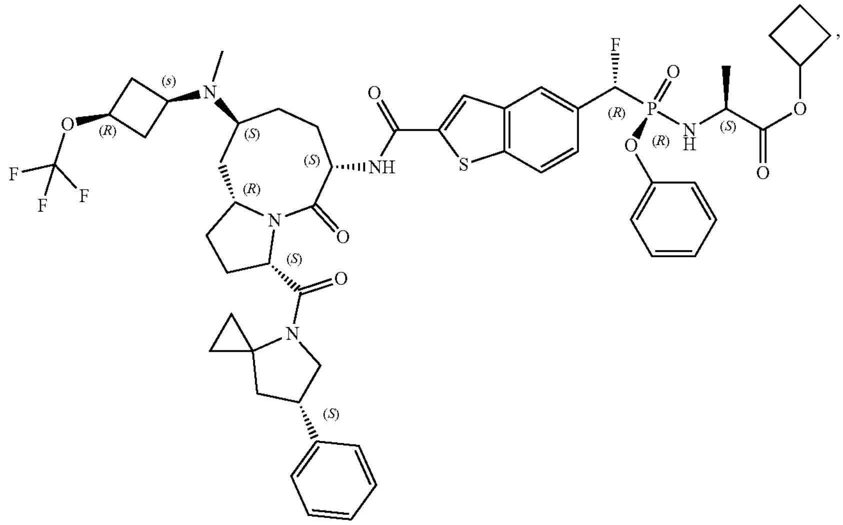
,

-continued
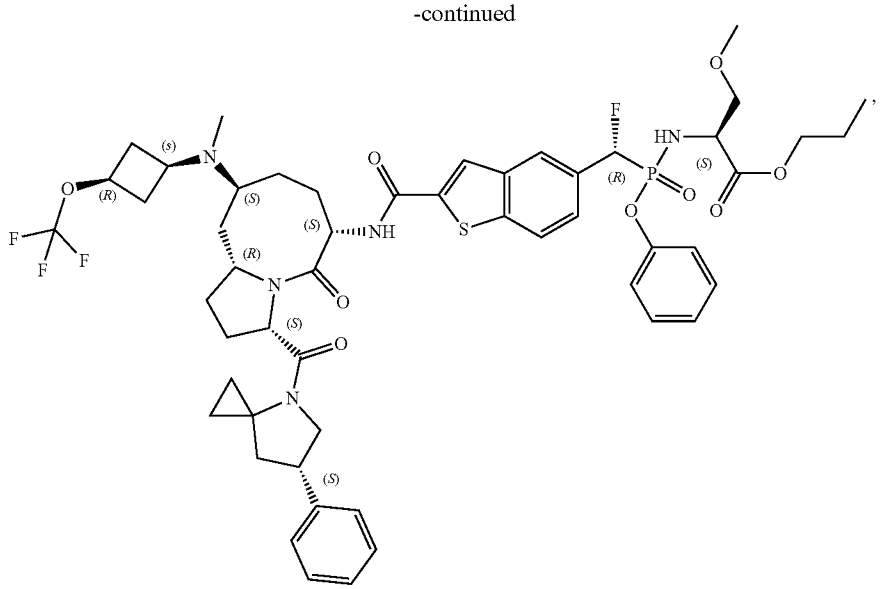
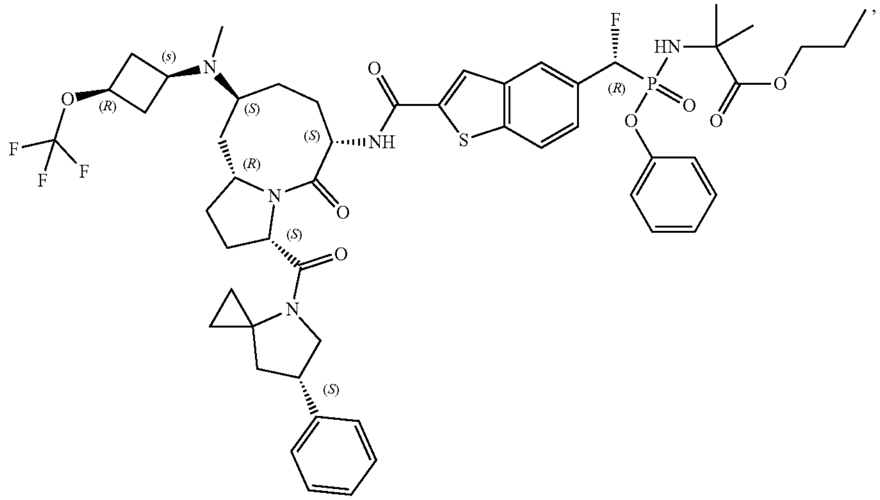
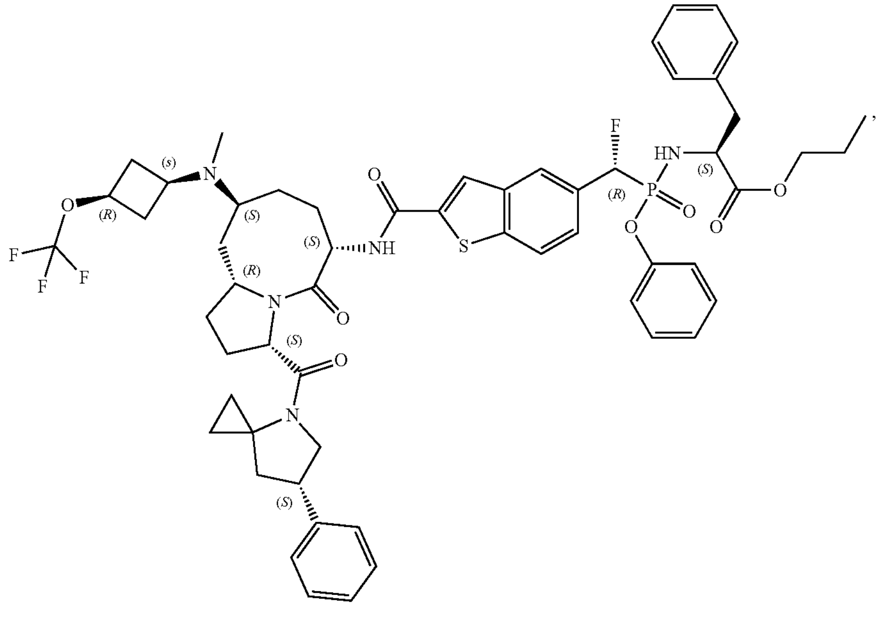

-continued
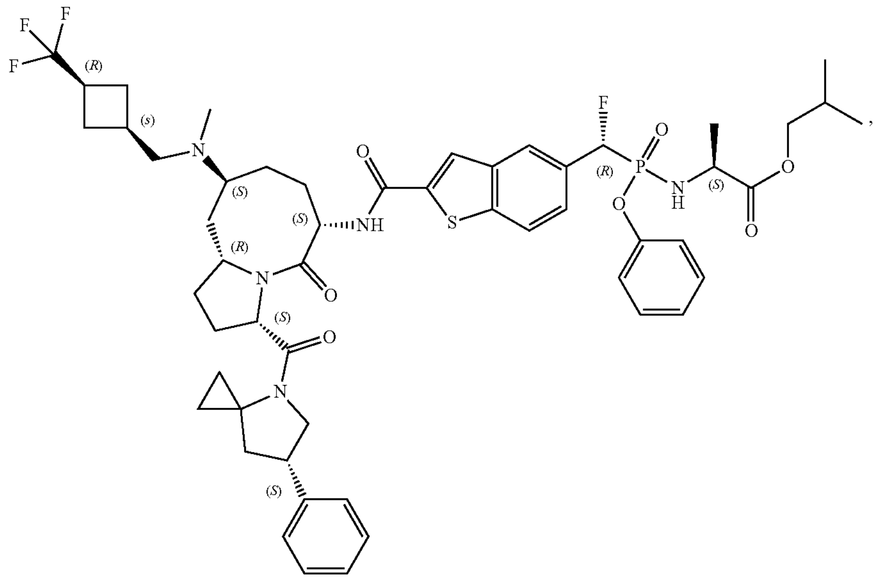
,
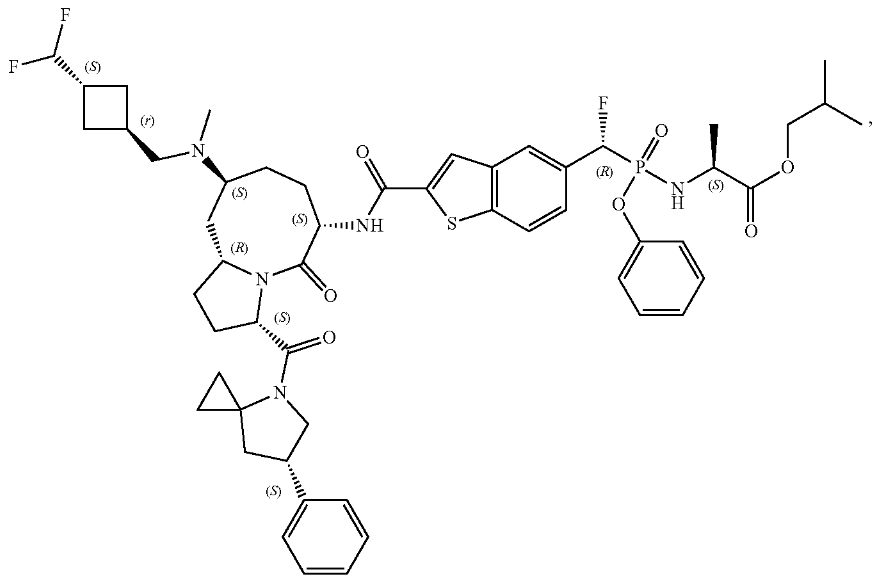
,
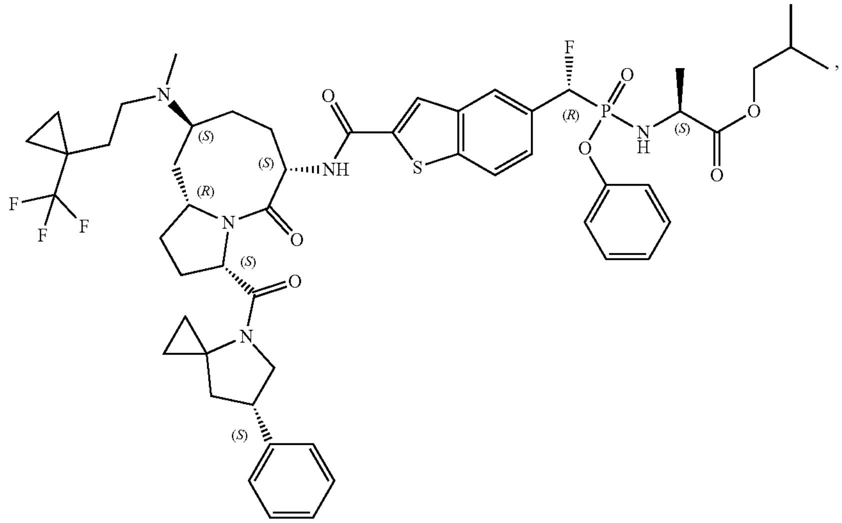
,

-continued
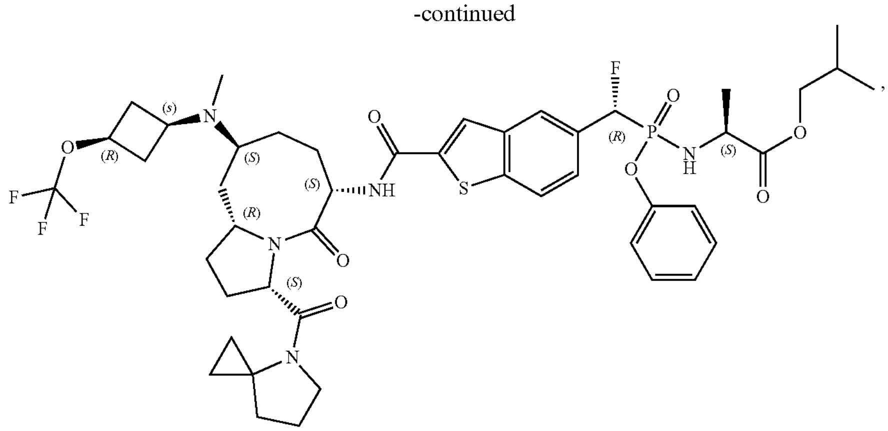
,
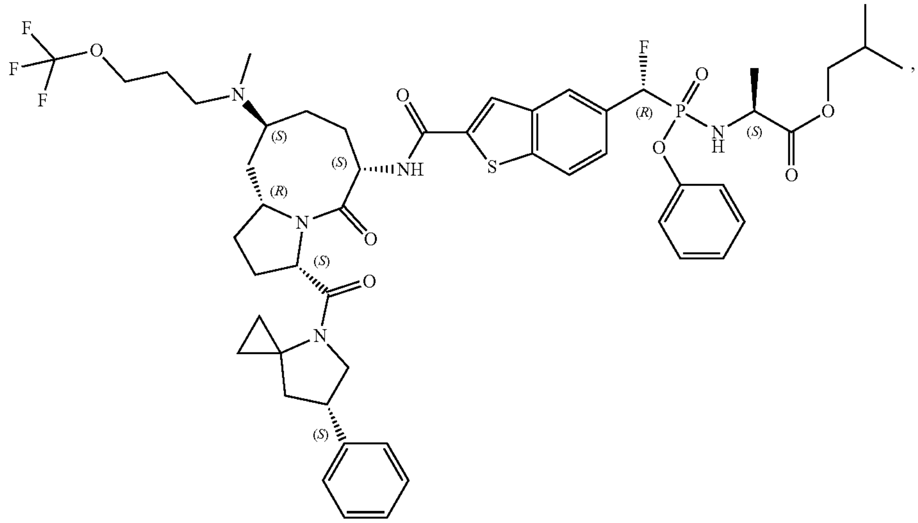
,
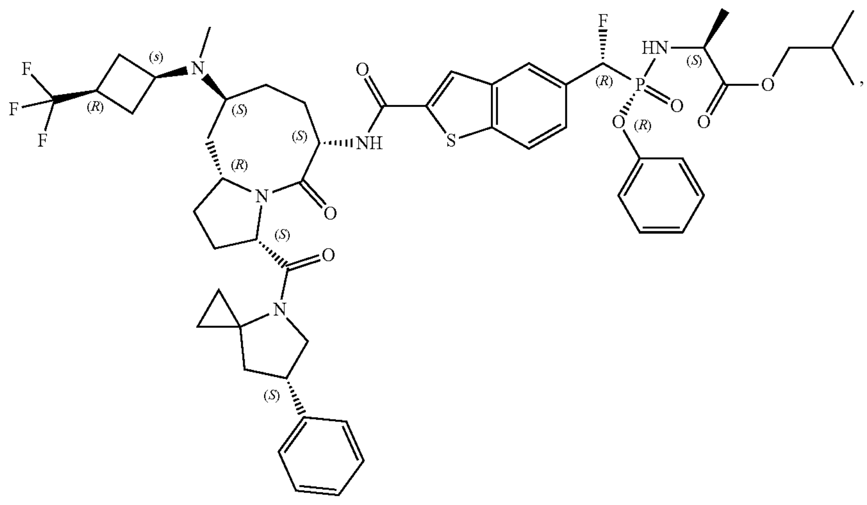
,

-continued
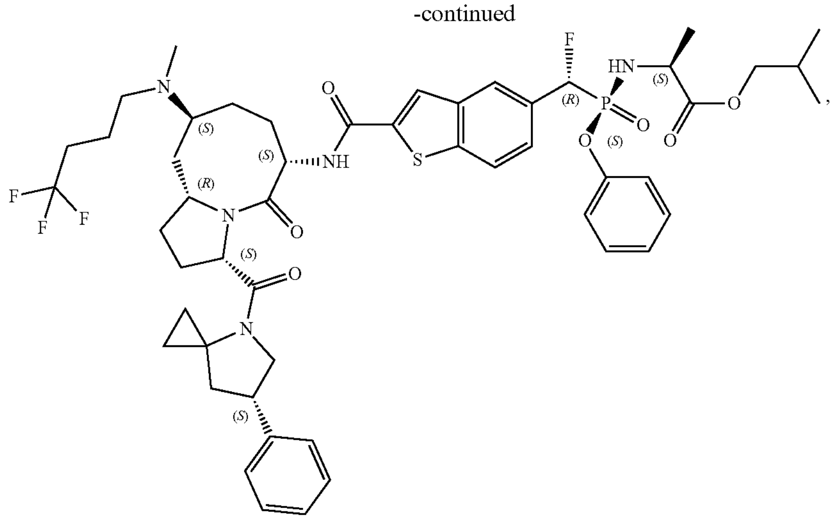
,
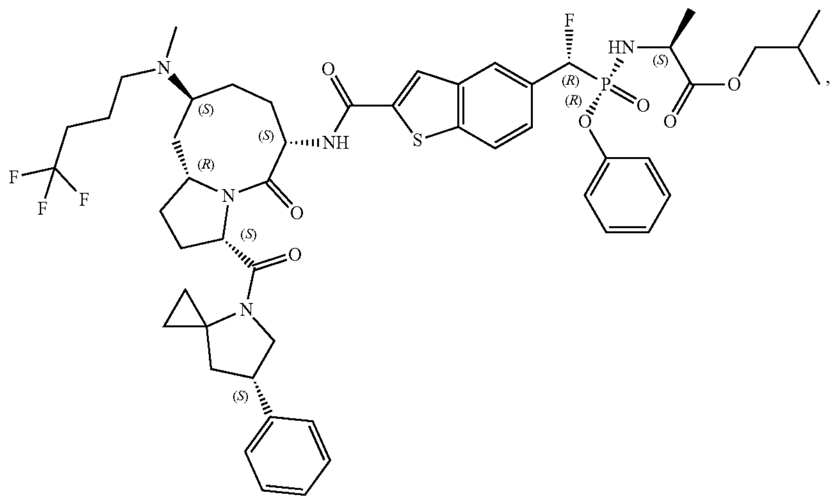
,
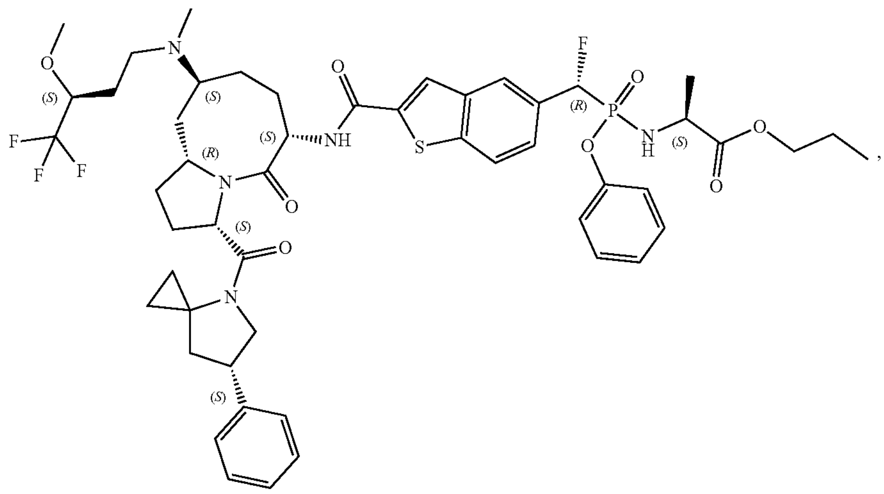
,

-continued
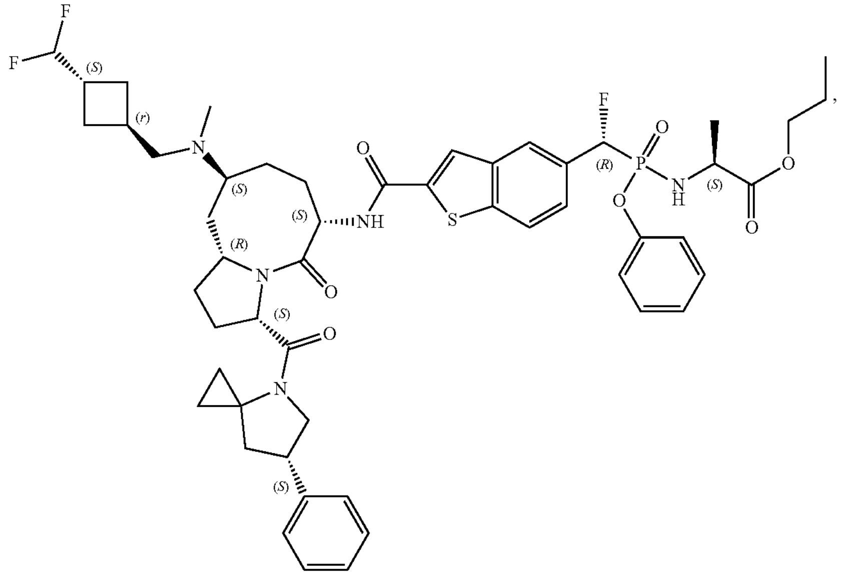
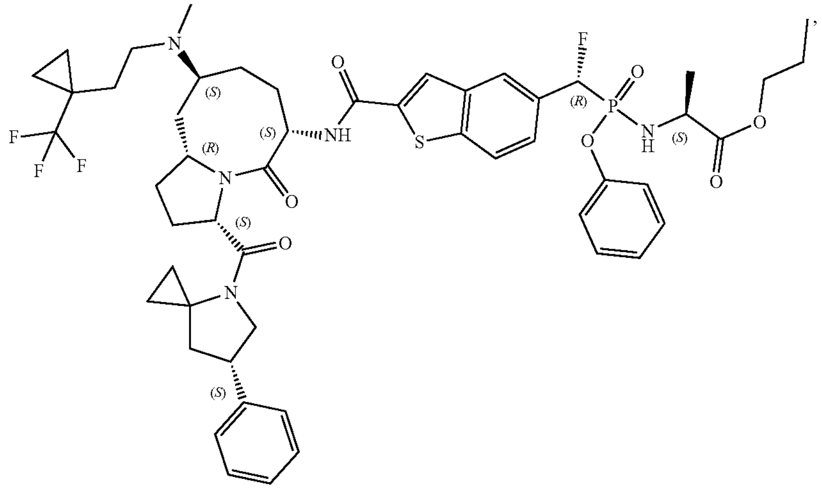
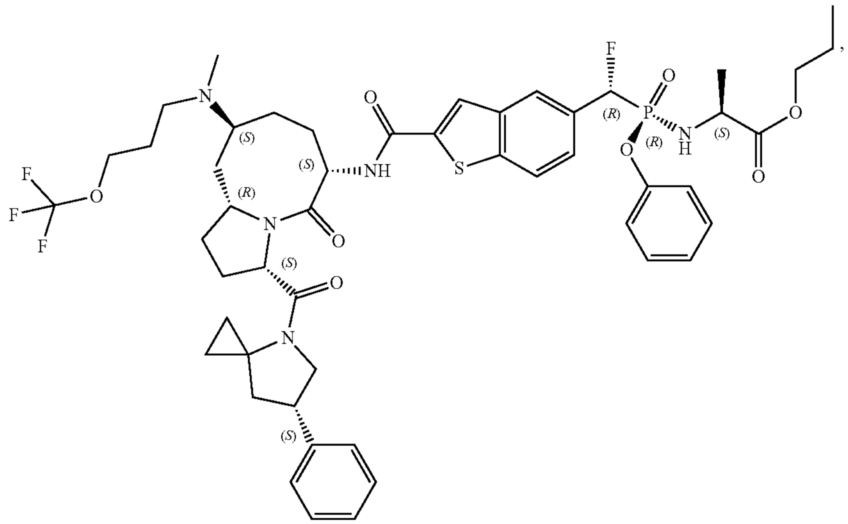

-continued
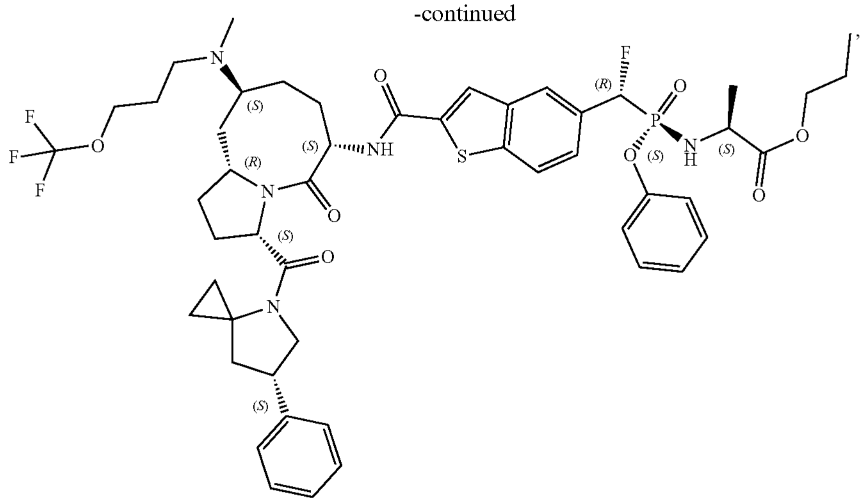
,
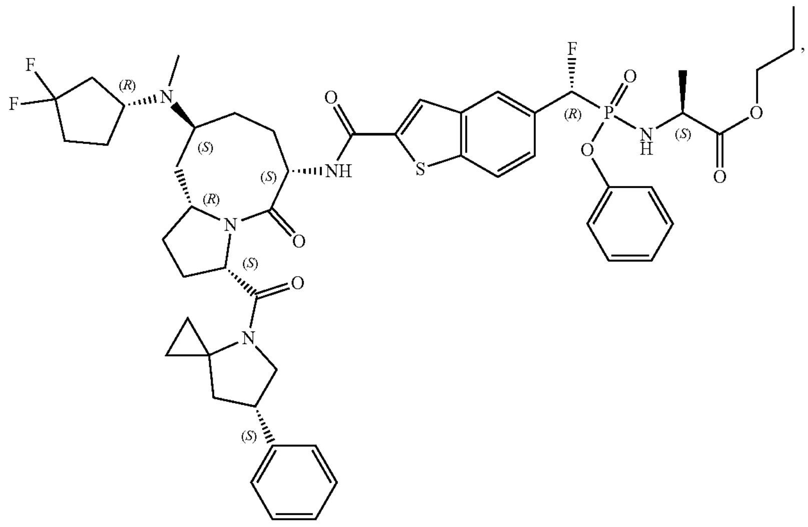
,
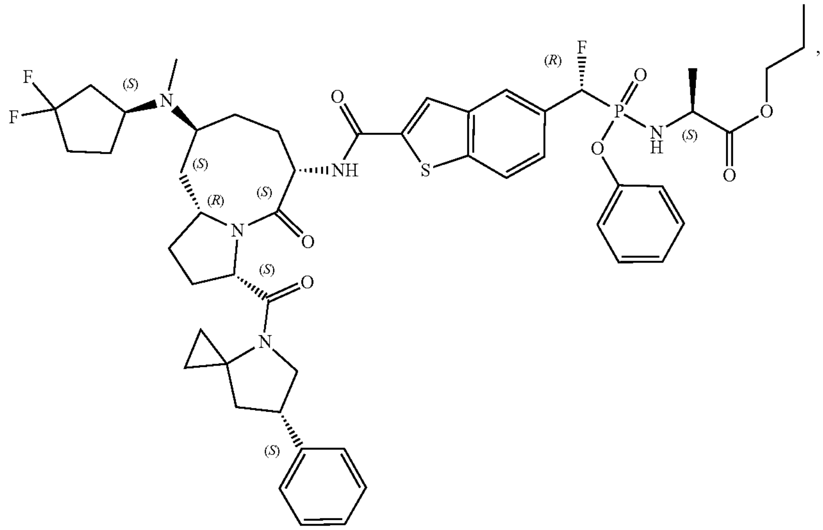
,

-continued
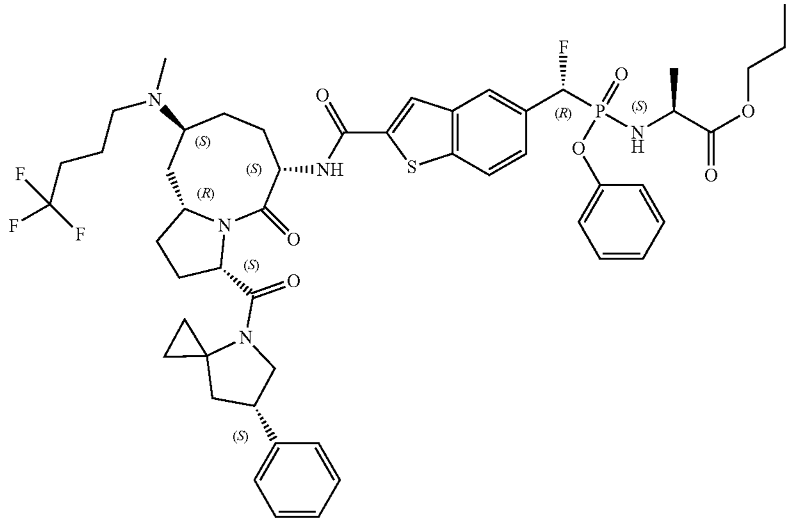
,
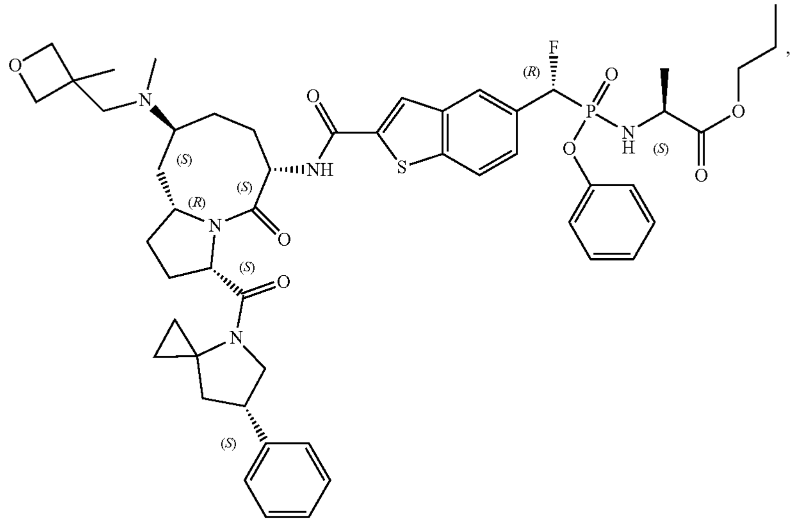
,
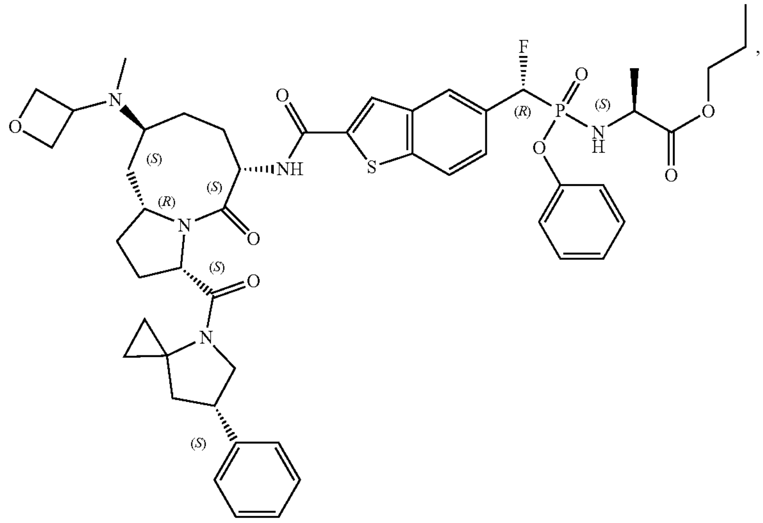
,

-continued
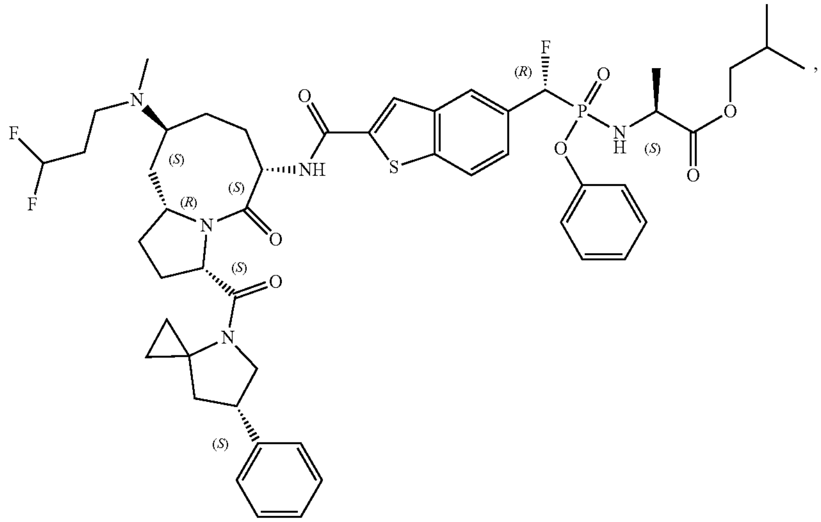
,
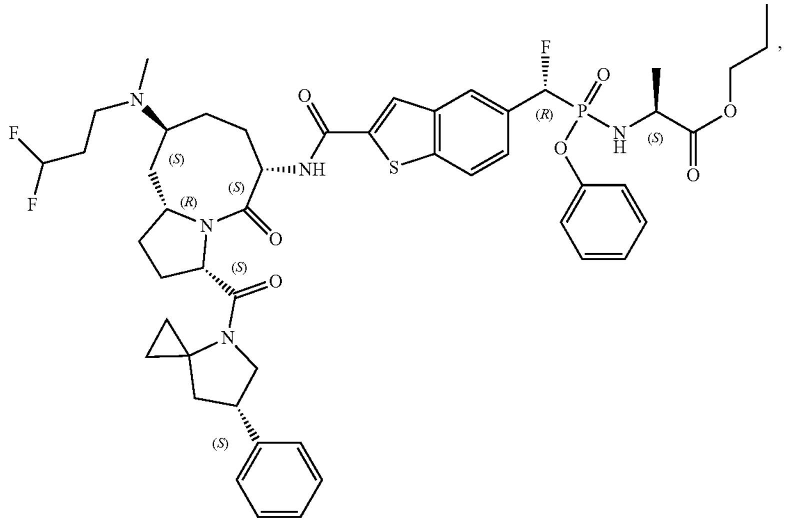
,
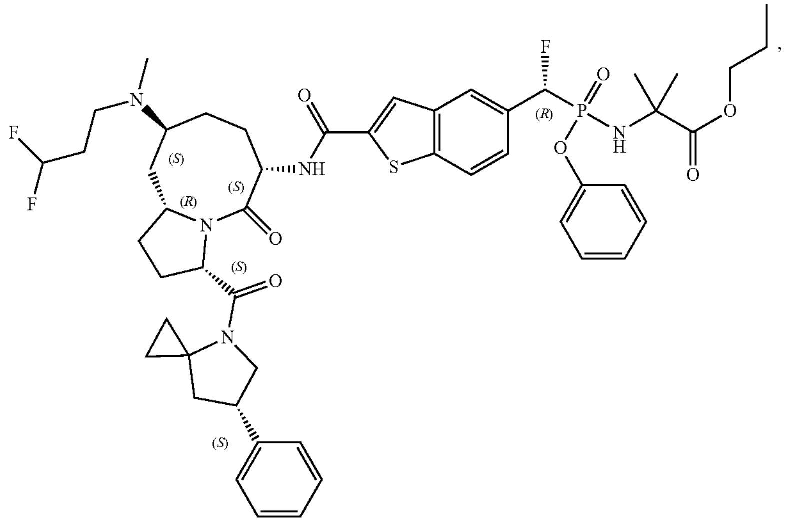
,

-continued
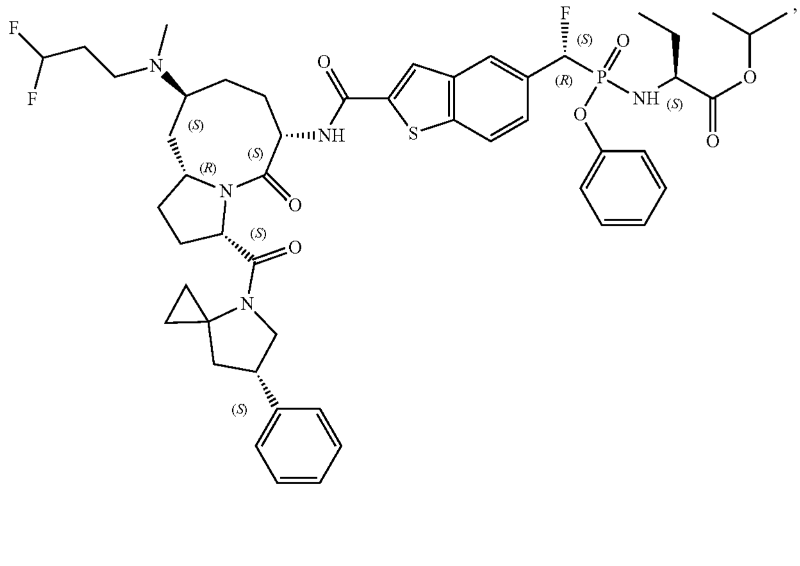
,
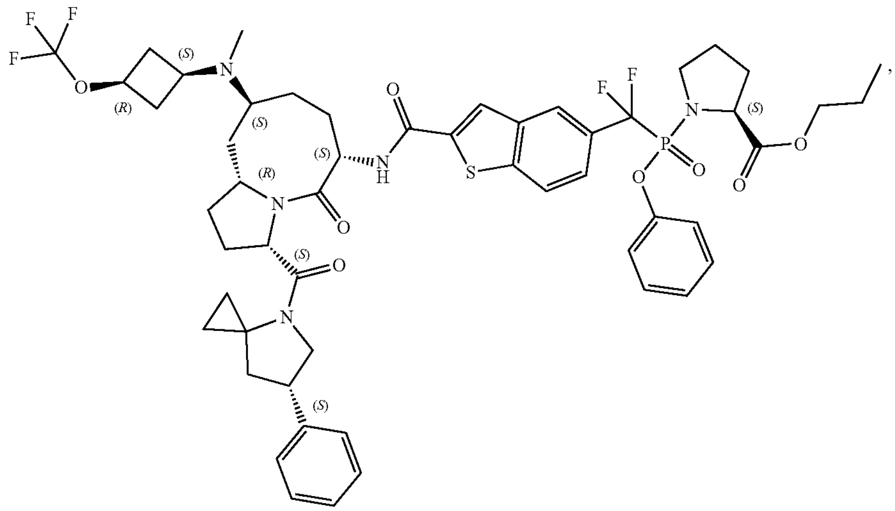
,
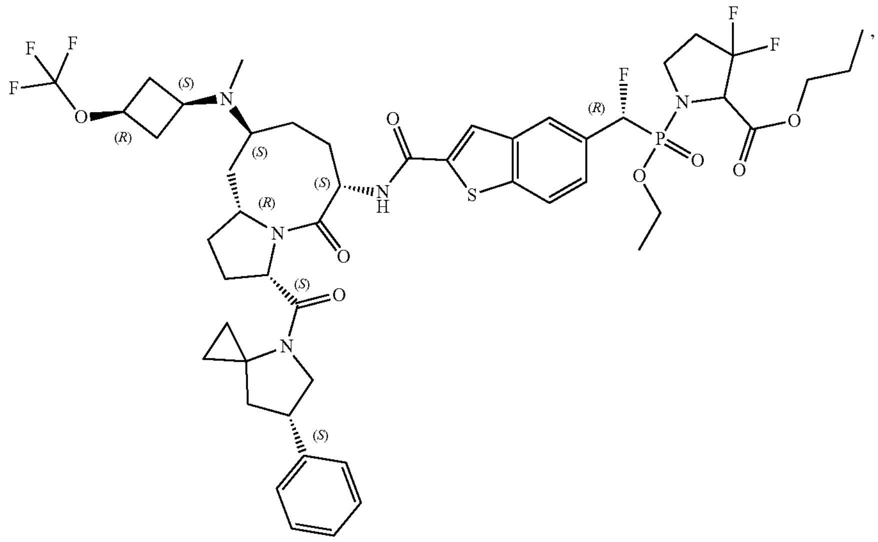
,

-continued
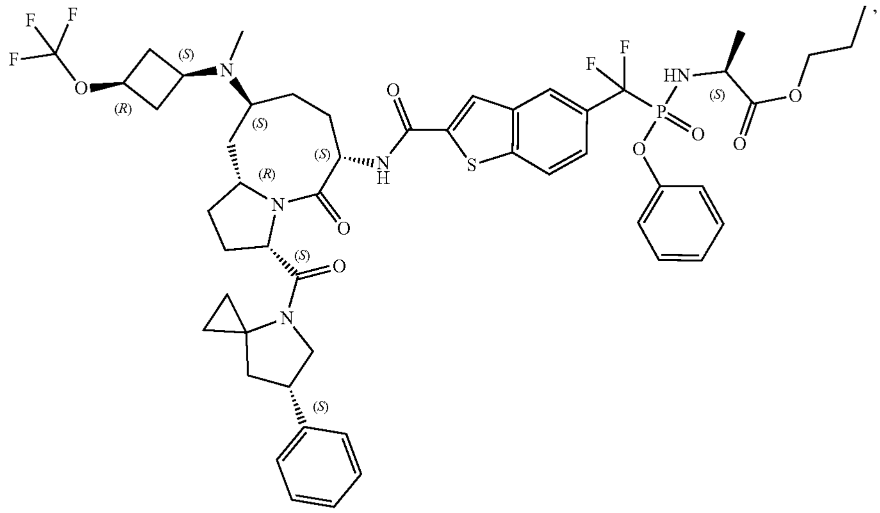
,
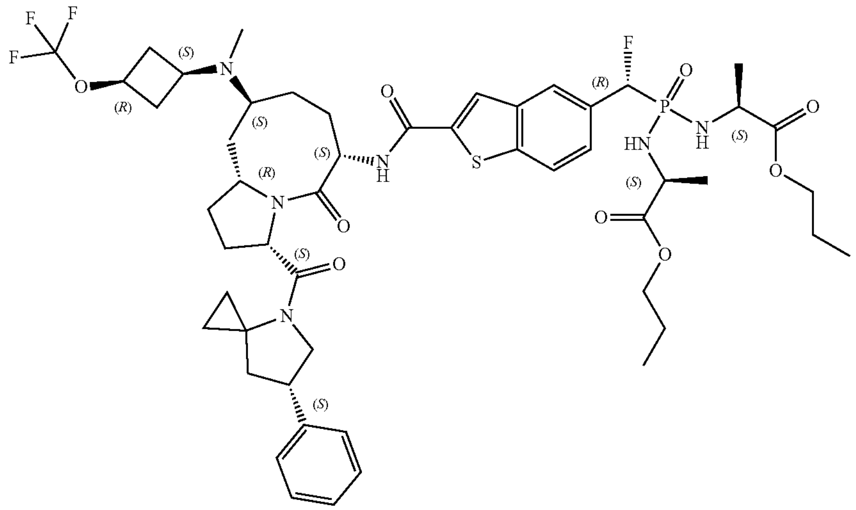
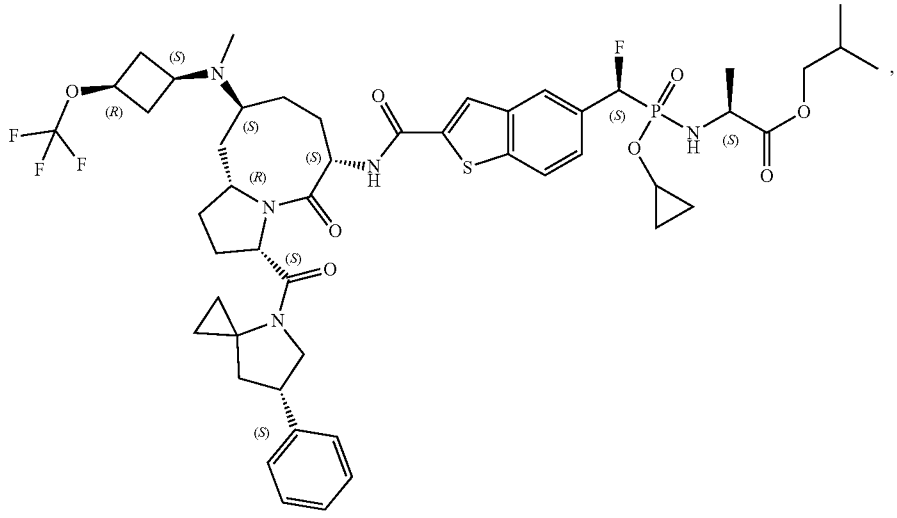
,

-continued
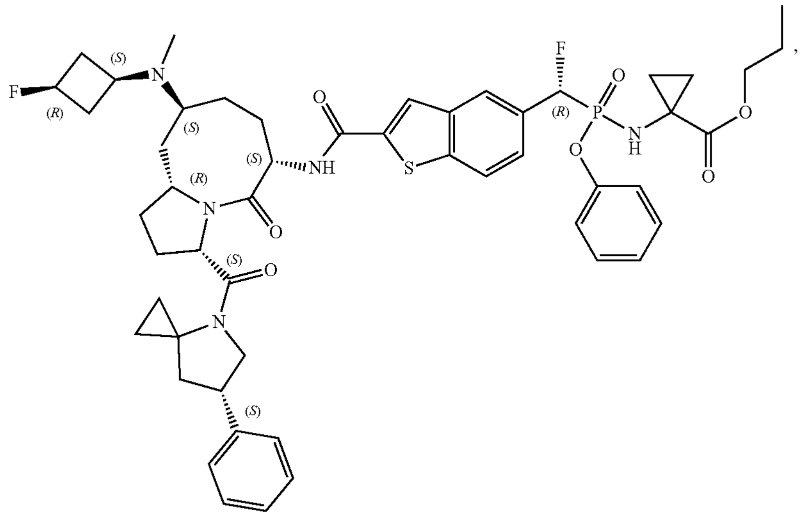
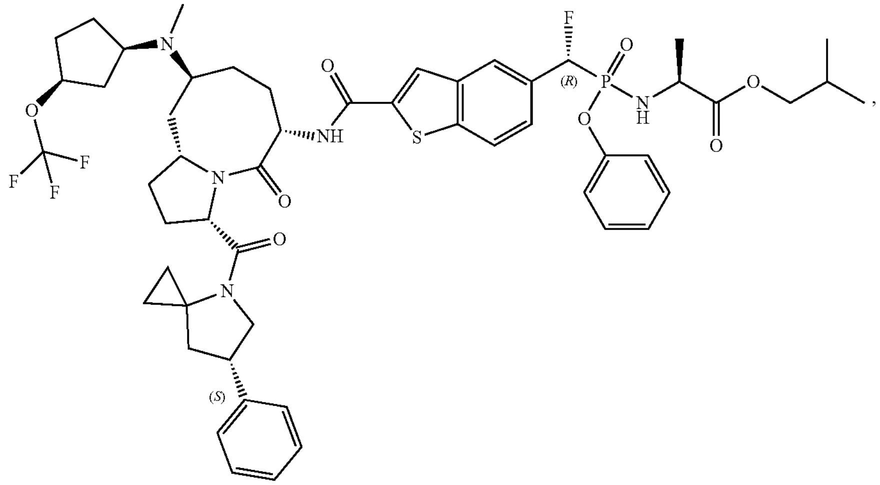
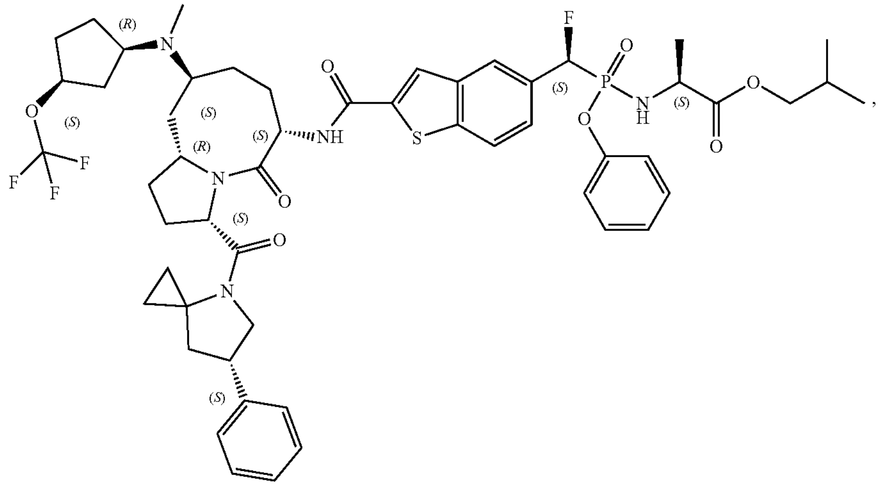

-continued
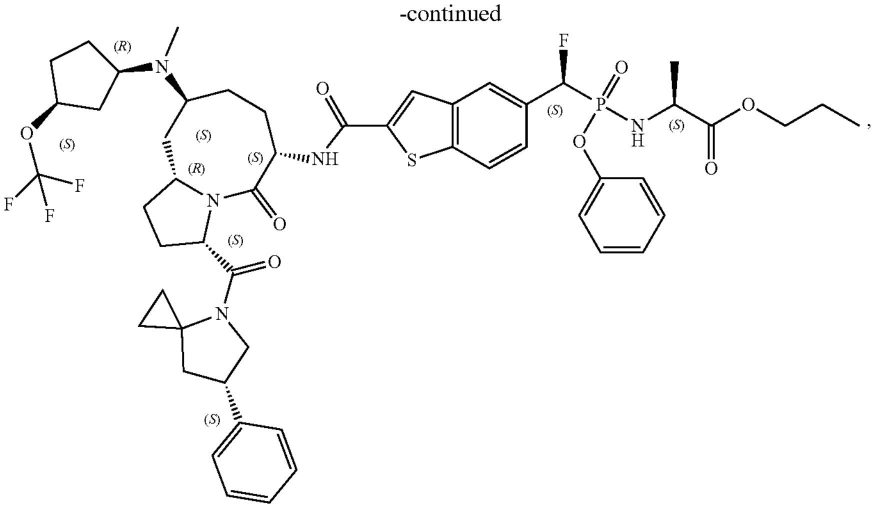
,
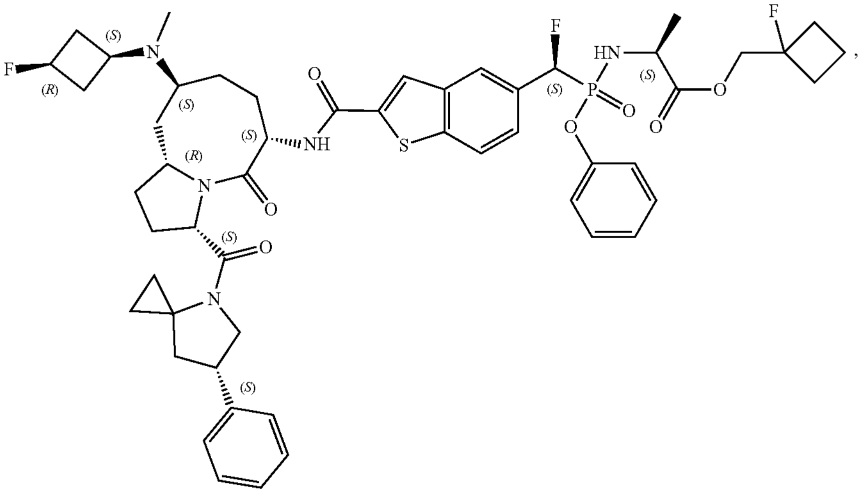
,
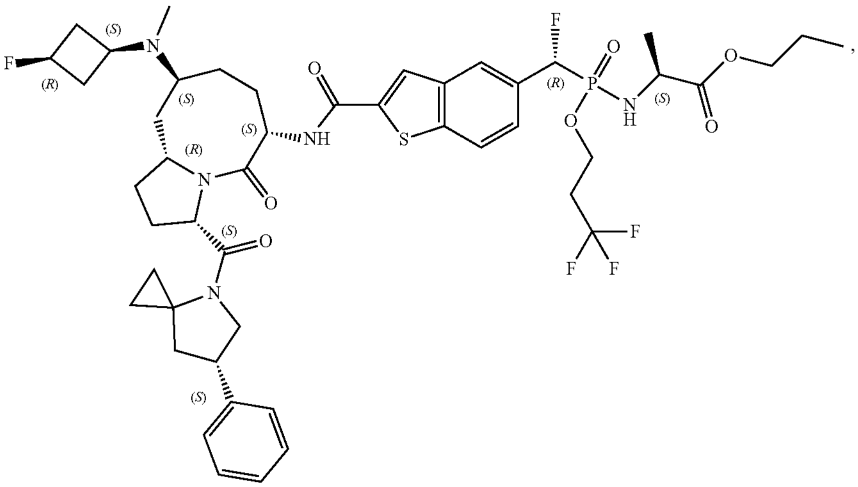
,

-continued
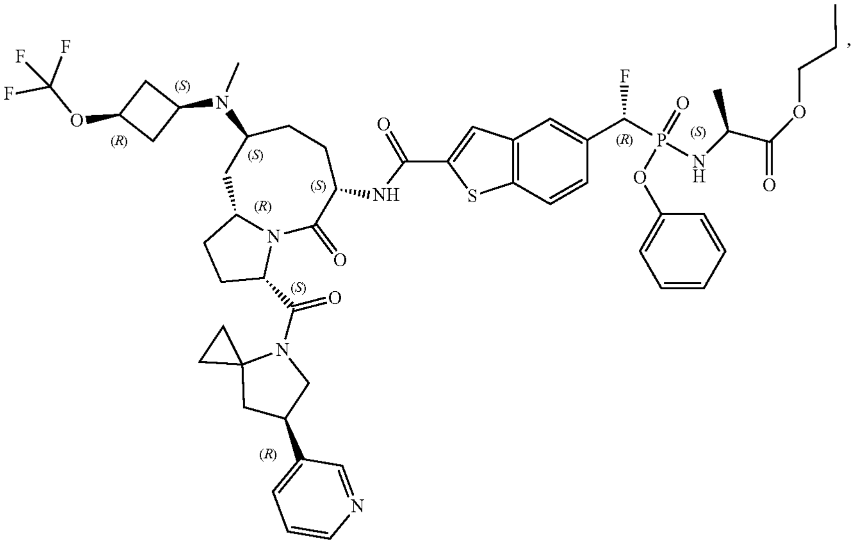
,
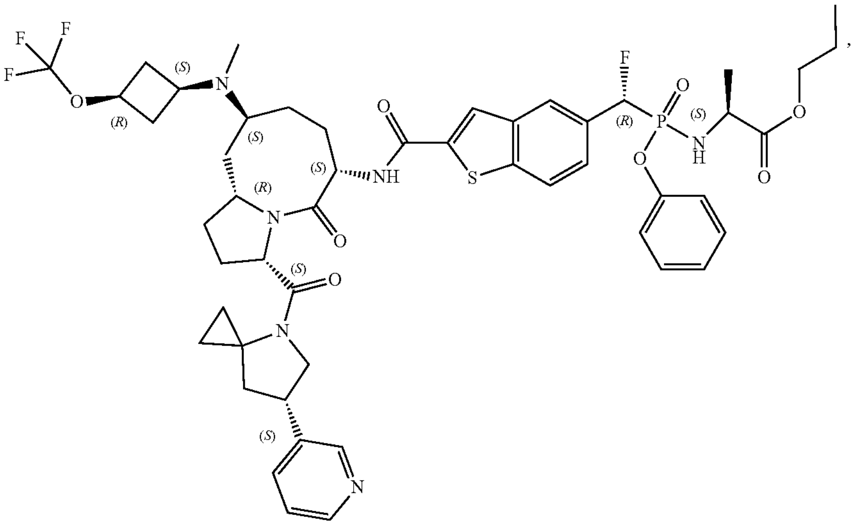
,
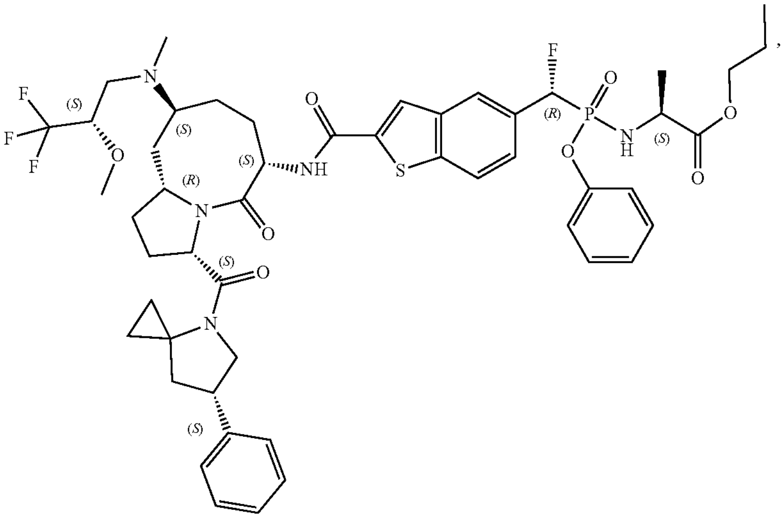
,

-continued
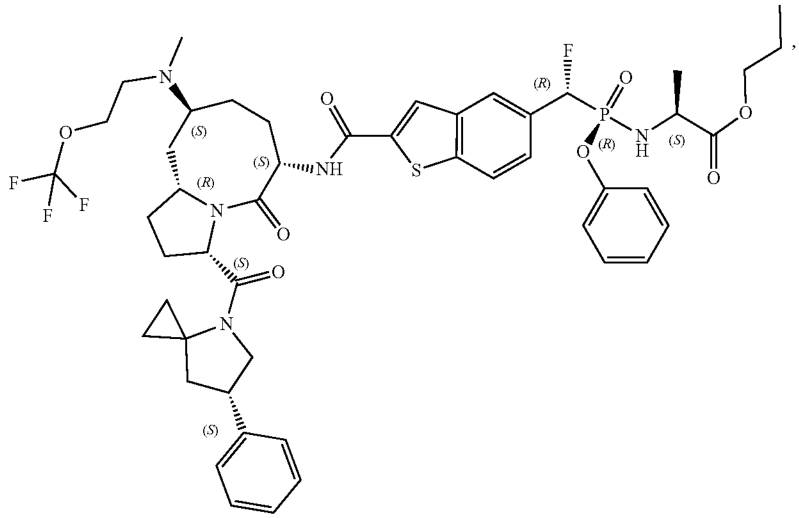
,
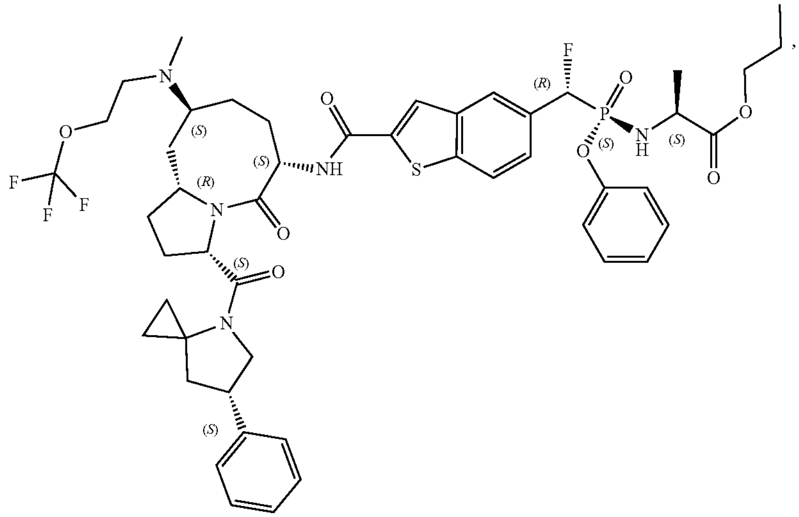
,
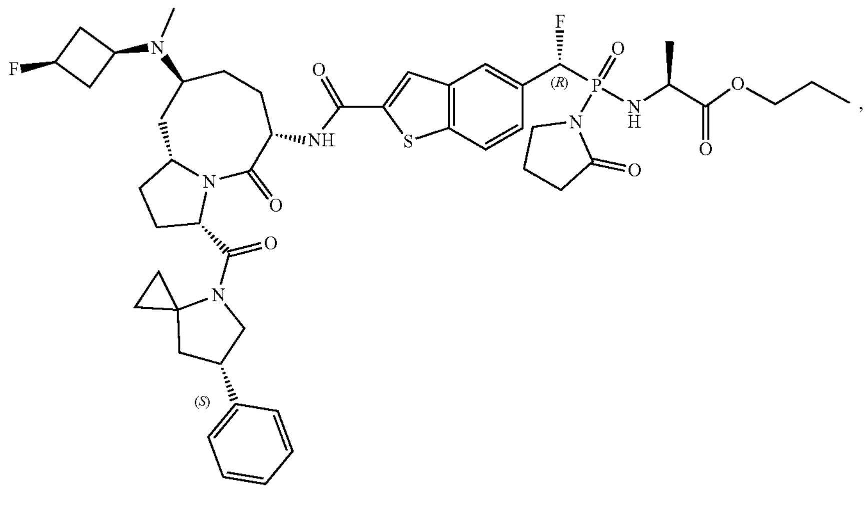
,

-continued
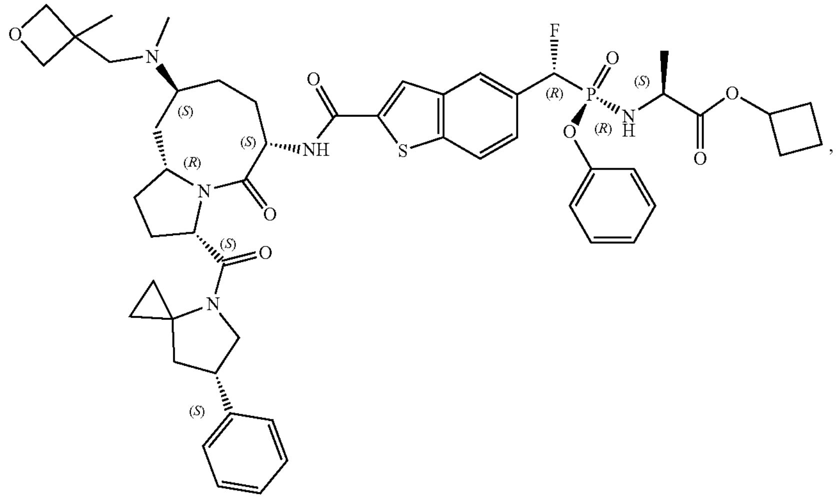
,
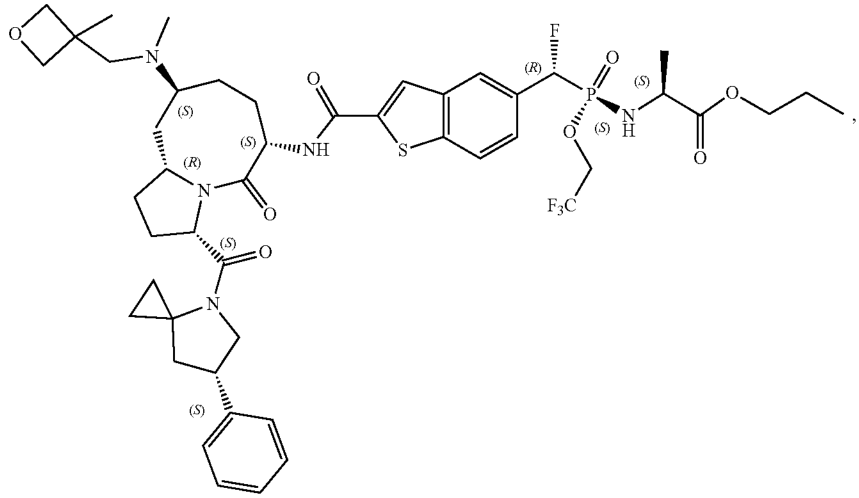
,
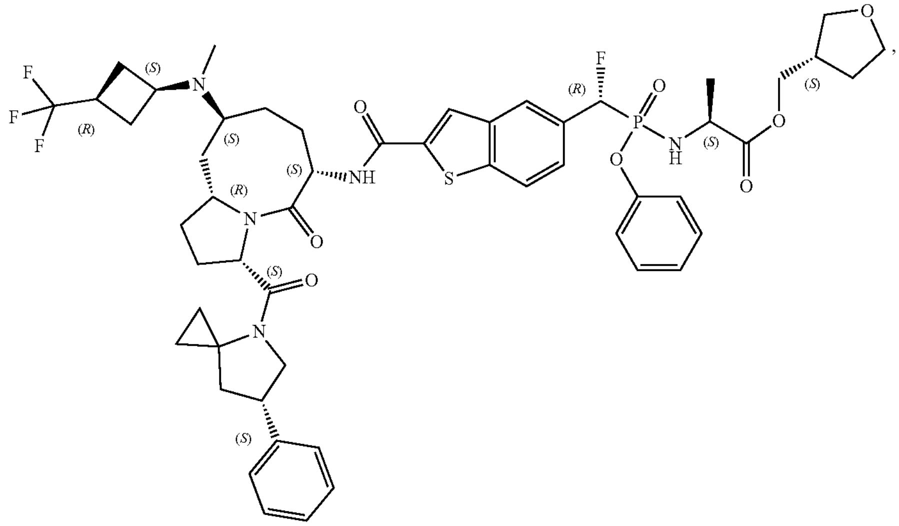
,

-continued
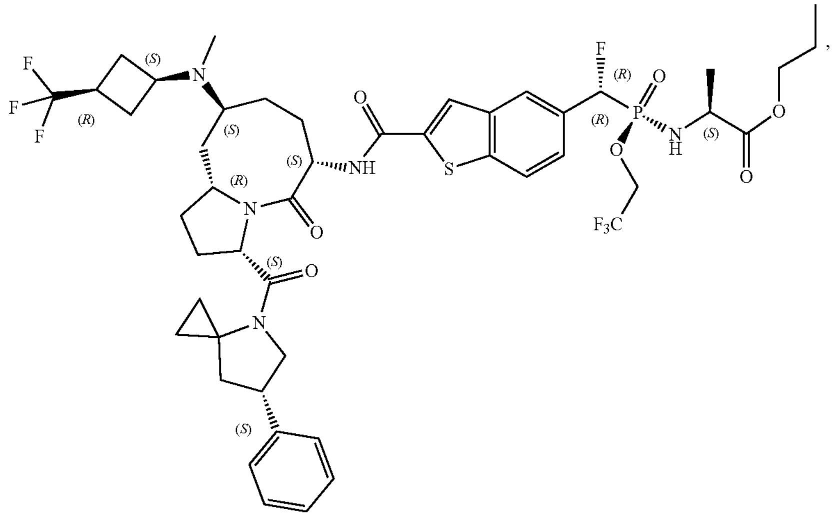
,
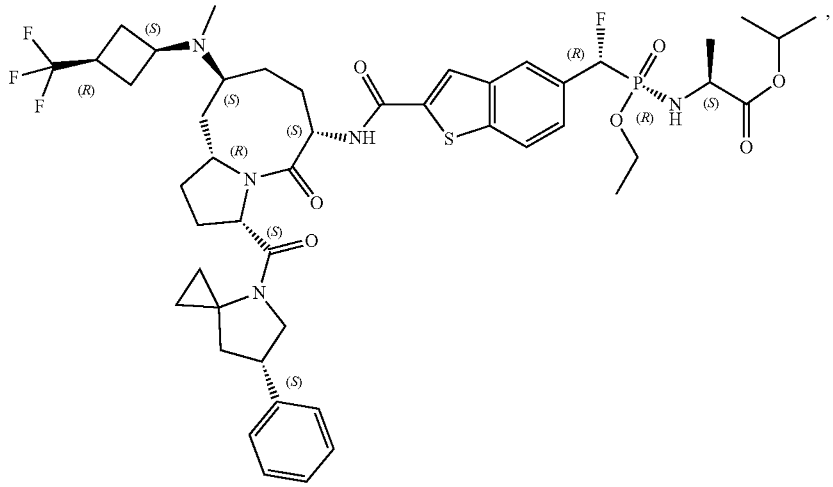
,
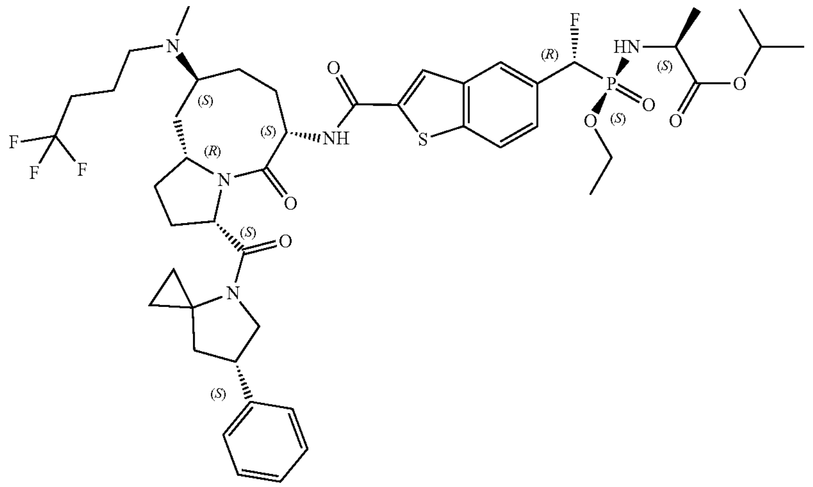
,

-continued
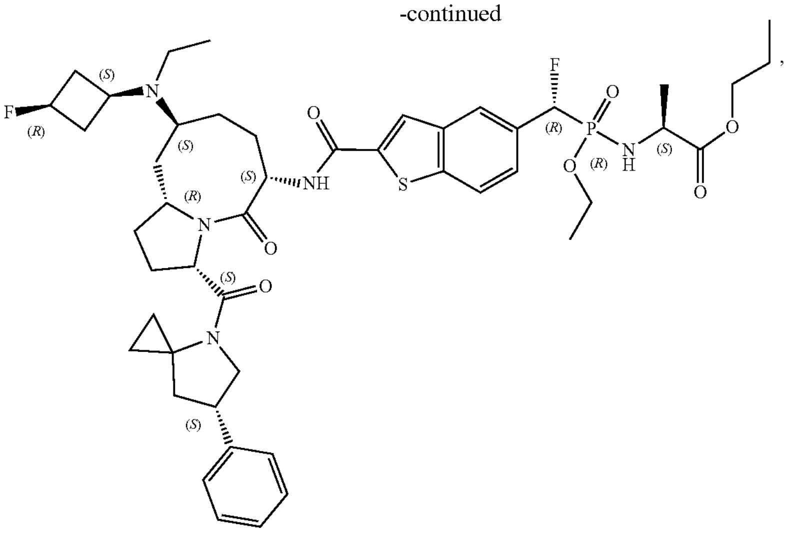
,
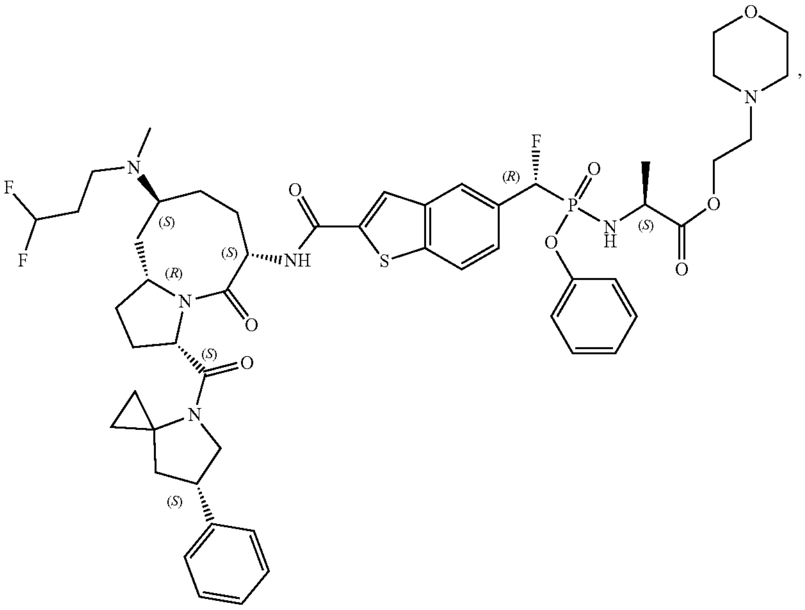
,
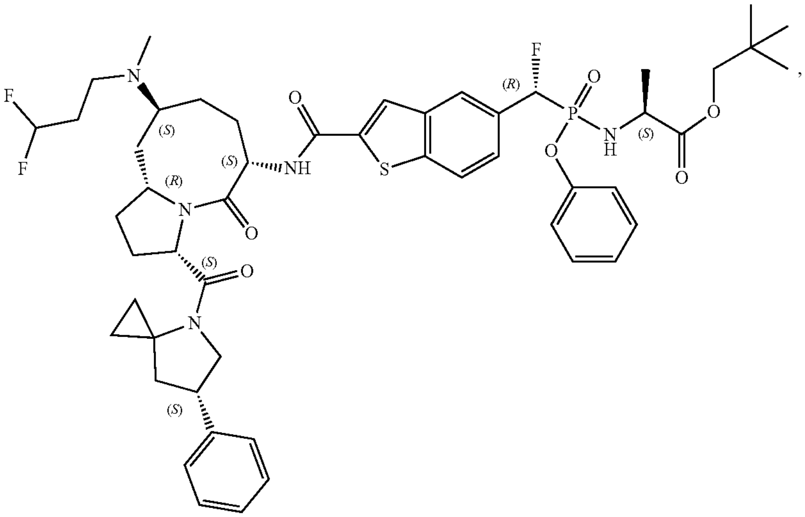
,

-continued
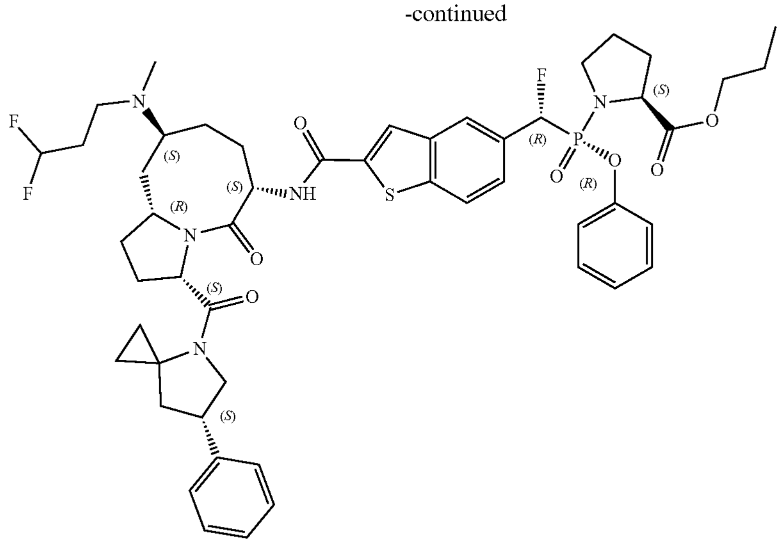
,
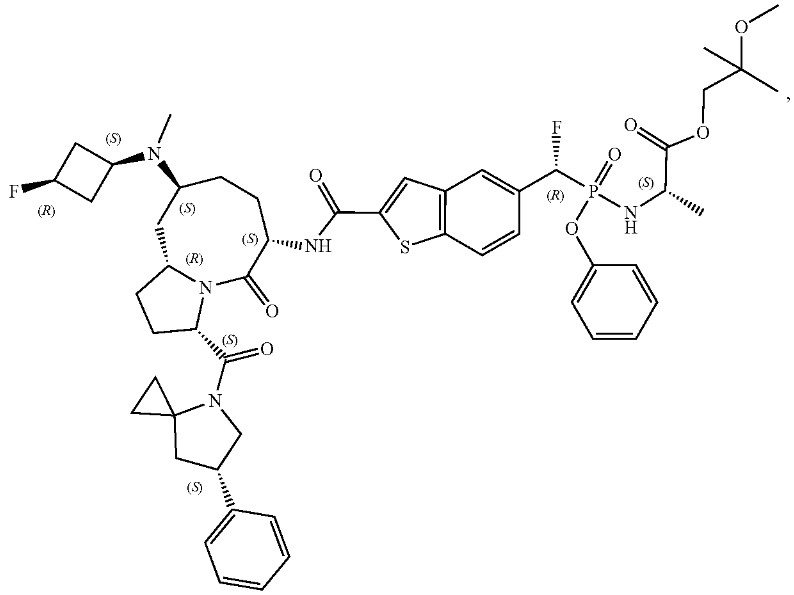
,
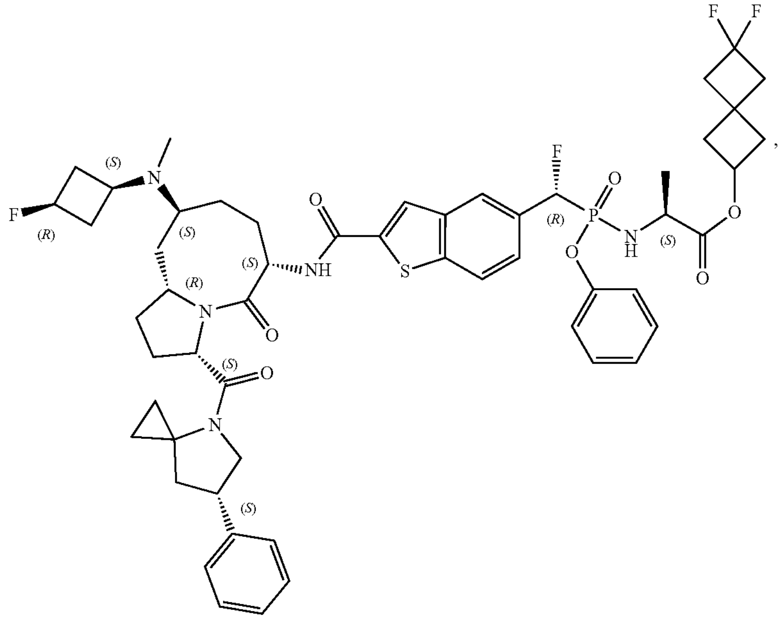
,

-continued
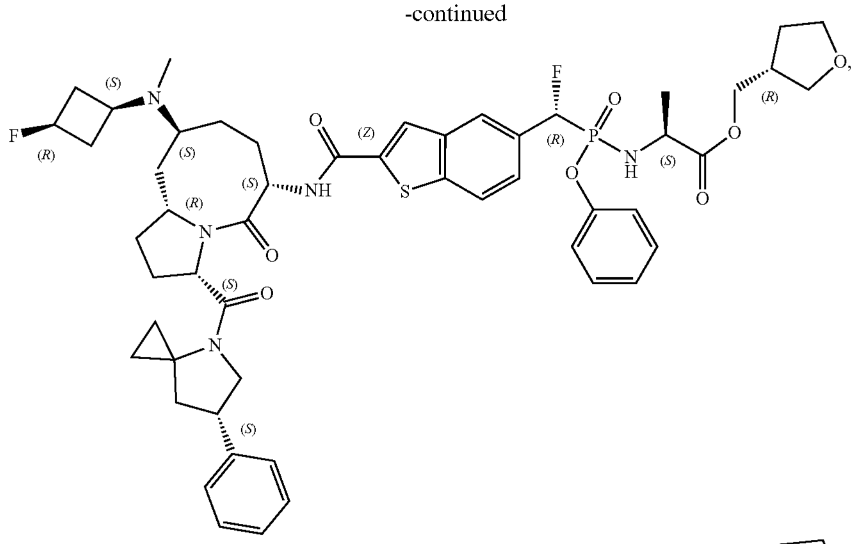
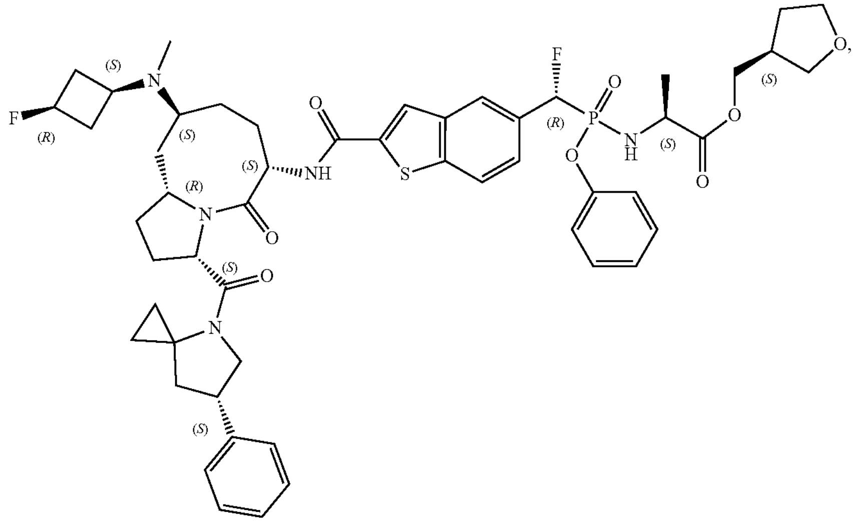
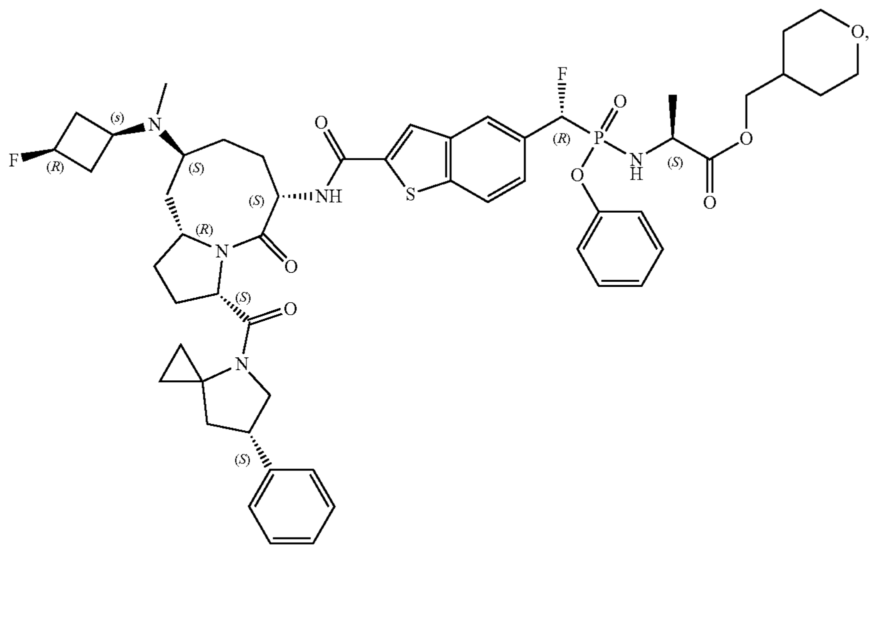

-continued
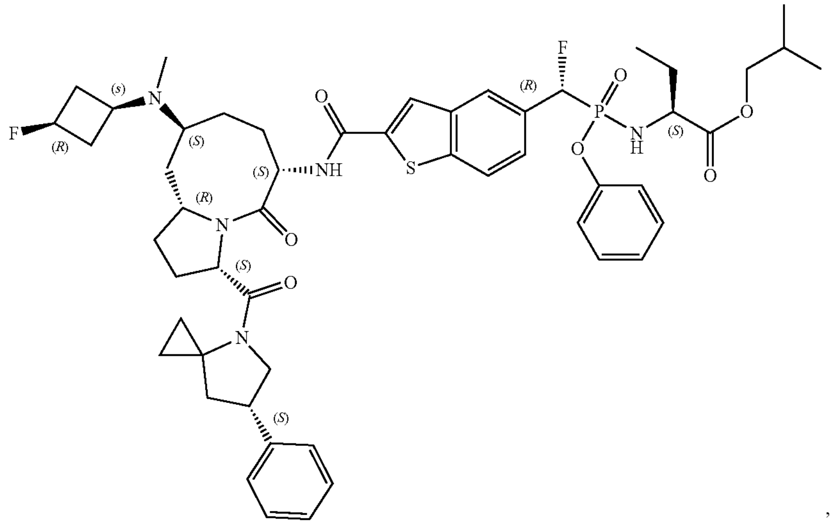
,
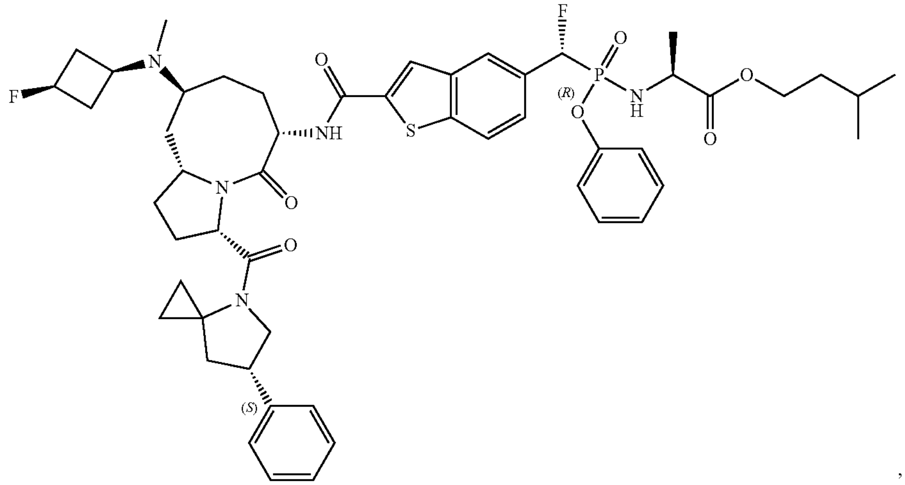
,
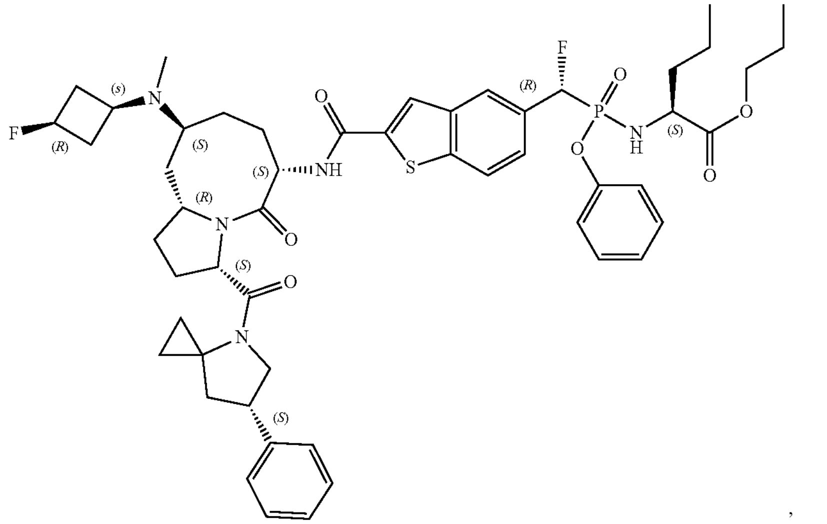
,

-continued
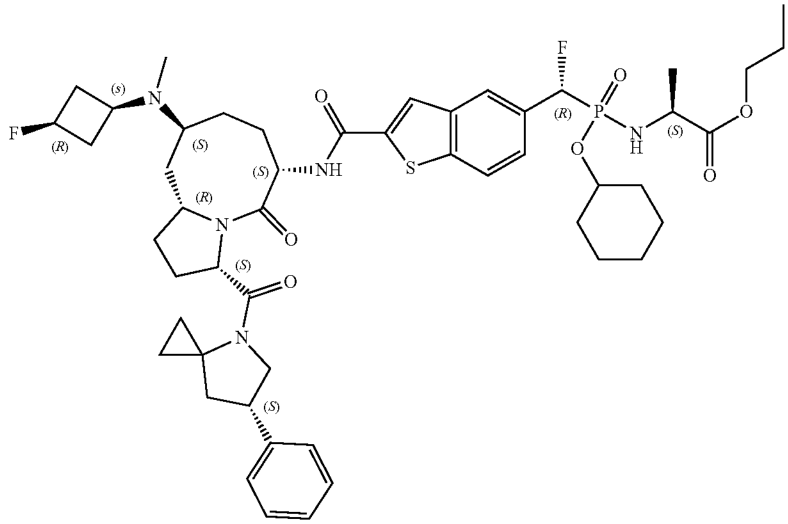
,
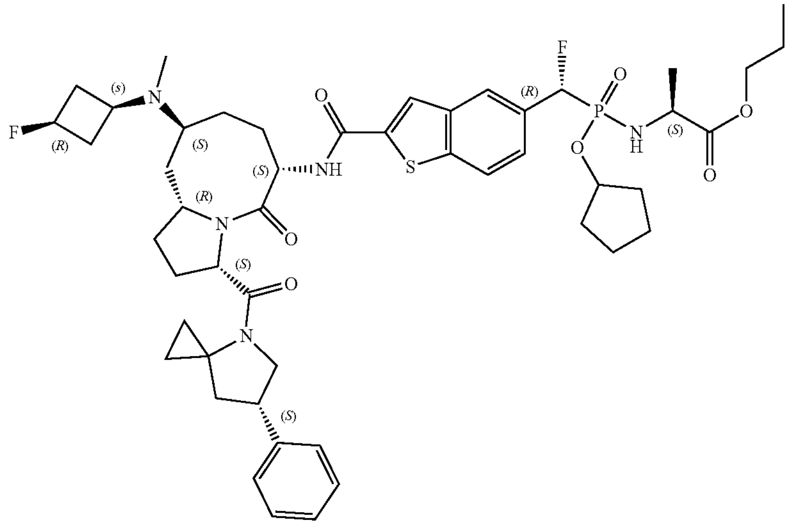
,
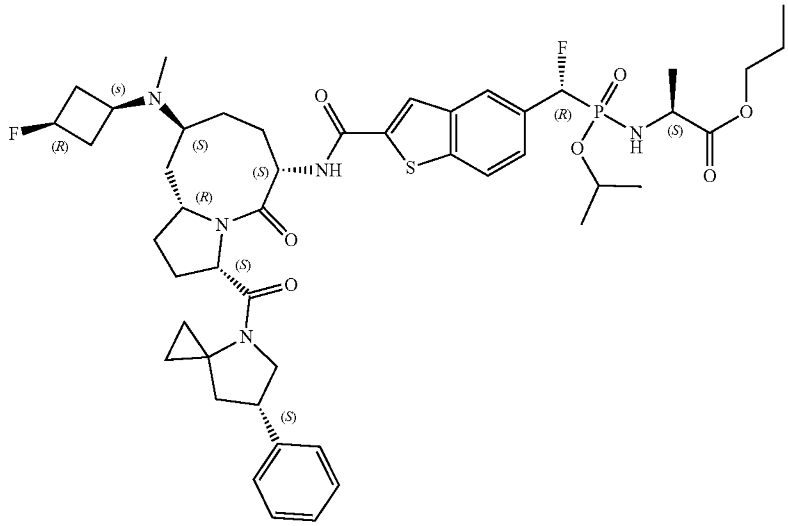
,

-continued
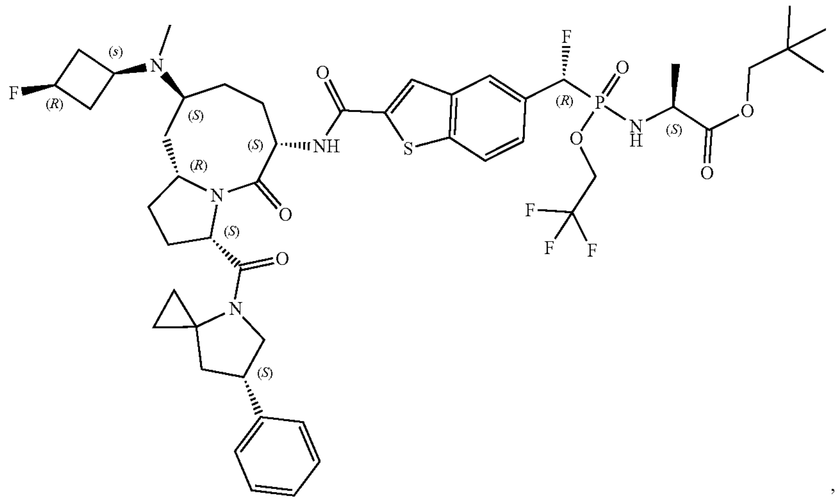
,
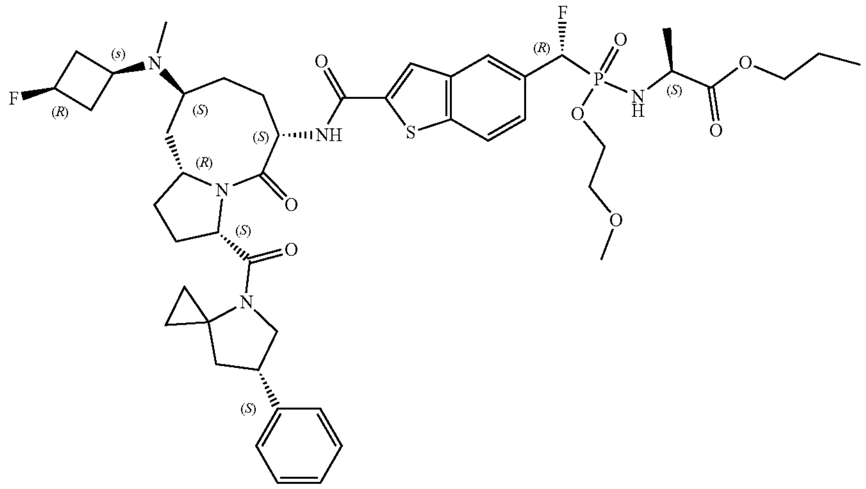
,
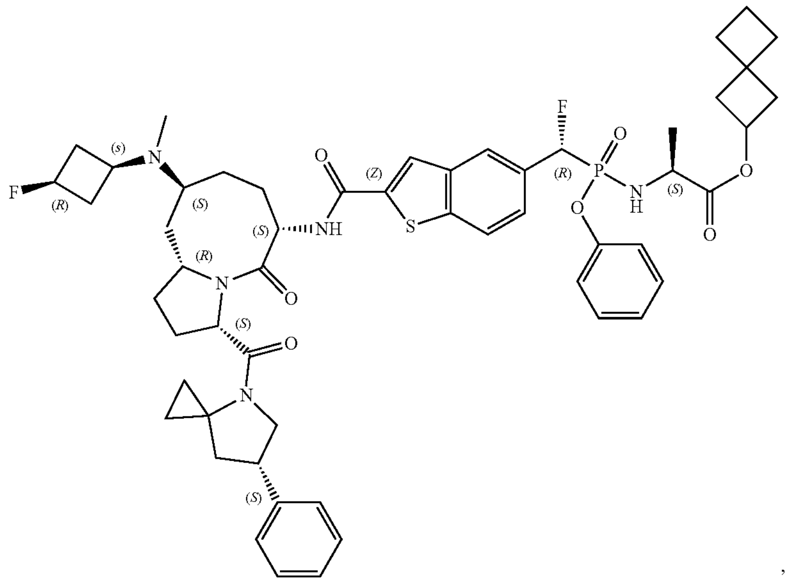
,

-continued
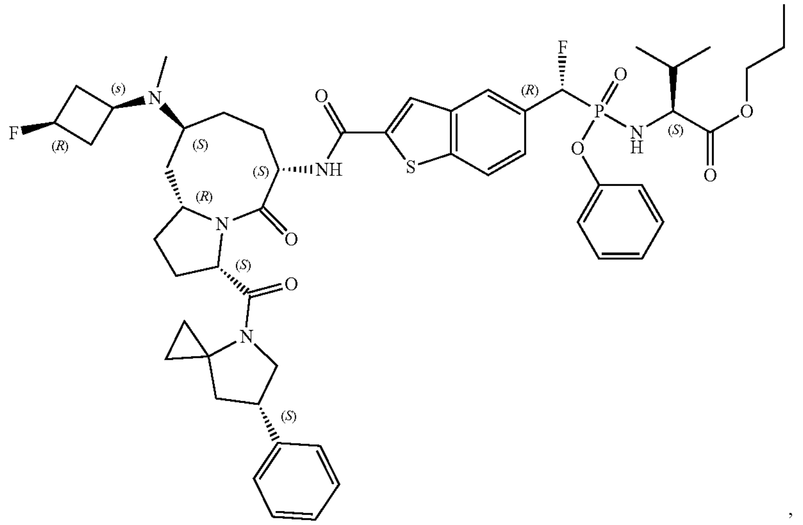
,
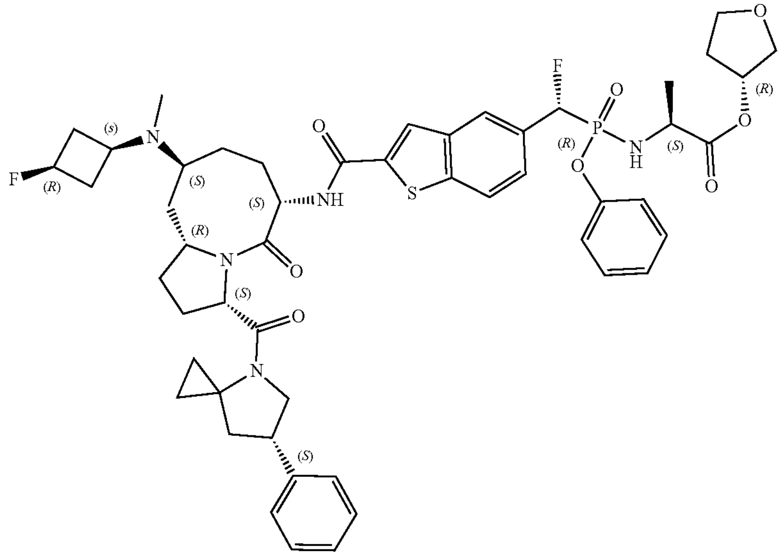
,
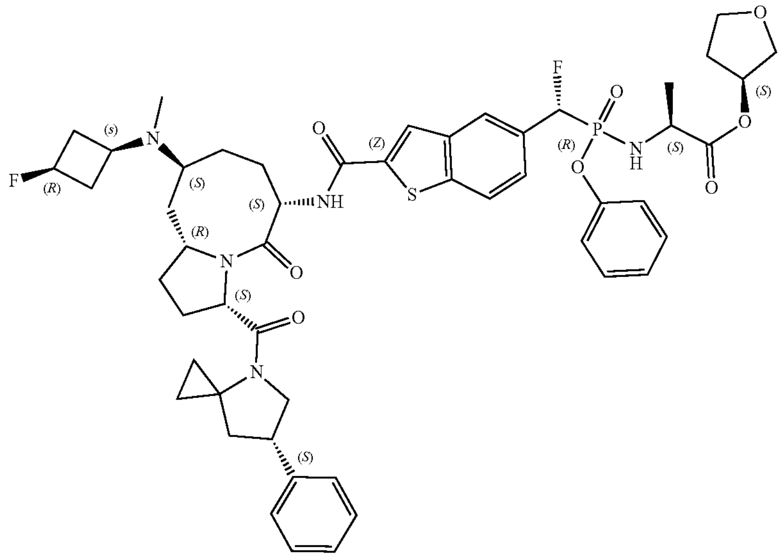
,

-continued
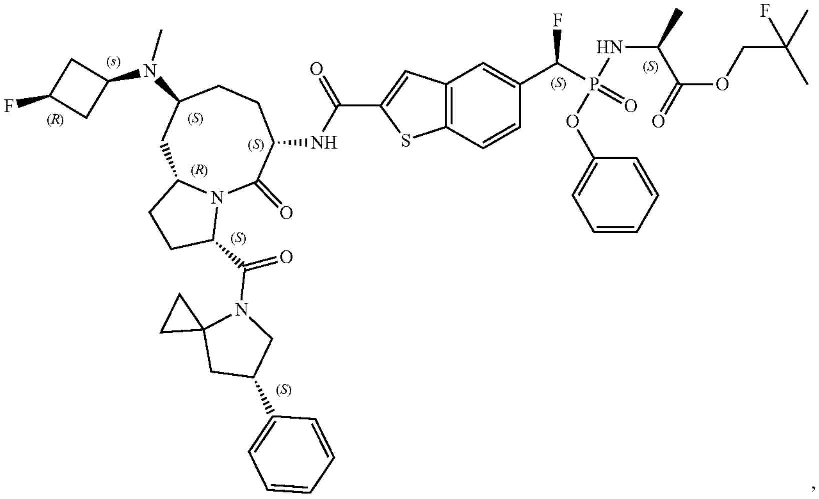
,
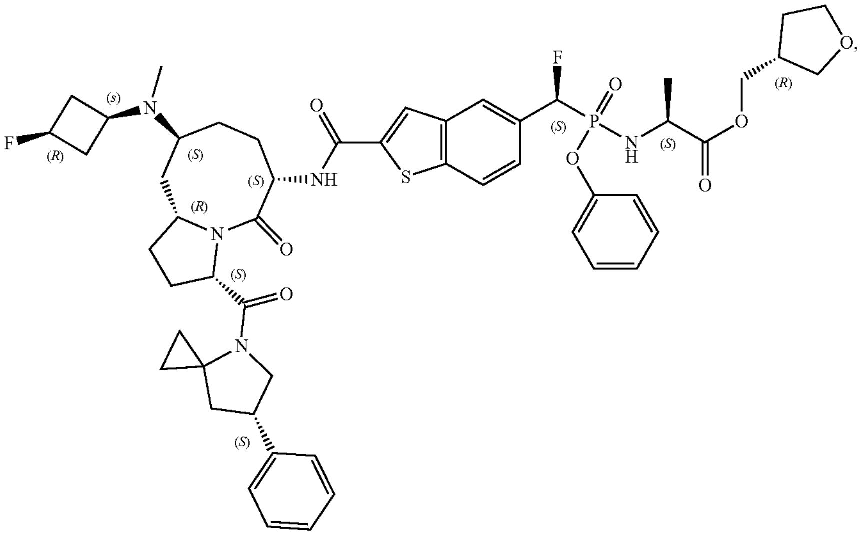
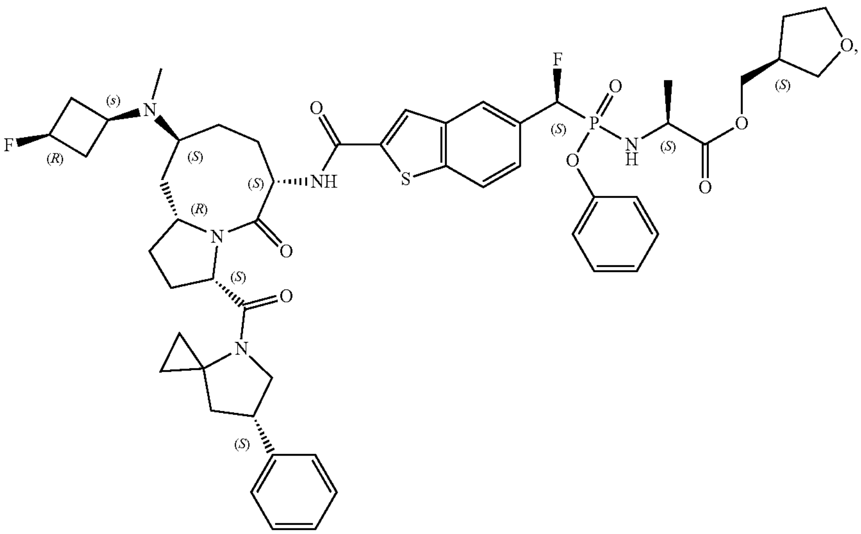

-continued
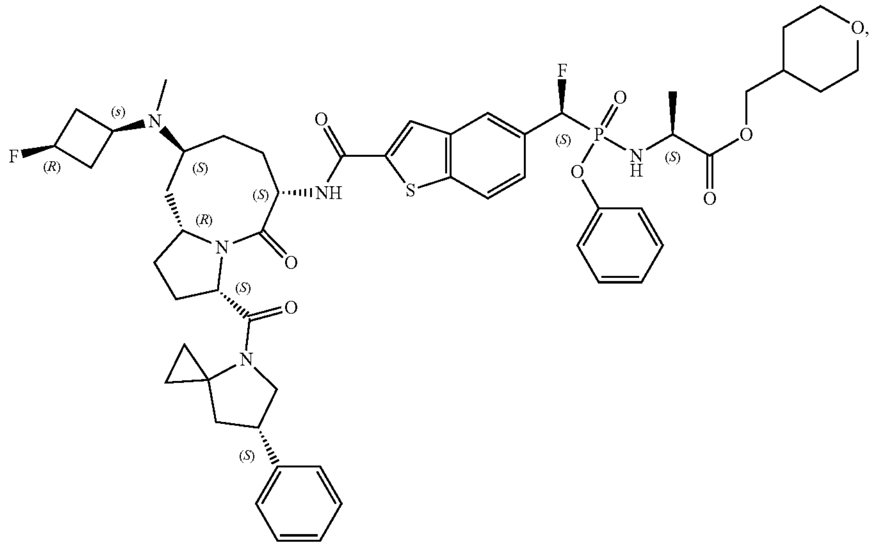
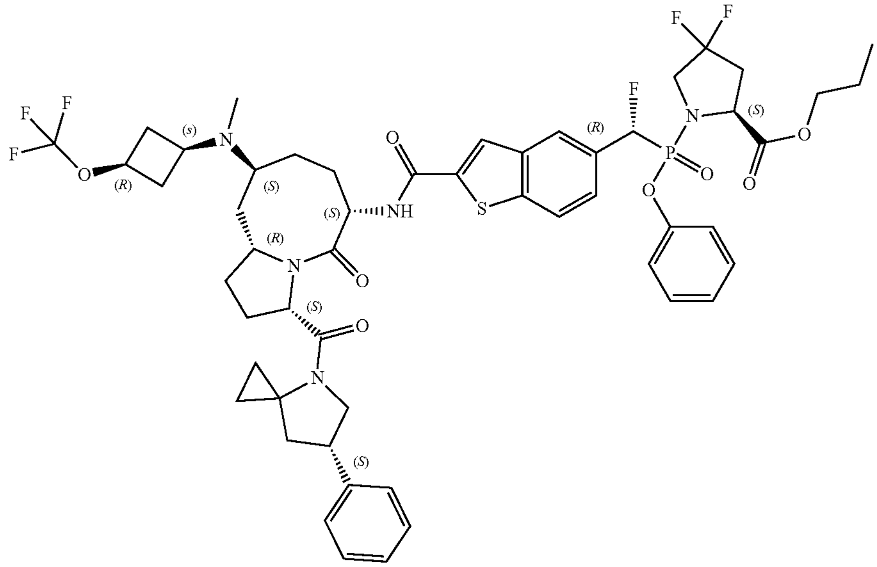
,
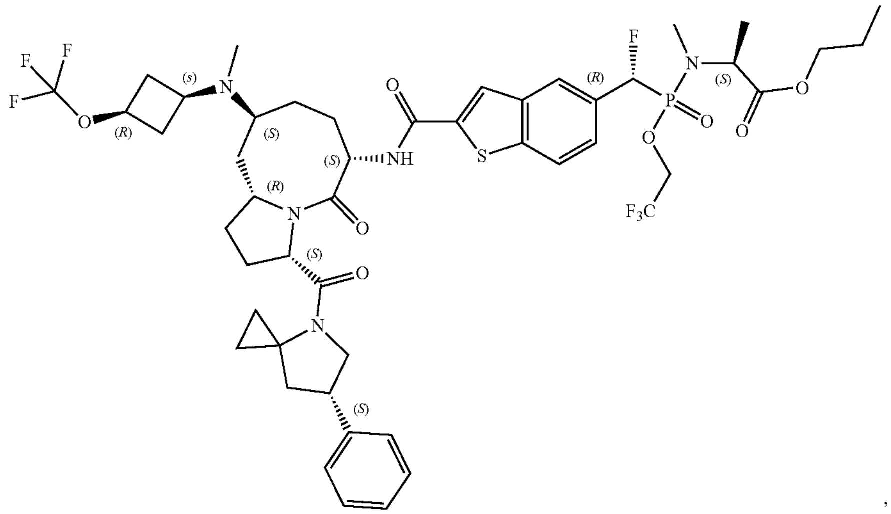
,

-continued
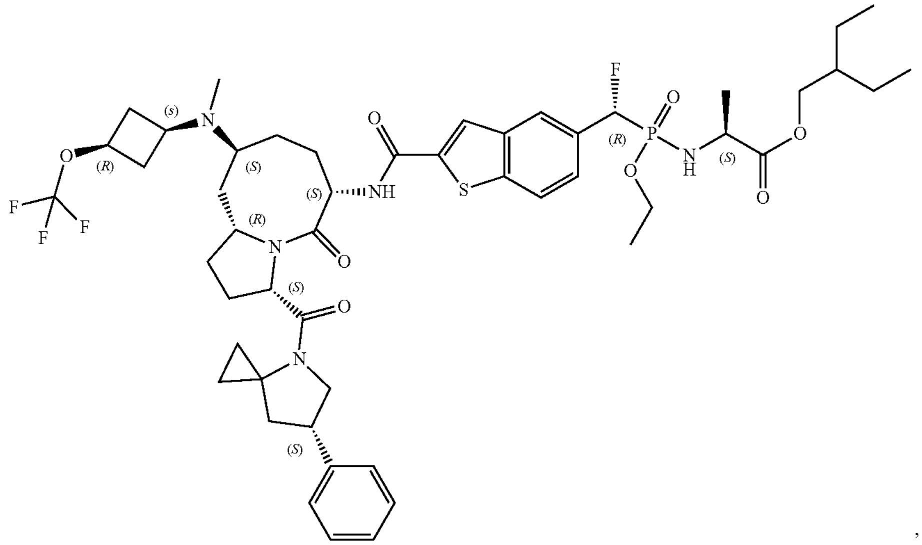
,
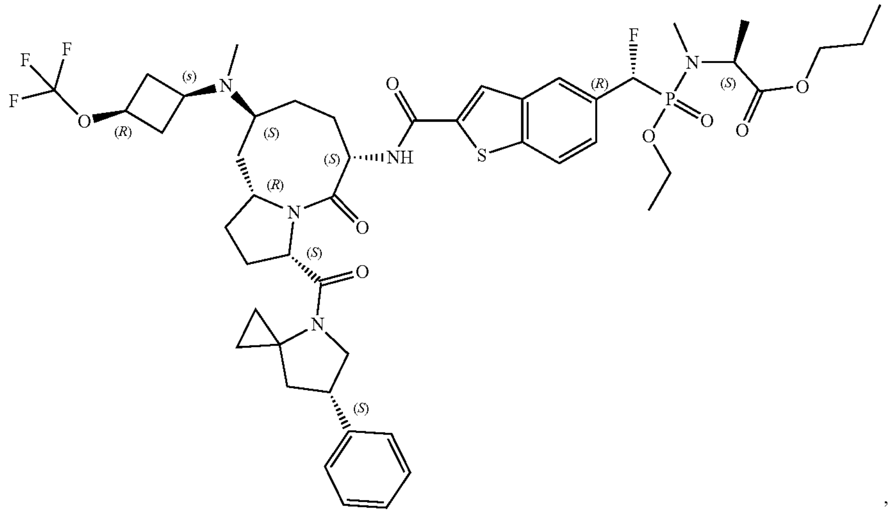
,
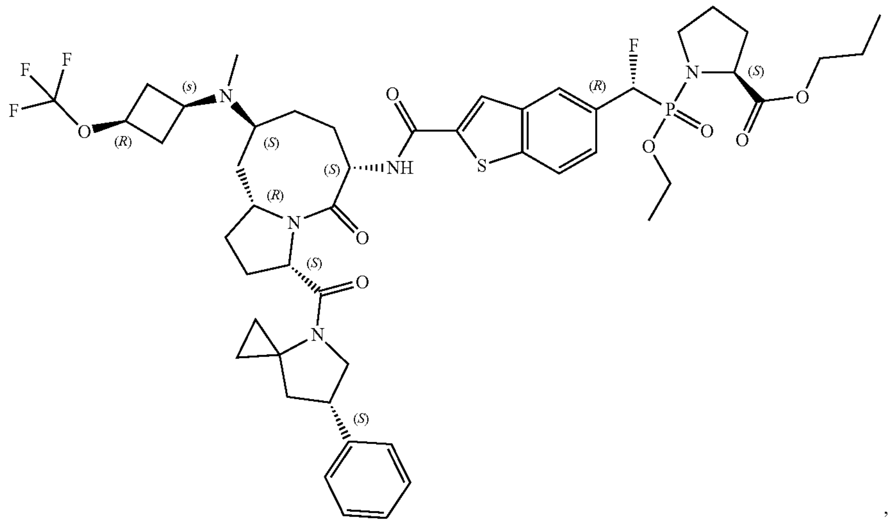
,

-continued
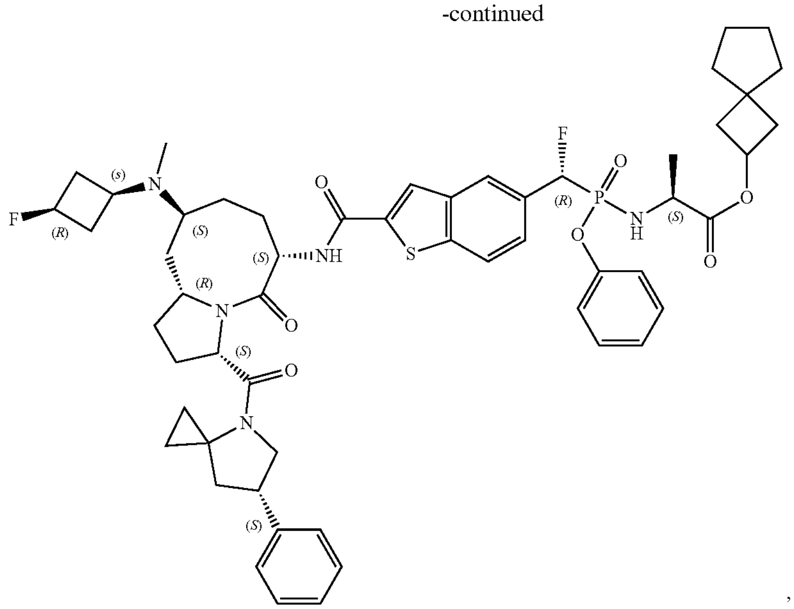
,
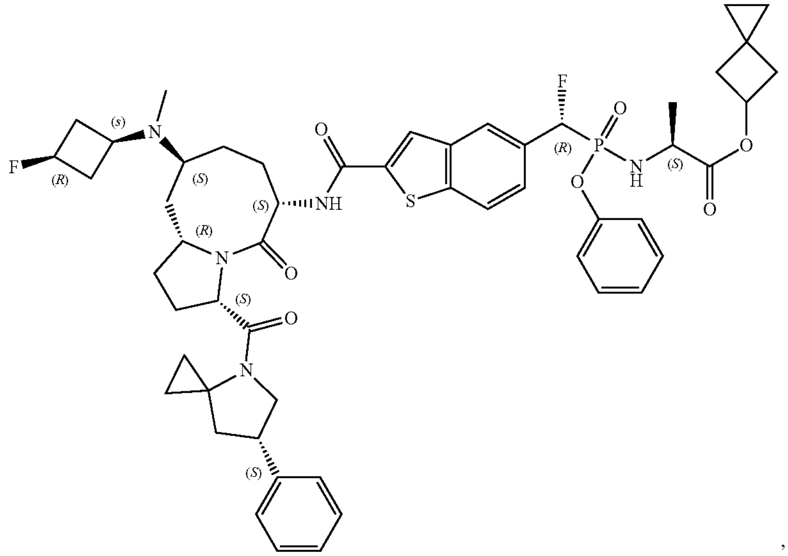
,
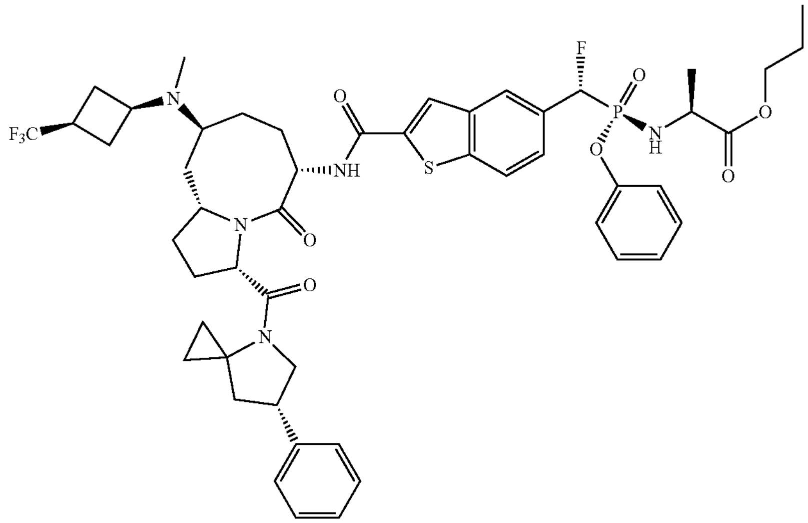
,

-continued
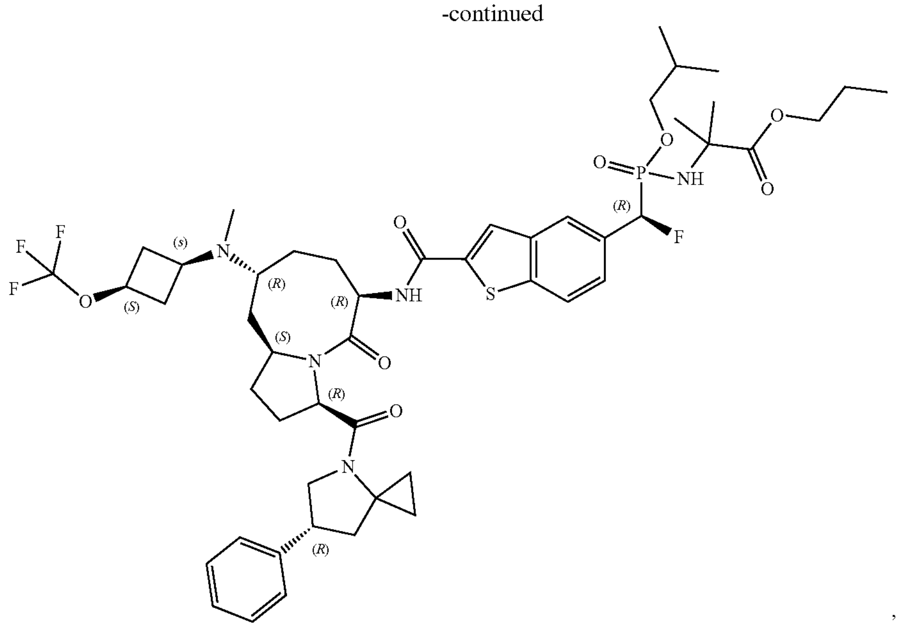
,
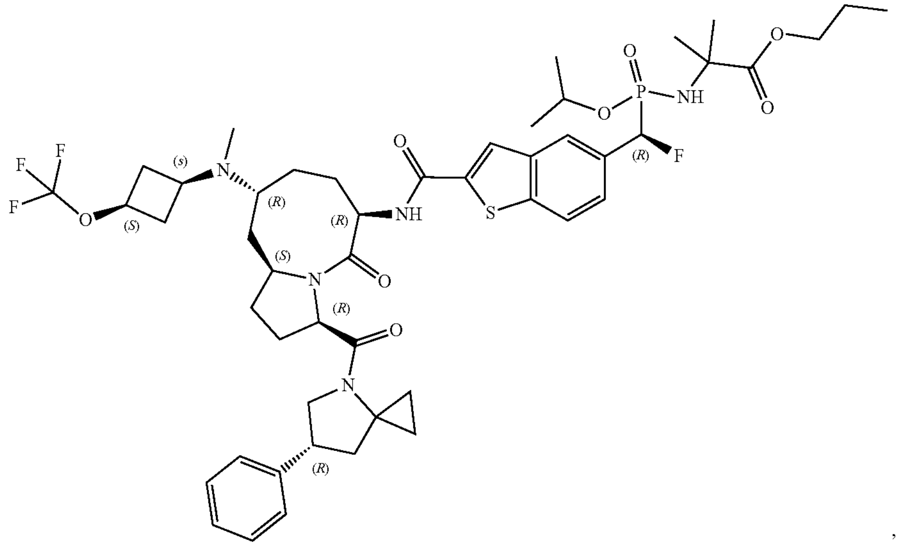
,
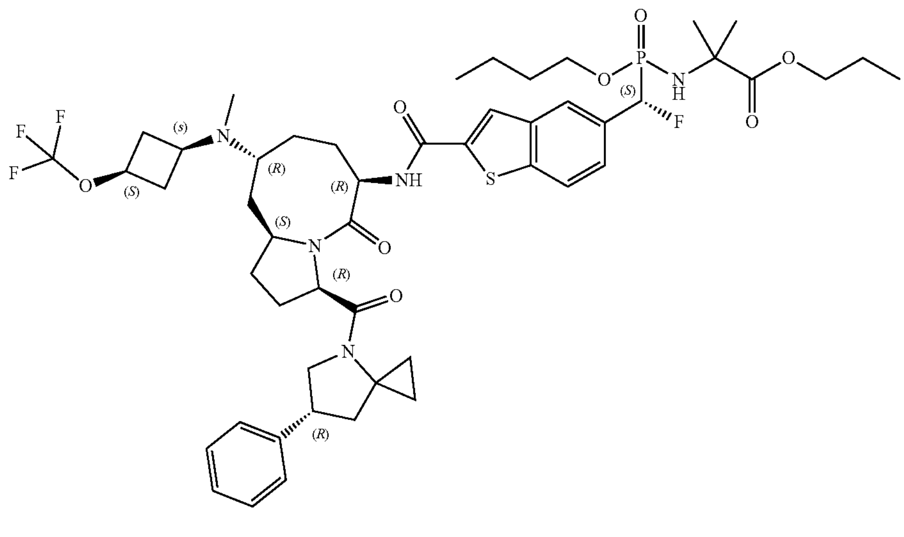
,

-continued
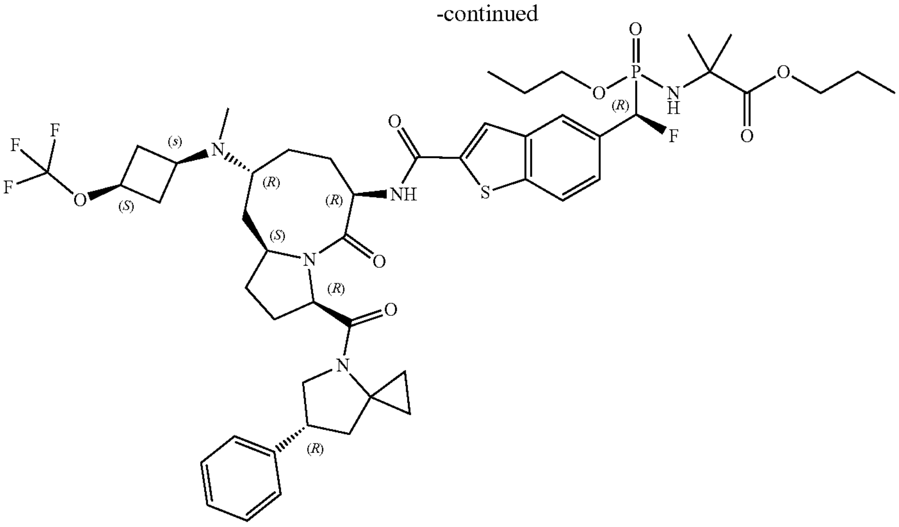
, and
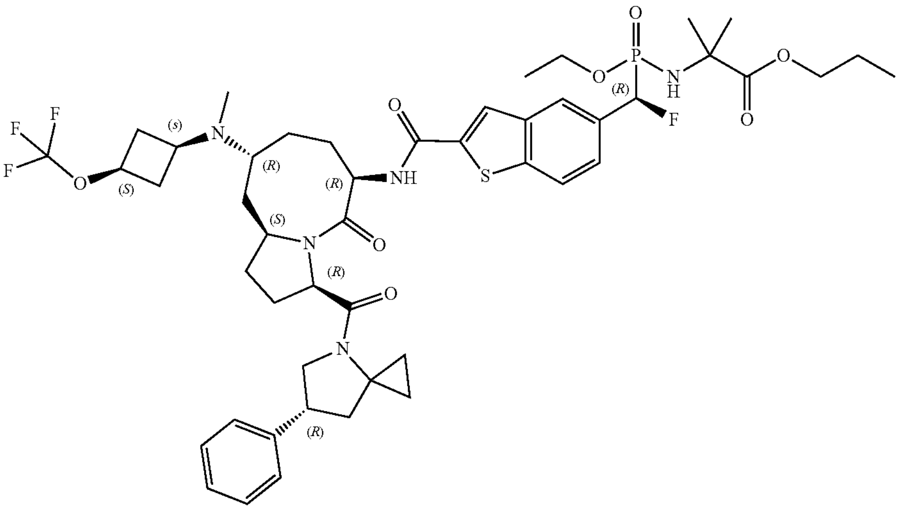
,
or a pharmaceutically acceptable salt thereof.
4. The compound of claim 1, or a pharmaceutically acceptable salt thereof, wherein $R^{P1}$ and $R^{P2}$ are each —OH.
5. The compound of claim 1, wherein the compound is selected from the group consisting of:
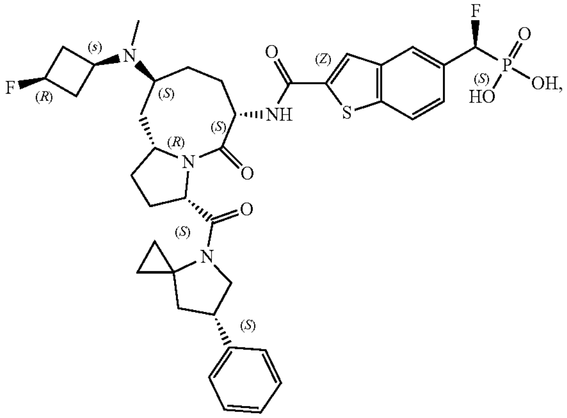
-continued
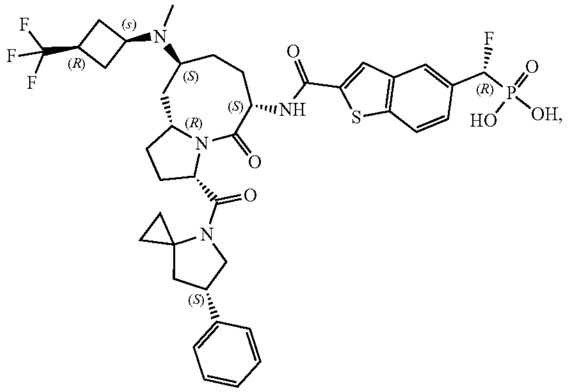

-continued
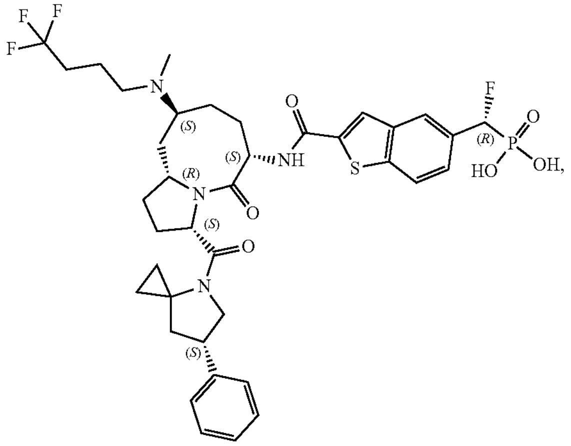
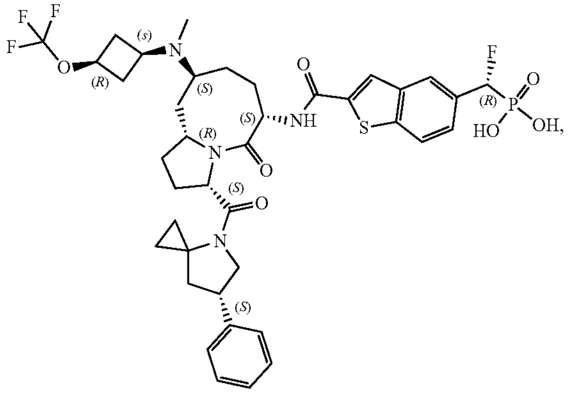
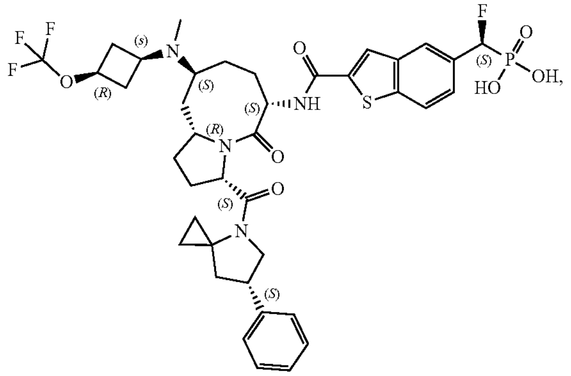
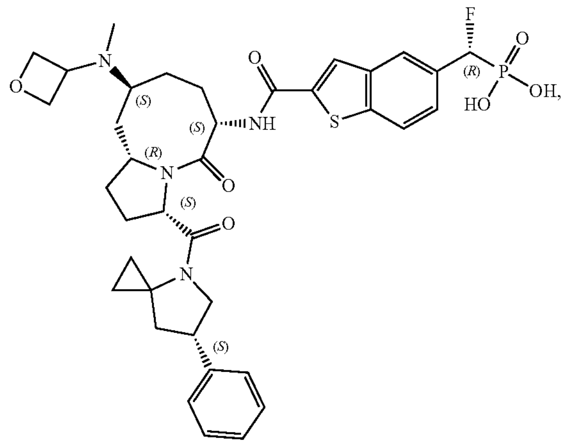
-continued
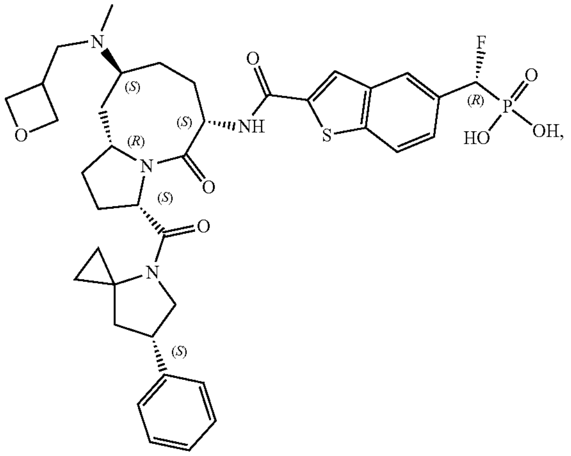
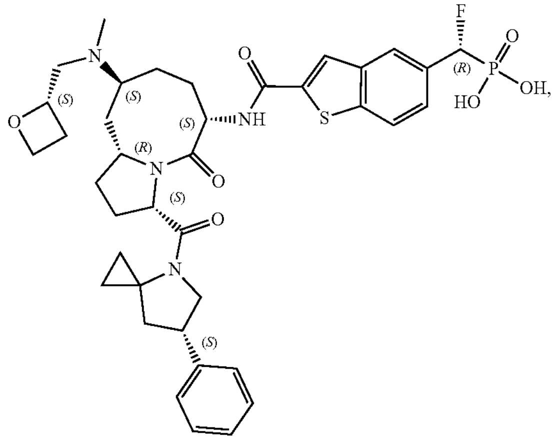
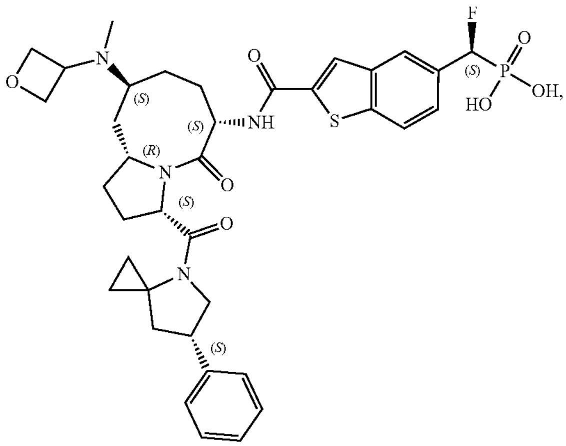

-continued
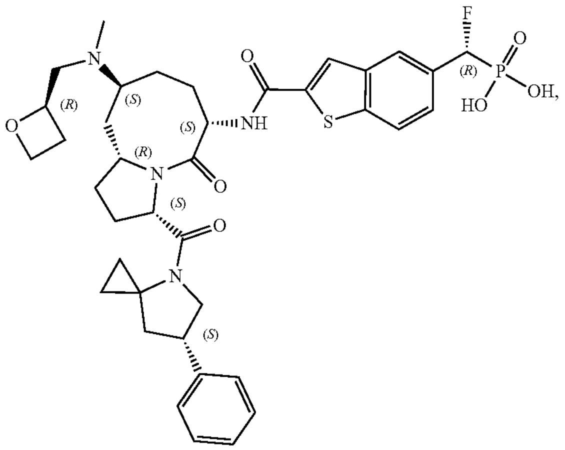
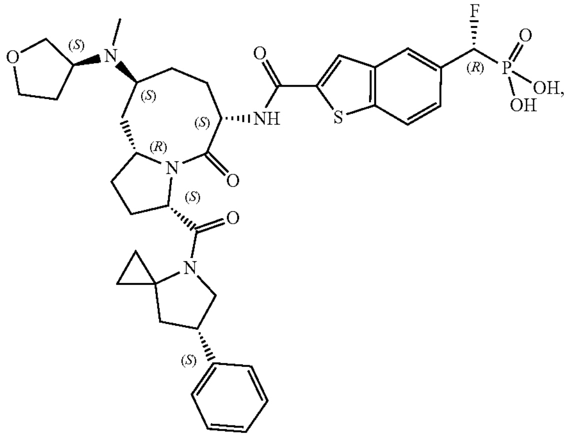
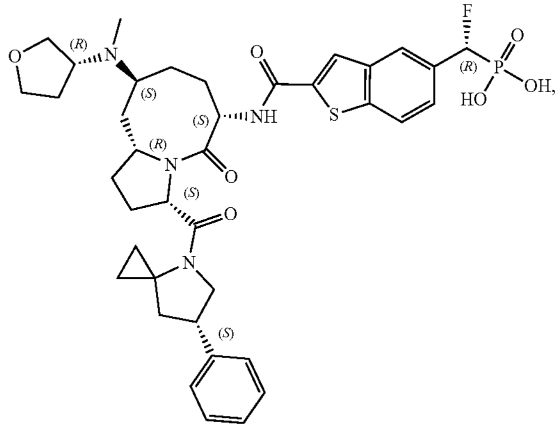
-continued
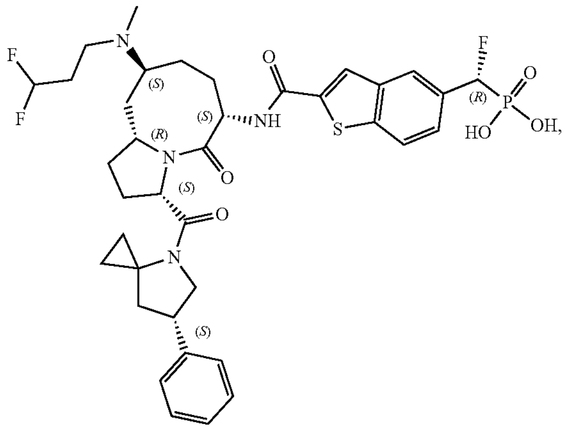
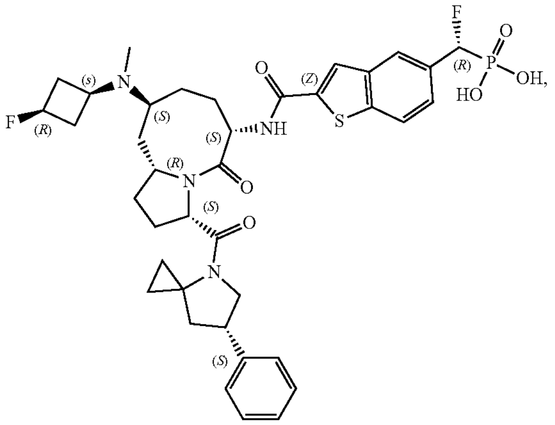
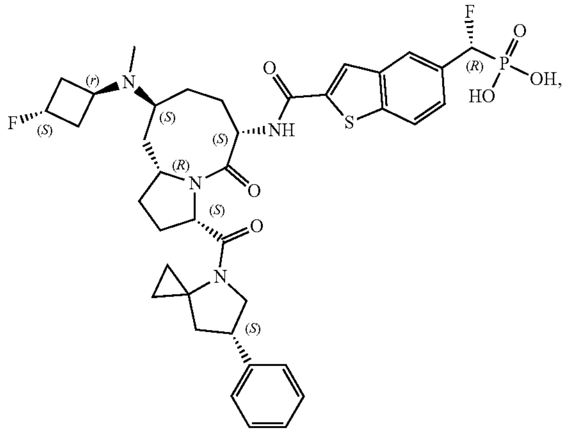
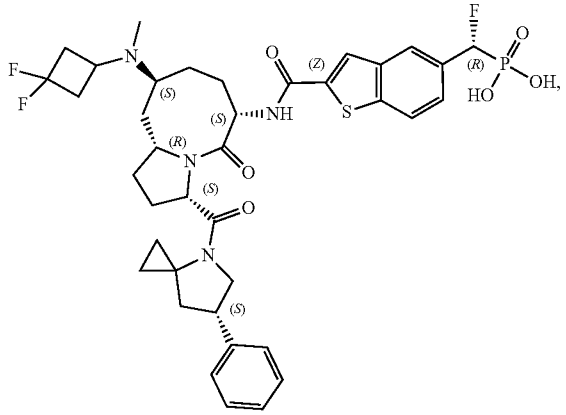

-continued
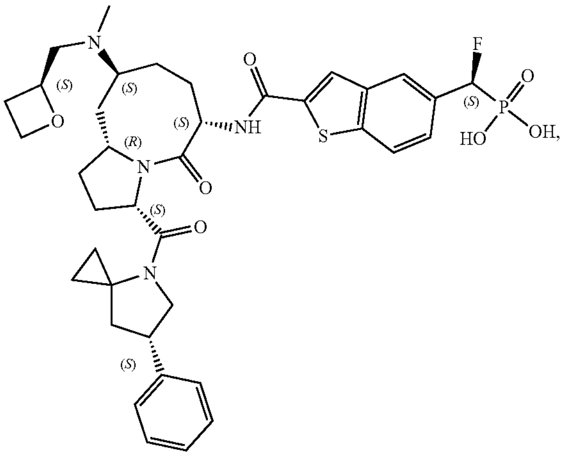
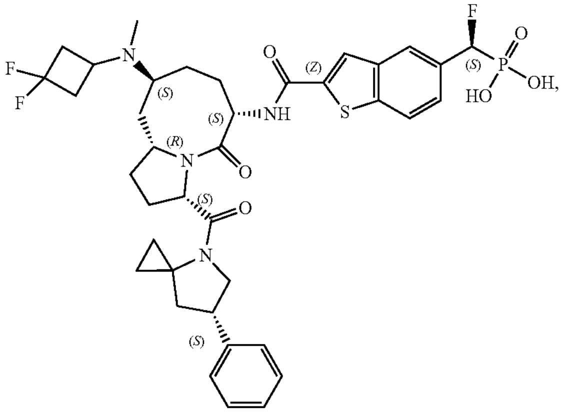
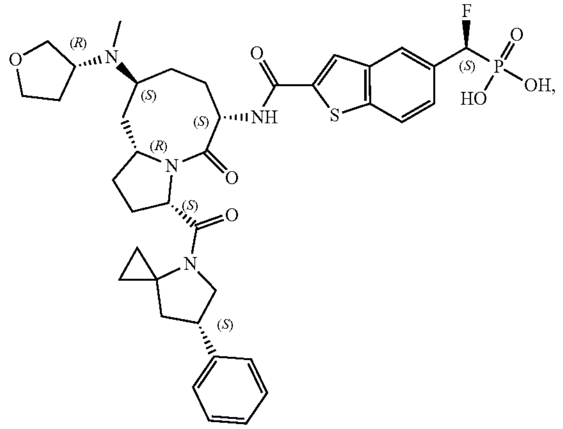
-continued
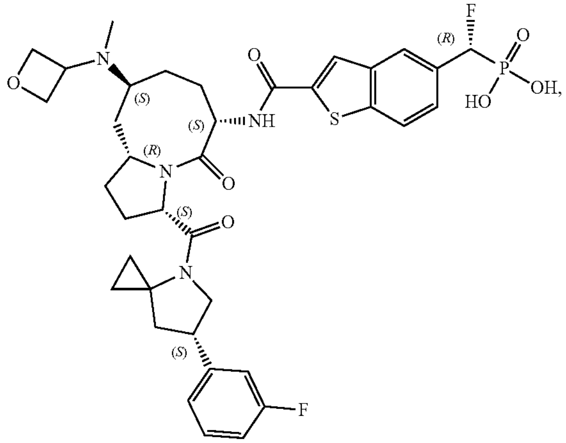
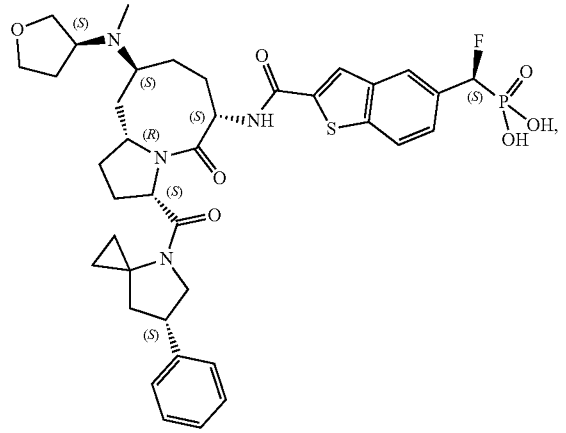
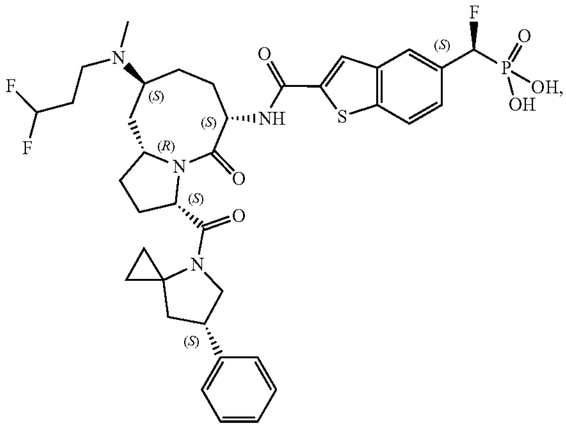
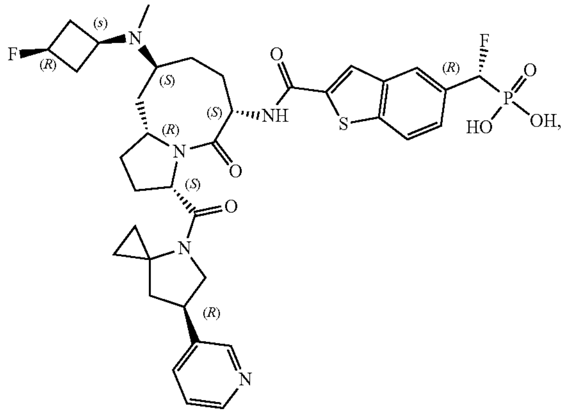

-continued
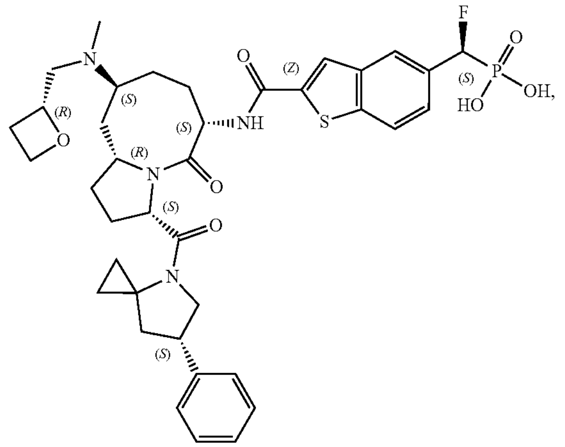
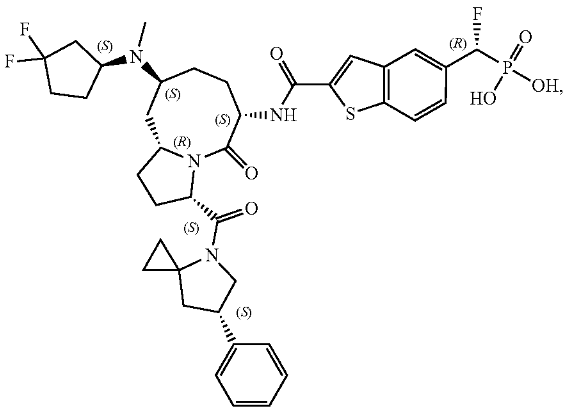
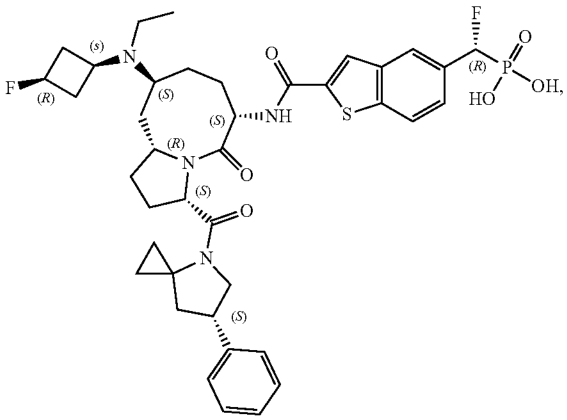
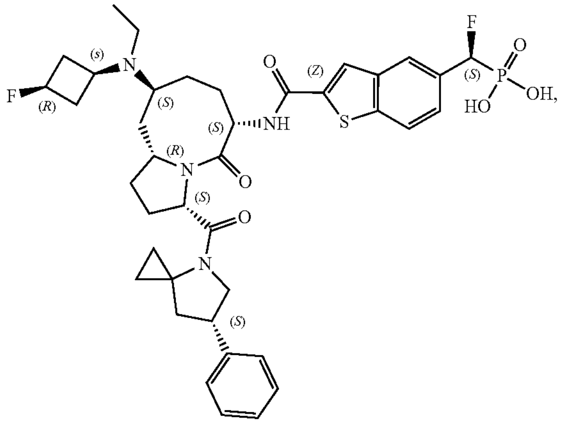
-continued
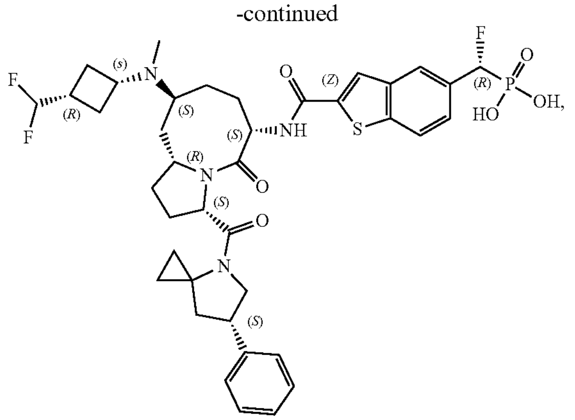
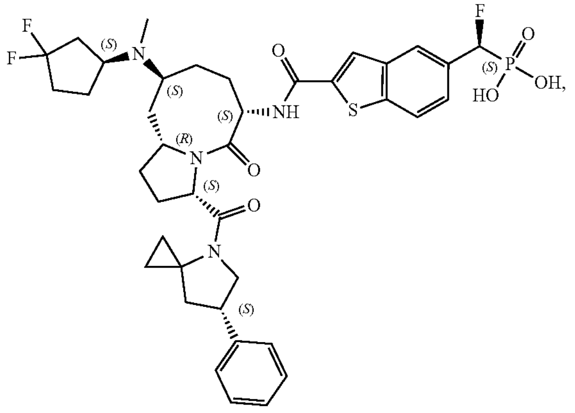
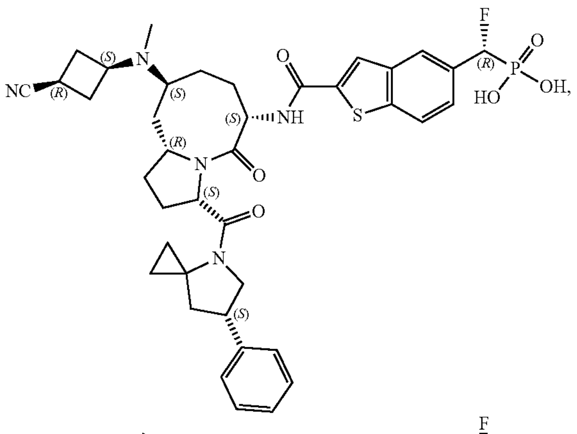
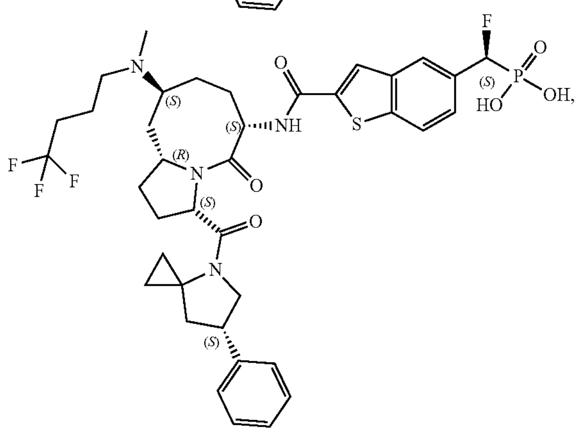

-continued
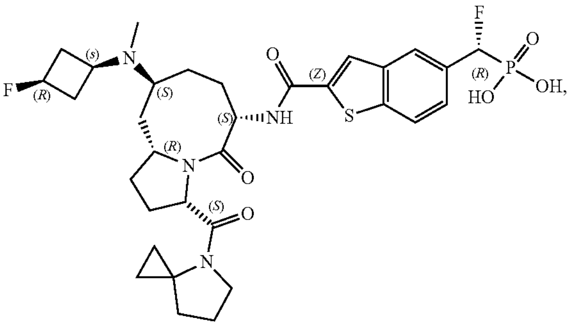
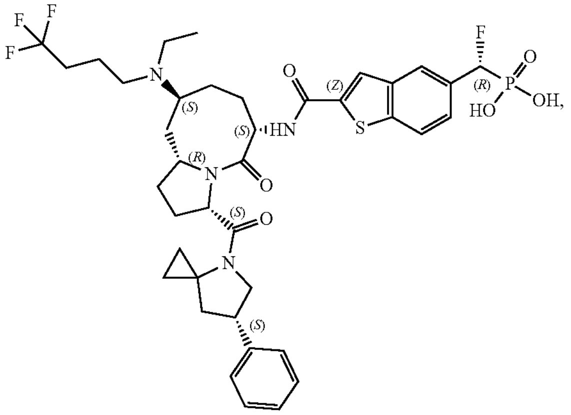
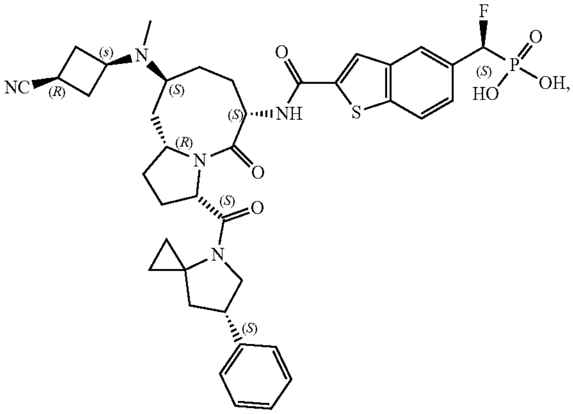
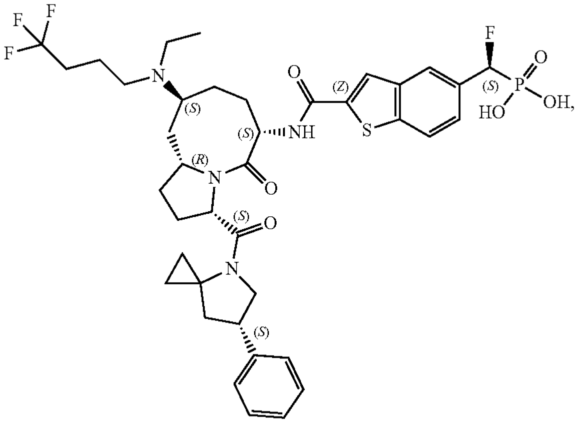
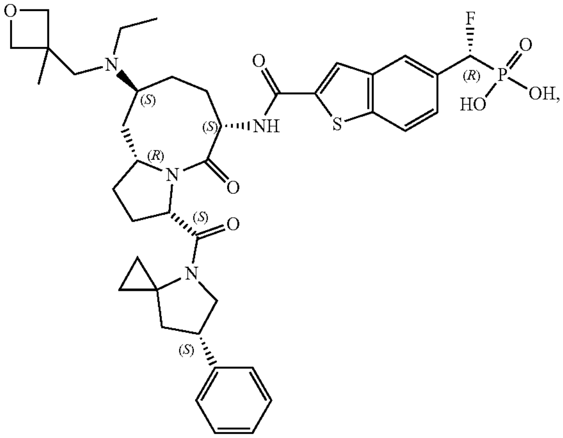
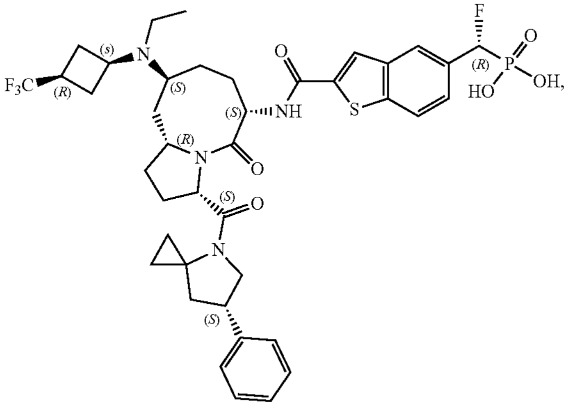
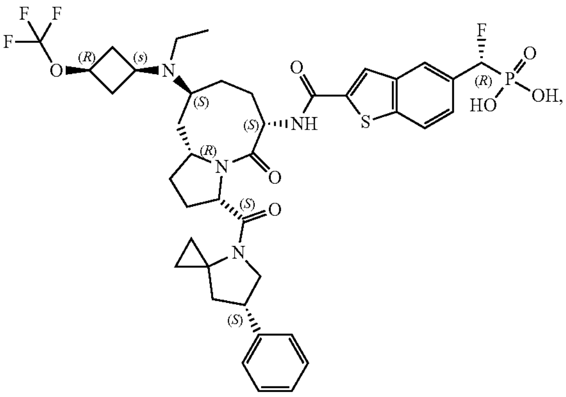
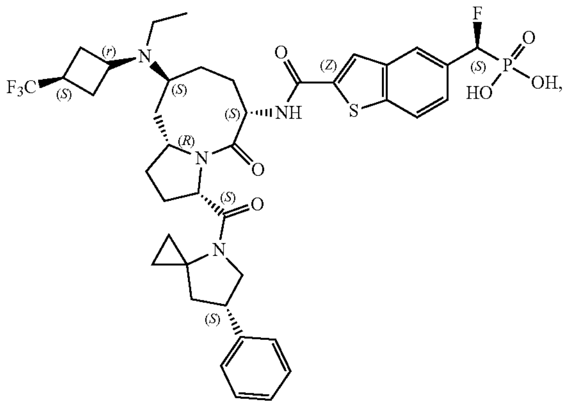

-continued
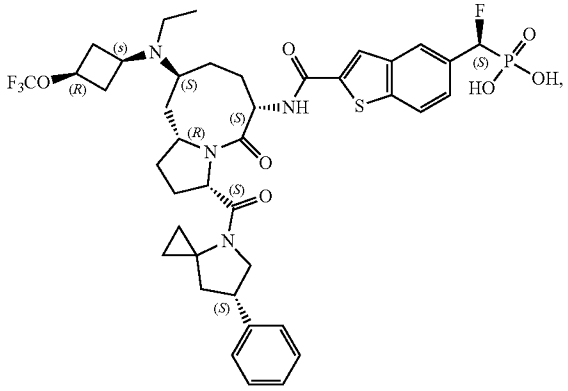 [SMILES: CN([C@H]1CC[C@H](NC(=O)c2cc3cc([C@@H](F)P(=O)(O)O)ccc3s2)C(=O)N2[C@H](CC[C@H]2C(=O)N2C[C@H](c3ccccc3)CC23CC3)C1)[C@H]1C[C@@H](C(F)(F)F)C1]
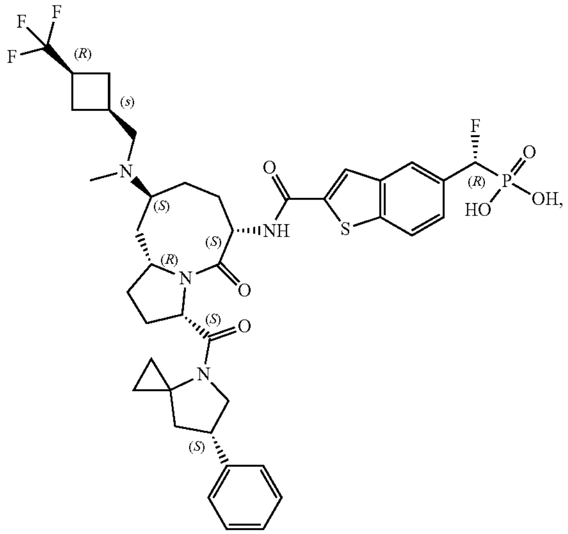
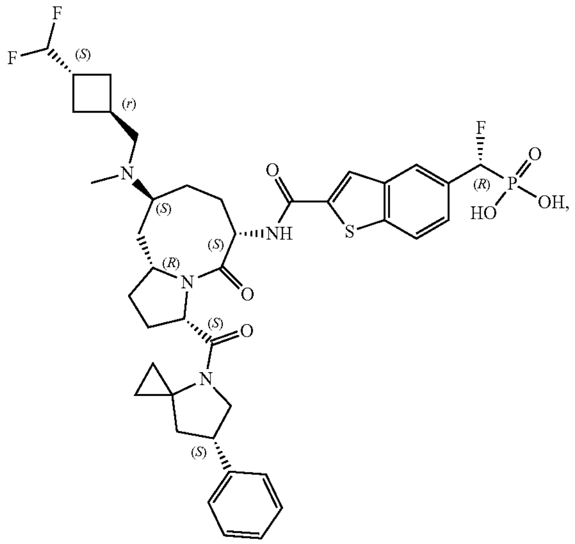
-continued
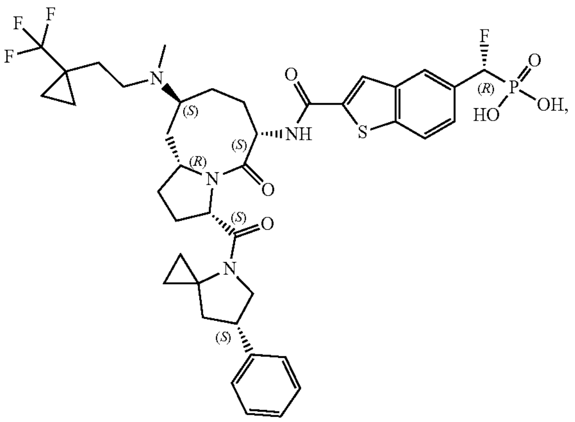
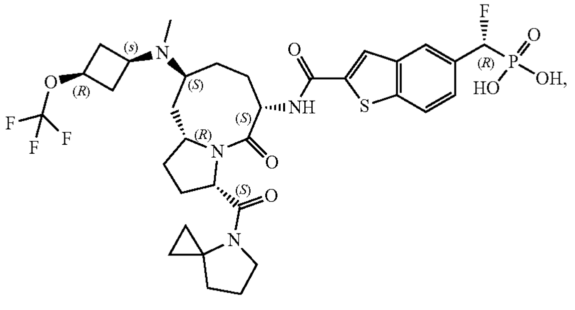
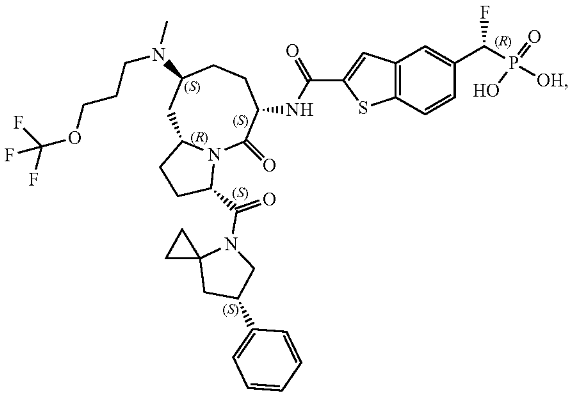
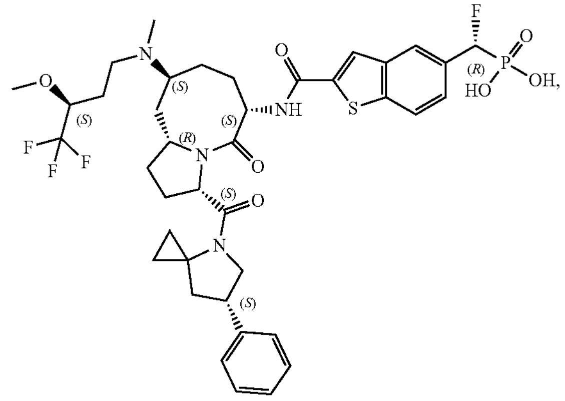

-continued
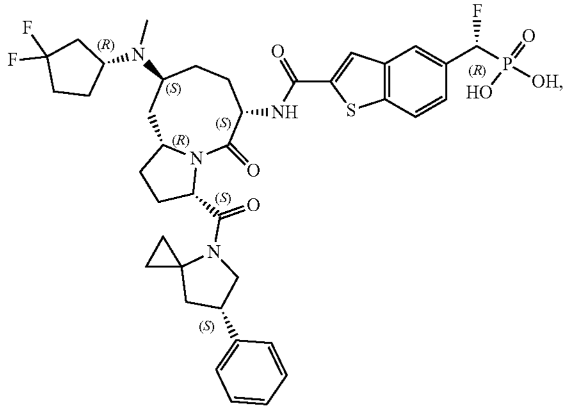
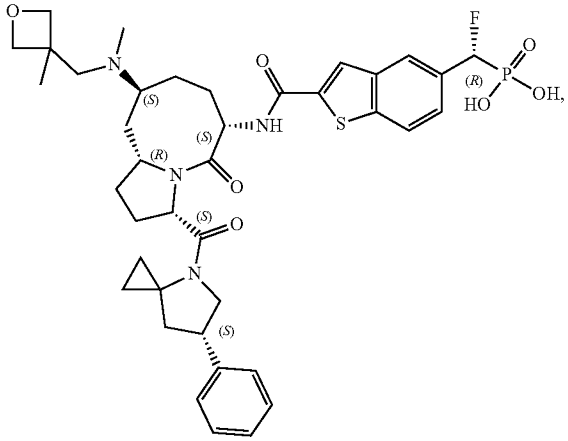
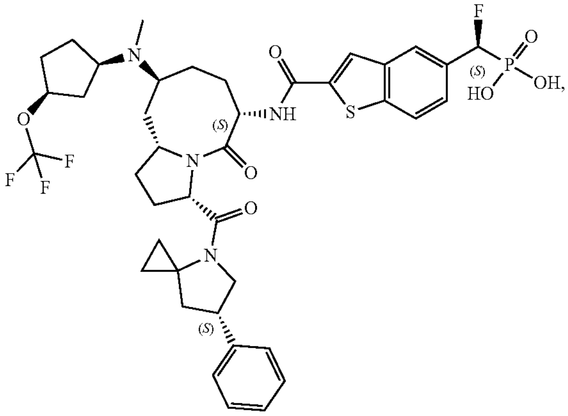
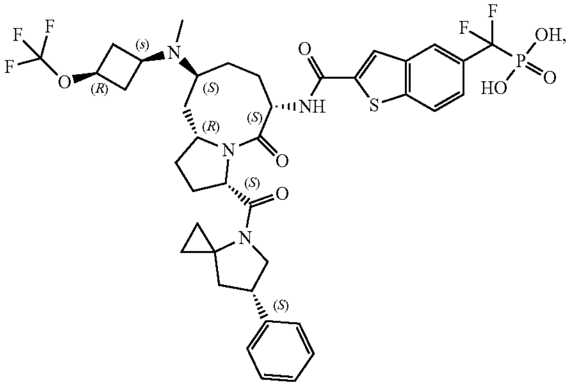
-continued
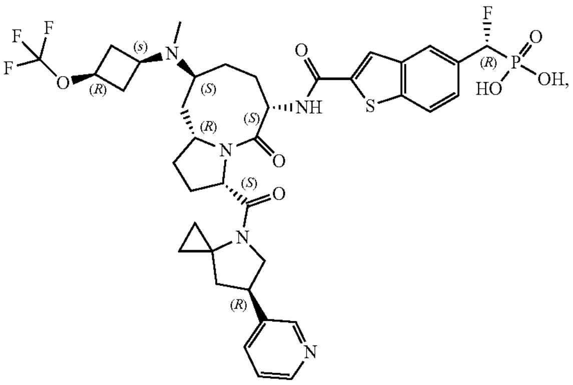
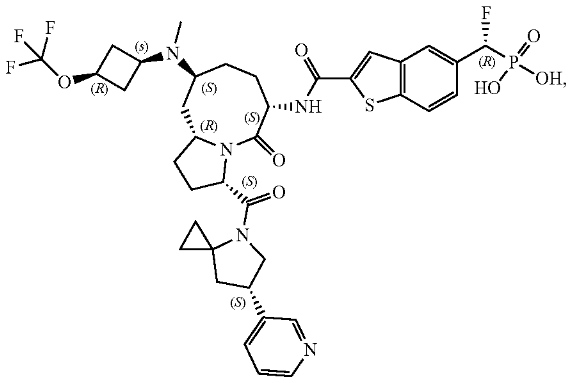
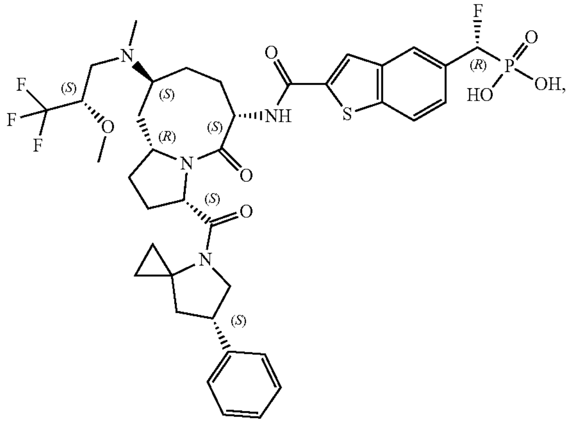
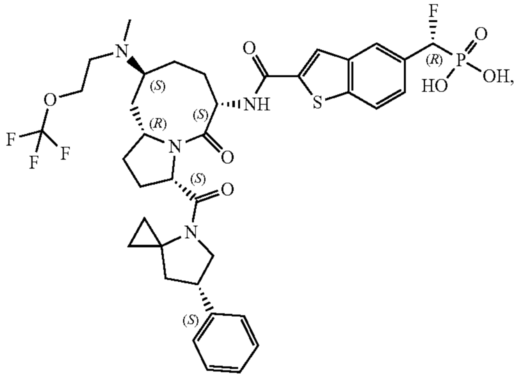
and -continued

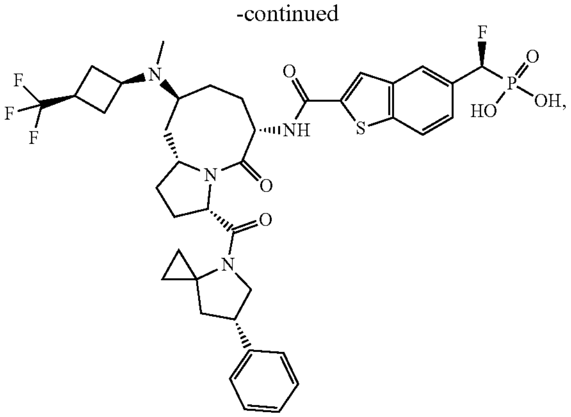

or a pharmaceutically acceptable salt thereof.

6. The compound of claim 1, or a pharmaceutically acceptable salt thereof, wherein $R^{P1}$ is —OH and $R^{P2}$ is N-linked amino acid, wherein:

N-linked amino acid is $—NR^{Paa1}CR^{Paa2}R^{Paa3}C(O)OH$;

$R^{Paa1}$ is H or $(C_1-C_6)$alkyl;

$R^{Paa2}$ is H or $(C_1-C_6)$alkyl; and $R^{Paa3}$ is H, $(C_1-C_6)$alkyl, —$(C_1-C_6)$alkylene-$(C_1-C_6)$ alkoxy;

or —$(C_1-C_6)$alkylene-$(C_6-C_{10})$aryl; or $R^{Paa2}$ and $R^{Paa3}$, together with the carbon atom to which they are attached, form $(C_3-C_6)$cycloalkyl.

7. The compound of claim 1, wherein the compound is selected from the group consisting of:

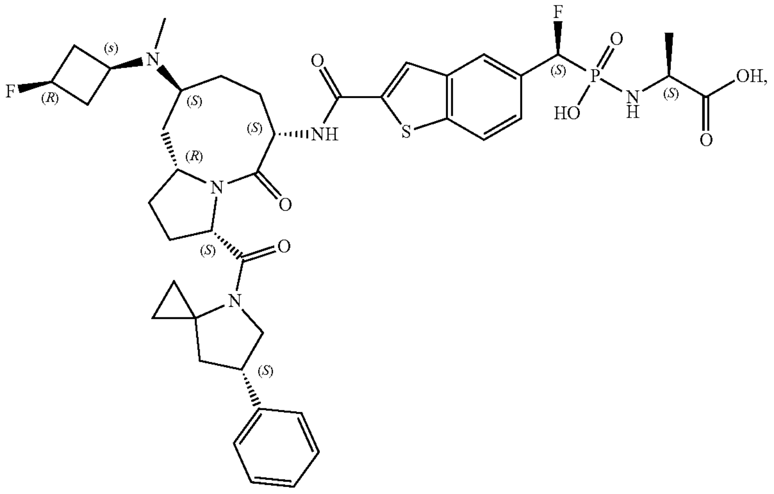

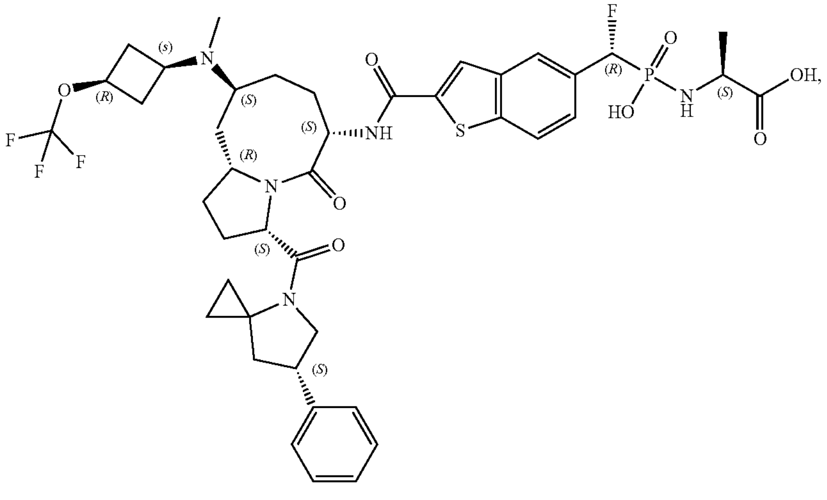

-continued
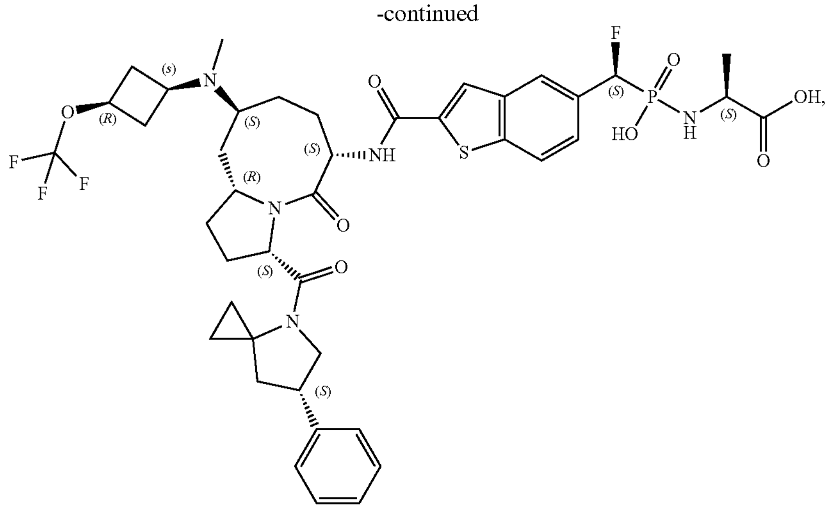
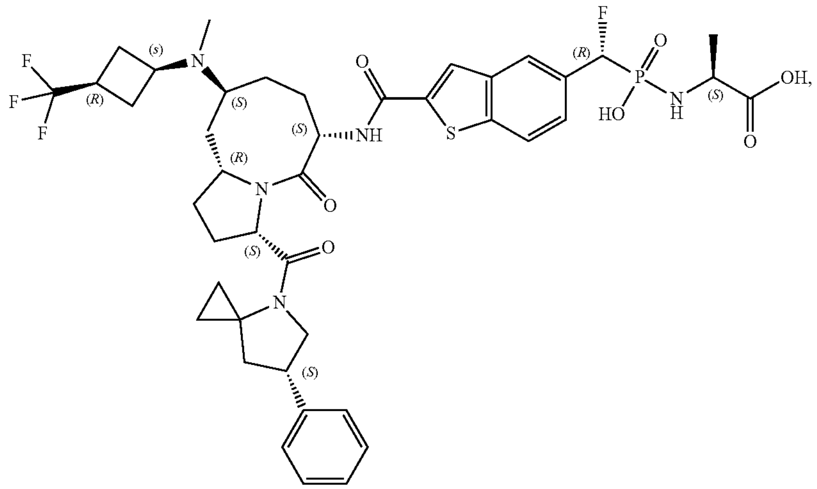
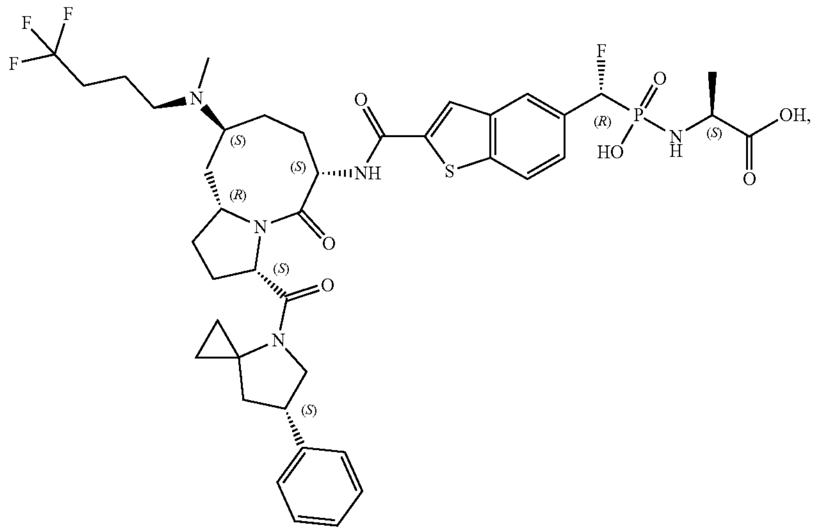

-continued
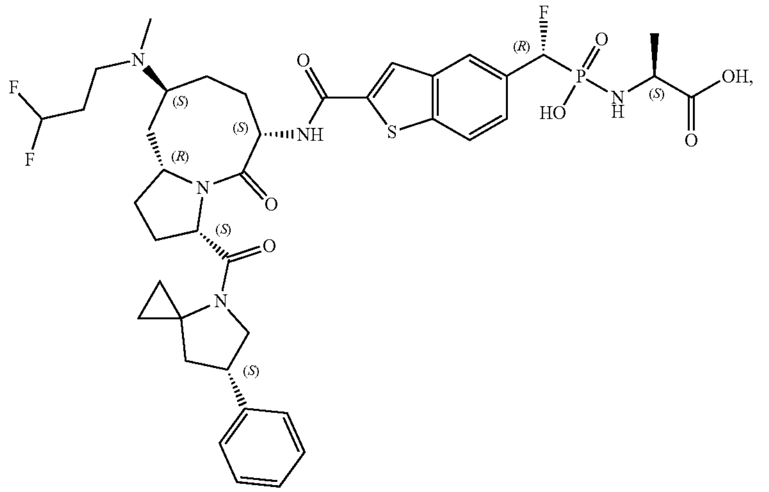
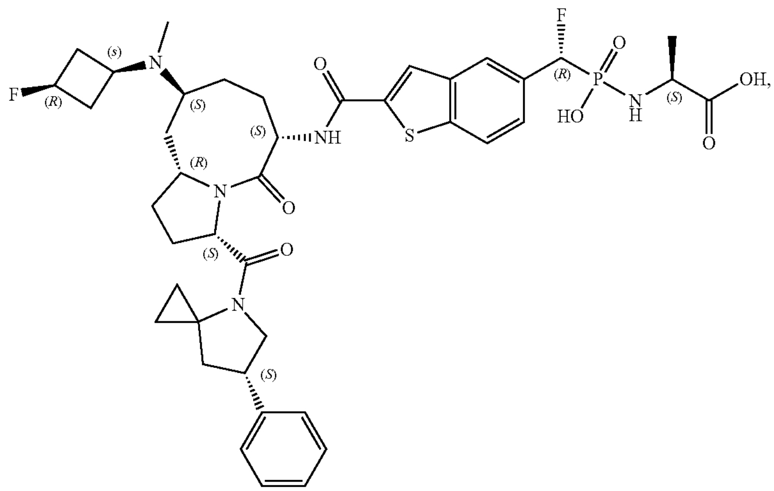
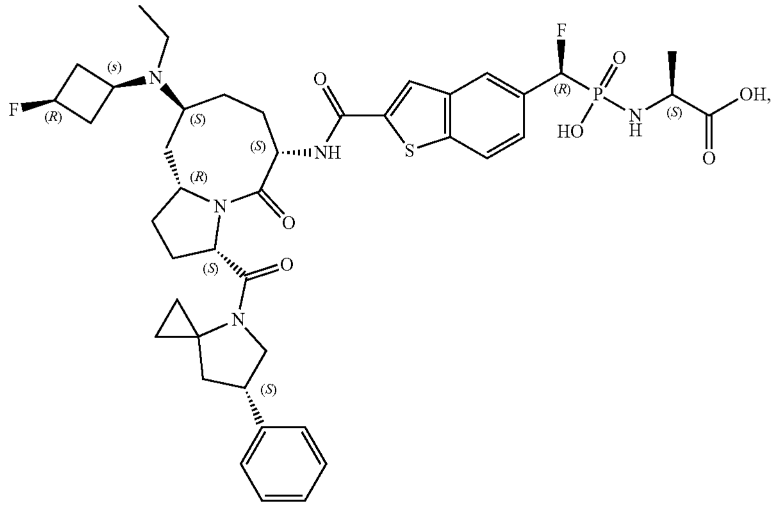

-continued
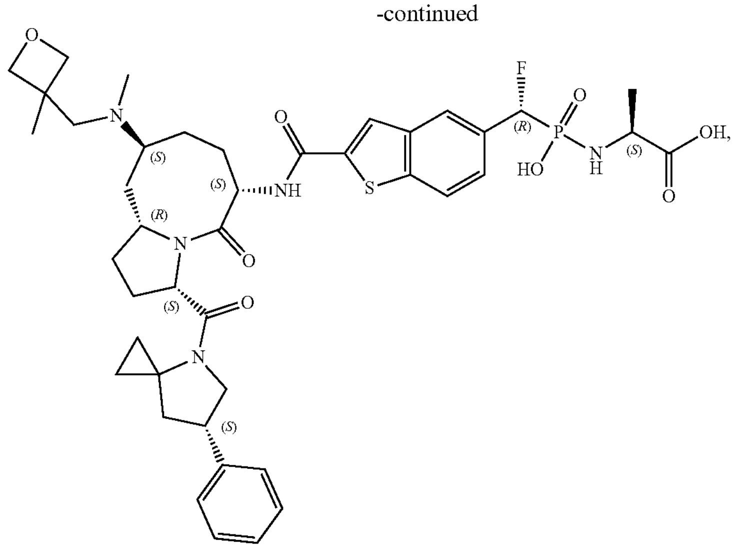
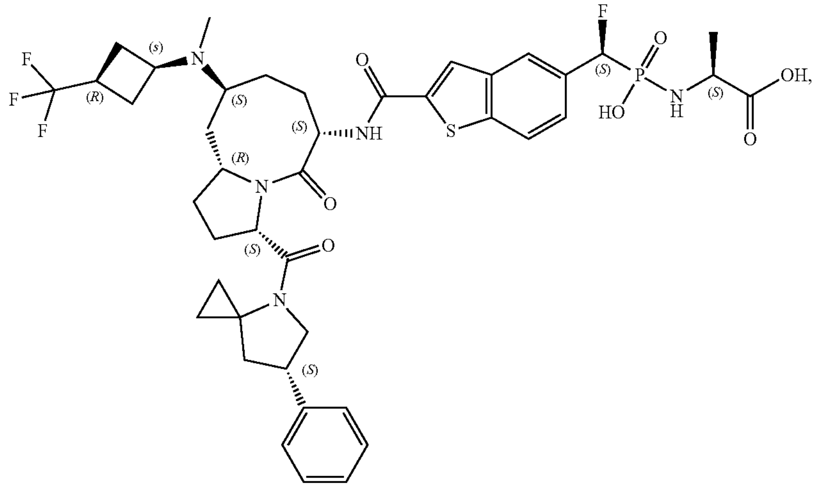
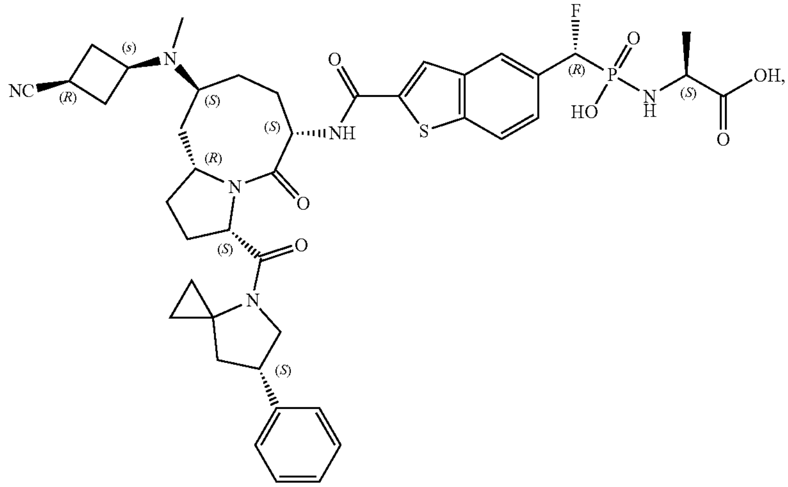

-continued
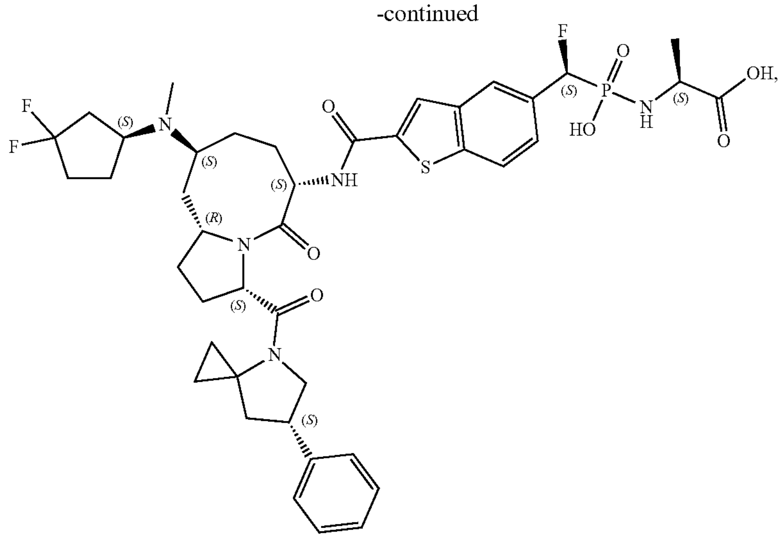
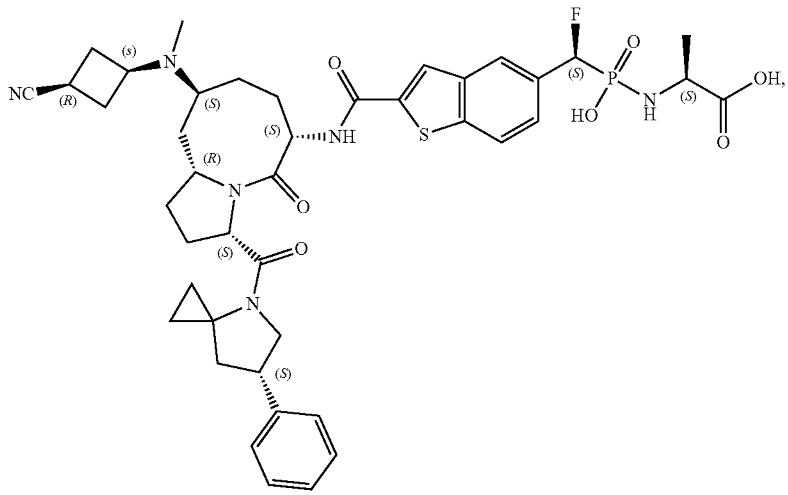
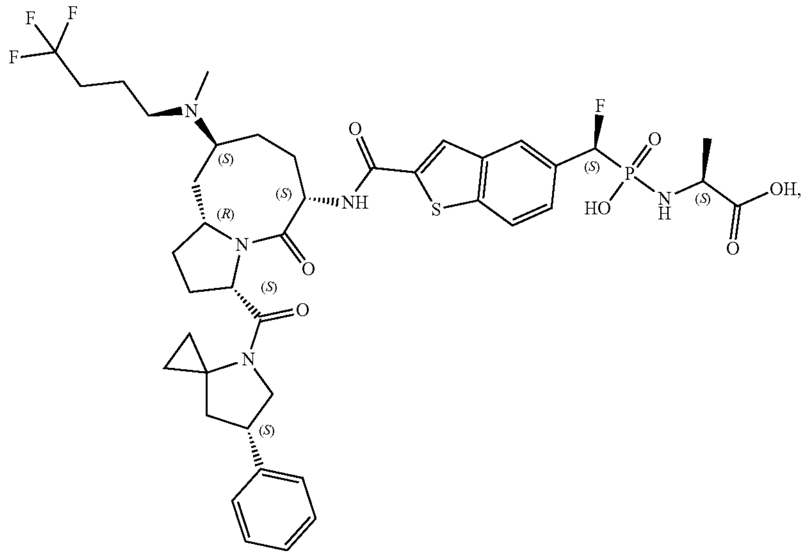

-continued
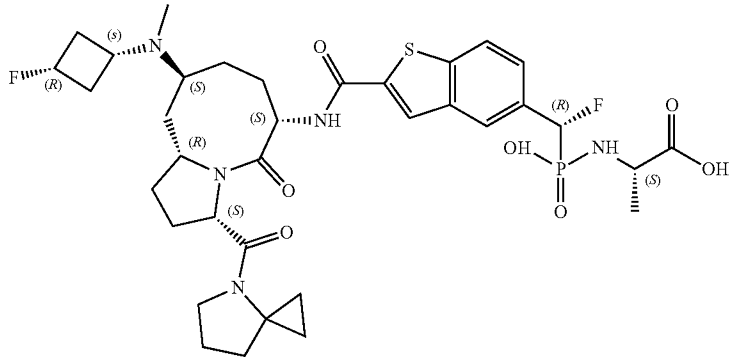
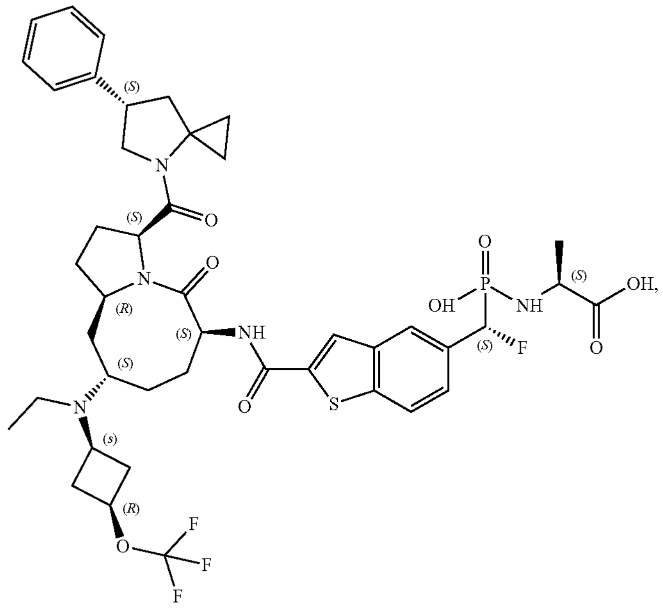
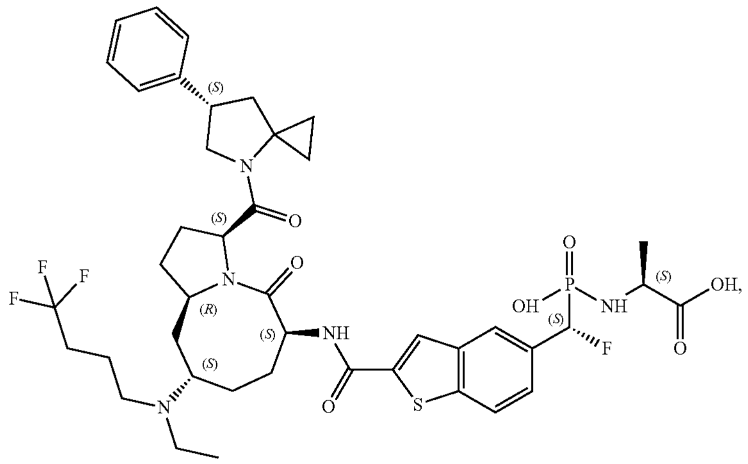

-continued
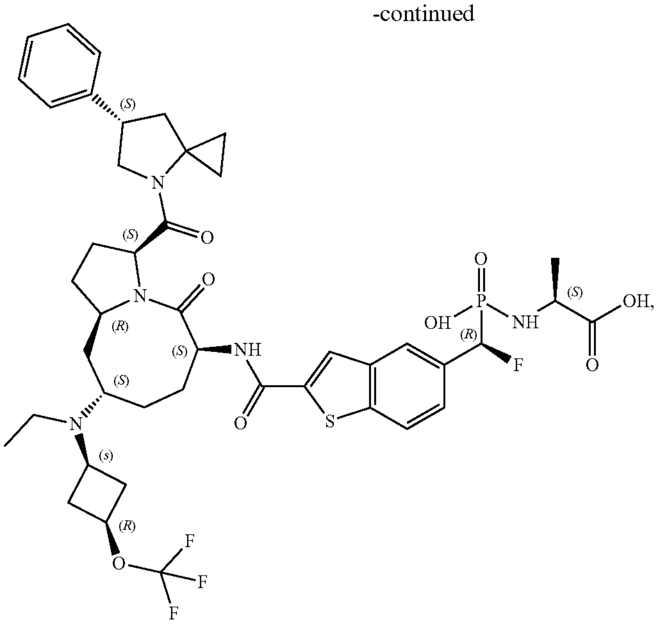
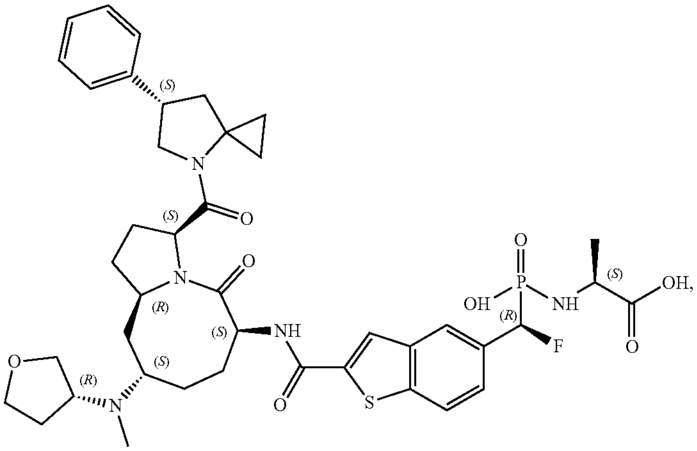
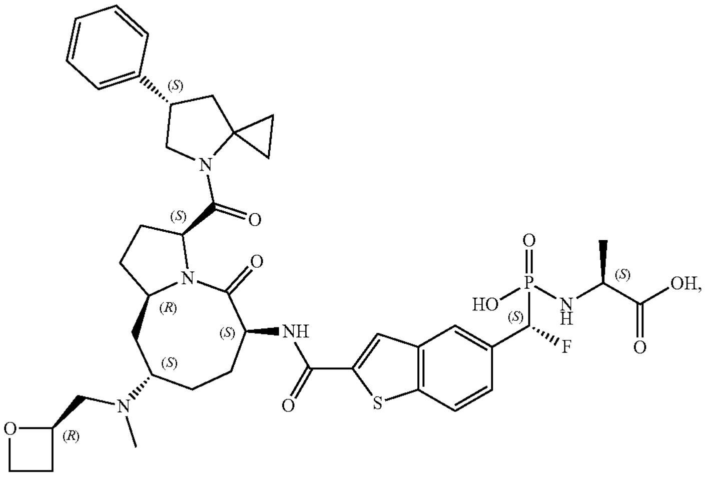

-continued
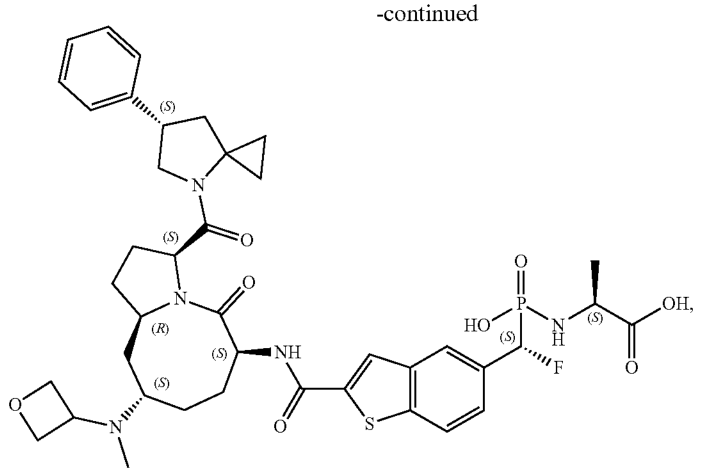
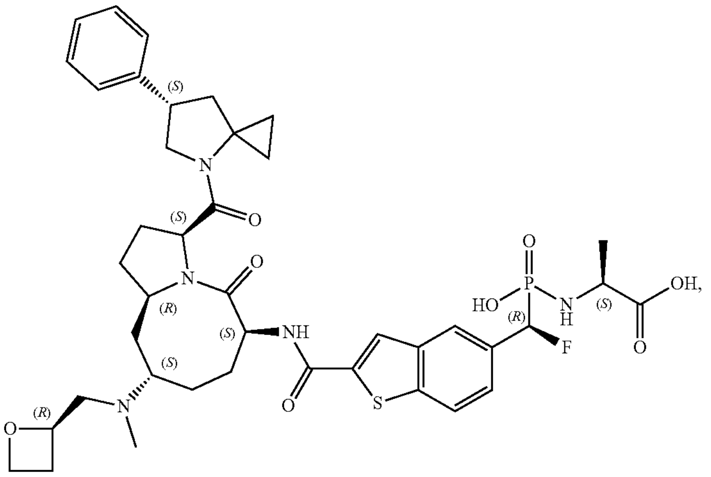
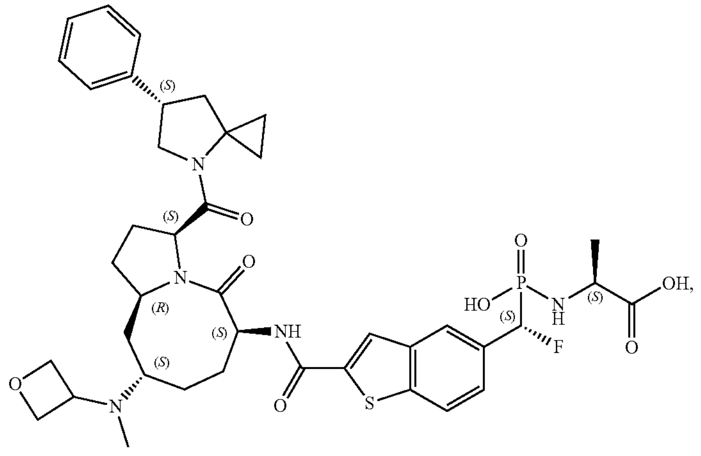

-continued
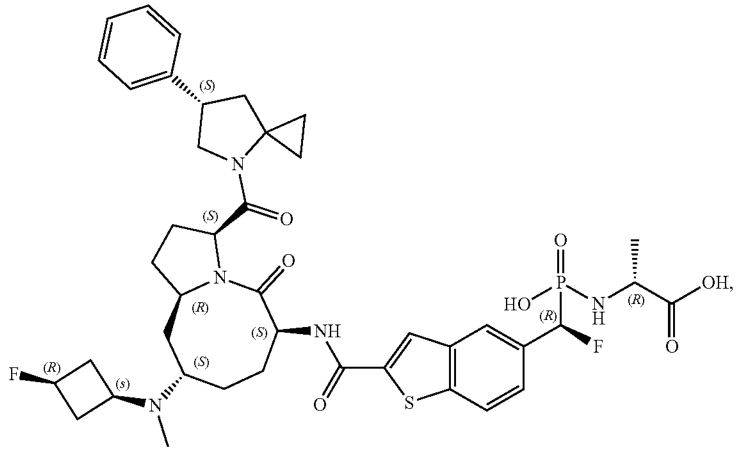
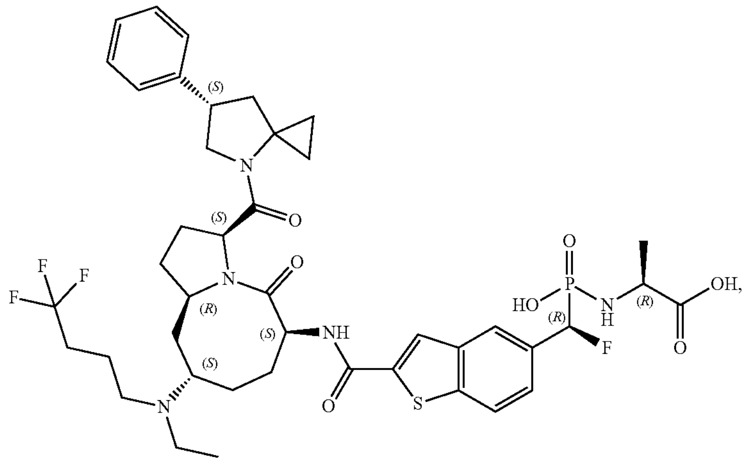
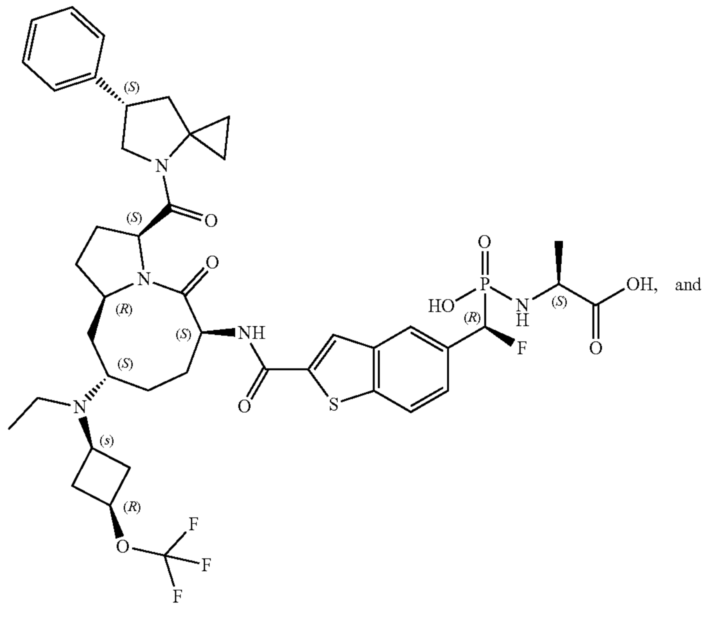
and

-continued

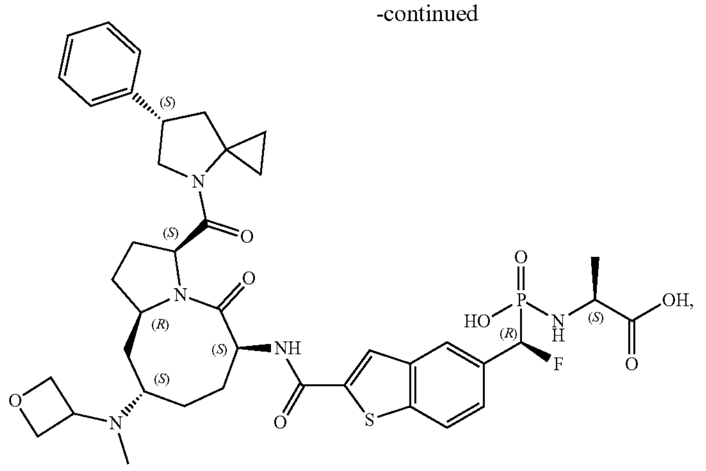

or a pharmaceutically acceptable salt thereof.

8. The compound of claim 1, wherein the compound is of Formula (I-C-3), (I-C-3)

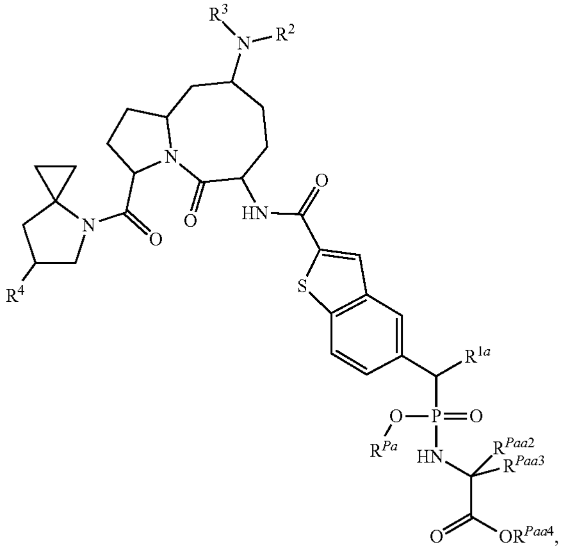

or a pharmaceutically acceptable salt thereof, wherein:

$R^{Pa}$ is $(C_1-C_6)$alkyl, halo$(C_1-C_6)$alkyl, $(C_6-C_{10})$aryl, or $(C_3-C_6)$cycloalkyl, wherein $(C_1-C_6)$alkyl is substituted with 0, 1, 2, or 3 substituents each independently selected from the group consisting of halo and $(C_1-C_6)$ alkoxy;

$R^{Paa2}$ is H or $(C_1-C_6)$alkyl;

$R^{Paa3}$ is H, $(C_1-C_6)$alkyl, —$(C_1-C_6)$alkylene-$(C_1-C_6)$ alkoxy, or —$(C_1-C_6)$alkylene-$(C_6-C_{10})$aryl; or $R^{Paa2}$ and $R^{Paa3}$, together with the carbon atom to which they are attached, form $(C_3-C_6)$cycloalkyl; and $R^{Paa4}$ is $(C_1-C_6)$alkyl, halo$(C_1-C_6)$alkyl, —$(C_1-C_6)$alkylene-$(C_1-C_6)$alkoxy, $(C_3-C_6)$cycloalkyl, $(C_5-C_8)$spirocycloalkyl, —$(C_1-C_6)$alkylene-$(C_6-C_{10})$aryl, —$(C_1-C_6)$alkylene-$(C_3-C_7)$cycloalkyl, 3- to 7-membered heterocyclyl, or —$(C_1-C_6)$alkylene-(3- to 7-membered heterocyclyl), wherein $(C_1-C_6)$alkyl, $(C_3-C_6)$cycloalkyl, $(C_5-C_8)$spirocycloalkyl, or $(C_3-C_7)$cycloalkyl of —$(C_1-C_6)$alkylene-$(C_3-C_7)$cycloalkyl is each substituted with 0, 1, 2, or 3 independently selected halogen.

9. The compound of claim 1, wherein the compound is of Formula (I-C-5), (I-C-5)

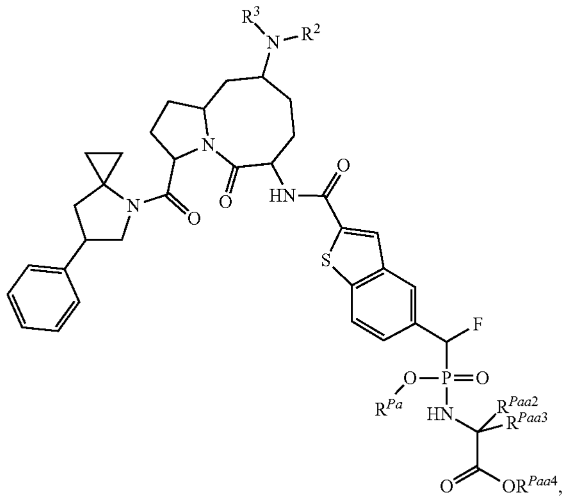

or a pharmaceutically acceptable salt thereof, wherein:

$R^{Pa}$ is $(C_1-C_6)$alkyl, halo$(C_1-C_6)$alkyl, $(C_6-C_{10})$aryl, or $(C_3-C_6)$cycloalkyl, wherein $(C_1-C_6)$alkyl is substituted with 0, 1, 2, or 3 substituents each independently selected from the group consisting of halo and $(C_1-C_6)$ alkoxy;

$R^{Paa2}$ is H or $(C_1-C_6)$alkyl;

$R^{Paa3}$ is H, $(C_1-C_6)$alkyl, —$(C_1-C_6)$alkylene-$(C_1-C_6)$ alkoxy, or —$(C_1-C_6)$alkylene-$(C_6-C_{10})$aryl; or $R^{Paa2}$ and $R^{Paa3}$, together with the carbon atom to which they are attached, form $(C_3-C_6)$cycloalkyl; and $R^{Paa4}$ is $(C_1-C_6)$alkyl, halo$(C_1-C_6)$alkyl, —$(C_1-C_6)$alkylene-$(C_1-C_6)$alkoxy, $(C_3-C_6)$cycloalkyl, $(C_5-C_8)$spirocycloalkyl, —$(C_1-C_6)$alkylene-$(C_6-C_{10})$aryl, —$(C_1-C_6)$alkylene-$(C_3-C_7)$cycloalkyl, 3- to 7-membered heterocyclyl, or —$(C_1-C_6)$alkylene-(3- to 7-membered heterocyclyl), wherein $(C_1-C_6)$alkyl, $(C_3-C_6)$cycloalkyl, $(C_5-C_8)$spirocycloalkyl, or $(C_3-C_7)$cycloalkyl of —$(C_1-C_6)$alkylene-$(C_3-C_7)$cycloalkyl is each substituted with 0, 1, 2, or 3 independently selected halogen.

10. The compound of claim 1, wherein the compound is of Formula (I-A-3), (I-A-3)

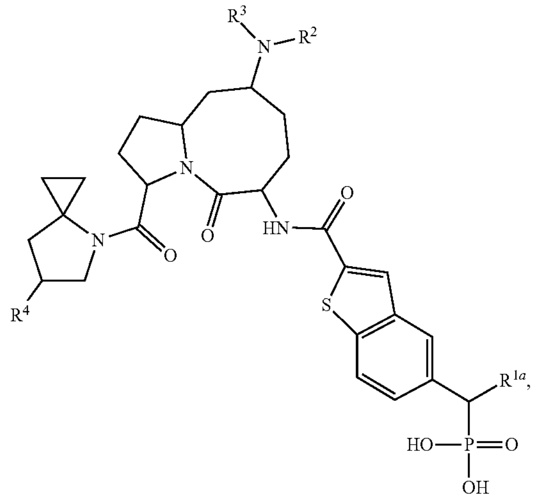

or a pharmaceutically acceptable salt thereof.

11. The compound of claim 1, wherein the compound is of Formula (I-A-5), (I-A-5)

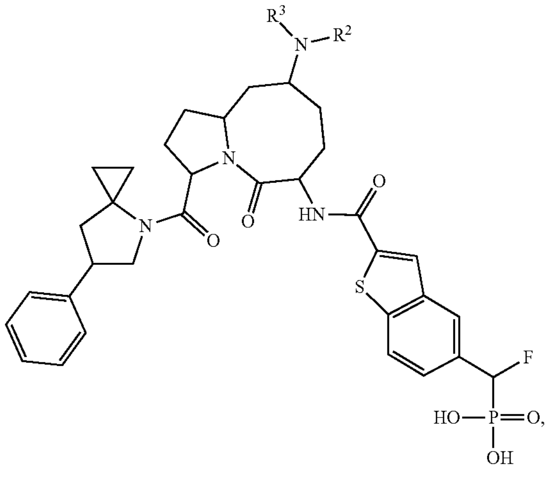

or a pharmaceutically acceptable salt thereof.

12. The compound of claim 1, wherein the compound is of Formula (I-B-3), (I-B-3)

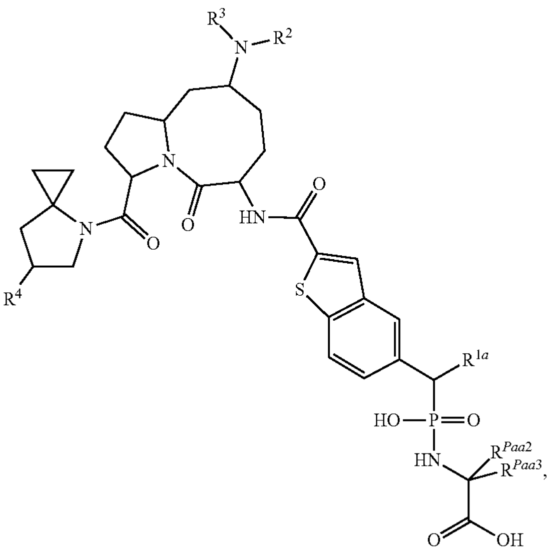

or a pharmaceutically acceptable salt thereof, wherein:

$R^{Paa2}$ is H or $(C_1-C_6)$alkyl; and $R^{Paa3}$ is H, $(C_1-C_6)$alkyl, —$(C_1-C_6)$alkylene-$(C_1-C_6)$alkoxy, or —$(C_1-C_6)$alkylene-$(C_6-C_{10})$aryl; or $R^{Paa2}$ and $R^{Paa3}$, together with the carbon atom to which they are attached, form $(C_3-C_6)$cycloalkyl.

13. The compound of claim 1, wherein the compound is of Formula (I-B-5), (I-B-5)

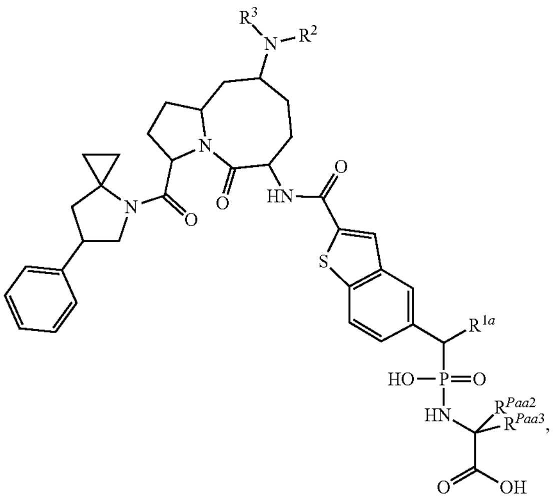

or a pharmaceutically acceptable salt thereof, wherein:

$R^{1a}$ is F;

$R^{Paa2}$ is H or $(C_1-C_6)$alkyl; and $R^{Paa3}$ is H, $(C_1-C_6)$alkyl, —$(C_1-C_6)$alkylene-$(C_1-C_6)$alkoxy, or —$(C_1-C_6)$alkylene-$(C_6-C_{10})$aryl; or $R^{Paa2}$ and $R^{Paa3}$, together with the carbon atom to which they are attached, form $(C_3-C_6)$cycloalkyl.

14. The compound of claim 1, wherein the compound is of Formula (I-H-3), (I-H-3)

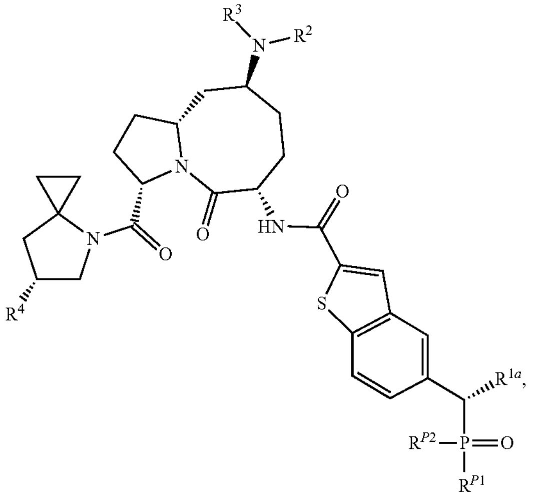

or a pharmaceutically acceptable salt thereof, wherein:

$R^{P1}$ and $R^{P2}$ are each independently —OH, —$OR^{Pa}$, —$NR^{Paa1}CR^{Paa2}R^{Paa3}C(O)OH$, —$NR^{Paa1}CR^{Paa2}R^{Paa3}C(O)OR^{Paa4}$, or Ring A;

Ring A is

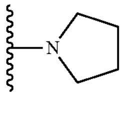 [SMILES: *N1CCCC1]

substituted with 0, 1, 2, or 3 substituents each independently selected from the group consisting of halo, oxo, COOH, and —$C(O)OR^{PE}$;

each $R^{Pa}$ is independently $(C_1\text{-}C_6)$alkyl, halo$(C_1\text{-}C_6)$alkyl, $(C_6\text{-}C_{10})$aryl, or $(C_3\text{-}C_6)$cycloalkyl, wherein $(C_1\text{-}C_6)$alkyl is substituted with 0, 1, 2, or 3 substituents each independently selected from the group consisting of halo and $(C_1\text{-}C_6)$alkoxy;

each $R^{PE}$ is independently $(C_1\text{-}C_6)$alkyl, halo$(C_1\text{-}C_6)$alkyl, —$(C_1\text{-}C_6)$alkylene-$(C_1\text{-}C_6)$alkoxy, $(C_3\text{-}C_6)$cycloalkyl, $(C_5\text{-}C_8)$spirocycloalkyl, —$(C_1\text{-}C_6)$alkylene-$(C_6\text{-}C_{10})$aryl, —$(C_1\text{-}C_6)$alkylene-$(C_3\text{-}C_7)$cycloalkyl, 3- to 7-membered heterocyclyl, or —$(C_1\text{-}C_6)$alkylene-(3- to 7-membered heterocyclyl), wherein $(C_1\text{-}C_6)$alkyl, $(C_3\text{-}C_6)$cycloalkyl, $(C_5\text{-}C_8)$spirocycloalkyl, or $(C_3\text{-}C_7)$cycloalkyl of —$(C_1\text{-}C_6)$alkylene-$(C_3\text{-}C_7)$cycloalkyl is each substituted with 0, 1, 2, or 3 independently selected halogen;

each $R^{Paa1}$ is independently H or $(C_1\text{-}C_6)$alkyl; each $R^{Paa2}$ is independently H or $(C_1\text{-}C_6)$alkyl;

each $R^{Paa3}$ is independently H, $(C_1\text{-}C_6)$alkyl, —$(C_1\text{-}C_6)$alkylene-$(C_1\text{-}C_6)$alkoxy, or —$(C_1\text{-}C_6)$alkylene-$(C_6\text{-}C_{10})$aryl;

or $R^{Paa2}$ and $R^{Paa3}$, together with the carbon atom to which they are attached form $(C_3\text{-}C_6)$cycloalkyl;

and each $R^{Paa4}$ is independently $(C_1\text{-}C_6)$alkyl, halo$(C_1\text{-}C_6)$alkyl, —$(C_1\text{-}C_6)$alkylene-$(C_1\text{-}C_6)$alkoxy, $(C_3\text{-}C_6)$cycloalkyl, $(C_5\text{-}C_8)$spirocycloalkyl, —$(C_1\text{-}C_6)$alkylene-$(C_6\text{-}C_{10})$aryl, —$(C_1\text{-}C_6)$alkylene-$(C_3\text{-}C_7)$cycloalkyl, 3- to 7-membered heterocyclyl, or —$(C_1\text{-}C_6)$alkylene-(3- to 7-membered heterocyclyl), wherein $(C_1\text{-}C_6)$alkyl, $(C_3\text{-}C_6)$cycloalkyl, $(C_5\text{-}C_8)$spirocycloalkyl, or $(C_3\text{-}C_7)$cycloalkyl of —$(C_1\text{-}C_6)$alkylene-$(C_3\text{-}C_7)$cycloalkyl is each substituted with 0, 1, 2, or 3 independently selected halogen.

15. The compound of claim 14, wherein the compound is of Formula (I-H-5), (I-H-5)

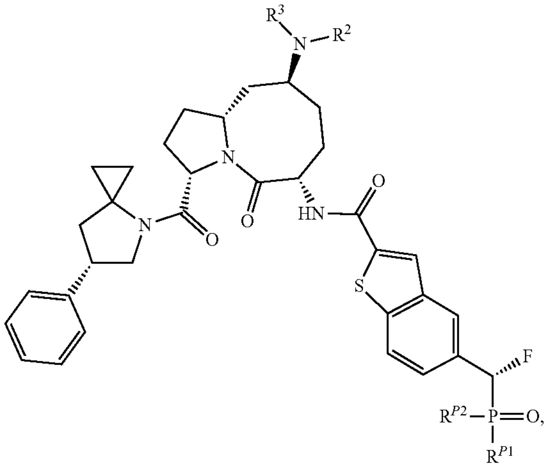

or a pharmaceutically acceptable salt thereof.

16. The compound of claim 1, wherein the compound is of Formula (I-H-4), (I-H-4)

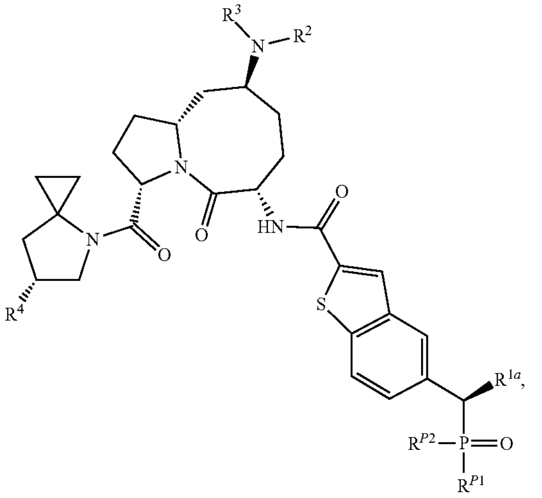

or a pharmaceutically acceptable salt thereof, wherein:

$R^{P1}$ and $R^{P2}$ are each independently —OH, —$OR^{Pa}$, —$NR^{Paa1}CR^{Paa2}R^{Paa3}C(O)OH$, —$NR^{Paa1}CR^{Paa2}R^{Paa3}C(O)OR^{Paa4}$, or Ring A;

Ring A is

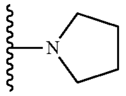 [SMILES: *N1CCCC1]

substituted with 0, 1, 2, or 3 substituents each independently selected from the group consisting of halo, oxo, COOH, and —C(O)$O^{PE}$;

each $R^{Pa}$ is independently ($C_1$-$C_6$)alkyl, halo($C_1$-$C_6$)alkyl, ($C_6$-$C_{10}$)aryl, or ($C_3$-$C_6$)cycloalkyl, wherein ($C_1$-$C_6$)alkyl is substituted with 0, 1, 2, or 3 substituents each independently selected from the group consisting of halo and ($C_1$-$C_6$)alkoxy;

each $R^{PE}$ is independently ($C_1$-$C_6$)alkyl, halo($C_1$-$C_6$)alkyl, —($C_1$-$C_6$)alkylene-($C_1$-$C_6$)alkoxy, ($C_3$-$C_6$)cycloalkyl, ($C_5$-$C_8$)spirocycloalkyl, —($C_1$-$C_6$)alkylene-($C_6$-$C_{10}$)aryl, —($C_1$-$C_6$)alkylene-($C_3$-$C_7$)cycloalkyl, 3-to 7-membered heterocyclyl, or —($C_1$-$C_6$)alkylene-(3- to 7-membered heterocyclyl), wherein ($C_1$-$C_6$)alkyl, ($C_3$-$C_6$)cycloalkyl, ($C_5$-$C_8$)spirocycloalkyl, or ($C_3$-$C_7$)cycloalkyl of —($C_1$-$C_6$)alkylene-($C_3$-$C_7$)cycloalkyl is each substituted with 0, 1, 2, or 3 independently selected halogen;

each $R^{Paa1}$ is independently H or ($C_1$-$C_6$)alkyl; each $R^{Paa2}$ is independently H or ($C_1$-$C_6$)alkyl;

each $R^{Paa3}$ is independently H, ($C_1$-$C_6$)alkyl, —($C_1$-$C_6$)alkylene-($C_1$-$C_6$)alkoxy, or —($C_1$-$C_6$)alkylene-($C_6$-$C_{10}$)aryl;

or $R^{Paa2}$ and $R^{Paa3}$, together with the carbon atom to which they are attached form ($C_3$-$C_6$)cycloalkyl;

and each $R^{Paa4}$ is independently ($C_1$-$C_6$)alkyl, halo($C_1$-$C_6$)alkyl, —($C_1$-$C_6$)alkylene-($C_1$-$C_6$)alkoxy, ($C_3$-$C_6$)cycloalkyl, ($C_5$-$C_8$)spirocycloalkyl, —($C_1$-$C_6$)alkylene-($C_6$-$C_{10}$)aryl, —($C_1$-$C_6$)alkylene-($C_3$-$C_7$)cycloalkyl, 3-to 7-membered heterocyclyl, or —($C_1$-$C_6$)alkylene-(3- to 7-membered heterocyclyl), wherein ($C_1$-$C_6$)alkyl, ($C_3$-$C_6$)cycloalkyl, ($C_5$-$C_8$)spirocycloalkyl, or ($C_3$-$C_7$)cycloalkyl of —($C_1$-$C_6$)alkylene-($C_3$-$C_7$)cycloalkyl is each substituted with 0, 1, 2, or 3 independently selected halogen.

17. The compound of claim 16, wherein the compound is of Formula (I-H-6), (I-H-6)

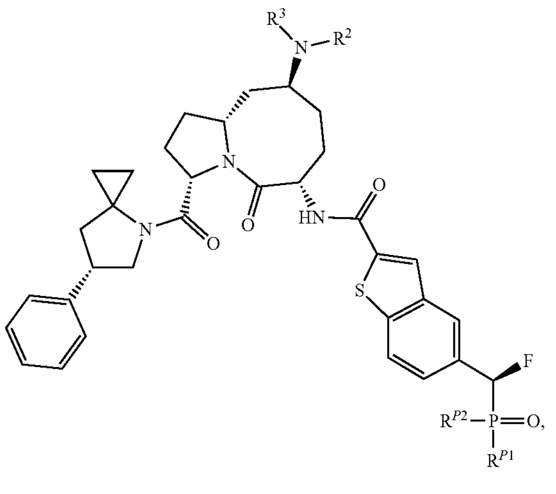

or a pharmaceutically acceptable salt thereof.

18. The compound of claim 2, or a pharmaceutically acceptable salt thereof, wherein $R^2$ is ($C_1$-$C_6$)alkyl; and $R^3$ is halo($C_1$-$C_6$)alkyl.

19. The compound of claim 4, or a pharmaceutically acceptable salt thereof, wherein $R^2$ is ($C_1$-$C_6$)alkyl; and $R^3$ is halo($C_1$-$C_6$)alkyl.

20. The compound of claim 2, or a pharmaceutically acceptable salt thereof, wherein $R^2$ is ($C_1$-$C_6$)alkyl; and $R^3$ is ($C_3$-$C_6$)cycloalkyl substituted with 0, 1, 2, or 3 substituents each independently selected from the group consisting of halogen, cyano, halo($C_1$-$C_6$)alkyl, and halo($C_1$-$C_6$) alkoxy.

21. The compound of claim 4, or a pharmaceutically acceptable salt thereof, wherein $R^2$ is ($C_1$-$C_6$)alkyl; and $R^3$ is ($C_3$-$C_6$)cycloalkyl substituted with 0, 1, 2, or 3 substituents each independently selected from the group consisting of halogen, cyano, halo($C_1$-$C_6$)alkyl, and halo($C_1$-$C_6$) alkoxy.

22. The compound of claim 2, wherein

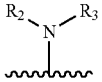

of formula (I) is

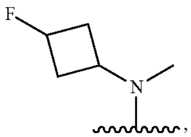,
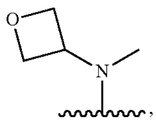,
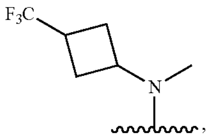,
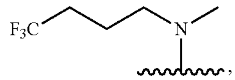,
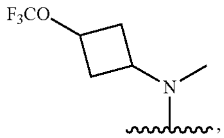,
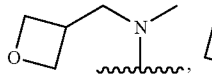,
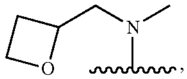,
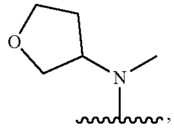,
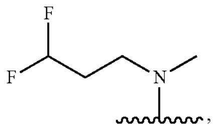,
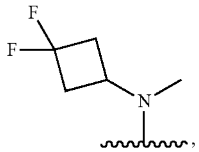,
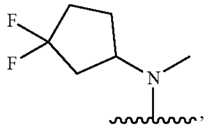,
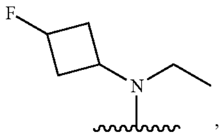,
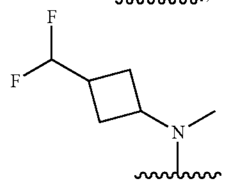,
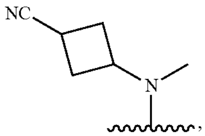,
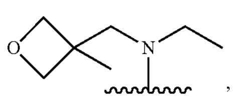,
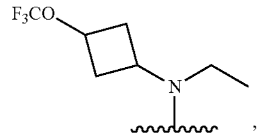, -continued

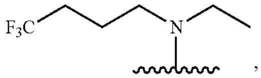,
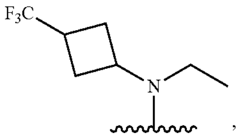,
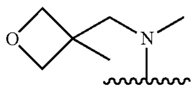,
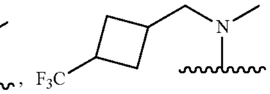,
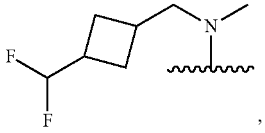,
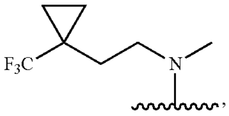,
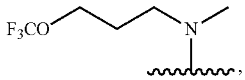,
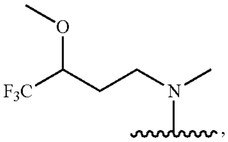,
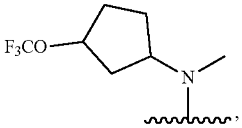, or
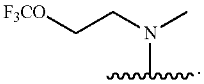.

23. The compound of claim 4, wherein

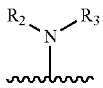

of Formula (I) is

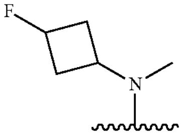,
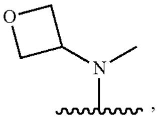,
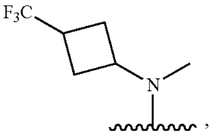,
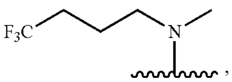,
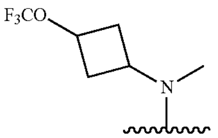,
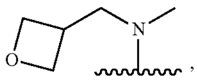,
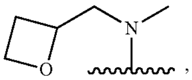,
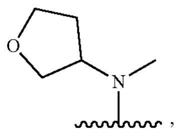,
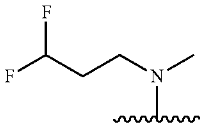,
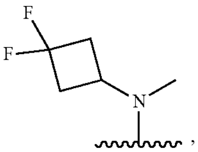, -continued

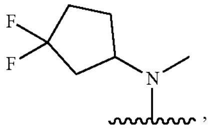,
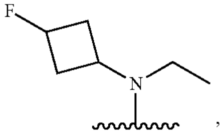,
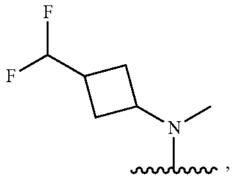,
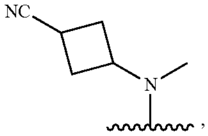,
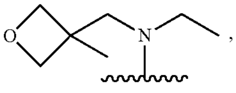,
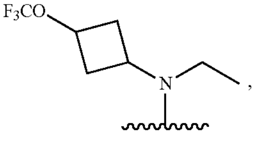,
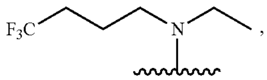,
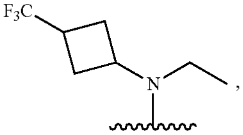,
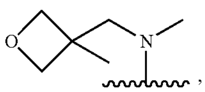,
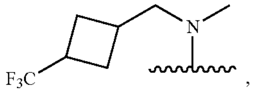,
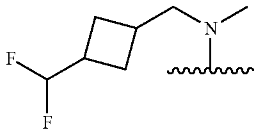,
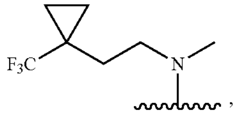,
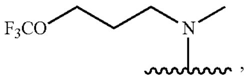,
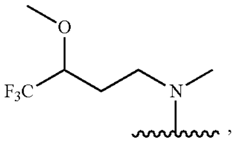,
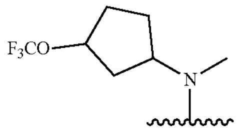, or
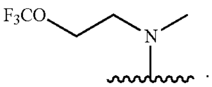.

24. The compound of claim 2, or a pharmaceutically acceptable salt thereof, wherein $R^{Pa}$ is phenyl; $R^{Paa1}$ is H; $R^{Paa2}$ is H; $R^{Paa3}$ is $(C_1-C_6)$alkyl; and $R^{Paa4}$ is $(C_1-C_6)$alkyl.

25. The compound of claim 2, or a pharmaceutically acceptable salt thereof, wherein $R^{Pa}$ is phenyl; $R^{Paa1}$ is H; $R^{Paa2}$ is H; $R^{Paa3}$ is methyl; and $R^{Paa4}$ is

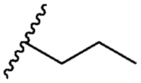.

26. A compound having the structure:

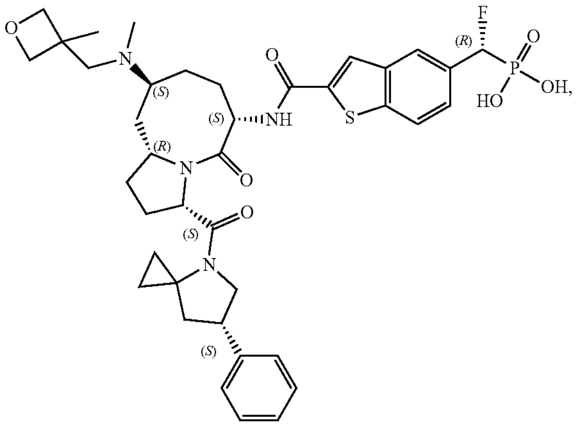

or a pharmaceutically acceptable salt thereof.

27. A compound having the structure:

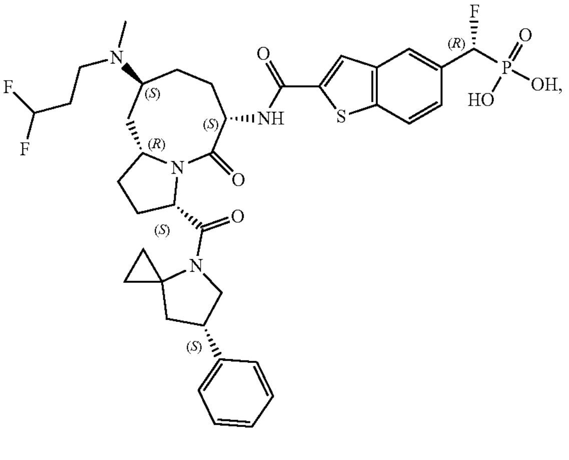

or a pharmaceutically acceptable salt thereof.

28. A compound having the structure:

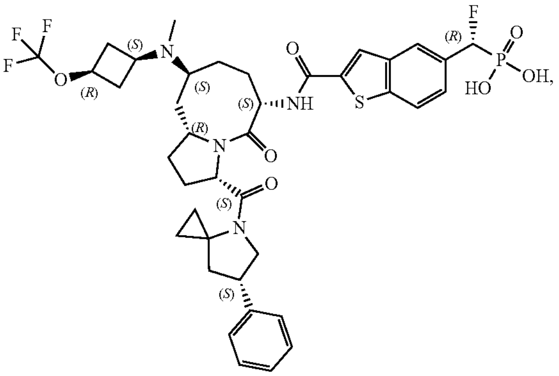

or a pharmaceutically acceptable salt thereof.

29. A compound having the structure:

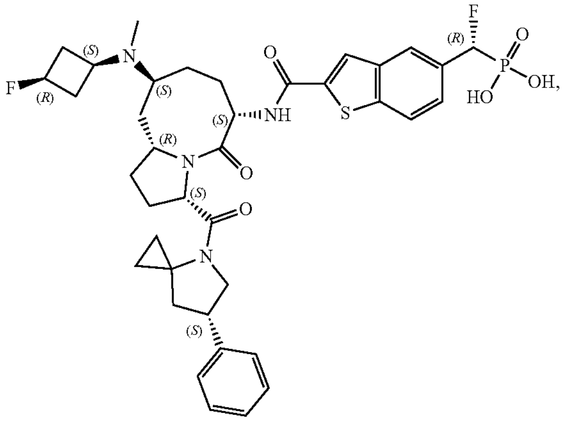

or a pharmaceutically acceptable salt thereof.

30. A compound having the structure:

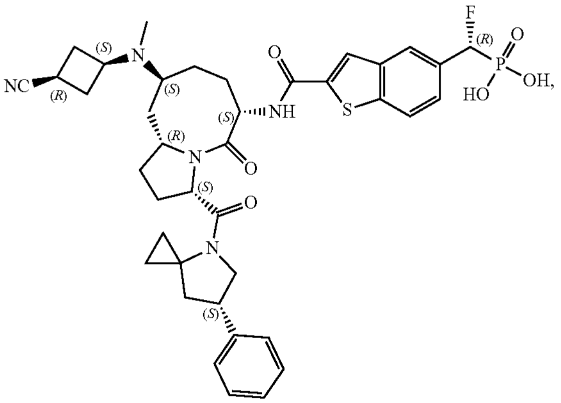

or a pharmaceutically acceptable salt thereof.

31. A compound having the structure:

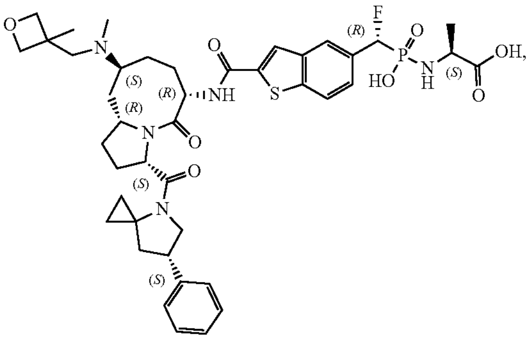

or a pharmaceutically acceptable salt thereof.

32. A compound having the structure:

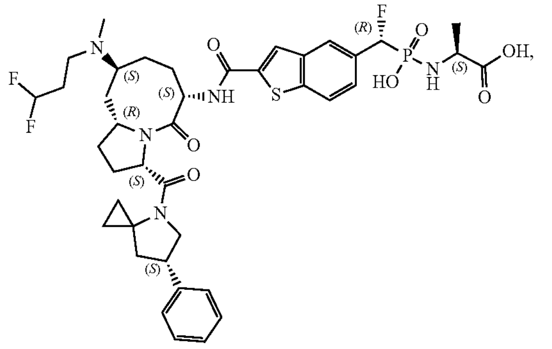

or a pharmaceutically acceptable salt thereof.

33. A compound having the structure:

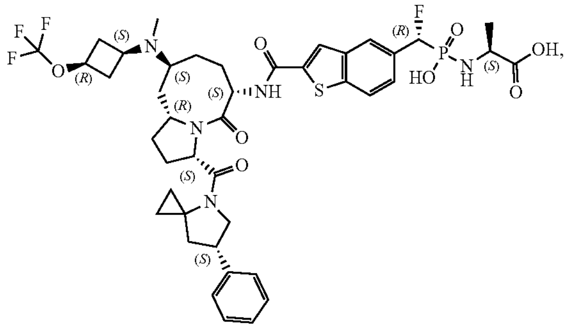

or a pharmaceutically acceptable salt thereof.

34. A compound having the structure:

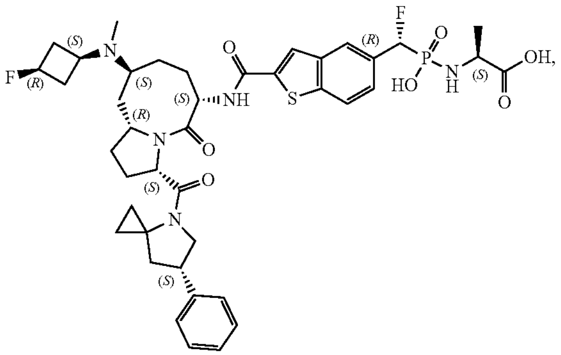

or a pharmaceutically acceptable salt thereof.

35. A compound having the structure:

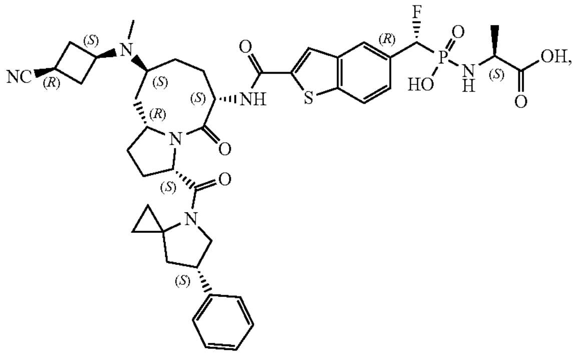

or a pharmaceutically acceptable salt thereof.

36. A compound having the structure:

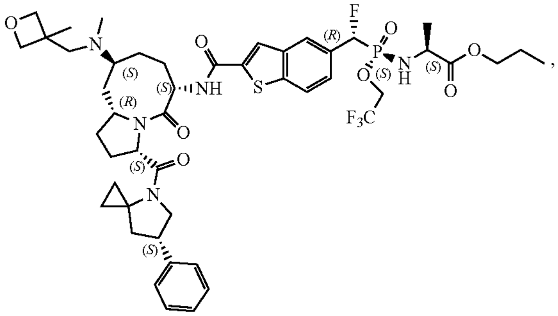

or a pharmaceutically acceptable salt thereof.

37. A compound having the structure:

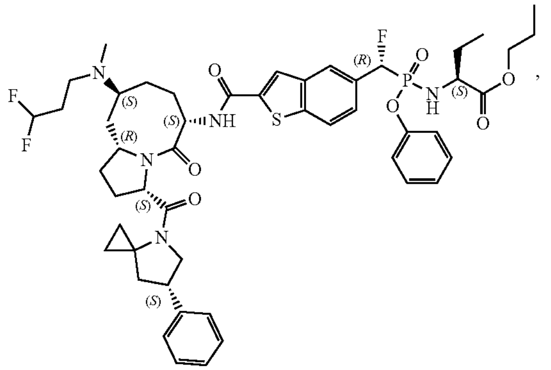

or a pharmaceutically acceptable salt thereof.

38. A compound having the structure:

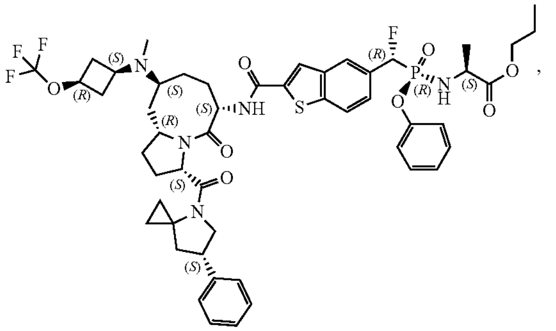

or a pharmaceutically acceptable salt thereof.

39. A compound having the structure:

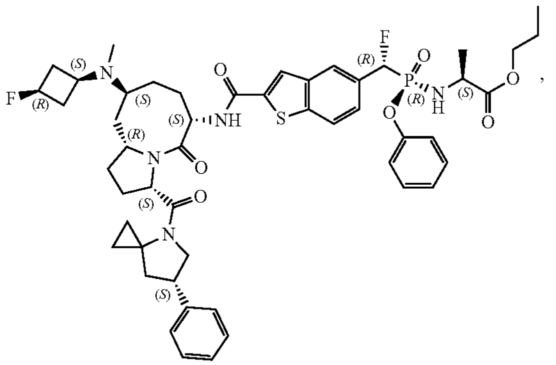

or a pharmaceutically acceptable salt thereof.

40. A compound having the structure:

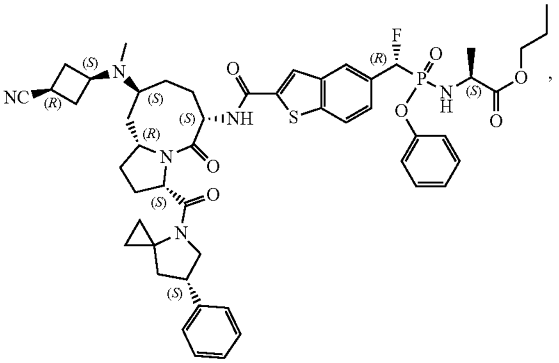

or a pharmaceutically acceptable salt thereof.

41. A pharmaceutical composition comprising the compound of claim 1, or a pharmaceutically acceptable salt thereof, and a pharmaceutically acceptable excipient.

42. A pharmaceutical composition comprising the compound of claim 2, or a pharmaceutically acceptable salt thereof, and a pharmaceutically acceptable excipient.

43. A pharmaceutical composition comprising the compound of claim 3, or a pharmaceutically acceptable salt thereof, and a pharmaceutically acceptable excipient.

44. A pharmaceutical composition comprising the compound of claim 5, or a pharmaceutically acceptable salt thereof, and a pharmaceutically acceptable excipient.

45. A pharmaceutical composition comprising the compound of claim 7, or a pharmaceutically acceptable salt thereof, and a pharmaceutically acceptable excipient.

46. A pharmaceutical composition comprising a compound having the structure:

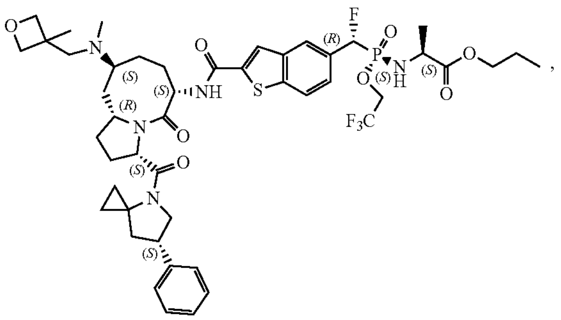

or a pharmaceutically acceptable salt thereof, and a pharmaceutically acceptable excipient.

47. A pharmaceutical composition comprising a compound having the structure:

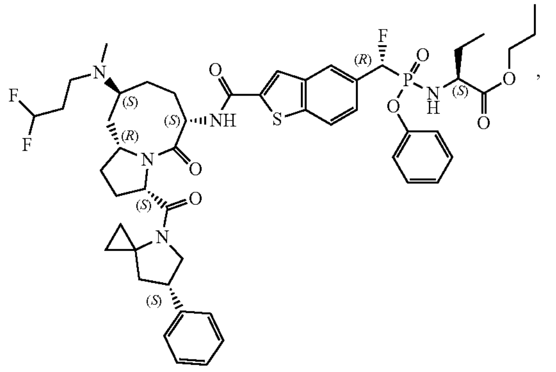

or a pharmaceutically acceptable salt thereof, and a pharmaceutically acceptable excipient.

48. A pharmaceutical composition comprising a compound having the structure:

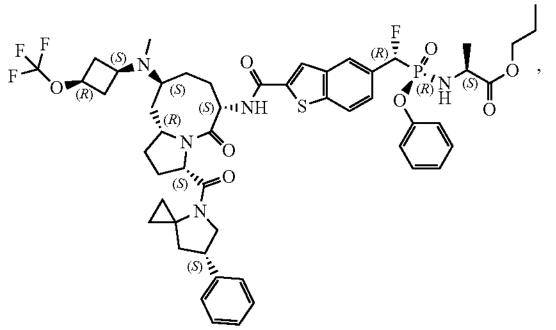

or a pharmaceutically acceptable salt thereof, and a pharmaceutically acceptable excipient.

49. A pharmaceutical composition comprising a compound having the structure:
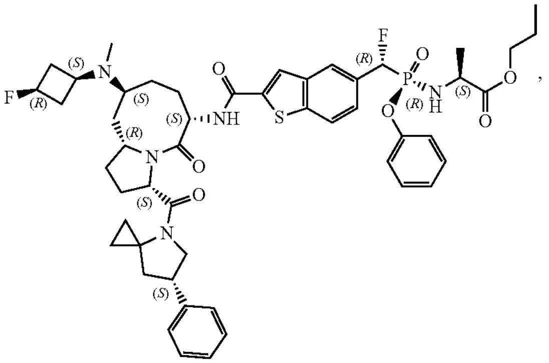
or a pharmaceutically acceptable salt thereof, and a pharmaceutically acceptable excipient.
50. A pharmaceutical composition comprising a compound having the structure:
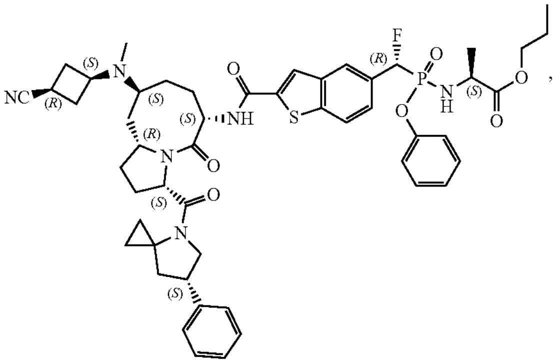
or a pharmaceutically acceptable salt thereof, and a pharmaceutically acceptable excipient.
* * * * *